(12) United States Patent
Matsushima et al.

(10) Patent No.: US 7,531,532 B2
(45) Date of Patent: May 12, 2009

(54) PYRIDINE DERIVATIVE AND PYRIMIDINE DERIVATIVE

(75) Inventors: Tomohiro Matsushima, Tsukuba (JP); Keiko Takahashi, Tsukuba (JP); Setsuo Funasaka, Tsukuba (JP); Hiroshi Obaishi, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 438 days.

(21) Appl. No.: 11/065,631

(22) Filed: Feb. 25, 2005

(65) Prior Publication Data

US 2005/0277652 A1 Dec. 15, 2005

(30) Foreign Application Priority Data

Feb. 27, 2004 (JP) ............................ P2004-054451
Dec. 22, 2004 (JP) ............................ P2004-370801

(51) Int. Cl.
C07D 213/75 (2006.01)
C07D 239/48 (2006.01)
C07D 239/47 (2006.01)
A61K 31/44 (2006.01)

(52) U.S. Cl. ............... 514/218; 514/235.8; 514/252.14; 514/252.18; 514/269; 540/575; 544/122; 544/319

(58) Field of Classification Search ................ 540/575; 544/122, 319; 514/218, 235.8, 252.14, 252.18, 514/269
See application file for complete search history.

(56) References Cited

U.S. PATENT DOCUMENTS

| | | |
|---|---|---|
| 6,790,852 B2 | 9/2004 | Brandt et al. |
| 2003/0199691 A1 | 10/2003 | Brandt et al. |
| 2004/0053908 A1 | 3/2004 | Yasuhiro |
| 2004/0214874 A1 | 10/2004 | Brandt et al. |
| 2004/0242603 A1 | 12/2004 | Fujiwara et al. |
| 2005/0009840 A1 | 1/2005 | Cui et al. |
| 2005/0014753 A1 | 1/2005 | Ding et al. |
| 2005/0245530 A1* | 11/2005 | Borzilleri et al. ........ 514/252.02 |
| 2005/0277652 A1 | 12/2005 | Matsushima et al. |

FOREIGN PATENT DOCUMENTS

| | | |
|---|---|---|
| EP | 1 473 043 A1 | 11/2004 |
| EP | 1 719 762 A1 | 11/2006 |
| WO | WO 02/32872 A1 | 4/2002 |
| WO | WO 02/096361 A2 | 12/2002 |
| WO | WO 03/000660 A1 | 1/2003 |
| WO | WO 03/087026 A1 | 10/2003 |
| WO | WO-2004/076412 A2 | 9/2004 |
| WO | WO-2004/089286 A2 | 10/2004 |
| WO | WO 2005/005389 A2 | 1/2005 |
| WO | WO-2005/030140 A2 | 4/2005 |
| WO | WO-2005/082855 A1 | 9/2005 |
| WO | WO-2005/117867 A2 | 12/2005 |
| WO | WO-2006/004636 A2 | 1/2006 |
| WO | WO-2006/014325 A2 | 2/2006 |
| WO | WO-2007/023768 A1 | 3/2007 |

OTHER PUBLICATIONS

Ulrich, Crystallization—4. Crystal Characteristics, Kirk-Othmer Encyclopedia of Chemical Technology, Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Christine Ting Ting To et al.; Oncology Reports 5: 1013-1024, 1998.
Eliot M. Rosen et al.; Advances in Cancer Research, 67, 257-279, 1995.
N. Maehara et al.; British Journal of Cancer, 84, 864-873, 2001.
Kunio Matsumoto et al.; Cancer Sci., 94, 321-327, 2003.
Matthias Ebert et al.; Cancer Research; 54, pp. 5775-5778, Nov. 15, 1994.
Hiroki Kuniyasu et al.; Biochemical and Biophysical Research Communications; vol. 189, No. 1, pp. 227-232; Nov. 30, 1992.
Chi Liu et al.; Oncogene; 7, pp. 181-185, 1992.
Rola A. D. Ghoussoub et al.; Cancer, 82, pp. 1513-1520, 1998.

(Continued)

*Primary Examiner*—Deepak Rao
(74) *Attorney, Agent, or Firm*—Birch, Stewart, Kolasch & Birch, LLP

(57) ABSTRACT

A compound represented by the following formula, a salt thereof or a hydrate of the foregoing has an excellent hepatocyte growth factor receptor (HGFR) inhibitory activity, and exhibits anti-tumor activity, angiogenesis inhibitory activity and cancer metastasis inhibitory activity.

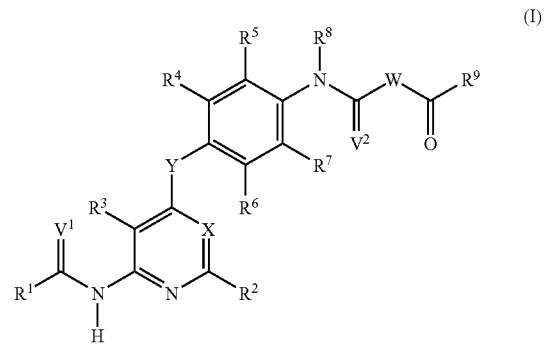

[$R^1$ represents $C_{1-6}$ alkyl or the like; $R^2$ and $R^3$ represent hydrogen; $R^4$, $R^5$, $R^6$, and $R^7$ may be the same or different and each represents hydrogen, halogen, $C_{1-6}$ alkyl or the like; $R^8$ represents hydrogen or the like; $R^9$ represents $C_{1-6}$ alkyl or the like; $V^1$ represents oxygen or the like; $V^2$ represents oxygen or sulfur; W represents —NH— or the like; X represents —CH=, nitrogen or the like; and Y represents oxygen or the like.]

25 Claims, No Drawings

OTHER PUBLICATIONS

Louis L. Pisters et al.; The Journal of Urology; vol. 154, pp. 293-298, Jul. 1995.

Iwao Takanami et al.; Oncology; 53; pp. 392-397, 1996.

Laura Schmidt et al.; Oncogene, 18, pp. 2343-2350, 1999.

Shahriar Koochekpour et al.; Cancer Research; 57; pp. 5391-5398, Dec. 1, 1997.

Janos Tanyi et al.; Pathology Oncology Research; vol. 5, No. 3; pp. 187-191, 1999.

Yoshitaka Imaizumi et al.; Clinical Cancer Research, 9, pp. 181-187, Jan. 2003.

Nakagawa et al., "A novel orally active c-Met and VEGFR-2 tyrosine kinase inhibitor exhibited potent antitumor effect and prolongation of survival in preclinical mice model," Proceedings of the American Association for Cancer Research, vol. 49, p. 1154, 2008, E7050, #4845., 2008.

Obaishi et al.. "A novel small molecule inhibitor the c-Met and VEGFR-2 tyrosine kinases," Proceedings of the American Association for Cancer Research, vol. 49, p. 1154, 2008, E7050, #4846., 2008.

"MET tyrosine kinase inhibitors", Nature Reviews Drug Discovery, vol. 7, 469 (2008).

"E7050: A novel orally active c-Met and VEGFR-2 tyrosine kinase inhibitor exhibited potent antitumor effect and prolongation of survival in preclinical mice model.", Nakagawa et al., Proceedings of the American Association for Cancer Research, vol. 49, p. 1154, #4845, 2008.

"E7050: A novel small molecule inhibitor the c-Met and VEGFR-2 tyrosine kinases.", Obaishi et al., Proceedings of the American Association for Cancer Research, vol. 49, p. 1154, #4846, 2008.

"E7050: A novel small molecule inhibitor of the c-Met and VEGFR-2 tyrosine kinases.", Obaishi et al., Abstract of a poster presentation P1-7 in Japanese Association for Molecular Target Therapy of Cancer 2008 meeting. Issue date of abstract May 25, 2008.

"E7050: A novel orally active c-Met and VEGFR-2 tyrosine kinase inhibitor exhibited potent antitumor effect and prolongation of survival in preclinical mice model", Nakagawa et al., Abstract of a poster presentation P1-8 in Japanese Association for Molecular Target Therapy of Cancer 2008 meeting. Issue date of abstract May 25, 2008.

"E7050: A novel orally active c-Met and VEGFR-2 tyrosine kinase inhibitor exhibited potent antitumor effect and prolongation of survival in preclinical mice model.", Nakagawa et al., Proceedings of the American Association for Cancer Research, vol. 49, p. 1154, #4845, 2008.

"E7050: A novel small moleculae inhibitor the c-Met and VEGFR-2 tyrosine kinases.", Obaishi et al., Proceedings of the American Association for Cancer Research, vol. 49, p. 1154, #4846, 2008.

* cited by examiner

PYRIDINE DERIVATIVE AND PYRIMIDINE DERIVATIVE

BACKGROUND OF THE INVENTION

1. Field of the Invention

The present invention relates to a novel pyridine derivative and pyrimidine derivative, a salt thereof or a hydrate of the foregoing, having inhibitory activity against hepatocyte growth factor receptor, anti-tumor activity, inhibitory activity against angiogenesis, inhibitory activity against cancer metastasis or the like.

2. Related Background of the Invention

Overexpression of hepatocyte growth factor receptor (hereafter referred to as "HGFR") is reported in various kinds of tumors such as a pancreatic cancer, a gastric cancer, a colorectal cancer, a breast cancer, a prostate cancer, a lung cancer, a renal cancer, a brain tumor or an ovarian cancer (non-patent document 1). HGFR expressed in these cancer cells is considered to be involved in cancer malignancy (aberrant growth, invasion or enhanced metastasis), because HGFR cause autophosphorylation of intracellular tyrosine kinase constitutively or upon stimulation by hepatocyte growth factor (hereafter referred to as HGF).

It is also reported that HGFR is expressed in vascular endothelial cells and is involved in tumor angiogenesis since HGF stimulates HGFR to facilitate proliferate and migration of vascular endothelial cells (non-patent document 2).

Furthermore, NK4, an antagonistic peptide for HGF, is reported to block HGF-HGFR signal to inhibit invasion of cancer cells and tumor angiogenesis (non-patent documents 3 and 4).

Therefore, a compound having inhibitory activity for HGFR is expected to be useful as an anti-tumor agent, an angiogenesis inhibitor or an inhibitor for cancer metastasis.

With regard to documents disclosing a low molecular weight compound having inhibitory activity for HGFR, the patent documents 1, 2 and 3 are listed. However, the patent document 1 discloses indolinone derivatives, the patent document 2 discloses quinoline derivatives and quinazoline derivatives, and the patent document 3 discloses imidazole derivatives; therefore the compounds disclosed in these documents are obviously different in the structure from pyridine derivatives and pyrimidine derivatives according to the present invention.

The patent document 4 discloses pyridine derivatives and pyrimidine derivatives similar in the structure to the compounds according to the present invention. The patent document 4, however, does not disclose inhibitory activity for HGFR of the compounds disclosed in the patent document 4 as well as the compounds according to the present invention.

[Patent document 1] WO 02/096361
[Patent document 2] WO 03/000660
[Patent document 3] WO 03/087026
[Patent document 4] WO 02/032872
[Non-patent document 1] Oncology Reports, 5, 1013-1024 (1998)
[Non-patent document 2] Advances in Cancer Research, 67, 257-279 (1995)
[Non-patent document 3] British Journal of Cancer, 84, 864-873 (2001)
[Non-patent document 4] Cancer Sci., 94, 321-327 (2003)

SUMMARY OF THE INVENTION

An object of the present invention is to provide a compound showing anti-tumor activity, inhibitory activity against angiogenesis or inhibitory activity against cancer metastasis by inhibiting cellular aberrant growth, morphological change and hypermobility via HGFR in vivo.

As a result of diligent studies in view of the above situation, the present inventors have succeeded in synthesizing novel pyridine derivatives and pyrimidine derivatives represented by the formula (I), salts thereof or hydrates of the foregoing, found out that the compounds, salts thereof or hydrates of the foregoing have excellent inhibitory activity for HGFR and also exhibit anti-tumor activity, inhibitory activity for angiogenesis or inhibitory activity for cancer metastasis, and completed the present invention.

Namely, the present invention provides

[1] A compound represented by the following formula, a salt thereof or a hydrate of the foregoing:

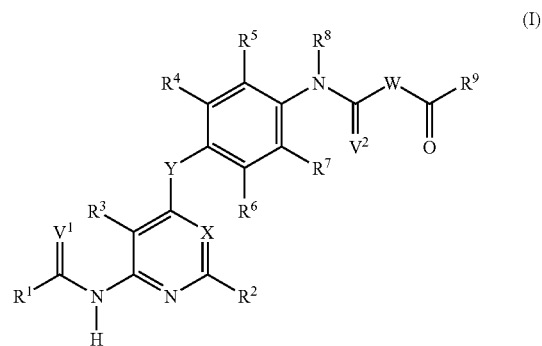

(I)

wherein $R^1$ represents $C_{1-6}$ alkyl, $C_{2-6}$ alkenyl, $C_{2-6}$ alkynyl, $C_{3-10}$ cycloalkyl, $C_{6-10}$ aryl, $C_{1-6}$ alkoxy, 5- to 10-membered heteroaryl, a 3- to 10-membered non-aromatic heterocyclic group or a group represented by the formula —$NR^{11a}R^{11b}$, and $R^1$ may be substituted with a substituent selected from Substituent Group A or Substituent Group B, wherein $R^{11a}$ and $R^{11b}$ may be the same or different and each represents hydrogen, $C_{1-6}$ alkyl, $C_{3-6}$ alkenyl, $C_{3-6}$ alkynyl, $C_{3-10}$ cycloalkyl, $C_{6-10}$ aryl, $C_{1-6}$ alkoxy, 5- to 10-membered heteroaryl or a 4- to 10-membered non-aromatic heterocyclic group, and $R^{11a}$ and $R^{11b}$ may be substituted with a substituent selected from Substituent Group A or Substituent Group B;

$R^2$ and $R^3$ represent hydrogen;

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino;

$R^8$ represents hydrogen or $C_{1-6}$ alkyl;

$R^9$ represents $C_{1-6}$ alkyl, $C_{2-6}$ alkenyl, $C_{2-6}$ alkynyl, $C_{3-10}$ cycloalkyl, $C_{6-10}$ aryl, $C_{3-10}$ cycloalkyl-$C_{1-6}$ alkyl, $C_{6-10}$ aryl-$C_{1-6}$ alkyl, $C_{1-6}$ alkoxy, 5- to 10-membered heteroaryl, a 3- to 10-membered non-aromatic heterocyclic group, 5- to 10-membered heteroaryl-$C_{1-6}$ alkyl, 3- to 10-membered non-aromatic heterocyclic-$C_{1-6}$ alkyl or a group represented by the formula —$NR^{11a}R^{11b}$, and $R^9$ may be substituted with a substituent selected from Substituent Group A or Substituent Group B, wherein $R^{11a}$ and $R^{11b}$ represent the same meaning as recited above;

$V^1$ and $V^2$ may be the same or different and each represents oxygen or sulfur;

W represents a group represented by the formula —N($R^{W3}$)—, wherein $R^{W3}$ represents hydrogen or $C_{1-6}$ alkyl;

X represents a group represented by the formula —C($R^{10}$)= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as recited above; and Y represents oxygen, sulfur, sulfinyl, sulfonyl, or a group represented by the formula —N($R^Y$)—, wherein $R^Y$ represents hydrogen or $C_{1-6}$ alkyl, wherein Substituent Group A consists of halogen, hydroxyl, mercapto, nitro, cyano and oxo;

wherein Substituent Group B consists of $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{3-6}$ alkenyloxy, $C_{3-6}$ alkynyloxy, $C_{3-10}$ cycloalkoxy, $C_{6-10}$ aryloxy, 5- to 10-membered heteroaryloxy, 4- to 10-membered non-aromatic heterocyclicoxy, $C_{1-6}$ alkylthio, $C_{3-6}$ alkenylthio, $C_{3-6}$ alkynylthio, $C_{3-10}$ cycloalkylthio, $C_{6-10}$ arylthio, 5- to 10-membered heteroarylthio, 4- to 10-membered non-aromatic heterocyclicthio and a group represented by the formula -$T^1$-$T^2$-$T^3$, and each group in Substituent Group B may be substituted with a substituent selected from Substituent Group C, wherein $T^1$ represents a direct bond or $C_{1-6}$ alkylene, $T^2$ represents carbonyl, sulfinyl, sulfonyl, a group represented by the formula —C(=O)—O—, a group represented by the formula —O—C(=O)—, a group represented by the formula —$SO_2$—O—, a group represented by the formula —O—$SO_2$—, a group represented by the formula —$NR^{T1}$—, a group represented by the formula —C(=O)—$NR^{T1}$—, a group represented by the formula —$NR^{T1}$—C(=O)—, a group represented by the formula —$SO_2$—$NR^{T1}$— or a group represented by the formula —$NR^{T1}$—$SO_2$—, T represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl, or a 4- to 10-membered non-aromatic heterocyclic group, and $R^{T1}$ represents hydrogen or $C_{1-6}$ alkyl; and wherein Substituent Group C consists of halogen, hydroxyl, mercapto, nitro, cyano, oxo, $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy and $C_{1-6}$ alkylthio.

[2] A compound according to [1], a salt thereof or a hydrate of the foregoing, wherein $R^1$ represents $C_{1-6}$ alkyl optionally substituted with a substituent selected from Substituent Group A or Substituent Group B recited in [1].

[3] A compound according to [1], a salt thereof or a hydrate of the foregoing, wherein $R^1$ represents $C_{1-6}$ alkyl optionally substituted with a substituent selected from Substituent Group D, wherein Substituent Group D consists of amino, mono-$C_{1-6}$ alkylamino and di-$C_{1-6}$ alkylamino.

[4] A compound according to [1], a salt thereof or a hydrate of the foregoing, wherein $R^1$ represents a 3- to 10-membered non-aromatic heterocyclic group optionally substituted with a substituent selected from Substituent Group A or Substituent Group B recited in [1].

[5] A compound according to [1], a salt thereof or a hydrate of the foregoing, wherein $R^1$ represent a group represented by the formula (II):

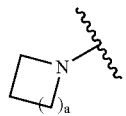

(II)

wherein a represents an integer of 1 to 4,
or a group represented by the formula (III):

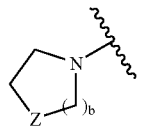

(III)

wherein b represents an integer of 1 to 3, and Z represents oxygen, sulfur, carbonyl, sulfonyl or a group represented by the formula —$NR^Z$—, wherein $R^Z$ represents hydrogen or $C_{1-6}$ alkyl, and the groups represented by the formula (II) or (III) may be substituted with a substituent selected from Substituent Group A or Substituent Group B recited in [1].

[6] A compound according to [1], a salt thereof or a hydrate of the foregoing, wherein $R^1$ represents azetidin-1-yl, pyrrolidin-1-yl, piperidin-1-yl, azepan-1-yl, piperazin-1-yl, diazepan-1-yl, morpholin-4-yl, thiomorpholin-4-yl or 1,1-dioxothiomorpholin-4-yl optionally substituted with a substituent selected from Substituent Group E, wherein Substituent Group E consists of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, diazepanyl and a group represented by -$T^4$-$T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino, where each group included in Substituent Group E may be substituted with hydroxyl, $C_{1-6}$ alkyl, di-$C_{1-6}$ alkylamino, azetidinyl or pyrrolidinyl.

[7] A compound according to [1], a salt thereof or a hydrate of the foregoing, wherein $R^1$ represents azetidin-1-yl, pyrrolidin-1-yl, piperidin-1-yl, azepan-1-yl, piperazin-1-yl, diazepan-1-yl or morpholin-4-yl optionally substituted with a substituent selected from Substituent Group E', wherein Substituent Group E' consists of methyl, ethyl, dimethylamino, azetidinyl, pyrrolidinyl, piperidinyl and piperazinyl, where each group included in Substituent Group E' may be substituted with hydroxyl, methyl, dimethylamino, azetidinyl or pyrrolidinyl.

[8] A compound according to [1], a salt thereof or a hydrate of the foregoing, wherein $R^1$ represents a group represented by the formula —$NR^{11a}R^{11b}$, wherein $R^{11a}$ and $R^{11b}$ represent the same meaning as recited in [1].

[9] A compound according to [1], a salt thereof or a hydrate of the foregoing, wherein $R^1$ represents a group represented by the formula —NR$^{11c}$R$^{11d}$, wherein R$^{11c}$ represents hydrogen or C$_{1-6}$ alkyl, and R$^{11d}$ represents C$_{1-6}$ alkyl or a group represented by the formula (IV):

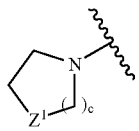

(IV)

wherein c represents an integer of 1 to 3, and Z$^1$ represents oxygen, sulfur, carbonyl, sulfonyl or a group represented by the formula —NR$^{Z1}$—, wherein R$^{Z1}$ represents hydrogen or C$_{1-6}$ alkyl, and R$^{11d}$ may be substituted with a substituent selected from Substituent Group A or Substituent Group B recited in [1].

[10] A compound according to [1], a salt thereof or a hydrate of the foregoing, wherein R$^1$ represents a group represented by the formula —NR$^{11e}$R$^{11f}$, wherein R$^{11e}$ represents hydrogen or C$_{1-6}$ alkyl, and R$^{11f}$ represents C$_{1-6}$ alkyl, pyrrolidin-3-yl, piperidin-3-yl, piperidin-4-yl, piperazin-4-yl or tetrahydropyran-4-yl, and R$^{11f}$ may be substituted with a substituent selected from Substituent Group E recited in [6].

[11] A compound according to [1], a salt thereof or a hydrate of the foregoing, wherein R$^1$ represents a group represented by the formula —NR$^{11g}$R$^{11h}$, wherein R$^{11g}$ represents hydrogen or methyl, and R$^{11h}$ represents n-propyl, n-butyl, pyrrolidin-3-yl, piperidin-3-yl, piperidin-4-yl or tetrahydropyran-4-yl, and R$^{11h}$ may be substituted with a substituent selected from Substituent Group E",
wherein Substituent Group E" consists of methyl, ethyl, n-propyl, acetyl, dimethylamino, diethylamino, azetidinyl, pyrrolidinyl and piperazinyl.
where each group included in Substituent Group E" may be substituted with methyl or diethylamino.

[12] A compound according to any one of [1] to [11], a salt thereof or a hydrate of the foregoing, wherein R$^4$, R$^5$, R$^6$ and R$^7$ may be the same or different and each represents hydrogen, halogen or C$_{1-6}$ alkyl.

[13] A compound according to any one of [1] to [12], a salt thereof or a hydrate of the foregoing, wherein R$^8$ represents hydrogen.

[14] A compound according to any one of [1] to [13], a salt thereof or a hydrate of the foregoing, wherein V$^1$ represents oxygen.

[15] A compound according to any one of [1] to [14], a salt thereof or a hydrate of the foregoing, wherein X represents a group represented by the formula —C(R$^{10a}$)=, wherein R$^{10a}$ represents hydrogen, halogen or cyano.

[16] A compound according to any one of [1] to [14], a salt thereof or a hydrate of the foregoing, wherein X represents nitrogen.

[17] A compound according to any one of [1] to [16], a salt thereof or a hydrate of the foregoing, wherein Y represents oxygen.

[18] A compound according to any one of [1] to [17], a salt thereof or a hydrate of the foregoing, wherein V$^2$ represents sulfur.

[19] A compound according to any one of [1] to [17], a salt thereof or a hydrate of the foregoing, wherein W represents a group represented by the formula —NH— and V$^2$ represents sulfur.

[20] A compound according to any one of [1] to [17], a salt thereof or a hydrate of the foregoing, wherein V$^2$ represents oxygen.

[21] A compound according to any one of [1] to [17], a salt thereof or a hydrate of the foregoing, wherein W represents a group represented by the formula —NH— and V$^2$ represents oxygen.

[22] A compound according to any one of [1] to [21], a salt thereof or a hydrate of the foregoing, wherein R$^9$ represents C$_{1-6}$ alkyl, C$_{3-10}$ cycloalkyl, C$_{3-10}$ cycloalkyl-C$_{1-6}$ alkyl, C$_{6-10}$ aryl-C$_{1-6}$ alkyl, 5- to 10-membered heteroaryl-C$_{1-6}$ alkyl or 3- to 10-membered non-aromatic heterocyclic-C$_{1-6}$ alkyl, and R$^9$ may be substituted with a substituent selected from Substituent Group A or Substituent Group B recited in [1].

[23] A compound according to any one of [1] to [21], a salt thereof or a hydrate of the foregoing, wherein R$^9$ represents C$_{3-10}$ cycloalkyl-C$_{1-6}$ alkyl or C$_{6-10}$ aryl-C$_{1-6}$ alkyl, and R$^9$ may be substituted with a substituent selected from Substituent Group A or Substituent Group B recited in [1].

[24] A pharmaceutical composition comprising a compound according to [1], a salt thereof or a hydrate of the foregoing.

[25] An inhibitor for hepatocyte growth factor receptor, comprising a compound according to [1], a salt thereof or a hydrate of the foregoing.

[26] An angiogenesis inhibitor comprising a compound according to [1], a salt thereof or a hydrate of the foregoing.

[27] An anti-tumor agent comprising a compound according to [1], a salt thereof or a hydrate of the foregoing.

[28] An anti-tumor agent according to [27], wherein tumor is a pancreatic cancer, a gastric cancer, a colorectal cancer, a breast cancer, a prostate cancer, a lung cancer, a renal cancer, a brain tumor or an ovarian cancer.

[29] An inhibitor for cancer metastasis, comprising a compound according to [1], a salt thereof or a hydrate of the foregoing.

[30] A prophylactic or therapeutic method for a disease for which inhibition of hepatocyte growth factor receptor is effective, comprising administering to a patient, a pharmacologically effective dose of a compound according to [1], a salt thereof or a hydrate of the foregoing.

[31] A prophylactic or therapeutic method for a disease for which angiogenesis inhibition is effective, comprising administering to a patient, a pharmacologically effective dose of a compound according to [1], a salt thereof or a hydrate of the foregoing.

[32] A prophylactic or therapeutic method for a tumor, comprising administering to a patient, a pharmacologically effective dose of a compound according to [1], a salt thereof or a hydrate of the foregoing.

[33] A prophylactic or therapeutic method for a tumor according to [32], wherein tumor is a pancreatic cancer, a gastric cancer, a colorectal cancer, a breast cancer, a prostate cancer, a lung cancer, a renal cancer, a brain tumor or an ovarian cancer.

[34] A prophylactic or therapeutic method for a cancer metastasis, comprising administering to a patient, a pharmacologically effective dose of a compound according to [1], a salt thereof or a hydrate of the foregoing.

The symbols and terms as used herein will be defined and the present invention will be described in details below.

Several of the structural formulas for the compounds throughout the present specification represent only one isomeric form for convenience, but the invention encompasses any and all of the geometric isomers as well as optical isomers based on asymmetric carbons, stereoisomers and tautomers, and mixtures of those isomers, which are implied by the structures of the compounds, without being limited to any of the formulas shown for convenience. The compounds of the invention therefore include all those having asymmetric carbons therein and existing in optically active or racemic form, with no particular restrictions on the invention. There are also no restrictions when polymorphic crystalline forms thereof exist, and the compounds may be in one crystalline form or a mixture of different crystalline forms, while anhydrates and hydrates of the compounds of the invention are also included.

The so-called metabolite, a compound which a compound according to the present invention is metabolized in a living body through oxidation, reduction, hydrolysis, conjugation and the others to provide, and the so-called prodrug, a compound which is metabolized in a living body through oxidation, reduction, hydrolysis, conjugation and the others to provide a compound according to the present invention, are also included within the claimed scope of the present invention.

The "salt" includes a salt of an inorganic acid, a salt of an organic acid, a salt of an inorganic base, a salt of an organic base and a salt of an acidic or basic amino acid, among them, a pharmacologically acceptable salt is preferable.

The preferable salt of an inorganic acid includes, for example, a salt of hydrochloric acid, hydrobromic acid, sulfuric acid, nitric acid and phosphoric acid. The preferable salt of an organic acid includes, for example, a salt of acetic acid, succinic acid, fumaric acid, maleic acid, tartaric acid, citric acid, lactic acid, stearic acid, benzoic acid, methanesulfonic acid, ethanesulfonic acid, and p-toluenesulfonic acid.

The preferable salt of an inorganic base includes, for example, an alkali metal salt such as sodium salt and potassium salt, an alkali earth metal salt such as calcium salt and magnesium salt, aluminum salt, and ammonium salt. The preferable salt of an organic base includes, for example, a salt of diethylamine, diethanolamine, meglumine, and N,N-dibenzylethylenediamine.

The preferable salt of an acidic amino acid includes, for example, a salt of aspartic acid and glutamic acid. The preferable salt of a basic amino acid includes, for example, a salt of arginine, lysine and ornithine.

The "halogen" represents fluorine, chlorine, bromine or iodine.

The "$C_{1-6}$ alkyl" represents an alkyl of straight or branched chain having a carbon number of 1 to 6, and includes, for specific example, methyl, ethyl, 1-propyl (n-propyl), 2-propyl (i-propyl), 2-methyl-1-propyl (i-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl.

The "$C_{2-6}$ alkenyl" represents an alkenyl of straight or branched chain having one double bond and a carbon number of 2 to 6, and includes, for specific example, ethenyl (vinyl), 1-propenyl, 2-propenyl (allyl), 1-butenyl, 2-butenyl, 3-butenyl, pentenyl, and hexenyl.

The "$C_{3-6}$ alkenyl" represents an alkenyl of straight or branched chain having one double bond and a carbon number of 3 to 6, and includes, for specific example, 2-propenyl (allyl), 2-butenyl, 3-butenyl, pentenyl, and hexenyl.

The "$C_{2-6}$ alkynyl" represents an alkynyl of straight or branched chain having one triple bond and a carbon number of 2 to 6, and includes, for specific example, ethynyl, 1-propynyl, 2-propynyl, 1-butynyl, 2-butynyl, 3-butynyl, pentynyl, and hexynyl.

The "$C_{3-6}$ alkynyl" represents an alkynyl of straight or branched chain having one triple bond and a carbon number of 3 to 6, and includes, for specific example, 2-propynyl, 2-butynyl, 3-butynyl, pentynyl, and hexynyl.

The "$C_{1-6}$ alkylene" represents a divalent group derived by eliminating further any one hydrogen from the "$C_{1-6}$ alkyl" defined above, and includes, for specific example, methylene, 1,2-ethylene, 1,1-ethylene, 1,3-propylene, tetramethylene, pentamethylene, and hexamethylene.

The "$C_{3-10}$ cycloalkyl" represents a mono- or di-cyclic saturated aliphatic hydrocarbon group having a carbon number of 3 to 10, and includes, for specific example, cyclopropyl, cyclobutyl, cyclopentyl, cyclohexyl, cycloheptyl, cyclooctyl, cyclononyl, cyclodecyl, bicyclo[2.1.0]pentyl, bicyclo[3.1.0]hexyl, bicyclo[2.1.1]hexyl, bicyclo[4.1.0]heptyl, bicyclo[2.2.1]heptyl (norbornyl), bicyclo[3.3.0]octyl, bicyclo[3.2.1]octyl, bicyclo[2.2.2]octyl, bicyclo[4.3.0]nonyl, bicyclo[3.3.1]nonyl, bicyclo[4.4.0]decyl (decalyl), and bicyclo[3.3.2]decyl.

The "$C_{6-10}$ aryl" represents an aromatic hydrocarbon ring group having a carbon number of 6 to 10, and includes, for specific example, phenyl, 1-naphthyl, 2-naphthyl, indenyl, azulenyl, and heptalenyl.

The "heteroatom" represents nitrogen, oxygen, or sulfur.

The "5- to 10-membered heteroaryl" represents an aromatic ring group having 5 to 10 atoms forming the ring and containing 1 to 5 heteroatoms, and includes, for specific example, furyl, thienyl, pyrrolyl, imidazolyl, triazolyl, tetrazolyl, thiazolyl, pyrazolyl, oxazolyl, isoxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthalazinyl, imidazopyridyl, imidazothiazolyl, imidazoxazolyl, benzothiazolyl, benzoxazolyl, benzimidazolyl, indolyl, isoindolyl, indazolyl, pyrrolopyridyl, thienopyridyl, furopyridyl, benzothiadiazolyl, benzoxadiazolyl, pyridopyrimidinyl, benzofuryl, benzothienyl, and thienofuryl. The preferable example of the "5- to 10-membered heteroaryl" includes furyl, thienyl, pyrrolyl, imidazolyl, thiazolyl, pyrazolyl, oxazolyl, isoxazolyl, isothiazolyl, pyridyl, and pyrimidinyl.

The "3- to 10-membered non-aromatic heterocyclic group" represents
(1) a monocyclic or a bicyclic non-aromatic heterocyclic group
(2) having 3 to 10 atoms in the ring,
(3) containing 1 to 2 heteroatoms among the atoms of the ring,
(4) optionally containing 1 to 2 double bonds in the ring,
(5) optionally containing 1 to 3 carbonyl, sulfinyl, or sulfonyl in the ring.

If the group contains nitrogen in the ring, the nitrogen may have a bond not participating in the formation of the ring. The group includes, for specific example, aziridinyl, azetidinyl, pyrrolidinyl, piperidinyl, azepanyl, azocanyl, piperazinyl, diazepanyl, diazocanyl, diazabicyclo[2.2.1]heptyl, morpholinyl, thiomorpholinyl, 1,1-dioxothiomorpholinyl, oxiranyl, oxetanyl, tetrahydrofuryl, tetrahydropyranyl, dioxanyl, tetrahydrothienyl, tetrahydrothiopyranyl, oxazolidinyl, and thiazolidinyl.

The preferable example of the "3- to 10-membered non-aromatic heterocyclic group" includes aziridinyl, azetidinyl, pyrrolidinyl, piperidinyl, azepanyl, piperazinyl, diazepanyl, morpholinyl, thiomorpholinyl, 1,1-dioxothiomorpholinyl, tetrahydrofuryl, and tetrahydropyranyl.

The "4- to 10-membered non-aromatic heterocyclic group" represents
(1) a monocyclic or a bicyclic non-aromatic heterocyclic group
(2) having 4 to 10 atoms in the ring,
(3) containing 1 to 2 heteroatoms among the atoms of the ring,
(4) optionally containing 1 to 2 double bonds in the ring,
(5) optionally containing 1 to 3 carbonyl, sulfinyl, or sulfonyl in the ring.

If the group contains nitrogen in the ring, the nitrogen may have a bond not participating in the formation of the ring. The group includes, for specific example, azethidinyl, pyrrolidinyl, piperidinyl, azepanyl, azocanyl, piperazinyl, diazepanyl, diazocanyl, diazabicyclo[2.2.1]heptyl, morpholinyl, thiomorpholinyl, 1,1-dioxothiomorpholinyl, oxetanyl, tetrahydrofuryl, tetrahydropyranyl, dioxanyl, tetrahydrothienyl, tetrahydrothiopyranyl, oxazolidinyl, and thiazolidinyl.

The preferable example of the "4- to 10-membered non-aromatic heterocyclic group" includes azetidinyl, pyrrolidinyl, piperidinyl, azepanyl, piperazinyl, diazepanyl, morpholinyl, thiomorpholinyl, 1,1-dioxothiomorpholinyl, tetrahydrofuryl, and tetrahydropyranyl.

The "$C_{3-10}$ cycloalkyl-$C_{1-6}$ alkyl" represents a group obtained by substituting any one hydrogen of the above defined "$C_{1-6}$ alkyl" with the above defined "$C_{3-10}$ cycloalkyl", and includes, for specific example, cyclopropylmethyl, cyclobutylmethyl, cyclopentylmethyl, cyclohexylmethyl, cycloheptylmethyl, cyclooctylmethyl, cyclononylmethyl, cyclodecylmethyl, bicyclo[2.2.1]heptylmethyl (norbornylmethyl), and bicyclo[4.4.0]decylmethyl (decarylmethyl).

The "$C_{6-10}$ aryl-$C_{1-6}$ alkyl" represents a group obtained by substituting any one hydrogen of the above defined "$C_{1-6}$ alkyl" with the above defined "$C_{6-10}$ aryl", and includes, for specific example, benzyl, 1-naphthylmethyl, 2-naphthylmethyl, phenethyl, 1-naphthylethyl, and 2-naphthylethyl.

The "5- to 10-membered heteroaryl-$C_{1-6}$ alkyl" represents a group obtained by substituting any one hydrogen of the above defined "$C_{1-6}$ alkyl" with the above defined "5- to 10-membered heteroaryl", and includes, for specific example, furylmethyl, thienylmethyl, pyrrolylmethyl, imidazolylmethyl, triazolylmethyl, tetrazolylmethyl, thiazolylmethyl, pyrazolylmethyl, oxazolylmethyl, isoxazolylmethyl, isothiazolylmethyl, furazanylmethyl, thiadiazolylmethyl, oxadiazolylmethyl, pyridylmethyl, pyrazinylmethyl, pyridazinylmethyl, pyrimidinylmethyl, triazinylmethyl, furylethyl, thienylethyl, pyrrolylethyl, imidazolylethyl, triazolylethyl, tetrazolylethyl, thiazolylethyl, pyrazolylethyl, oxazolylethyl, isoxazolylethyl, isothiazolylethyl, furazanylethyl, thiadiazolylethyl, oxadiazolylethyl, pyridylethyl, pyrazinylethyl, pyridazinylethyl, pyrimidinylethyl, and triazinylethyl.

The preferable example of the "5- to 10-membered heteroaryl $C_{1-6}$ alkyl" includes furylmethyl, thienylmethyl, pyrrolylmethyl, imidazolylmethyl, thiazolylmethyl, pyrazolylmethyl, oxazolylmethyl, isoxazolylmethyl, isothiazolylmethyl, pyridylmethyl, pyrimidinylmethyl, furylethyl, thienylethyl, pyrrolylethyl, imidazolylethyl, thiazolylethyl, pyrazolylethyl, oxazolylethyl, isoxazolylethyl, isothiazolylethyl, pyridylethyl, and pyrimidinylethyl.

The "3- to 10-membered non-aromatic heterocyclic-$C_{1-6}$ alkyl" represents a group obtained by substituting any one hydrogen of the above defined "$C_{1-6}$ alkyl" with the above defined "3- to 10-membered heterocyclic group", and includes, for specific example, aziridinylmethyl, azetidinylmethyl, pyrrolidinylmethyl, piperidinylmethyl, azepanylmethyl, azocanylmethyl, piperazinylmethyl, diazepanylmethyl, diazocanylmethyl, morpholinylmethyl, thiomorpholinylmethyl, 1,1-dioxothiomorpholinylmethyl, oxiranylmethyl, oxetanylmethyl, tetrahydrofurylmethyl, tetrahydropyranylmethyl, dioxanylmethyl, tetrahydrothienylmethyl, tetrahydrothiopyranylmethyl, oxazolidinylmethyl, thiazolidinylmethyl, aziridinylethyl, azetidinylethyl, pyrrolidinylethyl, piperidinylethyl, azepanylethyl, azocanylethyl, piperazinylethyl, diazepanylethyl, diazocanylethyl, morpholinylethyl, thiomorpholinylethyl, 1,1-dioxothiomorpholinylethyl, oxiranylethyl, oxetanylethyl, tetrahydrofurylethyl, tetrahydropyranylethyl, dioxanylethyl, tetrahydrothienylethyl, tetrahydrothiopyranylethyl, oxazolidinylethyl, and thiazolidinylethyl.

The preferable example of the "3- to 10-membered non-aromatic heterocyclic-$C_{1-6}$ alkyl" includes azetidinylmethyl, pyrrolidinylmethyl, piperidinylmethyl, azepanylmethyl, piperazinylmethyl, diazepanylmethyl, morpholinylmethyl, thiomorpholinylmethyl, tetrahydrofurylmethyl, azetidinylethyl, pyrrolidinylethyl, piperidinylethyl, azepanylethyl, piperazinylethyl, diazepanylethyl, morpholinylethyl, thiomorpholinylethyl, and tetrahydrofurylethyl.

The "$C_{1-6}$ alkoxy" represents a group obtained by adding oxygen to the terminal of the above defined "$C_{1-6}$ alkyl", and includes, for specific example, methoxy, ethoxy, 1-propoxy (n-propoxy), 2-propoxy (i-propoxy), 2-methyl-1-propoxy (i-butoxy), 2-methyl-2-propoxy (t-butoxy), 1-butoxy (n-butoxy), 2-butoxy (s-butoxy), 1-pentyloxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propoxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, and 2,3-dimethyl-2-butoxy.

The "$C_{1-6}$ alkylthio" represents a group obtained by adding sulfur to the terminal of the above defined "$C_{1-6}$ alkyl", and includes, for specific example, methylthio, ethylthio, 1-propylthio (n-propylthio), 2-propylthio (i-propylthio), 2-methyl-1-propylthio (i-butylthio), 2-methyl-2-propylthio (t-butylthio), 1-butylthio (n-butylthio), 2-butylthio (s-butylthio), 1-pentylthio, 2-pentylthio, 3-pentylthio, 2-methyl-1-butylthio, 3-methyl-1-butylthio, 2-methyl-2-butylthio, 3-methyl-2-butylthio, 2,2-dimethyl-1-propylthio, 1-hexylthio, 2-hexylthio, 3-hexylthio, 2-methyl-1-pentylthio, 3-methyl-1-pentylthio, 4-methyl-1-pentylthio, 2-methyl-2-pentylthio, 3-methyl-2-pentylthio, 4-methyl-2-pentylthio, 2-methyl-3-pentylthio, 3-methyl-3-pentylthio, 2,3-dimethyl-1-butylthio, 3,3-dimethyl-1-butylthio, 2,2-dimethyl-1-butylthio, 2-ethyl-1-butylthio, 3,3-dimethyl-2-butylthio, and 2,3-dimethyl-2-butylthio.

The "$C_{3-6}$ alkenyloxy" represents a group obtained by adding oxygen to the terminal of the above defined "$C_{3-6}$ alkenyl", and includes, for specific example, 2-propenyloxy (allyloxy), 2-butenyloxy, 3-butenyloxy, pentenyloxy, and hexenyloxy.

The "$C_{3-6}$ alkenylthio" represents a group obtained by adding sulfur to the terminal of the above defined "$C_{3-6}$ alkenyl", and includes, for specific example, 2-propenylthio (allylthio), 2-butenylthio, 3-butenylthio, pentenylthio, and hexenylthio.

The "$C_{3-6}$ alkynyloxy" represents a group obtained by adding oxygen to the terminal of the above defined "$C_{3-6}$ alkynyl", and includes, for specific example, 2-propynyloxy, 2-butynyloxy, 3-butynyloxy, pentynyloxy, and hexynyloxy.

The "$C_{3-6}$ alkynylthio" represents a group obtained by adding sulfur to the terminal of the above defined "$C_{3-6}$ alkynyl", and includes, for specific example, 2-propynylthio, 2-butynylthio, 3-butynylthio, pentynylthio, and hexynylthio.

The "$C_{3-10}$ cycloalkoxy" represents a group obtained by adding oxygen to the terminal of the above defined "$C_{3-10}$ cycloalkyl", and includes, for specific example, cyclopropoxy, cyclobutoxy, cyclopentyloxy, cyclohexyloxy, cycloheptyloxy, and cyclooctyloxy.

The "$C_{3-10}$ cycloalkylthio" represents a group obtained by adding sulfur to the terminal of the above defined "$C_{3-10}$ cycloalkyl", and includes, for specific example, cyclopropylthio, cyclobutylthio, cyclopentylthio, cyclohexylthio, cycloheptylthio, and cyclooctylthio.

The "$C_{6-10}$ aryloxy" represents a group obtained by adding oxygen to the terminal of the above defined "$C_{6-10}$ aryl", and includes, for specific example, phenoxy, 1-naphthoxy, 2-naphthoxy, indenyloxy, azulenyloxy, and heptalenyloxy.

The "$C_{6-10}$ arylthio" represents a group obtained by adding sulfur to the terminal of the above defined "$C_{6-10}$ aryl", and includes, for specific example, phenylthio, 1-naphthylthio, 2-naphthylthio, indenylthio, azulenylthio, and heptalenylthio.

The "5- to 10-membered heteroaryloxy" represents a group obtained by adding oxygen to the terminal of the above defined "5- to 10-membered heteroaryl", and includes, for specific example, furyloxy, thienyloxy, pyrrolyloxy, imidazolyloxy, triazolyloxy, thiazolyloxy, pyrazolyloxy, oxazolyloxy, isoxazolyloxy, isothiazolyloxy, furazanyloxy, thiadiazolyloxy, oxadiazolyloxy, pyridyloxy, pyrazinyloxy, pyridazinyloxy, pyrimidinyloxy, and triazinyloxy.

The "5- to 10-membered heteroarylthio" represents a group obtained by adding sulfur to the terminal of the above defined "5- to 10-membered heteroaryl", and includes, for specific example, furylthio, thienylthio, pyrrolylthio, imidazolylthio, triazolylthio, thiazolylthio, pyrazolylthio, oxazolylthio, isoxazolylthio, isothiazolylthio, furazanylthio, thiadiazolylthio, oxadiazolylthio, pyridylthio, pyrazinylthio, pyridazinylthio, pyrimidinylthio, and triazinylthio.

The "4- to 10-membered non-aromatic heterocyclicoxy group" represents a group obtained by adding oxygen to the terminal of the above defined "4- to 10-membered non-aromatic heterocyclic group", and includes, for specific example, azetidinyloxy, pyrrolidinyloxy, piperidinyloxy, azepanyloxy, azocanyloxy, piperazinyloxy, diazepanyloxy, diazocanyloxy, morpholinyloxy, thiomorpholinyloxy, 1,1-dioxothiomorpholinyloxy, oxetanyloxy, tetrahydrofuryloxy, tetrahydropyranyloxy, tetrahydrothienyloxy, and tetrahydrothiopyranyloxy.

The "4- to 10-membered non-aromatic heterocyclicthio group" represents a group obtained by adding sulfur to the terminal of the above defined "4- to 10-membered non-aromatic heterocyclic group", and includes, for specific example, azetidinylthio, pyrrolidinylthio, piperidinylthio, azepanylthio, azocanylthio, piperazinylthio, diazepanylthio, diazocanylthio, oxetanylthio, tetrahydrofurylthio, tetrahydropyranylthio, tetrahydrothienylthio, and tetrahydrothiopyranylthio.

The "mono-$C_{1-6}$ alkylamino" represents a group obtained by substituting one hydrogen of amino with the above defined "$C_{1-6}$ alkyl", and includes, for specific example, methylamino, ethylamino, 1-propylamino (n-propylamino), 2-propylamino (i-propylamino), 2-methyl-1-propylamino (i-butylamino), 2-methyl-2-propylamino (t-butylamino), 1-butylamino (n-butylamino), 2-butylamino (s-butylamino), 1-pentylamino, 2-pentylamino, 3-pentylamino, 2-methyl-1-butylamino, 3-methyl-1-butylamino, 2-methyl-2-butylamino, 3-methyl-2-butylamino, 2,2-dimethyl-1-propylamino, 1-hexylamino, 2-hexylamino, 3-hexylamino, 2-methyl-1-pentylamino, 3-methyl-1-pentylamino, 4-methyl-1-pentylamino, 2-methyl-2-pentylamino, 3-methyl-2-pentylamino, 4-methyl-2-pentylamino, 2-methyl-3-pentylamino, 3-methyl-3-pentylamino, 2,3-dimethyl-1-butylamino, 3,3-dimethyl-1-butylamino, 2,2-dimethyl-1-butylamino, 2-ethyl-1-butylamino, 3,3-dimethyl-2-butylamino, and 2,3-dimethyl-2-butylamino.

The "mono-$C_{3-10}$ cycloalkylamino" represents a group obtained by substituting one hydrogen of amino with the above defined "$C_{3-10}$ cycloalkyl", and includes, for specific example, cyclopropylamino, cyclobutylamino, cyclopentylamino, cyclohexylamino, cycloheptylamino, and cyclooctylamino.

The "mono-$C_{6-10}$ arylamino" represents a group obtained by substituting one hydrogen of amino with the above defined "$C_{6-10}$ aryl", and includes, for specific example, phenylamino, 1-naphthylamino, 2-naphthylamino, indenylamino, azulenylamino, and heptalenylamino.

The "mono-5- to 10-membered heteroarylamino" represents a group obtained by substituting one hydrogen of amino with the above defined "5- to 10-membered heteroaryl", and includes, for specific example, furylamino, thienylamino, pyrrolylamino, imidazolylamino, triazolylamino, tetrazolylamino, thiazolylamino, pyrazolylamino, oxazolylamino, isoxazolylamino, isothiazolylamino, furazanylamino, thiadiazolylamino, oxadiazolylamino, pyridylamino, pyrazinylamino, pyridazinylamino, pyrimidinylamino, and triazinylamino.

The preferable example of the "mono-5- to 10-membered heteroarylamino" includes furylamino, thienylamino, pyrrolylamino, imidazolylamino, thiazolylamino, pyrazolylamino, oxazolylamino, isoxazolylamino, isothiazolylamino, pyridylamino, and pyrimidinylamino.

The "mono-4- to 10-membered non-aromatic heterocyclic amino" represents a group obtained by substituting one hydrogen of amino with the above defined "4- to 10-membered non-aromatic heterocyclic group", and includes, for specific example, azetidinylamino, pyrrolidinylamino, piperidinylamino, azepanylamino, azocanylamino, piperazinylamino, diazepanylamino, diazocanylamino, morpholinylamino, thiomorpholinylamino, 1,1-dioxothiomorpholinylamino, oxetanylamino, tetrahydrofurylamino, tetrahydropyranylamino, tetrahydrothienylamino, and tetrahydrothiopyranylamino.

The preferable example of the "mono-4- to 10-membered non-aromatic heterocyclic amino" includes pyrrolidinylamino, piperidinylamino, azepanylamino, piperazinylamino, diazepanylamino, morpholinylamino, thiomorpholinylamino, and tetrahydrofurylamino.

The "di-$C_{1-6}$ alkylamino" represents a group obtained by substituting two hydrogen of amino with the same or different groups of the above defined "$C_{1-6}$ alkyl", and includes, for specific example, N,N-dimethylamino, N,N-diethylamino, N,N-di-n-propylamino, N,N-di-i-propylamino, N,N-di-n-butylamino, N,N-di-i-butylamino, N,N-di-s-butylamino, N,N-di-t-butylamino, N-ethyl-N-methylamino, N-n-propyl-N-methylamino, N-i-propyl-N-methylamino, N-n-butyl-N-methylamino, N-i-butyl-N-methylamino, N-s-butyl-N-methylamino, and N-t-butyl-N-methylamino.

Each of the substituents in the compound of the present invention represented by the above formula (I) will be described below.

(Meaning of $R^1$)

$R^1$ represents $C_{1-6}$ alkyl, $C_{2-6}$ alkenyl, $C_{2-6}$ alkynyl, $C_{3-10}$ cycloalkyl, $C_{6-10}$ aryl, $C_{1-6}$ alkoxy, 5- to 10-membered heteroaryl, a 3- to 10-membered non-aromatic heterocyclic group or a group represented by the formula —NR$^{11a}$R$^{11b}$, wherein R$^{11a}$ and R$^{11b}$ may be the same or different and each represents hydrogen, C$_{1-6}$ alkyl, C$_{3-6}$ alkenyl, C$_{3-6}$ alkynyl, C$_{3-10}$ cycloalkyl, C$_{6-10}$ aryl, C$_{1-6}$ alkoxy, 5- to 10-membered heteroaryl or a 4- to 10-membered non-aromatic heterocyclic group, and R$^{11a}$ and R$^{11b}$ may be substituted with a substituent selected from Substituent Group A or Substituent Group B.

R$^1$ may be substituted with a substituent selected from Substituent Group A or Substituent Group B.

The preferable example of R$^1$ includes C$_{1-6}$ alkyl optionally substituted with a substituent selected from Substituent Group A or Substituent Group B; a 3- to 10-membered non-aromatic heterocyclic group optionally substituted with a substituent selected from Substituent Group A or Substituent Group B; and a group represented by the formula —NR$^{11a}$R$^{11b}$, wherein R$^{11a}$ and R$^{11b}$ represent the same meaning as described above, and R$^{11a}$ and R$^{11b}$ may be substituted with a substituent selected from Substituent Group A or Substituent Group B.

The more preferable example of R$^1$ includes C$_{1-6}$ alkyl optionally substituted with a substituent selected from Substituent Group D;

a group represented by the formula (II):

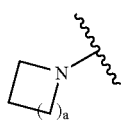

(II)

wherein a represents an integer of 1 to 4;
a group represented by the formula (III):

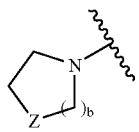

(III)

wherein b represents an integer of 1 to 3, and Z represents oxygen, sulfur, carbonyl, sulfonyl, or a group represented by the formula —NR$^Z$—, wherein R$^Z$ represents hydrogen or C$_{1-6}$ alkyl, and the groups represented by the formula (II) or (III) may be substituted with a substituent selected from Substituent Group A or Substituent Group B; or a group represented by the formula —NR$^{11c}$R$^{11d}$, wherein R$^{11c}$ represents hydrogen or C$_{1-6}$ alkyl, and R$^{11d}$ represents C$_{1-6}$ alkyl or a group represented by the formula (IV):

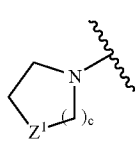

(IV)

wherein c represents an integer of 1 to 3, and Z$^1$ represents oxygen, sulfur, carbonyl, sulfonyl or a group represented by the formula —NR$^{Z1}$—, wherein R$^{Z1}$ represents hydrogen or C$_{1-6}$ alkyl, and R$^{11d}$ may be substituted with a substituent selected from Substituent Group A or Substituent Group B.

The even more preferable example of R$^1$ includes C$_{1-6}$ alkyl, azetidin-1-yl, pyrrolidin-1-yl, piperidin-1-yl, azepan-1-yl, piperazin-1-yl, diazepan-1-yl, morpholin-4-yl, thiomorpholin-4-yl, 1,1-dioxothiomorpholin-4-yl, or a group represented by the formula —NR$^{11e}$R$^{11f}$, wherein R$^{11e}$ represents hydrogen or C$_{1-6}$ alkyl, R$^{11f}$ represents C$_{1-6}$ alkyl, pyrrolidin-3-yl, piperidin-3-yl, piperidin-4-yl, piperazin-4-yl or tetrahydropyran-4-yl, and R$^{11f}$ may be substituted with a substituent selected from Substituent Group E, and each of the above substituents may be substituted with a substituent selected from Substituent Group E.

The especially preferable example of R$^1$ includes azetidin-1-yl, pyrrolidin-1-yl, piperidin-1-yl, piperazin-1-yl, diazepan-1-yl, morpholin-4-yl, and each of the above substituents may be substituted with a substituent selected from Substituent Group E', or a group represented by the formula —NR$^{11g}$R$^{11h}$, wherein R$^{11g}$ represents hydrogen or methyl, R$^{11h}$ represents n-propyl, n-butyl, pyrrolidin-3-yl, piperidin-3-yl, piperidin-4-yl or tetrahydropyran-4-yl, and R$^{11h}$ may be substituted with a substituent selected from Substituent Group E".

The most preferable example of R$^1$ includes a group represented by the formulas:

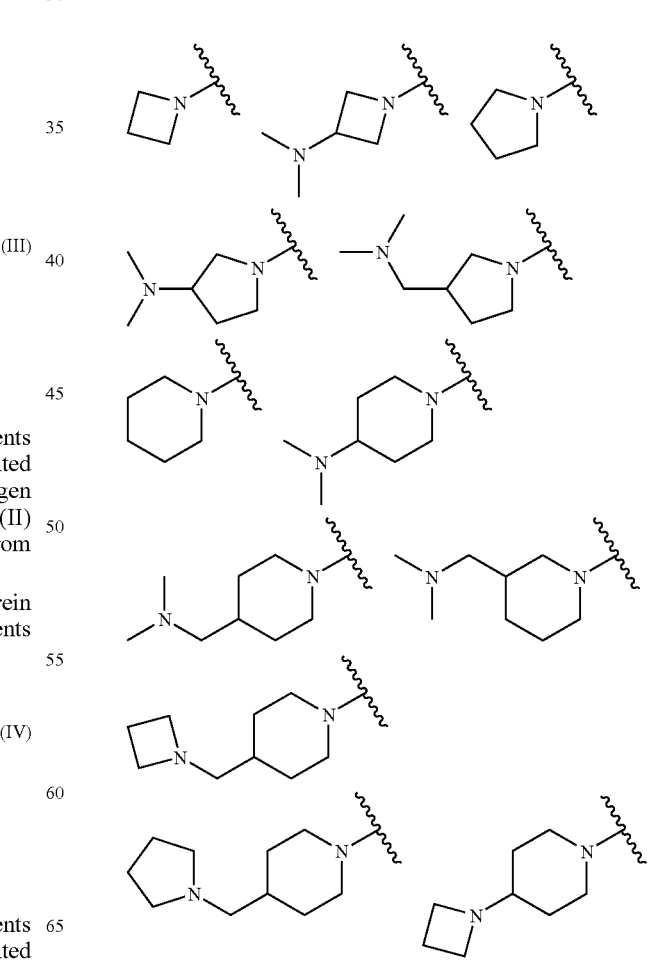

-continued
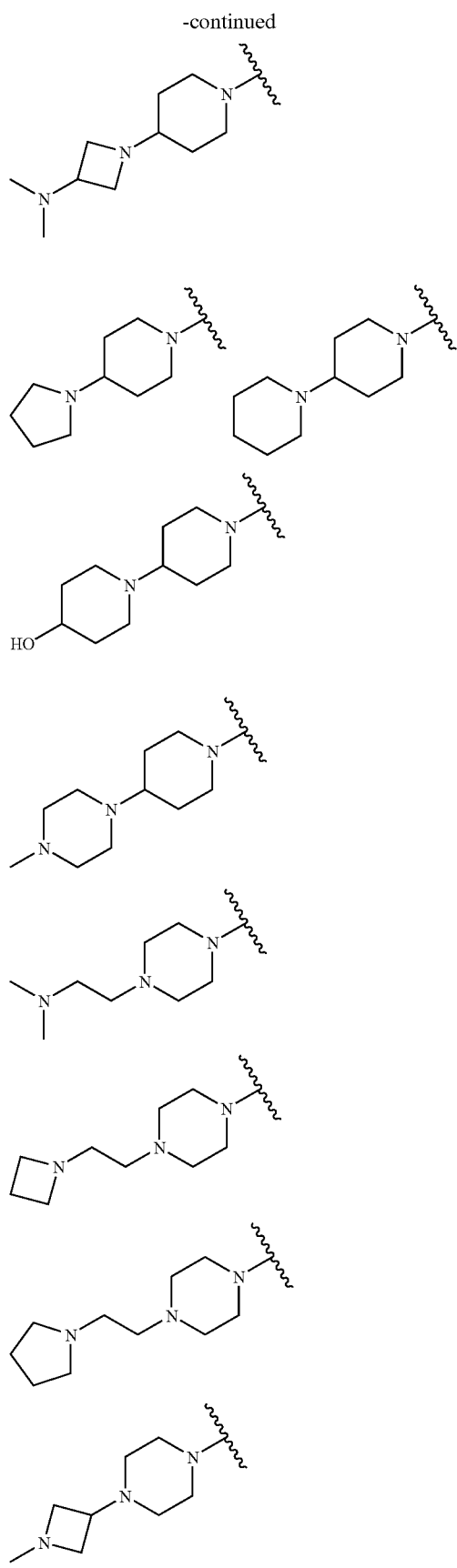
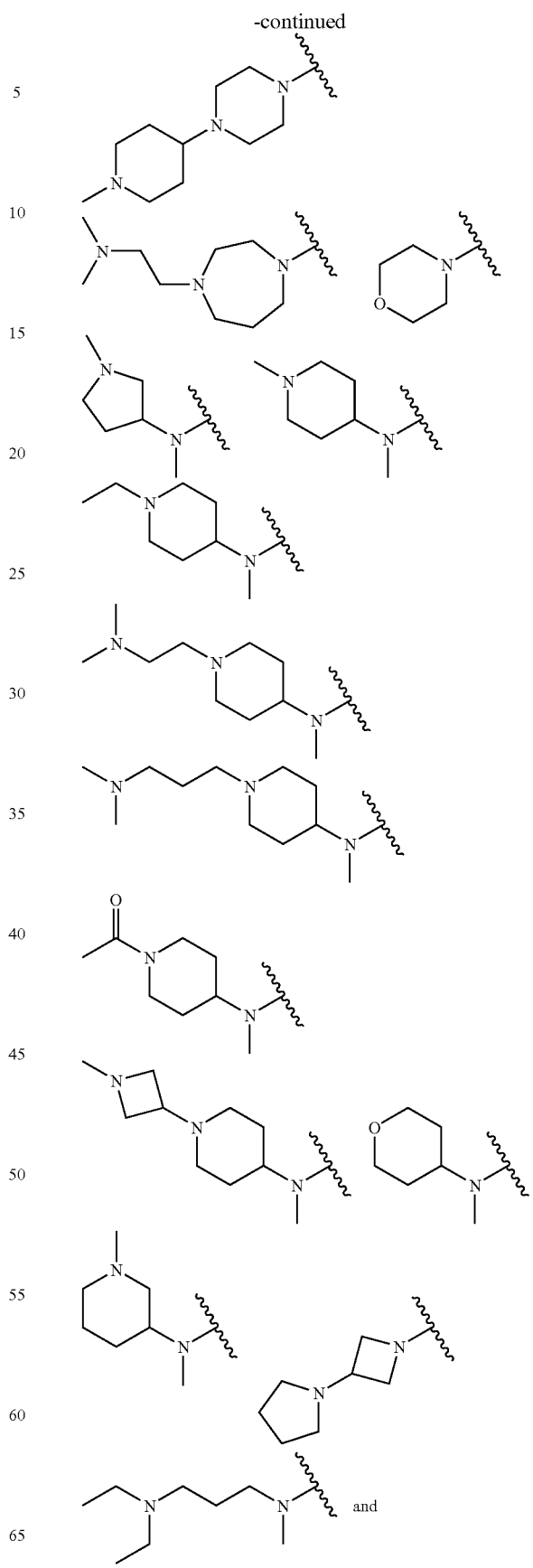

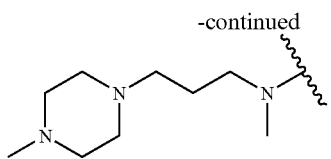

(Meaning of Substituent Group A)

The Substituent Group A represents a group consisting of halogen, hydroxyl, mercapto, nitro, cyano and oxo.

(Meaning of Substituent Group B)

The Substituent Group B represents a group consisting of $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{3-6}$ alkenyloxy, $C_{3-6}$ alkynyloxy, $C_{3-10}$ cycloalkoxy, $C_{6-10}$ aryloxy, 5- to 10-membered heteroaryloxy, 4- to 10-membered non-aromatic heterocyclicoxy, $C_{1-6}$ alkylthio, $C_{3-6}$ alkenylthio, $C_{3-6}$ alkynylthio, $C_{3-10}$ cycloalkylthio, $C_{6-10}$ arylthio, 5- to 10-membered heteroarylthio, 4- to 10-membered non-aromatic heterocyclicthio and a group represented by the formula $-T^1-T^2-T^3$, wherein $T^1$ represents a single bond or $C_{1-6}$ alkylene, $T^2$ represents carbonyl, sulfinyl, sulfonyl, a group represented by the formula $-C(=O)-O-$, a group represented by the formula $-O-C(=O)-$, a group represented by the formula $-SO_2-O-$, a group represented by the formula $-O-SO_2-$, a group represented by the formula $-NR^{T1}-$, a group represented by the formula $-C(=O)-NR^{T1}-$, a group represented by the formula $-NR^{T1}-C(=O)-$, a group represented by the formula $-SO_2-NR^{T1}-$ or a group represented by the formula $-NR^{T1}-SO_2-$, $T^3$ represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{T1}$ represents hydrogen or $C_{1-6}$ alkyl.

Each group included in Substituent Group B may be substituted with a substituent selected from Substituent Group C.

(Meaning of Substituent Group C)

The Substituent Group C represents a group consisting of halogen, hydroxyl, mercapto, nitro, cyano, oxo, $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy and $C_{1-6}$ alkylthio.

(Meaning of Substituent Group D)

The Substituent Group D represents a group consisting of amino, mono-$C_{1-6}$ alkylamino and di-$C_{1-6}$ alkylamino.

(Meaning of Substituent Group E)

The Substituent Group E represents a group consisting of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, diazepanyl and a group represented by $-T^4-T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino.

Each group included in Substituent Group E may be substituted with hydroxyl, $C_{1-6}$ alkyl, di-$C_{1-6}$ alkylamino, azetidinyl or pyrrolidinyl.

(Meaning of Substituent Group E')

The Substituent Group E' represents a group consisting of methyl, ethyl, dimethylamino, azetidinyl, pyrrolidinyl, piperidinyl and piperazinyl.

Each group included in Substituent Group E' may be substituted with hydroxyl, methyl, dimethylamino, azetidinyl or pyrrolidinyl.

(Meaning of Substituent Group E")

The Substituent Group E" represents a group consisting of methyl, ethyl, n-propyl, acetyl, dimethylamino, diethylamino, azetidinyl, pyrrolidinyl and piperazinyl.

Each group included in Substituent Group E" may be substituted with methyl or diethylamino.

(Meaning of $R^2$ and $R^3$)

$R^2$ and $R^3$ represent hydrogen.

(Meaning of $R^4$, $R^5$, $R^6$ and $R^7$)

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula $-CO-R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino.

The preferable example of $R^4$, $R^5$, $R^6$ and $R^7$ includes hydrogen, halogen, $C_{1-6}$ alkyl, $C_{1-6}$ alkoxy and trifluoromethyl.

The more preferable example of $R^4$, $R^5$, $R^6$ and $R^7$ includes hydrogen, halogen and $C_{1-6}$ alkyl.

The even more preferable example of $R^4$, $R^5$, $R^6$ and $R^7$ includes hydrogen, fluorine, chlorine and methyl.

$R^4$, $R^5$, $R^6$ and $R^7$ may be in any one of the following cases: (1) all of them represent hydrogen, (2) all of them represent substituents other than hydrogen, and (3) some of them represent hydrogen and the others represent substituents other than hydrogen. Preferably, 2 to 4 of $R^4$, $R^5$, $R^6$ and $R^7$ represent hydrogen.

Preferable example for a group represented by the formula:

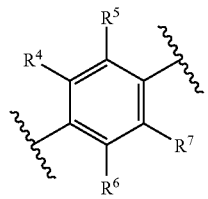

includes groups represented by the formulas:

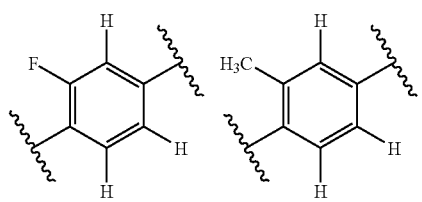

-continued

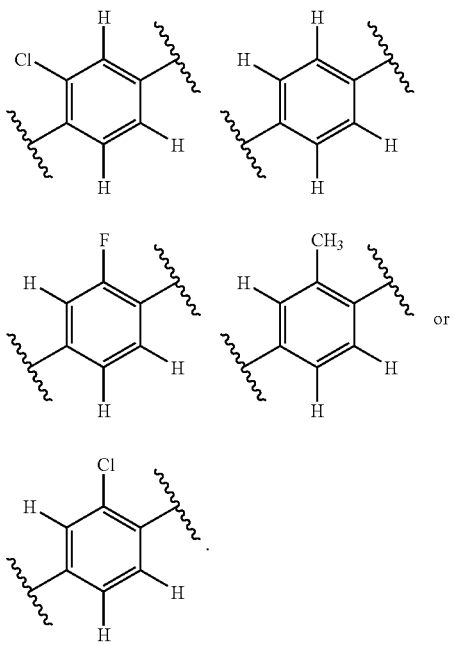

(Meaning of $R^8$)

$R^8$ represents hydrogen or $C_{1-6}$ alkyl.

The preferable example of $R^8$ includes hydrogen.

(Meaning of $R^9$)

$R^9$ represents $C_{1-6}$ alkyl, $C_{2-6}$ alkenyl, $C_{2-6}$ alkynyl, $C_{3-10}$ cycloalkyl, $C_{6-10}$ aryl, $C_{3-10}$ cycloalkyl-$C_{1-6}$ alkyl, $C_{6-10}$ aryl-$C_{1-6}$ alkyl, $C_{1-6}$ alkoxy, 5- to 10-membered heteroaryl, a 3- to 10-membered non-aromatic heterocyclic group, 5- to 10-membered heteroaryl-$C_{1-6}$ alkyl, 3- to 10-membered non-aromatic heterocyclic-$C_{1-6}$ alkyl or a group represented by the formula —$NR^{11a}R^{11b}$, wherein $R^{11a}$ and $R^{11b}$ represent the same meaning as described above.

$R^9$ may be substituted with a substituent selected from Substituent Group A or Substituent Group B.

(Meaning of $V^1$)

$V^1$ represents oxygen or sulfur.

The preferable example of $V^1$ includes oxygen.

(Meaning of $V^2$)

$V^2$ represents oxygen or sulfur.

(Meaning of W)

W represents a group represented by the formula —$N(R^{W3})$—, wherein $R^{W3}$ represents hydrogen or $C_{1-6}$ alkyl.

The preferable example of W includes a group represented by —NH—.

The preferable combination of W and $V^2$ includes:

(1) a combination where W represents a group represented by the formula —$N(R^{W3})$— and $V^2$ represents sulfur, wherein $R^{W3}$ represents the same meaning as described above; and (2) a combination where W represents a group represented by the formula —$N(R^{W3})$— and $V^2$ represents oxygen, wherein $R^{W3}$ represents the same meaning as described above.

The more preferable combination includes:

(1) a combination where W represents a group represented by the formula —NH— and $V^2$ represents sulfur; and (2) a combination where W represents a group represented by the formula —NH— and $V^2$ represents oxygen.

The preferable example of $R^9$ includes $C_{1-6}$ alkyl, $C_{3-10}$ cycloalkyl, $C_{3-10}$ cycloalkyl-$C_{1-6}$ alkyl, $C_{6-10}$ aryl-$C_{1-6}$ alkyl, 5- to 10-membered heteroaryl-$C_{1-6}$ alkyl, and 3- to 10-membered non-aromatic heterocyclic-$C_{1-6}$ alkyl, and $R^9$ may be substituted with a substituent selected from Substituent Group A or Substituent Group B.

The more preferable example of $R^9$ includes $C_{3-10}$ cycloalkyl-$C_{1-6}$ alkyl, and $C_{6-10}$ aryl-$C_{1-6}$ alkyl, and $R^9$ may be substituted with a substituent selected from Substituent Group A or Substituent Group B.

The even more preferable example of $R^9$ includes $C_{3-10}$ cycloalkyl-$C_{1-6}$ alkyl, and $C_{6-10}$ aryl-$C_{1-6}$ alkyl, and $R^9$ may be substituted with a substituent selected from Substituent Group F, wherein Substituent Group F consists of halogen, trifluoromethyl, cyano, $C_{1-6}$ alkyl and $C_{1-6}$ alkoxy.

The especially preferable example of $R^9$ includes cyclopentylmethyl, cyclohexylmethyl, cycloheptylmethyl, norbornan-2-ylmethyl and benzyl, and $R^9$ may be substituted with a substituent selected from Substituent Group F.

(Meaning of X)

X represents a group represented by the formula —$C(R^{10})$= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as described above.

The preferable example of X includes a group represented by the formula —$C(R^{10a})$= or nitrogen, wherein $R^{10a}$ represents hydrogen, halogen or cyano.

The more preferable example of X includes a group represented by the formula —CH= or nitrogen.

(Meaning of Y)

Y represents oxygen, sulfur, sulfinyl, sulfonyl or a group represented by the formula —$N(R^Y)$—, wherein $R^Y$ represents hydrogen or $C_{1-6}$ alkyl.

The preferable example of Y includes oxygen or a group represented by the formula —NH—.

The more preferable example of Y includes oxygen.

The preferable compound according to the present invention represented by the formula (I) includes a compound represented by the following formula (I-1):

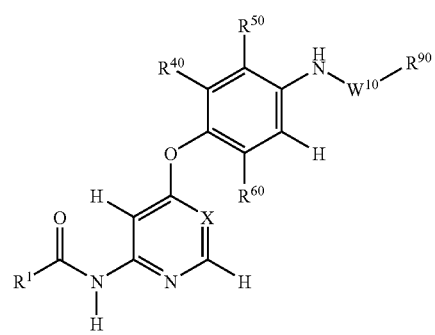

(I-1)

$R^1$ and X represent the same meanings as those in the above formula (I).

21

(Meaning of $W^{10}$)

$W^{10}$ represents a group represented by the formulas:

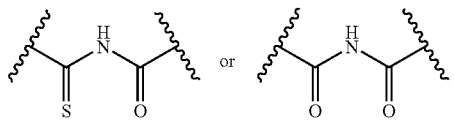

wherein the left bonding hands bond with —NH—, and the right bonding hands bond with $R^{90}$.

(Meaning of $R^{40}$, $R^{50}$ and $R^{60}$)

$R^{40}$, $R^{50}$ and $R^{60}$ may be the same or different and each represents hydrogen, halogen or $C_{1-6}$ alkyl.

Preferably, $R^{40}$, $R^{50}$ and $R^{60}$ may be the same or different and each represents hydrogen, fluorine, chlorine or methyl.

More preferably, $R^{40}$ and $R^{50}$ each represents hydrogen, fluorine, chlorine or methyl, and $R^{60}$ represents hydrogen.

(Meaning of $R^{90}$)

$R^{90}$ represents $C_{1-6}$ alkyl, $C_{3-10}$ cycloalkyl, $C_{6-10}$ aryl, 5- to 10-membered heteroaryl, $C_{3-10}$ cycloalkyl-$C_{1-6}$ alkyl, $C_{6-10}$ aryl-$C_{1-6}$ alkyl, or 5- to 10-membered heteroaryl-$C_{1-6}$ alkyl. $R^{90}$ may be substituted with a substituent selected from Substituent Group F, wherein Substituent Group F consists of halogen, trifluoromethyl, cyano, $C_{1-6}$ alkyl and $C_{1-6}$ alkoxy.

The preferable example of $R^{90}$ includes $C_{3-10}$ cycloalkyl-$C_{1-6}$ alkyl and $C_{6-10}$ aryl-$C_{1-6}$ alkyl, and $R^{90}$ may be substituted with a substituent selected from Substituent Group F.

The more preferable example of $R^{90}$ includes cyclopentylmethyl, cyclohexylmethyl, cycloheptylmethyl, norbornan-2-ylmethyl and benzyl, and $R^{90}$ may be substituted with a substituent selected from Substituent Group F.

The preferable compound of the formula (I) includes a compound obtained by selecting respective aspects of $R^1$, $R^2$, $R^3$, $R^4$, $R^5$, $R^6$, $R^7$, $R^8$, $R^9$, $V^1$, $V^2$, W, X and Y in the compound and combining them arbitrarily.

The preferable compound of the formula (I-1) includes a compound obtained by selecting respective aspects of $R^1$, $R^{40}$, $R^{50}$, $R^{60}$, $R^{90}$, $W^{10}$ and X in the compound and combining them arbitrarily.

The preferable compound of the formula (I) or the formula (I-1) includes, for specific example, Ex. 3, Ex. 13, Ex. 22, Ex. 28, Ex. 38, Ex. 39, Ex. 52, Ex. 100, Ex. 170, Ex. 172, Ex. 174, Ex. 178, Ex. 179, Ex. 180, Ex. 181, Ex. 182, Ex. 183, Ex. 184, Ex. 185, Ex. 188, Ex. 189, Ex. 190, Ex. 191, Ex. 192, Ex. 193, Ex. 194, Ex. 195, Ex. 196, Ex. 201, Ex. 208, Ex. 209, Ex. 219, Ex. 221, Ex. 223, Ex. 224, Ex. 225, Ex. 245, Ex. 246, Ex. 250, Ex. 254, Ex. 258, Ex. 261, Ex. 281, Ex. 285, Ex. 288, Ex. 289, Ex. 290, Ex. 301, Ex. 309, Ex. 311, Ex. 312, Ex. 314, Ex. 322, Ex. 326, Ex. 327, Ex. 329, Ex. 330, Ex. 331, Ex. 334, Ex. 335, Ex. 337, Ex. 339, Ex. 340, Ex. 341, Ex. 342, Ex. 343, Ex. 344, Ex. 345, Ex. 346, Ex. 347, Ex. 349, Ex. 353, Ex. 354, Ex. 362, Ex. 364, Ex. 373, Ex. 376, Ex. 377, Ex. 381, Ex. 383, Ex. 387, Ex. 389, Ex. 390, Ex. 391, Ex. 392, Ex. 393, Ex. 394, Ex. 395, Ex. 396, Ex. 397, and Ex. 398.

The phrase "may be substituted with a substituent selected from Substituent Group" or "optionally substituted with a substituent selected from Substituent Group" means "may be substituted with 1 to 3 substituents selected arbitrarily from the substituents described in the Substituent Group."

EFFECTS OF THE INVENTION

The compound according to the present invention has an inhibitory activity of HGFR tyrosine kinase (Pharmacological Test Examples 1 and 3), and thus inhibits proliferation of human cancer cells caused by HGFR activation (Pharmacological Test Example 2), whereby to exhibit inhibitory activity of tumor proliferation (Pharmacological Test Example 5). The compound according to the present invention also inhibits migration of human cancer cells (Pharmacological Test Example 4). Furthermore, the compound according to the present invention inhibits proliferation and tube formation of vascular endothelial cells via HGF-HGFR signal (Pharmacological Test Examples 6 and 7).

Overexpression of HGFR is reported to involve in malignancy of cancer (overgrowth, invasion and enhanced metastasis) in a pancreatic cancer, a gastric cancer, a colorectal cancer, a breast cancer, a prostate cancer, a lung cancer, a renal cancer, a brain tumor, an ovarian cancer and a blood cancer (Cancer Research, 54, 5775-5778 (1994); Biochemical and Biophysical Research Communication, 189, 227-232 (1992); Oncogene, 7, 181-185 (1992); Cancer, 82, 1513-1520 (1998); J. Urology, 154, 293-298 (1995); Oncology, 53, 392-397 (1996); Oncogene, 14, 2343-2350 (1999); Cancer Research, 57, 5391-5398 (1997); Pathology Oncology Research, 5, 187-191 (1999); Clinical Cancer Research, 9, 181-187 (2003)).

Additionally, HGFR activation in vascular endothelial cells is reported to facilitate tumor angiogenesis (Advances in Cancer Research, 67, 257-279 (1995)).

Therefore, the compound according to the present invention which has excellent inhibitory activity against HGFR is useful as an anti-tumor agent, an inhibitor against angiogenesis or a cancer metastasis inhibitor against various kinds of cancers such as a pancreatic cancer, a gastric cancer, a colorectal cancer, a breast cancer, a prostate cancer, a lung cancer, a renal cancer, a brain tumor and an ovarian cancer.

PHARMACOLOGICAL TEST EXAMPLES

The biological activity and pharmaceutical effect (inhibitory activity for hepatocyte growth factor receptor, anti-tumor activity, inhibitory activity for angiogenesis, and inhibitory activity for cancer metastasis) of the compound according to the present invention were evaluated by methods described below.

Abbreviations and terms used in the following Pharmacological Test Examples are listed as follows:

(Abbreviation List)
HGFR (Hepatocyte growth factor receptor)
DNA (Deoxyribonucleic acid)
Human placenta
PCR (Polymerase chain reaction)
VEGFR2 (Vascular endothelial growth factor receptor 2)
FGFR1 (Fibroblast growth factor receptor 1)
PDGFRβ (Platelet derived growth factor receptor β)
EGFR (Epidermal growth factor receptor)
FBS (Fetal bovine serum)
PBS (Phosphate buffered saline)
Tris (Tris(hydroxymethyl)aminomethane, Tris(buffer))
PMSF (Phenylmethylsulfonyl fluoride)
NP-40 (Nonidet P-40)
EGTA (O,O-Bis(2-aminoethyleneglycol)-N,N,N',N'-tetraacetic acid)
SDS (Sodium dodecyl sulfate)
BSA (Bovine serum albumin)
Hepes (N-[2-hydroxyethyl]piperazine-N'-[2-ethanesulfonic acid], Hepes (buffer))
ATP (Adenosine 5'-triphosphate)
EDTA (Ethylenediamine tetraacetic acid)
HTRF (Homogenous Time-Resolved Fluorescence)

HRP (Horseradish peroxidase)
ELISA (Enzyme-linked immunosorbent assay)
HGF (Hepatocyte growth factor)
HBSS (Hank's Balanced Salt solution)
MTT (3-[4,5-dimethylthiazol-2-yl]-2,5-diphenyltetrazolium bromide; Thiazolyl blue)
EGM-2 (Endothelial Cell Growth Medium-2)

Pharmacological Test Example 1

Inhibitory Activity Against Receptor Tyrosine Kinase Activity

1. Cloning of Receptor Tyrosine Kinases, and Preparation of the Recombinant Baculovirus Solutions The cytoplasmic domain of HGFR (Genbank Accession No. J02958) is a 1.3 kb DNA fragment beginning with Lys974 and including a stop codon, and described by Park et al. (Proc. Natl. Acad. Sci. U.S.A. 84(18), 6379-6383, 1987). The DNA fragment was isolated from the human placental cDNA library (purchased from Clontech) by PCR (TaKaRa Ex Taq™ Kit, purchased from TaKaRa) using two kinds of primers (SEQ ID NO: 1, 5'-CCGGCCGGATCCAAAAA-GAGAAAGCAAATTAAA-3' and SEQ ID NO: 2, 5'-TTAATTCTGCAGCTATGATGTCTCCCAGAAGGA-3', purchased from Invitrogen). The DNA fragment was cloned into a baculovirus transplace vector (pFastBac™-HT (purchased from GIBCO BRL)) to produce a recombinant construct. The construct was transfected into insect cells (*Spodoptera frugiperda* 9 (Sf9)) to produce a solution of HGFR transfected baculovirus (preparation of a recombinant baculovirus can be found in the standard text (Bac-to-Bac Baculovirus Expression System (GIBCO BRL)). The cloning of the other receptor tyrosine kinases and preparation of the recombinant baculovirus solutions were performed using a cytoplasmic fragment starting from Lys791 (VEGFR2, Genbank Accession No. L04947), a cytoplasmic fragment starting from Lys398 (FGFR1, Genbank Accession No. X52833) and a cytoplasmic fragment starting from Lys558 (PDGFRβ, Genbank Accession No. M21616) in stead of HGFR in the above method. EGFR was purchased from Sigma (Production No. E-2645).

2. Expression and Purification of Receptor Tyrosine Kinases

To the suspension of Sf9 cells ($3\times10^8$ cells) in SF-900II medium (purchased from Invitrogen) containing 2% FBS was added a solution of HGFR transfected baculovirus above (4 ml), followed by a shaking culture at 27° C. for 48 hrs. The cells infected with the HGFR transfected baculovirus were centrifuged at 1,000 rpm, 4° C. for 5 min to remove the supernatant. The precipitated infected cells were suspended in 80 ml of ice-cold PBS, and centrifuged at 1,000 rpm, 4° C. for 5 min to remove the supernatant. The precipitated infected cells were suspended in 40 ml of ice-cold Lysis Buffer (50 mM Tris-HCl (pH 8.5), 5 mM 2-mercaptoethanol, 100 mM KCl, 1 mM PMSF and 1% (v/v) NP-40). The suspension was centrifuged at 12,000 rpm, 4° C. for 30 min to provide a supernatant.

The supernatant was loaded onto an Ni-NTA agarose column (3 ml, purchased from Qiagen) equilibrated with 30 ml of Buffer A (20 mM Tris-HCl (pH 8.5), 5 mM 2-mercaptoethanol, 500 mM KCl, 20 mM imidazole and 10% (v/v) glycerol). The column was washed with 30 ml of Buffer A, 6 ml of Buffer B (20 mM Tris-HCl (pH 8.5), 5 mM 2-mercaptoethanol, 1 M KCl, and 10% (v/v) glycerol) and 6 ml of Buffer A in this order. Then, the column was eluted with 6 ml of Buffer C (20 mM Tris-HCl (pH 8.5), 5 mM 2-mercaptoethanol, 100 mM KCl, 100 mM imidazole, and 10% (v/v) glycerol) to provide a fraction. The fraction was entrapped in a dialysis membrane (purchased from Spectrum Laboratories), dialyzed at 4° C. overnight with 1 L of dialysis buffer (20 mM Tris-HCl (pH 7.5), 10% (v/v) glycerol, 1 mM dithiothreitol, 0.1 mM $Na_3VO_4$ and 0.1 mM EGTA), and stored at −80° C. until used. An aliquot of the dialyzed fraction was subjected to SDS electrophoresis, and then a recombinant protein (His6-HGFR, the HGFR cytoplasmic domain fused with six histidine at the N terminus) detected at a molecular weight of about 60 kDa when stained with Coomassie Brilliant Blue, was determined with regard to protein content using BSA (purchased from Sigma) as a standard. The VEGFR2 cytoplasmic domain, the FGFR1 cytoplasmic domain, and the PDGFRβ cytoplasmic domain were fused with six histidine at the N terminus by the similar method to produce respective recombinant proteins (His6-VEGFR2, His6-FGFR1, and His6-PDGFRβ)

3. Assay for the Inhibitory Activity Against HGFR Tyrosine Kinase Activity

To each well of a 96-well round plate (purchased from NUNC, Production No. 163320) were added 10 μl of a solution for kinase reaction (200 mM Hepes (pH 7.4), 80 mM $MgCl_2$, 16 mM $MnCl_2$ and 2 mM $Na_3VO_4$), 250 ng of biotinylated poly(Glu4: Tyr1) (biotin-poly(GT), purchased from Japan Schering) (6 μl, 15-fold diluted with distilled water), 30 ng of His6-HGFR (10 μl, 60-fold diluted with 0.4% BSA) and a test substance dissolved in dimethylsulfoxide (4 μl, 100-fold diluted with 0.1% BSA) to mess up to 30 μl. To the well was added 10 μl of 4 μM ATP (purchased from Sigma) diluted with distilled water to incubate at 30° C. for 10 min, followed by adding 10 μl of 500 mM EDTA (pH 8.0) (purchased from Wako Pure Chemicals) to provide a kinase reaction solution.

The tyrosine-phosphorylated biotin-poly(GT) was detected using the Homogenous Time-Resolved Fluorescence (HTRF) method (Analytical Biochemistry, 269, 94-104, 1999). That is, to each well of a 96-well half-area black plate (purchased from COSTAR, Production No. 3694) were added 20 μl of the above kinase reaction solution and 30 μl of a dilution solution (50 mM Hepes (pH 7.4), 20 mM $MgCl_2$, 4 mM $MnCl_2$, 0.5 mM $Na_3VO_4$, 0.1% BSA and 100 mM EDTA). To the well was added 7.5 ng of an europium cryptate-labelled anti-phosphotyrosine antibody (Eu(K)-PY20, purchased from Japan Schering) (25 μl, 250-fold diluted with 20 mM Hepes (pH 7.0), 0.5 M KF and 0.1% BSA) and 250 ng of XL665-labelled streptavidin (XL665-SA, purchased from Japan Schering) (25 μl, 62.5-fold diluted with 20 mM Hepes (pH 7.0), 0.5 M KF and 0.1% BSA), and using a discovery HTRF microplate analyzer (Packard), the well was instantly irradiated at an excitation wavelength of 337 nm to determine fluorescence intensities at 665 nm and 620 nm. The tyrosine phosphorylation rate of a biotin-poly (GT) was calculated using a delta F % value described in the text of a HTRF standard experiment method by Japan Schering. While defining the delta F % value of a well added with His6-HGFR and no test substance as 100% and the delta F % value of a well added with no His6-HGFR and no test substance as 0%, ratio (%) of the delta F % value of each well added with the test substance was calculated. The ratio (%) was used to calculate the concentration ($IC_{50}$) of the test substance necessary to inhibit HGFR kinase activity by 50%. The results are shown in Table 1-1 and 1-2.

TABLE 1-1

| Example | IC50 (μM) |
|---|---|
| 3 | 0.071 |
| 4 | 0.03 |
| 6 | 0.06 |
| 7 | 0.018 |
| 8 | 0.083 |
| 9 | 0.053 |
| 11 | 0.088 |
| 13 | 0.11 |
| 15 | <0.03 |
| 16 | 0.056 |
| 17 | 0.064 |
| 22 | 0.11 |
| 24 | 0.054 |
| 28 | 0.075 |
| 43 | 0.083 |
| 44 | 0.045 |
| 45 | 0.091 |
| 46 | 0.045 |
| 47 | 0.1 |
| 48 | 0.056 |
| 49 | 0.21 |
| 50 | 0.19 |
| 51 | 0.018 |
| 52 | 0.073 |
| 54 | 0.043 |
| 56 | 0.056 |
| 57 | 0.048 |
| 59 | 0.1 |
| 60 | 0.049 |
| 61 | <0.03 |
| 64 | 0.059 |
| 65 | 0.087 |
| 67 | 0.067 |
| 71 | 0.025 |
| 74 | 0.033 |
| 75 | 0.054 |
| 76 | 0.1 |
| 77 | 0.013 |
| 78 | 0.13 |
| 82 | 0.066 |
| 83 | 0.082 |
| 84 | 0.012 |
| 85 | 0.096 |
| 86 | 0.055 |
| 89 | 0.038 |
| 92 | 0.078 |
| 93 | 0.093 |
| 100 | 0.2 |
| 170 | 0.066 |
| 172 | 0.064 |
| 174 | 0.074 |
| 178 | 0.063 |
| 179 | 0.025 |
| 180 | 0.038 |
| 181 | 0.041 |
| 182 | 0.07 |
| 183 | 0.16 |
| 184 | 0.13 |
| 185 | 0.047 |
| 188 | 0.13 |
| 189 | 0.11 |
| 190 | 0.06 |
| 191 | 0.057 |
| 192 | 0.04 |
| 193 | 0.052 |
| 194 | 0.062 |
| 195 | 0.057 |
| 196 | 0.057 |
| 201 | 0.05 |
| 208 | 0.05 |
| 209 | 0.065 |
| 219 | 0.042 |
| 221 | 0.17 |
| 223 | 0.058 |
| 224 | 0.088 |
| 225 | 0.079 |
| 245 | 0.081 |

TABLE 1-1-continued

| Example | IC50 (μM) |
|---|---|
| 246 | 0.079 |
| 250 | 0.068 |
| 254 | 0.083 |
| 258 | 0.1 |
| 261 | 0.1 |
| 281 | 0.028 |
| 285 | 0.051 |
| 288 | 0.016 |
| 289 | 0.067 |
| 290 | 0.13 |
| 301 | 0.028 |
| 309 | 0.054 |
| 311 | 0.048 |
| 312 | 0.048 |
| 314 | 0.031 |
| 322 | 0.043 |
| 326 | 0.13 |
| 327 | 0.075 |
| 329 | 0.064 |
| 330 | 0.05 |
| 331 | 0.084 |
| 334 | 0.12 |
| 335 | 0.11 |

TABLE 1-2

| Example | IC50 (μM) |
|---|---|
| 335 | 0.11 |
| 337 | 0.15 |
| 339 | 0.13 |
| 340 | 0.077 |
| 341 | 0.1 |
| 342 | 0.059 |
| 343 | 0.12 |
| 344 | 0.11 |
| 345 | 0.12 |
| 346 | 0.1 |
| 347 | 0.062 |
| 349 | 0.087 |
| 353 | 0.18 |
| 354 | 0.16 |
| 362 | 0.13 |
| 364 | 0.097 |
| 373 | 0.077 |
| 376 | 0.065 |
| 377 | 0.068 |
| 381 | 0.083 |
| 383 | 0.094 |
| 387 | 0.12 |
| 389 | 0.13 |
| 390 | 0.12 |
| 391 | 0.083 |
| 392 | 0.055 |
| 393 | 0.056 |
| 394 | 0.045 |
| 395 | 0.047 |
| 397 | 0.055 |
| 398 | 0.047 |

4. Assay for the Inhibitory Activity Against Receptor Tyrosine Kinase Activities Other than HGFR The inhibitory activity against tyrosine kinase activities of VEGFR2, FGFR1, and EGFR were determined by the similar manner as in the assay for the inhibitory activity against HGFR tyrosine kinase activity described above, using 15 ng of His6-VEGFR2, 15 ng of His6-FGFR1 and 23 ng of EGFR, respectively in stead of HGFR.

The inhibitory activity against PDGFRβ tyrosine kinase activity was evaluated by obtaining a kinase reaction solution by the above method using 50 ng of His6-PDGFRβ, followed by detecting the tyrosine phosphorylated biotin-poly(GT) by a method described below.

To each well of a 96-well streptavidin-coated plate (purchased from PIERCE, Production No. 15129) were added 34 μl of the kinase reaction solution and 16 μl of a dilution solution, followed by incubation at room temperature for 30 min. Then, the well was washed three times with 150 μl of a washing solution (20 mM Tris-HCl (pH 7.6), 137 mM NaCl, 0.05% Tween-20 and 0.1% BSA), and to the well was added 70 μl of anti-phosphotyrosine (PY20)-HRP conjugate (purchased from Transduction Laboratories, Production No. P-11625) (2,000-fold diluted with 20 mM Tris-HCl (pH 7.6), 137 mM NaCl, 0.05% Tween-20 and 1% BSA), followed by incubation at room temperature for 1 hr. Then, each well was washed three times with 150 μl of the washing solution, and supplied with 100 μl of TMB Membrane Peroxidase Substrate (purchased from Funakoshi, Production No. 50-5077-03). After incubating the same at room temperature for 10 min, 100 μl of 1 M phosphoric acid was added to each well, and using a Plate Reader MTP-500 (Corona Electric), the absorbance of the well was determined at 450 nm. While defining the absorbance of a well supplied with His6-PDGFRβ and no test substance as 100% and the absorbance of a well supplied with no His6-PDGFRβ and no test substance as 0%, the absorbance ratio (%) of each well supplied with the test substance was calculated. The absorbance ratio (%) was used to calculate the concentration ($IC_{50}$) of the test substance necessary to inhibit PDGFRβ kinase activity by 50%.

Pharmacological Test Example 2

Inhibitory Activity Against the Proliferation of Human Gastric Cancer Cells (MKN-45)

Human gastric cancer cells (MKN-45) were suspended in a 1% FBS-containing RPMI1640 medium (purchased from Sigma). The cell suspension ($1 \times 10^4$ cells/ml) was added in a 96-well plate for cell culture (purchased from NUNC, Production No. 167008) at 0.1 ml/well, and then cultured in a 5% $CO_2$ incubator (37° C.) overnight. After the culture, each well was supplied with 0.1 ml of a test substance diluted with a 1% FBS-containing RPMI1640 medium, followed by culturing in a 5% $CO_2$ incubator (37° C.) for 3 days. After the culture, each well was supplied with 10 μl of Cell Counting Kit-8 (purchased from DOJINDO, Production No. 343-07623), followed by incubation in a 5% $CO_2$ incubator (37° C.) for about 1.5 hrs. After the incubation, using the Plate Reader MTP-500 (Corona Electric), the absorbance of each well was determined at a measurement wavelength of 450 nm and a reference wavelength of 660 nm. The ratio (%) of absorbance of each well supplied with a test substance to absorbance of the well supplied with no test substance was calculated, and the ratio was used to calculate the concentration ($IC_{50}$) of the test substance necessary to inhibit the cell proliferation by 50%. The results are shown in Table 2.

TABLE 2

| Example | IC50 (μM) |
|---|---|
| 3 | 0.04 |
| 9 | 0.033 |
| 11 | 0.18 |
| 13 | 0.023 |
| 15 | 0.048 |
| 17 | 0.57 |
| 22 | 0.033 |

TABLE 2-continued

| Example | IC50 (μM) |
|---|---|
| 24 | 0.18 |
| 28 | 0.0058 |
| 43 | 0.035 |
| 44 | 0.064 |
| 45 | 0.14 |
| 48 | 0.057 |
| 50 | 0.16 |
| 52 | 0.063 |
| 56 | 0.14 |
| 77 | 0.11 |
| 82 | 0.12 |
| 85 | 0.63 |
| 89 | 0.086 |
| 92 | 0.57 |

Pharmacological Test Example 3

Inhibitory Activity Against the HGFR Autophosphorylation Using ELISA

1. Preparation of Cell Extract

Human gastric cancer cells (MKN-45) were suspended in a 1% FBS-containing RPMI1640 medium (purchased from Sigma). The cell suspension ($1 \times 10^5$ cells/ml) was put in a 96-well plate for cell culture (purchased from NUNC, Production No. 167008) at 0.1 ml/well, and then cultured in a 5% $CO_2$ incubator (37° C.) overnight. After the culture, from each well was removed the supernatant solution, followed by adding 0.05 ml of a 1% FBS-containing RPMI1640 medium. Then, the well was supplied with 0.05 ml of the test substance dissolved in dimethyl sulfoxide (diluted with a 1% FBS-containing RPMI1640 medium), followed by culturing in a 5% $CO_2$ incubator (37° C.) for 1 hr. From each well was removed the supernatant, and each well was washed with 150 μl of PBS, followed by adding 100 μl of a lysis buffer (50 mM Hepes (pH 7.4), 150 mM NaCl, 10% (v/v) glycerol, 1% Triton X-100, 1.5 mM $MgCl_2$, 1 mM EDTA (pH 8.0), 100 mM NaF, 1 mM PMSF, 10 μg/ml Aprotinin, 50 μg/ml Leupeptin, 1 μg/ml Pepstatin A and 1 mM $Na_3VO_4$). The plate was shaken at 4° C. for 1 hr to prepare the cell extract.

2. Preparation of an Anti-Phosphotyrosine Antibody-Immobilized Plate

To a 96-well plate for ELISA (purchased from COSTAR, Production No. 3369) was added 50 μl of 60 mM bicarbonate buffer (pH 9.6) containing 50 μg/ml of an anti-phosphotyrosine antibody (PY20, purchased from Transduction Laboratory, Production No. P-11120). The plate was incubated at 4° C. overnight.

3. Assay for Inhibitory Activity Against HGFR Autophosphorylation

Each well of the plate prepared in 2. was washed three times with 200 μl of PBS, and supplied with 150 μl of 3% BSA/PBS, followed by incubating at room temperature for 2 hrs. Each well was washed three times with 200 μl of PBS, and supplied with 50 μl of the above cell extract, followed by incubating at 4° C. overnight. After the incubation, each well was washed three times with 250 μl of a washing solution (0.1% BSA, 20 mM Tris-HCl (pH 7.6), 137 mM NaCl, and 0.05% Tween-20), and supplied with 70 μl of anti-HGFR antibody (h-Met(C-12), purchased from Santa Cruz, Production No. sc-10) 2,000-fold diluted with a reaction solution (1% BSA, 20 mM Tris-HCl (pH 7.6), 137 mM NaCl and 0.05% Tween-20), followed by incubating at room temperature for 1 hr. The well was washed three times with 250 µl of the washing solution, and supplied with 70 µl of peroxidase-labelled anti-rabbit IgG antibody (purchased from Cell Signaling, Production No. 7074) 2,000-fold diluted with the reaction solution, followed by incubating at room temperature for 1 hr. Each well was washed three times with 250 µl of the washing solution, and supplied with 70 µl of TMB Membrane Peroxidase Substrate (purchased from Funakoshi, Production No. 50-5077-03), followed by incubating at room temperature for 10 min. Each well was supplied with 70 µl of 1 M phosphoric acid, and using the Plate Reader MTP-500 (Corona Electric), the absorbance of the well was instantly determined at a measurement wavelength of 450 nm. While defining the absorbance of a well supplied with the cell extract having no test substance as 100% HGFR autophosphorylation activity, and the absorbance of a well supplied with 50 µl of the lysis buffer as 0% HGFR autophosphorylation activity, the HGFR autophosphorylation activity (%) was calculated for each well. The concentration of the test substance was changed by several levels to calculate HGFR autophosphorylation activities (%) in respective cases, and to calculate the concentration ($IC_{50}$) of the test substance necessary to inhibit HGFR autophosphorylation activity by 50%. The results are shown in Table 3.

TABLE 3

| Example | IC50 (µM) |
|---|---|
| 3 | 0.02 |
| 9 | 0.02 |
| 11 | 0.043 |
| 13 | 0.0068 |
| 15 | 0.013 |
| 17 | 0.12 |
| 22 | <0.03 |
| 24 | 0.069 |
| 28 | 0.019 |
| 43 | 0.059 |
| 44 | 0.35 |
| 45 | 0.35 |
| 48 | 0.26 |
| 50 | 0.28 |
| 52 | 0.34 |
| 56 | 0.13 |
| 77 | 0.11 |
| 82 | 0.088 |
| 85 | 0.59 |
| 89 | 0.049 |
| 92 | 0.54 |

Pharmacological Test Example 4

Inhibitory Activity Against Migration of Human Pancreatic Cancer Cells (SUIT-2)

Human pancreatic cancer cells (SUIT-2) were suspended in a 1% FBS-containing RPMI1640 medium (purchased from Sigma) to prepare a cell suspension ($8 \times 10^5$ cells/ml). To the lower compartment of Transwell (purchased from COSTAR, Production No. 3422) was added 600 µl of a 1% FBS-containing RPMI1640 medium. To the upper compartment were added 50 µl of the above cell suspension and 25 µl of the test substance dissolved in dimethyl sulfoxide (diluted with the 1% FBS-containing RPMI1640 medium), followed by culturing in a 5% $CO_2$ incubator (37° C.) for 1 hr. After the culture, to the upper compartment of each Transwell was added 25 µl of human recombinant hepatocyte growth factor (HGF, purchased from Wako Pure Chemical Industry, Production No. 22949) diluted to 280 ng/ml with a 1% FBS-containing RPMI1640 medium, followed by culturing in a 5% $CO_2$ incubator (37° C.) for 24 hrs. The cells adhering to the lower compartment of each well were counted in five fields by a phase contrast microscope (200×) to calculate an average adhering cell number. While defining the average adhering cell number of a well supplied with HGFR and no test substance as 100% cell migration activity and the average adhering cell number of a well supplied with no HGFR and no test substance as 0% cell migration activity, the cell migration activity percent (%) was calculated for each well. The concentration of the test substance was varied at several levels to calculate the cell migration activity percent (%) for respective cases, and to calculate the concentration of the test substance necessary to inhibit the cell migration activity by 50% ($IC_{50}$). The results are shown in Table 4.

TABLE 4

| Example | IC50 (µM) |
|---|---|
| 3 | 0.05 |
| 13 | 0.0032 |
| 56 | 0.038 |

Pharmacological Test Example 5

Inhibitory Activity Against the Tumor Growth of Human Gastric Cancer Cells (MKN-45)

Human gastric cancer cells (MNK-45) were suspended in HBSS (purchased from GIBCO BRL). The cell suspension ($5 \times 10^7$ cells/ml) was transplanted under the right flank skin of seven-week-old female BALB/c (nu/nu) mice at a volume of 0.1 ml. When tumor volume of the site transplanted with MNK-45 cells grew to 100-200 mm$^3$, mice were grouped so that the groups might be equalized in average tumor volume. The test substance was suspended in 0.5% methylcellulose, a mixed solution of hydrochloric acid and glucose (0.1N hydrochloric acid:5% glucose=1:9) or a mixed solution of dimethyl sulfoxide-Tween-glucose (dimethyl sulfoxide:Tween 80:5% glucose (containing equimolar hydrochloric acid to the test substance)=7:13:80), were administered orally to the mice twice every day. The tumor volumes were determined at the fifth day after the initiation of the administration of the test substances. The major axis and the minor axis of tumor were measured by a caliper to calculate ½×(major axis×minor axis×minor axis) for the tumor volume. The experiment was conducted using 10 mice in the control group (solvent-administered group) and 5 mice in test substance-administered group. The ratio in tumor volume of the group for administrating the test substance relative to that of the control group was defined as a tumor proliferation rate (%) The results are shown in Table 5.

TABLE 5

| Example | Dose (mg/kg/time) | Tumor proliferation rate (%) |
|---|---|---|
| 3 | 30 | 69 |
| 3 | 100 | 37 |
| 13 | 10 | 68 |
| 13 | 30 | 47 |
| 13 | 100 | 26 |

Pharmacological Test Example 6

Inhibitory Activity Against Sandwich Tube Formation by Vascular Endothelial Cells Stimulated with Hepatocyte Growth Factor Human umbilical vein endothelial cells (HUVECs) were isolated according to the reported method (Shin Seikagaku Jikken Koza, "Cell culturing techniques", p 197-202), and then cultured in a 5% $CO_2$ incubator (37° C.) using EGM-2 medium (purchased from Clonetics) until the cells reached confluency.

To each well of a 24-well plate was added 0.4 ml of an ice-cold mixture of collagen:5×RPMI1640:reconstitution buffer (all purchased from Nitta Gelatin, Inc.) at 7:2:1, followed by incubating in a 5% $CO_2$ incubator (37° C.) for 40 min to allow the solution to gell. Then, each well was supplied with 1 ml of the cell suspension of HUVEC (1-1.2×10$^5$ cells were used, though the cell number varied slightly depending on the lot of the HUVEC to be used) diluted with a serum free medium for endothelial cell culture (SFM, purchased from GIBCO RBL) supplemented with 10 ng/ml of EGF, followed by culturing in a 5% $CO_2$ incubator (37° C.) overnight. The supernatant was removed from each well, and then 0.4 ml of an ice-cold mixture of collagen:5×RPMI1640:reconstitution buffer (all purchased from Nitta Gelatin, Inc.) at 7:2:1 was layered on each well, followed by incubating in a 5% $CO_2$ incubator (37° C.) for 4 hours to allow the solution to gell. To the upper compartment was added 1.5 ml of a SFM solution containing 30 ng/ml of HGF (purchased from R&D), an angiogenic factor, and a diluted test substance, followed by culturing in a 5% $CO_2$ incubator (37° C.). On the fourth day after the addition of the test substance, the supernatant was removed from each well, and 0.4 ml of a 3.3 mg/ml solution of MTT (purchased from Sigma) in PBS was added to each well, followed by culturing in a 5% $CO_2$ incubator (37° C.) for about 2 hours. The tube formed in the collagen gel of each well was stained with MTT, and then the tube image was loaded in a computer (Macintosh) to determine the total length of the tube by an image analysis software "Angiogenesis quantification software" (purchased from Kurabo). The ratio of the total length of a tube formed in a well supplied with the test substance relative to a tube formed in a well supplied with no test substance was expressed as a percentage. The value of the ratio was used to provide the concentration ($IC_{50}$) of the test substance necessary to inhibit the tube formation by 50%. The results are shown in Table 6.

TABLE 6

| Example | IC50 (µM) |
|---|---|
| 13 | 0.13 |

Pharmacological Test Example 7

Inhibitory Activity Against the Growth of Vascular Endothelial Cells by Stimulated with Hepatocyte Growth Factor Human umbilical vein endothelial cells (HUVECs) were isolated according to the reported method (Shin Seikagaku Jikken Koza, "Cell culturing techniques", p 197-202), and then cultured in a 5% $CO_2$ incubator (37° C.) using EGM-2 medium (purchased from Clonetics) until the cells reached confluency.

HUVECs were suspended in a serum-free medium for endothelial cell culture (SFM, purchased from GIBCO RBL) containing 2% FBS. The cell suspension (2×10$^4$ cells/ml) was put in a cell culturing 96-well plate (purchased from NUNC, Production No. 167008) at 0.1 ml/well, and then cultured in a 5% $CO_2$ incubator (37° C.) overnight. After the culture, each well was supplied with 50 µl of the test substance diluted with a 2% FBS-containing serum-free medium for endothelial cell culture and 50 µl of HGF (purchased from R&D) diluted at a concentration of 120 ng/ml with a 2% FBS-containing serum-free medium for endothelial cell culture, followed by culturing in a 5% $CO_2$ incubator (37° C.) On the third day after the addition of the test substance, each well was supplied with 10 µl of Cell Counting Kit-8 (purchased from DOJINDO, Production No. 343-07623), and then the plate was incubated in a 5% $CO_2$ incubator (37° C.) for about 2 hours. After the incubation, using a Plate Reader MTP-500 (Corona Electric), the absorbance of each well was determined at a measurement wavelength of 450 nm and a reference wavelength of 660 nm. While defining the absorbance of a well supplied with HGF and no test substance as 100% cell proliferation activity and the absorbance of the well supplied with no test substance and no HGF as 0% cell proliferation activity, the cell proliferation activity ratio (%) was calculated for each cell. The concentration of the test substance was changed at several levels to calculate the cell proliferation activity ratio (%) in respective cases, and to calculate the concentration ($IC_{50}$) of the test substance necessary to inhibit cell proliferation activity by 50%. The results are shown in Table 7.

TABLE 7

| Example | IC50 (µM) |
|---|---|
| 3 | 0.19 |
| 13 | 0.073 |

DESCRIPTION OF THE PREFERRED EMBODIMENTS (General Production Method)

The compound of the present invention can be produced by methods described below. But the method for producing the compound of the present invention is not limited to these methods.

[Production Method 1] A Method for Producing Intermediates (1m) and (1n)

[Production Method 1-A] A Method for Producing Intermediates (1m) and (1n) Via Coupling of a Derivative of 2-Aminopyridine or 6-Aminopyrimidine with a Derivative of Phenol, Thiophenol or Aniline

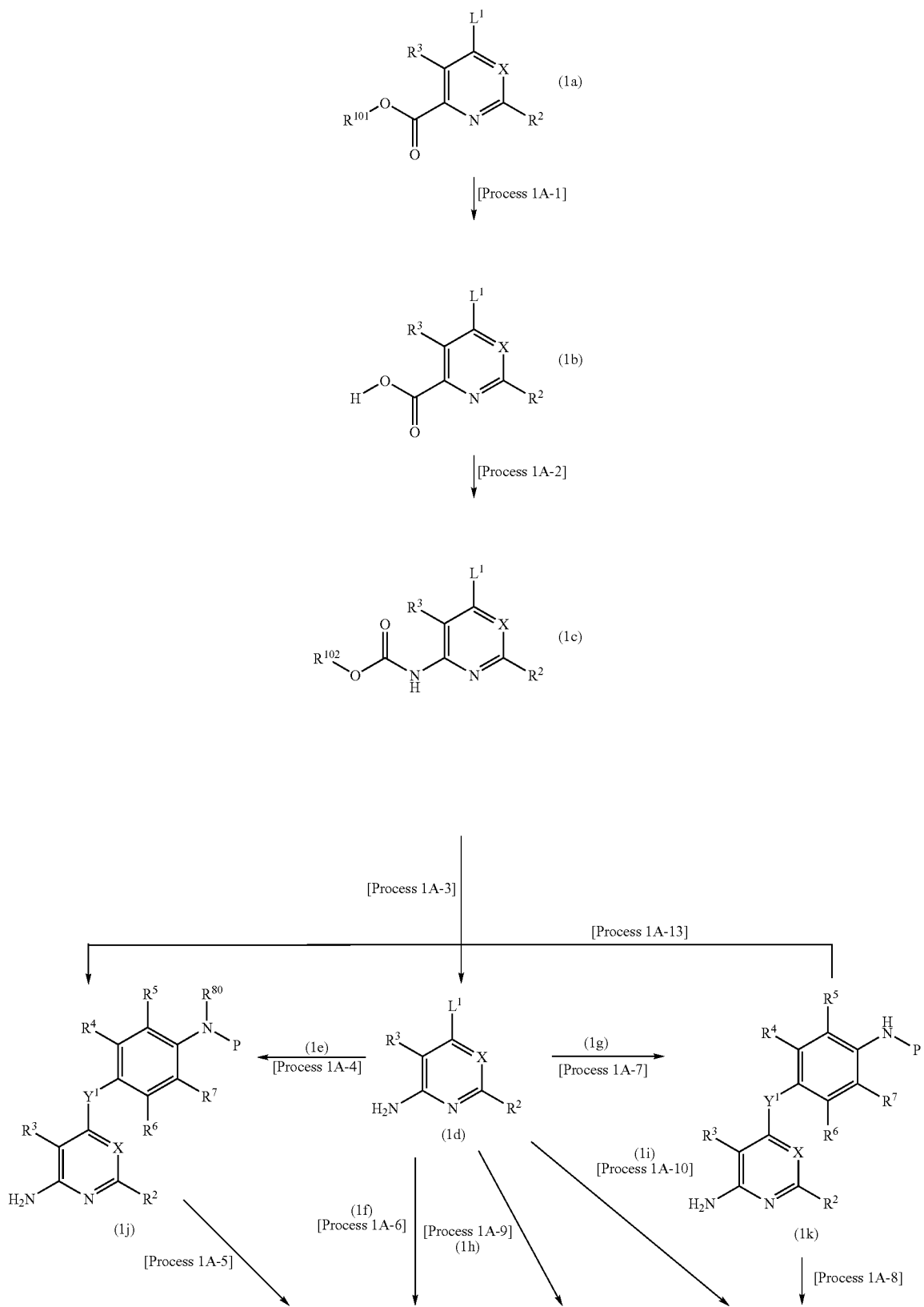

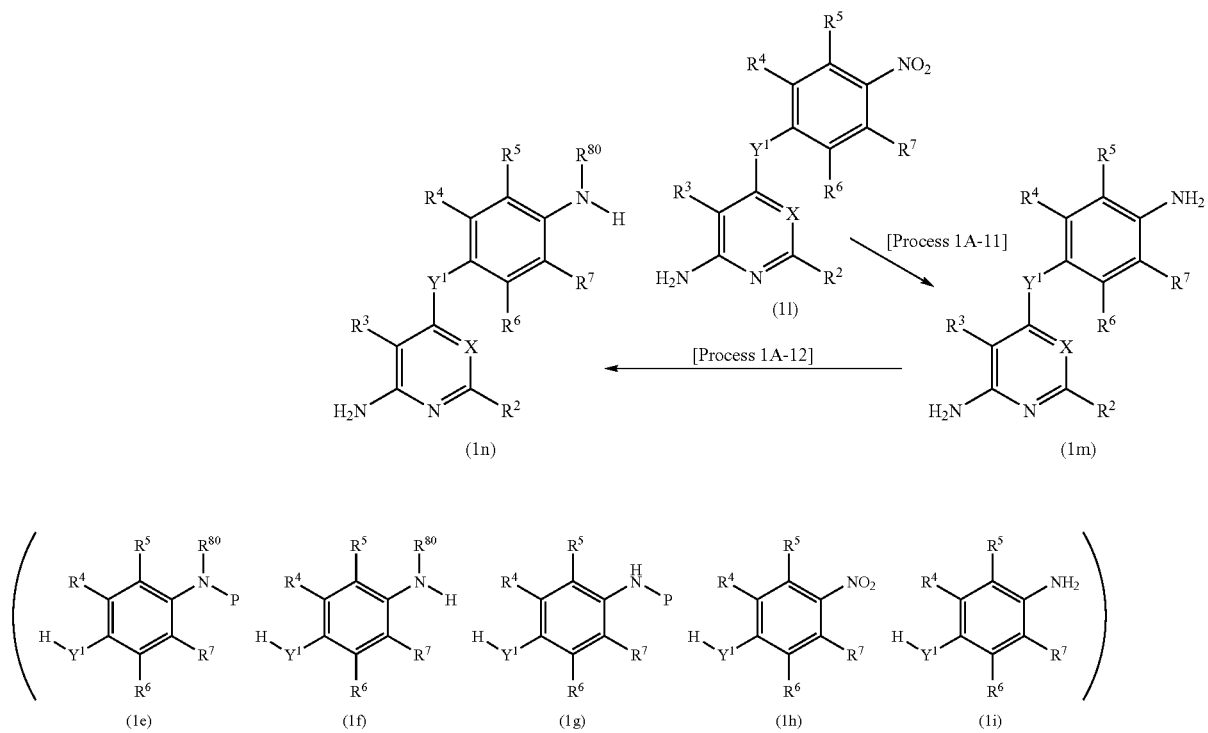

In the scheme, $Y^1$ represents oxygen, sulfur or the formula —N($R^{Y1}$)—, wherein $R^{Y1}$ represents hydrogen or $C_{1-6}$ alkyl; $L^1$ represents a leaving group; $R^{101}$ represents $C_{1-6}$ alkyl or benzyl; $R^{102}$ represents $C_{1-6}$ alkyl, benzyl or 2-(trimethylsilyl)ethyl; $R^{80}$ represents $C_{1-6}$ alkyl; P represents a protecting group for amino; and the other symbols represent the same meaning as defined above.

The compound (1a) includes, for example, 4-nitropicolinic acid ester, 4-chloropicolinic acid ester, 6-chloropyrimidine-4-carboxylic acid ester. 4-nitropicolinic acid ester and 4-chloropicolinic acid ester can be obtained by the esterification of 4-nitropicolinic acid and 4-chloropicolinic acid, both of which are commercially available (See Production Example 111). Among 6-chloropyrimidine-4-carboxylic acid ester, methyl 6-chloropyrimidine-4-carboxylate is described in Ukr. Kihm. Zh., 1982, Vol. 48, p 67 (CAS No. 6627-22-1). 6-chloropyrimidine-4-carboxylic acid ester also can be produced according to a method described in J. Heterocycl. Chem., 1, 130 (1964).

The compound (1d) includes, for example, commercially available compounds such as 2-amino-4-chloropyridine and 4-amino-6-chloropyrimidine. The compound (1d) also can be produced via <Process 1A-1>, <Process 1A-2> and <Process 1A-3> described below, using the compound (1a) as a starting material.

The compound (1f) includes, for example, commercially available compounds such as p-methylaminophenol sulfate and N-methyl-1,4-phenylenediamine dihydrochloride.

The compound (1e) can be obtained by protecting a group represented by the formula $R^{80}NH$— of the compound (1f). The general reaction for protecting amino can be used. For example, the compound (1e) can be obtained by a reaction of the compound (1f) with ethyl chloroformate, methyl chloroformate, benzyl chloroformate, di-t-butyl dicarbonate or trifluoroacetic anhydride.

The compound (1g) includes, for example, commercially available compounds such as acetaminophen, N-(hydroxyphenyl)formamide, 4-(N-t-butoxycarbonylamino)phenol, 4-trifluoroacetoamidophenol, 4-acetoamidothiophenol, 4-(methylcarbamyl)aniline and 4-(t-butylcarbamyl)aniline.

The compound (1 h) includes, for example, commercially available compounds such as 4-nitrophenol, 2-chloro-4-nitrophenol, 2-fluoro-4-nitrophenol, 3-fluoro-4-nitrophenol, 3-methyl-4-nitrophenol, 4-nitrothiophenol, 4-nitroaniline and 2-methoxy-4-nitroaniline.

The compound (1i) includes, for example, commercially available compounds such as 4-aminophenol, 4-amino-3-chlorophenol hydrochloride, 4-amino-2,5-dimethylphenol, 4-amino-2,6-dichlorophenol, 5-amino-2-hydroxybenzonitrile, 4-aminothiophenol, p-phenylenediamine and 2,5-diaminoanisol sulfate.

The above compounds can also be produced from commercially available compounds by a known method.

<Process 1A-1>

The process is a process for producing the compound (1b) from the compound (1a). For example, hydrolysis using a base can be used. As the base, an inorganic base such as sodium hydroxide, potassium hydroxide and lithium hydroxide can be used. As the solvent, methanol, ethanol, water or the like can be used. The reaction temperature is between 0° C. and a reflux temperature. The reaction time is between 10 minutes and 30 hours.

<Process 1A-2>

The process is a process for rearrangement of the compound (1b) to the compound (1c). The compound (1c) can be obtained by a reaction of the compound (1b) with an alcohol represented by the formula $R^{102}$—OH in the presence of diphenylphosphoryl azide and triethylamine. The preferable example of $R^{102}$ includes t-butyl, benzyl and 2-(trimethylsilyl)ethyl. As the solvent, N,N-dimethylformamide, N-methylpyrrolidone, toluene or the like can be used as well as t-butanol or benzylalcohol. The reaction temperature is between room temperature and a reflux temperature. The reaction time is between 10 minutes and 30 hours.

<Process 1A-3>

The process is a process for producing the compound (1d) from the compound (1c) by decarbamation. For the reaction, general deprotection for amino can be used and specific examples are deprotection using an acid such as hydrochloric acid and trifluoroacetic acid, deprotection using an inorganic base such as sodium hydroxide and potassium hydroxide, and deprotection using tetrabutylammonium fluoride. As the solvent, methanol, ethanol, water, tetrahydrofuran, N,N-dimethylformamide or the like can be used. The reaction temperature is between room temperature and a reflux temperature. The reaction time is between 10 minutes and 30 hours.

<Process 1A-4> <Process 1A-6> <Process 1A-7> <Process 1A-9> <Process 1A-10>

These processes are processes for coupling the compound (1d) with the compounds (1e), (1f), (1 g), (1 h) or (1i) to produce the compounds (1j), (1n), (1k), (1l) or (1m), respectively. As the solvent, N-methylpyrrolidone, N,N-dimethylformamide, dimethyl sulfoxide, 2-ethoxyethanol, chlorobenzene or the like can be used. A base or an acid may be added in the reaction system, and specifically an organic base such as triethylamine and diisopropylethylamine, an inorganic base such as potassium carbonate, cesium carbonate and sodium hydride, or an acid such as pyridine hydrochloride and hydrochloric acid can be used. The reaction temperature is between room temperature and a reflux temperature. The reaction time is between 10 minutes and 30 hours.

<Process 1A-5>

The process is a process for deprotecting the compound (1j) to produce the compound (1n). For the reaction, general deprotection for amino can be applied, for specific example, deprotection using an acid such as hydrochloric acid and trifluoroacetic acid, deprotection using an inorganic base such as sodium hydroxide and potassium hydroxide, and deprotection using tetrabutylammonium fluoride. When a protecting group is benzyloxycarbonyl and $R^4, R^5, R^6, R^7$ and $R^{10}$ are not any of chlorine, bromine and iodine, deprotection by catalytic hydrogenation using palladium-carbon or palladium hydroxide as a catalyst can also be used. As the solvent, methanol, ethanol, water, tetrahydrofuran, N,N-dimethylformamide or the like can be used. The reaction temperature is between room temperature and a reflux temperature. The reaction time is between 10 minutes and 30 hours.

<Process 1A-8>

The process is a process for deprotecting the compound (1k) to produce the compound (1m). The conditions similar to those in <Process 1A-5> can be used.

<Process 1A-11>

The process is a process for reducing nitro of the compound (1l) to produce the compound (1m). Generally used conditions for reduction from nitro to amino can be applied, for specific example, reduction using iron-ammonium chloride, or iron-acetic acid. When $R^4, R^5, R^6, R^7$ and $R^{10}$ are not any of chlorine, bromine and iodine, catalytic hydrogenation using palladium hydroxide or palladium-carbon as a catalyst also can be used. As the solvent, methanol, ethanol, water, N,N-dimethylformamide, ethyl acetate, tetrahydrofuran or the like can be used. The reaction temperature is between room temperature and a reflux temperature. The reaction time is between 10 minutes and 30 hours.

<Process 1A-12>

The process is a process for alkylating the compound (1m) to produce the compound (1n). Reductive amination of aldehyde or ketone can convert hydrogen to $C_{1-6}$ alkyl. As the reducing agent, sodium cyanoborohydride and sodium triacetoxyborohydride can be used. As the solvent, methanol, tetrahydrofuran, dichloromethane, dichloroethane or the like can be used.

A method for reducing a benzotriazole derivative with sodium borohydride can also be used, as described in Tetrahedron, 47(16), 2683 (1991). Specifically for example, the compound (1n) wherein $R^{80}$ is methyl can be obtained by reduction with sodium borohydride, a benzotriazol-1-ylmethylaniline derivative obtained by a reaction of the compound (1m) with 1-(hydroxymethyl)-1H-benzotriazole. In the process for producing a benzotriazol-1-ylmethylaniline derivative, an alcohol such as methanol or ethanol, or a mixed solvent of an alcohol with N,N-dimethylformamide, acetic acid or water can be used for the solvent. The reaction temperature is between −5° C. and a reflux temperature. The reaction time is between 10 minutes and 30 hours. In the process of reduction with sodium borohydride, tetrahydrofuran, dioxane, an alcohol such as methanol or ethanol, or a mixed solvent of an alcohol with N,N-dimethylformamide or the like can be used as the solvent. The reaction temperature is between −5° C. and a reflux temperature. The reaction time is between 10 minutes and 30 hours.

<Process 1A-13>

The process is an alternative method for producing the compound (1j) by alkylating the compound (1k) to produce the compound (1j). The compound (1j) can be obtained by a reaction with alkyl halide in the presence of a base such as potassium carbonate or sodium hydride. As the solvent, tetrahydrofuran, N,N-dimethylformamide or the like can be used. The reaction temperature is between 0° C. and a reflux temperature. The reaction time is between 10 minutes and 30 hours.

[Production Method 1-B] A Method for Producing an Intermediate (1n) Via Coupling of Pyridine-2-Carboxylic Acid Ester or Pyrimidine-6-Carboxylic Acid Ester with a Derivative of Phenol, Thiophenol or Aniline

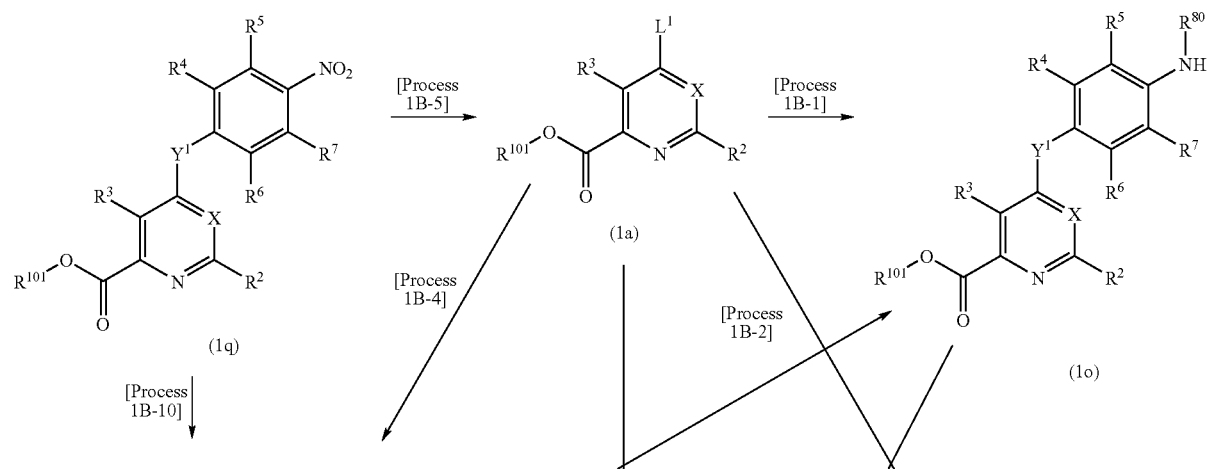
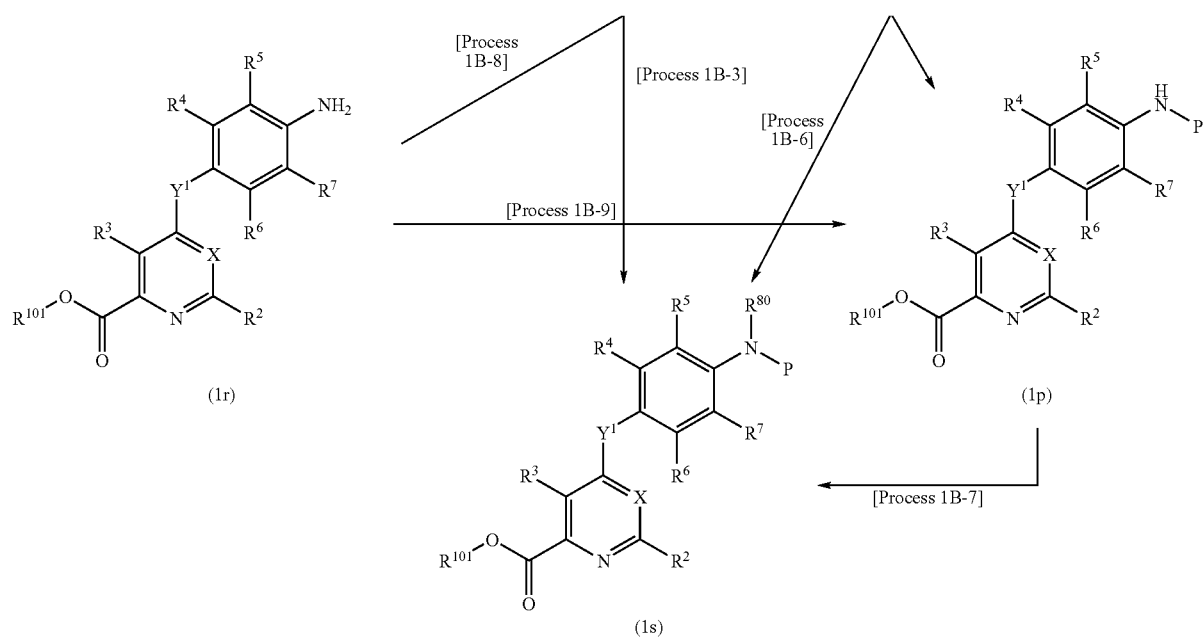
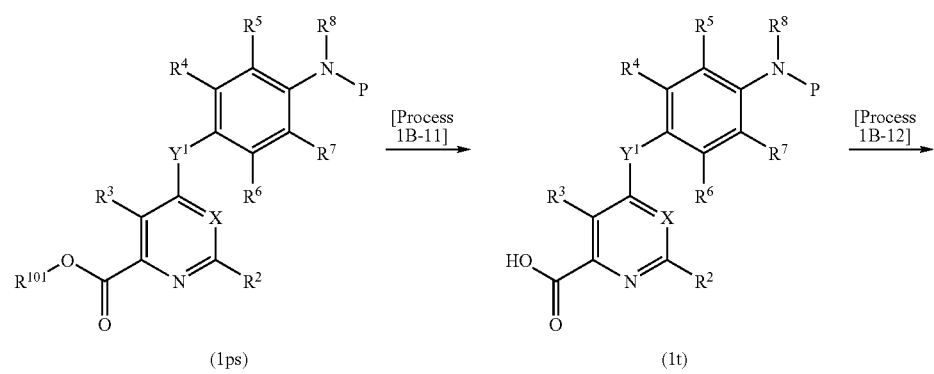

-continued
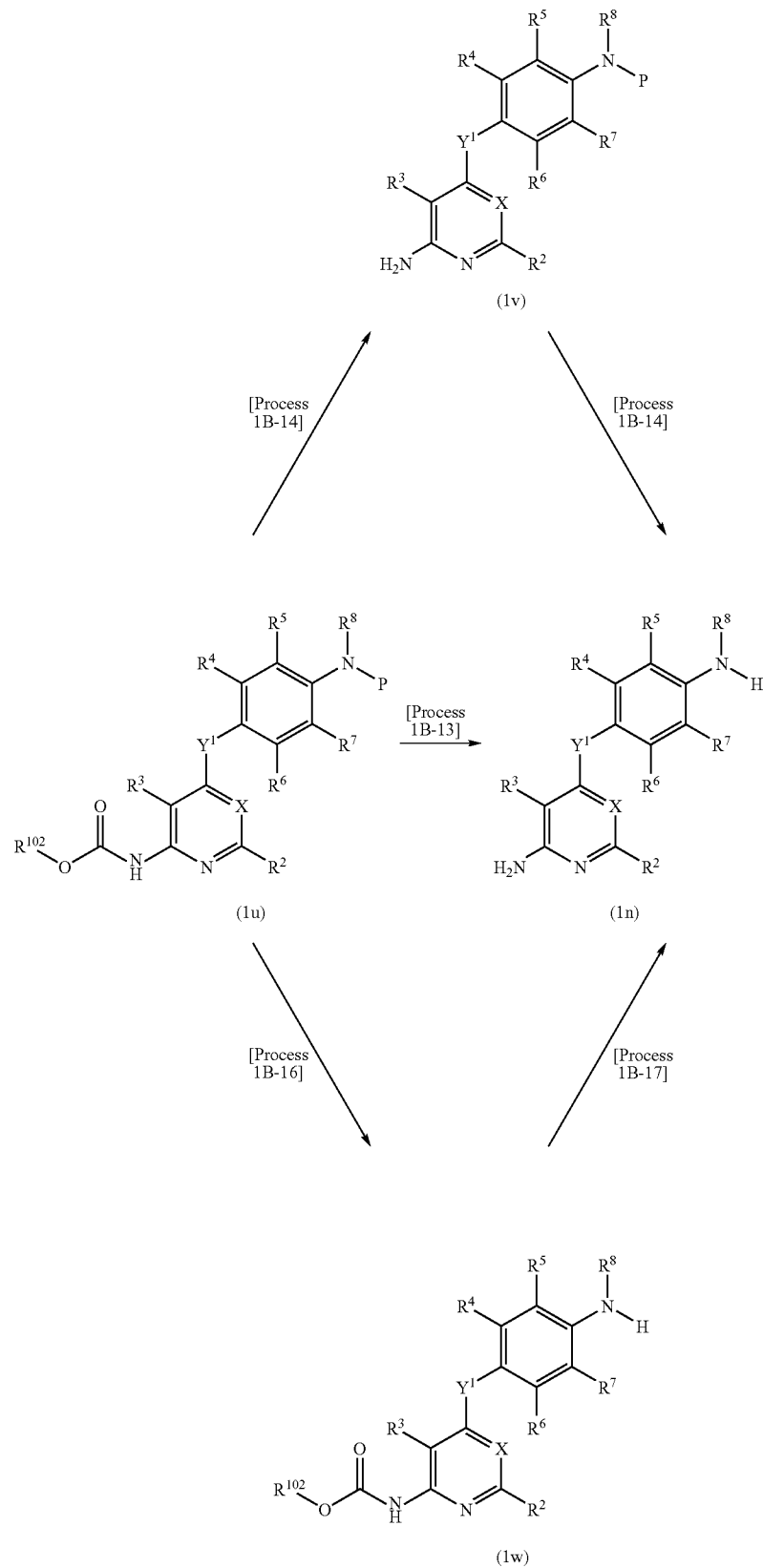

In the scheme, the symbols represent the same meaning as defined above.

<Process 1B-1> <Process 1B-2> <Process 1B-3> <Process 1B-4> <Process 1B-5>

These processes are processes for coupling the compound (1a) with the compound (1f), (1g), (1e), (1i) or (1h) to produce the compound (1o), (1p), (1s), (1r) or (1q), respectively. The methods similar to those in <Process 1A-4> can be used.

<Process 1B-6>

The process is a process for protecting amino of the compound (1o) to produce the compound (1s). A general reaction for protecting amino can be used. Specifically for example, a reaction with ethyl chloroformate, methyl chloroformate, benzyl chloroformate, di-t-butyl dicarbonate and trifluoroacetic anhydride can be used. A base may be added in the reaction system, and an organic base such as pyridine, triethylamine and diisopropylethylamine, and an inorganic base such as sodium carbonate, potassium carbonate and sodium hydrogencarbonate can be used. As the solvent, tetrahydrofuran, acetone, water, dioxane or the like can be used. The reaction temperature is between room temperature and a reflux temperature. The reaction time is between 10 minutes and 30 hours.

<Process 1B-7>

The process is a process for alkylating the compound (1p) to produce the compound (1s). The methods similar to those in <Process 1A-13> can be used.

<Process 1B-8>

The process is a process for alkylating the compound (1r) to produce the compound (1o). The methods similar to those in <Process 1A-12> can be used.

<Process 1B-9>

The process is a process for protecting amino of the compound (1r) to produce the compound (1p). The methods similar to those in <Process 1B-6> can be used.

<Process 1B-10>

The process is a process for reducing nitro of the compound (1q) to produce the compound (1r). The methods similar to those in <Process 1A-11> can be used.

<Process 1B-11>

The process is a process for producing the compound (1t) from the compound (1ps) (the compound (1ps) represents the compound (1p) or the compound (1s) described in [Production method 1-B]). The methods similar to those in <Process 1A-1> can be used.

<Process 1B-12>

The process is a process for producing the compound (1u) from the compound (1t). The methods similar to those in <Process 1A-2> can be used.

<Process 1B-13>

The process is a process for deprotecting the two protecting groups "$R^{102}$—O—C(=O)—" and "P" of the compound (1u) to produce the compound (1n). Depending on the kind of the protecting groups, deprotection using an acid such as hydrochloric acid and trifluoroacetic acid, deprotection using an inorganic base such as sodium hydroxide and potassium hydroxide, deprotection using tetrabutylammonium fluoride, and deprotection by catalytic hydrogenation using palladium-carbon or palladium hydroxide as a catalyst can be appropriately combined to produce the compound (1n).

<Production 1B-14> <Production 1B-16>

These processes are processes for deprotecting only one of the two protecting groups "$R^{102}$—O—C(=O)—" and "P" of the compound (1u) to produce the compound (1v) or the compound (1w), respectively. The process is applicable only when the two protecting groups "$R^{102}$—O—C(=O)—" and "P" are different. Specifically, for example, when a group represented by the formula $R^{102}$—O—C(=O)— is 2-(trimethylsilyl)ethoxycarbonyl and P is benzyloxycarbonyl, deprotection using tetrabutylammonium fluoride or deprotection by catalytic hydrogenation can be applied to deprotect selectively only one of the two protecting groups.

<Process 1B-15>

The process is a process for deprotecting the compound (1v) to produce the compound (1n). The method described in <Process 1A-5> can be used.

<Process 1B-17>

The process is a process for deprotecting the compound (1w) to produce the compound (1n). The method described in <Process 1A-5> can be used.

[Production Method 2] An Alternative Production Method of Intermediates (1l), (1m), (1k), (1j) and (1n) from a Pyridine or Pyrimidine Derivative (2a) Having Leaving Groups $L^1$ at the 4-Position and $L^2$ at the 2-Position or 6-Position

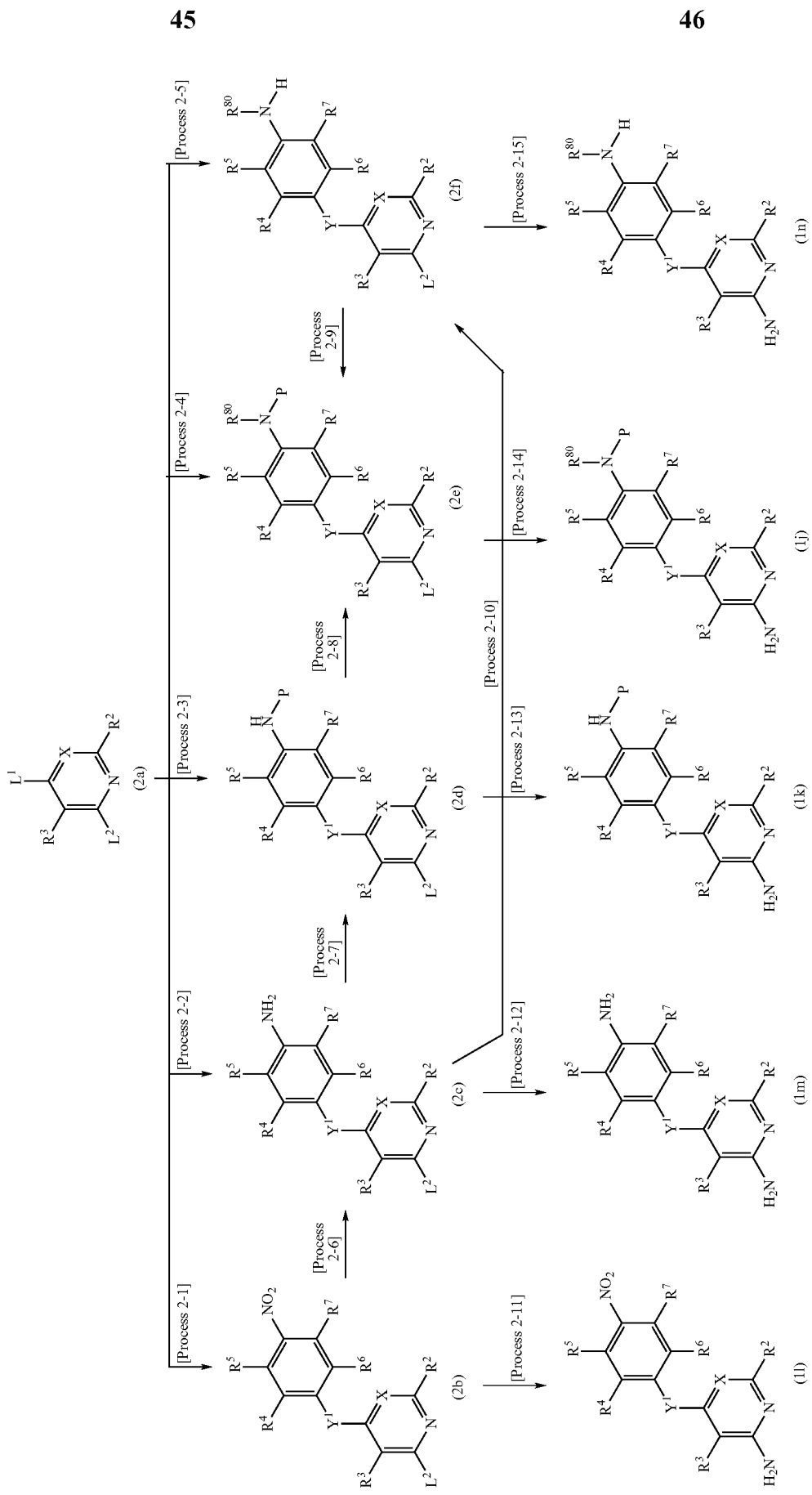

In the scheme, $L^2$ represents a leaving group. The other symbols represent the same meanings as defined above.

The compound (2a) includes, for example, commercially available compounds such as 4,6-dichloropyrimidine, 2-chloro-4-nitropyridine, and 2,4-dichloropyridine. The compound (2a) also can be produced from commercially available compounds by a known method.

<Process 2-1> <Process 2-2> <Process 2-3> <Process 2-4> <Process 2-5>

These processes are processes for coupling the compound (2a) with the compound (1h), (1i), (1g), (1e) or (1f) to produce the compound (2b), (2c), (2d), (2e) or (2f), respectively. Preferably, in (2a), $L^1$ is a reactive group higher than $L^2$. In a specific combination, for example, $L^1$ is nitro and $L^2$ is chlorine. The methods similar to those in <Process 1A-4> can be used for these processes.

<Process 2-6>

The process is a process for reducing nitro of the compound (2b) to produce the compound (2c). Generally used conditions of reduction from nitro to amino can be used. Specifically, for example a reduction using iron-ammonium chloride or iron-acetic acid can be used. As the solvent, methanol, ethanol, water, N,N-dimethylformamide, tetrahydrofuran or the like can be used. The reaction temperature is between room temperature and a reflux temperature. The reaction time is between 10 minutes and 30 hours.

<Process 2-7>

The process is a process for protecting amino of the compound (2c) to produce the compound (2d). The methods similar to those in <Process 1B-6> can be used.

<Process 2-8>

The process is a process for alkylating the compound (2d) to produce the compound (2e). The methods similar to those in <Process 1A-13> can be used.

<Process 2-9>

The process is a process for protecting amino of the compound (2f) to produce the compound (2e). The methods similar to those in <Process 1B-6> can be used.

<Process 2-10>

The process is a process for alkylating the compound (2c) to produce the compound (2f). The methods similar to those in <Process 1A-12> can be used.

<Process 2-11> <Process 2-12> <Process 2-13> <Process 2-14> <Process 2-15>

These process are processes for converting the leaving group $L^2$ of the compound (2b), (2c), (2d), (2e) or (2f) to amino to produce the compound (1l), (1m), (1k), (1j) or (1n), respectively. The process can be carried out using, for example, an ammonia-ethanol solution in a sealed tube. The reaction temperature is a reflux temperature. The reaction time is between 10 minutes and 100 hours.

[Production Method 3] A Method for Producing an Intermediate Represented by the Formula (XI)

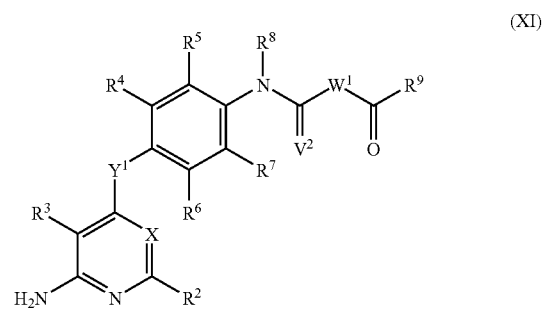

(XI)

In the formula, $W^1$ represents a direct bond, a group represented by the formula —C($R^{W1}$)($R^{W2}$)— or a group represented by the formula —NH—, wherein $R^{W1}$ and $R^{W2}$ may be the same or different and each represents hydrogen, halogen, $C_{1-6}$ alkyl or $C_{1-6}$ alkoxy; and the other symbols represent the same meanings as defined above.

[Production Method 3-A] A Method for Producing an Intermediate Product (3a), Wherein $V^2$ is Sulfur, $W^1$ is a Group Represented by the Formula —NH—, and $R^9$ is $R^{9a}$, Among the Intermediate Product Represented by the Formula (XI)

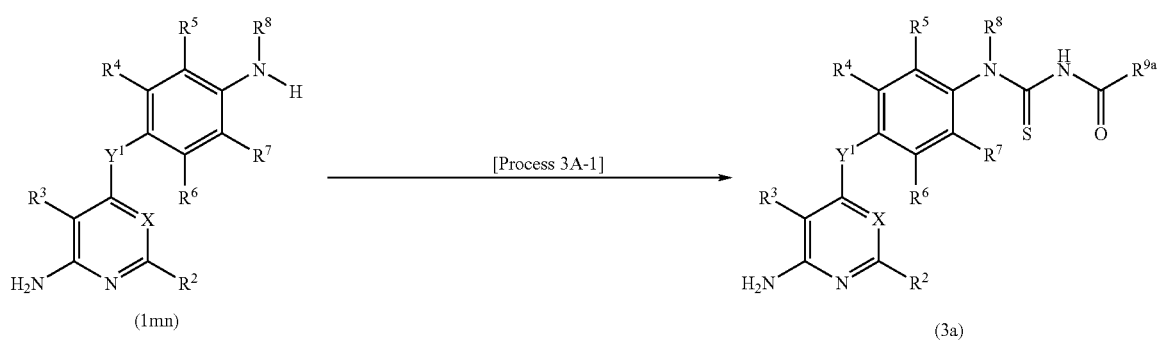

-continued

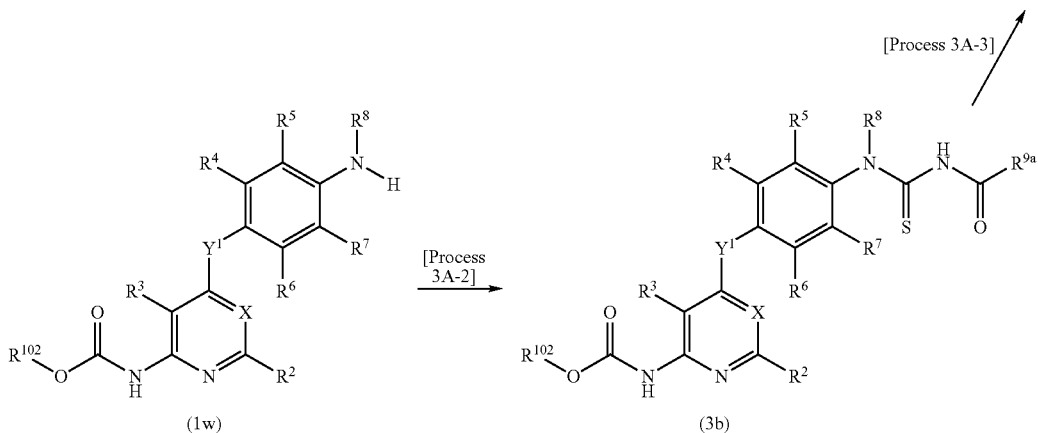

[Process 3A-3]

In the scheme, $R^{9a}$ represents $C_{1-6}$ alkyl, $C_{2-6}$ alkenyl, $C_{2-6}$ alkynyl, $C_{3-10}$ cycloalkyl, $C_{6-10}$ aryl, $C_{3-10}$ cycloalkyl-$C_{1-16}$ alkyl, $C_{6-10}$ aryl-$C_{1-6}$ alkyl, 5- to 10-membered heteroaryl, a 3- to 10-membered non-aromatic heterocyclic group (limited to the group having a bonding hand from a carbon forming the ring), 5- to 10-membered heteroaryl-$C_{1-6}$ alkyl, and 3- to 10-membered non-aromatic heterocyclic-$C_{1-6}$ alkyl, and $R^{9a}$ may be substituted with a substituent selected from Substituent Group A or Substituent Group B, and if $R^{9a}$ has hydroxyl, or primary or secondary amino as a substituent group, the substituent group may be protected by a suitable protecting group, and the other symbols represent the same meanings as defined above.

<Process 3A-1>

The process is a process for producing an acylthiourea derivative (3a) from the compound (1mn) (the compound (1mn) represents the compound (1m) or the compound (1n) described in [Production method 1-A], the same applies hereinafter). For the process, for example, a method for reacting acyl isothiocyanate represented by the formula $R^{9a}$—C(=O)—NCS with the compound (1mn) can be used. In the reaction system, an acid such as camphor sulfonic acid can be added. As the solvent, a mixed solvent of toluene-methanol, a mixed solvent of toluene-ethanol, acetonitrile, N,N-dimethylformamide, and tetrahydrofuran can be used. The reaction temperature is between room temperature and a reflux temperature. The reaction time is between 10 minutes and 30 hours. If hydroxyl, primary amino or secondary amino of $R^{9a}$ is protected, deprotection is suitably carried out in any process down to a final product.

The acyl isothiocyanate represented by the formula $R^{9a}$—C(=O)—NCS can be obtained by reacting an acyl chloride represented by the formula $R^{9a}$—C(=O)—Cl with potassium thiocyanate. As the solvent, acetonitrile, ethyl acetate or the like can be used. The reaction temperature is between room temperature and a reflux temperature. The reaction time is between 10 minutes and 100 hours.

<Process 3A-2>

The process is a process for providing the compound (3b) from the compound (1w). The methods similar to those in <Process 3A-1> can be used.

<Process 3A-3>

The process is a process for deprotecting the compound (3b) to produce the compound (3a). The methods similar to those in <Process 1A-5> can be used.

[Production Method 3-B] A Method for Producing an Intermediate (3f), Which is an Intermediate Represented by the Formula (XI), Wherein $V^2$ is Oxygen, $W^1$ is a Group Represented by the Formula —NH—, and $R^9$ is $R^{9a}$.

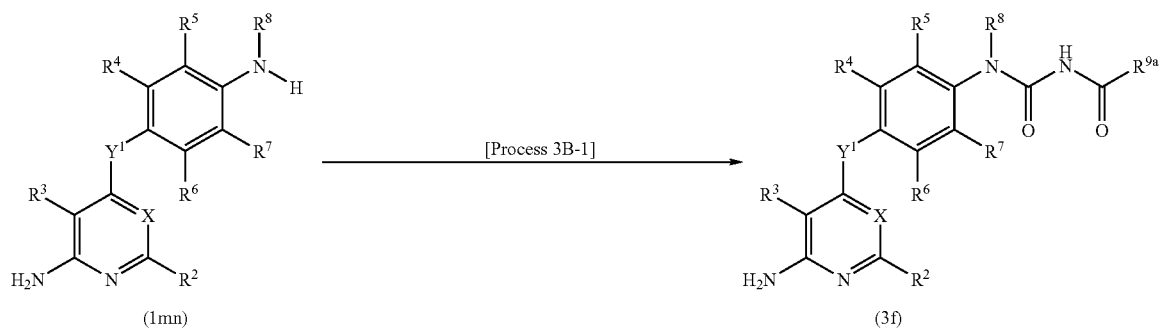

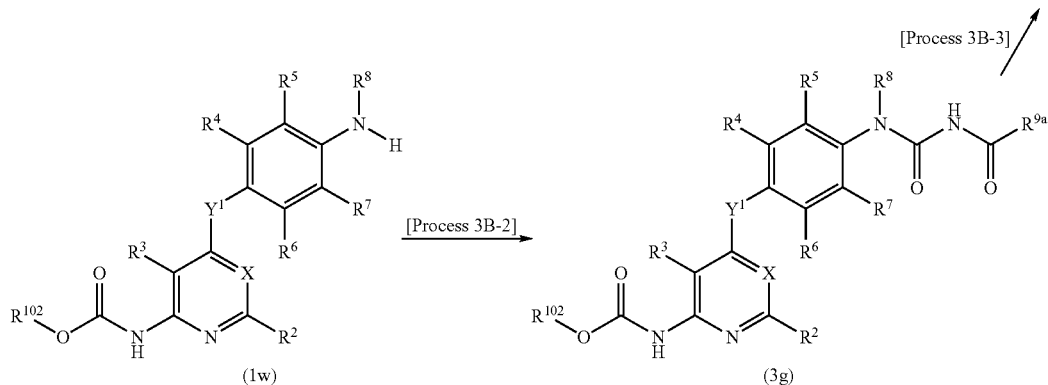

In the scheme, the symbols represent the same meanings as defined above.

<Process 3B-1>

The process is a process for producing the acylurea derivative (3f) from the compound (1mn). For the process, for example, a method for reacting acyl isocyanate represented by the formula $R^{9a}$—C(=O)—NCO with the compound (1n) can be used. As the solvent, N,N-dimethylformamide, tetrahydrofuran or the like can be used. The reaction temperature is between 0° C. and a reflux temperature. The reaction time is between 10 minutes and 30 hours. If hydroxyl, primary amino or secondary amino of $R^{9a}$ is protected, deprotection is suitably carried out in any process down to a final product.

The acyl isocyanate represented by the formula $R^{9a}$—C(=O)—NCO can be obtained by reacting an amide represented by the formula $R^{9a}$—C(=O)—NH$_2$ with oxalyl chloride. As the solvent, 1,2-dichloroethane or the like can be used. The reaction temperature is between room temperature and a reflux temperature. The reaction time is between 1 hour and 100 hours.

<Process 3B-2>

The process is a process for producing the acylurea derivative (3g) from the compound (1w). The methods similar to those in <Process 3B-1> can be used.

<Process 3B-3>

The process is a process for deprotecting the compound (3g) to produce the compound (3f). The methods similar to those in <Process 1A-5> can be used.

[Production Method 3-C] A Method for Producing an Intermediate (3o), Which is an Intermediate Represented by the Formula (XI), Wherein $V^2$ is Oxygen, $W^1$ is $W^2$, Wherein $W^2$ Represents a Direct Bond, a Group Represented by the Formula —C($R^{W1}$)($R^{W2}$)—, Wherein $R^{W1}$ and $R^{W2}$ may be the Same or Different and Each Represents Hydrogen, Halogen, $C_{1-6}$ Alkyl or $C_{1-6}$ Alkoxy, and $R^9$ is $R^{9b}$.

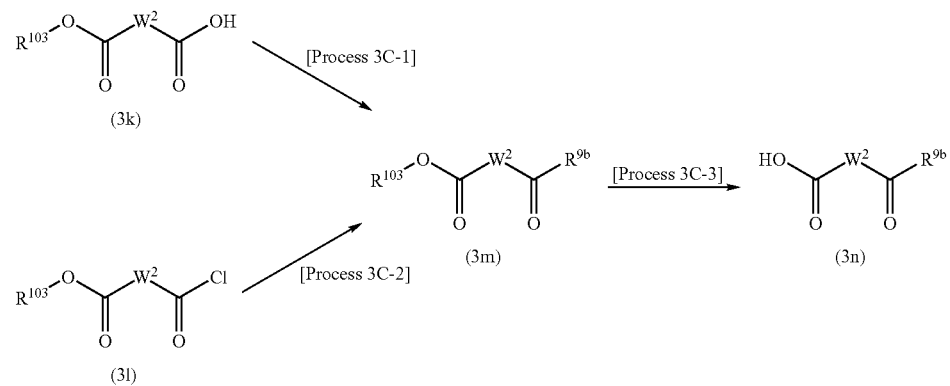

-continued

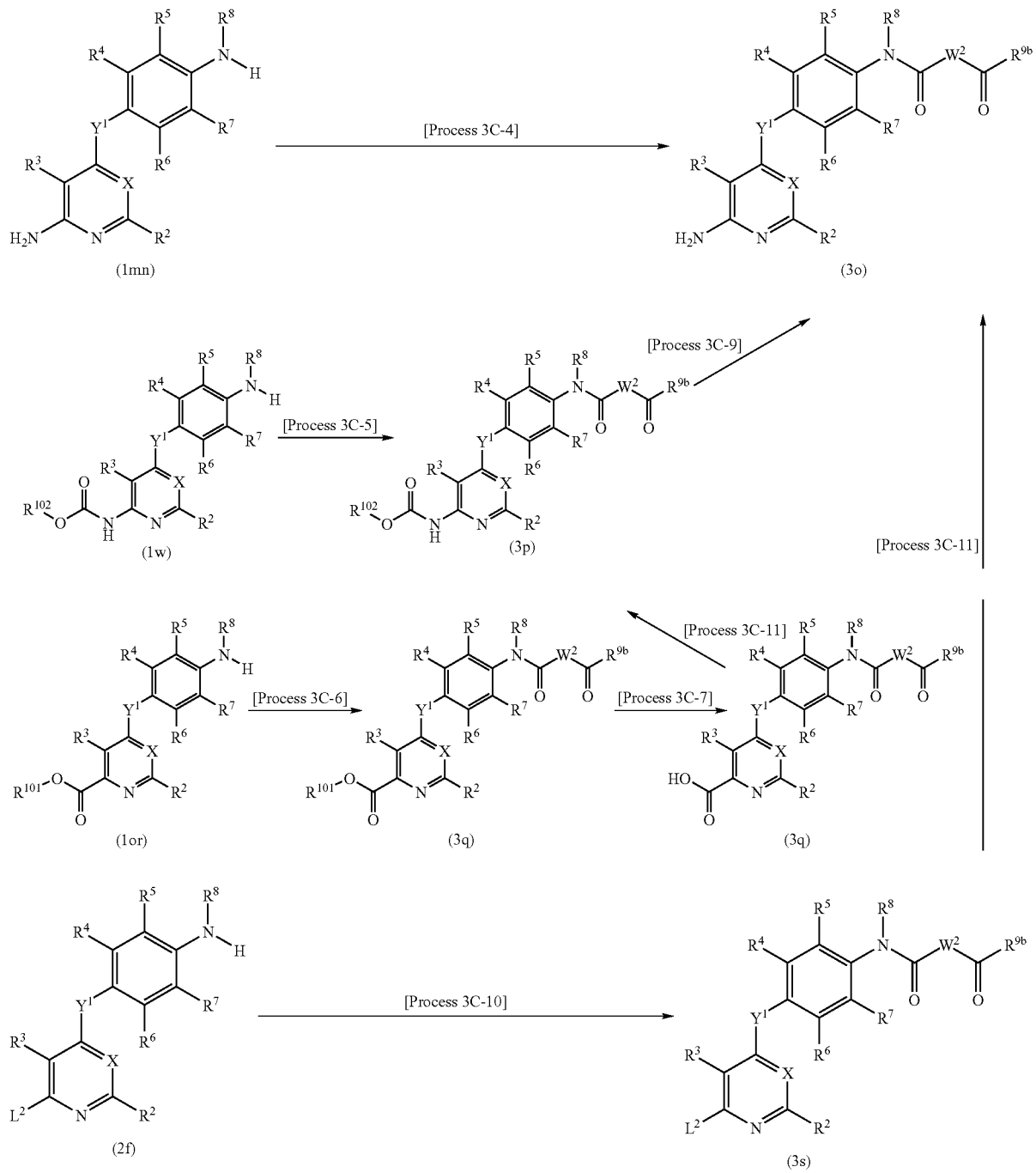

In the scheme, $R^{103}$ represents $C_{1-6}$ alkyl or benzyl; $R^{9b}$ represents 3- to 10-membered non-aromatic heterocyclic group (limited to a group having nitrogen as a ring constituent atom, the nitrogen having a bonding hand), or a group represented by the formula —$NR^{11a}R^{11b}$, wherein $R^{11a}$ and $R^{11b}$ represent the same meaning as defined above, and $R^{9b}$ may be substituted with a substituent selected from Substituent Group A or Substituent Group B, and if $R^{9b}$ has hydroxyl, primary amino, or secondary amino as a substituent group, the group may be protected by a suitable protecting group, and the other symbols represent the same meanings as defined above.

The compound (3k) includes, for example, commercially available compounds such as benzyl malonate, and monobenzyl 2-fluoromalonate.

The compound (3l) includes, for example, commercially available compounds such as ethyl malonyl chloride, methyl malonyl chloride, ethyl oxalyl chloride, and methyl oxalyl chloride.

The above compounds can also be produced from commercially available compounds by a known method.

<Process 3C-1>

The process is a process for condensing the compound (3k) with an amine represented by the formula $R^{9b}$—H or a salt thereof to produce the compound (3m). For the process, a general condensation of a carboxylic acid with an amine can be used. For specific example, as the solvent, N,N-dimethylformamide and tetrahydrofuran can be used, and for the condensing agent, carbonyldiimidazole, dicyclohexylcarbodiimide, 1-ethyl-3-(3-dimethylaminopropyl)carbodiimide hydrochloride, and (1H-1,2,3-benzotriazol-1-yloxy)(tri(dimethylamino))phosphonium hexafluorophosphate can be used. An organic base such as triethylamine also can be appropriately used. The reaction temperature is between 0° C. and a reflux temperature. The reaction time is between 10 minutes and 30 hours.

<Process 3C-2>

The process is a process for condensing the compound (3l) with an amine represented by the formula $R^{9b}$—H or a salt thereof to produce the compound (3m). As the solvent, N,N-dimethylformamide, tetrahydrofuran, dichloromethane or the like can be used. An organic base such as triethylamine also can be appropriately used. The reaction temperature is between 0° C. and a reflux temperature. The reaction time is between 10 minutes and 30 hours.

<Process 3C-3>

The process is a process for producing the compound (3n) from the compound (3m). For the process, hydrolysis using a base can be used. For the base, lithium hydroxide or the like can be used. If $R^{103}$ is a benzyl and $R^{9b}$ does not have chlorine, bromine and iodine as a substituent group, catalytic hydrogenation using palladium-carbon or palladium hydroxide as a catalyst also can be used. As the solvent, methanol, ethanol, water, N,N-dimethylformamide, tetrahydrofuran, ethyl acetate or the like can be used. The reaction temperature is between 0° C. and a reflux temperature. The reaction time is between 10 minutes and 30 hours.

<Process 3C-4>

The process is a process for condensing the compound (1mn) with the compound (3n) to produce the compound (3o). For the condensing agent, 1-ethyl-3-(3-dimethylaminopropyl)carbodiimide hydrochloride, (1H-1,2,3-benzotriazol-1-yloxy)(tri(dimethylamino))phosphonium hexafluorophosphate or the like can be used. An organic base such as triethylamine also can be appropriately used. As the solvent, tetrahydrofuran, N,N-dimethylformamide or the like can be used. The reaction temperature is between 0° C. and a reflux temperature. The reaction time is between 10 minutes and 30 hours.

<Process 3C-5> <Process 3C-6> <Process 3C-10>

These processes are processes for producing the compounds (3p), (3q) or (3s) from the compound (1w), (1or) (the compound (1or) represents the compound (1o) or the compound (1r) described in [Production method 1-B], the same applies hereinafter), or (2f), respectively. The methods similar to those in <Process 3C-4> can be used.

<Process 3C-7>

The process is a process for producing the compound (3r) from the compound (3q). The methods similar to those in <Process 1A-1> can be used.

<Process 3C-8>

The process is a process for rearrangement of the compound (3r) to the compound (3p). The methods similar to those in <Process 1A-2> can be used.

<Process 3C-9>

The process is a process for deprotecting the compound (3p) to produce the compound (3o). The methods similar to those in <Process 1A-5> can be used.

<Process 3C-11>

The process is a process for converting the leaving group $L^2$ of the compound (3s) to amino to produce the compound (3o). The methods similar to those in <Process 2-11> can be used.

[Production Method 3-D] A Method for Producing an Intermediate (3t), an Intermediate Represented by the Formula (XI), Wherein $V^2$ is Oxygen, $W^1$ is a Group Represented by the Formula —NH—, and $R^9$ is $R^{9b}$

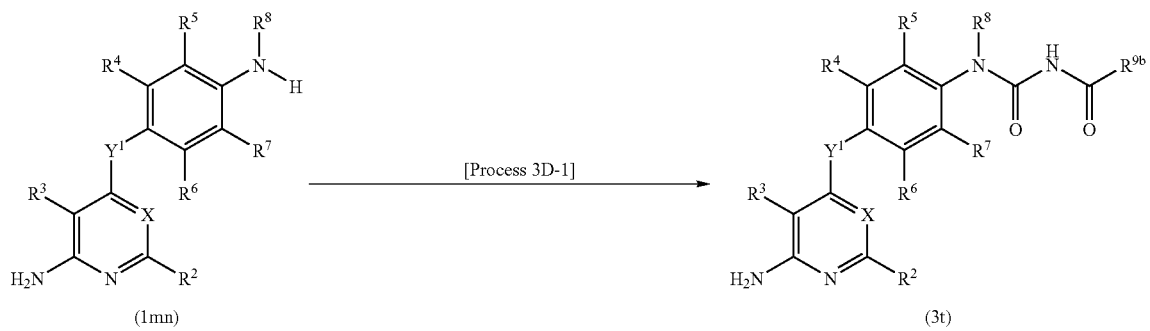

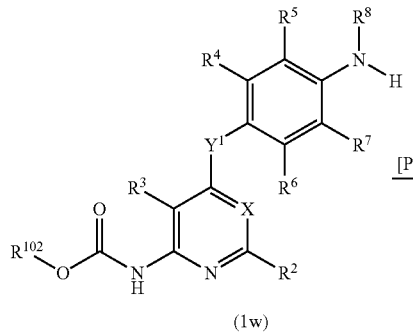

(1w)

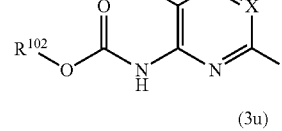

[Process 3D-2]

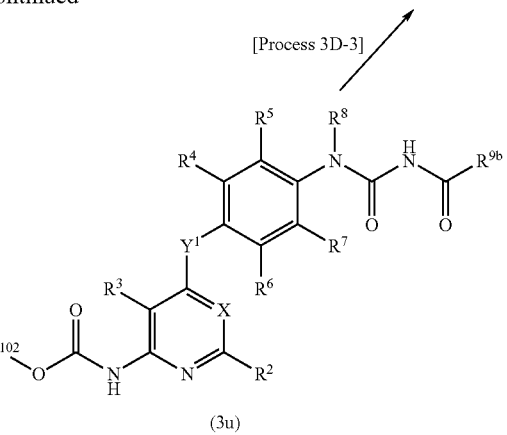

(3u)

In the scheme, the symbols represent the same meanings as defined above.

<Process 3D-1>

The process is a process for producing the compound (3t) from the compound (1mn). A method wherein the compound (1mn) is reacted with N-(chlorocarbonyl)isocyanate or phenyl isocyanateformate followed by reacting with an amine represented by the formula $R^{9b}$—H and the like can be used. A base such as diisopropylamine and triethylamine also may be used. As the solvent, dichloromethane, dichloroethane, tetrahydrofuran or the like can be used. The reaction temperature is between 0° C. and a reflux temperature. The reaction time is between 10 minutes and 30 hours.

<Process 3D-2>

The process is a process for producing the compound (3u) from the compound (1w). The methods similar to those in <Process 3D-1> can be used.

<Process 3D-3>

The process is a process for deprotecting the compound (3u) to produce the compound (3t). The methods similar to those in <Process 1A-5> can be used.

If a group represented by the formula $R^{9b}$ has amino or hydroxyl as a substituent group, or if $Y^1$ is a group represented by the formula —NH—, they can be appropriately protected in any preceding process and deprotected in any succeeding process of this process.

[Production Method 4] An Alternative Method for Synthesizing Various Intermediates in Production Method 3-C

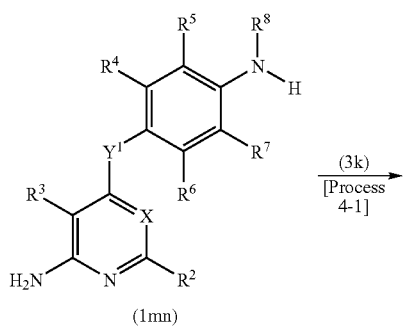

(1mn)

[Process 4-1]

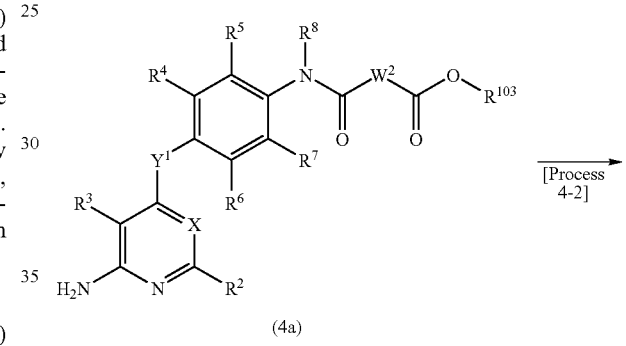

(4a)

[Process 4-2]

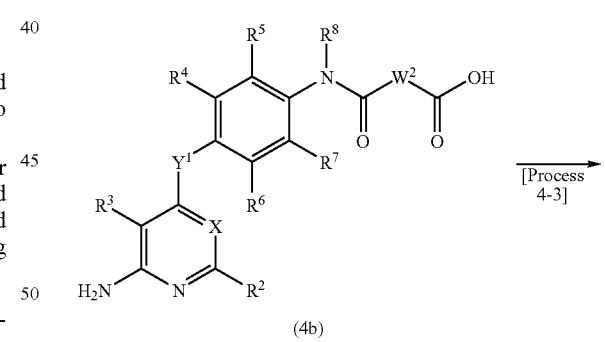

(4b)

[Process 4-3]

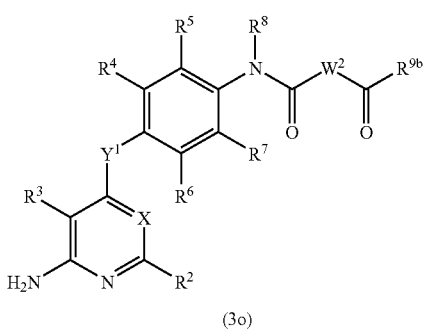

(3o)

-continued
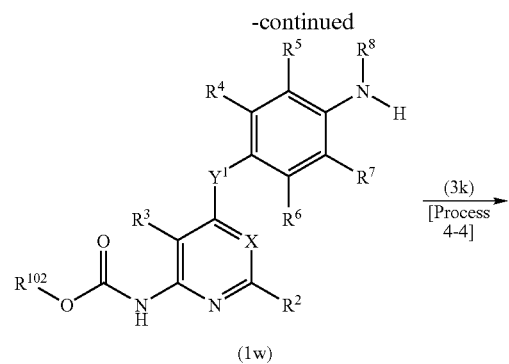
(1w)
→ (3k) [Process 4-4]
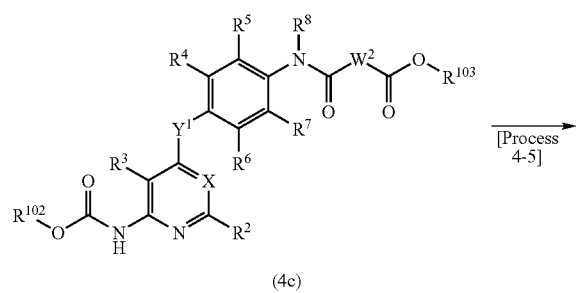
(4c)
→ [Process 4-5]
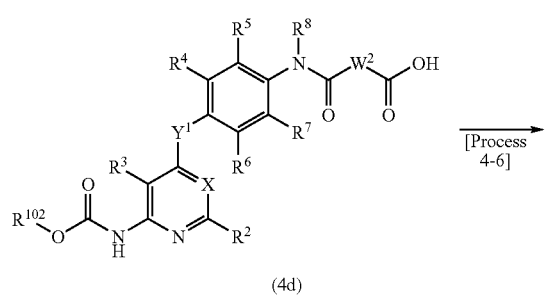
(4d)
→ [Process 4-6]
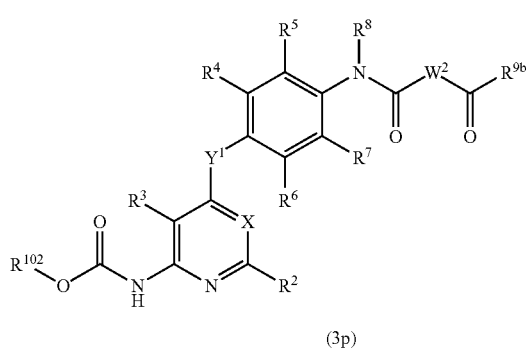
(3p)
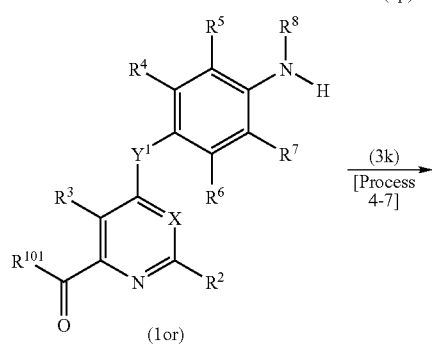
(1or)
→ (3k) [Process 4-7]
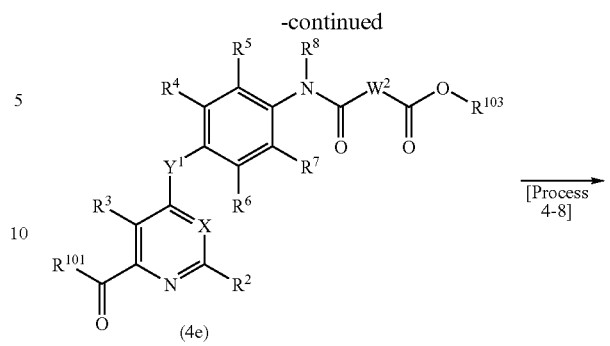
(4e)
→ [Process 4-8]
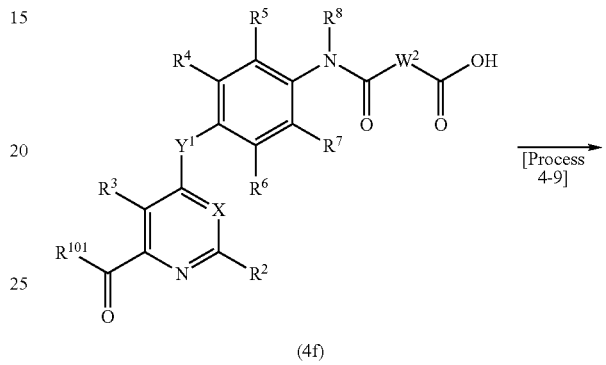
(4f)
→ [Process 4-9]
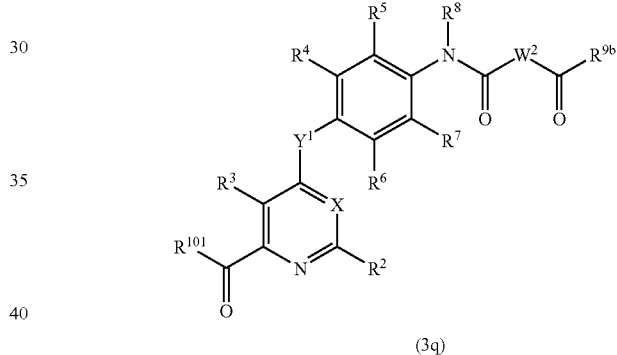
(3q)
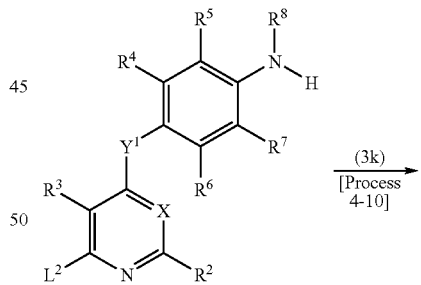
(2f)
→ (3k) [Process 4-10]
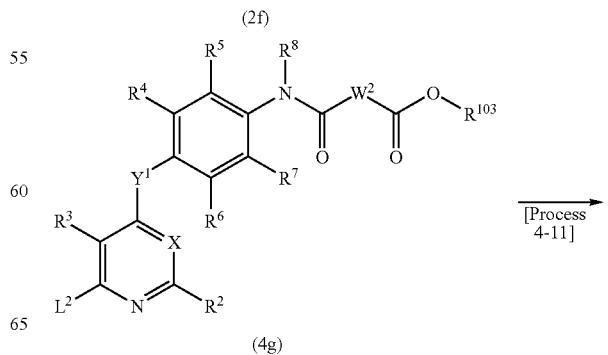
(4g)
→ [Process 4-11]

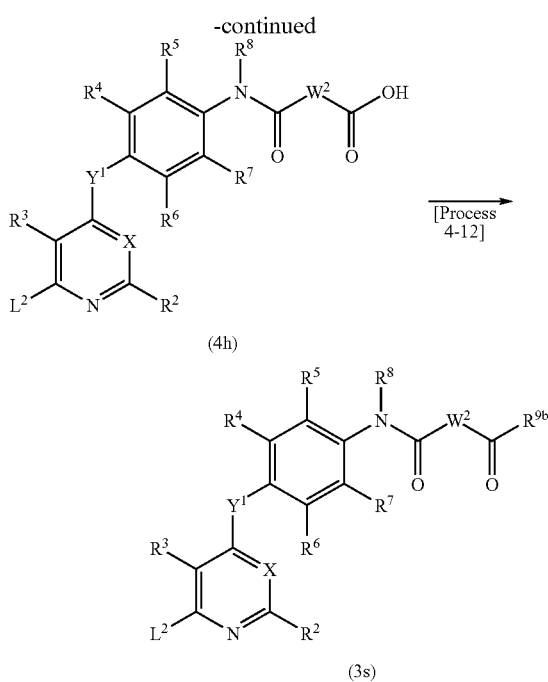

In the scheme, the symbols represent the same meanings as defined above.

<Process 4-1> <Process 4-4> <Process 4-7> <Process 4-10>

These processes are processes for condensing the compound (1mn), (1w), (1or) or (2f) with the compound (3k) to produce the compound (4a), (4c), (4e) or (4g), respectively. The method similar to those in <Process 3C-4> can be used.

<Process 4-2> <Process 4-5> <Process 4-8> <Process 4-11>

These processes are processes for producing the compound (4b), (4d), (4f) or (4h) from the compound (4a), (4c), (4e) or (4g), respectively. The methods similar to those in <Process 1A-1> can be used. But in <Process 4-5> and <Process 4-8> deprotection is carried out under such a condition that the protecting group of amino or carboxyl at 2-position of pyridine may not be deprotected. Specifically, for example, if $R^{101}$ or $R^{102}$ is $C_{1-6}$ alkyl or 2-(trimethylsilyl)ethyl and $R^{103}$ is benzyl, then catalytic hydrogenation can be carried out to produce the compound (4d) or (4f).

<Process 4-3> <Process 4-6> <Process 4-9> <Process 4-12>

These processes are processes for condensing the compound (4b), (4d), (4f) or (4h) with an amine represented by the formula $R^{9b}$—H or a salt thereof to produce the compound (3o), (3p), (3q) or (3s), respectively. The method similar to those in <Process 3C-1> can be used.

[Production Method 5]

A Method for Producing an Intermediate (5f)

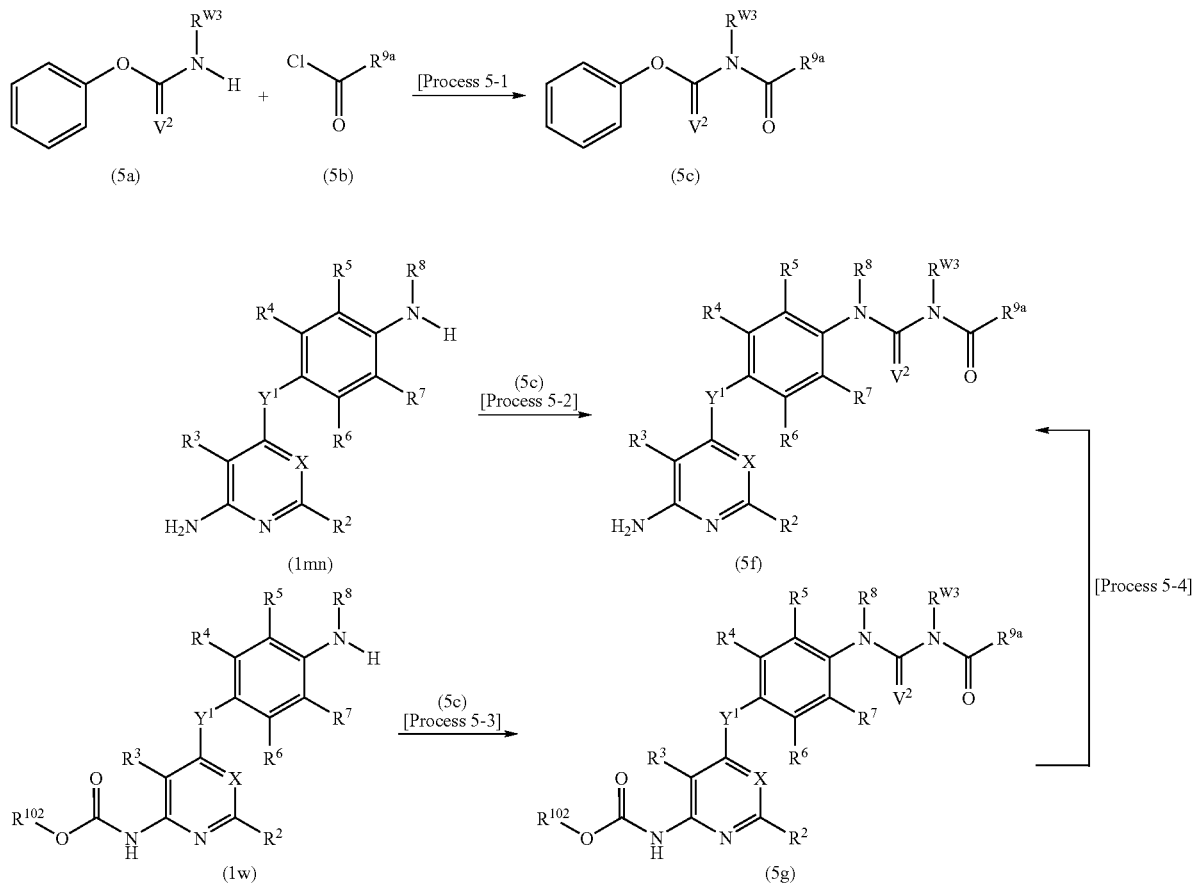

In the scheme, $R^{W3}$ represents hydrogen or $C_{1-6}$ alkyl, and the other symbols represent the same meanings as defined above.

The compound (5a) can be produced from an amine represented by the formula $R^{W3}$—NH with phenyl chloroformate or phenyl chlorothionoformate according to a method described in WO 02/32872 (Production method 16, Production example 316-1 or Production example 316-2), or a method described in J. Org. Chem., 2000, 65(19), 6237. As the amine represented by the formula $R^{W3}$—NH, commercially available compounds can be used.

The compound (5b) can be produced by a reaction of a carboxylic acid represented by the formula $R^{9a}$—C(=O)—OH with thionyl chloride or the like. For the carboxylic acid represented by the formula $R^{9a}$—C(=O)—OH, commercially available compounds can be used.

hydride, pyridine and triethylamine also may be used. The reaction temperature is between 0° C. and a reflux temperature. The reaction time is between 10 minutes and 30 hours.

If a group represented by the formula $R^{9a}$ has amino or hydroxyl as a substituent group, or if $Y^1$ is a group represented by the formula —NH—, they can be appropriately protected in any preceding process and deprotected in any succeeding process of this process, respectively.

<Process 5-4>

The process is a process for deprotecting the compound (5g) to produce the compound (5f). The methods similar to those in <Process 1A-5> can be used.

[Production Method 6] A Method for Producing an Intermediate (6c)

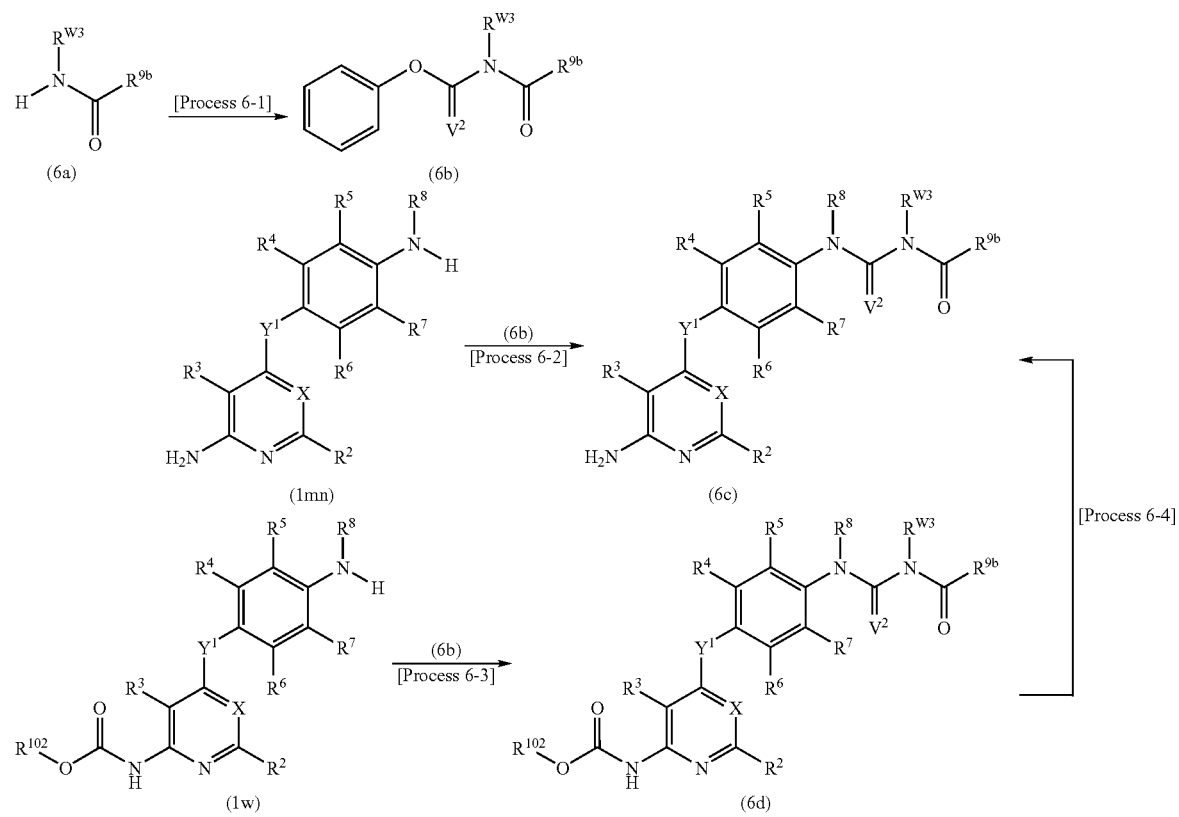

<Process 5-1> The process is a process for producing the compound (5c) from the compound (5a) by acylation using the compound (5b). As the solvent, tetrahydrofuran, benzene, toluene, xylene, chlorobenzene or the like can be used. A base such as sodium hydride, pyridine and triethylamine also may be used. The reaction temperature is between 0° C. and a reflux temperature. The reaction time is between 10 minutes and 30 hours.

<Process 5-2> <Process 5-3>

These processes are processes for producing the compound (5f) or (5g) by reacting the compound (1mn) or (1w) with the compound (5c), respectively. As the solvent, N,N-dimethylformamide, dimethylsulfoxide, N-methylpyrrolidone, tetrahydrofuran or the like can be used. A base such as sodium In the scheme, the symbols represent the same meanings as defined above.

The compound (6a) can be obtained by an urea formation reaction of an amine represented by the formula $R^{W3}$—NH and an amine represented by the formula $R^{9b}$—H. The compound can be produced according to a method described in Synthesis, 1189 (1997). As the amine represented by the formula $R^{W3}$—NH and the amine represented by the formula $R^{9b}$—H, commercially available compounds can be used.

<Process 6-1>

The process is a process for producing the compound (6b) from the compound (6a). As the reagent, phenyl chloroformate or phenyl chlorothionoformate is used. As the solvent, tetrahydrofuran, benzene, toluene, xylene, chlorobenzene or the like can be used. A base such as sodium hydride, pyridine and triethylamine also may be used. The reaction temperature is between 0° C. and a reflux temperature. The reaction time is between 10 minutes and 30 hours.

<Process 6-2> <Process 6-3>

These processes are processes for reacting the compound (1mn) or (1w) with the compound (6b) to produce the compound (6c) or (6d), respectively. As the solvent, N,N-dimethylformamide, dimethylsulfoxide, N-methylpyrrolidone, tetrahydrofuran or the like can be used. A base such as sodium hydride, pyridine and triethylamine also may be used. The reaction temperature is between 0° C. and a reflux temperature. The reaction time is between 10 minutes and 30 hours.

If a group represented by the formula $R^{9b}$ has amino or hydroxyl as a substituent group, or if $Y^1$ is a group represented by the formula —NH—, they can be appropriately protected in any preceding process and deprotected in any succeeding process of the process, respectively.

<Process 6-4>

The process is a process for deprotecting the compound (6d) to produce the compound (6c). The methods similar to those in <Process 1A-5> can be used.

[Production Method 7] A Method for Producing an Intermediate Represented by the Formula (XII)

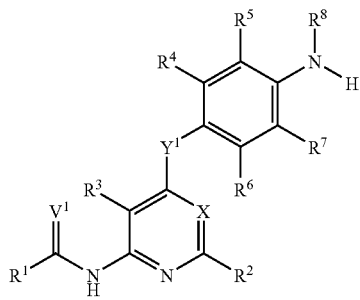

(XII)

In the formula, the symbols represent the same meanings as defined above.

[Production Method 7-A] A Method for Producing an Intermediate (7e), Which is an Intermediate Represented by the Formula (XII), Wherein $R^1$ is $R^{1a}$.

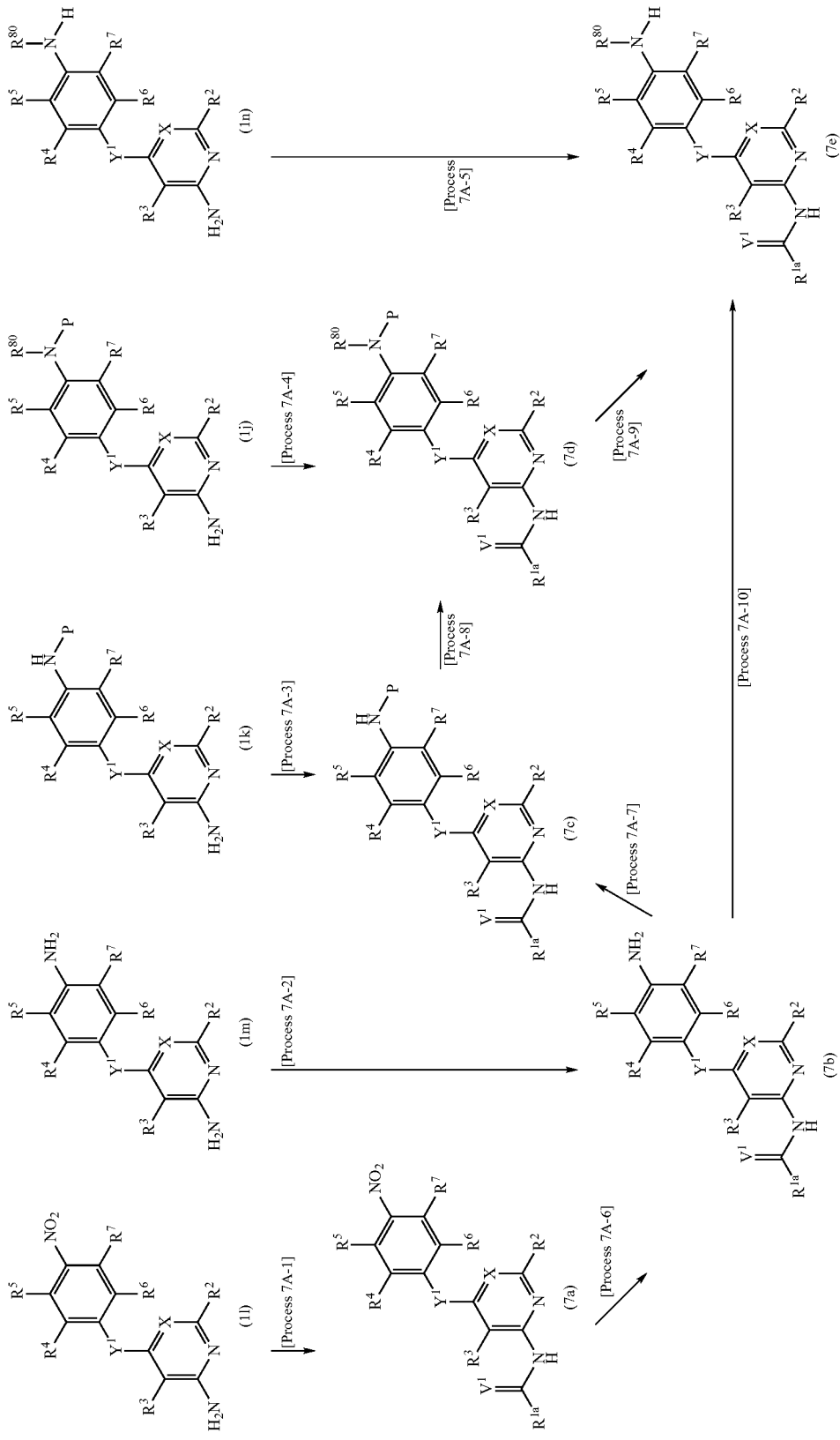

In the scheme, $R^{1a}$ represents 3- to 10-membered non-aromatic heterocyclic group (limited to a group having nitrogen as a ring constituent atom, and the nitrogen having a bonding hand), or a group represented by the formula —$NR^{11a}R^{11b}$, wherein $R^{11a}$ and $R^{11b}$ each represents the same meaning as defined above, and $R^{1a}$ may be substituted with a substituent selected from Substituent Group A or Substituent Group B, and if $R^{1a}$ has hydroxyl, primary amino or secondary amino as a substituent group, the group may be protected by a suitable protecting group; and the other symbols represent the same meanings as defined above.

<Process 7A-1> <Process 7A-2> <Process 7A-3> <Process 7A-4> <Process 7A-5>

These processes are processes for producing the compound (7a), (7b), (7c), (7d) or (7e) from the compound (1l), (1m), (1k), (1j) or (1n), respectively. For example, a method wherein the compound (1l), (1m), (1k), (1j) or (1n) is converted to a carbamic acid ester or carbamic acid thioester derivative using a compound represented by the formula Ar—OC(=O)—Cl, wherein Ar represents a phenyl group optionally substituted with one or two substituent(s) selected from halogen, methyl, methoxy and nitro, or a compound represented by the formula Ar—OC(=S)—Cl, wherein Ar represents the same meaning as defined above, followed by reacting with an amine can be used. Alternatively, the compound (1l), (1m), (1k), (1j) or (1n) can be reacted with a carbamate derivative, a thiocarbamate derivative, an isocyanate derivative or an isothiocyanate derivative to convert to a corresponding urea derivative or thiourea derivative. As the solvent, chloroform, toluene, N-methylpyrrolidone, N,N-dimethylformamide, dimethylsulfoxide, chlorobenzene or the like can be used. A mixed solvent of the above solvent and water also can be used. A base also can be used. Specifically, an organic base such as pyridine, triethylamine and diisopropylethylamine, and an inorganic base such as potassium carbonate, cesium carbonate, sodium hydride and sodium hydroxide can be used. The reaction temperature is between 0° C. and a reflux temperature. The reaction time is between 10 minutes and 30 hours.

After the process, in order to convert substituent groups on $R^{1a}$, generally used reactions such as oxidation, reduction, esterification, amidation, introduction of protecting groups, deprotection and hydrolysis can also be carried out in a suitable succeeding process. Specifically, for example, the method includes a method wherein the compound (1l), (1k) or (1j) is reacted with a ketone or aldehyde-containing amine, followed by reductive amination with an amine to introduce an amine side chain on $R^{1a}$. As the reducing agent, sodium cyanoborohydride and sodium triacetoxyborohydride or the like can be used. As the solvent, methanol, tetrahydrofuran, dichloromethane, dichloroethane or the like can be used. Furthermore, the compound (1l), (1k) or (1j) can be reacted with an ester-containing amine to produce a compound, an ester portion of which is then hydrolyzed with a base such as lithium hydroxide, sodium hydroxide and potassium hydroxide in hydrous ethanol, followed by converting with a condensing agent to an amide derivative. As the solvent, N,N-dimethylformamide, tetrahydrofuran or the like can be used. As the condensing agent, 1-ethyl-3-(3-dimethylaminopropyl) carbodiimide hydrochloride and (1H-1,2,3-benzotriazol-1-yloxy)(tri(dimethylamino))phosphonium hexafluorophosphate can be used. The reaction temperature is between 0° C. and a reflux temperature. The reaction time is between 10 minutes and 30 hours.

<Process 7A-6>

The process is a process for reducing the compound (7a) to produce the compound (7b). The methods similar to those in <Process 1A-11> can be used.

<Process 7A-7>

The process is a process for protecting amino of the compound (7b) to produce the compound (7c). The methods similar to those in <Process 1B-6> can be used.

<Process 7A-8>

The process is a process for alkylating the compound (7c) to produce the compound (7d). The methods similar to those in <Process 1A-13> can be used.

<Process 7A-9>

The process is a process for deprotecting the compound (7d) to produce the compound (7e). The methods similar to those in <Process 1A-5> can be used.

<Process 7A-10>

The process is a process for alkylating the compound (7b) to produce the compound (7e). The methods similar to those in <Process 1A-12> can be used.

[Production Method 7-B] A Method for Producing an Intermediate (7j), Which is an Intermediate Represented by the Formula (XII), Wherein $R^1$ is $R^{1b}$

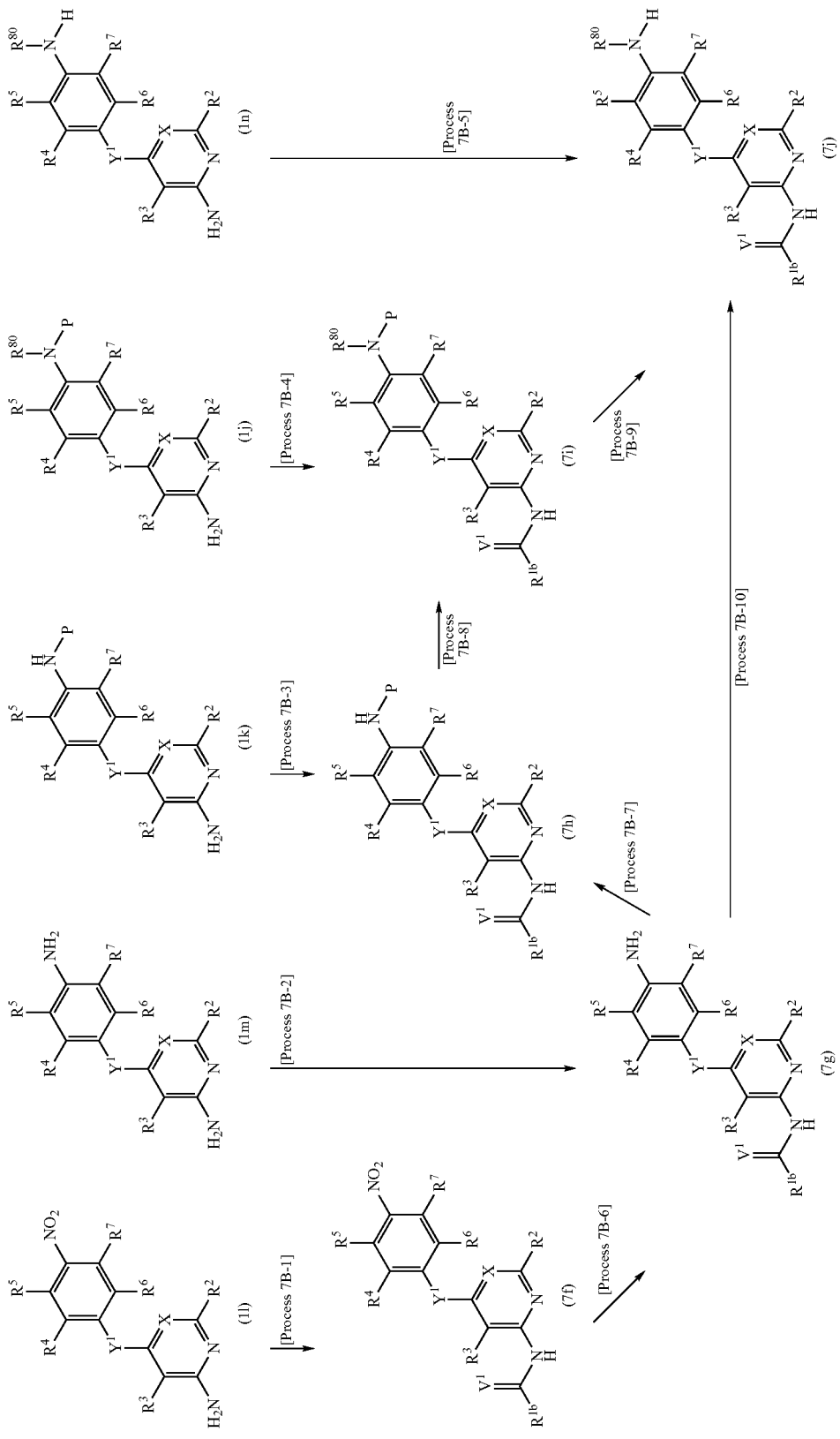

In the scheme, $R^{1b}$ represents $C_{1-6}$ alkyl, $C_{2-6}$ alkenyl, $C_{2-6}$ alkynyl, $C_{3-10}$ cycloalkyl, $C_{6-10}$ aryl, $C_{3-10}$ cycloalkyl-$C_{1-6}$ alkyl, $C_{6-10}$ aryl-$C_{1-6}$ alkyl, 5- to 10-membered heteroaryl, a 3- to 10-membered non-aromatic heterocyclic group (limited to the group having a bonding hand from a carbon forming the ring), 5- to 10-membered heteroaryl-$C_{1-6}$ alkyl, and 3- to 10-membered non-aromatic heterocyclic-$C_{1-6}$ alkyl, and $R^{1b}$ may be substituted with a substituent selected from Substituent Group A or Substituent Group B, and if $R^{1b}$ has a hydroxyl, or primary or secondary amino substituent group, the substituent group may be protected by a suitable protecting group; and the other symbols represent the same meanings as defined above.

<Process 7B-1> <Process 7B-2> <Process 7B-3> <Process 7B-4> <Process 7B-5>

These processes are processes for producing the compound (7f), (7g), (7h), (7i) or (7j) from the compound (1l), (1m), (1k), (1j) or (1n), respectively. Specifically, a method wherein the compound (1l), (1m), (1k), (1j) or (1n) is reacted with an acyl halide, a carboxylic anhydride or a thioacyl halide, or a method wherein the compound (1l), (1m), (1k), (1j) or (1n) is reacted with a carboxylic acid in the presence of a condensing agent such as (1H-1,2,3-benzotriazol-1-yloxy)(tri(dimethylamino))phosphonium hexafluorophosphate can be used to produce the compound (7f), (7g), (7h), (7i) or (7j), respectively. Furthermore, in order to obtain a thioamide derivative, an amide derivative can be synthesized, followed by converting with the Lawesson's reagent (Org. Synth., 1990, VII, 372; J. Org. Chem., 1990, 55(14), 4484) to the thioamide. As the solvent, tetrahydrofuran, chloroform, toluene, N-methylpyrrolidone, N,N-dimethylformamide, dimethylsulfoxide, chlorobenzene or the like can be used. A base also can be used, specifically, for example, an organic base such as pyridine, triethylamine and diisopropylethylamine, and an inorganic base such as potassium carbonate, cesium carbonate and sodium hydride can be used. The reaction temperature is between 0° C. and a reflux temperature. The reaction time is between 10 minutes and 30 hours.

After the process, in order to convert substituent groups on $R^{1b}$, generally used reactions such as oxidation, reduction, esterification, amidation, introduction of protecting groups, deprotection and hydrolysis can also be carried out in a suitable succeeding process, as described in <Process 7A-1> of the above [Production method 7-A].

<Process 7B-6>

The process is a process for reducing the compound (7f) to produce the compound (7g). The methods similar to those in <Process 1A-11> can be used.

<Process 7B-7>

The process is a process for protecting amino of the compound (7g) to produce the compound (7h). The methods similar to those in <Process 1B-6> can be used.

<Process 7B-8>

The process is a process for alkylating the compound (7h) to produce the compound (7i). The methods similar to those in <Process 1A-13> can be used.

<Process 7B-9>

The process is a process for deprotecting the compound (7i) to produce the compound (7j). The methods similar to those in <Process 1A-5> can be used.

<Process 7B-10>

The process is a process for alkylating the compound (7g) to produce the compound (7j). The methods similar to those in <Process 1A-12> can be used.

[Production Method 7-C] A Method for Producing an Intermediate (7o), Which is an Intermediate Represented by the Formula (XII), Wherein $R^1$ is $R^{1c}$

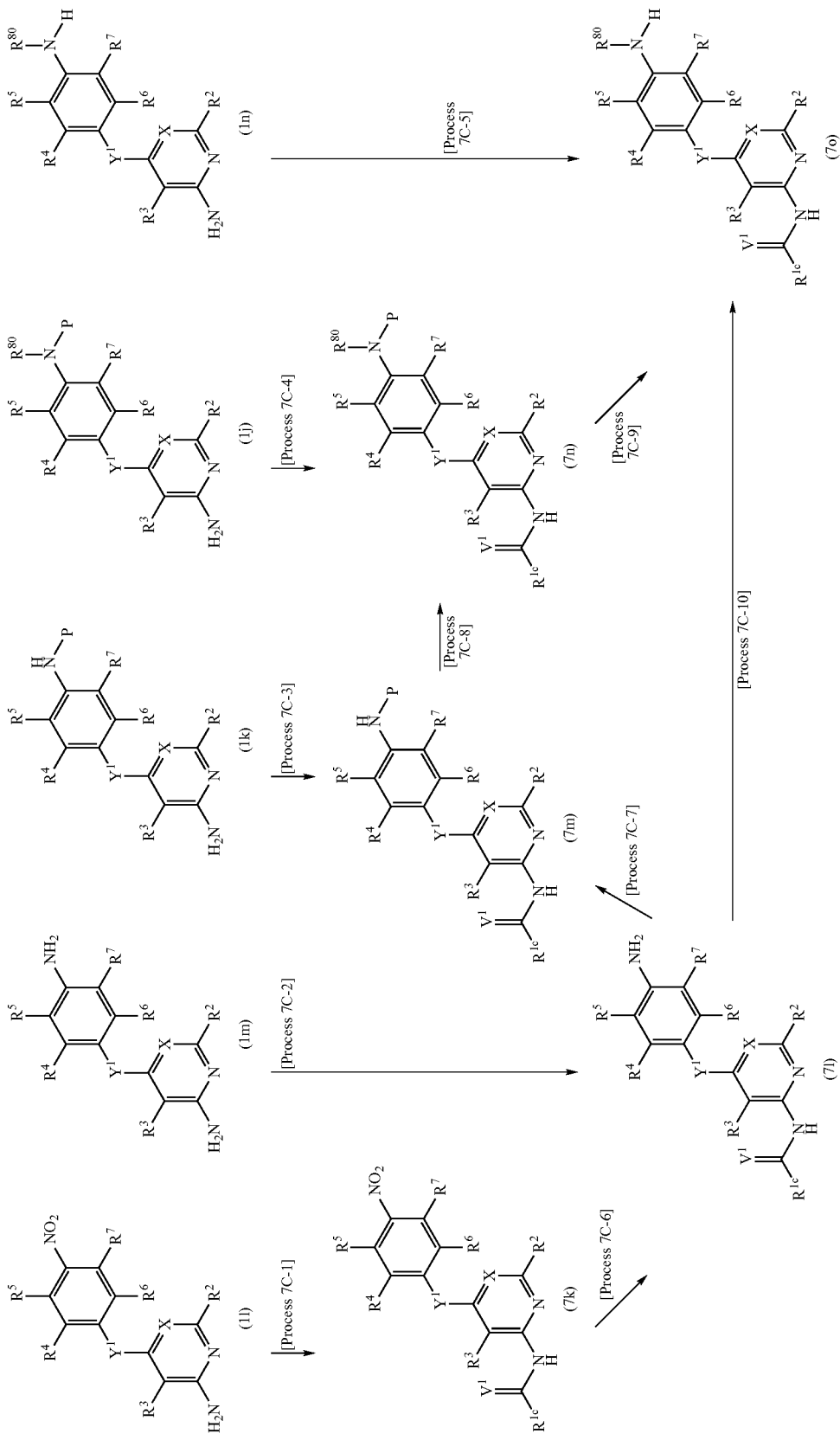

In the scheme, $R^{1c}$ represents $C_{1-6}$ alkoxy, and $R^{1c}$ may be substituted with a substituent selected from Substituent Group A or Substituent Group B, and if $R^{1c}$ has a hydroxyl, or primary or secondary amino substituent group, the substituent group may be protected by a suitable protecting group; and the other symbols represent the same meanings as defined above.

<Process 7C-1> <Process 7C-2> <Process 7C-3> <Process 7C-4> <Process 7C-5>

These processes are processes for producing the compound (7k), (7l), (7m), (7n) or (7o) from the compound (1l), (1m), (1k), (1j) or (1n), respectively. The compound (1l), (1m), (1k), (1j) or (1n) can be reacted with a chlorocarbonic acid ester, a chlorocarbonic acid thioester, a dialkyl dicarbonate or the like to produce the compound (7k), (7l), (7m), (7n) or (7o). A base also can be used, that is, an organic base such as pyridine, triethylamine and diisopropylethylamine, and an inorganic base such as potassium carbonate, cesium carbonate and sodium hydroxide can be used. As the solvent, tetrahydrofuran, chloroform, dichloroethane, N,N-dimethylformamide, dimethyl sulfoxide, chlorobenzene or the like can be used. A mixed solvent of the above solvent and water also can be used. The reaction temperature is between 0° C. and a reflux temperature. The reaction time is between 10 minutes and 30 hours.

After the process, in order to convert substituent groups on $R^{1c}$, generally used reactions such as oxidation, reduction, esterification, amidation, introduction of protecting groups, deprotection and hydrolysis can also be carried out in a suitable succeeding process, as described in <Process 7A-1> of the above [Production method 7-A].

<Process 7C-6>
The process is a process for reducing the compound (7k) to produce the compound (7l). The methods similar to those in <Process 1A-11> can be used.

<Process 7C-7>
The process is a process for protecting amino of the compound (7l) to produce the compound (7m). The methods similar to those in <Process 1B-6> can be used.

<Process 7C-8>
The process is a process for alkylating the compound (7m) to produce the compound (7n). The methods similar to those in <Process 1A-13> can be used.

<Process 7C-9>
The process is a process for deprotecting the compound (7n) to produce the compound (7o). The methods similar to those in <Process 1A-5> can be used.

<Process 7C-10>
The process is a process for alkylating the compound (7l) to produce the compound (7o). The methods similar to those in <Process 1A-12> can be used.

[Production Method 8] A Method for Producing the Compound of the Present Invention Represented by the Formula (I)

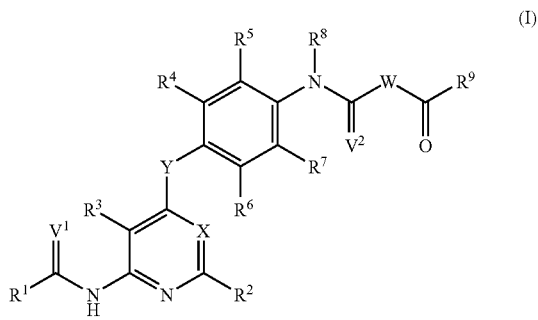

In the formula, the symbols represent the same meanings as defined above.

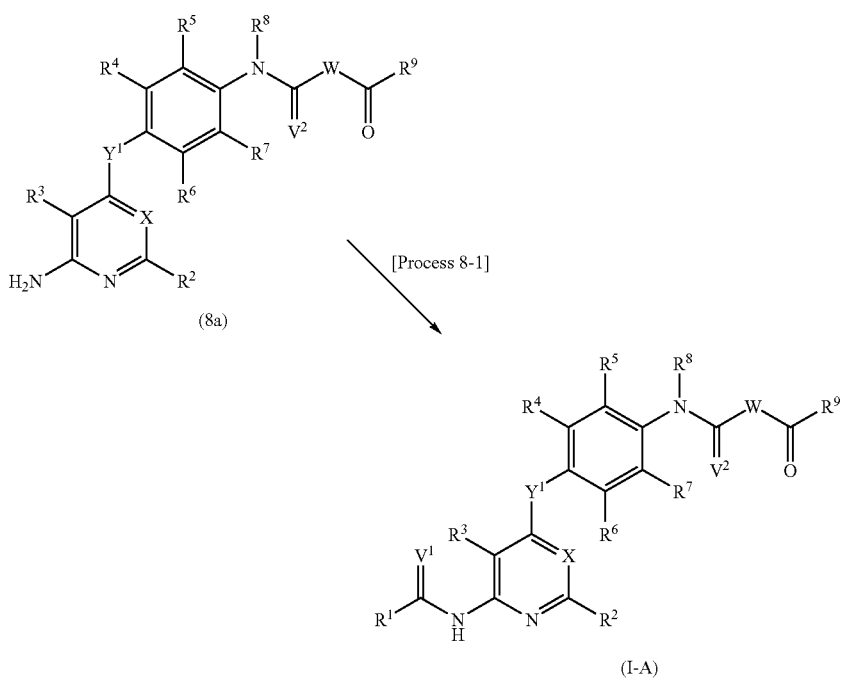

-continued

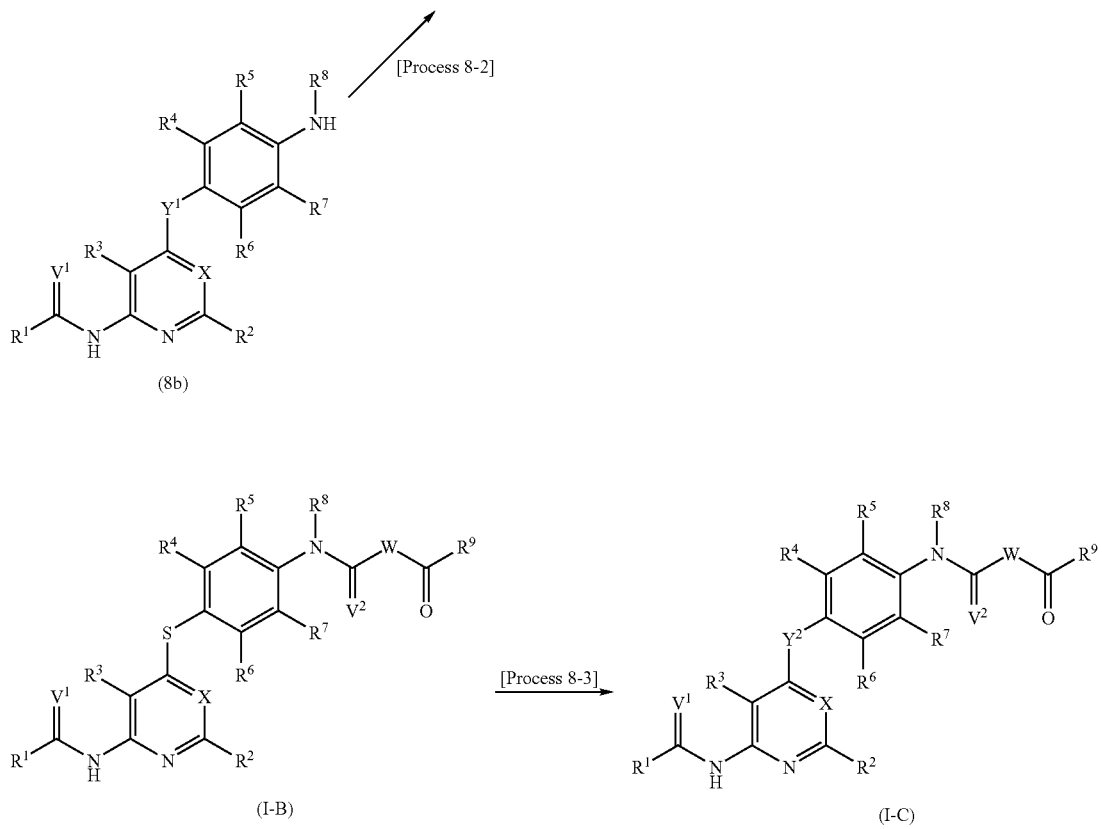

In the scheme, $Y^2$ represents sulfinyl or sulfonyl; and the other symbols represent the same meanings as defined above.

<Process 8-1>

The process is a process for producing the compound (I-A) of the present invention from the compound (8a), that is, the above intermediate (XI).

(1) When $R^1$ or $R^9$ does not contain hydroxyl, primary or secondary amino, and when Y is a group except a group represented by the formula —NH—:

(Method 1) Using a compound represented by the formula Ar—OC(=O)—Cl, wherein Ar represents the same meaning as defined above, a compound represented by the formula Ar—OC(=S)—Cl, wherein Ar represents the same meaning as defined above, or the like, the compound (8a) can be converted to a carbamic acid ester derivative or a carbamic acid thioester derivative, which is then reacted with an amine to produce the compound (I-A) of the present invention. Alternatively, the compound (8a) can be reacted with a carbamate derivative, a thiocarbamate derivative, an isocyanate derivative or an isothiocyanate derivative to convert to the compound (I-A) of the present invention. As the solvent, chloroform, toluene, N-methylpyrrolidone, N,N-dimethylformamide, dimethyl sulfoxide, chlorobenzene or the like can be used. A mixed solvent of the above solvent and water also can be used. A base also can be used, and specifically, an organic base such as pyridine, triethylamine and diisopropylethylamine, and an inorganic base such as potassium carbonate, cesium carbonate, sodium hydride and sodium hydroxide can be used. The reaction temperature is between 0° C. and a reflux temperature. The reaction time is between 10 minutes and 30 hours.

(Method 2) The compound (8a) can be reacted with an acyl halide, a carboxylic anhydride, a thioacyl halide or the like to produce the compound (I-A) of the present invention. Alternatively, the compound (8a) can be reacted with a carboxylic acid in the presence of a condensing agent such as (1H-1,2,3-benzotriazol-1-yloxy)(tri(dimethylamino))phosphonium hexafluorophosphate to produce the compound (I-A) of the present invention. As the solvent, tetrahydrofuran, chloroform, toluene, N-methylpyrrolidone, N,N-dimethylformamide, dimethyl sulfoxide, chlorobenzene or the like can be used. A base also can be used, and specifically, an organic base such as pyridine, triethylamine and diisopropylethylamine, and an inorganic base such as potassium carbonate, cesium carbonate and sodium hydride can be used. The reaction temperature is between 0° C. and a reflux temperature. The reaction time is between 10 minutes and 30 hours.

(Method 3)

The compound (8a) can be reacted with a chlorocarbonic acid ester, a chlorocarbonic acid thioester or a dialkyldicarbonate to produce the compound (I-A) of the present invention. A base also can be used, that is, an organic base such as pyridine, triethylamine and diisopropylethylamine, and an inorganic base such as potassium carbonate, cesium carbonate and sodium hydroxide can be used. As the solvent, tetrahydrofuran, chloroform, dichloroethane, N,N-dimethylformamide, dimethyl sulfoxide, chlorobenzene or the like can be used. A mixed solvent of the above solvent and water also can be used. The reaction temperature is between 0° C. and a reflux temperature. The reaction time is between 10 minutes and 30 hours.

(2) When $R^1$ or $R^9$ contains hydroxyl, primary or secondary amino, or when $Y^1$ is a group represented by the formula —NH—:

After these substituents are suitably protected, the above reaction can be carried out followed by deprotecting suitably to produce the compound (I-A) of the present invention.

(3) After the process, in order to convert substituent groups on $R^1$ or $R^9$, generally used reactions such as oxidation, reduction, esterification, amidation, protection, deprotection and hydrolysis can also be carried out in a suitable succeeding process, as described in <Process 7A-1> of the above [Production method 7-A].

<Process 8-2>

The process is a process for producing the compound (I-A) of the present invention from the compound (8b), that is, the above intermediate (XII).

(1) When $R^1$ or $R^9$ does not contain hydroxyl, primary or secondary amino, and when Y is a group except a group represented by the formula —NH—:

(Method 1)
The compound (8b) can be reacted with an acyl isothiocyanate to produce the compound (I-A) of the present invention. In the reaction system, an acid such as camphor sulfonic acid can also be added. As the solvent, a mixed solvent of toluene-methanol, a mixed solvent of toluene-ethanol, acetonitrile, N,N-dimethylformamide, tetrahydrofuran or the like can be used. The reaction temperature is between room temperature and a reflux temperature. The reaction time is between 10 minutes and 30 hours.

(Method 2)
The compound (8b) can be reacted with an acyl isocyanate to produce the compound (I-A) of the present invention. As the solvent, N,N-dimethylformamide, tetrahydrofuran or the like can be used. The reaction temperature is between 0° C. and a reflux temperature. The reaction time is between 10 minutes and 30 hours.

(Method 3)
The compound (8b) can be condensed with the compound (3n) to produce the compound (I-A) of the present invention. As a condensing agent, 1-ethyl-3-(3-dimethylaminopropyl) carbodiimide hydrochloride, (1H-1,2,3-benzotriazol-1-yloxy)(tri(dimethylamino))phosphonium hexafluorophosphate or the like can be used. An organic base such as triethylamine also can be used. The reaction temperature is between 0° C. and a reflux temperature. The reaction time is between 10 minutes and 30 hours.

(Method 4)
The compound (8b) can be reacted with N-(chlorocarbonyl) isocyanate or phenyl isocyanateformate, and then reacted with an amine to provide the compound (I-A) of the present invention. A base such as diisopropylamine and triethylamine also may be used. As the solvent, dichloromethane, dichloroethane, tetrahydrofuran or the like can be used. The reaction temperature is between 0° C. and a reflux temperature. The reaction time is between 10 minutes and 30 hours.

(Method 5)
The compound (8b) can be reacted with the compound (6b) to produce the compound (I-A) of the present invention. As the solvent, N,N-dimethylformamide, dimethyl sulfoxide, N-methylpyrrolidone, tetrahydrofuran or the like can be used. A base such as sodium hydride, pyridine and triethylamine also may be suitably used. The reaction temperature is between 0° C. and a reflux temperature. The reaction time is between 10 minutes and 30 hours.

(Method 6) When $R^1$, $R^9$ or $R^{10}$ does not contain alkoxycarbonyl:

The compound (8b) can be condensed with the compound (3k), $R^{103}$ of the resultant compound is then deprotected, followed by condensing with an amine or a salt thereof to produce the compound (I-A) of the present invention.

In condensation of the compound (8b) with the compound (3k), as the condensing agent, 1-ethyl-3-(3-dimethylaminopropyl) carbodiimide hydrochloride, (1H-1,2,3-benzotriazol-1-yloxy)(tri(dimethylamino))phosphonium hexafluorophosphate or the like can be used. A base such as triethylamine can also be suitably used. As the solvent, tetrahydrofuran, N,N-dimethylformamide or the like can be used. The reaction temperature is between 0° C. and a reflux temperature. The reaction time is between 10 minutes and 30 hours.

For the deprotection of $R^{103}$, hydrolysis using a base or the like can be used.

In condensation with an amine or a salt thereof, general condensation of a carboxylic acid with an amine can be used. Specifically for example, as the solvent, N,N-dimethylformamide and tetrahydrofuran can be used, and as the condensing agent, carbonyl diimidazole, dicyclohexyl carbodiimide, 1-ethyl-3-(3-dimethylaminopropyl)carbodiimide hydrochloride and (1H-1,2,3-benzotriazol-1-yloxy)(tri(dimethylamino))phosphonium hexafluorophosphate can be used. A base such as triethylamine can also be suitably used. The reaction temperature is between 0° C. and a reflux temperature. The reaction time is between 10 minutes and 30 hours.

(2) When $R^1$ or $R^9$ contains hydroxyl, primary or secondary amino, or when $Y^1$ is a group represented by the formula —NH—:

After the substituent is protected if necessary, the above reaction can be carried out, followed by deprotecting suitably to produce the compound (I-A) of the present invention.

(3) After the process, in order to convert substituent groups on $R^1$ or $R^9$, generally used reactions such as oxidation, reduction, esterification, amidation, protection, deprotection and hydrolysis can also be carried out, as described in <Process 7A-1> of the above [Production method 7-A].

<Process 8-3>

The process is a process for oxidation of the compound (I-B) of the present invention to the compound (I-C) of the present invention. As the oxidizing agent, hydrogen peroxide, peracetic acid, metaperiodic acid salt, 3-chloroperbenzoic acid or the like can be used. As the solvent, methanol, water, dichloromethane, chloroform or the like can be used. The reaction temperature is between 0° C. and a reflux temperature. The reaction time is between 10 minutes and 30 hours.

[Production Method 9] A Method for Producing an Intermediate (1d), Wherein X is a Group Represented by the Formula —C($R^{10b}$)=

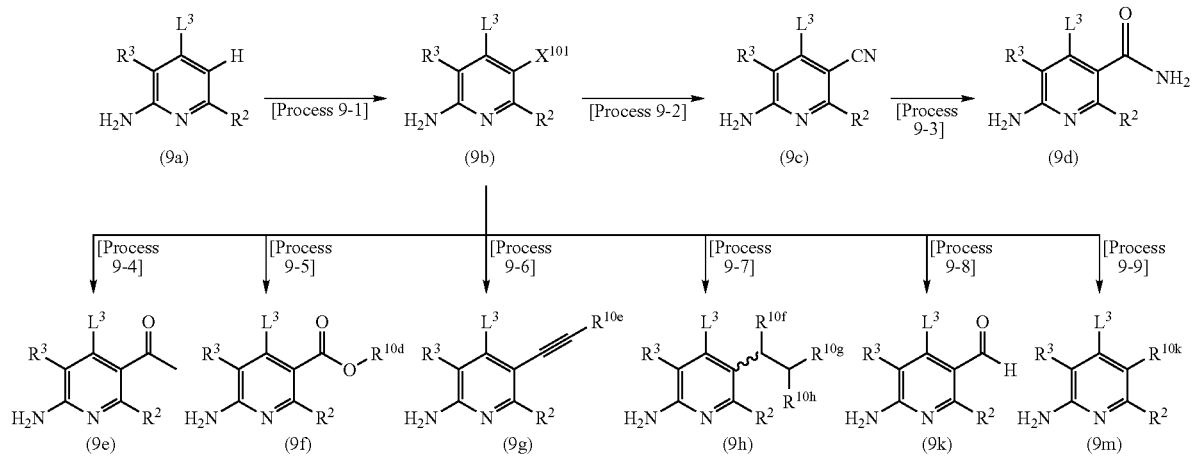

In the scheme, $L^3$ represents chlorine or bromine; $X^{101}$ represents chlorine, bromine or iodine; $R^{10b}$ represents halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as defined above; $R^{10d}$ represents $C_{1-6}$ alkyl; $R^{10e}$ represents hydrogen or $C_{1-4}$ alkyl; $R^{10f}$, $R^{10g}$ and $R^{10h}$ may be the same or different and each represents hydrogen or $C_{1-4}$ alkyl, with the proviso that the total carbon number of $R^{10f}$, $R^{10g}$ and $R^{10h}$ is 0 or more to 4 or less; $R^{10k}$ represents $C_{1-6}$ alkyl; and the other symbols represent the same meanings as defined above.

<Process 9-1>

The process is a process for chlorinating, brominating or iodinating the 5-position of the compound (9a) to produce the compound (9b). For example, a halogenating agent such as iodine, N-iodosuccinimide, bromine, N-bromosuccinimide and N-chlorosuccinimide can be used. As the solvent, for example, N,N-dimethylformamide, dimethyl sulfoxide, dichloromethane and acetonitrile can be used. The reaction temperature is between 0° C. and a reflux temperature. The reaction time is between 10 minutes and 48 hours.

<Process 9-2>

The process is a process for converting $X^{101}$ of the compound (9b) to cyano to produce the compound (9c). Concerning the combination of $L^3$ and $X^{101}$ upon cyanation, $X^{101}$ is preferably iodine or bromine when $L^3$ is chlorine, and $X^{101}$ is preferably iodine when $L^3$ is bromine. For example, in the presence of a palladium catalyst such as tetrakis (triphenylphosphine)palladium(0) and dichlorobis (triphenylphosphine)palladium(II), 0.5-0.6 equivalent of zinc cyanide is used relative to the compound (9b), or 1.0-1.2 equivalent of potassium cyanide or trimethylsilyl cyanide is used relative to the compound (9b). As the solvent, for example, N,N-dimethylformamide, dioxane or tetrahydrofuran can be used. The reaction temperature is between room temperature and a reflux temperature. The reaction time is between 10 minutes and 10 hours.

<Process 9-3>

The process is a process for producing the compound (9d) from the compound (9c). Hydrolysis using an inorganic base such as potassium carbonate and a hydrogen peroxide can be used. As the solvent, dimethyl sulfoxide or the like can be used. The reaction temperature is between 0° C. and a reflux temperature. The reaction time is between 10 minutes and 10 hours. A method of heating under reflux in a solvent such as toluene and tetrahydrofuran in the presence of potassium trimethylsilanolate, as described in Tetrahedron Lett., 41, 3747 (2000), also can be used. The reaction time is between 10 minutes and 60 hours.

<Process 9-4>

The process is a process for producing the compound (9e) from the compound (9b). A method of reacting with (1-ethoxyvinyl)tributyltin in the presence of a palladium catalyst such as dichlorobis(triphenylphosphine)palladium(II) and tetrakis (triphenylphosphine)palladium(0) can be used. In the reaction system, a salt such as lithium chloride may be added. As the solvent, tetrahydrofuran, N,N-dimethylformamide, N-methylpyrrolidone or the like can be used. The reaction temperature is between room temperature and a reflux temperature. The reaction time is between 10 minutes and 60 hours.

As for a document that complements the above method, Tetrahedron, 53 (14), 5159 (1997) can be mentioned.

<Process 9-5>

The process is a process for producing the compound (9f) from the compound (9b). A method of reacting an alcohol represented by the formula $R^{10d}$—OH with carbon monoxide in the presence of a palladium catalyst such as dichlorobis (triphenylphosphine)palladium(II) can be used. In the reaction system, a base such as triethylamine and diisopropylethylamine may be added. As the solvent, an alcohol represented by the formula $R^{10a}$—OH, tetrahydrofuran, N,N-dimethylformamide, N-methylpyrrolidone, dimethyl sulfoxide or the like can be used. The reaction temperature is between room temperature and a reflux temperature. The reaction time is between 10 minutes and 60 hours.

As for a document that complements the above method, Tetrahedron Lett., 25 (51), 5939 (1984) can be mentioned.

<Process 9-6>

The process is a process for producing the compound (9g) from the compound (9b). The compound (9b) can be reacted with an acetylene derivative in the presence of a palladium catalyst such as dichlorobis(triphenylphosphine)palladium (II) to produce the compound (9g). In the reaction system, an organic base such as triethylamine or an inorganic base such as potassium carbonate and sodium hydroxide may be added. A monovalent copper halide may coexist. As the solvent, tetrahydrofuran, N,N-dimethylformamide, N-methylpyrrolidone, dioxane, 1,2-dimethoxyethane, toluene, benzene, acetonitrile or the like can be used. The reaction temperature is between room temperature and a reflux temperature. The reaction time is between 10 minutes and 60 hours.

<Process 9-7>

The process is a process for producing the compound (9h) from the compound (9b). The compound (9b) can be reacted with a trialkylvinyltin derivative in the presence of a palladium catalyst such as dichlorobis(triphenylphosphine)palladium(II) to produce the compound (9h). In the reaction system, hexamethylphosphoramide or the like may be added. As the solvent, tetrahydrofuran, N,N-dimethylformamide, N-methylpyrrolidone, dimethyl sulfoxide or the like can be used. The reaction temperature is between room temperature and a reflux temperature. The reaction time is between 10 minutes and 60 hours.

As for a document that complements the above method, Tetrahedron, 53 (14), 5159 (1997) can be mentioned.

<Process 9-8>

The process is a process for producing the compound (9k) from the compound (9b). A method of reacting with carbon monoxide in the presence of a palladium catalyst such as dichlorobis(triphenylphosphine)palladium(II), and sodium formate, as described in Bull. Chem. Soc. Jpn., 67 (8), 2329 (1994), can be used. As the solvent, tetrahydrofuran, N,N-dimethylformamide, N-methylpyrrolidone, dimethyl sulfoxide or the like can be used. The reaction temperature is between room temperature and a reflux temperature. The reaction time is between 10 minutes and 60 hours.

<Process 9-9>

The process is a process for producing the compound (9m) from the compound (9b). A method of reacting with a reagent prepared from alkyl magnesium halide and zinc(II)chloride in the presence of a palladium catalyst such as dichlorobis(triphenylphosphine)palladium(II), as described in J. Org. Chem., 2001, 66 (20), 605, can be used. As the solvent, tetrahydrofuran or the like can be used. The reaction temperature is between room temperature and a reflux temperature. The reaction time is between 10 minutes and 60 hours. Alternatively, a method of reacting with tetraalkyltin in the presence of a palladium catalyst such as dichlorobis(triphenylphosphine)palladium(II), as described in Tetrahedron Lett. 1996, 37 (14), 2409-2412, can be used. As the solvent, toluene or the like can be used. The reaction temperature is between room temperature and a reflux temperature. The reaction time is between 10 minutes and 60 hours.

The reactions similar to described in the processes of <Process 9-1> to <Process 9-9> can be applied to the conversion of the substituent at the 5-position ($R^{10}$) of the pyridine ring of various intermediates described in [Production Method 1] to [Production Method 8].

The "leaving group" may be any group generally known as a leaving group in organic synthesis, and is not particularly limited. Specifically for example, it includes halogen such as chlorine, bromine and iodine; nitro; alkylsulfonyloxy such as methanesulfonyloxy, trifluoromethanesulfonyloxy and ethanesulfonyloxy; arylsulfonyloxy such as benzenesulfonyloxy and p-toluenesulfonyloxy; and alkanoyloxy such as acetoxy and trifluoroacetoxy.

The amino-protecting group may be any group generally known as an amino-protecting group in organic synthesis, and is not particularly limited. Specifically for example, it includes substituted or unsubstituted acyl such as formyl, acetyl, chloroacetyl, dichloroacetyl, propionyl, phenylacetyl, phenoxyacetyl and thienylacetyl; alkoxycarbonyl such as t-butoxycarbonyl; substituted or unsubstituted benzyloxycarbonyl such as benzyloxycarbonyl and 4-nitrobenzyloxycarbonyl; substituted or unsubstituted alkyl such as methyl, t-butyl and 2,2,2-trichloroethyl; substituted benzyl such as trityl, 4-methoxybenzyl, 4-nitrobenzyl and diphenylmethyl; alkylcarbonyloxyalkyl such as pivaloyloxymethyl; alkylsilyl such as trimethylsilyl and t-butyldimethylsilyl; and alkylsilylalkoxyalkyl such as trimethylsilylmethoxymethyl, trimethylsilylethoxymethyl, t-butyldimethylsilylmethoxymethyl, t-butyldimethylsilylethoxymethyl.

These protecting groups can be deprotected by a conventional method such as hydrolysis and reduction depending on the kind of the protecting group used.

The hydroxyl-protecting group may be any group generally known as a hydroxyl-protecting group in organic synthesis, and is not particularly limited. Specifically for example, it includes alkylsilyl such as trimethylsilyl and t-butyldimethylsilyl; alkoxymethyl such as methoxymethyl and 2-methoxyethoxymethyl; tetrahydropyranyl; substituted or unsubstituted benzyl such as benzyl, 4-methoxybenzyl, 2,4-dimethoxybenzyl, 2-nitrobenzyl, 4-nitrobenzyl and trityl; alkenyl such as allyl; and acyl such as formyl and acetyl.

These protecting groups can be deprotected by a conventional method such as hydrolysis and reduction depending on the kind of the protecting group used.

The carboxyl-protecting group may be any group generally known as a carboxyl-protecting group in organic synthesis, and is not particularly limited. For example, it includes substituted or unsubstituted alkyl such as methyl, ethyl, i-propyl, t-butyl, 2-iodoethyl and 2,2,2-trichloroethyl; alkoxymethyl such as methoxymethyl, ethoxymethyl and i-butoxymethyl; acyloxymethyl such as butylyloxymethyl and pivaloyloxymethyl; alkoxycarbonyloxyethyl such as 1-methoxycarbonyloxyethyl and 1-ethoxycarbonyloxyethyl; and substituted or unsubstituted benzyl such as benzyl, 4-methoxybenzyl, 2-nitrobenzyl and 4-nitrobenzyl.

These protecting groups can be deprotected by a conventional method such as hydrolysis and reduction depending on the kind of the protecting group used.

In addition to the above protecting groups, groups described in Greene et al., "Protective Groups in Organic Synthesis", 2nd Edition, JOHN WILEY & SONS, INC. can be used.

There have been described above the typical examples of a method for producing the compound (I) according to the present invention. Each of the starting materials and various reagents may be a salt, a hydrate or a solvate, varies depending on a starting material, a solvent and the like to be used, and is not limited to a particular one as long as it does not inhibit a reaction. A solvent to be used varies depending on a starting material, a reagent and the like, and is not limited to a particular one as long as it does not inhibit a reaction and can dissolve the starting material to some extent.

The compound (I) according to the present invention, if provided as a free form, can be converted to a form of a salt or a hydrate which the forgoing may form by a conventional method.

The compound (I) according to the present invention, if provided as the form of a salt or a hydrate of the compound (I), can be converted to a free form of the compound (I) by a conventional method.

The compound (I) according to the present invention and the various isomers (such as geometric isomers and optical isomers) of the compound (I) according to the present invention can be purified and isolated by a conventional separation means, including recrystallization, diastereomer salt method, enzyme separation method, and various chromatographies such as thin-layer chromatography, column chromatography and gas chromatography.

The compound (I) of the present invention is generally mixed with an appropriate additive and formulated to use as a medicament. But the compound of the present invention may be used alone without any additive.

The above additives include excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like. These also may be appropriately combined to use if desired.

The excipients include, for example, lactose, white soft sugar, glucose, corn starch, mannitol, sorbitol, starch, alpha starch, dextrin, crystalline cellulose, soft silicic anhydride, aluminum silicate, calcium silicate, magnesium aluminometasilicate and calcium hydrogenphosphate.

The binders include, for example, polyvinyl alcohol, methylcellulose, ethylcellulose, gum arabic, tragacanth, gelatin, shellac, hydroxypropylmethylcellulose, hydroxypropylcellulose, carboxymethylcellulose sodium, polyvinylpyrrolidone and macrogol.

The disintegrators includes, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch and carboxymethyl starch sodium.

The coloring agents include, for example, those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

The taste correctives include cocoa powder, menthol, aromatic powders, mentha oil, borneol, powdered cinnamon bark and the like.

The emulsifiers or surfactants include, for example, stearyl triethanolamine, sodium lauryl sulfate, lauryl aminopropionic acid, lecitin, glycerin monostearate, sucrose fatty acid esters and glycerin fatty acid esters.

The dissolving aids include, for example, polyethylene glycol, propylene glycol, benzyl benzoate, ethanol, cholesterol, triethanolamine, sodium carbonate, sodium citrate, polysorbate 80 and nicotinamide.

The suspending agents include, for example, hydrophilic polymers such as polyvinyl alcohol, polyvinylpyrrolidone, methylcellulose, hydroxymethylcellulose, hydroxyethylcellulose and hydroxypropylcellulose, in addition to the above surfactants.

The isotonizing agents include, for example, glucose, sodium chloride, mannitol and sorbitol.

The buffering agents include, for example, buffer solutions of phosphate, acetate, carbonate and citrate.

The antiseptics include, for example, methylparaben, propylparaben, chlorobutanol, benzyl alcohol, phenetyl alcohol, dehydroacetic acid and sorbic acid.

The antioxidants include, for example, sulfite, ascorbic acid and α-tocopherol.

The stabilizers include those commonly used in pharmaceuticals.

The absorption accelerators include those commonly used in pharmaceuticals.

The formulation may be in an oral form such as tablets, powders, granules, capsules, syrups, lozenges and inhalants; an external application form such as suppositories, ointment, eye salve, tape, eye drops, nose drops, ear drops, pap and lotion; and an injection.

An oral formulation may be formulated by combining appropriately the above additives, and may be coated on the surface if necessary.

An external application may be formulated by combining appropriately the above additives, particularly excipients, binders, taste correctives, emulsifiers, surfactants, dissolving aids, suspending agents, isotonizing agents, antiseptics, antioxidants, stabilizers and absorption accelerators.

An injection may be formulated by combining appropriately the above additives, particularly emulsifiers, surfactants, dissolving aids, suspending agents, isotonizing agents, buffering agents, antiseptics, antioxidants, stabilizers and absorption accelerators.

The dose of the compound according to the present invention for the pharmaceutical use varies depending on symptoms and age of the patients, but it will ordinary be 0.1 mg to 10 g (preferably 1 mg to 2 g) for an oral formulation, 0.01 mg to 10 g (preferably 0.1 mg to 2 g) for an external application, and 0.01 mg to 10 g (preferably 0.1 mg to 2 g) for an injection, which is administrated once or divided over two to four times a day.

EXAMPLE

The compound according to the present invention can be produced, for example, by the methods described in the below Production Examples and Examples. But these Examples are for illustrative purposes, and the compound according to the present invention is not limited to the following specific Examples in any case.

In the Production Examples and Examples, YMC SIL-60-400/230W was used as silica gel for purification unless otherwise described.

For conditions for purification by LC-MS, the condition described below was used unless otherwise described.

ODS column: WakopakR Combi ODS Column, or YMC Combi ODS-A

Solvent: Solution A (0.1% trifluoroacetic acid-water), Solution B (0.1% trifluoroacetic acid-acetonitrile)

Flow rate: 30 mL/min

Stop time: 10 min

Gradient:

0.00 min A: 99%, B: 1%

8.00 min A: 20%, B: 80%

8.20 min A: 0%, B: 100%

Production Example 1

0.5 M Solution of Phenylacetyl Isocyanate in Hexane

To a suspension of phenylacetamide (1.81 g, 13.4 mmol) in 1,2-dichloroetane (150 mL) was added oxalyl chloride (3.51 mL, 40.2 mmol) under a nitrogen atmosphere at room temperature, followed by stirring at 110° C. overnight. The reaction mixture was cooled to room temperature, concentrated under a reduced pressure, and n-hexane (26.8 mL) was added thereto, followed by sonication. The resultant supernatant (a portion of yellow solution) was hereinafter used as the titled reagent.

Production Example 2

N-(4-Fluorophenyl)malonic acid methyl ester

Chlorocarbonylacetic acid methyl ester (5.00 g) was dissolved in tetrahydrofuran (100 ml) under a nitrogen atmosphere, and triethylamine (5.58 ml) and 4-fluoroaniline (3.79 ml) were added thereto in an ice water bath, followed by raising the temperature up to room temperature and stirring for 4 hrs. The reaction mixture was partitioned between ethyl acetate and 1 N HCl. The organic layer was washed with a saturated aqueous solution of sodium hydrogencarbonate, water and brine in this order, dried over anhydrous sodium sulfate, concentrated under a reduced pressure, and dried in vacuum to provide the titled compound (8.02 g, quantitatively) as pale brown crystals.
$^1$H-NMR Spectrum (CDCl$_3$) δ (ppm): 3.49 (2H, s), 3.81 (3H, s), 6.99-7.10 (2H, m), 7.50-7.55 (2H, m), 9.19 (1H, brs).

Production Example 3

N-(4-Fluorophenyl)malonic acid

N-(4-fluorophenyl)malonic acid methyl ester (8.02 g) was dissolved in ethanol (80 ml), and lithium hydroxide monohydrate (3.19 g) was added thereto, followed by stirring for 3 hrs and 30 min. To the reaction mixture was added 1 N HCl (84 ml), followed by evaporating ethanol under a reduced pressure. The residue was salted out and extracted with ethyl acetate-tetrahydrofuran (1:1). The organic layer was dried over anhydrous sodium sulfate, and concentrated under a reduced pressure. To the resultant residue was added diethyl ether-hexane (1:1) to suspend. A solid was filtered off and dried under aeration to provide the titled compound (7.06 g, 94%) as pale brown powder.
$^1$H-NMR Spectrum (CD$_3$OD) δ (ppm): 3.40 (2H, s), 7.02-7.07 (2H, m), 7.50-7.58 (2H, m).

Production Example 4

N-(2,4-Difluorophenyl)malonic acid methyl ester

Chlorocarbonylacetic acid methyl ester (1.00 g) was dissolved in tetrahydrofuran (20 ml) under a nitrogen atmosphere, and triethylamine (1.12 ml) and 2,4-difluoroaniline (0.82 ml) were added thereto in an ice water bath, followed by raising the temperature up to room temperature and stirring for 3 hrs and 40 min. Triethylamine (0.56 ml) and 2,4-difluoroaniline (0.39 ml) were added further thereto, followed by stirring at room temperature overnight. Triethylamine (0.25 ml) and 2,4-difluoroaniline (0.17 ml) were added further thereto, followed by stirring at room temperature for 3 hrs. Triethylamine (0.25 ml) and 2,4-difluoroaniline (0.17 ml) were added further thereto, followed by stirring at room temperature for 1 hr and 20 min. The reaction mixture was partitioned between ethyl acetate and 1 N HCl. The organic layer was washed with a saturated aqueous solution of sodium hydrogencarbonate, water and brine in this order, dried over anhydrous sodium sulfate, and concentrated under a reduced pressure. The resultant residue was purified by silica gel column chromatography (Fuji Silysia NH, eluent; hexane: ethyl acetate=1:1). The solvent was evaporated to give a residue, to which diethyl ether-hexane (1:1) was added to suspend. A solid was filtered off and dried under aeration to provide the titled compound (1.14 g, 68.4%) as a pale purple solid.
$^1$H-NMR Spectrum (CDCl$_3$) δ (ppm): 3.53 (2H, s), 3.83 (3H, s), 6.82-6.94 (2H, m), 8.18-8.29 (1H, m), 9.42 (1H, brs).

Production Example 5

N-(2,4-Difluorophenyl)malonic acid

N-(2,4-difluorophenyl)malonic acid methyl ester (1.14 g) was dissolved in ethanol (10 ml), and lithium hydroxide monohydrate (417 mg) was added thereto, followed by stirring for 3 hrs and 30 min. To the reaction mixture was added 1 N HCl (20 ml), followed by evaporating ethanol under a reduced pressure. The residue was salted out and extracted with ethyl acetate-tetrahydrofuran (1:1). The organic layer was dried over anhydrous sodium sulfate, and concentrated under a reduced pressure. To the resultant residue was added diethyl ether-hexane (1:1) to suspend. A solid was filtered off and dried under aeration to provide the titled compound (1.01 g, 94.5%) as a pale purple solid.
$^1$H-NMR Spectrum (DMSO-d$_6$) δ (ppm): 3.33 (1H, brs), 3.40-3.48 (2H, m), 7.02-7.20 (1H, m), 7.28-7.45 (1H, m), 7.85-8.00 (1H, m), 9.98 (1H, s).

Production Example 6

N-(4-Fluorobenzyl)oxalic acid ethyl ester 4-fluorobenzylamine (1.252 g) was dissolved in tetrahydrofuran (30 ml) under a nitrogen atmosphere, and triethylamine (2.6 ml) and ethyl chlorooxalate (1.4 ml) were added dropwise therein while cooling in an ice water bath, followed by stirring at room temperature for 30 min. The reaction mixture was partitioned between ethyl acetate and a saturated aqueous solution of sodium hydrogencarbonate. The organic layer was washed with water, 1 N HCl, water, and brine in this order, and dried over anhydrous sodium sulfate. The solvent was evaporated under a reduced pressure to give a residue, which was purified by silica gel column chromatography (eluent; hexane:ethyl acetate=1:1) to provide the titled compound (1.851 g, 82%) as white crystals.
$^1$H-NMR Spectrum (CDCl$_3$) δ (ppm): 1.39 (3H, t, J=7.2 Hz), 4.35 (2H, q, J=7.2 Hz), 4.49 (2H, d, J=6.4 Hz), 7.01-7.07 (2H, m), 7.25-7.30 (2H, m), 7.39 (1H, br).

Production Example 7

N-(4-Fluorobenzyl)oxalic acid

N-(4-fluorobenzyl)oxalamide ethyl ester (1.85 g) was dissolved in methanol (20 ml)-water (5 ml), and lithium hydroxide monohydrate (671 mg) was added thereto, followed by stirring at room temperature for 30 min. To the reaction mixture was added 2 N HCl (10 ml). Methanol was evaporated under a reduced pressure to give a residue, which was partitioned between ethyl acetate and water. The organic layer was washed with water and brine in this order, and dried over anhydrous sodium sulfate. The solvent was evaporated under a reduced pressure to give a residue, to which diethyl ether-hexane was added to precipitate crystals. The crystals were filtered off and dried under aeration to provide the titled compound (1.346 g, 83%) as white crystals.
$^1$H-NMR Spectrum (CDCl$_3$) δ (ppm): 4.51 (2H, d, J=6.0 Hz), 7.00-7.10 (2H, m), 7.20-7.30 (2H, m), 7.57 (1H, br).

Production Example 8

N-(2-Phenylethyl)oxalic acid ethyl ester

2-Phenylethylamine (970 mg) was dissolved in tetrahydrofuran (30 ml) under a nitrogen atmosphere, and triethylamine (1.87 ml) and ethyl chlorooxalate (1.0 ml) were added dropwise therein while cooling in an ice water bath, followed by stirring at room temperature for 1 hr. The reaction mixture was partitioned between ethyl acetate and a saturated aqueous solution of sodium hydrogencarbonate. The organic layer was washed with water, 1 N HCl, water, and brine in this order, and dried over anhydrous sodium sulfate. The solvent was evaporated under a reduced pressure to provide a crude product of the titled compound (1.83 g) as a yellow oil.

$^1$H-NMR Spectrum (CDCl$_3$) δ (ppm): 1.38 (3H, t, J=7.2 Hz), 2.88 (2H, t, J=7.2 Hz), 3.61 (2H, q, J=7.2 Hz), 4.33 (2H, q, J=7.2 Hz), 7.13 (1H, br), 7.19-7.35 (5H, m).

Production Example 9

N-(2-Phenylethyl)oxalic acid

A crude product of N-(2-phenylethyl)oxalamide ethyl ester (1.83 g) was dissolved in methanol (20 ml)-water (5 ml), and lithium hydroxide monohydrate (671 mg) was added thereto, followed by stirring at room temperature for 1 hr. Methanol was evaporated under a reduced pressure to give a residue, to which 1 N HCl (50 ml) was added, followed by extracting with ethyl acetate. The organic layer was washed with water and brine, and dried over anhydrous sodium sulfate. The solvent was evaporated under a reduced pressure to give a residue, to which diethyl ether-hexane (1:5, 60 ml) was added to suspend. A solid was filtered off and dried under aeration to provide the titled compound (1.327 g) as white powder.

Production Example 10

N-(3-Phenylpropyl)oxalic acid ethyl ester

3-Phenylpropylamine (1.14 ml) was dissolved in tetrahydrofuran (30 ml) under a nitrogen atmosphere, and triethylamine (1.87 ml) and ethyl chlorooxalate (1.0 ml) were added dropwise therein in an ice water bath, followed by stirring at room temperature for 40 min. The reaction mixture was partitioned between ethyl acetate and a saturated aqueous solution of sodium hydrogencarbonate. The organic layer was washed with water, 1 N HCl, water and brine in this order, and dried over anhydrous sodium sulfate. The solvent was evaporated under a reduced pressure to provide a crude product of the titled compound (2.06 g) as a yellow oil.

$^1$H-NMR Spectrum (CDCl$_3$) δ (ppm): 1.39 (3H, t, J=7.2 Hz), 1.92 (2H, quint, J=7.2 Hz), 2.68 (2H, t, J=7.2 Hz), 3.38 (2H, q, J=7.2 Hz), 4.34 (2H, q, J=7.2 Hz), 7.10 (1H, br), 7.17-7.32 (5H, m).

Production Example 11

N-(3-Phenylpropyl)oxalic acid

A crude product of N-(3-phenylpropyl)oxalamide ethyl ester (2.06 g) was dissolved in methanol (20 ml)-water (5 ml), and lithium hydroxide monohydrate (671 mg) was added thereto, followed by stirring at room temperature for 1 hr. Methanol was evaporated under a reduced pressure to give a residue, to which 1 N HCl (50 ml) was added, followed by extracting with ethyl acetate. The organic layer was washed with water and brine in this order, and dried over anhydrous sodium sulfate. The solvent was evaporated under a reduced pressure to give a residue, to which diethyl ether-hexane (1:5, 60 ml) was added to suspend. A solid was filtered off and dried under aeration to provide the titled compound (1.579 g) as white powder.

Production Example 12

N-(4-Fluorophenyl)-difluoromalonic acid

Diethyl difluoromalonate (196 mg) was dissolved in toluene (2 ml), and then 4-fluoroaniline (0.1 ml) was added thereto, followed by heating under reflux overnight. The reaction mixture was allowed to stand down to room temperature, and then 1 N HCl (2.5 ml) was added thereto, followed by extracting with ethyl acetate. The organic layer was dried over anhydrous sodium sulfate, followed by evaporating the solvent to provide a brown solid residue. The residue (188 mg) was dissolved in ethanol (2 ml)-water (0.5 ml), and lithium hydroxide monohydrate (42 mg) was added thereto, followed by stirring for 1 hr. Ethanol was evaporated under a reduced pressure, and the resultant was partitioned between ethyl acetate and water. To the aqueous layer was added 1 N HCl (1.5 ml) to make it acidic, followed by extracting with ethyl acetate. The organic layer was dried over anhydrous sodium sulfate, followed by evaporating the solvent and drying in vacuum to provide a crude product of N-(4-fluorophenyl)-difluoromalonic acid (116 mg) as white powder.

Production Example 13

N,N-Diethyl-N'-methylpropane-1,3-diamine

To a solution of N,N-diethyl-1,3-propanediamine (10.0 ml) and triethylamine (10.0 ml) in tetrahydrofuran (150 ml) was added dropwise methyl chloroformate (5.15 ml) in an ice bath, followed by stirring at room temperature for 30 min. To the reaction mixture was added a saturated aqueous solution of sodium hydrogencarbonate (10 ml) to partition. The organic layer was dried over anhydrous sodium sulfate, and concentrated under a reduced pressure. The residue was dissolved in ethyl acetate (200 ml) again, dried over potassium carbonate, and concentrated under a reduced pressure to provide a pale yellow oil (8.90 g, ESI-MS (m/z):189). This residue was dissolved in tetrahydrofuran (200 ml), and then lithium aluminium hydride (2.00 g, 0.826 mmol) was gradually added thereto while cooling in an ice bath and stirring, followed by stirring under a nitrogen atmosphere at room temperature for 15 min and then at 65° C. for 1.5 hrs. The reaction mixture was cooled in an ice bath, and then supplied with water (2.0 mL), an 5 N aqueous solution of sodium hydroxide (2.0 mL) and water (10.0 mL), followed by stirring in an ice bath for 1 hr. The insoluble portion was filtered and washed with tetrahydrofuran to give a filtrate, which was concentrated under a reduced pressure to provide a crude product of the titled compound (9.2 g, 72.3%) as a pale yellow oil.

$^1$H-NMR Spectrum (CDCl$_3$) δ (ppm): 1.01 (6H, t, J=7.0 Hz), 1.65 (2H, m), 2.42 (3H, s), 2.47 (2H, t, J=7.0 Hz), 2.51 (4H, q, J=7.0 Hz), 2.62 (2H, t, J=7.0 Hz). ESI-MS (m/z): 145 [M+H]$^+$.

Production Example 14

Methyl-[3-(4-methylpiperazin-1-yl)propyl]amine

To a solution of 1-(3-aminopropyl)-4-methylpiperazine (1.50 g) in tetrahydrofuran (10 mL) was added triethylamine (1.53 mL), and then methyl chloroformate (0.811 ml) dropwise in an ice bath, followed by stirring at room temperature for 18 hrs. The reaction mixture was partitioned between ethyl acetate and a saturated aqueous solution of sodium hydrogencarbonate. The organic layer was washed with brine, dried over anhydrous sodium sulfate, and concentrated under a reduced pressure. The aqueous layer was also concentrated under a reduced pressure to give a residue, to which tetrahydrofuran (100 mL) was added to filter an insoluble portion. The filtrate was combined with the above residue, and concentrated under a reduced pressure to give a residue (549 mg). This residue was dissolved in tetrahydrofuran (10 mL), and then lithium aluminium hydride (107 mg) was gradually added thereto while cooling in an ice bath and stirring, followed by stirring under a nitrogen atmosphere at room temperature for 30 min and heating to stir at 65° C. for 2 hrs. The reaction mixture was cooled in an ice bath, and then water (0.11 mL), a 5 N aqueous solution of sodium hydroxide (0.11 mL) and water (0.55 mL) in this order were added thereto, followed by stirring in an ice bath for 1 hr. The insoluble portion was filtered, and washed with tetrahydrofuran to give a filtrate, which was concentrated under a reduced pressure to provide a crude product of the titled compound (1.63 g, 26.3%) as a yellow oil.

ESI-MS (m/z): 172 [M+H]$^+$.

Production Example 15

2-Amino-4-(2-fluoro-4-nitrophenoxy)pyridine

2-Amino-4-chloropyridine (8.00 g) was dissolved in N-methylpyrrolidone (65 ml), and then 2-fluoro-4-nitrophenol (19.55 g) and N,N-diisopropylethylamine (43.36 ml) were added thereto, followed by stirring at 160° C. for 41 hrs. The reaction mixture was cooled down to room temperature, and partitioned between ethyl acetate-tetrahydrofuran (1:1) and a 2 N aqueous solution of sodium hydroxide. The organic layer was washed with water and brine in this order. The aqueous layer was extracted again with ethyl acetate. The combined organic layer was dried over anhydrous sodium sulfate. The solvent was evaporated under a reduced pressure to give a residue, which was purified by silica gel column chromatography (eluent; hexane:ethyl acetate=1:2, then ethyl acetate). Fractions containing the target compound were concentrated to provide a residue, to which ethyl acetate was added to precipitate crystals. The crystals were filtered, and dried under aeration to provide the titled compound (3.02 g, 20%) as opaline crystals.

$^1$H-NMR Spectrum (CDCl$_3$) δ (ppm): 4.52 (2H, brs), 6.05 (1H, d, J=1.6 Hz), 6.30 (1H, dd, J=2.0, 5.6 Hz), 7.20-7.30 (1H, m), 8.02 (1H, d, J=5.6 Hz), 8.05-8.15 (2H, m).

Production Example 16

4-(2-Fluoro-4-nitrophenoxy)-2-[(pyrrolidin-1-yl)carbonylamino]pyridine

2-Amino-4-(2-fluoro-4-nitrophenoxy)pyridine (2.71 g) was dissolved in tetrahydrofuran (60 ml) under a nitrogen atmosphere, and then triethylamine (2.27 ml) and phenyl chloroformate (2.05 ml) were added dropwise thereto while cooling in an ice water bath, followed by stirring at room temperature for 25 min. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to provide a crude product of 4-(2-fluoro-4-nitrophenoxy)-2-(phenoxycarbonylamino)pyridine (5.00 g). The crude product was dissolved in tetrahydrofuran (50 ml), and then pyrrolidine (3.64 ml) was added at room temperature, followed by stirring for 1 hr. To the reaction mixture was added a saturated aqueous solution of ammonium chloride, followed by extracting with ethyl acetate. The organic layer was washed with a saturated aqueous solution of ammonium chloride and an brine in this order, and dried over anhydrous sodium sulfate. The solvent was evaporated under a reduced pressure to give a residue, which was purified by silica gel column chromatography (eluent; hexane:ethyl acetate=1:2 to 1:4, then ethyl acetate) to provide the titled compound (2.927 g, 78%) as pale brown crystals.

$^1$H-NMR Spectrum (CDCl$_3$) δ (ppm): 1.90-2.00 (4H, m), 3.40-3.50 (4H, m), 6.65 (1H, dd, J=2.4, 5.6 Hz), 7.12 (1H, brs), 7.27-7.33 (1H, m), 7.78 (1H, d, J=2.4 Hz), 8.07-8.15 (3H, m).

Production Example 17

4-(4-Amino-2-fluorophenoxy)-2-[(pyrrolidin-1-yl)carbonylamino]pyridine

To 4-(2-fluoro-4-nitrophenoxy)-2-[(pyrrolidin-1-yl)carbonylamino]pyridine (2.927 g) dissolved in ethanol (100 ml)-water (20 ml) were added electrolytic iron powder (3.0 g) and ammonium chloride (6.0 g), followed by heating under reflux for 1 hr. The reaction mixture was cooled down to room temperature, and then ethyl acetate-tetrahydrofuran (1:1) was added thereto, followed by stirring. An insoluble portion was filtered through celite, and washed with ethyl acetate and water. The organic layer of the filtrate was separated, washed with water and brine in this order, and dried over anhydrous sodium sulfate. The solvent was evaporated under a reduced pressure to give a residue, to which ethyl acetate-hexane was added to suspend. Crystals was filtered off and dried under aeration to provide the titled compound (2.378 g, 89%) as pale brown crystals.

$^1$H-NMR Spectrum (CDCl$_3$) δ (ppm): 1.90-2.00 (4H, m), 3.30-3.50 (4H, m), 3.73 (2H, s), 6.45 (1H, dd, J=2.4, 5.6 Hz), 6.50-6.60 (2H, m), 6.96 (1H, m), 7.03 (1H, brs), 7.67 (1H, d, J=2.4 Hz), 8.00 (1H, d, J=5.6 Hz).

Production Example 18

4-(4-Amino-2-fluorophenoxy)-2-{[4-(pyrrolidin-1-yl)piperidin-1-yl]carbonylamino}pyridine 2-Amino-4-(2-fluoro-4-nitrophenoxy)pyridine (187 mg) was dissolved in tetrahydrofuran (4 ml) under a nitrogen atmosphere, and then triethylamine (0.21 ml) and phenyl chloroformate (0.188 ml) were added dropwise thereto while cooling in an ice bath, followed by stirring at room temperature for 20 min. To the reaction mixture were added N,N-dimethylformamide (2 ml) and 4-(pyrrolidin-1-yl)piperidine (609 mg) at room temperature, followed by stirring overnight. The reaction mixture was partitioned between ethyl acetate and water. The organic layer was washed with brine, and dried over anhydrous sodium sulfate. The solvent was evaporated under a reduced pressure to give a residue, to which methanol (10 ml)-tetrahydrofuran (10 ml) was added to dissolve, and then 10% palladium carbon (200 mg) was added thereto under a nitrogen atmosphere, followed by replacing with hydrogen inside the system and stirring overnight. After replacing with nitrogen inside the system, the catalyst was filtered and washed with ethanol. The filtrate was concentrated under a reduced pressure to give a residue, which was purified by silica gel column chromatography (Fuji Silysia NH, eluent; ethyl acetate, then ethyl acetate:methanol=95:5) to provide the titled compound (214 mg, 71%) as colorless crystals.

$^1$H-NMR Spectrum (CDCl$_3$) δ (ppm): 1.40-1.60 (2H, m), 1.70-1.90 (4H, m), 1.90-2.00 (2H, m), 2.19 (1H, m), 2.50-2.60 (4H, m), 2.96 (2H, m), 3.74 (2H, brs), 4.03-4.10 (2H, m), 6.40-6.60 (3H, m), 6.96 (1H, m), 7.23 (1H, brs), 7.58 (1H, s), 8.01 (1H, d, J=5.6 Hz).

Production Example 19

2-[(Dimethylamino)carbonylamino]-4-(2-fluoro-4-nitrophenoxy)pyridine

2-Amino-4-(2-fluoro-4-nitrophenoxy)pyridine (249 mg) was dissolved in tetrahydrofuran (5 ml) under a nitrogen atmosphere, and then triethylamine (0.21 ml) and phenyl chloroformate (0.19 ml) were added dropwise thereto while cooling in an ice water bath, followed by stirring at room temperature for 15 min. To the reaction mixture was added 2 M solution of dimethylamine in methanol (4.0 ml), followed by stirring for 2 days. The solvent was evaporated under a reduced pressure to give a residue, which was purified by silica gel column chromatography (eluent; hexane:ethyl acetate=1:3, then ethyl acetate) to provide the titled compound (219 mg, 68%) as pale yellow crystals.

$^1$H-NMR Spectrum (CDCl$_3$) δ (ppm): 3.03 (6H, s), 6.64 (1H, dd, J=2.0, 5.6 Hz), 7.30 (2H, m), 7.51 (1H, d, J=5.6 Hz), 8.05-8.16 (3H, m).

Production Example 20

4-(4-Amino-2-fluorophenoxy)-2-[(dimethylamino)carbonylamino]pyridine

2-[(Dimethylamino)carbonylamino]-4-(2-fluoro-4-nitrophenoxy)pyridine (218 mg) was dissolved in ethanol (20 ml)-water (5 ml) to dissolve, and then electrolytic iron powder (250 mg) and ammonium chloride (500 mg) were added thereto, followed by heating under reflux for 1 hr. The reaction mixture was cooled down to room temperature, and then ethyl acetate-tetrahydrofuran (1:1) was added thereto, followed by stirring. An insoluble portion was filtered through celite, and washed with ethyl acetate and water. The organic layer of the filtrate was separated, washed with water and brine in this order, and dried over anhydrous sodium sulfate. The solvent was evaporated under a reduced pressure to give a residue, to which thus diethyl ether-hexane was then added to suspend. Crystals was filtered off and dried under aeration to provide the titled compound (180 mg, 91%) as pale yellow crystals.

$^1$H-NMR Spectrum (CDCl$_3$) δ (ppm): 3.02 (6H, s), 3.77 (2H, br), 6.40-6.60 (3H, m), 6.96 (1H, m), 7.20 (1H, brs), 7.63 (1H, d, J=2.0 Hz), 8.01 (1H, d, J=5.6 Hz).

Production Example 21

4-(4-Amino-2-fluorophenoxy)-2-[(methylamino)carbonylamino]pyridine

2-Amino-4-(2-fluoro-4-nitrophenoxy)pyridine (347 mg) was dissolved in tetrahydrofuran (7.5 ml) under a nitrogen atmosphere, and then triethylamine (0.314 ml) and phenyl chloroformate (0.282 ml) were added dropwise thereto while cooling in an ice water bath, followed by stirring at room temperature for 10 min. To the reaction mixture was added 2 M solution of methylamine in tetrahydrofuran (7.5 ml), followed by stirring for 2 days. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to give a residue (1028 mg), which was then dissolved in ethanol (20 ml)-N,N-dimethylformamide (5 ml)-water (5 ml), and then electrolytic iron powder (500 mg) and ammonium chloride (1.0 g) were added thereto, followed by heating under reflux for 2 hr. The reaction mixture was cooled down to room temperature, and then an insoluble portion was filtered through celite and washed with ethyl acetate and water. The organic layer of the filtrate was separated, washed with water and brine in this order, and dried over anhydrous sodium sulfate. The solvent was evaporated under a reduced pressure to give a residue, which was then purified by silica gel column chromatography (Fuji Silysia NH, eluent; hexane: ethyl acetate=1:3, then ethyl acetate). Fractions containing the target compound were concentrated to give a residue, to which diethyl ether-hexane was added to suspend. A solid was filtered off and dried under aeration to provide the titled compound (321.7 mg, 78% by the two processes) as pale yellow powder.

$^1$H-NMR Spectrum (CDCl$_3$) δ (ppm): 2.91 (3H, d, J=4.4 Hz), 3.79 (2H, brs), 6.16 (1H, m), 6.40-6.60 (3H, m), 6.93 (1H, m), 7.68 (1H, brs), 7.96 (1H, d, J=6.0 Hz), 9.14 (1H, brs).

Production Example 22

2-Amino-4-(4-amino-2-fluorophenoxy)pyridine

2-Amino-4-(2-fluoro-4-nitrophenoxy)pyridine (1.246 g) was dissolved in methanol (20 ml)-tetrahydrofuran (10 ml), and then 10% palladium carbon (1.0 g) was added thereto under a nitrogen atmosphere, followed by replacing with hydrogen inside the system and stirring for 6 days. After replacing with nitrogen inside the system, the catalyst was filtered and washed with ethanol. The filtrate was concentrated under a reduced pressure to provide the titled compound (1.182 g, quantitative) as brown crystals.

$^1$H-NMR Spectrum (CDCl$_3$) δ (ppm): 3.77 (2H, brs), 4.37 (2H, brs), 5.92 (1H, d, J=2.4 Hz), 6.27 (1H, dd, J=2.4, 5.6 Hz), 6.43 (1H, m), 6.51 (1H, dd, J=2.4, 12.0 Hz), 6.93 (1H, m), 7.91 (1H, d, J=5.6 Hz).

Production Example 23

N-(4-Fluorophenyl)-N'-[4-(2-aminopyridin-4-yloxy)-3-fluorophenyl]malonamide

2-Amino-4-(4-amino-2-fluorophenoxy)pyridine (1.14 g) was dissolved in N,N-dimethylformamide (20 ml) under a nitrogen atmosphere, and then N-(4-fluorophenyl)malonic acid (986 mg), triethylamine (0.697 ml), and (1H-1,2,3-benzotriazol-1-yloxy)[tri(dimethylamino)]phosphonium hexafluorophosphate (2.21 g) were added thereto at room temperature, followed by stirring for 23 hrs. The reaction mixture was partitioned between ethyl acetate-tetrahydrofuran (1:1) and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (Fuji Silysia NH, eluent; ethyl acetate, then ethyl acetate:methanol=95:5) to provide the titled compound (937 mg, 47%) as white crystals.

$^1$H-NMR Spectrum (CDCl$_3$) δ (ppm): 3.55 (2H, s), 4.43 (2H, s), 5.94 (1H, d, J=2.4 Hz), 6.28 (1H, dd, J=2.0, 5.6 Hz), 7.00-7.30 (4H, m), 7.50-7.54 (2H, m), 7.72 (1H, dd, J=2.4, 12.0 Hz), 7.94 (1H, d, J=5.6 Hz), 8.54 (1H, brs), 9.29 (1H, brs).

Production Example 24

4-(2-Fluoro-4-nitrophenoxy)-2-[(4-hydroxypiperidin-1-yl)carbonylamino]pyridine

2-Amino-4-(2-fluoro-4-nitrophenoxy)pyridine (124.6 mg) was dissolved in tetrahydrofuran (2.5 ml) under a nitrogen atmosphere, and then triethylamine (0.105 ml) and phenyl chloroformate (0.094 ml) were added dropwise thereto while cooling in an ice bath, followed by stirring at room temperature for 1 hr. The reaction mixture was concentrated under a reduced pressure to give a residue, which was dissolved in N,N-dimethylformamide (1.25 ml), and then 4-hydroxypiperidine (253 mg) was added thereto at room temperature, followed by stirring for 2 hrs. To the reaction mixture was added a saturated aqueous solution of ammonium chloride, followed by extracting with ethyl acetate. The organic layer was washed with a saturated aqueous solution of ammonium chloride and brine in this order, and dried over anhydrous sodium sulfate. The solvent was evaporated under a reduced pressure to give a residue, which was then purified by silica gel column chromatography (eluent; hexane:ethyl acetate=1:2 to 1:4, then ethyl acetate) to provide the titled compound (169 mg, 90%) as pale yellow powder.

$^1$H-NMR Spectrum (CDCl$_3$) δ (ppm): 1.40-1.70 (2H, m), 1.90-1.96 (2H, m), 3.20-3.29 (2H, m), 3.70-3.85 (2H, m), 3.96 (1H, m), 6.64 (1H, dd, J=2.4, 6.0 Hz), 7.27-7.36 (2H, m), 7.70 (1H, d, J=2.4 Hz), 8.08-8.20 (3H, m).

Production Example 25

2-Amino-4-{2-fluoro-4-[3-(2-phenylacetyl)thioureido]phenoxy}pyridine

2-Phenylacetyl chloride (0.481 ml) was dissolved in acetonitrile (30 ml) under a nitrogen atmosphere, and then potassium thiocyanate (707 mg) was added thereto at 50° C., followed by stirring at the same temperature for 1.5 hrs. After acetonitrile was evaporated under a reduced pressure, toluene (20 ml) and a saturated aqueous solution of sodium hydrogencarbonate (20 ml) were added, followed by stirring for 25 min. The toluene layer (12 ml) was added in a solution of 2-amino-4-(4-amino-2-fluorophenoxy)pyridine (400 mg) in ethanol (10 ml) at room temperature, followed by stirring for 1 hr. The reaction mixture was concentrated under a reduced pressure to give a residue, which was then purified by silica gel column chromatography (eluent; ethyl acetate). Fractions containing the target compound were concentrated under a reduced pressure to give a residue, to which diethyl ether (10 ml) was added to precipitate crystals, followed by diluting with hexane (50 ml). The crystals were filtered off and dried under aeration to provide the titled compound (298 mg, 41%) as white crystals.

$^1$H-NMR Spectrum (CDCl$_3$) δ (ppm): 3.75 (2H, s), 4.43 (2H, brs), 5.95 (1H, d, J=2.4 Hz), 6.29 (1H, dd, J=2.4, 5.6 Hz), 7.16 (1H, m), 7.30-7.47 (6H, m), 7.85 (1H, dd, J=2.4, 11.6 Hz), 7.95 (1H, d, J=5.6 Hz), 8.51 (1H, brs), 12.43 (1H, brs).

Production Example 26

N-(3-Fluoro-4-{2-[(pyrrolidine-1-carbonyl)amino]pyridin-4-yloxy}phenyl)malonic acid benzyl ester 4-(4-Amino-2-fluorophenoxy)-2-[(pyrrolidin-1-yl)carbonylamino]pyridine (350 mg) was dissolved in N,N-dimethylformamide (4 ml), and then malonic acid monobenzyl ester (51.0 mg), triethylamine (0.463 ml) and (1H-1,2,3-benzotriazol-1-yloxy)[tri(dimethylamino)]phosphonium hexafluorophosphate (1.47 g) were added thereto at 50° C., followed by stirring at the same temperature for 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:2 to 1:4) to provide the titled compound (545.7 mg, quantitative) as a yellow oil.

$^1$H-NMR Spectrum (CDCl$_3$) δ (ppm): 1.95 (4H, m), 3.43 (4H, m), 3.52 (2H, s), 5.24 (2H, s), 6.55 (1H, dd, J=2.4, 6.0 Hz), 7.06-7.26 (3H, m), 7.32-7.46 (5H, m), 7.62-7.78 (2H, m), 8.03 (1H, d, J=6.0 Hz), 9.38 (1H, brs).

Production Example 27

N-(3-Fluoro-4-{2-[(pyrrolidine-1-carbonyl)amino]pyridin-4-yloxy}phenyl)malonic acid N-(3-Fluoro-4-{2-[(pyrrolidine-1-carbonyl)amino]pyridin-4-yloxy}phenyl)malonic acid benzyl ester (546 mg) was dissolved in tetrahydrofuran (15 ml)-methanol (15 ml), and then 10% palladium carbon (236 mg) was added thereto under a nitrogen atmosphere, followed by replacing with hydrogen inside the system and stirring for 1 hr. After replacing with nitrogen inside the system, the catalyst was filtered and washed with methanol. The filtrate was concentrated under a reduced pressure and dried in vacuum to provide the titled compound (354.4 mg, 79.3%).

$^1$H-NMR Spectrum (DMSO-d$_6$) δ (ppm): 1.80 (4H, m), 3.00-3.80 (7H, m), 6.60 (1H, dd, J=2.4, 5.6 Hz), 7.28-7.45 (2H, m), 7.46 (1H, d, J=2.4 Hz), 7.78 (1H, dd, J=2.4, 13 Hz), 8.10 (1H, dd, J=0.4, 5.6 Hz), 8.69 (1H, brs), 10.6 (1H, brs).

Production Example 28

3-[4-(2-Fluoro-4-nitrophenoxy)pyridin-2-yl]-1-methyl-1-(1-methylpiperidin-4-yl)urea 4-(2-Fluoro-4-nitrophenoxy)pyridin-2-ylamine (200 mg) was dissolved in tetrahydrofuran (8 ml) under a nitrogen atmosphere, and then triethylamine (0.336 ml) and phenyl chloroformate (0.302 ml) were added dropwise thereto at room temperature, followed by stirring for 30 min. The reaction mixture was concentrated under a reduced pressure to give a residue, which was dissolved in N,N-dimethylformamide (5 ml), and then N-methyl-N-(1-methylpiperidin-4-yl)amine (0.467 ml) was added thereto at room temperature, followed by stirring for 4 hrs. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was purified by silica gel column chromatography (Fuji Silysia NH, eluent; ethyl acetate). The resultant fractions were concentrated under a reduced pressure, and dried in vacuum to provide the titled compound (245 mg, 75.5%) as a yellow solid.

$^1$H-NMR Spectrum (CDCl$_3$) δ (ppm): 1.50-1.70 (2H, m), 1.79 (2H, m), 2.04-2.13 (2H, m), 2.29 (3H, s), 2.88-2.98 (5H, m), 4.09-4.22 (1H, m), 6.66 (1H, dd, J=2.4, 5.6 Hz), 7.26-7.35 (1H, m), 7.74-7.78 (1H, m), 8.06-8.13 (2H, m), 8.13-8.19 (2H, m).

Production Example 29

3-[4-(4-Amino-2-fluorophenoxy)pyridin-2-yl]-1-methyl-1-(1-methylpiperidin-4-yl)urea 3-[4-(2-Fluoro-4-nitrophenoxy)pyridin-2-yl]-1-methyl-1-(1-methylpiperidin-4-yl)urea (243 mg) was dissolved in tetrahydrofuran (6 ml)-methanol (6 ml), and then 10% palladium carbon (128 mg) was added thereto under a nitrogen atmosphere, followed by replacing with hydrogen inside the reaction system and stirring for 3 hrs. After replacing with nitrogen inside the system, the catalyst was filtered and washed with methanol. The filtrate was concentrated under a reduced pressure to give a residue, which was then purified by silica gel column chromatography (Fuji Silysia NH, eluent; ethyl acetate) and concentrated under a reduced pressure to provide the titled compound (175 mg, 78.0%) as pale yellow powder.

$^1$H-NMR Spectrum (CDCl$_3$) δ (ppm): 1.50-1.70 (2H, m), 1.78 (2H, m), 1.98-2.18 (2H, m), 2.20-2.38 (3H, m), 2.82-3.02 (5H, m), 3.75 (2H, m), 4.08-4.26 (1H, m), 6.45 (1H, dd, J=3.2, 8.4 Hz), 6.47-6.66 (2H, m), 6.97 (1H, m), 7.17 (1H, brs), 7.65 (1H, d, J=2.0 Hz), 8.03 (1H, d, J=5.6 Hz). ESI-MS (m/z): 374 [M+H]$^+$.

Production Example 30

1-(3-Diethylaminopropyl)-3-[4-(2-fluoro-4-nitrophenoxy)pyridin-2-yl]-1-methylurea To a solution of 4-(2-fluoro-4-nitrophenoxy)pyridin-2-ylamine (300 mg, 1.2 mmol) and triethylamine (0.335 ml, 2.4 mmol) in tetrahydrofuran (30 ml) was added phenyl chloroformate (0.226 ml, 1.8 mmol) dropwise while stirring in an ice bath, followed by stirring for 0.5 hr. The reaction mixture was concentrated under a reduced pressure to give a residue, to which N,N-dimethylformamide (6.0 ml) and N,N-diethyl-N'-methyl-1,3-propanediamine (606 mg, 4.2 mmol) were added, followed by stirring at room temperature for 4 hrs and 45 min. To the reaction mixture was added ethyl acetate (150 ml), washed with a saturated aqueous solution of sodium hydrogencarbonate, and dried over anhydrous sodium sulfate. The solvent was evaporated to give a residue, which was filtered by silica gel (Fuji Silysia NH, hexane:ethyl acetate=3:1 to 1:1) to provide the titled compound (503 mg, 100%) as a yellow oil.

ESI-MS (m/z): 420 [M+H]$^+$.

Production Example 31

1-(3-Diethylaminopropyl)-3-[4-(4-amino-2-fluorophenoxy)pyridin-2-yl]-1-methylurea To a solution of 1-(3-diethylaminopropyl)-3-[4-(2-fluoro-4-nitrophenoxy)pyridin-2-yl]-1-methylurea (503 mg, 1.20 mmol) in methanol (40 ml)-tetrahydrofuran (20 ml) was added 10% palladium carbon (200 mg), followed by stirring under a hydrogen atmosphere at room temperature for 12 hrs. The catalyst was filtered and washed with methanol. The filtrate was concentrated under a reduced pressure to give a residue, which was then purified by silica gel column chromatography (Fuji Silysia NH, ethyl acetate, then ethyl acetate:methanol=10:1) to provide the titled compound (467 mg, 85.6%) as a yellow oil.

$^1$H-NMR Spectrum (DMSO-d$_6$) δ (ppm): 0.97 (6H, t, J=7.2 Hz), 1.68 (2H, m), 2.36 (2H, m), 2.52 (4H, m), 2.80 (3H, s), 3.29 (2H, m), 5.43 (2H, m), 6.40 (1H, dd, J=2.4, 8.8 Hz), 6.47-6.51 (2H, m), 6.94 (1H, dd, J=8.8, 8.8 Hz), 7.29 (1H, d, J=2.4 Hz), 8.02 (1H, d, J=5.6 Hz), 9.33 (1H, s).

Production Example 32

1-(3-Diethylaminopropyl)-3-[4-(2-fluoro-4-nitrophenoxy)pyridin-2-yl]urea

To a solution of 4-(2-fluoro-4-nitrophenoxy)pyridin-2-ylamine (400 mg, 1.61 mmol) and triethylamine (0.455 ml, 3.26 mmol) in tetrahydrofuran (40 ml) was added phenyl chloroformate (0.307 ml, 2.45 mmol) dropwise while stirring in an ice bath, followed by stirring for 0.5 hr. The reaction mixture was concentrated under a reduced pressure to give a residue, to which N,N-dimethylformamide (20 ml) and N,N-diethyl-1,3-propanediamine (606 mg, 4.2 mmol) were then added, followed by stirring at room temperature for 1 hr and 45 min. To the reaction mixture was added ethyl acetate (150 ml), washed with a saturated aqueous solution of sodium hydrogencarbonate, and dried over anhydrous sodium sulfate. The solvent was evaporated to give a residue, which was then purified by silica gel column chromatography (Fuji Silysia NH, eluent; hexane:ethyl acetate=1:2, then ethyl acetate) to provide the titled compound (653 mg, 83.8%) as a pale yellow oil.

ESI-MS (m/z): 406 [M+H]$^+$.

Production Example 33

1-(3-Diethylaminopropyl)-3-[4-(4-amino-2-fluorophenoxy)pyridin-2-yl]urea

To a solution of 1-(3-diethylaminopropyl)-3-[4-(2-fluoro-4-nitrophenoxy)pyridin-2-yl]urea (547 mg, 1.35 mmol) in methanol (40 ml)-tetrahydrofuran (20 ml) was added 10% palladium carbon (200 mg), followed by stirring under a hydrogen atmosphere at room temperature for 12 hrs. The catalyst was filtered and washed with methanol. The filtrate was concentrated under a reduced pressure to give a residue, which was then purified by silica gel column chromatography (Fuji Silysia NH, ethyl acetate, then ethyl acetate:methanol=10:1) to provide the titled compound (316 mg, 62.3%) as a yellow oil.

$^1$H-NMR Spectrum (DMSO-d$_6$) δ (ppm): 0.94 (6H, t, J=7.0 Hz), 1.53 (2H, m), 2.38 (2H, m), 2.43 (4H, q, J=7.0 Hz), 3.14 (2H, m), 5.45 (2H, m), 6.41 (1H, d, J=8.4 Hz), 6.47-6.52 (2H, m), 6.84 (1H, s), 6.95 (1H, m), 8.01 (1H, d, J=5.6 Hz), 8.11 (1H, m), 9.08 (1H, s).

Production Example 34

1-[4-(2-Aminopyridin-4-yloxy)-3-fluorophenyl]-3-[(4-fluorophenyl)acetyl]thiourea 4-Fluorophenyl acetate (169 mg, 1.1 mmol) was dissolved in thionyl chloride (651 mg, 5.48 mmol), followed by stirring at 100° C. for 1 hr. The reaction mixture was cooled down to room temperature, and thionyl chloride was evaporated under a reduced pressure. The resultant residue was dissolved in acetonitrile (10 ml), and then potassium thiocyanate (213 mg, 2.19 mmol) was added thereto, followed by stirring at 50° C. for 1 hr. The reaction mixture was cooled down to room temperature, and then 4-(4-amino-2-fluorophenoxy)pyridin-2-ylamine (160 mg, 0.912 mmol) was then added thereto, followed by stirring at room temperature for 59.5 hrs. The reaction mixture was partitioned between water (50 ml) and ethyl acetate (100 ml). The organic layer was washed with brine, and dried over sodium sulfate. The solvent was evaporated to give a residue, which was then purified by silica gel column chromatography (Fuji Silysia NH, hexane:ethyl acetate=1:2, ethyl acetate, and then ethyl acetate:methanol=10:1) to provide the titled compound (84.6 mg, 28%) as yellow powder.
ESI-MS (m/z): 415 [M+H]$^+$.

Production Example 35

4-Methylpiperazine-1-carboxylic acid [4-(2-fluoro-4-nitrophenoxy)pyridin-2-yl]amide To a solution of 4-(2-fluoro-4-nitrophenoxy)pyridin-2-ylamine (300 mg, 1.2 mmol) and triethylamine (0.335 ml, 2.4 mmol) in tetrahydrofuran (30 ml) was added phenyl chloroformate (0.226 ml, 1.8 mmol) dropwise while stirring in an ice bath, followed by stirring for 1 hr. The reaction mixture was concentrated under a reduced pressure to give a residue, to which was then added N,N-dimethylformamide (6.0 ml) and 1-methylpiperazine (537 µl, 4.84 mmol), followed by stirring at room temperature for 3 hrs. To the reaction mixture was added ethyl acetate (150 ml), washed with a saturated aqueous solution of sodium hydrogencarbonate, and dried over anhydrous sodium sulfate. The solvent was evaporated to give a residue, which was then purified by silica gel column chromatography (Fuji Silysia NH, eluent; hexane:ethyl acetate=1:2, then ethyl acetate) to provide the titled compound (450 mg, 75.3%) as a pale yellow oil.
$^1$H-NMR Spectrum (CDCl$_3$) δ (ppm): 2.31 (3H, s), 2.43 (4H, m), 3.51 (4H, m), 6.62 (1H, dd, J=2.0, 6.0H), 7.26-7.31 (1H, m), 7.48 (1H, m), 7.69 (1H, d, J=2.0 Hz), 8.06-8.13 (3H, m). ESI-MS (m/z): 376 [M+H]$^+$.

Production Example 36

4-Methylpiperazine-1-carboxylic acid [4-(4-amino-2-fluorophenoxy)pyridin-2-yl]amide To a solution of 4-methylpiperazine-1-carboxylic acid [4-(2-fluoro-4-nitrophenoxy)pyridin-2-yl]amide (339 mg, 0.903 mmol) in methanol (30 ml) was added 10% palladium carbon (100 mg), followed by stirring under a hydrogen atmosphere at room temperature for 2 hrs. The catalyst was filtered. The filtrate was concentrated under a reduced pressure to give a residue, which was then purified by silica gel column chromatography (Fuji Silysia NH, hexane:ethyl acetate=1:1, then ethyl acetate) to provide the titled compound (196 mg, 62.8%) as a yellow oil.
$^1$H-NMR Spectrum (CDCl$_3$) δ (ppm): 2.30 (3H, s), 2.41 (4H, m), 3.50 (4H, m), 3.79 (2H, brs), 6.43 (1H, ddd, J=1.2, 2.4, 8.8 Hz), 6.47-6.51 (2H, m), 6.93 (1H, m), 7.48 (1H, m), 7.56 (1H, m), 7.98 (1H, d, J=5.6 Hz).

Production Example 37 t-Butyl 4-[4-(2-fluoro-4-nitrophenoxy)pyridin-2-ylcarbamoyl]piperidine-1-carboxylate To a solution of 4-(2-fluoro-4-nitrophenoxy)pyridin-2-ylamine (400 mg, 1.61 mmol) in N,N-dimethylformamide (16 ml) were added Boc-isonipecotic acid (554 mg, 2.42 mmol), triethylamine (0.673 ml, 4.83 mmol) and benzotriazol-1-yloxytris(dimethylamino)phosphonium hexafluorophosphate (1.07 g, 2.42 mmol), followed by stirring at room temperature for 6.5 hrs. Boc-isonipecotic acid (554 mg, 2.42 mmol), triethylamine (0.673 ml, 4.83 mmol), and benzotriazol-1-yloxytris(dimethylamino)phosphonium hexafluorophosphate (1.07 g, 2.42 mmol) were further added thereto, followed by stirring at room temperature for 3 hrs. Furthermore, Boc-isonipecotic acid (554 mg, 2.42 mmol), triethylamine (0.673 ml, 4.83 mmol), and benzotriazol-1-yloxytris(dimethylamino)phosphonium hexafluorophosphate (1.07 g, 2.42 mmol) were added thereto, followed by stirring at room temperature for 3 days. To the reaction mixture was added ethyl acetate (150 ml), washed with a saturated aqueous solution of sodium hydrogencarbonate, and dried over anhydrous sodium sulfate. The solvent was evaporated to give a residue, which was then subjected to silica gel column chromatography (Fuji Silysia NH, eluent; hexane:ethyl acetate=1:1, then ethyl acetate) to provide a crude product of the titled compound (548 mg) as a yellow oil.
ESI-MS (m/z): 461 [M+H]$^+$.

Production Example 38 t-Butyl 4-[4-(4-amino-2-fluorophenoxy)pyridin-2-ylcarbamoyl]piperidine-1-carboxylate To a solution of a crude product of t-butyl 4-[4-(2-fluoro-4-nitrophenoxy)pyridin-2-ylcarbamoyl]piperidine-1-carboxylate (548 mg) in methanol (50 ml) was added 10% palladium carbon (100 mg), followed by stirring under a hydrogen atmosphere at room temperature for 2 hrs. The catalyst was filtered. The filtrate was concentrated under a reduced pressure to give a residue, which was then subjected to silica gel column chromatography (Fuji Silysia BW-300, eluent; hexane:ethyl acetate=1:1 to 1:2, then ethyl acetate) to provide a mixture of the starting material and the target compound. The mixture was dissolved in methanol (50 ml) again, and then 10% palladium carbon (100 mg) was added thereto, followed by stirring under a hydrogen atmosphere at room temperature for 2 hrs. The catalyst was filtered. The filtrate was concentrated under a reduced pressure to give a residue, which was then filtered by silica gel. The filtrate was concentrate under a reduced pressure to provide the titled compound (185 mg) as a yellow oil.
$^1$H-NMR Spectrum (CDCl$_3$) δ (ppm): 1.45 (9H, s), 1.62-1.73 (2H, m), 1.82-1.86 (2H, m), 2.37 (1H, m), 2.74 (2H, m), 4.14 (2H, m), 6.45 (1H, ddd, J=1.4, 2.4, 8.4 Hz), 6.51 (1H, m), 6.61 (1H, dd, J=2.4, 6.0 Hz), 6.94 (1H, m), 7.26 (1H, d, J=1.2H), 7.88 (1H, brs), 8.05 (1H, d, J=6.0 Hz), 8.67 (1H, brs).

Production Example 39 t-Butyl 4-{4-[2-fluoro-(3-phenylacetylureido)phenoxy]pyridin-2-ylcarbamoyl}piperidine-1-carboxylate To a solution of t-butyl 4-[4-(4-amino-2-fluorophenoxy)pyridin-2-ylcarbamoyl]piperidine-1-carboxylate (100 mg, 0.232 mmol) in tetrahydrofuran (4 ml) was added 0.5 M solution of phenylacetyl isocyanate in hexane (1.9 ml, 0.93 mmol, Production Example 1), followed by stirring under a nitrogen atmosphere at room temperature for 2 hrs. The reaction mixture was partitioned between ethyl acetate (100 ml) and a saturated aqueous solution of sodium hydrogencarbonate (50 ml). The organic layer was dried over anhydrous sodium sulfate and concentrated under a reduced pressure. The resultant residue was purified by silica gel column chromatography (Fuji Silysia NH, eluent; hexane:ethyl acetate=1:1, ethyl acetate, and then ethyl acetate:methanol=10:1) to provide the titled compound (60 mg, 43.7%) as a yellow oil.
$^1$H-NMR Spectrum (DMSO-d$_6$) δ (ppm): 1.44 (9H, s), 1.62-1.73 (2H, m), 1.85 (2H, m), 2.41 (1H, m), 2.75 (2H, m), 3.76 (2H, s), 4.14 (2H, m), 6.61 (1H, dd, J=2.4, 6.0 Hz), 7.10-7.18 (2H, m), 7.30-7.41 (5H, m), 7.66 (1H, dd, J=2.8, 11.8 Hz), 7.81 (1H, d, J=2.4 Hz), 8.08 (1H, d, J=6.0 Hz), 8.64 (1H, s), 9.10 (1H, s), 10.71 (1H, s).

Production Example 40 t-Butyl 4-(4-{2-fluoro-4-[3-(4-fluorophenyl)acetylthioureido]phenoxy}pyridin-2-ylcarbamoyl)piperidine-1-carboxylate To a solution of 1-[4-(2-aminopyridin-4-yloxy)-3-fluorophenyl]-3-[(4-fluorophenyl) acetyl]thiourea (84.6 mg, 0.204 mmol) in N,N-dimethylformamide (2.0 ml) were added Boc-isonipecotic acid (93.5 mg, 0.408 mmol), triethylamine (0.0853 ml, 0.612 mmol) and benzotriazol-1-yloxytris(dimethylamino)phosphonium hexafluorophosphate (180 mg, 0.408 mmol), followed by stirring at room temperature for 88 hrs. Boc-isonipecotic acid (93.5 mg, 0.408 mmol), triethylamine (0.0853 ml, 0.612 mmol) and benzotriazol-1-yloxytris(dimethylamino)phosphonium hexafluorophosphate (180 mg, 0.408 mmol) were further added thereto, followed by stirring at room temperature for 32.5 hrs. To the reaction mixture were added ethyl acetate (50 ml), tetrahydrofuran (50 ml) and a saturated aqueous solution of sodium hydrogencarbonate (50 ml) to partition. The organic layer was washed with a 1 N aqueous solution of sodium hydroxide (30 ml) and brine in this order, and dried over anhydrous sodium sulfate. The solvent was evaporated to give a residue, which was then subjected to silica gel column chromatography (Fuji Silysia BW-300; hexane:ethyl acetate=1:1, then ethyl acetate) to provide a crude product of the titled compound (548 mg) as a yellow oil.
ESI-MS (m/z): 648 [M+Na]$^+$.

Production Example 41

2-Amino-4-(2-chloro-4-nitrophenoxy)pyridine

2-Amino-4-chloropyridine (2.57 g) was dissolved in dimethylsulfoxide (30 ml), and then 2-chloro-4-nitrophenol (6.94 g) and N,N-diisopropylethylamine (14 ml) were added thereto, followed by stirring at 160° C. for 6 days. The reaction mixture was cooled down to room temperature, and partitioned between ethyl acetate and a 1 N aqueous solution of sodium hydroxide. The organic layer was washed with a 1 N aqueous solution of sodium hydroxide and brine in this order, and dried over anhydrous sodium sulfate. The solvent was evaporated to give a residue, which was purified by silica gel column chromatography (eluent; hexane:ethyl acetate=1:2, then ethyl acetate) to provide the titled compound (574 mg, 11%) as brown powder.
$^1$H-NMR Spectrum (CDCl$_3$) δ (ppm): 4.53 (2H, br), 6.04 (1H, d, J=2.4 Hz), 6.30 (1H, dd, J=2.4, 5.6 Hz), 7.19 (1H, d, J=8.8 Hz), 8.04 (1H, d, J=5.6 Hz), 8.16 (1H, dd, J=2.4, 8.8 Hz), 8.40 (1H, d, J=2.4 Hz).

Production Example 42

4-(4-Amino-2-chlorophenoxy)-2-[(pyrrolidin-1-yl)carbonylamino]pyridine

2-Amino-4-(2-chloro-4-nitrophenoxy)pyridine (574 mg) was dissolved in tetrahydrofuran (10 ml) under a nitrogen atmosphere, and then triethylamine (0.602 ml) and phenyl chloroformate (0.542 ml) were added dropwise thereto while cooling in an ice bath, followed by stirring at room temperature for 10 min. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to provide a crude product of 4-(2-chloro-4-nitrophenoxy)-2-(phenoxycarbonylamino)pyridine (1.272 g). The crude product (637.3 mg) was dissolved in tetrahydrofuran (6.5 ml), and then pyrrolidine (1.06 ml) was added at room temperature, followed by stirring for 1 hr and evaporating the solvents under a reduced pressure. The resultant residue was dissolved in ethanol (20 ml)-water (5 ml), and then electrolytic iron powder (500 mg) and ammonium chloride (1 g) were added thereto, followed by heating under reflux for 1 hr. The reaction mixture was cooled down to room temperature, and filtered through celite to remove an insoluble portion, which was washed with ethyl acetate-tetrahydrofuran (1:1) and water. The organic layer of the filtrate was separated, washed with water and brine in this order, dried over anhydrous sodium sulfate. The solvent was evaporated under a reduced pressure to give a residue, which was purified by silica gel column chromatography (eluent; ethyl acetate) to provide the titled compound (227 mg) as pale yellow powder.
$^1$H-NMR Spectrum (CDCl$_3$) δ (ppm): 1.90-2.00 (4H, m), 3.40-3.50 (4H, m), 3.70 (2H, br), 6.48 (1H, dd, J=2.4, 5.6 Hz), 6.59 (1H, dd, J=2.8, 8.8 Hz), 6.77 (1H, d, J=2.8 Hz), 6.96 (1H, d, J=8.8 Hz), 7.04 (1H, brs), 7.62 (1H, d, J=2.4 Hz), 8.01 (1H, d, J=5.6 Hz).

Production Example 43

4-(4-Amino-2-chlorophenoxy)-2-[(morpholin-4-yl)carbonylamino]pyridine

A crude product of 4-(2-chloro-4-nitrophenoxy)-2-(phenoxycarbonylamino)pyridine (634.8 mg) was dissolved in tetrahydrofuran (6.5 ml), and then morpholine (0.942 ml) was added thereto at room temperature, followed by stirring overnight and evaporating the solvent under a reduced pressure. The resultant residue was dissolved in ethanol (20 ml)-water (5 ml), and then electrolytic iron powder (500 mg) and ammonium chloride (1 g) were added thereto, followed by heating under reflux for 1 hr. The reaction mixture was cooled down to room temperature, and filtered through celite to remove an insoluble portion, which was washed with ethyl acetate-tetrahydrofuran (1:1) and water. The organic layer of the filtrate was separated, washed with water and brine in this order, dried over anhydrous sodium sulfate. The solvent was evaporated to give a residue, which was purified by silica gel column chromatography (eluent; ethyl acetate, then ethyl acetate:methanol=95:5) to provide the titled compound (283.3 mg) as pale yellow powder.

$^1$H-NMR Spectrum (CDCl$_3$) δ (ppm): 3.40-3.80 (10H, m), 6.49 (1H, dd, J=2.0, 6.0 Hz), 6.61 (1H, dd, J=2.8, 8.8 Hz), 6.79 (1H, d, J=2.8 Hz), 6.95-6.99 (2H, m), 7.55 (1H, brs), 8.02 (1H, d, J=6.0 Hz).

Production Example 44

4-Amino-6-(2-chloro-4-nitropenoxy)pyrimidine

4-Amino-6-chloropyrimidine (648 mg) was dissolved in N,N-dimethylformamide (5 ml), and 2-chloro-4-nitrophenol (1.736 g) and N,N-diisopropylethylamine (3.48 ml) were added thereto, followed by stirring at 160° C. overnight. The reaction mixture was cooled down to room temperature, and partitioned between ethyl acetate and a 1 N aqueous solution of sodium hydroxide. The organic layer was washed with a 1 N aqueous solution of sodium hydroxide and brine in this order, and dried over anhydrous sodium sulfate. The solvent was evaporated under a reducer pressure to give a residue, to which ethyl acetate (10 ml) was then added to precipitate crystals. The crystals were filtered and dried under aeration to provide the titled compound (230 mg, 17%) as pale yellow crystals.

$^1$H-NMR Spectrum (CDCl$_3$) δ (ppm): 5.00 (2H, br), 6.10 (1H, s), 7.38 (1H, d, J=8.8 Hz), 8.20 (1H, dd, J=2.8, 8.8 Hz), 8.22 (1H, s), 8.38 (1H, d, J=2.8 Hz).

Production Example 45

4-(4-Amino-2-chlorophenoxy)-6-[(pyrrolidin-1-yl)carbonylamino]pyrimidine

4-Amino-6-(2-chloro-4-nitropenoxy)pyrimidine (230 mg) was dissolved in tetrahydrofuran (5 ml) under a nitrogen atmosphere, and then triethylamine (0.24 ml) and phenyl chloroformate (0.216 ml) were added dropwise thereto while cooling in an ice bath, followed by stirring at room temperature for 1 hr. Pyrrolidine (0.507 ml) was added thereto, followed by stirring for another 1 hr. The reaction mixture was partitioned between ethyl acetate and a saturated aqueous solution of ammonium chloride. The organic layer was washed with a saturated aqueous solution of ammonium chloride, water, a saturated aqueous solution of sodium hydrogencarbonate and brine in this order, and dried over anhydrous sodium sulfate. The solvent was evaporated under a reduced pressure to give a residue, to which ethanol (20 ml)-water (5 ml) was added to dissolve, and then electrolytic iron powder (400 mg) and ammonium chloride (800 mg) were added thereto, followed by heating under reflux for 2 hr. The reaction mixture was cooled down to room temperature, and filtered through celite to remove an insoluble portion, which was washed with ethyl acetate-tetrahydrofuran (1:1) and water. The organic layer of the filtrate was separated, washed with water and brine in this order, and dried over anhydrous sodium sulfate. The solvent was evaporated under a reduced pressure to give a residue, which was then purified by silica gel column chromatography (eluent; hexane:ethyl acetate=1:4, then ethyl acetate) to provide the titled compound (145.5 mg, 51%) as white powder.

$^1$H-NMR Spectrum (CDCl$_3$) δ (ppm): 1.90-2.05 (4H, m), 3.40-3.55 (4H, m), 3.70 (2H, brs), 6.60 (1H, dd, J=2.4, 5.6 Hz), 6.77 (1H, d, J=2.4 Hz), 6.98 (1H, d, J=5.6 Hz), 7.15 (1H, brs), 7.60 (1H, d, J=0.8 Hz), 8.37 (1H, d, J=0.8 Hz).

Production Example 46

4-(2-Methyl-4-nitrophenoxy)pyridin-2-ylamine

2-Amino-4-chloropyridine (5.0 g), N-methyl pyrrolidone (40 ml), 2-hydroxy-5-nitrotoluene (11.9 g) and diisopropylethylamine (20.1 g) were put in a reaction vessel, followed by heating and stirring under a nitrogen atmosphere at 150° C. for 5 days. The reaction mixture was cooled down to room temperature and concentrated under a reduced pressure. To the resultant residue was added a saturated aqueous solution of sodium hydrogencarbonate, followed by stirring at room temperature overnight. To the reaction mixture was added tetrahydrofuran (200 ml) to partition. The aqueous layer was extracted with diethyl ether (100 ml). The organic layer was washed with brine (100 ml×2), dried over anhydrous sodium sulfate, and concentrated under a reduced pressure. The precipitated solid was suspended in diethyl ether and filtered off. The solid was washed with diethyl ether:ethyl acetate=1:1, and dried under aeration to provide the titled compound (4.36 g, 45.7%) as a yellow solid.

$^1$H-NMR Spectrum (DMSO-d$_6$) δ (ppm): 2.28 (3H, s), 5.89 (1H, d, J=2.0 Hz), 6.04 (2H, brs), 6.19 (1H, dd, J=2.4, 5.6 Hz), 7.23 (1H, d, J=8.8 Hz), 7.87 (1H, d, J=5.6 Hz), 8.14 (1H, d, J=2.8, 8.8 Hz), 8.29 (1H, d, J=2.8 Hz). ESI-MS (m/z): 246 [M+H]$^+$.

Production Example 47

Morpholine-4-carboxylic acid [4-(2-methyl-4-nitrophenoxy)pyridin-2-yl]amide

To a solution of 4-(2-methyl-4-nitrophenoxy)pyridin-2-ylamine (1.00 g, 4.08 mmol) in tetrahydrofuran (50 ml) was added triethylamine (1.14 ml, 8.16 mmol), and then phenyl chloroformate (0.768 ml) was added dropwise thereto while stirring in an ice bath, followed by stirring for 1 hr. Phenyl chloroformate (0.252 ml) was further added thereto while stirring in an ice bath, followed by stirring for 30 min. The reaction mixture was concentrated under a reduced pressure to give a residue, to which N,N-dimethylformamide (18.9 ml) and morpholine (1.42 ml) were added, followed by stirring at room temperature for 5 hrs. The reaction mixture was partitioned between ethyl acetate:tetrahydrofuran=1:1 (150 ml) and water (100 ml). The aqueous layer was extracted with ethyl acetate:tetrahydrofuran=1:1. The combined organic layer was washed with brine, and dried over anhydrous sodium sulfate. The solvent was evaporated to give a residue, which was then purified by silica gel column chromatography (Fuji Silysia NH, eluent; hexane:ethyl acetate=2:1 to 1:1, then ethyl acetate). The crude fraction was concentrated to give a residue, which was purified again by silica gel column chromatography (eluent; hexane:ethyl acetate=1:1, ethyl acetate, and then ethyl acetate:methanol=10:1) to provide the titled compound (772 mg, 52.8%) as a colorless solid.

$^1$H-NMR Spectrum (DMSO-d$_6$) δ (ppm): 2.29 (3H, s), 3.41 (4H, m), 3.54 (4H, m), 6.67 (1H, m), 7.27 (1H, d, J=8.8

Hz), 7.43 (1H, m), 8.15 (1H, d, J=8.8 Hz), 8.20 (1H, d, J=5.6 Hz), 8.32 (1H, s), 9.38 (1H, s).

Production Example 48

Morpholine-4-carboxylic acid [4-(4-amino-2-methylphenoxy)pyridin-2-yl]amide

To a solution of morpholine-4-carboxylic acid [4-(2-methyl-4-nitrophenoxy)pyridin-2-yl]amide (775 mg) in ethanol (50 ml) were added electrolytic iron powder (505 mg), ammonium chloride (967 mg) and water (10 ml), followed by stirring to heat at 90° C. for 20 min. The reaction mixture was cooled down to room temperature, and filtered to remove an insoluble portion, which was then washed with water and N,N-dimethylformamide in this order. The filtrate was concentrated under a reduced pressure to give a residue, which was then partitioned between ethyl acetate:tetrahydrofuran=1:1 (200 ml) and water (100 ml). The organic layer was washed with brine, and dried over anhydrous sodium sulfate. The solvent was evaporated to give a residue, which was then suspended in ethyl acetate (5 ml), and diluted with diethyl ether (30 ml). The solid was filtered, and dried under aeration to provide the titled compound (184 mg, 26.1%) as colorless powder. The mother liquor was concentrated to give a residue, which was suspended in diethyl ether (30 ml). The solid was filtered, and dried under aeration to further provide the titled compound (207 mg, 29.3%) as pale yellow powder.
$^1$H-NMR Spectrum (DMSO-$d_6$) δ (ppm): 1.94 (3H, s), 3.38 (4H, m), 3.54 (4H, m), 5.01 (2H, m), 6.42-6.48 (3H, m), 6.72 (1H, d, J=8.8 Hz), 7.23 (1H, s), 8.04 (1H, d, J=6.0 Hz), 9.13 (1H, s).

Production Example 49

Pyrrolidine-1-carboxylic acid [4-(2-methyl-4-nitrophenoxy)pyridin-2-yl]amide

To a solution of 4-(2-methyl-4-nitrophenoxy)pyridin-2-ylamine (1.00 g) in tetrahydrofuran (50 ml) was added triethylamine (1.14 ml), and then phenyl chloroformate (0.768 ml) was added dropwise thereto while stirring in an ice bath, followed by stirring for 1.5 hrs. Phenyl chloroformate (0.252 ml) was further added thereto while stirring in an ice bath, followed by stirring for 0.5 hr. The reaction mixture was concentrated under a reduced pressure to give a residue, to which N,N-dimethylformamide (20 ml) and pyrrolidine (1.36 ml) were added, followed by stirring at room temperature for 0.5 hr. The reaction mixture was partitioned between ethyl acetate (150 ml) and water (100 ml). The organic layer was washed with brine, and dried over anhydrous sodium sulfate. The solvent was evaporated to give a residue, which was purified by silica gel column chromatography (Fuji Silysia NH, eluent; hexane:ethyl acetate=2:1 to 1:1, then ethyl acetate) to provide the titled compound (988 mg, 70.7%) as a pale yellow solid.
$^1$H-NMR Spectrum (DMSO-$d_6$) δ (ppm): 1.81 (4H, m), 2.29 (3H, s), 3.35 (4H, m), 6.66 (1H, m), 7.27 (1H, d, J=9.0 Hz), 7.53 (1H, s), 8.15 (1H, m), 8.18 (1H, d, J=5.6 Hz), 8.32 (1H, m), 9.31 (1H, s).

Production Example 50

Pyrrolidine-1-carboxylic acid [4-(4-amino-2-methylphenoxy)pyridin-2-yl]amide

To a solution of pyrrolidine-1-carboxylic acid [4-(2-methyl-4-nitrophenoxy)pyridin-2-yl]amide (775 mg) in ethanol (50 ml) were added electrolytic iron powder (505 mg), ammonium chloride (967 mg) and water (10 ml), followed by stirring to heat at 90° C. for 30 min. The reaction mixture was cooled down to room temperature, and filtered to remove an insoluble portion, which was then washed with water and N,N-dimethylformamide in this order. The filtrate was concentrated under a reduced pressure to give a residue, which was partitioned between ethyl acetate (100 ml) and water (100 ml). The organic layer was washed with brine, and dried over anhydrous sodium sulfate. The solvent was evaporated to give a residue, to which ethyl acetate (10 ml) was added, followed by allowing to stand at room temperature. After a solid precipitated, diethyl ether (30 ml) was added thereto, followed by stirring at room temperature for 2 hrs. The solid was filtered off, and dried under aeration to provide the titled compound (467 mg, 66.2%) as powder.
$^1$H-NMR Spectrum (DMSO-$d_6$) δ (ppm): 1.80 (4H, m), 1.94 (3H, s), 3.34 (4H, m), 5.01 (2H, m), 6.42-6.45 (2H, m), 6.49 (1H, d, J=2.4 Hz), 6.72 (1H, d, J=8.4 Hz), 7.33 (1H, d, J=2.4 Hz), 8.02 (1H, d, J=5.6 Hz), 8.54 (1H, s).

Production Example 51

1-(3-Diethylaminopropyl)-3-[4-(2-methyl-4-nitrophenoxy)pyridin-2-yl]urea

To a solution of 4-(2-methyl-4-nitrophenoxy)pyridin-2-ylamine and triethylamine (500 mg) in tetrahydrofuran (50 ml) was added phenyl chloroformate (0.384 ml, 4.08 mmol) dropwise while stirring in an ice bath, followed by stirring for 0.5 hr. The reaction mixture was concentrated under a reduced pressure to give a residue, to which N,N-dimethylformamide (20 ml) and N,N-diethyl-1,3-propanediamine (1.28 ml) were then added, followed by stirring at room temperature for 2 hrs. The reaction mixture was partitioned between ethyl acetate (150 ml) and water (100 ml). The organic layer was washed with brine, dried over anhydrous sodium sulfate and concentrated under a reduced pressure. The resultant residue was purified by silica gel column chromatography (Fuji Silysia NH, eluent; hexane:ethyl acetate=1:1, then ethyl acetate) to provide the titled compound (794 mg, 96.9%) as a pale yellow oil.
ESI-MS (m/z): 402 [M+H]$^+$.

Production Example 52

1-[4-(4-Amino-2-methylphenoxy)pyridin-2-yl]-3-(3-diethylaminopropyl)urea

To a solution of 1-(3-diethylaminopropyl)-3-[4-(2-methyl-4-nitrophenoxy)pyridin-2-yl]urea (794 mg) in ethanol (50 ml) were added electrolytic iron powder (442 mg), ammonium chloride (847 mg) and water (10 ml), followed by stirring to heat at 90° C. for 1 hr. The reaction mixture was cooled down to room temperature, and filtered to remove an insoluble portion. The filtrate was concentrated under a reduced pressure to give a residue, which was then supplied with ethyl acetate (100 ml), washed with a saturated aqueous solution of sodium hydrogencarbonate, and dried over anhydrous sodium sulfate. The solvent was evaporated to give a residue, which was then purified by silica gel column chromatography (eluent; hexane:ethyl acetate=1:1 to 1:2, ethyl acetate, and then ethyl acetate:methanol=20:1 to 10:1) to provide the titled compound (110 mg, 15%).
$^1$H-NMR Spectrum (DMSO-$d_6$) δ (ppm): 0.93 (6H, t, J=7.2 Hz), 1.53 (2H, m), 1.93 (3H, s), 2.38 (2H, m), 2.43 (4H, q, J=7.2 Hz), 3.12 (2H, m), 5.03 (2H, m), 6.39 (1H, dd, J=2.4, 6.0 Hz), 6.44 (1H, dd, J=2.4, 8.4 Hz), 6.49 (1H, d, J=2.4 Hz), 6.72 (2H, m), 7.97 (1H, d, J=6.0 Hz), 8.22 (1H, brs), 9.04 (1H, s). ESI-MS (m/z): 372 [M+H]$^+$.

Production Example 53

1-[4-(4-Amino-3-chlorophenoxy)pyridin-2-yl]-3-ethylurea

2-Amino-4-(4-amino-3-chlorophenoxy)pyridine (707 mg) as disclosed in WO 02/32872 was dissolved in tetrahydrofuran (15 ml) under a nitrogen atmosphere, and then triethylamine (0.523 ml) and phenyl chloroformate (0.470 ml) were added dropwise thereto while cooling in an ice bath, followed by raising the temperature gradually to room temperature while stirring. After 6 hrs, the reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; hexane:ethyl acetate=3:2) to provide a crude product of 4-(4-amino-3-chlorophenoxy)-2-phenoxycarbonylaminopyridine (920 mg). The crude product was dissolved in N,N-dimethylformamide (9 ml), and then 2 M solution of ethylamine in tetrahydrofuran (4.5 ml) was added thereto, followed by stirring at room temperature for 23 hrs. The reaction mixture was partitioned between ethyl acetate and water. The organic layer was washed with brine, and dried over anhydrous sodium sulfate. The solvent was evaporated to give a residue, which was then purified by silica gel column chromatography (eluent; hexane:ethyl acetate=1:2). Fractions containing the target compound were concentrated to give a residue, to which hexane-ethyl acetate (5:1) was added to precipitate crystals. The crystals were filtered, and dried under aeration to provide the titled compound (298 mg, 32%) as white crystals.

$^1$H-NMR Spectrum (CDCl$_3$) δ (ppm): 1.22 (3H, t, J=7.2 Hz), 3.37 (2H, m), 4.05 (2H, s), 6.11 (1H, s), 6.45 (1H, dd, J=2.8, 6.0 Hz), 6.78-6.85 (2H, m), 7.03 (1H, d, J=2.8 Hz)$_1$ 7.98 (1H, d, J=6.0 Hz), 9.21 (1H, brs).

Production Example 54

4-(4-Amino-3-chlorophenoxy)-2-[(pyrrolidin-1-yl)carbonylamino]pyridine

2-Amino-4-(4-amino-3-chlorophenoxy)pyridine (471 mg) as disclosed in WO 02/32872 was dissolved in tetrahydrofuran (10 ml) under a nitrogen atmosphere, and then triethylamine (0.348 ml) and phenyl chloroformate (0.313 ml) were added dropwise thereto while cooling in an ice bath, followed by raising the temperature gradually to room temperature and stirring overnight. To the reaction mixture was added pyrrolidine (2 ml), followed by further stirring for 1 day. The reaction mixture was partitioned between ethyl acetate and water. The organic layer was washed with brine, and dried over anhydrous sodium sulfate. The solvent was evaporated to give a residue, which was then purified by silica gel column chromatography (eluent; ethyl acetate). Fractions containing the target compound were concentrated to give a residue, to which hexane-ethyl acetate (5:1) was added to precipitate crystals. The crystals were filtered off, and dried under aeration to provide the titled compound (232 mg, 35%) as white crystals.

$^1$H-NMR Spectrum (CDCl$_3$) δ (ppm): 1.90-2.00 (4H, m), 3.40-3.55 (4H, m), 4.00 (2H, s), 6.48 (1H, dd, J=2.0, 5.6 Hz), 6.78 (1H, d, J=8.8 Hz), 6.86 (1H, dd, J=2.8, 8.8 Hz), 7.01 (1H, brs), 7.04 (1H, d, J=2.8 Hz), 7.67 (1H, d, J=2.0 Hz), 8.01 (1H, d, J=5.6 Hz).

Production Example 55

1-[4-(4-Amino-3-chlorophenoxy)pyridin-2-yl]-3-diethylurea

2-Amino-4-(4-amino-3-chlorophenoxy)pyridine (236 mg) as disclosed in WO 02/32872 was dissolved in tetrahydrofuran (10 ml) under a nitrogen atmosphere, and then triethylamine (0.21 ml) and phenyl chloroformate (0.188 ml) were added dropwise thereto while cooling in an ice bath, followed by raising the temperature gradually to room temperature and stirring overnight. To the reaction mixture were added N,N-dimethylformamide (2 ml) and N,N-diethylamine (0.5 ml), followed by further stirring for 1 day. The reaction mixture was partitioned between ethyl acetate and water. The organic layer was washed with water and brine in this order, and dried over anhydrous sodium sulfate. The solvent was evaporated to give a residue, which was then purified by silica gel column chromatography (eluent; hexane:ethyl acetate=1:3). Fractions containing the target compound were concentrated to give a residue, to which diethyl ether-hexane (1:1) was added to suspend, followed by evaporating the solvent. The residue was dried in vacuum to provide the titled compound (121.5 mg, 36%) as white powder.

$^1$H-NMR Spectrum (CDCl$_3$) δ (ppm): 1.22 (6H, t, J=6.8 Hz), 3.36 (4H, q, J=6.8 Hz), 4.01 (2H, brs), 6.46 (1H, dd, J=2.4, 5.6 Hz), 6.78 (1H, d, J=8.8 Hz), 6.85 (1H, dd, J=2.4, 8.8 Hz), 7.04 (1H, d, J=2.4 Hz), 7.12 (1H, brs), 7.66 (1H, d, J=2.4 Hz), 8.01 (1H, d, J=5.6 Hz).

Production Example 56

4-(4-Amino-3-chlorophenoxy)-2-[(morpholin-4-yl)carbonylamino]pyridine

2-Amino-4-(4-amino-3-chlorophenoxy)pyridine (236 mg) as disclosed in WO 02/32872 was dissolved in tetrahydrofuran (10 ml) under a nitrogen atmosphere, and then triethylamine (0.21 ml) and phenyl chloroformate (0.188 ml) were added dropwise thereto while cooling in an ice bath, followed by raising the temperature gradually to room temperature and stirring overnight. To the reaction mixture were added N,N-dimethylformamide (2 ml) and morpholine (0.5 ml), followed by further stirring for 1 day. The reaction mixture was partitioned between ethyl acetate and water. The organic layer was washed with brine, and dried over anhydrous sodium sulfate. The solvent was evaporated to give a residue, which was then purified by silica gel column chromatography (eluent; ethyl acetate). Fractions containing the target compound were concentrated to give a residue, to which diethyl ether-hexane was added to suspend, followed by evaporating the solvent. The residue was dried in vacuum to provide the titled compound (172 mg, 49%) as white powder.

$^1$H-NMR Spectrum (CDCl$_3$) δ (ppm): 3.49-3.51 (4H, m), 3.72-3.80 (4H, m), 4.02 (2H, brs), 6.49 (1H, m), 6.79 (1H, dd, J=1.6, 8.0 Hz), 6.86 (1H, m), 7.05 (1H, m), 7.58 (1H, brs), 8.00-8.10 (2H, m).

Production Example 57

4-(4-Amino-3-chlorophenoxy)-2-[(4-methylpiperazin-1-yl)carbonylamino]pyridine 2-Amino-4-(4-amino-3-chlorophenoxy)pyridine (236 mg) as disclosed in WO 02/32872 was dissolved in tetrahydrofuran (10 ml) under a nitrogen atmosphere, and then triethylamine (0.21 ml) and phenyl chloroformate (0.188 ml) were added dropwise thereto while cooling in an ice bath, followed by stirring at room temperature for 1.5 hrs. To the reaction mixture were added N,N-dimethylformamide (2 ml) and 1-methylpiperazine (0.555 ml), followed by further stirring for 1 day. The reaction mixture was partitioned between ethyl acetate and water. The organic layer was washed with brine, and dried over anhydrous sodium sulfate. The solvent was evaporated to give a residue, which was then purified by silica gel column chromatography (eluent; ethyl acetate:methanol=95:5) to provide the titled compound (234 mg, 65%) as pale brown powder.

$^1$H-NMR Spectrum (CDCl$_3$) δ (ppm): 2.32 (3H, s), 2.35-2.50 (4H, m), 3.40-3.60 (4H, m), 4.02 (2H, brs), 6.48 (1H, dd, J=2.4, 5.6 Hz), 6.78 (1H, d, J=8.8 Hz), 6.86 (1H, dd, J=2.4, 8.8 Hz), 7.04 (1H, d, J=2.4 Hz), 7.26 (1H, m), 7.58 (1H, d, J=2.4 Hz), 8.01 (1H, d, J=5.6 Hz).

Production Example 58

4-(4-Amino-3-chlorophenoxy)-2-{1-[(t-butoxycarbonyl)piperidin-4-yl]carbonylamino}pyridine 2-Amino-4-(4-amino-3-chlorophenoxy)pyridine (471 mg) as disclosed in WO 02/32872 was dissolved in N,N-dimethylformamide (10 ml) under a nitrogen atmosphere, and then triethylamine (0.523 ml), 1-(t-butoxycarbonyl)piperidine-4-carboxylic acid (573 mg), and (1H-1,2,3-benzotriazol-1-yloxy)[tri(dimethylamino)]phosphonium hexafluorophosphate (1106 mg) were added thereto at room temperature, followed by stirring for 2.5 hrs. Triethylamine (0.523 ml), 1-(t-butoxycarbonyl)piperidine-4-carboxylic acid (573 mg), and (1H-1,2,3-benzotriazol-1-yloxy)[tri(dimethylamino)]phosphonium hexafluorophosphate (1106 mg) were further added thereto, followed by stirring overnight. The reaction mixture was partitioned between ethyl acetate and water. The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; ethyl acetate:hexane=2:1) to give a residue. To the residue was added diethyl ether-hexane to precipitate crystals. The crystals were filtered off, and dried under aeration to provide the titled compound (644 mg, 72%) as white crystals.

$^1$H-NMR Spectrum (CDCl$_3$) δ (ppm): 1.46 (9H, s), 1.60-1.80 (2H, m), 1.80-2.00 (2H, m), 2.37 (1H, m), 2.60-2.90 (2H, m), 4.03 (2H, brs), 4.10-4.30 (2H, m), 6.56 (1H, dd, J=2.4, 5.6 Hz), 6.79 (1H, d, J=8.8 Hz), 6.85 (1H, dd, J=2.4, 8.8 Hz), 7.04 (1H, d, J=2.4 Hz), 7.76 (1H, m), 7.92 (1H, brs), 8.07 (1H, d, J=5.6 Hz).

Production Example 59

4-{3-Chloro-4-[3-(2-phenylacetyl)thioureido]phenoxy}-2-{[1-(t-butoxycarbonyl)piperidin-4-yl]carbonylamino}pyridine To 4-(4-amino-3-chlorophenoxy)-2-{1-[(t-butoxycarbonyl)piperidin-4-yl]carbonylamino}pyridine (447 mg) was added a 0.11 M solution of phenylacetyl isothiocyanate in acetonitrile (47 ml) at room temperature, followed by stirring overnight. After an insoluble portion was filtered to remove, the filtrate was concentrated under a reduced pressure to give a residue, which was then purified by silica gel column chromatography (eluent; ethyl acetate:hexane=1:1). The resultant residue was dried in vacuum to provide the titled compound (527 mg) as pale yellow powder.

$^1$H-NMR Spectrum (CDCl$_3$) δ (ppm): 1.46 (9H, s), 1.60-1.80 (2H, m), 1.80-2.00 (2H, m), 2.40 (1H, m), 2.60-2.90 (2H, m), 3.77 (2H, s), 4.00-4.30 (2H, m), 6.23 (1H, m), 7.04 (1H, m), 7.20-7.50 (6H, m), 7.87 (1H, m), 8.07 (1H, brs), 8.13 (1H, m), 8.38 (1H, d, J=8.8 Hz), 8.61 (1H, brs), 12.45 (1H, s).

Production Example 60

4-(4-Amino-3-chlorophenoxy)-2-(ethoxycarbonylamino)pyridine

2-Amino-4-(4-amino-3-chlorophenoxy)pyridine (235.7 mg) as disclosed in WO 02/32872 was dissolved in tetrahydrofuran (10 ml) under a nitrogen atmosphere, and then triethylamine (0.21 ml) and ethyl chloroformate (0.143 ml) were added dropwise thereto while cooling in an ice bath, followed by stirring at room temperature for 9 hrs. The reaction mixture was partitioned between ethyl acetate and a saturated aqueous solution of sodium hydrogencarbonate. The organic layer was washed with brine, and dried over anhydrous sodium sulfate. The solvent was evaporated to give a residue, which was then purified by silica gel column chromatography (eluent; ethyl acetate:hexane=1:1) to provide 4-(4-amino-3-chlorophenoxy)-2-(bisethoxycarbonyl)aminopyridine (190 mg, 50%) as a colorless oil. 4-(4-amino-3-chlorophenoxy)-2-(bisethoxycarbonyl)aminopyridine (190 mg) was dissolved in ethanol (5 ml), and then a 1 N aqueous solution of sodium hydroxide (1.0 ml) was added thereto at room temperature, followed by stirring for 15 min. The reaction mixture was partitioned between ethyl acetate and water. The organic layer was washed with brine, and dried over anhydrous sodium sulfate. The solvent was evaporated under a reduced pressure to give a residue, to which diethyl ether-hexane (1:2) was added to precipitate crystals. The crystals were filtered off, and dried under aeration to provide the titled compound (121 mg, 79%) as pale brown crystals.

$^1$H-NMR Spectrum (CDCl$_3$) δ (ppm): 1.30 (3H, t, J=7.2 Hz), 4.03 (2H, brs), 4.21 (2H, q, J=7.2 Hz), 6.50 (1H, dd, J=2.4, 5.6 Hz), 6.79 (1H, d, J=8.8 Hz), 6.86 (1H, dd, J=2.4, 8.8 Hz), 7.05 (1H, d, J=2.4 Hz), 7.53 (1H, brs), 8.09 (1H, d, J=5.6 Hz), 8.18 (1H, brs).

Production Example 61

1-[4-(4-Amino-3-chlorophenoxy)pyridin-2-yl]-3-cyclopropylurea

Similarly to Production Example 53, the titled compound was obtained as pale brown powder (146 mg, 46%) from 2-amino-4-(4-amino-3-chlorophenoxy)pyridine (236 mg) as disclosed in WO 02/32872 and cyclopropylamine.

$^1$H-NMR Spectrum (CDCl$_3$) δ (ppm): 0.40-0.60 (2H, m), 0.70-0.80 (2H, m), 2.71 (1H, m), 4.05 (2H, brs), 6.46 (1H, dd, J=2.4, 5.6 Hz), 6.70-7.00 (4H, m), 7.03 (1H, d, J=2.4 Hz), 7.20-7.25 (1H, m), 7.96 (1H, d, J=5.6 Hz).

Production Example 62

1-[4-(4-Amino-3-chlorophenoxy)pyridin-2-yl]-3-[2-(N,N-diethylamino)ethyl]urea Similarly to Production Example 53, the titled compound was obtained as colorless oil (154.7 mg, 41%) from 2-amino-4-(4-amino-3-chlorophenoxy)pyridine (236 mg) as disclosed in WO 02/32872 and 2-(N,N-diethylamino)ethylamine.

$^1$H-NMR Spectrum (CDCl$_3$) δ (ppm): 1.04 (6H, t, J=6.4 Hz), 2.58 (4H, q, J=6.4 Hz), 2.64 (2H, m), 3.42 (2H, m), 4.07 (2H, brs), 6.43 (1H, m), 6.70-7.25 (5H, m), 7.97 (1H, d, J=5.6 Hz), 9.33 (1H, brs).

Production Example 63

4-(4-Amino-3-chlorophenoxy)-2-[4-(pyrrolidin-1-yl)piperidin-1-ylcarbonylamino]pyridine Similarly to Production Example 53, the titled compound was obtained as white powder (137.8 mg, 33%) from 2-amino-4-(4-amino-3-chlorophenoxy)pyridine (236 mg) as disclosed in WO 02/32872 and 4-(pyrrolidin-1-yl)piperidine.

$^1$H-NMR Spectrum (CDCl$_3$) δ (ppm): 1.20-1.30 (2H, m), 1.40-1.60 (2H, m), 1.70-1.80 (4H, m), 1.90-2.00 (2H, m), 2.21 (1H, m), 2.50-2.70 (4H, m), 2.97 (2H, m), 4.01 (2H, brs), 6.47 (1H, dd, J=2.4, 5.6 Hz), 6.78 (1H, d, J=8.8 Hz), 6.85 (1H, dd, J=2.4, 8.8 Hz), 7.04 (1H, d, J=2.4 Hz), 7.57 (1H, d, J=2.4 Hz), 8.00 (1H, d, J=8.8 Hz).

Production Example 64

4-(4-{3-Chloro-4-[2-(4-fluorophenylcarbamoyl)acetylamino]phenoxy}pyridin-2-ylcarbamoyl)piperidine-1-carboxylic acid t-butyl ester 4-(4-Amino-3-chlorophenoxy)-2-{1-[(t-butoxycarbonyl)piperidin-4-yl]carbonylamino}pyridine (196 mg) was dissolved in N,N-dimethylformamide (2 ml) under a nitrogen atmosphere, and then N-(4-fluorophenyl)malonic acid (260 mg), triethylamine (0.184 ml) and (1H-1,2,3-benzotriazol-1-yloxy)[tri(dimethylamino)]phosphonium hexafluorophosphate (584 mg) were added thereto at 50° C., followed by stirring for 1 hr. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (Fuji Silysia NH, eluent; hexane:ethyl acetate=1:3, then ethyl acetate). Fractions containing the target compound were concentrated to give a residue, which was dried in vacuum to provide the titled compound (234.1 mg, 85.2%) as a colorless oil.

$^1$H-NMR Spectrum (CDCl$_3$) δ (ppm): 1.39 (9H, s), 1.55-1.70 (2H, m), 1.75-1.85 (2H, m), 2.35-2.50 (1H, m), 2.60-2.75 (2H, m), 3.62 (2H, m), 4.07 (2H, m), 6.55 (1H, dd, J=2.4, 5.6 Hz), 6.85-6.98 (3H, m), 7.10 (1H, m), 7.43-7.52 (2H, m), 7.78 (1H, m), 8.05 (1H, d, J=5.6 Hz), 8.23 (1H, d, J=8.8 Hz), 9.18 (1H, brs), 9.67 (1H, s), 9.92 (1H, s).

Production Example 65

Pyrrolidine-1-carbothioic acid [4-(4-amino-3-chlorophenoxy)pyridin-2-yl]amide 2-Amino-4-(4-amino-3-chlorophenoxy)pyridine (250 mg) as disclosed in WO 02/32872 was dissolved in tetrahydrofuran (5 ml) under a nitrogen atmosphere, and then triethylamine (0.185 ml) and phenyl chlorothioformate (0.184 ml) were added dropwise thereto while cooling in an ice bath, followed by stirring at room temperature for 2.5 hrs. To the reaction mixture were further added triethylamine (0.074 ml) and phenyl chlorothioformate (0.073 ml), followed by stirring at room temperature for 40 min. To the reaction mixture was added pyrrolidine (0.530 ml), followed by stirring overnight. Pyrrolidine (0.530 ml) was further added thereto, followed by stirring for 1 hr. The reaction mixture was warmed to 40° C. and stirred for 30 min, and warmed to 50° C. and stirred for 2.5 hrs. The reaction mixture was partitioned between ethyl acetate and water. The organic layer was washed with brine, and dried over anhydrous sodium sulfate. The solvent was evaporated to give a residue, which was then purified by silica gel column chromatography (eluent; hexane:ethyl acetate=1:1 to 1:3). Fractions containing the target compound were concentrated to give a residue, which was dried in vacuum to provide the titled compound (73.2 mg, 19.8%) as a colorless solid.

$^1$H-NMR Spectrum (CDCl$_3$) δ (ppm): 1.80-2.30 (4H, m), 3.62 (2H, m), 3.84 (2H, m), 4.02 (2H, m), 6.14 (1H, m), 6.80 (1H, d, J=8.8 Hz), 6.90 (1H, dd, J=2.8, 8.8 Hz), 7.09 (1H, d, J=2.8 Hz), 7.67 (1H, m), 8.04 (1H, m), 8.23 (1H, m).

Production Example 66

1-[4-(4-Amino-3-chlorophenoxy)pyridin-2-yl]-3-(3-morpholin-4-ylpropyl)urea 4-(4-Amino-3-chlorophenoxy)pyridin-2-ylamine (750 mg, 3.18 mmol) was dissolved in tetrahydrofuran (30 ml), and then triethylamine (0.444 ml, 4.77 mmol) was added thereto. Phenyl chloroformate (0.399 ml, 4.77 mmol) was added dropwise thereto while ice-cooling, followed by stirring at room temperature for 4 hrs and 45 min. Triethylamine (0.222 ml) and phenyl chloroformate (0.200 ml) were further added thereto while ice-cooling, followed by stirring for 40 min. Triethylamine (0.111 ml) and phenyl chloroformate (0.100 ml) were further added thereto, followed by stirring for 40 min. The reaction mixture was concentrated under a reduced pressure to give a residue, to which N,N-dimethylformamide (10 ml) and 3-(morpholin-4-yl)propylamine (2.32 ml, 15.9 mmol) were added, followed by stirring at room temperature for 2 hrs. The reaction mixture was partitioned between ethyl acetate (50 ml) and water (20 ml). The organic layer was washed with a saturated aqueous solution of sodium hydrogencarbonate, and dried over anhydrous sodium sulfate. The solvent was evaporated to give a solid, which was then suspended in ethyl acetate, filtered, washed with ethyl acetate, and dried under aeration to provide the titled compound (359 mg, 0.844 mmol, 27.8%) as colorless powder.

$^1$H-NMR Spectrum (DMSO-d$_6$) δ (ppm): 1.59 (2H, m), 2.28 (2H, m), 2.32 (4H, m), 3.15 (2H, dd, J=6.4, 6.4 Hz), 3.56 (4H, t, J=4.4 Hz), 5.36-5.39 (2H, m), 6.47 (1H, dd, J=2.4, 5.6

Hz), 6.82-6.89 (3H, m), 7.08 (1H, d, J=2.4 Hz), 8.02 (1H, d, J=5.6 Hz), 8.11 (1H, brs), 9.06 (1H, s). ESI-MS (m/z): 406 [M+H]$^+$.

Production Example 67

1-[4-(4-Amino-3-chlorophenoxy)pyridin-2-yl]-3-[3-(1-methylpiperazin-4-yl)propyl]urea 4-(4-Amino-3-chlorophenoxy)pyridin-2-ylamine (750 mg, 3.18 mmol) was dissolved in tetrahydrofuran (30 ml), and then triethylamine (0.444 ml, 4.77 mmol) was added thereto. Phenyl chloroformate (0.399 ml, 4.77 mmol) was added dropwise thereto while ice-cooling, followed by stirring at room temperature for 4 hrs and 45 min. Triethylamine (0.222 ml) and phenyl chloroformate (0.200 ml) were further added thereto, followed by stirring for 40 min. Triethylamine (0.111 ml) and phenyl chloroformate (0.100 ml) were further added thereto, followed by stirring for 40 min. The reaction mixture was concentrated under a reduced pressure to give a residue, to which N,N-dimethylformamide (10 ml) and 3-(1-methylpiperazin-4-yl)propylamine (2.32 ml, 15.9 mmol) were added, followed by stirring at room temperature for 2 hrs. The reaction mixture was partitioned between ethyl acetate (50 ml) and water (20 ml). The organic layer was washed with a saturated aqueous solution of sodium hydrogencarbonate, and dried over anhydrous sodium sulfate. The solvent was evaporated to give a residue, which was then purified by silica gel column chromatography (Fuji Silysia NH, ethyl acetate, then ethyl acetate:methanol=10:1 to 20:3). The crude purified fraction was concentrated, and purified again by silica gel column chromatography (Fuji Silysia NH, hexane:ethyl acetate=1:1, ethyl acetate, then ethyl acetate:methanol=10:1 to 20:3) to provide the titled compound (691 mg, 1.65 mmol, 51.9%) as colorless powder.
$^1$H-NMR Spectrum (DMSO-d$_6$) δ (ppm): 1.57 (2H, m), 2.13 (3H, s), 2.24-2.45 (10H, m), 3.13 (2H, m), 5.38 (2H, m), 6.47 (1H, dd, J=2.4, 6.0 Hz), 6.82-6.91 (3H, m), 7.08 (1H, d, J=2.4 Hz), 8.01 (1H, d, J=6.0 Hz), 8.11 (1H, d, J=6.0 Hz), 9.04 (1H, s).

Production Example 68

Piperidine-1-carboxylic acid [4-(4-amino-3-chlorophenoxy)pyridin-2-yl]amide 4-(4-Amino-3-chlorophenoxy)pyridin-2-ylamine (750 mg, 3.18 mmol) was dissolved in tetrahydrofuran (30 ml), and then triethylamine (0.444 ml, 4.77 mmol) was added thereto. Phenyl chloroformate (0.399 ml, 4.77 mmol) was added dropwise thereto while ice-cooling, followed by stirring at room temperature for 3.5 hrs. Triethylamine (0.444 ml) and phenyl chloroformate (0.399 ml) were further added thereto while ice-cooling, followed by stirring for 15 min. N,N-dimethylformamide (6.0 ml) and piperidine (1.5 ml) were added thereto, followed by stirring at room temperature for 5.5 hrs. The reaction mixture was concentrated under a reduced pressure, and then N,N-dimethylformamide (4.0 ml) and piperidine (1.0 ml) were added thereto, followed by stirring at room temperature for 36 hrs. The reaction mixture was partitioned between ethyl acetate and water. The organic layer was washed with brine, and dried over anhydrous sodium sulfate. The solvent was evaporated to give a residue, which was then purified by silica gel column chromatography (eluent; hexane:ethyl acetate=1:1 to 1:2, ethyl acetate, then ethyl acetate:methanol=10:1). Fractions containing the target compound were concentrated to give a solid, which was suspended in diethyl ether, filtered, and dried under aeration to provide the titled compound (462 mg, 1.33 mmol, 41.9%) as a pale yellow solid.
$^1$H-NMR Spectrum (DMSO-d$_6$) δ (ppm): 1.44 (4H, m), 1.54 (2H, m), 3.38 (4H, m), 5.37 (2H, s), 6.49 (1H, dd, J=2.2, 5.6 Hz), 6.86-6.89 (2H, m), 7.07 (1H, d, J=2.0 Hz), 7.31 (1H, d, J=2.2 Hz), 8.06 (1H, d, J=5.6 Hz), 9.05 (1H, s). ESI-MS (m/z): 347 [M+H]$^+$.

Production Example 69

Azetidine-1-carboxylic acid [4-(4-amino-3-chlorophenoxy)pyridin-2-yl]amide 4-(4-Amino-3-chlorophenoxy)pyridin-2-ylamine (750 mg, 3.18 mmol) was dissolved in tetrahydrofuran (30 ml), and then triethylamine (0.444 ml, 4.77 mmol) was added thereto. Phenyl chloroformate (0.399 ml, 4.77 mmol) was added dropwise thereto while ice-cooling, followed by stirring at room temperature for 5 hrs. Triethylamine (0.222 ml) and phenyl chloroformate (0.200 ml) were further added thereto while ice-cooling, followed by stirring for 40 min. Triethylamine (0.111 ml) and phenyl chloroformate (0.100 ml) were further added thereto while ice-cooling, followed by stirring for 30 min. The reaction mixture was concentrated under a reduced pressure to give a residue, to which N,N-dimethylformamide (10 ml), azetidine hydrochloride (1.49 g, 15.9 mmol) and triethylamine (2.66 ml, 19.1 mmol) were added thereto, followed by stirring at room temperature for 3 hrs. To the reaction mixture were added ethyl acetate (50 ml) and water (20 ml), and was further added a saturated aqueous solution of sodium hydrogencarbonate to partition. The organic layer was washed with brine, and dried over anhydrous sodium sulfate. The solvent was evaporated to give a residue, which was then purified by silica gel column chromatography (hexane:ethyl acetate=1:1, ethyl acetate, then ethyl acetate:methanol=20:1 to 10:1). Fractions containing the target compound were concentrated to give a solid, which was suspended in diethyl ether, filtered, and dried under aeration to provide the titled compound (492 mg, 1.54 mmol, 48.5%) as colorless powder.
$^1$H-NMR Spectrum (DMSO-d$_6$) δ (ppm): 2.12 (2H, m), 3.93 (4H, t, J=7.8 Hz), 5.37 (2H, m), 6.50 (1H, dd, J=2.4, 5.8 Hz), 6.83-6.89 (2H, m), 7.07 (1H, d, J=2.4 Hz), 7.42 (1H, d, J=2.4 Hz), 8.05 (1H, d, J=5.8 Hz), 8.99 (1H, s). ESI-MS (m/z): 318 [M+H]$^+$.

Production Example 70

1-[4-(4-Amino-3-chlorophenoxy)pyridin-2-yl]-3-(3-diethylaminopropyl)urea 4-(4-Amino-3-chlorophenoxy)pyridin-2-ylamine (750 mg, 3.18 mmol) was dissolved in tetrahydrofuran (30 ml), and then triethylamine (0.444 ml, 4.77 mmol) was added thereto. Phenyl chloroformate (0.399 ml, 4.77 mmol) was added dropwise thereto while ice-cooling, followed by stirring at room temperature for 5 hrs. Triethylamine (0.222 ml) and phenyl chloroformate (0.200 ml) were further added thereto, followed by stirring for 40 min. Triethylamine (0.111 ml) and phenyl chloroformate (0.100 ml) were further added thereto, followed by stirring for 30 min. The reaction mixture was concentrated under a reduced pressure to give a residue, to which N,N-dimethylformamide (10 ml) and 3-(diethylamino)propylamine (2.49 ml, 15.9 mmol) were added, followed by stirring at room temperature for 3 hrs. To the reaction mixture were added ethyl acetate (50 ml) and water (20 ml), and further added a saturated aqueous solution of sodium hydrogencarbonate to partition. The organic layer was washed with brine, and dried over anhydrous sodium sulfate. The solvent was evaporated to give a residue, which was then dried in vacuum to provide the titled compound (645 mg, 1.65 mmol, 51.8%) as a pale yellow solid.

$^1$H-NMR Spectrum (DMSO-d$_6$) δ (ppm): 0.93 (6H, t, J=7.2 Hz), 1.53 (2H, m), 2.38 (2H, t, J=7.2 Hz), 2.43 (4H, q, J=7.2 Hz), 3.14 (2H, m), 5.39 (2H, s), 6.47 (1H, dd, J=2.2, 6.0 Hz), 6.80 (1H, d, J=2.2 Hz), 6.84-6.89 (2H, m), 7.08 (1H, d, J=2.2 Hz), 8.00 (1H, d, J=6.0 Hz), 8.19 (1H, brs), 9.07 (1H, s).

Production Example 71

4-(3-Methyl-4-nitrophenoxy)pyridin-2-ylamine

To a solution of 2-amino-4-chloropyridine (2.50 g, 19.4 mmol) in N-methylpyrrolidone (20 ml) were added 3-methyl-4-nitrophenol (5.94 g, 38,8 mmol) and diisopropylethylamine (13.5 ml, 77.5 mmol), followed by stirring at 150° C. under a nitrogen atmosphere. The reaction mixture was cooled down to room temperature, and diisopropylethylamine in the mixture was evaporated under a reduced pressure. The resultant residue was partitioned between ethyl acetate (150 ml) and a 1 N aqueous solution of sodium hydroxide (50 ml). The aqueous layer was extracted with ethyl acetate (50 ml). The combined organic layer was washed with brine, and dried over anhydrous sodium sulfate. The solvent was evaporated to give a residue, which was then purified by silica gel column chromatography (eluent; hexane/ethyl acetate=1/2, ethyl acetate, then ethyl acetate/methanol=20/1) to provide the titled compound (1.64 g, 34.4%) as a brown solid.

$^1$H-NMR Spectrum (DMSO-d$_6$) δ (ppm): 2.54 (3H, s), 5.98 (1H, d, J=2.4 Hz), 6.07 (2H, brs), 6.23 (1H, dd, J=2.4, 5.6 Hz), 7.14 (1H, dd, J=2.4, 8.8 Hz), 7.25 (1H, d, J=2.4 Hz), 7.89 (1H, d, J=5.6 Hz), 8.10 (1H, d, J=8.8 Hz). ESI-MS (m/z): 246 [M+H]$^+$.

Production Example 72

Morpholine-4-carboxylic acid [4-(4-amino-3-methylphenoxy)pyridin-2-yl]amide

To a solution of 4-(3-methyl-4-nitrophenoxy)pyridin-2-ylamine (553 mg, 2.26 mmol) in tetrahydrofuran (20 ml) was added triethylamine (0.471 ml, 3.38 mmol) under a nitrogen atmosphere. Phenyl chloroformate (0.424 ml, 3.38 mmol) was added thereto while ice-cooling, followed by stirring for 20 min. The reaction mixture was concentrated under a reduced pressure to give a residue, to which N,N-dimethylformamide (8.0 ml) and morpholine (0.786 ml, 9.02 mmol) was added, followed by stirring at room temperature for 11 hrs. The reaction mixture was partitioned between ethyl acetate (60 ml) and water (60 ml). The organic layer was washed with brine, dried over anhydrous sodium sulfate, and concentrated under a reduced pressure. The resultant residue was dissolved in ethanol (20 ml), and then electrolytic iron powder (505 mg, 9.04 mmol), ammonium chloride (967 ml, 18.1 mmol) and water (5 ml) were added thereto, followed by stirring to heat at 80° C. for 2 hrs. The reaction mixture was cooled down to room temperature, and filtered to remove an insoluble portion. The filtrate was concentrated under a reduced pressure to give a residue, which was then purified by silica gel column chromatography (eluent; hexane/ethyl acetate=1/1, ethyl acetate, then ethyl acetate/methanol=10/1) to provide the titled compound (283 mg, 38.1%) as a brown oil.

$^1$H-NMR Spectrum (DMSO-d$_6$) δ (ppm): 2.05 (3H, s), 3.39 (4H, m), 3.55 (4H, m), 4.85 (2H, m), 6.48 (1H, dd, J=2.4, 5.6 Hz), 6.63-6.70 (2H, m), 6.73 (1H, s), 7.29 (1H, d, J=2.4 Hz), 8.04 (1H, d, J=5.6 Hz), 9.13 (1H, s).

Production Example 73

Pyrrolidine-1-carboxylic acid [4-(4-amino-3-methylphenoxy)pyridin-2-yl]amide

To a solution of 4-(3-methyl-4-nitrophenoxy)pyridin-2-ylamine (553 mg, 2.26 mmol) in tetrahydrofuran (20 ml) was added triethylamine (0.471 ml, 3.38 mmol) under a nitrogen atmosphere. Phenyl chloroformate (0.424 ml, 3.38 mmol) was added thereto while ice-cooling, followed by stirring for 20 min. The reaction mixture was concentrated under a reduced pressure to give a residue, to which N,N-dimethylformamide (8.0 ml) and pyrrolidine (0.753 ml, 9.02 mmol), followed by stirring at room temperature for 10 min. The reaction mixture was partitioned between ethyl acetate (60 ml) and water (60 ml). The organic layer was washed with brine, dried over anhydrous sodium sulfate, and concentrated under a reduced pressure. The resultant residue was dissolved in ethanol (20 ml), and then electrolytic iron powder (505 mg, 9.04 mmol), ammonium chloride (967 ml, 18.1 mmol) and water (5 ml) were added thereto, followed by stirring to heat at 80° C. for 2 hrs. The reaction mixture was cooled down to room temperature, and filtered to remove an insoluble portion. The filtrate was concentrated under a reduced pressure to give a residue, which was then purified by silica gel column chromatography (eluent; hexane/ethyl acetate=1/1, ethyl acetate, then ethyl acetate/methanol=10/1) to provide the titled compound (277 mg, 39.2%) as orange powder.

$^1$H-NMR Spectrum (DMSO-d$_6$) δ (ppm): 1.80 (4H, m), 2.05 (3H, s), 3.30 (4H, m), 4.85 (2H, m), 6.46 (1H, dd, J=2.0, 5.6 Hz), 6.63-6.70 (2H, m), 6.73 (1H, d, J=2.4 Hz), 7.39 (1H, d, J=2.0 Hz), 8.02 (1H, d, J=5.6 Hz), 8.54 (1H, s).

Production Example 74

4-(4-Amino-3-methylphenoxy)pyridin-2-ylamine

To a solution of 4-(3-methyl-4-nitrophenoxy)pyridin-2-ylamine (1.64 g, 6.69 mmol) in methanol (75 ml) was added 10% palladium carbon (300 mg), followed by stirring under a hydrogen atmosphere at room temperature 14.5 hrs. The reaction mixture was filtered to remove the catalyst. The filtrate was concentrated under a reduced pressure to give a residue, which was purified by silica gel column chromatography (eluent; hexane:ethyl acetate=1:2, ethyl acetate, then ethyl acetate:methanol=20:1 to 10:1) to provide the titled compound (765 mg, 53.1%) as a brown solid.

$^1$H-NMR Spectrum (CDCl$_3$) δ (ppm): 2.14 (3H, s), 3.45 (2H, brs), 4.47 (2H, brs), 5.87 (1H, d, J=2.0 Hz), 6.23 (1H, dd, J=2.0, 6.0 Hz), 6.65 (1H, d, J=8.4 Hz), 6.74 (1H, dd, J=2.8, 8.4 Hz), 6.77 (1H, d, J=2.8 Hz), 7.85 (1H, d, J=6.0 Hz).

Production Example 75

N-[4-(2-Aminopyridin-4-yloxy)-2-methylphenyl]-N'-(4-fluorophenyl)malonamide

To a solution of 4-(4-amino-3-methylphenoxy)pyridin-2-ylamine (765 mg, 3.55 mmol) in N,N-dimethylformamide (15.0 ml) were added N-(4-fluorophenyl)malonic acid (770 mg, 3.91 mmol), triethylamine (0.544 ml, 3.91 mmol) and benzotriazol-1-yloxytris(dimethylamino)phosphonium hexafluorophosphate (1.73 g, 3.91 mmol), followed by stirring at room temperature for 13 hrs. The reaction mixture was partitioned between ethyl acetate (200 ml) and a saturated aqueous solution of sodium hydrogencarbonate (80 ml). The organic layer was washed with water and brine, and dried over anhydrous sodium sulfate. The solvent was evaporated to give a residue, which was then subjected to silica gel column chromatography (ethyl acetate, then ethyl acetate/methanol=20/1 to 10/1). To the resultant crude product were added ethanol (0.5 ml) and diethyl ether (10 ml) to suspend. A solid was filtered off, washed with diethyl ether, and dried under aeration to provide the titled compound (805 mg, 57.5%) as pale yellow powder.

$^1$H-NMR Spectrum (DMSO-d$_6$) δ (ppm): 2.25 (3H, s), 3.52 (2H, s), 5.81 (1H, d, J=2.0 Hz), 5.94 (2H, s), 6.14 (1H, dd, J=2.0, 6.0 Hz), 6.94 (1H, dd, J=2.0, 8.8 Hz), 7.02 (1H, d, J=2.0 Hz), 7.17 (2H, dd, J=9.0, 9.0 Hz), 7.54 (1H, d, J=8.8 Hz), 7.63 (2H, dd, J=5.0, 9.0 Hz), 7.79 (1H, d, J=6.0 Hz), 9.62 (1H, s), 10.26 (1H, s). ESI-MS (m/z): 395 [M+H]$^+$.

Production Example 76

4-(4-Nitro-3-trifluoromethylphenoxy)pyridin-2-ylamine

To a solution of 2-amino-4-chloropyridine (2.0 g, 15.6 mmol) in N-methylpyrrolidone (16 ml) were added 5-hydroxy-2-nitrobenzotrifluoride (4.85 g, 23.4 mmol) and diisopropylethylamine (8.15 ml, 46.8 mmol), followed by stirring under a nitrogen atmosphere to heat at 150° C. for 62 hrs. The reaction mixture was cooled down to room temperature and the diisopropylethylamine was evaporated under a reduced pressure. The resultant residue was partitioned between ethyl acetate:tetrahydrofuran=1:1 (300 ml) and a 1 N aqueous solution of sodium hydroxide (100 ml). The organic layer was washed with a 1 N aqueous solution of sodium hydroxide and brine in this order, and dried over anhydrous sodium sulfate. The solvent was evaporated to give a residue, which was then purified by silica gel column chromatography (eluent; heptane/ethyl acetate=1/2, ethyl acetate, then ethyl acetate/methanol=20/1). The crude product was subjected to silica gel filtration (Fuji Silysia NH) The filtrate was concentrated to give a solid, which was then suspended in diethyl ether: hexane=1:1, filtered, and dried under aeration to provide the titled compound (760 mg, 16.3%) as a brown solid.

$^1$H-NMR Spectrum (DMSO-d$_6$) δ (ppm): 6.05 (1H, s), 6.15 (2H, s), 6.30 (1H, m), 7.61 (1H, d, J=9.2 Hz), 7.77 (1H, s), 7.93 (1H, m), 8.26 (1H, d, J=9.2 Hz)

Production Example 77

4-(4-Amino-3-trifluoromethylphenoxy)pyridin-2-ylamine

To a solution of 4-(4-nitro-3-trifluoromethylphenoxy)pyridin-2-ylamin (400 mg, 1.34 mmol) in methanol (20 ml) was added 10% palladium carbon (146 mg), followed by stirring under a hydrogen atmosphere at room temperature for 10 hrs. The reaction mixture was filtered to remove the catalyst. The filtrate was concentrated under a reduced pressure to give a residue, which was then purified by silica gel column chromatography (eluent; ethyl acetate) to provide the titled compound (201 mg, 55.4%) as a brown oil.

$^1$H-NMR Spectrum (CDCl$_3$) δ (ppm): 4.27 (2H, brs), 4.56 (2H, brs), 5.85 (1H, d, J=2.4 Hz), 6.19 (1H, m), 6.74 (1H, d, J=8.6 Hz), 6.99 (1H, dd, J=2.4, 8.6 Hz), 7.13 (1H, d, J=2.4 Hz), 7.85 (1H, d, J=6.0 Hz).

Production Example 78

N-[4-(2-Aminopyridin-4-yloxy)-2-trifluoromethylphenyl]-N'-(4-fluorophenyl)malonamide To a solution of 4-(4-amino-3-trifluoromethylphenoxy)pyridin-2-ylamine (201 mg, 0.747 mmol) in N,N-dimethylformamide (2.0 ml) were added N-(4-fluorophenyl)malonic acid (221 mg, 1.12 mmol), triethylamine (0.156 ml, 1.12 mmol) and benzotriazol-1-yloxytris(dimethylamino)phosphonium hexafluorophosphate (496 mg, 1.12 mmol), followed by stirring at room temperature for 5 hrs. The reaction mixture was partitioned between ethyl acetate (100 ml) and water (50 ml). The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; ethyl acetate, then ethyl acetate:methanol=10:1) to provide the titled compound (335 mg, 17.6%) as a brown oil.

$^1$H-NMR Spectrum (CDCl$_3$) δ (ppm): 3.58 (2H, s), 4.71 (2H, brs), 5.95 (1H, d, J=2.0 Hz), 6.28 (1H, dd, J=2.0, 6.0 Hz), 7.01-7.04 (2H, m), 7.25 (1H, dd, J=2.8, 8.4 Hz), 7.36 (1H, d, J=2.8 Hz), 7.50-7.54 (2H, m). 7.93 (1H, d, J=6.0 Hz), 8.22 (1H, d, J=8.4 Hz), 9.27 (1H, s), 9.68 (1H, s).

Production Example 79

1-Benzyloxy-3-methoxy-4-nitrobenzene

3-Fluoro-4-nitrophenol (15.71 g) was dissolved in N,N-dimethylformamide (150 ml), and then potassium carbonate (16.59 g) and benzyl bromide (14.27 ml) were added thereto at 60° C., followed by stirring for 3 hrs. The reaction mixture was cooled down to room temperature, and partitioned between ethyl acetate and water. The organic layer was washed with water and brine in this order, and dried over anhydrous sodium sulfate. The solvent was evaporated to give a residue (35.09 g), which was dissolved in methanol (200 ml), and then potassium carbonate (27.64 g) was added thereto, followed by heating under reflux for 1 hr. The reaction mixture was cooled down to room temperature, and concentrated under a reduced pressure to give a residue, which was then partitioned between ethyl acetate and water. The organic layer was washed with water and brine in this order, and dried over anhydrous sodium sulfate. The solvent was evaporated to give a residue, to which diethyl ether (200 ml) was added, followed by stirring. The precipitated crystals were filtered and dried under aeration to provide the titled compound (21.10 g, 81%) as pale yellow crystals.

$^1$H-NMR Spectrum (CDCl$_3$) δ (ppm): 3.93 (3H, s), 5.14 (2H, s), 6.56-6.62 (2H, m), 7.30-7.50 (5H, m), 8.00 (1H, d, J=9.2 Hz).

Production Example 80

4-Amino-3-methoxyphenol

1-Benzyloxy-3-methoxy-4-nitrobenzene (11.0 g) was dissolved in tetrahydrofuran (100 ml)-methanol (100 ml), and then 10% palladium carbon (5.0 g) was added thereto, followed by replacing with hydrogen inside the system and stirring overnight. After replacing with nitrogen inside the system, the reaction mixture was filtered to remove the catalyst, which was washed with tetrahydrofuran, ethyl acetate and methanol in this order. The filtrate was concentrated under a reduced pressure to give a residue, which was dried in vacuum to provide the titled compound (5.88 g, quantitatively) as brown powder.

$^1$H-NMR Spectrum (CDCl$_3$) δ (ppm): 3.82 (3H, s), 6.27 (1H, dd, J=2.4, 8.0 Hz), 6.41 (1H, d, J=2.4 Hz), 6.59 (1H, d, J=8.0 Hz).

Production Example 81

2-Amino-4-(4-amino-3-methoxyphenoxy)pyridine

4-Amino-3-methoxyphenol (5.88 g) was dissolved in dimethyl sulfoxide (80 ml) while stirring, and then 60% sodium hydride (1.6 g) was added thereto gradually under a nitrogen stream, followed by stirring for 20 min. 2-amino-4-chloropyridine (2.75 g) was then added thereto, followed by stirring at 160° C. for 8 hrs. The reaction mixture was cooled down to room temperature, and partitioned between ethyl acetate and water. The organic layer was washed with water and brine in this order, and dried over anhydrous sodium sulfate. The solvent was evaporated under a reduced pressure to give a residue, which was then purified by silica gel column chromatography (eluent; ethyl acetate, then ethyl acetate:methanol=9:1). Fractions containing the target compound were concentrated to give a residue, to which diethyl ether was then added to precipitate crystals. The crystals were filtered and dried under aeration to provide the titled compound (1.56 g, 34%) as pale brown crystals.

$^1$H-NMR Spectrum (CDCl$_3$) δ (ppm): 3.77 (2H, br), 3.83 (3H, s), 4.34 (2H, br), 5.91 (1H, d, J=2.0 Hz), 6.28 (1H, dd, J=2.0, 5.6 Hz), 6.52-6.56 (2H, m), 6.70 (1H, dd, J=0.4, 8.0 Hz), 7.90 (1H, d, J=5.6 Hz).

Production Example 82

2-Amino-4-{3-methoxy-4-[3-(2-phenylacetyl)thioureido]phenoxy}pyridine

2-Phenylacetyl chloride (0.198 ml) was dissolved in acetonitrile (10 ml) under a nitrogen atmosphere, and then potassium thiocyanate (292 mg) was added at 60° C., followed by stirring at the same temperature for 3.5 hrs. The reaction mixture was cooled down to room temperature, and then 2-amino-4-(4-amino-3-methoxyphenoxy)pyridine (231.3 mg) was added thereto, followed by further stirring for 2 hrs. The reaction mixture was partitioned between ethyl acetate and a saturated aqueous solution of sodium hydrogencarbonate. The organic layer was washed with water and brine in this order, and dried over anhydrous sodium sulfate. The solvent was evaporated under a reduced pressure to give a residue, which was then purified by silica gel column chromatography (eluent; ethyl acetate, then ethyl acetate:methanol=9:1) to provide the titled compound (158 mg, 39%) as pale brown powder.

$^1$H-NMR Spectrum (CDCl$_3$) δ (ppm): 3.71 (3H, s), 3.77 (2H, s), 5.13 (2H, br), 5.86 (1H, d, J=2.4 Hz), 6.25 (1H, dd, J=2.4, 6.0 Hz), 6.54 (1H, d, J=2.4 Hz), 6.67 (1H, dd, J=2.4, 8.8 Hz), 7.30-7.45 (6H, m), 7.70 (1H, brs), 7.82 (1H, d, J=6.0 Hz), 8.35 (1H, d, J=8.8 Hz).

Production Example 83

Benzyl N-(4-aminophenyl)carbamate 1,4-Diaminobenzene (1.081 g) was dissolved in tetrahydrofuran (50 ml) under a nitrogen atmosphere while stirring, and then triethylamine (2.01 ml) and benzyl chloroformate (1.71 ml) were added dropwise thereto while cooling in an ice-bath, followed by raising the temperature gradually up to room temperature. After 7 hrs, to the reaction mixture was added a saturated aqueous solution of sodium hydrogencarbonate, followed by extracting with ethyl acetate. The organic layer was washed with brine, and dried over anhydrous sodium sulfate. The solvent was evaporated under a reduced pressure to give a residue, which was then purified by silica gel column chromatography (eluent; hexane:ethyl acetate=1:1). Fractions containing the target compound were concentrated to give a residue, which was then suspended in hexane-ethyl acetate. The solid was filtered off, and dried under aeration to provide the titled compound (1.093 g, 45%) as pale yellow powder.

$^1$H-NMR Spectrum (CDCl$_3$) δ (ppm): 3.56 (2H, brs), 5.18 (2H, s), 6.45 (1H, brs), 6.60-6.70 (2H, m), 7.10-7.20 (2H, m), 7.30-7.50 (5H, m).

Production Example 84

Benzyl N-[4-(6-aminopyrimidin-4-ylamino)phenyl]carbamate

6-Amino-4-chloropyrimidine (259 mg) was dissolved in 2-ethoxyethanol (10 ml), and then benzyl N-(4-aminophenyl)carbamate (533 mg) and 2 N HCl (2 ml) were added thereto, followed by stirring at 120° C. overnight. The reaction mixture was cooled down to room temperature, and partitioned between ethyl acetate and a saturated aqueous solution of sodium hydrogencarbonate. The organic layer was washed with brine, and dried over anhydrous sodium sulfate. The solvent was evaporated under a reduced pressure to give a residue, which was then purified by silica gel column chromatography (eluent; ethyl acetate:methanol=95:5). Fractions containing the target compound were concentrated to give a residue, to which ethyl acetate-hexane was then added to precipitate crystals. The solid was filtered, and dried under aeration to provide the titled compound (313.1 mg, 47%) as opaline crystals.

$^1$H-NMR Spectrum (CDCl$_3$) δ (ppm): 4.59 (2H, brs), 5.22 (2H, s), 5.72 (1H, m), 6.53 (1H, brs), 6.69 (1H, brs), 7.20 (2H, d, J=8.8 Hz), 7.30-7.50 (7H, m), 8.20 (1H, s).

Production Example 85

Benzyl N-{4-[6-(pyrrolidin-1-ylcarbonyl)aminopyrimidin-4-ylamino]phenyl}carbamate Benzyl N-[4-(6-aminopyrimidin-4-ylamino)phenyl]carbamate (313 mg) was dissolved in tetrahydrofuran (10 ml) under a nitrogen atmosphere, and then triethylamine (0.78 ml) and phenyl chloroformate (0.35 ml) were added dropwise thereto while cooling in an ice bath, followed by stirring at room temperature for 30 min. To the reaction mixture were added pyrrolidine (1.0 ml) and N,N-dimethylformamide (2 ml), followed by further stirring at room temperature overnight. The reaction mixture was partitioned between ethyl acetate and water. The organic layer was washed with brine, and dried over anhydrous sodium sulfate. The solvent was evaporated under a reduced pressure to give a residue, which was then purified by silica gel column chromatography (eluent; ethyl acetate, then ethyl acetate:methanol=95:5) to provide the titled compound (210 mg, 52%) as pale yellow powder.

$^1$H-NMR Spectrum (CDCl$_3$) δ (ppm): 1.90-2.00 (4H, m), 3.40-3.50 (4H, m), 5.20 (2H, s), 6.73 (1H, brs), 6.75 (1H, brs), 6.95 (1H, brs), 7.28-7.47 (10H, m), 8.28 (1H, d, J=1.2 Hz).

Production Example 86

4-(4-Aminophenylamino)-6-[(pyrrolidin-1-yl)carbonylamino]pyrimidine

Benzyl N-{4-[6-(pyrrolidin-1-ylcarbonyl)aminopyrimidin-4-ylamino]phenyl}carbamate (210 mg) was dissolved in tetrahydrofuran (5 ml)-methanol (5 ml), and then 10% palladium carbon (200 mg) was added thereto under a nitrogen atmosphere, followed by replacing with hydrogen inside the system and stirring for 5 hrs. After replacing with nitrogen inside the system, the reaction mixture was filtered to remove the catalyst, which was washed with tetrahydrofuran and ethanol in this order. The filtrate was concentrated under a reduced pressure to give a residue, to which hexane-ethyl acetate was added to precipitate crystals. The crystals were filtered, and dried under aeration to provide the titled compound (103 mg, 71%) as white crystals.

$^1$H-NMR Spectrum (CDCl$_3$) δ (ppm): 1.90-2.00 (4H, m), 3.30-3.50 (4H, m), 3.64 (2H, brs), 6.55 (1H, brs), 6.68-6.71 (2H, m), 6.90 (1H, brs), 7.10 (2H, d, J=8.4 Hz), 7.33 (1H, s), 8.24 (1H, s).

Production Example 87

Benzyl N-[4-(2-aminopyrimidin-4-ylamino)phenyl]carbamate

2-Amino-4-chloropyridine (257 mg) was dissolved in 2-ethoxyethanol (10 ml), and then benzyl N-(4-aminophenyl)carbamate (533 mg) and pyridine hydrochloride (462 mg) were added thereto, followed by stirring at 120° C. overnight. The reaction mixture was cooled down to room temperature, and partitioned between ethyl acetate and a saturated aqueous solution of sodium hydrogencarbonate. The organic layer was washed with brine, and dried over anhydrous sodium sulfate. The solvent was evaporated under a reduced pressure to give a residue, which was then purified by silica gel column chromatography (Fuji Silysia NH, eluent; ethyl acetate, then ethyl acetate:methanol=95:5). Fractions containing the target compound were concentrated to give a residue, to which ethyl acetate-hexane was then added to precipitate crystals. The solid was filtered, and dried under aeration to provide the titled compound (321.5 mg, 48%) as pale brown crystals.

$^1$H-NMR Spectrum (CDCl$_3$) δ (ppm): 4.28 (2H, brs), 5.21 (2H, s), 5.76 (1H, s), 5.95 (1H, m), 6.17 (1H, dd, J=2.0, 6.0 Hz), 6.66 (1H, brs), 7.12 (2H, d, J=8.8 Hz), 7.30-7.45 (7H, m), 7.79 (1H, d, J=6.0 Hz).

Production Example 88

4-(4-Aminophenylamino)-2-[(pyrrolidin-1-yl)carbonylamino]pyridine

Benzyl N-[4-(2-aminopyridin-4-ylamino)phenyl]carbamate (321 mg) was dissolved in tetrahydrofuran (10 ml) under a nitrogen atmosphere, and then triethylamine (0.803 ml) and phenyl chloroformate (0.36 ml) were added dropwise thereto while cooling in an ice bath, followed by stirring at room temperature for 1 hr. To the reaction mixture were added pyrrolidine (0.8 ml) and N,N-dimethylformamide (2 ml), followed by stirring further at room temperature overnight. The reaction mixture was partitioned between ethyl acetate and water. The organic layer was washed with brine, and dried over anhydrous sodium sulfate. The solvent was evaporated under a reduced pressure to give a residue (950 mg), which was then dissolved in dimethyl sulfoxide (5.0 ml), and then a 5 N aqueous solution of sodium hydroxide (1.0 ml) was added thereto, followed by stirring at 100° C. for 30 min. The reaction mixture was cooled down to room temperature, and partitioned between ethyl acetate and water. The organic layer was washed with water and brine in this order, and dried over anhydrous sodium sulfate. The solvent was evaporated to give a residue, which was then purified by silica gel column chromatography (Fuji Silysia NH, eluent; ethyl acetate, then ethyl acetate:methanol=95:5) to provide the titled compound (116 mg, 41%) as pale yellow crystals.

$^1$H-NMR Spectrum (CDCl$_3$) δ (ppm): 1.90-2.00 (4H, m), 3.40-3.50 (4H, m), 3.64 (2H, brs), 5.82 (1H, brs), 6.31 (1H, m), 6.65-6.75 (2H, m), 6.90 (1H, brs), 6.99-7.03 (2H, m), 7.53 (1H, d, J=2.4 Hz), 7.80 (1H, d, J=6.0 Hz).

Production Example 89

6-(2-Fluoro-4-nitrophenoxy)pyrimidin-4-ylamine

2-Fluoro-4-nitrophenol (1.736 g) was dissolved in dimethyl sulfoxide (10 ml), and then sodium hydride (400 mg) was added thereto, followed by stirring for 20 min. Then, 4-amino-6-chloropyrimidine (648 mg) was added thereto, followed by stirring at 100° C. for 45 min. The reaction mixture was heated up to 120° C., followed by stirring for 1 hr and 25 min. Then, the reaction mixture was heated up to 140° C., followed by stirring overnight. The reaction mixture was cooled down to room temperature, and then a 1 N aqueous solution of sodium hydroxide (10 ml) was added thereto, followed by stirring and extracting with ethyl acetate. The organic layer was washed with a 1 N aqueous solution of sodium hydroxide, water and brine in this order, and dried over anhydrous sodium sulfate. The solvent was evaporated under a reduced pressure to give a residue, which was then purified by silica gel column chromatography (eluent; hexane:ethyl acetate=1:2). The solvent was evaporated under a reduced pressure to give a residue, which was suspended in diethyl ether (7 ml)-hexane (3.5 ml). The solid was filtered off, and dried under aeration to provide the titled compound (201 mg, 16.0%) as pale brown powder.

$^1$H-NMR Spectrum (DMSO-d$_6$) δ (ppm): 6.02 (1H, m), 7.06 (2H, brs), 7.60 (1H, dd, J=8.0, 8.8 Hz), 8.04 (1H, m), 8.10-8.19 (1H, m), 8.30 (1H, dd, J=2, 10 Hz).

Production Example 90

Pyrrolidine-1-carboxylic acid [6-(2-fluoro-4-nitrophenoxy)pyrimidin-4-yl]amide 4-Amino-6-(2-fluoro-4-nitrophenoxy)pyrimidine (100 mg) was dissolved in tetrahydrofuran (3 ml) under a nitrogen atmosphere, and then triethylamine (0.112 ml) and phenyl chloroformate (0.100 ml) were added dropwise thereto, followed by stirring for 1.5 hrs. To the reaction mixture was added pyrrolidine (0.313 ml), followed by stirring for 30 min. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=2:1). The solvent was evaporated under a reduced pressure to give a residue, which was partitioned between ethyl acetate and a 1 N aqueous solution of sodium hydroxide. The organic layer was washed with water and brine in this order, and dried over anhydrous

Production Example 91

Pyrrolidine-1-carboxylic acid [6-(4-amino-2-fluorophenoxy)pyrimidin-4-yl]amide

Pyrrolidine-1-carboxylic acid [6-(2-fluoro-4-nitrophenoxy)pyrimidin-4-yl]amide (610 mg) was dissolved in ethanol (15 ml)-water (3 ml), and then electrolytic iron powder (610 mg) and ammonium chloride (1.20 g) were added thereto, followed by heating under reflux for 30 min. The reaction mixture was cooled down to room temperature, and ethyl acetate-tetrahydrofuran (1:1) was then added thereto, followed by stirring. The mixture was filtered through celite to remove an insoluble portion, which was washed with ethyl acetate and water. The organic layer of the filtrate was washed with water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1 to 1:5). Fractions containing the target compound was concentrated under a reduced pressure, and dried in vacuum to provide the titled compound (495 mg, 88.6%) as a pale yellow solid.

$^1$H-NMR Spectrum (CDCl$_3$) δ (ppm): 1.99 (4H, m), 3.48 (4H, m), 3.74 (2H, m), 6.43 (1H, m), 6.44-6.53 (1H, m), 6.94 (1H, m), 7.17 (1H, m), 7.63 (1H, s), 8.37 (1H, s).

Production Example 92

Morpholine-4-carboxylic acid [6-(2-fluoro-4-nitrophenoxy)pyrimidin-4-yl]amide

4-Amino-6-(2-fluoro-4-nitrophenoxy)pyrimidine (89 mg) was dissolved in tetrahydrofuran (3 ml) under a nitrogen atmosphere, and then triethylamine (0.099 ml) and phenyl chloroformate (0.089 ml) were added dropwise thereto while cooling in an ice bath, followed by stirring at room temperature for 45 min. To the reaction mixture was added morpholine (0.249 ml), followed by stirring at room temperature overnight. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1). Fractions containing the target compound was concentrated under a reduced pressure, and dried in vacuum to provide the titled compound (80.2 mg, 62.0%) as a colorless solid.

$^1$H-NMR Spectrum (CDCl$_3$) δ (ppm): 3.55 (4H, m), 3.77 (4H, m), 7.36-7.44 (2H, m), 7.74 (1H, d, J=0.8 Hz), 8.06-8.16 (2H, m), 8.33 (1H, m).

Production Example 93

Morpholine-4-carboxylic acid [6-(4-amino-2-fluorophenoxy)pyrimidin-4-yl]amide

Morpholine-4-carboxylic acid [6-(2-fluoro-4-nitrophenoxy)pyrimidin-4-yl]amide (107 mg) was dissolved in ethanol (5 ml)-water (1 ml), and then electrolytic iron powder (110 mg) and ammonium chloride (220 mg) were added thereto, followed by heating under reflux for 30 min. The reaction mixture was cooled down to room temperature, and ethyl acetate-tetrahydrofuran (1:1) was then added thereto, followed by stirring. The reaction mixture was filtered through celite to remove an insoluble portion, which was washed with ethyl acetate and water. The organic layer of the filtrate was washed with water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1). Fractions containing the target compound were concentrated under a reduced pressure, and dried in vacuum to provide the titled compound (82.4 mg, 85.2%) as a yellow solid.

$^1$H-NMR Spectrum (CDCl$_3$) δ (ppm): 3.52 (4H, m), 3.74 (6H, m), 6.42-6.48 (1H, m), 6.50 (1H, m), 6.97 (1H, m), 7.52 (1H, m), 7.66 (1H, m), 8.37 (1H, m).

Production Example 94

Piperidine-1-carboxylic acid [6-(2-fluoro-4-nitrophenoxy)pyrimidin-4-yl]amide

4-Amino-6-(2-fluoro-4-nitrophenoxy)pyrimidine (300 mg) was dissolved in tetrahydrofuran (5 ml) under a nitrogen atmosphere, and then triethylamine (0.335 ml) and phenyl chloroformate (0.301 ml) were added dropwise thereto while cooling in an ice bath, followed by stirring at room temperature for 45 min. To the reaction mixture was added piperidine (0.446 ml), followed by stirring at room temperature for 45 min. The reaction mixture was partitioned between ethyl acetate and a saturated aqueous solution of ammonium chloride. The organic layer was washed with a saturated aqueous solution of ammonium chloride, a 1 N aqueous solution of sodium hydroxide, water and brine in this order, and dried over anhydrous sodium sulfate. The solvent was evaporated under a reduced pressure to give a residue, which was then purified by silica gel column chromatography (eluent; hexane:ethyl acetate=3:2). Fractions containing the target compound was concentrated under a reduced pressure, and dried in vacuum to provide the titled compound (275.4 mg, 63.5%) as a pale yellow oil.

$^1$H-NMR Spectrum (CDCl$_3$) δ (ppm): 1.54-1.76 (4H, m), 3.50 (6H, m), 7.38-7.48 (2H, m), 7.74 (1H, s), 8.06-8.16 (2H, m), 8.32 (1H, s).

Production Example 95

Piperidine-1-carboxylic acid [6-(4-amino-2-fluorophenoxy)pyrimidin-4-yl]amide

Piperidine-1-carboxylic acid [6-(2-fluoro-4-nitrophenoxy)pyrimidin-4-yl]amide (273 mg) was dissolved in ethanol (15 ml)-water (3 ml), and then electrolytic iron powder (275 mg) and ammonium chloride (550 mg) were added thereto, followed by heating under reflux for 30 min. The reaction mixture was cooled down to room temperature, and ethyl acetate-tetrahydrofuran (1:1) was then added thereto,

---

(continued from previous page) sodium sulfate. The solvent was evaporated under a reduced pressure to give a residue, which was then dried in vacuum to provide the titled compound (96.6 mg, 69.5%) as a yellow solid.

$^1$H-NMR Spectrum (CDCl$_3$) δ (ppm): 2.02 (4H, m), 3.51 (4H, m), 7.22 (1H, m), 7.41 (1H, m), 7.81 (1H, d, J=1.2 Hz), 8.07-8.15 (2H, m), 8.32 (1H, m).

followed by stirring. The reaction mixture was filtered through celite to remove an insoluble portion, which was washed with ethyl acetate and water. The organic layer of the filtrate was washed with water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1 to 1:5). Fractions containing the target compound was concentrated under a reduced pressure, and dried in vacuum to provide the titled compound (235.8 mg, 94.1%) as a pale yellow solid.

$^1$H-NMR Spectrum (CDCl$_3$) δ (ppm): 1.63 (6H, m), 3.47 (4H, m), 3.74 (2H, brs), 6.45 (1H, m), 6.50 (1H, dd, J=2, 12 Hz), 6.97 (1H, m), 7.36 (1H, brs), 7.56 (1H, m), 8.36 (1H, m).

Production Example 96

3-[6-(2-Fluoro-4-nitrophenoxy)pyrimidin-4-yl]-1,1-dimethylurea

4-Amino-6-(2-fluoro-4-nitrophenoxy)pyrimidine (500 mg) was dissolved in tetrahydrofuran (10 ml) under a nitrogen atmosphere, and then triethylamine (0.418 ml) and phenyl chloroformate (0.376 ml) were added dropwise thereto while cooling in an ice bath, followed by stirring at room temperature for 1 hr and 10 min. Triethylamine (0.139 ml) and phenyl chloroformate (0.125 ml) were added further thereto while cooling in an ice bath, followed by stirring at room temperature for 30 min. Triethylamine (0.139 ml) and phenyl chloroformate (0.125 ml) were added further thereto, followed by stirring at room temperature for 30 min. To the reaction mixture was added 2 M dimethylamine (a methanol solution) (5.0 ml), followed by stirring at room temperature overnight. The reaction mixture was partitioned between ethyl acetate and a saturated aqueous solution of ammonium chloride. The organic layer was washed with a saturated aqueous solution of ammonium chloride, a saturated aqueous solution of sodium hydrogencarbonate, water and brine in this order, and dried over anhydrous sodium sulfate. The solvent was evaporated under a reduced pressure to give a residue, which was then suspended in diethyl ether. The solid was filtered, and dried under aeration to provide the titled compound (378.9 mg, 59.0%) as pale yellow powder.

$^1$H-NMR Spectrum (CDCl$_3$) δ (ppm): 3.08 (6H, s), 7.41 (2H, m), 7.77 (1H, brs), 8.11 (2H, m), 8.32 (1H, brs).

Production Example 97

3-[6-(4-Amino-2-fluorophenoxy)pyrimidin-4-yl]-1,1-dimethylurea

3-[6-(2-Fluoro-4-nitrophenoxy)pyrimidin-4-yl]-1,1-dimethylurea (227 mg) was dissolved in ethanol (15 ml)-water (3 ml), and then electrolytic iron powder (230 mg) and ammonium chloride (460 mg) were added thereto, followed by heating under reflux for 30 min. The reaction mixture was cooled down to room temperature, and ethyl acetate-tetrahydrofuran (1:1) was then added thereto, followed by stirring. The reaction mixture was filtered through celite to remove an insoluble portion, which was washed with ethyl acetate and water. The organic layer of the filtrate was washed with water and brine in this order, and dried over anhydrous sodium sulfate. The solvent was evaporated under a reduced pressure to give a residue, which was then purified by silica gel column chromatography (eluent; hexane:ethyl acetate=1:3). Fractions containing the target compound were concentrated under a reduced pressure to give a residue, which was suspended in diethyl ether (4 ml)-hexane (4 ml). The solid was filtered and dried under aeration to provide the titled compound (172 mg, 83.4%) as a pale yellow solid.

$^1$H-NMR Spectrum (CDCl$_3$) δ (ppm): 3.05 (6H, m), 3.74 (2H, brs), 6.45 (1H, m), 6.50 (1H, m), 6.97 (1H, m), 7.32 (1H, brs), 7.60 (1H, d, J=1.2 Hz), 8.37 (1H, d, J=1.2 Hz).

Production Example 98

N-{4-[6-(3,3-Dimethylureido)pyrimidin-4-yloxy]-3-fluorophenyl}malonic acid benzyl ester 3-[6-(4-Amino-2-fluorophenoxy)pyrimidin-4-yl]-1,1-dimethylurea (92.0 mg) was dissolved in N,N-dimethylformamide (2 ml) under a nitrogen atmosphere, and then malonic acid monobenzyl ester (184.0 mg), triethylamine (0.132 ml), and (1H-1,2,3-benzotriazol-1-yloxy)[tri(dimethylamino)]phosphonium hexafluorophosphate (419 mg) at 50° C., followed by stirring at the same temperature for 1 hr. The reaction mixture was cooled down to room temperature, and partitioned between ethyl acetate and a saturated aqueous solution of sodium hydrogencarbonate. The organic layer was washed with a saturated aqueous solution of sodium hydrogencarbonate, a saturated aqueous solution of ammonium chloride, water and brine in this order, and dried over anhydrous sodium sulfate. The solvent was evaporated under a reduced pressure to give a residue, which was then purified by silica gel column chromatography (eluent; hexane:ethyl acetate=1:1 to 1:5). Fractions containing the target compound were concentrated under a reduced pressure to provide the titled compound (119.4 mg, 80.8%) as a colorless oil.

$^1$H-NMR Spectrum (CDCl$_3$) δ (ppm): 3.06 (6H, s), 3.53 (2H, s), 5.24 (2H, s), 7.12-7.25 (2H, m), 7.35-7.46 (6H, m), 7.65 (1H, s), 7.68 (1H, dd, J=2, 12 Hz), 8.34 (1H, s), 9.32 (1H, brs).

Production Example 99

N-{4-[6-(3,3-Dimethylureido)pyrimidin-4-yloxy]-3-fluorophenyl}malonic acid

N-{4-[6-(3,3-Dimethylureido)pyrimidin-4-yloxy]-3-fluorophenyl}malonic acid benzyl ester (119 mg) was dissolved in tetrahydrofuran (3 ml)-methanol (3 ml), and then 10% palladium carbon (54 mg) was added thereto under a nitrogen atmosphere, followed by replacing with hydrogen inside the system and stirring for 1 hrs. After replacing with nitrogen inside the system, the reaction mixture was filtered to remove the catalyst, which was washed with methanol. The filtrate was concentrated under a reduced pressure to give a residue, which was suspended in diethyl ether-hexane (1:1). The solid was filtered, and dried under aeration to provide the titled compound (76.8 mg, 79.8%) as a white solid.

$^1$H-NMR Spectrum (DMSO-d$_6$) δ (ppm): 2.94 (6H, s), 3.17 (1H, brs), 3.18-3.54 (2H, m), 7.44-7.48 (2H, m), 7.36 (1H, d, J=1.2 Hz), 7.74 (1H, m), 8.39 (1H, d, J=1.2 Hz), 9.56 (1H, brs), 10.6 (1H, brs).

Production Example 100

N-(3-Fluoro-4-{6-[(pyrrolidine-1-carbonyl)amino]pyrimidin-4-yloxy}phenyl)malonic acid benzyl ester Pyrrolidine-1-carboxylic acid [6-(4-amino-2-fluorophenoxy)pyrimidin-4-yl]amide (290 mg) was dissolved in N,N-dimethylformamide (3 ml) under a nitrogen atmosphere, and then malonic acid monobenzyl ester (534 mg), triethylamine (0.383 ml) and (1H-1,2,3-benzotriazol-1-yloxy)[tri(dimethylamino)]phosphonium hexafluorophosphate (1.22 g) at 50° C., followed by stirring for 30 min. The reaction mixture was cooled down to room temperature, and partitioned between ethyl acetate and a saturated aqueous solution of sodium hydrogencarbonate. The organic layer was washed with a saturated aqueous solution of sodium hydrogencarbonate, a saturated aqueous solution of ammonium chloride, water and brine in this order, and dried over anhydrous sodium sulfate. The solvent was evaporated under a reduced pressure to give a residue, which was then purified by silica gel column chromatography (eluent; hexane:ethyl acetate=1:1 to 1:2). Fractions containing the target compound were concentrated under a reduced pressure to provide the titled compound (523.7 mg, quantitatively) as a pale yellow oil.

$^1$H-NMR Spectrum (CDCl$_3$) δ (ppm): 2.00 (4H, m), 3.49 (4H, m), 3.53 (2H, s), 5.24 (2H, s), 7.10-7.25 (3H, m), 7.39 (4H, m), 7.68 (2H, m), 8.02 (1H, brs), 8.34 (1H, m), 9.33 (1H, brs).

Production Example 101

N-(3-Fluoro-4-{6-[(pyrrolidine-1-carbonyl)amino] pyrimidin-4-yloxy}phenyl)malonic acid N-(3-Fluoro-4-{6-[(pyrrolidine-1-carbonyl)amino]pyrimidin-4-yloxy}phenyl}malonic acid benzyl ester (430 mg) was dissolved in tetrahydrofuran (13 ml)-methanol (13 ml), and then 10% palladium carbon (191 mg) was added thereto under a nitrogen atmosphere, followed by replacing with hydrogen inside the system and stirring for 30 min. After replacing with nitrogen inside the system, the reaction mixture was filtered to remove the catalyst, which was washed with methanol. The filtrate was concentrated under a reduced pressure to give a residue, which was suspended in diethyl ether-hexane (1:1). The solid was filtered, and dried under aeration to provide the titled compound (361.5 mg, quantitatively) as a pale yellow solid.

$^1$H-NMR Spectrum (DMSO-d$_6$) δ (ppm): 1.83 (4H, brs), 3.10-3.50 (7H, m), 7.32 (2H, m), 7.45 (1H, s), 7.74 (1H, m), 8.39 (1H, m), 9.40 (1H, brs), 10.50 (1H, brs).

Production Example 102

[1,4']Bipiperidinyl-1'-carboxylic acid [6-(4-nitro-2-fluorophenoxy)pyrimidin-4-yl]amide 4-Amino-6-(2-fluoro-4-nitrophenoxy)pyrimidine (40 mg) was dissolved in tetrahydrofuran (2 ml) under a nitrogen atmosphere, and then triethylamine (0.045 ml) and phenyl chloroformate (0.040 ml) were added dropwise thereto, followed by stirring at room temperature for 1 hr. The reaction mixture was concentrated under a reduced pressure to give a residue, which was then dissolved in N,N-dimethylformamide (2 ml). 4-(Piperidin-1-yl)piperidine (108 mg) was added thereto, followed by stirring for 10 min. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1 to 1:2). Fractions containing the target compound were concentrated under a reduced pressure, and dried in vacuum to provide the titled compound (43.9 mg, 61.7%) as a yellow solid.

$^1$H-NMR Spectrum (CDCl$_3$) δ (ppm): 1.36-1.82 (8H, m), 1.92 (2H, m), 2.52 (5H, m), 2.94 (2H, m), 4.15 (2H, m), 7.41 (1H, m), 7.46 (1H, m), 7.73 (1H, m), 8.11 (2H, m), 8.32 (1H, m).

Production Example 103

4-(Pyrrolidin-1-yl)piperidine-1-carboxylic acid [6-(4-amino-2-fluorophenoxy)pyrimidin-4-yl]amide 4-Amino-6-(2-fluoro-4-nitrophenoxy)pyrimidine (50 mg) was dissolved in tetrahydrofuran (3 ml) under a nitrogen atmosphere, and then triethylamine (0.056 ml) and phenyl chloroformate (0.050 ml) were added dropwise thereto, followed by stirring at room temperature for 30 min. The reaction mixture was concentrated under a reduced pressure to give a residue, which was then dissolved in N,N-dimethylformamide (3 ml). 4-(Pyrrolidin-1-yl)piperidine (123 mg) was added thereto, followed by stirring at room temperature for 2 hrs. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:5). The solvent was evaporated under a reduced pressure, and dried in vacuum to provide a crude product of 4-(pyrrolidin-1-yl)piperidine-1-carboxylic acid [6-(2-fluoro-4-nitrophenoxy)pyrimidin-4-yl]amide. The crude product (86 mg) was dissolved in tetrahydrofuran (2 ml)-methanol (2 ml), and then 10% palladium carbon (43 mg) was added thereto under a nitrogen atmosphere, followed by replacing with hydrogen inside the system and stirring overnight. After replacing with nitrogen inside the system, the reaction mixture was filtered to remove the catalyst, which was washed with methanol. The filtrate was concentrated under a reduced pressure to give a residue, which was purified by silica gel column chromatography (Fuji Silysia NH, eluent; hexane:ethyl acetate=1:5, then ethyl acetate). Fractions containing the target compound were concentrated under a reduced pressure to provide the titled compound (53.5 mg, 66.8%).

$^1$H-NMR Spectrum (DMSO-d$_6$) δ (ppm): 1.31 (2H, m), 1.66 (4H, m), 1.81 (2H, m), 2.14 (1H, m), 2.47 (4H, m), 2.92 (2H, m), 3.97 (2H, m), 5.30-5.42 (2H, m), 6.37 (1H, dd, J=2.0, 8.8 Hz), 6.46 (1H, m), 6.94 (1H, dd, J=8.8, 8.8 Hz), 7.23 (1H, m), 8.37 (1H, m), 9.75 (1H, brs).

Production Example 104

3-[4-(4-Amino-2-fluorophenoxy)pyridin-2-yl]-1-methyl-1-[3-(4-methylpiperazin-1-yl)propyl]urea 4-(2-Fluoro-4-nitrophenoxy)pyridin-2-ylamine (200 mg) was dissolved in tetrahydrofuran (8 ml) under a nitrogen atmosphere, and then triethylamine (0.336 ml) and phenyl chloroformate (0.302 ml) were added dropwise thereto at room temperature, followed by stirring for 30 min. The reaction mixture was concentrated under a reduced pressure to give a residue, which was then dissolved in N,N-dimethylformamide (5 ml). N-methyl-N-[3-(4-methylpiperazin-1-yl)propyl]amine (0.300 ml) was added thereto, followed by stirring at room temperature overnight. N-methyl-N-[3-(4-methylpiperazin-1-yl)propyl]amine (0.200 ml) was further added thereto, followed by stirring at room temperature for 1 day. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; heptane:ethyl acetate=1:1). The solvent was evaporated under a reduced pressure to provide a crude product of 3-[4-(2-fluoro-4-nitrophenoxy)pyridin-2-yl]-1-methyl-1-[3-(4-methylpiperazin-1-yl)propyl]urea. The crude product (357 mg) was dissolved in tetrahydrofuran (8 ml)-methanol (8 ml), and then 10% palladium carbon (170 mg) was added thereto under a nitrogen atmosphere, followed by replacing with hydrogen inside the system and stirring for 2 hrs. After replacing with nitrogen inside the system, the reaction mixture was filtered to remove the catalyst, which was washed with methanol. The filtrate was concentrated under a reduced pressure to give a residue, which was purified by silica gel column chromatography (Fuji Silysia NH, eluent; heptane:ethyl acetate=1:1, then ethyl acetate). Fractions containing the target compound were concentrated to give a residue, which was then suspended in diethyl ether-hexane (2:1). The solid was filtered and dried under aeration to provide the titled compound (91.0 mg, 27.3%) as pale yellow powder.

$^1$H-NMR Spectrum (CDCl$_3$) δ (ppm): 1.65 (2H, m), 1.77 (2H, m), 2.33 (3H, s), 2.39 (2H, t, J=6.0 Hz), 2.50 (2H, brs), 2.66 (4H, m), 2.90 (3H, s), 3.38 (2H, t, J=6.0 Hz), 3.64-3.80 (2H, m), 6.39-6.53 (3H, m), 6.95 (1H, m), 7.56 (1H, s), 8.00 (1H, d, J=1.2, 5.6 Hz), 9.30 (1H, brs).

Production Example 105

[6-(2-Fluoro-4-nitrophenoxy)pyrimidin-4-yl]carbamic acid phenyl ester 6-(2-Fluoro-4-nitrophenoxy)pyrimidin-4-ylamine (400 mg) was dissolved in tetrahydrofuran (16 ml) under a nitrogen atmosphere, and then triethylamine (0.669 ml) and phenyl chloroformate (0.602 ml) were added dropwise thereto while cooling in an ice bath, followed by warming the reaction mixture to room temperature and stirring for 10 min. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml) and brine (20 ml) in this order, and dried over anhydrous sodium sulfate. The solvent was evaporated to give a residue, which was then purified by silica gel column chromatography (Fuji Silysia NH, eluent; ethyl acetate). Fractions containing the target compound were concentrated to give a residue, which was then suspended in diethyl ether (4 ml)-hexane (4 ml). The solid was filtered and dried under aeration to provide the titled compound (396 mg, 66.8%) as pale yellow powder.

$^1$H-NMR Spectrum (CDCl$_3$) δ (ppm):7.14-7.25 (2H, m), 7.26-7.35 (1H, m), 7.38-7.48 (3H, m), 7.72 (1H, d, J=0.8 Hz), 8.06-8.18 (2H, m), 8.49 (1H, d, J=0.8 Hz), 8.93 (1H, brs). ESI-MS (m/z) (neg.): 369 [M−H]$^−$.

Production Example 106

3-[6-(4-Amino-2-fluorophenoxy)pyrimidin-4-yl]-1-methyl-1-(1-methylpiperidin-4-yl)urea

[6-(2-Fluoro-4-nitrophenoxy)pyrimidin-4-yl]carbamic acid phenyl ester (200 mg) was dissolved in tetrahydrofuran (16 ml), and then 1-methyl-4-(methylamino)piperidine (0.236 ml) was added thereto while stirring, followed by stirring for 20 min. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml) and brine (20 ml) in this order, and dried over anhydrous sodium sulfate. The solvent was evaporated to give a crude product (218 mg) of 3-[6-(2-fluoro-4-nitrophenoxy)pyrimidin-4-yl]-1-methyl-1-(1-methylpiperidin-4-yl)urea. The crude product (218 mg) was dissolved in methanol (5 ml)-tetrahydrofuran (5 ml), and then 10% palladium carbon (115 mg) was added thereto under a nitrogen atmosphere, followed by replacing with hydrogen inside the system and stirring for 3 hrs. The reaction mixture was filtered to remove the catalyst, which was washed with ethanol. The filtrate was concentrated under a reduced pressure to give a residue, which was then suspended in diethyl ether (2 ml)-hexane (4 ml). The solid was filtered off and dried under aeration to provide the titled compound (91.0 mg, 45%) as yellow powder.

$^1$H-NMR Spectrum (CDCl$_3$) δ (ppm):1.56-1.74 (2H, m), 1.80 (2H, ddd, J=3.6, 12, 12.4 Hz), 2.07 (2H, m), 2.30 (3H, s), 2.86-3.00 (5H, m), 3.74 (2H, brs), 4.18 (1H, m), 6.45 (1H, m), 6.51 (1H, m), 6.98 (1H, m), 7.29 (1H, brs), 7.61 (1H, m), 8.34 (1H, m). ESI-MS (m/z): 375 [M+H]$^+$.

Production Example 107

4-Amino-3-fluorophenol

To a solution of 3-fluoro-4-nitrophenol (20 g) in ethanol (200 ml)-tetrahydrofuran (125 ml) was added 10% palladium carbon (6.0 g), followed by stirring under a hydrogen atmosphere at room temperature for 4.5 hrs. The mixture was filtered to remove the catalyst, which was washed with ethanol. The filtrate was concentrated under a reduced pressure to provide the titled compound (16.1 g, 100%) as a pale yellow solid.

$^1$H-NMR Spectrum (DMSO-d$_6$) δ (ppm): 4.38 (2H, m), 6.34 (1H, m), 6.43 (1H, m), 6.59 (1H, dd, J=8.4, 10.4 Hz), 8.78 (1H, s).

Production Example 108

4-(4-Amino-3-fluorophenoxy)pyridin-2-ylamine

Sodium hydride (1.1 g) was suspended in dimethyl sulfoxide (60 ml) under a nitrogen stream, and 4-chloro-2-pyridinamine (2.9 g) described in WO 02/32872 and then 4-amino-3-fluorophenol (3.6 g, 28 mmol) were added thereto at room temperature while stirring, followed by stirring under a nitrogen stream at 150° C. for 9 hrs. The reaction mixture was cooled down to room temperature, and partitioned between 10% aqueous ammonia (150 ml) and ethyl acetate (350 ml). The organic layer was washed twice with 10% aqueous ammonia (150 ml). The combined aqueous layer was extracted with ethyl acetate (150 ml) again. The combined organic layer was washed twice with a saturated aqueous solution of sodium hydrogencarbonate (100 ml), and dried over anhydrous sodium sulfate. The solvent was evaporated to give a residue, which was then purified by silica gel column chromatography (eluent; hexane:ethyl acetate=1:1, ethyl acetate, then ethyl acetate:methanol=10:1). Crude fractions containing the target compound were concentrated to give a residue, which was then purified by silica gel column chromatography (eluent; ethyl acetate). Fractions containing the target compound were concentrated to provide the titled compound (1.3 g, 26%) as a purple solid.

$^1$H-NMR Spectrum (DMSO-d$_6$) δ (ppm): 5.11 (2H, s), 5.76 (1H, d, J=2.0 Hz), 5.87 (2H, s), 6.09 (1H, dd, J=2.0, 5.6 Hz), 6.69 (1H, m), 6.80 (1H, dd, J=8.8, 10.0 Hz), 6.88 (1H, dd, J=4.4, 11.8 Hz), 7.75 (1H, d, J=5.6 Hz). ESI-MS (m/z): 220 [M+H]$^+$.

Production Example 109

Morpholine-4-carboxylic acid [4-(4-amino-3-fluorophenoxy)pyridin-2-yl]amide

To a solution of 4-(4-amino-3-fluorophenoxy)pyridin-2-ylamine (500 mg) in tetrahydrofuran (23 ml) was added triethylamine (0.318 ml), and then phenyl chloroformate (0.357 ml, 2.28 mmol) was added thereto while stirring in an ice bath, followed by stirring under a nitrogen atmosphere for 1 hr and 20 min. The reaction mixture was concentrated under a reduced pressure to give a residue, to which N,N-dimethylformamide (20 ml) and morpholine (0.994 ml) were added, followed by stirring at room temperature for 8 hrs. The reaction mixture was partitioned between ethyl acetate (100 ml) and water (100 ml). The organic layer was washed with a saturated aqueous solution of sodium hydrogencarbonate, and dried over anhydrous sodium sulfate. The solvent was evaporated to give a residue, which was then purified by silica gel column chromatography (eluent; hexane:ethyl acetate=1:1, ethyl acetate, then ethyl acetate:methanol=10:1). The resultant solid was suspended in ethyl acetate:diethyl ether (1:10), filtered, washed with diethyl ether, and dried under aeration to provide the titled compound (48 mg, 6.3%) as pale red powder.

$^1$H-NMR Spectrum (DMSO-d$_6$) δ (ppm): 3.40 (4H, m), 3.55 (4H, m), 5.16 (2H, m), 6.53 (1H, dd, J=2.4, 5.8 Hz), 6.74 (1H, ddd, J=2.4, 9.4, 9.4 Hz), 6.82 (1H, dd, J=9.4, 9.4 Hz), 6.93 (1H, dd, J=2.4, 12.0 Hz), 7.32 (1H, d, J=2.4 Hz), 8.07 (1H, d, J=5.8 Hz), 9.19 (1H, s).

Production Example 110

Pyrrolidine-1-carboxylic acid [4-(4-amino-3-fluorophenoxy)pyridin-2-yl]amide

To a solution of 4-(4-amino-3-fluorophenoxy)pyridin-2-ylamine (500 mg) in tetrahydrofuran (10 ml) was added triethylamine (0.223 ml), and then phenyl chloroformate (0.200 ml) was added thereto while stirring in an ice bath, followed by stirring under a nitrogen atmosphere for 2 hr. The reaction mixture was concentrated under a reduced pressure to give a residue, to which N,N-dimethylformamide (10 ml) and pyrrolidine (0.667 ml) were then added, followed by stirring at room temperature for 21 hrs. The reaction mixture was partitioned between ethyl acetate (100 ml) and water (100 ml). The organic layer was washed with brine, and dried over anhydrous sodium sulfate. The solvent was evaporated to give a residue, which was then purified by silica gel column chromatography (eluent; hexane:ethyl acetate=1:2, ethyl acetate, then ethyl acetate:methanol=10:1). Fractions containing the target compound were concentrated to provide the titled compound (94 mg, 13%) as a purple oil.

$^1$H-NMR Spectrum (DMSO-d$_6$) δ (ppm): 1.80 (4H, m), 3.31 (4H, m), 5.15 (2H, m), 6.51 (1H, dd, J=2.4, 5.8 Hz), 6.72 (1H, dd, J=2.2, 8.8 Hz), 6.81 (1H, m), 6.92 (1H, dd, J=2.2, 12.0 Hz), 7.42 (1H, d, J=2.4 Hz), 8.05 (1H, d, J=5.8 Hz), 8.61 (1H, s).

Production Example 111

Methyl 4-chloropyridine-2-carboxylate

Thionyl chloride (500 ml) was stirred at room temperature, and then picolinic acid (200 g) was added gradually thereto. Under a nitrogen atmosphere, the reaction mixture was stirred at 85° C. for 20 min and further at 100° C. for 157 hrs. The reaction mixture was cooled down to room temperature, and thionyl chloride was evaporated under a reduced pressure. To the resultant residue was slowly added methanol (500 ml) while cooling in an ice bath, followed by stirring for 1 hr in an ice bath and further at room temperature for 17.5 hrs. The reaction mixture was concentrated under a reduced pressure to give a residue, which was then partitioned between ethyl acetate:tetrahydrofuran=2:1 (1.0 l) and a 1 N aqueous solution of sodium hydroxide (500 ml). The aqueous layer was extracted twice with ethyl acetate (500 ml). The combined organic layer was washed with brine (500 ml), and dried over anhydrous sodium sulfate. The solvent was evaporated to give a residue, to which hexane (200 ml) and diethyl ether (40 ml) were added, followed by stirring at room temperature for 13 hrs. The precipitated solid was filtered off, washed twice with a mixed solvent of hexane (100 ml) and diethyl ether (20 ml), and dried under aeration to provide the titled compound (182 mg, 65.2%).

$^1$H-NMR Spectrum (DMSO-d$_6$) δ (ppm): 3.99 (3H, s), 7.83 (1H, dd, J=2.0, 5.2 Hz), 8.09 (1H, d, J=2.0 Hz), 8.70 (1H, d, J=5.2 Hz).

Production Example 112

Methyl 4-(3-fluoro-4-nitrophenoxy)pyridine-2-carboxylate

A mixture of methyl 4-chloropyridine-2-carboxylate (200 mg), 3-fluoro-4-nitrophenol (202 mg) and chlorobenzene (0.6 ml) was stirred under a nitrogen atmosphere at 120° C. for 2 hrs and 20 min. The reaction mixture was cooled down to room temperature to give a solidified reaction mixture, which was then dissolved in a small amount of N,N-dimethylformamide and subjected to silica gel column chromatography (eluent; hexane:ethyl acetate=1:2, ethyl acetate, then ethyl acetate:methanol=20:1 to 10:1). Fractions containing the target compound were concentrated to provide the titled compound (94 mg, 27.5%) as a pale yellow solid.

$^1$H-NMR Spectrum (DMSO-d$_6$) δ (ppm): 3.89 (3H, s), 7.25 (1H, m), 7.45 (1H, dd, J=1.6, 5.6 Hz), 7.58 (1H, m), 7.71 (1H, d, J=1.6 Hz), 8.29 (1H, m), 8.72 (1H, d, J=5.6 Hz).

Production Example 113

Methyl 4-(4-amino-3-fluorophenoxy)pyridine-2-carboxylate

To a solution of methyl 4-(3-fluoro-4-nitrophenoxy)pyridine-2-carboxylate (200 mg) in methanol (40 ml) was added 10% palladium carbon, followed by stirring under a hydrogen atmosphere at room temperature for 4.5 hrs. The reaction mixture was filtered to remove the catalyst, which was then washed with methanol. The filtrate was concentrated under a reduced pressure to give a residue, which was purified by silica gel column chromatography (eluent; ethyl acetate). Fractions containing the target compound were concentrated to provide a crude product of the titled compound (181 mg) as a brown oil.

$^1$H-NMR Spectrum (CDCl$_3$) δ (ppm): 3.98 (3H, s), 6.71 (1H, m), 6.78-6.85 (2H, m), 6.98 (1H, dd, J=2.4, 5.6 Hz), 7.61 (1H, d, J=2.4 Hz), 8.56 (1H, d, J=5.6 Hz).

Production Example 114

Methyl 4-{3-fluoro-4-[2-(4-fluorophenylcarbamoyl)acetamino]phenoxy}pyridine-2-carboxylate To a solution of methyl 4-(4-amino-3-fluorophenoxy)pyridine-2-carboxylate (179 mg) in N,N-dimethylformamide (2.0 ml) were added N-(4-fluorophenyl)malonic acid (202 mg, 1.02 mmol), and benzotriazol-1-yloxytris(dimethylamino)phosphonium hexafluorophosphate (453 mg, 1.02 mmol), followed by stirring under a nitrogen atmosphere at room temperature for 21 hrs. The reaction mixture was partitioned between ethyl acetate (100 ml) and brine (50 ml). The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; ethyl acetate, then ethyl acetate:methanol=20:1). Fractions containing the target compound were concentrated to give a solid, which was suspended in diethyl ether, filtered, and dried under aeration to provide the titled compound (96.3 mg, 31.9%) as purple brown powder.

$^1$H-NMR Spectrum (DMSO-$d_6$) δ (ppm): 3.59 (2H, s), 3.86 (3H, s), 7.10 (1H, d, J=8.8 Hz), 7.17 (2H, m), 7.25 (1H, dd, J=2.4, 5.6 Hz), 7.36 (1H, m), 7.49 (1H, d, J=2.4 Hz), 7.63 (1H, d, J=5.0, 8.8 Hz), 8.09 (1H, m), 8.61 (1H, d, J=5.6 Hz), 10.14 (1H, s), 10.26 (1H, s).

Production Example 115

4-{3-Fluoro-4-[2-(4-fluorophenylcarbamoyl)acetamino]phenoxy}pyridine-2-carboxylic acid A solution of methyl 4-{3-fluoro-4-[2-(4-fluorophenylcarbamoyl)acetamino]phenoxy}pyridine-2-carboxylate (96.3 mg) in ethanol (2.0 ml) were added water (0.50 ml) and lithium hydroxide monohydrate (15.7 mg), followed by stirring at room temperature for 4 hrs. To the reaction mixture was added 1 N HCl (30 ml), followed by concentrating under a reduced pressure. To the resultant residue was added ethyl acetate (100 ml)-tetrahydrofuran (100 ml) to partition. The organic layer was washed with brine, and dried over anhydrous sodium sulfate. The solvent was evaporated to give a solid, which was then suspended in hexane, filtered, and dried under aeration to provide a crude product of the titled compound (99.5 mg) as pale yellow solid.

$^1$H-NMR Spectrum (DMSO-$d_6$) δ (ppm): 3.60 (2H, s), 7.08-7.11 (1H, m), 7.17 (2H, m), 7.25 (1H, dd, J=2.4, 5.6 Hz), 7.37 (2H, dd, J=2.4, 11.4 Hz), 7.50 (1H, d, J=2.4 Hz), 7.63 (2H, dd, J=5.2, 9.2 Hz), 8.09 (1H, m), 8.60 (1H, d, J=5.6 Hz), 10.15 (1H, s), 10.27 (1H, s).

Production Example 116-1

2-(Trimethylsilyl)ethyl (4-{3-fluoro-4-[2-(4-fluorophenylcarbamoyl)acetylamino]phenoxy}pyridin-2-yl) carbamate

Production Example 116-2

N-[4-(2-Aminopyridin-4-yloxy)-2-fluorophenyl]-N'-(4-fluorophenyl)malonamide

To a solution of 4-{3-fluoro-4-[2-(4-fluorophenylcarbamoyl)acetamino]phenoxy}pyridine-2-carboxylic acid (93.2 mg, 0.218 mmol) in N,N-dimethylformamide (1.0 ml) were added triethylamine (0.0759 ml, 0.545 mmol) and 2-(trimethylsilyl)ethanol (0.0344 ml, 0.240 mmol), and then diphenylphosphoryl azide (0.0517 ml, 0.240 mmol) was added thereto at room temperature, followed by stirring under a nitrogen atmosphere at room temperature for 30 min and at 110° C. for 2 hrs. The reaction mixture was cooled down to room temperature and partitioned between ethyl acetate (100 ml) and a saturated aqueous solution of sodium hydrogencarbonate (100 ml). The organic layer was washed with brine, and dried over anhydrous sodium sulfate. The solvent was evaporated to give a residue, which was then purified by silica gel column chromatography (Fuji Silysia NH, eluent; ethyl acetate, then ethyl acetate:methanol=10:1) to provide 2-(trimethylsilyl)ethyl (4-{3-fluoro-4-[2-(4-fluorophenylcarbamoyl)acetylamino]phenoxy}pyridin-2-yl)carbamate (Production Example 116-1) (24.0 mg, 20.3%) and N-[4-(2-aminopyridin-4-yloxy)-2-fluorophenyl]-N'-(4-fluorophenyl)malonamide (Production Example 116-2) (31.2 mg, 35.9%).

(Production Example 116-1) $^1$H-NMR Spectrum (CDCl$_3$) δ (ppm): 0.02 (9H, s), 0.99-1.03 (2H, m), 3.59 (2H, s), 4.18-4.23 (2H, m), 6.53 (1H, dd, J=1.6, 6.0 Hz), 6.86-6.90 (2H, m), 6.98 (2H, dd, J=4.4, 4.8 Hz), 7.51 (2H, dd, J=4.8, 8.8 Hz), 7.58 (1H, d, J=1.6 Hz), 8.14 (1H, d, J=6.0 Hz), 8.20 (1H, m), 9.07 (1H, brs), 9.25 (1H, brs), 9.43 (1H, brs).

(Production Example 116-2) $^1$H-NMR Spectrum (CDCl$_3$) δ (ppm): 3.61 (2H, s), 4.65 (2H, brs), 5.95 (1H, d, J=2.2 Hz), 6.26 (1H, dd, J=2.2, 6.0 Hz), 6.29-6.88 (2H, m), 6.97-7.02 (2H, m), 7.49 (2H, m), 7.90 (1H, d, J=6.0 Hz), 8.12 (1H, dd, J=9.0, 9.0 Hz), 9.34 (1H, s), 9.49 (1H, s).

Alternative synthesis method for Production Example 116-2 will be described below.

To a solution of 4-(4-amino-3-fluorophenoxy)pyridin-2-ylamine (100 mg) in N,N-dimethylformamide (2.0 ml) were added N-(4-fluorophenyl)malonic acid (189 mg), and benzotriazol-1-yloxytris(dimethylamino)phosphonium hexafluorophosphate (424 mg), followed by stirring at room temperature. The reaction mixture was partitioned between ethyl acetate (100 ml) and brine (80 ml). The aqueous layer was extracted with ethyl acetate (50 ml). The combined organic layer was washed with a saturated aqueous solution of sodium hydrogencarbonate and brine, and dried over anhydrous sodium sulfate. The solvent was evaporated to give a residue, which was then purified by silica gel column chromatography (eluent; ethyl acetate, ethyl acetate:methanol=10:1). Fractions containing the target compound were concentrated to provide the titled compound (182 mg, 66.1%) as brown crystals.

Production Example 117

Methyl 4-(4-benzyloxycarbonylamino-3-fluorophenyl)pyridine-2-carboxylate

To a solution of methyl 4-(3-fluoro-4-nitrophenoxy)pyridine-2-carboxylate (851 mg) in tetrahydrofuran (200 ml) was added palladium hydroxide (309 mg, a palladium content of 20%), followed by stirring under a hydrogen atmosphere at room temperature for 2.5 hrs. The mixture was filtered to remove the catalyst, washed with tetrahydrofuran, and concentrated under a reduced pressure to a liquid volume of about 20 ml. Water (15 ml), acetone (30 ml) and sodium carbonate (771 mg) were added thereto, followed by stirring in an ice bath. Benzyloxycarbonyl chloride (0.449 ml) was added dropwise thereto, followed by stirring at room temperature for 4 hrs. The reaction mixture was concentrated under a reduced pressure to give a residue, which was then partitioned between ethyl acetate (200 ml) and brine (100 ml). The aqueous layer was extracted with ethyl acetate (50 ml×2). The combined organic layer was washed with brine, and dried over anhydrous sodium sulfate. The solvent was evaporated to give a residue, which was then purified by silica gel column chromatography (eluent; heptane:ethyl acetate=1:2, then ethyl acetate). Fractions containing the target compound were concentrated to provide the titled compound (738 mg, 64%) as pale yellow crystals.

$^1$H-NMR Spectrum (CDCl$_3$) δ (ppm): 3.98 (3H, s), 5.24 (2H, s), 6.87-6.93 (2H, m), 6.99 (1H, m), 7.01 (1H, dd, J=2.4, 5.4 Hz), 7.36-7.44 (5H, m), 6.40 (1H, d, J=2.4 Hz), 8.20 (1H, m), 8.59 (1H, d, J=5.4 Hz). ESI-MS (m/z): 397 [M+H]$^+$, 419 [M+Na]$^+$.

Production Example 118

4-(4-Benzyloxycarbonylamino-3-fluorophenyl)pyridine-2-carboxylic acid

Methyl 4-(4-benzyloxycarbonylamino-3-fluorophenyl) pyridine-2-carboxylate (1.02 g) was dissolved in a mixed solvent of ethanol (25 ml), methanol (50 ml) and N,N-dimethylformamide (7.5 ml), and then water (7.5 ml) was added. Lithium hydroxide monohydrate (185 mg) was added thereto at room temperature while stirring, followed by stirring at room temperature for 1.5 hrs. To the reaction mixture was added 1 N HCl (30 ml), followed by concentrating under a reduced pressure. To the resultant residue was added a mixed solvent of ethyl acetate (100 ml) and tetrahydrofuran (100 ml) to partition. The organic layer was washed with brine (50 ml×3), and dried over anhydrous sodium sulfate. The solvent was evaporated to give a solid, which was then suspended in a mixed solvent of diethyl ether (20 ml) and hexane (20 ml), filtered, and dried under aeration to provide the titled compound (846 mg, 86.1%) as a pale brown solid.

$^1$H-NMR Spectrum (DMSO-d$_6$) δ (ppm): 5.18 (0.2H, s), 7.08 (1H, m), 7.23 (1H, m), 7.24-7.46 (8H, m), 7.75 (1H, m), 8.59 (1H, d, J=5.6 Hz), 9.59 (1H, s).

Production Example 119-1

Benzyl [4-(2-aminopyridin-4-yloxy)-2-fluorophenyl] carbamate

Production Example 119-2

2-(Trimethylsilyl)ethyl [4-(4-benzyloxycarbonylamino-3-fluorophenoxy)pyridin-2-yl]carbamate To a solution of 4-(4-benzyloxycarbonylamino-3-fluorophenyl)pyridine-2-carboxylic acid (2.85 g) in N-methylpyrrolidone (30 ml) were added triethylamine (2.59 ml) and 2-(trimethylsilyl)ethanol (1.28 ml), and then diphenylphosphoryl azide (2.59 ml) was added thereto, followed by stirring under a nitrogen atmosphere at room temperature for 1 hr and at 90° C. for 2 hrs. The reaction mixture was cooled down to room temperature and partitioned between ethyl acetate (100 ml) and a saturated aqueous solution of sodium hydrogencarbonate (100 ml). The organic layer was washed with brine. The solvent was evaporated to give a residue, which was then purified by silica gel column chromatography (eluent; heptane:ethyl acetate=1:1 to 1:2, ethyl acetate, then ethyl acetate: methanol=20:1 to 10:1). Fractions containing the two respective target compounds were concentrated respectively to provide 2-(trimethylsilyl)ethyl [4-(4-benzyloxycarbonylamino-3-fluorophenoxy)pyridin-2-yl]carbamate (Production Example 119-2: 747 mg, 20.2%) as a yellow solid, and benzyl [4-(2-aminopyridin-4-yloxy)-2-fluorophenyl]carbamate (Production Example 119-1: 618 mg, 23.5%) as a brown solid.

Production Example 119-2

$^1$H-NMR Spectrum (CDCl$_3$) δ (ppm): 0.06 (9H, m), 1.03 (2H, m), 4.24 (2H, m), 5.23 (2H, s), 6.54 (1H, dd, J=2.0, 5.6 Hz), 6.59-6.64 (1H, m), 6.66-6.93 (3H, m), 7.34-7.42 (5H, m), 7.61 (1H, m), 8.10 (1H, d, J=5.6 Hz), 8.15 (1H, m). ESI-MS: 520 [M+Na]$^+$.

Production Example 119-1

$^1$H-NMR Spectrum (CDCl$_3$) δ (ppm): 4.49 (2H, m), 5.23 (2H, s), 5.95 (1H, d, J=2.0 Hz), 6.26 (1H, dd, J=2.0, 6.0 Hz), 6.84-6.90 (2H, m), 7.00 (1H, m), 7.34-7.42 (5H, m), 7.94 (1H, d, J=6.0 Hz), 8.10 (1H, m). ESI-MS: 354 [M+H]$^+$.

Production Example 120

Benzyl {4-[2-(3,3-dimethylureido)pyridin-4-yloxy]-2-fluorophenyl}carbamate

To a solution of benzyl [4-(2-aminopyridin-4-yloxy)-2-fluorophenyl]carbamate (163 mg, 0.461 mmol) in tetrahydrofuran (4.50 ml) was added triethylamine (0.128 ml, 0.918 mmol), and then phenyl chloroformate (0.0872 ml, 0.695 mmol) was added dropwise thereto, followed by stirring at room temperature for 10 min. The reaction mixture was concentrated under a reduced pressure to give a residue, to which N,N-dimethylformamide (2.0 ml), dimethylamine hydrochloride (188 mg, 2.31 mmol) and triethylamine (0.386 ml) were then added, followed by stirring at room temperature for 8 hrs. The reaction mixture was partitioned between ethyl acetate (50 ml) and water (30 ml). The organic layer was washed with brine (30 ml×3), and dried over anhydrous sodium sulfate. The solvent was evaporated to give a residue, which was then purified by silica gel column chromatography (eluent; ethyl acetate, then ethyl acetate:methanol=20:1) to provide the titled compound (165 mg, 47.5%) as pale yellow powder.

$^1$H-NMR Spectrum (CDCl$_3$) δ (ppm): 3.02 (6H, s), 5.22 (2H, s), 6.51 (1H, dd, J=2.0, 6.0 Hz), 6.87-6.90 (3H, m), 7.20 (1H, m), 7.25-7.42 (5H, m), 7.66 (1H, d, J=2.0 Hz), 8.03 (1H, d, J=6.0 Hz), 8.12 (1H, brs). ESI-MS (m/z): 425 [M+H]$^+$, 447 [M+Na]$^+$.

Production Example 121

1-[4-(2-Aminopyridin-4-yloxy)-2-fluorophenyl]-3-[2-(4-fluorophenyl)acetyl]thiourea To a solution of 2-(trimethylsilyl)ethyl [4-(4-benzyloxycarbonylamino-3-fluorophenoxy)pyridin-2-yl]carbamate (222 mg) in tetrahydrofuran (7.0 ml) was added 10% palladium carbon (71.2 mg), followed by stirring under a hydrogen atmosphere at room temperature for 25 hrs. The reaction mixture was filtered to remove the catalyst, which was then washed with methanol (5.0 ml). 4-Fluorophenyl acetic acid (103 mg) and thionyl chloride (0.448 ml) were put in another vessel, stirred at 90° C. for 30 min, and concentrated under a reduced pressure. The resultant residue was dissolved in acetonitrile (5.0 ml), and then potassium thiocyanate (130 mg, 1.34 mmol) was added thereto, followed by stirring at 50° C. for 1 hr. The reaction mixture was added to the above filtrate, followed by stirring at room temperature for 1 hr. To the reaction mixture were added ethyl acetate (50 ml) and brine (30 ml) to partition. The organic layer was washed with brine (30 ml×3), and dried over anhydrous sodium sulfate. The solvent was evaporated to give a residue, which was then dissolved in tetrahydrofuran (5.0 ml), and then 1 M solution of tetrabutylammonium fluoride in tetrahydrofuran (0.891 ml) was added thereto, followed by stirring at room temperature for 30 min. The reaction mixture was concentrated, and then 1 M solution of tetrabutylammonium fluoride in tetrahydrofuran (0.1 ml) was further added thereto, followed by stirring at room temperature for 30 min. Then, 1 M solution of tetrabutylammonium fluoride in tetrahydrofuran (0.5 ml) was further added thereto, followed by stirring at room temperature overnight. To the reaction mixture were added ethyl acetate (50 ml) and brine (30 ml) to partition. The organic layer was washed with brine (30 ml×3), and dried over anhydrous sodium sulfate. The solvent was evaporated to give a residue, which was then purified by silica gel column chromatography (Fuji Silysia NH, eluent; heptane:ethyl acetate=1:2, ethyl acetate, then ethyl acetate:methanol=20:1 to 10:1) to provide the target compound (75.4 mg, 43.5%) as a pale yellow oil.

$^1$H-NMR Spectrum (CDCl$_3$) δ (ppm): 3.73 (2H, s), 4.52 (2H, m), 6.02 (1H, dd, J=0.4, 2.0 Hz), 6.31 (1H, dd, J=2.0, 5.8 Hz), 6.88-6.92 (2H, m), 7.08-7.13 (2H, m), 7.27-7.31 (2H, m), 7.98 (1H, dd, J=0.4, 5.8 Hz), 8.26 (1H, m), 8.98 (1H, brs), 12.30 (1H, s). ESI-MS (m/z): 415 [M+H]$^+$.

Alternative synthesis method for Production Example 121 will be described below.

4-Fluorophenylacetic acid (482 mg) was dissolved in thionyl chloride (1.09 ml), and stirred at 60° C. for 1 hr. The reaction mixture was cooled down to room temperature, and thionyl chloride was evaporated under a reduced pressure to give a residue, which was then azeotropically distilled with toluene. The resultant residue was dissolved in acetonitrile (34.2 ml), and then potassium thiocyanate (607 mg) was added thereto, followed by stirring at 50° C. for 1 hr. The reaction mixture was cooled down to room temperature, and then 4-(4-amino-3-fluorophenoxy)pyridin-2-ylamine (500 mg) was added thereto, followed by stirring at room temperature for 18 hrs. The reaction mixture was partitioned between water (50 ml) and ethyl acetate (100 ml). The organic layer was washed with brine, and dried over anhydrous sodium sulfate. The solvent was evaporated to give a residue, which was then purified by silica gel column chromatography (Fuji Silysia NH, eluent; heptane:ethyl acetate=1:2, ethyl acetate, then ethyl acetate:methanol=10:1). Fractions containing the target compound was concentrated to give a crude product (945 mg, crude yield: 42.9%) of the titled compound as a brown oil. To the crude product (220 mg) was added ethanol (0.5 ml)-diethyl ether (2.5 ml) to precipitate crystals, which was then filtered, washed with diethyl ether, and dried under aeration to provide the titled compound (42 mg) as pale brown crystals.

Production Example 122

1-[4-(2-Aminopyridin-4-yloxy)-2-fluorophenyl]-3-phenylacetylthiourea

To a solution of 2-(trimethylsilyl)ethyl [4-(4-benzyloxycarbonylamino-3-fluorophenoxy)pyridin-2-yl]carbamate (200 mg) in tetrahydrofuran (20 ml) was added 10% palladium carbon (85.6 mg), followed by stirring under a hydrogen atmosphere at room temperature for 25 hrs. The reaction mixture was filtered to remove the catalyst, which was then washed with tetrahydrofuran. The filtrate was concentrated to a volume of 20 ml. A solution of 2-phenylacetyl chloride (0.0862 ml) in acetonitrile (10 ml) and potassium thiocyanate (117 mg) were put in another vessel, stirred under a nitrogen atmosphere at 60° C. for 2 hrs, and cooled down to room temperature. To the mixture was added the above concentrated filtrate, followed by stirring at room temperature for 2 hr. To the reaction mixture were added ethyl acetate (50 ml) and brine (30 ml) to partition. The organic layer was washed with brine (30 ml×3), and dried over anhydrous sodium sulfate. The solvent was evaporated to give a residue, which was then purified by silica gel column chromatography (eluent; heptane:ethyl acetate=1:1 to 1:2, then ethyl acetate) to give a pale yellow oil (250 mg). The pale yellow oil was dissolved in tetrahydrofuran (0.80 ml), and then a 1 M solution of tetrabutylammonium fluoride in tetrahydrofuran (0.804 ml) was added thereto, followed by stirring at room temperature for 30 min. A 1 M solution of tetrabutylammonium fluoride in tetrahydrofuran (0.804 ml) was further added thereto, followed by stirring at room temperature for 30 min. To the reaction mixture were added ethyl acetate (50 ml) and brine (30 ml) to partition. The organic layer was washed with brine (30 ml×3), and dried over anhydrous sodium sulfate. The solvent was evaporated to give a residue, which was then purified by silica gel column chromatography (eluent; heptane:ethyl acetate=1:1 to 1:2, ethyl acetate, then ethyl acetate:methanol=10:1) to provide the titled product (58.9 mg, 37%) as colorless powder.

$^1$H-NMR Spectrum (CDCl$_3$) δ (ppm): 3.75 (2H, s), 4.83 (2H, brs), 6.00 (1H, d, J=2.4 Hz), 6.32 (1H, dd, J=2.4, 6.0 Hz), 6.88-6.93 (2H, m), 7.26-7.45 (5H, m), 7.93 (1H, d, J=6.0 Hz), 8.25-8.29 (1H, m), 8.87 (1H, brs), 12.34 (1H, s). ESI-MS (m/z): 397 [M+H]$^+$.

Alternative synthesis method for Production Example 122 will be described below.

To a solution of 2-phenylacetyl chloride (0.378 ml, 3.00 mmol) in acetonitrile (30 ml) was added potassium thiocyanate (583 mg, 6.00 mmol), followed by stirring under a nitrogen atmosphere at 50° C. for 1.5 hrs. The reaction mixture was cooled down to room temperature, and then 4-(4-amino-3-fluorophenoxy)pyridin-2-ylamine (438 mg, 2.00 mmol) was added thereto, followed by stirring at room temperature for 13 hrs. The reaction mixture was partitioned between water (50 ml) and ethyl acetate (100 ml). The organic layer was washed with a saturated aqueous solution of sodium hydrogencarbonate and brine in this order, and dried over anhydrous sodium sulfate. The solvent was evaporated to give a residue, which was then purified by silica gel column chromatography (Fuji Silysia NH, eluent; heptane:ethyl acetate=1:1, ethyl acetate, then ethyl acetate:methanol=10:1). Fractions containing the target compound were concentrated to provide the titled compound (271 mg, 34.2%) as a brown oil.

Production Example 123

Benzyl (2-fluoro-4-{2-[3-methyl-3-(1-methylpiperidin-4-yl)ureido]pyridin-4-yloxy}phenyl)carbamate To a solution of Benzyl [4-(2-aminopyridin-4-yloxy)-2-fluorophenyl]carbamate (200 mg) in tetrahydrofuran (5.0 ml) was added triethylamine (0.197 ml), and then phenyl chloroformate (0.107 ml) was added dropwise thereto, followed by stirring at room temperature for 10 min. The reaction mixture was concentrated under a reduced pressure to give a residue, to which N,N-dimethylformamide (2.0 ml) and 1-methyl-4-(methylamino)piperidine (0.329 ml) were then added, followed by stirring at room temperature for 18 hrs. To the reaction mixture was added ethyl acetate (50 ml) and water (30 ml) to partition. The organic layer was washed with brine (30 ml×3), and dried over anhydrous sodium sulfate. The solvent was evaporated to give a residue, which was then purified by silica gel column chromatography (FUJI Silysia NH, heptane:ethyl acetate=1:2, ethyl acetate, then ethyl acetate:methanol=20:1 to 10:1) to provide the titled compound (117 mg, 40.7%) as pale yellow powder.

$^1$H-NMR Spectrum (CDCl$_3$) δ (ppm): 1.63-1.67 (2H, m), 1.72-1.82 (2H, m), 2.04-2.11 (2H, m), 2.28 (3H, s), 2.88-2.92 (5H, m), 4.17 (1H, m), 5.23 (2H, s), 6.52 (1H, dd, J=2.4, 6.0 Hz), 6.85-6.92 (3H, m), 7.22 (1H, m), 7.34-7.44 (5H, m), 7.68 (1H, d, J=2.4 Hz), 8.05 (1H, d, J=6.0 Hz), 8.12 (1H, m). ESI-MS (m/z): 508 [M+H]$^+$, 530 [M+Na]$^+$.

Production Example 124

3-[4-(4-Amino-3-fluorophenoxy)pyridin-2-yl]-1-methyl-1-(1-methylpiperidin-4-yl)urea To a solution of benzyl (2-fluoro-4-{2-[3-methyl-3-(1-methylpiperidin-4-yl)ureido]pyridin-4-yloxy}phenyl)carbamate (110 mg) in tetrahydrofuran (10 ml) was 10% palladium carbon (46.2 mg), followed by stirring under a hydrogen atmosphere at room temperature for 18 hrs. The reaction mixture was filtered to remove the catalyst, which was then washed with tetrahydrofuran. The filtrate was dried over anhydrous sodium sulfate, and concentrated to a volume of 40 ml to give a solution of the target compound in tetrahydrofuran (40 ml) as a pale yellow solution. Assuming that the reaction preceded quantitatively, the solution was used for a next reaction.

ESI-MS (m/z): 374 [M+H]$^+$, 396 [M+Na]$^+$.

Production Example 125

2-Amino-4-(4-nitrophenoxy)pyridine

2-Amino-4-chloropyridine (2.00 g) was dissolved in N-methylpyrrolidone (31.8 ml), and then 4-nitrophenol (6.51 g) and N,N-diisopropylethylamine (15.9 ml) were added thereto under a nitrogen atmosphere, followed by stirring at 150° C. for 3 days. The reaction mixture was cooled down to room temperature, and partitioned between ethyl acetate and a 1 N aqueous solution of sodium hydroxide (32 ml). The organic layer was washed with water and brine in this order, and dried over anhydrous sodium sulfate. The solvent was evaporated under a reduced pressure to give a residue, which was then purified by silica gel column chromatography (eluent; hexane:ethyl acetate=1:2 to 1:5). Fractions containing the target compound were concentrated under a reduced pressure to give a residue, which was then dried in vacuum to provide the titled compound (764 mg, 21.2%) as a brown solid.

$^1$H-NMR Spectrum (CDCl$_3$) δ (ppm): 4.54 (2H, brs), 6.11 (1H, s), 6.35 (1H, m), 7.17 (2H, m), 8.05 (1H, d, J=5.6 Hz), 8.27 (2H, m).

Production Example 126

Pyrrolidine-1-carboxylic acid [4-(4-nitrophenoxy)pyridin-2-yl]amide

2-Amino-4-(4-nitrophenoxy)pyridine (490 mg) was dissolved in tetrahydrofuran (10 ml) under a nitrogen atmosphere, and then triethylamine (0.886 ml) and phenyl chloroformate (0.798 ml) were added dropwise, followed by stirring for 20 min. To the reaction mixture was added pyrrolidine (1.42 ml), followed by stirring for 40 min. The reaction mixture was partitioned between ethyl acetate and a saturated aqueous solution of ammonium chloride. The organic layer was washed with a saturated aqueous solution of ammonium chloride, a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:1 to 1:3). Fractions containing the target compound were concentrated under a reduced pressure to give a residue, which was then dried in vacuum to provide the titled compound (639 mg, 91.8%) as a brown solid.

$^1$H-NMR Spectrum (CDCl$_3$) δ (ppm): 1.98 (4H, m), 3.46 (4H, m), 6.65 (1H, dd, J=2.4, 5.6 Hz), 7.08 (1H, brs), 7.19 (2H, m), 7.84 (1H, d, J=2.4 Hz), 8.16 (1H, d, J=5.6 Hz), 8.28 (2H, m).

Production Example 127

Pyrrolidine-1-carboxylic acid [4-(4-aminophenoxy)pyridin-2-yl]amide

Pyrrolidine-1-carboxylic acid [4-(4nitrophenoxy)pyridin-2-yl]amide (636 mg) was dissolved in tetrahydrofuran (18 ml)-methanol (18 ml), and then 10% palladium carbon (412 mg) was added thereto under a nitrogen atmosphere, followed by replacing with hydrogen inside the system and stirring overnight. After replacing with nitrogen inside the system, the reaction mixture was filtered to remove the catalyst, which was washed with methanol. The filtrate was concentrated under a reduced pressure to give a residue, which was suspended in diethyl ether (10 ml)-hexane (10 ml). The solid was filtered off, and dried in vacuum to provide the titled compound (524.9 mg, 90.7%).

$^1$H-NMR Spectrum (CDCl$_3$) δ (ppm): 1.95 (4H, m), 3.44 (4H, m), 3.64 (2H, brs), 6.48 (1H, dd, J=2.4, 5.6 Hz), 6.69 (2H, m), 6.90 (2H, m), 6.95 (1H, m), 7.66 (1H, m), 7.99 (1H, m).

Production Example 128

3-[4-(4-Nitrophenoxy)pyridin-2-yl]-1,1-dimethylurea

2-Amino-4-(4-nitrophenoxy)pyridine (761 mg) was dissolved in tetrahydrofuran (14 ml) under a nitrogen atmosphere, and then triethylamine (1.16 ml) and phenyl chloroformate (1.05 ml) were added dropwise while cooling in an ice water bath, followed by stirring for 30 min. To the reaction mixture was added 2 N dimethylamine (a solution in methanol) (6.95 ml), followed by stirring overnight. The reaction mixture was partitioned between ethyl acetate and a saturated aqueous solution of ammonium chloride. The organic layer was washed with a saturated aqueous solution of ammonium chloride, a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:1 to 1:5). Fractions containing the target compound were concentrated under a reduced pressure to give a residue, which was then dried in vacuum to provide the titled compound (609 mg, 72.5%) as a brown solid.

$^1$H-NMR Spectrum (CDCl$_3$) δ (ppm): 3.03 (6H, s), 6.65 (1H, dd, J=2.4, 5.6 Hz), 7.19 (2H, m), 7.21 (1H, m), 7.80 (1H, d, J=2.4 Hz), 8.16 (1H, d, J=5.6 Hz), 8.28 (2H, m).

Production Example 129

3-[4-(4-Aminophenoxy)pyridin-2-yl]-1,1-dimethylurea

3-[4-(4-Nitrophenoxy)pyridin-2-yl]-1,1-dimethylurea (607 mg) was dissolved in tetrahydrofuran (20 ml)-methanol (20 ml), and then 10% palladium carbon (236 mg) was added thereto under a nitrogen atmosphere, followed by replacing with hydrogen inside the system and stirring overnight. After replacing with nitrogen inside the system, the reaction mixture was filtered to remove the catalyst, which was washed with methanol. The filtrate was concentrated under a reduced pressure to give a residue, which was dried in vacuum to provide the titled compound (529.5 mg, 96.7%).

$^1$H-NMR Spectrum (CDCl$_3$) δ (ppm): 3.01 (6H, m), 3.64 (2H, brs), 6.48 (1H, dd, J=2.0, 6.0 Hz), 6.70 (2H, m), 6.90 (2H, m), 7.11 (1H, brs), 7.61 (1H, d, J=2.0 Hz), 7.99 (1H, d, J=6.0 Hz).

Production Example 130

[4-(4-Nitrophenoxy)pyridin-2-yl]carbamic acid phenyl ester

2-Amino-4-(4-nitrophenoxy)pyridine (600 mg) was dissolved in tetrahydrofuran (12 ml) under a nitrogen atmosphere, and then triethylamine (1.09 ml) and phenyl chloroformate (0.979 ml) were added dropwise thereto, followed by stirring for 20 min. To the reaction mixture was added morpholine (1.81 ml), followed by stirring for 25 min. The reaction mixture was partitioned between ethyl acetate and a saturated aqueous solution of ammonium chloride. The organic layer was washed with a saturated aqueous solution of ammonium chloride, a saturated aqueous solution of sodium hydrogencarbonate, water and brine in this order, and dried over anhydrous sodium sulfate. The solvent was evaporated under a reduced pressure to give a residue, which was then suspended in diethyl ether. The solid was filtered off, and dried under aeration to provide the titled compound (854 mg, 93.8%) as a brown solid.

$^1$H-NMR Spectrum (CDCl$_3$) δ (ppm): 6.73 (1H, dd, J=2.4, 5.6 Hz), 7.14-7.24 (4H, m), 7.32-7.46 (3H, m), 7.71 (1H, d, J=2.0 Hz), 8.27 (2H, m), 8.32 (1H, d, J=5.6 Hz), 9.07 (1H, brs).

Production Example 131

Morpholine-4-carboxylic acid [4-(4-nitrophenoxy)pyridin-2-yl]amide

[4-(4-Nitrophenoxy)pyridin-2-yl]carbamic acid phenyl ester (250 mg) was dissolved in tetrahydrofuran (7 ml) under a nitrogen atmosphere, and then morpholine (0.187 ml) was added thereto. The reaction mixture was stirred overnight at room temperature. To the reaction mixture was further added morpholine (0.187 ml), followed by stirring for 2 hrs and 15 min. The reaction mixture was warmed up to 50° C., followed by stirring for 1 hr. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (eluent; hexane:ethyl acetate=1:1 to 1:5). Fractions containing the target compound were concentrated under a reduced pressure to give a residue, which was then dried in vacuum to provide the titled compound (152 mg, 61.9%) as a brown solid.

$^1$H-NMR Spectrum (CDCl$_3$) δ (ppm): 3.49 (4H, m), 3.73 (4H, m), 6.66 (1H, dd, J=2.4, 5.6 Hz), 7.19 (1H, m), 7.21 (1H, m), 7.29 (1H, brs), 7.75 (1H, m), 8.17 (1H, d, J=5.6 Hz), 8.28 (1H, m), 8.30 (1H, m).

Production Example 132

Morpholine-4-carboxylic acid [4-(4-aminophenoxy)pyridin-2-yl]amide

Morpholine-4-carboxylic acid [4-(4-nitrophenoxy)pyridin-2-yl]amide (227 mg) was dissolved in ethanol (10 ml)-water (2 ml), and then electrolytic iron powder (150 mg) and ammonium chloride (300 mg) were added thereto, followed by heating under reflux for 1 hr. The reaction mixture was cooled down to room temperature, and then ethyl acetate-tetrahydrofuran (1:1) was added, followed by stirring. The mixture was filtered through celite to remove an insoluble portion, which was washed with ethyl acetate and water. The organic layer of the filtrate was washed with water and brine, and dried over anhydrous sodium sulfate. The solvent was evaporated under a reduced pressure to give a residue, which was then purified by silica gel column chromatography (eluent; hexane:ethyl acetate=1:5, then ethyl acetate). Fractions containing the target compound were concentrated under a reduced pressure to give a residue, which was then suspended in diethyl ether (6 ml)-hexane (12 ml). The solid was filtered, and dried under aeration to provide the titled compound (81.3 mg, 59.3%) as a pale yellow solid.

$^1$H-NMR Spectrum (CDCl$_3$) δ (ppm): 3.48 (4H, m), 3.65 (2H, brs), 3.71 (4H, m), 6.44-6.56 (1H, m), 6.71 (2H, d, J=8.8 Hz), 6.90 (2H, d, J=8.8 Hz), 7.21 (1H, brs), 7.57 (1H, brs), 7.99 (1H, m).

Production Example 133

4-(Pyrrolidin-1-yl)piperidine-1-carboxylic acid [4-(4-aminophenoxy)pyridin-2-yl]amide

[4-(4-Nitrophenoxy)pyridin-2-yl]carbamic acid phenyl ester (100 mg) was dissolved in tetrahydrofuran (2 ml) under a nitrogen atmosphere, and then 4-(pyrrolidin-1-yl)piperidine (148 mg) was added thereto, followed by stirring for 50 min. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:2 to 1:8). The solvent was evaporated under a reduced pressure to give a residue, which was then dried in vacuum to provide 4-(pyrrolidin-1-yl)piperidine-1-carboxylic acid [4-(4-nitrophenoxy)pyridin-2-yl]amide as a crude product.

4-(Pyrrolidin-1-yl)piperidine-1-carboxylic acid [4-(4-nitrophenoxy)pyridin-2-yl]amide (117 mg) was dissolved in tetrahydrofuran (3 ml)-methanol (3 ml), and then 10% palladium carbon (61 mg) was added thereto under a nitrogen atmosphere, followed by replacing with hydrogen inside the system and stirring overnight. After replacing with nitrogen inside the system, the reaction mixture was filtered to remove the catalyst, which was washed with ethanol. The filtrate was concentrated under a reduced pressure to give a residue, which was then suspended in diethyl ether (2 ml)-hexane (2 ml). The solid was filtered and dried under aeration to provide the titled compound (59.5 mg, 54.7%).

$^1$H-NMR Spectrum (DMSO-$d_6$) δ (ppm): 1.27 (2H, m), 1.66 (4H, m), 1.78 (2H, m), 2.11 (1H, m), 2.46 (4H, m), 2.85 (2H, m), 3.96 (2H, m), 5.04-5.15 (2H, m), 6.46 (1H, dd, J=2.0, 5.6 Hz), 6.60 (2H, d, J=8.8 Hz), 6.80 (2H, d, J=8.8 Hz), 7.29 (1H, d, J=2.0 Hz), 8.03 (1H, d, J=5.6 Hz), 9.06 (1H, brs).

Production Example 134

4-(Piperidin-1-yl)piperidine-1-carboxylic acid [4-(4-aminophenoxy)pyridin-2-yl]amide

[4-(4-Nitrophenoxy)pyridin-2-yl]carbamic acid phenyl ester (100 mg) was dissolved in tetrahydrofuran (2 ml) under a nitrogen atmosphere, and then 4-(piperidin-1-yl)piperidine (144 mg) was added thereto, followed by stirring for 30 min. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:2 to 1:8). The solvent was evaporated under a reduced pressure to give a residue, which was then dried in vacuum to provide 4-(piperidin-1-yl)piperidine-1-carboxylic acid [4-(4-nitrophenoxy)pyridin-2-yl]amide as a crude product.

4-(Piperidin-1-yl)piperidine-1-carboxylic acid [4-(4-nitrophenoxy)pyridin-2-yl]amide (121 mg) was dissolved in tetrahydrofuran (3 ml)-methanol (3 ml), and then 10% palladium carbon (61 mg) was added thereto under a nitrogen atmosphere, followed by replacing with hydrogen inside the system and stirring overnight. After replacing with nitrogen inside the system, the reaction mixture was filtered to remove the catalyst, which was washed with ethanol. The filtrate was concentrated under a reduced pressure to give a residue, which was then suspended in diethyl ether (2 ml)-hexane (2 ml). The solid was filtered off and dried under aeration to provide the titled compound (84.8 mg, 75.2%).

$^1$H-NMR Spectrum (CDCl$_3$) δ (ppm): 1.38-1.78 (8H, m), 1.86 (2H, m), 2.38-2.54 (5H, m), 2.85 (2H, m), 3.65 (2H, brs), 4.12 (2H, m), 6.48 (1H, dd, J=2.0, 5.6 Hz), 6.66-6.76 (2H, m), 6.86-6.94 (2H, m), 7.20 (1H, m), 7.57 (1H, m), 7.99 (1H, d, J=5.6 Hz).

Production Example 135

3-[4-(4-Aminophenoxy)pyridin-2-yl]-1-methyl-1-(1-methylpiperidin-4-yl)urea

[4-(4-Nitrophenoxy)pyridin-2-yl]carbamic acid phenyl ester (150 mg) was dissolved in N,N-dimethylformamide (4 ml) under a nitrogen atmosphere, and then N-methyl-N-(1-methylpiperidin-4-yl)amine (0.186 mg) was added thereto, followed by stirring for 1 hr. The reaction mixture was partitioned between ethyl acetate (40 ml) and a saturated aqueous solution of ammonium chloride (10 ml). The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (Fuji Silysia NH, eluent; heptane:ethyl acetate=1:1, then ethyl acetate). Fractions containing the target compound were concentrated under a reduced pressure to provide 3-[4-(4-nitrophenoxy)pyridin-2-yl]-1-methyl-1-(1-methylpiperidin-4-yl)urea (117.7 mg, 71.5%) as a crude product.

3-[4-(4-Nitrophenoxy)pyridin-2-yl]-1-methyl-1-(1-methylpiperidin-4-yl)urea was dissolved in tetrahydrofuran (4 ml)-methanol (4 ml), and then 10% palladium carbon (65 mg) was added thereto under a nitrogen atmosphere, followed by replacing with hydrogen inside the system and stirring overnight. After replacing with nitrogen inside the system, the reaction mixture was filtered to remove the catalyst, which was washed with methanol. The filtrate was concentrated under a reduced pressure to give a residue, which was then purified by silica gel column chromatography (Fuji Silysia NH, eluent; ethyl acetate). Fractions containing the target compound were concentrated under a reduced pressure to provide the titled compound (113.5 mg, quantitatively) as colorless powder.

$^1$H-NMR Spectrum (CDCl$_3$) δ (ppm):1.25-1.32 (1H, m), 1.77 (2H, m), 2.08 (2H, m), 2.29 (3H, s), 2.84-2.96 (6H, m), 3.65 (2H, brs), 4.20 (1H, m), 6.48 (1H, dd, J=2.4, 6.0 Hz), 6.70 (2H, m), 6.90 (2H, m), 7.14 (1H, brs), 7.62 (1H, m), 8.00 (1H, d, J=6.0 Hz). ESI-MS (m/z): 356 [M+H]$^+$.

Production Example 136

4-(4-Amino-2-fluorophenoxy)-2-[(4-hydroxypiperidin-1-yl)carbonylamino]pyridine 4-(2-Fluoro-4-nitrophenoxy)-2-[(4-hydroxypiperidin-1-yl)carbonylamino]pyridine (169 mg) was dissolved in methanol (5 ml)-tetrahydrofuran (5 ml), and then 10% palladium carbon (200 mg) was added thereto under a nitrogen atmosphere, followed by replacing with hydrogen inside the system and stirring for 2 hrs. After replacing with nitrogen inside the system, the reaction mixture was filtered to remove the catalyst, which was washed with ethyl acetate. The filtrate was concentrated under a reduced pressure to provide the titled compound (168 mg, quantitatively) as pale yellow powder.

$^1$H-NMR Spectrum (CDCl$_3$) δ (ppm): 1.40-1.70 (2H, m), 1.80-2.00 (2H, m), 3.10-3.30 (2H, m), 3.74 (2H, brs), 3.80-4.00 (3H, m), 6.40-6.55 (3H, m), 6.90-7.30 (2H, m), 7.58 (1H, s), 8.01 (1H, d, J=6.0 Hz).

Production Example 137

Morpholine-4-carboxylic acid [4-(2-fluoro-4-nitrophenoxy)pyridin-2-yl]amide

To a solution of 4-(2-fluoro-4-nitrophenoxy)pyridin-2-ylamine (1.00 g) in tetrahydrofuran (50 ml) were added triethylamine (1.12 ml) and phenyl chloroformate (0.906 ml) while stirring in an ice bath, followed by stirring in an ice bath for 1 hr. The reaction mixture was concentrated under a reduced pressure to give a residue, to which N,N-dimethylformamide (16 ml) and morpholine (1.4 ml) were added, followed by stirring at room temperature for 4.5 hrs. The reaction mixture was partitioned between ethyl acetate (150 ml) and water (100 ml). The organic layer was washed with a 1 N aqueous solution of sodium hydroxide, brine, 1 N HCl and brine in this order, and dried over anhydrous sodium sulfate. The solvent was evaporated under a reduced pressure to give a solid, which was then suspended in diethyl ether (50 ml), filtered, and dried under aeration to provide the titled compound (941 mg, 64.8%) as pale yellow powder.

¹H-NMR Spectrum (DMSO-$d_6$) δ (ppm): 3.42 (4H, m), 3.56 (4H, m), 6.77 (1H, dd, J=2.4, 5.8 Hz), 7.51 (1H, d, J=2.4 Hz), 7.59 (1H, d, J=2.4 Hz), 8.19 (1H, m), 8.23 (1H, d, J=5.8 Hz), 8.43 (1H, dd, J=2.4, 10.4 Hz), 9.44 (1H, s).

Production Example 138

Morpholine-4-carboxylic acid [4-(4-amino-2-fluorophenoxy)pyridin-2-yl]amide

To a suspension of morpholine-4-carboxylic acid [4-(2-fluoro-4-nitrophenoxy)pyridin-2-yl]amide (941 mg) in ethanol (50 ml) were added water (10 ml), electrolytic iron powder (581 mg), ammonium chloride (1.11 g) and N,N-dimethylformamide (0.75 ml), followed by stirring to heat at 90° C. for 30 min. The reaction mixture was cooled down to room temperature, and filtered to remove an insoluble portion, which was washed with water and N,N-dimethylformamide in this order. The filtrate was concentrated under a reduced pressure to give a residue, to which ethyl acetate (100 ml) and water (100 ml) were added to partition. The aqueous layer was extracted with ethyl acetate. The combined organic layer was washed with water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1 to 1:2, ethyl acetate, then ethyl acetate:methanol=20:1 to 10:1). Fractions containing the target compound were concentrated to provide the titled compound (759 mg, 87.8%) as a pale yellow oil.

¹H-NMR Spectrum (DMSO-$d_6$) δ (ppm): 3.40 (4H, m), 3.55 (4H, m), 5.44 (2H, m), 6.40 (1H, dd, J=2.4, 8.4 Hz), 6.49 (1H, dd, J=2.4, 13.0 Hz), 6.54 (1H, dd, J=2.4, 5.6 Hz), 6.95 (1H, m), 7.32 (1H, d, J=2.4 Hz), 8.07 (1H, d, J=5.6 Hz), 9.20 (1H, s).

Production Example 139

3-[6-(2-Fluoro-4-nitrophenoxy)pyrimidin-4-yl]-1-(3-diethylaminopropyl)-1-methylurea 6-(2-Fluoro-4-nitrophenoxy)pyrimidin-4-ylamine (50 mg) was dissolved in tetrahydrofuran (2 ml) under a nitrogen atmosphere, and then triethylamine (0.0697 ml) and phenyl chloroformate (0.0627 ml) were added thereto while cooling in an ice bath, followed by stirring at room temperature for 30 min. The reaction mixture was concentrated under a reduced pressure to give a residue, to which N,N-dimethylformamide (2 ml) and N,N-diethyl-N'-methylpropane-1,3-diamine (115 mg) were added, followed by stirring at room temperature for 2 hrs. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated under a reduced pressure to give a residue, which was then purified by silica gel column chromatography (eluent; hexane:ethyl acetate=2:1 to 1:1, then ethyl acetate:ethanol=19:1). Fractions containing the target compound were concentrated under a reduced pressure to give a residue, which was then dried in vacuum to provide the titled compound (55.7 mg, 66.2%) as a yellow solid.

¹H-NMR Spectrum (CDCl₃) δ (ppm):1.08 (6H, m), 1.82 (2H, m), 2.51 (2H, t, J=6.0 Hz), 2.68 (4H, q, J=7.2 Hz), 2.94 (3H, s), 3.41 (2H, t, J=6.0 Hz), 7.39 (1H, m), 7.56 (1H, s), 8.10 (2H, m), 8.29 (1H, s), 11.70 (1H, brs).

Production Example 140

3-[6-(4-Amino-2-fluorophenoxy)pyrimidin-4-yl]-1-(3-diethylaminopropyl)-1-methylurea 3-[6-(2-Fluoro-4-nitrophenoxy)pyrimidin-4-yl]-1-(3-diethylaminopropyl)-1-methylurea (54.0 mg) was dissolved in tetrahydrofuran (2 ml)-methanol (2 ml), and then 10% palladium carbon (27.2 mg) was added thereto, followed by replacing with hydrogen inside the system and stirring overnight. After replacing with nitrogen inside the system, the reaction mixture was filtered to remove the catalyst, which was washed with methanol. The filtrate was concentrated under a reduced pressure to give a residue, which was then purified by silica gel column chromatography (Fuji Silysia NH, eluent; hexane:ethyl acetate=1:1, then ethyl acetate). Fractions containing the target compound were concentrated under a reduced pressure to provide the titled compound (34.3 mg, 68.6%) as a pale yellow solid.

¹H-NMR Spectrum (CDCl₃) δ (ppm):1.07 (6H, t, J=7.2 Hz), 1.79 (2H, m), 2.49 (2H, t, J=6 Hz), 2.67 (4H, q, J=7.2 Hz), 2.91 (3H, m), 3.39 (2H, m), 3.70 (2H, brs), 6.45 (1H, m), 6.49 (1H, dd, J=2.4, 11.6 Hz), 6.97 (1H, m), 7.20-7.30 (1H, m), 7.40 (1H, m), 8.33 (1H, m). ESI-MS (m/z):391 [M+H]⁺

Production Example 141

Benzyl (2-fluoro-4-{2-[(4-pyrrolidin-1-ylpiperidine-1-carbonyl)amino]pyridin-4-yloxy}phenyl)carbamate To a solution of benzyl [4-(2-aminopyridin-4-yloxy)-2-fluorophenyl]carbamate (230 mg) in tetrahydrofuran (6.50 ml) was added triethylamine (0.181 ml), and then phenyl chloroformate (0.123 ml) was added dropwise thereto while stirring in an ice bath, followed by stirring for 10 min. The reaction mixture was concentrated under a reduced pressure to give a residue, to which N,N-dimethylformamide (2.0 ml) and 4-(1-pyrrolidinyl)piperidine (301 mg) were then added, followed by stirring at room temperature for 11 hrs. To the reaction mixture was added ethyl acetate (50 ml) and water (30 ml) to partition. The organic layer was washed with brine (30 ml×3), and dried over anhydrous sodium sulfate. The solvent was evaporated under a reduced pressure to give a residue, which was then purified by silica gel column chromatography (FUJI Silysia NH, eluent; heptane:ethyl acetate=1:2, ethyl acetate, then ethyl acetate:methanol=10:1) to provide the titled compound (165 mg, 47.5%) as pale yellow powder.

¹H-NMR Spectrum (CDCl₃) δ (ppm): 1.27 (2H, m), 1.47-1.56 (2H, m), 1.93 (4H, m), 2.20 (1H, m), 2.57 (4H, m), 3.00 (2H, m), 4.02 (2H, m), 5.23 (2H, s), 6.50 (1H, dd, J=2.0, 5.6 Hz), 6.85-6.91 (3H, m), 7.34-7.44 (5H, m), 7.62 (1H, d, J=2.0 Hz), 8.04 (1H, d, J=5.6 Hz), 8.12 (1H, brs). ESI-MS (m/z): 534 [M+H]⁺.

Production Example 142

4-(Pyrrolidin-1-yl)piperidine-1-carboxylic acid [4-(4-amino-3-fluorophenoxy)pyridin-2-yl]amide To a solution of benzyl (2-fluoro-4-{2-[(4-pyrrolidin-1-ylpiperidine-1-carbonyl)amino]pyridin-4-yloxy}phenyl)carbamate (91 mg) in tetrahydrofuran (10 ml) was 10% palladium carbon (36.4 mg), followed by stirring under a hydrogen atmosphere at room temperature for 3.5 hrs. Ethanol (5.0 ml) was added thereto, followed by stirring under a hydrogen atmosphere at room temperature for 1.5 hrs. The reaction mixture was filtered to remove the catalyst, and washed with a small amount of tetrahydrofuran to give a solution of the titled compound in tetrahydrofuran. The solution was concentrated to almost dryness, which was then used for succeeding reactions without further purification.

ESI-MS (m/z): 400 [M+H]$^+$.

Example 1

Pyrrolidine-1-carboxylic acid {6-[2-fluoro-4-(3-phenylacetylthioureido)phenoxy]pyrimidin-4-yl}amide 2-Phenylacetyl chloride (0.079 ml) was dissolved in acetonitrile (3 ml) under a nitrogen atmosphere, and then potassium thiocyanate (116.6 mg) was added thereto at 60° C., followed by stirring at the same temperature for 2 hrs. The reaction mixture was cooled down to room temperature, and then a solution of 4-(4-amino-2-fluorophenoxy)-6-[(pyrroridin-1-yl)carbonylamino]pyrimidine (76.0 mg) in acetonitrile (3 ml) was added thereto, followed by stirring for 1 hr. The reaction mixture was partitioned between ethyl acetate and a saturated aqueous solution of sodium hydrogencarbonate. The organic layer was washed with a saturated aqueous solution of sodium hydrogencarbonate, water and brine in this order, dried over anhydrous sodium sulfate. The solvent was evaporated under a reduced pressure to give a residue, which was then purified by silica gel column chromatography (eluent; hexane:ethyl acetate=1:4). Fractions containing the target compound were concentrated to give a residue, which was suspended in diethyl ether (3 ml)-hexane (3 ml). The solid was filtered and dried under aeration to provide the titled compound (58.3 mg, 45.3%) as white powder.

$^1$H-NMR Spectrum (CDCl$_3$) δ (ppm): 2.00 (4H, m), 3.49 (4H, m), 3.74 (2H, s), 7.42-7.50 (8H, m), 7.71 (1H, m), 7.86 (1H, dd, J=2.8, 11.6 Hz), 8.83 (1H, m), 8.51 (1H, m), 12.43 (1H, s).

Example 2

Morpholine-4-carboxylic acid {6-[2-fluoro-4-(3-phenylacetylthioureido)phenoxy]pyrimidin-4-yl}amide 2-Phenylacetyl chloride (0.064 ml) was dissolved in acetonitrile (3 ml) under a nitrogen atmosphere, and then potassium thiocyanate (94.8 mg) was added thereto at 60° C., followed by stirring at the same temperature for 2 hrs. The reaction mixture was cooled down to room temperature, and then a solution of morpholine-4-carboxylic acid [6-(4-amino-2-fluorophenoxy)pyrimidin-4-yl}amide (65.0 mg) in acetonitrile (3 ml) was added thereto, followed by stirring for 1 hr. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:4). Fractions containing the target compound were concentrated to give a residue, which was suspended in diethyl ether (3 ml)-hexane (3 ml). The solid was filtered off and dried under aeration to provide the titled compound (54.4 mg, 54.6%) as white powder.

$^1$H-NMR Spectrum (CDCl$_3$) δ (ppm): 3.53 (4H, m), 3.75 (6H, m), 7.42-7.50 (8H, m), 7.64 (1H, m), 7.86 (1H, dd, J=2.4, 11.6 Hz), 8.34 (1H, m), 8.51 (1H, m), 12.44 (1H, s).

Example 3

Pyrrolidine-1-carboxylic acid [6-(2-fluoro-4-{3-[2-(4-fluorophenyl)acetyl]thioureido}phenoxy)pyrimidin-4-yl]amide 2-(4-Fluorophenyl)acetyl chloride (135 mg) was dissolved in acetonitrile (5 ml) under a nitrogen atmosphere, and then potassium thiocyanate (152 mg) was added thereto at 60° C., followed by stirring at the same temperature for 1.5 hrs. The reaction mixture was cooled down to room temperature, and then a solution of 4-(4-amino-2-fluorophenoxy)-6-[(pyrrolidin-1-yl)carbonylamino]pyrimidine (99.6 mg) in acetonitrile (3 ml) was added thereto, followed by stirring for 15 min. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:3). Fractions containing the target compound were concentrated to give a residue, which was suspended in diethyl ether (5 ml)-hexane (5 ml). The solid was filtered off and dried under aeration to provide the titled compound (111.8 mg, 69.5%) as a pale yellow solid.

$^1$H-NMR Spectrum (DMSO-d$_6$) δ (ppm): 1.83 (4H, m), 3.41 (4H, m), 3.83 (2H, m), 7.18 (2H, dd, J=8.8, 8.8 Hz), 7.46-7.50 (4H, m), 7.50 (1H, s), 7.88 (1H, d, J=12.4 Hz), 8.40 (1H, s), 9.43 (1H, brs), 11.79 (1H, brs), 12.39 (1H, brs).

Example 4

Morpholine-4-carboxylic acid [6-[2-fluoro-4-{3-[2-(4-fluorophenyl)acetyl]thioureido}phenoxy)pyrimidin-4-yl]amide 2-(4-Fluorophenyl)acetyl chloride (103 mg) was dissolved in acetonitrile (3 ml) under a nitrogen atmosphere, and then potassium thiocyanate (116 mg) was added thereto at 60° C., followed by stirring at the same temperature for 2 hrs. The reaction mixture was cooled down to room temperature, and then a solution of 4-(4-amino-2-fluorophenoxy)-6-[(morpholin-4-yl)carbonylamino]pyrimidine (79.5 mg) in acetonitrile (3 ml) was added thereto, followed by stirring for 10 min. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:3). Fractions containing the target compound were concentrated to give a residue, which was suspended in diethyl ether (5 ml)-hexane (5 ml). The solid was filtered off and dried under aeration to provide the titled compound (71.9 mg, 56.9%) as a pale yellow solid.

$^1$H-NMR Spectrum (CDCl$_3$) δ (ppm): 3.53 (4H, m), 3.71 (2H, m), 3.75 (4H, m), 7.12 (2H, m), 7.22 (1H, m), 7.25-7.34 (2H, m), 7.36 (1H, d, J=7.6 Hz), 7.43 (1H, brs), 7.65 (1H, s), 7.86 (1H, dd, J=2.4, 11.6 Hz), 8.34 (1H, s), 8.57 (1H, brs), 12.40 (1H, brs).

151

Example 5

Piperidine-1-carboxylic acid {6-[2-fluoro-4-(3-phenylacetylthioureido)phenoxy]pyrimidin-4-yl}amide 2-Phenylacetyl chloride (0.068 ml) was dissolved in acetonitrile (5 ml) under a nitrogen atmosphere, and then potassium thiocyanate (100 mg) was added thereto at 60° C., followed by stirring at the same temperature for 1.5 hrs. The reaction mixture was cooled down to room temperature, and then a solution of piperidine-1-carboxylic acid [6-(4-amino-2-fluorophenoxy)pyrimidin-4-yl]amide (114 mg) in acetonitrile (3 ml) was added thereto, followed by stirring for 30 min. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:1). Fractions containing the target compound were concentrated to give a residue, which was suspended in diethyl ether (5 ml)-hexane (5 ml). The solid was filtered off and dried under aeration to provide the titled compound (88.8 mg, 50.8%) as a pale yellow solid.

$^1$H-NMR Spectrum (CDCl$_3$) δ (ppm): 1.54-1.74 (6H, m), 3.48 (4H, m), 3.74 (2H, s), 7.18-7.50 (8H, m), 7.64 (1H, s), 7.86 (1H, dd, J=2.4, 11.2 Hz), 8.33 (1H, s), 8.50 (1H, brs), 12.43 (1H, brs).

Example 6

Piperidine-1-carboxylic acid [6-(2-fluoro-4-{3-[2-(4-fluorophenyl)acetyl]thioureido}phenoxy)pyrimidin-4-yl]amide 2-(4-Fluorophenyl)acetyl chloride (92 mg) was dissolved in acetonitrile (5 ml) under a nitrogen atmosphere, and then potassium thiocyanate (104 mg) was added thereto at 60° C., followed by stirring at the same temperature for 1.5 hrs. The reaction mixture was cooled down to room temperature, and then a solution of piperidine-1-carboxylic acid [6-(4-amino-2-fluorophenoxy)pyrimidin-4-yl]amide (118 mg) in acetonitrile (3 ml) was added thereto, followed by stirring for 30 min. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (Fuji Silysia NH, eluent; hexane:ethyl acetate=1:1). Fractions containing the target compound were concentrated to give a residue, which was suspended in diethyl ether (5 ml)-hexane (5 ml). The solid was filtered off and dried under aeration to provide the titled compound (98.4 mg, 52.5%) as a pale yellow solid.

$^1$H-NMR Spectrum (CDCl$_3$) δ (ppm): 1.52-1.74 (6H, m), 3.48 (4H, m), 3.71 (2H, s), 7.05-7.15 (2H, m), 7.22 (1H, m), 7.25-7.32 (2H, m), 7.35-7.45 (2H, m), 7.64 (1H, s), 7.86 (1H, dd, J=2.8, 11.6 Hz), 8.33 (1H, s), 8.55 (1H, brs), 12.39 (1H, brs).

Example 7

3-[6-(2-Fluoro-4-{3-[2-(4-fluorophenyl)acetyl]thioureido}phenoxy)pyrimidin-4-yl]-1,1-dimethylurea 2-(4-Fluorophenyl)acetyl chloride (148 mg) was dissolved in acetonitrile (5 ml) under a nitrogen atmosphere, and then potassium thiocyanate (104 mg) was added thereto at 60° C., followed by stirring at the same temperature for 5 hrs. The reaction mixture was cooled down to room temperature, and then a solution of 1-[4-(4-amino-2-fluorophenoxy)pyrimidin-6-yl]-3-dimethylurea (100 mg) in acetonitrile (3 ml) was added thereto, followed by stirring for 40 min. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:2). Fractions containing the target compound were concentrated to give a residue, which was suspended in diethyl ether (1.5 ml)-hexane (1.5 ml). The solid was filtered off and dried under aeration to provide the titled compound (125.7 mg, 75.3%) as a pale yellow solid.

$^1$H-NMR Spectrum (DMSO-d$_6$) δ (ppm): 2.95 (6H, s), 3.83 (2H, s), 7.19 (2H, m), 7.30-7.50 (5H, m), 7.88 (1H, m), 8.40 (1H, m), 9.60 (1H, s), 11.79 (1H, brs), 12.41 (1H, brs).

Example 8

4-(Pyrrolidin-1-yl)piperidine-1-carboxylic acid {6-[2-fluoro-4-(3-phenylacetylthioureido)phenoxy]pirimidin-4-yl}amide 2-Phenylacetyl chloride (0.053 ml) was dissolved in acetonitrile (4 ml) under a nitrogen atmosphere, and then potassium thiocyanate (77.7 mg) was added thereto at 60° C., followed by stirring at the same temperature for 2 hrs. The reaction mixture was cooled down to room temperature, and partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated to give a residue, to which was added a solution of 4-(pyrrolidin-1-yl)piperidin-1-carboxylic acid [6-(4-amino-2-fluorophenoxy)pyrimidin-4-yl]amide (49.0 mg) in acetonitrile (5 ml) under a nitrogen atmosphere, followed by stirring at room temperature for 1 hr. The reaction mixture was partitioned between ethyl acetate and water. The organic layer was washed with brine, and dried over anhydrous sodium sulfate. The solvent was evaporated under a reduced pressure to give a residue, which was then purified by silica gel column chromatography (FUJI Silysia NH, eluent; ethyl acetate:methanol=19:1). The resultant crude product was purified again by silica gel column chromatography (FUJI Silysia NH, eluent; ethyl acetate:methanol=19:1). Fractions containing the target compound were concentrated to give a residue, which was suspended in diethyl ether (0.5 ml)-hexane (1.0 ml). The solid was filtered off and dried under aeration to provide the titled compound (8.1 mg, 11.5%) as a white solid.

$^1$H-NMR Spectrum (CDCl$_3$) δ (ppm): 1.48-1.70 (2H, m), 1.81 (4H, m), 1.97 (2H, m), 2.25 (1H, m), 2.59 (4H, m), 3.04

(2H, m), 3.70-3.80 (2H, m), 4.03 (2H, m), 7.18-7.50 (8H, m), 7.63 (1H, s), 7.86 (1H, dd, J=2.4, 11.6 Hz), 8.33 (1H, s), 8.49 (1H, brs), 12.43 (1H, brs).

Example 9

Pyrrolidine-1-carboxylic acid [4-(4-{3-[2-(4-fluorophenyl)acetyl]thioureido}phenoxy)pyridin-2-yl] amide 2-(4-Fluorophenyl)acetyl chloride (72.5 mg) was dissolved in acetonitrile (2 ml) under a nitrogen atmosphere, and then potassium thiocyanate (81.6 mg) was added thereto at 60° C., followed by stirring at the same temperature for 2 hrs. The reaction mixture was cooled down to room temperature, and then a solution of 4-(4-aminophenoxy)-2-[(pyrrolidin-1-yl)carbonylamino]pyridine (50 mg) in acetonitrile (3 ml) was added thereto, followed by stirring for 1 hr. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated under a reduced pressure to give a residue, which was then purified by silica gel column chromatography (eluent; hexane:ethyl acetate=1:1 to 1:3). Fractions containing the target compound were concentrated to give a residue, which was suspended in diethyl ether (0.5 ml)-hexane (1.5 ml). The solid was filtered off and dried under aeration to provide the titled compound (15.8 mg, 19.1%) as a pale yellow solid.

$^1$H-NMR Spectrum (CDCl$_3$) δ (ppm): 1.96 (4H, m), 3.45 (4H, m), 3.70 (2H, s), 6.55 (1H, dd, J=2.4, 5.6 Hz), 7.01 (1H, brs), 7.11 (4H, m), 7.29 (2H, m), 7.68 (2H, m), 7.73 (1H, d, J=2.4 Hz), 8.05 (1H, d, J=5.6 Hz), 8.57 (1H, m), 12.26 (1H, brs).

Example 10

4-{2-Chloro-4-[3-(2-phenylacetyl)thioureido]phenoxy}-2-[(pyrrolidin-1-yl)carbonylamino]pyridine 2-Phenylacetyl chloride (0.73 ml) was dissolved in acetonitrile (5 ml) under a nitrogen atmosphere, and then potassium thiocyanate (107 mg) was added thereto at 60° C., followed by stirring at the same temperature for 2 hrs. The reaction mixture was cooled down to room temperature, and then a solution of 4-(4-amino-2-chlorophenoxy)-2-[(pyrrolidin-1-yl)carbonylamino]pyridine (122 mg) in acetonitrile (5 ml) was added thereto, followed by stirring at room temperature for 1.5 hr. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to give a residue, which was then purified by silica gel column chromatography (eluent; hexane:ethyl acetate=1:4, then ethyl acetate). Fractions containing the target compound were concentrated to give a residue, to which a small amount of diethyl ether was added to precipitate crystals. A suspension containing the crystals was diluted with a small amount of hexane. The crystals were filtered off and dried under aeration to provide the titled compound (66.7 mg, 36%) as pale yellow crystals.

$^1$H-NMR Spectrum (DMSO-d$_6$) δ (ppm): 1.75-1.85 (4H, m), 3.20-3.40 (4H, m), 3.83 (2H, s), 6.56 (1H, dd, J=2.4, 5.6 Hz), 7.20-7.30 (6H, m), 7.45 (1H, d, J=2.4 Hz), 7.63 (1H, dd, J=2.4, 8.8 Hz), 8.10 (1H, d, J=2.4 Hz), 8.13 (1H, d, J=5.6 Hz), 8.68 (1H, s), 11.81 (1H, s), 12.44 (1H, s).

Example 11

4-{2-Chloro-4-[3-(2-phenylacetyl)thioureido]phenoxy}-2-[(morpholin-4-yl)carbonylamino]pyridine 2-Phenylacetyl chloride (0.93 ml) was dissolved in acetonitrile (5 ml) under a nitrogen atmosphere, and then potassium thiocyanate (137 mg) was added thereto at 60° C., followed by stirring at the same temperature for 3 hrs. The reaction mixture was cooled down to room temperature, and then a solution of 4-(4-amino-2-chlorophenoxy)-2-[(morpholin-4-yl)carbonylamino]pyridine (164 mg) in acetonitrile (5 ml) was added thereto, followed by stirring at room temperature for 1 hr. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to give a residue, which was then purified by silica gel column chromatography (eluent; hexane:ethyl acetate=1:4, then ethyl acetate). Fractions containing the target compound were concentrated to give a residue, to which hexane/ethyl acetate (1/5) was added to suspend. The resultant solid was filtered off and dried under aeration to provide the titled compound (115 mg, 47%) as pale yellow powder.

$^1$H-NMR Spectrum (DMSO-d$_6$) δ (ppm): 3.30-3.40 (4H, m), 3.50-3.60 (4H, m), 3.83 (2H, s), 6.56 (1H, dd, J=2.4, 6.0 Hz), 7.20-7.40 (7H, m), 7.64 (1H, dd, J=2.8, 8.8 Hz), 8.09 (1H, d, J=2.8 Hz), 8.14 (1H, d, J=6.0 Hz), 9.30 (1H, s), 11.81 (1H, s), 12.43 (1H, s).

Example 12

4-{2-Chloro-4-[3-(2-phenylacetyl)thioureido]phenoxy}-6-[(pyrrolidin-1-yl)carbonylamino]pyridine 2-Phenylacetyl chloride (0.86 ml) was dissolved in acetonitrile (5 ml) under a nitrogen atmosphere, and then potassium thiocyanate (127 mg) was added thereto at 60° C., followed by stirring at the same temperature for 3 hrs. The reaction mixture was cooled down to room temperature, and then a solution of 4-(4-amino-2-chlorophenoxy)-6-[(pyrrolidin-1-yl)carbonylamino]pyridine (145 mg) in acetonitrile (5 ml) was added thereto, followed by stirring at room temperature for 1.5 hr. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to give a residue, which was then purified by silica gel column chromatography (eluent; hexane:ethyl acetate=1:2). Fractions containing the target compound were concentrated to give a residue, to which diethyl ether/hexane (1/2) was added to suspend. The resultant solid was filtered off and dried under aeration to provide the titled compound (122 mg, 55%) as white powder.

$^1$H-NMR Spectrum (DMSO-d$_6$) δ (ppm): 1.80-1.90 (4H, m), 3.20-3.40 (4H, m), 3.83 (2H, s), 7.20-7.40 (6H, m), 7.48 (1H, d, J=0.8 Hz), 7.59 (1H, dd, J=2.4, 8.8 Hz), 8.00 (1H, d, J=2.4 Hz), 8.39 (1H, d, J=0.8 Hz), 9.41 (1H, s), 11.80 (1H, s), 12.39 (1H, s).

Example 13

4-(2-Fluoro-4-{3-[2-(4-fluorophenyl)acetyl]thioureido}phenoxy)-2-[(pyrrolidin-1-yl)carbonylamino]pyridine Thionyl chloride (2.0 ml) was added to 2-(4-fluorophenyl)acetic acid (694 mg) under a nitrogen atmosphere, followed by stirring at 50° C. for 1 hr. The reaction mixture was concentrated under a reduced pressure to give a residue. The residue was dissolved in acetonitrile (100 ml) under a nitrogen atmosphere, and then potassium thiocyanate (875 mg) was added thereto at 50° C., followed by stirring at the same temperature for 2 hrs. The reaction mixture was cooled down to room temperature, and then 4-(4-amino-2-fluorophenoxy)-2-[(pyrrolidin-1-yl)carbonylamino]pyridine (949 mg) was added thereto, followed by stirring for 1 hr. The reaction mixture was concentrated under a reduced pressure to give a residue, which was then partitioned between ethyl acetate and a saturated aqueous solution of sodium hydrogencarbonate. The organic layer was washed with brine, and dried over anhydrous sodium sulfate. The solvent was evaporated under a reduced pressure to give a residue, which was then purified by silica gel column chromatography (eluent; hexane:ethyl acetate=1:2 to 1:3). Fractions containing the target compound were concentrated to give a residue, to which diethyl ether (20 ml) was added to precipitate crystals. The crystals were filtered off and dried under aeration to provide the titled compound (834.5 mg, 54%) as white crystals.

$^1$H-NMR Spectrum (DMSO-$d_6$) δ (ppm): 1.70-1.90 (4H, m), 3.20-3.40 (4H, m), 3.83 (2H, s), 6.60 (1H, dd, J=2.4, 5.6 Hz), 7.18 (2H, m), 7.30-7.60 (5H, m), 7.98 (1H, m), 8.13 (1H, d, J=5.6 Hz), 8.73 (1H, s), 11.80 (1H, s), 12.47 (1H, s).

Example 14

4-{2-Fluoro-4-[3-(2-phenylacetyl)thioureido]phenoxy}-2-[(pyrrolidin-1-yl)carbonylamino]pyridine 2-Phenylacetyl chloride (100 mg) was dissolved in acetonitrile (2 ml) under a nitrogen atmosphere, and then potassium thiocyanate (126 mg) was added thereto at 50° C., followed by stirring at the same temperature for 1.5 hrs. A solution of 4-(4-amino-2-fluorophenoxy)-2-[(pyrrolidin-1-yl)carbonylamino]pyridine (41 mg) in acetonitrile (4 ml) was added thereto, followed by stirring at room temperature for 2.5 hr. The reaction mixture was cooled down to room temperature, and then partitioned between ethyl acetate and a saturated aqueous solution of sodium hydrogencarbonate. The organic layer was washed with brine, and dried over anhydrous sodium sulfate. The solvent was evaporated under a reduced pressure to give a residue, which was then purified by silica gel column chromatography (eluent; hexane:ethyl acetate=1:4). Fractions containing the target compound were concentrated to give a residue, to which a small amount of diethyl ether was added to precipitate crystals. A suspension containing the crystals was diluted with a small amount of hexane. The crystals were filtered off and dried under aeration to provide the titled compound (21.4 mg, 34%) as pale yellow crystals.

$^1$H-NMR Spectrum (DMSO-$d_6$) δ (ppm): 1.70-1.90 (4H, m), 3.20-3.40 (4H, m), 3.83 (2H, s), 6.60 (1H, m), 7.20-7.40 (6H, m), 7.50-7.60 (2H, m), 7.99 (1H, m), 8.13 (1H, d, J=5.6 Hz), 8.75 (1H, s), 11.81 (1H, s), 12.50 (1H, s).

Example 15

4-{2-Fluoro-4-[3-(2-phenylacetyl)thioureido]phenoxy}-2-[(4-hydroxypiperidin-1-yl)carbonylamino]pyridine 2-Phenylacetyl chloride (0.180 ml) was dissolved in acetonitrile (20 ml) under a nitrogen atmosphere, and then potassium thiocyanate (197 mg) was added thereto at 50° C., followed by stirring at the same temperature for 2 hrs. The reaction mixture was concentrated under a reduced pressure to give a residue, to which ethyl acetate (20 ml) and a saturated aqueous solution of sodium hydrogencarbonate (20 ml) were then added, followed by stirring for 30 min. The organic layer was separated, washed with brine, and dried over anhydrous sodium sulfate. The solvent was evaporated to provide 2-phenylacetyl isothiocyanate, which was used to prepare a solution in toluene (5 ml)-ethanol (5 ml). To the solution was added 4-(4-amino-2-fluorophenoxy)-2-[(4-hydroxypiperidin-1-yl)carbonylamino]pyridine (168 mg), followed by stirring overnight. The reaction mixture was concentrated under a reduced pressure to give a residue, which was then purified by silica gel column chromatography (eluent; ethyl acetate:methanol=95:5). Fractions containing the target compound were concentrated to give a residue, to which diethyl ether (20 ml) was added to suspend. The resultant solid was filtered off and dried under aeration to provide the titled compound (106 mg, 42%) as white powder.

$^1$H-NMR Spectrum (DMSO-$d_6$) δ (ppm): 1.20-1.40 (2H, m), 1.60-1.80 (2H, m), 3.00-3.20 (2H, m), 3.64 (1H, m), 3.70-3.85 (2H, m), 3.83 (2H, s), 4.68 (1H, d, J=4.4 Hz), 6.58 (1H, dd, J=2.4, 6.0 Hz), 7.20-7.40 (7H, m), 7.50 (1H, m), 8.00 (1H, m), 8.13 (1H, d, J=6.0 Hz), 9.22 (1H, s), 11.81 (1H, s), 12.49 (1H, s).

Example 16

2-[(Dimethylamino)carbonylamino]-4-{2-fluoro-4-[3-(2-cyclohexylacetylthio)ureido]phenoxy}pyridine 2-Cyclohexylacetyl chloride (80 mg) was dissolved in acetonitrile (5 ml) under a nitrogen atmosphere, and then potassium thiocyanate (97 mg) was added thereto at 50° C., followed by stirring at the same temperature for 1 hr. The reaction mixture was cooled down to room temperature, and then 4-(4-amino-2-fluorophenoxy)-2-[(dimethylamino)carbonylamino]pyridine (58 mg) was added thereto, followed by stirring for 30 min. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated under a reduced pressure to give a residue, which was then purified by silica gel column chromatography (eluent; hexane:ethyl acetate=1:3). Fractions containing the target compound were concentrated to give a residue, to which diethyl ether (10 ml) was added to precipitate crystals. A suspension containing the crystals was diluted with hexane (20 ml). The crystals were filtered off and dried under aeration to provide the titled compound (45.6 mg, 48%) as white crystals.

$^1$H-NMR Spectrum (DMSO-$d_6$) δ (ppm): 0.80-1.80 (11H, m), 2.36 (2H, d, J=6.8 Hz), 2.89 (6H, s), 6.61 (1H, dd, J=2.4, 5.6 Hz), 7.36-7.43 (2H, m), 7.53 (1H, dd, J=1.2, 8.8 Hz), 8.03 (1H, dd, J=2.4, 12.0 Hz), 8.13 (1H, d, J=5.6 Hz), 8.94 (1H, s), 11.54 (1H, s), 12.68 (1H, s).

Example 17

2-[(Dimethylamino)carbonylamino]-4-{2-fluoro-4-[3-(2-norbornaneacetylthio)ureido]phenoxy}pyridine 2-Norbornaneacetic acid (66 mg) was dissolved in thionyl chloride (0.5 ml) under a nitrogen atmosphere, followed by stirring at 50° C. for 1 hr. The reaction mixture was concentrated under a reduced pressure to provide a crude product of 2-norbornaneacetyl chloride. The crude product of 2-norbornaneacetyl chloride was dissolved in acetonitrile (5 ml) under a nitrogen atmosphere, and then potassium thiocyanate (84 mg) was added thereto at 50° C., followed by stirring at the same temperature for 1 hr. The reaction mixture was cooled down to room temperature, and then 4-(4-amino-2-fluorophenoxy)-2-[(dimethylamino)carbonylamino]pyridine (50 mg) was added thereto, followed by stirring for 30 min. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; hexane:ethyl acetate=1:4). Fractions containing the target compound were concentrated to give a residue, to which diethyl ether (5 ml) was added to precipitate crystals. A suspension containing the crystals was diluted with hexane (10 ml). The crystals were filtered off and dried under aeration to provide the titled compound (39,7 mg, 48%) as white crystals.

$^1$H-NMR Spectrum (DMSO-$d_6$) δ (ppm): 0.60-2.30 (13H, m), 2.90 (6H, s), 6.61 (1H, dd, J=2.4, 5.6 Hz), 7.36-7.43 (2H, m), 7.52 (1H, d, J=8.8 Hz), 8.03 (1H, dd, J=2.4, 12.0 Hz), 8.13 (1H, d, J=5.6 Hz), 8.94 (1H, s), 11.54 (1H, s), 12.65 (1H, s). ESI-MS (m/z): 486 [M+1]$^+$.

Example 18

Morpholine-4-carboxylic acid {4-[3-fluoro-4-(3-phenylacetylthioureido)phenoxy]pyridin-2-yl}amide To a solution of 1-[4-(2-aminopyridin-4-yloxy)-2-fluorophenyl]-3-(2-phenylacetyl)thiourea (270 mg) in tetrahydrofuran (12 ml) was added triethylamine (0.142 ml), and then phenyl chloroformate (0.160 ml) was added while stirring in an ice bath, followed by stirring under a nitrogen atmosphere for 30 min. A portion of the solution (4.0 ml) was concentrated under a reduced pressure, and then N,N-dimethylformamide (1.5 ml) and morpholine (0.989 ml, 1.14 mmol) were added thereto, followed by stirring at room temperature for 5 hrs. The reaction mixture was partitioned between ethyl acetate (40 ml) and water (40 ml). The organic layer was washed with brine, and dried over anhydrous sodium sulfate. The solvent was evaporated to give a residue, which was then purified by silica gel column chromatography (eluent; hexane:ethyl acetate=1:1, ethyl acetate, then ethyl acetate:methanol=10:1). Fractions containing the target compound were concentrated to give a solid, which was suspended in diethyl ether. The solid was filtered off, washed with diethyl ether, and dried under aeration to provide the titled compound (42 mg) as pale brown powder.

$^1$H-NMR Spectrum (DMSO-$d_6$) δ (ppm): 3.41 (4H, m), 3.56 (4H, m), 3.83 (2H, s), 6.63 (1H, dd, J=2.2, 5.6 Hz), 7.05 (1H, d, J=8.8 Hz), 7.25-7.35 (6H, m), 7.46 (1H, m), 8.02 (1H, dd, J=8.8, 8.8 Hz), 8.17 (1H, d, J=5.6 Hz), 9.33 (1H, s), 11.88 (1H, s), 12.24 (1H, s). ESI-MS (m/z): 510 [M+1]$^+$.

Example 19

Piperidine-1-carboxylic acid (4-{3-fluoro-4-[3-(2-phenylacetyl)thioureido]phenoxy}pyridin-2-yl) amide To a solution of 1-[4-(2-aminopyridin-4-yloxy)-2-fluorophenyl]-3-(2-phenylacetyl)thiourea (270 mg) in tetrahydrofuran (12 ml) was added triethylamine (0.142 ml), and then phenyl chloroformate (0.160 ml) was added while stirring in an ice bath, followed by stirring under a nitrogen atmosphere for 30 min. One third of the solution was concentrated under a reduced pressure, and then N,N-dimethylformamide (1.5 ml) and piperidine (0.112 ml) were added thereto, followed by stirring at room temperature for 5 hrs. The reaction mixture was partitioned between ethyl acetate (40 ml) and water (40 ml). The organic layer was washed with brine, and dried over anhydrous sodium sulfate. The solvent was evaporated to give a residue, which was then purified by silica gel column chromatography (eluent; hexane:ethyl acetate=1:1, then ethyl acetate). Fractions containing the target compound were concentrated to give a solid, which was suspended in diethyl ether. The solid was filtered off, washed with diethyl ether, and dried under aeration to provide the titled compound (50 mg) as pale brown powder.

$^1$H-NMR Spectrum (DMSO-$d_6$) δ (ppm): 1.45 (4H, m), 1.54 (2H, m), 3.39 (4H, m), 3.83 (2H, s), 6.60 (1H, dd, J=2.4, 5.6 Hz), 7.03 (1H, m), 7.24-7.36 (6H, m), 7.46 (1H, d, J=2.4 Hz), 8.01 (1H, m), 8.15 (1H, d, J=5.6 Hz), 9.19 (1H, s), 11.87 (1H, s), 12.23 (1H, s).

Example 20

Pyrrolidine-1-carboxylic acid {4-[3-fluoro-4-(3-phenylacetylthioureido)phenoxy]pyridin-2-yl}amide To a solution of 2-phenylacetyl chloride (0.054 ml, 0.43 mmol) in acetonitrile (4.3 ml) was added potassium thiocyanate (83 mg) at room temperature, followed by stirring under a nitrogen atmosphere at 60° C. for 1.5 hrs. The reaction mixture was cooled in an ice bath, and then a solution of pyrrolidine-1-carboxylic acid [4-(4-amino-3-fluorophenoxy)pyridin-2-yl]amide (90 mg) in acetonitrile (4.0 ml) was added thereto, followed by warming the reaction mixture to room temperature and stirring for 3 hrs. The reaction mixture was partitioned between ethyl acetate and water. The organic layer was washed with brine, and dried over anhydrous sodium sulfate. The solvent was evaporated to give a residue, which was then purified by silica gel column chromatography (eluent; hexane:ethyl acetate=1:1 to 1:2, then ethyl acetate). Fractions containing the target compound were concentrated to give a solid, which was suspended in diethyl ether. The solid was filtered off, washed with diethyl ether, and dried under aeration to provide the titled compound (18 mg, 13%) as colorless powder.

$^1$H-NMR Spectrum (DMSO-$d_6$) δ (ppm): 1.81 (4H, m), 3.36 (4H, m), 3.83 (2H, s), 6.62 (1H, d, J=5.6 Hz), 7.04 (1H, m), 7.25-7.36 (6H, m), 7.57 (1H, s), 8.02 (1H, m), 8.15 (1H, d, J=5.6 Hz), 8.75 (1H, s), 11.88 (1H, s), 12.24 (1H, s).

Example 21

Morpholine-4-carboxylic acid {4-[2-fluoro-4-(3-phenylacetylthioureido)phenoxy]pyridin-2-yl}amide To a solution of morpholine-4-carboxylic acid [4-(4-amino-2-fluorophenoxy)pyridin-2-yl]amide (50 mg) in N,N-dimethylformamide (1.0 ml) was added phenylacetyl isothiocyanate (42 mg), followed by stirring at room temperature for 22 hrs. The reaction mixture was partitioned between ethyl acetate and water. The organic layer was washed with brine, and dried over anhydrous sodium sulfate. The solvent was evaporated to give a residue, which was then purified by silica gel column chromatography (eluent; hexane:ethyl acetate=1:1, ethyl acetate, then ethyl acetate:methanol=10:1). Fractions containing the target compound were concentrated to give a solid, which was suspended in diethyl ether. The solid was filtered off, washed with diethyl ether, and dried under aeration to provide the titled compound (22 mg, 0.043 mmol, 29%) as colorless solid.
$^1$H-NMR Spectrum (DMSO-d$_6$) δ (ppm): 3.40 (4H, m), 3.55 (4H, m), 3.83 (2H, s), 6.61 (1H, d, J=5.8 Hz), 7.30 (1H, m), 7.36 (6H, m), 7.51 (1H, d, J=9.6 Hz), 7.99 (1H, m), 8.14 (1H, d, J=5.8 Hz), 9.32 (1H, s), 11.81 (1H, s), 12.49 (1H, s). ESI-MS (m/z): 510 [M+H]$^+$.

Example 22

1-(3-Diethylaminopropyl)-3-[4-(2-fluoro-4-{3-[2-(4-fluorophenyl)acetyl]thioureido}phenoxy)pyridin-2-yl]-1-methylurea To a solution of 1-[4-(2-aminopyridin-4-yloxy)-3-fluorophenyl]-3-[(4-fluorophenyl)acetyl]thiourea (100 mg) in tetrahydrofuran (10 ml) was added triethylamine (0.101 ml), and then phenyl chloroformate (0.0454 ml) was added while stirring in an ice bath, followed by stirring under a nitrogen atmosphere for 10 min. The reaction mixture was concentrated under a reduced pressure to give a residue, to which N,N-dimethylformamide (2.0 ml) and N,N-diethyl-N'-methyl-1,3-propanediamine (151 mg) were then added, followed by stirring at room temperature for 2.5 hrs. The reaction mixture was diluted with ethyl acetate (150 ml), washed with a saturated aqueous solution of sodium hydrogencarbonate, and dried over anhydrous sodium sulfate. The solvent was evaporated to give a residue, which was then purified by silica gel column chromatography (FUJI Silysia NH, hexane:ethyl acetate=1:2, then ethyl acetate). Fractions containing the target compound were concentrated to give a solid, which was further purified by LC-MS. Fractions containing the target compound were concentrated to give a solid, to which a saturated aqueous solution of sodium hydrogencarbonate was then added to make it alkaline. The mixture was extracted with ethyl acetate, and the organic layer was dried over anhydrous sodium sulfate. The solvent was evaporated to provide the titled compound (2.7 mg, 1.9%) as a pale yellow oil.
$^1$H-NMR Spectrum (CDCl$_3$) δ (ppm): 1.09 (6H, m), 1.60-1.90 (2H, m), 2.06 (2H, m), 2.75 (4H, m), 2.88 (3H, s), 3.34 (2H, m), 3.65 (2H, s), 6.44 (1H, dd, J=2.4, 6.0 Hz), 7.00-7.09 (3H, m), 7.20-7.26 (3H, m), 7.47 (1H, m), 7.80 (1H, dd, J=2.4, 11.6 Hz), 7.99 (1H, d, J=6.0 Hz), 8.96 (1H, brs), 12.36 (1H, s). ESI-MS (m/z) (neg.): 583 [M−H]$^-$.

Example 23

Morpholine-4-carboxylic acid {4-[2-methyl-4-(3-phenylacetylthioureido)phenoxy]pyridin-2-yl}amide To a solution of 2-phenylacetyl chloride (0.0523 ml) in acetonitrile (5.0 ml) was added potassium thiocyanate (35.6 mg), followed by stirring under a nitrogen atmosphere at 50° C. for 1 hr. The reaction mixture was cooled down to room temperature, and then morpholine-4-carboxylic acid [4-(4-amino-2-methylphenoxy)pyridine-2-yl]amide (80 mg) and N,N-dimethylformamide (1 ml) were added thereto, followed by stirring under a nitrogen atmosphere at room temperature for 21 hrs. The reaction mixture was partitioned between ethyl acetate (100 ml) and water (40 ml). The organic layer was washed with brine, and dried over anhydrous sodium sulfate. The solvent was evaporated to give a residue, which was then purified by silica gel column chromatography (eluent; ethyl acetate). Fractions containing the target compound were concentrated to give a solid, which was suspended in diethyl ether (4 ml)-ethanol (0.8 ml). The solid was filtered off, washed with diethyl ether, and dried under aeration to provide the titled compound (38 mg, 31%) as colorless powder.
$^1$H-NMR Spectrum (DMSO-d$_6$) δ (ppm): 2.10 (3H, s), 3.39 (4H, m), 3.55 (4H, m), 3.82 (2H, s), 6.51 (1H, dd, J=2.4, 5.6 Hz), 7.10 (1H, d, J=8.4 Hz), 7.28-7.36 (6H, m), 7.60-7.64 (2H, m), 8.11 (1H, d, J=5.6 Hz), 9.24 (1H, s), 11.72 (1H, s), 12.43 (1H, s). ESI-MS (m/z) (neg.): 504 [M−H]$^-$.

Example 24

Morpholine-4-carboxylic acid (4-{2-methyl-4-[3-(4-fluorophenyl)acetylthioureido]phenoxy}pyridin-2-yl)amide To a solution of 2-(4-fluorophenyl)acetyl chloride (63.2 mg) in acetonitrile (30 ml) was added potassium thiocyanate (35.6 mg), followed by stirring under a nitrogen atmosphere at 50° C. for 1 hr. The reaction mixture was cooled down to room temperature, and then morpholine-4-carboxylic acid [4-(4-amino-2-methylphenoxy)pyridine-2-yl]amide (80 mg) was added thereto, followed by stirring under a nitrogen atmosphere for 2 hrs. The reaction mixture was partitioned between ethyl acetate (100 ml) and water (60 ml). The organic layer was washed with brine, and dried over anhydrous sodium sulfate. The solvent was evaporated to give a residue, which was then purified by silica gel column chromatography (eluent; hexane:ethyl acetate=2:5, then ethyl acetate). Fractions containing the target compound were concentrated to give an oil, which was then added in diethyl ether concentrated under a reduced pressure again to give a solid. The resultant solid was then suspended in diethyl ether (4 ml)-ethanol (0.4 ml), filtered off, washed with diethyl ether, and dried under aeration to provide the titled compound (14 mg, 11%) as colorless powder.
$^1$H-NMR Spectrum (DMSO-d$_6$) δ (ppm): 2.10 (3H, s), 3.39 (4H, m), 3.55 (4H, m), 3.82 (2H, s), 6.51 (1H, dd, J=2.4, 6.0 Hz), 7.10 (1H, d, J=8.4 Hz), 7.18 (2H, m), 7.31 (1H, d, J=2.4 Hz), 7.38 (2H, dd, J=5.8, 8.8 Hz), 7.60-7.66 (2H, m), 8.11 (1H, d, J=6.0 Hz), 9.24 (1H, s), 11.72 (1H, s), 12.40 (1H, s). ESI-MS (m/z) (neg.): 522 [M−H]⁻.

Example 25

Pyrrolidine-1-carboxylic acid {4-[2-methyl-4-(3-phenylacetylthioureido)phenoxy]pyridin-2-yl}amide To a solution of 2-phenylacetyl chloride (0.0549 ml) in acetonitrile (5.0 ml) was added potassium thiocyanate (37.3 mg, 0.384 mmol), followed by stirring under a nitrogen atmosphere at 50° C. for 1 hr. The reaction mixture was cooled down to room temperature, and then pyrrolidine-1-carboxylic acid [4-(4-amino-2-methylphenoxy)pyridin-2-yl]amide (80 mg) was added thereto, followed by stirring under a nitrogen atmosphere for 21 hrs. The reaction mixture was partitioned between ethyl acetate (100 ml) and water (40 ml). The organic layer was washed with brine, and dried over anhydrous sodium sulfate. The solvent was evaporated to give a residue, which was then purified by silica gel column chromatography (eluent; ethyl acetate). Fractions containing the target compound were concentrated to give a solid, which was suspended in diethyl ether (4 ml). The solid was filtered off, and dried under aeration to provide the titled compound (51 mg, 41%) as colorless powder.

¹H-NMR Spectrum (DMSO-d₆) δ (ppm): 1.80 (4H, m), 2.11 (3H, s), 3.33 (4H, m), 3.83 (2H, s), 6.49 (1H, d, J=5.6 Hz), 7.00 (1H, d, J=9.0 Hz), 7.30 (1H, m), 7.35 (4H, m), 7.42 (1H, s), 7.61 (1H, s), 7.64 (1H, d, J=9.0 Hz), 8.09 (1H, d, J=5.6 Hz), 8.66 (1H, s), 11.72 (1H, s), 12.44 (1H, s). ESI-MS (m/z) (neg.): 488 [M−H]⁻.

Example 26

Pyrrolidine-1-carboxylic acid (4-{2-methyl-4-[3-(4-fluorophenyl)acetylthioureido]phenoxy}pyridin-2-yl)amide To a solution of 2-(4-fluorophenyl)acetyl chloride (66.3 mg) in acetonitrile (30 ml) was added potassium thiocyanate (37.3 mg), followed by stirring under a nitrogen atmosphere at 50° C. for 1 hr. The reaction mixture was cooled down to room temperature, and then pyrrolidine-1-carboxylic acid [4-(4-amino-2-methylphenoxy)pyridin-2-yl]amide (80 mg) was added thereto, followed by stirring under a nitrogen atmosphere for 2 hrs. The reaction mixture was partitioned between ethyl acetate (100 ml) and water (60 ml). The organic layer was washed with brine, and dried over anhydrous sodium sulfate. The solvent was evaporated to give a residue, which was then purified by silica gel column chromatography (eluent; hexane:ethyl acetate=1:3, then ethyl acetate). Fractions containing the target compound were concentrated to give a residue, to which diethyl ether was then added and concentrated under a reduced pressure again to give a solid. The resultant solid was then suspended in diethyl ether (4 ml)-ethanol (0.4 ml), filtered off, washed with diethyl ether, and dried under aeration to provide the titled compound (15 mg, 11.5%) as colorless powder.

¹H-NMR Spectrum (DMSO-d₆) δ (ppm): 1.80 (4H, m), 2.10 (3H, s), 3.33 (4H, m), 3.82 (2H, s), 6.50 (1H, dd, J=2.4, 5.6 Hz), 7.10 (1H, d, J=8.8 Hz), 7.18 (2H, m), 7.38 (2H, dd, J=6.0, 8.4 Hz), 7.42 (1H, d, J=2.4 Hz), 7.59-7.65 (2H, m), 8.09 (1H, d, J=5.6 Hz), 8.65 (1H, s), 11.71 (1H, s), 12.41 (1H, s). ESI-MS (m/z) (neg.): 506 [M−H]⁻.

Example 27

1-(3-Dimethylaminopropyl)-3-{6-[2-fluoro-4-(3-phenylacetylthioureido)phenoxy]pyrimidin-4-yl}-1-methylurea 2-Phenylacetyl chloride (0.032 ml) was dissolved in acetonitrile (3 ml) under a nitrogen atmosphere, and then potassium thiocyanate (46.6 mg) was added thereto at 60° C., followed by stirring at the same temperature for 2 hrs. The reaction mixture was cooled down to room temperature, and then ethyl acetate and a saturated aqueous solution of sodium hydrogencarbonate were added thereto, followed by stirring for 30 min. The organic layer was separated, washed with a saturated aqueous solution of sodium hydrogencarbonate, water and brine in this order, and dried over anhydrous sodium sulfate. The solvent was evaporated to give a residue, which was then dissolved in toluene (1 ml)-ethanol (1 ml), and then a solution of 3-[6-(4-amino-2-fluorophenoxy)pyrimidin-4-yl]-1-(3-diethylaminopropyl)-1-methylurea in toluene (1.5 ml)-ethanol (1.5 ml) was added thereto under a nitrogen atmosphere, followed by stirring at room temperature for 2 hrs. The reaction mixture was partitioned between ethyl acetate and water. The organic layer was washed with brine, and dried over anhydrous sodium sulfate. The solvent was evaporated to give a residue, which was then purified by silica gel column chromatography (FUJI Silysia NH, eluent; heptane:ethyl acetate=1:1). Fractions containing the crude product were concentrated to give a residue, which was then purified by silica gel column chromatography (FUJI Silysia NH, eluent; heptane:ethyl acetate=1:1). Fractions containing the target compound were concentrated to give a residue, which was dried in vacuum to provide the titled compound (6.0 mg, 12.5%) as a white solid.

¹H-NMR Spectrum (CDCl₃) δ (ppm): 1.07 (6H, t, J=6.8 Hz), 1.80 (2H, m), 2.50 (2H, t, J=5.6 Hz), 2.68 (4H, m), 2.92 (3H, s), 3.40 (2H, t, J=5.6 Hz), 3.74 (2H, s), 7.15-7.52 (9H, m), 7.84 (1H, dd, J=2.4, 11.6 Hz), 8.30 (1H, s), 8.43 (1H, brs), 12.40 (1H, brs). ESI-MS (m/z): 568 [M+H]⁺.

Example 28

3-{4-[2-Fluoro-4-(3-phenylacetylthioureido)phenoxy]pyridin-2-yl}-1-methyl-1-(1-methylpiperidin-4-yl)urea 2-Phenylacetyl chloride (0.032 ml) was dissolved in acetonitrile (3 ml) under a nitrogen atmosphere, and then potassium thiocyanate (46.6 mg) was added thereto at 60° C., followed by stirring at the same temperature for 2 hrs. The reaction mixture was cooled down to room temperature, and then ethyl acetate and a saturated aqueous solution of sodium hydrogencarbonate were added thereto, followed by stirring for 30 min. The organic layer was separated, washed with a saturated aqueous solution of sodium hydrogencarbonate, water and brine in this order, and dried over anhydrous sodium sulfate. The solvent was evaporated to give a residue, to which was added toluene (1 ml)-ethanol (1 ml) to prepare a solution. 3-[4-(4-Amino-2-fluorophenoxy)pyridin-2-yl]-1-methyl-1-(1-methylpiperidin-4-yl)urea (40.0 mg) was dissolved in ethanol (1 ml) under a nitrogen atmosphere, and then D-10-camphorsulfonic acid (24.9 mg) was added thereto, followed by stirring for 5 min. To the reaction mixture was added the solution of 2-phenylacetyl isothiocyanate in toluene-ethanol (2 ml) synthesized above, followed by stirring at room temperature for 30 min. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate). Fractions containing the target compound were concentrated to give a residue, to which diethyl ether (0.5 ml)-hexane (1.0 ml) was then added to suspend. The solid was filtered off and dried under aeration to provide the titled compound (10.3 mg, 17.5%) as a white solid.

$^1$H-NMR Spectrum (CDCl$_3$) δ (ppm): 1.50-1.70 (2H, m), 1.79 (2H, m), 2.10 (2H, m), 2.29 (3H, m), 2.84-3.00 (5H, m), 3.75 (2H, m), 4.18 (1H, m), 6.54 (1H, m), 7.19 (2H, m), 7.20-7.50 (6H, m), 7.69 (1H, d, J=2.4 Hz), 7.89 (1H, dd, J=2.4, 11.6 Hz), 8.06 (1H, d, J=5.6 Hz), 8.49 (1H, brs), 12.44 (1H, brs). ESI-MS (m/z): 551 [M+H]$^+$.

Example 29

3-{4-[2-Fluoro-4-(3-phenylacetylthioureido)phenoxy]pyridin-2-yl}-1-methyl-1-[3-(4-methylpiperazin-1-yl)propyl]urea 2-Phenylacetyl chloride (0.032 ml) was dissolved in acetonitrile (3 ml) under a nitrogen atmosphere, and then potassium thiocyanate (46.6 mg) was added thereto at 60° C., followed by stirring at the same temperature for 2 hrs. The reaction mixture was cooled down to room temperature, and then ethyl acetate and a saturated aqueous solution of sodium hydrogencarbonate were added thereto, followed by stirring for 30 min. The organic layer was separated, washed with a saturated aqueous solution of sodium hydrogencarbonate, water and brine in this order, and dried over anhydrous sodium sulfate. The solvent was evaporated to give a residue, to which was added acetonitrile (2 ml) to prepare a solution. 3-[4-(4-Amino-2-fluorophenoxy)pyridin-2-yl]-1-methyl-1-[3-(4-methylpiperazin-1-yl)propyl]urea (50.0 mg) was dissolved in ethanol (1 ml) under a nitrogen atmosphere, and then D-10-camphorsulfonic acid (24.9 mg) was added thereto, followed by stirring for 5 min. To the reaction mixture was added the solution of 2-phenylacetyl isothiocyanate in acetonitrile (2 ml) synthesized above, followed by stirring under a nitrogen atmosphere at room temperature overnight. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; heptane:ethyl acetate=1:5 to 1:8). Fractions containing the target compound were concentrated to give a residue, to which diethyl ether (1.5 ml)-hexane (1.5 ml) was then added to suspend. The solid was filtered off and dried under aeration to provide the titled compound (35.0 mg, 49.1%) as a white solid.

$^1$H-NMR Spectrum (CDCl$_3$) δ (ppm): 1.61 (4H, m), 1.78 (2H, m), 2.35 (3H, s), 2.40 (2H, t, J=6.0 Hz), 2.69 (4H, m), 2.89 (3H, s), 3.39 (2H, t, J=6.0 Hz), 3.74 (2H, s), 6.50 (1H, dd, J=2.4, 5.6 Hz), 7.16 (1H, m), 7.26 (1H, s), 7.31 (3H, m), 7.34-7.48 (3H, m), 7.60 (1H, d, J=2.4 Hz), 7.88 (1H, dd, J=2.4, 12.0 Hz), 8.05 (1H, d, J=5.6 Hz), 8.55 (1H, brs), 12.43 (1H, brs). ESI-MS (m/z): 594 [M+H]$^+$.

Example 30

1-(1-Methylpiperidin-4-yl)-3-{4-[2-fluoro-4-(3-phenylacetylthioureido)phenoxy]pyridin-2-yl}urea 1-[4-(2-Aminopyridin-4-yloxy)-3-fluorophenyl]-3-phenylacetylthiourea (50 mg) was dissolved in tetrahydrofuran (1.3 ml) while stirring, and then N-methylmorpholine (0.040 ml) and phenyl chloroformate (0.040 ml) in this order were added thereto under a nitrogen atmosphere while cooling in an ice bath, followed by raising up to room temperature and stirring for 10 min. The reaction mixture was partitioned between ethyl acetate (15 ml) and a saturated aqueous solution of sodium hydrogencarbonate (10 ml). The organic layer was washed with a saturated aqueous solution of sodium hydrogencarbonate (10 ml), water (10 ml) and brine (10 ml) in this order, and dried over anhydrous sodium sulfate. The solvent was evaporated to provide {4-[2-fluoro-4-(3-phenylacetylthioureido)phenoxy]pyridin-2-yl}carbamic acid phenyl eater as a crude product. The crude product was dissolved in N,N-dimethylformamide (1.3 ml), and then N-methylmorpholine (0.100 ml) and 4-amino-1-methylpiperidine (101 mg) were added thereto at room temperature, followed by stirring for 1 hr. The reaction mixture was partitioned between ethyl acetate (15 ml) and a saturated aqueous solution of sodium hydrogencarbonate (10 ml). The organic layer was washed with a saturated aqueous solution of sodium hydrogencarbonate (10 ml), water (10 ml) and brine (10 ml) in this order, and dried over anhydrous sodium sulfate. The solvent was evaporated to give a residue, which was then purified by silica gel column chromatography (FUJI Silysia NH, eluent; ethyl acetate, then ethyl acetate:ethanol=9:1). Fractions containing the target compound were concentrated to give a residue, to which diethyl ether (1 ml)-hexane (2 ml) was then added to suspend. The solid was filtered off and dried under aeration to provide the titled compound (67.6 mg, 56.2%) as a white solid.

$^1$H-NMR Spectrum (CDCl$_3$) δ (ppm): 1.50-1.72 (2H, m), 2.01 (2H, m), 2.19 (2H, m), 2.29 (3H, s), 2.73 (2H, m), 3.72-3.85 (3H, m), 6.13 (1H, m), 6.54 (1H, dd, J=2.4, 6.0 Hz), 7.16 (1H, m), 7.27-7.46 (7H, m), 7.89 (1H, dd, J=2.4, 12.0 Hz), 8.05 (1H, d, J=6.0 Hz), 9.44 (2H, m), 12.58 (1H, brs). ESI-MS (m/z): 537 [M+H]$^+$.

Example 31

1-Methyl-1-(1-methylpiperidin-4-yl)-3-{4-[4-(3-phenylacetylthioureido)phenoxy]pyridin-2-yl}urea 3-[4-(4-Aminophenoxy)pyridin-2-yl]-1-methyl-1-(1-methylpiperidin-4-yl)urea (60 mg) was dissolved in ethanol (1 ml) while stirring, and then D-10-camphorsulfonic acid (39.3 mg) was added thereto under a nitrogen atmosphere, followed by stirring for 5 min. Phenylacetyl isothiocyanate (toluene solution, 1.82 M, 0.074 ml) was added thereto, followed by stirring further for 1.5 hrs. The reaction mixture was partitioned between ethyl acetate (30 ml) and a saturated aqueous solution of sodium hydrogencarbonate (20 ml). The organic layer was washed with a saturated aqueous solution of sodium hydrogencarbonate, water and brine in this order, and dried over anhydrous sodium sulfate. The solvent was evaporated to give a residue, which was then purified by silica gel column chromatography (Fuji Silysia NH, eluent; hexane:ethyl acetate=1:5, then ethyl acetate). Fractions containing the crude product were concentrated to give a residue, which was then purified by LC-MS. The fractions containing the target compound were concentrated to give a residue, to which a saturated aqueous solution of sodium hydrogencarbonate was added to extract with ethyl acetate. The organic layer was separated, dried over anhydrous sodium sulfate. The solvent was evaporated to give a residue, which was then purified by silica gel column chromatography (Fuji Silysia NH, eluent; ethyl acetate, then ethyl acetate:ethanol=9:1). Fractions containing the target compound were concentrated to give a residue, to which diethyl ether (0.3 ml)-hexane (0.1 ml) was then added to suspend. The solid was filtered off and dried under aeration to provide the titled compound (2.0 mg, 2.2%) as a white solid.

$^1$H-NMR Spectrum (CDCl$_3$) δ (ppm):1.45-1.63 (2H, m), 1.78 (2H, m), 2.09 (2H, m), 2.29 (3H, s), 2.88-2.96 (5H, m), 3.75 (2H, s), 4.18 (1H, m), 6.54 (1H, dd, J=2.0, 5.6 Hz), 7.11 (2H, m), 7.18 (1H, brs), 7.32 (2H, m), 7.37-7.47 (3H, m), 7.66-7.72 (3H, m), 8.06 (1H, d, J=5.6 Hz), 8.44 (1H, brs), 12.30 (1H, brs). ESI-MS (m/z): 533 [M+H]$^+$.

Example 32

4-(Pyrrolidin-1-yl)piperidine-1-carboxylic acid {4-[3-fluoro-4-(3-phenylacetylthioureido)phenoxy]pyridin-2-yl}amide 4-(Pyrrolidin-1-yl)piperidine-1-carboxylic acid [4-(4-amino-3-fluorophenoxy)pyridin-2-yl]amide was dissolved in ethanol (3.0 ml), and then (S)-(+)-10-camphorsulfonic acid (75.5 mg) was added thereto, followed by stirring at room temperature for 15 min. A solution of phenylacetyl isothiocyanate (45.5 mg) in toluene (3.0 ml) was added thereto, followed by stirring at room temperature for 2.5 hrs. The reaction mixture was partitioned between ethyl acetate (50 ml) and a saturated aqueous solution of sodium hydrogencarbonate (30 ml). The organic layer was washed with brine (30 ml×3), and dried over anhydrous sodium sulfate. The solvent was evaporated to give a residue, which was then purified by silica gel column chromatography (FUJI Silysia NH, eluent; heptane:ethyl acetate=1:2, ethyl acetate, then ethyl acetate). Fractions containing the target compound were concentrated to give a solid, to which diethyl ether (3 ml) and hexane (3 ml) in this order were then added to suspend. The solid was filtered off, washed with diethyl ether (1 ml), and dried under aeration to provide the titled compound (17.8 mg, 18%) as colorless powder.

$^1$H-NMR Spectrum (DMSO-d$_6$) δ (ppm): 1.28 (2H, m), 1.66 (4H, m), 1.79 (2H, m), 2.13 (1H, m), 2.47 (4H, m), 2.87 (2H, m), 3.83 (2H, s), 3.97 (2H, m), 6.60 (1H, dd, J=2.4, 5.6 Hz), 7.03 (1H, d, J=9.2 Hz), 7.24-7.38 (6H, m), 7.45 (1H, d, J=2.4 Hz), 8.01 (1H, m), 8.15 (1H, d, J=5.6 Hz), 9.25 (1H, s), 11.88 (1H, brs), 12.23 (1H, brs). ESI-MS (m/z): 577 [M+H]$^+$.

Example 33

1-(3-Diethylaminopropyl)-3-{4-[3-fluoro-4-(3-phenylacetylthioureido)phenoxy]pyridin-2-yl}-1-methylurea To a solution of 1-[4-(2-aminopyridin-4-yloxy)-2-fluorophenyl]-3-phenylacetylthiourea (69.4 mg) in tetrahydrofuran (2.0 ml) were added triethylamine (0.0488 ml) and phenyl chloroformate (0.0329 ml) in this order under a nitrogen atmosphere, followed by stirring at room temperature for 10 min. The solution was concentrated under a reduced pressure, and then N,N-dimethylformamide (1.0 ml) and N,N-diethyl-N'-methylpropane-1,3-diamine (101 mg) were then added thereto, followed by stirring at room temperature for 10.5 hrs. The reaction mixture was partitioned between water (30 ml) and ethyl acetate (50 ml). The organic layer was washed with brine (30 ml), and dried over anhydrous sodium sulfate. The solvent was evaporated to give a residue, which was then purified by silica gel column chromatography (Fuji Silysia NH, heptane:ethyl acetate=1:2, ethyl acetate, then ethyl acetate:methanol=20:1). Fractions containing the target compound were concentrated to give a solid, to which diethyl ether (1 ml) and hexane (1 ml) were added to suspend. The solid was filtered off and dried under aeration to provide the titled compound (15.8 mg, 15.9%) as colorless powder.

$^1$H-NMR Spectrum (CDCl$_3$) δ (ppm): 1.06 (6H, t, J=7.2 Hz), 1.77 (2H, m), 2.49 (2H, m), 2.65 (4H, q, J=7.2 Hz), 2.90 (3H, s), 3.39 (2H, m), 3.75 (2H, s), 6.48 (1H, dd, J=2.4, 5.6 Hz), 6.89 (2H, m), 7.31-7.45 (5H, m), 7.61 (1H, d, J=2.4 Hz), 8.07 (1H, d, J=5.6 Hz), 8.27 (1H, m), 8.52 (1H, brs), 12.29 (1H, s). ESI-MS (m/z): 567 [M+H]$^+$.

Example 34

3-{4-[3-Fluoro-4-(3-phenylacetylthioureido)phenoxy]pyridin-2-yl}-1-methyl-1-(1-methylpiperidin-4-yl)urea A solution in tetrahydrofuran (20 ml) of 3-[4-(4-amino-3-fluorophenoxy)pyridin-2-yl]-1-methyl-1-(1-methylpiperidin-4-yl)urea synthesized in Production Example 124 was concentrated to almost dryness. Then, to the residue was added ethanol (3.0 ml), and then (S)-(+)-10-camphorsulfonic acid (48.1 mg) was added thereto, followed by stirring at room temperature for 15 min. A solution of phenylacetyl isothiocyanate (29 mg) in toluene (3.0 ml) was added thereto, followed by stirring at room temperature for 2.5 hrs. The reaction mixture was partitioned between ethyl acetate (50 ml) and a saturated aqueous solution of sodium hydrogencarbonate (30 ml). The organic layer was washed with brine (30 ml×3), and dried over anhydrous sodium sulfate. The solvent was evaporated to give a residue, which was then purified by silica gel column chromatography (FUJI Silysia NH, eluent; heptane:ethyl acetate=1:2, ethyl acetate, then ethyl acetate:methanol=20:1). Fractions containing the target compound were concentrated to give a residue, to which diethyl ether (1 ml) and hexane (5 ml) were then added to suspend. After allowing to stand for 10 min, a supernatant was removed, and remaining solvent was evaporated under a reduced pressure. The resultant solid was dried in vacuum to provide the titled compound (20.5 mg, 34.2%) as colorless powder.

$^1$H-NMR Spectrum (CDCl$_3$) δ (ppm): 1.64-1.82 (4H, m), 2.05-2.11 (2H, m), 2.29 (3H, s), 2.88-2.93 (5H, m), 3.76 (2H, s), 4.17 (1H, m), 6.56 (1H, dd, J=2.0, 5.6 Hz), 6.90-6.93 (2H, m), 7.17 (1H, brs), 7.31-7.33 (2H, m), 7.37-7.46 (3H, m), 7.75 (1H, d, J=2.0 Hz), 8.31 (1H, m), 8.47 (1H, brs), 12.33 (1H, s). ESI-MS (m/z): 551 [M+H]$^+$, 573 [M+Na]$^+$.

Example 35

3-[4-(3-Fluoro-4-{3-[2-(4-fluorophenyl)acetyl]thioureido}phenoxy)pyridin-2-yl]-1,1-dimethylurea To a solution of 1-[4-(2-aminopyridin-4-yloxy)-2-fluorophenyl]-3-[2-(4-fluorophenyl)acetyl]thiourea (26 mg) in tetrahydrofuran (2.0 ml) were added triethylamine (0.0175 ml) and phenyl chloroformate (0.0118 ml) in this order under a nitrogen atmosphere, followed by stirring at room temperature for 10 min. The solution was concentrated under a reduced pressure to give a residue, which was then dissolved in N,N-dimethylformamide (1.0 ml). Triethylamine (0.0873 ml) and dimethylamine hydrochloride (25.6 mg) were then added thereto, followed by stirring at room temperature for 24 hrs. To the reaction mixture was added water (30 ml) and ethyl acetate (50 ml), followed by stirring at room temperature for 4 hrs. The organic layer was separated, washed with brine (30 ml), and dried over anhydrous sodium sulfate. The solvent was evaporated to give a residue, which was then purified by silica gel column chromatography (Fuji Silysia NH, heptane:ethyl acetate=1:2, ethyl acetate, then ethyl acetate:methanol=20:1). Fractions containing the target compound were concentrated to give a residue, which was purified again by silica gel column chromatography (eluent; heptane:ethyl acetate=1:2, ethyl acetate, then ethyl acetate:methanol=20:1). Fractions containing the target compound were concentrated to give a pale yellow solid (83.7 mg), which was suspended in ethyl acetate (1 ml) and hexane (3 ml). The solid was filtered off and dried under aeration to provide the titled compound (4.8 mg, 15.8%) as colorless powder.

$^1$H-NMR Spectrum (CDCl$_3$) δ (ppm): 3.03 (6H, s), 3.72 (2H, s), 6.56 (1H, dd, J=2.4, 5.6 Hz), 6.92 (2H, m), 7.12 (2H, m), 7.21 (1H, m), 7.21-7.28 (2H, m), 7.73 (1H, d, J=2.4 Hz), 8.08 (1H, m), 8.33 (1H, m), 8.54 (1H, brs), 11.29 (1H, s). ESI-MS (m/z) (neg.): 484 [M−H]$^-$.

Example 36

4-{4-[3-(2-Phenylacetyl)thioureido]phenoxy}-2-{[4-(pyrrolidin-1-yl)piperidin-1-yl]carbonylamino}pyridine 2-Phenylacetyl chloride (0.040 ml) was dissolved in acetonitrile (2.0 ml) under a nitrogen atmosphere, and then potassium thiocyanate (60 mg) was added thereto at 50° C., followed by stirring at the same temperature for 3 hrs. The acetonitrile was evaporated under a reduced pressure to give a residue, to which toluene (2.0 ml) and a saturated aqueous solution of sodium hydrogencarbonate (2.0 ml) were added, followed by stirring for 15 min. The toluene layer (0.7 ml) was added to a solution of 4-(4-aminophenoxy)-2-{[4-(pyrrolidin-1-yl)piperidin-1-yl]carbonylamino}pyridine (27 mg) and (S)-(+)-10-camphorsulfonic acid (32 mg) in ethanol (1.0 ml) at room temperature, followed by stirring for 30 min. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (Fuji Silysia NH, eluent; ethyl acetate). Fractions containing the target compound were concentrated under a reduced pressure to give a residue, which was then dried in vacuum to provide the titled compound (17.2 mg, 44%) as white powder.

$^1$H-NMR Spectrum (CDCl$_3$) δ (ppm): 1.45-1.60 (2H, m), 1.70-1.90 (4H, m), 1.90-2.00 (2H, m), 2.23 (1H, m), 2.50-2.65 (4H, m), 2.97 (2H, m), 3.74 (2H, s), 4.03 (2H, m), 6.53 (1H, dd, J=2.4, 5.6 Hz), 7.11 (2H, d, J=8.8 Hz), 7.30-7.50 (6H, m), 7.64 (1H, d, J=2.4 Hz), 7.68 (2H, d, J=8.8 Hz), 8.03 (1H, d, J=5.6 Hz), 8.50-8.70 (1H, br), 12.31 (1H, s). ESI-MS (m/z): 559 [M+1]$^+$ Example 37

4-{2-Fluoro-4-[3-(2-phenylacetyl)thioureido]phenoxy}-2-[(4-oxopiperidin-1-yl)carbonylamino]pyridine 2-Amino-4-{2-fluoro-4-[3-(2-phenylacetyl)thioureido]phenoxy}pyridine (100 mg) was dissolved in tetrahydrofuran (2.5 ml) under a nitrogen atmosphere, and then N-methylmorpholine (0.080 ml) and phenyl chloroformate (0.080 ml) were added dropwise thereto while cooling in an ice bath, followed by raising the temperature up to room temperature and stirring for 20 min. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then dissolved in N,N-dimethylformamide (2.5 ml), and then N-methylmorpholine (0.2 ml) and 4-oxopiperidine hydrochloride monohydrate (272 mg) were added thereto at room temperature, followed by stirring for 23 hrs. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; ethyl acetate). Fractions containing the target compound were concentrated under a reduced pressure to give a residue, which was dried in vacuum to provide the titled compound (83.1 mg, 63%) as white powder.

$^1$H-NMR Spectrum (CDCl$_3$) δ (ppm): 2.40-2.60 (4H, m), 3.75 (2H, s), 3.76-3.83 (4H, m), 6.57 (1H, m), 7.20-7.45 (8H, m), 7.64 (1H, s), 7.91 (1H, dd, J=2.4, 12.0 Hz), 8.07 (1H, d, J=5.6 Hz), 8.48 (1H, s), 12.46 (1H, s).

Example 38

2-{[4-(Dimethylamino)piperidin-1-yl]carbonylamino}-4-{2-fluoro-4-[3-(2-phenylacetyl)thioureido]phenoxy}pyridine To a solution of 4-{2-fluoro-4-[3-(2-phenylacetyl)thioureido]phenoxy}-2-[(4-oxopiperidin-1-yl)carbonylamino]pyridine (38 mg) in dichloromethane (2.0 ml) were added dimethylamine HCl (15 mg) and sodium triacetoxyborohydride (40 mg) at room temperature, followed by stirring overnight. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (Fuji Silysia NH, eluent; ethyl acetate:methanol=95:5). Fractions containing the target compound were concentrated under a reduced pressure to give a residue, which was dried in vacuum to provide the titled compound (22.8 mg, 57%) as white powder.

$^1$H-NMR Spectrum (CDCl$_3$) δ (ppm): 1.40-1.55 (2H, m), 1.80-1.95 (2H, m), 2.28 (6H, s), 2.34 (1H, m), 2.85-2.95 (2H, m), 3.74 (2H, s), 4.05-4.15 (2H, m), 6.53 (1H, dd, J=2.4, 5.6 Hz), 7.10-7.45 (8H, m), 7.63 (1H, d, J=2.4 Hz), 7.89 (1H, dd, J=2.4, 12.0 Hz), 8.05 (1H, d, J=5.6 Hz), 8.51 (1H, br), 12.44 (1H, s). ESI-MS (m/z): 551 [M+1]$^+$ Example 39

2-{[4-(Azetidin-1-yl)piperidin-1-yl]carbonylamino}-4-{2-fluoro-4-[3-(2-phenylacetyl)thioureido]phenoxy}pyridine To a solution of 4-{2-fluoro-4-[3-(2-phenylacetyl)thioureido]phenoxy}-2-[(4-oxopiperidin-1-yl)carbonylamino]pyridine (38 mg) in dichloromethane (2.0 ml) were added azetidine hydrochloride (17 mg) and sodium triacetoxyborohydride (40 mg) at room temperature, followed by stirring overnight. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (Fuji Silysia NH, eluent; ethyl acetate:methanol=95:5). Fractions containing the target compound were concentrated under a reduced pressure to give a residue, which was dried in vacuum to provide the titled compound (31.9 mg, 78%) as white powder.

$^1$H-NMR Spectrum (CDCl$_3$) δ (ppm): 1.50-1.80 (4H, m), 2.00-2.10 (2H, m), 2.19 (1H, m), 3.00-3.07 (2H, m), 3.10-3.20 (4H, m), 3.74 (2H, s), 3.80-3.95 (2H, m), 6.53 (1H, dd, J=2.4, 5.6 Hz), 7.10-7.45 (8H, m), 7.62 (1H, d, J=2.4 Hz), 7.88 (1H, dd, J=2.4, 12.0 Hz), 8.04 (1H, d, J=5.6 Hz), 8.51 (1H, br), 12.44 (1H, s). ESI-MS (m/z): 563 [M+1]$^+$ Example 40

4-{2-Fluoro-4-[3-(2-phenylacetyl)thioureido]phenoxy}-2-{[4-(pyrrolidin-1-yl)piperidin-1-yl]carbonylamino}pyridine 2-Amino-4-{2-fluoro-4-[3-(2-phenylacetyl)thioureido]phenoxy}pyridine (66.6 mg) was dissolved in tetrahydrofuran (2.0 ml) under a nitrogen atmosphere, and then N-methylmorpholine (0.0462 ml) and phenyl chloroformate (0.0527 ml) in this order were added dropwise thereto while cooling in an ice bath, followed by raising the temperature up to room temperature and stirring for 15 min. The solvent was evaporated to give a residue, which was dissolved in N,N-dimethylformamide (2.0 ml), and then 4-(pyrrolidin-1-yl)piperidine (136 mg) was added thereto at room temperature, followed by stirring for 2 hr. The reaction mixture was partitioned between ethyl acetate and a saturated aqueous solution of sodium hydrogencarbonate. The organic layer was washed with a saturated aqueous solution of sodium hydrogencarbonate and brine in this order, and dried over anhydrous sodium sulfate. The solvent was evaporated to give a residue, which was then purified by silica gel column chromatography (Fuji Silysia NH, eluent; ethyl acetate:methanol=95:5). Fractions containing the target compound were concentrated under a reduced pressure to give a residue, which was dried in vacuum to provide the titled compound (46.3 mg, 48%) as white powder.

$^1$H-NMR Spectrum (CDCl$_3$) δ (ppm): 1.50-1.60 (2H, m), 1.75-1.85 (4H, m), 1.90-1.96 (2H, m), 2.20 (1H, m), 2.50-2.60 (4H, m), 2.97 (2H, m), 3.74 (2H, s), 3.95-4.05 (2H, m), 6.53 (1H, dd, J=2.4, 5.6 Hz), 7.15-7.47 (8H, m), 7.63 (1H, d, J=2.4 Hz), 7.89 (1H, dd, J=2.4, 12.0 Hz), 8.05 (1H, d, J=5.6 Hz), 8.47 (1H, brs), 12.43 (1H, s). ESI-MS (m/z): 577 [M+1]$^+$.

Example 41

3-{6-[2-Fluoro-4-(3-phenylacetylthioureido)phenoxy]pyrimidin-4-yl}-1-methyl-1-(1-methylpiperidin-4-yl)urea 3-[6-(4-Amino-2-fluorophenoxy)pyrimidin-4-yl]-1-methyl-1-(1-methylpiperidin-4-yl)urea (50 mg) was dissolved in ethanol (1 ml), and then D-10-camphorsulfonic acid (62.3 mg) was added thereto, followed by stirring for 5 min. Phenylacetyl isothiocyanate (toluene solution, 0.355 M, 0.565 ml) was added thereto, followed by stirring further for 1 hr. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml) and brine (20 ml) in this order, and dried over anhydrous sodium sulfate. The solvent was evaporated to give a residue, which was then purified by silica gel column chromatography (Fuji Silysia NH, eluent; ethyl acetate). Fractions containing the target compound were concentrated to give a residue, to which diethyl ether (0.5 ml)-hexane (2.0 ml) was then added to suspend a solid. The solid was filtered off and dried under aeration to provide the titled compound (12.4 mg, 16.8%) as pale yellow powder.

$^1$H-NMR Spectrum (CDCl$_3$) δ (ppm):1.30-1.72 (2H, m), 1.81 (2H, m), 2.11 (2H, m), 2.31 (3H, s), 2.60-3.10 (5H, m), 3.74 (2H, s), 4.19 (1H, m), 7.00-7.60 (8H, m), 7.68 (1H, s), 7.86 (1H, dd, J=2, 11 Hz), 8.34 (1H, s), 8.45 (1H, brs), 12.43 (1H, brs). ESI-MS (m/z): 552 [M+H]$^+$.

Example 42

1,1-Dimetyl-3-{4-[4-(3-phenylacetylureido)phenoxy]pyridin-2-yl}urea

2-Phenylacetamide (149 mg) was dissolved in 1,2-dichloroethane (10 ml) under a nitrogen atmosphere, and then oxalyl chloride (0.175 ml) was added thereto, followed by stirring at 110° C. overnight. The reaction mixture was concentrated under a reduced pressure to give a residue, which was then dissolved in N,N-dimethylformamide (3.4 ml) under a nitrogen atmosphere. 3-[4-(4-Aminophenoxy)pyridin-2-yl]-1,1-dimethylurea (100 mg) was then added thereto, followed by stirring for 30 min. The reaction mixture was partitioned between ethyl acetate and water. The organic layer was washed with water and brine in this order, and dried over anhydrous sodium sulfate. The solvent was evaporated to give a residue, which was then purified by silica gel column chromatography (eluent; hexane:ethyl acetate=1:3). Fractions containing a crude product were concentrated under a reduced pressure to give a residue, which was then partitioned between ethyl acetate and 1N hydrochloric acid. To the aqueous layer was added a 1 N aqueous solution of sodium hydroxide to make it alkaline, which was then extracted with ethyl acetate. The organic layer was washed with water and brine in this order, and dried over anhydrous sodium sulfate. The solvent was evaporated to give a crude product, which was then partitioned between ethyl acetate and 1N hydrochloric acid again. To the aqueous layer was added a 1 N aqueous solution of sodium hydroxide to make it alkaline, which was then extracted with ethyl acetate. The organic layer was washed with water and brine in this order, and dried over anhydrous sodium sulfate. The solvent was evaporated to give a crude product, which was then partitioned between ethyl acetate and 1N hydrochloric acid again. To the aqueous layer was added a 1 N aqueous solution of sodium hydroxide to make it alkaline, which was then extracted with ethyl acetate. The organic layer was washed with water and brine in this order, and dried over anhydrous sodium sulfate. The solvent was evaporated to give a crude product, which was then partitioned between ethyl acetate and 1N hydrochloric acid. To the aqueous layer was added a 1 N aqueous solution of sodium hydroxide to make it alkaline, which was then extracted with ethyl acetate. The organic layer was washed with water and brine in this order, and dried over anhydrous sodium sulfate. The solvent was evaporated to give a residue, to which were added a small amount of ethyl acetate and a small amount of hexane to precipitate crystals. The crystals were filtered off and dried under aeration to provide the titled compound (8.1 mg, 5.1%) as pale yellow crystals.

$^1$H-NMR Spectrum (DMSO-d$_6$) δ (ppm): 2.88 (6H, s), 3.73 (2H, brs), 6.56 (1H, m), 7.11 (2H, d, J=8.4 Hz), 7.25-7.45 (6H, m), 7.60 (2H, d, J=8.4 Hz), 8.09 (1H, d, J=5.6 Hz), 8.86 (1H, brs), 10.52 (1H, brs), 10.98 (1H, brs).

Example 43

4-{2-Fluoro-4-[3-(2-phenylacetyl)ureido]phenoxy}-2-[(pyrrolidin-1-yl)carbonylamino]pyridine 2-Phenylacetamide (128 mg) was dissolved in 1,2-dichloroethane (10 ml) under a nitrogen atmosphere, and then oxalyl chloride (0.103 ml) was added thereto, followed by stirring at 120° C. overnight. The reaction mixture was concentrated under a reduced pressure to give a residue, which was then dissolved in N,N-dimethylformamide (3.2 ml) under a nitrogen atmosphere. 4-(4-amino-2-fluorophenoxy)-2-[(pyrrolidin-1-yl)carbonylamino]pyridine (100 mg) was then added thereto, followed by stirring for 30 min. The reaction mixture was partitioned between ethyl acetate and a saturated aqueous solution of sodium hydrogencarbonate. The organic layer was washed with water and brine in this order, and dried over anhydrous sodium sulfate. The solvent was evaporated to give a residue, which was purified by silica gel column chromatography (FUJI Silysia NH, eluent; hexane:ethyl acetate=1:3). Fractions containing the target compound were concentrated to give a residue, to which ethyl acetate (2 ml)-hexane (10 ml) was added to precipitate crystals. The crystals were filtered off and dried under aeration to provide the titled compound (113 mg, 75%) as white crystals.

$^1$H-NMR Spectrum (DMSO-d$_6$) δ (ppm): 1.70-1.90 (4H, m), 3.20-3.40 (4H, m), 3.74 (2H, s), 6.60 (1H, m), 7.20-7.50 (8H, m), 7.77 (1H, m), 8.10 (1H, d, J=5.6 Hz), 8.70 (1H, s), 10.61 (1H, s), 11.04 (1H, s).

Example 44

2-[(Dimethylamino)carbonylamino]-4-{2-fluoro-4-[3-(2-phenylacetyl)ureido]phenoxy}pyridine 2-Phenylacetamide (126 mg) was dissolved in 1,2-dichloroethane (10 ml) under a nitrogen atmosphere, and then oxalyl chloride (0.101 ml) was added thereto, followed by stirring at 110° C. overnight. The reaction mixture was concentrated under a reduced pressure to give a residue, which was then dissolved in N,N-dimethylformamide (3 ml) under a nitrogen atmosphere. 4-(4-Amino-2-fluorophenoxy)-2-[(dimethylamino)carbonylamino]pyridine (90 mg) was then added thereto, followed by stirring for 20 min. The reaction mixture was partitioned between ethyl acetate and water. The organic layer was washed with a saturated aqueous solution of sodium hydrogencarbonate and brine in this order, and dried over anhydrous sodium sulfate. The solvent was evaporated to give a residue, which was then purified by silica gel column chromatography (FUJI Silysia NH, eluent; hexane:ethyl acetate=1:3). Fractions containing the target compound were concentrated to give a residue, to which ethyl acetate (1.5 ml) was added to precipitate crystals. The crystals were filtered off and dried under aeration to provide the titled compound (36.3 mg, 26%) as white crystals.

$^1$H-NMR Spectrum (CDCl$_3$) δ (ppm): 3.01 (6H, s), 3.75 (2H, s), 6.53 (1H, m), 7.00-7.80 (10H, m), 8.04 (1H, m), 8.20 (1H, s), 10.61 (1H, s).

Example 45

4-{2-Fluoro-4-[3-(2-phenylacetyl)ureido]phenoxy}-2-{[4-(pyrrolidin-1-yl)piperidin-1-yl]carbonylamino}pyridine 2-Phenylacetamide (203 mg) was dissolved in 1,2-dichloroethane (20 ml) under a nitrogen atmosphere, and then oxalyl chloride (0.174 ml) was added thereto, followed by stirring at 120° C. overnight. The reaction mixture was concentrated under a reduced pressure to give a residue, which was then dissolved in N,N-dimethylformamide (5 ml) under a nitrogen atmosphere. 4-(4-Amino-2-fluorophenoxy)-2-{[4-(pyrrolidin-1-yl)piperidin-1-yl]carbonylamino}pyridine (295 mg) was then added thereto, followed by stirring for 1 hr. The reaction mixture was partitioned between ethyl acetate and a saturated aqueous solution of sodium hydrogencarbonate. The organic layer was washed with water and brine in this order, and dried over anhydrous sodium sulfate. The solvent was evaporated to give a residue, which was then purified by silica gel column chromatography (FUJI Silysia NH, eluent; ethyl acetate:methanol=98:2). Fractions containing the target compound were concentrated under a reduced pressure to give a brown powder residue, which was then dissolved in ethyl acetate (10 ml) to extract with 1 N hydrochloric acid (5 ml). To the aqueous layer was added a 1 N aqueous solution of sodium hydroxide dropwise to make it neutral, followed by stirring overnight. The precipitated solid was filtered off, washed with water, and dried under aeration at 60° C. to provide the titled compound (116 mg, 28%) as pale pink powder.

$^1$H-NMR Spectrum (CDCl$_3$) δ (ppm): 1.40-1.60 (2H, m), 1.60-1.80 (4H, m), 1.90-2.00 (2H, m), 2.20 (1H, m), 2.50-2.60 (4H, m), 2.90-3.00 (2H, m), 3.75 (2H, s), 3.90-4.05 (2H, m), 6.52 (1H, dd, J=2.4, 5.6 Hz), 7.10-7.45 (8H, m), 7.59-7.64 (2H, m), 7.78 (1H, s), 8.03 (1H, d, J=5.6 Hz), 10.57 (1H, s).

Example 46

Pyrrolidine-1-carboxylic acid {6-[2-fluoro-4-(3-phenylacetylureido)phenoxy]pyrimidin-4-yl}amide To a suspension of 2-phenylacetamide (905 mg, 6.7 mmol) in dichloroethane (90 ml) was added oxalyl chloride (1.75 ml, 20.1 mmol) under a nitrogen atmosphere, followed by stirring at 110° C. for 12 hrs. The reaction mixture was cooled down to room temperature, and concentrated under a reduced pressure to give a residue, to which hexane (13.4 ml) was added to prepare a solution of phenylacetyl isocyanate in hexane. To a solution of pyrrolidine-1-carboxylic acid [6-(4-amino-2-fluorophenoxy)pyrimidin-4-yl]amide (40 mg) in N,N-dimethylformamide (1.0 ml) was added the above solution of phenylacetyl isocyanate in hexane (supernatant, 0.948 ml) under a nitrogen atmosphere, followed by stirring at room temperature for 1 hr. The reaction mixture was partitioned between ethyl acetate (50 ml) and a saturated aqueous solution of sodium hydrogencarbonate (20 ml). The organic layer was dried over anhydrous sodium sulfate. The solvent was evaporated to give a residue, to which ethyl acetate (1.0 ml) was added to suspend. The solid was filtered off, washed with diethyl ether, and dried under aeration to provide the titled compound (47.1 mg, 78.1%) as pale yellow powder.

$^1$H-NMR Spectrum (DMSO-d$_6$) δ (ppm):1.83 (4H, m), 3.40 (4H, m), 3.73 (2H, s), 7.25-7.36 (7H, m), 7.44 (1H, s), 7.69 (1H, m), 8.37 (1H, dd, J=1.2 Hz), 9.38 (1H, s), 10.56 (1H, s), 11.01 (1H, s). ESI-MS (m/z): 479 [M+H]$^+$, 501 [M+Na]$^+$.

Example 47

Pyrrolidine-1-carboxylic acid {4-[3-chloro-4-(3-phenylacetylureido)phenoxy]pyridin-2-yl}amide Pyrrolidine-1-carboxylic acid [4-(4-amino-3-chlorophenoxy)pyridin-2-yl]amide (20 mg) was dissolved in N,N-dimethylformamide (1.0 ml), and then a solution of phenylacetyl isocyanate in hexane (0.019 ml, Production Example 1) was added thereto, followed by stirring at room temperature for 1 hr. To the reaction mixture was added ethyl acetate and water to partition. The organic layer was washed with brine, and dried over anhydrous sodium sulfate. The solvent was evaporated to give a residue, which was then suspended in ethyl acetate:methanol=1:1. The solid was filtered off, washed with methanol, and dried under aeration to provide the titled compound (10 mg, 34%) as pale yellow powder.
$^1$H-NMR Spectrum (DMSO-$d_6$) δ (ppm): 1.78 (4H, m), 3.36 (4H, m), 3.74 (2H, s), 6.56 (1H, dd, J=2.4, 5.6 Hz), 7.17 (1H, dd, J=2.4, 9.2 Hz), 7.26-7.35 (5H, m), 7.42 (1H, d, J=2.4 Hz), 7.47 (1H, d, J=2.4 Hz), 8.10 (1H, d, J=5.6 Hz), 8.30 (1H, d, J=9.2 Hz), 8.69 (1H, s), 11.04 (1H, s), 11.18 (1H, s).

Example 48

Morpholine-4-carboxylic acid {4-[2-fluoro-4-(3-phenylacetylureido)phenoxy]pyridin-2-yl}amide To a solution of morpholine-4-carboxylic acid [4-(4-amino-2-fluorophenoxy)pyridin-2-yl]amide (54 mg) in N,N-dimethylformamide (1.0 ml) was added a solution of phenylacetyl isocyanate in hexane (0.972 ml, Production Example 1), followed by stirring at room temperature for 25 hrs. The reaction mixture was partitioned between ethyl acetate (50 ml) and water (30 ml). The organic layer was washed with brine, and dried over anhydrous sodium sulfate. The solvent was evaporated to give a residue, which was then purified by silica gel column chromatography (eluent; hexane:ethyl acetate=1:1 to 1:2, ethyl acetate, ethyl acetate:methanol=20:1 to 10:1). Fractions containing the target compound were concentrated to give a solid, which was suspended in ethyl acetate. The solid was filtered off, washed with ethyl acetate, and dried under aeration to provide the titled compound (9.5 mg, 12%) as colorless powder.
$^1$H-NMR Spectrum (DMSO-$d_6$) δ (ppm): 3.40 (4H, m), 3.55 (4H, m), 3.74 (2H, s), 6.61 (1H, dd, J=2.0, 5.6 Hz), 7.27-7.40 (8H, m), 7.77 (1H, dd, J=2.4, 8.8 Hz), 8.13 (1H, d, J=5.6 Hz), 9.28 (1H, s), 10.61 (1H, s), 11.05 (1H, s). ESI-MS (m/z): 516 [M+Na]$^+$.

Example 49

1-(3-Diethylaminopropyl)-3-{4-[2-fluoro-4-(3-phenylacetylureido)phenoxy]pyridin-2-yl}-1-methylurea To a solution of 1-(3-diethylaminopropyl)-3-[4-(4-amino-2-fluorophenoxy)pyridin-2-yl]-1-methylurea (100 mg) in tetrahydrofuran (2.0 ml) was added a solution of phenylacetyl isocyanate in hexane (3.4 ml, Production Example 1), followed by stirring under a nitrogen atmosphere at room temperature for 30 min. A solution of phenylacetyl isocyanate in hexane (1.0 ml, Production Example 1) was further added thereto, followed by stirring at room temperature for 30 min. The reaction mixture was partitioned between a mixed solvent of ethyl acetate-tetrahydrofuran (1:1, 200 ml) and a saturated aqueous solution of sodium hydrogencarbonate (15 ml). The organic layer was washed with a 1 N aqueous solution of sodium hydroxide, and dried over anhydrous sodium sulfate. The solvent was evaporated to give a residue, which was then purified by silica gel column chromatography (FUJI Silysia NH, eluent; ethyl acetate). Fractions containing a crude product were concentrated to give a residue, which was then dissolved in ethyl acetate and washed with a 1 N aqueous solution of sodium hydroxide. The organic layer was dried over anhydrous sodium sulfate. The solvent was evaporated to give a residue, to which diethyl ether (3 ml) and hexane (3 ml) were then added to precipitate a solid. The solid was filtered off, washed with diethyl ether, and dried under aeration to provide the titled compound (8.3 mg, 5.9%) as colorless powder.
$^1$H-NMR Spectrum (DMSO-$d_6$) δ (ppm): 0.97 (6H, t, J=7.2 Hz), 1.67 (2H, m), 2.35 (2H, m), 2.52 (4H, m), 2.79 (3H, s), 3.28 (2H, m), 3.74 (2H, s), 6.54 (1H, dd, J=2.4, 5.6 Hz), 7.27-7.40 (8H, m), 7.76 (1H, dd, J=2.4, 8.8 Hz), 8.07 (1H, d, J=5.6 Hz), 10.60 (1H, s), 11.04 (1H, s). ESI-MS (m/z): 551 [M+H]$^+$.

Example 50

4-Methylpiperazine-1-carboxylic acid {4-[2-fluoro-4-(3-phenylacetylureido)phenoxy]pyridin-2-yl}amide To a solution of 4-methylpiperazine-1-carboxylic acid [4-(4-amino-2-fluorophenoxy)pyridin-2-yl]amide (80 mg) in tetrahydrofuran (2.3 ml) was added a solution of phenylacetyl isocyanate in hexane (1.4 ml, Production Example 1), followed by stirring under a nitrogen atmosphere at room temperature for 2 hrs. The reaction mixture was partitioned between ethyl acetate (100 ml) and a saturated aqueous solution of sodium hydrogencarbonate (50 ml). The organic layer was dried over anhydrous sodium sulfate, and concentrated under a reduced pressure. The residue was purified by silica gel column chromatography (FUJI Silysia NH, eluent; hexane:ethyl acetate=1:1, ethyl acetate, then ethyl acetate:methanol=10:1). Fractions containing the target compound were concentrated to give a crude product, to which diethyl ether was then added to precipitate a solid. The solid was filtered off, washed with diethyl ether, and dried under aeration to provide the titled compound (55.2 mg, 47%) as colorless powder.
$^1$H-NMR Spectrum (DMSO-$d_6$) δ (ppm): 2.16 (3H, s), 2.25 (4H, m), 3.40 (4H, m), 3.74 (2H, s), 6.59 (1H, dd, J=2.4, 5.6 Hz), 7.27-7.40 (8H, m), 7.76 (1H, dd, J=2.4, 8.8 Hz), 8.11 (1H, d, J=5.6 Hz), 9.23 (1H, s), 10.60 (1H, s), 11.04 (1H, s). ESI-MS (m/z): 507 [M+H]$^+$

Example 51

3-[6-(2-Fluoro-4-{3-[2-(4-fluorophenyl)acetyl]ureido}phenoxy)pyrimidin-4-yl]-1,1-dimethylurea 2-(4-Fluorophenyl)acetamide (125 mg) was dissolved in 1,2-dichloroethane (9 ml) under a nitrogen atmosphere, and then oxalyl chloride (0.10 ml) was added thereto, followed by stirring at 110° C. overnight. The reaction mixture was concentrated under a reduced pressure to give a residue, which was then dissolved in N,N-dimethylformamide (1 ml) under a nitrogen atmosphere. A solution of 3-[6-(4-amino-2-fluorophenoxy)pyrimidin-4-yl]-1,1-dimethylurea (90 mg) in N,N-dimethylformamide (2 ml) was then added thereto, followed by stirring for 30 min. The reaction mixture was partitioned between ethyl acetate and water. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (eluent: hexane:ethyl acetate=1:3). Fractions containing the target compound were concentrated to give a residue, to which diethyl ether (2 ml)-hexane (1 ml) was added to suspend. The solid was filtered off and dried under aeration to provide the titled compound (72.4 mg, 49.8%) as a pale yellow solid.

$^1$H-NMR Spectrum (CDCl$_3$) δ (ppm): 3.06 (6H, m), 3.72 (2H, s), 7.10 (2H, m), 7.16 (2H, m), 7.20-7.40 (3H, m), 7.50-7.70 (2H, m), 8.34 (2H, brs), 10.58 (1H, brs). ESI-MS (m/z) (neg.): 469 [M–H]$^-$.

Example 52

3-{4-[2-Fluoro-4-(3-phenylacetylureido)phenoxy] pyridin-2-yl]-1-methyl-1-(1-methylpiperidin-4-yl) urea 3-[4-(4-Amino-2-fluorophenoxy)pyridin-2-yl]-1-methyl-1-(1-methylpiperidin-4-yl)urea (50.0 mg) was dissolved in tetrahydrofuran (2 ml) under a nitrogen atmosphere, and then a solution of phenylacetyl isocyanate in toluene (0.80 ml, 0.5 M solution in toluene, Production Example 1) was added thereto, followed by stirring for 1 hr. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate:ethanol=9:1) Fractions containing the target compound were concentrated to give a residue, to which diethyl ether (1 ml)-hexane (0,5 ml) was added to suspend. The solid was filtered off and dried under aeration to provide the titled compound (63.1 mg, 88.1%) as a pale yellow solid.

$^1$H-NMR Spectrum (CDCl$_3$) δ (ppm): 1.40-1.62 (2H, m), 1.70-1.84 (2H, m), 2.05 (2H, m), 2.28 (3H, s), 2.84-2.94 (5H, m), 3.76 (2H, s), 4.16 (1H, m), 6.52 (1H, m), 7.08-7.19 (3H, m), 7.30 (2H, m), 7.34-7.46 (3H, m), 7.58-7.74 (3H, m), 8.04 (1H, d, J=6.0 Hz), 10.57 (1H, brs). ESI-MS (m/z): 535 [M+H]$^+$.

Example 53

4-(Pyrrolidin-1-yl)piperidine-1-carboxylic acid {4-[3-fluoro-4-(3-phenylacetylureido)phenoxy]pyridin-2-yl}amide To a solution of benzyl 2-[fluoro-4-(2-{[4(pyrrolidin-1-yl) piperidine-1-carbonyl]amino}pyridin-4-yloxy)phenyl]carbamate (165 mg) in tetrahydrofuran (5.0 ml) was added 10% palladium carbon (32.9 mg), followed by stirring under a hydrogen atmosphere at room temperature for 25 hrs. After replacing hydrogen with nitrogen, tetrahydrofuran (5.0 ml) and 10% palladium carbon (32.9 mg) were further added thereto, followed by stirring under a hydrogen atmosphere at room temperature for 2 hrs. The reaction mixture was filtered to remove the catalyst, which was washed with a small amount of tetrahydrofuran (4 ml). To the filtrate was added phenylacetyl isocyanate (1.84 ml, a solution in hexane, Production Example 1), followed by stirring under a nitrogen atmosphere at room temperature for 1 hr. Phenylacetyl isocyanate (1.84 ml, a solution in hexane, Production Example 1) was further added thereto, followed by stirring for 1 hr. To the reaction mixture were added ethyl acetate (50 ml) and brine (30 ml) to partition. The organic layer was washed with brine (30 ml×3), and dried over anhydrous sodium sulfate. The solvent was evaporated to give a residue, which was then purified by silica gel column chromatography (FUJI Silysia NH, eluent; heptane:ethyl acetate=1:2, ethyl acetate, then ethyl acetate:ethanol=20:1). Fractions containing the target compound were concentrated to give a pale red solid (94 mg), which was then suspended in diethyl ether (3 ml). The solid was filtered off, washed with diethyl ether, and dried under aeration to provide the titled compound (75.4 mg, 43.5%) as pale red powder.

$^1$H-NMR Spectrum (DMSO-d$_6$) δ (ppm): 1.28 (2H, m), 1.66 (4H, m), 1.78 (2H, m), 2.12 (1H, m), 2.46 (4H, m), 2.86 (2H, m), 3.75 (2H, s), 3.97 (2H, m), 6.58 (1H, dd, J=2.0, 5.6 Hz), 7.02 (1H, d, J=9.2 Hz), 7.26-7.39 (7H, m), 8.12 (1H, d, J=5.6 Hz), 8.17 (1H, m), 9.21 (1H, s), 10.76 (1H, s), 11.17 (1H, s). ESI-MS (m/z): 561 [M+H]$^+$.

Example 54

3-{4-[3-Fluoro-4-(3-phenylacetylureido)phenoxy] pyridin-2-yl}-1,1-dimethylurea

To a solution of benzyl {4-[2-(3,3-dimethyluerido)pyridin-4-yloxy]-2-fluorophenyl}carbamate (86.9 mg) in tetrahydrofuran (5.0 ml) was added 10% palladium carbon (21.8 mg), followed by stirring under a hydrogen atmosphere at room temperature for 25 hrs. The reaction mixture was filtered to remove the catalyst, which was washed with a small amount of tetrahydrofuran. To the resultant filtrate was added phenylacetyl isocyanate (1.23 ml, a solution in hexane, Production Example 1), followed by stirring under a nitrogen atmosphere at room temperature for 1 hr. To the reaction mixture were added ethyl acetate (50 ml) and water (30 ml) to partition. The organic layer was washed with brine (30 ml×3), and dried over anhydrous sodium sulfate. The solvent was evaporated to give a residue, which was then purified by silica gel column chromatography (eluent; ethyl acetate, ethyl acetate:methanol=20:1). Fractions containing the target compound were concentrated to give a pale yellow solid (83.7 mg), to which ethyl acetate (1 ml)-diethyl ether (3 ml) was added to suspend. The solid was filtered off, and dried under aeration to provide the titled compound (48.0 mg, 51.9%) as colorless powder.

$^1$H-NMR Spectrum (DMSO-d$_6$) δ (ppm): 2.90 (6H, s), 3.75 (2H, s), 6.60 (1H, dd, J=2.4, 6.0 Hz), 7.03 (1H, d, J=8.8 Hz), 7.22-7.46 (7H, m), 8.12 (1H, m), 8.18 (1H, m), 8.92 (1H, s), 10.76 (1H, s), 11.17 (1H, s). ESI-MS (m/z): 474 [M+Na]$^+$.

Example 55

N-(3-Fluoro-4-{2-[(morpholine-4-carbonyl)amino] pyridin-4-yloxy}phenyl)-N'-(fluorophenyl)malonamide 4-(4-Amino-2-fluorophenoxy)-2-[(morpholin-1-yl)carbonylamino]pyridine (106 mg) was dissolved in N,N-dimethylformamide (2 ml) under a nitrogen atmosphere, and then N-(4-fluorophenyl)malonic acid (189 mg), triethylamine (0.134 ml) and (1H-1,2,3-benzotriazol-1-yloxy)[tri(dimethylamino)]phosphonium hexafluorophosphate (424 mg) were added thereto at 50° C., followed by stirring at the same temperature for 1 hr and 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate, then ethyl acetate:ethanol=19:1). Fractions containing the target compound were concentrated to give a residue, to which diethyl ether (5 ml)-hexane (5 ml) was added to suspend. The solid was filtered off and dried under aeration to provide the titled compound (116 mg, 70.6%) as white powder.

$^1$H-NMR Spectrum (DMSO-d 6) δ (ppm): 3.37-3.41 (4H, m), 3.50 (2H, m), 3.52-3.60 (4H, m), 6.62 (1H, dd, J=2.4, 6.0 Hz), 7.17 (2H, m), 7.30-7.45 (3H, m), 7.63 (2H, dd, J=5.2, 8.8 Hz), 7.83 (1H, m), 8.12 (1H, d, J=6.0 Hz), 9.29 (1H, s), 10.27 (1H, brs), 10.52 (1H, brs).

Example 56

N-(4-Fluorophenyl)-N'-(3-fluoro-4-{2[(pyrrolidine-1-carbonyl)amino]pyridin-4-yloxy}phenyl)malonamide 4-(4-Amino-2-fluorophenoxy)-2-[(pyrrolidin-1-yl)carbonylamino]pyridine (47.8 mg) was dissolved in N,N-dimethylformamide (2 ml) under a nitrogen atmosphere, and then N-(4-fluorophenyl)malonic acid (89.3 mg), triethylamine (0.063 ml) and (1H-1,2,3-benzotriazol-1-yloxy)[tri(dimethylamino)]phosphonium hexafluorophosphate (200 mg) were added thereto at 50° C., followed by stirring at the same temperature for 1 hr. The reaction mixture was cooled down to room temperature, followed by further stirring overnight. The reaction mixture was partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate, then ethyl acetate:ethanol=95:5). Fractions containing the target compound were concentrated to give a residue, to which diethyl ether-hexane (1:1) was added to suspend. The solid was filtered off and dried under aeration to provide the titled compound (28.7 mg, 38.4%) as pale yellow powder.

$^1$H-NMR Spectrum (CDCl$_3$) δ (ppm): 1.92 (4H, m), 3.39 (4H, m), 3.47 (2H, m), 6.74 (1H, d, J=2, 6.0 Hz), 6.90 (2H, m), 7.07 (1H, m), 7.23 (2H, m), 7.51 (2H, m), 7.56 (1H, m), 7.62 (1H, d, J=10.8 Hz), 8.09 (1H, d, J=6.0 Hz), 9.62 (1H, s), 10.08 (1H, brs).

Example 57

N-(3-Fluoro-4-{2-[(pyrrolidine-1-carbonyl)amino]pyridin-4-yloxy}phenyl)-N'-(2,4-difluorophenyl)malonamide 4-(4-Amino-2-fluorophenoxy)-2-[pyrrolidin-1-yl)carbonylamino]pyridine (50 mg) was dissolved in N,N-dimethylformamide (2 ml) under a nitrogen atmosphere, and then N-(2,4-difluorophenyl)malonic acid (51.0 mg), triethylamine (0.033 ml) and (1H-1,2,3-benzotriazol-1-yloxy)[tri(dimethylamino)]phosphonium hexafluorophosphate (105 mg) were added thereto at 50° C., followed by stirring at the same temperature for 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; hexane:ethyl acetate=1:1 to 1:3). Fractions containing the target compound were concentrated to give a residue, to which diethyl ether-hexane (3:1) was added to suspend, and the solid was filtered off. The resultant solid was then suspended in ethyl acetate (1 ml), filtered off and dried under aeration to provide the titled compound (12.5 mg, 15.4%) as pale brown powder.

$^1$H-NMR Spectrum (DMSO-d$_6$) δ (ppm): 1.80 (4H, m), 3.31 (4H, m), 3.59 (2H, m), 6.61 (1H, d, J=5.6 Hz), 7.09 (1H, m), 7.20-7.45 (3H, m), 7.47 (1H, s), 7.82 (1H, d, J=12.8 Hz), 7.94 (1H, dd, J=8.0, 15.2 Hz), 8.11 (1H, d, J=5.6 Hz), 8.70 (1H, s), 10.06 (1H, m), 10.53 (1H, m).

Example 58

N-(2-Fluorophenyl)-N'-(3-fluoro-4-{2-[(pyrrolidine-1-carbonyl) amino]pyridin-4-yloxy}phenyl)malonamide N-(3-Fluoro-4-{2-[(pyrrolidine-1-carbonyl)amino]pyridin-4-yloxy}phenyl)malonic acid (20.0 mg) was dissolved in N,N-dimethylformamide (1 ml) under a nitrogen atmosphere, and then 2-fluorophenylamine (0.010 ml), triethylamine (0.014 ml) and (1H-1,2,3-benzotriazol-1-yloxy)[tri(dimethylamino)]phosphonium hexafluorophosphate (44 mg) were added thereto at room temperature, followed by stirring for 3 hr. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated to give a residue, which was then purified by silica gel column chromatography (eluent; hexane:ethyl acetate=1:5, then ethyl acetate). Fractions containing the target compound were concentrated to give a residue, to which diethyl ether (1 ml)-hexane (1 ml) was added to suspend. The solid was filtered off and dried under aeration to provide the titled compound (15.3 mg, 62.1%) as white powder.

$^1$H-NMR Spectrum (DMSO-d$_6$) δ (ppm): 1.80 (4H, m), 3.26-3.44 (4H, m), 3.61 (2H, s), 6.60 (1H, dd, J=2.4, 6.0 Hz), 7.10-7.23 (2H, m), 7.24-7.32 (1H, m), 7.35 (1H, d, J=8.8 Hz), 7.39 (1H, m), 7.46 (1H, dd, J=2.0 Hz), 7.82 (1H, dd, J=2.4, 12.8 Hz), 7.99 (1H, m), 8.11 (1H, d, J=5.6 Hz), 8.70 (1H, s), 10.05 (1H, brs), 10.51 (1H, brs).

Example 59

N-(2,6-Difluorophenyl)-N'-(3-fluoro-4-{2-[(pyrrolidine-1-carbonyl)amino]pyridin-4-yloxy}phenyl)malonamide N-(3-Fluoro-4-{2-[(pyrrolidine-1-carbonyl)amino]pyridin-4-yloxy}phenyl)malonic acid (20.0 mg) was dissolved in N,N-dimethylformamide (1 ml) under a nitrogen atmosphere, and then 2,6-difluorophenylamine (0.010 ml), triethylamine (0.014 ml) and (1H-1,2,3-benzotriazol-1-yloxy)[tri(dimethylamino)]phosphonium hexafluorophosphate (44 mg) were added thereto at room temperature, followed by stirring for 3 hr. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated to give a residue, which was then purified by silica gel column chromatography (eluent; hexane:ethyl acetate=1:

5, then ethyl acetate). Fractions containing the target compound were concentrated to give a residue, to which diethyl ether (1 ml)-hexane (1 ml) was added to suspend. The solid was filtered off and dried under aeration to provide the titled compound (11.4 mg, 44.7%) as white powder.

$^1$H-NMR Spectrum (DMSO-d$_6$) δ (ppm): 1.80 (4H, m), 3.26-3.42 (4H, m), 3.56 (2H, s), 6.60 (1H, dd, J=2.4, 6.0 Hz), 7.18 (2H, m), 7.25-7.44 (3H, m), 7.47 (1H, d, J=2.4 Hz), 7.83 (1H, dd, J=2.4, 13.2 Hz), 8.10 (1H, d, J=6.0 Hz), 8.70 (1H, m), 9.96 (1H, brs), 10.52 (1H, brs).

Example 60

N-(2-methoxyphenyl)-N'-(3-fluoro-4-{2-[(pyrrolidine-1-carbonyl)amino]pyridin-4-yloxy}phenyl) malonamide N-(3-Fluoro-4-{2-[(pyrrolidine-1-carbonyl)amino]pyridin-4-yloxy}phenyl)malonic acid (20.0 mg) was dissolved in N,N-dimethylformamide (1 ml) under a nitrogen atmosphere, and then 2-methoxyphenylamine (0.011 ml), triethylamine (0.014 ml) and (1H-1,2,3-benzotriazol-1-yloxy)[tri(dimethylamino)]phosphonium hexafluorophosphate (44 mg) were added thereto at room temperature, followed by stirring for 30 min. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated to give a residue, which was then purified by silica gel column chromatography (FUJI Silysia NH, eluent; hexane:ethyl acetate=1:5, then ethyl acetate). Fractions containing the target compound were concentrated to give a residue, to which diethyl ether (1 ml)-hexane (1 ml) was added to suspend. The solid was filtered off and dried under aeration to provide the titled compound (15.0 mg, 59.1%) as white powder.

$^1$H-NMR Spectrum (CDCl$_3$) δ (ppm): 1.95 (4H, m), 3.44 (4H, m), 3.55 (2H, brs), 3.90 (3H, s), 6.56 (1H, dd, J=2.4, 5.6 Hz), 6.90 (1H, dd, J=1.2, 8.0 Hz), 6.99 (1H, m), 7.01 (1H, brs), 7.05-7.18 (2H, m), 7.23 (1H, m), 7.69 (1H, d, J=2.4 Hz), 7.75 (1H, dd, J=2.8, 12 Hz), 8.05 (1H, d, J=6.0 Hz), 8.31 (1H, dd, J=1.6, 8.0 Hz), 8.54 (1H, brs), 9.64 (1H, brs).

Example 61

N-Cycloheptyl-N'-(3-fluoro-4-{2-[(pyrrolidine-1-carbonyl)amino]pyridin-4-yloxy}phenyl)malonamide N-(3-Fluoro-4-{2-[(pyrrolidine-1-carbonyl)amino]pyridin-4-yloxy}phenyl)malonic acid (20.8 mg) was dissolved in N,N-dimethylformamide (1 ml) under a nitrogen atmosphere, and then cycloheptylamine (0.010 ml), triethylamine (0.014 ml) and (1H-1,2,3-benzotriazol-1-yloxy)[tri(dimethylamino)]phosphonium hexafluorophosphate (46 mg) were added thereto at room temperature, followed by stirring for 30 min. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated to give a residue, which was then purified by silica gel column chromatography (eluent; hexane:ethyl acetate=1:5, then ethyl acetate). Fractions containing the target compound were concentrated to give a residue, to which diethyl ether (1 ml)-hexane (1 ml) was added to suspend. The solid was filtered off and dried under aeration to provide the titled compound (19.7 mg, 76.6%) as white powder.

$^1$H-NMR Spectrum (CDCl$_3$) δ (ppm): 1.40-1.74 (10H, m), 1.95 (6H, m), 3.28 (2H, s), 3.44 (4H, m), 3.99 (1H, m), 6.16 (1H, m), 6.54 (1H, dd, J=2.4, 6.0 Hz), 7.03 (1H, brs), 7.12 (1H, m), 7.22 (1H, m), 7.67 (1H, d, J=2.4 Hz), 7.73 (1H, dd, J=2.4, 12 Hz), 8.03 (1H, d, J=6.0 Hz), 9.85 (1H, brs).

Example 62

N-(2-Chloro-4-{2-[(morpholine-4-carbonyl)amino]pyridin-4-yloxy}phenyl)-N'-(4-fluorophenyl)malonamide Morpholine-4-carboxylic acid [4-(4-amino-3-chlorophenoxy)pyridin-2-yl]amide (93.2 mg) was dissolved in N,N-dimethylformamide (2 ml) under a nitrogen atmosphere, and then N-(4-fluorophenyl)malonic acid (105 mg), triethylamine (0.074 ml) and (1H-1,2,3-benzotriazol-1-yloxy)[tri (dimethylamino)]phosphonium hexafluorophosphate (236 mg) were added thereto at 50° C., followed by stirring at the same temperature for 1 hr. To the reaction mixture were further added N-(4-fluorophenyl)malonic acid (62.6 mg), triethylamine (0.027 ml), and (1H-1,2,3-benzotriazol-1-yloxy) [tri(dimethylamino)]phosphonium hexafluorophosphate (118 mg), followed by stirring for 2 hr and 45 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; hexane:ethyl acetate=1:3) Fractions containing the target compound were concentrated to give a residue, to which hexane (20 ml)-ethyl acetate (2 ml) was added to precipitate crystals. The crystals were filtered off and dried under aeration to provide the titled compound (77.1 mg, 54.7%) as white crystals.

$^1$H-NMR Spectrum (DMSO-d$_6$) δ (ppm): 3.36-3.44 (4H, m), 3.55 (4H, m), 3.61 (2H, m), 6.63 (1H, m), 7.17 (3H, m), 7.41 (2H, m), 7.62 (2H, m), 7.99 (1H, m), 8.14 (1H, m), 9.31 (1H, brs), 10.06 (1H, brs), 10.31 (1H, brs).

Example 63

N-(4-Fluorophenyl)-N'-[2-chloro-4-(2-{[(4-pyrrolidin-1-yl)piperidine-1-carbonyl]amino}pyridin-4-yloxy)phenyl]malonamide 4-(Pyrrolidin-1-yl)piperidine-1-carboxylic acid [4-(4-amino-3-chlorophenoxy)pyridin-2-yl]amide (129 mg) was dissolved in N,N-dimethylformamide (2 ml) under a nitrogen atmosphere, and then N-(4-fluorophenyl)malonic acid (183 mg), triethylamine (0.130 ml) and (1H-1,2,3-benzotriazol-1-yloxy)[tri(dimethylamino)]phosphonium hexafluorophosphate (411 mg) were added thereto at 50° C., followed by stirring at the same temperature for 5 hrs and 30 min. The reaction mixture was cooled down to room temperature, followed by stirring for 2 days. The reaction mixture was partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate:ethanol=19:1). Fractions containing the target compound were concentrated to give a residue, to which diethyl ether was added to precipitate crystals. The crystals were filtered off and dried under aeration to provide the titled compound (64.7 mg, 35.1%) as white crystals.

$^1$H-NMR Spectrum (DMSO-d$_6$) δ (ppm): 1.09 (2H, t, J=7 Hz), 1.20-1.35 (2H, m), 1.65 (4H, m), 1.78 (2H, m), 2.12 (1H, m), 2.46 (2H, m), 2.86 (2H, m), 3.61 (2H, brs), 3.97 (2H, m), 6.32 (1H, dd, J=2.0, 6.0 Hz), 7.10-7.25 (3H, m), 7.41 (2H, m), 7.63 (2H, m), 7.99 (1H, m), 8.13 (1H, d, J=6.0 Hz), 9.21 (1H, s), 10.06 (1H, brs), 10.31 (1H, brs).

Example 64

N-(2-Chloro-4-{2-[(azetidine-1-carbonyl)amino] pyridin-4-yloxy}phenyl)-N'-(4-fluorophenyl)malonamide Azetidine-1-carboxylic acid [4-(4-amino-3-chlorophenoxy)pyridin-2-yl]amide (100 mg) was dissolved in N,N-dimethylformamide (2 ml) under a nitrogen atmosphere, and then N-(4-fluorophenyl)malonic acid (186 mg), triethylamine (0.131 ml) and (1H-1,2,3-benzotriazol-1-yloxy)[tri(dimethylamino)]phosphonium hexafluorophosphate (417 mg) were added thereto at 50° C., followed by stirring at the same temperature for 1 hr. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, to which diethyl ether was added to suspend. The solid was filtered off and dried under aeration to provide the titled compound (128 mg, 81.7%) as pale brown powder.

$^1$H-NMR Spectrum (DMSO-d$_6$) δ (ppm): 2.08-2.20 (2H, m), 3.61 (2H, m), 3.94 (4H, m), 6.60 (1H, dd, J=2.4, 6.0 Hz), 7.14-7.25 (3H, m), 7.42 (1H, d, J=2.8 Hz), 7.51 (1H, d, J=2.4 Hz), 7.63 (2H, m), 8.00 (1H, m), 8.12 (1H, d, J=6.0 Hz), 9.10 (1H, brs), 10.05 (1H, brs), 10.30 (1H, brs).

Example 65

N-(2-Chloro-4-{2-[(piperidine-1-carbonyl)amino] pyridin-4-yloxy}phenyl)-N'-(4-fluorophenyl)malonamide Piperidine-1-carboxylic acid [4-(4-amino-3-chlorophenoxy)pyridin-2-yl]amide (100 mg) was dissolved in N,N-dimethylformamide (2 ml) under a nitrogen atmosphere, and then N-(4-fluorophenyl)malonic acid (171 mg), triethylamine (0.121 ml) and (1H-1,2,3-benzotriazol-1-yloxy)[tri(dimethylamino)]phosphonium hexafluorophosphate (383 mg) were added thereto at 50° C., followed by stirring at the same temperature for 1 hr and 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was purified by silica gel column chromatography (FUJI Silysia NH, eluent; ethyl acetate:ethanol=49:1). Fractions containing a crude product were concentrated to give a residue, which was then further purified by silica gel column chromatography (FUJI Silysia NH, eluent; ethyl acetate:ethanol=49:1). Fractions containing the target compound were concentrated to give a residue, to which diethyl ether (5 ml)-hexane (5 ml) was added to suspend. The solid was filtered off and dried under aeration to provide the titled compound (123 mg, 81.3%) as white powder.

$^1$H-NMR Spectrum (DMSO-d$_6$) δ (ppm): 0.86 (2H, m), 1.24 (2H, m), 1.45 (4H, m), 1.54 (2H, m), 3.61 (2H, m), 6.60 (1H, dd, J=2.0, 6.0 Hz), 7.14-7.25 (3H, m), 7.35-7.45 (2H, m), 7.63 (2H, dd, J=5.2, 9.2 Hz), 7.99 (1H, d, J=9.2 Hz), 8.13 (1H, d, J=6.0 Hz), 9.16 (1H, s), 10.06 (1H, brs), 10.31 (1H, brs).

Example 66

N-(2-Chloro-4-{2-[(pyrrolidine-1-carbonyl)amino] pyridin-4-yloxy}phenyl)-N'-(4-fluorophenyl)malonamide Pyrrolidine-1-carboxylic acid [4-(4-amino-3-chlorophenoxy)pyridin-2-yl]amide (79.6 mg) was dissolved in N,N-dimethylformamide (1.5 ml) under a nitrogen atmosphere, and then N-(4-fluorophenyl)malonic acid (142 mg), triethylamine (0.100 ml), and (1H-1,2,3-benzotriazol-1-yloxy)[tri(dimethylamino)]phosphonium hexafluorophosphate (318 mg) were added thereto at 50° C., followed by stirring at the same temperature for 2 hrs and 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (eluent; ethyl acetate). Fractions containing the target compound were concentrated to give a residue, to which diethyl ether (5 ml)-hexane (5 ml) was added to suspend. The solid was filtered off and dried under aeration to provide the titled compound (94.5 mg, 76.9%) as white powder.

$^1$H-NMR Spectrum (DMSO-d$_6$) δ (ppm): 1.81 (4H, m), 3.27-3.42 (4H, m), 3.61 (2H, m), 6.61 (1H, dd, J=2.4, 5.6 Hz), 7.15-7.25 (3H, m), 7.42 (1H, d, J=2.8 Hz), 7.51 (1H, d, J=2.4 Hz), 7.63 (2H, dd, J=4.8, 8.8 Hz), 8.00 (1H, d, J=8.8 Hz), 8.13 (1H, d, J=5.6 Hz), 8.72 (1H, s), 10.05 (1H, s), 10.31 (1H, brs).

Example 67

N-(3-Chloro-4-{2-[(pyrrolidine-1-carbonyl)amino] pyridin-4-yloxy}phenyl)-N'-(4-fluorophenyl)malonamide 4-(4-Amino-2-chlorophenoxy)-2-[(pyrrolidin-1-yl)carbonylamino]pyridine (99 mg) was dissolved in N,N-dimethylformamide (2 ml) under a nitrogen atmosphere, and then N-(4-fluorophenyl)malonic acid (176 mg), triethylamine (0.124 ml) and (1H-1,2,3-benzotriazol-1-yloxy)[tri(dimethylamino)]phosphonium hexafluorophosphate (394 mg) were added thereto at 50° C., followed by stirring at the same temperature for 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate, then ethyl acetate:ethanol=95:5). Fractions containing the target compound were concentrated to give a residue, to which diethyl ether was added to suspend. The solid was filtered off and dried under aeration to provide the titled compound (102.9 mg, 67.7%) as white powder.

$^1$H-NMR Spectrum (CDCl$_3$) δ (ppm): 1.65 (4H, m), 3.32-3.44° (4H, m), 3.46 (2H, m), 6.74 (1H, dd, J=2.4, 5.6 Hz), 6.92 (2H, m), 7.11 (2H, d, J=8.8 Hz), 7.40-7.57 (4H, m), 7.74 (1H, d, J=2.4 Hz), 8.11 (1H, d, J=5.6 Hz), 9.41 (1H, brs), 9.92 (1H, brs).

Example 68

N-(3-Chloro-4-{2-[(morpholine-4-carbonyl)amino]pyridin-4-yloxy}phenyl)-N'-(4-fluorophenyl)malonamide 4-(4-Amino-2-chlorophenoxy)-2-[(morpholin-1-yl)carbonylamino]pyridine (119 mg) was dissolved in N,N-dimethylformamide (2 ml) under a nitrogen atmosphere, and then N-(4-fluorophenyl)malonic acid (202 mg), triethylamine (0.143 ml) and (1H-1,2,3-benzotriazol-1-yloxy) [tri(dimethylamino)]phosphonium hexafluorophosphate (452 mg) were added thereto at 50° C., followed by stirring at the same temperature for 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (FUJI Silysia NH, eluent; ethyl acetate, then ethyl acetate:ethanol=19:1). Fractions containing the target compound were concentrated to give a residue, to which diethyl ether-hexane (1:1) was added to precipitate crystals. The crystals were filtered off and dried under aeration to provide the titled compound (106.1 mg, 58.9%) as white crystals.

$^1$H-NMR Spectrum (DMSO-d$_6$) δ (ppm): 3.39 (4H, m), 3.50 (2H, m), 3.55 (4H, m), 6.57 (1H, dd, J=2.4, 6.0 Hz), 7.17 (2H, m), 7.32 (2H, m), 7.56 (1H, dd, J=2.4, 8.8 Hz), 7.63 (2H, m), 8.01 (1H, d, J=2.4 Hz), 8.12 (1H, d, J=6.0 Hz), 9.27 (1H, s), 10.27 (1H, brs), 10.50 (1H, brs).

Example 69

N-(4-Fluorophenyl)-N'-(4-{2-[(pyrrolidine-1-carbonyl)amino]pyridin-4-yloxy}phenyl)malonamide 4-(4-Aminophenoxy)-2-[(pyrrolidin-1-yl)carbonylamino]pyridine (30 mg) was dissolved in N,N-dimethylformamide (1 ml) under a nitrogen atmosphere, and then N-(4-fluorophenyl)malonic acid (59.5 mg), triethylamine (0.042 ml) and (1H-1,2,3-benzotriazol-1-yloxy)[tri(dimethylamino)]phosphonium hexafluorophosphate (134 mg) were added thereto at 50° C., followed by stirring at the same temperature for 30 min. The reaction mixture was cooled down to room temperature, and partitioned between ethyl acetate and a 1 N aqueous solution of sodium hydroxide. The organic layer was washed with a saturated aqueous solution of sodium hydrogencarbonate, a saturated aqueous solution of ammonium chloride, water and brine in this order, and dried over anhydrous sodium sulfate. The solvent was evaporated to give a residue, which was then purified by silica gel column chromatography (eluent; hexane:ethyl acetate=1:5, then ethyl acetate). Fractions containing the target compound were concentrated to give a residue, to which diethyl ether (2 ml)-hexane (2 ml) was added to suspend. The solid was filtered off and dried under aeration to provide the titled compound (40.4 mg, 83.4%) as a pale brown solid.

$^1$H-NMR Spectrum (DMSO-d$_6$) δ (ppm): 1.80 (4H, m), 3.30-3.40 (4H, m), 3.48 (2H, m), 6.56 (1H, dd, J=2.4, 5.6 Hz), 7.15 (4H, m), 7.46 (1H, d, J=2.0 Hz), 7.63 (2H, dd, J=5.2, 8.8 Hz), 7.69 (2H, d, J=9.2 Hz), 8.09 (1H, s), 8.65 (1H, s), 10.25 (1H, m), 10.31 (1H, s).

Example 70

N-{4-[2-(3,3-Dimethylureido)pyridin-4-yloxy]phenyl}-N'-(4-fluorophenyl)malonamide 1-[4-(4-Aminophenoxy)pyridin-2-yl]-3,3dimethylurea (30 mg) was dissolved in N,N-dimethylformamide (1 ml) under a nitrogen atmosphere, and then N-(4-fluorophenyl)malonic acid (65.1 mg), triethylamine (0.046 ml) and (1H-1,2,3-benzotriazol-1-yloxy)[tri(dimethylamino)]phosphonium hexafluorophosphate (146 mg) were added thereto at 50° C., followed by stirring at the same temperature for 1.5 hr. The reaction mixture was cooled down to room temperature, and partitioned between ethyl acetate and a 1 N aqueous solution of sodium hydroxide. The organic layer was washed with a saturated aqueous solution of sodium hydrogencarbonate, a saturated aqueous solution of ammonium chloride, water and brine in this order, and dried over anhydrous sodium sulfate. The solvent was evaporated to give a residue, which was then purified by silica gel column chromatography (FUJI Silysia NH, eluent; hexane:ethyl acetate=1:5 to 1:8). Fractions containing the target compound were concentrated to give a residue, to which diethyl ether (2 ml)-hexane (2 ml) was added to suspend. The solid was filtered off and dried under aeration to provide the titled compound (43.4 mg, 87.4%) as a white solid.

$^1$H-NMR Spectrum (DMSO-d$_6$) δ (ppm): 2.89 (6H, s), 3.48 (2H, s), 6.56 (1H, dd, J=2.8, 6.0 Hz), 7.15 (4H, m), 7.37 (1H, d, J=2.0 Hz), 7.63 (2H, dd, J=5.2, 9.2 Hz), 7.69 (2H, d, J=9.2 Hz), 8.09 (1H, d, J=6.0 Hz), 8.85 (1H, s), 10.26 (1H, s), 10.31 (1H, s).

Example 71

N-(4-Fluorophenyl)-N'-(4-{2-[(morpholine-4-carbonyl)amino]pyridin-4-yloxy}phenyl)malonamide 4-(4-Aminophenoxy)-2-[(morpholin-1-yl)carbonylamino]pyridine (30 mg) was dissolved in N,N-dimethylformamide (1 ml) under a nitrogen atmosphere, and then N-(4-fluorophenyl)malonic acid (30.0 mg), triethylamine (0.027 ml) and (1H-1,2,3-benzotriazol-1-yloxy)[tri(dimethylamino)]phosphonium hexafluorophosphate (85 mg) were added thereto at room temperature, followed by stirring overnight. The reaction mixture was cooled down to room temperature, and partitioned between ethyl acetate and a 1 N aqueous solution of sodium hydroxide. The organic layer was washed with a saturated aqueous solution of sodium hydrogencarbonate, a saturated aqueous solution of ammonium chloride, water and brine in this order, and dried over anhydrous sodium sulfate. The solvent was evaporated to give a residue, which was then purified by silica gel column chromatography (FUJI Silysia NH, eluent; hexane:ethyl acetate=1:3, then ethyl acetate). Fractions containing the target compound were concentrated to give a residue, to which diethyl ether (1 ml)-hexane (1 ml) was added to suspend. The solid was filtered off and dried under aeration to provide the titled compound (45.9 mg, 97.5%) as a pale brown solid.

$^1$H-NMR Spectrum (DMSO-d$_6$) δ (ppm): 3.40 (4H, m), 3.47 (2H, s), 3.55 (4H, m), 6.58 (1H, dd, J=2.4, 6.0 Hz), 7.08-7.24 (4H, m), 7.35 (1H, d, J=2.4 Hz), 7.58-7.66 (2H, m), 7.70 (2H, d, J=2.4 Hz), 8.11 (1H, d, J=6.0 Hz), 9.23 (1H, brs), 10.25 (1H, brs), 10.31 (1H, brs).

Example 72

N-(4-Fluorophenyl)-N'-[3-fluoro-4-(2-{[4-(pyrrolidin-1-yl)piperidin-1-yl]carbonylamino}pyridin-4-yloxy)phenyl]malonamide 4-(4-Amino-2-fluorophenoxy)-2-{[4-(pyrrolidin-1-yl)carbonylamino}pyridine (78.6 mg) was dissolved in N,N-dimethylformamide (2 ml) under a nitrogen atmosphere, and then N-(4-fluorophenyl)malonic acid (77.6 mg), triethylamine (0.055 ml) and (1H-1,2,3-benzotriazol-1-yloxy)[tri(dimethylamino)]phosphonium hexafluorophosphate (174 mg) were added thereto at room temperature, followed by stirring for 2 hrs. The reaction mixture was partitioned between ethyl acetate and a saturated aqueous solution of sodium hydrogencarbonate. The organic layer was washed with water and brine in this order, and dried over anhydrous sodium sulfate. The solvent was evaporated to give a residue, which was then purified by silica gel column chromatography (FUJI Silysia NH, eluent; ethyl acetate, then ethyl acetate:methanol=95:5 to 9:1). Fractions containing the target compound were concentrated to give a residue, to which ethyl acetate/hexane (1/5) was added to suspend. The solid was filtered off and dried under aeration to provide the titled compound (33.3 mg, 29%) as pale rosy powder.

$^1$H-NMR Spectrum (DMSO-$d_6$) δ (ppm): 1.20-1.40 (2H, m), 1.60-1.70 (4H, m), 1.70-1.80 (2H, m), 2.12 (1H, m), 2.40-2.60 (4H, m), 2.86 (2H, m), 3.50 (2H, s), 3.90-4.05 (2H, m), 6.59 (1H, dd, J=2.4, 5.6 Hz), 7.16 (2H, m), 7.30-7.40 (3H, m), 7.60-7.70 (2H, m), 7.82 (1H, m), 8.11 (1H, d, J=5.6 Hz), 9.19 (1H, s), 10.26 (1H, s), 10.51 (1H, s).

Example 73

N-(4-Fluorophenyl)-N'-[4-{[2-(dimethylamino)carbonylamino]pyridin-4-yloxy}-3-fluorophenyl)malonamide 4-(4-Amino-2-fluorophenoxy)-2-[(dimethylamino)carbonylamino]pyridine (22 mg) was dissolved in N,N-dimethylformamide (1 ml) under a nitrogen atmosphere, and then N-(4-fluorophenyl)malonic acid (45 mg), triethylamine (0.032 ml) and (1H-1,2,3-benzotriazol-1-yloxy)[tri(dimethylamino)]phosphonium hexafluorophosphate (100 mg) were added thereto at room temperature, followed by stirring at 50° C. for 1.5 hrs. The reaction mixture was partitioned between ethyl acetate and a saturated aqueous solution of sodium hydrogencarbonate. The organic layer was washed with a saturated aqueous solution of sodium hydrogencarbonate, water and brine in this order, and dried over anhydrous sodium sulfate. The solvent was evaporated to give a residue, which was then purified by silica gel column chromatography (eluent; ethyl acetate, then ethyl acetate:methanol=9:1). Fractions containing the target compound were concentrated to give a residue, to which diethyl ether/hexane (1/2) was added to suspend. The solid was filtered off and dried under aeration to provide the titled compound (29 mg, 82%) as white powder.

$^1$H-NMR Spectrum (CDCl$_3$) δ (ppm): 3.00 (6H, s), 3.47 (2H, s), 6.66 (1H, dd, J=2.4, 6.0 Hz), 6.96-7.01 (2H, m), 7.11 (1H, m), 7.20-7.30 (2H, m), 7.50-7.54 (2H, m), 7.56 (1H, d, J=2.4 Hz), 7.67 (1H, dd, J=2.4, 12.0 Hz), 8.08 (1H, d, J=6.0 Hz), 9.03 (1H, s), 9.53 (1H, s).

Example 74

N-(4-Fluorophenyl)-N'-[4-(2-acetylaminopyridin-4-yloxy)-2-fluorophenyl]malonamide N-(4-Fluorophenyl)-N'-[4-(2-aminopyridin-4-yloxy)-2-fluorophenyl]malonamide (20.6 mg) was dissolved in N,N-dimethylformamide (0.5 ml), and then triethylamine (0.043 ml) and acetyl chloride (0.011 ml) were added dropwise thereto under a nitrogen atmosphere at room temperature, followed by stirring overnight. To the reaction mixture was added a 1 N aqueous solution of sodium hydroxide (1.5 ml), followed by stirring and extracting with ethyl acetate. The organic layer was concentrated under a reduced pressure to give a residue, which was purified by silica gel column chromatography (FUJI Silysia NH, eluent; ethyl acetate). Fractions containing the target compound were concentrated to give a residue, which was then dried in vacuum to provide the titled compound (9.3 mg, 41%) as white powder.

$^1$H-NMR Spectrum (CDCl$_3$) δ (ppm): 2.17 (3H, s), 3.60 (2H, s), 6.62 (1H, dd, J=2.4, 5.6 Hz), 6.88-6.93 (2H, m), 7.00-7.05 (2H, m), 7.51-7.56 (2H, m), 7.80 (1H, s), 8.12 (1H, d, J=5.6 Hz), 8.24 (1H, m), 8.35 (1H, m), 9.04 (1H, brs), 9.22 (1H, brs).

Example 75

N-(4-Fluorophenyl)-N'-[4-(2-propionylaminopyridin-4-yloxy)-2-fluorophenyl]malonamide N-(4-Fluorophenyl)-N'-[4-(2-aminopyridin-4-yloxy)-2-fluorophenyl]malonamide (20.2 mg) was dissolved in N,N-dimethylformamide (0.5 ml), and then triethylamine (0.042 ml) and propionyl chloride (0.013 ml) were added dropwise thereto under a nitrogen atmosphere at room temperature, followed by stirring overnight. To the reaction mixture was added a 1 N aqueous solution of sodium hydroxide (1.5 ml), followed by stirring and extracting with ethyl acetate. The organic layer was concentrated under a reduced pressure to give a residue, which was purified by silica gel column chromatography (FUJI Silysia NH, eluent; ethyl acetate). Fractions containing the target compound were concentrated to give a residue, which was then dried in vacuum to provide the titled compound (9.0 mg, 39%) as pale yellow powder.

$^1$H-NMR Spectrum (CDCl$_3$) δ (ppm): 1.21 (3H, t, J=7.6 Hz), 2.40 (2H, q, J=7.6 Hz), 3.58 (2H, s), 6.62 (1H, m), 6.89-6.92 (2H, m), 7.00-7.05 (2H, m), 7.50-7.57 (2H, m), 7.81 (1H, s), 8.00-8.20 (2H, m), 8.25 (1H, m), 8.90 (1H, brs), 9.11 (1H, brs).

Example 76

N-(4-Fluorophenyl)-N'-[4-(2-isobutylylaminopyridin-4-yloxy)-2-fluorophenyl]malonamide N-(4-Fluorophenyl)-N'-[4-(2-aminopyridin-4-yloxy)-2-fluorophenyl]malonamide (20.1 mg) was dissolved in N,N-dimethylformamide (0.5 ml), and then triethylamine (0.040 ml) and isobutylyl chloride (0.008 ml) were added dropwise thereto under a nitrogen atmosphere at room temperature, followed by stirring for 1 hr. To the reaction mixture was added a 1 N aqueous solution of sodium hydroxide (1.0 ml), followed by stirring and extracting with ethyl acetate. The organic layer was concentrated under a reduced pressure to give a residue, which was purified by silica gel column chromatography (FUJI Silysia NH, eluent; ethyl acetate). Fractions containing the target compound were concentrated to give a residue, which was then dried in vacuum to provide the titled compound (11.7 mg, 49%) as pale yellow powder.

$^1$H-NMR Spectrum (CDCl$_3$) δ (ppm): 1.21 (3H, d, J=6.8 Hz), 1.23 (3H, d, J=6.8 Hz), 2.53 (1H, m), 3.60 (2H, s), 6.64 (1H, dd, J=2.0, 3.2 Hz), 6.89-6.92 (2H, m), 7.00-7.04 (2H, m), 7.40-7.60 (2H, m), 7.82 (1H, s), 8.00-8.20 (2H, m), 8.25 (1H, m), 9.07 (1H, brs), 9.23 (1H, brs).

Example 77

N-(4-Fluorophenyl)-N'-{4-[2-(cyclopropanecarbonylamino)pyridin-4-yloxy]-2-fluorophenyl}malonamide N-(4-Fluorophenyl)-N'-[4-(2-aminopyridin-4-yloxy)-2-fluorophenyl]malonamide (21.3 mg) was dissolved in N,N-dimethylformamide (0.5 ml), and then triethylamine (0.030 ml) and cyclopropanecarbonyl chloride (0.010 ml) were added dropwise thereto under a nitrogen atmosphere at room temperature, followed by stirring for 1 hr. To the reaction mixture were added a 1 N aqueous solution of sodium hydroxide (1.0 ml) and methanol (1.0 ml), followed by stirring and extracting with ethyl acetate. The organic layer was concentrated under a reduced pressure to give a residue, which was purified by silica gel column chromatography (FUJI Silysia NH, eluent; ethyl acetate). Fractions containing the target compound were concentrated to give a residue, which was then dried in vacuum to provide the titled compound (9.6 mg, 39%) as white powder.

$^1$H-NMR Spectrum (CDCl$_3$) δ (ppm): 0.80-1.60 (5H, m), 3.56 (2H, s), 6.61 (1H, m), 6.93-7.08 (4H, m), 7.50-7.55 (2H, m), 7.79 (1H, s), 8.12-8.17 (2H, m), 8.28 (1H, m), 8.57 (1H, m), 8.79 (1H, m).

Example 78

N-(4-Fluorophenyl)-N'-{2-fluoro-4-[({[4-(piperidin-1-yl)piperidin-1-yl]carbonyl}amino)pyridin-4-yloxy]phenyl}malonamide N-(4-Fluorophenyl)-N'-[4-(2-aminopyridin-4-yloxy)-2-fluorophenyl]malonamide (17.0 mg) was dissolved in tetrahydrofuran (1.0 ml), and then triethylamine (0.015 ml) and phenyl chloroformate (0.013 ml) were added dropwise thereto under a nitrogen atmosphere at room temperature, followed by stirring for 30 min. The reaction mixture was concentrated under a reduced pressure to give a residue, which was then dissolved in N,N-dimethylformamide (0.5 ml). 4-(Piperidin-1-yl)piperidine (80 mg) was added thereto at room temperature, followed by stirring for 23 hrs. The reaction mixture was partitioned between ethyl acetate and water. The organic layer was washed with water, a saturated aqueous solution of ammonium chloride and brine in this order, and dried over anhydrous sodium sulfate. The solvent was evaporated to give a residue, to which ethyl acetate (2.5 ml) was added to precipitate crystals. The crystals were filtered off and dried under aeration to provide the titled compound (10.4 mg, 41%) as white crystals.

$^1$H-NMR Spectrum (DMSO-d$_6$) δ (ppm): 1.20-3.50 (17H, m), 3.59 (2H, s), 4.20-4.30 (2H, m), 6.64 (1H, m), 7.01 (1H, d, J=8.8 Hz), 7.15-7.27 (3H, m), 7.40 (1H, s), 7.50-7.70 (2H, m), 8.03 (1H, m), 8.15 (1H, m), 9.39 (1H, brs), 10.13 (1H, brs), 10.32 (1H, brs).

Example 79

N-(4-Fluorophenyl)-N'-{4-[2-(cyclopropanecarbonylamino)pyridin-4-yloxy]-3-fluorophenyl}malonamide N-(4-Fluorophenyl)-N'-[4-(2-aminopyridin-4-yloxy)-3-fluorophenyl]malonamide (34 mg) was dissolved in N,N-dimethylformamide (0.5 ml), and then triethylamine (0.047 ml) and cyclopropanecarbonyl chloride (0.016 ml) were added dropwise thereto under a nitrogen atmosphere at room temperature, followed by stirring for 1 hr. To the reaction mixture were added a 1 N aqueous solution of sodium hydroxide (1.5 ml) and methanol (1.0 ml), followed by stirring and extracting with ethyl acetate. The organic layer was washed with water and a saturated aqueous solution of ammonium chloride in this order, and dried over anhydrous sodium sulfate. The solvent was evaporated to give a residue, which was then purified by silica gel column chromatography (FUJI Silysia NH, eluent; ethyl acetate). Fractions containing the target compound were concentrated to give a residue, which was then dried in vacuum to provide the titled compound (21.1 mg, 53%) as white powder.

$^1$H-NMR Spectrum (CDCl$_3$) δ (ppm): 0.80-1.60 (5H, m), 3.52 (2H, s), 6.64 (1H, m), 7.01-7.26 (4H, m), 7.50-7.55 (2H, m), 7.70-7.80 (2H, m), 8.12 (1H, d, J=5.6 Hz), 8.22 (1H, s), 8.74 (1H, s), 9.30 (1H, s).

Example 80

N-(2-Fluoro-4-{2-[(morpholine-4-carbonyl)amino]pyridin-4-yloxy}phenyl)-N'-(4-fluorophenyl)malonamide To a solution of morpholine-4-carboxylic acid [4-(4-amino-3-fluorophenoxy)pyridin-2-yl]amide (48 mg) in N,N-dimethylformamide (3.0 ml) were added N-(4-fluorophenyl) malonic acid (48 mg), and benzotriazol-1-yloxytris(dimethylamino)phosphonium hexafluorophosphate (96 mg), followed by stirring at 50° C. for 2.5 hrs and at room temperature for 56 hrs. N-(4-Fluorophenyl)malonic acid (48 mg) and (1H-1,2,3-benzotriazol-1-yloxy)[tri(dimethylamino)]phosphonium hexafluorophosphate (96 mg) were added thereto, followed by stirring at 50° C. for 2 hr. The reaction mixture was cooled down to room temperature, followed by stirring further for 3.3 hrs. N-(4-Fluorophenyl)malonic acid (48 mg) and (1H-1,2,3-benzotriazol-1-yloxy)[tri(dimethylamino)]phosphonium hexafluorophosphate (96 mg) were further added thereto, followed by stirring at 50° C. for 2.5 hr. The reaction mixture was partitioned between ethyl acetate (100 ml) and a saturated aqueous solution of sodium hydrogencarbonate (100 ml). The organic layer was washed with brine, and dried over anhydrous sodium sulfate. The solvent was evaporated to give a residue, which was then purified by LC-MS. Fractions containing the target compound were concentrated to give a residue, to which a saturated aqueous solution of sodium hydrogencarbonate was added to extract with ethyl acetate. The organic layer was dried over anhydrous sodium sulfate, and concentrated under a reduced pressure. The solid was suspended in diethyl ether, filtered off, washed with diethyl ether, and dried under aeration to provide the titled compound (15 mg, 21%) as colorless powder.

$^1$H-NMR Spectrum (DMSO-d$_6$) δ (ppm):3.37 (2H, s), 3.40 (4H, m), 3.56 (4H, m), 6.63 (1H, dd, J=2.4, 5.6 Hz), 7.01 (1H, m), 7.19 (2H, m), 7.25 (1H, dd, J=2.4, 11.6 Hz), 7.40 (1H, d, J=2.4 Hz), 7.62 (2H, dd, J=5.2, 8.8 Hz), 8.03 (1H, m), 8.14 (1H, d, J=5.6 Hz), 9.29 (1H, s), 10.11 (1H, s), 10.27 (1H, s).

Example 81

N-(2-Fluoro-4-{2-[(pyrrolidine-1-carbonyl)amino] pyridin-4-yloxy}phenyl)-N'-(4-fluorophenyl)malonamide To a solution of N-[4-(2-aminopyridin-4-yloxy)-2-fluorophenyl]-N'-(4-fluorophenyl)malonamide (30 mg) in tetrahydrofuran (2.4 ml) was added triethylamine (0.021 ml), and then phenyl chloroformate (0.0189 ml) was added dropwise thereto while cooling in an ice water bath, followed by stirring for 20 min. The reaction mixture was concentrated under a reduced pressure. To a suspension of the residue in N,N-dimethylformamide (1.2 ml) was added pyrrolidine (0.0251 ml) while cooling in an ice water bath, followed by raising the temperature to room temperature and stirring for 1 hr. The reaction mixture was partitioned between ethyl acetate (50 ml) and a 1 N aqueous solution of sodium hydroxide (30 ml). The organic layer was washed with brine, and dried over anhydrous sodium sulfate. The solvent was evaporated to give a residue, which was then purified by silica gel column chromatography (eluent; hexane:ethyl acetate=1:2, ethyl acetate, then ethyl acetate:methanol=10:1). Fractions containing the target compound were concentrated to give a residue, which was then further subjected to silica gel filtration (FUJI Silysia NH). The filtrate was concentrated under a reduced pressure to give a residue, to which hexane (3 ml), diethyl ether (1 ml) and ethanol (1 drop) were added to suspend. The solid was filtered off and dried under aeration to provide the titled compound (12.3 mg, 33.0%) as pale red powder.

$^1$H-NMR Spectrum (DMSO-d$_6$) δ (ppm): 1.81 (4H, m), 3.33 (4H, m), 3.58 (2H, s), 6.61 (1H, dd, J=2.4, 5.8 Hz), 7.00 (1H, m), 7.17 (2H, m), 7.24 (1H, m), 7.50 (1H, d, J=2.4 Hz), 7.62 (2H, m), 8.03 (1H, m), 8.12 (1H, d, J=5.8 Hz), 8.71 (1H, s), 10.10 (1H, s), 10.25 (1H, s). ESI-MS (m/z): 496 [M+H]$^+$.

Example 82

N-(4-Fluorophenyl)-N'-[2-fluoro-4-(2-{[4(pyrrolidin-1-yl)piperidine-1-carbonyl]amino}pyridin-4-yloxy)phenyl]malonamide To a solution of N-[4-(2-aminopyridin-4-yloxy)-2-fluorophenyl]-N'-(4-fluorophenyl)malonamide (20 mg) in tetrahydrofuran (1.6 ml) was added triethylamine (0.014 ml), and then phenyl chloroformate (0.0126 ml) was added dropwise thereto while cooling in an ice water bath, followed by stirring for 30 min. The reaction mixture was concentrated under a reduced pressure, and then N,N-dimethylformamide (0.8 ml) and 4-(1-pyrrolidinyl)piperidine (31 mg) were added thereto, followed by stirring at room temperature for 1 hr. The reaction mixture was partitioned between ethyl acetate (50 ml) and a 1 N aqueous solution of sodium hydroxide (30 ml). The organic layer was washed with brine, dried over anhydrous sodium sulfate, and concentrated under a reduced pressure. The resultant residue was purified by silica gel column chromatography (FUJI Silysia NH, eluent; hexane:ethyl acetate=1:2, ethyl acetate, then ethyl acetate:methanol=20:1). Fractions containing the target compound were concentrated to give a solid, which was then suspended in hexane (3 ml) and diethyl ether (1 ml), and filtered to provide the titled compound (5.0 mg, 17%) as pale yellow powder.

$^1$H-NMR Spectrum (DMSO-d$_6$) δ (ppm): 1.26 (2H, m), 1.66 (4H, m), 1.79 (2H, m), 2.12 (1H, m), 2.46 (4H, m), 2.86 (2H, m), 3.58 (2H, s), 3.97 (2H, m), 6.60 (1H, dd, J=1.6, 6.0 Hz), 7.01 (1H, m), 7.17 (2H, m), 7.24 (1H, dd, J=2.4, 11.6 Hz), 7.63 (2H, dd, J=5.2, 8.8 Hz), 8.03 (1H, m), 8.12 (1H, d, J=6.0 Hz), 9.02 (1H, s), 10.11 (1H, s), 10.27 (1H, s). ESI-MS (m/z): 579 [M+H]$^+$.

Example 83

N-(4-{2-[3-(3-Diethylaminopropyl)-3-methylureido] pyridin-4-yloxy}phenyl)-N'-(4-fluorophenyl)malonamide To a solution of N-[4-(2-aminopyridin-4-yloxy)-2-fluorophenyl]-N'-(4-fluorophenyl)malonamide (35 mg) in tetrahydrofuran (2.8 ml) was added triethylamine (0.025 ml), and then phenyl chloroformate (0.022 ml) was added dropwise thereto while cooling in an ice water bath, followed by stirring for 30 min. The reaction mixture was concentrated under a reduced pressure. To a suspension of the residue in N,N-dimethylformamide (1.4 ml) was added N,N-diethyl-N'-methylpropane-1,3-diamine (54.3 mg) while cooling in an ice water bath, followed by stirring at room temperature for 30 min. The reaction mixture was partitioned between ethyl acetate (50 ml) and a 1 N aqueous solution of sodium hydroxide (30 ml). The organic layer was washed with brine, and dried over anhydrous sodium sulfate. The solvent was evaporated to give a residue, which was then purified by silica gel column chromatography (FUJI Silysia NH, eluent; hexane:ethyl acetate=1:1, then ethyl acetate). Fractions containing a crude product were concentrated to give a residue, which was further purified by LC-MS. Fractions containing the target compound were concentrated to give a residue, to which a saturated aqueous solution of sodium hydrogencarbonate was added to extract with ethyl acetate. The organic layer was washed with brine, and concentrated under a reduced pressure to give a residue, which was dried in vacuum to provide the titled compound (4.1 mg, 8.2%) as pale brown powder.

$^1$H-NMR Spectrum (DMSO-d$_6$) δ (ppm): 1.00 (6H, t, J=6.8 Hz), 1.70 (2H, m), 2.35-2.70 (6H, m), 2.83 (3H, s), 3.30 (2H, m), 3.58 (2H, s), 6.57 (1H, m), 7.00 (1H, m), 7.17 (2H, m), 7.23 (1H, dd, J=2.6, 11.4 Hz), 7.39 (1H, d, J=2.4 Hz), 7.63 (2H, dd, J=5.2, 8.8 Hz), 8.03 (1H, m), 8.10 (1H, d, J=5.6 Hz), 10.09 (1H, s), 10.25 (1H, s). ESI-MS (m/z): 569 [M+H]$^+$.

Example 84

N-{4-[2-(3,3-Dimethylureido)pyridin-4-yloxy]-2-fluorophenyl}-N'-(4-fluorophenyl)malonamide To a solution of N-[4-(2-aminopyridin-4-yloxy)-2-fluorophenyl]-N'-(4-fluorophenyl)malonamide (35 mg) in tetrahydrofuran (2.8 ml) was added triethylamine (0.0245 ml), and then phenyl chloroformate (0.0221 ml) was added dropwise thereto while cooling in an ice water bath, followed by stirring for 30 min. The reaction mixture was concentrated under a reduced pressure. To a suspension of the residue in N,N-dimethylformamide (1.4 ml) was added dimethylamine (0.175 ml, 2.0 M solution in tetrahydrofuran), followed by stirring at room temperature for 5 hrs. Diethylamine hydrochloride (35.8 mg) and triethylamine (0.2 ml) were added further, followed by stirring at room temperature for 2 hrs. The reaction mixture was partitioned between ethyl acetate (50 ml) and a 1 N aqueous solution of sodium hydroxide (30 ml). The organic layer was washed with a 1 N aqueous solution of sodium hydroxide and brine in this order, and dried over anhydrous sodium sulfate. The solvent was evaporated to give a residue, which was then subjected to silica gel filtration (FUJI Silysia NH). The filtrate was concentrated under a reduced pressure to give a residue, which was then purified by silica gel column chromatography (eluent; hexane:ethyl acetate=1:2, ethyl acetate, then ethyl acetate:methanol=20:1 to 10:1). Fractions containing the target compound were concentrated to give a solid, which was then suspended in ethanol (0.5 ml)-diethyl ether (2.5 ml), filtered off, and dried under aeration to provide the titled compound (12.4 mg, 30%) as pale brown powder.

$^1$H-NMR Spectrum (DMSO-$d_6$) δ (ppm): 2.89 (6H, s), 3.58 (2H, s), 6.61 (1H, m), 7.01 (1H, m), 7.17 (2H, m), 7.24 (1H, m), 7.43 (1H, s), 7.63 (2H, m), 8.03 (1H, m), 8.13 (1H, d, J=5.6 Hz), 8.92 (1H, s), 10.10 (1H, s), 10.26 (1H, s). ESI-MS (m/z) (neg).: 468 [M−H]$^-$.

Example 85

N-(4-Fluorophenyl)-N'-[2-methyl-4-(2-{[(4-pyrrolidin-1-yl)piperidine-1-carbonyl]amino}pyridin-4-yloxy)phenyl]malonamide To a solution of N-[4-(2-aminopyridin-4-yloxy)-2-methylphenyl]-N'-(4-fluorophenyl)malonamide (60 mg) in tetrahydrofuran (6 ml)-N,N-dimethylformamide (0.090 ml) was added triethylamine (0.042 ml), and then phenyl chloroformate (0.0378 ml) was added thereto while cooling in an ice water bath, followed by stirring for 20 min. The reaction mixture was concentrated under a reduced pressure. To a suspension of the residue in N,N-dimethylformamide (2.4 ml) was added 4-(1-pyrrolidinyl)piperidine (93 mg), followed by stirring at room temperature for 5 hrs. The reaction mixture was partitioned between ethyl acetate (50 ml) and a 1 N aqueous solution of sodium hydroxide (30 ml). The organic layer was washed with brine, dried over anhydrous sodium sulfate, and subjected to silica gel filtration (FUJI Silysia NH). The filtrate was concentrated under a reduced pressure to give a residue, which was then suspended in ethanol (0.5 ml) and ethyl acetate (1 ml)-diethyl ether (5 ml). The solid was filtered off, washed with diethyl ether and dried under aeration to provide the titled compound (62.4 mg, 71.4%) as colorless powder.

$^1$H-NMR Spectrum (DMSO-$d_6$) δ (ppm): 1.22-1.54 (2H, m), 1.66 (4H, m), 1.74-1.83 (2H, m), 2.13 (1H, m), 2.26 (3H, s), 2.47 (4H, m), 2.86 (2H, m), 3.52 (2H, s), 3.97 (2H, m), 6.55 (1H, dd, J=2.4, 5.6 Hz), 6.96 (1H, dd, J=2.4, 8.4 Hz), 7.05 (1H, d, J=2.4 Hz), 7.17 (2H, dd, J=8.8, 8.8 Hz), 7.37 (1H, d, J=2.4 Hz), 7.57 (1H, d, J=8.4 Hz), 7.64 (2H, dd, J=5.2, 8.8 Hz), 8.10 (1H, d, J=5.6 Hz), 9.16 (1H, s), 9.64 (1H, s), 10.27 (1H, s). ESI-MS (m/z): 575 [M+H]$^+$.

Example 86

N-{4-[2-(3,3-Dimethylureido)pyridin-4-yloxy]-2-methylphenyl}-N'-(4-fluorophenyl)malonamide To a solution of N-[4-(2-aminopyridin-4-yloxy)-2-methylphenyl]-N'-(4-fluorophenyl)malonamide (60 mg) in tetrahydrofuran (6 ml)-N,N-dimethylformamide (0.090 ml) was added triethylamine (0.042 ml), and then phenyl chloroformate (0.038 ml) was added thereto while cooling in an ice water bath, followed by stirring for 20 min. The reaction mixture was concentrated under a reduced pressure. To a suspension of the residue in N,N-dimethylformamide (2.4 ml) were added diethylamine hydrochloride (61 mg) and triethylamine (0.106 ml), followed by stirring at room temperature for 7 hrs and 20 min. The reaction mixture was partitioned between ethyl acetate (50 ml) and a 1 N aqueous solution of sodium hydroxide (30 ml). The organic layer was washed with brine, and dried over anhydrous sodium sulfate. The solvent was evaporated to give a residue, which was then suspended in ethanol (0.5 ml)-diethyl ether (5 ml), filtered off, washed with diethyl ether and dried under aeration to provide the titled compound (52.7 mg, 75%) as colorless powder.

$^1$H-NMR Spectrum (DMSO-$d_6$) δ (ppm): 2.26 (3H, s), 2.89 (6H, s), 3.52 (2H, s), 6.56 (1H, d, J=5.6 Hz), 6.97 (1H, d, J=8.4 Hz), 7.05 (1H, s), 7.17 (2H, dd, J=8.4, 8.4 Hz), 7.39 (1H, s), 7.57 (1H, d, J=8.4 Hz), 7.64 (2H, dd, J=5.2, 8.4 Hz), 8.10 (1H, d, J=5.6 Hz), 8.87 (1H, s), 9.65 (1H, s), 10.27 (1H, s). ESI-MS (m/z): 466 [M+H]$^+$.

Example 87

N-(4-Fluorophenyl)-N'-(2-methyl-4-{2-[(pyrrolidine-1-carbonyl)amino]pyridin-4-yloxy}phenyl)malonamide To a solution of pyrrolidine-1-carboxylic acid [4-(4-amino-3-methylphenoxy)pyridin-2-yl]amide (100 mg) in N,N-dimethylformamide (2.0 ml) were added N-(4-fluorophenyl)malonic acid (189 mg), triethylamine (0.5 ml) and (1H-1,2,3-benzotriazol-1-yloxy)[tri(dimethylamino)]phosphonium hexafluorophosphate (425 mg) at room temperature, followed by stirring at 50° C. for 5 hrs. The reaction mixture was partitioned between ethyl acetate (60 ml) and water (60 ml). The organic layer was washed with a saturated aqueous solution of sodium hydrogencarbonate and brine in this order, and dried over anhydrous sodium sulfate. The solvent was evaporated to give a residue, which was then purified by silica gel column chromatography (eluent; ethyl acetate-ethyl acetate:methanol=10:1). Fractions containing the target compound were concentrated to give a solid, which was suspended in ethyl acetate, filtered off, washed with diethyl ether and dried under aeration to provide the titled compound (70 mg, 45%) as colorless powder.

$^1$H-NMR Spectrum (DMSO-$d_6$) δ (ppm): 1.81 (4H, m), 2.26 (3H, s), 3.35 (4H, m), 3.52 (2H, s), 6.55 (1H, dd, J=2.0, 6.0 Hz), 6.97 (1H, dd, J=2.8, 8.8 Hz), 7.05 (1H, d, J=2.0 Hz), 7.17 (2H, dd, J=9.0, 9.0 Hz), 7.48 (1H, d, J=2.8 Hz), 7.58 (1H, d, J=8.8 Hz), 7.64 (2H, dd, J=5.3, 9.0 Hz), 8.09 (1H, d, J=6.0 Hz), 8.65 (1H, s), 9.64 (1H, s), 10.26 (1H, s).

Example 88

N-(4-Fluorophenyl)-N'-(2-methyl-4-{2-[(morpholine-4-carbonyl)amino]pyridin-4-yloxy}phenyl)malonamide To a solution of morpholine-4-carboxylic acid [4-(4-amino-3-methylphenoxy)pyridin-2-yl]amide (100 mg) in N,N-dimethylformamide (2.0 ml) were added N-(4-fluorophenyl)malonic acid (180 mg), triethylamine (0.5 ml), and (1H-1,2,3-benzotriazol-1-yloxy)[tri(dimethylamino)]phosphonium hexafluorophosphate (404 mg) at room temperature, followed by stirring at 50° C. for 5 hrs. The reaction mixture was partitioned between ethyl acetate (60 ml) and water (60 ml). The organic layer was washed with a saturated aqueous solution of sodium hydrogencarbonate and brine in this order, and dried over anhydrous sodium sulfate. The solvent was evaporated to precipitate crystals, which was then suspended in ethyl acetate, and filtered. The filtrate was concentrated again to give a residue, which was purified by silica gel column chromatography (eluent; ethyl acetate-ethyl acetate:methanol=10:1). Fractions containing the target compound were concentrated to give a solid, which was suspended in diethyl ether, filtered off, washed with diethyl ether, and dried under aeration to provide the titled compound (13 mg, 8.4%) as pale yellow powder.

¹H-NMR Spectrum (DMSO-d₆) δ (ppm): 2.26 (3H, s), 3.40 (4H, m), 3.52 (2H, s), 3.55 (4H, m), 6.57 (1H, dd, J=2.4, 5.6 Hz), 6.97 (1H, dd, J=2.4, 8.4 Hz), 7.05 (1H, d, J=2.4 Hz), 7.17 (2H, dd, J=8.8, 8.8 Hz), 7.39 (1H, d, J=2.4 Hz), 7.57 (1H, d, J=8.4 Hz), 7.63 (2H, dd, J=5.2, 8.8 Hz), 8.11 (1H, d, J=5.6 Hz), 9.24 (1H, s), 9.64 (1H, s), 10.26 (1H, s).

Example 89

N-(3-Fluoro-4-{2-[3-methyl-3-(1-methylpiperidin-4-yl)ureido]pyridin-4-yloxy}phenyl)-N'-(4-fluorophenyl)malonamide 3-[4-(4-Amino-2-fluorophenoxy)pyridin-2-yl]-1-methyl-1-(1-methylpiperidin-4-yl)urea (30.0 mg) was dissolved in N,N-dimethylformamide (1 ml) under a nitrogen atmosphere, and then N-(4-fluorophenyl)malonic acid (31.7 mg), triethylamine (0.022 ml) and (1H-1,2,3-benzotriazol-1-yloxy)[tri(dimethylamino)]phosphonium hexafluorophosphate (71 mg) were added thereto at room temperature, followed by stirring for 3 hrs. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was evaporated to give a residue, which was then purified by silica gel column chromatography (FUJI Silysia NH, eluent; ethyl acetate:ethanol=9:1) Fractions containing the target compound were concentrated to give a residue, to which diethyl acetate (1 ml) was added to suspend. The solid was filtered off and dried under aeration to provide the titled compound (15.0 mg, 33.8%) as a white solid.

¹H-NMR Spectrum (CDCl₃) δ (ppm): 1.50-1.68 (2H, t, J=7 Hz), 1.74 (2H, m), 1.96 (2H, t, J=11.6 Hz), 2.23 (3H, s), 2.86 (5H, m), 3.49 (2H, m), 4.05 (1H, m), 6.63 (1H, dd, J=2.0, 6.0 Hz), 7.02 (2H, m), 7.11 (1H, m), 7.21 (1H, d, J=8.8 Hz), 7.24-7.36 (1H, m), 7.48-7.62 (3H, m), 7.68 (1H, m), 8.08 (1H, d, J=6.0 Hz), 8.89 (1H, brs), 9.42 (1H, brs). ESI-MS (m/z): 553 [M+H]⁺.

Example 90

N-(4-Fluorophenyl)-N'-(4-{2-[3-methyl-3-(1-methylpiperidin-4-yl)ureido]pyridin-4-yloxy}phenyl)malonamide 3-[4-(4-Aminophenoxy)pyridin-2-yl]-1-methyl-1-(1-methylpiperidin-4-yl)urea (20 mg) was dissolved in N,N-dimethylformamide (1 ml), and then N-(4-fluorophenyl)malonic acid (22.3 mg), triethylamine (0.016 ml) and (1H-1,2,3-benzotriazol-1-yloxy)[tri(dimethylamino)]phosphonium hexafluorophosphate (49.8 mg) were added thereto at room temperature, followed by stirring for 30 min. The reaction mixture was partitioned between ethyl acetate (30 ml) and a saturated aqueous solution of sodium hydrogencarbonate (10 ml). The organic layer was washed with a saturated aqueous solution of sodium hydrogencarbonate (10 ml), water (10 ml) and brine (10 ml) in this order, and dried over anhydrous sodium sulfate. The solvent was evaporated to give a residue, which was then purified by silica gel column chromatography (FUJI Silysia NH, eluent; ethyl acetate-ethyl acetate:ethanol=9:1). Fractions containing the target compound were concentrated to give a residue, to which diethyl acetate (2 ml)-hexane (2 ml) was added to suspend. The solid was filtered off and dried under aeration to provide the titled compound (21.3 mg, 70.8%) as a white solid.

¹H-NMR Spectrum (CDCl₃) δ (ppm): 1.50-1.68 (2H, m), 1.75 (2H, m), 1.99 (2H, t, J=12 Hz), 2.25 (3H, s), 2.87 (5H, m), 3.48 (2H, s), 4.09 (1H, m), 6.58 (1H, dd, J=2.0, 6.0 Hz), 7.02 (2H, m), 7.08 (2H, d, J=8.8 Hz), 7.20 (1H, brs), 7.53 (2H, m), 7.56-7.68 (3H, m), 8.06 (1H, d, J=6.0 Hz), 8.87-9.12 (2H, m). ESI-MS (m/z): 557 [M+Na]⁺.

Example 91

N-(2-Fluoro-4-{2-[3-methyl-3-(1-methylpiperidin-4-yl)ureido]pyridin-4-yloxy}phenyl)-N'-(4-fluorophenyl)malonamide To a solution of 3-[4-(4-amino-3-fluorophenoxy)pyridin-2-yl]-1-methyl-1-(1-methylpiperidin-4-yl)urea (40.5 mg) in tetrahydrofuran (20 ml) (Production Example 124) was added N,N-dimethylformamide (2 ml) under a nitrogen atmosphere, followed by evaporating the tetrahydrofuran under a reduced pressure. To the solution thus concentrated were added N-(4-fluorophenyl)malonic acid (42.6 mg), triethylamine (0.030 ml) and (1H-1,2,3-benzotriazol-1-yloxy)[tri(dimethylamino)]phosphonium hexafluorophosphate (95.5 mg) at room temperature, followed by stirring for 1 hr. The reaction mixture was partitioned between ethyl acetate (30 ml) and a saturated aqueous solution of ammonium chloride (15 ml). The organic layer was washed with a saturated aqueous solution of ammonium chloride (15 ml), water (15 ml) and brine (15 ml) in this order, and dried over anhydrous sodium sulfate. The solvent was evaporated to give a residue, which was then purified by silica gel column chromatography (FUJI Silysia NH, eluent; ethyl acetate-ethyl acetate:ethanol=95:5). Fractions containing the target compound were concentrated to give a residue, to which diethyl ether (1 ml) was added to suspend. The solid was filtered off and dried under aeration to provide the titled compound (29.1 mg, 48.8%) as a pale green and yellow solid.

¹H-NMR Spectrum (CDCl₃) δ (ppm): 1.48-1.71 (2H, m), 1.78 (2H, m), 2.07 (2H, m), 2.29 (3H, s), 2.80-3.00 (5H, m), 3.55 (2H, m), 4.16 (1H, m), 6.55 (1H, dd, J=2.4, 6.0 Hz), 6.92 (2H, d, J=8.8 Hz), 7.05 (2H, m), 7.21 (1H, brs), 7.53 (2H, m), 7.69 (1H, d, J=2.4 Hz), 8.08 (1H, d, J=6.0 Hz), 8.26 (1H, m), 8.63 (1H, brs), 8.80 (1H, brs). ESI-MS (m/z): 553 [M+H]⁺.

Example 92

N-(2-Fluoro-4-{2-[(4-methyl-[1,4]diazepane-1-carbonyl)amino]pyridin-4-yloxy}phenyl)-N'-(4-fluorophenyl)malonamide To a solution of N-[4-(2-aminopyridin-4-yloxy)-2-fluorophenyl]-N'-(4-fluorophenyl)malonamide (17.6 mg) in tetrahydrofuran (2.0 ml) was added triethylamine (0.0154 ml), and then phenyl chloroformate (0.00833 ml) was added dropwise thereto while cooling in an ice water bath, followed by stirring for 10 min. The reaction mixture was concentrated under a reduced pressure. To the resultant residue were added N,N-dimethylformamide (1.0 ml) and 1-methylhomopiperazine (0.0193 ml), followed by stirring at room temperature for 8 hrs. The reaction mixture was partitioned between ethyl acetate (50 ml) and water (30 ml). The organic layer was washed with brine (30 ml×3), and dried over anhydrous sodium sulfate. The solvent was evaporated to give a solid, which was then suspended in hexane:diethyl ether=1:1 (3.0 ml), filtered off and dried under aeration to provide the titled compound (10.2 mg, 42.8%) as pale yellow powder.

$^1$H-NMR Spectrum (DMSO-d$_6$) δ (ppm): 1.25 (2H, m), 1.78 (2H, m), 2.24 (3H, s), 2.45 (2H, m), 3.51 (4H, m), 3.58 (2H, m), 6.61 (1H, dd, J=2.4, 5.6 Hz), 7.02 (1H, m), 7.17 (2H, dd, J=9.0, 9.0 Hz), 7.25 (1H, dd, J=2.4, 8.0 Hz), 7.48 (1H, d, J=2.4 Hz), 7.63 (2H, dd, J=5.0, 9.0 Hz), 8.04 (1H, m), 8.13 (1H, d, J=5.6 Hz), 8.82 (1H, s), 10.10 (1H, s), 10.26 (1H, s). ESI-MS (m/z): 539 [M+H]$^+$.

Example 93

N-[2-Fluoro-4-(2-{3-methyl-3-[3-(4-methylpiperazin-1-yl)propyl]ureido}pyridin-4-yloxy)phenyl]-N'-(4-fluorophenyl)malonamide To a solution of N-[4-(2-aminopyridin-4-yloxy)-2-fluorophenyl]-N'-(4-fluorophenyl)malonamide (17.6 mg) in tetrahydrofuran (2.0 ml) was added triethylamine (0.0154 ml), and then phenyl chloroformate (0.00833 ml) was added dropwise thereto while cooling in an ice bath, followed by stirring for 10 min. The reaction mixture was concentrated under a reduced pressure. To the resultant residue were added N,N-dimethylformamide (1.0 ml) and methyl-[3-(4-methylpiperazin-1-yl)propyl]amine (67.1 mg), followed by stirring at room temperature for 3 hrs. Methyl-[3-(4-methylpiperazin-1-yl)propyl]amine (34.5 mg) was further added thereto, followed by stirring at room temperature for 3 hrs. Additionally, methyl-[3-(4-methylpiperazin-1-yl)propyl]amine (34.5 mg) was further added thereto, followed by stirring at room temperature for 2.5 hrs. The reaction mixture was partitioned between ethyl acetate (50 ml) and water (30 ml). The organic layer was washed with brine (30 ml×3), and dried over anhydrous sodium sulfate. The solvent was evaporated to give a residue, which was then purified by silica gel column chromatography (FUJI Silysia NH, eluent; ethyl acetate:methanol=20:1-10:1). Fractions containing the target compound were concentrated to give a residue, to which ethyl acetate (0.5 ml) and hexane (2.5 ml) were added to suspend. After a solid was precipitated, the supernatant was removed. The remaining solvent was evaporated under a reduced pressure to give a residue, which was dried in vacuum to provide the titled compound (46.7 mg, 12.4%) as colorless powder.

$^1$H-NMR Spectrum (DMSO-d$_6$) δ (ppm): 1.68 (2H, m), 2.11-2.60 (11H, m), 2.81 (3H, s), 3.31 (4H, m), 3.58 (2H, s), 6.59 (1H, dd, J=2.0, 5.6 Hz), 7.01 (1H, m), 7.17 (2H, dd, J=8.8, 8.8 Hz), 7.24 (1H, dd, J=2.8, 7.6 Hz), 7.42 (1H, d, J=2.0 Hz), 7.63 (2H, dd, J=4.8, 8.8 Hz), 8.03 (1H, d, J=5.6 Hz), 8.10 (1H, d, J=5.6 Hz), 9.47 (1H, brs), 10.10 (1H, s), 10.26 (1H, s). H-NMR Spectrum (CDCl$_3$) δ (ppm): 1.78 (2H, m), 2.26-2.78 (11H, m), 2.89 (3H, s), 3.38 (4H, m), 3.55 (2H, s), 6.52 (1H, dd, J=2.2, 5.6 Hz), 6.88 (2H, m), 7.01 (2H, m), 7.51-7.57 (3H, m), 8.06 (1H, d, J=5.6 Hz), 8.20 (1H, m), 9.07 (1H, s), 9.13 (1H, s). ESI-MS (m/z): 596 [M+H]$^+$.

The following Examples were synthesized similarly to the methods described in Examples 1 to 93.

Example 94

Pyrrolidine-1-carbothioic acid {4-[3-chloro-4-(3-phenylacetylthioureido)phenoxy]pyridin-2-yl}amide The titled compound (15.7 mg, 14.5%) was obtained as a pale yellow solid from 2-phenylacetyl chloride (0.067 ml), potassium thiocyanate (99.1 mg) and 4-(4-amino-2-fluorophenoxy)-2-[(pyrrolidin-1-yl)thiocarbonylamino]pyridine (99.6 mg).

$^1$H-NMR Spectrum (CDCl$_3$) δ (ppm): 2.05 (4H, m), 3.40-4.10 (6H, m), 6.62 (1H, m), 7.09 (1H, dd, J=2.8, 9.2 Hz), 7.20-7.50 (6H, m), 7.72 (1H, m), 8.11 (1H, m), 8.36 (2H, dd, J=9.2 Hz), 8.55 (1H, m), 12.42 (1H, s).

Example 95

4-{3-chloro-4-[3-(2-phenylacetyl)thioureido]phenoxy}-2-[(pyrrolidin-1-yl)carbonylamino]pyridine The titled compound (88.8 mg, 35%) was obtained as white crystals from 2-phenylacetyl chloride (0.2 ml), potassium thiocyanate (292 mg) and 4-(4-amino-3-chlorophenoxy)-2-[(pyrrolidin-1-yl)carbonylamino]pyridine (166 mg).

$^1$H-NMR Spectrum (DMSO-d$_6$) δ (ppm): 1.70-1.90 (4H, m), 3.20-3.40 (4H, m), 3.82 (2H, s), 6.59 (1H, dd, J=2.4, 5.6 Hz), 7.18 (1H, m), 7.20-7.40 (5H, m), 7.43 (1H, d, J=3.2 Hz), 7.53 (1H, d, J=2.0 Hz), 8.04 (1H, d, J=8.8 Hz), 8.13 (1H, d, J=5.6 Hz), 8.74 (1H, s), 11.88 (1H, s), 12.36 (1H, s).

Example 96

4-{3-Chloro-4-[3-(2-phenylacetyl)thioureido]phenoxy}-2-[(morpholin-4-yl)carbonylamino]pyridine The titled compound (34.3 mg, 41%) was obtained as white powder from 2-phenylacetyl chloride (125 mg), potassium thiocyanate (157 mg) and 4-(4-amino-3-chlorophenoxy)-2-[(morpholin-4-yl)carbonylamino]pyridine (56.2 mg).

$^1$H-NMR Spectrum (DMSO-d$_6$) δ (ppm): 3.30-3.40 (4H, m), 3.50-3.60 (4H, m), 3.84 (2H, s), 6.62 (1H, dd, J=2.4, 5.6 Hz), 7.20-7.50 (8H, m), 8.06 (1H, d, J=8.8 Hz), 8.16 (1H, d, J=5.6 Hz), 9.33 (1H, s), 11.90 (1H, s), 12.38 (1H, s).

Example 97

4-{4-[3-(2-Cyclopropylacetyl)thioureido]-2-fluorophenoxy}-2-[(pyrrolidin-1-yl)carbonylamino]pyridine The titled compound (61.9 mg, 42%) was obtained as pale yellow crystals from 2-cyclopropylacetic acid (114.2 mg)., oxalyl chloride (0.105 ml), potassium thiocyanate (222 mg) and 4-(4-amino-2-fluorophenoxy)-2-[(pyrrolidin-1-yl)carbonylamino]pyridine (103 mg).

$^1$H-NMR Spectrum (DMSO-d$_6$) δ (ppm): 0.15-0.25 (2H, m), 0.40-0.60 (2H, m), 1.02 (1H, m), 1.80-1.90 (4H, m), 2.38 (2H, d, J=7.2 Hz), 3.20-3.40 (4H, m), 6.61 (1H, dd, J=2.4, 6.0 Hz), 7.30-7.60 (3H, m), 8.03 (1H, m), 8.13 (1H, d, J=6.0 Hz), 8.74 (1H, s), 11.51 (1H, s), 12.66 (1H, s).

Example 98

4-{4-[-3-(3-ethoxypropionyl)thioureido]phenoxy}-2-[(pyrrolidin-1-yl)carbonylamino]pyridine The titled compound (10.2 mg, 13%) was obtained as pale yellow powder from 3-ethoxypropionic acid (50 mg), thionyl chloride (0.5 ml), potassium thiocyanate (81 mg) and 4-(4-aminophenoxy)-2-[(pyrrolidin-1-yl)carbonylamino]pyridine (50 mg).

$^1$H-NMR Spectrum (DMSO-d$_6$)° (ppm): 1.11 (3H, t, J=7.2 Hz), 1.70-1.90 (4H, m), 2.70-2.75 (2H, m), 3.20-3.70 (8H, m), 6.60 (1H, dd, J=2.4, 5.6 Hz), 7.18-7.21 (2H, m), 7.52 (1H, s), 7.72-7.75 (2H, m), 8.13 (1H, d, J=5.6 Hz), 8.72 (1H, s), 11.50 (1H, s), 12.51 (1H, s).

Example 99

Piperidine-1-carboxylic acid {4-[3-chloro-4-(3-phenylacetylthioureido)phenoxy]pyridin-2-yl}amide The titled compound (20 mg, 0.038 mmol, 25%) was obtained as colorless powder from piperidine-1-carboxylic acid [4-(4-amino-3-chlorophenoxy)pyridin-2-yl]amide (52 mg, 0.15 mmol) and a 0.1 M solution of phenylacetyl isothiocyanate in acetonitrile (7.5 ml, 0.75 mmol).

$^1$H-NMR Spectrum (DMSO-$d_6$) δ (ppm): 1.45 (4H, m), 1.54 (2H, m), 3.39 (4H, m), 3.84 (2H, s), 6.59 (1H, dd, J=2.4, 5.6 Hz), 7.19 (1H, dd, J=2.6, 8.8 Hz), 7.29 (1H, m), 7.33-7.38 (4H, m), 7.45 (2H, m), 8.06 (1H, d, J=8.8 Hz), 8.15 (1H, d, J=5.6 Hz), 9.19 (1H, s), 11.90 (1H, s), 12.38 (1H, s). ESI-MS (m/z): 524 [M+H]$^+$.

Example 100

Azetidine-1-carboxylic acid {4-[3-chloro-4-(3-phenylacetylthioureido)phenoxy]pyridin-2-yl}amide The titled compound (27 mg, 0.054 mmol, 36%) was obtained as colorless powder from azetidine-1-carboxylic acid [4-(4-amino-3-chlorophenoxy)pyridin-2-yl]amide (48 mg, 0.15 mmol) and a 0.1 M solution of phenylacetyl isothiocyanate in acetonitrile (7.5 ml, 0.75 mmol).

$^1$H-NMR Spectrum (DMSO-$d_6$) δ (ppm): 2.13 (2H, m), 3.84 (2H, s), 3.95 (4H, m), 6.60 (1H, dd, J=2.0, 6.0 Hz), 7.19 (1H, dd, J=2.8, 8.4 Hz), 7.27 (1H, m), 7.35 (4H, m), 7.45 (1H, d, J=2.8 Hz), 7.56 (1H, d, J=2.0 Hz), 8.07 (1H, d, J=8.4 Hz), 8.14 (1H, d, J=6.0 Hz), 9.13 (1H, s), 11.90 (1H, s), 12.38 (1H, s).

Example 101

1-(3-Diethylaminopropyl)-3-[4-(2-fluoro-4-{3-[(4-fluorophenyl)acetyl]thioureido}phenoxy)pyridin-2-yl]urea The titled compound (0.8 mg, 0.6%) was obtained as colorless powder from 1-[4-(2-aminopyridin-4-yloxy)-3-fluorophenyl]-3-[(4-fluorophenyl)acetyl]thiourea (100 mg), phenyl chloroformate (0.0454 ml), and N,N-diethyl-1,3-propanediamine (0.151 ml).

$^1$H-NMR Spectrum (CDCl$_3$) δ (ppm): 1.26 (6H, t, J=7.2 Hz), 1.98 (2H, m), 3.07 (6H, m), 3.31 (2H, m), 3.68 (2H, s), 6.64 (1H, dd, J=2.0, 6.6 Hz), 7.05 (2H, dd, J=8.4, 8.4 Hz), 7.15 (1H, dd, J=8.8, 8.8 Hz), 7.19-7.25 (3H, m), 7.35 (1H, m), 7.86 (1H, d, J=6.6 Hz), 7.94 (1H, dd, J=2.2, 11.4 Hz), 8.41 (1H, brs), 8.74 (1H, s), 12.04 (1H, brs), 12.46 (1H, s). ESI-MS (m/z): 571 [M+H]$^+$.

Example 102

1-Methylpiperidine-4-carboxylic acid (4-{2-fluoro-4-[3-(4-fluorophenyl)acetylthioureido]phenoxy}pyridin-2-yl)amide t-Butyl 4-(4-{2-fluoro-4-[3-(4-fluorophenyl)acetylthioureido]phenoxy}pyridin-2-ylcarbamoyl)piperidine-1-carboxylate (38.8 mg, 0.062 mmol) and trifluoroacetic acid (0.50 ml) gave a crude product of piperidine-4-carboxylic acid (4-{2-fluoro-4-[3-(4-fluorophenyl)acetylthioureido]phenoxy}pyridin-2-yl}amide (ESI-MS (m/z):526). The crude product, formalin (37% aqueous solution; 0.0231 ml), acetic acid (0.0142 ml) and sodium triacetoxyborohydride (26.3 mg) gave the titled compound (1.1 mg, 3.29%) as colorless powder.

$^1$H-NMR Spectrum (DMSO-$d_6$) δ (ppm): 1.70-1.83 (2H, m), 1.99 (2H, m), 2.67 (1H, m), 2.76 (3H, m), 2.84-2.98 (2H, m), 3.45 (2H, m), 3.83 (2H, s), 6.74 (1H, dd, J=2.4, 6.0 Hz), 7.18 (2H, m), 7.36-7.42 (3H, m), 7.53 (1H, m), 7.67 (1H, d, J=2.4 Hz), 8.00 (1H, dd, J=2.2, 12.2 Hz), 8.23 (1H, d, J=6.0 Hz), 10.76 (1H, s), 11.81 (1H, s), 12.47 (1H, s). ESI-MS (m/z): 540 [M+H]$^+$.

Example 103

Morpholine-4-carboxylic acid {4-[3-methyl-4-(3-phenylacetylthioureido)phenoxy]pyridin-2-yl}amide The titled compound (7.0 mg, 6.9%) was obtained as a pale brown solid from 2-phenylacetyl chloride (0.038 ml), potassium thiocyanate (58 mg) and morpholine-4-carboxylic acid [4-(4-amino-3-methylphenoxy)pyridin-2-yl]amide (66 mg).

$^1$H-NMR Spectrum (DMSO-$d_6$) δ (ppm): 2.19 (3H, s), 3.41 (4H, m), 3.56 (4H, m), 3.83 (2H, s), 6.57 (1H, m), 7.01 (1H, d, J=8.4 Hz), 7.10 (1H, s), 7.30 (1H, m), 7.35 (4H, m), 7.44 (1H, m), 7.65 (1H, m), 8.14 (1H, m), 9.27 (1H, m), 11.74 (1H, s), 12.04 (1H, s). ESI-MS (m/z) (neg.): 504 [M–H]$^-$.

Example 104

Pyrrolidine-1-carboxylic acid {4-[3-methyl-4-(3-phenylacetylthioureido)phenoxy]pyridin-2-yl}amide The titled compound (18 mg, 18%) was obtained as colorless powder from 2-phenylacetyl chloride (0.038 ml), potassium thiocyanate (58 mg) and pyrrolidine-1-carboxylic acid 4-(4-amino-3-methylphenoxy)pyridin-2-yl]amide (62 mg).

$^1$H-NMR Spectrum (DMSO-$d_6$) δ (ppm): 1.81 (4H, m), 2.19 (3H, s), 3.35 (4H, m), 3.83 (2H, s), 6.55 (1H, m), 7.01 (1H, m), 7.10 (1H, s), 7.28-7.36 (5H, m), 7.53 (1H, s), 7.66 (1H, m), 8.12 (1H, d, J=6.0 Hz), 8.70 (1H, brs), 11.73 (1H, s), 12.04 (1H, s).

Example 105

4-{3-Chloro-4-[3-(2-phenylacetyl)thioureido]phenoxy}-2-(cyclopropylcarbonylamino)pyridine 2-Amino-4-(4-amino-3-chlorophenoxy)pyridine (471 mg), triethylamine (0.384 ml), cyclopropanecarboxylic acid (0.22 ml) and (1H-1,2,3-benzotriazol-1-yloxy)[tri(dimethylamino)]phosphonium hexafluorophosphate (1216 mg) gave a crude product of 4-(4-amino-3-chlorophenoxy)-2-(cyclopropylcarbonylamino)pyridine (63 mg). The crude product (63 mg), 2-phenylacetyl chloride (97 mg) and potassium thiocyanate (122 mg) gave the titled compound (30.6 mg, two processes 6.4%) as white crystals.

$^1$H-NMR Spectrum (DMSO-$d_6$) δ (ppm): 0.87 (2H, m), 1.25 (2H, m), 1.99 (1H, m), 3.85 (2H, s), 6.71 (1H, m), 7.21 (1H, m), 7.22-7.40 (5H, m), 7.48 (1H, d, J=3.2 Hz), 7.72 (1H, d, J=2.0 Hz), 8.08 (1H, d, J=8.8 Hz), 8.23 (1H, d, J=5.6 Hz), 10.91 (1H, s), 11.91 (1H, s), 12.40 (1H, s).

Example 106

4-{2-Fluoro-4-[3-(2-cyclopropylacetyl)ureido]phenoxy}-2-[(pyrrolidin-1-yl)carbonylamino]pyridine The titled compound (8.5 mg, 7.7%) was obtained as white crystals from 2-cyclopropylacetamide (124 mg), oxalyl chloride (0.109 ml) and 4-(4-amino-2-fluorophenoxy)-2-[(pyrrolidin-1-yl)carbonylamino]pyridine (79 mg).
$^1$H-NMR Spectrum (DMSO-$d_6$) δ (ppm): 0.17-0.21 (2H, m), 0.47-0.52 (2H, m), 1.03 (1H, m), 1.70-1.90 (4H, m), 2.29 (2H, d, J=7.2 Hz), 3.20-3.40 (4H, m), 6.60 (1H, dd, J=2.4, 5.6 Hz), 7.30-7.48 (3H, m), 7.79 (1H, dd, J=2.4, 8.8 Hz), 8.11 (1H, d, J=5.6 Hz), 8.70 (1H, s), 10.70-10.74 (2H, m).

Example 107

4-(2-Fluoro-4-{3-[2-(4-fluorophenyl)acetyl]ureido}phenoxy)-2-[(methylamino)carbonylamino]pyridine The titled compound (9.8 mg, 5.6%) was obtained as pale yellow powder from 2-(4-fluorophenyl)acetamide (153.2 mg), oxalyl chloride (0.110 ml) and 4-(4-amino-2-fluorophenoxy)-2-[(methylamino)carbonylamino]pyridine (107 mg).
$^1$H-NMR Spectrum (DMSO-$d_6$) δ (ppm): 2.67 (3H, d, J=4.4 Hz), 3.75 (2H, s), 6.55 (1H, dd, J=2.4, 5.6 Hz), 6.91 (1H, s), 7.15-7.41 (6H, m), 7.77 (1H, dd, J=2.4, 8.8 Hz), 7.82 (1H, m), 8.06 (1H, d, J=5.6 Hz), 9.15 (1H, s), 10.58 (1H, s), 11.03 (1H, s).

Example 108

1-(3-Diethylaminopropyl)-3-{4-[2-fluoro-4-(3-phenylacetylureido)phenoxy]pyridin-2-yl}urea The titled compound (27.1 mg, 19%) was obtained as colorless powder from 1-(3-diethylaminopropyl)-3-[4-(4-amino-2-fluorophenoxy)pyridin-2-yl]urea (100 mg, 0.266 mmol) and a 0.5 M solution of phenylacetyl isocyanate in hexane (3.4 ml, Production Example 1).
$^1$H-NMR Spectrum (DMSO-$d_6$) δ (ppm): 0.93 (6H, t, J=7.0 Hz), 1.53 (2H, m), 2.35-2.46 (6H, m), 3.13 (2H, m), 3.74 (2H, s), 6.55 (1H, d, J=5.6 Hz), 6.90 (1H, s), 7.27-7.41 (7H, m), 7.78 (1H, d, J=8.8 Hz), 8.01 (1H, m), 8.05 (1H, d, J=5.6 Hz), 9.11 (1H, s), 10.61 (1H, s), 11.05 (1H, s). ESI-MS (m/z): 537 [M+H]$^+$.

Example 109

1-Methylpiperidine-4-carboxylic acid {4-[2-fluoro-4-(3-phenylacetylureido)phenoxy]pyridin-2-yl}amide t-Butyl 4-{4-[2-fluoro-4-(3-phenylacetylureido)phenoxy]pyridin-2-ylcarbamoyl}piperidine-1-carboxylate (60 mg, 0.101 mmol) and trifluoroacetic acid (0.50 ml) gave a crude product of piperidine-4-carboxylic acid {4-[2-fluoro-4-(3-phenylacetylureido)phenoxy]pyridin-2-yl}amide (ESI-MS (m/z):492). The crude product, formalin (37% aqueous solution; 0.0376 ml, 0.505 mmol), acetic acid (0.0231 ml, 0.404 mmol) and sodium triacetoxyborohydride (42.8 mg, 0.202 mmol) gave the titled compound (51.1 mg, 22.5%) as colorless powder.
$^1$H-NMR Spectrum (DMSO-$d_6$) δ (ppm): 1.49-1.61 (2H, m), 1.67 (2H, m), 1.80 (2H, m), 2.13 (3H, s), 2.39 (1H, m), 2.76 (2H, m), 3.74 (2H, s), 6.71 (1H, m), 7.25-7.42 (7H, m), 7.64 (1H, d, J=1.6 Hz), 7.78 (1H, m), 8.19 (1H, d, J=6.0 Hz), 10.51 (1H, s), 10.62 (1H, s), 11.05 (1H, s). ESI-MS (m/z): 506 [M+H]$^+$.

Example 110

Pyrrolidine-1-carboxylic acid {4-[3-methyl-4-(3-phenylacetylureido)phenoxy]pyridin-2-yl}amide The titled compound (6.8 mg, 4.5%) was obtained as colorless powder from pyrrolidine-1-carboxylic acid [4-(4-amino-3-methylphenoxy)pyridin-2-yl]amide (100 mg, 0.32 mmol) and phenylacetyl isocyanate (2.0 ml, 1.0 mmol, 0.5 M solution in hexane, Production Example 1).
$^1$H-NMR Spectrum (DMSO-$d_6$) δ (ppm): 1.80 (4H, m), 2.22 (3H, s), 3.34 (4H, m), 3.75 (2H, s), 6.54 (1H, dd, J=2.4, 5.6 Hz), 6.99 (1H, dd, J=2.4, 8.4 Hz), 7.07 (1H, d, J=2.4 Hz), 7.27-7.37 (5H, m), 7.46 (1H, d, J=2.4 Hz), 8.01 (1H, d, J=8.4 Hz), 8.08 (1H, d, J=5.6 Hz), 8.64 (1H, s), 10.48 (1H, s), 11.04 (1H, s). ESI-MS (m/z): 474 [M+H]$^+$.

Example 111

Morpholine-4-carboxylic acid {4-[2-methyl-4-(3-phenylacetylureido)phenoxy]pyridin-2-yl}amide The titled compound (10.5 mg, 8.8%) was obtained as colorless powder from morpholine-4-carboxylic acid [4-(4-amino-2-methylphenoxy)pyridin-2-yl]amide (80 mg, 0.24 mmol) and phenylacetyl isocyanate (0.5 M solution in hexane; 2.0 ml).
$^1$H-NMR Spectrum (DMSO-$d_6$) δ (ppm): 2.07 (3H, s), 3.39 (4H, m), 3.55 (4H, m), 3.73 (2H, s), 6.51 (1H, dd, J=2.4, 5.6 Hz), 7.04 (1H, d, J=8.8 Hz), 7.26-7.35 (6H, m), 7.46 (1H, d, J=9.2 Hz), 7.50 (1H, s), 8.09 (1H, d, J=5.6 Hz), 9.21 (1H, s), 10.49 (1H, s), 10.97 (1H, s). ESI-MS (m/z): 512 [M+Na]$^+$.

Example 112

Pyrrolidine-1-carboxylic acid {4-[2-methyl-4-(3-phenylacetylureido)phenoxy]pyridin-2-yl}amide The titled compound (11.3 mg, 9.32%) was obtained as colorless powder from pyrrolidine-1-carboxylic acid [4-(4-amino-2-methylphenoxy)pyridin-2-yl]amide (80 mg, 0.256 mmol) and phenylacetyl isocyanate (0.5 M solution in hexane; 2.0 ml).
$^1$H-NMR Spectrum (DMSO-$d_6$) δ (ppm): 1.80 (4H, m), 2.07 (3H, s), 3.32 (4H, m), 3.74 (2H, s), 6.49 (1H, d, J=6.0 Hz), 7.04 (1H, d, J=9.0 Hz), 7.23-7.38 (6H, m), 7.45 (1H, d, J=9.0 Hz), 7.50 (1H, s), 8.07 (1H, d, J=6.0 Hz), 8.62 (1H, s), 10.49 (1H, s), 10.96 (1H, s). ESI-MS (m/z): 496 [M+Na]$^+$.

Example 113

N-(4-Fluorobenzyl)-N'-(3-fluoro-4-{2-[(pyrrolidin-1-yl)carbonylamino]pyridin-4-yloxy}phenyl)oxalamide The titled compound (74.4 mg, 48%) was obtained as white crystals from 4-(4-amino-2-fluorophenoxy)-2-[(prrrolidin-1-yl)carbonylamino]pyridine (100 mg), triethylamine (0.132 ml), N-(4-fluorobenzyl)oxalic acid (187 mg) and (1H-1,2,3-benzotriazol-1-yloxy)[tri(dimethylamino)]phosphonium hexafluorophosphate (419 mg).
$^1$H-NMR Spectrum (DMSO-$d_6$) δ (ppm): 1.70-1.90 (4H, m), 3.20-3.40 (4H, m), 4.38 (2H, d, J=6.0 Hz), 6.61 (1H, dd, J=2.4, 5.6 Hz), 7.16 (2H, m), 7.34-7.40 (3H, m), 7.46 (1H, d, J=2.0 Hz), 7.78 (1H, d, J=8.8 Hz), 7.97 (1H, m), 8.11 (1H, d, J=5.6 Hz), 8.70 (1H, s), 9.63 (1H, t, J=6.0 Hz), 11.03 (1H, s).

Example 114

N-(4-Fluorophenyl)-N'-{4-[2-(2,2-dimethylpropionylamino)pyridin-4-yloxy]-2-fluorophenyl}malonamide The titled compound (3.7 mg, 15%) was obtained as pale yellow powder from N-(4-fluorophenyl)-N'-[4-(2-aminopyridin-4-yloxy)-2-fluorophenyl}malonamide (20.0 mg), triethylamine (0.020 ml) and pivaloyl chloride (0.009 ml).

$^1$H-NMR Spectrum (CDCl$_3$) δ (ppm): 1.29 (9H, s), 3.57 (2H, s), 6.63 (1H, m), 6.90-6.93 (2H, m), 7.02-7.07 (2H, m), 7.51-7.55 (2H, m), 7.85 (1H, d, J=2.4 Hz), 8.03 (1H, s), 8.13 (1H, d, J=5.6 Hz), 8.28 (1H, m), 8.69 (1H, brs), 8.90 (1H, brs).

Example 115

N-(4-Fluorophenyl)-N'-(4-{2-[(2-dimethylamino)acetylamino]pyridin-4-yloxy}-2-fluorophenyl)malonamide The titled compound (8.6 mg, 14%) was obtained as white powder from N-(4-fluorophenyl)-N'-[4-(2-aminopyridin-4-yloxy)-2-fluorophenyl]malonamide (50 mg), triethylamine (0.088 ml), N,N-dimethylglycine (65 mg) and (1H-1,2,3-benzotriazol-1-yloxy)[tri(dimethylamino)]phosphonium hexafluorophosphate (278 mg).

$^1$H-NMR Spectrum (CDCl$_3$) δ (ppm): 2.37 (6H, s), 3.06 (2H, s), 3.55 (2H, s), 6.63 (1H, dd, J=2.4, 5.6 Hz), 6.93 (2H, d, J=8.8 Hz), 7.05 (2H, m), 7.30-7.55 (2H, m), 7.87 (1H, m), 8.17 (1H, d, J=5.6 Hz), 8.29 (1H, m), 8.57 (1H, brs), 8.79 (1H, brs), 9.69 (1H, brs).

Example 116

(4-{3-Fluoro-4-[2-(4-fluorophenylcarbamoyl)acetylamino]phenoxy}pyridin-2-yl)carbamic acid methyl ester The titled compound (5.0 mg, 39%) was obtained as white powder from N-(4-fluorophenyl)-N'-[4-(2-aminopyridin-4-yloxy)-2-fluorophenyl]malonamide (11.3 mg), triethylamine (0.016 ml) and methyl chloroformate (0.0044 ml).

$^1$H-NMR Spectrum (DMSO-d$_6$) δ (ppm): 3.59 (2H, s), 3.63 (3H, s), 6.68 (1H, m), 7.00-7.30 (4H, m), 7.41 (1H, s), 7.50-7.70 (2H, m), 8.05 (1H, m), 8.16 (1H, m), 10.11 (1H, s), 10.26 (1H, s), 10.29 (1H, s).

Example 117

N-(4-{2-[3-(3-diethylaminopropyl)-3-methylureido]pyridin-4-yloxy}-3-fluorophenyl)-N'-(4-fluorophenyl)malonamide The titled compound (31 mg, 42%) was obtained as pale yellow powder from 1-(3-diethylaminopropyl)-3-[4-(4-amino-2-fluorophenoxy)pyridin-2-yl]-1-methylurea (50 mg), N-(4-fluorophenyl)malonic acid (76.3 mg), triethylamine (0.0539 ml), and (1H-1,2,3-benzotriazol-1-yloxy)[tri(dimethylamino)]phosphonium hexafluorophosphate (171 mg).

$^1$H-NMR Spectrum (DMSO-d$_6$) δ (ppm): 0.97 (6H, t, J=7.0 Hz), 1.68 (2H, m), 2.31-2.60 (6H, m), 2.79 (3H, s), 3.28 (2H, m), 3.49 (2H, s), 6.55 (1H, dd, J=2.4, 6.0 Hz), 7.17 (2H, dd, J=9.2, 9.2 Hz), 7.30-7.41 (3H, m), 7.63 (2H, dd, J=5.2, 9.2 Hz), 7.82 (1H, dd, J=2.4, 8.8 Hz), 8.07 (1H, d, J=6.0 Hz), 10.21 (1H, brs), 10.26 (1H, s), 10.50 (1H, s).

Example 118

N-(4-{2-[3-(3-Diethylaminopropyl)ureido]pyridin-4-yloxy}-3-fluorophenyl)-N'-(4-fluorophenyl)malonamide The titled compound (31 mg, 42%) was obtained as pale yellow powder from 1-(3-diethylaminopropyl)-3-[4-(4-amino-2-fluorophenoxy)pyridin-2-yl] urea (50 mg), N-(4-fluorophenyl)malonic acid (78.7 mg), triethylamine (0.2 ml) and (1H-1,2,3-benzotriazol-1-yloxy)[tri(dimethylamino)]phosphonium hexafluorophosphate (176 mg).

$^1$H-NMR Spectrum (DMSO-d$_6$) δ (ppm): 0.93 (6H, t, J=6.8 Hz), 1.53 (2H, m), 2.37 (2H, m), 2.43 (4H, q, J=6.8 Hz), 3.13 (2H, m), 3.49 (2H, s), 6.56 (1H, dd, J=2.4, 5.8 Hz), 6.89 (1H, d, J=2.4 Hz), 7.17 (2H, dd, J=8.8, 8.8 Hz), 7.31-7.41 (2H, m), 7.63 (2H, dd, J=5.0, 8.8 Hz), 7.83 (1H, dd, J=2.4, 13.0 Hz), 8.01 (1H, m), 8.05 (1H, d, J=5.8 Hz), 9.10 (1H, s), 10.26 (1H, s), 10.51 (1H, s). ESI-MS (m/z): 555 [M+H]$^+$.

Example 119

N-(4-{2-[3-(3-Dimethylaminopropyl)-3-methylureido]pyridin-4-yloxy}-2-methylphenyl)-N'-(4-fluorophenyl)malonamide The titled compound (7.4 mg, 8.6%) was obtained as colorless powder from N-[4-(2-aminopyridin-4-yloxy)-2-methylphenyl]-N'-(4-fluorophenyl)malonamide (60 mg), triethylamine (0.042 ml), phenyl chloroformate (0.038 ml) and N,N-diethyl-N'-methylpropane-1,3-diamine (93.1 mg).

$^1$H-NMR Spectrum (DMSO-d$_6$) δ (ppm): 0.97 (6H, t, J=7.0 Hz), 1.68 (2H, m), 2.26 (3H, s), 2.36 (2H, m), 2.53 (2H, m), 2.80 (3H, s), 3.31 (4H, m), 3.52 (2H, s), 6.50 (1H, dd, J=2.4, 5.6 Hz), 6.96 (1H, d, J=2.4, 8.8 Hz), 7.04 (1H, d, J=2.4 Hz), 7.17 (2H, dd, J=9.2, 9.2 Hz), 7.35 (1H, d, J=2.4 Hz), 7.57 (1H, d, J=8.8 Hz), 7.64 (2H, dd, J=5.2, 9.2 Hz), 8.06 (1H, d, J=5.6 Hz), 9.64 (1H, s), 10.02 (1H, brs), 10.27 (1H, s). ESI-MS (m/z): 565 [M+H]$^+$.

Example 120

N-[4-(2-Acetaminopyridin-4-yloxy)-2-methylphenyl]-N'-(4-fluorophenyl)malonamide

The titled compound (33.7 mg, 51%) was obtained as colorless crystals from N-[4-(2-aminopyridin-4-yloxy)-2-methylphenyl]-N'-(4-fluorophenyl)malonamide (60 mg), triethylamine (0.027 ml) and acetyl chloride (0.053 ml).

$^1$H-NMR Spectrum (DMSO-d$_6$) δ (ppm): 2.04 (3H, s), 2.26 (3H, s), 3.53 (2H, s), 6.64 (1H, d, J=5.6 Hz), 6.99 (1H, d, J=8.2 Hz), 7.07 (1H, s), 7.17 (2H, dd, J=8.6, 8.6 Hz), 7.58 (1H, d, J=8.2 Hz), 7.62-7.66 (3H, m), 8.17 (1H, d, J=5.6 Hz), 9.65 (1H, s), 10.27 (1H, s), 10.53 (1H, s). ESI-MS (m/z): 459 [M+Na]$^+$.

Example 121

N-(4-Fluorophenyl)-N'-(3-methyl-4-{2-[(morpholine-4-carbonyl)amino]pyridin-4-yloxy}phenyl)malonamide The titled compound (14 mg, 18%) was obtained as colorless powder from morpholine-4-carboxylic acid [4-(4-amino-2-methylphenoxy)pyridin-2-yl]amide (50 mg), N-(4-fluorophenyl)malonic acid (90 mg) and (1H-1,2,3-benzotriazol-1-yloxy)[tri(dimethylamino)]phosphonium hexafluorophosphate (202 mg).

$^1$H-NMR Spectrum (DMSO-$d_6$) δ (ppm): 2.08 (3H, s), 3.39 (4H, m), 3.47 (2H, s), 3.53 (4H, m), 6.51 (1H, m), 7.05 (1H, d, J=9.2 Hz), 7.16 (2H, dd, J=9.0, 9.0 Hz), 7.26 (1H, s), 7.51 (1H, m), 7.61-7.65 (3H, m), 8.09 (1H, d, J=6.0 Hz), 9.20 (1H, s), 10.23 (2H, s). ESI-MS (m/z): 508 [M+H]$^+$.

Example 122

N-(4-Fluorophenyl)-N'-(3-methyl-4-{2-[(pyrrolidine-1-carbonyl)amino]pyridin-4-yloxy}phenyl)malonamide The titled compound (27 mg, 34%) was obtained as colorless powder from pyrrolidine-1-carboxylic acid [4-(4-amino-2-methylphenoxy)pyridin-2-yl]amide (50 mg), N-(4-fluorophenyl)malonic acid (95 mg) and (1H-1,2,3-benzotriazol-1-yloxy)[tri(dimethylamino)]phosphonium hexafluorophosphate (212 mg).

$^1$H-NMR Spectrum (DMSO-$d_6$) δ (ppm): 1.80 (4H, m), 2.08 (3H, s), 3.22 (4H, m), 3.47 (2H, s), 6.50 (1H, d, J=8.8 Hz), 7.04 (1H, dd, J=8.8 Hz), 7.16 (1H, dd, J=8.8, 8.8 Hz), 7.36 (1H, d, J=2.4 Hz), 7.51 (2H, dd, J=2.4, 8.8 Hz), 7.60-7.65 (3H, m), 8.07 (1H, d, J=6.0 Hz), 8.61 (1H, s), 10.23 (2H, s). ESI-MS (m/z): 492 [M+H]$^+$.

Example 123

N-(4-{2-[3-(3-Diethylaminoethyl)ureido]pyridin-4-yloxy}-2-chlorophenyl)-N'-(4-fluorophenyl) malonamide The titled compound (79.7 mg, 56.3%) was obtained as pale yellow powder from 1-[4-(4-amino-3-chlorophenoxy)pyridin-2-yl]-3-(2-diethylaminoethyl)urea (95.9 mg), N-(4-fluorophenyl)malonic acid (150 mg), triethylamine (0.106 ml) and (1H-1,2,3-benzotriazol-1-yloxy)[tri(dimethylamino)]phosphonium hexafluorophosphate (337 mg).

$^1$H-NMR Spectrum (DMSO-$d_6$) δ (ppm): 1.00 (6H, t, J=7.2 Hz), 2.49-2.52 (6H, m), 3.19-3.21 (2H, m), 3.61 (2H, m), 6.56 (1H, dd, J=2.4, 5.6 Hz), 6.91 (1H, s), 7.10-7.25 (3H, m), 7.43 (1H, d, J=2.4 Hz), 7.63 (2H, dd, J=5, 7 Hz), 7.99-8.01 (1H, m), 8.07 (1H, d, J=6.0 Hz), 8.20 (1H, m), 9.24 (1H, brs), 10.05 (1H, s), 10.30 (1H, s).

Example 124

N-(2-Chloro-4-{2-[3-(3-morpholin-4-ylpropyl)ureido]pyridin-4-yloxy}phenyl)-N'-(4-fluorophenyl)malonamide The titled compound (90.1 mg, 62.4%) was obtained as white powder from 1-[4-(4-amino-3-chlorophenoxy)pyridin-2-yl]-3-(3-morpholin-4-ylpropyl)urea (100 mg), N-(4-fluorophenyl)malonic acid (146 mg), triethylamine (0.103 ml) and (1H-1,2,3-benzotriazol-1-yloxy)[tri(dimethylamino)]phosphonium hexafluorophosphate (328 mg).

$^1$H-NMR Spectrum (DMSO-$d_6$) δ (ppm): 1.59 (2H, m), 2.22-2.40 (6H, m), 3.15 (2H, m), 3.56 (4H, m), 3.62 (2H, m), 6.57 (1H, dd, J=2.0, 6.0 Hz), 6.94 (1H, m), 7.10-7.25 (3H, m), 7.43 (1H, d, J=2.8 Hz), 7.55-7.70 (2H, m), 7.99-8.06 (2H, m), 8.08 (1H, d, J=6.0 Hz), 9.13 (1H, s), 10.05 (1H, brs), 10.30 (1H, brs).

Example 125

N-[2-Chloro-4-(2-{3-[3-(4-methylpiperazin-1-yl)propyl]ureido}pyridin-4-yloxy)phenyl]-N'-(4-fluorophenyl)malonamide The titled compound (79.7 mg, 55.8%) was obtained as white powder from 1-[4-(4-amino-3-chlorophenoxy)pyridin-2-yl]-3-[3-(4-methylpiperazin-1-yl)propyl]urea (100 mg), N-(4-fluorophenyl)malonic acid (151 mg), triethylamine (0.107 ml) and (1H-1,2,3-benzotriazol-1-yloxy)[tri(dimethylamino)]phosphonium hexafluorophosphate (339 mg).

$^1$H-NMR Spectrum (DMSO-$d_6$) δ (ppm): 1.58 (2H, m), 2.18 (3H, m), 2.22-2.48 (10H, m), 3.14 (2H, m), 3.61 (2H, m), 6.57 (1H, dd, J=2.4, 6.0 Hz), 6.94 (1H, m), 7.10-7.25 (3H, m), 7.43 (1H, d, J=2.0 Hz), 7.60-7.70 (2H, m), 8.01 (2H, m), 8.08 (1H, d, J=6.0 Hz), 9.12 (1H, s), 10.06 (1H, m), 10.30 (1H, brs).

Example 126

N-[2-Chloro-4-(2-{3-[3-(diethylamino)propyl]ureido}pyridin-4-yloxy)phenyl]-N'-(4-fluorophenyl)malonamide The titled compound (70.9 mg, 48.7%) was obtained as white powder from 1-[4-(4-amino-3-chlorophenoxy)pyridin-2-yl]-3-(3-(diethylaminopropyl)urea (100 mg), N-(4-fluorophenyl)malonic acid (151 mg), triethylamine (0.107 ml) and (1H-1,2,3-benzotriazol-1-yloxy)[tri(dimethylamino)]phosphonium hexafluorophosphate (339 mg).

$^1$H-NMR Spectrum (DMSO-$d_6$) δ (ppm): 0.94 (6H, m), 1.55 (2H, m), 2.46 (3H, m), 3.15 (2H, m), 3.23 (3H, m), 3.62 (2H, m), 6.57 (1H, dd, J=2, 5.6 Hz), 6.92 (1H, m), 7.15-7.20 (3H, m), 7.43 (1H, d, J=2.4 Hz), 7.60-7.65 (2H, dd, J=4.8, 8.8 Hz), 8.00 (1H, m), 8.07 (2H, m), 9.14 (1H, s), 10.06 (1H, brs), 10.31 (1H, brs).

Example 127

N-(3-Fluoro-4-{2-[(pyrrolidine-1-carbonyl)amino]pyridin-4-yloxy}phenyl)-N'-(pyridin-2-yl)malonamide The titled compound (11.9 mg, 14.3%) was obtained as a pale brown solid from N-(3-fluoro-4-{2-[(pyrrolidine-1-carbonyl)amino]pyridin-4-yloxy}phenyl)malonic acid (70.0 mg), 2-aminopyridine (16.4 mg), triethylamine (0.0363 ml) and (1H-1,2,3-benzotriazol-1-yloxy)[tri(dimethylamino)]phosphonium hexafluorophosphate (116.0 mg).

$^1$H-NMR Spectrum (DMSO-$d_6$) δ (ppm): 1.80 (4H, m), 3.31 (4H, m), 3.61 (2H, m), 6.60 (1H, m), 7.12 (1H, m), 7.35 (2H, m), 7.46 (1H, s), 7.81 (2H, m), 8.10 (2H, m), 8.33 (1H, m), 8.70 (1H, s), 10.49 (1H, s), 10.68 (1H, s).

Example 128

N-(3-Fluoro-4-{2-[(pyrrolidine-1-carbonyl)amino]pyridin-4-yloxy}phenyl)-N'-(thiophen-2-yl)malonamide The titled compound (50.1 mg, 59.5%) was obtained as white powder from N-(3-fluoro-4-{2-[(pyrrolidine-1-carbonyl)amino]pyridin-4-yloxy}phenyl)malonic acid (70.0 mg), thiophen-2-ylamine (69.4 mg), triethylamine (0.097 ml) and (1H-1,2,3-benzotriazol-1-yloxy)[tri(dimethylamino)]phosphonium hexafluorophosphate (77.0 mg).

$^1$H-NMR Spectrum (DMSO-$d_6$) δ (ppm): 1.80 (4H, m), 3.25-3.42 (4H, m), 3.52 (2H, m), 6.60 (1H, dd, J=2.4, 5.6 Hz), 6.71 (1H, dd, J=1.2, 3.6 Hz), 6.86 (1H, dd, J=3.6, 5.6 Hz), 6.97 (1H, dd, J=1.2, 5.6 Hz), 7.19 (2H, m), 7.47 (1H, d, J=2.0 Hz), 7.82 (1H, dd, J=2.0, 13.2 Hz), 8.11 (1H, d, J=6.0 Hz), 8.70 (1H, s), 10.54 (1H, brs), 11.40 (1H, brs).

Example 129

N-(3-Fluoro-4-{2-[(pyrrolidine-1-carbonyl)amino]pyridin-4-yloxy}phenyl)-N'-methyl-N'-phenylmalonamide The titled compound (45.4 mg, 53.1%) was obtained as white powder from N-(3-fluoro-4-{2-[(pyrrolidine-1-carbonyl)amino]pyridin-4-yloxy}phenyl)malonic acid (70.0 mg), methylphenylamine (0.0283 ml), triethylamine (0.0243 ml) and (1H-1,2,3-benzotriazol-1-yloxy)[tri(dimethylamino)]phosphonium hexafluorophosphate (77.0 mg).

$^1$H-NMR Spectrum (CDCl$_3$) δ (ppm): 1.95 (4H, m), 3.22 (2H, s), 3.35 (3H, s), 3.44 (4H, m), 6.53 (1H, dd, J=2.0, 6.0 Hz), 7.12 (2H, m), 7.16-7.30 (3H, m), 7.36-7.60 (3H, m), 7.68 (1H, d, J=2.0 Hz), 7.73 (1H, dd, J=2.4, 12 Hz), 8.03 (1H, d, J=6.0 Hz), 10.39 (1H, brs).

Example 130

N-{4-[6-(3,3-Dimethylureido)pyrimidin-4-yloxy]-3-fluorophenyl}-N'-(4-fluorophenyl)malonamide The titled compound (33.2 mg, 74.0%) was obtained as a white solid from N-{4-[6-(3,3-dimethylureido)pyrimidin-4-yloxy]-3-fluorophenyl}malonic acid (36.0 mg), 4-fluorophenylamine (0.014 ml), triethylamine (0.013 ml) and (1H-1,2,3-benzotriazol-1-yloxy)[tri(dimethylamino)]phosphonium hexafluorophosphate (42.2 mg).

$^1$H-NMR Spectrum (CDCl$_3$) δ (ppm): 3.05 (6H, s), 3.53 (2H, s), 7.04 (2H, m), 7.17 (1H, m), 7.23 (1H, m), 7.38 (1H, brs), 7.46-7.56 (2H, m), 7.63 (1H, m), 7.70 (1H, dd, J=2.4, 12.0 Hz), 8.35 (1H, m), 8.82 (1H, brs), 9.25 (1H, brs).

Example 131

N-(4-Fluorophenyl)-N'-(3-fluoro-4-{6-[(pyrrolidine-1-carbonyl)amino]pyrimidin-4-yloxy}phenyl)malonamide The titled compound (68.0 mg, 86.7%) was obtained as a pale brown solid from 4-(4-amino-2-fluorophenoxy)-6-[(pyrrolidin-1-yl)carbonylamino]pyridine (50 mg), N-(4-fluorophenyl)malonic acid (93.5 mg), triethylamine (0.066 ml) and (1H-1,2,3-benzotriazol-1-yloxy)[tri(dimethylamino)]phosphonium hexafluorophosphate (210 mg).

$^1$H-NMR Spectrum (DMSO-$d_6$) δ (ppm): 1.83 (4H, m), 3.32-3.48 (4H, m), 3.49 (2H, s), 7.17 (2H, m), 7.34 (2H, m), 7.45 (1H, s), 7.63 (2H, dd, J=5, 9 Hz), 7.77 (1H, m), 8.39 (1H, s), 9.39 (1H, brs), 10.26 (1H, brs), 10.47 (1H, brs).

Example 132

N-(2,4-Difluorophenyl)-N'-(3-fluoro-4-{6-[(pyrrolidine-1-carbonyl)amino]pyrimidin-4-yloxy}phenyl)malonamide The titled compound (74.3 mg, 91.4%) was obtained as a pale brown solid from 4-(4-amino-2-fluorophenoxy)-6-[(pyrrolidin-1-yl)carbonylamino]pyridine (50 mg), N-(2,4-difluorophenyl)malonic acid (102 mg), triethylamine (0.066 ml) and (1H-1,2,3-benzotriazol-1-yloxy) [tri (dimethylamino)]phosphonium hexafluorophosphate (210 mg).

$^1$H-NMR Spectrum (DMSO-$d_6$) δ (ppm): 1.83 (4H, brs), 3.41 (4H, brs), 3.58 (2H, s), 7.08 (1H, m), 7.34 (3H, m), 7.46 (1H, s), 7.76 (1H, m), 7.93 (1H, m), 8.40 (1H, s), 9.40 (1H, s), 10.04 (1H, brs), 10.47 (1H, brs).

Example 133

N-(2,4-Difluorophenyl)-N'-{4-[6-(3,3-dimethylureido) pyrimidin-4-yloxy]-3-fluorophenyl}malonamide The titled compound (5.4 mg, 10.7%) was obtained as a pale yellow solid from 1-[4-(4-amino-2-fluorophenoxy)pyrimidin-6-yl]-3-dimethylurea (30 mg), N-(2,4-difluorophenyl)malonic acid (66.5 mg), triethylamine (0.043 ml) and (1H-1,2,3-benzotriazol-1-yloxy) [tri (dimethylamino)] phosphonium hexafluorophosphate (137 mg).

$^1$H-NMR Spectrum (DMSO-$d_6$) δ (ppm): 2.94 (6H, s), 3.58 (2H, s), 7.09 (1H, m), 7.25-7.42 (4H, m), 7.76 (1H, m), 7.92 (1H, m), 8.40 (1H, m), 9.57 (1H, brs), 10.04 (1H, brs), 10.47 (1H, brs).

Example 134

N-(4-Fluorophenyl)-N'-(3-fluoro-4-(6-{[4-(pyrrolidin-1-yl)piperidine-1-carbonyl]amino}pyrimidin-4-yloxy)phenyl]malonamide The titled compound (31.0 mg, 71.4%) was obtained as a pale yellow solid from 4-(pyrrolidin-1-yl)piperidine-1-carboxylic acid [6-(4-amino-2-fluorophenoxy)pyrimidin-4-yl]amide (30 mg), N-(4-fluorophenyl)malonic acid (30 mg), triethylamine (0.021 ml) and (1H-1,2,3-benzotriazol-1-yloxy)[tri(dimethylamino)]phosphonium hexafluorophosphate (66 mg).

$^1$H-NMR Spectrum (CDCl$_3$) δ (ppm): 1.45-1.60 (2H, m), 1.80 (4H, m), 1.96 (2H, m), 2.18-2.28 (1H, m), 2.58 (4H, m), 3.04 (2H, m), 3.53 (2H, s), 4.02 (2H, m), 7.05 (2H, m), 7.16 (1H, m), 7.20 (1H, m), 7.43 (1H, brs), 7.51 (2H, m), 7.58 (1H, s), 7.70 (1H, dd, J=2, 12 Hz), 8.34 (1H, m), 8.76 (1H, brs), 9.20 (1H, brs).

Example 135

N-(4-{6-[([1,4']Bipiperidinyl-1'-carbonyl)amino]pyrimidin-4-yloxy}-3-fluorophenyl)-N'-(4-fluorophenyl)malonamide

[1,4']Bipiperidinyl-1'-carboxylic acid [6-(2-fluoro-4-nitrophenoxy)pyrimidin-4-yl]amide (43 mg) and 10% palladium carbon (21 mg) gave a crude product of [1,4']bipiperidinyl-1'-carboxylic acid [6-(4-amino-2-fluorophenoxy) pyrimidin-4-yl]amide. The crude product, N-(4- fluorophenyl)malonic acid (38 mg), triethylamine (0.027 ml) and (1H-1,2,3-benzotriazol-1-yloxy)[tri(dimethylamino)]phosphonium hexafluorophosphate (85 mg) gave the titled compound (28.8 mg, 50.2%) as a white solid.

$^1$H-NMR Spectrum (CDCl$_3$) δ (ppm): 0.89 (2H, m), 1.26 (2H, m), 1.38-1.78 (5H, m), 1.90 (2H, m), 2.44-2.62 (4H, m), 2.92 (2H, m), 3.53 (2H, s), 4.14 (2H, m), 7.05 (2H, m), 7.17 (1H, m), 7.23 (1H, m), 7.44 (1H, brs), 7.51 (2H, m), 7.60 (1H, s), 7.70 (1H, m), 8.34 (1H, brs), 8.72 (1H, brs), 9.18 (1H, brs). ESI-MS (m/z): 594 [M+H]$^+$.

Example 136

N-(4-Fluorophenyl)-N'-[4-(2-{[4-(pyrrolidin-1-yl)piperidine-1-carbonyl]amino}pyridin-4-yloxy)phenyl]malonamide The titled compound (22.6 mg, 51.3%) was obtained as a white solid from 4-(4-aminophenoxy)-2-{[4-(pyrrolidin-1-yl)piperidin-1-yl]carbonylamino}pyridine (30 mg), N-(4-fluorophenyl)malonic acid (31 mg), triethylamine (0.016 ml) and (1H-1,2,3-benzotriazol-1-yloxy)[tri(dimethylamino)]phosphonium hexafluorophosphate (69 mg).

$^1$H-NMR Spectrum (CDCl$_3$) δ (ppm): 1.50 (2H, m), 1.79 (4H, m), 1.92 (2H, m), 2.20 (1H, m), 2.56 (4H, m), 2.96 (2H, m), 3.51 (2H, m), 3.98 (2H, m), 6.58 (1H, m), 6.96-7.10 (4H, m), 7.33 (1H, m), 7.44-7.66 (5H, m), 8.04 (1H, d, J=6.0 Hz), 8.98-9.18 (2H, m)

Example 137

N-(4-{2-[([1,4']Bipiperidinyl-1'-carbonyl)amino]pyridin-4-yloxy}phenyl)-N'-(4-fluorophenyl)malonamide The titled compound (37.9 mg, 86.9%) was obtained as a white solid from 4-(4-aminophenoxy)-2-{[4-(piperidin-1-yl)piperidin-1-yl]carbonylamino}pyridine (30 mg), N-(4-fluorophenyl)malonic acid (30 mg), triethylamine (0.021 ml) and (1H-1,2,3-benzotriazol-1-yloxy)[tri(dimethylamino)]phosphonium hexafluorophosphate (67 mg).

$^1$H-NMR Spectrum (CDCl$_3$) δ (ppm):0.88 (2H, m), 1.27 (2H, m), 1.35-1.75 (5H, m), 1.85 (2H, m), 2.36-2.54 (4H, m), 2.85 (2H, m), 3.44-3.54 (2H, m), 4.09 (2H, m), 6.56 (1H, dd, J=2.4, 6.0 Hz),6.94-7.10 (4H, m), 7.30 (1H, m), 7.45-7.64 (5H, m), 8.04 (1H, d, J=6.0 Hz), 9.01 (2H, brs).

Example 138

N-(4-{2-[3-(3-Diethylaminopropyl)-3-methylureido]pyridin-4-yloxy}phenyl)-N'-(4-fluorophenyl)malonamide

[4-(4-Nitrophenoxy)pyridin-2-yl]carbamic acid phenyl ester (60 mg) and N,N-diethyl-N'-methylpropane-1,3-diamine (98.6 mg) gave a crude product of 3-[4-(4-nitrophenoxy)pyridin-2-yl]-1-(3-diethylaminopropyl)-1-methylurea. The crude product (69 mg) was subjected to catalytic hydrogenation using 10% palladium carbon (72 mg) to give a crude product of 3-[4-(4-aminophenoxy)pyridin-2-yl]-1-(3-diethylaminopropyl)-1-methylurea. The compound (63.5 mg), N-(4-fluorophenyl)malonic acid (67 mg), triethylamine (0.048 ml) and (1H-1,2,3-benzotriazol-1-yloxy)[tri(dimethylamino)]phosphonium hexafluorophosphate (151 mg) gave the titled compound (37.9 mg, 86.9%) as a white solid.

$^1$H-NMR Spectrum (CDCl$_3$) δ (ppm): 1.06 (6H, t, J=7.2 Hz), 1.78 (2H, m), 2.51 (2H, m), 2.60-2.73 (4H, m), 2.86 (3H, s), 3.38 (2H, t, J=6.4 Hz), 3.48 (2H, brs), 6.55 (1H, m), 6.98 (2H, m), 7.04 (2H, m), 7.43 (1H, brs), 7.46-7.62 (4H, m), 7.71 (1H, dd, J=3.2, 5.6 Hz), 8.05 (1H, d, J=5.6 Hz), 9.21 (2H, brs).

Example 139

N-{4-[6-(3,3-Dimethylureido)pyrimidin-4-yloxy]-3-fluorophenyl}-N'-(4-fluorophenyl)malonamide The titled compound (33.2 mg, 74.0%) was obtained as a white solid from N-{4-[6-(3,3-dimethylureido)pyrimidin-4-yloxy]-3-fluorophenyl}malonic acid (36.0 mg), 4-fluorophenylamine (0.014 ml), triethylamine (0.013 ml) and (1H-1,2,3-benzotriazol-1-yloxy)[tri(dimethylamino)]phosphonium hexafluorophosphate (42.2 mg).

$^1$H-NMR Spectrum (CDCl$_3$) δ (ppm): 3.05 (6H, s), 3.53 (2H, s), 7.04 (2H, m), 7.17 (1H, m), 7.23 (1H, m), 7.38 (1H, brs), 7.46-7.56 (2H, m), 7.63 (1H, m), 7.70 (1H, dd, J=2.4, 12.0 Hz), 8.35 (1H, m), 8.82 (1H, brs), 9.25 (1H, brs).

Example 140

1-(4-{3-Chloro-4-[3-(2-phenylacetyl)thioureido]phenoxy}pyridin-2-yl)-3-diethylurea $^1$H-NMR Spectrum (DMSO-d$_6$) δ (ppm): 1.05 (6H, t, J=7.2 Hz), 3.20-3.60 (4H, m), 3.84 (2H, s), 6.61 (1H, dd, J=2.0, 5.6 Hz), 7.20 (1H, dd, J=2.8, 8.8 Hz), 7.20-7.40 (5H, m), 7.45 (1H, d, J=2.4 Hz), 7.53 (1H, s), 8.06 (1H, d, J=8.8 Hz), 8.16 (1H, d, J=5.6 Hz), 8.77 (1H, s), 11.90 (1H, s), 12.37 (1H, s).

Example 141

4-{3-Chloro-4-[3-(2-phenylacetyl)thioureido]phenoxy}-2-[(4-methylpiperazin-1-yl)carbonylamino]pyridine $^1$H-NMR Spectrum (CDCl$_3$) δ (ppm): 2.32 (3H, s), 2.40-2.45 (4H, m), 3.49-3.54 (4H, m), 3.81 (2H, s), 6.48 (1H, dd, J=2.4, 5.6 Hz), 6.99-7.07 (2H, m), 7.20-7.60 (7H, m), 7.68 (1H, d, J=2.4 Hz), 8.07 (1H, d, J=5.6 Hz), 8.41 (1H, d, J=8.8 Hz), 8.51 (1H, brs). ESI-MS (m/z): 561 [M+Na]$^+$

Example 142

4-{3-Chloro-4-[3-(2-phenylacetyl)thioureido]phenoxy}-2-[(1-methylpiperidin-4-yl)carbonylamino]pyridine $^1$H-NMR Spectrum (DMSO-d$_6$) δ (ppm): 1.50-1.90 (6H, m), 2.13 (3H, s), 2.41 (1H, m), 2.75-2.79 (2H, m), 3.85 (2H, s), 6.71 (1H, m), 7.20-7.40 (6H, m), 7.48 (1H, m), 7.74 (1H, m), 8.07 (1H, d, J=8.8 Hz), 8.23 (1H, d, J=5.6 Hz), 10.54 (1H, s), 11.90 (1H, brs), 12.39 (1H, brs).

Example 143

4-{3-Chloro-4-[3-(2-phenylacetyl)thioureido]phenoxy}-2-(ethoxycarbonylamino)pyridine $^1$H-NMR Spectrum (DMSO-d$_6$) δ (ppm): 1.20 (3H, t, J=7.2 Hz), 3.84 (2H, s), 4.10 (2H, q, J=7.2 Hz), 6.66 (1H, dd, J=2.0, 5.6 Hz), 7.22 (1H, dd, J=2.4, 8.8 Hz), 7.28-7.40 (5H, m), 7.44 (1H, d, J=2.0 Hz), 7.48 (1H, d, J=2.4 Hz), 8.08 (1H, d, J=8.8 Hz), 8.18 (1H, d, J=5.6 Hz), 10.23 (1H, s), 11.91 (1H, s), 12.39 (1H, s).

Example 144

4-{3-Methoxy-4-[3-(2-phenylacetyl)thioureido]phenoxy}-2-[(pyrrolidin-1-yl)carbonylamino]pyridine ¹H-NMR Spectrum (DMSO-d$_6$) δ (ppm): 1.70-1.90 (4H, m), 3.20-3.40 (4H, m), 3.75 (2H, s), 3.83 (3H, s), 6.56 (1H, dd, J=2.4, 6.0 Hz), 6.67 (1H, dd, J=2.4, 8.8 Hz), 6.90 (1H, d, J=2.4 Hz), 7.20-7.40 (6H, m), 7.49 (1H, d, J=2.4 Hz), 7.95 (1H, d, J=8.8 Hz), 8.09 (1H, m), 8.64 (1H, s), 9.35 (1H, s).

Example 145

4-{3-Methoxy-4-[3-(2-phenylacetyl)thioureido]phenoxy}-2-[(morpholin-4-yl)carbonylamino]pyridine ¹H-NMR Spectrum (CDCl$_3$) δ (ppm): 3.40-3.50 (4H, m), 3.70 (3H, s), 3.65-3.75 (4H, m), 3.77 (2H, s), 6.49 (1H, dd, J=2.4, 6.0 Hz), 6.58 (1H, d, J=2.4 Hz), 6.67 (1H, dd, J=2.0, 8.8 Hz), 7.23 (1H, brs), 7.30-7.45 (6H, m), 7.59 (1H, brs), 7.70 (1H, brs), 8.01 (1H, d, J=6.0 Hz), 8.36 (1H, d, J=8.8 Hz).

Example 146

4-{4-[3-(2-Phenylacetyl)thioureido]phenyl}amino-6-[(pyrrolidin-1-yl)carbonylamino]pyrimidine ¹H-NMR Spectrum (DMSO-d$_6$) δ (ppm): 1.80-2.00 (4H, m), 3.00-3.60 (4H, m), 3.81 (2H, s), 7.20-7.50 (6H, m), 7.51 (2H, d, J=8.8 Hz), 7.64 (2H, d, J=8.8 Hz), 8.32 (1H, s), 8.74 (1H, s), 9.55 (1H, s), 11.65 (1H, s), 10.31 (1H, s).

Example 147

2-[(Dimethylamino)carbonylamino]-4-{2-fluoro-3-[2-(tert-butyl)acetylthio]ureidophenoxy}pyridine ¹H-NMR Spectrum (DMSO-d$_6$) δ (ppm): 1.04 (9H, s), 2.38 (2H, s), 2.90 (6H, s), 6.61 (1H, dd, J=2.4, 6.0 Hz), 7.36-7.43 (2H, m), 7.54 (1H, m), 8.05 (1H, dd, J=2.4, 8.8 Hz), 8.13 (1H, d, J=6.0 Hz), 8.94 (1H, s), 11.47 (1H, s), 12.72 (1H, s).

Example 148

1-{4-[3-Chloro-4-(3-phenylacetylthioureido)phenoxy]pyridin-2-yl}-3-[3-(morpholin-4-yl)propyl]urea ¹H-NMR Spectrum (DMSO-d$_6$) δ (ppm): 1.59 (2H, m), 2.27-2.36 (6H, m), 3.16 (2H, m), 3.56 (4H, m), 3.85 (2H, s), 6.56 (1H, d, J=5.6 Hz), 7.00 (1H, s), 7.21 (1H, d, J=9.2 Hz), 7.29 (1H, m), 7.35 (4H, m), 7.47 (1H, s), 8.02 (1H, m), 8.09 (2H, m), 9.17 (1H, s), 11.91 (1H, brs), 12.39 (1H, brs).

Example 149

1-{4-[3-Chloro-4-(3-phenylacetylthioureido)phenoxy]pyridin-2-yl}-3-[3-(1-methylpiperazin-4-yl)propyl]urea ¹H-NMR Spectrum (DMSO-d$_6$) δ (ppm): 1.57 (2H, m), 2.13 (3H, s), 2.29 (10H, m), 3.14 (2H, m), 3.85 (2H, s), 6.56 (1H, dd, J=2.4, 5.6 Hz), 6.99 (1H, d, J=2.4 Hz), 7.20 (1H, dd, J=2.8, 8.8 Hz), 7.29 (1H, m), 7.35 (4H, m), 7.47 (1H, d, J=2.8 Hz), 8.01 (1H, m), 8.09 (1H, d, J=8.8 Hz), 8.10 (1H, d, J=5.6 Hz), 9.16 (1H, s), 11.91 (1H, brs), 12.39 (1H, brs). ESI-MS (m/z): 596 [M+H]⁺.

Example 150

1-{4-[3-Chloro-4-(3-phenylacetylthioureido)phenoxy]pyridin-2-yl}-3-(3-diethylaminopropyl)urea ¹H-NMR Spectrum (DMSO-d$_6$) δ (ppm): 0.94 (6H, t, J=7.0 Hz), 1.55 (2H, m), 2.44 (6H, m), 3.15 (2H, m), 3.85 (2H, s), 6.56 (1H, dd, J=2.4, 5.6 Hz), 6.98 (1H, d, J=2.4 Hz), 7.21 (1H, dd, J=2.8, 8.8 Hz), 7.30 (1H, m), 7.36 (4H, m), 7.47 (1H, d, J=2.8 Hz), 8.09 (3H, m), 9.19 (1H, s), 11.91 (1H, brs), 12.39 (1H, brs). ESI-MS (m/z): 569 [M+H]⁺.

Example 151

3-[4-(4-{3-[2-(4-Fluorophenyl)acetyl]thioureido}phenoxy)pyridin-2-yl]-1,1-dimethylurea ¹H-NMR Spectrum (CDCl$_3$) δ (ppm): 3.00 (6H, s), 3.71 (2H, s), 6.51 (1H, dd, J=2.0, 5.6 Hz), 7.03 (2H, m), 7.06-7.24 (5H, m), 7.32 (2H, m), 7.47 (2H, m), 7.60 (1H, d, J=2.0 Hz), 8.02 (1H, d, J=5.6 Hz).

Example 152

1-(4-{3-Chloro-4-[3-(2-phenylacetyl)thioureido]phenoxy}pyridin-2-yl)-3-ethylurea ¹H-NMR Spectrum (DMSO-d$_6$) δ (ppm): 1.04 (3H, t, J=7.2 Hz), 3.12 (2H, m), 3.82 (2H, s), 6.54 (1H, dd, J=2.4, 5.6 Hz), 6.99 (1H, s), 7.18 (1H, dd, J=2.8, 8.8 Hz), 7.20-7.40 (5H, m), 7.45 (1H, d, J=2.4 Hz), 7.92 (1H, brs), 8.00-8.10 (2H, m), 9.13 (1H, s), 11.89 (1H, s), 12.38 (1H, s).

Example 153

Morpholine-4-carboxylic acid {4-[3-methyl-4-(3-phenylacetylureido)phenoxy]pyridin-2-yl}amide ¹H-NMR Spectrum (DMSO-d$_6$) δ (ppm): 2.22 (3H, s), 3.41 (4H, m), 3.55 (4H, m), 3.75 (2H, s), 6.56 (1H, dd, J=2.4, 5.4 Hz), 7.00 (1H, d, J=8.4 Hz), 7.07 (1H, d, J=2.4 Hz), 7.27-7.37 (5H, m), 8.01 (1H, d, J=9.2 Hz), 8.10 (1H, d, J=5.4 Hz), 9.23 (1H, s), 10.48 (1H, s), 11.05 (1H, s). ESI-MS (m/z): 512 [M+Na]⁺.

Example 154

1-(3-Diethylaminopropyl)-3-{4-[2-methyl-4-(3-phenylacetylureido)phenoxy]pyridin-2-yl}urea ¹H-NMR Spectrum (DMSO-d$_6$) δ (ppm): 0.93 (6H, t, J=7.2 Hz), 1.53 (2H, m), 2.06 (3H, s), 2.38 (2H, m), 2.43 (4H, q, J=7.2 Hz), 3.13 (2H, m), 3.73 (2H, s), 6.44 (1H, dd, J=2.0, 5.6 Hz), 6.78 (1H, d, J=2.0 Hz), 7.04 (1H, d, J=8.8 Hz), 7.24-7.37 (5H, m), 7.46 (1H, dd, J=2.8, 8.8 Hz), 7.51 (1H, d, J=2.8 Hz), 8.02 (1H, d, J=5.6 Hz), 8.11 (1H, brs), 9.07 (1H, s), 10.50 (1H, s), 10.97 (1H, s). ESI-MS (m/z): 533 [M+H]⁺.

Example 155

N-(4-Fluorophenyl)-N'-(4-{[2-(dimethylamino)carbonylamino]pyridin-4-yloxy}phenyl)-difluoromalonamide ¹H-NMR Spectrum (DMSO-d$_6$) δ (ppm): 2.94 (6H, s), 6.90 (1H, m), 7.11 (1H, m), 7.20-7.31 (4H, m), 7.72-7.76 (2H, m), 7.86-7.89 (2H, m), 8.20 (1H, m), 11.05 (1H, s), 11.14 (1H, s).

ESI Mass: 488 [M+1]$^+$

Example 156

N-(3-Fluoro-4-{2-[(dimethylamino)carbonylamino]pyridin-4-yloxy}phenyl)-N'-(2-phenylethyl)oxalamide $^1$H-NMR Spectrum (DMSO-d$_6$) δ (ppm): 2.91 (2H, t, J=7.2 Hz), 3.01 (6H, s), 3.65 (2H, q, J=7.2 Hz), 6.54 (1H, m), 7.10-7.40 (8H, m), 7.59 (1H, br), 7.65 (1H, s), 7.77 (1H, m), 8.05 (1H, d, J=5.6 Hz), 9.34 (1H, brs).

Example 157

N-(3-Fluoro-4-{2-[(dimethylamino)carbonylamino]pyridin-4-yloxy}phenyl)-N'-(3-phenylpropyl)oxalamide $^1$H-NMR Spectrum (DMSO-d$_6$) δ (ppm): 1.96 (2H, quint, J=7.2 Hz), 2.71 (2H, t, J=7.2 Hz), 3.01 (6H, s), 3.42 (2H, q, J=7.2 Hz), 6.54 (1H, dd, J=2.4, 5.6 Hz), 7.10-7.40 (8H, m), 7.53 (1H, m), 7.66 (1H, d, J=2.4 Hz), 7.78 (1H, dd, J=2.4, 12.0 Hz), 8.05 (1H, d, J=5.6 Hz), 9.32 (1H, s).

Example 158

N-(4-Fluorophenyl)-N'-(4-{[2-(pyrrolidin-1-ylcarbonyl)amino]pyridin-4-yloxy}-2-trifluoromethylphenyl)malonamide $^1$H-NMR Spectrum (CDCl$_3$) δ (ppm): 1.88 (4H, m), 3.37 (4H, m), 3.49 (2H, s), 6.46 (1H, d, J=5.4 Hz), 6.94 (2H, m), 7.10 (1H, m), 7.20 (1H, m), 7.29 (1H, s), 7.43 (2H, dd, J=4.8, 8.0 Hz), 7.64 (1H, s), 7.97 (1H, d, J=8.8 Hz), 7.99 (1H, d, J=5.4 Hz), 8.81 (1H, s), 9.21 (1H, s). ESI-MS (m/z): 546 [M+H]$^+$, 568 [M+Na]$^+$.

Example 159

N-{4-[2-(Cyclopropylcarbonylamino)pyridin-4-yloxy]-2-trifluoromethylphenyl}-N'-(4-fluorophenyl)malonamide $^1$H-NMR Spectrum (DMSO-d$_6$) δ (ppm): 0.78 (4H, m), 1.23 (1H, m), 3.56 (2H, s), 6.73 (1H, d, J=5.4 Hz), 7.16 (2H, m), 7.49-7.63 (4H, m), 7.68 (1H, s), 7.76 (1H, d, J=8.4 Hz), 8.22 (1H, d, J=5.4 Hz), 10.03 (1H, s), 10.27 (1H, s), 10.90 (1H, s). ESI-MS (m/z): 517 [M+H]$^+$, 539 [M+Na]$^+$.

Example 160

N-{2-Chloro-4-[2-(3-cyclopropylureido)pyridin-4-yloxy]phenyl}-N'-(4-fluorophenyl)malonamide $^1$H-NMR Spectrum (DMSO-d$_6$) δ (ppm): 0.40-0.42 (2H, m), 0.61-0.64 (2H, m), 2.53-2.56 (1H, m), 3.62 (2H, m), 6.57 (1H, dd, J=2.4, 5.6 Hz), 7.01 (1H, m), 7.14-7.20 (3H, m), 7.43 (1H, d, J=2.4 Hz), 7.61-7.64 (3H, m), 8.01 (1H, d, J=9.2 Hz), 8.08 (1H, d, J=5.6 Hz), 9.03 (1H, s), 10.06 (1H, s), 10.30 (1H, s).

Example 161

N-(2-Chloro-4-{2-[(1-methylpiperidine-4-carbonyl)amino]pyridin-4-yloxy}phenyl)-N'-(4-fluorophenyl)malonamide $^1$H-NMR Spectrum (DMSO-d$_6$) δ (ppm): 1.48-1.62 (2H, m), 1.68 (2H, m), 1.80 (2H, m), 2.12 (3H, s), 2.39 (1H, m), 2.58 (1H, m), 2.76 (2H, m), 3.78 (1H, m), 6.71 (1H, dd, J=2.4, 5.6 Hz), 7.13-7.23 (3H, m), 7.43 (1H, m), 7.55-7.72 (3H, m), 7.96 (1H, m), 8.15 (1H, d, J=5.6 Hz), 9.71 (1H, d, J=12 Hz), 10.32 (1H, brs), 10.52 (1H, s).

Example 162

N-Cyclopropyl-N'-(3-fluoro-4-{2-[(pyrrolidine-1-carbonyl)amino]pyridin-4-yloxy}phenyl)malonamide $^1$H-NMR Spectrum (DMSO-d$_6$) δ (ppm): 0.42 (2H, m), 0.63 (2H, m), 1.80 (4H, m), 2.65 (1H, m), 3.21 (2H, m), 3.25-3.45 (4H, m), 6.59 (1H, dd, J=2.4, 5.6 Hz), 7.33 (2H, m), 7.46 (1H, d, J=2.4 Hz), 7.81 (1H, dd, J=2.4, 13 Hz), 8.10 (1H, d, J=5.6 Hz), 8.18 (1H, d, J=4.0 Hz), 8.69 (1H, s), 10.41 (1H, brs).

Example 163

N-{4-[6-(3,3-Dimethylureido)pyrimidin-4-yloxy]-3-fluorophenyl}-N'-methyl-N'-phenylmalonamide $^1$H-NMR Spectrum (CDCl$_3$) δ (ppm): 3.06 (6H, s), 3.22 (2H, s), 3.35 (3H, s), 7.10-7.30 (4H, m), 7.32 (1H, brs), 7.38-7.45 (1H, m), 7.45-7.52 (2H, m), 7.64 (1H, s), 7.73 (1H, dd, J=2.4, 12.0 Hz), 8.35 (1H, m), 10.40 (1H, brs).

Example 164

N-(3-Fluoro-4-{6-[(pyrrolidine-1-carbonyl)amino]pyrimidin-4-yloxy}phenyl)-N'-methyl-N'-phenylmalonamide $^1$H-NMR Spectrum (DMSO-d$_6$) δ (ppm): 1.83 (4H, brs), 3.21 (5H, brs), 3.25-3.55 (0.4H, m), 7.10-7.55 (8H, m), 7.68 (1H, m), 8.39 (1H, brs), 9.39 (1H, brs), 10.19 (1H, brs).

Example 165

N-(4-Fluorophenyl)-N'-(4-{2-[(pyrrolidin-1-yl)carbonylamino]pyridin-4-ylamino}phenyl)malonamide $^1$H-NMR Spectrum (DMSO-d$_6$) δ (ppm): 1.70-1.90 (4H, m), 3.20-3.40 (4H, m), 3.45 (2H, s), 6.47 (1H, m), 7.00-7.20 (4H, m), 7.40-7.70 (5H, m), 7.83 (1H, d, J=6.0 Hz), 8.16 (1H, s), 8.63 (1H, s), 10.13 (1H, s), 10.23 (1H, s).

Example 166

1-{6-[2-Fluoro-4-(3-phenylacetylthioureido)phenoxy]pyrimidin-4-yl}-3-(1-methylpiperidin-4-yl)urea

[6-(2-Fluoro-4-nitrophenoxy)pyrimidin-4-yl]carbamic acid phenyl ester (190 mg) was dissolved in N,N-dimethylformamide (2 ml), and then 4-amino-1-methylpiperidine (176 mg)-N,N-dimethylformamide (3 ml) was added thereto, followed by stirring for 4 hrs. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml) and brine (20 ml), and dried over anhydrous sodium sulfate. The solvent was evaporated to give a crude product of 1-[6-(2-fluoro-4-nitrophenoxy)pyrimidin-4-yl]-3-(1-methylpiperidin-4-yl)urea (200 mg). The crude product (200 mg) was dissolved in methanol (5 ml)-tetrahydrofuran (5 ml), and then 10% palladium carbon (109 mg) was added thereto under a nitrogen atmosphere, followed by replacing with hydrogen inside the system and stirring overnight. After replacing with nitrogen inside the system, the catalyst was filtered, and washed with ethanol. The filtrate was concentrated under a reduced pressure to give a residue, to which diethyl ether (2.5 ml)-hexane (5.0 ml) was added to suspend. The solid was filtered off, and dried under aeration to provide a crude product of 1-[6-(4-amino-2-fluorophenoxy)pyrimidin-4-yl]-3-(1-methylpiperidin-4-yl)urea (183 mg).

To 2-phenylacetyl chloride (36.6 mg) was added potassium thiocyanate (53.8 mg) and acetonitrile (3 ml) under a nitrogen atmosphere, followed by stirring at 60° C. for 2 hrs. The reaction mixture was cooled down to room temperature, and then ethyl acetate (20 ml) and a saturated aqueous solution of sodium hydrogencarbonate (20 ml) were added thereto, followed by stirring for 30 min. After partitioning the solution, the separated organic layer was washed with a saturated aqueous solution of sodium hydrogencarbonate (20 ml), water (20 ml) and brine (20 ml) in this order, and dried over anhydrous sodium sulfate. The solvent was evaporated to provide phenylacetyl isothiocyanate as a yellow oil.

1-[6-(4-Amino-2-fluorophenoxy)pyrimidin-4-yl]-3-(1-methylpiperidin-4-yl)urea (50 mg) was dissolved in ethanol, and then D-10-camphorsulfonic acid (64.6 mg) was added thereto, followed by stirring for 5 min. A solution of phenylacetyl isothiocyanate in toluene (1.5 ml) was added thereto, followed by stirring for 4 hrs. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml) and brine (20 ml), and dried over anhydrous sodium sulfate. The solvent was evaporated to give a residue, which was then purified by silica gel column chromatography (Fuji Silysia NH, eluent; ethyl acetate). Fractions containing the target compound were concentrated to give a residue, to which diethyl ether (0.5 ml)-hexane (2.0 ml) was then added to suspend. The solid was filtered off, and dried under aeration to provide the titled compound (13.5 mg, 18.1%) as white powder.

$^1$H-NMR Spectrum (CDCl$_3$) δ (ppm):1.40-1.62 (2H, m), 1.95-2.10 (2H, m), 2.20 (2H, m), 2.29 (3H, s), 2.74 (2H, m), 3.76 (2H, s), 3.80 (1H, m), 6.27 (1H, s), 7.20 (1H, m), 7.25-7.52 (6H, m), 7.86 (1H, dd, J=2.4, 11.6 Hz), 7.93 (1H, brs), 8.38 (1H, s), 8.73 (1H, brs), 8.96 (1H, m), 12.47 (1H, s). ESI-MS (m/z): 538 [M+H]$^+$.

The compound of Production Example 29 may also be synthesized by the following method.

Production Example 29

3-[4-(4-Amino-2-fluorophenoxy)pyridin-2-yl]-1-methyl-1-(1-methylpiperidin-4-yl)urea After dissolving (3-fluoro-4-{2-[3-methyl-3-(1-methylpiperidin-4-yl)ureido]pyridin-4-yloxy}phenyl)carbamic acid benzyl ester (38.7 mg) in tetrahydrofuran (1.5 ml) and methanol (1.5 ml), 10% palladium-carbon (16 mg) was added under a nitrogen atmosphere. The atmosphere in the reaction vessel was replaced with hydrogen, and the mixture was stirred for 5 hours at room temperature. The catalyst was filtered and then washed with methanol. The filtrate was concentrated under reduced pressure to provide a crude product of the title compound as a pale yellow oil (28.5 mg).
ESI-MS (m/z): 374 [M+H]$^+$.

Production Example 29-1

4-(4-Amino-2-fluorophenoxy)pyridine-2-carboxylic acid methyl ester dihydrochloride After dissolving 4-chloropyridine-2-carboxylic acid methyl ester (30 g) and 2-fluoro-4-nitrophenol (41.2 g) in chlorobenzene (24 ml), the reaction mixture was stirred for 4 hours at 120° C. under a nitrogen atmosphere. The reaction mixture was brought to room temperature, methanol (100 ml) was added, and the mixture was stirred for 30 minutes. After distilling off the solvent under reduced pressure, the resultant residue was partitioned between ethyl acetate (300 ml) and 1N aqueous sodium hydroxide (150 ml). The separated organic layer was washed with 1N aqueous sodium hydroxide (100 ml) and brine (150 ml) and then dried over anhydrous sodium sulfate. The solvent was distilled off under reduced pressure, and then ethanol (200 ml) was added to the resultant residue and the mixture was stirred for 30 minutes. After filtering the solid, the filtrate was purified by silica gel column chromatography (YMC, SIL-60-400/230W, eluent; heptane: ethyl acetate=1:1). Fractions containing the target compound were concentrated under reduced pressure, and the obtained solid was combined with the previously obtained solid to provide 4-(2-fluoro-4-nitrophenoxy)pyridine-2-carboxylic acid methyl ester (20.0 g, 40.0%) as a pale brown solid.

After dissolving this purified product (9.90 g) in methanol (340 ml) and tetrahydrofuran (340 ml), 20% palladium hydroxide-carbon (2.4 g) was added while stirring under a nitrogen atmosphere, the reaction system was hydrogen-replaced, and the mixture was stirred for 16 hours. The atmosphere in the reaction vessel was then replaced with nitrogen and the catalyst was filtered and washed with methanol. After adding 4N hydrochloric acid-ethyl acetate (4.18 ml) to the filtrate, the mixture was concentrated under reduced pressure to provide a crude product of the title compound as a pale yellow solid (11.5 g).
ESI-MS (m/z): 263 [M+H]$^+$.

Production Example 29-2

4-(4-Benzyloxycarbonylamino-2-fluorophenoxy) pyridine-2-carboxylic acid methyl ester 4-(4-Amino-2-fluorophenoxy)pyridine-2-carboxylic acid methyl ester (11.5 g) was dissolved in acetone (340 ml) and water (170 ml). Next, sodium hydrogencarbonate (17.3 g) was added to the reaction mixture, benzyl chloroformate (9.79 ml) was added while cooling in an ice water bath, and the mixture was stirred for 15 minutes. The reaction mixture was allowed to warm to room temperature and then the mixture was stirred for 2 hours. Benzyl chloroformate (2.45 ml) was further added to the reaction mixture while cooling in an ice water bath, and the mixture was stirred for 18 hours. After concentrating the reaction mixture under reduced pressure, ethyl acetate (500 ml) and brine (200 ml) were added to the resultant residue for partition. The separated organic layer was washed with water (100 ml) and brine (200 ml) and dried over anhydrous sodium sulfate. The solvent was distilled off under reduced pressure, and then ethyl acetate (50 ml) and hexane (30 ml) were added to the resultant solid for suspension. After filtering the solid, it was subjected to aeration drying to provide the title compound (9.6 g, 70.6%) as a pale yellow solid.

$^1$H-NMR Spectrum (CDCl$_3$) δ (ppm): 3.95-4.10 (3H, m), 5.23 (2H, m), 6.84 (1H, m), 7.00 (1H, m), 7.11 (2H, m), 7.34-7.50 (5H, m), 7.56 (1H, m), 7.62 (1H, m), 8.59 (1H, m).

Production Example 29-3

4-(4-Benzyloxycarbonylamino-2-fluorophenoxy)pyridine-2-carboxylic acid

After dissolving 4-(4-benzyloxycarbonylamino-2-fluorophenoxy)pyridine-2-carboxylic acid methyl ester (10.7 g) in methanol (450 ml) and N,N-dimethylformamide (150 ml), water (75 ml) and lithium hydroxide (1.36 g) were added and the mixture was stirred for 1 hour at room temperature. After adding 1N hydrochloric acid (100 ml), the reaction mixture was concentrated under reduced pressure, ethyl acetate (500 ml) was added for partition, and the precipitated solid was filtered. The resultant solid was washed with water and hexane and then subjected to aeration drying. The organic layer of the obtained filtrate was washed with water (100 ml×2) and brine (200 ml) and then dried over anhydrous sodium sulfate. The solvent was distilled off under reduced pressure, and then the obtained solid was washed with water and hexane and subjected to aeration drying. This solid was combined with the previously obtained solid and dried at 60° C. overnight to provide the title compound (9.53 g, 92.3%) as white powder.

$^1$H-NMR Spectrum (CDCl$_3$) δ (ppm): 3.32 (1H, brs), 5.19 (2H, s), 7.21 (1H, m), 7.25-7.58 (8H, m), 7.64 (1H, d, J=12.8 Hz), 8.59 (1H, d, J=5.6 Hz), 10.18 (1H, brs).

Production Example 29-4

[4-(4-Benzyloxycarbonylamino-2-fluorophenoxy)pyridin-2-yl]carbamic acid tert-butyl ester After dissolving 4-(4-benzyloxycarbonylamino-2-fluorophenoxy)pyridine-2-carboxylic acid (500 mg) in tert-butyl alcohol (5 ml), triethylamine (0.457 ml) and diphenylphosphoryl azide (0.310 ml) were added at room temperature under a nitrogen atmosphere, and the mixture was stirred for 1.5 hours. The reaction mixture was heated to 30° C. and stirred for 1 hour, and was then stirred at 40° C. for 45 minutes. Next, the reaction mixture was heated to 50° C. and stirred for 30 minutes, and subsequently heated to 60° C. and stirred for 30 minutes. After then heating the reaction mixture to 70° C. and stirring for 30 minutes, it was stirred at 80° C. for 30 minutes. The reaction mixture was then heated to 90° C. and stirred for 1.5 hours, and subsequently cooled to room temperature and stirred for 15 hours. It was then partitioned between ethyl acetate (50 ml) and saturated aqueous sodium hydrogencarbonate (30 ml). The organic layer was washed with water (30 ml) and brine (30 ml) in that order and dried over anhydrous sodium sulfate. The solvent was distilled off under reduced pressure, and then the resultant residue was purified by silica gel column chromatography (Fuji Silysia NH, eluent; heptane:ethyl acetate=3:2). After concentrating fractions containing the target compound under reduced pressure, diethyl ether (3 ml) and hexane (3 ml) were added to the resultant residue for suspension. The solid was filtered and then subjected to aeration drying to provide the title compound (277 mg, 46.6%) as a pale yellow solid.

$^1$H-NMR Spectrum (CDCl$_3$) δ (ppm): 1.49 (9H, s), 5.22 (2H, s), 6.46 (1H, dd, J=2.0, 6.0 Hz), 6.77 (1H, brs), 6.99-7.14 (2H, m), 7.28-7.48 (7H, m), 7.52 (1H, m), 8.06 (1H, d, J=6.0 Hz). ESI-MS (m/z): 476 [M+Na]$^+$.

Production Example 29-5

[4-(2-Aminopyridin-4-yloxy)-3-fluorophenyl]carbamic acid benzyl ester

[4-(4-Benzyloxycarbonylamino-2-fluorophenoxy)pyridin-2-yl]carbamic acid tert-butyl ester (510 mg) was added to a 4N hydrochloric acid-ethyl acetate (30 ml) while cooling in an ice water bath. The reaction mixture was allowed to warm to room temperature and then stirred for 16 hours. Diethyl ether (10 ml) and 5N aqueous sodium hydroxide (1 ml) were added to the reaction mixture and stirred therewith for 30 minutes. The separated organic layer was washed with saturated aqueous sodium hydrogencarbonate (20 ml), water (20 ml) and brine (20 ml) and dried over anhydrous sodium sulfate. The solvent was distilled off under reduced pressure, and then the resultant residue was purified by silica gel column chromatography (Fuji Silysia NH, eluent; heptane:ethyl acetate=1:2) and fractions containing the target compound were concentrated under reduced pressure. Diethyl ether (4 ml) and hexane (6 ml) were added to the resultant residue to produce a suspension of the precipitated solid. After filtering the solid, it was subjected to aeration drying to provide the title compound (46.6 mg, 11.7%) as pale yellow powder.

$^1$H-NMR Spectrum (CDCl$_3$) δ (ppm): 3.35 (2H, brs), 5.19 (2H, m), 6.14 (1H, brs), 6.69 (1H, m), 7.30-7.52 (6H, m), 7.66 (1H, m), 7.83 (1H, m), 7.97 (1H, m), 10.24 (1H, brs).

Production Example 29-6

(3-Fluoro-4-{2-[3-methyl-3-(1-methylpiperidin-4-yl)ureido]pyridin-4-yloxy}phenyl)carbamic acid benzyl ester After dissolving [4-(2-aminopyridin-4-yloxy)-3-fluorophenyl]carbamic acid benzyl ester (41 mg) in N,N-dimethylformamide (2 ml) under a nitrogen atmosphere, triethylamine (0.0485 ml) and phenyl chloroformate (0.0545 ml) were added while stirring in an ice water bath. The reaction mixture was brought to room temperature and the mixture was stirred for 30 minutes. Methyl-(1-methylpiperidin-4-yl)amine (0.0675 ml) was added to the reaction mixture and stirred therewith for 20 hours. The reaction mixture was partitioned between ethyl acetate (30 ml) and saturated aqueous ammonium chloride (20 ml). The separated organic layer was washed with saturated aqueous ammonium chloride (20 ml), water (20 ml) and brine (20 ml) and dried over anhydrous sodium sulfate. The solvent was distilled off under reduced pressure and then the resultant residue was purified by silica gel column chromatography (Fuji Silysia NH, eluent; heptane:ethyl acetate=2:3 to 1:5). Fractions containing the target compound were concentrated under reduced pressure to provide the title compound (38.7 mg, 65.7%) as a colorless oil. ESI-MS (neg.) (m/z): 506[M−H]$^−$.

The compound of Production Example 118 may also be synthesized by the following method.

Production Example 118

4-(4-Benzyloxycarbonylamino-3-fluorophenoxy) pyridine-2-carboxylic acid

After suspending ethyl 4-(4-benzyloxycarbonylamino-3-fluorophenoxy)pyridine-2-carboxylate (7.51 g) in ethanol (100 ml) and water (20 ml), lithium hydroxide (657 mg) was added at room temperature. The reaction mixture was stirred for 1 hour at room temperature. The reaction mixture was stirred while cooling in an ice bath and then 1N hydrochloric acid (60 ml) was added thereto. After stirring for 5 minutes, the reaction mixture was concentrated. After concentration, the crystals precipitated in the reaction mixture were filtrated, and the crystals were washed with water. The crystals were then dissolved in ethyl acetate-tetrahydrofuran, the solution was dried over anhydrous sodium sulfate. The dried solution was concentrated under reduced pressure. The obtained precipitate was suspended in hexane and the precipitate was filtered. The solid was dried to provide the title compound (5.04 g, 72.0%) as a pale yellow solid.

Production Example 118-1

Ethyl 4-chloropyridine-2-carboxylate

A mixture of 4-chloropyridine-2-carboxylic acid (39.4 g) and thionyl chloride (64 ml) was heated and stirred for 6 hours at 100° C. under a nitrogen atmosphere. The reaction mixture was then cooled to room temperature. After concentration under reduced pressure, it was azeotropically distilled with toluene. The residue was gradually added to ethanol while stirring in an ice bath. The reaction mixture was stirred for 25.5 hours at room temperature. The reaction mixture was then concentrated under reduced pressure. Saturated aqueous sodium hydrogencarbonate was added to the residue and the mixture was extracted with ethyl acetate. The organic layer was washed with brine and dried over anhydrous sodium sulfate. The dried organic layer was concentrated under reduced pressure to provide the title compound (38.8 g, 83.6%) as a brown oil.

$^1$H-NMR Spectrum (CDCl$_3$) δ (ppm): 1.46 (3H, t, J=7.2 Hz), 4.50 (2H, q, J=7.2 Hz), 7.49 (1H, dd, J=2.0, 5.2 Hz), 8.15 (1H, d, J=2.0 Hz), 8.67 (1H, d, J=5.2 Hz).

Production Example 118-2

Ethyl 4-(3-fluoro-4-nitrophenoxy)pyridine-2-carboxylate

After adding 3-fluoro-4-nitrophenol (24.7 g) and chlorobenzene (7.0 ml) to ethyl 4-chloropyridine-2-carboxylate (19.4 g), the mixture was heated and stirred for 4 hours at 120° C. under a nitrogen atmosphere. The reaction mixture was then cooled to room temperature. Ethyl acetate (400 ml) and saturated aqueous sodium carbonate (400 ml) were added thereto and the mixture was stirred for 27 hours at room temperature. The stirring was paused and the aqueous layer was separated. Saturated aqueous sodium carbonate was again added to the organic layer, and the mixture was stirred at room temperature for 2 days. The stirring was again paused and the aqueous layer was separated. The aqueous layer was then extracted with ethyl acetate (300 ml). The organic layers were combined and washed with brine. The organic layer was dried over anhydrous sodium sulfate and then concentrated under reduced pressure. The residue was purified by silica gel column chromatography (eluent; heptane:ethyl acetate=2:1 to 1:1, then ethyl acetate). Fractions containing the target compound were concentrated to provide the title compound (12.9 g, 40.2%) as a brown oil.

$^1$H-NMR Spectrum (CDCl$_3$) δ (ppm): 1.45 (3H, t, J=7.2 Hz), 4.49 (2H, q, J=7.2 Hz), 6.97-7.01 (2H, m), 7.16 (1H, dd, J=2.4, 5.6 Hz), 7.79 (1H, d, J=2.4 Hz), 8.20 (1H, m), 8.76 (1H, d, J=5.6 Hz). ESI-MS (m/z): 329 [M+Na]$^+$.

Production Example 118-3

Ethyl 4-(4-benzyloxycarbonylamino-3-fluorophenoxy)pyridine-2-carboxylate

After adding 20% palladium hydroxide-carbon (1.0 g) to a solution of ethyl 4-(3-fluoro-4-nitrophenoxy)pyridine-2-carboxylate (8.56 g) in ethanol (150 ml), the reaction mixture was stirred for 9.5 hours at room temperature under a hydrogen atmosphere. The catalyst was then filtered. A 4N hydrochloric acid-ethyl acetate solution (14 ml) was added to the filtrate and the mixture was concentrated. Concentration was stopped before dryness. Water (75 ml), acetone (150 ml) and sodium hydrogencarbonate (11.8 g) were added thereto. The mixture was then stirred while cooling in an ice bath, and benzyloxycarbonyl chloride (6.00 ml) was added. The reaction mixture was stirred for 4 hours at room temperature. The reaction mixture was then concentrated under reduced pressure. The residue was extracted with ethyl acetate. The organic layer was washed with brine and dried over anhydrous sodium sulfate. It was then concentrated under reduced pressure, and the residue was purified by silica gel column chromatography (eluent; heptane:ethyl acetate 1:1 to 1:2, then ethyl acetate). Fractions containing the target compound were concentrated under reduced pressure. Hexane was added to the obtained solid to produce a suspension of the solid. After allowing it to stand for a while, the supernatant was removed off with a pipette. The residue was dried to provide the title compound (7.51 g, 65.4%) as a pale yellow solid.

$^1$H-NMR Spectrum (CDCl$_3$) δ (ppm): 1.43 (3H, m), 4.45-4.52 (2H, m), 5.24 (2H, s), 6.87-6.92 (2H, m), 6.99 (1H, dd, J=2.4, 5.6 Hz), 7.35-7.45 (6H, m), 7.65 (1H, d, J=2.4 Hz), 8.19 (1H, m), 8.60 (1H, d, J=5.6 Hz).

The compound of Production Example 119-1 may also be synthesized by the following method.

Production Example 119-1

Benzyl [4-(2-aminopyridin-4-yloxy)-2-fluorophenyl] carbamate

A 4N hydrochloric acid-ethyl acetate solution (120 ml) was cooled in an ice bath. After adding tert-butyl [4-(4-benzyloxycarbonylamino-3-fluorophenoxy)pyridin-2-yl]carbamate (3.92 g) thereto while stirring, the stirring was continued for 10 minutes in an ice bath. The reaction mixture was then stirred for 3.5 hours at room temperature. The reaction mixture was concentrated under reduced pressure. Ethyl acetate (150 ml) and saturated aqueous sodium hydrogencarbonate (70 ml) were added thereto for partition. The aqueous layer was extracted with ethyl acetate (50 ml). The combined organic layers were washed with brine and dried over anhydrous sodium sulfate. The dried organic layer was concentrated under reduced pressure. The obtained crystals were then suspended in a mixed solvent of hexane-ethyl acetate (5:1). The crystals were filtered off and washed with a mixed solvent of hexane-ethyl acetate (5:1). They were then dried by aspiration at room temperature to provide the title compound (2.93 g, 95.9%) as pale yellow crystals.

Production Example 119-3 tert-Butyl [4-(4-benzyloxycarbonylamino-3-fluorophenoxy)pyridin-2-yl]carbamate

Triethylamine (4.6 ml) was added to a suspension of 4-(4-benzyloxycarbonylamino-3-fluorophenoxy)pyridine-2-carboxylic acid (5.04 g) in tert-butanol (50 ml) at room temperature, and the mixture was stirred. After adding diphenylphosphoryl azide (3.13 ml) thereto at room temperature, the mixture was stirred for 30 minutes at room temperature under a nitrogen atmosphere. It was then heated and stirred at 90° C. for 30 minutes and at 100° C. for 4 hours. The reaction mixture was subsequently cooled to room temperature. Ethyl acetate (25 ml) was added thereto, and the reaction mixture was stirred for 30 minutes while cooling in an ice bath. The precipitated crystals were filtered and washed with diethyl ether. They were then subjected to aeration drying for 1 hour at room temperature to provide the title compound (3.92 g, 65.5%) as colorless crystals.
$^1$H-NMR Spectrum (DMSO-$d_6$) δ (ppm): 1.42 (9H, s), 5.17 (2H, s), 6.62 (1H, dd, J=2.4, 5.6 Hz), 7.01 (1H, dd, J=2.2, 8.8 Hz), 7.21 (1H, dd, J=2.2, 11.2 Hz), 7.35-7.42 (6H, m), 7.70 (1H, m), 8.14 (1H, d, J=5.6 Hz), 9.53 (1H, s), 9.83 (1H, s).

Example 167

4-(Azetidin-1-yl)piperidine-1-carboxylic acid {6-[2-fluoro-4-(3-phenylacetylthioureido)phenoxy]pyrimidin-4-yl}amide After dissolving 4-(azetidin-1-yl)piperidine-1-carboxylic acid [6-(4-amino-2-fluorophenoxy)pyrimidin-4-yl]amide (40 mg) in ethanol (1 ml) under a nitrogen atmosphere, D-10-camphorsulfonic acid (22.3 mg) was added and the mixture was stirred for 5 minutes. Phenylacetyl isothiocyanate (34.1 mg)-acetonitrile (0.5 ml×3) was added thereto, and the mixture was stirred for 30 minutes. Ethyl acetate (30 ml) and saturated aqueous sodium hydrogencarbonate (20 ml) were added to the reaction mixture for partition, and the organic layer was washed with saturated aqueous sodium hydrogencarbonate (20 ml), water (20 ml) and brine (20 ml) and then dried over anhydrous sodium sulfate. The solvent was distilled off under reduced pressure. The resultant residue was purified by silica gel column chromatography (Fuji Silysia NH, eluent; ethyl acetate) and then fractions containing the target compound were concentrated under reduced pressure. Diethyl ether (1.5 ml) and hexane (1.5 ml) were added to the resultant residue to produce a suspension. After filtering the solid, it was subjected to aeration drying to provide the title compound (33.5 mg, 61.8%) as white powder.
$^1$H-NMR Spectrum (CDCl$_3$) δ (ppm): 1.22-1.50 (2H, m), 1.74 (2H, m), 2.07 (2H, m), 2.25 (1H, m), 3.11 (2H, m), 3.20 (4H, m), 3.74 (2H, s), 3.89 (2H, m), 7.08-7.55 (8H, m), 7.62 (1H, m), 7.86 (1H, dd, J=2.4, 11.6 Hz), 8.33 (1H, m), 8.41 (1H, brs), 12.42 (1H, brs). ESI-MS (m/z): 564[M+H]$^+$.

Production Example 167-1

4-(Azetidin-1-yl)-1-benzylpiperidine dihydrochloride

Triethylamine (3.51 ml) was added to a suspension of azetidine hydrochloride (2.35 g) in tetrahydrofuran (60 ml). 1-Benzyl-4-piperidone (3.71 ml) and acetic acid (2.29 ml) were added thereto and the mixture was stirred in an ice bath. Sodium triacetoxyborohydride (6.36 g) and dichloroethane (60 ml) were further added, and the mixture was stirred for 3.3 hours at room temperature. After adding sodium carbonate to the reaction mixture until foaming ceased, water (50 ml), ethyl acetate (300 ml) and brine (50 ml) were added for partition. The aqueous layer was extracted with ethyl acetate (200 ml). The organic layers were combined and washed with saturated aqueous sodium hydrogencarbonate and dried over anhydrous sodium sulfate. The dried organic layer was concentrated under reduced pressure to provide a pale brown oil. This was dissolved in diethyl ether (20 ml)-hexane (20 ml) and a 4N hydrochloric acid-ethyl acetate solution (11 ml) was added. The precipitated solid was filtered and washed with hexane. This was subjected to aeration drying to provide a crude product of the title compound (6.55 g, quantitative) as a white solid.
ESI-MS (m/z): 231[M+H]$^+$.

Production Example 167-2

4-(Azetidin-1-yl)piperidine dihydrochloride

After adding 10% palladium-carbon (600 mg) to a solution of the crude 4-(azetidin-1-yl)-1-benzylpiperidine dihydrochloride (6.55 g) in 2-propanol (50 ml)-water (50 ml), the mixture was stirred for 23 hours at room temperature under a hydrogen atmosphere. The catalyst was filtered and washed with 2-propanol, and then the filtrate was concentrated. Ethanol (10 ml)-hexane (50 ml) was added to the residue to produce suspended precipitate. It was then filtered and washed with 10 ml of ethanol. The filtered precipitate was subjected to aeration drying to provide the title compound (4.26 g) as white powder.
$^1$H-NMR Spectrum (CD$_3$OD) δ (ppm): 1.70-1.80 (2H, m), 2.25 (2H, m), 2.49 (2H, m), 2.86-3.12 (2H, m), 3.55 (2H, m), 3.60 (1H, m), 4.22 (4H, m). ESI-MS (m/z): 141[M+H]$^+$.

Production Example 167-3

4-(Azetidin-1-yl)piperidine-1-carboxylic acid [6-(2-fluoro-4-nitrophenoxy)pyrimidin-4-yl]amide After adding triethylamine (0.278 ml) and phenyl chloroformate (0.176 ml) to a solution of 6-(2-fluoro-4-nitrophenoxy)pyrimidin-4-ylamine (200 mg) in tetrahydrofuran (10 ml) at room temperature, the mixture was stirred for 15 minutes at room temperature. The reaction mixture was partitioned between ethyl acetate (60 ml) and water (50 ml). The organic layer was dried over anhydrous magnesium sulfate and concentrated under reduced pressure. After then adding N,N-dimethylformamide (3.0 ml), triethylamine (1.0 ml) and 4-(azetidin-1-yl)piperidine dihydrochloride (681 mg) to the residue, the mixture was stirred for 10 hours at room temperature. The reaction mixture was partitioned between 1N aqueous sodium hydroxide (50 ml) and ethyl acetate (100 ml). The organic layer was washed with brine and dried over anhydrous sodium sulfate. The dried organic layer was concentrated under reduced pressure. The residue was purified by silica gel column chromatography (Fuji Silysia NH, eluent; ethyl acetate, then ethyl acetate:methanol=10:1). Fractions containing the target compound were concentrated to provide a crude product of the title compound as a pale yellow solid (364 mg).
ESI-MS (m/z): 417[M+H]$^+$.

Production Example 167-4

4-(Azetidin-1-yl)piperidine-1-carboxylic acid [6-(4-amino-2-fluorophenoxy)pyrimidin-4-yl]amide After adding 10% palladium-carbon (85 mg) to a solution of 4-(azetidin-1-yl)piperidine-1-carboxylic acid (6-(2-fluoro-4-nitrophenoxy)pyrimidin-4-yl)amide (364 mg) in methanol (20 ml), the mixture was stirred for 12 hours at room temperature under a hydrogen atmosphere. The catalyst was filtered and the filtrate was concentrated under reduced pressure. The obtained solid was suspended in ethyl acetate and diluted with diethyl ether. The solid was filtered and washed with diethyl ether. It was then subjected to aeration drying to provide the title compound (160 mg) as white powder.

$^1$H-NMR Spectrum (DMSO-$d_6$) δ (ppm): 1.09 (2H, m), 1.57 (2H, m), 1.90 (2H, m), 2.15 (1H, m), 3.05 (6H, m), 3.79 (2H, m), 5.38 (2H, m), 6.37 (1H, dd, J=2.4, 8.2 Hz), 6.46 (1H, dd, J=2.4, 13.2 Hz), 6.93 (1H, m), 7.22 (1H, d, J=1.0 Hz), 8.37 (1H, d, J=1.0 Hz), 9.71 (1H, m). ESI-MS (m/z): 387[M+H]$^+$.

Example 168

4-(Azetidin-1-yl)piperidine-1-carboxylic acid {4-[3-fluoro-4-(3-phenylacetylthioureido)phenoxy]pyridin-2-yl}amide After adding 10% palladium-carbon (26.2 mg) to a solution of benzyl [4-(2-{[4-(azetidin-1-yl)piperidine-1-carbonyl]amino}pyridin-4-yloxy)-2-fluorophenyl]carbamate (128 mg) in tetrahydrofuran (10 ml), the mixture was stirred for 16 hours at room temperature under a hydrogen atmosphere. The catalyst was filtered and washed with tetrahydrofuran (4 ml). A 7 ml portion thereof was concentrated to almost dryness. A solution of 2-phenylacetyl isothiocyanate (32.8 mg) in toluene (3.0 ml) was added to a solution of the residue in ethanol (3.0 ml) at room temperature, and the mixture was stirred for 2 hours at room temperature. The reaction mixture was partitioned between ethyl acetate (60 ml) and saturated aqueous sodium hydrogencarbonate (30 ml). The organic layer was washed with brine and dried over anhydrous sodium sulfate. The organic layer was then concentrated under reduced pressure. The residue was purified by silica gel column chromatography (Fuji Silysia NH, eluent; ethyl acetate, then ethyl acetate:methanol=20:1). Fractions containing the target compound were concentrated. The residue was purified by LC-MS. Fractions containing the target compound were concentrated, and then partitioned between saturated aqueous sodium hydrogencarbonate and ethyl acetate. The organic layer was dried over anhydrous sodium sulfate and concentrated under reduced pressure. Hexane was added to the obtained solid to produce a suspension. The solid was filtered and washed with hexane. It was then subjected to aeration drying to provide the title compound (8.9 mg, 12.9%) as white powder.

$^1$H-NMR Spectrum (CD$_3$OD) δ (ppm): 1.16 (2H, m), 1.80 (2H, m), 2.11 (2H, m), 2.37 (1H, m), 2.91 (2H, m), 3.30 (4H, m), 3.76 (2H, s), 4.09 (2H, m), 6.64 (1H, dd, J=2.4, 6.0 Hz), 6.97 (1H, m), 7.05 (1H, dd, J=2.4, 10.8 Hz), 7.26-7.35 (6H, m), 7.49 (1H, d, J=2.4 Hz), 8.11 (1H, d, J=6.0 Hz), 8.27 (1H, m). ESI-MS (m/z): 563[M+H]$^+$, 585[M+Na]$^+$.

Production Example 168-1

Benzyl [4-(2-{[4-(azetidin-1-yl)piperidine-1-carbonyl]amino}pyridin-4-yloxy)-2-fluorophenyl]carbamate After adding triethylamine (0.0814 ml) and phenyl chloroformate (0.0641 ml) to a solution of benzyl [4-(2-aminopyridin-4-yloxy)-2-fluorophenyl]carbamate (103 mg) in tetrahydrofuran (5.0 ml) at room temperature, the mixture was stirred for 15 minutes at room temperature. The reaction mixture was then concentrated. N,N-dimethylformamide (3.0 ml), triethylamine (1.0 ml) and 4-(azetidin-1-yl)piperidine dihydrochloride (249 mg) were added to the residue, and the mixture was stirred for 10.5 hours at room temperature. The reaction mixture was partitioned between 1N aqueous sodium hydroxide (50 ml) and ethyl acetate (100 ml). The organic layer was washed with brine and dried over anhydrous sodium sulfate. The dried organic layer was concentrated under reduced pressure. The residue was purified by silica gel column chromatography (Fuji Silysia NH, eluent; ethyl acetate, then ethyl acetate:methanol=10:1). Fractions containing the target compound were concentrated to provide the title compound (128 mg, 84.4%) as a pale yellow oil.

$^1$H-NMR Spectrum (CDCl$_3$) δ (ppm): 1.26 (2H, m), 1.69 (2H, m), 2.06 (2H, m), 2.19 (1H, m), 3.01 (2H, m), 3.18 (4H, m), 3.90 (2H, m), 5.22 (2H, s), 6.50 (1H, dd, J=2.0, 5.8 Hz), 6.84-6.89 (3H, m), 6.99 (1H, s), 7.33-7.41 (5H, m), 7.62 (1H, d, J=2.0 Hz), 8.03 (1H, d, J=5.8 Hz), 8.11 (1H, m). ESI-MS (m/z): 520[M+H]$^+$.

Example 169

4-Dimethylaminopiperidine-1-carboxylic acid {4-[3-fluoro-4-(3-phenylacetylthioureido)phenoxy]pyridin-2-yl}amide After adding 10% palladium-carbon (21.2 mg) to a solution of benzyl (4-{2-[(4-dimethylaminopiperidine-1-carbonyl)amino]pyridin-4-yloxy}-2-fluorophenyl)carbamate (101 mg) in tetrahydrofuran (10 ml), the mixture was stirred for 16 hours at room temperature under a hydrogen atmosphere. The catalyst was filtered and washed with tetrahydrofuran (4 ml) to provide a solution of 4-dimethylaminopiperidine-1-carboxylic acid [4-(4-amino-3-fluorophenoxy)pyridin-2-yl] amide in tetrahydrofuran (14 ml). A 7 ml portion thereof was concentrated to almost dryness. A solution of 2-phenylacetyl isothiocyanate (26.4 mg) in toluene (3.0 ml) was added to a solution of the residue in ethanol (3.0 ml) at room temperature, and the mixture was stirred for 2 hours at room temperature. The reaction mixture was partitioned between ethyl acetate (60 ml) and saturated aqueous sodium hydrogencarbonate (30 ml). The organic layer was washed with brine and dried over anhydrous sodium sulfate. The organic layer was then concentrated under reduced pressure. The residue was purified by silica gel column chromatography (Fuji Silysia NH, eluent; ethyl acetate, then ethyl acetate:methanol 20:1). The obtained solid was suspended in hexane and filtered. It was then washed with hexane. It was subsequently purified by LC-MS (eluent; acetonitrile-water-trifluoroacetic acid system). Fractions containing the target compound were concentrated, and then the residue was partitioned between saturated aqueous sodium hydrogencarbonate and ethyl acetate. The organic layer was dried over anhydrous sodium sulfate. The organic layer was then concentrated to provide the title compound (8.4 mg) as white powder.

$^1$H-NMR Spectrum (CD$_3$OD) δ (ppm): 1.37-1.47 (2H, m), 1.92 (2H, m), 2.31 (6H, s), 2.47 (1H, m), 2.88 (2H, m), 3.76 (2H, s), 4.20 (2H, m), 6.40 (1H, dd, J=2.4, 6.0 Hz), 6.97 (1H, m), 7.04 (1H, dd, J=2.6, 11.0 Hz), 7.26-7.36 (6H, m), 7.49 (1H, d, J=2.4 Hz), 8.11 (1H, d, J=6.0 Hz), 8.27 (1H, m). ESI-MS (m/z): 551[M+H]$^+$, 573[M+Na]$^+$.

Production Example 169-1

4-Dimethylamino-1-benzylpiperidine dihydrochloride

After adding 1-benzyl-4-piperidone (20 ml) and acetic acid (6.15 ml) to a suspension of dimethylamine hydrochloride (11.0 g) in dichloroethane (300 ml), the mixture was stirred in an ice bath. Sodium triacetoxyborohydride (34.3 g) was added thereto, and after stirring in an ice bath for 20 minutes, the mixture was further stirred for 5.5 hours at room temperature. Water (200 ml) was then added to the reaction mixture. Sodium carbonate was further added thereto until the aqueous layer became weakly alkaline, and the mixture was stirred for 10 minutes at room temperature. It was then partitioned and the aqueous layer was extracted with ethyl acetate. The combined organic layer was dried over anhydrous sodium sulfate. The dried organic layer was concentrated under reduced pressure. Diethyl ether (100 ml) and a 4N hydrochloric acid-ethyl acetate solution (59.5 ml) were added to the residue. This was diluted with diethyl ether (50 ml) and hexane (50 ml), and then the solid was filtered. The filtered solid was washed with diethyl ether. It was then subjected to aeration drying to provide a crude product of the title compound (30.0 g) as a pale brown solid.
ESI-MS (m/z): 219[M+H]$^+$.

Production Example 169-2

4-Dimethylaminopiperidine dihydrochloride

After adding 10% palladium-carbon (2.0 g) to a solution of the crude 4-dimethylamino-1-benzylpiperidine dihydrochloride (30.0 g) in 2-propanol (300 ml)-water (300 ml), the mixture was stirred for 22 hours at room temperature under a hydrogen atmosphere. The catalyst was filtered and washed with 2-propanol. The filtrate was then concentrated. The obtained crystals were suspended in ethanol (50 ml). They were then diluted with diethyl ether (50 ml). The crystals were subsequently filtered and washed with methanol (10 ml). They were then subjected to aeration drying to provide the title compound (16.4 g) as colorless crystals.
$^1$H-NMR Spectrum (CD$_3$OD) δ (ppm): 1.94-2.05 (2H, m), 2.35 (2H, m), 2.89 (6H, s), 3.06-3.16 (2H, m), 3.52-3.62 (3H, m).

Production Example 169-3

Benzyl (4-{2-[(4-dimethylaminopiperidine-1-carbonyl)amino]pyridin-4-yloxy}-2-fluorophenyl)carbamate After adding triethylamine (0.0814 ml) and phenyl chloroformate (0.0641 ml) to a solution of benzyl [4-(2-aminopyridin-4-yloxy)-2-fluorophenyl]carbamate (103 mg) in tetrahydrofuran (5.0 ml) at room temperature, the mixture was stirred for 15 minutes at room temperature. The reaction mixture was concentrated under reduced pressure, and then N,N-dimethylformamide (3.0 ml), triethylamine (1.0 ml) and 4-dimethylaminopiperidine dihydrochloride (235 mg) were added thereto and the mixture was stirred at room temperature. The reaction mixture was partitioned between 1N aqueous sodium hydroxide (50 ml) and ethyl acetate (100 ml). The organic layer was washed with brine and dried over anhydrous sodium sulfate. The organic layer was then concentrated under reduced pressure. The residue was purified by silica gel column chromatography (Fuji Silysia NH, eluent; ethyl acetate, then ethyl acetate:methanol=10:1). Fractions containing the target compound were concentrated to provide the title compound (101 mg, 68.1%) as a pale yellow oil.
$^1$H-NMR Spectrum (CDCl$_3$) δ (ppm): 1.27-1.55 (2H, m), 1.86 (2H, m), 2.27 (6H, s), 2.34 (1H, m), 2.87 (2H, m), 4.09-4.15 (2H, m), 5.22 (2H, s), 6.51 (1H, dd, J=2.0, 5.6 Hz), 6.85-6.93 (3H, m), 7.06 (1H, brs), 7.33-7.41 (4H, m), 7.51 (1H, brs), 7.63 (1H, d, J=2.0 Hz), 8.03 (1H, d, J=5.6 Hz), 8.11 (1H, m). ESI-MS (m/z): 508[M+H]$^+$, 530[M+Na]$^+$.

Example 170

3-[6-(2-Fluoro-4-{3-[2-(4-fluorophenyl)acetyl]thioureido}phenoxy)pyrimidin-4-yl]-1-methyl-1-(1-methylpiperidin-4-yl)urea After dissolving 3-[6-(4-amino-2-fluorophenoxy)pyrimidin-4-yl]-1-methyl-1-(1-methylpiperidin-4-yl)urea (70.3 mg) in ethanol (2 ml) under a nitrogen atmosphere, D-10-camphorsulfonic acid (43.7 mg) was added and the mixture was stirred for 5 minutes. A 0.24 M solution of 2-(4-fluorophenyl)acetyl isothiocyanate in toluene (1.02 ml) was added thereto, and the mixture was stirred for 17.5 hours. Then, a 0.24 M solution of 2-(4-fluorophenyl)acetyl isothiocyanate in toluene (0.3 ml) was further added to the reaction mixture, and stirring was continued for 30 minutes. Ethyl acetate (30 ml) and saturated aqueous sodium hydrogencarbonate (20 ml) were added to the reaction mixture for partition. The organic layer was washed with saturated aqueous sodium hydrogencarbonate (20 ml), water (20 ml) and brine (20 ml) and then dried over anhydrous sodium sulfate. The solvent was distilled off under reduced pressure. The resultant residue was purified by silica gel column chromatography (Fuji Silysia NH, eluent; heptane:ethyl acetate=1:8), and then fractions containing the target compound were concentrated under reduced pressure. Diethyl ether (1 ml) and hexane (2 ml) were added to the resultant residue to produce a suspension. After filtering the solid, it was subjected to aeration drying to provide the title compound (39.4 mg, 36.8%) as pale yellow powder.
$^1$H-NMR Spectrum (CDCl$_3$) δ (ppm): 1.50-1.73 (2H, m), 1.81 (2H, m), 2.12 (2H, m), 2.31 (3H, s), 2.93 (3H, s), 2.96 (2H, m), 3.72 (2H, s), 4.20 (1H, m), 7.13 (2H, m), 7.17-7.42 (5H, m), 7.69 (1H, m), 7.87 (1H, dd, J=2.8, 11.6 Hz), 8.35 (1H, m), 8.48 (1H, brs), 12.39 (1H, brs). ESI-MS (m/z): 570[M+H]$^+$.

Example 171

4-Dimethylaminopiperidine-1-carboxylic acid [6-(2-fluoro-4-{3-[2-(4-fluorophenyl)acetyl]thioureido}phenoxy)pyrimidin-4-yl]amide After dissolving 4-dimethylaminopiperidine-1-carboxylic acid [6-(4-amino-2-fluorophenoxy)pyrimidin-4-yl]amide (89.3 mg) in ethanol (2 ml), D-10-camphorsulfonic acid (55.3 mg) was added and the mixture was stirred for 5 minutes under a nitrogen atmosphere. A 0.24 M solution of 2-(4-fluorophenyl)acetyl isothiocyanate in toluene (0.4 ml) was then added and the mixture was stirred for 1 hour. Then, a 0.24

M solution of 2-(4-fluorophenyl)acetyl isothiocyanate in toluene (0.4 ml) was further added to the reaction mixture and stirring was continued for 1 hour. Ethyl acetate (30 ml) and saturated aqueous sodium hydrogencarbonate (20 ml) were added to the reaction mixture for partition, and the organic layer was washed with saturated aqueous sodium hydrogencarbonate (20 ml), water (20 ml) and brine (20 ml) and then dried over anhydrous sodium sulfate. The solvent was distilled off under reduced pressure. The resultant residue was purified by silica gel column chromatography (Fuji Silysia NH, eluent; heptane:ethyl acetate=8:1), and then fractions containing the target compound were concentrated under reduced pressure. Diethyl ether (0.5 ml) and hexane (4.0 ml) were added to the resultant residue to produce a suspension. After filtering the solid, it was subjected to aeration drying to provide the title compound (24.9 mg, 18.4%) as a white solid.

$^1$H-NMR Spectrum (CDCl$_3$) δ (ppm): 1.50 (2H, m), 1.91 (2H, m), 2.30 (6H, s), 2.38 (1H, m), 2.96 (2H, m), 3.71 (2H, brs), 4.12 (2H, m), 7.12 (2H, m), 7.16-7.50 (5H, m), 7.63 (1H, s), 7.86 (1H, m), 8.33 (1H, s), 8.46 (1H, brs), 12.38 (1H, brs). ESI-MS (m/z): 570[M+H]$^+$.

Example 172

4-(Azetidin-1-yl)piperidine-1-carboxylic acid [6-(2-fluoro-4-{3-[2-(4-fluorophenyl)acetyl]thioureido}phenoxy)pyrimidin-4-yl]amide After adding potassium thiocyanate (65.3 mg) and acetonitrile (4 ml) to 2-(4-fluorophenyl)acetyl chloride (58 mg) under a nitrogen atmosphere, the mixture was stirred for 2 hours at 60° C. The reaction mixture was cooled to room temperature, and then ethyl acetate (30 ml) and saturated aqueous sodium hydrogencarbonate (20 ml) were added to the reaction mixture and stirring was continued for 30 minutes. After partitioning the reaction mixture, the separated organic layer was washed with saturated aqueous sodium hydrogencarbonate (20 ml), water (20 ml) and brine (20 ml) and dried over anhydrous sodium sulfate. The solvent was distilled off under reduced pressure to provide a crude product of 2-(4-fluorophenyl)acetyl isothiocyanate as a yellow oil. After dissolving 4-(azetidin-1-yl)piperidine-1-carboxylic acid [6-(4-amino-2-fluorophenoxy)pyrimidin-4-yl]amide (70 mg) in ethanol (2 ml), D-10-camphorsulfonic acid (43 mg) was added and the mixture was stirred for 5 minutes under a nitrogen atmosphere. Then, 2-(4-fluorophenyl)acetyl isothiocyanate-acetonitrile (0.5 ml×3) was added and the mixture was stirred for 2 hours. Ethyl acetate (30 ml) and saturated aqueous sodium hydrogencarbonate (20 ml) were added to the reaction mixture for partition, and the organic layer was washed with saturated aqueous sodium hydrogencarbonate (20 ml), water (20 ml) and brine (20 ml) and then dried over anhydrous sodium sulfate. The filtrate was concentrated under reduced pressure. The resultant residue was purified by silica gel column chromatography (Fuji Silysia NH, eluent; heptane:ethyl acetate=1:5), and then fractions containing the target compound were concentrated under reduced pressure. Diethyl ether (0.5 ml) and hexane (4 ml) were added to the resultant residue to produce a suspension of the solid. After filtering the solid, it was subjected to aeration drying to provide the title compound (36.9 mg, 37.8%) as white powder.

$^1$H-NMR Spectrum (CDCl$_3$) δ (ppm): 1.23-1.40 (2H, m), 1.63-1.84 (2H, m), 2.07 (2H, m), 2.25 (1H, m), 3.11 (2H, m), 3.20 (4H, m), 3.71 (2H, s), 3.80-4.00 (2H, m), 7.12 (2H, m), 7.18-7.50 (5H, m), 7.62 (1H, s), 7.86 (1H, dd, J=2.4, 11.6 Hz), 8.33 (1H, s), 8.49 (1H, brs), 12.38 (1H, brs). ESI-MS (m/z): 582[M+H]$^+$.

Example 173

4-(Pyrrolidin-1-yl)piperidine-1-carboxylic acid [6-(2-fluoro-4-{3-[2-(4-fluorophenyl)acetyl]thioureido}phenoxy)pyrimidin-4-yl]amide After adding potassium thiocyanate (388 mg) and acetonitrile (20 ml) to (4-fluorophenyl)acetyl chloride (345 mg) under a nitrogen atmosphere, the mixture was stirred for 2 hours at 60° C. The reaction mixture was cooled to room temperature, and then the reaction mixture was concentrated under reduced pressure, toluene (10 ml) and saturated aqueous sodium hydrogencarbonate (10 ml) were added to the resultant residue and the mixture was stirred for 20 minutes to prepare a 0.2 M solution of 2-(4-fluorophenyl)acetyl isothiocyanate in toluene.

After suspending a crude product of 4-(pyrrolidin-1-yl)piperidine-1-carboxylic acid [6-(4-amino-2-fluorophenoxy)pyrimidin-4-yl]amide (88.4 mg) in ethanol (3 ml), D-10-camphorsulfonic acid (51.3 mg) was added and the mixture was stirred for 5 minutes. A 0.2 M solution of 2-(4-fluorophenyl)acetyl isothiocyanate in toluene (1.3 ml) was added thereto and the mixture was stirred for 62 hours. Ethyl acetate (30 ml) and saturated aqueous sodium hydrogencarbonate (20 ml) were added to the reaction mixture for partition, and then the organic layer was washed with saturated aqueous sodium hydrogencarbonate (20 ml), water (20 ml) and brine (20 ml) and then dried over anhydrous sodium sulfate. The solvent was distilled off under reduced pressure, and then the resultant residue was purified by silica gel column chromatography (Fuji Silysia NH, eluent; heptane:ethyl acetate=1:9). Fractions containing the target compound were concentrated, and then diethyl ether (1 ml) and hexane (1.5 ml) were added to the resultant residue to produce a suspension. After filtering the solid, it was subjected to aeration drying to provide the title compound (44.7 mg, 34%) as pale pink powder.

$^1$H-NMR Spectrum (CDCl$_3$) δ (ppm): 1.27 (2H, m), 1.81 (4H, m), 1.97 (2H, m), 2.24 (1H, m), 2.59 (4H, m), 3.04 (2H, m), 3.71 (2H, brs), 4.03 (2H, m), 7.12 (2H, m), 7.18-7.32 (3H, m), 7.33-7.46 (2H, m), 7.63 (1H, m), 7.86 (1H, dd, J=2.4, 11.6 Hz), 8.33 (1H, m), 8.48 (1H, brs), 12.38 (1H, brs). ESI-MS (m/z): 596[M+H]$^+$.

Production Example 173-1

4-(Pyrrolidin-1-yl)piperidine-1-carboxylic acid [6-(4-amino-2-fluorophenoxy)pyrimidin-4-yl]amide After dissolving 6-(2-fluoro-4-nitrophenoxy)pyrimidin-4-ylamine (150 mg) in tetrahydrofuran (6 ml) under a nitrogen atmosphere, triethylamine (0.251 ml) and phenyl chloroformate (0.226 ml) were added while cooling in an ice water bath. The reaction mixture was brought to room temperature, stirred for 30 minutes, and then concentrated under reduced pressure. After adding 4-(pyrrolidin-1-yl)piperidine (370 mg) in N,N-dimethylformamide (6 ml) to the resultant residue, the mixture was stirred for 15.5 hours. Ethyl acetate (30 ml) and saturated aqueous ammonium chloride (20 ml) were added to the reaction mixture for partition. The organic layer was washed with saturated aqueous ammonium chloride (20 ml), water (20 ml) and brine (20 ml) and then dried over anhydrous sodium sulfate. The solvent was distilled off under reduced pressure, and then the resultant residue was purified by silica gel column chromatography (Fuji Silysia NH, eluent; heptane:ethyl acetate=1:5). Fractions containing the target compound were concentrated under reduced pressure to provide a crude product of 4-(pyrrolidin-1-yl)piperidine-1-carboxylic acid [6-(2-fluoro-4-nitrophenoxy)pyrimidin-4-yl]amide (88.4 mg) as a pale yellow oil.

After adding methanol (6 ml) and tetrahydrofuran (6 ml) to the crude product (88.4 mg) to dissolution, 10% palladium-carbon (128 mg) was added under a nitrogen atmosphere. The atmosphere in the reaction vessel was replaced with hydrogen and the reaction mixture was stirred for 3 hours, and then the atmosphere in the reaction vessel was replaced with nitrogen. The catalyst was filtered and subsequently washed with ethanol, and the filtrate was concentrated under reduced pressure. The resultant residue was purified by silica gel column chromatography (Fuji Silysia NH, eluent; ethyl acetate:ethanol=19:1), and then fractions containing the target compound were concentrated under reduced pressure to provide a crude product of the title compound (88.4 mg) as a yellow oil.

ESI-MS (m/z): 401[M+H]$^+$.

Example 174

4-(Pyrrolidin-1-yl)piperidine-1-carboxylic acid [4-(2-fluoro-4-{3-[2-(4-fluorophenyl)acetyl]ureido}phenoxy)pyridin-2-yl]amide 1,2-Dichloroethane (20 ml) was added to 2-(4-fluorophenyl)acetamide (282 mg) at room temperature under a nitrogen atmosphere. The reaction mixture was heated to 110° C. while stirring, and then oxalyl chloride (0.201 ml) was added to the reaction mixture and stirred therewith for 14.5 hours. The reaction mixture was cooled to room temperature and then concentrated under reduced pressure.

After adding N,N-dimethylformamide (4.5 ml) to the resultant residue under a nitrogen atmosphere, 4-(pyrrolidin-1-yl)piperidine-1-carboxylic acid [4-(4-amino-2-fluorophenoxy)pyridin-2-yl]amide (245 mg)-N,N-dimethylformamide (0.5 ml×3) was added and the mixture was stirred for 1.5 hours. The reaction mixture was partitioned between ethyl acetate (200 ml) and saturated aqueous sodium hydrogencarbonate (50 ml). The separated organic layer was washed with saturated aqueous sodium hydrogencarbonate (50 ml), water (50 ml) and brine (100 ml) in that order and then dried over anhydrous sodium sulfate. The solvent was distilled off under reduced pressure, and then the resultant residue was purified by silica gel column chromatography (Fuji Silysia NH, eluent; heptane:ethyl acetate=1:5 to 1:8). Fractions containing the target compound were concentrated under reduced pressure, and then diethyl ether (3.0 ml) and hexane (3.0 ml) were added to the resultant residue to produce a suspension of the solid. The solid was filtered and then subjected to aeration drying to provide the title compound (171.2 mg, 48.3%) as white powder.

$^1$H-NMR Spectrum (CDCl$_3$) δ (ppm): 1.44-1.66 (2H, m), 1.79 (4H, m), 1.93 (2H, m), 2.20 (1H, m), 2.57 (4H, m), 2.96 (2H, m), 3.72 (2H, s), 4.01 (2H, m), 6.23 (1H, dd, J=2.4, 5.6 Hz), 7.02-7.40 (4H, m), 7.21-7.34 (3H, m), 7.55-7.66 (2H, m), 7.94-8.13 (2H, m), 10.55 (1H, brs). ESI-MS (m/z): 579 [M+H]$^+$.

Example 175

3-[6-(3-Fluoro-4-{3-[2-(4-fluorophenyl)acetyl]thioureido}phenoxy)pyrimidin-4-yl]-1-methyl-1-(1-methylpiperidin-4-yl)urea Benzyl N-(2-fluoro-4-{6-[3-methyl-3-(1-methylpiperidin-4-yl)ureido]pyrimidin-4-yloxy}phenyl)carbamate (189 mg) was dissolved in tetrahydrofuran (20 ml). After adding 20% palladium hydroxide-carbon (104 mg), the mixture was stirred for 10 hours under a hydrogen atmosphere. The catalyst was filtered and washed with ethyl acetate. The filtrate and the washings were combined and concentrated under reduced pressure to provide crude 3-[6-(4-amino-3-fluorophenoxy)pyrimidin-4-yl]-1-methyl-1-(1-methylpiperidin-4-yl)urea as a colorless oil [ESI-MS (m/z): 375[M+H]$^+$].

After adding a solution of 2-(4-fluorophenyl)acetyl isothiocyanate in toluene (0.2 M, 3.4 ml) to a solution of crude 3-[6-(4-amino-3-fluorophenoxy)pyrimidin-4-yl]-1-methyl-1-(1-methylpiperidin-4-yl)urea and (+)-10-camphorsulfonic acid (86.2 mg) in ethanol (2.5 ml) at room temperature, the mixture was stirred for 4 hours. The reaction mixture was then partitioned between ethyl acetate and saturated aqueous sodium hydrogencarbonate. The organic layer was washed with saturated aqueous sodium hydrogencarbonate and brine in that order and dried over anhydrous sodium sulfate. The solvent was distilled off and the residue was purified by silica gel column chromatography (Fuji Silysia NH, eluent; ethyl acetate). Fractions containing the target compound were concentrated under reduced pressure, and diethyl ether (2.0 ml) was added to the resultant residue to precipitate crystals. The crystals were filtered and then subjected to aeration drying to provide the title compound (21.0 mg, 10%) as white crystals.

$^1$H-NMR Spectrum (CDCl$_3$) δ (ppm): 1.64-1.72 (2H, m), 1.74-1.88 (2H, m), 2.04-2.16 (2H, m), 2.31 (3H, s), 2.86-2.98 (5H, m), 3.72 (2H, s), 4.18 (1H, m), 6.95-7.05 (2H, m), 7.09-7.15 (2H, m), 7.20-7.40 (3H, m), 7.62 (1H, d, J=0.8 Hz), 8.35-8.42 (2H, m), 8.48 (1H, brs), 12.32 (1H, brs).

Production Example 175-1

4-Chloro-6-(3-fluoro-4-nitrophenoxy)pyrimidine

After dissolving 2,6-dichloropyrimidine (5.0 g) and 3-fluoro-4-nitrophenol (6.11 g) in 1-methyl-2-pyrrolidinone (25 ml) at room temperature under a nitrogen atmosphere, diisopropylethylamine (6.81 ml) was added and the mixture was stirred for 13 hours at 50° C. The reaction mixture was cooled to room temperature and then partitioned between ethyl acetate and water. The separated organic layer was washed with water, 1N aqueous sodium hydroxide, water, 10% aqueous potassium hydrogen sulfate and brine in that order and then dried over anhydrous sodium sulfate. The solvent was distilled off under reduced pressure, and then ethyl acetate (25 ml) was added to the residue to precipitate crystals. The crystals were filtered and subjected to aeration drying to provide the title compound (2.61 g, 30%) as white crystals. The filtrate was concentrated under reduced pressure, and then diethyl ether (30 ml) was added to the resultant residue and the mixture was stirred. The precipitated crystals were filtered, washed with diethyl ether (5 ml×2) and subjected to aeration drying to provide the title compound (3.98 g, 44%) as white crystals.

$^1$H-NMR Spectrum (CDCl$_3$) δ (ppm): 7.09 (1H, s), 7.14 (1H, m), 7.20 (1H, m), 8.20 (1H, dd, J=8.8, 8.8 Hz), 8.62 (1H, s).

Production Example 175-2

4-(4-Amino-3-fluorophenoxy)-6-chloropyrimidine

After dissolving 4-chloro-6-(3-fluoro-4-nitrophenoxy)pyrimidine (9.726 g) in ethanol (100 ml)-N,N-dimethylformamide (100 ml) at room temperature, water (50 ml), ammonium chloride (20 g) and electrolytic iron powder (10 g) were added and the mixture was stirred for 1 hour at 100° C. The reaction mixture was cooled to room temperature. The insoluble portion was removed using celite prior to washing with ethyl acetate. The filtrate was concentrated under reduced pressure, and then the residue was partitioned between ethyl acetate and water. The separated organic layer was washed with water and brine in that order and dried over anhydrous sodium sulfate. The solvent was distilled off, and the residue was dried under reduced pressure to provide the title compound (8.204 g, 95%) as pale yellow crystals.

$^1$H-NMR Spectrum (CDCl$_3$) δ (ppm): 3.76 (2H, br), 6.74-6.90 (4H, m), 8.60 (1H, s).

Production Example 175-3

4-Amino-6-(4-amino-3-fluorophenoxy)pyrimidine

After dissolving 4-(4-amino-3-fluorophenoxy)-6-chloropyrimidine (2.25 g) in tetrahydrofuran (25 ml) and a 7N ammonia solution in methanol (50 ml), the mixture was heated in a sealed tube for 3 days at 130° C. The reaction mixture was cooled to room temperature and then partitioned between ethyl acetate and 1N aqueous sodium hydroxide. The separated organic layer was washed with brine. The aqueous layer was then re-extracted with ethyl acetate. The combined organic layers were dried over anhydrous sodium sulfate. The solvent was distilled off, and the residue was purified by silica gel column chromatography (eluent; heptane:ethyl acetate=1:3, then ethyl acetate) to provide the title compound (0.73 g, 35%) as a purple solid.

$^1$H-NMR Spectrum (CDCl$_3$) δ (ppm): 3.69 (2H, br), 4.81 (2H, br), 5.80 (1H, s), 6.70-6.86 (3H, m), 8.29 (1H, Production Example 175-4

Benzyl N-[4-(6-aminopyrimidin-4-yloxy)-2-fluorophenyl]carbamate

After dissolving 4-amino-6-(4-amino-3-fluorophenoxy) pyrimidine (730 mg) in acetone (60 ml)-water (30 ml), sodium hydrogencarbonate (335 mg) and benzyl chloroformate (0.550 ml) were added while cooling in an ice water bath and the mixture was stirred at the same temperature. After 3.5 hours, sodium hydrogencarbonate (140 mg) and benzyl chloroformate (0.120 ml) were added and stirring was continued for 1 hour. The reaction mixture was concentrated under reduced pressure, ethyl acetate (50 ml)-tetrahydrofuran (100 ml) and saturated aqueous sodium hydrogencarbonate (50 ml) were added to the residue, and the mixture was stirred. The organic layer was separated and washed with a small amount of brine, and then the organic layer was concentrated under reduced pressure. Ethyl acetate (25 ml) was added to the residue and the mixture was stirred. The precipitated insoluble portion was filtered prior to washing with ethyl acetate (5 ml×3). The filtrate was concentrated under reduced pressure and the resultant residue was purified by silica gel column chromatography (eluent; heptane:ethyl acetate=1:2 to 1:4) to provide the title compound (514 mg, 44%) as pale brown powder.

$^1$H-NMR Spectrum (CDCl$_3$) δ (ppm): 4.86 (2H, brs), 5.23 (2H, s), 5.86 (1H, d, J=0.8 Hz), 6.86 (1H, brs), 6.90-6.95 (2H, m), 7.30-7.45 (5H, m), 8.13 (1H, m), 8.28 (1H, s).

Production Example 175-5

Benzyl N-(2-fluoro-4-{6-[3-methyl-3-(1-methylpiperidin-4-yl)ureido]pyrimidin-4-yloxy}phenyl)carbamate After adding a solution of 1-methyl-4-methylaminopiperidine (0.355 ml) in N,N-dimethylformamide (2.5 ml) to crude phenyl N-[6-(4-benzyloxycarbonylamino-3-fluorophenoxy) pyrimidin-4-yl]-N-(phenoxycarbonyl)carbamate (358 mg) at room temperature, the mixture was stirred for 2 hours. The reaction mixture was partitioned between ethyl acetate and water. The separated organic layer was washed with 1N aqueous sodium hydroxide and brine in that order and then dried over anhydrous sodium sulfate. The solvent was distilled off, and the residue was purified by silica gel column chromatography (Fuji Silysia NH, eluent; ethyl acetate, then ethyl acetate:methanol=95:5) to provide the title compound (189.4 mg) as white powder.

$^1$H-NMR Spectrum (CDCl$_3$) δ (ppm): 1.60-1.90 (4H, m), 2.04-2.14 (2H, m), 2.30 (3H, s), 2.80-3.00 (5H, m), 4.18 (1H, m), 5.23 (2H, s), 6.88 (1H, m), 6.92-6.96 (2H, m), 7.29 (1H, brs), 7.30-7.45 (5H, m), 7.58 (1H, s), 8.16 (1H, m), 8.38 (1H, s).

Example 176

4-(Pyrrolidin-1-yl)piperidine-1-carboxylic acid [4-(3-fluoro-4-{3-[2-(4-fluorophenyl)acetyl] thioureido}phenoxy)pyridin-2-yl]amide After adding 20% palladium hydroxide-carbon (40.7 mg) to a solution of benzyl [2-fluoro-4-(2-{[4-(pyrrolidin-1-yl) piperidine-1-carbonyl]amino}pyridin-4-yloxy)phenyl]carbamate (155 mg) in tetrahydrofuran (10 ml), the mixture was stirred for 13 hours at room temperature under a hydrogen atmosphere. Then, 20% palladium hydroxide-carbon (81.4 mg) was added to the reaction mixture and stirring was continued for 3.5 hours at room temperature under a hydrogen atmosphere. The catalyst was filtered and was washed with tetrahydrofuran to provide a solution of 4-(pyrrolidin-1-yl) piperidine-1-carboxylic acid [4-(4-amino-3-fluorophenoxy) pyridin-2-yl]amide in tetrahydrofuran (22 ml) (ESI-MS (m/z): 400[M+H]$^+$). To an 11 ml portion thereof were added ethanol (4.0 ml) and (1S)-(+)-10-camphorsulfonic acid (67.4 mg), and the mixture was stirred for 5 minutes at room temperature. A 0.2 M solution of 2-(4-fluorophenyl)acetyl isothiocyanate in toluene (0.870 ml) was then added thereto at room temperature and the mixture was stirred at room temperature for 1 hour. A 0.2 M solution of 2-(4-fluorophenyl) acetyl isothiocyanate in toluene (0.400 ml) was added next, and the mixture was stirred at room temperature for 2 hours. A 0.2 M solution of 2-(4-fluorophenyl)acetyl isothiocyanate in toluene (0.400 ml) was then added, and the mixture was stirred at room temperature for 2 hours. A 0.2 M solution of 2-(4-fluorophenyl)acetyl isothiocyanate in toluene (0.700 ml) was then further added, and the mixture was stirred at room temperature for 45 minutes. The reaction mixture was partitioned between saturated aqueous sodium hydrogencarbonate and ethyl acetate. The organic layer was washed with brine and dried over anhydrous sodium sulfate. This was concentrated under reduced pressure and purified by silica gel column chromatography (Fuji Silysia NH, eluent; heptane: ethyl acetate=1:1 to 1:2, then ethyl acetate). Fractions containing the target compound were concentrated under reduced pressure. The residue was purified by LC-MS (eluent; water-acetonitrile based, with addition of trifluoroacetic acid). The fractions containing the target compound were concentrated just before dryness under reduced pressure and partitioned between saturated aqueous sodium hydrogencarbonate and ethyl acetate. The organic layer was washed with brine and then dried over anhydrous sodium sulfate. The organic layer was concentrated under reduced pressure to provide a crude product of the target compound (24.5 mg, 28.4%). To this was added diethyl ether:heptane=1:1 to produce a solid. The solid was suspended, filtered, and the crystals were washed with hexane. They were then subjected to aeration drying to provide the title compound (15.4 mg) as white powder.

$^1$H-NMR Spectrum (CDCl$_3$) δ (ppm): 1.48-1.58 (2H, m), 1.80 (4H, m), 1.94 (2H, m), 2.22 (1H, m), 2.58 (4H, m), 2.98 (2H, m), 3.72 (2H, s), 4.02 (2H, m), 6.56 (1H, dd, J=2.4, 6.0 Hz), 6.91 (2H, d, J=8.8 Hz), 7.09-7.14 (2H, m), 7.25-7.32 (3H, m), 7.68 (1H, d, J=2.4 Hz), 8.08 (2H, d, J=6.0 Hz), 8.32 (1H, m), 12.30 (1H, brs). ESI-MS (m/z): 595[M+H]$^+$.

Example 177

4-(Azetidin-1-yl)piperidine-1-carboxylic acid [4-(3-fluoro-4-{3-[2-(4-fluorophenyl)acetyl]thioureido}phenoxy)pyridin-2-yl]amide After adding 10% palladium-carbon (26.2 mg) to a solution of benzyl [4-(2-{[4-(azetidin-1-yl)piperidine-1-carbonyl]amino}pyridin-4-yloxy)-2-fluorophenyl]carbamate (128 mg) in tetrahydrofuran (10 ml), the mixture was stirred for 16 hours at room temperature under a hydrogen atmosphere. The catalyst was filtered and washed with tetrahydrofuran (4 ml) to provide a solution of 4-(azetidin-1-yl)piperidine-1-carboxylic acid [4-(4-amino-3-fluorophenoxy)pyridin-2-yl]amide in tetrahydrofuran (approximately 14 ml)

(ESI-MS (m/z): 386[M+H]$^+$). It was concentrated under reduced pressure to 4.5 ml, and to 1.5 ml of the concentrate were added ethanol (1.0 ml) and (1S)-(+)-10-camphorsulfonic acid (36.4 mg) and the mixture was stirred for 5 minutes at room temperature. A 0.2 M solution of 2-(4-fluorophenyl)acetyl isothiocyanate in toluene (0.588 ml) was added thereto at room temperature, and the mixture was stirred at room temperature for 2 hours. The reaction mixture was partitioned between saturated aqueous sodium hydrogencarbonate and ethyl acetate. The organic layer was dried over anhydrous sodium sulfate. It was then concentrated under reduced pressure and purified by silica gel column chromatography (Fuji Silysia NH, eluent; heptane:ethyl acetate=1:2, then ethyl acetate). Fractions containing the target compound were concentrated under reduced pressure. The residue was purified by LC-MS (eluent; water-acetonitrile based, with addition of trifluoroacetic acid). The fractions containing the target compound were concentrated and then partitioned between saturated aqueous sodium hydrogencarbonate and ethyl acetate. The organic layer was washed with brine and then dried over anhydrous sodium sulfate. The organic layer was concentrated under reduced pressure to provide a crude product of the target compound (15.5 mg). To this crude product was added hexane (1 ml), to solidify. The resultant solid was suspended, filtered and then washed with hexane. It was then subjected to aeration drying to provide the title compound (11.0 mg) as white powder.

$^1$H-NMR Spectrum (CDCl$_3$) δ (ppm): 1.23-1.47 (2H, m), 1.74 (2H, m), 2.08 (2H, m), 2.26 (1H, m), 3.04 (2H, m), 3.24 (4H, m), 3.72 (2H, s), 3.92 (2H, m), 6.55 (1H, dd, J=2.4, 5.6 Hz), 6.91 (2H, d, J=9.2 Hz), 7.11 (2H, m), 7.29 (3H, m), 7.67 (1H, d, J=2.4 Hz), 8.07 (1H, d, J=5.6 Hz), 8.32 (1H, m), 8.64 (1H, s), 12.29 (1H, s). ESI-MS (m/z): 581[M+H]$^+$.

Example 178

4-(Azetidin-1-yl)piperidine-1-carboxylic acid [4-(3-fluoro-4-{3-[2-(4-fluorophenyl)acetyl]ureido}phenoxy)pyridin-2-yl]amide After adding 10% palladium-carbon (26.2 mg) to a solution of benzyl [4-(2-{[4-(azetidin-1-yl)piperidine-1-carbonyl]amino}pyridin-4-yloxy)-2-fluorophenyl]carbamate (128 mg) in tetrahydrofuran (10 ml), the mixture was stirred for 16 hours at room temperature under a hydrogen atmosphere. The catalyst was filtered and washed with tetrahydrofuran (4 ml) to provide a solution of 4-(azetidin-1-yl)piperidine-1-carboxylic acid [4-(4-amino-3-fluorophenoxy)pyridin-2-yl]amide in tetrahydrofuran (approximately 14 ml)

(ESI-MS (m/z): 386[M+H]$^+$). It was concentrated under reduced pressure to 4.5 ml, and to 3.0 ml of the concentrate was added 2-(4-fluorophenyl)acetyl isocyanate (0.25 M solution in tetrahydrofuran, 1.57 ml) at room temperature, and the mixture was stirred for 0.5 hour at room temperature. Then, 2-(4-fluorophenyl)acetyl isocyanate (0.25 M solution in tetrahydrofuran, 0.89 ml) was added to the reaction mixture at room temperature, and stirring was carried out for 0.5 hour at room temperature. The reaction mixture was partitioned between saturated aqueous sodium hydrogencarbonate and ethyl acetate. The organic layer was dried over anhydrous sodium sulfate. It was then concentrated under reduced pressure and purified by silica gel column chromatography (Fuji Silysia NH, eluent; heptane:ethyl acetate=1:2, then ethyl acetate). Fractions containing the target compound were concentrated under reduced pressure. The residue was purified by LC-MS (eluent; water-acetonitrile based, with addition of trifluoroacetic acid). The fractions containing the target compound were concentrated just before dryness under reduced pressure, and then partitioned between saturated aqueous sodium hydrogencarbonate and ethyl acetate. The organic layer was washed with brine and then dried over anhydrous sodium sulfate. The organic layer was concentrated under reduced pressure to provide a crude product of the target compound (30.3 mg). Diethyl ether (1 ml), hexane (1 ml) and acetone (0.2 ml) were added thereto and the precipitated solid formed as a suspension. The solid was filtered off and washed with diethyl ether. It was then subjected to aeration drying to provide the title compound (11.3 mg, 24.2%) as white powder.

$^1$H-NMR Spectrum (CDCl$_3$) δ (ppm): 1.24-1.33 (2H, m), 1.68-1.73 (2H, m), 2.06 (2H, m), 2.21 (1H, m), 3.03 (2H, m), 3.19 (4H, m), 3.73 (2H, s), 3.90 (2H, m), 6.52 (1H, dd, J=2.0, 6.0 Hz), 6.87-6.92 (2H, m), 7.08 (2H, m), 7.26-7.34 (3H, m), 7.62 (1H, d, J=2.0 Hz), 8.04 (1H, d, J=6.0 Hz), 8.15 (1H, m), 8.90 (1H, m), 10.72 (1H, brs). ESI-MS (m/z): 565[M+H]$^+$.

Example 179

4-{[(3S)-3-(Dimethylaminomethyl)pyrrolidin-1-yl]carbonylamino}-6-(2-fluoro-4-{3-[2-(4-fluorophenyl)acetyl]thioureido}phenoxy)pyrimidine After adding a 2-(4-fluorophenyl)acetyl isothiocyanate-toluene (0.2 M, 2.2 ml) solution to a solution of 4-(4-amino-2-fluorophenoxy)-6-{[(3S)-3-(dimethylaminomethyl)pyrrolidin-1-yl]carbonylamino}pyrimidine (105 mg) and (+)-10-camphorsulfonic acid (65 mg) in ethanol (2.5 ml) at room temperature, the mixture was stirred for 1 hour. The reaction mixture was partitioned between ethyl acetate and saturated aqueous sodium hydrogencarbonate. The organic layer was washed with saturated aqueous sodium hydrogencarbonate and brine and dried over anhydrous sodium sulfate. The solvent was distilled off, and the residue was purified by silica gel column chromatography (Fuji Silysia NH, eluent; ethyl acetate:heptane=2:1, then ethyl acetate) to provide the title compound (60.5 mg, 38%) as white powder.

$^1$H-NMR Spectrum (CDCl$_3$) δ (ppm): 1.72 (1H, m), 2.10 (1H, m), 2.25 (6H, s), 2.29-2.32 (2H, m), 2.50 (1H, m), 3.20 (1H, m), 3.40-3.70 (3H, m), 3.71 (2H, s), 7.10-7.40 (7H, m), 7.70 (1H, s), 7.86 (1H, dd, J=2.4, 11.2 Hz), 8.32 (1H, s), 8.44 (1H, brs), 12.38 (1H, brs).

Production Example 179-1

4-{[(3S)-3-(Dimethylaminomethyl)pyrrolidin-1-yl]carbonylamino}-6-(2-fluoro-4-nitrophenoxy)pyrimidine 4-Amino-6-(2-fluoro-4-nitrophenoxy)pyrimidine (125 mg) was dissolved in tetrahydrofuran (2 ml) under a nitrogen atmosphere. Triethylamine (0.167 ml) and phenyl chloroformate (0.150 ml) were added dropwise while cooling in an ice water bath. After stirring for 12 minutes at room temperature, the solvent was distilled off under reduced pressure. A solution of (3S)-3-(dimethylaminomethyl)pyrrolidine dihydrochloride (503 mg) in N,N-dimethylformamide (2.5 ml) and triethylamine (0.841 ml) were added to the resultant residue at room temperature under a nitrogen atmosphere and the mixture was stirred for 3.5 hours. The reaction mixture was partitioned between ethyl acetate and water. The organic layer was washed with 1N aqueous sodium hydroxide and brine and dried over anhydrous sodium sulfate. The solvent was distilled off under reduced pressure, and then the residue was purified by silica gel column chromatography (Fuji Silysia NH, eluent, ethyl acetate:heptane=2:1, then ethyl acetate) to provide the title compound (124 mg, 61%) as a colorless oil.

ESI-MS (m/z): 427[M+Na]$^+$.

Production Example 179-2

4-(4-Amino-2-fluorophenoxy)-6-{[(3S)-3-(dimethylaminomethyl)pyrrolidin-1-yl]carbonylamino}pyrimidine 4-{[(3S)-3-(Dimethylaminomethyl)pyrrolidin-1-yl]carbonylamino}-6-(2-fluoro-4-nitrophenoxy)pyrimidine (124 mg) was dissolved in tetrahydrofuran (15 ml). After adding 20% palladium hydroxide-carbon (86 mg), the mixture was stirred overnight under a hydrogen atmosphere. The catalyst was filtered and washed with tetrahydrofuran. The filtrate and the washings were combined and concentrated under reduced pressure, and then the resultant residue was dried under reduced pressure to provide the title compound (105 mg, 91%) as a pale yellow oil.

ESI-MS (m/z): 397[M+Na]$^+$.

Example 180

4-{[4-(Dimethylaminomethyl)piperidin-1-yl]carbonylamino}-6-(2-fluoro-4-{3-[2-(4-fluorophenyl)acetyl]thioureido}phenoxy)pyrimidine After adding a solution of 2-(4-fluorophenyl)acetyl isothiocyanate in toluene (0.2 M, 3.0 ml) to a solution of 4-(4-amino-2-fluorophenoxy)-6-{[4-(dimethylaminomethyl)piperidin-1-yl]carbonylamino}pyrimidine (118 mg) and (+)-10-camphorsulfonic acid (70.6 mg) in ethanol (3.0 ml) at room temperature, the mixture was stirred for 2 hours. The reaction mixture was partitioned between ethyl acetate and saturated aqueous sodium hydrogencarbonate. The organic layer was washed with saturated aqueous sodium hydrogencarbonate and brine and dried over anhydrous sodium sulfate. The solvent was distilled off, and the residue was purified by silica gel column chromatography (Fuji Silysia NH, eluent; ethyl acetate:heptane=4:1) to provide the title compound (70.0 mg, 40%) as white powder.

$^1$H-NMR Spectrum (CDCl$_3$) δ (ppm): 1.10-1.40 (2H, m), 1.70 (1H, m), 1.80-1.90 (2H, m), 2.10-2.15 (2H, m), 2.22 (6H, s), 2.85-3.00 (2H, m), 3.71 (2H, s), 4.05-4.15 (2H, m), 7.10-7.40 (7H, m), 7.64 (1H, d, J=0.8 Hz), 7.86 (1H, dd, J=2.4, 11.2 Hz), 8.33 (1H, d, J=0.8 Hz), 8.49 (1H, brs), 12.38 (1H, brs). ESI-MS (m/z): 584[M+H]$^+$.

Production Example 180-1

4-{[4-(Dimethylaminomethyl)piperidin-1-yl]carbonylamino}-6-(2-fluoro-4-nitrophenoxy)pyrimidine 4-Amino-6-(2-fluoro-4-nitrophenoxy)pyrimidine (125 mg) was dissolved in tetrahydrofuran (2 ml) under a nitrogen atmosphere. Triethylamine (0.167 ml) and phenyl chloroformate (0.150 ml) were added dropwise while cooling in an ice water bath. After stirring for 10 minutes at room temperature, the solvent was distilled off under reduced pressure. A solution of 4-(dimethylaminomethyl)piperidine dihydrochloride (538 mg) in N,N-dimethylformamide (2.5 ml) and triethylamine (0.841 ml) were added to the resultant residue at room temperature under a nitrogen atmosphere and the mixture was stirred for 2 hours. The reaction mixture was partitioned between ethyl acetate and water. The organic layer was washed with 1N aqueous sodium hydroxide and brine and dried over anhydrous sodium sulfate. The solvent was distilled off under reduced pressure, and then the residue was purified by silica gel column chromatography (Fuji Silysia NH, eluent; ethyl acetate:heptane=2:1, then ethyl acetate) to provide the title compound (136 mg, 65%) as white crystals.

$^1$H-NMR Spectrum (CDCl$_3$) δ (ppm): 1.20-1.40 (2H, m), 1.72 (1H, m), 1.80-1.90 (2H, m), 2.10-2.20 (2H, m), 2.22 (6H, s), 2.90-3.00 (2H, m), 4.05-4.15 (2H, m), 7.41 (1H, m), 7.45 (1H, brs), 7.73 (1H, d, J=0.8 Hz), 8.06-8.16 (2H, m), 8.32 (1H, d, J=0.8 Hz).

Production Example 180-2

4-(4-Amino-2-fluorophenoxy)-6-{[4-(dimethylaminomethyl)piperidin-1-yl]carbonylamino}pyrimidine 4-{[4-(Dimethylaminomethyl)piperidin-1-yl]carbonylamino}-6-(2-fluoro-4-nitrophenoxy)pyrimidine (136 mg) was dissolved in tetrahydrofuran (15 ml). After adding 20% palladium hydroxide-carbon (100 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (118 mg, 94%) as a colorless oil.

ESI-MS (m/z): 389[M+H]$^+$.

Example 181

4-{[4-(2-Dimethylaminoethyl)piperazin-1-yl]carbonylamino}-6-(2-fluoro-4-{3-[2-(4-fluorophenyl)acetyl]thioureido}phenoxy)pyrimidine After adding a solution of 2-(4-fluorophenyl)acetyl isothiocyanate in toluene (0.2 M, 3.5 ml) to a solution of 4-(4-amino-2-fluorophenoxy)-6-{[4-(2-dimethylaminoethyl)piperazin-1-yl]carbonylamino}pyrimidine (150 mg) and (+)-10-camphorsulfonic acid (173 mg) in ethanol (3.5 ml) at room temperature, the mixture was stirred for 2 hours. The reaction mixture was partitioned between ethyl acetate and saturated aqueous sodium hydrogencarbonate. The organic layer was washed with saturated aqueous sodium hydrogencarbonate and brine in that order and dried over anhydrous sodium sulfate. The solvent was distilled off, and the residue was purified by silica gel column chromatography (Fuji Silysia NH, eluent; ethyl acetate, then ethyl acetate:methanol=95:5) to provide the title compound (84.8 mg, 38%) as white powder.
$^1$H-NMR Spectrum (CDCl$_3$) δ (ppm): 2.26 (6H, s), 2.42-2.58 (8H, m), 3.52-3.60 (4H, m), 3.71 (2H, s), 7.09-7.40 (7H, m), 7.63 (1H, d, J=0.8 Hz), 7.86 (1H, dd, J=2.4, 12.0 Hz), 8.33 (1H, d, J=0.8 Hz), 8.49 (1H, brs), 12.38 (1H, brs). ESI-MS (m/z): 599[M+H]$^+$.

Production Example 181-1

4-{[4-(2-Dimethylaminoethyl)piperazin-1-yl]carbonylamino}-6-(2-fluoro-4-nitrophenoxy)pyrimidine 4-Amino-6-(2-fluoro-4-nitrophenoxy)pyrimidine (125 mg) was dissolved in tetrahydrofuran (2 ml) under a nitrogen atmosphere. Triethylamine (0.174 ml) and phenyl chloroformate (0.157 ml) were added dropwise while cooling in an ice water bath. After stirring for 20 minutes at room temperature, the solvent was distilled off under reduced pressure. A solution of 1-(2-dimethylaminoethyl)piperazine (393 mg) in N,N-dimethylformamide (2.5 ml) was added to the resultant residue at room temperature under a nitrogen atmosphere and the mixture was stirred for 2.5 hours. The reaction mixture was partitioned between ethyl acetate and water. The organic layer was washed with 1N aqueous sodium hydroxide and brine in that order and dried over anhydrous sodium sulfate. The solvent was distilled off under reduced pressure, and then the residue was purified by silica gel column chromatography (Fuji Silysia NH, eluent; ethyl acetate, then ethyl acetate:methanol=95:5) to provide the title compound (167 mg, 77%) as pale yellow powder.
$^1$H-NMR Spectrum (CDCl$_3$) δ (ppm): 2.26 (6H, s), 2.40-2.60 (8H, m), 3.50-3.60 (4H, m), 7.39-7.45 (2H, m), 7.73 (1H, d, J=0.8 Hz), 8.07-8.15 (2H, m), 8.32 (1H, d, J=0.8 Hz).

Production Example 181-2

4-(4-Amino-2-fluorophenoxy)-6-{[4-(2-dimethylaminoethyl)piperazin-1-yl]carbonylamino}pyrimidine 4-{[4-(2-Dimethylaminoethyl)piperazin-1-yl]carbonylamino}-6-(2-fluoro-4-nitrophenoxy)pyrimidine (167 mg) was dissolved in tetrahydrofuran (16 ml). After adding 20% palladium hydroxide-carbon (108 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (150 mg, 97%) as pale yellow powder.
ESI-MS (m/z): 404[M+H]$^+$.

Example 182

4-{2-Fluoro-4-[3-(2-phenylacetyl)thioureido]phenoxy}-2-{[4-(1-methylpiperazin-4-yl)piperidin-1-yl]carbonylamino}pyridine After adding a solution of 2-phenylacetyl isothiocyanate in toluene (0.2 M, 2.0 ml) to a solution of 4-(4-amino-2-fluorophenoxy)-2-{[4-(1-methylpiperazin-4-yl)piperidin-1-yl]carbonylamino}pyridine (85 mg) and (+)-10-camphorsulfonic acid (92 mg) in ethanol (2.0 ml) at room temperature, the mixture was stirred for 25 minutes. The reaction mixture was partitioned between ethyl acetate and saturated aqueous sodium hydrogencarbonate. The organic layer was washed with saturated aqueous sodium hydrogencarbonate and brine and dried over anhydrous sodium sulfate. The solvent was distilled off, and the residue was purified by silica gel column chromatography (Fuji Silysia NH, eluent; ethyl acetate:methanol=98:2 to 95:5) to provide the title compound (30.5 mg, 25%) as white powder.
$^1$H-NMR Spectrum (CDCl$_3$) δ (ppm): 1.50-1.95 (5H, m), 2.28 (3H, s), 2.36-2.70 (8H, m), 2.89 (2H, m), 3.74 (2H, s), 4.04-4.16 (2H, m), 6.53 (1H, dd, J=2.4, 5.6 Hz), 7.10-7.50 (8H, m), 7.62 (1H, d, J=2.4 Hz), 7.89 (1H, dd, J=2.4, 11.6 Hz), 8.05 (1H, d, J=5.6 Hz), 8.47 (1H, brs), 12.44 (1H, brs). ESI-MS (m/z): 606[M+H]$^+$.

Production Example 182-1

4-(2-Fluoro-4-nitrophenoxy)-2-{[4-(1-methylpiperazin-4-yl)piperidin-1-yl]carbonylamino}pyridine 2-Amino-4-(2-fluoro-4-nitrophenoxy)pyridine (100 mg) was dissolved in tetrahydrofuran (2 ml) under a nitrogen atmosphere. Triethylamine (0.140 ml) and phenyl chloroformate (0.126 ml) were added dropwise while cooling in an ice water bath. After stirring for 20 minutes at room temperature, the solvent was distilled off under reduced pressure. A solution of 4-(1-methylpiperazin-4-yl)piperidine (368 mg) in N,N-dimethylformamide (2.0 ml) was added to the resultant residue at room temperature under a nitrogen atmosphere and the mixture was stirred overnight. The reaction mixture was partitioned between ethyl acetate and water. The organic layer was washed with 1N aqueous sodium hydroxide and brine and dried over anhydrous sodium sulfate. The solvent was distilled off under reduced pressure, and then the residue was purified by silica gel column chromatography (Fuji Silysia NH, eluent; ethyl acetate:methanol=98:2 to 95:5) to provide the title compound (138 mg, 75%) as pale yellow powder.
$^1$H-NMR Spectrum (CDCl$_3$) δ (ppm): 1.60-2.00 (5H, m), 2.28 (3H, s), 2.40-3.00 (10H, m), 4.00-4.20 (2H, m), 6.64 (1H, dd, J=2.4, 5.6 Hz), 7.20-7.40 (2H, m), 7.70 (1H, d, J=2.4 Hz), 8.00-8.20 (3H, m).

Production Example 182-2

4-(4-Amino-2-fluorophenoxy)-2-{[4-(1-methylpiperazin-4-yl)piperidin-1-yl]carbonylamino}pyridine 4-(2-Fluoro-4-nitrophenoxy)-2-{[4-(1-methylpiperazin-4-yl)piperidin-1-yl]carbonylamino}pyridine (138 mg) was dissolved in tetrahydrofuran (30 ml). After adding 20% palladium hydroxide-carbon (89 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (85 mg, 66%) as pale yellow powder.

ESI-MS (m/z): 429[M+H]$^+$.

Example 183

1-[1-(2-Dimethylaminoethyl)piperidin-4-yl]-3-[4-(3-fluoro-4-{3-[2-(4-fluorophenyl)acetyl]thioureido}phenoxypyridin-2-yl)-1-methylurea After adding 20% palladium hydroxide-carbon (20 mg) to a solution of benzyl [4-(2-{3-[1-(2-dimethylaminoethyl)piperidin-4-yl]-3-methylureido}pyridin-4-yloxy)-2-fluorophenyl]carbamate (51.3 mg) in tetrahydrofuran (5.0 ml), the mixture was stirred for 6 hours at room temperature under a hydrogen atmosphere. The catalyst was then filtered. The filtrate was concentrated to provide 3-[4-(4-amino-3-fluorophenoxy)pyridin-2-yl]-1-[1-(2-dimethylaminoethyl)piperidin-4-yl]-1-methylurea (ESI-MS (m/z): 431[M+H]$^+$) as a pale yellow oil. This was dissolved in ethanol (0.68 ml), and then (1S)-(+)-10-camphorsulfonic acid (40.1 mg) was added thereto and the mixture was stirred for 5 minutes at room temperature. After adding 2-(4-fluorophenyl)acetyl isothiocyanate (0.2 M solution in toluene, 0.682 ml) thereto, the mixture was stirred at room temperature for 1 hour. After further adding 2-(4-fluorophenyl)acetyl isothiocyanate (0.2 M solution in toluene, 1.24 ml), the mixture was further stirred at room temperature for 1 hour. After still further adding 2-(4-fluorophenyl)acetyl isothiocyanate (0.2 M solution in toluene, 0.205 ml), stirring was continued at room temperature for 1 hour. Finally, additional 2-(4-fluorophenyl) acetyl isothiocyanate (0.2 M solution in toluene, 0.205 ml) was added and the mixture was stirred at room temperature for 3 hours. The reaction mixture was partitioned between ethyl acetate and saturated aqueous sodium hydrogencarbonate. The organic layer was dried over anhydrous sodium sulfate and concentrated under reduced pressure. The residue was purified by LC-MS (eluent; acetonitrile-water-trifluoroacetic acid system). Fractions containing the target compound were concentrated, and the residue was partitioned between ethyl acetate and saturated aqueous sodium hydrogencarbonate. The organic layer was dried over anhydrous sodium sulfate and concentrated under reduced pressure. Hexane:ethyl acetate=5:1 was added to the resultant residue to precipitate a solid. The solid was filtered and washed with hexane, and then dried to provide the title compound (8.5 mg, 14.9%) as pale yellow powder.

$^1$H-NMR Spectrum (CDCl$_3$) δ (ppm): 1.65 (2H, m), 1.79 (2H, m), 2.12 (2H, m), 2.29 (6H, s), 2.49 (4H, m), 2.89 (3H, s), 3.01 (2H, m), 3.72 (2H, s), 4.17 (1H, m), 6.57 (1H, dd, J=2.4, 6.0 Hz), 6.91 (2H, d, J=8.8 Hz), 7.11 (2H, m), 7.23-7.31 (3H, m), 7.74 (1H, d, J=2.4 Hz), 8.09 (1H, d, J=6.0 Hz), 8.32 (1H, m), 12.30 (1H, s). ESI-MS (m/z): 626[M+H]$^+$.

Production Example 183-1 tert-Butyl [1-(2-dimethylaminoacetyl)piperidin-4-yl]carbamate

After adding N,N-dimethylglycine (2.97 g), 1-hydroxybenzotriazole (3.89 g) and 1-ethyl-3-(3-dimethylaminopropyl)carbodiimide hydrochloride (5.27 g) to a solution of 4-(tert-butoxycarbonylamino)piperidine (5.0 g) in N,N-dimethylformamide (70 ml), the mixture was stirred for 46 hours at room temperature under a nitrogen atmosphere. Ethyl acetate (400 ml), brine (200 ml) and 1N aqueous sodium hydroxide (50 ml) were added to the reaction mixture and stirred therewith at room temperature for 30 minutes, and then the mixture was partitioned. The aqueous layer was extracted with ethyl acetate. The organic layers were combined and then washed with 1N aqueous sodium hydroxide and brine in that order and then dried over anhydrous sodium sulfate. The dried organic layer was concentrated under reduced pressure to provide the title compound (8.03 g, quantitative) as colorless crystals.

ESI-MS (m/z): 286[M+H]$^+$.

Production Example 183-2

N-[1-(2-Dimethylaminoethyl)piperidin-4-yl]-N-methylamine trihydrochloride

A solution of tert-butyl [1-(2-dimethylaminoacetyl)piperidin-4-yl]carbamate (702 mg) in tetrahydrofuran (10.5 ml) was stirred while cooling in an ice bath under a nitrogen atmosphere. Lithium aluminum hydride (280 mg) was added thereto, and the mixture was stirred in an ice bath for 15 minutes and at room temperature for 15 minutes. The reaction mixture was heated to reflux for 8 hours at 100° C. under a nitrogen atmosphere. The reaction mixture was then cooled on ice. Water (0.280 ml), 5N aqueous sodium hydroxide (0.280 ml) and water (0.840 ml) were added thereto in that order, and the mixture was stirred for 1 hour. The insoluble portion was filtered, and a 4N hydrochloric acid-ethyl acetate solution (1.23 ml) was added to the filtrate. The resulting mixture was concentrated to provide the title compound (673 mg, quantitative) as pale yellow crystals.

$^1$H-NMR Spectrum (CD$_3$OD) δ (ppm): 1.70-1.80 (2H, m), 2.07 (2H, m), 2.19 (2H, m), 2.70 (3H, s), 2.73 (2H, m), 2.89 (6H, s), 3.02-3.13 (3H, m), 3.26 (2H, m). ESI-MS (m/z): 186[M+H]$^+$.

Production Example 183-3

Benzyl [4-(2-{3-[1-(2-dimethylaminoethyl)piperidin-4-yl]-3-methylureido}pyridin-4-yloxy)-2-fluorophenyl]carbamate After adding triethylamine (0.127 ml) and phenyl chloroformate (0.100 ml) to a solution of benzyl [4-(2-aminopyridin-4-yloxy)-2-fluorophenyl]carbamate (113 mg) in tetrahydrofuran (5.0 ml), the mixture was stirred for 30 minutes at room temperature under a nitrogen atmosphere. The reaction mixture was partitioned between ethyl acetate (50 ml) and brine (30 ml). The organic layer was dried over anhydrous sodium sulfate and then concentrated under reduced pressure. To this residue was added a suspension (4 ml) produced by adding tetrahydrofuran (6.0 ml) and triethylamine (2.0 ml) to N-[1-(2-dimethylaminoethyl)piperidin-4-yl]-N-methylamine trihydrochloride (673 mg), and the resulting mixture was stirred at room temperature for 27 hours. Ethyl acetate (30 ml) and 1N aqueous sodium hydroxide (10 ml) were added to the reaction mixture, and stirring was carried out for 5 hours at room temperature. Brine was added thereto and the mixture was extracted with ethyl acetate. The aqueous layer was then extracted with ethyl acetate. The organic layers were combined and washed with 1N aqueous sodium hydroxide and brine in that order, and dried over anhydrous sodium sulfate. The dried organic layer was concentrated and the residue was purified by silica gel column chromatography (Fuji Silysia NH, eluent; ethyl acetate:methanol=20:1 to 10:1). Fractions containing the target compound were concentrated to provide a white solid. Methanol (3 ml) and 5N aqueous sodium hydroxide (1 ml) were added thereto, and the mixture was stirred at room temperature for 1 hour. The reaction mixture was then partitioned between ethyl acetate and brine. The organic layer was washed with brine and then dried over anhydrous sodium sulfate. It was subsequently concentrated. The residue was purified by LC-MS (eluent; acetonitrile-water-trifluoroacetic acid system). Fractions containing the target compound were concentrated, respectively. The residue was partitioned between ethyl acetate and saturated aqueous sodium hydrogencarbonate. The organic layer was dried over anhydrous sodium sulfate. It was then concentrated to provide the title compound (51.3 mg, 28.4%) as a colorless oil.

$^1$H-NMR Spectrum (CDCl$_3$) δ (ppm): 1.64 (2H, m), 1.78 (2H, m), 2.11 (2H, m), 2.27 (6H, s), 2.48 (4H, m), 2.88 (3H, s), 3.01 (2H, m), 4.16 (1H, m), 5.23 (2H, s), 6.52 (1H, dd, J=2.4, 6.0 Hz), 6.85-6.91 (3H, m), 7.20 (1H, s), 7.33-7.43 (5H, m), 7.68 (1H, d, J=2.4 Hz), 8.05 (1H, d, J=6.0 Hz), 8.12 (1H, brs). ESI-MS (m/z): 565[M+H]$^+$.

Example 184

1-[1-(2-Dimethylaminoethyl)piperidin-4-yl]-3-[6-(2-fluoro-4-{3-[2-(4-fluorophenyl)acetyl]thioureido}phenoxy)pyrimidin-4-yl]-1-methylurea After adding (1S)-(+)-10-camphorsulfonic acid (101 mg) to a solution of 3-[6-(4-amino-2-fluorophenoxy)pyrimidin-4-yl]-1-[1-(2-dimethylaminoethyl)piperidin-4-yl]-1-methylurea (110 mg) in ethanol (2.0 ml), the mixture was stirred for 15 minutes at room temperature. After adding 2-(4-fluorophenyl)acetyl isothiocyanate (3.06 ml, 0.25 M solution in toluene) thereto, the mixture was further stirred at room temperature for 1 hour. The reaction mixture was partitioned between saturated aqueous sodium hydrogencarbonate (10 ml) and ethyl acetate (30 ml). The organic layer was washed with brine and dried over anhydrous sodium sulfate. The dried organic layer was concentrated and the residue was purified by silica gel column chromatography (Fuji Silysia NH, eluent; ethyl acetate, then ethyl acetate:methanol=20:1 to 10:1). Fractions containing the target compound were concentrated. Diethyl ether:hexane=1:1 was added to the obtained solid to produce a suspension. The precipitate was filtered and then washed with diethyl ether to provide the title compound (50.5 mg, 31.6%) as pale yellow powder.

$^1$H-NMR Spectrum (CDCl$_3$) δ (ppm): 1.69 (2H, m), 1.83 (2H, m), 2.15 (2H, m), 2.30 (6H, s), 2.51 (4H, m), 2.92 (3H, s), 3.05 (2H, m), 3.71 (2H, s), 4.19 (1H, m), 7.10 (2H, m), 7.20-7.37 (5H, m), 7.68 (1H, s), 7.86 (1H, dd, J=2.4, 7.6 Hz), 8.34 (1H, s), 8.50 (1H, brs), 12.38 (1H, s). ESI-MS (m/z): 627[M+H]$^+$ Production Example 184-1

N-[1-(2-Dimethylaminoethyl)piperidin-4-yl]-N-methylamine

A solution of tert-butyl [1-(2-dimethylaminoacetyl)piperidin-4-yl]carbamate (702 mg) in tetrahydrofuran (10.5 ml) was stirred while cooling in an ice bath under a nitrogen atmosphere. Lithium aluminum hydride (280 mg) was added thereto, and the mixture was stirred in an ice bath for 15 minutes and at room temperature for 15 minutes. The reaction mixture was heated to reflux for 11 hours at 100° C. under a nitrogen atmosphere. The reaction mixture was then cooled in an ice bath. Water (2.8 ml), 5N aqueous sodium hydroxide (2.8 ml) and water (14.0 ml) were added in that order, and the mixture was stirred for 2 hours. The insoluble portion was filtered. The filtrate was concentrated to provide the title compound (4.65 g, quantitative) as a yellow oil.

$^1$H-NMR Spectrum (CDCl$_3$) δ (ppm): 1.34-1.43 (2H, m), 1.87-1.90 (2H, m), 2.02-2.08 (2H, m), 2.25 (6H, s), 2.31-2.50 (7H, m), 2.90 (2H, m), 3.14-3.27 (1H, m). ESI-MS (m/z): 186[M+H]$^+$.

Production Example 184-2

3-[6-(2-Fluoro-4-nitrophenoxy)pyrimidin-4-yl]-1-[1-(2-dimethylaminoethyl)piperidin-4-yl]-1-methylurea After adding triethylamine (0.266 ml) and phenyl chloroformate (0.221 ml) to a solution of 6-(2-fluoro-4-nitrophenoxy)pyrimidin-4-ylamine (200 mg) in tetrahydrofuran (10.0 ml), the mixture was stirred for 30 minutes at room temperature under a nitrogen atmosphere. The reaction mixture was then concentrated. After adding N,N-dimethylformamide (6.0 ml) and N-[1-(2-dimethylaminoethyl)piperidin-4-yl]-N-methylamine (593 mg) to the residue, the mixture was stirred for 8 hours at room temperature. Ethyl acetate (30 ml) and 1N aqueous sodium hydroxide (10 ml) were added to the reaction mixture, and stirring was carried out at room temperature for 5 hours. Brine was added thereto and the mixture was extracted with ethyl acetate. The aqueous layer was extracted with ethyl acetate. The organic layers were then combined and washed with 1N aqueous sodium hydroxide and brine in that order, and dried over anhydrous sodium sulfate. The dried organic layer was concentrated and the residue was purified by silica gel column chromatography (Fuji Silysia NH, eluent; ethyl acetate:methanol=20:1 to 10:1). Fractions containing the target compound were concentrated. Diethyl ether-hexane (1:1) was added to the obtained solid to produce a suspension, and the supernatant was removed off. This was dried to provide the title compound (240 mg, 65.0%) as pale yellow powder.

$^1$H-NMR Spectrum (CDCl$_3$) δ (ppm): 1.67 (2H, m), 1.85 (2H, m), 2.15 (2H, m), 2.30 (6H, s), 2.52 (4H, m), 2.94 (3H, s), 3.06 (2H, m), 4.20 (1H, m), 7.36 (1H, s), 7.42 (1H, m), 7.77 (1H, d, J=0.8 Hz), 8.08-8.24 (2H, m), 8.33 (1H, d, J=0.8 Hz). ESI-MS (m/z): 462[M+H]$^+$.

Production Example 184-3

3-[6-(4-Amino-2-fluorophenoxy)pyrimidin-4-yl]-1-[1-(2-dimethylaminoethyl)piperidin-4-yl]-1-methylurea After adding 20% palladium hydroxide-carbon (18.3 mg) to a solution of 3-[6-(2-fluoro-4-nitrophenoxy)pyrimidin-4-yl]-1-[1-(2-dimethylaminoethyl)piperidin-4-yl]-1-methylurea (240 mg) in tetrahydrofuran (10 ml), the mixture was stirred for 15.5 hours at room temperature under a hydrogen atmosphere. The catalyst was filtered and washed with methanol. The filtrate was then concentrated to provide the title compound (220 mg, 98.0%) as a yellow amorphous substance.

ESI-MS (m/z): 432[M+H]$^+$.

Example 185

4-{2-Fluoro-4-[3-(2-phenylacetyl)thioureido]phenoxy}-2-{[4-(4-hydroxypiperidin-1-yl)piperidin-1-yl]carbonylamino}pyridine After adding a solution of 2-phenylacetyl isothiocyanate in toluene (0.2 M, 4.0 ml) to a solution of 4-(4-amino-2-fluorophenoxy)-2-{[4-(4-hydroxypiperidin-1-yl)piperidin-1-yl]carbonylamino}pyridine (164 mg) and (+)-10-camphorsulfonic acid (85 mg) in ethanol (4.0 ml) at room temperature, the mixture was stirred for 1 hour. The reaction mixture was partitioned between ethyl acetate and saturated aqueous sodium hydrogencarbonate. The organic layer was washed with saturated aqueous sodium hydrogencarbonate and brine in that order and dried over anhydrous sodium sulfate. The solvent was distilled off, and the residue was purified by silica gel column chromatography (Fuji Silysia NH, eluent; ethyl acetate:methanol=98:2 to 95:5) to provide the title compound (127 mg, 57%) as white powder.
$^1$H-NMR Spectrum (CDCl$_3$) δ (ppm): 1.40-2.00 (8H, m), 2.25-2.40 (2H, m), 2.49 (1H, m), 2.75-2.90 (4H, m), 3.70 (1H, m), 3.74 (2H, s), 4.05-4.20 (2H, m), 6.53 (1H, dd, J=2.4, 5.6 Hz), 7.10-7.50 (8H, m), 7.62 (1H, d, J=2.4 Hz), 7.89 (1H, dd, J=2.4, 11.6 Hz), 8.04 (1H, d, J=5.6 Hz), 8.53 (1H, brs), 12.44 (1H, brs). ESI-MS (m/z): 607[M+H]$^+$.

Production Example 185-1

4-(2-Fluoro-4-nitrophenoxy)-2-{[4-(4-hydroxypiperidin-1-yl)piperidin-1-yl]carbonylamino}pyridine 2-Amino-4-(2-fluoro-4-nitrophenoxy)pyridine (100 mg) was dissolved in tetrahydrofuran (2 ml) under a nitrogen atmosphere. Triethylamine (0.140 ml) and phenyl chloroformate (0.126 ml) were added dropwise while cooling in an ice water bath. After stirring for 20 minutes at room temperature, the solvent was distilled off under reduced pressure. A solution of 4-(4-hydroxypiperidin-1-yl)piperidine (412 mg) in N,N-dimethylformamide (5.0 ml) was added to the resultant residue at room temperature under a nitrogen atmosphere and the mixture was stirred overnight. The reaction mixture was partitioned between ethyl acetate and water. The organic layer was washed with 1N aqueous sodium hydroxide and brine in that order and dried over anhydrous sodium sulfate. The solvent was distilled off under reduced pressure, and then the residue was purified by silica gel column chromatography (Fuji Silysia NH, eluent; ethyl acetate:methanol=98:2 to 95:5) to provide the title compound (168 mg, 91%) as pale yellow powder.
$^1$H-NMR Spectrum (CDCl$_3$) δ (ppm): 1.40-2.00 (8H, m), 2.31 (2H, m), 2.52 (1H, m), 2.70-2.95 (4H, m), 3.70 (1H, m), 4.00-4.20 (2H, m), 6.64 (1H, dd, J=2.4, 5.6 Hz), 7.20-7.40 (2H, m), 7.70 (1H, d, J=2.4 Hz), 8.00-8.20 (3H, m).

Production Example 185-2

4-(4-Amino-2-fluorophenoxy)-2-{[4-(4-hydroxypiperidin-1-yl)piperidin-1-yl]carbonylamino}pyridine 4-(2-Fluoro-4-nitrophenoxy)-2-{[4-(4-hydroxypiperidin-1-yl)piperidin-1-yl]carbonylamino}pyridine (168 mg) was dissolved in tetrahydrofuran (20 ml). After adding 20% palladium hydroxide-carbon (103 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (164 mg) as pale yellow powder.
ESI-MS (m/z): 430[M+H]$^+$.

Example 186

4-(Dimethylaminomethyl)piperidine-1-carboxylic acid {6-[2-fluoro-4-(3-phenylacetylthioureido)phenoxy]pyrimidin-4-yl}amide After adding tetrahydrofuran (2 ml) and methanol (2 ml) to 4-(dimethylaminomethyl)piperidine-1-carboxylic acid [6-(2-fluoro-4-nitrophenoxy)pyrimidin-4-yl]amide (88 mg) under a nitrogen atmosphere, 10% palladium-carbon (45 mg) was added, the atmosphere in the reaction vessel was replaced with hydrogen, and the mixture was stirred for 9 hours. The atmosphere in the reaction vessel was then replaced with nitrogen and the catalyst was filtered and washed with methanol. The filtrate was concentrated under reduced pressure to provide a crude product of 4-(dimethylaminomethyl)piperidine-1-carboxylic acid [6-(4-amino-2-fluorophenoxy)pyrimidin-4-yl]amide (90 mg) as a pale yellow amorphous substance.

After dissolving this crude product (81.6 mg) in ethanol (1 ml) under a nitrogen atmosphere, D-10-camphorsulfonic acid (49 mg) was added and the mixture was stirred for 5 minutes. A 0.5 M solution of 2-phenylacetyl isothiocyanate in toluene (0.63 ml) was added to the reaction mixture and the mixture was stirred for 1 hour. The reaction mixture was then partitioned between ethyl acetate (50 ml) and saturated aqueous sodium hydrogencarbonate (30 ml). The organic layer was washed with saturated aqueous sodium hydrogencarbonate (30 ml), water (30 ml) and brine (30 ml) in that order and then dried over anhydrous sodium sulfate. The solvent was distilled off under reduced pressure, and the resultant residue was purified by silica gel column chromatography (Fuji Silysia NH, eluent; heptane:ethyl acetate=1:1 to 2:3). Fractions containing the target compound were concentrated under reduced pressure, and then diethyl ether (1.0 ml) and hexane (3.0 ml) were added to the resultant residue to produce a suspension. After filtering the solid, it was subjected to aeration drying to provide the title compound (34.0 mg, 28.6%) as white powder.
$^1$H-NMR Spectrum (CDCl$_3$) δ (ppm): 1.50-1.56 (3H, m), 1.85 (2H, m), 2.14 (2H, t, J=7.2 Hz), 2.22 (6H, s), 2.93 (2H, m), 3.74 (2H, brs), 4.09 (2H, m), 7.16-7.50 (8H, m), 7.64 (1H, m), 7.86 (1H, dd, J=2.4, 11.6 Hz), 8.33 (1H, m), 8.44 (1H, brs), 12.43 (1H, brs). ESI-MS (m/z): 566[M+H]$^+$.

Example 187

4-(2-Dimethylaminoethyl)piperazine-1-carboxylic acid {6-[2-fluoro-4-(3-phenylacetylthioureido)phenoxy]pyrimidin-4-yl}amide After adding tetrahydrofuran (2 ml) and methanol (2 ml) to 4-(2-dimethylaminoethyl)piperazine-1-carboxylic acid [6-(2-fluoro-4-nitrophenoxy)pyrimidin-4-yl]amide (94 mg) under a nitrogen atmosphere, 10% palladium-carbon (46 mg) was added, the atmosphere in the reaction vessel was replaced with hydrogen, and the mixture was stirred for 9 hours. The atmosphere in the reaction vessel was then replaced with nitrogen, and the catalyst was filtered and washed with methanol. The filtrate was concentrated under reduced pressure to provide a crude product of 4-(2-dimethylaminoethyl)

piperazine-1-carboxylic acid [6-(4-amino-2-fluorophenoxy) pyrimidin-4-yl]amide (91 mg) as a pale yellow amorphous substance.

After dissolving this crude product (81 mg) in ethanol (1 ml) under a nitrogen atmosphere, D-10-camphorsulfonic acid (51 mg) was added and the mixture was stirred for 5 minutes. A 0.5 M solution of 2-phenylacetyl isothiocyanate in toluene (0.651 ml) was added to the reaction mixture and stirring was carried out for 1 hour. The reaction mixture was partitioned between ethyl acetate (50 ml) and saturated aqueous sodium hydrogencarbonate (30 ml). The organic layer was washed with saturated aqueous sodium hydrogencarbonate (30 ml), water (30 ml) and brine (30 ml) in that order, and then dried over anhydrous sodium sulfate. The solvent was distilled off under reduced pressure, and then the resultant residue was purified by silica gel column chromatography (Fuji Silysia NH, eluent; heptane:ethyl acetate=1:5, then ethyl acetate). Fractions containing the target compound were concentrated under reduced pressure, and then diethyl ether (1.0 ml) and hexane (3.0 ml) were added to the resultant residue to produce a suspension of the solid. After filtering the solid, it was subjected to aeration drying to provide the title compound (47.8 mg, 37.9%) as white powder.

$^1$H-NMR Spectrum (CDCl$_3$) δ (ppm): 2.27 (6H, s), 2.46 (2H, m), 2.53 (6H, m), 3.55 (4H, m), 3.74 (2H, s), 7.15-7.52 (8H, m), 7.63 (1H, m), 7.86 (1H, dd, J=2.8, 11.6 Hz), 8.33 (1H, m), 8.43 (1H, brs), 12.42 (1H, brs). ESI-MS (m/z): 581[M+H]$^+$.

Example 188

2-{[4-(Dimethylaminomethyl)piperidin-1-yl]carbonylamino}-4-(4-{3-[2-(4-fluorophenyl)acetyl]thioureido}phenoxy)pyridine After adding a solution of 2-(4-fluorophenyl)acetyl isothiocyanate in toluene (0.2 M, 3.0 ml) to a solution of 4-(4-aminophenoxy)-2-{[4-(dimethylaminomethyl)piperidin-1-yl]carbonylamino}pyridine (79 mg) and (+)-10-camphorsulfonic acid (49.7 mg) in ethanol (3.0 ml) at room temperature, the mixture was stirred overnight. The reaction mixture was partitioned between ethyl acetate and saturated aqueous sodium hydrogencarbonate. The organic layer was washed with saturated aqueous sodium hydrogencarbonate and brine in that order and dried over anhydrous sodium sulfate. The solvent was distilled off, and the residue was purified by silica gel column chromatography (Fuji Silysia NH, eluent; ethyl acetate:heptane=4:1) to provide the title compound (36.5 mg, 30%) as white powder.

$^1$H-NMR Spectrum (CDCl$_3$) δ (ppm): 1.10-1.20 (2H, m), 1.50-1.90 (3H, m), 2.10-2.15 (2H, m), 2.21 (6H, s), 2.80-2.95 (2H, m), 3.71 (2H, s), 4.00-4.15 (2H, m), 6.53 (1H, dd, J=2.4, 5.6 Hz), 7.10-7.40 (7H, m), 7.60-7.70 (3H, m), 8.04 (1H, d, J=5.6 Hz), 8.63 (1H, brs), 12.27 (1H, brs). ESI-MS (m/z): 565[M+H]$^+$.

Production Example 188-1

4-(4-Amino-3-chlorophenoxy)-2-{[4-(dimethylaminomethyl)piperidin-1-yl]carbonylamino}pyridine 2-Amino-4-(4-amino-3-chlorophenoxy)pyridine (100 mg) was dissolved in tetrahydrofuran (2 ml) under a nitrogen atmosphere. Triethylamine (0.118 ml) and phenyl chloroformate (0.106 ml) were added dropwise while cooling in an ice water bath. After stirring for 15 minutes at room temperature, the solvent was distilled off under reduced pressure. A solution of 4-(dimethylaminomethyl)piperidine dihydrochloride (456 mg) in N,N-dimethylformamide (4.0 ml) and triethylamine (0.591 ml) were added to the resultant residue at room temperature under a nitrogen atmosphere and the mixture was stirred overnight. The reaction mixture was partitioned between ethyl acetate and water. The organic layer was washed with 1N aqueous sodium hydroxide and brine in that order and dried over anhydrous sodium sulfate. The solvent was distilled off under reduced pressure, and then the residue was purified by silica gel column chromatography (Fuji Silysia NH, eluent; ethyl acetate:heptane=2:1, then ethyl acetate) to provide the title compound (122 mg, 71%) as pale yellow powder.

ESI-MS (m/z): 404[M+H]$^+$.

Production Example 188-2

4-(4-Aminophenoxy)-2-{[4-(dimethylaminomethyl)piperidin-1-yl]carbonylamino}pyridine 4-(4-Amino-3-chlorophenoxy)-2-{[4-(dimethylaminomethyl)piperidin-1-yl]carbonylamino}pyridine (122 mg) was dissolved in methanol (15 ml). After then adding 10% palladium-carbon (123 mg), the mixture was stirred for 3 days under a hydrogen atmosphere. The catalyst was filtered and washed with methanol. The filtrate and the washings were combined and concentrated under reduced pressure, and the resultant residue was dried under reduced pressure to provide the title compound (79 mg, 71%) as a colorless oil.

ESI-MS (m/z): 370[M+H]$^+$.

Example 189

4-[3-(Dimethylamino)azetidin-1-yl]piperidine-1-carboxylic acid [4-(3-fluoro-4-{3-[2-(4-fluorophenyl)acetyl]thioureido}phenoxy)pyridin-2-yl]amide After adding 20% palladium hydroxide-carbon (50 mg) to a solution of benzyl {4-[2-({4-[3-(dimethylamino)azetidin-1-yl]piperidine-1-carbonyl}amino)pyridin-4-yloxy]-2-fluorophenyl}carbamate (135 mg) in tetrahydrofuran (10.0 ml), the mixture was stirred for 8 hours at room temperature under a hydrogen atmosphere. The catalyst was filtered and the filtrate was concentrated to 3 ml of solvent to provide a crude product of 4-[3-(dimethylamino)azetidin-1-yl]piperidine-1-carboxylic acid [4-(4-amino-3-fluorophenoxy)pyridin-2-yl]amide (ESI-MS (m/z): 429[M+H]$^+$). Ethanol (3.0 ml) and (1S)-(+)-10-camphorsulfonic acid (68.3 mg) were added to the crude product. After stirring at room temperature for 10 minutes, 2-(4-fluorophenyl)acetyl isothiocyanate (0.2 M solution in toluene, 3.15 ml) was added and the mixture was stirred at room temperature. After 30 minutes, 2-(4-fluorophenyl)acetyl isothiocyanate (0.2 M solution in toluene, 4.26 ml) was added and stirring was continued at room temperature for 3.5 hours. Ethyl acetate and saturated aqueous sodium hydrogencarbonate were then added to the reaction solution, and the mixture was stirred at room temperature for 2 hours and then partitioned. The aqueous layer was extracted with ethyl acetate, and then the separated organic layer was washed with brine. It was then dried over anhydrous sodium sulfate and concentrated. The residue was purified by silica gel column chromatography (Fuji Silysia NH, eluent; ethyl acetate, then ethyl acetate:methanol=10:1). Fractions containing the target compound were concentrated. Diethyl ether and hexane were added thereto, and the produced precipitate (41.3 mg) was filtered. After removing 12 mg of the powder, the remaining 29.3 mg was again purified by silica gel column chromatography (Fuji Silysia NH, eluent; ethyl acetate, then ethyl acetate:methanol=10:1). Fractions containing the target compound were combined and concentrated. Diethyl ether and hexane were added thereto, and the produced precipitate was filtered. It was then subjected to aeration drying to provide the title compound (12.8 mg) as white powder.

$^1$H-NMR Spectrum (CDCl$_3$) δ (ppm): 1.24-1.35 (2H, m), 1.71 (2H, m), 2.11 (6H, s), 2.26 (1H, m), 2.84 (3H, m), 3.06 (2H, m), 3.49 (2H, m), 3.72 (2H, s), 3.88 (2H, m), 6.55 (1H, dd, J=2.4, 5.6 Hz), 6.91 (2H, d, J=8.8 Hz), 7.11 (2H, m), 7.13-7.31 (3H, m), 7.67 (1H, d, J=2.4 Hz), 8.07 (1H, d, J=5.6 Hz), 8.32 (1H, m), 8.64 (1H, brs), 12.29 (1H, s). ESI-MS (m/z): 624[M+H]$^+$.

Production Example 189-1 tert-Butyl 3-dimethylaminoazetidine-1-carboxylate

After adding a 2 M solution of dimethylamine in tetrahydrofuran (21.9 ml), acetic acid (1.73 ml) and 10% palladium-carbon (2.15 g) to a solution of 1-Boc-azetidin-3-one (3.45 g) in methanol (175 ml), the mixture was stirred for 14 hours at room temperature under a hydrogen atmosphere. The catalyst was filtered and the filtrate was concentrated under reduced pressure. The residue was partitioned between ethyl acetate and saturated aqueous sodium hydrogencarbonate. The combined organic layers were dried over anhydrous sodium sulfate. This was followed by concentration to provide the title compound (4.07 g, 101%) as a colorless oil.

$^1$H-NMR Spectrum (CDCl$_3$) δ (ppm): 1.43 (9H, m), 2.17 (6H, s), 3.01 (1H, m), 3.79 (2H, m), 3.91 (2H, m).

Production Example 189-2

N-[1-(1-Benzylpiperidin-4-yl)azetidin-3-yl]-N,N-dimethylamine trihydrochloride tert-Butyl 3-dimethylaminoazetidine-1-carboxylate (7.00 g) was stirred while cooling in an ice bath, trifluoroacetic acid (21.6 ml) was added thereto, and the mixture was stirred for 30 minutes in an ice bath and then for 1.5 hours at room temperature. The reaction mixture was concentrated to provide a crude product of 3-(dimethylamino)azetidine ditrifluoroacetate (ESI-MS (m/z): 101[M+H]$^+$) as a brown oil. This was dissolved in dichloromethane (350 ml), and then 1-benzyl-4-piperidone (6.49 ml) was added and the mixture was stirred for 10 minutes at room temperature. It was then cooled on ice, sodium triacetoxyborohydride (11.1 g) was added thereto, and the mixture was stirred at room temperature for 2 hours. The reaction mixture was concentrated. Ethyl acetate (300 ml), brine and potassium carbonate were added to the residue and stirred therewith at room temperature for 20 minutes, and then the mixture was partitioned. The aqueous layer was extracted with ethyl acetate:tetrahydrofuran=1:1. The organic layers were combined and a 4N hydrochloric acid-ethyl acetate solution (26.3 ml) was added to the dried organic layer. The mixture was concentrated to provide a crude product of the title compound (14.1 g) as colorless crystals.

ESI-MS (m/z): 274[M+H]$^+$.

Production Example 189-3

N,N-Dimethyl-N-[1-(piperidin-4-yl)azetidin-3-yl] amine trihydrochloride

After adding 10% palladium-carbon (5.0 g) to a solution of the crude N-[1-(1-benzylpiperidin-4-yl)azetidin-3-yl]-N,N-dimethylamine trihydrochloride (14.1 g) in 2-propanol (380 ml)-water (380 ml), the mixture was stirred for 12 hours at room temperature under a hydrogen atmosphere. The catalyst was then filtered. The filtrate was concentrated under reduced pressure to provide a crude product of the title compound (10.7 g) as colorless crystals.

ESI-MS (m/z): 184(M+H]$^+$.

Production Example 189-4

Benzyl {4-[2-({4-[3-(dimethylamino)azetidin-1-yl] piperidine-1-carbonyl}amino)pyridin-4-yloxy]-2-fluorophenyl}carbamate After adding triethylamine (0.169 ml) and phenyl chloroformate (0.133 ml) to a solution of benzyl [4-(2-aminopyridin-4-yloxy)-2-fluorophenyl]carbamate (150 mg) in tetrahydrofuran (6.64 ml), the mixture was stirred for 23 hours at room temperature under a nitrogen atmosphere. The reaction mixture was concentrated under reduced pressure. After adding N,N-dimethylformamide (1.5 ml), dimethyl-[1-(piperidin-4-yl)azetidin-3-yl]amine trihydrochloride (498 mg) and triethylamine (0.200 ml) to the residue, the mixture was stirred for 12 hours at room temperature. Ethyl acetate (30 ml) and 1N aqueous sodium hydroxide (10 ml) were added to the reaction mixture, and stirring was carried out at room temperature for 1 hour. Brine was added thereto and the mixture was extracted with ethyl acetate. The aqueous layer was extracted with ethyl acetate. The organic layers were combined and washed with 1N aqueous sodium hydroxide and brine in that order, and then dried over anhydrous sodium sulfate. The dried organic layer was concentrated and the residue was purified by silica gel column chromatography (Fuji Silysia NH, eluent; ethyl acetate, then ethyl acetate: methanol=19:1). Fractions containing the target compound were concentrated to provide the title compound (118 mg, 49.3%) as a pale yellow solid.

$^1$H-NMR Spectrum (CDCl$_3$) δ (ppm): 1.26-1.35 (2H, m), 1.73 (2H, m), 2.12 (6H, s), 2.25 (1H, m), 2.83 (3H, m), 3.05 (2H, m), 3.49 (2H, m), 3.88 (2H, m), 5.23 (2H, s), 6.50 (1H, dd, J=2.4, 6.0 Hz), 6.85-6.91 (3H, m), 7.23-7.26 (2H, m), 7.35-7.42 (4H, m), 7.61 (1H, d, J=2.4 Hz), 8.04 (1H, d, J=6.0 Hz), 8.14 (1H, brs). ESI-MS (m/z): 563[M+H]$^+$.

Example 190

2-{[4-(4-Hydroxypiperidin-1-yl)piperidin-1-yl]carbonylamino}-4-(4-{3-[2-(4-fluorophenyl)acetyl] thioureido}phenoxy)pyridine After adding a solution of 2-(4-fluorophenyl)acetyl isothiocyanate in toluene (0.25 M, 3.0 ml) to a solution of 4-(4-aminophenoxy)-2-{[4-(4-hydroxypiperidin-1-yl)piperidin-1-yl]carbonylamino}pyridine (214 mg) and (+)-10-camphorsulfonic acid (105 mg) in ethanol (4.0 ml) at room temperature, the mixture was stirred for 4 hours. The reaction mixture was partitioned between ethyl acetate and saturated aqueous sodium hydrogencarbonate. The organic layer was washed with saturated aqueous sodium hydrogencarbonate and brine and dried over anhydrous sodium sulfate. The solvent was distilled off, and the residue was purified by silica gel column chromatography (Fuji Silysia NH, eluent; ethyl acetate:methanol=100:0 to 97:3) to provide the title compound (58.6 mg, 19%) as white powder.

$^1$H-NMR Spectrum (CDCl$_3$) δ (ppm): 1.40-2.00 (8H, m), 2.32 (2H, m), 2.51 (1H, m), 2.75-2.95 (4H, m), 3.60-3.80 (3H, m), 4.05-4.20 (2H, m), 6.54 (1H, dd, J=2.4, 5.6 Hz), 7.10-7.40

(7H, m), 7.63 (1H, d, J=2.4 Hz), 7.67-7.70 (2H, m), 8.04 (1H, d, J=5.6 Hz), 8.50 (1H, brs), 12.26 (1H, brs). ESI-MS (m/z): 607[M+H]$^+$.

Production Example 190-1

2-{[4-(4-Hydroxypiperidin-1-yl)piperidin-1-yl]carbonylamino}-4-(4-nitrophenoxy)pyridine 2-Amino-4-(4-nitrophenoxy)pyridine (116 mg) was dissolved in tetrahydrofuran (2.5 ml) under a nitrogen atmosphere. Triethylamine (0.175 ml) and phenyl chloroformate (0.157 ml) were then added dropwise while cooling in an ice water bath. After stirring for 30 minutes at room temperature, the solvent was distilled off under reduced pressure. A solution of 4-(4-hydroxypiperidin-1-yl)piperidine (500 mg) in N,N-dimethylformamide (5.0 ml) was added to the resultant residue at room temperature under a nitrogen atmosphere and the mixture was stirred overnight. The reaction mixture was partitioned between ethyl acetate and water. The organic layer was washed with 1N aqueous sodium hydroxide and brine and dried over anhydrous sodium sulfate. The solvent was distilled off under reduced pressure, and then the residue was purified by silica gel column chromatography (Fuji Silysia NH, eluent; ethyl acetate:methanol=100:0 to 97:3) to provide the title compound (243 mg) as a pale yellow oil.
$^1$H-NMR Spectrum (CDCl$_3$) δ (ppm): 1.40-2.00 (8H, m), 2.33 (2H, m), 2.52 (1H, m), 2.75-3.00 (4H, m), 3.71 (1H, m), 4.00-4.20 (2H, m), 6.64 (1H, dd, J=2.4, 5.6 Hz), 7.15-7.30 (3H, m), 7.75 (1H, d, J=2.4 Hz), 8.16 (1H, d, J=5.6 Hz), 8.25-8.30 (2H, m)

Production Example 190-2

4-(4-Aminophenoxy)-2-{[4-(4-hydroxypiperidin-1-yl)piperidin-1-yl]carbonylamino}pyridine 2-{[4-(4-Hydroxypiperidin-1-yl)piperidin-1-yl]carbonylamino}-4-(4-nitrophenoxy)pyridine (243 mg) was dissolved in tetrahydrofuran (25 ml). After then adding 20% palladium hydroxide-carbon (140 mg), the mixture was stirred overnight under a hydrogen atmosphere. The catalyst was filtered and washed with tetrahydrofuran. The filtrate and the washings were then combined and concentrated under reduced pressure, and the resultant residue was dried under reduced pressure to provide the title compound (214 mg) as pale yellow powder.
ESI-MS (m/z): 412[M+H]$^+$.

Example 191

4-(4-{3-[2-(4-Fluorophenyl)acetyl]thioureido}phenoxy)-2-{[4-(1-methylpiperazin-4-yl)piperidin-1-yl]carbonylamino}pyridine After adding a solution of 2-(4-fluorophenyl)acetyl isothiocyanate in toluene (0.25 M, 3.0 ml) to a solution of 4-(4-aminophenoxy)-2-{[4-(1-methylpiperazin-4-yl)piperidin-1-yl]carbonylamino}pyridine (149 mg) and (+)-10-camphorsulfonic acid (152 mg) in ethanol (4.0 ml) at room temperature, the mixture was stirred for 3 hours. The reaction mixture was partitioned between ethyl acetate and saturated aqueous sodium hydrogencarbonate. The organic layer was washed with saturated aqueous sodium hydrogencarbonate and brine and dried over anhydrous sodium sulfate. The solvent was then distilled off, and the residue was purified by silica gel column chromatography (Fuji Silysia NH, eluent; ethyl acetate:methanol=98:2 to 97:3) to provide the title compound (88.2 mg, 40%) as white powder.
$^1$H-NMR Spectrum (CDCl$_3$) δ (ppm): 1.40-2.00 (5H, m), 2.34 (3H, s), 2.40-3.00 (10H, m), 3.71 (2H, s), 4.05-4.20 (2H, m), 6.54 (1H, dd, J=2.4, 5.6 Hz), 7.10-7.40 (7H, m), 7.63 (1H, d, J=2.4 Hz), 7.67-7.70 (2H, m), 8.04 (1H, d, J=5.6 Hz), 8.47 (1H, brs), 12.26 (1H, brs). ESI-MS (m/z): 606[M+H]$^+$.

Production Example 191-1

2-{[4-(1-Methylpiperazin-4-yl)piperidin-1-yl]carbonylamino}-4-(4-nitrophenoxy)pyridine 2-Amino-4-(4-nitrophenoxy)pyridine (116 mg) was dissolved in tetrahydrofuran (2.5 ml) under a nitrogen atmosphere. Triethylamine (0.175 ml) and phenyl chloroformate (0.157 ml) were then added dropwise while cooling in an ice water bath. After stirring for 30 minutes at room temperature, the solvent was distilled off under reduced pressure. A solution of 4-(1-methylpiperazin-4-yl)piperidine (500 mg) in N,N-dimethylformamide (5.0 ml) was added to the resultant residue at room temperature under a nitrogen atmosphere and the mixture was stirred overnight. The reaction mixture was partitioned between ethyl acetate and water. The organic layer was washed with 1N aqueous sodium hydroxide and brine and dried over anhydrous sodium sulfate. The solvent was distilled off under reduced pressure, and then the residue was purified by silica gel column chromatography (Fuji Silysia NH, eluent; ethyl acetate:methanol=100:0 to 97:3) to provide the title compound (163 mg, 74%) as a pale yellow oil.
$^1$H-NMR Spectrum (CDCl$_3$) δ (ppm): 1.40-2.00 (5H, m), 2.31 (3H, s), 2.40-3.00 (10H, m), 4.00-4.20 (2H, m), 6.64 (1H, dd, J=2.4, 5.6 Hz), 7.15-7.30 (3H, m), 7.75 (1H, d, J=2.4 Hz), 8.15 (1H, d, J=5.6 Hz), 8.25-8.30 (2H, m).

Production Example 191-2

4-(4-Aminophenoxy)-2-{[4-(1-methylpiperazin-4-yl)piperidin-1-yl]carbonylamino}pyridine 2-{[4-(1-Methylpiperazin-4-yl)piperidin-1-yl]carbonylamino}-4-(4-nitrophenoxy)pyridine (163 mg) was dissolved in tetrahydrofuran (20 ml). After adding 20% palladium hydroxide-carbon (104 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (149 mg, 98%) as pale yellow powder.
ESI-MS (m/z): 411[M+H]$^+$.

Example 192

4-(2-Fluoro-4-{3-[2-(4-fluorophenyl)acetyl]thioureido}phenoxy)-6-{[4-(1-methylpiperazin-4-yl)piperidin-1-yl]carbonylamino}pyrimidine After adding a solution of 2-(4-fluorophenyl)acetyl isothiocyanate in toluene (0.25 M, 2.0 ml) to a solution of 4-(4-amino-2-fluorophenoxy)-6-{[4-(1-methylpiperazin-4-yl)piperidin-1-yl]carbonylamino}pyrimidine (98 mg) and (+)-10-camphorsulfonic acid (79 mg) in ethanol (2.0 ml) at room temperature, the mixture was stirred for 3.5 hours. The reaction mixture was partitioned between ethyl acetate and saturated aqueous sodium hydrogencarbonate. The organic layer was washed with saturated aqueous sodium hydrogencarbonate and brine and dried over anhydrous sodium sulfate. The solvent was then distilled off, and the residue was purified by silica gel column chromatography (Fuji Silysia NH, eluent; ethyl acetate, then ethyl acetate:methanol=97:3) to provide the title compound (65.2 mg, 46%) as white powder.

$^1$H-NMR Spectrum (CDCl$_3$) δ (ppm): 1.40-2.00 (5H, m), 2.30 (3H, s), 2.40-3.00 (10H, m), 3.71 (2H, s), 4.00-4.20 (2H, m), 7.10-7.40 (7H, m), 7.62 (1H, d, J=0.8 Hz), 7.86 (1H, dd, J=2.4, 11.6 Hz), 8.33 (1H, d, J=0.8 Hz), 8.64 (1H, brs), 12.40 (1H, brs). ESI-MS (m/z): 625[M+H]$^+$.

Production Example 192-1

4-(2-Fluoro-4-nitrophenoxy)-6-{[4-(1-methylpiperazin-4-yl)piperidin-1-yl]carbonylamino}pyrimidine 4-Amino-6-(2-fluoro-4-nitrophenoxy)pyrimidine (100 mg) was dissolved in tetrahydrofuran (2 ml) under a nitrogen atmosphere. Triethylamine (0.139 ml) and phenyl chloroformate (0.125 ml) were added dropwise while cooling in an ice water bath. After stirring for 15 minutes at room temperature, the solvent was distilled off under reduced pressure. A solution of 4-(1-methylpiperazin-4-yl)piperidine (440 mg) in N,N-dimethylformamide (4.0 ml) was added to the resultant residue at room temperature under a nitrogen atmosphere and the mixture was stirred for 2 hours. The reaction mixture was partitioned between ethyl acetate and water. The organic layer was washed with 1N aqueous sodium hydroxide and brine and dried over anhydrous sodium sulfate. The solvent was distilled off under reduced pressure, and then the residue was purified by silica gel column chromatography (Fuji Silysia NH, eluent; ethyl acetate, then ethyl acetate:methanol=97:3) to provide the title compound (104 mg, 57%) as a pale yellow oil.

$^1$H-NMR Spectrum (CDCl$_3$) δ (ppm): 1.40-2.00 (5H, m), 2.34 (3H, s), 2.40-3.00 (10H, m), 4.00-4.20 (2H, m), 7.35-7.45 (2H, m), 7.73 (1H, d, J=0.8 Hz), 8.07-8.15 (2H, m), 8.32 (1H, d, J=0.8 Hz).

Production Example 192-2

4-(4-Amino-2-fluorophenoxy)-6-{[4-(1-methylpiperazin-4-yl)piperidin-1-yl]carbonylamino}pyrimidine 4-(2-Fluoro-4-nitrophenoxy)-6-{[4-(1-methylpiperazin-4-yl)piperidin-1-yl]carbonylamino}pyrimidine (104 mg) was dissolved in tetrahydrofuran (15 ml). After adding 20% palladium hydroxide-carbon (70 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (98 mg, quantitative) as a pale yellow oil.

ESI-MS (m/z): 430[M+H]$^+$.

Example 193

4-(2-Fluoro-4-{3-[2-(4fluorophenyl)acetyl]thioureido}phenoxy)-6-{[4-(1-methylpiperidin-4-yl)piperazin-1-yl]carbonylamino}pyrimidine After adding a solution of 2-(4-fluorophenyl)acetyl isothiocyanate in toluene (0.25 M, 2.5 ml) to a solution of 4-(4-amino-2-fluorophenoxy)-6-{[4-(1-methylpiperidin-4-yl)piperazin-1-yl]carbonylamino}pyrimidine (134 mg) and (+)-10-camphorsulfonic acid (109 mg) in ethanol (3.0 ml) at room temperature, the mixture was stirred for 3.5 hours. The reaction mixture was partitioned between ethyl acetate and saturated aqueous sodium hydrogencarbonate. The organic layer was washed with saturated aqueous sodium hydrogencarbonate and brine in that order and dried over anhydrous sodium sulfate. The solvent was distilled off, and the residue was purified by silica gel column chromatography (Fuji Silysia NH, eluent; ethyl acetate, then ethyl acetate:methanol=98:2). Fractions containing the target compound were concentrated to provide the title compound (60.7 mg, 31%) as white powder.

$^1$H-NMR Spectrum (CDCl$_3$) δ (ppm): 1.50-2.10 (6H, m), 2.20-2.40 (4H, m), 2.55-2.65 (4H, m), 2.90-3.10 (2H, m), 3.50-3.60 (4H, m), 3.71 (2H, s), 7.10-7.40 (7H, m), 7.63 (1H, d, J=0.8 Hz), 7.87 (1H, dd, J=2.4, 11.6 Hz), 8.33 (1H, d, J=0.8 Hz), 8.44 (1H, brs), 12.38 (1H, brs). ESI-MS (m/z): 625[M+H]$^+$.

Production Example 193-1

4-(2-Fluoro-4-nitrophenoxy)-6-{[4-(1-methylpiperidin-4-yl)piperazin-1-yl]carbonylamino}pyrimidine 4-Amino-6-(2-fluoro-4-nitrophenoxy)pyrimidine (100 mg) was dissolved in tetrahydrofuran (2 ml) under a nitrogen atmosphere. Triethylamine (0.139 ml) and phenyl chloroformate (0.125 ml) were then added dropwise while cooling in an ice water bath. After stirring for 15 minutes at room temperature, the solvent was distilled off under reduced pressure. A solution of 4-(1-methylpiperidin-4-yl)piperazine (440 mg) in N,N-dimethylformamide (4.0 ml) was added to the resultant residue at room temperature under a nitrogen atmosphere and the mixture was stirred for 2 hours. The reaction mixture was then partitioned between ethyl acetate and water. The organic layer was washed with 1N aqueous sodium hydroxide and brine in that order and dried over anhydrous sodium sulfate. The solvent was distilled off under reduced pressure, and then the residue was purified by silica gel column chromatography (Fuji Silysia NH, eluent; ethyl acetate, then ethyl acetate:methanol=97:3) to provide the title compound (145 mg, 79%) as a pale yellow oil.

$^1$H-NMR Spectrum (CDCl$_3$) δ (ppm): 1.60-2.00 (6H, m), 2.20-2.30 (1H, m), 2.28 (3H, s), 2.55-2.65 (4H, m), 2.80-3.00 (2H, m), 3.40-3.60 (4H, m), 7.35-7.45 (2H, m), 7.73 (1H, d, J=0.8 Hz), 8.07-8.15 (2H, m), 8.32 (1H, d, J=0.8 Hz).

Production Example 193-2

4-(4-Amino-2-fluorophenoxy)-6-{[4-(1-methylpiperidin-4-yl)piperazin-1-yl]carbonylamino}pyrimidine 4-(2-Fluoro-4-nitrophenoxy)-6-{[4-(1-methylpiperidin-4-yl)piperazin-1-yl]carbonylamino}pyrimidine (145 mg) was dissolved in tetrahydrofuran (20 ml). After adding 20% palladium hydroxide-carbon (100 mg), the mixture was stirred overnight under a hydrogen atmosphere. The catalyst was filtered and washed with tetrahydrofuran. The filtrate and the washings were combined and concentrated under reduced pressure, and the resultant residue was dried under reduced pressure to provide the title compound (134 mg, 99%) as a pale yellow oil.

ESI-MS (m/z): 430[M+H]$^+$.

Example 194) 1-[1-(2-Dimethylaminoethyl)piperidin-4-yl]-3-[4-(4-{3-[2-(4-fluorophenyl)acetyl]thioureido}phenoxy)pyridin-2-yl]-1-methylurea After adding (1S)-(+)-10-camphorsulfonic acid (119 mg) to a solution of 3-[4-(4-aminophenoxy)pyridin-2-yl]-1-[1-(2-dimethylaminoethyl)piperidin-4-yl]-1-methylurea (121 mg) in ethanol (2.0 ml), the mixture was stirred for 10 minutes at room temperature. Next, 2-(4-fluorophenyl)acetyl isothiocyanate (2.34 ml, 0.25 M solution in toluene) was added thereto and the mixture was stirred at room temperature for 50 minutes. The reaction mixture was then partitioned between ethyl acetate and saturated aqueous sodium hydrogencarbonate. The organic layer was dried over anhydrous sodium sulfate and concentrated. The residue was purified by silica gel column chromatography (Fuji Silysia NH, ethyl acetate, then ethyl acetate:methanol=20:1 to 10:1). Fractions containing the target compound were combined and concentrated. The residue was purified by LC-MS (eluent; acetonitrile-water-trifluoroacetic acid system). Fractions containing the target compound were concentrated, and saturated aqueous sodium hydrogencarbonate was added to the resultant residue. The mixture was extracted with ethyl acetate, and the organic layer was washed with brine and dried over anhydrous sodium sulfate. It was then concentrated to provide the title compound (26.3 mg, 14.8%) as white powder.

$^1$H-NMR Spectrum (CDCl$_3$) δ (ppm): 1.64 (2H, m), 1.78 (2H, m), 2.10 (2H, m), 2.28 (6H, s), 2.47 (4H, m), 2.88 (3H, s), 3.10 (2H, m), 3.70 (2H, s), 4.16 (1H, m), 6.55 (1H, dd, J=2.4, 5.6 Hz), 7.08-7.16 (4H, m), 7.20 (1H, brs), 7.25-7.31 (2H, m), 7.66-7.69 (2H, m), 8.06 (1H, d, J=5.6 Hz), 8.82 (1H, brs), 12.28 (1H, s). ESI-MS (m/z): 608[M+H]$^+$.

Production Example 194-1

1-[1-(2-Dimethylaminoethyl)piperidin-4-yl]-1-methyl-3-[4-(4-nitrophenoxy)pyridin-2-yl]urea After adding triethylamine (0.209 ml) and phenyl chloroformate (0.157 ml) to a solution of 4-(4-nitrophenoxy)pyridin-2-ylamine (116 mg) in tetrahydrofuran (5.0 ml) at room temperature, the mixture was stirred for 30 minutes at room temperature under a nitrogen atmosphere. The reaction mixture was then concentrated. After adding N,N-dimethylformamide (2.0 ml) and N-[1-(2-dimethylaminoethyl)piperidin-4-yl]-N-methylamine (463 mg) to the residue, stirring was carried out at room temperature for 6 hours. Ethyl acetate and 1N aqueous sodium hydroxide were added to the reaction mixture and stirred therewith for 15 minutes, and then the mixture was partitioned. The aqueous layer was extracted with ethyl acetate. The organic layers were combined, and then washed with brine and dried over anhydrous sodium sulfate. After concentration, the residue was purified by silica gel column chromatography (Fuji Silysia NH, eluent; ethyl acetate, then ethyl acetate:methanol=20:1 to 10:1). Fractions containing the target compound were concentrated to provide the title compound (186 mg, 84.1%) as a pale yellow oil.

$^1$H-NMR Spectrum (CDCl$_3$) δ (ppm): 1.65 (2H, m), 1.79 (2H, m), 2.10 (2H, m), 2.25 (6H, s), 2.40-2.50 (4H, m), 2.90 (3H, s), 3.01 (2H, m), 4.15 (1H, m), 6.65 (1H, dd, J=2.4, 5.6 Hz), 7.18 (2H, d, J=9.2 Hz), 7.25 (1H, brs), 7.80 (1H, d, J=2.4 Hz), 8.17 (1H, d, J=5.6 Hz), 8.27 (2H, d, J=9.2 Hz). ESI-MS (m/z): 443[M+H]$^+$.

Production Example 194-2

3-[4-(4-Aminophenoxy)pyridin-2-yl]-1-[1-(2-dimethylaminoethyl)piperidin-4-yl]-1-methylurea After adding 20% palladium hydroxide-carbon (50 mg) to a solution of 1-[1-(2-dimethylaminoethyl)piperidin-4-yl]-1-methyl-3-[4-(4-nitrophenoxy)pyridin-2-yl]urea (186 mg) in tetrahydrofuran (5.0 ml), the mixture was stirred for 12 hours at room temperature under a hydrogen atmosphere. The catalyst was filtered. The filtrate was concentrated to provide the title compound (121 mg, 69.8%) as a pale yellow oil.

$^1$H-NMR Spectrum (CDCl$_3$) δ (ppm): 1.64 (2H, m), 1.78 (2H, m), 2.10 (2H, m), 2.26 (6H, s), 2.42-2.51 (4H, m), 2.87 (3H, s), 2.97-3.04 (2H, m), 4.18 (1H, m), 6.48 (1H, dd, J=2.4, 6.0 Hz), 6.70 (2H, d, J=8.8 Hz), 6.90 (2H, d, J=8.8 Hz), 7.21 (1H, brs), 7.62 (1H, d, J=2.4 Hz), 7.99 (1H, d, J=6.0 Hz). ESI-MS (m/z): 413[M+H]$^+$.

Example 195

4-[3-(Dimethylamino)azetidin-1-yl]piperidine-1-carboxylic acid [4-(4-{3-[2-(4-fluorophenyl)acetyl]thioureido}phenoxy)pyridin-2-yl]amide After adding (1S)-(+)-10-camphorsulfonic acid (90.7 mg) to a solution of 4-[3-(dimethylamino)azetidin-1-yl]piperidine-1-carboxylic acid [4-(4-aminophenoxy)pyridin-2-yl]amide (91.5 mg) in ethanol (2.0 ml), the mixture was stirred for 10 minutes at room temperature. Then, 2-(4-fluorophenyl)acetyl isothiocyanate (1.28 ml, 0.25 M solution in toluene) was added and stirring was carried out at room temperature for 50 minutes. The reaction mixture was partitioned between ethyl acetate and saturated aqueous sodium hydrogencarbonate. The organic layer was dried over anhydrous sodium sulfate and concentrated. The residue was purified by silica gel column chromatography (Fuji Silysia NH, ethyl acetate, then ethyl acetate:methanol=20:1 to 10:1). Fractions containing the target compounds were combined and concentrated. The residue was then purified by LC-MS (eluent; acetonitrile-water-trifluoroacetic acid system). Fractions containing the target compound were combined and concentrated, and then saturated aqueous sodium hydrogencarbonate was added to the residue. The mixture was extracted with ethyl acetate, and the organic layer was washed with brine and dried over anhydrous sodium sulfate. It was then concentrated, and the obtained precipitate was suspended in diethyl ether-hexane and filtered. The filtered solid was washed with diethyl ether. It was then dried by aspiration to provide the title compound (14.2 mg, 10.5%) as white powder.

$^1$H-NMR Spectrum (CDCl$_3$) δ (ppm): 1.31 (2H, m), 1.72 (2H, m), 2.16 (6H, s), 2.33 (1H, m), 2.94 (3H, m), 3.04 (2H, m), 3.56 (2H, m), 3.71 (2H, s), 3.90 (2H, m), 6.53 (1H, dd, J=2.4, 6.0 Hz), 7.12 (4H, m), 7.26-7.31 (3H, m), 7.63-7.69 (3H, m), 8.04 (1H, d, J=6.0 Hz), 8.55 (1H, s), 12.26 (1H, s). ESI-MS (m/z): 606[M+H]$^+$, 628[M+Na]$^+$.

Production Example 195-1

4-[3-(Dimethylamino)azetidin-1-yl]piperidine-1-carboxylic acid [4-(4-nitrophenoxy)pyridin-2-yl]amide After adding triethylamine (0.209 ml) and phenyl chloroformate (0.157 ml) to a solution of 4-(4-nitrophenoxy)pyridin-2-ylamine (116 mg) in tetrahydrofuran (5.0 ml) at room temperature, the mixture was stirred for 30 minutes at room temperature under a nitrogen atmosphere. The reaction mixture was then concentrated. Triethylamine (0.697 ml), N,N-dimethyl-N-[1-(piperidin-4-yl)azetidin-3-yl]amine trihydrochloride (5.0 ml, 0.5 M solution in N,N-dimethylformamide) and water (0.2 ml) were added to the residue, and stirring was carried out at room temperature for 6 hours. Ethyl acetate and 1N aqueous sodium hydroxide were added to the reaction mixture and stirred therewith for 15 minutes, and then the mixture was partitioned. The aqueous layer was extracted with ethyl acetate. The organic layers were combined, and then washed with brine and dried over anhydrous sodium sulfate. It was concentrated and the residue was purified by silica gel column chromatography (Fuji Silysia NH, eluent; ethyl acetate, then ethyl acetate:methanol=20:1 to 10:1). Fractions containing the target compound were concentrated to provide the title compound (112 mg, 50.9%) as a pale yellow oil.

$^1$H-NMR Spectrum (CDCl$_3$) δ (ppm): 1.32 (2H, m), 1.71-1.77 (2H, m), 2.12 (6H, s), 2.27 (1H, m), 2.84 (3H, m), 3.07 (2H, m), 3.48-3.53 (2H, m), 3.85-3.91 (2H, m), 6.40 (1H, dd, J=2.0, 5.6 Hz), 7.09 (1H, m), 7.18 (2H, d, J=9.2 Hz), 7.74 (1H, d, J=2.0 Hz), 8.15 (1H, d, J=5.6 Hz), 8.27 (2H, d, J=9.2 Hz). ESI-MS (m/z): 441[M+H]$^+$.

Production Example 195-2

4-[3-(Dimethylamino)azetidin-1-yl]piperidine-1-carboxylic acid [4-(4-aminophenoxy)pyridin-2-yl] amide After adding 20% palladium hydroxide-carbon (50 mg) to a solution of 4-[3-(dimethylamino)azetidin-1-yl]piperidine-1-carboxylic acid [4-(4-nitrophenoxy)pyridin-2-yl]amide (112 mg) in tetrahydrofuran (5.0 ml), the mixture was stirred for 12 hours at room temperature under a hydrogen atmosphere. The catalyst was filtered. The filtrate was concentrated to provide the title compound (91.5 mg, 87.8%) as a pale yellow oil.

$^1$H-NMR Spectrum (CDCl$_3$) δ (ppm): 1.30 (2H, m), 1.70-1.78 (2H, m), 2.12 (6H, s), 2.26 (1H, m), 2.82-2.87 (3H, m), 3.02 (2H, m), 3.48-3.55 (2H, m), 3.90 (2H, m), 6.47 (1H, dd, J=2.4, 5.6 Hz), 6.69 (2H, d, J=8.8 Hz), 6.89 (2H, d, J=8.8 Hz), 7.40 (1H, brs), 7.55 (1H, m), 7.96 (1H, d, J=5.6 Hz). ESI-MS (m/z): 411[M+H]$^+$.

Example 196

4-(1-Methylazetidin-3-yl)piperazine-1-carboxylic acid [6-(2-fluoro-4-{3-[2-(4-fluorophenyl)acetyl] thioureido}phenoxy)pyrimidin-4-yl]amide After adding (1S)-(+)-10-camphorsulfonic acid (29.4 mg) to a solution of 4-(1-methylazetidin-3-yl)piperazine-1-carboxylic acid [6-(4-amino-2-fluorophenoxy)pyrimidin-4-yl] amide (31.8 mg) in ethanol (1.5 ml), the mixture was stirred for 10 minutes at room temperature. A solution of 2-(4-fluorophenyl)acetyl isothiocyanate in toluene (0.25 M, 0.634 ml) was added thereto, and stirring was carried out at room temperature for 30 minutes. The reaction mixture was partitioned between saturated aqueous sodium hydrogencarbonate and ethyl acetate. The organic layer was washed with brine and dried over anhydrous sodium sulfate. It was then concentrated, and the residue was purified by LC-MS (eluent; acetonitrile-water-trifluoroacetic acid system). Fractions containing the target compound were concentrated, and saturated aqueous sodium hydrogencarbonate was added to the residue. The mixture was then extracted with ethyl acetate. The organic layer was washed with brine and dried over anhydrous sodium sulfate. It was concentrated to provide the title compound (8.0 mg, 16.9%) as white powder.

$^1$H-NMR Spectrum (CDCl$_3$) δ (ppm): 2.36 (4H, m), 2.43 (3H, s), 3.03 (3H, m), 3.55 (4H, m), 3.62 (2H, m), 3.71 (2H, s), 7.12 (2H, m), 7.21 (1H, m), 7.26-7.30 (2H, m), 7.34-7.39 (2H, m), 7.63 (1H, d, J=0.8 Hz), 7.86 (1H, dd, J=2.4, 11.2 Hz), 8.33 (1H, d, J=0.8 Hz), 8.59 (1H, brs), 12.39 (1H, s). ESI-MS (m/z): 597[M+H]$^+$.

Production Example 196-1

1-(1-Methylazetidin-3-yl)piperazine trihydrochloride

After adding 1-Boc-azetidin-3-one (495 mg) and acetic acid (0.182 ml) to a solution of 1-benzylpiperazine (0.500 ml) in methanol (25 ml), the mixture was stirred for 5 minutes at room temperature. Then, 10% palladium-carbon (308 mg) was added thereto and the mixture was stirred for 15 hours at room temperature under a hydrogen atmosphere. The catalyst was then filtered. The residue was partitioned between ethyl acetate and saturated aqueous sodium hydrogencarbonate. The organic layer was washed with brine and then dried over anhydrous sodium sulfate. It was concentrated to provide a crude product of 4-benzyl-1-(1-Boc-azetidin-3-yl)piperazine (ESI-MS (m/z): 332[M+H]$^+$). It was dissolved in tetrahydrofuran (10 ml). Lithium aluminum hydride (219 mg) was then added thereto while stirring the mixture in an ice bath. After stirring for 15 minutes in an ice bath under a nitrogen atmosphere and for 15 minutes at room temperature, the mixture was heated to reflux for 3.5 hours at 100° C. The reaction mixture was cooled in an ice bath. Water (0.22 ml), 5N aqueous sodium hydroxide (0.22 ml) and water (1.1 ml) were added thereto, and the mixture was stirred in an ice bath for 1 hour. The insoluble portion was filtered. A solution of 4N hydrochloric acid-ethyl acetate (2.17 ml) was added to the filtrate, and the mixture was concentrated to provide a crude product of 4-benzyl-1-(1-methylazetidin-3-yl)piperazine trihydrochloride (ESI-MS (m/z): 246[M+H]$^+$). It was dissolved in water (25 ml) and 2-propanol (25 ml). After adding 10% palladium-carbon (615 mg), the mixture was stirred for 12 hours at room temperature under a hydrogen atmosphere. The catalyst was filtered. The filtrate was concentrated to provide a crude product of the title compound (382 mg) as a white solid.

ESI-MS (m/z): 156[M+H]$^+$.

Production Example 196-2

4-(1-Methylazetidin-3-yl)piperazine-1-carboxylic acid [6-(2-fluoro-4-nitrophenoxy)pyrimidin-4-yl] amide After adding triethylamine (0.167 ml) and phenyl chloroformate (0.126 ml) to a solution of 6-(2-fluoro-4-nitrophenoxy)pyrimidin-4-ylamine (100 mg) in tetrahydrofuran (5.0 ml), the mixture was stirred for 30 minutes at room temperature. The reaction mixture was concentrated, and then N,N-dimethylformamide (3.0 ml), 1-(1-methylazetidin-3-yl)piperazine trihydrochloride (382 mg), triethylamine (0.669 ml) and water (0.30 ml) were added thereto and the mixture was stirred at room temperature for 2.5 hours. Ethyl acetate and 1N aqueous sodium hydroxide were added to the reaction mixture, and stirring was carried out at room temperature for 20 minutes. This was followed by extraction with ethyl acetate. The organic layer was washed with brine and dried over anhydrous sodium sulfate. It was then concentrated, and the residue was purified by silica gel column chromatography (Fuji Silysia NH, eluent; ethyl acetate, ethyl acetate:methanol=20:1 to 10:1). Fractions containing the target compound were concentrated to provide the title compound (69.1 mg, 40.0%) as a yellow amorphous substance.

$^1$H-NMR Spectrum (CDCl$_3$) δ (ppm): 2.34-2.38 (7H, m), 2.91-3.02 (3H, m), 3.51-3.58 (6H, m), 7.42 (1H, m), 7.51 (1H, brs), 7.73 (1H, d, J=1.2 Hz), 8.11 (2H, m), 8.32 (1H, d, J=1.2 Hz). ESI-MS (m/z): 432[M+H]$^+$.

Production Example 196-3

4-(1-Methylazetidin-3-yl)piperazine-1-carboxylic acid [6-(4-amino-2-fluorophenoxy)pyrimidin-4-yl] amide After adding 20% palladium hydroxide (150 mg) to a solution of 4-(1-methylazetidin-3-yl)piperazine-1-carboxylic acid [6-(2-fluoro-4-nitrophenoxy)pyrimidin-4-yl]amide (69.1 mg) in tetrahydrofuran, the mixture was stirred for 7 hours at room temperature under a hydrogen atmosphere. The catalyst was then filtered. The filtrate was concentrated to provide the title compound (31.8 mg, 64.2%) as a yellow oil.

ESI-MS (m/z): 402[M+H]$^+$.

Example 197) 1-[1-(2-Dimethylaminoethyl)piperidin-4-yl]-3-[6-(4-{3-[2-(4-fluorophenyl)acetyl] thioureido}phenoxy)pyrimidin-4-yl]-1-methylurea After adding (1S)-(+)-10-camphorsulfonic acid (127 mg) to a solution of crude 3-[6-(4-aminophenoxy)pyrimidin-4-yl]-1-[1-(2-dimethylaminoethyl)piperidin-4-yl]-1-methylurea (119 mg) in ethanol (3.0 ml), the mixture was stirred for 15 minutes at room temperature. After then adding 2-(4-fluorophenyl)acetyl isothiocyanate (4.08 ml, 0.25 M solution in toluene) thereto, the mixture was stirred at room temperature for 2 hours. The reaction mixture was partitioned between saturated aqueous sodium hydrogencarbonate (10 ml) and ethyl acetate (30 ml). The organic layer was washed with brine and dried over anhydrous sodium sulfate. The dried organic layer was concentrated and the residue was purified by silica gel column chromatography (Fuji Silysia NH, eluent; ethyl acetate, then ethyl acetate:methanol=20:1 to 10:1). Fractions containing the target compound were concentrated, and the residue was purified by LC-MS (water-acetonitrile-trifluoroacetic acid system). Fractions containing the target compound were concentrated, saturated aqueous sodium hydrogencarbonate was added to the residue, and the mixture was extracted with ethyl acetate. The organic layer was then dried over anhydrous sodium sulfate. The dried organic layer was concentrated. Diethyl ether was added to the obtained solid to produce a suspension. The resulting precipitate was filtered and then dried to provide the title compound (12.4 mg) as white powder.

$^1$H-NMR Spectrum (CDCl$_3$) δ (ppm): 1.86 (2H, m), 2.20 (2H, m), 2.46 (6H, brs), 2.62 (4H, m), 2.92 (3H, s), 3.07 (2H, m), 3.71 (2H, s), 4.22 (1H, m), 7.12 (2H, m), 7.17 (2H, d, J=8.8 Hz), 7.26-7.31 (5H, m), 7.59 (1H, s), 7.71 (2H, d, J=8.8 Hz), 8.38 (1H, s), 8.46 (1H, brs), 12.27 (1H, s). ESI-MS (m/z): 609[M+H]$^+$.

Production Example 197-1

1-[1-(2-Dimethylaminoethyl)piperidin-4-yl]-1-methyl-3-[6-(4-nitrophenoxy)pyrimidin-4-yl]urea After adding triethylamine (0.112 ml) and phenyl chloroformate (0.089 ml) to a solution of 6-(4-nitrophenoxy)pyrimidin-4-ylamine (75.0 mg) in tetrahydrofuran (4.0 ml) at room temperature, the mixture was stirred for 30 minutes at room temperature. The reaction mixture was concentrated, N,N-dimethylformamide (3.0 ml) and N-[1-(2-dimethylaminoethyl)piperidin-4-yl]-N-methylamine (341 mg) were added to the residue, and the mixture was stirred at room temperature for 46 hours. Ethyl acetate (30 ml) and 1N aqueous sodium hydroxide (20 ml) were added to the reaction mixture and stirring was carried out at room temperature for 1 hour. The reaction mixture was then partitioned. The aqueous layer was extracted with ethyl acetate (50 ml). The organic layer was dried over anhydrous sodium sulfate and concentrated. The obtained solid was suspended in diethyl ether:hexane=1:3. The supernatant was removed off, and the remaining portion was dried to provide the title compound (131 mg, 91.4%) as yellow powder.

$^1$H-NMR Spectrum (CDCl$_3$) δ (ppm): 1.66 (2H, m), 1.80 (2H, m), 2.12 (2H, m), 2.26 (6H, s), 2.47 (4H, m), 2.90 (3H, s), 3.04 (2H, m), 4.17 (1H, m), 7.31 (2H, d, J=9.0 Hz), 7.42 (1H, brs), 7.70 (1H, s), 8.30 (2H, d, J=9.0 Hz), 8.39 (1H, s). ESI-MS (m/z): 444[M+H]$^+$.

Production Example 197-2

3-[6-(4-Aminophenoxy)pyrimidin-4-yl]-1-[1-(2-dimethylaminoethyl)piperidin-4-yl]-1-methylurea After adding 20% palladium hydroxide-carbon (51.8 mg) to a solution of 1-[1-(2-dimethylaminoethyl)piperidin-4-yl]-1-methyl-3-[6-(4-nitrophenoxy)pyrimidin-4-yl]urea (131 mg) in tetrahydrofuran (10.0 ml), the mixture was stirred for 10.5 hours at room temperature under a hydrogen atmosphere. The catalyst was filtered and the then washed with methanol. The filtrate was concentrated to provide a crude product of the title compound (122 mg) as a yellow oil.

ESI-MS (m/z): 414[M+H]$^+$.

Example 198

4-[2-(Pyrrolidin-1-yl)ethyl]piperazine-1-carboxylic acid {6-[2-fluoro-4-(3-phenylacetylthioureido)phenoxy]pyrimidin-4-yl}amide After dissolving 4-[2-(pyrrolidin-1-yl)ethyl]piperazine-1-carboxylic acid [6-(4-amino-2-fluorophenoxy)pyrimidin-4-yl]amide (49 mg) in ethanol (2 ml) under a nitrogen atmosphere, D-10-camphorsulfonic acid (53 mg) was added and the mixture was stirred for 5 minutes. A 0.25 M solution of 2-phenylacetyl isothiocyanate in toluene (0.684 ml) was added to the reaction mixture and stirring was carried out for 1 hour. The reaction mixture was partitioned between ethyl acetate (50 ml) and saturated aqueous sodium hydrogencarbonate (30 ml). The organic layer was washed with saturated aqueous sodium hydrogencarbonate (30 ml), water (30 ml) and brine (30 ml) in that order and then dried over anhydrous sodium sulfate. The solvent was distilled off under reduced pressure, and then the resultant residue was purified by silica gel column chromatography (Fuji Silysia NH, eluent; heptane:ethyl acetate=1:8). Fractions containing the target compound were concentrated under reduced pressure, and then diethyl ether (1.0 ml) and hexane (1.5 ml) were added to the resultant residue to produce a suspension of the solid. After filtering the solid, it was subjected to aeration drying to provide the title compound (5.8 mg, 8.4%) as white powder.

$^1$H-NMR Spectrum (CDCl$_3$) δ (ppm): 1.81 (4H, m), 2.40-2.65 (10H, m), 2.66 (2H, m), 3.55 (4H, m), 3.74 (2H, s), 7.00-7.45 (8H, m), 7.64 (1H, brs), 7.86 (1H, dd, J=2.0, 11.6 Hz), 8.33 (1H, brs), 8.44 (1H, m), 12.42 (1H, brs). ESI-MS (m/z): 607[M+H]$^+$.

Production Example 198-1

4-[2-(Pyrrolidin-1-yl)ethyl]piperazine-1-carboxylic acid [6-(2-fluoro-4-nitrophenoxy)pyrimidin-4-yl] amide After dissolving 6-(2-fluoro-4-nitrophenoxy)pyrimidin-4-ylamine (100 mg) in tetrahydrofuran (3 ml) under a nitrogen atmosphere, triethylamine (0.167 ml) and phenyl chloroformate (0.151 ml) were added while stirring in an ice water bath. The reaction mixture was allowed to warm to room temperature and stirred for 30 minutes. The reaction mixture was then partitioned between ethyl acetate (50 ml) and saturated aqueous sodium hydrogencarbonate (30 ml). The separated organic layer was washed with saturated aqueous sodium hydrogencarbonate (30 ml), water (30 ml) and brine (30 ml) in that order and then dried over anhydrous sodium sulfate. The solution was distilled off under reduced pressure, N,N-dimethylformamide (3 ml) was added to the resultant residue, and then 1-[2-(pyrrolidin-1-yl)ethyl]piperazine (295 mg)-N,N-dimethylformamide (0.5 ml×3) was added and the mixture was stirred for 18 hours. The reaction mixture was partitioned between ethyl acetate (50 ml) and saturated aqueous ammonium chloride (30 ml). The separated organic layer was washed with saturated aqueous ammonium chloride (30 ml), water (30 ml) and brine (30 ml) in that order and then dried over anhydrous sodium sulfate. The solution was distilled off under reduced pressure, and then the resultant residue was purified by silica gel column chromatography (Fuji Silysia NH, eluent; heptane:ethyl acetate=1:1, ethyl acetate, then ethyl acetate:ethanol=19:1). Fractions containing the target compound were concentrated under reduced pressure to provide a crude product of the title compound (130 mg, 70.7%) as a pale brown oil.

$^1$H-NMR Spectrum (CDCl$_3$) δ (ppm): 1.80 (4H, m), 2.40-2.80 (12H, m), 3.56 (4H, m), 7.34-7.50 (2H, m), 7.73 (1H, s), 8.11 (2H, m), 8.32 (1H, m).

Production Example 198-2

4-[2-(Pyrrolidin-1-yl)ethyl]piperazine-1-carboxylic acid [6-(4-amino-2-fluorophenoxy)pyrimidin-4-yl] amide After adding tetrahydrofuran (3 ml) and methanol (3 ml) to a crude product of 4-[2-(pyrrolidin-1-yl)ethyl]piperazine-1-carboxylic acid [6-(2-fluoro-4-nitrophenoxy)pyrimidin-4-yl] amide (129 mg) under a nitrogen atmosphere, 10% palladium-carbon (60 mg) was added, the atmosphere in the reaction vessel was replaced with hydrogen, and the mixture was stirred for 4.5 hours. The atmosphere in the reaction vessel was then replaced with nitrogen, and the catalyst was filtered and washed with methanol. The filtrate was concentrated under reduced pressure. The resultant residue was purified by silica gel column chromatography (Fuji Silysia NH, eluent; ethyl acetate:methanol=19:1), and then Fractions containing the target compound were concentrated under reduced pressure to provide a crude product of the title compound (98.4 mg) as a pale yellow amorphous substance.

$^1$H-NMR Spectrum (CDCl$_3$) δ (ppm): 1.79 (4H, m), 2.45-2.60 (10H, m), 2.60-2.69 (2H, m), 3.54 (4H, m), 3.73 (2H, brs), 6.44 (1H, m), 6.50 (1H, dd, J=2.8, 12.0 Hz), 6.98 (1H, m), 7.32 (1H, m), 7.55 (1H, m), 8.36 (1H, m)

Example 199

1-[6-(2-Fluoro-4-{3-[2-(4-fluorophenyl)acetyl] thioureido}phenoxy)pyrimidin-4-yl]-3-(1-methylpiperidin-4-yl)urea The title compound (50.2 mg, 44.1%) was obtained as pale yellow powder from a crude product of 1-[6-(4-amino-2-fluorophenoxy)pyrimidin-4-yl]-3-(1-methylpiperidin-4-yl) urea (73.9 mg) and a 0.2 M solution of 2-(4-fluorophenyl) acetyl isothiocyanate in toluene (1.6 ml).

$^1$H-NMR Spectrum (CDCl$_3$) δ (ppm): 1.41 (2H, m), 1.80 (2H, m), 2.03 (2H, m), 2.15 (3H, m), 2.52-2.72 (2H, m), 3.49 (1H, m), 3.83 (2H, s), 7.18 (3H, m), 7.26 (2H, m), 7.30-7.50 (4H, m), 7.88 (1H, m), 8.37 (1H, s), 9.48 (1H, brs), 11.78 (1H, m). ESI-MS (m/z): 556[M+H]$^+$.

Production Example 199-1

1-[6-(4-Amino-2-fluorophenoxy)pyrimidin-4-yl]-3-(1-methylpiperidin-4-yl)urea

A crude product of the title compound (73.9 mg) was obtained as a yellow oil from 1-[6-(2-fluoro-4-nitrophenoxy) pyrimidin-4-yl]-3-(1-methylpiperidin-4-yl)urea (80 mg). ESI-MS (m/z): 361[M+H]$^+$.

Example 200

4-(Pyrrolidin-1-yl)piperidine-1-carboxylic acid [4-(4-{3-[2-(4-fluorophenyl)acetyl] thioureido}phenoxy)pyridin-2-yl]amide The title compound (15.3 mg, 15.5%) was obtained as white powder from a crude product of 4-(pyrrolidin-1-yl) piperidine-1-carboxylic acid [4-(4-aminophenoxy)pyridin-2-yl]amide (65.3 mg), D-10-camphorsulfonic acid (79.4 mg) and a 0.2 M solution of 2-(4-fluorophenyl)acetyl isothiocyanate in toluene (0.2 ml).

$^1$H-NMR Spectrum (CDCl$_3$) δ (ppm): 1.18-1.36 (4H, m), 1.65 (4H, m), 1.78 (2H, m), 2.12 (1H, m), 2.38-2.60 (2H, m), 2.86 (2H, m), 3.82 (2H, s), 3.96 (2H, m), 6.56 (1H, dd, J=2.0, 5.6 Hz), 7.10-7.29 (4H, m), 7.30-7.56 (3H, m), 7.71 (2H, d, J=8.8 Hz), 8.12 (1H, d, J.=5.6 Hz), 9.19 (1H, brs), 11.72 (1H, m), 12.37 (1H, m). ESI-MS (m/z): 577[M+H]$^+$.

Production Example 200-1

4-(Pyrrolidin-1-yl)piperidine-1-carboxylic acid [4-(4-aminophenoxy)pyridin-2-yl]amide A crude product of the title compound (65.3 mg) was obtained as a yellow oil from 4-(pyrrolidin-1-yl)piperidine-1-carboxylic acid [4-(4-nitrophenoxy)pyridin-2-yl]amide (87.6 mg) synthesized from [4-(4-nitrophenoxy)pyridin-2-yl]carbamic acid phenyl ester (75 mg), N,N-dimethylformamide (3 ml) and 4-(pyrrolidin-1-yl)piperidine (98.6 mg)
ESI-MS (m/z): 382[M+H]$^+$.

Example 201

3-[6-(2-Fluoro-4-{3-[2-(4-fluorophenyl)acetyl] thioureido}phenoxy)pyrimidin-4-yl]-1-methyl-1-[(3S)-1-methylpyrrolidin-3-yl]urea The title compound (23.0 mg, 17%) was obtained as white crystals from 3-[6-(4-amino-2-fluorophenoxy)pyrimidin-4- yl]-1-methyl-1-[(3S)-1-methylpyrrolidin-3-yl]urea (90 mg), (+)-10-camphorsulfonic acid (53.3 mg) and a solution of 2-(4-fluorophenyl)acetyl isothiocyanate in toluene (0.1 M, 3 ml).

$^1$H-NMR Spectrum (CDCl$_3$) δ (ppm): 1.99 (1H, m), 2.13 (1H, m), 2.30-2.40 (2H, m), 2.44 (3H, s), 3.05 (1H, m), 3.08 (3H, s), 3.24 (1H, m), 3.71 (2H, s), 4.12 (1H, m), 7.10-7.40 (7H, m), 7.71 (1H, d, J=0.8 Hz), 7.84 (1H, dd, J=2.4, 11.2 Hz), 8.34 (1H, d, J=0.8 Hz), 8.42 (1H, brs), 12.36 (1H, brs).

Production Example 201-1

3-[6-(2-Fluoro-4-nitrophenoxy)pyrimidin-4-yl]-1-methyl-1-[(3S)-1-methylpyrrolidin-3-yl]urea The title compound (93 mg, 60%) was obtained as white crystals from 4-amino-6-(2-fluoro-4-nitrophenoxy)pyrimidine (100 mg), triethylamine (0.140 ml), phenyl chloroformate (0.125 ml), a solution of (3S)-1-methyl-3-methylaminopyrrolidine dihydrochloride (468 mg) in N,N-dimethylformamide (2.5 ml), and triethylamine (0.7 ml).

$^1$H-NMR Spectrum (CDCl$_3$) δ (ppm): 2.00 (1H, m), 2.14 (1H, m), 2.35-2.45 (2H, m), 2.46 (3H, s), 3.07 (1H, m), 3.09 (3H, s), 3.27 (1H, m), 4.10 (1H, m), 7.39 (1H, m), 7.81 (1H, d, J=0.8 Hz), 8.07-8.14 (2H, m), 8.33 (1H, d, J=0.8 Hz).

Production Example 201-2

3-[6-(4-Amino-2-fluorophenoxy)pyrimidin-4-yl]-1-methyl-1-[(3S)-1-methylpyrrolidin-3-yl]urea The title compound (90 mg, quantitative) was obtained as white powder from 3-[6-(2-fluoro-4-nitrophenoxy)pyrimidin-4-yl]-1-methyl-1-[(3S)-1-methylpyrrolidin-3-yl]urea (93 mg).

ESI-MS (m/z): 361[M+H]$^+$.

Example 202

(1S,4S)-5-Methyl-2,5-diazabicyclo[2.2.1]heptane-2-carboxylic acid [6-(2-fluoro-4-{3-[2-(4-fluorophenyl)acetyl]thioureido}phenoxy)pyrimidin-4-yl]amide The title compound (48.2 mg, 73%) was obtained as white powder from (1S,4S)-5-methyl-2,5-diazabicyclo[2.2.1]heptane-2-carboxylic acid [6-(4-amino-2-fluorophenoxy)pyrimidin-4-yl]amide (42.7 mg), (+)-10-camphorsulfonic acid (27.6 mg) and a solution of 2-(4-fluorophenyl)acetyl isothiocyanate in toluene (0.1 M, 1.5 ml).

$^1$H-NMR Spectrum (CDCl$_3$) δ (ppm): 1.77 (1H, m), 1.97 (1H, m), 2.44 (3H, s), 2.73 (1H, m), 2.93 (1H, m), 3.33 (1H, dd, J=2.4, 8.8 Hz), 3.53 (1H, brs), 3.62 (1H, m), 3.71 (2H, s), 4.54 (1H, m), 7.00-7.40 (7H, m), 7.69 (1H, d, J=0.8 Hz), 7.86 (1H, dd, J=2.4, 11.2 Hz), 8.33 (1H, d, J=0.8 Hz), 8.43 (1H, brs), 12.38 (1H, brs).

Production Example 202-1

(1S,4S)-5-Methyl-2,5-diazabicyclo[2.2.1]heptane-2-carboxylic acid [6-(2-fluoro-4-nitrophenoxy)pyrimidin-4-yl]amide The title compound (95 mg, 61%) was obtained as pale yellow powder from 4-amino-6-(2-fluoro-4-nitrophenoxy)pyrimidine (100 mg), triethylamine (0.139 ml), phenyl chloroformate (0.125 ml) and a solution of (1S,4S)-2-methyl-2,5-diazabicyclo[2.2.1]heptane (359 mg) in N,N-dimethylformamide (3.2 ml).

$^1$H-NMR Spectrum (CDCl$_3$) δ (ppm): 1.78 (1H, m), 1.98 (1H, m), 2.45 (3H, s), 2.76 (1H, m), 2.92 (1H, m), 3.35 (1H, dd, J=2.4, 8.8 Hz), 3.54 (1H, s), 3.63 (1H, m), 4.56 (1H, br), 7.14 (1H, brs), 7.41 (1H, m), 7.79 (1H, s), 8.08-8.15 (2H, m), 8.32 (1H, s).

Production Example 202-2

(1S,4S)-5-Methyl-2,5-diazabicyclo[2.2.1]heptane-2-carboxylic acid [6-(4-amino-2-fluorophenoxy)pyrimidin-4-yl]amide The title compound (42.7 mg, 49%) was obtained as white powder from (1S,4S)-5-methyl-2,5-diazabicyclo[2.2.1]heptane-2-carboxylic acid [6-(2-fluoro-4-nitrophenoxy)pyrimidin-4-yl]amide (95 mg).

ESI-MS (m/z): 359[M+H]$^+$.

Example 203

3-[6-(2-Fluoro-4-{3-[2-(2-fluorophenyl)acetyl]thioureido}phenoxy)pyrimidin-4-yl]-1-methyl-1-(1-methylpiperidin-4-yl)urea The title compound (15.3 mg, 17.7%) was obtained as white powder from 3-[6-(4-amino-2-fluorophenoxy)pyrimidin-4-yl]-1-methyl-1-(1-methylpiperidin-4-yl)urea (57.0 mg), D-10-camphorsulfonic acid (35.3 mg) and a crude product of 2-(2-fluorophenyl)acetyl isothiocyanate.

$^1$H-NMR Spectrum (CDCl$_3$) δ (ppm): 1.50-1.76 (2H, m), 1.81 (2H, m), 2.12 (2H, m), 2.31 (3H, s), 2.86-3.04 (5H, m), 3.77 (2H, s), 4.20 (1H, m), 7.08-7.50 (7H, m), 7.68 (1H, s), 7.87 (1H, dd, J=2.4, 11.6 Hz), 8.34 (1H, s), 8.63 (1H, brs), 12.36 (1H, brs). ESI-MS (m/z): 592[M+Na]$^+$.

Example 204

3-[6-(2-Fluoro-4-{3-[2-(3-fluorophenyl)acetyl]thioureido}phenoxy)pyrimidin-4-yl]-1-methyl-1-(1-methylpiperidin-4-yl)urea The title compound (15.3 mg, 17.4%) was obtained as white powder from 3-[6-(4-amino-2-fluorophenoxy)pyrimidin-4-yl]-1-methyl-1-(1-methylpiperidin-4-yl)urea (57.5 mg), D-10-camphorsulfonic acid (35.8 mg) and a crude product of 2-(3-fluorophenyl)acetyl isothiocyanate.

$^1$H-NMR Spectrum (CDCl$_3$) δ (ppm): 1.62-1.75 (2H, m), 1.82 (2H, m), 2.12 (2H, m), 2.31 (3H, s), 2.85-3.02 (5H, m), 3.77 (2H, s), 4.20 (1H, m), 7.10-7.50 (7H, m), 7.68 (1H, d, J=1.2 Hz), 7.87 (1H, dd, J=2.8, 11.6 Hz), 8.34 (1H, d, J=1.2 Hz), 8.59 (1H, brs), 12.35 (1H, brs). ESI-MS (m/z): 592[M+Na]$^+$.

Example 205

4-Methylpiperazine-1-carboxylic acid [6-(2-fluoro-4-{3-[2-(4-fluorophenyl)acetyl]thioureido}phenoxy)pyrimidin-4-yl]amide The title compound (65 mg, 35%) was obtained as white powder from 4-methylpiperazine-1-carboxylic acid [6-(4-amino-2-fluorophenoxy)pyrimidin-4-yl]amide (119 mg), (+)-10-camphorsulfonic acid (79.9 mg) and a solution of 2-(4-fluorophenyl)acetyl isothiocyanate in toluene (0.1 M, 4.5 ml).

$^1$H-NMR Spectrum (CDCl$_3$) δ (ppm): 2.34 (3H, s), 2.42-2.50 (4H, m), 3.52-3.58 (4H, m), 3.71 (2H, s), 7.10-7.40 (7H, m), 7.63 (1H, d, J=0.8 Hz), 7.86 (1H, dd, J=2.4, 11.2 Hz), 8.33 (1H, d, J=0.8 Hz), 8.45 (1H, brs), 12.38 (1H, brs).

Production Example 205-1

4-Methylpiperazine-1-carboxylic acid [6-(2-fluoro-4-nitrophenoxy)pyrimidin-4-yl]amide The title compound (135.5 mg, 72%) was obtained as white powder from 4-amino-6-(2-fluoro-4-nitrophenoxy)pyrimidine (125 mg), triethylamine (0.180 ml), phenyl chloroformate (0.160 ml) and 1-methylpiperazine (0.424 ml).

$^1$H-NMR Spectrum (CDCl$_3$) δ (ppm): 2.35 (3H, s), 2.45-2.49 (4H, m), 3.55-3.59 (4H, m), 7.39-7.44 (2H, m), 7.73 (1H, s), 8.08-8.15 (2H, m), 8.32 (1H, s).

Production Example 205-2

4-Methylpiperazine-1-carboxylic acid [6-(4-amino-2-fluorophenoxy)pyrimidin-4-yl]amide The title compound (119 mg, 96%) was obtained as white powder from 4-methylpiperazine-1-carboxylic acid [6-(2-fluoro-4-nitrophenoxy)pyrimidin-4-yl]amide (135 mg).
ESI-MS (m/z): 369[M+Na]$^+$.

Example 206

1-(3-Dimethylaminopropyl)-3-[6-(2-fluoro-4-{3-[2-(4-fluorophenyl)acetyl]thioureido}phenoxy)pyrimidin-4-yl]-1-methylurea The title compound (35.4 mg, 21%) was obtained as white powder from 3-[6-(4-amino-2-fluorophenoxy)pyrimidin-4-yl]-1-(3-dimethylaminopropyl)-1-methylurea (111 mg), (+)-10-camphorsulfonic acid (72.5 mg) and a solution of 2-(4-fluorophenyl)acetyl isothiocyanate in toluene (0.1 M, 4.0 ml).

$^1$H-NMR Spectrum (CDCl$_3$) δ (ppm): 1.72-1.82 (2H, m), 2.30 (6H, s), 2.34-2.42 (2H, m), 2.92 (3H, s), 3.36-3.44 (2H, m), 3.71 (2H, s), 7.10-7.40 (7H, m), 7.52 (1H, s), 7.83 (1H, dd, J=2.4, 11.2 Hz), 8.32 (1H, s), 8.44 (1H, brs), 12.36 (1H, brs).

Production Example 206-1

1-(3-Dimethylaminopropyl)-3-[6-(2-fluoro-4-nitrophenoxy)pyrimidin-4-yl]-1-methylurea The title compound (128 mg, 68%) was obtained as white crystals from 4-amino-6-(2-fluoro-4-nitrophenoxy)pyrimidine (120 mg), triethylamine (0.167 ml), phenyl chloroformate (0.150 ml) and N,N,N'-trimethyl-1,3-propanediamine (0.45 ml).

$^1$H-NMR Spectrum (CDCl$_3$) δ (ppm): 1.75-1.85 (2H, m), 2.31 (6H, s), 2.35-2.41 (2H, m), 2.94 (3H, s), 3.40-3.44 (2H, m), 7.40 (1H, m), 7.60 (1H, d, J=0.8 Hz), 8.06-8.13 (2H, m), 8.31 (1H, d, J=0.8 Hz).

Production Example 206-2

3-[6-(4-Amino-2-fluorophenoxy)pyrimidin-4-yl]-1-(3-dimethylaminopropyl)-1-methylurea The title compound (111 mg) was obtained as a colorless oil from 1-(3-dimethylaminopropyl)-3-[6-(2-fluoro-4-nitrophenoxy)pyrimidin-4-yl]-1-methylurea (128 mg).
ESI-MS (m/z): 363[M+H]$^+$.

Example 207

3-(Pyrrolidin-1-yl)azetidine-1-carboxylic acid [6-(2-fluoro-4-{3-[2-(4-fluorophenoxy)acetyl]thioureido}phenoxy)pyrimidin-4-yl]amide The title compound (8.3 mg, 6.53%) was obtained as white powder from 3-(pyrrolidin-1-yl)azetidine-1-carboxylic acid [6-(4-amino-2-fluorophenoxy)pyrimidin-4-yl]amide (ESI-MS (m/z): 395[M+Na]$^+$) synthesized from 3-(pyrrolidin-1-yl)azetidine-1-carboxylic acid [6-(2-fluoro-4-nitrophenoxy)pyrimidin-4-yl]amide (90.3 mg), (1S)-(+)-10-camphorsulfonic acid (8.5 mg), and 2-(4-fluorophenyl)acetyl isothiocyanate (0.2 M solution in toluene, 1.12 ml).

$^1$H-NMR Spectrum (CDCl$_3$) δ (ppm): 1.84 (4H, m), 2.52 (4H, m), 3.39 (1H, m), 3.71 (2H, s), 4.01 (2H, m), 4.13 (2H, m), 6.89 (1H, s), 7.12 (2H, m), 7.21 (2H, m), 7.29 (1H, m), 7.36 (1H, m), 7.65 (1H, d, J=0.8 Hz), 7.86 (1H, dd, J=2.4, 11.6 Hz), 8.33 (1H, d, J=0.8 Hz), 8.47 (1H, s), 12.38 (1H, s).
ESI-MS (m/z): (neg.): 566[M–H]$^-$.

Production Example 207-1

3-(Pyrrolidin-1-yl)azetidine-1-carboxylic acid [6-(2-fluoro-4-nitrophenoxy)pyrimidin-4-yl]amide The title compound (90.3 mg, 37.4%) was obtained as a pale yellow amorphous substance from 6-(2-fluoro-4-nitrophenoxy)pyrimidin-4-ylamine (150 mg), triethylamine (0.209 ml), phenyl chloroformate (0.150 ml), 3-(pyrrolidin-1-yl)azetidine ditrifluoroacetate (1.06 g) and triethylamine (1.0 ml).

$^1$H-NMR Spectrum (CDCl$_3$) δ (ppm): 1.68 (4H, m), 2.53 (4H, m), 3.39 (1H, m), 4.03 (2H, m), 4.16 (2H, m), 7.06 (1H, s), 7.41 (1H, m), 7.55 (1H, d, J=0.8 Hz), 8.08-8.14 (2H, m), 8.32 (1H, d, J=0.8 Hz). ESI-MS (m/z): 425[M+Na]$^+$.

Example 208

3-Dimethylaminoazetidine-1-carboxylic acid [6-(2-fluoro-4-{3-[2-(4-fluorophenyl)acetyl]thioureido}phenoxy)pyrimidin-4-yl]amide The title compound (22 mg) was obtained as white powder from a 1/2 amount of crude 3-dimethylaminoazetidine-1-carboxylic acid [6-(4-amino-2-fluorophenoxy)pyrimidin-4-yl]amide (ESI-MS (m/z): 369[M+Na]$^+$) synthesized from 3-dimethylaminoazetidine-1-carboxylic acid [6-(2-fluoro-4-nitrophenoxy)pyrimidin-4-yl]amide (88 mg), (1S)-(+)-10-camphorsulfonic acid (25.8 mg), and 2-(4-fluorophenyl)acetyl isothiocyanate (0.2 M solution in toluene, 0.556 ml).

$^1$H-NMR Spectrum (CDCl$_3$) δ (ppm): 2.20 (6H, s), 3.16 (1H, m), 3.71 (2H, s), 3.95 (2H, m), 4.09 (2H, m), 6.97 (1H, s), 7.09 (2H, m), 7.21 (2H, m), 7.26-7.37 (2H, m), 7.66 (1H, s), 7.86 (1H, dd, J=2.4, 11.2 Hz), 8.33 (1H, s), 8.74 (1H, brs), 12.41 (1H, s). ESI-MS (m/z): 564[M+Na]$^+$.

Production Example 208-1

3-Dimethylaminoazetidine-1-carboxylic acid [6-(2-fluoro-4-nitrophenoxy)pyrimidin-4-yl]amide The title compound (88.0 mg, 39.0%) was obtained as a pale yellow amorphous substance from 6-(2-fluoro-4-nitrophenoxy)pyrimidin-4-ylamine (150 mg), phenyl chloroformate (0.150 ml), crude 3-(pyrrolidin-1-yl)azetidine ditrifluoroacetate (1.28 g) and triethylamine.

$^1$H-NMR Spectrum (CDCl$_3$) δ (ppm): 2.21 (6H, s), 3.18 (1H, m), 3.97 (2H, m), 4.12 (2H, m), 7.00 (1H, s), 7.41 (1H, m), 7.76 (1H, s), 8.11 (2H, m), 8.32 (1H, s). ESI-MS (m/z): 398[M+Na]$^+$.

Example 209) 4-{[(3R)-3-(Dimethylaminomethyl)pyrrolidin-1-yl]carbonylamino}-6-(2-fluoro-4-{3-[2-(4-fluorophenyl)acetyl]thioureido}phenoxy)pyrimidine The title compound (41.4 mg, 29%) was obtained as white powder from 4-(4-amino-2-fluorophenoxy)-6-{[(3R)-3-(dimethylaminomethyl)pyrrolidin-1-yl]carbonylamino}pyrimidine (95.3 mg), (+)-10-camphorsulfonic acid (57.5 mg) and a solution of 2-(4-fluorophenyl)acetyl isothiocyanate in toluene (0.1 M, 3.3 ml).

$^1$H-NMR Spectrum (CDCl$_3$) δ (ppm): 1.72 (1H, m), 2.10 (1H, m), 2.25 (6H, s), 2.29-2.32 (2H, m), 2.50 (1H, m), 3.20 (1H, m), 3.40-3.70 (3H, m), 3.71 (2H, s), 7.10-7.40 (7H, m), 7.70 (1H, s), 7.86 (1H, dd, J=2.4, 11.2 Hz), 8.32 (1H, s), 8.44 (1H, brs), 12.38 (1H, brs).

Production Example 209-1

4-{[(3R)-3-(Dimethylaminomethyl)pyrrolidin-1-yl]carbonylamino}-6-(2-fluoro-4-nitrophenoxy)pyrimidine The title compound (112 mg, 55%) was obtained as a colorless oil from 4-amino-6-(2-fluoro-4-nitrophenoxy)pyrimidine (125 mg), phenyl chloroformate (0.150 ml), a solution of (3R)-3-(dimethylaminomethyl)pyrrolidine dihydrochloride (603 mg) in N,N-dimethylformamide (3.5 ml), and triethylamine.

$^1$H-NMR Spectrum (CDCl$_3$) δ (ppm): 2.05-2.25 (2H, m), 2.26 (6H, s), 2.30-2.32 (2H, m), 2.52 (1H, m), 3.22 (1H, dd, J=3.2, 9.6 Hz), 3.48 (1H, m), 3.60-3.70 (2H, m), 7.23 (1H, brs), 7.41 (1H, m), 7.79 (1H, d, J=0.8 Hz), 8.07-8.14 (2H, m), 8.31 (1H, d, J=0.8 Hz).

Production Example 209-2

4-(4-Amino-2-fluorophenoxy)-6-{[(3R)-3-(dimethylaminomethyl)pyrrolidin-1-yl]carbonylamino}pyrimidine The title compound (95.3 mg, 92%) was obtained as a pale yellow oil from 4-{[(3R)-3-(dimethylaminomethyl)pyrrolidin-1-yl]carbonylamino}-6-(2-fluoro-4-nitrophenoxy)pyrimidine (112 mg).

ESI-MS (m/z): 375[M+H]$^+$.

Example 210

3-[6-(2-Fluoro-4-{3-[2-(4-fluorophenyl)acetyl]thioureido}phenoxy)pyrimidin-4-yl]-1-methyl-1-[(3S)-(1-methylpyrrolidin-3-yl) methyl]urea The title compound (76.8 mg, 32%) was obtained as white powder from 3-[6-(4-amino-2-fluorophenoxy)pyrimidin-4-yl]-1-methyl-1-[(3S)-(1-methylpyrrolidin-3-yl)methyl]urea (162 mg), (+)-10-camphorsulfonic acid (97.1 mg) and a solution of 2-(4-fluorophenyl)acetyl isothiocyanate in toluene (0.1 M, 5.6 ml).

$^1$H-NMR Spectrum (CDCl$_3$) δ (ppm): 1.48 (1H, m), 2.01 (1H, m), 2.21 (1H, m), 2.32 (1H, m), 2.38 (3H, s), 2.48 (1H, m), 2.66 (1H, m), 2.98 (3H, s), 3.02-3.20 (2H, m), 3.49 (1H, dd, J=11.2, 14.8 Hz), 3.71 (2H, s), 7.10-7.40 (7H, m), 7.61 (1H, s), 7.85 (1H, dd, J=2.4, 11.2 Hz), 8.33 (1H, s), 8.48 (1H, brs), 12.37 (1H, brs).

Production Example 210-1

3-[6-(2-Fluoro-4-nitrophenoxy)pyrimidin-4-yl]-1-methyl-1-[(3S)-(1-methylpyrrolidin-3-yl)methyl]urea The title compound (174 mg, 86%) was obtained as a colorless oil from 4-amino-6-(2-fluoro-4-nitrophenoxy)pyrimidine (125 mg), triethylamine (0.167 ml), phenyl chloroformate (0.150 ml) and a solution of (3R)-1-methyl-3-(methylaminomethyl)pyrrolidine (449 mg) in N,N-dimethylformamide (3.5 ml).

ESI-MS (m/z): 427[M+Na]$^+$.

Production Example 210-2

3-[6-(4-Amino-2-fluorophenoxy)pyrimidin-4-yl]-1-methyl-1-[(3S)-(1-methylpyrrolidin-3-yl) methyl]urea The title compound (163 mg) was obtained as a pale yellow oil from 3-[6-(2-fluoro-4-nitrophenoxy)pyrimidin-4-yl]-1-methyl-1-[(3S)-(1-methylpyrrolidin-3-yl)methyl]urea (174 mg).

ESI-MS (m/z): 375[M+H]$^+$.

Example 211

4-(Pyrrolidin-1-yl)piperidine-1-carboxylic acid [6-(2-fluoro-4-{3-[2-(4-fluorophenyl)acetyl]ureido}phenoxy)pyrimidin-4-yl]amide The title compound (98.9 mg, 30.3%) was obtained as white powder from 4-(pyrrolidin-1-yl)piperidine-1-carboxylic acid [6-(4-amino-2-fluorophenoxy)pyrimidin-4-yl]amide (226 mg) and a 1.0 M solution of 2-(4-fluorophenyl)acetyl isocyanate in N,N-dimethylformamide (1.7 ml) under a nitrogen atmosphere.

$^1$H-NMR Spectrum (CDCl$_3$) δ (ppm): 1.50-1.68 (2H, m), 1.80 (4H, m), 1.97 (2H, m), 2.24 (1H, m), 2.58 (4H, m), 3.04 (2H, m), 3.72 (2H, s), 4.02 (2H, m), 7.10 (2H, m), 7.14-7.21 (2H, m), 7.24-7.34 (2H, m), 7.38 (1H, brs), 7.56-7.66 (2H, m), 7.96 (1H, brs), 8.34 (1H, brs), 10.53 (1H, brs). ESI-MS (m/z): 602[M+Na]$^+$.

Example 212

4-Dimethylaminopiperidine-1-carboxylic acid [4-(3-fluoro-4-{3-[2-(4-fluorophenyl)acetyl]thioureido}phenoxy)pyridin-2-yl]amide The title compound (18.5 mg) was obtained as white powder from a 1/2 amount of crude 4-dimethylaminopiperidine-1-carboxylic acid [4-(4-amino-3-fluorophenoxy)pyridin-2-yl]amide (ESI-MS (m/z): 374[M+H]$^+$) synthesized from benzyl (4-{2-[(4-dimethylaminopiperidine-1-carbonyl)amino]pyridin-4-yloxy}-2-fluorophenyl)carbamate (122 mg), (1S)-(+)-camphorsulfonic acid (55.8 mg), and a 0.2 M solution of 2-(4-fluorophenyl)acetyl isothiocyanate in toluene (1.12 ml).

$^1$H-NMR Spectrum (CDCl$_3$) δ (ppm): 1.42-1.53 (2H, m), 1.88 (2H, m), 2.30 (6H, s), 2.40 (1H, m), 2.91 (2H, m), 3.72 (2H, s), 4.12 (2H, m), 6.57 (1H, dd, J=2.0, 6.0 Hz), 6.91 (2H, d, J=8.4 Hz), 6.93-7.14 (2H, m), 7.25-7.31 (2H, m), 7.37 (1H, brs), 7.68 (1H, d, J=2.0 Hz), 8.08 (1H, d, J=6.0 Hz), 8.32 (1H, m), 8.79 (1H, brs), 12.31 (1H, s). ESI-MS (m/z): 569[M+H]$^+$.

Example 213

4-(Pyrrolidin-1-yl)piperidine-1-carboxylic acid [4-(3-fluoro-4-{3-[2-(4-fluorophenyl)acetyl]ureido}phenoxy)pyridin-2-yl]amide The title compound (2.6 mg) was obtained as pale yellow powder from a 1/2 amount of 4-(pyrrolidin-1-yl)piperidine-1-carboxylic acid [4-(4-amino-3-fluorophenoxy)pyridin-2-yl]amide (ESI-MS (m/z): 400[M+H]$^+$) synthesized from benzyl [2-fluoro-4-(2-{[4-(pyrrolidin-1-yl)piperidine-1-carbonyl]amino}pyridin-4-yloxy)phenyl]carbamate (155 mg), and a 1.0 M solution of 2-(4-fluorophenyl)acetyl isocyanate in toluene (0.635 ml).

$^1$H-NMR Spectrum (CDCl$_3$) δ (ppm): 1.55 (2H, m), 1.82 (4H, m), 1.95 (2H, m), 2.30 (1H, m), 2.64 (4H, m), 2.96 (2H, m), 3.73 (2H, s), 4.04 (2H, m), 6.52 (1H, dd, J=2.0, 5.6 Hz), 6.87-6.92 (2H, m), 7.07-7.12 (2H, m), 7.26-7.32 (2H, m), 7.62 (2H, d, J=2.0 Hz), 8.05 (1H, d, J=5.6 Hz), 8.15 (1H, m), 8.23 (1H, s), 10.66 (1H, s). ESI-MS (m/z): 579[M+H]$^+$.

Example 214

4-Dimethylaminopiperidine-1-carboxylic acid [4-(3-fluoro-4-{3-[2-(4-fluorophenyl)acetyl]ureido}phenoxy)pyridin-2-yl]amide The title compound (0.55 mg, 0.83%) was obtained from a 1/2 amount of 4-dimethylaminopiperidine-1-carboxylic acid [4-(4-amino-3-fluorophenoxy)pyridin-2-yl]amide (ESI-MS (m/z): 374[M+H]$^+$) synthesized from benzyl (4-{2-[(4-dimethylaminopiperidine-1-carbonyl)amino]pyridin-4-yloxy}-2-fluorophenyl)carbamate (122 mg), and a 1.0 M solution of 2-(4-fluorophenyl)acetyl isocyanate in toluene (0.360 ml).

$^1$H-NMR Spectrum (CDCl$_3$) δ (ppm): 1.42-1.55 (2H, m), 1.90 (2H, m), 2.33 (6H, s), 2.43 (1H, m), 2.90 (2H, m), 3.73 (2H, s), 4.13 (2H, m), 6.53 (1H, dd, J=2.0, 5.6 Hz), 6.85-6.92 (2H, m), 7.11 (2H, m), 7.29 (2H, m), 7.45-7.69 (3H, m), 8.05 (1H, d, J=5.6 Hz), 8.16 (1H, m), 10.13 (1H, s). ESI-MS (m/z): 553[M+H]$^+$, 575[M+Na]$^+$.

Example 215

1-[4-(3-Fluoro-4-{3-[2-(4-fluorophenyl)acetyl]thioureido}phenoxy)pyridin-2-yl]-3-(1-methylpiperidin-4-yl)urea The title compound (18.5 mg) was obtained as white powder from a 1/2 amount of 1-[4-(4-amino-3-fluorophenoxy)pyridin-2-yl]-3-(1-methylpiperidin-4-yl)urea synthesized from crude benzyl (2-fluoro-4-{2-[3-(1-methylpiperidin-4-yl)ureido]pyridin-4-yloxy}phenyl)carbamate (97.0 mg), (1S)-(+)-10-camphorsulfonic acid (51.6 mg), and 2-(4-fluorophenyl)acetyl isothiocyanate (0.2 M solution in toluene, 0.833 ml).

$^1$H-NMR Spectrum (CDCl$_3$) δ (ppm): 1.58-1.70 (2H, m), 1.98-2.06 (2H, m), 2.18 (1H, m), 2.30 (3H, s), 2.75 (2H, m), 3.76 (3H, s), 3.81 (1H, m), 6.18 (1H, d, J=2.0 Hz), 6.55 (1H, dd, J=2.0, 6.0 Hz), 6.90 (2H, m), 7.10 (2H, m), 7.28-7.33 (2H, m), 8.08 (1H, d, J=6.0 Hz), 8.30 (1H, m), 9.43 (1H, brs), 12.38 (1H, s). ESI-MS (m/z): 555[M+H]$^+$.

Production Example 215-1

Benzyl (2-fluoro-4-{2-[3-(1-methylpiperidin-4-yl)ureido]pyridin-4-yloxy}phenyl)carbamate A crude product of the title compound (97 mg) was obtained as a pale yellow oil from a 1/6 amount of a reaction intermediate obtained using benzyl [4-(2-aminopyridin-4-yloxy)-2-fluorophenyl]carbamate (2.1 g), triethylamine (2.49 ml) and phenyl chloroformate (1.64 ml), and 4-amino-1-methylpiperidine (566 mg).

ESI-MS (m/z): 494[M+H]$^+$.

Example 216

4-{[(3R)-3-Dimethylaminopyrrolidin-1-yl]carbonylamino}-6-(2-fluoro-4-{3-[2-(4-fluorophenyl)acetyl]thioureido}phenoxy)pyrimidine The title compound (88.9 mg, 47%) was obtained as white powder from 4-(4-amino-2-fluorophenoxy)-6-{[(3R)-3-dimethylaminopyrrolidin-1-yl]carbonylamino}pyrimidine (130 mg), (+)-10-camphorsulfonic acid (78.5 mg), and a solution of 2-(4-fluorophenyl)acetyl isothiocyanate in toluene (0.2 M, 2.75 ml).

$^1$H-NMR Spectrum (CDCl$_3$) δ (ppm): 1.92 (1H, m), 2.21 (1H, m), 2.30 (6H, s), 2.78 (1H, m), 3.26 (1H, m), 3.40-3.52 (1H, m), 3.64-3.84 (2H, m), 3.72 (2H, s), 7.10-7.40 (7H, m), 7.70 (1H, d, J=0.8 Hz), 7.87 (1H, dd, J=2.4, 11.2 Hz), 8.34 (1H, d, J=0.8 Hz), 8.44 (1H, brs), 12.39 (1H, brs).

Production Example 216-1

4-{[(3R)-3-Dimethylaminopyrrolidin-1-yl]carbonylamino}-6-(2-fluoro-4-nitrophenoxy)pyrimidine The title compound (132 mg, 68%) was obtained as pale yellow powder from 4-amino-6-(2-fluoro-4-nitrophenoxy)pyrimidine (125 mg), triethylamine (0.167 ml), phenyl chloroformate (0.150 ml) and (3R)-3-dimethylaminopyrrolidine (0.330 ml).

Production Example 216-2

4-(4-Amino-2-fluorophenoxy)-6-{[(3R)-3-dimethylaminopyrrolidin-1-yl]carbonylamino}pyrimidine The title compound (130 mg) was obtained as white powder from 4-{[(3R)-3-dimethylaminopyrrolidin-1-yl]carbonylamino}-6-(2-fluoro-4-nitrophenoxy)pyrimidine (132 mg).
ESI-MS (m/z): 383[M+Na]$^+$.

Example 217

3-[6-(2-Fluoro-4-{3-[2-(4-fluorophenoxy)acetyl]thioureido}phenoxy)pyrimidin-4-yl]-1-methyl-1-[3-(pyrrolidin-1-yl)propyl]urea The title compound (43.8 mg, 23.3%) was obtained as white powder from 3-[6-(4-amino-2-fluorophenoxy)pyrimidin-4-yl]-1-methyl-1-[3-(pyrrolidin-1-yl)propyl]urea (ESI-MS (m/z): 389[M+H]$^+$) synthesized from 3-[6-(2-fluoro-4-nitrophenoxy)pyrimidin-4-yl]-1-methyl-1-[3-(pyrrolidin-1-yl)propyl]urea (135 mg), (1S)-(+)-10-camphorsulfonic acid (142 mg), and 2-(4-fluorophenyl)acetyl isothiocyanate (0.2 M solution in toluene, 3.42 ml).
$^1$H-NMR Spectrum (CDCl$_3$) δ (ppm): 1.78 (2H, m), 1.96 (4H, m), 2.50 (2H, m), 2.57 (4H, m), 2.93 (3H, s), 3.43 (2H, m), 3.71 (2H, s), 7.12 (2H, m), 7.21 (1H, m), 7.25-7.35 (3H, m), 7.51 (1H, s), 7.84 (1H, dd, J=2.4, 11.6 Hz), 8.28 (1H, s), 8.51 (1H, s), 11.54 (1H, brs), 12.36 (1H, s). ESI-MS (m/z): 584[M+H]$^+$.

Production Example 217-1

3-[6-(2-Fluoro-4-nitrophenoxy)pyrimidin-4-yl]-1-methyl-1-[3-(pyrrolidin-1-yl)propyl]urea The title compound (135 mg, 67.2%) was obtained as pale yellow crystals from 6-(2-fluoro-4-nitrophenoxy)pyrimidin-4-ylamine (120 mg), triethylamine (0.334 ml), phenyl chloroformate (0.181 ml) and methyl-(3-pyrrolidin-1-ylpropyl)amine (341 mg).
$^1$H-NMR Spectrum (CDCl$_3$) δ (ppm): 1.80 (2H, m), 1.96 (4H, m), 2.52 (2H, t, J=6.0 Hz), 2.58 (4H, m), 2.94 (3H, s), 3.45 (2H, t, J=6.0 Hz), 7.40 (1H, m), 7.60 (1H, s), 8.07-8.13 (2H, m), 8.26 (1H, s), 11.64 (1H, brs). ESI-MS (m/z): 419 [M+H]$^+$.

Example 218

3-[6-(2-Fluoro-4-{3-[2-(4-fluorophenoxy)acetyl]thioureido}phenoxy)pyrimidin-4-yl]-1-methyl-1-[3-(azetidin-1-yl)propyl]urea The title compound (12.9 mg, 8.81%) was obtained as white powder from 3-[6-(4-amino-2-fluorophenoxy)pyrimidin-4-yl]-1-methyl-1-[3-(azetidin-1-yl)propyl]urea (ESI-MS (m/z): 375[M+H]$^+$, 397[M+Na]$^+$) synthesized from 3-[6-(2-fluoro-4-nitrophenoxy)pyrimidin-4-yl]-1-methyl-1-[3-(azetidin-1-yl)propyl]urea (104 mg), (1S)-(+)-10-camphorsulfonic acid (142 mg), and a 0.2 M solution of (4-fluorophenyl)acetyl isothiocyanate in toluene (2.73 ml).
$^1$H-NMR Spectrum (CDCl$_3$) δ (ppm): 1.63 (2H, m), 2.26 (2H, m), 2.46 (2H, m), 2.89 (3H, s), 3.29 (4H, m), 3.37 (2H, m), 3.71 (2H, s), 7.12 (2H, m), 7.29-7.35 (4H, m), 7.52 (1H, s), 7.85 (1H, dd, J=2.4, 11.6 Hz), 8.35 (1H, s), 8.48 (1H, s), 12.36 (1H, s). ESI-MS (m/z): 570[M+H]$^+$.

Production Example 218-1 tert-Butyl (3-azetidin-1-yl-3-oxopropyl)carbamate

After adding azetidine hydrochloride (2.96 g) to a solution of triethylamine (4.42 ml) in N,N-dimethylformamide, the mixture was stirred for 10 minutes at room temperature. Boc-beta-ALA-OH (5.00 g), 1-ethyl-3-(3-dimethylaminopropyl)carbodiimide hydrochloride (7.59 g) and 1-hydroxybenzotriazole (5.35 g) were added thereto, and the mixture was stirred at room temperature for 3 days. The reaction mixture was partitioned between ethyl acetate and brine. The organic layer was washed with brine and dried over anhydrous sodium sulfate. It was then concentrated under reduced pressure. The residue was purified by silica gel column chromatography (eluent; ethyl acetate, then ethyl acetate:methanol=10:1). Fractions containing the target compound were concentrated under reduced pressure to provide the title compound (5.99 g, 99.4%) as a pale yellow oil.
$^1$H-NMR Spectrum (CDCl$_3$) δ (ppm): 1.43 (9H, s), 2.28 (4H, m), 3.37 (2H, m), 4.03 (2H, m), 4.12 (2H, m), 5.27 (1H, brs). ESI-MS (m/z): 251[M+Na]$^+$.

Production Example 218-2

Methyl-(3-azetidin-1-ylpropyl)amine

Lithium aluminum hydride (2.98 g) was gradually added to a solution of tert-butyl (3-azetidin-1-yl-3-oxopropyl)carbamate (5.99 g) in tetrahydrofuran (150 ml) while stirring in an ice bath. The mixture was stirred under a nitrogen atmosphere, for 15 minutes in an ice bath and for 45 minutes at room temperature. It was then heated and stirred for 8 hours at 80° C. under a nitrogen atmosphere. The reaction mixture was further heated to reflux for 34 hours at 100° C. under a nitrogen atmosphere. It was then cooled in an ice bath. Water (2.98 ml), 5N aqueous sodium hydroxide (2.98 ml) and water (8.94 ml) were added thereto in that order while stirring, and the mixture was stirred at room temperature for 3 days. The insoluble portion was then filtered. The filtrate was concentrated under reduced pressure to provide the title compound (2.78 g, 82.8%) as a brown oil.
$^1$H-NMR Spectrum (CDCl$_3$) δ (ppm): 1.52 (2H, m), 2.05 (2H, m), 2.41 (3H, s), 2.43 (2H, m), 2.59 (2H, m), 3.15 (4H, m). ESI-MS (m/z): 129[M+H]$^+$.

Production Example 218-3

3-[6-(2-Fluoro-4-nitrophenoxy)pyrimidin-4-yl]-1-methyl-1-[3-(azetidin-1-yl)propyl]urea The title compound (104 mg, 53.6%) was obtained from 6-(2-fluoro-4-nitrophenoxy)pyrimidin-4-ylamine (120 mg), triethylamine (0.334 ml), phenyl chloroformate (0.181 ml) and methyl-(3-azetidin-1-ylpropyl)amine (341 mg).
$^1$H-NMR Spectrum (CDCl$_3$) δ (ppm): 1.65 (2H, m), 2.27 (2H, m), 2.47 (2H, t, J=6.0 Hz), 2.91 (3H, s), 3.30 (4H, m), 3.38 (2H, t, J=5.6 Hz), 7.41 (1H, dd, J=7.0, 9.0 Hz), 7.61 (1H, s), 8.07-8.13 (2H, m), 8.34 (1H, s), 12.56 (1H, brs). ESI-MS (m/z): 405[M+H]$^+$.

Example 219

(3S)-3-Dimethylaminomethylpyrrolidine-1-carboxylic acid [4-(3-fluoro-4-{3-[2-(4-fluorophenyl)acetyl]thioureido}phenoxy)pyridin-2-yl]amide The title compound (17.5 mg) was obtained as white powder from (3S)-3-dimethylaminomethylpyrrolidine-1-carboxylic acid [4-(4-amino-3-fluorophenoxy)pyridin-2-yl]amide synthesized from a crude product of benzyl (4-{2-[(3S)-3-dimethylaminomethylpyrrolidine-1-carbonyl]amino}pyridin-4-yloxy)-2-fluorophenyl)carbamate (128 mg), (1S)-(+)-10-camphorsulfonic acid (58.5 mg), and 2-(4-fluorophenyl)acetyl isothiocyanate (1.89 ml, 0.2 M solution in toluene).

$^1$H-NMR Spectrum (CDCl$_3$) δ (ppm): 1.70 (1H, m), 2.08 (1H, m), 2.24 (6H, s), 2.28 (2H, m), 2.47 (1H, m), 3.17 (1H, m), 3.43 (1H, m), 3.54-3.68 (2H, m), 3.72 (2H, s), 6.55 (1H, dd, J=2.0, 6.0 Hz), 6.92 (2H, d, J=8.8 Hz), 7.11 (3H, m), 7.26-7.31 (2H, m), 7.76 (1H, d, J=2.0 Hz), 8.07 (1H, d, J=6.0 Hz), 8.32 (1H, m), 8.67 (1H, s), 12.29 (1H, s). ESI-MS (m/z): 569[M+H]$^+$.

Production Example 219-1

Benzyl [(4-{2-[(3S)-3-dimethylaminomethylpyrrolidine-1-carbonyl]amino}pyridin-4-yloxy)-2-fluorophenyl]carbamate A crude product of the title compound (128 mg) was obtained from benzyl [4-(2-aminopyridin-4-yloxy)-2-fluorophenyl]carbamate (300 mg), phenyl chloroformate (0.266 ml), (3S)-3-(dimethylaminomethyl)pyrrolidine dihydrochloride (4.25 ml, 1.0 M solution in N,N-dimethylformamide) and triethylamine.

Example 220

3-[6-(2-Fluoro-4-{3-[2-(4-fluorophenyl)acetyl]thioureido}phenoxy)pyrimidin-4-yl]-1-methyl-1-[4-(pyrrolidin-1-yl)butyl]urea The title compound (13.4 mg, 12.7%) was obtained as pale yellow powder from 3-[6-(4-amino-2-fluoro-phenoxy)pyrimidin-4-yl]-1-methyl-1-[4-(pyrrolidin-1-yl)butyl]urea (ESI-MS (m/z): 403[M+H]$^+$) synthesized from 3-[6-(2-fluoro-4-nitrophenoxy)pyrimidin-4-yl]-1-methyl-1-[4-(pyrrolidin-1-yl)butyl]urea (76 mg), (1S)-(+)-10-camphorsulfonic acid (30.8 mg), and 2-(4-fluorophenyl)acetyl isothiocyanate.

$^1$H-NMR Spectrum (CDCl$_3$) δ (ppm): 1.59 (4H, m), 1.81 (4H, m), 2.56 (6H, m), 3.04 (3H, s), 3.39 (2H, m), 3.71 (2H, s), 7.12 (3H, m), 7.19-7.31 (3H, m), 7.35 (1H, m), 7.57 (1H, brs), 7.68 (1H, d, J=1.2 Hz), 7.85 (1H, dd, J=2.4, 11.2 Hz), 8.33 (1H, d, J=1.2 Hz), 12.38 (1H, s). ESI-MS (m/z): 598[M+H]$^+$.

Production Example 220-1

3-[6-(2-Fluoro-4-nitrophenoxy)pyrimidin-4-yl]-1-methyl-1-[4-(pyrrolidin-1-yl)butyl]urea The title compound (76 mg, 54.9%) was obtained as pale yellow crystals from 6-(2-fluoro-4-nitrophenoxy)pyrimidin-4-ylamine (80 mg), triethylamine (0.166 ml), phenyl chloroformate (0.124 ml) and methyl-[4-(pyrrolidin-1-yl)butyl]amine (250 mg).

$^1$H-NMR Spectrum (CDCl$_3$) δ (ppm): 1.54-1.72 (4H, m), 1.80 (4H, m), 2.52 (6H, m), 3.04 (3H, m), 3.40 (2H, m), 7.41 (1H, m), 7.74 (1H, brs), 7.78 (1H, s), 8.11 (2H, m), 8.32 (1H, s). ESI-MS (m/z): 433[M+H]$^+$.

Example 221

1-[1-(3-Dimethylaminopropyl)piperidin-4-yl]-3-[6-(2-fluoro-4-{3-[2-(4-fluorophenyl)acetyl]thioureido}phenoxy)pyrimidin-4-yl]-1-methylurea The title compound (41.3 mg, 22.7%) was obtained as white powder from 1-[1-(3-dimethylaminopropyl)piperidin-4-yl]-3-[6-(2-fluoro-4-nitrophenoxy)pyrimidin-4-yl]-1-methylurea (135 mg), 20% palladium hydroxide-carbon (50 mg), (1S)-(+)-10-camphorsulfonic acid (99 mg) and 2-(4-fluorophenyl)acetyl isothiocyanate.

$^1$H-NMR Spectrum (CDCl$_3$) δ (ppm): 1.58-1.84 (6H, m), 2.07 (2H, m), 2.23 (6H, s), 2.29 (2H, m), 2.37 (2H, m), 2.92 (3H, s), 3.03 (2H, m), 3.71 (2H, s), 4.18 (1H, s), 7.12 (2H, m), 7.22 (1H, m), 7.26-7.31 (3H, m), 7.36 (2H, m), 7.68 (1H, s), 7.86 (1H, dd, J=2.4, 11.4 Hz), 8.34 (1H, s), 12.38 (1H, s). ESI-MS (m/z): 641[M+H]$^+$.

Production Example 221-1 tert-Butyl [1-(3-dimethylaminopropionyl)piperidin-4-yl]carbamate

After adding N,N-dimethylaminopropionic acid hydrochloride (1.46 g), triethylamine (1.45 ml), 1-hydroxybenzotriazole (1.93 g) and 1-ethyl-3-(3-dimethylaminopropyl)carbodiimide hydrochloride (2.19 g) to a solution of 4-(tert-butoxycarbonylamino)piperidine (1.9 g) in N,N-dimethylformamide (30 ml), the mixture was stirred for 27.5 hours at room temperature under a nitrogen atmosphere. Ethyl acetate (200 ml), brine (50 ml) and 1N aqueous sodium hydroxide (50 ml) were added to the reaction mixture and stirred therewith at room temperature for 30 minutes, and then the mixture was partitioned. The aqueous layer was extracted with ethyl acetate. The organic layers were combined, and then washed with 1N aqueous sodium hydroxide and brine and dried over anhydrous sodium sulfate. The dried organic layer was concentrated under reduced pressure to provide the title compound (2.96 g, quantitative) as pale yellow crystals.

ESI-MS (m/z): 300[M+H]$^+$.

Production Example 221-2

N-[1-(3-Dimethylaminopropyl)piperidin-4-yl]-N-methylamine

A solution of tert-butyl [1-(3-dimethylaminopropionyl)piperidin-4-yl]carbamate (2.73 g) in tetrahydrofuran (30 ml) was stirred in an ice bath, and lithium aluminum hydride (1.04 g) was gradually added thereto. The mixture was stirred under a nitrogen atmosphere, for 15 minutes in an ice bath and for 15 minutes at room temperature. It was further heated to reflux for 7 hours under a nitrogen atmosphere. The reaction mixture was cooled in an ice bath, and then water (1.0 ml), 5N aqueous sodium hydroxide (1.0 ml) and water (5.0 ml) were added thereto in that order and stirring was carried out on ice. The insoluble portion was filtered. The filtrate was concentrated to provide the title compound (1.51 g, 83.2%) as a pale yellow oil.

$^1$H-NMR Spectrum (CDCl$_3$) δ (ppm): 1.32-1.42 (2H, m), 1.67 (2H, m), 1.89 (2H, m), 1.98 (2H, m), 2.22 (6H, s), 2.28 (2H, m), 2.32-2.38 (2H, m), 2.43 (3H, s), 2.90 (2H, m), 3.16-3.24 (1H, m). ESI-MS (m/z): 200[M+H]$^+$.

Production Example 221-3

1-[1-(3-Dimethylaminopropyl)piperidin-4-yl]-3-[6-(2-fluoro-4-nitrophenoxy)pyrimidin-4-yl]-1-methylurea The title compound (135 mg, 59.1%) was obtained as pale yellow powder from 6-(2-fluoro-4-nitrophenoxy)pyrimidin-4-ylamine (120 mg), triethylamine (0.191 ml), phenyl chloroformate (0.150 ml) and N-[1-(3-dimethylaminopropyl)piperidin-4-yl]-N-methylamine (478 mg).

$^1$H-NMR Spectrum (CDCl$_3$) δ (ppm): 1.63-1.86 (6H, m), 2.08 (2H, m), 2.23 (6H, s), 2.29 (2H, t, J=7.0 Hz), 2.38 (2H, t, J=7.8 Hz), 2.94 (3H, s), 3.03 (2H, m), 4.18 (1H, m), 7.40-7.43 (2H, m), 7.78 (1H, d, J=1.2 Hz), 8.03-8.14 (2H, m), 8.33 (1H, d, J=1.2 Hz). ESI-MS (m/z): 476[M+H]$^+$.

Example 222

1-[1-(3-Dimethylaminopropyl)piperidin-4-yl]-3-[4-(3-fluoro-4-{3-[2-(4-fluorophenyl)acetyl]thioureido}phenoxy)pyridin-2-yl]-1-methylurea The title compound (51.3 mg, 22.5%) was obtained as white powder from benzyl [4-(2-{3-[1-(3-dimethylaminopropyl)piperidin-4-yl]-3-methylureido}pyridin-4-yloxy)-2-fluorophenyl]carbamate (206 mg), 20% palladium hydroxide-carbon (50 mg), (1S)-(+)-10-camphorsulfonic acid (116 mg) and 2-(4-fluorophenyl)acetyl isothiocyanate (0.2 M solution in toluene, 2.67 ml).

$^1$H-NMR Spectrum (CDCl$_3$) δ (ppm): 1.62-1.85 (6H, m), 2.07 (2H, m), 2.27 (6H, s), 2.33-2.40 (4H, m), 2.90 (3H, s), 3.01 (2H, m), 3.72 (2H, s), 4.17 (1H, m), 6.57 (1H, dd, J=2.0, 5.6 Hz), 6.92 (2H, d, J=8.8 Hz), 7.12 (2H, m), 7.14-7.31 (4H, m), 7.74 (1H, d, J=2.0 Hz), 8.09 (1H, d, J=5.6 Hz), 8.33 (1H, m), 12.30 (1H, s). ESI-MS (m/z): 640[M+H]$^+$.

Production Example 222-1

Benzyl [4-(2-{3-[1-(3-dimethylaminopropyl)piperidin-4-yl]-3-methylureido}pyridin-4-yloxy)-2-fluorophenyl]carbamate The title compound (206 mg, 83.8%) was obtained as a pale yellow oil from benzyl [4-(2-aminopyridin-4-yloxy)-2-fluorophenyl]carbamate (150 mg), triethylamine (0.169 ml), phenyl chloroformate (0.133 ml) and N-[1-(3-dimethylaminopropyl)piperidin-4-yl]-N-methylamine (424 mg).

$^1$H-NMR Spectrum (CDCl$_3$) δ (ppm): 1.62-1.74 (6H, m), 2.02 (2H, m), 2.22 (6H, s), 2.26-2.38 (4H, m), 2.89 (3H, s), 3.00 (2H, m), 4.16 (1H, m), 5.23 (2H, s), 6.52 (1H, dd, J=2.4, 5.6 Hz), 6.85-6.90 (3H, m), 7.21 (1H, brs), 7.34-7.42 (5H, m), 7.68 (1H, d, J=2.4 Hz), 8.05 (1H, d, J=5.6 Hz), 8.12 (1H, brs). ESI-MS (m/z): 579[M+H]$^+$.

Example 223

1-[1-(2-Dimethylaminoethyl)piperidin-4-yl]-3-{4-[2-fluoro-4-(3-phenylacetylthioureido)phenoxy]pyridin-2-yl}-1-methylurea The title compound (19.4 mg, 13.8%) was obtained as white powder from 3-[4-(4-amino-2-fluorophenoxy)pyridin-2-yl]-1-[1-(2-dimethylaminoethyl)piperidin-4-yl]-1-methylurea (100 mg), (1S)-(+)-10-camphorsulfonic acid (116 mg) and 2-phenylacetyl isothiocyanate (0.2 M solution in N,N-dimethylformamide, 1.74 ml).

$^1$H-NMR Spectrum (CDCl$_3$) δ (ppm): 1.64 (2H, m), 1.78 (2H, m), 2.11 (2H, m), 2.28 (6H, s), 2.48 (4H, m), 2.88 (3H, s), 3.01 (2H, m), 3.74 (2H, s), 4.16 (1H, m), 6.55 (1H, dd, J=2.4, 6.0 Hz), 7.17 (2H, m), 7.30-7.45 (6H, m), 7.67 (1H, d, J=2.4 Hz), 7.89 (1H, dd, J=2.4, 11.6 Hz), 8.06 (1H, d, J=6.0 Hz), 8.69 (1H, brs), 12.45 (1H, s). ESI-MS (m/z): 608[M+H]$^+$.

Production Example 223-1

3-[4-(2-Fluoro-4-nitrophenoxy)pyridin-2-yl]-1-[1-(2-dimethylaminoethyl)piperidin-4-yl]-1-methylurea The title compound (296 mg, 80.0%) was obtained from 4-(2-fluoro-4-nitrophenoxy)pyridin-2-ylamine (200 mg), triethylamine (0.252 ml), phenyl chloroformate (0.252 ml) and N-[1-(2-dimethylaminoethyl)piperidin-4-yl]-N-methylamine (595 mg).

$^1$H-NMR Spectrum (CDCl$_3$) δ (ppm): 1.63 (2H, m), 1.79 (2H, m), 2.10 (2H, m), 2.26 (6H, s), 2.47 (4H, m), 2.88 (3H, s), 3.01 (2H, m), 4.14 (1H, m), 6.65 (1H, dd, J=2.4, 5.6 Hz), 7.23 (1H, brs), 7.30 (1H, m), 7.75 (1H, d, J=2.4 Hz), 8.11 (2H, m), 8.16 (1H, d, J=5.6 Hz). ESI-MS (m/z): 461[M+H]$^+$.

Production Example 223-2

3-[4-(4-Amino-2-fluorophenoxy)pyridin-2-yl]-1-[1-(2-dimethylaminoethyl)piperidin-4-yl]-1-methylurea The title compound (260 mg, 93.9%) was obtained as a yellow oil from 3-[4-(2-fluoro-4-nitrophenoxy)pyridin-2-yl]-1-[1-(2-dimethylaminoethyl)piperidin-4-yl]-1-methylurea (296 mg) and 20% palladium hydroxide-carbon (70 mg).

$^1$H-NMR Spectrum (CDCl$_3$) δ (ppm): 1.63 (2H, m), 1.72-1.82 (2H, m), 2.10 (2H, m), 2.26 (6H, s), 2.27-2.50 (4H, m), 2.85 (3H, s), 3.00 (2H, m), 3.75 (2H, brs), 4.15 (1H, m), 6.42-6.45 (1H, m), 6.48-6.53 (2H, m), 6.95 (1H, m), 7.21 (1H, m), 7.64 (1H, d, J=2.4 Hz), 8.02 (1H, d, J=6.0 Hz). ESI-MS (m/z): 431[M+H]$^+$.

Example 224) 1-[1-(2-Dimethylaminoethyl)piperidin-4-yl]-3-[4-(2-fluoro-4-{3-[2-(4-fluorophenyl)acetyl]thioureido}phenoxy)pyridin-2-yl]-1-methylurea The title compound (19.2 mg, 13.2%) was obtained as white powder from 3-[4-(4-amino-2-fluorophenoxy)pyridin-2-yl]-1-[1-(2-dimethylaminoethyl)piperidin-4-yl]-1-methylurea (100 mg), (1S)-(+)-10-camphorsulfonic acid (116 mg) and 2-(4-fluorophenyl)acetyl isothiocyanate.

$^1$H-NMR Spectrum (CDCl$_3$) δ (ppm): 1.65 (2H, m), 1.72-1.90 (2H, m), 2.14 (2H, m), 2.36 (6H, s), 2.54 (4H, m), 2.88 (3H, s), 3.03 (2H, m), 3.72 (2H, s), 4.18 (1H, m), 6.55 (1H, dd, J=2.4, 6.0 Hz), 7.10-7.36 (7H, m), 7.67 (1H, d, J=2.4 Hz), 7.89 (1H, dd, J=2.4, 11.6 Hz), 8.06 (1H, d, J=6.0 Hz), 8.57 (1H, brs), 12.40 (1H, s). ESI-MS (m/z): 626[M+H]$^+$.

Example 225

1-[1-(3-Dimethylaminopropyl)piperidin-4-yl]-3-[4-(2-fluoro-4-{3-[2-(4-fluorophenyl)acetyl]thioureido}phenoxy)pyridin-2-yl]-1-methylurea The title compound (12.8 mg) was obtained as white powder from a crude product of 3-[4-(4-amino-2-fluorophenoxy)pyridin-2-yl]-1-[1-(3-dimethylaminopropyl)piperidin-4-yl]-1-methylurea (102 mg), (1S)-(+)-10-camphorsulfonic acid (90.4 mg) and 2-(4-fluorophenyl)acetyl isothiocyanate (1.83 ml, 0.25 M toluene solution).

$^1$H-NMR Spectrum (CDCl$_3$) δ (ppm): 1.67 (2H, m), 1.83-1.93 (4H, m), 2.14 (2H, m), 2.43 (6H, s), 2.46 (2H, m), 2.57 (2H, m), 2.89 (3H, s), 3.05 (2H, m), 3.73 (2H, s), 4.19 (1H, m), 6.55 (1H, dd, J=2.4, 6.0 Hz), 7.10-7.20 (4H, m), 7.27-7.35 (4H, m), 7.64 (1H, d, J=2.4 Hz), 7.90 (1H, dd, J=2.4, 11.6 Hz), 8.06 (1H, d, J=6.0 Hz), 12.41 (1H, s). ESI-MS (m/z): 640[M+H]$^+$.

Production Example 225-1

3-[4-(2-Fluoro-4-nitrophenoxy)pyridin-2-yl]-1-[1-(3-dimethylaminopropyl)piperidin-4-yl]-1-methylurea The title compound (226 mg, 59.3%) was obtained as white powder from 4-(2-fluoro-4-nitrophenoxy)pyridin-2-ylamine (200 mg), triethylamine (0.252 ml), phenyl chloroformate (0.252 ml) and N-[1-(3-dimethylaminopropyl)piperidin-4-yl]-N-methylamine (595 mg).

$^1$H-NMR Spectrum (CDCl$_3$) δ (ppm): 1.60-1.84 (6H, m), 2.05 (2H, m), 2.26 (6H, s), 2.35 (4H, m), 2.90 (3H, s), 3.01 (2H, m), 4.15 (1H, m), 6.65 (1H, dd, J=2.4, 5.6 Hz), 7.25 (1H, brs), 7.30 (1H, m), 7.75 (1H, d, J=2.4 Hz), 8.11 (2H, m), 8.16 (1H, d, J=5.6 Hz). ESI-MS (m/z): 475[M+H]$^+$.

Production Example 225-2

3-[4-(4-Amino-2-fluorophenoxy)pyridin-2-yl]-1-[1-(3-dimethylaminopropyl)piperidin-4-yl]-1-methylurea The title compound (205 mg, 96.8%) was obtained as a pale yellow oil from 3-[4-(2-fluoro-4-nitrophenoxy)pyridin-2-yl]-1-[1-(3-dimethylaminopropyl)piperidin-4-yl]-1-methylurea (226 mg) and 20% palladium hydroxide-carbon (70 mg).

$^1$H-NMR Spectrum (CDCl$_3$) δ (ppm): 1.64-1.78 (4H, m), 2.05 (2H, m), 2.25 (6H, s), 2.31-2.38 (4H, m), 2.88 (3H, s), 3.00 (2H, m), 3.75 (2H, m), 4.16 (1H, m), 6.49-6.52 (3H, m), 6.95 (1H, m), 7.27 (1H, m), 7.64 (1H, d, J=2.0 Hz), 8.01 (1H, d, J=5.6 Hz). ESI-MS (m/z): 445[M+H]$^+$.

Example 226

4-(2-Dimethylaminoethyl)-[1,4]diazepane-1-carboxylic acid [6-(2-fluoro-4-{3-[2-(4-fluorophenyl)acetyl]thioureido}phenoxy)pyrimidin-4-yl]amide The title compound (20.5 mg, 20.4%) was obtained as white powder from a crude product of 4-(2-dimethylaminoethyl)-[1,4]diazepane-1-carboxylic acid [6-(4-amino-2-fluorophenoxy)pyrimidin-4-yl]amide (68.6 mg) synthesized from 4-(2-dimethylaminoethyl)-[1,4]diazepane-1-carboxylic acid [6-(2-fluoro-4-nitrophenoxy)pyrimidin-4-yl]amide (144 mg), D-10-camphorsulfonic acid (76.4 mg), and a 0.25 M solution of 2-(4-fluorophenyl)acetyl isothiocyanate in toluene (1.31 ml).

$^1$H-NMR Spectrum (CDCl$_3$) δ (ppm): 1.95 (2H, m), 2.25 (6H, s), 2.42 (2H, m), 2.64 (2H, m), 2.71 (2H, m), 2.80 (2H, m), 3.59 (2H, m), 3.64 (2H, m), 3.71 (2H, s), 7.12 (2H, m), 7.16-7.38 (5H, m), 7.68 (1H, m), 7.86 (1H, dd, J=2.4, 11.6 Hz), 8.33 (1H, m), 8.49 (1H, brs), 12.38 (1H, brs). ESI-MS (m/z): 613[M+H]$^+$.

Production Example 226-1

(2-[1,4]Diazepan-1-ylethyl)dimethylamine trihydrochloride

After adding N,N-dimethylformamide (20 ml) to [1,4]diazepane-1-carboxylic acid benzyl ester (2 ml) under a nitrogen atmosphere, potassium carbonate (6.67 g) and 2-dimethylaminoethyl chloride (1.67 g) were added at room temperature. The reaction mixture was heated to 70° C. and stirred for 2 hours. It was then heated to 80° C. and stirred for 1 hour. Next, 2-dimethylaminoethyl chloride (420 mg) was further added and the reaction mixture was stirred for 2 hours. The reaction mixture was then cooled to room temperature. It was subsequently partitioned between ethyl acetate (100 ml) and saturated aqueous ammonium chloride (50 ml). The separated organic layer was washed with saturated aqueous ammonium chloride (50 ml), water (50 ml) and brine (50 ml) in that order and then dried over anhydrous sodium sulfate. The solvent was distilled off under reduced pressure, and then the resultant residue was purified by silica gel column chromatography (FUJI SILYSIA NH, eluent; heptane:ethyl acetate=4:1). Fractions containing the target compound were concentrated under reduced pressure to provide a crude product of 4-(2-dimethylaminoethyl)-[1,4]diazepane-1-carboxylic acid benzyl ester (724 mg, 24.5%) as a pale yellow oil.

After adding methanol (72 ml) to the crude product (724 mg), 20% palladium hydroxide (1.07 g) was added under a nitrogen atmosphere and the mixture was stirred for 4 hours with a pressurized hydrogenation apparatus. After replacing the atmosphere in the reaction vessel with nitrogen, the catalyst was filtered. It was then washed with methanol and the filtrate was concentrated. A 4N hydrochloric acid-ethyl acetate solution (4.15 ml) was added to the residue and the mixture was stirred. The excess hydrochloric acid was distilled off by stirring under reduced pressure. The solvent was distilled off under reduced pressure, and then the resultant residue was dried under reduced pressure to provide the title compound (660 mg, 99.2%) as a brown solid.

ESI-MS (m/z): 172[M+H]$^+$.

Production Example 226-2

4-(2-Dimethylaminoethyl)-[1,4]diazepane-1-carboxylic acid [6-(2-fluoro-4-nitrophenoxy)pyrimidin-4-yl]amide The title compound (144 mg, 80.3%) was obtained as a pale yellow oil from 6-(2-fluoro-4-nitrophenoxy)pyrimidin-4-ylamine (100 mg), tetrahydrofuran (4 ml), phenyl chloroformate (0.151 ml), (2-[1,4]diazepan-1-ylethyl)dimethylamine trihydrochloride (337 mg) and triethylamine (0.167 ml).

ESI-MS (m/z): 448[M+H]$^+$.

Example 227

1-[1-(3-Dimethylaminopropyl)piperidin-4-yl]-3-[4-(4-{3-[2-(4-fluorophenyl)acetyl]thioureido}phenoxy)pyridin-2-yl]-1-methylurea The title compound (26.4 mg, 17.4%) was obtained as white powder from 3-[4-(4-Aminophenoxy)pyridin-2-yl]-1-[1-(3-dimethylaminopropyl)piperidin-4-yl]-1-methylurea (104 mg), (1S)-(+)-10-camphorsulfonic acid (96.4 mg) and 2-(4-fluorophenyl)acetyl isothiocyanate (1.95 ml, 0.25 M solution in toluene).

$^1$H-NMR Spectrum (CDCl$_3$) δ (ppm): 1.62-1.94 (6H, m), 2.05 (2H, m), 2.26 (6H, s), 2.35 (4H, m), 2.89 (3H, s), 3.00 (2H, m), 3.71 (2H, s), 4.15 (1H, m), 6.55 (1H, dd, J=2.0, 5.6 Hz), 7.09-7.13 (4H, m), 7.18 (1H, s), 7.26-7.31 (3H, m), 7.67-7.69 (3H, m), 8.06 (1H, d, J=5.6 Hz), 12.28 (1H, s). ESI-MS (m/z): 622[M+H]$^+$.

Production Example 227-1

1-[1-(3-Dimethylaminopropyl)piperidin-4-yl]-1-methyl-3-[4-(4-nitrophenoxy)pyridin-2-yl]urea The title compound (140 mg, 76.7%) was obtained as a pale yellow oil from 4-(4-nitrophenoxy)pyridin-2-ylamine (92.5 mg), triethylamine (0.167 ml), phenyl chloroformate (0.157 ml) and N-[1-(3-dimethylaminopropyl)piperidin-4-yl]-N-methylamine (319 mg).

$^1$H-NMR Spectrum (CDCl$_3$) δ (ppm): 1.62-1.80 (6H, m), 2.04 (2H, m), 2.22 (6H, s), 2.26-2.31 (2H, m), 2.34-2.39 (2H, m), 2.90 (3H, s), 3.00 (2H, m), 4.15 (1H, m), 6.65 (1H, dd, J=2.4, 6.0 Hz), 7.19 (2H, d, J=9.0 Hz), 7.25 (1H, brs), 7.81 (1H, d, J=2.4 Hz), 8.17 (1H, d, J=6.0 Hz), 8.27 (2H, d, J=9.0 Hz). ESI-MS (m/z): 457[M+H]$^+$.

Production Example 227-2

3-[4-(4-Aminophenoxy)pyridin-2-yl]-1-[1-(3-dimethylaminopropyl)piperidin-4-yl]-1-methylurea The title compound (104 mg, 79.4%) was obtained as a pale yellow oil from 1-[1-(3-dimethylaminopropyl)piperidin-4-yl]-1-methyl-3-[4-(4-nitrophenoxy)pyridin-2-yl]urea (140 mg) and 10% palladium-carbon (100 mg).

$^1$H-NMR Spectrum (CDCl$_3$) δ (ppm): 1.64-1.82 (6H, m), 2.06 (2H, m), 2.62 (6H, s), 2.32-2.40 (4H, m), 2.71 (2H, brs), 2.88 (3H, s), 3.01 (2H, m), 4.17 (1H, m), 6.48 (1H, dd, J=2.0, 6.0 Hz), 6.70 (2H, d, J=8.8 Hz), 6.90 (2H, d, J=8.8 Hz), 7.25 (1H, brs), 7.62 (1H, d, J=2.0 Hz), 7.98 (1H, d, J=6.0 Hz). ESI-MS (m/z): 427[M+H]$^+$.

Example 228

3-[6-(4-{3-[2-(4-Fluorophenyl)acetyl]thioureido}phenoxy)pyrimidin-4-yl]-1-methyl-1-(1-methylpiperidin-4-yl)urea The title compound (46.3 mg, 23%) was obtained as white crystals from 3-[6-(4-aminophenoxy)pyrimidin-4-yl]-1-methyl-1-(1-methylpiperidin-4-yl)urea (131 mg), (+)-10-camphorsulfonic acid (81 mg) and a solution of 2-(4-fluorophenyl)acetyl isothiocyanate in toluene (0.25 M, 3.0 ml).

$^1$H-NMR Spectrum (CDCl$_3$) δ (ppm): 1.60-2.00 (4H, m), 2.10-2.20 (2H, m), 2.33 (3H, s), 2.90-3.05 (5H, m), 3.71 (2H, s), 4.21 (1H, m), 7.10-7.35 (7H, m), 7.59 (1H, d, J=0.8 Hz), 7.69-7.74 (2H, m), 8.37 (1H, d, J=0.8 Hz), 8.44 (1H, brs), 12.27 (1H, brs). ESI-MS (m/z): 552[M+H]$^+$.

Production Example 228-1

1-Methyl-1-(1-methylpiperidin-4-yl)-3-[6-(4-nitrophenoxy)pyrimidin-4-yl]urea The title compound (160 mg, 96%) was obtained as a colorless oil from 1-methyl-4-(methylamino)piperidine (331 mg), 4-amino-6-(4-nitrophenoxy)pyrimidine (100 mg), triethylamine (0.150 ml) and phenyl chloroformate (0.135 ml).

$^1$H-NMR Spectrum (CDCl$_3$) δ (ppm): 1.60-2.00 (4H, m), 2.09-2.16 (2H, m), 2.32 (3H, s), 2.80-3.00 (5H, m), 4.20 (1H, m), 7.29-7.38 (3H, m), 7.70 (1H, d, J=0.8 Hz), 8.14-8.33 (2H, m), 8.39 (1H, d, J=0.8 Hz)

Production Example 228-2

3-[6-(4-Aminophenoxy)pyrimidin-4-yl]-1-methyl-1-(1-methylpiperidin-4-yl)urea The title compound (132 mg, 90%) was obtained as white powder from 1-methyl-1-(1-methylpiperidin-4-yl)-3-[6-(4-nitrophenoxy)pyrimidin-4-yl]urea (160 mg) and 20% palladium hydroxide-carbon (120 mg).

ESI-MS (m/z): 357[M+H]$^+$.

Example 229

4-{[4-(Dimethylaminomethyl)piperidin-1-yl]carbonylamino}-6-(4-{3-[2-(4-fluorophenyl)acetyl]thioureido}phenoxy)pyrimidine The title compound (46 mg, 25%) was obtained as white powder from 4-(4-aminophenoxy)-6-{[4-(dimethylaminomethyl)piperidin-1-yl]carbonylamino}pyrimidine (120 mg), (+)-10-camphorsulfonic acid (71.5 mg) and a solution of 2-(4-fluorophenyl)acetyl isothiocyanate in toluene (0.25 M, 2.6 ml).

$^1$H-NMR Spectrum (CDCl$_3$) δ (ppm): 1.10-1.30 (2H, m), 1.75 (1H, m), 1.80-2.00 (2H, m), 2.10-2.45 (8H, m), 2.85-3.00 (2H, m), 3.71 (2H, s), 4.00-4.20 (2H, m), 7.10-7.35 (7H, m), 7.54 (1H, d, J=0.8 Hz), 7.69-7.73 (2H, m), 8.36 (1H, d, J=0.8 Hz), 8.44 (1H, brs), 12.27 (1H, brs). ESI-MS (m/z): 566[M+H]$^+$.

Production Example 229-1

4-{[4-(Dimethylaminomethyl)piperidin-1-yl]carbonylamino}-6-(4-nitrophenoxy)pyrimidine The title compound (137 mg, 79%) was obtained as pale yellow crystals from 4-amino-6-(4-nitrophenoxy)pyrimidine (100 mg), phenyl chloroformate (0.135 ml), 4-(dimethylaminomethyl)piperidine dihydrochloride (464 mg) and triethylamine (1.06 ml).

$^1$H-NMR Spectrum (CDCl$_3$) δ (ppm): 1.10-1.30 (2H, m), 1.73 (1H, m), 1.80-1.90 (2H, m), 2.10-2.20 (2H, m), 2.24 (6H, s), 2.80-3.00 (2H, m), 4.00-4.20 (2H, m), 7.29-7.33 (2H, m), 7.39 (1H, brs), 7.67 (1H, d, J=0.8 Hz), 8.28-8.33 (2H, m), 8.38 (1H, d, J=0.8 Hz).

Production Example 229-2

4-(4-Aminophenoxy)-6-{[4-(dimethylaminomethyl)piperidin-1-yl]carbonylamino}pyrimidine The title compound (120 mg, 95%) was obtained as white powder from 4-{[4-(dimethylaminomethyl)piperidin-1-yl]carbonylamino}-6-(4-nitrophenoxy)pyrimidine (137 mg) and 20% palladium hydroxide-carbon (100 mg).
ESI-MS (m/z): 371[M+H]$^+$.

Example 230

4-(4-{3-[2-(4-Fluorophenyl)acetyl]thioureido}phenoxy)-6-{[4-(1-methylpiperazin-4-yl)piperidin-1-yl]carbonylamino}pyrimidine The title compound (45.3 mg, 23%) was obtained as white powder from 4-(4-aminophenoxy)-6-{[4-(1-methylpiperazin-4-yl)piperidin-1-yl]carbonylamino}pyrimidine (133 mg), (+)-10-camphorsulfonic acid (135 mg) and a solution of 2-(4-fluorophenyl)acetyl isothiocyanate in toluene (0.25 M, 2.6 ml).
$^1$H-NMR Spectrum (CDCl$_3$) δ (ppm): 1.40-2.00 (5H, m), 2.33 (3H, s), 2.40-3.00 (10H, m), 3.71 (2H, s), 4.05-4.20 (2H, m), 7.10-7.40 (7H, m), 7.54 (1H, d, J=0.8 Hz), 7.69-7.73 (2H, m), 8.37 (1H, d, J=0.8 Hz), 8.45 (1H, brs), 12.27 (1H, brs). ESI-MS (m/z): 607[M+H]$^+$.

Production Example 230-1

4-{[4-(1-Methylpiperazin-4-yl)piperidin-1-yl]carbonylamino}-6-(4-nitrophenoxy)pyrimidine The title compound (148 mg, 78%) was obtained as a pale yellow oil from 4-amino-6-(4-nitrophenoxy)pyrimidine (100 mg), triethylamine (0.150 ml), phenyl chloroformate (0.135 ml) and 4-(1-methylpiperazin-4-yl)piperidine (400 mg).
$^1$H-NMR Spectrum (CDCl$_3$) δ (ppm): 1.40-2.00 (5H, m), 2.31 (3H, s), 2.40-3.00 (10H, m), 4.00-4.20 (2H, m), 7.27-7.33 (2H, m), 7.41 (1H, brs), 7.65 (1H, d, J=0.8 Hz), 8.29-8.32 (2H, m), 8.38 (1H, d, J=0.8 Hz).

Production Example 230-2

4-(4-Aminophenoxy)-6-{[4-(1-methylpiperazin-4-yl)piperidin-1-yl]carbonylamino}pyrimidine The title compound (133 mg, 97%) was obtained as pale yellow powder from 4-{[4-(1-methylpiperazin-4-yl)piperidin-1-yl]carbonylamino}-6-(4-nitrophenoxy)pyrimidine (148 mg) and 20% palladium hydroxide-carbon (100 mg).
ESI-MS (m/z): 412[M+H]$^+$.

Example 231

4-(4-{3-[2-(4-Fluorophenyl)acetyl]thioureido}phenoxy)-6-{[4-(1-methylpiperidin-4-yl)piperazin-1-yl]carbonylamino}pyrimidine The title compound (44.3 mg, 23%) was obtained as white powder from 4-(4-aminophenoxy)-6-{[4-(1-methylpiperidin-4-yl)piperazin-1-yl]carbonylamino}pyrimidine (131 mg), (+)-10-camphorsulfonic acid (133 mg) and a solution of 2-(4-fluorophenyl)acetyl isothiocyanate in toluene (0.25 M, 2.6 ml).
$^1$H-NMR Spectrum (CDCl$_3$) δ (ppm): 1.50-2.00 (6H, m), 2.26-2.36 (4H, m), 2.54-2.64 (4H, m), 2.90-3.04 (2H, m), 3.48-3.56 (4H, m), 3.71 (2H, s), 7.10-7.35 (7H, m), 7.54 (1H, d, J=0.8 Hz), 7.69-7.73 (2H, m), 8.37 (1H, d, J=0.8 Hz), 8.44 (1H, brs), 12.27 (1H, brs). ESI-MS (m/z): 607[M+H]$^+$.

Production Example 231-1

4-{[4-(1-Methylpiperidin-4-yl)piperazin-1-yl]carbonylamino}-6-(4-nitrophenoxy)pyrimidine The title compound (142 mg, 75%) was obtained as a pale yellow oil from 4-amino-6-(4-nitrophenoxy)pyrimidine (100 mg), triethylamine (0.150 ml), phenyl chloroformate (0.135 ml) and 4-(1-methylpiperidin-4-yl)piperazine (452 mg).
$^1$H-NMR Spectrum (CDCl$_3$) δ (ppm): 1.60-2.00 (6H, m), 2.20-2.40 (4H, m), 2.50-2.70 (4H, m), 2.80-3.00 (2H, m), 3.40-3.60 (4H, m), 7.29-7.34 (2H, m), 7.37 (1H, brs), 7.66 (1H, d, J=0.8 Hz), 8.28-8.33 (2H, m), 8.38 (1H, d, J=0.8 Hz).

Production Example 231-2

4-(4-Aminophenoxy)-6-{[4-(1-methylpiperidin-4-yl)piperazin-1-yl]carbonylamino}pyrimidine The title compound (131 mg, 99%) was obtained as pale yellow powder from 4-{[4-(1-methylpiperidin-4-yl)piperazin-1-yl]carbonylamino}-6-(4-nitrophenoxy)pyrimidine (142 mg) and 20% palladium hydroxide-carbon (100 mg).
ESI-MS (m/z): 412[M+H]$^+$.

Example 232

N-(3-Fluoro-4-{2-[3-(1-methylpiperidin-4-yl)ureido]pyridin-4-yloxy}phenyl)-N'-(4-fluorophenyl)malonamide $^1$H-NMR Spectrum (CDCl$_3$) δ (ppm): 1.50-2.07 (4H, m), 2.24 (2H, m), 2.32 (3H, s), 2.76 (2H, m), 3.63 (2H, s), 3.81 (1H, m), 6.27 (1H, m), 6.66 (1H, dd, J=1.2, 6.0 Hz), 7.01 (2H, m), 7.14 (1H, m), 7.28 (1H, m), 7.54 (2H, m), 7.67 (1H, m), 8.05 (1H, d, J=6.0 Hz), 8.35 (1H, brs), 9.35 (1H, brs), 9.72 (2H, m). ESI-MS (m/z): 539[M+H]$^+$.

Example 233

N-(4-{2-[(4-Dimethylaminopiperidine-1-carbonyl)amino]pyridin-4-yloxy}-3-fluorophenyl)-N'-(4-fluorophenyl)malonamide $^1$H-NMR Spectrum (CDCl$_3$) δ (ppm): 1.45 (2H, m), 1.86 (2H, m), 2.28 (6H, s), 2.34 (1H, m), 2.90 (2H, m), 3.49 (2H, s), 4.07 (2H, m), 6.59 (1H, dd, J=2.4, 6.0 Hz), 7.03 (2H, m), 7.13 (1H, m), 7.16-7.40 (2H, m), 7.45-7.60 (3H, m), 7.70 (1H, dd, J=2.4, 12.0 Hz), 8.06 (1H, d, J=6.0 Hz), 8.68 (1H, brs), 9.24 (1H, s). ESI-MS (m/z): 553[M+H]$^+$.

Example 234

4-{2-Fluoro-4-[3-(2-phenylacetyl)ureido]phenoxy}-2-[(4-oxopiperidin-1-yl)carbonylamino]pyridine $^1$H-NMR Spectrum (CDCl$_3$) δ (ppm): 2.40-2.60 (4H, m), 3.76 (2H, s), 3.76-3.83 (4H, m), 6.54 (1H, m), 7.00-7.65 (11H, m), 8.04 (1H, m), 10.58 (1H, s). ESI-MS (m/z): 528 [M+Na]$^+$.

Production Example 234-1

4-(2-Fluoro-4-nitrophenoxy)-2-[(4-oxopiperidin-1-yl)carbonylamino]pyridine $^1$H-NMR Spectrum (CDCl$_3$) δ (ppm): 2.40-2.70 (4H, m), 3.70-3.90 (4H, m), 6.67 (1H, dd, J=2.4, 5.6 Hz), 7.33 (1H, m), 7.48 (1H, brs), 7.73 (1H, d, J=2.4 Hz), 8.10-8.30 (3H, m).

Production Example 234-2

4-(4-Amino-2-fluorophenoxy)-2-[(4-oxopiperidin-1-yl)carbonylamino]pyridine $^1$H-NMR Spectrum (CDCl$_3$) δ (ppm): 2.50-2.60 (4H, m), 3.76 (2H, brs), 3.79-3.83 (4H, m), 6.45 (1H, dd, J=2.4, 5.6 Hz), 6.50-6.52 (1H, m), 6.90-7.00 (1H, m), 7.43 (1H, br), 7.61 (1H, brs), 8.03 (1H, m)

Example 235

2-{[4-(Dimethylamino)piperidin-1-yl]carbonylamino}-4-{2-fluoro-4-[3-(2-phenylacetyl)ureido]phenoxy}pyridine $^1$H-NMR Spectrum (CDCl$_3$) δ (ppm): 1.40-1.60 (2H, m), 1.80-2.00 (2H, m), 2.28 (6H, s), 2.35 (1H, m), 2.80-3.00 (2H, m), 3.75 (2H, s), 4.00-4.20 (2H, m), 6.53 (1H, m), 7.10-7.69 (10H, m), 7.70 (1H, s), 8.04 (1H, d, J=5.6 Hz), 10.57 (1H, s). ESI-MS (m/z): 535[M+H]$^+$.

Example 236

2-{[4-(Azetidin-1-yl)piperidin-1-yl]carbonylamino}-4-{2-fluoro-4-[3-(2-phenylacetyl)ureido]phenoxy}pyridine $^1$H-NMR Spectrum (CDCl$_3$) δ (ppm): 1.20-1.35 (2H, m), 1.60-1.80 (2H, m), 2.00-2.10 (2H, m), 2.20 (1H, m), 2.95-3.05 (2H, m), 3.10-3.20 (4H, m), 3.75 (2H, s), 3.80-3.95 (2H, m), 6.52 (1H, m), 7.05-7.45 (8H, m), 7.55-7.65 (2H, m), 8.02 (1H, d, J=5.6 Hz), 8.11 (1H, s), 10.60 (1H, s). ESI-MS (m/z): 547[M+H]$^+$.

Example 237

4-Dimethylaminopiperidine-1-carboxylic acid {6-[2-fluoro-4-(3-phenylacetylthioureido)phenoxy]pyrimidin-4-yl}amide $^1$H-NMR Spectrum (CDCl$_3$) δ (ppm): 1.50 (2H, m), 1.91 (2H, m), 2.30 (6H, s), 2.39 (1H, m), 2.96 (2H, m), 3.74 (2H, s), 4.12 (2H, m), 7.21 (1H, m), 7.28-7.32 (2H, m), 7.32-7.48 (5H, m), 7.63 (1H, m), 7.86 (1H, dd, J=2.4, 11.6 Hz), 8.33 (1H, m), 8.40 (1H, brs), 12.42 (1H, brs). ESI-MS (m/z): 552[M+H]$^+$.

Production Example 237-1

4-Dimethylaminopiperidine-1-carboxylic acid [6-(4-amino-2-fluorophenoxy)pyrimidin-4-yl]amide $^1$H-NMR Spectrum (CDCl$_3$) δ (ppm): 1.49 (2H, m), 1.90 (2H, m), 2.30 (6H, m), 2.37 (1H, m), 2.95 (2H, m), 3.73 (2H, brs), 4.11 (2H, m), 6.45 (1H, m), 6.50 (1H, m), 6.97 (1H, m), 7.32 (1H, brs), 7.56 (1H, s), 8.37 (1H, s). ESI-MS (m/z): 375[M+H]$^+$.

Example 238

N-(2-Fluoro-4-{2-[3-(1-methylpiperidin-4-yl)ureido]pyridin-4-yloxy}phenyl)-N'-(4-fluorophenyl)malonamide $^1$H-NMR Spectrum (DMSO-d$_6$) δ (ppm): 1.34-1.44 (2H, m), 1.78 (2H, m), 2.03 (2H, m), 2.15 (3H, s), 2.58 (2H, m), 3.48 (1H, m), 3.58 (2H, m), 6.57 (1H, dd, J=2.4, 6.0 Hz), 7.01 (2H, m), 7.17 (2H, m), 7.25 (1H, dd, J=2.4, 7.6 Hz), 7.63 (2H, dd, J=5.0, 8.6 Hz), 7.91 (1H, m), 8.04 (1H, m), 8.09 (1H, d, J=6.0 Hz), 9.03 (1H, s), 10.11 (1H, s), 11.26 (1H, s). ESI-MS (m/z): 539[M+H]$^+$.

Example 239

N-[4-(2-{[4-(Azetidin-1-yl)piperidine-1-carbonyl]amino}pyridin-4-yloxy)-2-fluorophenyl]-N'-(4-fluorophenyl)malonamide $^1$H-NMR Spectrum (DMSO-d$_6$) δ (ppm): 1.06 (2H, m), 1.55 (2H, m), 1.90 (2H, m), 2.12 (1H, m), 2.98 (2H, m), 3.05 (4H, m), 3.58 (2H, s), 3.79 (2H, m), 6.60 (1H, dd, J=2.0, 5.6 Hz), 7.00 (1H, m), 7.17 (2H, m), 7.24 (1H, dd, J=2.6, 7.4 Hz), 7.40 (1H, d, J=2.0 Hz), 7.63 (2H, dd, J=5.4, 9.2 Hz), 8.03 (1H, m), 8.12 (1H, d, J=5.2 Hz), 9.17 (1H, s), 10.10 (1H, s), 10.25 (1H, s). ESI-MS (m/z): 565[M+H]$^+$.

Example 240

N-(4-{2-[(4-Dimethylaminopiperidine-1-carbonyl)amino]pyridin-4-yloxy}-2-fluorophenyl)-N'-(4-fluorophenyl)malonamide $^1$H-NMR Spectrum (DMSO-d$_6$) δ (ppm): 1.18-1.31 (2H, m), 1.72 (2H, m), 2.15 (6H, s), 2.23 (1H, m), 2.75 (2H, m), 3.58 (2H, s), 4.09 (2H, m), 6.60 (1H, dd, J=2.0, 5.2 Hz), 7.01 (1H, m), 7.17 (2H, m), 7.24 (1H, dd, J=2.8, 7.6 Hz), 7.40 (1H, d, J=2.0 Hz), 7.63 (2H, dd, J=5.0, 9.0 Hz), 8.03 (1H, m), 8.13 (1H, d, J=5.2 Hz), 9.21 (1H, s), 10.10 (1H, s), 10.25 (1H, s). ESI-MS (m/z): 553[M+H]$^+$.

Example 241

4-Dimethylaminopiperidine-1-carboxylic acid {6-[2-fluoro-4-(3-phenylacetylureido)phenoxy]pyrimidin-4-yl}amide $^1$H-NMR Spectrum (CDCl$_3$) δ (ppm): 1.40-1.78 (2H, m), 1.92 (2H, m), 2.33 (6H, brs), 2.30-2.52 (1H, m), 2.96 (2H, m), 3.75 (2H, s), 4.13 (2H, m), 7.10-7.20 (2H, m), 7.29 (2H, m), 7.32-7.46 (4H, m), 7.55-7.66 (3H, m), 8.34 (1H, s), 10.55 (1H, brs). ESI-MS (m/z): 536[M+H]$^+$.

Example 242

4-(Azetidin-1-yl)piperidine-1-carboxylic acid {6-[2-fluoro-4-(3-phenylacetylureido)phenoxy]pyrimidin-4-yl}amide $^1$H-NMR Spectrum (CDCl$_3$) δ (ppm): 1.32 (2H, m), 1.73 (2H, m), 2.07 (2H, m), 2.24 (1H, m), 3.11 (2H, m), 3.19 (4H, m), 3.75 (2H, s), 3.89 (2H, m), 7.15 (2H, m), 7.22-7.46 (6H, m), 7.58-7.65 (2H, m), 7.80 (1H, brs), 8.33 (1H, m), 10.57 (1H, brs). ESI-MS (m/z): 548[M+H]$^+$.

Example 243

4-(Azetidin-1-yl)piperidine-1-carboxylic acid {4-[3-fluoro-4-(3-phenylacetylureido)phenoxy]pyridin-2-yl}amide $^1$H-NMR Spectrum (CD$_3$OD) δ (ppm): 1.15 (2H, m), 1.78 (2H, m), 2.09 (2H, m), 2.34 (1H, m), 2.90 (2H, m), 3.31 (4H, m), 3.72 (2H, s), 4.08 (2H, m), 6.60 (1H, dd, J=2.0, 5.8 Hz), 6.95 (1H, m), 7.04 (1H, dd, J=2.8, 11.6 Hz), 7.26-7.36 (6H, m), 8.08 (1H, d, J=5.8 Hz), 8.20 (1H, m). ESI-MS (m/z): 547[M+H]$^+$.

Example 244

4-Dimethylaminopiperidine-1-carboxylic acid {4-[3-fluoro-4-(3-phenylacetylureido)phenoxy]pyridin-2-yl}amide $^1$H-NMR Spectrum (CD$_3$OD) δ (ppm): 1.40 (2H, m), 1.92 (2H, m), 2.30 (6H, s), 2.43 (1H, m), 2.87 (2H, m), 3.72 (2H, s), 4.18 (2H, m), 6.61 (1H, dd, J=2.4, 5.8 Hz), 6.95 (1H, m), 7.04 (1H, dd, J=2.4, 11.2 Hz), 7.26-7.36 (6H, m), 8.09 (1H, d, J=5.8 Hz), 8.21 (1H, m). ESI-MS (m/z): 535[M+H]$^+$.

Example 245

2-{[(3R)-3-Dimethylaminopyrrolidin-1-yl]carbonylamino}-4-{2-fluoro-4-[3-(2-phenylacetyl)thioureido]phenoxy}pyridine $^1$H-NMR Spectrum (CDCl$_3$) δ (ppm): 1.86 (1H, m), 2.17 (1H, m), 2.27 (6H, s), 2.74 (1H, m), 3.21 (1H, m), 3.41 (1H, m), 3.65 (1H, m), 3.70-3.80 (1H, m), 3.74 (2H, s), 6.56 (1H, dd, J=2.4, 5.6 Hz), 7.00 (1H, s), 7.18 (1H, m), 7.30-7.47 (6H, m), 7.69 (1H, d, J=2.4 Hz), 7.89 (1H, dd, J=2.4, 12.0 Hz), 8.05 (1H, d, J=5.6 Hz), 8.49 (1H, brs), 12.44 (1H, s). ESI-MS (m/z): 537[M+H]$^+$.

Production Example 245-1

2-{[(3R)-3-Dimethylaminopyrrolidin-1-yl]carbonylamino}-4-(2-fluoro-4-nitrophenoxy)pyridine $^1$H-NMR Spectrum (CDCl$_3$) δ (ppm): 1.91 (1H, m), 2.19 (1H, m), 2.28 (6H, s), 2.76 (1H, m), 3.23 (1H, m), 3.41 (1H, m), 3.60-3.80 (2H, m), 6.67 (1H, dd, J=2.4, 5.6 Hz), 6.83 (1H, m), 7.10 (1H, brs), 7.78 (1H, d, J=2.4 Hz), 8.09-8.17 (3H, m).

Production Example 245-2

4-(4-Amino-2-fluorophenoxy)-2-{[(3R)-3-dimethylaminopyrrolidin-1-yl]carbonylamino}pyridine $^1$H-NMR Spectrum (CDCl$_3$) δ (ppm): 1.86 (1H, m), 2.17 (1H, m), 2.27 (6H, s), 2.73 (1H, m), 3.21 (1H, m), 3.40 (1H, m), 3.65 (1H, m), 3.70-3.80 (3H, m), 6.42-6.55 (3H, m), 6.90-7.00 (2H, m), 7.65 (1H, d, J=2.4 Hz), 8.01 (1H, d, J=5.6 Hz).

Example 246

2-{[(3S)-3-Dimethylaminopyrrolidin-1-yl]carbonylamino}-4-{2-fluoro-4-[3-(2-phenylacetyl)thioureido]phenoxy}pyridine

Production Example 246-1

2-{[(3S)-3-Dimethylaminopyrrolidin-1-yl]carbonylamino}-4-(2-fluoro-4-nitrophenoxy)pyridine ESI-MS (m/z) (neg.): 388[M−H]$^-$.

Production Example 246-2

4-(4-Amino-2-fluorophenoxy)-2-{[(3S)-3-dimethylaminopyrrolidin-1-yl]carbonylamino}pyridine

Example 247

N-(4-Fluorophenyl)-N'-[3-fluoro-4-(2-{[(3R)-3-dimethylaminopyrrolidin-1-yl]carbonylamino}pyridin-4-yloxy)phenyl]malonamide $^1$H-NMR Spectrum (CDCl$_3$) δ (ppm): 1.84 (1H, m), 2.14 (1H, m), 2.24 (6H, s), 2.74 (1H, m), 3.19 (1H, m), 3.38 (1H, m), 3.48 (2H, s), 3.61 (1H, m), 3.67 (1H, m), 6.66 (1H, dd, J=2.4, 5.6 Hz), 6.95-7.05 (3H, m), 7.11 (1H, m), 7.22 (1H, m), 7.49-7.54 (2H, m), 7.59 (1H, d, J=2.4 Hz), 7.66 (1H, dd, J=2.4, 12.0 Hz), 8.08 (1H, d, J=8.8 Hz), 8.93 (1H, brs), 9.47 (1H, brs).

Example 248

N-(4-Fluorophenyl)-N'-[3-fluoro-4-(2-{[(3S)-3-dimethylaminopyrrolidin-1-yl]carbonylamino}pyridin-4-yloxy)phenyl]malonamide

Example 249

2-{[(3R)-3-Dimethylaminopyrrolidin-1-yl]carbonylamino}-4-{2-fluoro-4-[3-(2-phenylacetyl)ureido]phenoxy}pyridine $^1$H-NMR Spectrum (CDCl$_3$) δ (ppm): 1.86 (1H, m), 2.17 (1H, m), 2.27 (6H, s), 2.73 (1H, m), 3.20 (1H, m), 3.40 (1H, m), 3.65 (1H, m), 3.73 (1H, m), 3.75 (2H, s), 6.54 (1H, dd, J=2.4, 5.6 Hz), 7.01 (1H, s), 7.10-7.20 (2H, m), 7.29-7.45 (5H, m), 7.64 (1H, dd, J=2.4, 12.0 Hz), 7.66 (1H, d, J=2.4 Hz), 7.93 (1H, brs), 8.04 (1H, d, J=5.6 Hz), 10.59 (1H, s). ESI-MS (m/z): 521[M+H]$^+$.

Example 250

2-{[(3S)-3-Dimethylaminopyrrolidin-1-yl]carbonylamino}-4-{2-fluoro-4-[3-(2-phenylacetyl)ureido]phenoxy}pyridine

Example 251

4-{2-Fluoro-4-[3-(2-phenylacetyl)thioureido]phenoxy}-2-{[(2S)-2-hydroxymethylpyrrolidin-1-yl]carbonylamino}pyridine $^1$H-NMR Spectrum (CDCl$_3$) δ (ppm): 1.60-1.70 (1H, m), 1.90-2.10 (3H, m), 3.40-3.80 (4H, m), 3.75 (2H, s), 4.15 (1H, m), 6.52 (1H, m), 7.10-7.50 (8H, m), 7.89 (1H, m), 8.06 (1H, m), 8.45 (1H, brs), 12.45 (1H, brs). ESI-MS (m/z): 524[M+H]$^+$.

Production Example 251-1

4-(2-Fluoro-4-nitrophenoxy)-2-{[(2S)-2-hydroxymethylpyrrolidin-1-yl]carbonylamino}pyridine $^1$H-NMR Spectrum (CDCl$_3$) δ (ppm): 1.69 (1H, m), 1.90-2.00 (2H, m), 2.06 (1H, m), 3.40-3.80 (4H, m), 4.14 (1H, m), 6.62 (1H, dd, J=2.4, 5.6 Hz), 7.30 (1H, m), 7.75 (1H, d, J=2.4 Hz), 8.08-8.16 (3H, m)

Production Example 251-2

4-(4-Amino-2-fluorophenoxy)-2-{[(2S)-2-hydroxymethylpyrrolidin-1-yl]carbonylamino}pyridine $^1$H-NMR Spectrum (CDCl$_3$) δ (ppm): 1.66 (1H, m), 1.90-2.20 (3H, m), 3.40-3.80 (6H, m), 4.15 (1H, m), 6.45 (1H, m), 6.47-6.53 (2H, m), 6.95 (1H, m), 7.63 (1H, brs), 8.01 (1H, d, J=5.6 Hz).

Example 252

4-{2-Fluoro-4-[3-(2-phenylacetyl)thioureido]phenoxy}-2-{[(2R)-2-hydroxymethylpyrrolidin-1-yl]carbonylamino}pyridine

Production Example 252-1

4-(2-Fluoro-4-nitrophenoxy)-2-{[(2R)-2-hydroxymethylpyrrolidin-1-yl]carbonylamino}pyridine ESI-MS (m/z): 399[M+Na]$^+$.

Production Example 252-2

4-(4-Amino-2-fluorophenoxy)-2-{[(2R)-2-hydroxymethylpyrrolidin-1-yl]carbonylamino}pyridine

Example 253

N-(4-{2-[(3-Dimethylaminoazetidine-1-carbonyl)amino]pyridin-4-yloxy}-2-fluorophenyl)-N'-(4-fluorophenyl)malonamide $^1$H-NMR Spectrum (CDCl$_3$) δ (ppm): 2.18 (6H, s), 3.13 (1H, m), 3.55 (2H, s), 3.90 (2H, m), 4.04 (2H, m), 6.55 (1H, dd, J=2.4, 5.6 Hz), 6.81 (1H, s), 6.91 (2H, d, J=9.6 Hz), 7.04 (2H, m), 7.53 (2H, m), 7.65 (1H, d, J=2.4 Hz), 8.06 (1H, d, J=5.6 Hz), 8.27 (1H, m), 8.67 (1H, s), 8.78 (1H, s). ESI-MS (m/z): 525[M+H]$^+$, 547[M+Na]$^+$.

Example 254

4-{[(3S)-3-Dimethylaminopyrrolidin-1-yl]carbonylamino}-6-(2-fluoro-4-{3-[2-(4-fluorophenyl)acetyl]thioureido}phenoxy)pyrimidine $^1$H-NMR Spectrum (CDCl$_3$) δ (ppm): 1.92 (1H, m), 2.21 (1H, m), 2.30 (6H, s), 2.78 (1H, m), 3.26 (1H, m), 3.40-3.52 (1H, m), 3.64-3.84 (2H, m), 3.72 (2H, s), 7.10-7.40 (7H, m), 7.70 (1H, d, J=0.8 Hz), 7.87 (1H, dd, J=2.4, 11.2 Hz), 8.34 (1H, d, J=0.8 Hz), 8.44 (1H, brs), 12.39 (1H, brs). ESI-MS (m/z) (neg.): 554[M−H]$^-$.

Production Example 254-1

4-{[(3S)-3-Dimethylaminopyrrolidin-1-yl]carbonylamino}-6-(2-fluoro-4-nitrophenoxy)pyrimidine $^1$H-NMR Spectrum (CDCl$_3$) δ (ppm): 1.92 (1H, m), 2.21 (1H, m), 2.30 (6H, s), 2.80 (1H, m), 3.28 (1H, m), 3.47 (1H, m), 3.60-3.85 (2H, m), 7.19 (1H, s), 7.42 (1H, m), 7.80 (1H, d, J=1.2 Hz), 8.08-8.15 (2H, m), 8.33 (1H, d, J=1.2 Hz).

Production Example 254-2

4-(4-Amino-2-fluorophenoxy)-6-{[(3S)-3-dimethylaminopyrrolidin-1-yl]carbonylamino}pyrimidine $^1$H-NMR Spectrum (CDCl$_3$) δ (ppm): 1.89 (1H, m), 2.20 (1H, m), 2.30 (6H, s), 2.77 (1H, m), 3.25 (1H, m), 3.44 (1H, m), 3.60-3.90 (4H, m), 6.30-6.55 (2H, m), 6.97 (1H, m), 7.12 (1H, s), 7.61 (1H, s), 8.37 (1H, s).

Example 255

3-(4-{2-Fluoro-4-[3-(2-phenylacetyl)thioureido]phenoxy}pyridin-2-yl)-1-[(2R)-2-hydroxy-3-(pyrrolidin-1-yl)propyl]-1-methylurea $^1$H-NMR Spectrum (CDCl$_3$) δ (ppm): 1.76-1.84 (4H, m), 2.37 (1H, dd, J=4.0, 12.0 Hz), 2.46-2.56 (2H, m), 2.64-2.74 (3H, m), 3.00 (3H, s), 3.32-3.44 (2H, m), 3.74 (2H, s), 3.93 (1H, m), 6.49 (1H, dd, J=2.4, 5.6 Hz), 7.16 (1H, m), 7.30-7.46 (7H, m), 7.57 (1H, d, J=2.4 Hz), 7.88 (1H, dd, J=2.4, 12.0 Hz), 8.08 (1H, d, J=5.6 Hz), 12.42 (1H, s). ESI-MS (m/z): 581[M+H]$^+$.

Production Example 255-1

N-Benzyl-N-methyl-N-(2S)-oxiranylmethylamine

Sodium hydride (60%, 88 mg) was suspended in tetrahydrofuran (5 ml) at room temperature under nitrogen atmosphere, and N-methylbenzylamine (0.284 ml) was added dropwise while stirring. After 1 hour, (2R)-glycidyl tosylate (457 mg) was added thereto and the reaction mixture was stirred overnight at room temperature, then at 50° C. for 7.5 hours. The reaction mixture was partitioned between ethyl acetate and water. The organic layer was washed with brine and dried over anhydrous sodium sulfate. The solvent was evaporated to give a residue, which was the purified by silica gel column chromatography (eluent; ethyl acetate) to provide the titled compound (225 mg, 64%) as a colorless oil.

$^1$H-NMR Spectrum (CDCl$_3$) δ (ppm): 2.33 (3H, s), 2.36 (1H, m), 2.49 (1H, m), 2.72-2.79 (2H, m), 3.12 (1H, m), 3.52 (1H, d, J=13.2 Hz), 3.67 (1H, d, J=13.2 Hz), 7.20-7.40 (5H, m).

Production Example 255-2

(2R)-1-(Benzylmethylamino)-3-(pyrrolidin-1-yl)-2-propanol

N-Benzyl-N-methyl-N-(2S)-oxiranylmethylamine (318 mg) was dissolved in tetrahydrofuran (3.5 ml) at room temperature under nitrogen atmosphere, and pyrrolidine (1.5 ml) was added dropwise while stirring. The reaction mixture was stirred overnight at room temperature, then overnight at 70° C. The reaction mixture was evaporated to give a residue, which was purified by silica gel column chromatography (Fuji Silysia NH, eluent; ethyl acetate) to provide the titled compound (420 mg, 95%) as a colorless oil.

¹H-NMR Spectrum (CDCl₃) δ (ppm): 1.74-1.80 (4H, m), 2.25 (3H, s), 2.37-2.65 (8H, m), 3.52 (1H, d, J=13.2 Hz), 3.63 (1H, d, J=13.2 Hz), 3.87 (1H, m), 7.20-7.40 (5H, m).

Production Example 255-3

(2S)-1-(Methylamino)-3-(pyrrolidin-1-yl)-2-propanol (2R)-1-(Benzylmethylamino)-3-(pyrrolidin-1-yl)-2-propanol (420 mg) was dissolved in methanol (10 ml). 10% Palladium hydroxide carbon (460 mg) was added thereto, followed by stirring under hydrogen atmosphere for 4.5 hours. The reaction mixture was filtered to remove the catalyst, and the catalyst was washed with methanol. The filtrate and the washings were combined and concentrated under reduced pressure to give a residue, which was dried under reduced pressure to provide the titled compound (232 mg, 87%) as a colorless oil.

¹H-NMR Spectrum (CDCl₃) δ (ppm): 1.75-1.85 (4H, m), 2.34 (1H, m), 2.40-2.60 (3H, m), 2.46 (3H, s), 2.60-2.75 (4H, m), 3.82 (1H, m).

Production Example 255-4

3-[4-(4-Amino-2-fluorophenoxy)pyridin-2-yl]-1-[(2R)-2-hydroxy-3-(pyrrolidin-1-yl)propyl]-1-methylurea ¹H-NMR Spectrum (CDCl₃) δ (ppm): 1.70-1.90 (4H, m), 2.37 (1H, dd, J=4.0, 12.0 Hz), 2.40-2.60 (2H, m), 2.60-2.80 (3H, m), 3.01 (3H, s), 3.30-3.50 (2H, m), 3.72 (2H, brs), 3.93 (1H, m), 6.40-6.60 (3H, m), 6.95 (1H, m), 7.53 (1H, d, J=1.6 Hz), 8.04 (1H, d, J=6.0 Hz).

Example 256

3-(4-{2-Fluoro-4-[3-(2-phenylacetyl)thioureido]phenoxy}pyridin-2-yl)-1-[(2S)-2-hydroxy-3-(pyrrolidin-1-yl)propyl]-1-methylurea Production Example 256-1

N-Benzyl-N-methyl-N-(2R)-oxiranylmethylamine

The titled compound was obtained as a colorless oil (534 mg, 60%) under nitrogen atmosphere from sodium hydride (60%, 220 mg), N-methylbenzylamine (0.710 ml) and (2S)-glycidyl tosylate (1.14 g).

Production Example 256-2

(2S)-1-(Benzylmethylamino)-3-(pyrrolidin-1-yl)-2-propanol

The titled compound was obtained as a colorless oil (718 mg, 96%) under nitrogen atmosphere from N-benzyl-N-methyl-N-(2R)-oxiranylmethylamine (533 mg).

Production Example 256-3

(2R)-1-(Methylamino)-3-(pyrrolidin-1-yl)-2-propanol

The titled compound was obtained as a colorless oil (418 mg, 91%) from (2S)-1-(benzylmethylamino)-3-(pyrrolidin-1-yl)-2-propanol (718 mg).
ESI-MS (m/z): 159[M+H]⁺.

Production Example 256-4

3-[4-(4-Amino-2-fluorophenoxy)pyridin-2-yl]-1-[(2S)-2-hydroxy-3-(pyrrolidin-1-yl)propyl]-1-methylurea ESI-MS (m/z): 404[M+H]⁺.

Example 257

N-(3-Fluoro-4-{2-[3-methyl-3-(1-methylpiperidin-4-yl)ureido]pyridin-4-yloxy}phenyl)-N'-phenylmalonamide ¹H-NMR Spectrum (CDCl₃) δ (ppm): 1.50-1.80 (4H, m), 2.01 (2H, m), 2.25 (3H, s), 2.87 (3H, s), 2.90 (2H, m), 3.51 (2H, s), 4.10 (1H, m), 6.60 (1H, dd, J=2.4, 6.0 Hz), 7.08-7.20 (2H, m), 7.20-7.30 (2H, m), 7.34 (2H, m), 7.56 (2H, m), 7.62 (1H, d, J=2.4 Hz), 7.71 (1H, dd, J=2.4, 12.0 Hz), 8.07 (1H, d, J=6.0 Hz), 8.75 (1H, brs), 9.48 (1H, brs). ESI-MS (m/z): 535[M+H]⁺.

Example 258

4-{2-Fluoro-4-[3-(2-phenylacetyl)thioureido]phenoxy}-2-{[4-(morpholin-4-yl)piperidin-1-yl]carbonylamino}pyridine ¹H-NMR Spectrum (CDCl₃) δ (ppm): 1.40-1.55 (2H, m), 1.85-1.95 (2H, m), 2.38 (1H, m), 2.50-2.60 (4H, m), 2.85-2.95 (2H, m), 3.70-3.73 (4H, m), 3.74 (2H, s), 4.05-4.15 (2H, m), 6.54 (1H, dd, J=2.4, 5.6 Hz), 7.16 (1H, m), 7.30-7.45 (7H, m), 7.61 (1H, s), 7.89 (1H, dd, J=2.4, 11.2 Hz), 8.05 (1H, d, J=5.6 Hz), 8.71 (1H, brs), 12.46 (1H, s). ESI-MS (m/z) (neg.): 591[M-H]⁻.

Production Example 258-1

4-(2-Fluoro-4-nitrophenoxy)-2-{[4-(morpholin-4-yl)piperidin-1-yl]carbonylamino}pyridine ¹H-NMR Spectrum (CDCl₃) δ (ppm): 1.43-1.60 (2H, m), 1.85-1.95 (2H, m), 2.39 (1H, m), 2.50-2.60 (4H, m), 2.85-2.97 (2H, m), 3.65-3.80 (4H, m), 4.00-4.15 (2H, m), 6.64 (1H, dd, J=2.4, 5.6 Hz), 7.20-7.36 (2H, m), 7.69 (1H, d, J=2.0 Hz), 8.06-8.18 (3H, m).

Production Example 258-2

4-(4-Amino-2-fluorophenoxy)-2-{[4-(morpholin-4-yl)piperidin-1-yl]carbonylamino}pyridine ¹H-NMR Spectrum (CDCl₃) δ (ppm): 1.45-1.60 (2H, m), 1.80-1.95 (2H, m), 2.39 (1H, m), 2.50-2.60 (4H, m), 2.85-2.95 (2H, m), 3.65-3.80 (6H, m), 4.05-4.15 (2H, m), 6.46 (1H, m), 6.48-6.56 (2H, m), 6.96 (1H, m), 7.21 (1H, brs), 7.58 (1H, d, J=1.6 Hz), 8.01 (1H, d, J=5.6 Hz)

Example 259

4-{2-Fluoro-4-[3-(2-phenylacetyl)ureido]phenoxy}-2-{[4-(morpholin-4-yl)piperidin-1-yl]carbonylamino}pyridine ¹H-NMR Spectrum (CDCl₃) δ (ppm): 1.30-1.45 (2H, m), 1.65-1.80 (2H, m), 2.31 (1H, m), 2.40-2.50 (4H, m), 2.70-2.80 (2H, m), 3.50-3.60 (4H, m), 3.74 (2H, s), 4.05-4.15 (2H, m), 6.58 (1H, m), 7.20-7.50 (8H, m), 7.76 (1H, d, J=12.0 Hz), 8.11 (1H, d, J=5.6 Hz), 9.21 (1H, s), 10.61 (1H, s), 11.05 (1H, brs). ESI-MS (m/z): 577[M+H]⁺.

Example 260

N-(4-Fluorophenyl)-N'-(2-fluoro-4-{2-[(3-pyrrolidin-1-ylazetidine-1-carbonyl)amino]pyridin-4-yloxy}phenyl)malonamide ¹H-NMR Spectrum (CDCl₃) δ (ppm): 1.83 (4H, m), 2.50 (4H, m), 3.35 (1H, m), 3.55 (2H, s), 3.96 (2H, m), 4.10 (2H, m), 6.55 (1H, dd, J=2.4, 5.8 Hz), 6.81 (1H, s), 6.91 (2H, m), 7.04 (2H, m), 7.53 (2H, m), 7.65 (1H, d, J=2.4 Hz), 8.05 (1H, d, J=5.8 Hz), 8.26 (1H, m), 8.72 (1H, brs), 8.81 (1H, brs). ESI-MS: 551[M+H]⁺, 573[M+Na]⁺.

Example 261

3-(Pyrrolidin-1-yl)azetidine-1-carboxylic acid {4-[2-fluoro-4-(3-phenylacetylthioureido)phenoxy]pyridin-2-yl}amide ¹H-NMR Spectrum (CDCl₃) δ (ppm): 1.83 (4H, m), 2.51 (4H, m), 3.36 (1H, m), 3.74 (2H, s), 3.96 (2H, m), 4.08 (2H, m), 6.55 (1H, dd, J=2.0, 6.0 Hz), 6.83 (1H, s), 7.17 (1H, m), 7.30-7.46 (5H, m), 7.66 (1H, d, J=2.0 Hz), 7.89 (1H, dd, J=2.8, 11.8 Hz), 8.04 (1H, d, J=6.0 Hz), 8.59 (1H, s), 12.44 (1H, s). ESI-MS: 549[M+H]⁺.

Production Example 261-1

3-(Pyrrolidin-1-yl)azetidine-1-carboxylic acid [4-(2-fluoro-4-nitrophenoxy)pyridin-2-yl]amide ¹H-NMR Spectrum (CD₃OD) δ (ppm): 1.84 (4H, m), 2.56 (4H, m), 3.36 (1H, m), 3.93 (2H, m), 4.13 (2H, m), 6.71 (1H, dd, J=2.4, 5.6 Hz), 7.49 (1H, dd, J=8.0, 8.8 Hz), 7.57 (1H, d, J=2.4 Hz), 8.15-8.19 (2H, m), 8.25 (1H, dd, J=2.8, 10.2 Hz)

Production Example 261-2

3-(Pyrrolidin-1-yl)azetidine-1-carboxylic acid [4-(4-amino-2-fluorophenoxy)pyridin-2-yl]amide ¹H-NMR Spectrum (CDCl₃) δ (ppm): 1.83 (4H, m), 2.50 (4H, m), 3.36 (1H, m), 3.73 (2H, s), 3.96 (2H, m), 4.07 (2H, m), 6.44 (1H, m), 6.49 (1H, dd, J=2.8, 11.6 Hz), 6.53 (1H, dd, J=2.4, 6.0 Hz), 6.75 (1H, brs), 6.95 (1H, m), 7.61 (1H, d, J=2.4 Hz), 8.00 (1H, d, J=6.0 Hz)

Example 262

N-(2-Fluoro-4-{2-[(3-hydroxyazetidine-1-carbonyl)amino]pyridin-4-yloxy}phenyl)-N'-(4-fluorophenyl)malonamide ¹H-NMR Spectrum (CDCl₃) δ (ppm): 3.60 (2H, s), 3.91-3.94 (2H, m), 4.24 (2H, m), 4.60 (1H, m), 5.09 (1H, m), 6.52 (1H, d, J=5.6 Hz), 6.89 (2H, m), 7.01 (2H, m), 7.19 (1H, s), 7.59 (2H, dd, J=4.0, 7.6 Hz), 7.67 (1H, s), 8.05 (1H, d, J=5.6 Hz), 8.23 (1H, m), 9.91 (1H, s), 9.97 (1H, s). ESI-MS (m/z): 498[M+H]⁺, 520[M+Na]⁺.

Example 263

3-[4-(2-Fluoro-4-{3-[2-(2-fluorophenyl)acetyl]thioureido}phenoxy)pyridin-2-yl]-1-methyl-1-(1-methylpiperidin-4-yl)urea ¹H-NMR Spectrum (CDCl₃) δ (ppm): 1.40-1.88 (4H, m), 2.08 (2H, m), 2.28 (3H, s), 2.88 (3H, s), 2.92 (2H, m), 3.77 (2H, s), 4.17 (1H, m), 6.54 (1H, m), 7.10-7.26 (4H, m), 7.27-7.47 (3H, m), 7.69 (1H, m), 7.90 (1H, m), 8.06 (1H, d, J=5.6 Hz), 8.65 (1H, brs), 12.37 (1H, brs). ESI-MS (m/z): 569[M+H]⁺.

Example 264

3-[4-(2-Fluoro-4-{3-[2-(4-methoxyphenyl)acetyl]thioureido}phenoxy)pyridin-2-yl]-1-methyl-1-(1-methylpiperidin-4-yl)urea ¹H-NMR Spectrum (CDCl₃) δ (ppm): 1.57-1.70 (2H, m), 1.76 (2H, m), 2.08 (2H, m), 2.29 (3H, s), 2.88 (3H, s), 2.92 (2H, m), 3.69 (2H, s), 3.84 (3H, s), 4.17 (1H, m), 6.54 (1H, dd, J=2.8, 5.6 Hz), 6.96 (2H, dd, J=2.8, 8.8 Hz), 7.10-7.31 (4H, m), 7.35 (1H, m), 7.69 (1H, brs), 7.89 (1H, dd, J=2.8, 11.6 Hz), 8.06 (1H, m), 8.44 (1H, brs), 12.46 (1H, brs). ESI-MS (m/z): 581[M+H]⁺.

Example 265

3-[4-(2-Fluoro-4-{3-[2-(2-methoxyphenyl)acetyl]thioureido}phenoxy)pyridin-2-yl]-1-methyl-1-(1-methylpiperidin-4-yl)urea ¹H-NMR Spectrum (CDCl₃) δ (ppm): 1.66 (2H, m), 1.77 (2H, m), 2.08 (2H, m), 2.29 (3H, s), 2.88 (3H, s), 2.92 (2H, m), 3.72 (2H, s), 4.01 (3H, s), 4.17 (1H, m), 6.53 (1H, dd, J=2.4, 5.6 Hz), 7.01 (3H, m), 7.13-7.20 (2H, m), 7.31-7.40 (2H, m), 7.69 (1H, d, J=2.4 Hz), 7.89 (1H, dd, J=2.4, 12.0 Hz), 8.05 (1H, brs), 9.41 (1H, brs), 12.36 (1H, brs). ESI-MS (m/z): 581[M+H]⁺.

Example 266

3-[4-(2-Fluoro-4-{3-[2-(3-fluorophenyl)acetyl]thioureido}phenoxy)pyridin-2-yl]-1-methyl-1-(1-methylpiperidin-4-yl)urea ¹H-NMR Spectrum (CDCl₃) δ (ppm): 1.50-1.70 (2H, m), 1.77 (2H, m), 2.07 (2H, m), 2.28 (3H, s), 2.88 (3H, s), 2.92 (2H, m), 3.73 (2H, s), 4.16 (1H, m), 6.55 (1H, m), 7.00-7.13 (3H, m), 7.30 (2H, m), 7.32-7.46 (2H, m), 7.68 (1H, m), 7.88 (1H, m), 8.06 (1H, m), 8.60 (1H, brs), 12.38 (1H, brs). ESI-MS (m/z): 569[M+H]⁺.

Example 267

4-(2-Fluoro-4-{3-[2-(4-fluorophenyl)acetyl]thioureido}phenoxy)-6-{[(3S)-3-(pyrrolidin-1-yl)pyrrolidin-1-yl]carbonylamino}pyrimidine $^1$H-NMR Spectrum (CDCl$_3$) δ (ppm): 1.78-1.90 (4H, m), 1.99 (1H, m), 2.17 (1H, m), 2.50-2.63 (4H, m), 2.83 (1H, m), 3.34 (1H, m), 3.47 (1H, m), 3.62-3.78 (2H, m), 3.71 (2H, s), 7.10-7.40 (7H, m), 7.70 (1H, d, J=0.8 Hz), 7.86 (1H, dd, J=2.4, 11.2 Hz), 8.33 (1H, d, J=0.8 Hz), 8.47 (1H, brs), 12.38 (1H, brs).

Production Example 267-1

4-(2-Fluoro-4-nitrophenoxy)-6-{[(3S)-3-(pyrrolidin-1-yl)pyrrolidin-1-yl]carbonylamino}pyrimidine $^1$H-NMR Spectrum (CDCl$_3$) δ (ppm): 1.80-1.85 (4H, m), 2.01 (1H, m), 2.19 (1H, m), 2.50-2.65 (4H, m), 2.85 (1H, m), 3.37 (1H, m), 3.47 (1H, m), 3.71 (1H, m), 6.92 (1H, m), 7.42 (1H, dd, J=7.6, 8.8 Hz), 8.02 (1H, s), 8.08-8.15 (2H, m), 8.33 (1H, s).

Production Example 267-2

4-(4-Amino-2-fluorophenoxy)-6-{[(3S)-3-(pyrrolidin-1-yl)pyrrolidin-1-yl]carbonylamino}pyrimidine ESI-MS (m/z): 387[M+H]$^+$.

Example 268

3-[6-(2-Fluoro-4-{3-[2-(4-fluorophenyl)acetyl]thioureido}phenoxy)pyrimidin-4-yl]-1-methyl-1-[(3R)-1-methylpyrrolidin-3-yl]urea

Production Example 268-1

3-[6-(2-Fluoro-4-nitrophenoxy)pyrimidin-4-yl]-1-methyl-1-[(3R)-1-methylpyrrolidin-3-yl]urea

Production Example 268-2

3-[6-(4-Amino-2-fluorophenoxy)pyrimidin-4-yl]-1-methyl-1-[(3R)-1-methylpyrrolidin-3-yl]urea

Example 269

3-[4-(2-Fluoro-4-{3-[2-(3-methoxyphenyl)acetyl]thioureido}phenoxy)pyridin-2-yl]-1-methyl-1-(1-methylpiperidin-4-yl)urea $^1$H-NMR Spectrum (CDCl$_3$) δ (ppm): 1.50-1.72 (2H, m), 1.79 (2H, m), 2.00-2.16 (2H, m), 2.30 (3H, s), 2.82-3.00 (5H, m), 3.72 (2H, s), 3.85 (3H, s), 4.17 (1H, m), 6.55 (1H, m), 6.75-7.88 (3H, m), 7.05-7.42 (4H, m), 7.69 (1H, m), 7.90 (1H, dd, J=2.4, 11.6 Hz), 8.07 (1H, d, J=6.0 Hz), 8.55 (1H, m), 12.44 (1H, brs). ESI-MS (m/z): 581[M+H]$^+$.

Example 270

3-(4-{2-Fluoro-4-[3-(2-o-tolylacetyl)thioureido]phenoxy}pyridin-2-yl)-1-methyl-1-(1-methylpiperidin-4-yl)urea $^1$H-NMR Spectrum (CDCl$_3$) δ (ppm): 1.50-1.72 (2H, m), 1.77 (2H, m), 2.08 (2H, m), 2.29 (3H, s), 2.36 (3H, s), 2.80-2.98 (5H, m), 3.77 (2H, s), 4.17 (1H, m), 6.54 (1H, dd, J=2.4, 6.0 Hz), 7.02-7.40 (7H, m), 7.69 (1H, d, J=2.4 Hz), 7.80 (1H, dd, J=2.4, 12.0 Hz), 8.06 (1H, d, J=6.0 Hz), 8.39 (1H, m), 12.47 (1H, brs). ESI-MS (m/z): 565[M+H]$^+$.

Example 271

3-(4-{2-Fluoro-4-[3-(2-m-tolylacetyl)thioureido]phenoxy}pyridin-2-yl)-1-methyl-1-(1-methylpiperidin-4-yl)urea $^1$H-NMR Spectrum (CDCl$_3$) δ (ppm): 1.50-1.90 (4H, m), 2.08 (2H, m), 2.29 (3H, s), 2.39 (3H, s), 2.80-3.10 (5H, m), 3.70 (2H, s), 4.17 (1H, m), 6.55 (1H, dd, J=2.4, 5.6 Hz), 7.00-7.50 (7H, m), 7.69 (1H, d, J=2.4 Hz), 7.89 (1H, dd, J=2.4, 11.6 Hz), 8.06 (1H, d, J=5.6 Hz), 8.59 (1H, brs), 12.47 (1H, brs). ESI-MS (m/z): 565[M+H]$^+$.

Example 272

4-(2-Fluoro-4-{3-[2-(4-fluorophenyl)acetyl]thioureido}phenoxy)-6-{[(2R)-2-(pyrrolidin-1-ylmethyl)pyrrolidin-1-yl]carbonylamino}pyrimidine $^1$H-NMR Spectrum (CDCl$_3$) δ (ppm): 1.63 (1H, m), 1.75-2.18 (7H, m), 2.49 (1H, m), 2.55-2.65 (2H, m), 2.70-2.95 (3H, m), 3.37 (1H, m), 3.70 (2H, s), 3.79 (1H, m), 3.93 (1H, m), 7.00-7.40 (7H, m), 7.58 (1H, d, J=0.8 Hz), 7.83 (1H, dd, J=2.4, 11.2 Hz), 8.28 (1H, d, J=0.8 Hz), 8.44 (1H, brs), 12.35 (1H, brs).

Production Example 272-1

4-(4-Amino-2-fluorophenoxy)-6-{[(2R)-2-(pyrrolidin-1-ylmethyl)pyrrolidin-1-yl]carbonylamino}pyrimidine $^1$H-NMR Spectrum (CDCl$_3$) δ (ppm): 1.63 (1H, m), 1.77-2.16 (7H, m), 2.49 (1H, m), 2.55-2.65 (2H, m), 2.70-2.95 (3H, m), 3.37 (1H, m), 3.70 (2H, brs), 3.78 (1H, m), 3.93 (1H, m), 6.42 (1H, m), 6.45 (1H, dd, J=2.8, 11.6 Hz), 6.97 (1H, m), 7.50 (1H, d, J=0.8 Hz), 8.31 (1H, d, J=0.8 Hz), 12.87 (1H, brs). ESI-MS (m/z): 401[M+H]$^+$.

Example 273

3-Methylimidazolidine-1-carboxylic acid [6-(2-fluoro-4-{3-[2-(4-fluorophenyl)acetyl]thioureido}phenoxy)pyrimidin-4-yl]amide $^1$H-NMR Spectrum (CDCl$_3$) δ (ppm): 2.44 (3H, s), 2.90-3.02 (2H, m), 3.52-3.61 (2H, m), 3.71 (2H, s), 4.14 (2H, s), 7.00-7.40 (7H, m), 7.61 (1H, d, J=0.8 Hz), 7.86 (1H, dd, J=2.4, 11.2 Hz), 8.34 (1H, d, J=0.8 Hz), 8.57 (1H, brs), 12.39 (1H, brs). ESI-MS (m/z): 550[M+Na]$^+$.

Production Example 273-1

1-[6-(2-Fluoro-4-nitrophenoxy)pyrimidin-4-yl]-3-(2-methylaminoethyl)urea $^1$H-NMR Spectrum (CDCl$_3$) δ (ppm): 2.49 (3H, s), 2.83 (2H, m), 3.50 (2H, m), 6.63 (1H, brs), 7.41 (1H, m), 8.09-8.15 (2H, m), 8.37 (1H, s), 8.85 (1H, br)

Production Example 273-2

1-[6-(4-Amino-2-fluorophenoxy)pyrimidin-4-yl]-3-(2-methylaminoethyl)urea

ESI-MS (m/z): 321[M+H]$^+$.

Production Example 273-3

3-Methylimidazolidine-1-carboxylic acid [6-(4-amino-2-fluorophenoxy)pyrimidin-4-yl]amide To 1-[6-(4-amino-2-fluorophenoxy)pyrimidin-4-yl]-3-(2-methylaminoethyl)urea (56.8 mg) dissolved in tetrahydrofuran (5 ml) was added paraformaldehyde (59 mg), followed by stirring at 80° C. for 1 hour. The reaction mixture was cooled to room temperature, and partitioned between ethyl acetate and 2N aqueous solution of sodium hydroxide. The separated organic layer was washed with water and brine, and dried over anhydrous sodium sulfate. The solvent was evaporated to give a residue, which was purified by silica gel column chromatography (Fuji Silysia NH, eluent; ethyl acetate, then ethyl acetate:methanol=95:5) to provide the titled compound (22.4 mg, 38%) as white powder.

$^1$H-NMR Spectrum (CDCl$_3$) δ (ppm): 2.44 (3H, d, J=2.8 Hz), 2.98 (2H, m), 3.57 (2H, m), 3.73 (2H, brs), 4.13 (2H, d, J=2.8 Hz), 6.46 (1H, m), 6.51 (1H, dd, J=2.4, 12.0 Hz), 6.96 (1H, m), 7.05 (1H, brs), 7.61 (1H, d, J=0.8 Hz), 8.37 (1H, d, J=0.8 Hz).

Example 274

3-(4-{2-Fluoro-4-[3-(2-p-tolylacetyl)thioureido]phenoxy}pyridin-2-yl)-1-methyl-1-(1-methylpiperidin-4-yl)urea $^1$H-NMR Spectrum (CDCl$_3$) δ (ppm): 1.65 (2H, m), 1.72 (2H, m), 2.07 (2H, m), 2.28 (3H, s), 2.38 (3H, s), 2.88 (3H, s), 2.92 (2H, m), 3.71 (2H, s), 4.16 (1H, m), 6.54 (1H, dd, J=2.0, 6.0 Hz), 7.15-7.30 (6H, m), 7.34 (1H, m), 7.69 (1H, d, J=2.0 Hz), 7.89 (1H, dd, J=2.8, 11.6 Hz), 8.06 (1H, d, J=6.0 Hz), 8.44 (1H, brs), 12.45 (1H, brs). ESI-MS (m/z): 565[M+H]$^+$.

Example 275

1-(2-Dimethylaminoethyl)-3-[6-(2-fluoro-4-{3-[2-(4-fluorophenyl)acetyl]thioureido}phenoxy)pyrimidin-4-yl]-1-methylurea $^1$H-NMR Spectrum (CDCl$_3$) δ (ppm): 2.41 (6H, s), 2.58-2.64 (2H, m), 3.00 (3H, s), 3.32-3.40 (2H, m), 3.71 (2H, s), 7.10-7.40 (7H, m), 7.48 (1H, s), 7.84 (1H, dd, J=2.4, 11.2 Hz), 8.33 (1H, s), 8.44 (1H, brs), 12.36 (1H, brs).

Production Example 275-1

1-(2-Dimethylaminoethyl)-3-[6-(2-fluoro-4-nitrophenoxy)pyrimidin-4-yl]-1-methylurea $^1$H-NMR Spectrum (CDCl$_3$) δ (ppm): 2.42 (6H, s), 2.60-2.63 (2H, m), 3.01 (3H, s), 3.36-3.39 (2H, m), 7.40 (1H, m), 7.57 (1H, d, J=0.8 Hz), 8.07-8.13 (2H, m), 8.31 (1H, d, J=0.8 Hz).

Production Example 275-2

3-[6-(4-Amino-2-fluorophenoxy)pyrimidin-4-yl]-1-(2-dimethylaminoethyl)-1-methylurea ESI-MS (m/z): 371[M+Na]$^+$.

Example 276

1-[4-(2-Fluoro-4-{3-[2-(4-fluorophenyl)acetyl]thioureido}phenoxy)pyridin-2-yl]-3-(4-methylpiperazin-1-yl)urea $^1$H-NMR Spectrum (CDCl$_3$) δ (ppm): 2.32 (3H, s), 2.36 (2H, m), 2.65 (2H, m), 2.77 (2H, m), 3.05 (2H, m), 3.71 (2H, s), 6.60 (1H, dd, J=2.4, 5.6 Hz), 7.00-7.38 (7H, m), 7.73 (1H, m), 7.88 (1H, dd, J=2.8, 11.6 Hz), 8.11 (1H, d, J=5.6 Hz), 8.50-8.80 (2H, m), 12.40 (1H, brs). ESI-MS (m/z): 556[M+H]$^+$.

Production Example 276-1

1-[4-(2-Fluoro-4-nitrophenoxy)pyridin-2-yl]-3-(4-methylpiperazin-1-yl)urea $^1$H-NMR Spectrum (CDCl$_3$) δ (ppm): 2.20-2.46 (5H, m), 2.50-3.60 (6H, m), 6.65 (1H, dd, J=2.4, 5.6 Hz), 7.10-7.40 (2H, m), 7.81 (1H, m), 8.10 (1H, m), 8.14 (1H, d, J=2.4 Hz), 8.21 (1H, d, J=5.6 Hz), 8.71 (1H, m). ESI-MS (m/z): 413[M+Na]$^+$.

Production Example 276-2

1-[4-(4-Amino-2-fluorophenoxy)pyridin-2-yl]-3-(4-methylpiperazin-1-yl)urea $^1$H-NMR Spectrum (CDCl$_3$) δ (ppm): 2.32 (3H, s), 2.36 (2H, m), 2.64 (2H, m), 2.77 (2H, m), 3.04 (2H, m), 3.75 (2H, m), 5.44 (1H, m), 6.38-6.47 (1H, m), 6.48-6.60 (2H, m), 6.91-6.99 (1H, m), 7.70 (1H, m), 8.07 (1H, d, J=12.0 Hz), 8.60 (1H, m). ESI-MS (m/z): 383[M+Na]$^+$.

Example 277

3-[6-(2-Fluoro-4-{3-[2-(4-fluorophenoxy)acetyl]thioureido}phenoxy)pyrimidin-4-yl]-1-methyl-1-[(1-methylazetidin-3-yl)methyl]urea $^1$H-NMR Spectrum (CDCl$_3$) δ (ppm): 2.35 (3H, s), 2.75 (1H, m), 3.04 (3H, s), 3.07 (2H, m), 3.39 (2H, m), 3.63 (2H, m), 3.71 (2H, s), 7.12 (2H, s), 7.21 (1H, m), 7.28 (2H, m), 7.35 (1H, m), 7.68 (1H, s), 7.84 (2H, m), 8.34 (1H, s), 8.54 (1H, brs), 12.38 (1H, s). ESI-MS (m/z): 556[M+H]$^+$.

Production Example 277-1

1-Benzhydrylazetidin-3-carboxylic acid methylamide

To a solution of 1-benzhydrylazetidin-3-carboxylic acid (654 mg) in N,N-dimethylformamide (4.0 ml) were added triethylamine (1.0 ml), benzotriazol-1-yloxytris(dimethylamino)phosphonium hexafluorophosphate (1.63 g) and methylamine hydrochloride (248 mg), followed by stirring at room temperature for 61.5 hours. The reaction mixture was partitioned between ethyl acetate and water. The organic layer was washed with brine, and dried over anhydrous sodium sulfate. The organic layer was concentrated to give a residue, which was purified by silica gel column chromatography (eluent; ethyl acetate). Fractions containing the target compound were concentrated to provide the titled compound (509 mg, 74.1%) as yellow crystals.

$^1$H-NMR Spectrum (CDCl$_3$) δ (ppm): 2.85 (3H, d, J=4.8 Hz), 3.11 (1H, m), 3.35 (2H, m), 3.45 (2H, m), 4.51 (1H, s), 6.10 (1H, br), 7.21 (2H, m), 7.29 (4H, m), 7.39 (4H, d, J=7.6 Hz). ESI-MS (m/z): 281[M+H]$^+$, 303[M+Na]$^+$.

Production Example 277-2 tert-Butyl 3-methylcarbamoylazetidine-1-carboxylate

To a solution of crude 1-benzhydrylazetidine-3-carboxylic acid methylamide (2.72 g) in methanol (200 ml) were added hydrochloric acid (3.0 ml) and 20% palladium hydroxide carbon (1.0 g), followed by stirring under hydrogen atmosphere (0.40 MPa) for 5 hours. The reaction mixture was filtered to remove the catalyst, which was washed with methanol, and the filtrate was concentrated. To the resultant residue was added hexane, allowed to stand for a while, the supernatant was removed using a pipette. The remain was evaporated to provide a crude product of azetidine-3-carboxylic acid methylamide hydrochloride (ESI-MS (m/z): 115[M+H]$^+$). To the crude product was added water (20 ml), followed by stirring in an ice water bath, and to the reaction mixture were added tetrahydrofuran (10 ml), di-tert-butyl dicarbonate (2.34 g) and sodium hydrogencarbonate (2.25 g), followed by stirring at room temperature for 12.5 hours. The reaction mixture was partitioned between ethyl acetate (200 ml) and brine (50 ml). The organic layer was dried over anhydrous sodium sulfate and concentrated under reduced pressure. The resultant residue was purified by silica gel column chromatography (eluent; heptane:ethyl acetate=1:1 to 1:2, ethyl acetate, then ethyl acetate:methanol=10:1 to 5:1) to provide the titled compound (696 mg) as colorless crystals.

$^1$H-NMR Spectrum (CDCl$_3$) δ (ppm): 1.43 (9H, s), 2.85 (3H, d, J=4.8 Hz), 3.15 (1H, m), 4.01-4.14 (4H, m), 5.53 (1H, br). ESI-MS (m/z): 237[M+Na]$^+$.

Production Example 277-3

N-Methyl-N-[(1-methylazetidin-3-yl)methyl]amine dihydrochloride

To a solution of tert-butyl 3-methylcarbamoylazetidine-1-carboxylate (696 mg) in tetrahydrofuran (10 ml) was added gradually lithium aluminum hydride (296 mg) while stirring in an ice bath. The reaction mixture was stirred under nitrogen atmosphere in an ice bath for 5 minutes, then at room temperature for 5 minutes. The reaction mixture was further stirred under nitrogen atmosphere at 65° C. for 1 hour and refluxed for 3 hours. The reaction mixture was cooled to room temperature, and tetrahydrofuran (10 ml) was added thereto. The reaction mixture was stirred in an ice bath, and lithium aluminum hydride (296 mg) was added gradually thereto. The reaction mixture was stirred under nitrogen atmosphere in an ice bath for 5 minutes and at room temperature for 5 minutes, and refluxed for 7 hours. The reaction mixture was stirred in an ice bath, and water (0.60 ml), 5N aqueous solution of sodium hydroxide (0.60 ml) and water (1.8 ml) were added in that order. The reaction mixture was stirred in an ice bath for 1 hour. The reaction mixture was filtered to remove insoluble material, 4N hydrochloric acid-ethyl acetate (1.6 ml) was added to the filtrate, and the solvent was evaporated. The resultant crystals were dried to provide the titled compound (552 mg, 90.8%) as colorless crystals.

$^1$H-NMR Spectrum (CD$_3$OD) δ (ppm): 2.71 (3H, s), 2.94 (3H, s), 3.30 (2H, m), 3.38 (2H, m), 4.11 (2H, m), 4.30 (2H, m). ESI-MS (m/z): 115[M+H]$^+$.

Production Example 277-4

3-[6-(2-Fluoro-4-nitrophenoxy)pyrimidin-4-yl]-1-methyl-1-[(1-methylazetidin-3-yl)methyl]urea $^1$H-NMR Spectrum (CDCl$_3$) δ (ppm): 2.34 (3H, s), 2.72 (1H, m), 3.05 (5H, m), 3.35 (2H, m), 3.65 (2H, m), 7.41 (1H, m), 7.77 (1H, s), 8.08-8.14 (3H, m), 8.33 (1H, s). ESI-MS (m/z): 391[M+H]$^+$.

Example 278

3-[6-(2-Fluoro-4-{3-[2-(4-fluorophenyl)acetyl]thioureido}phenoxy)pyrimidin-4-yl]-1-methyl-1-(1-methylazetidin-3-yl)urea $^1$H-NMR Spectrum (CDCl$_3$) δ (ppm): 2.50 (3H, s), 2.85 (2H, m), 2.93 (3H, s), 3.71 (3H, m), 3.93 (1H, m), 4.13 (1H, m), 7.10 (2H, m), 7.22 (1H, m), 7.26-7.36 (3H, m), 7.54 (1H, m), 7.52-7.87 (2H, m), 8.42 (1H, s), 8.55 (1H, brs), 12.38 (1H, s). ESI-MS (m/z): 542[M+H]$^+$.

Production Example 278-1 tert-Butyl 3-methylaminoazetidine-1-carboxylate

To a solution of 1-Boc-azetidin-3-on (240 mg) in methanol (20 ml) were added methylamine hydrochloride (1.42 g) and 10% palladium carbon (1.0 g), followed by stirring under hydrogen atmosphere at room temperature for 60 hours. The reaction mixture was filtered to remove the catalyst. To the filtrate was added again 10% palladium carbon (1.0 g), followed by stirring under hydrogen atmosphere (0.40 MPa) at room temperature for 9 hours. The reaction mixture was filtered to remove the catalyst, and the filtrate was concentrated under reduced pressure. To the resultant residue were added a saturated aqueous solution of sodium hydrogencarbonate, ethyl acetate and potassium carbonate, followed by partition. The aqueous layer was extracted with ethyl acetate. The combined organic layer was dried over anhydrous sodium sulfate, concentrated under reduced pressure to provide a crude product of the title compound (216 mg) as a pale yellow oil.

¹H-NMR Spectrum (CDCl₃) δ (ppm): 1.44 (9H, s), 2.38 (3H, s), 3.50 (1H, m), 3.64 (2H, m), 4.07 (2H, m).

Production Example 278-2

Methyl-(1-methylazetidin-3-yl)amine dihydrochloride

To a solution of crude tert-butyl 3-methylaminoazetidine-1-carboxylate (627 mg) in tetrahydrofuran (20 ml) was added gradually lithium aluminium hydride (256 mg) while stirring in an ice bath. The reaction mixture was stirred under nitrogen atmosphere in an ice bath for 5 minutes, at room temperature for 5 minutes, and at 80° C. for 5 hours. To the reaction mixture were added water (0.256 ml), 5N aqueous solution of sodium hydroxide (0.256 ml) and water (0.768 ml) while stirring in an ice bath, followed by stirring in an ice bath for 2 hours. The reaction mixture was filtered to remove insoluble material, and 4N hydrochloric acid-ethyl acetate (1.6 ml) was added to the filtrate. The solvent was evaporated to provide a crude product of the title compound (395 mg) as pale yellow oil.

ESI-MS (m/z): 101[M+H]⁺.

Production Example 278-3

3-[6-(2-Fluoro-4-nitrophenoxy)pyrimidin-4-yl]-1-methyl-1-(1-methylazetidin-3-yl)urea ¹H-NMR Spectrum (CDCl₃) δ (ppm): 2.49 (3H, s), 2.84 (2H, m), 2.95 (3H, s), 3.73 (1H, m), 3.94 (1H, m), 4.14 (1H, m), 7.41 (1H, m), 7.96 (1H, s), 8.08-8.14 (3H, m), 8.41 (1H, s). ESI-MS (m/z): 377[M+H]⁺, 399[M+Na]⁺.

Example 279

4-{[(2R)-2-(Dimethylaminomethyl)pyrrolidin-1-yl]carbonylamino}-6-(2-fluoro-4-{3-[2-(4-fluorophenyl)acetyl]thioureido}phenoxy)pyrimidine ¹H-NMR Spectrum (CDCl₃) δ (ppm): 1.55-1.65 (1H, m), 1.75-1.90 (2H, m), 2.09 (1H, m), 2.30-2.50 (7H, m), 2.63 (1H, m), 3.37 (1H, m), 3.71 (2H, s), 3.79 (1H, m), 3.93 (1H, m), 7.00-7.40 (6H, m), 7.56 (1H, s), 7.84 (1H, m), 8.33 (1H, s), 8.70 (1H, brs), 12.38 (1H, brs), 13.12 (1H, brs).

Production Example 279-1

4-{[(2R)-2-(Dimethylaminomethyl)pyrrolidin-1-yl]carbonylamino}-6-(2-fluoro-4-nitrophenoxy)pyrimidine ¹H-NMR Spectrum (CDCl₃) δ (ppm): 1.64 (1H, m), 1.80-1.90 (2H, m), 2.14 (1H, m), 2.40-2.48 (7H, m), 2.65 (1H, dd, J=10.0, 13.2 Hz), 3.39 (1H, m), 3.82 (1H, m), 3.96 (1H, m), 7.41 (1H, m), 7.69 (1H, d, J=0.8 Hz), 8.07-8.13 (2H, m), 8.32 (1H, d, J=0.8 Hz), 13.32 (1H, brs).

Production Example 279-2

4-(4-Amino-2-fluorophenoxy)-6-{[(2R)-2-(dimethylaminomethyl)pyrrolidin-1-yl]carbonylamino}pyrimidine ESI-MS (m/z): 375[M+H]⁺.

Example 280

3-[6-(2-Fluoro-4-{3-[2-(4-fluorophenyl)acetyl]thioureido}phenoxy)pyrimidin-4-yl]-1-methyl-1-[(2R)-(1-methylpyrrolidin-2-yl)methyl]urea ¹H-NMR Spectrum (CDCl₃) δ (ppm): 1.68 (1H, m), 1.76-1.88 (2H, m), 1.97 (1H, m), 2.41 (1H, m), 2.49 (3H, s), 2.77 (1H, m), 3.02 (3H, s), 3.16-3.28 (2H, m), 3.50 (1H, m), 3.71 (2H, s), 7.10-7.40 (7H, m), 7.49 (1H, dd, J=2.4, 11.2 Hz), 8.33 (1H, s), 8.42 (1H, brs), 12.36 (1H, brs)

Production Example 280-1

3-[6-(2-Fluoro-4-nitrophenoxy)pyrimidin-4-yl]-1-methyl-1-[(2R)-(1-methylpyrrolidin-2-yl)methyl]urea ¹H-NMR Spectrum (CDCl₃) δ (ppm): 1.64-2.08 (4H, m), 2.38-2.46 (2H, m), 2.50 (3H, s), 2.80 (1H, m), 3.03 (3H, s), 3.25 (1H, m), 3.53 (1H, m), 7.40 (1H, m), 7.59 (1H, s), 8.06-8.14 (2H, m), 8.32 (1H, s).

Production Example 280-2

3-[6-(4-Amino-2-fluorophenoxy)pyrimidin-4-yl]-1-methyl-1-[(2R)-(1-methylpyrrolidin-2-yl)methyl]urea ESI-MS (m/z): 397[M+Na]⁺.

Example 281

3-[6-(3-Fluoro-4-{3-[2-(4-fluorophenyl)acetyl]thioureido}phenoxy)pyrimidin-4-yl]-1-methyl-1-[(3S)-1-methylpyrrolidin-3-yl]urea ¹H-NMR Spectrum (CDCl₃) δ (ppm): 1.99 (1H, m), 2.13 (1H, m), 2.32-2.45 (2H, m), 2.45 (3H, s), 3.05 (1H, m), 3.07 (3H, s), 3.25 (1H, m), 3.72 (2H, s), 4.10 (1H, m), 6.97-7.04 (2H, m), 7.09-7.14 (2H, m), 7.20-7.35 (3H, m), 7.67 (1H, s), 8.34-8.39 (2H, m), 8.50 (1H, brs), 12.30 (1H, brs).

Production Example 281-1

Benzyl N-[2-fluoro-4-(6-{3-methyl-3-[(3S)-1-methylpyrrolidin-3-yl]ureido}pyrimidin-4-yloxy)phenyl]carbamate ¹H-NMR Spectrum (CDCl₃) δ (ppm): 1.99 (1H, m), 2.13 (1H, m), 2.30-2.40 (2H, m), 2.44 (3H, s), 3.05 (1H, m), 3.07 (3H, s), 3.24 (1H, m), 4.13 (1H, m), 5.23 (2H, s), 6.86 (1H, m), 6.90-6.95 (2H, m), 7.20-7.45 (6H, m), 7.62 (1H, d, J=0.8 Hz), 8.14 (1H, m), 8.38 (1H, d, J=0.8 Hz).

Example 282

4-{[(3S)-3-Dimethylaminopyrrolidin-1-yl]carbonylamino}-6-(3-fluoro-4-{3-[2-(4-fluorophenyl)acetyl]thioureido}phenoxy)pyrimidine ¹H-NMR Spectrum (CDCl₃) δ (ppm): 1.91 (1H, m), 2.20 (1H, m), 2.29 (6H, s), 2.78 (1H, m), 3.26 (1H, m), 3.45 (1H, m), 3.60-3.80 (4H, m), 6.90-7.05 (2H, m), 7.09-7.15 (2H, m), 7.20-7.40 (3H, m), 7.64 (1H, d, J=0.8 Hz), 8.36-8.42 (2H, m), 8.50 (1H, brs), 12.32 (1H, brs).

Production Example 282-1

Benzyl N-(4-{6-[(3S)-(3-dimethylaminopyrrolidin-1-ylcarbonyl)amino]pyrimidin-4-yloxy}-2-fluorophenyl)carbamate $^1$H-NMR Spectrum (CDCl$_3$) δ (ppm): 1.90 (1H, m), 2.20 (1H, m), 2.29 (6H, s), 2.78 (1H, m), 3.25 (1H, m), 3.46 (1H, m), 3.60-3.90 (2H, m), 5.23 (2H, s), 6.88 (1H, m), 6.92-6.96 (2H, m), 7.13 (1H, brs), 7.33-7.45 (5H, m), 7.60 (1H, d, J=0.8 Hz), 8.17 (1H, m), 8.37 (1H, d, J=0.8 Hz).

Example 283

3-(6-{2-Fluoro-4-[3-(2-o-tolylacetyl)thioureido]phenoxy}pyrimidin-4-yl)-1-methyl-1-(1-methylpiperidin-4-yl)urea $^1$H-NMR Spectrum (CDCl$_3$) δ (ppm): 1.20-3.00 (17H, m), 3.76 (2H, m), 4.19 (1H, m), 7.18-7.50 (7H, m), 7.68 (1H, m), 7.87 (1H, dd, J=2.4, 11.6 Hz), 8.34 (2H, m), 12.45 (1H, m). ESI-MS (m/z): 566[M+H]$^+$.

Example 284

3-[6-(2-Fluoro-4-{3-[2-(4-fluorophenyl)acetyl]thioureido}phenoxy)pyrimidin-4-yl]-1-methyl-1-(1-methylpiperidin-4-ylmethyl)urea $^1$H-NMR Spectrum (CDCl$_3$) δ (ppm): 1.20-1.80 (5H, m), 1.99 (2H, m), 2.20-2.36 (3H, m), 2.84-3.00 (2H, m), 3.02-3.14 (3H, m), 3.22-3.34 (2H, m), 3.68-3.80 (2H, m), 7.03-7.54 (7H, m), 7.68-7.80 (1H, m), 7.82-7.96 (1H, m), 8.30-8.43 (1H, m), 8.46-8.66 (1H, m), 12.34-12.56 (1H, m). ESI-MS (m/z): 584[M+H]$^+$.

Production Example 284-1

3-[6-(4-Amino-2-fluorophenoxy)pyrimidin-4-yl]-1-methyl-1-(1-methylpiperidin-4-ylmethyl)urea ESI-MS (m/z): 389[M+H]$^+$.

Example 285

1-(1-Ethylpiperidin-4-yl)-3-[6-(2-fluoro-4-{3-[2-(4-fluorophenyl)acetyl]thioureido}phenoxy)pyrimidin-4-yl]-1-methylurea $^1$H-NMR Spectrum (CDCl$_3$) δ (ppm): 1.10 (3H, t, J=7.2 Hz), 1.70 (2H, m), 1.78 (2H, m), 2.05 (2H, m), 2.43 (2H, m), 2.88-2.96 (3H, m), 3.05 (2H, m), 3.68-3.78 (2H, m), 4.19 (1H, m), 7.02-7.16 (2H, m), 7.17-7.50 (5H, m), 7.60-7.75 (1H, m), 7.86 (1H, dd, J=2.8, 11.6 Hz), 8.29-8.40 (1H, m), 8.48 (1H, m), 12.30-12.50 (1H, m). ESI-MS (m/z): 584[M+H]$^+$.

Production Example 285-1

N-(1-Ethylpiperidin-4-yl)-N-methylamine

To a 40% solution of methylamine in methanol (1.26 g) were added acetonitrile (150 ml), 1-ethyl-4-piperidone (2.0 ml) and acetic acid (0.932 ml), then was added sodium triacetoxyborohydride (6.59 g), followed by stirring for 1 hour. After addition of a saturated aqueous solution of sodium hydrogencarbonate (20 ml), the reaction mixture was concentrated under reduced pressure. To the resultant residue was added methanol (20 ml) to suspend, and the reaction mixture was filtered to remove a solid, which was washed with methanol (20 ml). The filtrate was concentrated under reduced pressure, and tetrahydrofuran (50 ml) was added to the resultant residue to suspend. The reaction mixture was filtered to remove a solid, which was washed with tetrahydrofuran (100 ml). The filtrate was concentrated under reduced pressure to provide a crude product of the titled compound (3.33 g) as pale yellow oil.

ESI-MS (m/z): 143[M+H]$^+$.

Production Example 285-2

3-[6-(4-Amino-2-fluorophenoxy)pyrimidin-4-yl]-1-(1-ethylpiperidin-4-yl)-1-methylurea ESI-MS (m/z): 389[M+H]$^+$.

Example 286

1-Cyclopropyl-3-[6-(2-fluoro-4-{3-[2-(4-fluorophenyl)acetyl]thioureido}phenoxy)pyrimidin-4-yl]-1-(1-methylpiperidin-4-yl)urea $^1$H-NMR Spectrum (CDCl$_3$) δ (ppm): 0.89 (1H, m), 0.98 (2H, m), 1.08 (2H, m), 1.02-1.90 (2H, m), 2.12 (4H, m), 2.34 (3H, s), 2.99 (2H, m), 3.72 (2H, m), 4.10 (1H, m), 7.00-7.42 (6H, m), 7.71 (1H, s), 7.86 (1H, m), 8.26 (1H, s), 8.36 (1H, m), 8.51 (1H, brs), 12.39 (1H, brs). ESI-MS (m/z): 596[M+H]$^+$.

Production Example 286-1

3-[6-(4-Amino-2-fluorophenoxy)pyrimidin-4-yl]-1-cyclopropyl-1-(1-methylpiperidin-4-yl)urea ESI-MS (m/z): 401[M+H]$^+$.

Example 287

1-Ethyl-3-[6-(2-fluoro-4-{3-[2-(4-fluorophenyl)acetyl]thioureido}phenoxy)pyrimidin-4-yl]-1-(1-methylpiperidin-4-yl)urea $^1$H-NMR Spectrum (CDCl$_3$) δ (ppm): 1.28 (3H, m), 1.60-1.88 (4H, m), 1.98-2.20 (2H, m), 2.24-2.48 (3H, m), 2.95 (2H, m), 3.32 (2H, m), 3.64-3.76 (2H, m), 4.16 (1H, m), 7.00-7.16 (2H, m), 7.16-7.46 (5H, m), 7.70 (1H, m), 7.86 (1H, dd, J=2.4, 11.2 Hz), 8.34 (1H, m), 8.46 (1H, m), 12.37 (1H, m). ESI-MS (m/z): 606[M+Na]$^+$.

Example 288

3-[6-(2-Fluoro-4-{3-[2-(4-fluorophenyl)acetyl]thioureido}phenoxy)pyrimidin-4-yl]-1-methyl-1-(tetrahydropyran-4-yl)urea $^1$H-NMR Spectrum (CDCl$_3$) δ (ppm): 1.64 (2H, m), 1.80 (2H, ddd, J=4.4, 12.0, 12.8 Hz), 2.94 (3H, s), 3.51 (2H, m), 3.71 (2H, s), 4.06 (2H, dd, J=4.4, 11.6 Hz), 4.47 (1H, m), 7.12 (2H, m), 7.18-7.40 (5H, m), 7.68 (1H, s), 7.87 (1H, dd, J=2.8, 11.6 Hz), 8.35 (1H, m), 8.47 (1H, brs), 12.38 (1H, brs). ESI-MS (m/z): 579[M+Na]$^+$.

Production Example 288-1

3-[6-(2-Fluoro-4-nitrophenoxy)pyrimidin-4-yl]-1-methyl-1-(tetrahydropyran-4-yl)urea $^1$H-NMR Spectrum (CDCl$_3$) δ (ppm): 1.61 (2H, m), 1.81 (2H, m), 2.95 (3H, s), 3.52 (2H, m), 4.07 (2H, dd, J=4.8, 12.0 Hz), 4.47 (1H, m), 7.20-7.52 (2H, m), 7.78 (1H, s), 8.12 (2H, m), 8.34 (1H, s).

Example 289

3-[4-(3-Fluoro-4-{3-[2-(4-fluorophenyl)acetyl]thioureido}phenoxy)pyridin-2-yl]-1-methyl-1-(1-methylpiperidin-4-yl)urea $^1$H-NMR Spectrum (CDCl$_3$) δ (ppm): 1.66 (2H, m), 1.80 (2H, m), 2.10 (2H, m), 2.30 (3H, s), 2.89 (3H, s), 2.93 (2H, m), 3.72 (2H, s), 4.18 (1H, m), 6.58 (1H, dd, J=2.4, 6.0 Hz), 6.92 (2H, d, J=8.8 Hz), 7.09-7.14 (2H, m), 7.24-7.32 (3H, m), 7.74 (1H, d, J=2.4 Hz), 8.09 (1H, d, J=6.0 Hz), 8.32 (1H, m), 8.80 (1H, brs), 12.31 (1H, s). ESI-MS (m/z): 569[M+H]$^+$.

Example 290

3-[4-(3-Fluoro-4-{3-[2-(4-fluorophenyl)acetyl]ureido}phenoxy)pyridin-2-yl]-1-methyl-1-(1-methylpiperidin-4-yl)urea $^1$H-NMR Spectrum (CDCl$_3$) δ (ppm): 1.83 (4H, m), 2.15 (2H, m), 2.34 (3H, s), 2.89 (3H, s), 2.99 (2H, m), 3.73 (2H, s), 4.20 (1H, m), 6.54 (1H, dd, J=2.2, 5.8 Hz), 6.87-6.92 (2H, m), 7.06-7.12 (2H, m), 7.22-7.28 (3H, m), 7.69 (1H, d, J=2.2 Hz), 8.56 (1H, d, J=5.8 Hz), 8.15 (2H, m), 10.66 (1H, s). ESI-MS (m/z): 553[M+H]$^+$, 575[M+Na]$^+$.

Example 291

1-(3-Dimethylaminopropyl)-3-[4-(3-fluoro-4-{3-[2-(4-fluorophenyl)acetyl]thioureido}phenoxy)pyridin-2-yl]-1-methylurea $^1$H-NMR Spectrum (CDCl$_3$) δ (ppm): 1.83 (2H, m), 2.37-2.63 (8H, m), 2.93 (3H, s), 3.42 (3H, t, J=6.0 Hz), 3.72 (2H, s), 6.51 (1H, dd, J=2.4, 5.6 Hz), 6.89 (2H, m), 7.11 (2H, m), 7.29 (3H, m), 7.65 (1H, d, J=2.4 Hz), 8.27 (1H, m), 8.71 (1H, brs), 12.27 (1H, brs). ESI-MS (m/z): 557[M+H]$^+$.

Production Example 291-1

Benzyl (4-{2-[3-(3-dimethylaminopropyl)-3-methylureido]pyridin-4-yloxy}-2-fluorophenyl)carbamate $^1$H-NMR Spectrum (CDCl$_3$) δ (ppm): 1.74 (2H, m), 2.28 (6H, s), 2.35 (2H, t, J=6.0 Hz), 2.88 (3H, s), 3.40 (3H, t, J=6.0 Hz), 5.23 (2H, s), 6.43 (1H, dd, J=2.4, 6.0 Hz), 6.83-6.89 (3H, m), 7.35-7.42 (5H, m), 7.61 (1H, d, J=2.4 Hz), 8.05 (1H, d, J=6.0 Hz), 8.10 (1H, brs). ESI-MS (m/z): 496[M+H]$^+$, 518 [M+Na]$^+$.

Example 292

1-[4-(3-Fluoro-4-{3-[2-(4-fluorophenyl)acetyl]ureido}phenoxy)pyridin-2-yl]-3-(1-methylpiperidin-4-yl)urea $^1$H-NMR Spectrum (DMSO-d$_6$) δ (ppm): 1.38 (2H, m), 1.78 (2H, m), 2.02 (2H, m), 2.15 (3H, s), 2.58 (2H, m), 3.47 (1H, m), 3.75 (2H, s), 6.55 (1H, dd, J=2.4, 5.8 Hz), 7.00 (1H, d, J=2.4 Hz), 7.03 (1H, m), 7.17 (2H, m), 7.29 (1H, dd, J=2.4, 11.6 Hz), 7.35-7.38 (2H, m), 7.86 (1H, brs), 8.08 (1H, d, J=5.8 Hz), 8.17 (1H, m), 9.02 (1H, s), 10.73 (1H, brs), 11.16 (1H, s). ESI-MS (m/z): 539[M+H]$^+$.

Example 293

1-(3-Dimethylaminopropyl)-3-[4-(3-fluoro-4-{3-[2-(4-fluorophenyl)acetyl]ureido}phenoxy)pyridin-2-yl]-1-methylurea $^1$H-NMR Spectrum (CDCl$_3$) δ (ppm): 1.77 (2H, m), 2.32 (6H, brs), 2.37 (2H, m), 2.89 (3H, s), 3.40 (2H, m), 3.73 (2H, s), 6.46 (1H, dd, J=2.4, 5.8 Hz), 6.85-6.90 (2H, m), 7.10 (2H, m), 7.27-7.35 (3H, m), 7.61 (1H, d, J=2.4 Hz), 7.99 (1H, m), 8.06 (1H, d, J=5.8 Hz), 8.12 (1H, m), 10.62 (1H, s). ESI-MS (m/z): 541[M+H]$^+$.

Example 294

3-[6-(2-Fluoro-4-{3-[2-(4-fluorophenyl)acetyl]thioureido}phenoxy)pyrimidin-4-yl]-1-isopropyl-1-(1-methylpiperidin-4-yl)urea $^1$H-NMR Spectrum (CDCl$_3$) δ (ppm): 0.60-5.50 (21H, m), 6.90-7.75 (8H, m), 7.85 (1H, m), 8.33 (1H, m), 8.49 (1H, m), 12.38 (1H, m). ESI-MS (m/z): 598[M+H]$^+$.

Example 295

N-{3-Fluoro-4-[2-(3-methyl-3-phenylureido)pyridin-4-yloxy]phenyl}-N'-(4-fluorophenyl)malonamide $^1$H-NMR Spectrum (CDCl$_3$) δ (ppm): 3.27 (3H, s), 3.51 (2H, s), 6.59 (1H, dd, J=2.4, 5.6 Hz), 6.96-7.08 (3H, m), 7.14 (1H, m), 7.19-7.33 (3H, m), 7.34-7.42 (1H, m), 7.43-7.58 (4H, m), 7.66 (1H, d, J=2.4 Hz), 7.71 (1H, dd, J=2.4, 12.0 Hz), 7.98 (1H, d, J=5.6 Hz), 8.90 (1H, brs), 9.40 (1H, brs). ESI-MS (m/z): 554[M+Na]$^+$.

Production Example 295-1

3-[4-(2-Fluoro-4-nitrophenoxy)pyridin-2-yl]-1-methyl-1-phenylurea $^1$H-NMR Spectrum (CDCl$_3$) δ (ppm): 3.31 (3H, s), 6.61 (1H, dd, J=2.0, 5.6 Hz), 7.10 (1H, m), 7.25-7.36 (3H, m), 7.40 (1H, m), 7.49 (2H, m), 7.82 (1H, d, J=2.0 Hz), 8.06 (1H, d, J=5.6 Hz), 8.13 (2H, m).

Production Example 295-2

3-[4-(4-Amino-2-fluorophenoxy)pyridin-2-yl]-1-methyl-1-phenylurea $^1$H-NMR Spectrum (CDCl$_3$) δ (ppm): 3.31 (3H, s), 3.75 (2H, brs), 6.42-6.57 (3H, m), 6.96 (1H, m), 7.00 (1H, m), 7.27-7.33 (2H, m), 7.36 (1H, m), 7.47 (2H, m), 7.70 (1H, d, J=2.4 Hz), 7.91 (1H, d, J=5.6 Hz). ESI-MS (m/z): 375[M+Na]$^+$.

Example 296

N-[4-(2-Fluoro-4-{3-[2-(4-fluorophenyl)acetyl]ureido}phenoxy)pyridin-2-yl]-2-(1-methylpiperidin-4-yl)acetamide $^1$H-NMR Spectrum (CDCl$_3$) δ (ppm): 1.30-1.50 (2H, m), 1.70-1.80 (2H, m), 1.87 (1H, m), 1.96-2.06 (2H, m), 2.22-

2.32 (5H, m), 2.82-2.92 (2H, m), 3.73 (2H, s), 6.59 (1H, dd, J=2.4, 5.6 Hz), 7.10-7.30 (6H, m), 7.64 (1H, dd, J=2.0, 12.0 Hz), 7.79 (1H, m), 7.90 (1H, m), 7.94 (1H, brs), 8.09 (1H, d, J=5.6 Hz), 10.56 (1H, brs).

Production Example 296-1 tert-Butyl 4-{[4-(2-fluoro-4-nitrophenoxy)pyridin-2-ylcarbamoyl]methyl}piperidine-1-carboxylate 2-Amino-4-(2-fluoro-4-nitrophenoxy)pyridine (400 mg) was dissolved in dimethylformamide (4.0 ml) under nitrogen atmosphere. To the solution were added 2-[1-(tert-butoxycarbonyl)piperidin-4-yl]acetic acid (487 mg), triethylamine (0.335 ml) and BOP reagent (1.06 g) at room temperature, followed by stirring at 60° C. for 3 hours. The reaction mixture was partitioned between ethyl acetate and water. The separated organic layer was washed with a saturated aqueous solution of sodium hydrogencarbonate and brine, and dried over anhydrous sodium sulfate. The solvent was evaporated to give a residue, which was purified by silica gel column chromatography (eluent; ethyl acetate:heptane=1:2 to 1:1) to provide the titled compound (328 mg, 43%) as pale yellow powder.

$^1$H-NMR Spectrum (CDCl$_3$) δ (ppm): 1.20-1.50 (2H, m), 1.45 (9H, s), 1.55-1.75 (2H, m), 2.02 (1H, m), 2.28-2.30 (2H, m), 2.60-2.80 (2H, m), 4.00-4.20 (2H, m), 6.71 (1H, dd, J=2.0, 5.6 Hz), 7.32 (1H, m), 7.88 (1H, d, J=2.0 Hz), 8.01 (1H, brs), 8.10-8.16 (2H, m), 8.20 (1H, d, J=5.6 Hz).

Production Example 296-2 tert-Butyl 4-{[4-(4-amino-2-fluorophenoxy)pyridin-2-ylcarbamoyl]methyl}piperidine-1-carboxylate ESI-MS (m/z): 467[M+Na]$^+$.

Production Example 296-3 tert-Butyl 4-{[4-(2-fluoro-4-{3-[2-(4-fluorophenyl)acetyl]ureido}phenoxy)pyridin-2-ylcarbamoyl]methyl}piperidine-1-carboxylate ESI-MS (m/z): 646[M+Na]$^+$.

Example 297

N-[4-(2-Fluoro-4-{3-[2-(4-fluorophenyl)acetyl]thioureido}phenoxy)pyridin-2-yl]-2-(morpholin-4-yl)acetamide $^1$H-NMR Spectrum (CDCl$_3$) δ (ppm): 2.56-2.64 (4H, m), 3.13 (2H, s), 3.72 (2H, s), 3.76-3.82 (4H, m), 6.63 (1H, dd, J=2.4, 5.6 Hz), 7.10-7.40 (6H, m), 7.86 (1H, d, J=2.4 Hz), 7.91 (1H, dd, J=2.4, 12.0 Hz), 8.17 (1H, d, J=5.6 Hz), 8.48 (1H, brs), 9.52 (1H, brs), 12.41 (1H, brs). ESI-MS (m/z): 564[M+Na]$^+$.

Production Example 297-1

N-[4-(2-Fluoro-4-nitrophenoxy)pyridin-2-yl]-2-(morpholin-4-yl)acetamide $^1$H-NMR Spectrum (CDCl$_3$) δ (ppm): 2.60-2.65 (4H, m), 3.14 (2H, s), 3.78-3.82 (4H, m), 6.72 (1H, dd, J=2.4, 5.6 Hz), 7.32 (1H, m), 7.92 (1H, d, J=2.4 Hz), 8.10-8.16 (2H, m), 8.26 (1H, d, J=5.6 Hz), 9.61 (1H, brs).

Production Example 297-2

N-[4-(4-Amino-2-fluorophenoxy)pyridin-2-yl]-2-(morpholin-4-yl)acetamide

ESI-MS (m/z): 369[M+Na]$^+$.

Example 298

N-[4-(2-Fluoro-4-{3-[2-(4-fluorophenyl)acetyl]thioureido}phenoxy)pyridin-2-yl]-2-(4-methylpiperazin-1-yl)acetamide $^1$H-NMR Spectrum (CDCl$_3$) δ (ppm): 2.32 (3H, s), 2.44-2.70 (8H, m), 3.12 (2H, s), 3.72 (2H, s), 6.62 (1H, dd, J=2.4, 5.6 Hz), 7.10-7.40 (6H, m), 7.87 (1H, d, J=2.4 Hz), 7.91 (1H, dd, J=2.4, 12.0 Hz), 8.17 (1H, d, J=5.6 Hz), 8.48 (1H, brs), 9.57 (1H, brs), 12.41 (1H, brs). ESI-MS (m/z): 555[M+H]$^+$.

Production Example 298-1

N-[4-(2-Fluoro-4-nitrophenoxy)pyridin-2-yl]-2-(4-methylpiperazin-1-yl)acetamide $^1$H-NMR Spectrum (CDCl$_3$) δ (ppm): 2.33 (3H, s), 2.40-2.80 (8H, m), 3.14 (2H, s), 6.72 (1H, dd, J=2.4, 5.6 Hz), 7.32 (1H, m), 7.93 (1H, d, J=2.4 Hz), 8.19-8.17 (2H, m), 8.27 (1H, d, J=5.6 Hz), 9.66 (1H, brs).

Production Example 298-2

N-[4-(4-Amino-2-fluorophenoxy)pyridin-2-yl]-2-(4-methylpiperazin-1-yl)acetamide

ESI-MS (m/z): 382[M+Na]$^+$.

Example 299

4-Methylpiperazine-1-carboxylic acid [4-(3-fluoro-4-{3-[2-(4-fluorophenyl)acetyl]thioureido}phenoxy)pyridin-2-yl]amide $^1$H-NMR Spectrum (CDCl$_3$) δ (ppm): 2.32 (3H, s), 2.44 (4H, m), 3.52 (4H, m), 3.72 (2H, s), 6.57 (1H, dd, J=2.0, 5.6 Hz), 6.92 (2H, d, J=9.2 Hz), 7.10 (2H, m), 7.28 (2H, m), 7.31 (1H, d, J=2.0 Hz), 7.69 (1H, d, J=2.0 Hz), 8.08 (1H, d, J=5.6 Hz), 8.33 (1H, m), 8.65 (1H, brs), 12.29 (1H, s). ESI-MS: 541[M+H]$^+$, 563[M+Na]$^+$.

Production Example 299-1

Benzyl (2-fluoro-4-{2-[(4-methylpiperazine-1-carbonyl)amino]pyridin-4-yloxy}phenyl)carbamate $^1$H-NMR Spectrum (CDCl$_3$) δ (ppm): 2.31 (3H, s), 2.42 (4H, m), 3.51 (4H, m), 5.23 (2H, s), 6.52 (1H, dd, J=2.0, 5.8 Hz), 6.85-6.95 (3H, m), 7.34-7.44 (6H, m), 7.63 (1H, d, J=2.0 Hz), 8.04 (1H, d, J=2.0 Hz), 8.13 (1H, brs). ESI-MS: 480[M+H]$^+$, 502[M+Na]$^+$.

Example 300

3-[4-[2-Fluoro-4-{3-[2-(4-fluorophenyl)acetyl]thioureido}phenoxy]pyridin-2-yl]-1-methyl-1-phenylurea $^1$H-NMR Spectrum (CDCl$_3$) δ (ppm): 3.31 (3H, s), 3.72 (2H, s), 6.52 (1H, dd, J=2.4, 6.0 Hz), 7.03 (1H, brs), 7.10-7.33 (7H, m), 7.38 (2H, m), 7.48 (2H, m), 7.75 (1H, d, J=2.4 Hz), 7.91 (1H, dd, J=2.4, 11.6 Hz), 7.97 (1H, d, J=6.0 Hz), 8.57 (1H, brs), 12.41 (1H, brs). ESI-MS (m/z): 548[M+H]$^+$.

Example 301

1-(1-Acetylpiperidin-4-yl)-3-[4-(2-fluoro-4-{3-[2-(4-fluorophenyl)acetyl]thioureido}phenoxy)pyridin-2-yl]-1-methylurea $^1$H-NMR Spectrum (CDCl$_3$) δ (ppm): 1.10-1.90 (4H, m), 2.12 (3H, s), 2.59 (1H, m), 2.87 (3H, m), 3.16 (1H, m), 3.72 (2H, s), 3.89 (1H, m), 4.46 (1H, m), 4.76 (1H, m), 6.57 (1H, dd, J=2.4, 5.6 Hz), 7.08-7.40 (7H, m), 7.67 (1H, d, J=2.4 Hz), 7.91 (1H, dd, J=2.4, 11.2 Hz), 8.07 (1H, d, J=5.6 Hz), 8.60 (1H, brs), 12.42 (1H, brs). ESI-MS (m/z): 619[M+Na]$^+$.

Production Example 301-1

1-(1-Acetylpiperidin-4-yl)-3-[4-(2-fluoro-4-nitrophenoxy)pyridin-2-yl]-1-methylurea $^1$H-NMR Spectrum (CDCl$_3$) δ (ppm): 1.44-1.82 (4H, m), 2.12 (3H, s), 2.59 (1H, m), 2.89 (3H, s), 3.16 (1H, m), 3.89 (1H, m), 4.44 (1H, m), 4.76 (1H, m), 6.67 (1H, dd, J=2.4, 5.6 Hz), 7.16-7.44 (2H, m), 7.75 (1H, d, J=2.4 Hz), 8.02-8.26 (3H, m)

Production Example 301-2

1-(1-Acetylpiperidin-4-yl)-3-[4-(4-amino-2-fluorophenoxy)pyridin-2-yl]-1-methylurea $^1$H-NMR Spectrum (CDCl$_3$) δ (ppm): 1.30-1.90 (4H, m), 2.11 (3H, s), 2.59 (1H, m), 2.86 (3H, m), 3.16 (1H, m), 3.76 (2H, brs), 3.89 (1H, m), 4.46 (1H, m), 4.75 (1H, m), 6.50-6.60 (3H, m), 6.96 (1H, m), 7.23 (1H, m), 7.62 (1H, m), 8.02 (1H, d, J=5.6 Hz). ESI-MS (m/z): 424[M+Na]$^+$.

Example 302

3-[6-[2-Fluoro-4-{3-[2-(4-fluorophenyl)acetyl]thioureido}phenoxy]pyrimidin-4-yl]-1-(4-methoxyphenyl)-1-methylurea $^1$H-NMR Spectrum (CDCl$_3$) δ (ppm): 3.31 (3H, s), 3.71 (2H, s), 3.85 (3H, s), 6.99 (2H, m), 7.12 (2H, m), 7.18-7.40 (7H, m), 7.74 (1H, s), 7.85 (1H, dd, J=2.4, 11.2 Hz), 8.24 (1H, s), 8.51 (1H, brs), 12.38 (1H, brs). ESI-MS (m/z): 601[M+Na]$^+$.

Production Example 302-1

3-[6-(2-Fluoro-4-nitrophenoxy)pyrimidin-4-yl]-1-(4-methoxyphenyl)-1-methylurea $^1$H-NMR Spectrum (CDCl$_3$) δ (ppm): 3.33 (3H, s), 3.86 (3H, s), 7.01 (2H, m), 7.19 (1H, brs), 7.20-7.37 (2H, m), 7.41 (1H, m), 7.84 (1H, s), 8.11 (2H, m), 8.23 (1H, s). ESI-MS (m/z): 436[M+Na]$^+$.

Production Example 302-2

3-[6-(4-Amino-2-fluorophenoxy)pyrimidin-4-yl]-1-(4-methoxyphenyl)-1-methylurea $^1$H-NMR Spectrum (CDCl$_3$) δ (ppm): 3.30 (3H, s), 3.73 (2H, brs), 3.85 (3H, s), 6.48 (2H, m), 6.90-7.02 (3H, m), 7.09 (1H, m), 7.18-7.30 (2H, m), 7.66 (1H, m), 8.27 (1H, m). ESI-MS (m/z): 406[M+Na]$^+$.

Example 303

1-(4-Dimethylaminophenyl)-3-[6-(2-fluoro-4-{3-[2-(4-fluorophenyl)acetyl]thioureido}phenoxy)pyrimidin-4-yl]-1-methylurea $^1$H-NMR Spectrum (CDCl$_3$) δ (ppm): 3.00 (6H, s), 3.29 (3H, s), 3.71 (2H, s), 6.74 (2H, d, J=8.8 Hz), 7.00-7.18 (4H, m), 7.19-7.36 (5H, m), 7.75 (1H, m), 7.85 (1H, dd, J=2.4, 11.2 Hz), 8.23 (1H, m), 8.54 (1H, brs), 12.38 (1H, brs). ESI-MS (m/z): 614[M+Na]$^+$.

Production Example 303-1

3-[6-(2-Fluoro-4-nitrophenoxy)pyrimidin-4-yl]-1-(4-dimethylaminophenyl)-1-methylurea $^1$H-NMR Spectrum (CDCl$_3$) δ (ppm): 3.01 (6H, s), 3.31 (3H, s), 6.75 (2H, m), 7.14 (2H, m), 7.28 (1H, m), 7.41 (1H, m), 7.85 (1H, s), 8.10 (2H, m), 8.22 (1H, s).

Production Example 303-2

3-[6-(4-Amino-2-fluorophenoxy)pyrimidin-4-yl]-1-(4-dimethylaminophenyl)-1-methylurea $^1$H-NMR Spectrum (CDCl$_3$) δ (ppm): 3.00 (6H, s), 3.29 (3H, s), 3.73 (2H, brs), 6.45 (1H, m), 6.50 (1H, dd, J=2.8, 12.0 Hz), 6.74 (2H, m), 6.97 (1H, m), 7.13 (2H, m), 7.19 (1H, brs), 7.67 (1H, m), 8.27 (1H, m). ESI-MS (m/z): 419[M+Na]$^+$.

Example 304

1-(2-Cyanoethyl)-3-{4-[2-fluoro-4-(3-phenylacetylthioureido)phenoxy]pyridin-2-yl}-1-methylurea $^1$H-NMR Spectrum (CDCl$_3$) δ (ppm): 2.67 (2H, t, J=6.4 Hz), 3.20 (3H, s), 3.66 (2H, t, J=6.4 Hz), 3.75 (2H, s), 6.56 (1H, dd, J=2.4, 5.6 Hz), 7.10-7.58 (8H, m), 7.65 (1H, m), 7.91 (1H, dd, J=2.4, 12.0 Hz), 8.08 (1H, d, J=5.6 Hz), 8.54 (1H, brs), 12.46 (1H, m). ESI-MS (m/z): 507[M+H]$^+$.

Production Example 304-1

3-[4-(2-Fluoro-4-nitrophenoxy)pyridin-2-yl]-1-(2-cyanoethyl)-1-methylurea $^1$H-NMR Spectrum (CDCl$_3$) δ (ppm): 2.67 (2H, t, J=6.4 Hz), 3.22 (3H, s), 3.66 (2H, t, J=6.4 Hz), 6.66 (1H, dd, J=2.0, 5.6 Hz), 7.20-7.40 (2H, m), 7.72 (1H, d, J=2.0 Hz), 8.07-8.19 (3H, m).

Production Example 304-2

3-[4-(4-Amino-2-fluorophenoxy)pyridin-2-yl]-1-(2-cyanoethyl)-1-methylurea $^1$H-NMR Spectrum (CDCl$_3$) δ (ppm): 2.67 (2H, t, J=6.4 Hz), 3.19 (3H, s), 3.66 (2H, t, J=6.4 Hz), 3.76 (2H, brs), 6.46 (1H, m), 6.52 (2H, m), 6.96 (1H, m), 7.26 (1H, m), 7.60 (1H, brs), 8.03 (1H, d, J=6.0 Hz).

Example 305

4-Acetylpiperazine-1-carboxylic acid {4-[2-fluoro-4-(3-phenylacetylthioureido)phenoxy]pyridin-2-yl}amide $^1$H-NMR Spectrum (CDCl$_3$) δ (ppm): 2.13 (3H, s), 3.44-3.65 (6H, m), 3.69 (2H, m), 3.75 (2H, s), 6.56 (1H, m), 7.10-7.50 (8H, m), 7.61 (1H, brs), 7.90 (1H, dd, J=2.4, 11.6 Hz), 8.06 (1H, d, J=5.6 Hz), 8.54 (1H, brs), 12.45 (1H, brs). ESI-MS (m/z): 573[M+Na]$^+$.

Production Example 305-1

4-Acetylpiperazine-1-carboxylic acid [4-(4-amino-2-fluorophenoxy)pyridin-2-yl]amide $^1$H-NMR Spectrum (CDCl$_3$) δ (ppm): 2.13 (3H, s), 3.43-3.60 (6H, m), 3.68 (2H, m), 3.76 (2H, brs), 6.45 (1H, dd, J=2.4, 8.8 Hz), 6.48-6.54 (2H, m), 6.98 (1H, m), 7.34 (1H, brs), 7.57 (1H, brs), 8.02 (1H, d, J=6.0 Hz).

Example 306

N-[4-(2-Fluoro-4-{3-[2-(4-fluorophenyl)acetyl]thioureido}phenoxy)pyridin-2-yl]-2-(4-hydroxypiperidin-1-yl)acetamide $^1$H-NMR Spectrum (CDCl$_3$) δ (ppm): 1.60-1.75 (2H, m), 1.90-2.00 (2H, m), 2.35-2.45 (2H, m), 2.80-2.90 (2H, m), 3.11 (2H, s), 3.72 (2H, s), 3.78 (1H, m), 6.62 (1H, dd, J=2.4, 5.6 Hz), 7.10-7.40 (6H, m), 7.86 (1H, d, J=2.4 Hz), 7.91 (1H, dd, J=2.4, 12.0 Hz), 8.17 (1H, d, J=5.6 Hz), 8.47 (1H, brs), 9.62 (1H, brs), 12.41 (1H, brs). ESI-MS (m/z): 578[M+Na]$^+$.

Production Example 306-1

N-[4-(2-Fluoro-4-nitrophenoxy)pyridin-2-yl]-2-(4-hydroxypiperidin-1-yl)acetamide $^1$H-NMR Spectrum (CDCl$_3$) δ (ppm): 1.65-1.80 (2H, m), 1.90-2.10 (2H, m), 2.30-2.45 (2H, m), 2.80-2.90 (2H, m), 3.12 (2H, s), 3.79 (2H, s), 6.72 (1H, dd, J=2.4, 5.6 Hz), 7.32 (1H, m), 7.92 (1H, d, J=2.4 Hz), 8.09-8.16 (2H, m), 8.26 (1H, d, J=5.6 Hz), 9.70 (1H, brs).

Production Example 306-2

N-[4-(4-Amino-2-fluorophenoxy)pyridin-2-yl]-2-(4-hydroxypiperidin-1-yl)acetamide ESI-MS (m/z): 383[M+Na]$^+$.

Example 307

N-[4-(2-Fluoro-4-{3-[2-(4-fluorophenyl)acetyl]thioureido}phenoxy)pyridin-2-yl]-2-(1-methylpiperidin-4-yl)acetamide $^1$H-NMR Spectrum (CDCl$_3$) δ (ppm): 1.28-1.40 (2H, m), 1.70-1.80 (2H, m), 1.86 (1H, m), 1.90-2.00 (2H, m), 2.20-2.30 (5H, m), 2.78-2.88 (2H, m), 3.72 (2H, s), 6.61 (1H, dd, J=2.4, 5.6 Hz), 7.10-7.40 (6H, m), 7.83 (1H, d, J=2.4 Hz), 7.91 (1H, dd, J=2.4, 12.0 Hz), 7.94 (1H, brs), 8.11 (1H, d, J=5.6 Hz), 8.52 (1H, brs), 12.42 (1H, brs). ESI-MS (m/z): 554[M+H]$^+$.

Production Example 307-1 tert-Butyl 4-{[4-(2-fluoro-4-{3-[2-(4-fluorophenyl)acetyl]thioureido}phenoxy)pyridin-2-ylcarbamoyl]methyl}piperidine-1-carboxylate $^1$H-NMR Spectrum (CDCl$_3$) δ (ppm): 1.10-1.30 (2H, m), 1.45 (9H, s), 1.70-1.80 (2H, m), 2.02 (1H, m), 2.25-2.30 (2H, m), 2.60-2.80 (2H, m), 3.72 (2H, s), 4.00-4.20 (2H, m), 6.61 (1H, dd, J=2.4, 5.6 Hz), 7.10-7.40 (6H, m), 7.82 (1H, d, J=2.4 Hz), 7.91 (1H, dd, J=2.4, 12.0 Hz), 8.02 (1H, brs), 8.11 (1H, d, J=5.6 Hz), 8.49 (1H, brs), 12.42 (1H, brs).

Example 308

2-{[4-(2-Hydroxyethyl)piperazin-1-yl]carbonylamino}-4-(2-fluoro-4-{3-[2-(phenyl)acetyl]thioureido}phenoxy)pyridine $^1$H-NMR Spectrum (CDCl$_3$) δ (ppm): 2.50-2.60 (6H, m), 3.50-3.56 (4H, m), 3.62-3.68 (2H, m), 3.75 (2H, s), 6.55 (1H, dd, J=2.4, 5.6 Hz), 7.16-7.50 (8H, m), 7.63 (1H, d, J=2.4 Hz), 7.90 (1H, dd, J=2.4, 11.6 Hz), 8.05 (1H, d, J=5.6 Hz), 8.51 (1H, brs), 12.44 (1H, brs). ESI-MS (m/z): 575[M+Na]$^+$.

Production Example 308-1

2-{[4-(2-Hydroxyethyl)piperazin-1-yl]carbonylamino}-4-(2-fluoro-4-nitrophenoxy)pyridine $^1$H-NMR Spectrum (CDCl$_3$) δ (ppm): 2.40-2.70 (6H, m), 3.40-3.60 (4H, m), 3.66 (2H, t, J=5.6 Hz), 6.65 (1H, dd, J=2.4, 5.6 Hz), 7.26-7.35 (2H, m), 7.70 (1H, d, J=2.4 Hz), 8.00-8.16 (3H, m).

Production Example 308-2

4-(4-Amino-2-fluorophenoxy)-2-{[4-(2-hydroxyethyl)piperazin-1-yl]carbonylamino}pyridine ESI-MS (m/z): 398[M+Na]$^+$.

Example 309

2-{[4-(2-Dimethylaminoethyl)piperazin-1-yl]carbonylamino}-4-(2-fluoro-4-{3-[2-(phenyl)acetyl]thioureido}phenoxy)pyridine $^1$H-NMR Spectrum (CDCl$_3$) δ (ppm): 2.26 (6H, s), 2.40-2.56 (8H, m), 3.48-3.56 (4H, m), 3.75 (2H, s), 6.54 (1H, dd, J=2.4, 5.6 Hz), 7.10-7.50 (8H, m), 7.64 (1H, d, J=2.4 Hz), 7.89 (1H, dd, J=2.4, 11.6 Hz), 8.05 (1H, d, J=5.6 Hz), 8.48 (1H, brs), 12.44 (1H, brs). ESI-MS (m/z): 580[M+H]$^+$.

Production Example 309-1

2-{[4-(2-Dimethylaminoethyl)piperazin-1-yl]carbonylamino}-4-(2-fluoro-4-nitrophenoxy)pyridine $^1$H-NMR Spectrum (CDCl$_3$) δ (ppm): 2.25 (6H, s), 2.40-2.55 (8H, m), 3.45-3.55 (4H, m), 6.64 (1H, dd, J=2.4, 5.6 Hz), 7.26-7.40 (2H, m), 7.71 (1H, d, J=2.4 Hz), 8.05-8.16 (3H, m).

Production Example 309-2

4-(4-Amino-2-fluorophenoxy)-2-{[4-(2-dimethylaminoethyl)piperazin-1-yl]carbonylamino}pyridine ESI-MS (m/z): 403[M+H]$^+$.

Example 310

N-[4-(2-Fluoro-4-{3-[2-(4-fluorophenyl)acetyl]thioureido}phenoxy)pyridin-2-yl]-2-(4-dimethylaminopiperidin-1-yl)acetamide $^1$H-NMR Spectrum (CDCl$_3$) δ (ppm): 1.50-1.70 (2H, m), 1.78-1.86 (2H, m), 2.10-2.28 (3H, m), 2.29 (6H, s), 2.90-2.98 (2H, m), 3.09 (2H, s), 3.72 (2H, s), 6.62 (1H, dd, J=2.4, 5.6 Hz), 7.10-7.40 (6H, m), 7.86 (1H, d, J=2.4 Hz), 7.90 (1H, dd, J=2.4, 12.0 Hz), 8.16 (1H, d, J=5.6 Hz), 8.48 (1H, m), 9.60 (1H, brs), 12.40 (1H, brs). ESI-MS (m/z): 583[M+H]$^+$.

Production Example 310-1

N-[4-(2-Fluoro-4-nitrophenoxy)pyridin-2-yl]-2-(4-dimethylaminopiperidin-1-yl)acetamide $^1$H-NMR Spectrum (CDCl$_3$) δ (ppm): 1.50-1.90 (4H, m), 2.10-2.28 (3H, m), 2.30 (6H, s), 2.90-3.00 (2H, m), 3.11 (2H, s), 6.72 (1H, dd, J=2.4, 5.6 Hz), 7.30 (1H, m), 7.93 (1H, d, J=2.4 Hz), 8.10-8.14 (2H, m), 8.26 (1H, d, J=5.6 Hz), 9.70 (1H, brs).

Production Example 310-2

N-[4-(4-Amino-2-fluorophenoxy)pyridin-2-yl]-2-(4-dimethylaminopiperidin-1-yl)acetamide ESI-MS (m/z): 388[M+H]$^+$.

Example 311

2-{[4-(Dimethylaminomethyl)piperidin-1-yl]carbonylamino}-4-(2-fluoro-4-{3-[2-(phenyl)acetyl]thioureido}phenoxy)pyridine $^1$H-NMR Spectrum (CDCl$_3$) δ (ppm): 1.10-1.20 (2H, m), 1.65 (1H, m), 1.75-1.85 (2H, m), 2.10-2.15 (2H, m), 2.20 (6H, s), 2.80-2.95 (2H, m), 3.74 (2H, s), 4.00-4.10 (2H, m), 6.53 (1H, dd, J=2.4, 5.6 Hz), 7.17 (1H, m), 7.20-7.50 (7H, m), 7.64 (1H, d, J=2.4 Hz), 7.89 (1H, dd, J=2.4, 12.0 Hz), 8.05 (1H, d, J=5.6 Hz), 8.53 (1H, brs), 12.44 (1H, brs). ESI-MS (m/z): 565[M+H]$^+$.

Production Example 311-1

2-{[4-(Dimethylaminomethyl)piperidin-1-yl]carbonylamino}-4-(2-fluoro-4-nitrophenoxy)pyridine $^1$H-NMR Spectrum (CDCl$_3$) δ (ppm): 1.10-1.30 (2H, m), 1.60-1.90 (3H, m), 2.10-2.20 (2H, m), 2.21 (6H, s), 2.80-3.00 (2H, m), 4.00-4.20 (2H, m), 6.64 (1H, dd, J=2.4, 5.6 Hz), 7.26-7.40 (2H, m), 7.72 (1H, d, J=2.4 Hz), 8.00-8.20 (3H, m).

Production Example 311-2

4-(4-Amino-2-fluorophenoxy)-2-{[4-(dimethylaminomethyl)piperidin-1-yl]carbonylamino}pyridine ESI-MS (m/z): 388[M+H]$^+$.

Example 312

3-[6-(2-Fluoro-4-{3-[2-(4-fluorophenyl)acetyl]thioureido}phenoxy)pyrimidin-4-yl]-1-methyl-1-[(3R)-1-methylpiperidin-3-yl]urea $^1$H-NMR Spectrum (CDCl$_3$) δ (ppm): 1.50-1.85 (4H, m), 2.00 (1H, m), 2.16 (1H, m), 2.31 (3H, s), 2.74 (1H, m), 2.82 (1H, m), 2.96 (3H, s), 3.72 (2H, s), 4.10 (1H, m), 7.06-7.16 (3H, m), 7.17-7.32 (3H, m), 7.35 (1H, m), 7.69 (1H, s), 7.85 (1H, dd, J=2.4, 11.2 Hz), 8.33 (1H, s), 8.62 (1H, brs), 12.39 (1H, brs). ESI-MS (m/z): 592[M+Na]$^+$.

Production Example 312-1

3-[6-(4-Amino-2-fluorophenoxy)pyrimidin-4-yl]-1-methyl-1-[(3R)-1-methylpiperidin-3-yl]urea $^1$H-NMR Spectrum (CDCl$_3$) δ (ppm): 1.43-1.84 (4H, m), 1.97 (1H, m), 2.11 (1H, m), 2.30 (3H, s), 2.74 (1H, m), 2.81 (1H, dd, J=3.6, 10.8 Hz), 2.94 (3H, s), 3.73 (2H, brs), 4.00-4.10 (1H, m), 6.45 (1H, dd, J=2.8, 8.4 Hz), 6.50 (1H, m), 6.97 (1H, m), 7.22-7.27 (1H, m), 7.61 (1H, s), 8.36 (1H, s)

Example 313

3-[6-(4-{3-[2-(4-Chlorophenyl)acetyl]thioureido}-2-fluorophenoxy)pyrimidin-4-yl]-1-methyl-1-(1-methylpiperidin-4-yl)urea $^1$H-NMR Spectrum (CDCl$_3$) δ (ppm): 1.69 (2H, m), 1.83 (2H, m), 2.14 (2H, m), 2.32 (3H, s), 2.85-3.04 (5H, m), 3.71 (2H, s), 4.21 (1H, m), 7.18-7.31 (3H, m), 7.36 (2H, m), 7.37-7.44 (2H, m), 7.68 (1H, m), 7.86 (1H, dd, J=2.8, 11.6 Hz), 8.34 (1H, m), 8.55 (1H, m), 12.36 (1H, brs). ESI-MS (m/z): 586[M+H]$^+$.

Example 314

1-(1-Acetylpiperidin-4-yl)-3-[6-(2-fluoro-4-{3-[2-(4-fluorophenyl)acetyl]thioureido}phenoxy)pyrimidin-4-yl]-1-methylurea $^1$H-NMR Spectrum (CDCl$_3$) δ (ppm): 1.50-1.68 (2H, m), 1.69-1.85 (2H, m), 2.13 (3H, s), 2.62 (1H, m), 2.90 (3H, m), 3.19 (1H, m), 3.72 (2H, s), 3.92 (1H, m), 4.48 (1H, m), 4.79 (1H, m), 7.12 (2H, m), 7.18-7.32 (3H, m), 7.34-7.40 (2H, m), 7.70 (1H, m), 7.87 (1H, dd, J=2.4, 11.6 Hz), 8.35 (1H, s), 8.60 (1H, brs), 12.40 (1H, brs). ESI-MS (m/z): 620[M+Na]$^+$.

Example 315

4-(2-Dimethylaminoacetyl)piperazine-1-carboxylic acid {4-[2-fluoro-4-(3-phenylacetylthioureido)phenoxy]pyridin-2-yl}amide ¹H-NMR Spectrum (CDCl₃) δ (ppm): 2.28 (6H, s), 3.13 (2H, s), 3.44-3.60 (4H, m), 3.62-3.70 (4H, m), 3.75 (2H, s), 6.56 (1H, m), 7.00-7.52 (8H, m), 7.62 (1H, s), 7.90 (1H, dd, J=2.4, 11.6 Hz), 8.06 (1H, m), 8.59 (1H, m), 12.46 (1H, brs). ESI-MS (m/z): 594[M+H]⁺.

Production Example 315-1

4-(2-Dimethylaminoacetyl)piperazine-1-carboxylic acid [4-(2-fluoro-4-nitrophenoxy)pyridin-2-yl]amide ¹H-NMR Spectrum (CDCl₃) δ (ppm): 2.28 (6H, s), 3.13 (2H, s), 3.59 (4H, m), 3.68 (4H, m), 6.65 (1H, dd, J=2.0, 5.6 Hz), 7.28-7.35 (1H, m), 7.38 (1H, m), 7.70 (1H, d, J=2.0 Hz), 8.06-8.19 (3H, m).

Example 316

3-[6-(4-{3-[2-(3-Chlorophenyl)acetyl]thioureido}-2-fluorophenoxy)pyrimidin-4-yl]-1-methyl-1-(1-methylpiperidin-4-yl)urea ¹H-NMR Spectrum (CDCl₃) δ (ppm): 1.58-1.74 (2H, m), 1.81 (2H, m), 2.11 (2H, m), 2.30 (3H, s), 2.86-3.00 (5H, m), 3.88 (2H, s), 4.19 (1H, m), 7.21 (1H, m), 7.30-7.42 (5H, m), 7.49 (1H, m), 7.68 (1H, m), 7.92 (1H, dd, J=2.4, 11.6 Hz), 8.34 (1H, s), 8.60 (1H, brs), 12.37 (1H, brs). ESI-MS (m/z): 608[M+Na]⁺.

Example 317

3-[6-(4-{3-[2-(2-Chlorophenyl)acetyl]thioureido}-2-fluorophenoxy)pyrimidin-4-yl]-1-methyl-1-(1-methylpiperidin-4-yl)urea ¹H-NMR Spectrum (CDCl₃) δ (ppm): 1.10-2.25 (6H, m), 2.34 (3H, brs), 2.93 (3H, s), 3.00 (2H, m), 3.71 (2H, s), 4.23 (1H, m), 7.08-7.49 (7H, m), 7.69 (1H, m), 7.86 (1H, dd, J=2.4, 11.2 Hz), 8.35 (1H, m), 8.56 (1H, brs), 12.36 (1H, brs). ESI-MS (m/z): 608[M+Na]⁺.

Example 318

4-{2-Fluoro-4-[3-(2-phenylacetyl)thioureido]phenoxy}-2-({4-[(2-hydroxyethyl)-methyl-amino]piperidin-1-yl}carbonylamino)pyridine ¹H-NMR Spectrum (CDCl₃) δ (ppm): 1.40-1.85 (4H, m), 2.26 (3H, s), 2.55-2.70 (3H, m), 2.85 (2H, m), 3.56 (2H, m), 3.75 (2H, s), 4.10-4.20 (2H, m), 6.54 (1H, dd, J=2.4, 5.6 Hz), 7.10-7.50 (8H, m), 7.63 (1H, d, J=2.4 Hz), 7.90 (1H, dd, J=2.4, 12.0 Hz), 8.05 (1H, d, J=5.6 Hz), 8.50 (1H, brs), 12.44 (1H, brs). ESI-MS (m/z): 581[M+H]⁺.

Production Example 318-1

4-(2-Fluoro-4-nitrophenoxy)-2-({4-[(2-hydroxyethyl)-methyl-amino]piperidin-1-yl}carbonylamino)pyridine ¹H-NMR Spectrum (CDCl₃) δ (ppm): 1.40-1.60 (2H, m), 1.70-1.90 (2H, m); 2.27 (3H, s), 2.60-2.70 (3H, m), 2.80-2.90 (2H, m), 3.55-3.59 (2H, m), 4.00-4.20 (2H, m), 6.64 (1H, dd, J=2.4, 5.6 Hz), 7.20-7.40 (2H, m), 7.71 (1H, d, J=2.4 Hz), 8.05-8.16 (3H, m)

Production Example 318-2

4-(4-Amino-2-fluorophenoxy)-2-({4-[(2-hydroxyethyl)-methyl-amino]piperidin-1-yl}carbonylamino)pyridine ESI-MS (m/z): 404[M+H]⁺.

Example 319

4-{2-Fluoro-4-[3-(2-phenylacetyl)thioureido]phenoxy}-2-({4-[(3R)-3-hydroxypyrrolidin-1-yl]piperidin-1-yl}carbonylamino)pyridine ¹H-NMR Spectrum (CDCl₃) δ (ppm): 1.40-2.00 (5H, m), 2.10-2.40 (3H, m), 2.60 (1H, m), 2.76 (1H, m), 2.90-3.05 (3H, m), 3.74 (2H, s), 3.90-4.10 (2H, m), 4.34 (1H, m), 6.54 (1H, dd, J=2.4, 5.6 Hz), 7.10-7.50 (8H, m), 7.62 (1H, d, J=2.4 Hz), 7.89 (1H, dd, J=2.4, 12.0 Hz), 8.05 (1H, d, J=5.6 Hz), 8.53 (1H, brs), 12.44 (1H, brs). ESI-MS (m/z): 593[M+H]⁺.

Production Example 319-1

2-({4-[(3R)-3-Hydroxypyrrolidin-1-yl]piperidin-1-yl}carbonylamino)-4-(2-fluoro-4-nitrophenoxy)pyridine ¹H-NMR Spectrum (CDCl₃) δ (ppm): 1.35-1.55 (2H, m), 1.70-1.95 (3H, m), 2.10-2.40 (3H, m), 2.60 (1H, m), 2.76 (1H, m), 2.90-3.10 (3H, m), 3.99 (1H, m), 4.20 (1H, m), 4.36 (1H, m), 6.64 (1H, dd, J=2.4, 5.6 Hz), 7.20-7.40 (2H, m), 7.70 (1H, d, J=2.4 Hz), 8.05-8.15 (3H, m).

Production Example 319-2

4-(4-Amino-2-fluorophenoxy)-2-({4-[(3R)-3-hydroxypyrrolidin-1-yl]piperidin-1-yl}carbonylamino)pyridine ESI-MS (m/z): 416[M+H]⁺.

Example 320

4-(2-Methoxyacetyl)piperazine-1-carboxylic acid {4-[2-fluoro-4-(3-phenylacetylthioureido)phenoxy]pyridin-2-yl}amide ¹H-NMR Spectrum (CDCl₃) δ (ppm): 3.43 (3H, s), 3.44-3.62 (6H, m), 3.68 (2H, m), 3.75 (2H, s), 4.13 (2H, s), 6.56 (1H, m), 7.18 (1H, m), 7.22-7.52 (7H, m), 7.61 (1H, brs), 7.90 (1H, m), 8.06 (1H, d, J=5.6 Hz), 8.55 (1H, brs), 12.46 (1H, brs). ESI-MS (m/z): 603[M+Na]⁺.

Production Example 320-1

4-(2-Methoxyacetyl)piperazine-1-carboxylic acid [4-(2-fluoro-4-nitrophenoxy)pyridin-2-yl]amide $^1$H-NMR Spectrum (CDCl$_3$) δ (ppm): 3.43 (3H, s), 3.46-3.75 (8H, m), 4.13 (2H, s), 6.66 (1H, dd, J=2.4, 5.6 Hz), 7.31 (1H, m), 7.39 (1H, brs), 7.69 (1H, d, J=2.4 Hz), 8.05-8.24 (3H, m).

Example 321

4-{2-Fluoro-4-[3-(2-phenylacetyl)thioureido]phenoxy}-2-{[4-(3-hydroxyazetidin-1-yl)piperidin-1-yl]carbonylamino}pyridine $^1$H-NMR Spectrum (CDCl$_3$) δ (ppm): 1.20-1.40 (2H, m), 1.65-1.80 (2H, m), 2.25 (1H, m), 2.85-2.90 (2H, m), 3.00-3.10 (2H, m), 3.60-3.70 (2H, m), 3.74 (2H, s), 3.80-3.95 (2H, m), 4.45 (1H, m), 6.53 (1H, dd, J=2.4, 5.6 Hz), 7.10-7.50 (8H, m), 7.62 (1H, d, J=2.4 Hz), 7.89 (1H, dd, J=2.4, 11.6 Hz), 8.04 (1H, d, J=5.6 Hz), 8.50 (1H, m), 12.43 (1H, brs). ESI-MS (m/z): 579[M+H]$^+$.

Production Example 321-1

4-(2-Fluoro-4-nitrophenoxy)-2-{[4-(3-hydroxyazetidin-1-yl)piperidin-1-yl]carbonylamino}pyridine $^1$H-NMR Spectrum (CDCl$_3$) δ (ppm): 1.20-1.40 (2H, m), 1.60-1.80 (2H, m), 2.26 (1H, m), 2.80-3.00 (2H, m), 3.00-3.15 (2H, m), 3.60-3.70 (2H, m), 3.80-3.90 (2H, m), 4.46 (1H, m), 6.64 (1H, dd, J=2.4, 5.6 Hz), 7.20-7.40 (2H, m), 7.69 (1H, d, J=2.4 Hz), 8.00-8.20 (3H, m).

Production Example 321-2

4-(4-Amino-2-fluorophenoxy)-2-{[4-(3-hydroxyazetidin-1-yl)piperidin-1-yl]carbonylamino}pyridine ESI-MS (m/z): 402[M+H]$^+$.

Example 322

3-[6-(2-Fluoro-4-{3-[2-(4-fluorophenyl)acetyl]thioureido}phenoxy)pyrimidin-4-yl]-1-methyl-1-[(3S)-1-methylpiperidin-3-yl]urea $^1$H-NMR Spectrum (CDCl$_3$) δ (ppm): 1.47-1.80 (4H, m), 2.01 (1H, m), 2.16 (1H, m), 2.31 (3H, s), 2.72 (1H, m), 2.81 (1H, m), 2.96 (3H, m), 3.71 (2H, s), 4.09 (1H, m), 7.00-7.42 (7H, m), 7.69 (1H, m), 7.86 (1H, dd, J=2.4, 11.6 Hz), 8.33 (1H, m), 8.49 (1H, brs), 12.38 (1H, brs). ESI-MS (m/z): 570[M+H]$^+$.

Example 323

3-{4-[2-Fluoro-4-(3-phenylacetylthioureido)phenoxy]pyridin-2-yl}-1-(2-hydroxyethyl)-1-methylurea $^1$H-NMR Spectrum (CDCl$_3$) δ (ppm): 3.02 (3H, s), 3.44-3.60 (3H, m), 3.74 (2H, s), 3.85 (2H, t, J=4.8 Hz), 6.52 (1H, dd, J=2.4, 5.6 Hz), 7.16 (1H, m), 7.27-7.48° (8H, m), 7.57 (1H, brs), 7.89 (1H, dd, J=2.4, 11.6 Hz), 8.05 (1H, d, J=5.6 Hz), 8.61 (1H, brs). ESI-MS (m/z): 498[M+H]$^+$.

Production Example 323-1

3-[4-(2-Fluoro-4-nitrophenoxy)pyridin-2-yl]-1-(2-hydroxyethyl)-1-methylurea $^1$H-NMR Spectrum (CDCl$_3$) δ (ppm): 3.03 (3H, s), 3.35 (1H, brs), 3.52 (2H, t, J=4.8 Hz), 3.87 (2H, t, J=4.8 Hz), 6.61 (1H, dd, J=2.4, 5.6 Hz), 7.31 (1H, m), 7.65 (1H, m), 8.05-8.16 (4H, m). ESI-MS (m/z): 373[M+Na]$^+$.

Example 324

3-{6-[2-Fluoro-4-(3-phenylacetylthioureido)phenoxy]pyrimidin-4-yl}-1-(2-methoxyethyl)-1-methylurea $^1$H-NMR Spectrum (CDCl$_3$) δ (ppm): 3.04 (3H, s), 3.48 (3H, s), 3.52 (2H, t, J=4.4 Hz), 3.62 (2H, t, J=4.4 Hz), 3.74 (2H, s), 7.18-7.49 (8H, m), 7.53 (1H, s), 7.85 (1H, dd, J=2.4, 11.6 Hz), 8.35 (1H, m), 8.43 (1H, brs), 12.41 (1H, brs). ESI-MS (m/z): 535[M+Na]$^+$.

Example 325

4-{2-Fluoro-4-[3-(2-phenylacetyl)thioureido]phenoxy}-2-({4-[(3S)-3-hydroxypyrrolidin-1-yl]piperidin-1-yl}carbonylamino)pyridine $^1$H-NMR Spectrum (CDCl$_3$) δ (ppm): 1.40-2.00 (5H, m), 2.10-2.40 (3H, m), 2.60 (1H, m), 2.76 (1H, m), 2.90-3.05 (3H, m), 3.74 (2H, s), 3.90-4.10 (2H, m), 4.34 (1H, m), 6.54 (1H, dd, J=2.4, 5.6 Hz), 7.10-7.50 (8H, m), 7.62 (1H, d, J=2.4 Hz), 7.89 (1H, dd, J=2.4, 12.0 Hz), 8.05 (1H, d, J=5.6 Hz), 8.53 (1H, brs), 12.44 (1H, brs).

Production Example 325-1

2-({4-[(3S)-3-Hydroxypyrrolidin-1-yl]piperidin-1-yl}carbonylamino)-4-(2-fluoro-4-nitrophenoxy)pyridine ESI-MS (m/z): 446[M+H]$^+$.

Production Example 325-2

4-(4-Amino-2-fluorophenoxy)-2-({4-[(3S)-3-hydroxypyrrolidin-1-yl]piperidin-1-yl}carbonylamino)pyridine ESI-MS (m/z): 416[M+H]$^+$.

Example 326

4-{2-Fluoro-4-[3-(2-phenylacetyl)thioureido]phenoxy}-2-{[4-(1-methylpiperidin-4-yl)piperazin-1-yl]carbonylamino}pyridine $^1$H-NMR Spectrum (CDCl$_3$) δ (ppm): 1.50-2.00 (6H, m), 2.20-2.45 (4H, m), 2.50-2.65 (4H, m), 2.85-2.95 (2H, m), 3.45-3.55 (4H, m), 3.74 (2H, s), 6.54 (1H, dd, J=2.4, 5.6 Hz), 7.10-7.50 (8H, m), 7.63 (1H, d, J=2.4 Hz), 7.89 (1H, dd, J=2.4, 11.6 Hz), 8.04 (1H, d, J=5.6 Hz), 8.50 (1H, m), 12.44 (1H, brs). ESI-MS (m/z): 606[M+H]$^+$.

Production Example 326-1

4-(2-Fluoro-4-nitrophenoxy)-2-{[4-(1-methylpiperidin-4-yl)piperazin-1-yl]carbonylamino}pyridine $^1$H-NMR Spectrum (CDCl$_3$) δ (ppm): 1.70-2.00 (5H, m), 2.20-2.30 (1H, m), 2.26 (3H, s), 2.55-2.60 (4H, m), 2.80-3.00 (3H, m), 3.40-3.60 (4H, m), 6.64 (1H, dd, J=2.4, 5.6 Hz), 7.20-7.40 (2H, m), 7.70 (1H, d, J=2.4 Hz), 8.08-8.16 (3H, m).

Production Example 326-2

4-(4-Amino-2-fluorophenoxy)-2-{[4-(1-methylpiperidin-4-yl)piperazin-1-yl]carbonylamino}pyridine ESI-MS (m/z): 429[M+H]$^+$.

Example 327

2-{[4-(2-Dimethylaminoethyl)piperazin-1-yl]carbonylamino}-4-(4-{3-[2-(4-fluorophenyl)acetyl]thioureido}phenoxy)pyridine $^1$H-NMR Spectrum (CDCl$_3$) δ (ppm): 2.25 (6H, s), 2.40-2.56 (8H, m), 3.48-3.56 (4H, m), 3.71 (2H, s), 6.54 (1H, dd, J=2.4, 5.6 Hz), 7.10-7.40 (7H, m), 7.60-7.75 (3H, m), 8.04 (1H, d, J=5.6 Hz), 8.56 (1H, brs), 12.26 (1H, brs). ESI-MS (m/z): 580[M+H]$^+$.

Production Example 327-1

4-(4-Amino-3-chlorophenoxy)-2-{[4-(2-dimethylaminoethyl)piperazin-1-yl]carbonylamino}pyridine ESI-MS (m/z): 419[M+H]$^+$.

Production Example 327-2

4-(4-Aminophenoxy)-2-{[4-(2-dimethylaminoethyl)piperazin-1-yl]carbonylamino}pyridine ESI-MS (m/z): 385[M+H]$^+$.

Example 328

4-[3-(Dimethylamino)azetidin-1-yl]piperidine-1-carboxylic acid [6-(2-fluoro-4-{3-[2-(4-fluorophenyl)acetyl]thioureido}phenoxy)pyrimidin-4-yl]amide ESI-MS (m/z): 625[M+H]$^+$.

Production Example 328-1

4-[3-(Dimethylamino)azetidin-1-yl]piperidine-1-carboxylic acid [6-(2-fluoro-4-nitrophenoxy)pyrimidin-4-yl]amide $^1$H-NMR Spectrum (CDCl$_3$) δ (ppm): 1.31-1.39 (2H, m), 1.76 (2H, m), 2.13 (6H, s), 2.31 (1H, m), 2.86 (3H, m), 3.14 (2H, m), 3.50 (2H, m), 3.90 (2H, m), 7.41 (1H, m), 7.50 (1H, m), 7.72 (1H, s), 8.11 (2H, m), 8.31 (1H, s). ESI-MS (m/z): 460[M+H]$^+$.

Example 329

4-(4-{3-[2-(4-Fluorophenyl)acetyl]thioureido}phenoxy)-2-{[4-(1-methylpiperidin-4-yl)piperazin-1-yl]carbonylamino}pyridine $^1$H-NMR Spectrum (CDCl$_3$) δ (ppm): 1.50-2.05 (6H, m), 2.20-2.40 (4H, m), 2.50-2.65 (4H, m), 2.85-3.00 (2H, m), 3.40-3.60 (4H, m), 3.71 (2H, s), 6.54 (1H, dd, J=2.4, 5.6 Hz), 7.10-7.40 (7H, m), 7.60-7.75 (3H, m), 8.04 (1H, d, J=5.6 Hz), 8.50 (1H, brs), 12.26 (1H, brs). ESI-MS (m/z): 606[M+H]$^+$.

Production Example 329-1

2-{[4-(1-Methylpiperidin-4-yl)piperazin-1-yl]carbonylamino}-4-(4-nitrophenoxy)pyridine $^1$H-NMR Spectrum (CDCl$_3$) δ (ppm): 1.70-2.00 (6H, m), 2.20-2.30 (1H, m), 2.28 (3H, s), 2.55-2.65 (4H, m), 2.80-3.00 (2H, m), 3.40-3.60 (4H, m), 6.64 (1H, dd, J=2.4, 5.6 Hz), 7.15-7.40 (3H, m), 7.75 (1H, d, J=2.4 Hz), 8.15 (1H, d, J=5.6 Hz), 8.25-8.30 (2H, m)

Production Example 329-2

4-(4-Aminophenoxy)-2-{[4-(1-methylpiperidin-4-yl)piperazin-1-yl]carbonylamino}pyridine ESI-MS (m/z): 411[M+H]$^+$.

Example 330

3-{4-[2-Fluoro-4-(3-phenylacetylthioureido)phenoxy]pyridin-2-yl}-1-methyl-1-[1-(1-methylazetidin-3-yl)piperidin-4-yl]urea $^1$H-NMR Spectrum (CDCl$_3$) δ (ppm): 1.64-1.77 (4H, m), 1.91 (2H, m), 2.39 (3H, s), 2.81 (2H, m), 2.88 (3H, s), 2.93 (3H, m), 3.57 (2H, m), 3.74 (2H, s), 4.17 (1H, m), 6.55 (1H, dd, J=2.4, 5.6 Hz), 7.14-7.50 (9H, m), 7.67 (1H, d, J=2.4 Hz), 7.90 (1H, dd, J=2.4, 11.6 Hz), 8.06 (1H, d, J=5.6 Hz), 11.46 (1H, s). ESI-MS (m/z): 606[M+H]$^+$, 628[M+Na]$^+$.

Production Example 330-1 tert-Butyl 3-(4-tert-butoxycarbonylaminopiperidin-1-yl)azetidine-1-carboxylate

To 1-Boc-azetidin-3-on (1.00 g) and 4-(tert-butoxycarbonylamino)piperidine (1.17 g) dissolved in methanol (50 ml) were added acetic acid (0.368 ml) and 10% palladium carbon (1.0 g), followed by stirring under hydrogen atmosphere at room temperature for 12 hours. The reaction mixture was stirred under hydrogen atmosphere (0.4 MPa) at room temperature for 4 hours. The reaction mixture was filtered to remove the catalyst. The filtrate was concentrated under reduced pressure. Ethyl acetate and a saturated aqueous solution of sodium hydrogencarbonate were added thereto, followed by partition. The aqueous layer was extracted with ethyl acetate. The combined organic layer was washed with brine, and dried over anhydrous sodium sulfate. The organic layer was concentrated. The resultant crystals were suspended in diethyl ether-hexane, collected by filtration, and washed with hexane. There crystals were dried under aeration to provide the title compound (1.21 g) as colorless crystals.

ESI-MS (m/z): 356[M+H]$^+$.

Production Example 330-2

Methyl-[1-(1-methylazetidin-3-yl)piperidin-4-yl]amine trihydrochloride

To a solution of tert-butyl 3-(4-tert-butoxycarbonylaminopiperidin-1-yl)azetidine-1-carboxylate (675 mg) in tetrahydrofuran (25 ml) was added lithium aluminium hydride (216 mg) in an ice bath, followed by stirring in an ice bath for 0.5 hours. The reaction mixture was stirred at 80° C. for 4 hours. The reaction mixture was cooled in an ice bath. To the reaction mixture were added water (0.216 ml), 5N aqueous solution of sodium hydroxide (0.216 ml) and water (1.08 ml) while stirring, followed by stirring in an ice bath for 3 hours. The reaction mixture was filtered to remove insoluble material, and 4N hydrochloric acid-ethyl acetate solution (1.43 ml) was added to the filtrate. This solution was concentrated to provide a crude product of the title compound (555 mg) as a pale yellow solid.
ESI-MS (m/z): 184[M+H]$^+$.

Production Example 330-3

3-[4-(2-Fluoro-4-nitrophenoxy)pyridin-2-yl]-1-methyl-1-[1-(1-methylazetidin-3-yl)piperidin-4-yl]urea ESI-MS (m/z): 459[M+H]$^+$.

Production Example 330-4

3-[4-(4-Amino-2-fluorophenoxy)pyridin-2-yl]-1-methyl-1-[1-(1-methylazetidin-3-yl)piperidin-4-yl]urea ESI-MS (m/z): 429[M+H]$^+$, 451[M+Na]$^+$.

Example 331

3-(4-{4-[3-(4-Fluorophenyl)acetylthioureido]phenoxy}pyridin-2-yl)-1-methyl-1-[1-(1-methylazetidin-3-yl)piperidin-4-yl]urea $^1$H-NMR Spectrum (CDCl$_3$) δ (ppm): 1.62-1.78 (4H, m), 1.92 (2H, m), 2.44 (3H, s), 2.81 (2H, m), 2.89 (3H, s), 3.00 (3H, m), 3.65 (2H, m), 3.71 (2H, s), 4.18 (1H, m), 6.55 (1H, dd, J=2.4, 5.8 Hz), 7.04-7.18 (4H, m), 7.25-7.31 (3H, m), 7.66-7.70 (3H, m), 8.06 (1H, d, J=5.8 Hz), 8.64 (1H, brs), 12.27 (1H, s). ESI-MS (m/z): 606[M+H]$^+$, 628[M+Na]$^+$.

Production Example 331-1

1-Methyl-1-[1-(1-methylazetidin-3-yl)piperidin-4-yl]-3-[4-(4-nitrophenoxy)pyridin-2-yl]urea $^1$H-NMR Spectrum (CDCl$_3$) δ (ppm): 1.64-1.98 (6H, m), 2.34 (3H, s), 2.79-2.93 (8H, m), 3.51 (2H, m), 4.17 (1H, m), 6.65 (1H, dd, J=2.0, 5.6 Hz), 7.18 (2H, d, J=9.0 Hz), 7.26 (1H, brs), 7.80 (1H, d, J=2.0 Hz), 8.17 (1H, d, J=5.6 Hz), 8.27 (2H, d, J=9.0 Hz). ESI-MS (m/z): 441[M+H]$^+$.

Production Example 331-2

3-[4-(4-Aminophenoxy)pyridin-2-yl]-1-methyl-1-[1-(1-methylazetidin-3-yl)piperidin-4-yl]urea $^1$H-NMR Spectrum (CDCl$_3$) δ (ppm): 1.64-1.77 (4H, m), 1.92 (2H, m), 2.39 (3H, s), 2.81 (2H, m), 2.95 (3H, s), 3.18 (5H, m), 3.60 (2H, m), 4.18 (1H, m), 6.48 (1H, dd, J=2.0, 5.6 Hz), 6.70 (2H, d, J=8.8 Hz), 6.90 (2H, d, J=8.8 Hz), 7.30 (1H, brs), 7.61 (1H, d, J=2.0 Hz), 7.98 (1H, d, J=5.6 Hz). ESI-MS (m/z): 411[M+H]$^+$, 433[M+Na]$^+$.

Example 332

(3S)-3-Dimethylaminomethylpiperidine-1-carboxylic acid [6-(2-fluoro-4-{3-[2-(4-fluorophenyl)acetyl]thioureido}phenoxy)pyrimidin-4-yl]amide $^1$H-NMR Spectrum (CDCl$_3$) δ (ppm): 1.43-1.74 (3H, m), 1.80 (1H, m), 1.92-2.08 (2H, m), 2.31 (6H, s), 2.61 (1H, m), 2.82 (1H, m), 3.14 (1H, m), 3.71 (2H, s), 3.89 (1H, m), 4.30 (1H, m), 7.12 (2H, m), 7.21 (1H, m), 7.25-7.31 (2H, m), 7.34 (1H, m), 7.46 (1H, s), 7.84 (1H, dd, J=2.4, 11.6 Hz), 8.33 (1H, s), 8.51 (1H, brs), 10.80 (1H, brs), 12.37 (1H, brs). ESI-MS (m/z): 584[M+H]$^+$.

Production Example 332-1

(3S)-3-Dimethylaminomethylpiperidine-1-carboxylic acid [6-(4-amino-2-fluorophenoxy)pyrimidin-4-yl]amide $^1$H-NMR Spectrum (CDCl$_3$) δ (ppm): 1.44-1.88 (4H, m), 1.90-2.09 (2H, m), 2.23-2.35 (6H, m), 2.60 (1H, m), 2.84 (1H, m), 3.16 (1H, m), 3.71 (2H, m), 3.87 (1H, m), 4.27 (1H, m), 6.43 (1H, dd, J=1.2, 2.8 Hz), 6.50 (1H, dd, J=2.8, 11.6 Hz), 6.97 (1H, m), 7.39 (1H, m), 8.36 (1H, m), 10.64 (1H, m)

Example 333

(3R)-3-Dimethylaminomethylpiperidine-1-carboxylic acid [6-(2-fluoro-4-{3-[2-(4-fluorophenyl)acetyl]thioureido}phenoxy)pyrimidin-4-yl]amide $^1$H-NMR Spectrum (CDCl$_3$) δ (ppm): 1.46-1.72 (3H, m), 1.80 (1H, m), 1.94-2.10 (2H, m), 2.31 (6H, s), 2.61 (1H, m), 2.82 (1H, m), 3.15 (1H, m), 3.71 (2H, s), 3.89 (1H, m), 4.30 (1H, m), 7.12 (2H, m), 7.21 (1H, m), 7.24-7.40 (3H, m), 7.46 (1H, s), 7.86 (1H, dd, J=2.4, 11.6 Hz), 8.32 (1H, s), 8.51 (1H, brs), 10.79 (1H, brs), 12.34 (1H, brs). ESI-MS (m/z): 584[M+H]$^+$.

Production Example 333-1

(3R)-3-Dimethylaminomethylpiperidine-1-carboxylic acid [6-(4-amino-2-fluorophenoxy)pyrimidin-4-yl]amide $^1$H-NMR Spectrum (CDCl$_3$) δ (ppm): 1.43-1.86 (4H, m), 1.95-2.08 (2H, m), 2.30 (6H, m), 2.60 (1H, m), 2.83 (1H, m), 3.15 (1H, m), 3.71 (2H, m), 3.83-3.79 (2H, m), 4.27 (1H, m), 6.40-6.55 (2H, m), 6.97 (1H, m), 7.38 (1H, m), 10.64 (1H, m).

Example 334

4-(2-Dimethylaminoethyl)-[1,4]diazepane-1-carboxylic acid {4-[2-fluoro-4-(3-phenylacetylthioureido)phenoxy]pyridin-2-yl}amide $^1$H-NMR Spectrum (CDCl$_3$) δ (ppm): 1.93 (2H, m), 2.24 (6H, m), 2.41 (2H, t, J=7.2 Hz), 2.63 (2H, t, J=7.2 Hz), 2.70 (2H, m), 2.77 (2H, m), 3.57 (2H, m), 3.62 (2H, m), 3.75 (2H, s), 6.53 (1H, dd, J=2.4, 5.6 Hz), 7.00-7.53 (8H, m), 7.70 (1H, m), 7.90 (1H, dd, J=2.4, 11.6 Hz), 8.06 (1H, d, J=5.6 Hz), 8.53 (1H, brs), 12.45 (1H, brs). ESI-MS (m/z): 594[M+H]$^+$.

Production Example 334-1

4-(2-Dimethylaminoethyl)-[1,4]diazepane-1-carboxylic acid [4-(4-amino2-fluorophenoxy)pyridin-2-yl]amide $^1$H-NMR Spectrum (CDCl$_3$) δ (ppm): 1.93 (2H, m), 2.25 (6H, s), 2.41 (2H, t, J=7.2 Hz), 2.63 (2H, t, J=7.2 Hz), 2.69 (2H, m), 2.77 (2H, m), 3.56 (2H, m), 3.60 (2H, m), 3.74 (2H, brs), 6.44 (1H, dd, J=2.8, 8.4 Hz), 6.49 (1H, d, J=2.8 Hz), 6.52 (1H, m), 6.96 (1H, m), 7.19 (1H, m), 7.64 (1H, m), 8.01 (1H, m).

Example 335

(3S)-3-Dimethylaminomethylpiperidine-1-carboxylic acid {4-[2-fluoro-4-(3-phenylacetylthioureido)phenoxy]pyridin-2-yl}amide $^1$H-NMR Spectrum (CDCl$_3$) δ (ppm): 1.26 (1H, m), 1.36-1.56 (2H, m), 1.78 (1H, m), 1.95 (2H, m), 2.28 (6H, s), 2.55 (1H, m), 2.95 (1H, m), 3.23 (1H, m), 3.70 (1H, m), 3.74 (2H, s), 4.05 (1H, m), 6.48 (1H, dd, J=2.4, 5.6 Hz), 7.15 (1H, m), 7.31 (3H, m), 7.42 (3H, m), 7.55 (1H, d, J=2.0 Hz), 7.87 (1H, dd, J=2.4, 11.6 Hz), 8.05 (1H, d, J=5.6 Hz), 8.56 (1H, brs), 9.72 (1H, brs), 12.42 (1H, brs). ESI-MS (m/z): 565[M+H]$^+$.

Production Example 335-1

(3S)-3-Dimethylaminomethylpiperidine-1-carboxylic acid [4-(4-amino-2-fluorophenoxy)pyridin-2-yl]amide $^1$H-NMR Spectrum (CDCl$_3$) δ (ppm): 1.25-1.50 (3H, m), 1.76 (1H, m), 1.94 (2H, m), 2.27 (6H, s), 2.53 (1H, m), 2.99 (1H, m), 3.26 (1H, m), 3.50-3.82 (3H, m), 4.01 (1H, m), 6.25-6.60 (3H, m), 6.93 (1H, m), 7.51 (1H, m), 8.01 (1H, d, J=5.6 Hz), 9.53 (1H, brs).

Example 336

(3R)-3-Dimethylaminomethylpiperidine-1-carboxylic acid {4-[2-fluoro-4-(3-phenylacetylthioureido)phenoxy]pyridin-2-yl}amide $^1$H-NMR Spectrum (CDCl$_3$) δ (ppm): 1.27 (1H, m), 1.36-1.60 (2H, m), 1.78 (1H, m), 1.95 (2H, m), 2.28 (6H, s), 2.55 (1H, m), 2.95 (1H, m), 3.24 (1H, m), 3.70 (1H, m), 3.74 (2H, s), 4.05 (1H, m), 6.48 (1H, dd, J=2.4, 5.6 Hz), 7.15 (1H, m), 7.32 (3H, m), 7.41 (3H, m), 7.54 (1H, d, J=2.4 Hz), 7.87 (1H, dd, J=2.4, 12.0 Hz), 8.06 (1H, d, J=5.6 Hz), 8.61 (1H, brs), 9.73 (1H, brs), 12.42 (1H, brs). ESI-MS (m/z): 565[M+H]$^+$.

Production Example 336-1

(3R)-3-Dimethylaminomethylpiperidine-1-carboxylic acid [4-(4-amino-2-fluorophenoxy)pyridin-2-yl]amide $^1$H-NMR Spectrum (CDCl$_3$) δ (ppm): 1.28-2.08 (6H, m), 2.32 (6H, s), 2.57 (1H, m), 3.08 (1H, m), 3.37 (1H, m), 3.59 (1H, m), 3.72 (2H, m), 3.91 (1H, m), 6.38-6.58 (4H, m), 6.95 (1H, m), 7.52 (1H, d, J=2.0 Hz), 8.01 (1H, d, J=5.6 Hz).

Example 337

4-(1-Methylazetidin-3-yl)piperazine-1-carboxylic acid [4-(4-{3-[2-(4-fluorophenyl)acetyl]thioureido}phenoxy)pyridin-2-yl]amide $^1$H-NMR Spectrum (CDCl$_3$) δ (ppm): 2.33 (4H, m), 2.40 (3H, s), 2.98 (3H, m), 3.51 (4H, m), 3.57 (2H, m), 3.71 (2H, s), 6.55 (1H, m), 7.12 (4H, m), 7.20-7.38 (3H, m), 7.63 (1H, s), 7.69 (2H, d, J=8.8 Hz), 8.05 (1H, d, J=1.6 Hz), 8.60 (1H, brs), 12.27 (1H, s). ESI-MS (m/z): 578[M+H]$^+$.

Production Example 337-1

4-(1-Methylazetidin-3-yl)piperazine-1-carboxylic acid [4-(4-nitrophenoxy)pyridin-2-yl]amide $^1$H-NMR Spectrum (CDCl$_3$) δ (ppm): 2.32-2.38 (7H, m), 2.93 (3H, m), 3.52 (6H, m), 6.65 (1H, dd, J=2.4, 5.6 Hz), 7.19 (2H, d, J=9.2 Hz), 7.36 (1H, m), 7.75 (1H, d, J=2.4 Hz), 8.16 (1H, d, J=5.6 Hz), 8.28 (2H, d, J=9.2 Hz). ESI-MS (m/z): 413[M+H]$^+$.

Production Example 337-2

4-(1-Methylazetidin-3-yl)piperazine-1-carboxylic acid [4-(4-aminophenoxy)pyridin-2-yl]amide ESI-MS (m/z): 383[M+H]$^+$, 405[M+Na]$^+$.

Example 338

4-(Azetidin-1-yl)piperidine-1-carboxylic acid [4-(4-{3-[2-(4-fluorophenyl)acetyl]thioureido}phenoxy)pyridin-2-yl]amide $^1$H-NMR Spectrum (CDCl$_3$) δ (ppm): 1.24-1.27 (2H, m), 1.72 (2H, m), 2.06 (2H, m), 2.21 (1H, m), 3.04 (2H, m), 3.19 (4H, m), 3.71 (2H, s), 3.90 (2H, m), 6.53 (1H, dd, J=2.0, 6.0 Hz), 7.08-7.13 (4H, m), 7.24-7.31 (3H, m), 7.63 (1H, d, J=2.0 Hz), 7.68 (2H, d, J=8.8 Hz), 8.04 (1H, d, J=6.0 Hz), 8.62 (1H, brs), 12.26 (1H, s). ESI-MS (m/z): 563[M+H]$^+$.

Production Example 338-1

4-(Azetidin-1-yl)piperidine-1-carboxylic acid [4-(4-nitrophenoxy)pyridin-2-yl]amide $^1$H-NMR Spectrum (CDCl$_3$) δ (ppm): 1.31 (2H, m), 1.72 (2H, m), 2.07 (2H, m), 2.22 (1H, m), 3.06 (2H, m), 3.19 (4H, m), 3.89 (2H, m), 6.64 (1H, dd, J=2.0, 5.6 Hz), 7.19 (2H, d, J=9.2 Hz), 7.29 (1H, brs), 7.74 (1H, d, J=2.0 Hz), 8.15 (1H, d, J=5.6 Hz), 8.28 (2H, d, J=9.2 Hz). ESI-MS (m/z): 398[M+H]$^+$.

Production Example 338-2) 4-(Azetidin-1-yl)piperidine-1-carboxylic acid [4-(4-aminophenoxy)pyridin-2-yl]amide ESI-MS (m/z): 368[M+H]$^+$.

Example 339

4-(2-Pyrrolidin-1-ylethyl)piperazine-1-carboxylic acid [6-(2-fluoro-4-{3-[2-(4-fluorophenyl)acetyl]thioureido}phenoxy)pyrimidin-4-yl]amide $^1$H-NMR Spectrum (CDCl$_3$) δ (ppm): 1.81 (4H, m), 2.45-2.67 (10H, m), 2.68 (2H, m), 3.55 (4H, t, J=4.8 Hz), 3.71 (2H, s), 7.00-7.52 (7H, m), 7.64 (1H, m), 7.86 (1H, dd, J=2.4, 11.6 Hz), 8.33 (1H, brs), 8.49 (1H, m), 12.38 (1H, brs). ESI-MS (m/z): 625[M+H]$^+$.

Example 340

4-{2-Fluoro-4-[3-(2-phenylacetyl)ureido]phenoxy}-2-{[4-(1-methylpiperazin-4-yl)piperidin-1-yl]carbonylamino}pyridine To a solution of 4-(4-amino-2-fluorophenoxy)-2-{[4-(1-methylpiperazin-4-yl)piperidin-1-yl]carbonylamino}pyridine (66.2 mg) in tetrahydrofuran (4.0 ml) was added a solution of 2-phenylacetyl isocyanate in hexane (0.25 M, 1.5 ml) at room temperature, followed by stirring overnight. The reaction mixture was concentrated under reduced pressure. The resultant residue was then purified by silica gel column chromatography (Fuji Silysia NH, eluent; ethyl acetate:methanol=97:3) to provide the titled compound (49.5 mg, 55%) as white powder.
$^1$H-NMR Spectrum (CDCl$_3$) δ (ppm): 1.40-1.95 (5H, m), 2.32 (3H, s), 2.40-2.80 (8H, m), 2.88 (2H, m), 3.75 (2H, s), 4.04-4.15 (2H, m), 6.52 (1H, dd, J=2.4, 5.6 Hz), 7.10-7.45 (8H, m), 7.58-7.65 (2H, m), 7.68 (1H, brs), 8.03 (1H, d, J=5.6 Hz), 10.57 (1H, brs). ESI-MS (m/z): 590 [M+H]$^+$.

Example 341

4-{2-Fluoro-4-[3-(2-phenylacetyl)ureido]phenoxy}-2-{[4-(1-methylpiperidin-4-yl)piperazin-1-yl]carbonylamino}pyridine To a solution of 4-(4-amino-2-fluorophenoxy)-2-{[4-(1-methylpiperidin-4-yl)piperazin-1-yl]carbonylamino}pyridine (811 mg) in tetrahydrofuran (50 ml) was added a solution of 2-phenylacetyl isocyanate in hexane (0.25 M, 17 ml) at room temperature, followed by stirring for 5 hours. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, ethyl acetate:methanol=97:3). Fractions containing the target compound were concentrated to give a residue, which was then suspended in ethyl acetate (8 ml) and hexane (16 ml). The crystals were filtered off and dried under aeration to provide the titled compound (629 mg, 61%) as white crystals.
$^1$H-NMR Spectrum (CDCl$_3$) δ (ppm): 1.50-2.10 (6H, m), 2.20-2.40 (4H, m), 2.50-2.60 (4H, m), 2.90-3.00 (2H, m), 3.45-3.55 (4H, m), 3.75 (2H, s), 6.52 (1H, dd, J=2.4, 5.6 Hz), 7.10-7.45 (8H, m), 7.55-7.70 (3H, m), 8.03 (1H, d, J=5.6 Hz), 10.57 (1H, brs). ESI-MS (m/z): 590 [M+H]$^+$.

Example 342

2-{[4-(Dimethylaminomethyl)piperidin-1-yl]carbonylamino}-4-{2-fluoro-4-[3-(2-phenylacetyl)ureido]phenoxy}pyridine To a solution of 4-(4-amino-2-fluorophenoxy)-2-{[4-(dimethylaminomethyl)piperidin-1-yl]carbonylamino}pyridine (62.7 mg) in tetrahydrofuran (4.0 ml) was added a solution of 2-phenylacetyl isocyanate in hexane (0.25 M, 1.6 ml) at room temperature, followed by stirring overnight. The reaction mixture was concentrated under reduced pressure. The resultant residue was then purified by silica gel column chromatography (Fuji Silysia NH, eluent; ethyl acetate) to provide the titled compound (48.0 mg, 54%) as white powder.
$^1$H-NMR Spectrum (CDCl$_3$) δ (ppm): 1.10-1.20 (2H, m), 1.65 (1H, m), 1.75-1.85 (2H, m), 2.10-2.15 (2H, m), 2.23 (6H, s), 2.80-2.90 (2H, m), 3.75 (2H, s), 4.00-4.10 (2H, m), 6.52 (1H, dd, J=2.4, 5.6 Hz), 7.10-7.45 (8H, m), 7.60-7.65 (2H, m), 8.03 (1H, brs), 8.30 (1H, d, J=5.6 Hz), 10.58 (1H, brs). ESI-MS (m/z): 549 [M+H]$^+$.

Example 343

4-(2-Fluoro-4-{3-[2-(4-fluorophenyl)acetyl]ureido}phenoxy)-2-{[4-(1-methylpiperazin-4-yl)piperidin-1-yl]carbonylamino}pyridine To a solution of 4-(4-amino-2-fluorophenoxy)-2-{[4-(1-methylpiperazin-4-yl)piperidin-1-yl]carbonylamino}pyridine (71 mg) in tetrahydrofuran (2.0 ml) was added a solution of 2-(4-fluorophenyl)acetyl isocyanate in tetrahydrofuran (0.25 M, 1.65 ml) at room temperature, followed by stirring for 3 days. The reaction mixture was concentrated under reduced pressure. The resultant residue was then purified by silica gel column chromatography (Fuji Silysia NH, eluent; ethyl acetate:methanol=97:3) to provide the titled compound (7.1 mg, 7.1%) as white powder.
$^1$H-NMR Spectrum (CDCl$_3$) δ (ppm): 1.40-1.95 (5H, m), 2.36 (3H, s), 2.40-2.80 (8H, m), 2.88 (2H, m), 3.73 (2H, s), 4.04-4.15 (2H, m), 6.52 (1H, dd, J=2.4, 5.6 Hz), 7.00-7.30 (7H, m), 7.57-7.62 (2H, m), 7.86 (1H, m), 8.03 (1H, d, J=5.6 Hz), 10.53 (1H, brs). ESI-MS (m/z): 608 [M+H]$^+$.

Example 344

4-(4-{3-[2-(4-Fluorophenyl)acetyl]ureido}phenoxy)-2-{[4-(1-methylpiperazin-4-yl)piperidin-1-yl]carbonylamino}pyridine To a solution of 4-(4-aminophenoxy)-2-{[4-(1-methylpiperazin-4-yl)piperidin-1-yl]carbonylamino}pyridine (86.9 mg) in tetrahydrofuran (2.5 ml) was added a solution of 2-(4-fluorophenyl)acetyl isocyanate in tetrahydrofuran (0.25 M, 2.12 ml) at room temperature, followed by stirring for 3 days. The reaction mixture was concentrated under reduced pressure. The resultant residue was then purified by silica gel column chromatography (Fuji Silysia NH, eluent; ethyl acetate:methanol=97:3) to provide the titled compound (22.5 mg, 18%) as white powder.
$^1$H-NMR Spectrum (CDCl$_3$) δ (ppm): 1.40-1.95 (5H, m), 2.34 (3H, s), 2.40-2.80 (8H, m), 2.88 (2H, m), 3.72 (2H, s), 4.05-4.15 (2H, m), 6.51 (1H, dd, J=2.4, 5.6 Hz), 7.00-7.35 (7H, m), 7.50-7.54 (2H, m), 7.58 (1H, d, J=2.4 Hz), 7.78 (1H, brs), 8.02 (1H, d, J=5.6 Hz), 10.43 (1H, brs). ESI-MS (m/z): 590 [M+H]$^+$.

Example 345

4-(2-Fluoro-4-{3-[2-(4-fluorophenyl)acetyl]
ureido}phenoxy)-2-{[4-(1-methylpiperidin-4-yl)
piperazin-1-yl]carbonylamino}pyridine To a solution of 4-(4-amino-2-fluorophenoxy)-2-{[4-(1-methylpiperidin-4-yl)piperazin-1-yl]
carbonylamino}pyridine (81.2 mg) in tetrahydrofuran (2.0 ml) was added a solution of 2-(4-fluorophenyl)acetyl isocyanate in tetrahydrofuran (0.25 M, 1.9 ml) at room temperature, followed by stirring for 3 days. The reaction mixture was concentrated under reduced pressure. The resultant residue was then purified by silica gel column chromatography (Fuji Silysia NH, eluent; ethyl acetate:methanol=97:3 to 95:5) to provide the titled compound (9.7 mg, 8.5%) as white powder.
$^1$H-NMR Spectrum (CDCl$_3$) δ (ppm): 1.50-2.10 (6H, m), 2.20-2.40 (4H, m), 2.50-2.60 (4H, m), 2.90-3.10 (2H, m), 3.45-3.55 (4H, m), 3.73 (2H, s), 6.52 (1H, dd, J=2.4, 5.6 Hz), 7.00-7.30 (7H, m), 7.59-7.70 (2H, m), 7.77 (1H, m), 8.03 (1H, d, J=5.6 Hz), 10.53 (1H, brs). ESI-MS (m/z): 608 [M+H]$^+$.

Example 346

4-(4-{3-[2-(4-Fluorophenyl)acetyl]ureido}phenoxy)-
2-{[4-(1-methylpiperidin-4-yl)piperazin-1-yl]
carbonylamino}pyridine To a solution of 4-(4-aminophenoxy)-2-{[4-(1-methylpiperidin-4-yl)piperazin-1-yl]carbonylamino}pyridine (834 mg) in tetrahydrofuran (45 ml) was added a solution of 2-(4-fluorophenyl)acetyl isocyanate in ethyl acetate (0.25 M, 15 ml) at room temperature, followed by stirring for 3.5 hours. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=97:3). Fractions containing the target compound were concentrated to give a residue, which was then suspended in ethyl acetate (8 ml) and hexane (16 ml). The crystals were filtered off and dried under aeration to provide the titled compound (546 mg, 49%) as white crystals.
$^1$H-NMR Spectrum (CDCl$_3$) δ (ppm): 1.50-2.02 (6H, m), 2.22-2.34 (4H, m), 2.54-2.62 (4H, m), 2.88-2.96 (2H, m), 3.44-3.54 (4H, m), 3.72 (2H, s), 6.51 (1H, dd, J=2.4, 5.6 Hz), 7.00-7.30 (7H, m), 7.50-7.54 (2H, m), 7.60 (1H, d, J=2.4 Hz), 8.02 (1H, d, J=5.6 Hz), 8.27 (1H, brs), 10.47 (1H, brs). ESI-MS (m/z): 590 [M+H]$^+$.

Example 347

2-{[4-(Dimethylaminomethyl)piperidin-1-yl]carbo-
nylamino}-4-(2-fluoro-4-{3-[2-(4-fluorophenyl)
acetyl]ureido}phenoxy)pyridine To a solution of 4-(4-amino-2-fluorophenoxy)-2-{[4-(dimethylaminomethyl)piperidin-1-yl]
carbonylamino}pyridine (61.1 mg) in tetrahydrofuran (2.0 ml) was added a solution of 2-(4-fluorophenyl)acetyl isocyanate in tetrahydrofuran (0.25 M, 1.6 ml) at room temperature, followed by stirring for 3 days. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate) to provide the titled compound (13.3 mg, 15%) as white powder.
$^1$H-NMR Spectrum (CDCl$_3$) δ (ppm): 1.10-1.25 (2H, m), 1.65 (1H, m), 1.75-1.90 (2H, m), 2.10-2.30 (8H, m), 2.80-2.90 (2H, m), 3.72 (2H, s), 4.00-4.10 (2H, m), 6.52 (1H, dd, J=2.4, 5.6 Hz), 7.10-7.30 (7H, m), 7.59-7.64 (2H, m), 7.95 (1H, brs), 8.03 (1H, d, J=5.6 Hz), 10.54 (1H, brs). ESI-MS (m/z): 567 [M+H]$^+$.

Example 348

2-{[4-(Dimethylaminomethyl)piperidin-1-yl]carbo-
nylamino}-4-(4-{3-[2-(4-fluorophenyl)acetyl]
ureido}phenoxy)pyridine To a solution of 4-(4-aminophenoxy)-2-{[4-(dimethylaminomethyl)piperidin-1-yl]carbonylamino}pyridine (61.8 mg) in tetrahydrofuran (2.0 ml) was added a solution of 2-(4-fluorophenyl)acetyl isocyanate in tetrahydrofuran (0.25 M, 1.7 ml) at room temperature, followed by stirring for 3 days. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate) to provide the titled compound (32.6 mg, 36%) as white powder.
$^1$H-NMR Spectrum (CDCl$_3$) δ (ppm): 1.15-1.25 (2H, m), 1.65 (1H, m), 1.70-1.80 (2H, m), 2.10-2.30 (8H, m), 2.80-2.90 (2H, m), 3.72 (2H, s), 4.00-4.10 (2H, m), 6.50 (1H, dd, J=2.4, 5.6 Hz), 7.00-7.30 (7H, m), 7.50-7.54 (2H, m), 7.60 (1H, d, J=2.4 Hz), 7.94 (1H, m), 8.02 (1H, d, J=5.6 Hz), 10.44 (1H, brs). ESI-MS (m/z): 549 [M+H]$^+$.

Example 349

4-(Pyrrolidin-1-ylmethyl)piperidine-1-carboxylic
acid [6-(2-fluoro-4-{3-[2-(4-fluorophenyl)acetyl]
thioureido}phenoxy)pyrimidin-4-yl]amide 6-(2-Fluoro-4-nitrophenoxy)pyrimidin-4-ylamine (200 mg) was dissolved in tetrahydrofuran (8 ml) under a nitrogen atmosphere, and then triethylamine (0.334 ml) and phenyl chloroformate (0.301 ml) were added thereto while cooling in an ice water bath, followed by warming to room temperature and stirring for 1.5 hrs. The reaction mixture was partitioned between ethyl acetate (200 ml) and a saturated aqueous solution of sodium hydrogencarbonate (50 ml). The organic layer was washed with a saturated aqueous solution of sodium hydrogencarbonate (50 ml), water (50 ml), brine (100 ml) in this order, and dried over anhydrous sodium sulfate. The solvent was evaporated to give a residue, to which was added N,N-dimethylformamide (8 ml). 4-(Pyrrolidin-1-ylmethyl) piperidine dihydrochloride (771 mg) and triethylamine (0.896 ml) were added thereto, followed by stirring for 4 hrs. The reaction mixture was partitioned between ethyl acetate (100 ml) and a saturated aqueous solution of ammonium chloride (50 ml). The organic layer was washed with a saturated aqueous solution of ammonium chloride (50 ml), water (50 ml), and brine (50 ml) in this order, and dried over anhydrous sodium sulfate. The solvent was evaporated to give a residue, which was then purified by silica gel column chromatography (Fuji Silysia NH, heptane:ethyl acetate=1:1, then ethyl acetate). Fractions containing the target compound were concentrated to provide 4-(pyrrolidin-1-ylmethyl)piperidine- 1-carboxylic acid [6-(2-fluoro-4-nitrophenoxy)pyrimidin-4-yl]amide (350 mg) as a pale yellow oil.

4-(Pyrrolidin-1-ylmethyl)piperidine-1-carboxylic acid [6-(2-fluoro-4-nitrophenoxy)pyrimidin-4-yl]amide (350 mg) was dissolved in tetrahydrofuran (8 ml) and methanol (8 ml), and then 10% palladium carbon (162 mg) was added, followed by stirring under a hydrogen atmosphere for 6 hrs. The reaction mixture was filtered to remove the catalyst. The filtrate was concentrated under reduced pressure to give a residue, which was purified by silica gel column chromatography (eluent; ethyl acetate:methanol=9:1). Fractions containing the target compound were concentrated to provide a crude product of 4-(pyrrolidin-1-ylmethyl)piperidine-1-carboxylic acid [6-(4-amino-2-fluorophenoxy)pyrimidin-4-yl]amide (201.4 mg) as pale yellow foam.

4-(Pyrrolidin-1-ylmethyl)piperidine-1-carboxylic acid [6-(4-amino-2-fluorophenoxy)pyrimidin-4-yl]amide (100 mg) was dissolved in ethanol (1.0 ml) under a nitrogen atmosphere, and then (S)-(+)-10-camphorsulfonic acid (56 mg) was added thereto, followed by stirring for 5 min. A 0.25 M solution of 2-(4-fluorophenyl)acetyl isothiocyanate in toluene (1.45 ml) was added thereto, followed by stirring for 1 hr. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml), brine (20 ml) in this order, and dried over anhydrous sodium sulfate. The solvent was evaporated to give a residue, which was then purified by silica gel column chromatography (FUJI Silysia NH, eluent; heptane:ethyl acetate=1:3). Fractions containing the target compound were concentrated to give a residue, to which diethyl ether (1.5 ml) and hexane (2.0 ml) were then added to suspend. The solid was filtered off, and dried under aeration to provide the titled compound (32.7 mg) as pale yellow powder.

$^1$H-NMR Spectrum (CDCl$_3$) δ (ppm): 1.10-1.40 (1H, m), 1.50-1.75 (2H, m), 1.78 (4H, m), 1.89 (2H, m), 2.35 (2H, d, J=7.2 Hz), 2.49 (4H, m), 2.92 (2H, m), 3.71 (2H, s), 4.09 (2H, m), 7.00-7.45 (7H, m), 7.64 (1H, m), 7.86 (1H, dd, J=2.4, 11.2 Hz), 8.33 (1H, m), 8.53 (1H, brs), 12.38 (1H, brs). ESI-MS (m/z): 610 [M+H]$^+$.

Example 350

4-(Pyrrolidin-1-ylmethyl)piperidine-1-carboxylic acid {6-[2-fluoro-4-(3-phenylacetylthioureido)phenoxy]pyrimidin-4-yl}amide 4-(Pyrrolidin-1-ylmethyl)piperidine-1-carboxylic acid [6-(4-amino-2-fluorophenoxy)pyrimidin-4-yl]amide (100 mg) was dissolved in ethanol (1.0 ml) under a nitrogen atmosphere, and then (S)-(+)-10-camphorsulfonic acid (56 mg) was added thereto, followed by for stirring 5 min. A 0.25 M solution of phenylacetyl isothiocyanate in toluene (1.45 ml) was added thereto, followed by stirring for 1 hr. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml), brine (20 ml) in this order, and dried over anhydrous sodium sulfate. The solvent was evaporated to give a residue, which was then purified by silica gel column chromatography (FUJI Silysia NH, eluent; heptane:ethyl acetate=1:3). Fractions containing the target compound were concentrated to give a residue, to which diethyl ether (1.5 ml) and hexane (2.0 ml) in this order were then added to suspend. The solid was filtered off, and dried under aeration to provide the titled compound (37.6 mg, 26.4%) as pale yellow powder.

$^1$H-NMR Spectrum (CDCl$_3$) δ (ppm): 1.10-1.40 (1H, m), 1.40-1.72 (2H, m), 1.78 (4H, m), 1.89 (2H, m), 2.34 (2H, d, J=7.2 Hz), 2.48 (4H, m), 2.92 (2H, m), 3.74 (2H, brs), 4.09 (2H, m), 7.00-7.53 (8H, m), 7.64 (1H, m), 7.86 (1H, dd, J=2.4, 11.2 Hz), 8.33 (1H, m), 8.48 (1H, brs), 12.42 (1H, brs). ESI-MS (m/z): 592 [M+H]$^+$.

Example 351

4-(4-Methylpiperazin-1-yl)piperidine-1-carboxylic acid {6-[2-fluoro-4-(3-phenylacetylthioureido)phenoxy]pyrimidin-4-yl}amide 4-(4-Methylpiperazin-1-yl)piperidine-1-carboxylic acid [6-(4-amino-2-fluorophenoxy)pyrimidin-4-yl]amide (81 mg) was dissolved in ethanol (1 ml), and then (S)-(+)-10-camphorsulfonic acid (44 mg) was added thereto, followed by stirring for 5 min. A 0.25 M solution of 2-phenylacetyl isothiocyanate in toluene (1.14 ml) was added thereto, followed by stirring for 1 hr. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml), brine (20 ml) in this order, and dried over anhydrous sodium sulfate. The solvent was evaporated to give a residue, which was then purified by silica gel column chromatography (FUJI Silysia NH, eluent; heptane:ethyl acetate=1:5 to 1:10, then ethyl acetate). Fractions containing the target compound were concentrated under reduced pressure to give a residue, to which diethyl ether (1.5 ml) and hexane (3.0 ml) were then added to suspend. The solid was filtered off, and dried under aeration to provide the titled compound (61.1 mg, 53.3%) as white powder.

$^1$H-NMR Spectrum (CDCl$_3$) δ (ppm): 1.21-1.40 (1H, m), 1.53 (2H, m), 1.93 (2H, m), 2.30 (3H, s), 2.47 (4H, m), 2.61 (4H, m), 2.95 (2H, m), 3.74 (2H, s), 4.12 (2H, m), 7.10-7.50 (8H, m), 7.62 (1H, s), 7.86 (1H, dd, J=2.4, 11.2 Hz), 8.33 (1H, s), 8.45 (1H, brs), 12.42 (1H, brs). ESI-MS (m/z): 607 [M+H]$^+$.

Example 352

4-(1-Methylpiperidin-4-yl)piperazine-1-carboxylic acid {6-[2-fluoro-4-(3-phenylacetylthioureido)phenoxy]pyrimidin-4-yl}amide 4-(1-Methylpiperidin-4-yl)piperazine-1-carboxylic acid [6-(4-amino-2-fluorophenoxy)pyrimidin-4-yl]amide (110 mg) was dissolved in ethanol (1 ml), and then (S)-(+)-10-camphorsulfonic acid (60 mg) was added thereto, followed by stirring for 5 min. A 0.25 M solution of 2-phenylacetyl isothiocyanate in toluene (1.54 ml) was added thereto, followed by stirring for 1 hr. The reaction mixture was partitioned between ethyl acetate (30 ml) and a saturated aqueous solution of sodium hydrogencarbonate (20 ml). The organic layer was washed with a saturated aqueous solution of sodium hydrogencarbonate (20 ml), water (20 ml), brine (20 ml) in this order, and dried over anhydrous sodium sulfate. The solvent was evaporated to give a residue, which was then purified by silica gel column chromatography (FUJI Silysia NH, eluent; heptane:ethyl acetate=1:5 to 1:10, then ethyl acetate). Fractions containing the target compound were concentrated to give a residue, to which diethyl ether (1.5 ml) and hexane (3.0 ml) were then added to suspend. The solid was filtered off, and dried under aeration to provide the titled compound (24.3 mg, 15.6%) as white powder.

$^1$H-NMR Spectrum (CDCl$_3$) δ (ppm): 1.21-1.35 (1H, m), 1.50-1.72 (2H, m), 1.78 (2H, m), 1.96 (2H, m), 2.27 (3H, s), 2.61 (4H, m), 2.92 (2H, m), 3.53 (4H, m), 3.74 (2H, m), 7.10-7.50 (8H, m), 7.63 (1H, s), 7.86 (1H, dd, J=2.4, 11.2 Hz), 8.33 (1H, s), 8.46 (1H, brs), 12.42 (1H, brs). ESI-MS (m/z): 607 [M+H]$^+$.

Example 353

1-[1-(2-Dimethylaminoethyl)piperidin-4-yl]-3-{4-[2-fluoro-4-(3-phenylacetylureido)phenoxy]pyridin-2-yl}-1-methylurea To a solution of 3-[4-(4-amino-2-fluorophenoxy)pyridin-2-yl]-1-[1-(2-dimethylaminoethyl)piperidin-4-yl]-1-methylurea (61 mg) in tetrahydrofuran (3.0 ml) was added a solution of 2-phenylacetyl isocyanate in hexane (0.2 M, 1.70 ml) at room temperature, followed by stirring at room temperature for 9.5 hrs. The reaction mixture was partitioned between ethyl acetate and a saturated aqueous solution of sodium hydrogencarbonate. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=10:1). Fractions containing a target compound were concentrated to give a residue, to which diethyl ether (1 ml) and hexane (1 ml) were added to give a precipitate. The precipitate was filtered off, and dried under aeration to provide the titled compound (17.8 mg, 21%) as white powder.

$^1$H-NMR Spectrum (CDCl$_3$) δ (ppm): 1.66 (2H, m), 1.79 (2H, m), 2.12 (2H, m), 2.28 (6H, s), 2.49 (4H, m), 2.88 (3H, s), 3.01 (2H, m), 3.76 (2H, s), 4.16 (1H, m), 6.52 (1H, dd, J=2.0, 5.6 Hz), 7.10-7.44 (8H, m), 7.60-7.65 (2H, m), 7.79 (1H, brs), 8.04 (1H, d, J=5.6 Hz), 10.57 (1H, s). ESI-MS (m/z): 592 [M+H]$^+$.

Example 354

1-[1-(2-Dimethylaminoethyl)piperidin-4-yl]-3-[4-(4-{3-[2-(4-fluorophenyl)acetyl]ureido}phenoxy)pyridin-2-yl]-1-methylurea To a solution of 3-[4-(4-aminophenoxy)-pyridin-2-yl]-1-[1-(2-dimethylaminoethyl)piperidin-4-yl]-1-methylurea (154 mg) in tetrahydrofuran (5.0 ml) was added a solution of 2-(4-fluorophenyl)acetyl isocyanate in tetrahydrofuran (0.25 M, 3.73 ml) at room temperature, followed by stirring at room temperature for 10.5 hrs. The reaction mixture was partitioned between ethyl acetate and a saturated aqueous solution of sodium hydrogencarbonate. The organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=10:1). Fractions containing a target compound were concentrated to give a residue, to which diethyl ether (1 ml) and hexane (1 ml) were added to give a precipitate. The precipitate was filtered off, and dried under aeration to provide the titled compound (29.8 mg, 13.5%) as white powder.

$^1$H-NMR Spectrum (CDCl$_3$) δ (ppm): 1.66 (2H, m), 1.79 (2H, m), 2.11 (2H, m), 2.27 (6H, s), 2.48 (4H, m), 2.87 (3H, s), 3.01 (2H, m), 3.72 (2H, s), 4.16 (1H, m), 6.51 (1H, d, J=5.6 Hz), 7.05-7.11 (5H, m), 7.29 (2H, m), 7.53 (2H, d, J=8.8 Hz), 7.66 (1H, s), 8.03 (1H, d, J=5.6 Hz), 8.33 (1H, brs), 10.47 (1H, s). ESI-MS (m/z): 592 [M+H]$^+$.

Example 355

3-{6-[2-Fluoro-4-(3-phenylacetylthioureido)phenoxy]pyrimidin-4-yl}-1-methyl-1-[1-(1-methylazetidin-3-yl)piperidin-4-yl]urea To a solution of 3-[6-(4-amino-2-fluorophenoxy)pyrimidin-4-yl]-1-methyl-1-[1-(1-methylazetidin-3-yl)piperidin-4-yl]urea (68.0 mg) in ethanol (2.0 ml) was added (1S)-(+)-10-camphorsulfonic acid (70.2 mg), followed by stirring at room temperature for 10 min. A solution of 2-phenylacetyl isothiocyanate in toluene (0.25 M, 1.91 ml) was added to the reaction mixture, followed by stirring at room temperature for 30 min. The reaction mixture was partitioned between ethyl acetate (50 ml) and a saturated aqueous solution of sodium hydrogencarbonate (20 ml). The organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=25:1). Fractions containing the target compound were concentrated to give a residue, which was added diethyl ether (2 ml) to give a precipitate. The precipitate was filtered off, washed with diethyl ether, and dried under aeration to provide the titled compound (12.9 mg, 13.4%) as white powder.

$^1$H-NMR Spectrum (CDCl$_3$) δ (ppm): 1.68-1.98 (6H, m), 2.40 (3H, s), 2.85 (2H, m), 2.92-3.00 (6H, m), 3.59 (2H, m), 3.74 (2H, s), 4.20 (1H, m), 7.21 (1H, m), 7.29-7.46 (7H, m), 7.67 (1H, s), 7.86 (1H, dd, J=2.4, 11.6 Hz), 8.34 (1H, s), 8.50 (1H, br), 12.43 (1H, s). ESI-MS (m/z): 607 [M+H]$^+$.

Production Example 355-1

Methyl-[1-(1-methylazetidin-3-yl)piperidin-4-yl]amine

To a solution of tert-butyl 3-[4-(tert-butoxycarbonylamino)piperidin-1-yl]azetidine-1-carboxylate (2.49 g) in tetrahydrofuran (100 ml) was added lithium aluminium hydride (930 mg) while stirring in an ice bath, followed by stirring under a nitrogen atmosphere in an ice bath for 10 min and at room temperature for 10 min. The reaction mixture was refluxed under a nitrogen atmosphere for 1.5 hrs. The reaction mixture was cooled in an ice bath, and then water (0.93 ml), a 5N aqueous solution of sodium hydroxide (0.93 ml), and water (4.65 ml) were added thereto in this order, followed by stirring at room temperature for 24 hrs. The insoluble portion was filtered off and washed with ethyl acetate to give a filtrate, which was concentrated to provide the titled compound (1.07 g, 83.4%) as a pale yellow oil.

$^1$H-NMR Spectrum (CDCl$_3$) δ (ppm): 1.35 (2H, m), 1.82-1.90 (4H, m), 2.35 (3H, s), 2.43 (3H, s), 2.71 (2H, m), 2.88 (3H, m), 3.52 (2H, m), 3.68 (1H, m). ESI-MS (m/z): 184 [M+H]$^+$.

Production Example 355-2

3-[6-(2-Fluoro-4-nitrophenoxy)pyrimidin-4-yl]-1-methyl-1-[1-(1-methylazetidin-3-yl)piperidin-4-yl]urea To a solution of 6-(2-fluoro-4-nitrophenoxy)pyrimidin-4-ylamine (250 mg) in tetrahydrofuran (10 ml) were added triethylamine (0.307 ml) and phenyl chloroformate (0.264 ml) in this order, followed by stirring at room temperature for 30 min. The reaction mixture was concentrated to give a residue. To the residue was added N,N-dimethylformamide (5.0 ml), methyl-[1-(1-methylazetidin-3-yl)piperidin-4-yl]amine (1.07 g), followed by stirring at room temperature for 36 hrs. The reaction mixture was partitioned between ethyl acetate and an 1N aqueous solution of sodium hydroxide. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing a target compound were concentrated to give a powder, which was suspended hexane (5 ml). It was filtered off, dried under aeration to provide the titled compound (193 mg, 42.0%) as yellow powder.

$^1$H-NMR Spectrum (CDCl$_3$) δ (ppm): 1.68-1.83 (4H, m), 1.95 (2H, m), 2.36 (3H, s), 2.85-2.97 (8H, m), 3.53 (2H, m), 4.20 (1H, m), 7.34 (1H, brs), 7.42 (1H, m), 7.77 (1H, m), 8.08-8.14 (2H, m), 8.33 (1H, m). ESI-MS (m/z): 460 [M+H]$^+$.

Production Example 355-3

3-[6-(4-Amino-2-fluorophenoxy)pyrimidin-4-yl]-1-methyl-1-[1-(1-methylazetidin-3-yl)piperidin-4-yl] urea To a solution of 3-[6-(2-fluoro-4-nitrophenoxy)pyrimidin-4-yl]-1-methyl-1-[1-(1-methylazetidin-3-yl)piperidin-4-yl] urea (193 mg) in tetrahydrofuran (100 ml) was added 20% palladium hydroxide carbon (590 mg), followed by stirring under a hydrogen atmosphere at room temperature for 6.5 hrs. The reaction mixture was filtered to remove the catalyst, and the catalyst was washed with methanol. The filtrate was concentrated to provide the titled compound (136 mg, 75.4%) as pale yellow solid.

ESI-MS (m/z): 430 [M+H]$^+$.

Example 356

4-(3-Dimethylaminoazetidin-1-yl)piperidine-1-carboxylic acid [4-(4-{3-[2-(4-fluorophenyl)acetyl]ureido}phenoxy)pyridin-2-yl]amide To a solution of 4-(3-dimethylaminoazetidin-1-yl)piperidine-1-carboxylic acid [4-(4-aminophenoxy)pyridin-2-yl]amide (60 mg) in tetrahydrofuran (5.0 ml) was added a solution of 2-(4-fluorophenyl)acetyl isocyanate in tetrahydrofuran (0.25 M, 1.75 ml) at room temperature, followed by stirring at room temperature for 0.5 hr. To the reaction mixture was added a saturated aqueous solution of sodium hydrogencarbonate, followed by stirring at room temperature for 0.5 hr. The reaction mixture was extracted with ethyl acetate. The organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=10:1). Fractions containing a target compound were concentrated to give a solid, which was suspended in diethyl ether (1 ml) and hexane (2 ml). The solid was filtered off, washed with diethyl ether:hexane=1:2, and dried under aeration to provide the titled compound (23.2 mg, 27%) as white powder.

$^1$H-NMR Spectrum (CDCl$_3$) δ (ppm): 1.27-1.35 (2H, m), 1.73 (2H, m), 2.14 (6H, s), 2.31 (1H, m), 2.90 (3H, m), 3.04 (2H, m), 3.52 (2H, m), 3.72 (2H, s), 3.89 (2H, m), 6.50 (1H, dd, J=2.0, 6.0 Hz), 7.05-7.12 (4H, m), 7.23 (1H, m), 7.29 (2H, m), 7.53 (2H, d, J=8.8 Hz), 7.59 (1H, d, J=2.0 Hz), 8.02 (1H, d, J=6.0 Hz), 8.09 (1H, brs), 10.45 (1H, s). ESI-MS (m/z): 590 [M+H]$^+$, 612 [M+Na]$^+$.

Example 357

2-{[4-(Azetidin-1-yl)piperidin-1-yl]carbonylamino}-4-(4-{3-[2-(4-fluorophenyl)acetyl]ureido}phenoxy)pyridine To a solution of 4-(4-aminophenoxy)-2-{[4-(azetidin-1-yl)piperidin-1-yl]carbonylamino}pyridine (67.8 mg) in tetrahydrofuran (2.5 ml) was added a solution of 2-(4-fluorophenyl)acetyl isocyanate in tetrahydrofuran (0.25 M, 2.2 ml) at room temperature, followed by stirring for 2 hours. A solution of 2-(4-fluorophenyl)acetyl isocyanate in tetrahydrofuran (0.25 M, 1.5 ml) was further added thereto at room temperature. After 6 hours, a solution of 2-(4-fluorophenyl)acetyl isocyanate in tetrahydrofuran (0.25 M, 1.85 ml) and diisopropylethylamine (0.322 ml) were added thereto at room temperature, followed by stirring for 2 days. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=97:3). Fractions containing the target compound were concentrated to give a residue, which was then suspended in ethyl acetate (1 ml). The solid was filtered off and dried under aeration to provide the titled compound (17.0 mg, 17%) as white powder.

$^1$H-NMR Spectrum (CDCl$_3$) δ (ppm): 1.20-1.35 (2H, m) 1.60-1.75 (2H, m), 2.00-2.10 (2H, m), 2.19 (1H, m), 3.03 (2H, m), 3.16-3.20 (4H, m), 3.72 (2H, s), 3.85-3.95 (2H, m), 6.50 (1H, dd, J=2.4, 5.6 Hz), 7.00-7.35 (7H, m), 7.50-7.55 (2H, m), 7.59 (1H, d, J=2.4 Hz), 8.02 (1H, d, J=5.6 Hz), 8.33 (1H, brs), 10.47 (1H, brs). ESI-MS (m/z): 547 [M+H]$^+$.

Example 358

2-{[4-(1-Methylpiperazin-4-yl)piperidin-1-yl]carbonylamino}-4-{4-[3-(2-phenylacetyl)ureido]phenoxy}pyridine To a solution of 4-(4-aminophenoxy)-2-{[4-(1-methylpiperazin-4-yl)piperidin-1-yl]carbonylamino}pyridine (75.2 mg) in tetrahydrofuran (4.0 ml) was added a solution of 2-phenylacetyl isocyanate in hexane (0.25 M, 1.83 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=98:2) to provide the titled compound (48.5 mg, 46%) as white powder.

$^1$H-NMR Spectrum (CDCl$_3$) δ (ppm): 1.40-1.95 (5H, m), 2.32 (3H, s), 2.40-2.75 (8H, m), 2.88 (2H, m), 3.75 (2H, s), 4.06-4.16 (2H, m), 6.50 (1H, dd, J=2.4, 5.6 Hz), 7.00-7.10 (2H, m), 7.21 (1H, brs), 7.25-7.45 (5H, m), 7.50-7.55 (2H, m), 7.59 (1H, d, J=2.4 Hz), 7.67 (1H, brs), 8.02 (1H, d, J=5.6 Hz), 10.47 (1H, brs). ESI-MS (m/z): 572 [M+H]$^+$.

Example 359

2-{[4-(1-Methylpiperidin-4-yl)piperazin-1-yl]carbonylamino}-4-{4-[3-(2-phenylacetyl)ureido]phenoxy}pyridine To a solution of 4-(4-aminophenoxy)-2-{[4-(1-methylpiperidin-4-yl)piperazin-1-yl]carbonylamino}pyridine (80.7 mg) in tetrahydrofuran (4.0 ml) was added a solution of 2-phenylacetyl isocyanate in hexane (0.25 M, 1.96 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=95:5) to provide the titled compound (73.7 mg, 66%) as white powder.
$^1$H-NMR Spectrum (CDCl$_3$) δ (ppm): 1.50-2.10 (6H, m), 2.20-2.36 (4H, m), 2.50-2.60 (4H, m), 2.90-3.00 (2H, m), 3.44-3.54 (4H, m), 3.75 (2H, s), 6.50 (1H, dd, J=2.4, 5.6 Hz), 7.00-7.10 (2H, m), 7.17 (1H, brs), 7.26-7.45 (5H, m), 7.50-7.55 (2H, m), 7.60 (1H, d, J=2.4 Hz), 7.75 (1H, m), 8.02 (1H, d, J=5.6 Hz), 10.47 (1H, brs). ESI-MS (m/z): 572 [M+H]$^+$.

Example 360

2-{[4-(Dimethylaminomethyl)piperidin-1-yl]carbonylamino}-4-{4-[3-(2-phenylacetyl)ureido]phenoxy}pyridine To a solution of 4-(4-aminophenoxy)-2-{[4-(dimethylaminomethyl)piperidin-1-yl]carbonylamino}pyridine (60.6 mg) in tetrahydrofuran (4.0 ml) was added a solution of 2-phenylacetyl isocyanate in hexane (0.25 M, 1.64 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate) to provide the titled compound (59.5 mg, 68%) as white powder.
$^1$H-NMR Spectrum (CDCl$_3$) δ (ppm): 1.10-1.25 (2H, m), 1.65 (1H, m), 1.75-1.85 (2H, m), 2.10-2.20 (2H, m), 2.22 (6H, s), 2.87 (2H, m), 3.75 (2H, s), 4.00-4.10 (2H, m), 6.49 (1H, dd, J=2.4, 5.6 Hz), 7.00-7.10 (2H, m), 7.21 (1H, brs), 7.25-7.45 (5H, m), 7.50-7.55 (2H, m), 7.61 (1H, d, J=2.4 Hz), 7.94 (1H, brs), 8.02 (1H, d, J=5.6 Hz), 10.49 (1H, brs). ESI-MS (m/z): 531 [M+H]$^+$.

Example 361

2-{[4-(Azetidin-1-yl)piperidin-1-yl]carbonylamino}-4-{4-[3-(2-phenylacetyl)ureido]phenoxy}pyridine To a solution of 4-(4-aminophenoxy)-2-{[4-(azetidin-1-yl)piperidin-1-yl]carbonylamino}pyridine (62.8 mg) in tetrahydrofuran (4.0 ml) was added a solution of 2-phenylacetyl isocyanate in hexane (0.25 M, 1.71 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=98:2) to provide the titled compound (50.0 mg, 55%) as white powder.
$^1$H-NMR Spectrum (CDCl$_3$) δ (ppm): 1.20-1.45 (2H, m), 1.65-1.75 (2H, m), 2.00-2.10 (2H, m), 2.20 (1H, m), 3.03 (2H, m), 3.14-3.24 (4H, m), 3.75 (2H, s), 3.85-3.95 (2H, m), 6.49 (1H, dd, J=2.4, 5.6 Hz), 7.00-7.10 (2H, m), 7.17 (1H, brs), 7.25-7.45 (5H, m), 7.50-7.55 (2H, m), 7.60 (1H, d, J=2.4 Hz), 7.69 (1H, m), 8.01 (1H, d, J=5.6 Hz), 10.46 (1H, brs). ESI-MS (m/z): 529 [M+H]$^+$.

Example 362

2-{[4-(2-Dimethylaminoethyl)piperazin-1-yl]carbonylamino}-4-(2-fluoro-4-{3-[2-(4-fluorophenyl)acetyl]ureido}phenoxy)pyridine To a solution of 4-(4-amino-2-fluorophenoxy)-2-{[4-(2-dimethylaminoethyl)piperazin-1-yl]carbonylamino}pyridine (84.3 mg) in tetrahydrofuran (2.5 ml) were added a solution of 2-(4-fluorophenyl)acetyl isocyanate in tetrahydrofuran (0.25 M, 5.02 ml) and diisopropylethylamine (0.218 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=95:5) to provide the titled compound (34.0 mg, 28%) as white powder.
$^1$H-NMR Spectrum (CDCl$_3$) δ (ppm): 2.29 (6H, s), 2.40-2.58 (8H, m), 3.44-3.54 (4H, m), 3.73 (2H, s), 6.54 (1H, dd, J=2.4, 5.6 Hz), 7.00-7.35 (7H, m), 7.59-7.63 (2H, m), 8.00-8.10 (2H, m), 10.56 (1H, brs). ESI-MS (m/z): 604 [M+Na]$^+$.

Example 363

2-{[4-(2-Dimethylaminoethyl)piperazin-1-yl]carbonylamino}-4-(4-{3-[2-(4-fluorophenyl)acetyl]ureido}phenoxy)pyridine To a solution of 4-(4-aminophenoxy)-2-{[4-(2-dimethylaminoethyl)piperazin-1-yl]carbonylamino}pyridine (86.7 mg) in tetrahydrofuran (2.5 ml) were added a solution of 2-(4-fluorophenyl)acetyl isocyanate in tetrahydrofuran (0.25 M, 5.4 ml) and diisopropylethylamine (0.235 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=95:5) to provide the titled compound (36.2 mg, 29%) as white powder.
$^1$H-NMR Spectrum (CDCl$_3$) δ (ppm): 2.30 (6H, s), 2.40-2.58 (8H, m), 3.44-3.54 (4H, m), 3.72 (2H, s), 6.52 (1H, dd, J=2.4, 5.6 Hz), 7.00-7.30 (7H, m), 7.50-7.55 (2H, m), 7.60

Example 364

2-{[4-(2-Dimethylaminoethyl)piperazin-1-yl]carbonylamino}-4-{2-fluoro-4-[3-(2-phenylacetyl)ureido]phenoxy}pyridine To a solution of 4-(4-amino-2-fluorophenoxy)-2-{[4-(2-dimethylaminoethyl)piperazin-1-yl]carbonylamino}pyridine (87.4 mg) in tetrahydrofuran (4.5 ml) was added a solution of 2-phenylacetyl isocyanate in hexane (0.25 M, 2.2 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=95:5) to provide the titled compound (82 mg, 67%) as white powder.

$^1$H-NMR Spectrum (CDCl$_3$) δ (ppm): 2.27 (6H, s), 2.40-2.54 (8H, m), 3.46-3.56 (4H, m), 3.75 (2H, s), 6.52 (1H, dd, J=2.4, 5.6 Hz), 7.00-7.45 (8H, m), 7.55-7.65 (2H, m), 7.87 (1H, brs), 8.03 (1H, d, J=5.6 Hz), 10.58 (1H, brs). ESI-MS (m/z): 564 [M+H]$^+$.

Example 365

2-{[4-(2-Dimethylaminoethyl)piperazin-1-yl]carbonylamino}-4-{4-[3-(2-phenylacetyl)ureido]phenoxy}pyridine To a solution of 4-(4-aminophenoxy)-2-{[4-(2-dimethylaminoethyl)piperazin-1-yl]carbonylamino}pyridine (97.2 mg) in tetrahydrofuran (5 ml) was added a solution of 2-phenylacetyl isocyanate in hexane (0.25 M, 2.6 ml) at room temperature, followed by stirring overnight. The reaction mixture was partitioned between ethyl acetate and a saturated aqueous solution of sodium hydrogencarbonate. The organic layer was washed with brine and dried over anhydrous sodium sulfate. The solvent was evaporated to give a residue, which was then purified by silica gel column chromatography (Fuji Silysia NH, eluent; ethyl acetate, then ethyl acetate:methanol=95:5) to provide the titled compound (100 mg, 72%) as white powder.

$^1$H-NMR Spectrum (CDCl$_3$) δ (ppm): 2.28 (6H, s), 2.42-2.56 (8H, m), 3.46-3.54 (4H, m), 3.75 (2H, s), 6.50 (1H, dd, J=2.4, 5.6 Hz), 7.00-7.10 (2H, m), 7.18 (1H, brs), 7.25-7.45 (5H, m), 7.50-7.55 (2H, m), 7.60 (1H, d, J=2.4 Hz), 7.77 (1H, brs), 8.02 (1H, d, J=5.6 Hz), 10.48 (1H, brs). ESI-MS (m/z): 546 [M+H]$^+$.

Example 366

2-{[4-(1-Methylpiperazin-4-yl)piperidin-1-yl]carbonylamino}-4-{4-[3-(2-phenylacetyl)thioureido]phenoxy}pyridine To a solution of 4-(4-aminophenoxy)-2-{[4-(1-methylpiperazin-4-yl)piperidin-1-yl]carbonylamino}pyridine (130 mg) and (+)-10-camphorsulfonic acid (138 mg) in ethanol (3.0 ml) was added a solution of 2-phenylacetyl isothiocyanate in toluene (0.25 M, 2.5 ml) at room temperature, followed by stirring for 3 hours. The reaction mixture was partitioned between ethyl acetate and a saturated aqueous solution of sodium hydrogencarbonate. The organic layer was washed with a saturated aqueous solution of sodium hydrogencarbonate and brine in this order, dried over anhydrous sodium sulfate. The solvent was evaporated to give a residue, which was then purified by silica gel column chromatography (Fuji Silysia NH, eluent; ethyl acetate, then ethyl acetate:methanol=98:2) to provide the titled compound (48.5 mg, 26%) as white powder.

$^1$H-NMR Spectrum (CDCl$_3$) δ (ppm): 1.40-2.00 (5H, m), 2.30 (3H, s), 2.40-2.94 (10H, m), 3.74 (2H, s), 4.05-4.16 (2H, m), 6.53 (1H, dd, J=2.4, 5.6 Hz), 7.09-7.15 (2H, m), 7.22 (1H, brs), 7.30-7.45 (5H, m), 7.67 (1H, d, J=2.4 Hz), 7.69-7.70 (2H, m), 8.04 (1H, d, J=5.6 Hz), 8.46 (1H, brs), 12.30 (1H, brs). ESI-MS (m/z): 588 [M+H]$^+$.

Example 367

2-{[4-(1-Methylpiperidin-4-yl)piperazin-1-yl]carbonylamino}-4-{4-[3-(2-phenylacetyl)thioureido]phenoxy}pyridine To a solution of 4-(4-aminophenoxy)-2-{[4-(1-methylpiperidin-4-yl)piperazin-1-yl]carbonylamino}pyridine (153 mg) and (+)-10-camphorsulfonic acid (162 mg) in ethanol (4.0 ml) was added a solution of 2-phenylacetyl isothiocyanate in toluene (0.25 M, 2.93 ml) at room temperature, followed by stirring for 3 hours. The reaction mixture was partitioned between ethyl acetate and a saturated aqueous solution of sodium hydrogencarbonate. The organic layer was washed with a saturated aqueous solution of sodium hydrogencarbonate and brine in this order, dried over anhydrous sodium sulfate. The solvent was evaporated to give a residue, which was then purified by silica gel column chromatography (Fuji Silysia NH, eluent; ethyl acetate, then ethyl acetate:methanol=98:2) to provide the titled compound (71.8 mg, 33%) as white powder.

$^1$H-NMR Spectrum (CDCl$_3$) δ (ppm): 1.50-2.05 (6H, m), 2.20-2.40 (4H, m), 2.50-2.65 (4H, m), 2.85-3.00 (2H, m), 3.44-3.54 (4H, m), 3.75 (2H, s), 6.53 (1H, dd, J=2.4, 5.6 Hz), 7.09-7.15 (2H, m), 7.19 (1H, brs), 7.30-7.46 (5H, m), 7.65 (1H, d, J=2.4 Hz), 7.67-7.70 (2H, m), 8.04 (1H, d, J=5.6 Hz), 8.45 (1H, brs), 12.30 (1H, brs). ESI-MS (m/z): 588 [M+H]$^+$.

Example 368

2-{[4-(2-Dimethylaminoethyl)piperazin-1-yl]carbonylamino}-4-{4-[3-(2-phenylacetyl)thioureido]phenoxy}pyridine To a solution of 4-(4-aminophenoxy)-2-{[4-(2-dimethylaminoethyl)piperazin-1-yl]carbonylamino}pyridine (137 mg) and (+)-10-camphorsulfonic acid (151 mg) in ethanol (3.5 ml) was added a solution of 2-phenylacetyl isothiocyanate in toluene (0.25 M, 2.73 ml) at room temperature, followed by stirring for 3 hours. The reaction mixture was partitioned between ethyl acetate and a saturated aqueous solution of sodium hydrogencarbonate. The organic layer was washed with a saturated aqueous solution of sodium hydrogencarbonate and brine in this order, dried over anhydrous sodium sulfate. The solvent was evaporated to give a residue, which was then purified by silica gel column chromatography (Fuji Silysia NH, eluent; ethyl acetate, then ethyl acetate:methanol=98:2) to provide the titled compound (86.5 mg, 45%) as white powder.

$^1$H-NMR Spectrum (CDCl$_3$) δ (ppm): 2.27 (6H, s), 2.40-2.56 (8H, m), 3.48-3.56 (4H, m), 3.74 (2H, s), 6.53 (1H, dd, J=2.4, 5.6 Hz), 7.08-7.13 (2H, m), 7.19 (1H, brs), 7.30-7.46 (5H, m), 7.65 (1H, d, J=2.4 Hz), 7.66-7.70 (2H, m), 8.04 (1H, d, J=5.6 Hz), 8.48 (1H, brs), 12.30 (1H, brs). ESI-MS (m/z): 562 [M+H]$^+$.

Example 369

2-{[4-(4-Hydroxypiperidin-1-yl)piperidin-1-yl]carbonylamino}-4-{4-[3-(2-phenylacetyl)thioureido]phenoxy}pyridine To a solution of 4-(4-aminophenoxy)-2-{[4-(4-hydroxypiperidin-1-yl)piperidin-1-yl]carbonylamino}pyridine (131 mg) and (+)-10-camphorsulfonic acid (70 mg) in ethanol (3.0 ml) was added a solution of 2-phenylacetyl isothiocyanate in toluene (0.25 M, 2.54 ml) at room temperature, followed by stirring for 2 days. The reaction mixture was partitioned between ethyl acetate and a saturated aqueous solution of sodium hydrogencarbonate. The organic layer was washed with a saturated aqueous solution of sodium hydrogencarbonate and brine in this order, dried over anhydrous sodium sulfate. The solvent was evaporated to give a residue, which was then purified by silica gel column chromatography (Fuji Silysia NH, eluent; ethyl acetate, then ethyl acetate:methanol=97:3). Fractions containing the target compound were concentrated to give a residue, which was then suspended in ethyl acetate (1 ml) and hexane (3 ml). The solid was filtered off and dried under aeration to provide the titled compound (46.5 mg, 25%) as white powder.

$^1$H-NMR Spectrum (CDCl$_3$) δ (ppm): 1.40-2.00 (8H, m), 2.25-2.45 (2H, m), 2.51 (1H, m), 2.75-2.95 (4H, m), 3.70 (1H, m), 3.74 (2H, s), 4.05-4.20 (2H, m), 6.53 (1H, d, J=2.4, 5.6 Hz), 7.09-7.13 (2H, m), 7.26-7.50 (6H, m), 7.64 (1H, d, J=2.4 Hz), 7.66-7.71 (2H, m), 8.04 (1H, d, J=5.6 Hz), 8.51 (1H, brs), 12.31 (1H, brs). ESI-MS (m/z): 589 [M+H]$^+$.

Example 370

4-(Pyrrolidin-1-ylmethyl)piperidine-1-carboxylic acid {4-[2-fluoro-4-(3-phenylacetylureido)phenoxy]pyridin-2-yl}amide 4-(2-Fluoro-4-nitrophenoxy)pyridin-2-ylamine (160 mg) was dissolved in tetrahydrofuran (7 ml) under a nitrogen atmosphere, and then triethylamine (0.268 ml) and phenyl chloroformate (0.242 ml) were added thereto while cooling in an ice water bath, followed by warming to room temperature and stirring for 1 hr. The reaction mixture was partitioned between ethyl acetate (200 ml) and a saturated aqueous solution of sodium hydrogencarbonate (50 ml). The organic layer was washed with a saturated aqueous solution of sodium hydrogencarbonate (50 ml), water (50 ml) and brine (100 ml) in this order, and dried over anhydrous sodium sulfate. The solvent was evaporated to give a residue, and N,N-dimethylformamide (7 ml) was added thereto. And then 4-(pyrrolidin-1-ylmethyl)piperidine dihydrochloride (619 mg) and triethylamine (0.716 ml) were added thereto, followed by stirring for 4 hrs. The reaction mixture was partitioned between ethyl acetate (100 ml) and a saturated aqueous solution of ammonium chloride (50 ml). The organic layer was washed with a saturated aqueous solution of ammonium chloride (50 ml), water (50 ml) and brine (50 ml) in this order, and dried over anhydrous sodium sulfate. The solvent was evaporated to give a residue, which was then purified by silica gel column chromatography (Fuji Silysia NH, eluent; heptane:ethyl acetate=1:1, then ethyl acetate). Fractions containing a target compound were concentrated to provide a crude product of 4-(pyrrolidin-1-ylmethyl)piperidine-1-carboxylic acid [4-(2-fluoro-4-nitrophenoxy)pyridin-2-yl]amide (290 mg) as pale yellow oil.

4-(Pyrrolidin-1-ylmethyl)piperidine-1-carboxylic acid [4-(2-fluoro-4-nitrophenoxy)pyridin-2-yl]amide (290 mg) was dissolved in tetrahydrofuran (7 ml) and methanol (7 ml) under a nitrogen atmosphere, and then 10% palladium carbon (139 mg) was added, followed by stirring under a hydrogen atmosphere for 10 hrs. The reaction mixture was filtered to remove the catalyst, and the catalyst was washed with methanol. The filtrate was concentrated to give a residue, which was then purified by silica gel column chromatography (Fuji Silysia NH, eluent; ethyl acetate). Fractions containing a target compound were concentrated to provide a crude product of 4-(pyrrolidin-1-ylmethyl)piperidine-1-carboxylic acid [4-(4-amino-2-fluorophenoxy)pyridin-2-yl]amide (270 mg) as white foam.

4-(Pyrrolidin-1-ylmethyl)piperidine-1-carboxylic acid [4-(4-amino-2-fluorophenoxy)pyridin-2-yl]amide (50 mg) was dissolved in N,N-dimethylformamide (1.5 ml) under a nitrogen atmosphere, and then 0.25 M phenylacetyl isocyanate in hexane (1.45 ml) was added, followed by stirring for 64.5 hrs. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml) and brine (50 ml) in this order, and dried over anhydrous sodium sulfate. The solvent was evaporated to give a residue, which was then purified by silica gel column chromatography (Fuji Silysia NH, eluent; ethyl acetate). Fractions containing the target compound were concentrated to give a residue, which was then suspended in diethyl ether (3 ml) and hexane (3 ml). The solid was filtered off, and dried under aeration to provide the titled compound (49.6 mg) as white powder.

$^1$H-NMR Spectrum (CDCl$_3$) δ (ppm): 1.10-1.35 (2H, m), 1.55-1.75 (1H, m), 1.77 (4H, m), 1.84 (2H, m), 2.32 (2H, d, J=7.2 Hz), 2.47 (4H, m), 2.86 (2H, m), 3.75 (2H, s), 4.06 (2H, m), 6.51 (1H, dd, J=2.4, 5.6 Hz), 7.07-7.20 (2H, m), 7.20-7.50 (6H, m), 7.57-7.68 (2H, m), 7.94 (1H, brs), 8.03 (1H, d, J=5.6 Hz), 10.58 (1H, brs). ESI-MS (m/z): 575[M+H]$^+$.

Example 371

4-(Pyrrolidin-1-ylmethyl)piperidine-1-carboxylic acid {4-[4-(3-phenylacetylureido)phenoxy]pyridin-2-yl}amide 4-(4-Nitrophenoxy)pyridin-2-ylamine (160 mg) was dissolved in tetrahydrofuran (7 ml) under a nitrogen atmosphere, and then triethylamine (0.289 ml) and phenyl chloroformate (0.260 ml) were added thereto while cooling in an ice water bath, followed by warming to room temperature and stirring for 1 hr. The reaction mixture was partitioned between ethyl acetate (200 ml) and a saturated aqueous solution of sodium hydrogencarbonate (50 ml). The organic layer was washed with a saturated aqueous solution of sodium hydrogencarbonate (50 ml), water (50 ml) and brine (50 ml) in this order, and dried over anhydrous sodium sulfate. The solvent was evaporated to give a residue, and N,N-dimethylformamide (8 ml) was added thereto. And then 4-(pyrrolidin-1-ylmethyl)piperidine dihydrochloride (668 mg) and triethylamine (0.772 ml) were added thereto, followed by stirring for 4 hrs. The reaction mixture was partitioned between ethyl acetate (100 ml) and a saturated aqueous solution of ammonium chloride (50 ml). The organic layer was washed with a saturated aqueous solution of ammonium chloride (50 ml), water (50 ml) and brine (50 ml) in this order, and dried over anhydrous sodium sulfate. The solvent was evaporated to give a residue, which was then purified by silica gel column chromatography (Fuji Silysia NH, eluent; heptane:ethyl acetate=1:1, then ethyl acetate). Fractions containing a target compound were concentrated to provide a crude product of 4-(pyrrolidin-1-ylmethyl)piperidine-1-carboxylic acid [4-(4-nitrophenoxy)pyridin-2-yl]amide (295 mg) as pale yellow oil.

4-(Pyrrolidin-1-ylmethyl)piperidine-1-carboxylic acid [4-(4-nitrophenoxy)pyridin-2-yl]amide (295 mg) was dissolved in tetrahydrofuran (7 ml) and methanol (7 ml) under a nitrogen atmosphere, and then 10% palladium carbon (147 mg) was added, followed by stirring under a hydrogen atmosphere for 10 hrs. The reaction mixture was filtered to remove the catalyst, and the catalyst was washed with methanol. The filtrate was concentrated to give a residue, which was then purified by silica gel column chromatography (Fuji Silysia NH, eluent; ethyl acetate). Fractions containing a target compound were concentrated to provide 4-(pyrrolidin-1-ylmethyl)piperidine-1-carboxylic acid [4-(4-aminophenoxy)pyridin-2-yl]amide (233.7 mg) as white foam.

4-(Pyrrolidin-1-ylmethyl)piperidine-1-carboxylic acid [4-(4-amino-2-fluorophenoxy)pyridin-2-yl]amide (50 mg) was dissolved in N,N-dimethylformamide (1.5 ml) under a nitrogen atmosphere, and then 0.25 M 2-phenylacetyl isocyanate in hexane (1.45 ml) was added, followed by stirring for 64.5 hrs. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml) and brine (50 ml) in this order, and dried over anhydrous sodium sulfate. The solvent was evaporated to give a residue, which was then purified by silica gel column chromatography (Fuji Silysia NH, eluent; ethyl acetate). Fractions containing the target compound were concentrated to give a residue, which was then suspended in diethyl ether (3 ml) and hexane (3 ml). The solid was filtered off, and dried under aeration to provide the titled compound (49.1 mg) as white powder.

$^1$H-NMR Spectrum (CDCl$_3$) δ (ppm): 1.08-1.33 (2H, m), 1.55-1.73 (1H, m), 1.77 (4H, m), 1.84 (2H, m), 2.31 (2H, d, J=7.2 Hz), 2.46 (4H, m), 2.86 (2H, m), 3.75 (2H, s), 4.06 (2H, m), 6.49 (1H, dd, J=2.4, 6.0 Hz), 7.00-7.10 (2H, m), 7.16-7.48 (6H, m), 7.52 (2H, m), 7.62 (1H, d, J=2.4 Hz), 7.99 (1H, brs), 8.02 (1H, d, J=6.0 Hz), 10.49 (1H, brs). ESI-MS (m/z):557 [M+H]$^+$.

Example 372

1-[1-(2-Dimethylaminoethyl)piperidin-4-yl]-3-{6-[2-fluoro-4-(3-phenylacetylthioureido)phenoxy]pyrimidin-4-yl}-1-methylurea To a solution of 3-[6-(4-amino-2-fluorophenoxy)pyrimidin-4-yl]-1-[1-(2-dimethylaminoethyl)piperidin-4-yl]-1-methylurea (110 mg) in ethanol (2.0 ml) was added (1S)-(+)-10-camphorsulfonic acid (101 mg), followed by stirring at room temperature for 15 min. A solution of 2-phenylacetyl isothiocyanate in toluene (0.25 M, 3.06 ml) was added to the reaction mixture, followed by stirring at room temperature for 2 hrs. The reaction mixture was partitioned between ethyl acetate (30 ml) and a saturated aqueous solution of sodium hydrogencarbonate (10 ml). The organic layer was washed with brine, and dried over anhydrous sodium sulfate. The organic layer was concentrated to give a residue, which was then purified by silica gel column chromatography (FUJI Silysia NH, eluent; ethyl acetate, ethyl acetate:methanol=20: 1, then 10:1). Fractions containing a target compound were concentrated to give a solid, which was suspended in diethyl ether:hexane=1:1. The solid was filtered off, and washed with diethyl ether to provide the titled compound (25.3 mg, 16.3%) as pale yellow powder.

$^1$H-NMR Spectrum (CDCl$_3$) δ (ppm): 1.64-1.90 (4H, m), 2.15 (2H, m), 2.30 (6H, s), 2.52 (4H, m), 2.92 (3H, s), 3.05 (2H, m), 3.74 (2H, s), 4.19 (1H, m), 7.19-7.46 (8H, m), 7.68 (1H, s), 7.86 (1H, dd, J=2.0, 11.6 Hz), 8.34 (1H, s), 8.51 (1H, brs), 12.43 (1H, s). ESI-MS (m/z): 609 [M+H]$^+$.

Example 373

4-(3-Dimethylaminoazetidin-1-yl)piperidine-1-carboxylic acid {4-[2-fluoro-4-(3-phenylacetylthioureido)phenoxy]pyridin-2-yl}amide To a solution of 4-(3-dimethylaminoazetidin-1-yl)piperidine-1-carboxylic acid [4-(4-amino-2-fluorophenoxy)pyridin-2-yl]amide (156 mg) in ethanol (5.0 ml) was added (1S)-(+)-10-camphorsulfonic acid (152 mg), followed by stirring at room temperature for 15 min. A solution of 2-phenylacetyl isothiocyanate in toluene (0.25 M, 4.37 ml) was added to the reaction mixture, followed by stirring at room temperature for 2 hrs. Ethyl acetate (50 ml) and a saturated aqueous solution of sodium hydrogencarbonate (20 ml) were added to the reaction mixture, and the organic layer was separated. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing a crude product were concentrated to give a residue, to which diethyl ether (5 ml) and hexane (5 ml) were added to give a precipitate. The precipitate was suspended in the solvent. Then the precipitate was filtered off, washed with hexane, and dried under aeration to provide the titled compound (56.6 mg, 25.7%) as pale yellow powder.

$^1$H-NMR Spectrum (CDCl$_3$) δ (ppm): 1.25-1.35 (4H, m), 1.72 (2H, m), 2.13 (6H, s), 2.27 (1H, m), 2.85 (3H, m), 3.05 (2H, m), 3.74 (2H, s), 3.88 (2H, m), 6.53 (1H, dd, J=2.4, 5.6 Hz), 7.18 (1H, m), 7.24 (1H, m), 7.30-7.46 (6H, m), 7.62 (1H, d, J=2.4 Hz), 7.89 (1H, dd, J=2.4, 11.6 Hz), 8.05 (1H, d, J=5.6 Hz), 8.51 (1H, s), 12.43 (1H, s). ESI-MS (m/z): 606 [M+H]$^+$, 628 [M+Na]$^+$.

Production Example 373-1

4-(3-Dimethylaminoazetidin-1-yl)piperidine-1-carboxylic acid [4-(2-fluoro-4-nitrophenoxy)pyridin-2-yl]amide To a solution of 4-(2-fluoro-4-nitrophenoxy)pyridin-2-ylamine (140 mg) in tetrahydrofuran (7.0 ml) were added triethylamine (0.172 ml) and phenyl chloroformate (0.141 ml) in this order at room temperature, followed by stirring at room temperature for 30 min. The reaction mixture was concentrated to give a residue. To the residue were added N,N-dimethylformamide (5.0 ml), triethylamine (0.940 ml), N,N-Dimethyl-N-[1-(piperidin-4-yl)azetidin-3-yl]amine trihydrochloride (658 mg) and water (0.050 ml), followed by stirring at room temperature for 2 days. An 1N aqueous solution of sodium hydroxide (30 ml) was added thereto, followed by stirring at room temperature for 5 hrs. The reaction mixture was extracted with ethyl acetate (100 ml). The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing the target compound were concentrated to provide the titled compound (258 mg, 100%) as a pale yellow oil.

$^1$H-NMR Spectrum (CDCl$_3$) δ (ppm): 1.25-1.35 (4H, m), 1.73 (2H, m), 2.13 (6H, s), 2.27 (1H, m), 2.83-2.89 (3H, m), 3.04 (2H, m), 3.87 (2H, m), 6.64 (1H, dd, J=2.4, 5.6 Hz), 7.30 (1H, m), 7.43 (1H, brs), 7.69 (1H, d, J=2.4 Hz), 8.08-8.16 (3H, m). ESI-MS (m/z): 459 [M+H]$^+$, 481 [M+Na]$^+$.

Production Example 373-2

4-(3-Dimethylaminoazetidin-1-yl)piperidine-1-carboxylic acid [4-(4-amino-2-fluorophenoxy)pyridin-2-yl]amide To a solution of 4-(3-dimethylaminoazetidin-1-yl)piperidine-1-carboxylic acid [4-(2-fluoro-4-nitrophenoxy)pyridin-2-yl]amide (258 mg) in tetrahydrofuran (50 ml) was added 20% palladium hydroxide carbon (198 mg), followed by stirring under a hydrogen atmosphere at room temperature for 12 hrs. The reaction mixture was filtered to remove the catalyst, and the catalyst was washed with tetrahydrofuran:methanol=1:1. The filtrate was concentrated to provide the titled compound (236 mg, 97.8%) as a yellow amorphous substance.

ESI-MS (m/z): 429 [M+H]$^+$, 451 [M+Na]$^+$.

Example 374

4-(1-Methylazetidin-3-yl)piperazine-1-carboxylic acid {4-[4-(3-phenylacetylthioureido)phenoxy]pyridin-2-yl}amide To a solution of 4-(1-methylazetidin-3-yl)piperazine-1-carboxylic acid [4-(4-aminophenoxy)pyridin-2-yl]amide (130 mg) in ethanol (6.0 ml)-tetrahydrofuran (6.0 ml) was added (1S)-(+)-10-camphorsulfonic acid (150 mg), followed by stirring at room temperature for 15 min. A solution of 2-phenylacetyl isothiocyanate in toluene (0.25 M, 4.08 ml) was added to the reaction mixture, followed by stirring at room temperature for 2 hrs. Ethyl acetate (50 ml) and a saturated aqueous solution of sodium hydrogencarbonate (20 ml) were added to the reaction mixture, and the organic layer was separated. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing the titled compound were concentrated to give a residue, to which diethyl ether (5 ml) and hexane (10 ml) were added to give a precipitate. The precipitate was suspended in the solvent. Then the precipitate was filtered off, washed with hexane, and dried under aeration to provide the titled compound (44.3 mg, 23.3%) as pale yellow powder.

$^1$H-NMR Spectrum (CDCl$_3$) δ (ppm): 2.32-2.38 (7H, m), 2.93 (3H, m), 3.50 (6H, m), 3.75 (2H, s), 6.55 (1H, dd, J=2.4, 5.6 Hz), 7.12 (2H, d, J=8.8 Hz), 7.23-7.46 (7H, m), 7.65-7.71 (3H, m), 8.06 (1H, d, J=5.6 Hz), 12.32 (1H, s). ESI-MS (m/z): 560 [M+H]$^+$.

Example 375

4-(3-Dimethylaminoazetidin-1-yl)piperidine-1-carboxylic acid {4-[2-fluoro-4-(3-phenylacetylureido)phenoxy]pyridin-2-yl}amide To a solution of 4-(3-dimethylaminoazetidin-1-yl)piperidine-1-carboxylic acid [4-(4-amino-2-fluorophenoxy)pyridin-2-yl]amide (78 mg) in tetrahydrofuran (6.0 ml) was added a solution of 2-phenylacetyl isocyanate in hexane (0.25 M, 1.82 ml), followed by stirring at room temperature for 11 hrs. The reaction mixture was partitioned between ethyl acetate and a saturated aqueous solution of sodium hydrogencarbonate. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate:methanol=100:7). Fractions containing a target compound were concentrated to give a residue, to which diethyl ether (2 ml) and hexane (2 ml) were added to give a precipitate. The precipitate was suspended in the solvent. Then the precipitate was filtered off, washed with diethyl ether, and dried under aeration to provide the titled compound (34.9 mg, 33%) as pale yellow powder.

$^1$H-NMR Spectrum (CDCl$_3$) δ (ppm): 1.29 (4H, m), 1.72 (2H, m), 2.12 (6H, s), 2.26 (1H, m), 2.85 (3H, m), 3.04 (2H, m), 3.75 (2H, s), 3.87 (2H, m), 6.51 (1H, dd, J=2.4, 6.0 Hz), 7.10-7.17 (2H, m), 7.25 (1H, brs), 7.30 (2H, m), 7.35-7.44 (3H, m), 7.59 (1H, d, J=2.4 Hz), 7.62 (1H, dd, J=2.0, 12.0 Hz), 7.89 (1H, m), 8.03 (1H, d, J=6.0 Hz), 10.58 (1H, s). ESI-MS (m/z): 590 [M+H]$^+$, 612 [M+Na]$^+$.

Example 376

4-(1-Methylazetidin-3-yl)piperazine-1-carboxylic acid [4-(4-{3-[2-(4-fluorophenyl)acetyl]ureido}phenoxy)pyridin-2-yl]amide To a solution of 4-(1-methylazetidin-3-yl)piperazine-1-carboxylic acid [4-(4-aminophenoxy)pyridin-2-yl]amide (100 mg) in tetrahydrofuran (5.0 ml) was added a solution of 2-(4-fluorophenyl)acetyl isocyanate in ethyl acetate (0.25 M, 2.61 ml) at room temperature, followed by stirring at room temperature for 4.5 hrs. The reaction mixture was partitioned between ethyl acetate and a saturated aqueous solution of sodium hydrogencarbonate. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate:methanol=100:7). Fractions containing a target compound were concentrated to give a residue, to which diethyl ether was added to give a precipitate. The precipitate was suspended in the solvent. Then the precipitate was filtered off, washed with diethyl ether, and dried under aeration to provide the titled compound (70.4 mg, 48.0%) as pale yellow powder.

$^1$H-NMR Spectrum (CDCl$_3$) δ (ppm): 2.32 (4H, m), 2.36 (3H, s), 2.93 (3H, m), 3.50 (6H, m), 3.72 (2H, s), 6.52 (1H, dd, J=2.0, 5.6 Hz), 7.05-7.11 (4H, m), 7.26-7.31 (3H, m), 7.53 (2H, d, J=8.4 Hz), 7.59 (1H, m), 8.03 (1H, d, J=5.6 Hz), 8.58 (1H, m), 10.50 (1H, s). ESI-MS (m/z): 562 [M+H]$^+$.

Example 377

4-(1-Methylazetidin-3-yl)piperazine-1-carboxylic acid {4-[2-fluoro-4-(3-phenylacetylureido)phenoxy]pyridin-2-yl}amide To a solution of 4-(1-methylazetidin-3-yl)piperazine-1-carboxylic acid [4-(4-amino-2-fluorophenoxy)pyridin-2-yl]amide (37 mg) in tetrahydrofuran (5.0 ml) was added a solution of 2-phenylacetyl isocyanate in hexane (0.25 M, 0.849 ml), followed by stirring at room temperature for 11 hrs.

A solution of 2-phenylacetyl isocyanate in hexane (0.25 M, 0.300 ml) and tetrahydrofuran (10 ml) were added to the reaction mixture, followed by stirring at room temperature for 3 hrs. The reaction mixture was partitioned between ethyl acetate and a saturated aqueous solution of sodium hydrogencarbonate. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate:methanol=10:1). Fractions containing a target compound were concentrated to give a residue, to which diethyl ether (2 ml) and hexane (2 ml) were added to give a precipitate. The precipitate was suspended in the solvent. Then the precipitate was filtered off, washed with diethyl ether, and dried under aeration to provide the titled compound (11.9 mg, 23%) as pale yellow powder.

$^1$H-NMR Spectrum (CDCl$_3$) δ (ppm): 2.32 (4H, m), 2.40 (3H, s), 2.98 (3H, m), 3.46-3.52 (6H, m), 3.76 (2H, s), 6.52 (1H, dd, J=2.0, 5.6 Hz), 7.10-7.14 (2H, m), 7.26-7.31 (3H, m), 7.35-7.44 (3H, m), 7.59 (1H, d, J=2.0 Hz), 7.63 (1H, dd, J=2.0, 12.0 Hz), 7.88 (1H, brs), 8.03 (1H, d, J=5.6 Hz), 10.58 (1H, s). ESI-MS (m/z): 562 [M+H]$^+$.

Production Example 377-1

4-(1-Methylazetidin-3-yl)piperazine-1-carboxylic acid [4-(2-fluoro-4-nitrophenoxy)pyridin-2-yl]amide To a solution of 4-(2-fluoro-4-nitrophenoxy)pyridin-2-ylamine (70.0 mg) in tetrahydrofuran (3.5 ml) were added triethylamine (0.0862 ml) and phenyl chloroformate (0.0705 ml) in this order at room temperature, followed by stirring at room temperature for 30 min. The reaction mixture was concentrated to give a residue, to which were added N,N-dimethylformamide (2.5 ml), triethylamine (0.470 ml), 1-(1-methylazetidin-3-yl)piperazine trihydrochloride (329 mg) and water (0.025 ml), followed by stirring at room temperature for 2 days. An 1N aqueous solution of sodium hydroxide (30 ml) was added thereto, followed by stirring at room temperature for 5 hrs. The reaction mixture was extracted with ethyl acetate (100 ml). The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing the target compound were concentrated to provide the titled compound (121 mg, 92.6%) as a pale yellow oil.

$^1$H-NMR Spectrum (CDCl$_3$) δ (ppm): 2.32-2.37 (7H, m), 2.89-3.00 (3H, m), 3.48-3.52 (6H, m), 6.64 (1H, dd, J=2.4, 6.0 Hz), 7.28-7.38 (2H, m), 7.70 (1H, d, J=2.4 Hz), 8.08-8.15 (3H, m). ESI-MS (m/z): 431 [M+H]$^+$, 453 [M+Na]$^+$.

Production Example 377-2

4-(1-Methylazetidin-3-yl)piperazine-1-carboxylic acid [4-(4-amino-2-fluorophenoxy)pyridin-2-yl]amide To a solution of 4-(1-methyl-azetidin-3-yl)piperazine-1-carboxylic acid [4-(2-fluoro-4-nitrophenoxy)pyridin-2-yl]amide (121 mg) in tetrahydrofuran (50 ml) was added 20% palladium hydroxide carbon (91.3 mg), followed by stirring under a hydrogen atmosphere at room temperature for 12 hrs. The reaction mixture was filtered to remove the catalyst, and the catalyst was washed with tetrahydrofuran:methanol=1:1. The filtrate was concentrated to provide the titled compound (113 mg, 100%) as a yellow amorphous substance.

ESI-MS (m/z): 401 [M+H]$^+$, 423 [M+Na]$^+$.

Example 378

4-(1-Methylazetidin-3-yl)piperazine-1-carboxylic acid {4-[4-(3-phenylacetylureido)phenoxy]pyridin-2-yl}amide To a solution of 4-(1-methylazetidin-3-yl)piperazine-1-carboxylic acid [4-(4-aminophenoxy)pyridin-2-yl]amide (100 mg) in tetrahydrofuran (5.0 ml) was added a solution of 2-phenylacetyl isocyanate in hexane (0.25 M, 2.61 ml), followed by stirring at room temperature for 11 hrs.

A solution of 2-phenylacetyl isocyanate in hexane (0.25 M, 1.00 ml) was added to the reaction mixture, followed by stirring at room temperature for 3 hrs. The reaction mixture was partitioned between ethyl acetate and a saturated aqueous solution of sodium hydrogencarbonate. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate:methanol=10:1). Fractions containing a target compound were concentrated to give a residue, to which diethyl ether (10 ml) was added to give a precipitate. The precipitate was suspended in the solvent. Then the precipitate was filtered off, washed with diethyl ether, and dried under aeration to provide the titled compound (62.3 mg, 43.9%) as pale yellow powder.

$^1$H-NMR Spectrum (CDCl$_3$) δ (ppm): 2.32 (4H, m), 2.37 (3H, s), 2.94 (3H, m), 3.50 (6H, m), 3.75 (2H, s), 6.52 (1H, dd, J=2.0, 6.0 Hz), 7.06 (2H, d, J=8.8 Hz), 7.22 (1H, brs), 7.31 (2H, d, J=8.8 Hz), 7.37-7.44 (3H, m), 7.53 (2H, d, J=8.8 Hz), 7.60 (1H, d, J=2.0 Hz), 7.92 (1H, brs), 8.02 (1H, d, J=6.0 Hz), 10.49 (1H, s). ESI-MS (m/z): 544 [M+H]$^+$.

Example 379

1-[1-(2-Dimethylaminoethyl)piperidin-4-yl]-1-methyl-3-{4-[4-(3-phenylacetylthioureido)phenoxy]pyridin-2-yl}urea To a solution of 3-[4-(4-aminophenoxy)pyridin-2-yl]-1-[1-(2-dimethylaminoethyl)piperidin-4-yl]-1-methylurea (96 mg) in ethanol (5.0 ml) was added (1S)-(+)-10-camphorsulfonic acid (103 mg), followed by stirring at room temperature for 15 min. A solution of 2-phenylacetyl isothiocyanate in toluene (0.25 M, 2.80 ml) was added to the reaction mixture, followed by stirring at room temperature for 4 hrs. Ethyl acetate (50 ml) and a saturated aqueous solution of sodium hydrogencarbonate (20 ml) were added to the reaction mixture, and the organic layer was separated. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing a target compound were concentrated to give a residue, to which diethyl ether (5 ml) and hexane (25 ml) were added to give a precipitate. The precipitate was suspended in the solvent. Then the precipitate was filtered off, washed with diethyl ether, and dried under aeration to provide the titled compound (57.4 mg, 42%) as white powder.

$^1$H-NMR Spectrum (CDCl$_3$) δ (ppm): 1.64 (2H, m), 1.78 (2H, m), 2.11 (2H, m), 2.26 (6H, s), 2.46 (4H, m), 2.88 (3H, s), 3.01 (2H, m), 3.74 (2H, s), 4.17 (1H, m), 6.54 (1H, dd, J=2.0, 6.0 Hz), 7.11 (2H, d, J=8.8 Hz), 7.17 (1H, m), 7.31 (2H, d, J=8.8 Hz), 7.36-7.45 (3H, m), 7.69 (3H, m), 8.05 (1H, d, J=6.0 Hz), 8.52 (1H, brs), 12.30 (1H, s). ESI-MS (m/z): 590 [M+H]$^+$.

Example 380

1-[1-(2-Dimethylaminoethyl)piperidin-4-yl]-1-methyl-3-{4-[4-(3-phenylacetylureido)phenoxy]pyridin-2-yl}urea To a solution of 3-[4-(4-aminophenoxy)pyridin-2-yl]-1-[1-(2-dimethylaminoethyl)piperidin-4-yl]-1-methylurea (96 mg) in tetrahydrofuran (10 ml) was added a solution of 2-phenylacetyl isocyanate in hexane (0.25 M, 2.33 ml), followed by stirring at room temperature for 2.5 hrs. A solution of 2-phenylacetyl isocyanate in hexane (0.25 M, 0.800 ml) was added to the reaction mixture, followed by stirring at room temperature for 30 min. The reaction mixture was partitioned between ethyl acetate and a saturated aqueous solution of sodium hydrogencarbonate. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate:methanol=100:7). Fractions containing a target compound were concentrated to provide the titled compound (64.5 mg, 48%) as pale yellow powder.

$^1$H-NMR Spectrum (CDCl$_3$) δ (ppm): 1.62-1.82 (4H, m), 2.10 (2H, m), 2.25 (6H, s), 2.45 (4H, m), 2.87 (3H, s), 3.00 (2H, m), 3.75 (2H, s), 4.16 (1H, m), 6.50 (1H, dd, J=2.0, 5.6 Hz), 7.06 (2H, d, J=8.8 Hz), 7.17 (1H, s), 7.30-7.43 (5H, m), 7.53 (2H, d, J=8.8 Hz), 7.66 (1H, d, J=2.0 Hz), 8.03 (1H, d, J=5.6 Hz), 8.21 (1H, brs), 10.51 (1H, s). ESI-MS (m/z): 574 [M+H]$^+$.

Example 381

4-(1-Methylazetidin-3-yl)piperazine-1-carboxylic acid {4-[2-fluoro-4-(3-phenylacetylthioureido)phenoxy]pyridin-2-yl}amide To a solution of 4-(1-methylazetidin-3-yl)piperazine-1-carboxylic acid [4-(4-amino-2-fluorophenoxy)pyridin-2-yl]amide (76 mg) in ethanol (2.0 ml) was added (1S)-(+)-10-camphorsulfonic acid (83.9 mg), followed by stirring at room temperature for 15 min. A solution of 2-phenylacetyl isothiocyanate in toluene (0.25 M, 2.28 ml) was added to the reaction mixture, followed by stirring at room temperature for 2 hrs. Ethyl acetate (50 ml) and a saturated aqueous solution of sodium hydrogencarbonate (20 ml) were added to the reaction mixture, and the organic layer was separated. The aqueous layer was extracted with ethyl acetate. The combined organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=20:1). Fractions containing a target compound were concentrated to give crystals, which were suspended in diethyl ether (5 ml). Then the crystals were filtered off, washed with hexane, and dried under aeration to provide the titled compound (32.1 mg, 29%) as colorless crystals.

$^1$H-NMR Spectrum (CDCl$_3$) δ (ppm): 2.33 (4H, m), 2.37 (3H, s), 2.94 (3H, m), 3.45-3.52 (6H, m), 3.75 (2H, s), 6.54 (1H, dd, J=2.4, 5.6 Hz), 7.18 (1H, m), 7.22 (1H, m), 7.30-7.46 (6H, m), 7.63 (1H, d, J=2.4 Hz), 7.89 (1H, dd, J=2.4, 12.0 Hz), 8.05 (1H, d, J=5.6 Hz), 8.50 (1H, brs), 12.44 (1H, s). ESI-MS (m/z): 578 [M+H]$^+$.

Example 382

2-{[4-(Dimethylaminomethyl)piperidin-1-yl]carbonylamino}-4-{4-[3-(2-phenylacetyl)thioureido]phenoxy}pyridine To a solution of 4-(4-aminophenoxy)-2-{[4-(dimethylaminomethyl)piperidin-1-yl]carbonylamino}pyridine (105.6 mg) and (+)-10-camphorsulfonic acid (62 mg) in ethanol (2.5 ml) was added a solution of 2-phenylacetyl isothiocyanate in toluene (0.25 M, 2.5 ml) at room temperature, followed by stirring for 1 hour. The reaction mixture was partitioned between ethyl acetate and a saturated aqueous solution of sodium hydrogencarbonate. The organic layer was washed with a saturated aqueous solution of sodium hydrogencarbonate and brine in this order, dried over anhydrous sodium sulfate. The solvent was evaporated to give a residue, which was then purified by silica gel column chromatography (Fuji Silysia NH, eluent; ethyl acetate:heptane=1:1 to 4:1) to provide the titled compound (70.2 mg, 46%) as white powder.

$^1$H-NMR Spectrum (CDCl$_3$) δ (ppm): 1.10-1.25 (2H, m), 1.69 (1H, m), 1.75-1.90 (2H, m), 2.10-2.20 (2H, m), 2.23 (6H, s), 2.80-2.95 (2H, m), 3.74 (2H, s), 4.00-4.15 (2H, m), 6.53 (1H, d, J=2.4, 5.6 Hz), 7.08-7.13 (2H, m), 7.20-7.50 (6H, m), 7.65 (1H, d, J=2.4 Hz), 7.67-7.71 (2H, m), 8.04 (1H, d, J=5.6 Hz), 8.46 (1H, brs), 12.30 (1H, brs). ESI-MS (m/z): 547 [M+H]$^+$.

Example 383

4-(1-Methylazetidin-3-yl)piperazine-1-carboxylic acid [4-(2-fluoro-4-{3-[2-(4-fluorophenyl)acetyl]ureido}phenoxy)pyridin-2-yl]amide To a solution of 4-(1-methylazetidin-3-yl)piperazine-1-carboxylic acid [4-(4-amino-2-fluorophenoxy)pyridin-2-yl]amide (40.0 mg) in tetrahydrofuran (15 ml) was added a solution of 2-(4-fluorophenyl)acetyl isocyanate in ethyl acetate (0.25 M, 1.60 ml), followed by stirring at room temperature for 1 hr. To the reaction mixture was added a saturated aqueous solution of sodium hydrogencarbonate, followed by stirring at room temperature for 15 min. The organic layer was separated, and dried over anhydrous sodium sulfate. The organic layer was concentrated to give a residue, which was then purified by silica gel column chromatography (FUJI Silysia NH, eluent; ethyl acetate, ethyl acetate:methanol=20:1, then 10:1). Fractions containing a target compound were concentrated to give a solid, to which diethyl ether (1 ml) and hexane (1 ml) were added to suspend. The solid was filtered off, washed with diethyl ether, and dried under aeration to provide the titled compound (18.5 mg, 31.9%) as pale yellow powder.

$^1$H-NMR Spectrum (CDCl$_3$) δ (ppm): 2.32 (4H, m), 2.41 (3H, s), 2.98 (3H, m), 3.45-3.51 (4H, m), 3.58 (2H, m), 3.73 (2H, s), 6.55 (1H, dd, J=2.0, 5.6 Hz), 7.07-7.17 (4H, m), 7.26-7.31 (3H, m), 7.58-7.66 (2H, m), 8.05 (1H, d, J=5.6 Hz), 8.56 (1H, brs), 10.61 (1H, s). ESI-MS (m/z): 580 [M+H]$^+$.

Example 384

4-(Azetidin-1-ylmethyl)piperidine-1-carboxylic acid {4-[2-fluoro-4-(3-phenylacetylureido)phenoxy]pyridin-2-yl}amide 4-(Azetidin-1-ylmethyl)piperidine-1-carboxylic acid [4-(2-fluoro-4-nitrophenoxy)pyridin-2-yl]amide (33 mg) was dissolved in tetrahydrofuran (1 ml) and methanol (1 ml), and then 10% palladium carbon (17 mg) was added thereto, followed by stirring under a hydrogen atmosphere for 5 hrs. The reaction mixture was filtered to remove the catalyst, and the catalyst was washed with methanol. The filtrate was concentrated under reduced pressure to give a crude product of 4-(azetidin-1-ylmethyl)piperidine-1-carboxylic acid [4-(4-amino-2-fluorophenoxy)pyridin-2-yl]amide (30 mg) as a pale yellow oil.

To a solution of 4-(azetidin-1-ylmethyl)piperidine-1-carboxylic acid [4-(4-amino-2-fluorophenoxy)pyridin-2-yl]amide (30 mg) in N,N-dimethylformamide (1 ml) was added a solution of 0.25 M 2-phenylacetyl isocyanate in hexane (0.901 ml) under a nitrogen atmosphere, followed by stirring for 1 hr. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate, then ethyl acetate:methanol=9:1). Fractions containing the target compound were concentrated to give a residue, to which were added diethyl ether (1.5 ml) and hexane (3 ml) to suspend. The solid was filtered off and dried under aeration to provide the titled compound (14.0 mg) as white powder.

$^1$H-NMR Spectrum (CDCl$_3$) δ (ppm): 1.05-1.35 (2H, m), 1.51 (1H, m), 1.75 (2H, m), 2.07 (2H, m), 2.29 (2H, d, J=7.2 Hz), 2.84 (2H, m), 3.17 (4H, m), 3.75 (2H, s), 4.03 (2H, m), 6.51 (1H, dd, J=2.0, 5.6 Hz), 7.05-7.20 (2H, m), 7.20-7.50 (6H, m), 7.54-7.69 (2H, m), 7.91 (1H, brs), 8.03 (1H, d, J=5.6 Hz), 10.58 (1H, brs). ESI-MS (m/z): 561 [M+H]$^+$.

Production Example 384-1

4-(Azetidin-1-ylmethyl)piperidine-1-carboxylic acid [4-(2-fluoro-4-nitrophenoxy)pyridin-2-yl]amide 4-(2-Fluoro-4-nitrophenoxy)pyridin-2-ylamine (60 mg) was dissolved in tetrahydrofuran (3 ml) under a nitrogen atmosphere, and then triethylamine (0.101 ml) and phenyl chloroformate (0.0908 ml) were added thereto while cooling in an ice water bath, followed by warming to room temperature and stirring for 1.5 hrs. The solution was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, to which was added N,N-dimethylformamide (3 ml). 4-(Azetidin-1-ylmethyl)piperidine dihydrochloride (192 mg) and triethylamine (0.235 ml) were added thereto, followed by stirring for 8 hrs. The reaction mixture was partitioned between ethyl acetate (100 ml) and a saturated aqueous solution of ammonium chloride (50 ml). The organic layer was washed with a saturated aqueous solution of ammonium chloride (50 ml), water (50 ml), and brine (50 ml), and dried over anhydrous sodium sulfate. The solvent was evaporated to give a residue, which was then purified by silica gel column chromatography (Fuji Silysia NH, heptane:ethyl acetate=1:1, then ethyl acetate). Fractions containing the target compound were concentrated to provide the titled compound (34 mg) as a pale yellow oil.

$^1$H-NMR Spectrum (CDCl$_3$) δ (ppm): 1.05-1.48 (2H, m), 1.48-1.65 (1H, m), 1.70-1.85 (2H, m), 2.08 (2H, m), 2.30 (2H, d, J=6.8 Hz), 2.86 (2H, m), 3.19 (4H, m), 4.04 (2H, m), 6.63 (1H, dd, J=2.0, 5.6 Hz), 7.22-7.40 (1H, m), 7.49-7.58 (1H, m), 7.68-7.74 (1H, m), 8.06-8.18 (3H, m).

Example 385

4-(Azetidin-1-ylmethyl)piperidine-1-carboxylic acid {4-[4-(3-phenylacetylureido)phenoxy]pyridin-2-yl}amide 4-(Azetidin-1-ylmethyl)piperidine-1-carboxylic acid [4-(4-nitrophenoxy)pyridin-2-yl]amide (33 mg) was dissolved in tetrahydrofuran (1 ml) and methanol (1 ml), and then 10% palladium carbon (17 mg) was added thereto, followed by stirring under a hydrogen atmosphere for 5 hrs. The reaction mixture was filtered to remove the catalyst, and the catalyst was washed with methanol. The filtrate was concentrated under reduced pressure to give a crude product of 4-(azetidin-1-ylmethyl)piperidine-1-carboxylic acid [4-(4-aminophenoxy)pyridin-2-yl]amide (31 mg) as a pale yellow oil.

To a solution of 4-(azetidin-1-ylmethyl)piperidine-1-carboxylic acid [4-(4-aminophenoxy)pyridin-2-yl]amide (31 mg) in N,N-dimethylformamide (1 ml) was added a solution of 0.25 M 2-phenylacetyl isocyanate in hexane (0.982 ml) under a nitrogen atmosphere, followed by stirring for 1 hr. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate, then ethyl acetate:methanol=9:1). Fractions containing the target compound were concentrated to give a residue, which was then suspended in diethyl ether (1.5 ml) and hexane (3 ml). The solid was filtered off and dried under aeration to provide the titled compound (28.0 mg, 63.1%) as white powder.

$^1$H-NMR Spectrum (CDCl$_3$) δ (ppm): 1.08-1.38 (2H, m), 1.52 (1H, m), 1.75 (2H, m), 2.07 (2H, m), 2.29 (2H, d, J=7.2 Hz), 2.84 (2H, m), 3.18 (4H, m), 3.75 (2H, s), 4.05 (2H, m), 6.49 (1H, dd, J=2.0, 6.0 Hz), 7.00-7.10 (2H, m), 7.15-7.48

(6H, m), 7.48-7.58 (2H, m), 7.61 (1H, d, J=2.0 Hz), 7.90 (1H, brs), 8.02 (1H, d, J=6.0 Hz), 10.48 (1H, brs). ESI-MS (m/z): 543 [M+H]$^+$.

Production Example 385-1

4-(Azetidin-1-ylmethyl)piperidine-1-carboxylic acid [4-(4-nitrophenoxy)pyridin-2-yl]amide 4-(4-Nitrophenoxy)pyridin-2-ylamine (60 mg) was dissolved in tetrahydrofuran (3 ml) under a nitrogen atmosphere, and then triethylamine (0.109 ml) and phenyl chloroformate (0.0975 ml) were added thereto while cooling in an ice water bath, followed by warming to room temperature and stirring for 1.5 hrs. The solution was partitioned between ethyl acetate (200 ml) and a saturated aqueous solution of sodium hydrogencarbonate (50 ml). The organic layer was washed with a saturated aqueous solution of sodium hydrogencarbonate (50 ml), water (50 ml), brine (100 ml) in this order, and dried over anhydrous sodium sulfate. The solvent was evaporated to give a residue, to which was added N,N-dimethylformamide (3 ml). 4-(Azetidin-1-ylmethyl) piperidine dihydrochloride (207 mg) and triethylamine (0.254 ml) were added thereto, followed by stirring for 7 hrs. The reaction mixture was partitioned between ethyl acetate (100 ml) and a saturated aqueous solution of ammonium chloride (50 ml). The organic layer was washed with a saturated aqueous solution of ammonium chloride (50 ml), water (50 ml), and brine (50 ml), and dried over anhydrous sodium sulfate. The solvent was evaporated to give a residue, which was then purified by silica gel column chromatography (Fuji Silysia NH, heptane:ethyl acetate=1:1, then ethyl acetate). Fractions containing the target compound were concentrated to provide a crude product of the titled compound (70.4 mg) as a pale yellow solid.

$^1$H-NMR Spectrum (CDCl$_3$) δ (ppm): 1.08-1.29 (2H, m), 1.53 (1H, m), 1.78 (2H, m), 2.07 (2H, m), 2.30 (2H, d, J=6.8 Hz), 2.87 (2H, m), 3.18 (4H, m), 4.05 (2H, m), 6.64 (1H, dd, J=2.0, 5.6 Hz), 7.14-7.22 (2H, m), 7.29 (1H, m), 7.76 (1H, d, J=2.0 Hz), 8.15 (1H, d, J=5.6 Hz), 8.27 (2H, m).

Example 386

4-(Azetidin-1-ylmethyl)piperidine-1-carboxylic acid [4-(4-{3-[2-(4-fluorophenyl)acetyl]ureido}phenoxy)pyridin-2-yl]amide To a solution of 4-(azetidin-1-ylmethyl)piperidine-1-carboxylic acid [4-(4-aminophenoxy)pyridin-2-yl]amide (36.2 mg) in N,N-dimethylformamide (1 ml) was added a solution of 0.25 M 2-(4-fluorophenyl)acetyl isocyanate in ethyl acetate (1.14 ml) under a nitrogen atmosphere, followed by stirring for 1 hr. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate, ethyl acetate:methanol=9:1). Fractions containing the target compound were concentrated to give a residue, which was then suspended in diethyl ether (1.5 ml) and hexane (3 ml). The solid was filtered off and dried under aeration to provide the titled compound (23.4 mg, 44.0%) as white powder.

$^1$H-NMR Spectrum (CDCl$_3$) δ (ppm): 1.08-1.40 (2H, m), 1.45-1.62 (1H, m), 1.68-1.78 (2H, m), 2.10 (2H, m), 2.30 (2H, d, J=6.8 Hz), 2.89 (2H, m), 3.19 (4H, m), 3.73 (2H, s), 3.96-4.12 (2H, m), 6.51 (1H, dd, J=2.4, 6.0 Hz), 7.00-7.18 (4H, m), 7.20-7.48 (3H, m), 7.48-7.56 (2H, m), 7.61 (1H, d, J=2.4 Hz), 8.03 (1H, d, J=6.0 Hz), 8.18 (1H, brs), 10.47 (1H, brs). ESI-MS (m/z): 561 [M+H]$^+$.

Example 387

4-[2-(Azetidin-1-yl)ethyl]piperazine-1-carboxylic acid {4-[2-fluoro-4-(3-phenylacetylureido)phenoxy]pyridin-2-yl}amide To a solution of 4-[2-(azetidin-1-yl)ethyl]piperazine-1-carboxylic acid [4-(4-amino-2-fluorophenoxy)pyridin-2-yl]amide (71 mg) in N,N-dimethylformamide (2 ml) was added a solution of 0.25 M 2-phenylacetyl isocyanate in hexane (2.05 ml) under a nitrogen atmosphere, followed by stirring for 1 hr. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate, then ethyl acetate:methanol=9:1). Fractions containing the target compound were concentrated to give a residue, which was then suspended in diethyl ether (1.5 ml) and hexane (3 ml). The solid was filtered off and dried under aeration to provide the titled compound (63.0 mg, 64.0%) as white powder.

$^1$H-NMR Spectrum (CDCl$_3$) δ (ppm): 2.00-2.14 (2H, m), 2.35 (2H, m), 2.40-2.62 (6H, m), 3.21 (4H, m), 3.30-3.60 (4H, m), 3.75 (2H, s), 6.46-6.60 (1H, m), 7.00-7.20 (3H, m), 7.20-7.50 (5H, m), 7.52-7.70 (2H, m), 7.95 (1H, m), 8.03 (1H, d, J=5.6 Hz), 10.59 (1H, brs). ESI-MS (m/z): 576 [M+H]$^+$.

Production Example 387-1

(4-Benzoylpiperazin-1-yl)acetic acid ethyl ester 1-(Ethoxycarbonylmethyl)piperazine (5.1 g) was dissolved in tetrahydrofuran (300 ml) under a nitrogen atmosphere, and then triethylamine (8.25 ml) and benzoyl chloride (3.44 ml) were added thereto while cooling in an ice water bath, followed by warming to room temperature and stirring for 4 hrs. The reaction mixture was partitioned between ethyl acetate (200 ml) and a saturated aqueous solution of sodium hydrogencarbonate (100 ml). The organic layer was washed with a saturated aqueous solution of sodium hydrogencarbonate (100 ml), water (100 ml), brine (100 ml) and dried over anhydrous sodium sulfate. The solvent was evaporated to provide the titled compound (8.19 g, quant.) as a colorless oil.

$^1$H-NMR Spectrum (CDCl$_3$) δ (ppm): 1.28 (3H, t, J=7.2 Hz), 2.20-2.85 (4H, m), 3.26 (2H, m), 3.48 (2H, m), 3.85 (2H, m), 4.19 (2H, m), 7.41 (5H, m).

Production Example 387-2

1-(Azetidin-1-yl)-2-(4-benzoylpiperazin-1-yl)ethanone (4-Benzoylpiperazin-1-yl)acetic acid ethyl ester (8.19 g) was dissolved in methanol (300 ml) and water (50 ml), and then lithium hydroxide (1.34 g) was added thereto while cooling in an ice water bath, followed by stirring for 10 min. The reaction mixture was warmed to room temperature and then the mixture was stirred for 24 hrs. 1 N Hydrochloric acid (55.9 ml) was added to the reaction mixture, and the reaction mixture was concentrated under reduced pressure. Ethanol (200 ml) was added to the residue. The mixture was passed through Celite to remove the precipitated insoluble material.

The obtained filtrate was concentrated under reduced pressure to provide a crude product of (4-benzoylpiperazin-1-yl) acetic acid (8.6 g) as a white solid.

To (4-benzoylpiperazin-1-yl)acetic acid (2 g) was added N,N-dimethylformamide (80 ml) at room temperature, and then azetidine hydrochloride (1.51 g) and triethylamine (4.49 ml), 1-ethyl-3-(3-dimethylaminopropyl)carbodiimide hydrochloride (3.09 g) and 1-hydroxybenzotriazole (2.18 g) were added thereto in this order, and the mixture was stirred at room temperature for 66 hrs. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) in this order and dried over anhydrous sodium sulfate The solvent was evaporated to give a residue, which was then purified by silica gel column chromatography (Fuji Silysia NH, eluent; ethyl acetate). Fractions containing the target compound were concentrated to give a residue, which was then suspended in diethyl ether (10 ml). The solid was filtered off and dried under aeration to provide the titled compound (731.5 mg) as white powder.

$^1$H-NMR Spectrum (CDCl$_3$) δ (ppm): 2.40-2.80 (6H, m), 3.03 (2H, s), 3.47 (2H, m), 3.83 (2H, m), 4.06 (2H, m), 4.22 (2H, m), 7.30-7.50 (5H, m).

Production Example 387-3

1-[2-(Azetidin-1-yl)ethyl]-4-benzylpiperazine

A suspension of lithium aluminum hydride (405 mg) in tetrahydrofuran (10 ml) was stirred while cooling in an ice water bath under a nitrogen atmosphere. 1-(Azetidin-1-yl)-2-(4-benzoylpiperazin-1-yl)ethanone (730 mg) and tetrahydrofuran (5 ml×3) were added thereto. The reaction mixture was stirred at 60° C. for 3 hrs. The reaction mixture was then cooled to room temperature. Water (0.40 ml), 5N aqueous sodium hydroxide (0.40 ml) and water (1.2 ml) were added thereto, and the reaction mixture was stirred for 13 hrs. The reaction mixture was passed through Celite to remove the insoluble material. The insoluble material was washed with ethyl acetate (100 ml). The solvent was evaporated to provide a crude product of the titled compound (687 mg) as a pale yellow oil.

ESI-MS (m/z): 260 [M+H]$^+$.

Production Example 387-4

1-[2-(Azetidin-1-yl)ethyl]piperazine trihydrochloride

1-[2-(Azetidin-1-yl)ethyl]-4-benzylpiperazine (687 mg) was dissolved in methanol (30 ml). 20% Palladium hydroxide-carbon (372 mg) was added thereto. The mixture was stirred under a hydrogen atmosphere (0.4 MPa) for 10 hrs. The catalyst was filtered and washed with methanol. After adding 4 N hydrochloric acid-ethyl acetate (1.33 ml) to the filtrate, the excess hydrochloric acid was removed by stirring under reduced pressure. The solvent was distilled off under reduced pressure to provide the title compound (736 mg, quant.) as a brown oil.

ESI-MS (m/z): 170 [M+H]$^+$.

Production Example 387-5

4-[2-(Azetidin-1-yl)ethyl]piperazine-1-carboxylic acid [4-(2-fluoro-4-nitrophenoxy)pyridin-2-yl]amide 4-(2-Fluoro-4-nitrophenoxy)pyridin-2-ylamine (60 mg) was dissolved in tetrahydrofuran (3 ml) under a nitrogen atmosphere. Triethylamine (0.101 ml) and phenyl chloroformate (0.0908 ml) were added thereto while cooling in an ice water bath, followed by warming to room temperature and stirring for 25 min. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml), and dried over anhydrous sodium sulfate. The solvent was evaporated to give a residue, N,N-dimethylformamide (3 ml) was added thereto. Then an 1.0 M solution of 1-[2-(azetidin-1-yl) ethyl]piperazine trihydrochloride in methanol (0.819 ml) and triethylamine (0.343 ml) were added to the mixture, followed by stirring for 4 hrs. The reaction mixture was partitioned between ethyl acetate (50 ml) and a saturated aqueous solution of ammonium chloride (30 ml). The organic layer was washed with a saturated aqueous solution of ammonium chloride (30 ml), water (30 ml), and brine (30 ml), and dried over anhydrous sodium sulfate. The solvent was evaporated to give a residue, which was then purified by silica gel column chromatography (Fuji Silysia NH, ethyl acetate, then ethyl acetate:methanol=9:1). Fractions containing the target compound were concentrated to provide a crude product of the titled compound (114 mg) as a pale yellow oil.

$^1$H-NMR Spectrum (CDCl$_3$) δ (ppm): 2.00-2.15 (2H, m), 2.30-2.42 (2H, m), 2.43-2.65 (6H, m), 3.13-3.28 (4H, m), 3.40-3.56 (4H, m), 6.64 (1H, dd, J=2.4, 5.6 Hz), 7.06-7.42 (2H, m), 7.66-7.75 (1H, m), 8.04-8.20 (3H, m)

Production Example 387-6

4-[2-(Azetidin-1-yl)ethyl]piperazine-1-carboxylic acid [4-(4-amino-2-fluorophenoxy)pyridin-2-yl] amide 4-[2-(Azetidin-1-yl)ethyl]piperazine-1-carboxylic acid [4-(2-fluoro-4-nitrophenoxy)pyridin-2-yl]amide (114 mg) was dissolved in tetrahydrofuran (3 ml) and methanol (3 ml). 10% Palladium carbon (55 mg) was added, followed by stirring under a hydrogen atmosphere for 22 hrs. The reaction mixture was filtered to remove the catalyst, and the catalyst was washed with methanol. The filtrate was concentrated under reduced pressure to give a residue, which was then purified by silica gel column chromatography (Fuji Silysia NH, eluent; ethyl acetate:methanol=9:1). Fractions containing the target compound were concentrated to give a crude product of the titled compound (71 mg) as a pale yellow oil.

$^1$H-NMR Spectrum (CDCl$_3$) δ (ppm): 2.08 (2H, m), 2.35 (2H, m), 2.38-2.62 (6H, m), 3.21 (4H, m), 3.40-3.58 (4H, m), 3.74 (2H, m), 6.36-6.59 (3H, m), 6.95 (1H, m), 7.06-7.42 (1H, m), 7.50-7.65 (1H, m), 8.01 (1H, d, J=5.6 Hz).

Example 388

4-[2-(Azetidin-1-yl)ethyl]piperazine-1-carboxylic acid {4-[4-(3-phenylacetylureido)phenoxy]pyridin-2-yl}amide To a solution of 4-[2-(azetidin-1-yl) ethyl]piperazine-1-carboxylic acid [4-(4-aminophenoxy)pyridin-2-yl]amide (36.3 mg) in N,N-dimethylformamide (1 ml) was added a solution of 0.25 M 2-phenylacetyl isocyanate in hexane (1.1 ml) under a nitrogen atmosphere, followed by stirring for 1 hr. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate, then ethyl acetate: methanol=9:1). Fractions containing the target compound were concentrated to give a residue, which was then suspended in diethyl ether (3.0 ml) and hexane (1.5 ml). The solid was filtered off and dried under aeration to provide the titled compound (28.6 mg, 56.0%) as white powder.

$^1$H-NMR Spectrum (CDCl$_3$) δ (ppm): 2.00-2.14 (2H, m), 2.35 (2H, m), 2.46 (4H, m), 2.56 (2H, m), 3.21 (4H, m), 3.30-3.60 (4H, m), 3.75 (2H, s), 6.50 (1H, m), 7.06 (2H, m), 7.15-7.50 (7H, m), 7.53 (1H, m), 7.60 (1H, m), 7.90-8.10 (2H, m), 10.49 (1H, brs). ESI-MS (m/z): 558 [M+H]$^+$.

Production Example 388-1

4-[2-(Azetidin-1-yl)ethyl]piperazine-1-carboxylic acid [4-(4-nitrophenoxy)pyridin-2-yl]amide 4-(4-Nitrophenoxy)pyridin-2-ylamine (60 mg) was dissolved in tetrahydrofuran (3 ml) under a nitrogen atmosphere. Triethylamine (0.109 ml) and phenyl chloroformate (0.0975 ml) were added thereto while cooling in an ice water bath, followed by warming to room temperature and stirring for 30 min. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, to which was then added N-dimethylformamide (3 ml). And then an 1.0 M solution of 1-[2-(azetidin-1-yl)ethyl]piperazine trihydrochloride in methanol (0.884 ml) and triethylamine (0.261 ml) were added thereto, followed by stirring for 4 hrs. The reaction mixture was partitioned between ethyl acetate (50 ml) and a saturated aqueous solution of ammonium chloride (30 ml). The organic layer was washed with a saturated aqueous solution of ammonium chloride (30 ml), water (30 ml), and brine (30 ml), and dried over anhydrous sodium sulfate. The solvent was evaporated to give a residue, which was then purified by silica gel column chromatography (Fuji Silysia NH, ethyl acetate, then ethyl acetate:methanol=9:1). Fractions containing the target compound were concentrated to provide a crude product of the titled compound (122 mg) as a pale yellow solid.

$^1$H-NMR Spectrum (CDCl$_3$) δ (ppm): 1.95-2.15 (2H, m), 2.27-2.75 (8H, m), 3.05-3.30 (4H, m), 3.40-3.60 (4H, m), 6.64 (1H, dd, J=1.6, 5.6 Hz), 7.00-7.40 (3H, m), 7.75 (1H, d, J=1.6 Hz), 8.16 (1H, d, J=5.6 Hz), 8.20-8.32 (2H, m).

Production Example 388-2

4-[2-(Azetidin-1-yl)ethyl]piperazine-1-carboxylic acid [4-(4-aminophenoxy)pyridin-2-yl]amide 4-[2-(Azetidin-1-yl)ethyl]piperazine-1-carboxylic acid [4-(4-nitrophenoxy)pyridin-2-yl]amide (122 mg) was dissolved in tetrahydrofuran (3 ml) and methanol (3 ml). 10% Palladium carbon (61 mg) was added, followed by stirring under a hydrogen atmosphere for 22 hrs. The reaction mixture was filtered to remove the catalyst, and the catalyst was washed with methanol. The filtrate was concentrated under reduced pressure to give a residue, which was then purified by silica gel column chromatography (Fuji Silysia NH, eluent; ethyl acetate:methanol=9:1). Fractions containing the target compound were concentrated to give a crude product of the titled compound (70 mg) as a pale yellow oil.

$^1$H-NMR Spectrum (CDCl$_3$) δ (ppm): 2.08 (2H, m), 2.35 (2H, m), 2.40-2.62 (6H, m), 3.20 (4H, m), 3.40-3.56 (4H, m), 3.65 (2H, m), 6.48 (1H, dd, J=1.6, 5.6 Hz), 6.66-6.75 (2H, m), 6.85-6.96 (2H, m), 7.17 (1H, m), 7.57 (1H, m), 7.99 (1H, d, J=5.6 Hz).

Example 389

4-[2-(Azetidin-1-yl)ethyl]piperazine-1-carboxylic acid [4-(4-{3-[2-(4-fluorophenyl)acetyl] ureido}phenoxy)pyridin-2-yl]amide To a solution of 4-[2-(azetidin-1-yl)ethyl]piperazine-1-carboxylic acid [4-(4-aminophenoxy)pyridin-2-yl]amide (32.4 mg) in N,N-dimethylformamide (1 ml) was added a solution of 0.25 M 2-(4-fluorophenyl)acetyl isocyanate in ethyl acetate (0.98 ml) under a nitrogen atmosphere, followed by stirring for 1 hr. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate, then ethyl acetate:methanol=9:1). Fractions containing the target compound were concentrated to give a residue, which was then suspended in diethyl ether (1.5 ml) and hexane (1.5 ml). The solid was filtered off and dried under aeration to provide the titled compound (9.2 mg, 19.6%) as white powder.

$^1$H-NMR Spectrum (CDCl$_3$) δ (ppm): 2.00-2.14 (2H, m), 2.32-2.41 (2H, m), 2.42-2.52 (4H, m), 2.52-2.64 (2H, m), 3.22 (4H, m), 3.34-3.60 (4H, m), 3.72 (2H, s), 6.51 (1H, dd, J=2.0, 5.6 Hz), 6.95-7.16 (5H, m), 7.16-7.40 (2H, m), 7.45-7.57 (2H, m), 7.60 (1H, d, J=2.0 Hz), 8.02 (1H, d, J=5.6 Hz), 8.06 (1H, m), 10.45 (1H, brs). ESI-MS (m/z): 576 [M+H]$^+$.

Example 390

4-(Pyrrolidin-1-ylmethyl)piperidine-1-carboxylic acid [4-(4-{3-[2-(4-fluorophenyl)acetyl] ureido}phenoxy)pyridin-2-yl]amide To a solution of 4-(pyrrolidin-1-ylmethyl)piperidine-1-carboxylic acid [4-(4-aminophenoxy)pyridin-2-yl]amide (50 mg) in N,N-dimethylformamide (1.5 ml) was added a solution of 0.25 M 2-(4-fluorophenyl)acetyl isocyanate in ethyl acetate (1.51 ml) under a nitrogen atmosphere, followed by stirring for 17 hrs. The reaction mixture was partitioned between ethyl acetate (100 ml) and a saturated aqueous solution of sodium hydrogencarbonate (50 ml). The organic layer was washed with a saturated aqueous solution of sodium hydrogencarbonate (50 ml), water (50 ml), brine (50 ml) and dried over anhydrous sodium sulfate. The solvent was evaporated to give a residue, which was then purified by silica gel column chromatography (Fuji Silysia NH, eluent; ethyl acetate). Fractions containing the target compound were concentrated to give a residue, which was then suspended in ethyl acetate (1.5 ml) and hexane (1.5 ml). The solid was filtered off and dried under aeration to provide the titled compound (45.7 mg, 63.1%) as white powder.

$^1$H-NMR Spectrum (CDCl$_3$) δ (ppm): 1.08-1.35 (2H, m), 1.50-1.70 (1H, m), 1.77 (4H, m), 1.84 (2H, m), 2.32 (2H, m), 2.47 (4H, m), 2.86 (2H, m), 3.72 (2H, s), 4.06 (2H, m), 6.50

(1H, dd, J=1.6, 5.6 Hz), 7.04-7.20 (5H, m), 7.20-7.38 (2H, m), 7.40-7.58 (2H, m), 7.61 (1H, d, J=1.6 Hz), 8.02 (1H, d, J=5.6 Hz), 8.21 (1H, m), 10.46 (1H, brs). ESI-MS (m/z): 575 [M+H]$^+$.

Example 391

3-(6-{2-Fluoro-4-[3-(4-fluorophenyl)acetylthioureido]phenoxy}pyrimidin-4-yl)-1-methyl-1-[1-(1-methylazetidin-3-yl)piperidin-4-yl]urea To a solution of 3-[6-(4-amino-2-fluorophenoxy)pyrimidin-4-yl]-1-methyl-1-[1-(1-methylazetidin-3-yl)piperidin-4-yl]urea (68.0 mg) in ethanol (2.0 ml) was added (1S)-(+)-10-camphorsulfonic acid (70.2 mg), followed by stirring at room temperature for 10 min. A solution of 2-(4-fluorophenyl)acetyl isothiocyanate in toluene (0.25 M, 1.91 ml) was added to the reaction mixture, followed by stirring at room temperature for 30 min. The reaction mixture was partitioned between ethyl acetate (50 ml) and a saturated aqueous solution of sodium hydrogencarbonate (20 ml). The organic layer was washed with brine, and dried over anhydrous sodium sulfate. The organic layer was concentrated to give a residue, which was then purified by silica gel column chromatography (FUJI Silysia NH, eluent; ethyl acetate, then ethyl acetate:methanol=25:1). Fractions containing the target compound were concentrated to give a residue, to which were added diethyl ether (2 ml) and hexane (2 ml) to give a precipitate. The precipitate was filtered off, washed with diethyl ether, and dried under aeration to provide the titled compound (10.9 mg, 11.0%) as white powder.

$^1$H-NMR Spectrum (CDCl$_3$) δ (ppm): 1.67-1.99 (6H, m), 2.50 (3H, s), 2.84 (2H, m), 2.93 (3H, s), 3.03 (3H, m), 3.67 (2H, m), 3.72 (2H, s), 4.20 (1H, m), 7.12 (2H, m), 7.22 (1H, m), 7.26-7.30 (3H, m), 7.36 (1H, m), 7.67 (1H, s), 8.24 (1H, dd, J=2.4, 11.6 Hz), 8.34 (1H, s), 8.50 (1H, br), 12.39 (1H, s). ESI-MS (m/z): 625 [M+H]$^+$.

Example 392

4-(Azetidin-1-ylmethyl)piperidine-1-carboxylic acid [6-(2-fluoro-4-{3-[2-(4-fluorophenyl)acetyl]thioureido}phenoxy)pyrimidin-4-yl]amide 4-(Azetidin-1-ylmethyl)piperidine-1-carboxylic acid [6-(4-amino-2-fluorophenoxy)pyrimidin-4-yl]amide (111 mg) was dissolved in ethanol (3 ml) under a nitrogen atmosphere, and then (S)-(+)-10-camphorsulfonic acid (65 mg) was added thereto, followed by stirring for 5 min. A 0.25 M solution of 2-(4-fluorophenyl)acetyl isothiocyanate in toluene (1.66 ml) was added thereto, followed by stirring for 1 hr. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, then ethyl acetate). Fractions containing the target compound were concentrated under reduced pressure to give a residue, to which diethyl ether (4 ml) and hexane (4 ml) were then added to suspend. The solid was filtered off, and dried under aeration to provide the titled compound (81.5 mg) as white powder.

$^1$H-NMR Spectrum (CDCl$_3$) δ (ppm): 1.10-1.38 (2H, m), 1.40-1.75 (1H, m), 1.82 (2H, m), 2.11 (2H, m), 2.36 (2H, m), 2.91 (2H, m), 3.24 (4H, m), 3.71 (2H, s), 4.07 (2H, m), 7.12 (2H, m), 7.12-7.42 (5H, m), 7.63 (1H, s), 7.86 (1H, dd, J=2.4, 11.6 Hz), 8.33 (1H, s), 8.46 (1H, brs), 12.38 (1H, brs). ESI-MS (m/z): 596 [M+H]$^+$.

Production Example 392-1

4-(Azetidin-1-ylmethyl)piperidine-1-carboxylic acid [6-(2-fluoro-4-nitrophenoxy)pyrimidin-4-yl]amide 6-(2-Fluoro-4-nitrophenoxy)pyrimidin-4-ylamine (200 mg) was dissolved in tetrahydrofuran (8 ml) under a nitrogen atmosphere, and then triethylamine (0.335 ml) and phenyl chloroformate (0.300 ml) were added thereto while cooling in an ice water bath, followed by warming to room temperature and stirring for 30 min. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, to which was added N,N-dimethylformamide (3 ml). 4-(Azetidin-1-ylmethyl)piperidine dihydrochloride (600 mg) and triethylamine (0.781 ml) were added thereto, followed by stirring for 7 hrs. The reaction mixture was partitioned between ethyl acetate (100 ml) and a saturated aqueous solution of ammonium chloride (50 ml). The organic layer was washed with a saturated aqueous solution of ammonium chloride (50 ml), water (50 ml), and brine (50 ml) in this order, and dried over anhydrous sodium sulfate. The solvent was evaporated to give a residue, which was then purified by silica gel column chromatography (Fuji Silysia NH, heptane:ethyl acetate=1:8, then ethyl acetate). Fractions containing the target compound were concentrated to provide a crude product of the titled compound (340 mg) as a pale yellow oil.

ESI-MS (m/z): 431 [M+H]$^+$.

Production Example 392-2

4-(Azetidin-1-ylmethyl)piperidine-1-carboxylic acid [6-(4-amino-2-fluorophenoxy)pyrimidin-4-yl]amide 4-(Azetidin-1-ylmethyl)piperidine-1-carboxylic acid [6-(2-fluoro-4-nitrophenoxy)pyrimidin-4-yl]amide (340 mg) was dissolved in tetrahydrofuran (8 ml) and methanol (8 ml), and then 10% palladium carbon (170 mg) was added, followed by stirring under a hydrogen atmosphere for 13 hrs. The catalyst was filtered off and washed with methanol. The filtrate and washings were concentrated under reduced pressure to give the titled compound (221 mg) as pale yellow solid.

$^1$H-NMR Spectrum (CDCl$_3$) δ (ppm): 1.05-1.40 (2H, m), 1.45-1.70 (1H, m), 1.70-1.95 (2H, m), 2.08 (2H, m), 2.59 (2H, d, J=6.4 Hz), 2.89 (2H, m), 3.20 (4H, m), 3.60-3.85 (2H, m), 4.06 (2H, m), 6.44 (1H, m), 6.50 (1H, dd, J=2.8, 11.6 Hz), 6.97 (1H, m), 7.31 (1H, brs), 7.55 (1H, m), 8.36 (1H, m). ESI-MS (m/z): 401 [M+H]$^+$.

Example 393

4-(Azetidin-1-ylmethyl)piperidine-1-carboxylic acid {6-[2-fluoro-4-(3-phenylacetylthioureido)phenoxy]pyrimidin-4-yl}amide 4-(Azetidin-1-ylmethyl)piperidine-1-carboxylic acid [6-(4-amino-2-fluorophenoxy)pyrimidin-4-yl]amide (110 mg) was dissolved in ethanol (3 ml) under a nitrogen atmosphere, and then (S)-(+)-10-camphorsulfonic acid (64 mg) was added thereto, followed by stirring for 5 min. A 0.25 M solution of phenylacetyl isothiocyanate in toluene (1.65 ml) was added thereto, followed by stirring for 1 hr. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, then ethyl acetate). Fractions containing the target compound were concentrated under reduced pressure to give a residue, to which diethyl ether (4 ml) and hexane (4 ml) were then added to suspend. The solid was filtered off, and dried under aeration to provide the titled compound (76.1 mg) as white powder.

$^1$H-NMR Spectrum (CDCl$_3$) δ (ppm): 1.10-1.40 (2H, m), 1.59 (1H, m), 1.81 (2H, m), 2.11 (2H, m), 2.35 (2H, m), 2.90 (2H, m), 3.24 (4H, m), 3.74 (2H, s), 4.07 (2H, m), 7.10-7.50 (8H, m), 7.63 (1H, s), 7.86 (1H, dd, J=2.4, 11.2 Hz), 8.33 (1H, s), 8.44 (1H, brs), 12.42 (1H, brs). ESI-MS (m/z): 578 [M+H]$^+$.

Example 394

4-(Azetidin-1-ylmethyl)piperidine-1-carboxylic acid [4-(4-{3-[2-(4-fluorophenyl)acetyl]thioureido}phenoxy)pyridin-2-yl]amide 4-(Azetidin-1-ylmethyl)piperidine-1-carboxylic acid [4-(4-aminophenoxy)pyridin-2-yl]amide (143 mg) was dissolved in ethanol (4 ml) under a nitrogen atmosphere, and then (S)-(+)-10-camphorsulfonic acid (131 mg) was added thereto, followed by stirring for 5 min. A 0.25 M solution of 2-(4-fluorophenyl)acetyl isothiocyanate in toluene (2.25 ml) was added thereto, followed by stirring for 1 hr. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, then ethyl acetate). Fractions containing the target compound were concentrated under reduced pressure to give a residue, to which diethyl ether (4 ml) and hexane (4 ml) were then added to suspend. The solid was filtered off, and dried under aeration to provide the titled compound (74.0 mg, 34.2%) as white powder.

$^1$H-NMR Spectrum (CDCl$_3$) δ (ppm): 1.05-1.35 (2H, m), 1.40-1.70 (1H, m), 1.70-1.90 (2H, m), 2.11 (2H, m), 2.34 (2H, m), 2.85 (2H, m), 3.23 (4H, m), 3.71 (2H, s), 3.95-4.15 (2H, m), 6.53 (1H, dd, J=2.4, 6.0 Hz), 7.00-7.16 (4H, m), 7.18 (1H, m), 7.19-7.40 (2H, m), 7.55-7.75 (3H, m), 8.05 (1H, d, J=6.0 Hz), 8.50 (1H, brs), 12.26 (1H, brs). ESI-MS (m/z): 577 [M+H]$^+$.

Example 395

4-(Azetidin-1-ylmethyl)piperidine-1-carboxylic acid {4-[2-fluoro-4-(3-phenylacetylthioureido)phenoxy]pyridin-2-yl}amide 4-(Azetidin-1-ylmethyl)piperidine-1-carboxylic acid [4-(4-amino-2-fluorophenoxy)pyridin-2-yl]amide (127 mg) was dissolved in ethanol (3 ml) under a nitrogen atmosphere, and then (S)-(+)-10-camphorsulfonic acid (148 mg) was added thereto, followed by stirring for 5 min. A 0.25 M solution of phenylacetyl isothiocyanate in toluene (1.91 ml) was added thereto, followed by stirring for 12 hrs. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, ethyl acetate, then ethyl acetate:ethanol=95:5). Fractions containing the target compound were concentrated under reduced pressure to give a residue, to which diethyl ether (3 ml) and hexane (3 ml) were then added to suspend. The solid was filtered off, and dried under aeration to provide the titled compound (104.1 mg, 56.8%) as white powder.

$^1$H-NMR Spectrum (CDCl$_3$) δ (ppm): 1.08-1.45 (2H, m), 1.55 (1H, m), 1.76 (2H, m), 2.09 (2H, m), 2.32 (2H, m), 2.84 (2H, m), 3.22 (4H, m), 3.74 (2H, s), 4.04 (2H, m), 6.53 (1H, dd, J=2.4, 6.0 Hz), 7.10-7.50 (8H, m), 7.63 (1H, m), 7.89 (1H, dd, J=2.4, 11.2 Hz), 8.05 (1H, d, J=6.0 Hz), 8.52 (1H, brs), 12.44 (1H, brs). ESI-MS (m/z): 577 [M+H]$^+$.

Example 396

4-[2-(Azetidin-1-yl)ethyl]piperazine-1-carboxylic acid [6-(2-fluoro-4-{3-[2-(4-fluorophenyl)acetyl]thioureido}phenoxy)pyrimidin-4-yl]amide 4-[2-(Azetidin-1-yl)ethyl]piperazine-1-carboxylic acid [6-(4-amino-2-fluorophenoxy)pyrimidin-4-yl]amide (31 mg) was dissolved in ethanol (1 ml) under a nitrogen atmosphere, and then (S)-(+)-10-camphorsulfonic acid (47 mg) was added thereto, followed by stirring for 5 min. A 0.25 M solution of 2-(4-fluorophenyl)acetyl isothiocyanate in toluene (0.448 ml) was added thereto, followed by stirring for 15 hrs. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, ethyl acetate, then ethyl acetate:ethanol=95:5). Fractions containing the target compound were concentrated under reduced pressure to give a residue, which was then purified by LC-MS. Fractions containing the target compound were concentrated to give a residue, which was then partitioned between ethyl acetate (50 ml) and a saturated aqueous solution of sodium hydrogencarbonate (30 ml). The organic layer was washed with brine (30 ml), and dried over anhydrous sodium sulfate. The solvent was evaporated to provide the titled compound (0.9 mg) as a colorless oil.

ESI-MS (m/z): 611 [M+H]$^+$.

Production Example 396-1

4-[2-(Azetidin-1-yl)ethyl]piperazine-1-carboxylic acid [6-(2-fluoro-4-nitrophenoxy)pyrimidin-4-yl]amide 6-(2-Fluoro-4-nitrophenoxy)pyrimidin-4-ylamine (60 mg) was dissolved in tetrahydrofuran (3 ml) under a nitrogen atmosphere, and then triethylamine (0.100 ml) and phenyl chloroformate (0.0903 ml) were added thereto while cooling in an ice water bath, followed by warming to room temperature and stirring for 20 min. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, to which was added N,N-dimethylformamide (3 ml). 1-[2-(Azetidin-1-yl)ethyl]piperazine trihydrochloride (214 mg) and triethylamine (0.234 ml) were added thereto, followed by stirring for 6 hrs. The reaction mixture was partitioned between ethyl acetate (50 ml) and a saturated aqueous solution of ammonium chloride (30 ml). The organic layer was washed with a saturated aqueous solution of ammonium chloride (30 ml), water (30 ml), and brine (30 ml) in this order, and dried over anhydrous sodium sulfate. The solvent was evaporated to give a residue, which was then purified by silica gel column chromatography (Fuji Silysia NH, heptane:ethyl acetate=1:1, ethyl acetate, then ethyl acetate:methanol=9:1). Fractions containing the target compound were concentrated under reduced pressure to provide a crude product of the titled compound (110 mg) as a pale yellow oil.

ESI-MS (m/z): 446 [M+H]$^+$.

Production Example 396-2

4-[2-(Azetidin-1-yl)ethyl]piperazine-1-carboxylic acid [6-(4-amino-2-fluorophenoxy)pyrimidin-4-yl]amide 4-[2-(Azetidin-1-yl)ethyl]piperazine-1-carboxylic acid [6-(2-fluoro-4-nitrophenoxy)pyrimidin-4-yl]amide (110 mg) was dissolved in tetrahydrofuran (3 ml) and methanol (3 ml), and then 10% palladium carbon (53 mg) was added, followed by stirring under a hydrogen atmosphere for 16.5 hrs. The catalyst was filtered off and washed with methanol. The filtrate and washings were concentrated under reduced pressure to give a residue, which was then purified by silica gel column chromatography (Fuji Silysia NH, heptane: ethyl acetate: ethanol=95:5 to 90:10). Fractions containing the target compound were concentrated to provide a crude product of the titled compound (32.4 mg) as a yellow oil.

$^1$H-NMR Spectrum (CDCl$_3$) δ (ppm): 2.14 (2H, m), 2.43 (2H, m), 2.51 (4H, m), 2.55-2.80 (2H, m), 3.32 (4H, m), 3.53 (4H, m), 3.73 (2H, s), 6.45 (1H, m), 6.50 (1H, dd, J=2.4, 11.6 Hz), 6.90-7.02 (1H, m), 7.36 (1H, m), 7.55 (1H, m), 8.36 (1H, m). ESI-MS (m/z): 438 [M+Na]$^+$.

Example 397

4-[2-(Azetidin-1-yl)ethyl]piperazine-1-carboxylic acid {4-[2-fluoro-4-(3-phenylacetylthioureido)phenoxy]pyridin-2-yl}amide 4-[2-(Azetidin-1-yl)ethyl]piperazine-1-carboxylic acid [4-(4-amino-2-fluorophenoxy)pyridin-2-yl]amide (60 mg) was dissolved in ethanol (1.5 ml) under a nitrogen atmosphere, and then (S)-(+)-10-camphorsulfonic acid (101 mg) was added thereto, followed by stirring for 5 min. A 0.25 M solution of phenylacetyl isothiocyanate in toluene (0.87 ml) was added thereto, followed by stirring for 13 hrs. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, ethyl acetate, then ethyl acetate:ethanol=95:5). Fractions containing the target compound were concentrated under reduced pressure to give a residue, to which diethyl ether (2 ml) and hexane (2 ml) were then added to suspend. The solid was filtered off, and dried under aeration to provide the titled compound (37.2 mg, 43.3%) as white powder.

$^1$H-NMR Spectrum (CDCl$_3$) δ (ppm): 2.14 (2H, m), 2.41 (2H, m), 2.48 (4H, m), 2.62 (2H, m), 3.31 (4H, m), 3.50 (4H, m), 3.74 (2H, s), 6.54 (1H, dd, J=2.4, 6.0 Hz), 7.10-7.50 (8H, m), 7.62 (1H, m), 7.89 (1H, dd, J=2.4, 11.6 Hz), 8.05 (1H, d, J=6.0 Hz), 8.48 (1H, brs), 12.44 (1H, brs). ESI-MS (m/z): 592 [M+H]$^+$.

Example 398

4-[2-(Azetidin-1-yl)ethyl]piperazine-1-carboxylic acid [4-(4-{3-[2-(4-fluorophenyl)acetyl]thioureido}phenoxy)pyridin-2-yl]amide 4-[2-(Azetidin-1-yl)ethyl]piperazine-1-carboxylic acid [4-(4-aminophenoxy)pyridin-2-yl]amide (63 mg) was dissolved in ethanol (1.5 ml) under a nitrogen atmosphere, and then (S)-(+)-10-camphorsulfonic acid (111 mg) was added thereto, followed by stirring for 5 min. A 0.25 M solution of 2-(4-fluorophenyl)acetyl isothiocyanate in toluene (0.954 ml) was added thereto, followed by stirring for 13.5 hrs. The reaction mixture was partitioned between ethyl acetate (50 ml) and a saturated aqueous solution of sodium hydrogencarbonate (30 ml). The organic layer was washed with a saturated aqueous solution of sodium hydrogencarbonate (30 ml), water (30 ml), brine (30 ml) in this order, and dried over anhydrous sodium sulfate. The solvent was evaporated to give a residue, which was then purified by silica gel column chromatography (FUJI Silysia NH, eluent; heptane:ethyl acetate=1:8, ethyl acetate, then ethyl acetate:ethanol=95:5). Fractions containing the target compound were concentrated under reduced pressure to give a residue, to which diethyl ether (2 ml) and hexane (2 ml) were then added to suspend. The solid was filtered off, and dried under aeration to provide the titled compound (34.1 mg, 36.2%) as white powder.

$^1$H-NMR Spectrum (CDCl$_3$) δ (ppm): 2.15 (2H, m), 2.42 (2H, m), 2.48 (4H, m), 2.63 (2H, m), 3.33 (4H, m), 3.50 (4H, m), 3.71 (2H, s), 6.54 (1H, dd, J=2.4, 5.6 Hz), 7.05-7.15 (4H, m), 7.19 (1H, brs), 7.23-7.40 (2H, m), 7.64 (1H, m), 7.65-7.75 (2H, m), 8.05 (1H, d, J=5.6 Hz), 8.52 (1H, brs), 12.26 (1H, brs). ESI-MS (m/z): 592 [M+H]$^+$.

Chemical formulas of the compounds provided in Production Examples and Examples described above are shown in Table 8 to Table 45 below.

TABLE 8
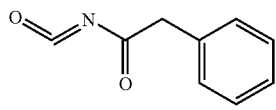
Pro. Ex. 1
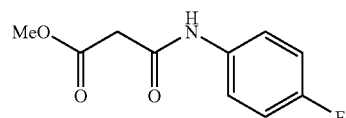
Pro. Ex. 2
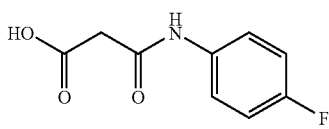
Pro. Ex. 3
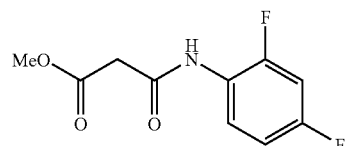
Pro. Ex. 4
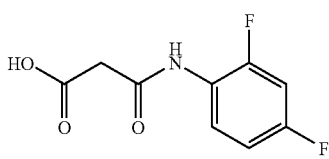
Pro. Ex. 5
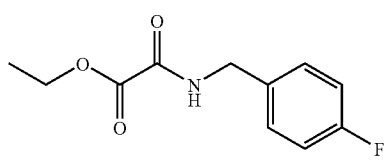
Pro. Ex. 6
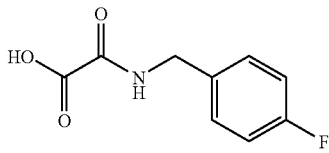
Pro. Ex. 7
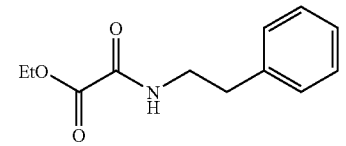
Pro. Ex. 8
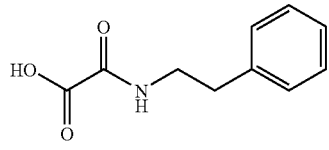
Pro. Ex. 9
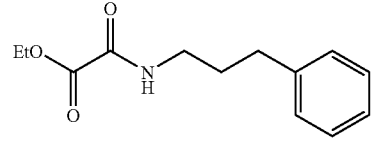
Pro. Ex. 10
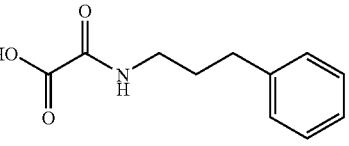
Pro. Ex. 11
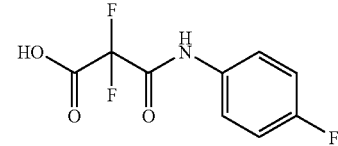
Pro. Ex. 12
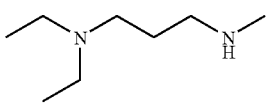
Pro. Ex. 13
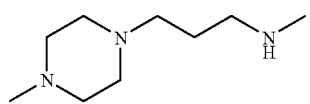
Pro. Ex. 14
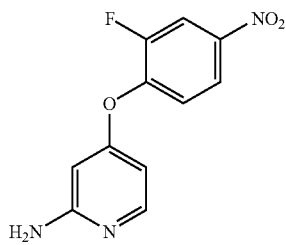
Pro. Ex. 15
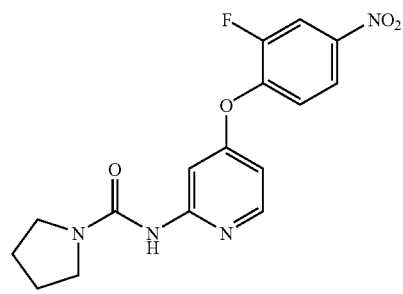
Pro. Ex. 16

TABLE 8-continued
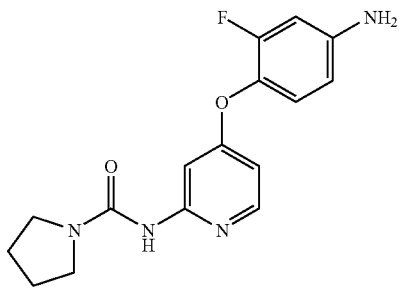
Pro. Ex. 17
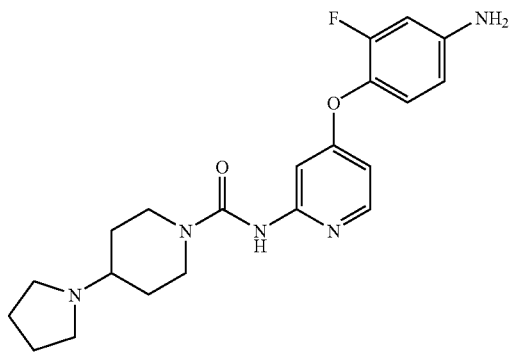
Pro. Ex. 18
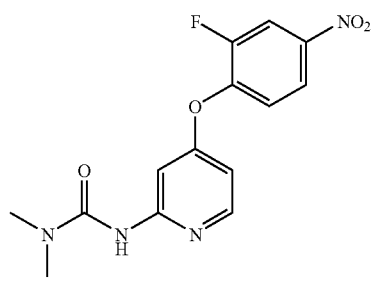
Pro. Ex. 19
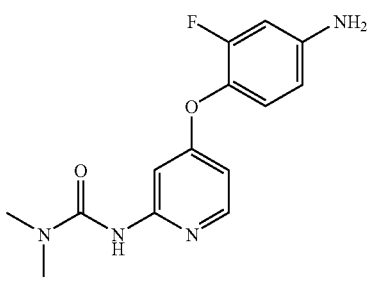
Pro. Ex. 20
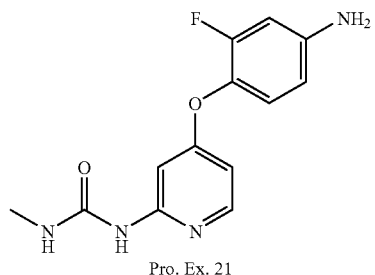
Pro. Ex. 21
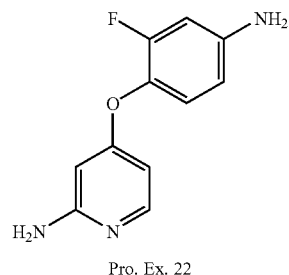
Pro. Ex. 22
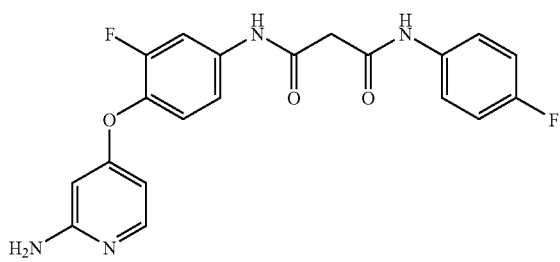
Pro. Ex. 23
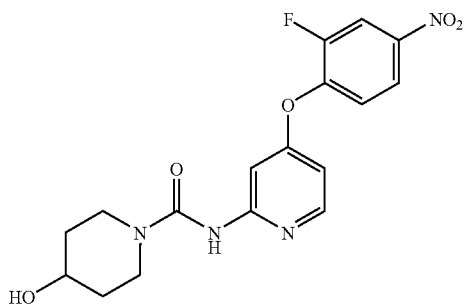
Pro. Ex. 24
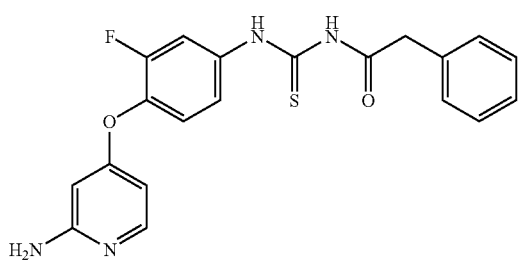
Pro. Ex. 25

TABLE 8-continued
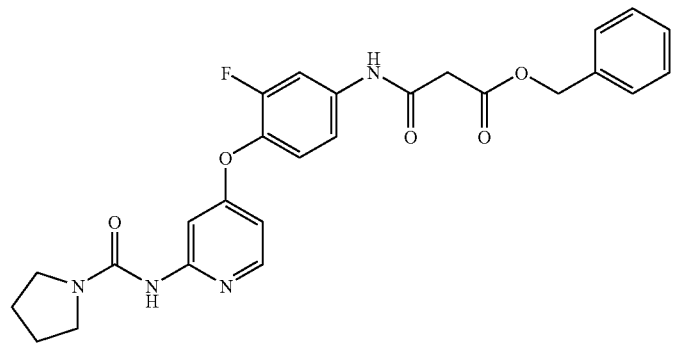
Pro. Ex. 26
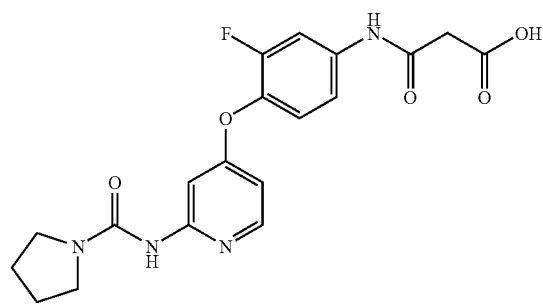
Pro. Ex. 27
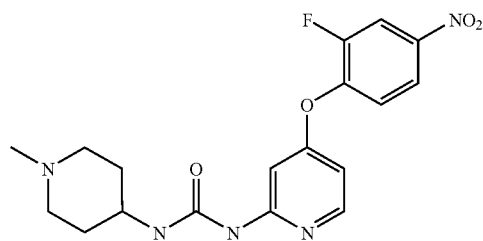
Pro. Ex. 28
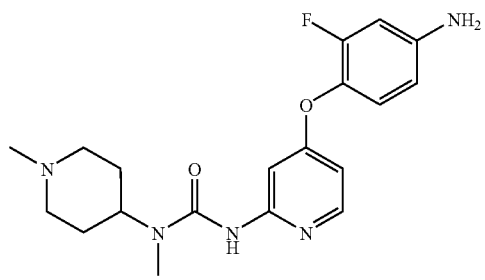
Pro. Ex. 29
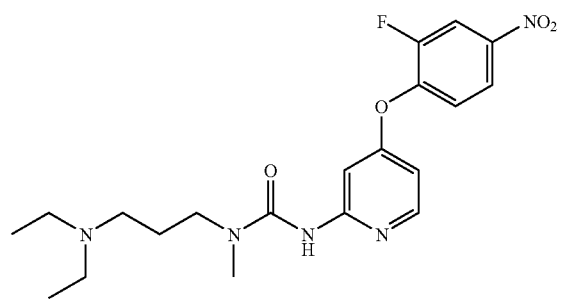
Pro. Ex. 30
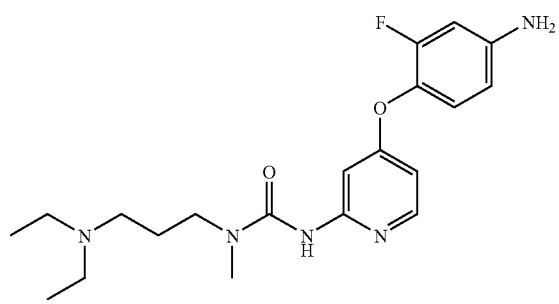
Pro. Ex. 31
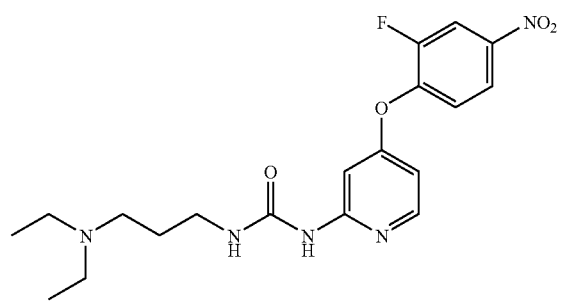
Pro. Ex. 32

TABLE 9
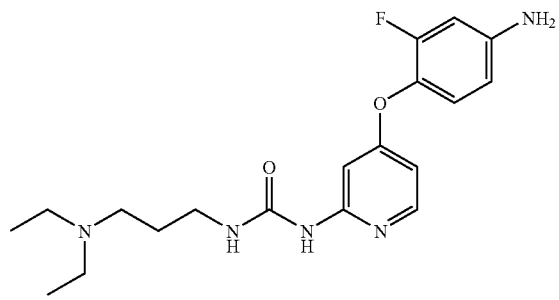
Pro. Ex. 33
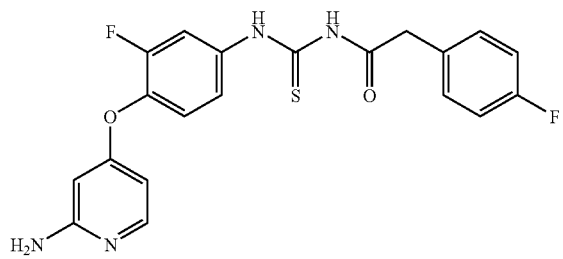
Pro. Ex. 34
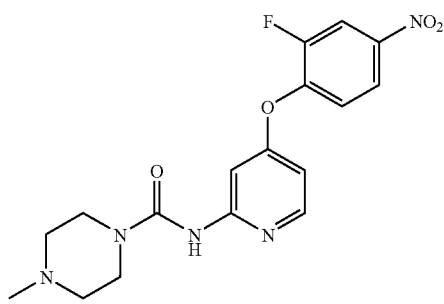
Pro. Ex. 35
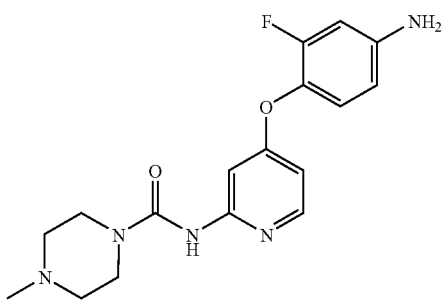
Pro. Ex. 36
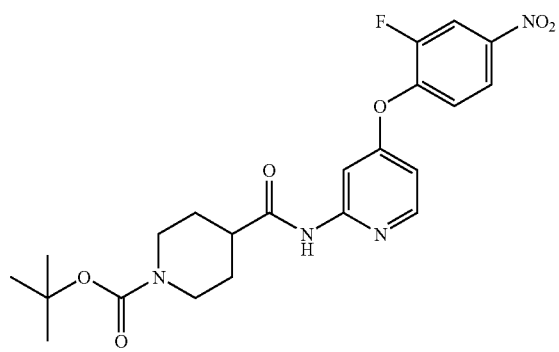
Pro. Ex. 37
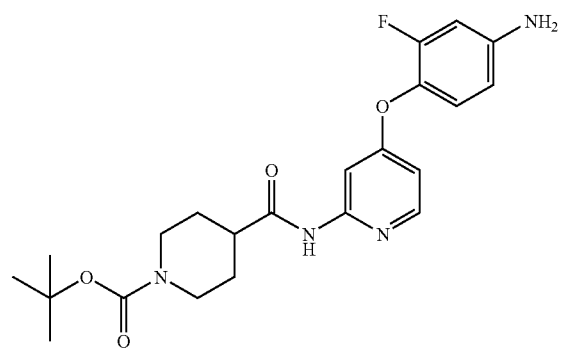
Pro. Ex. 38
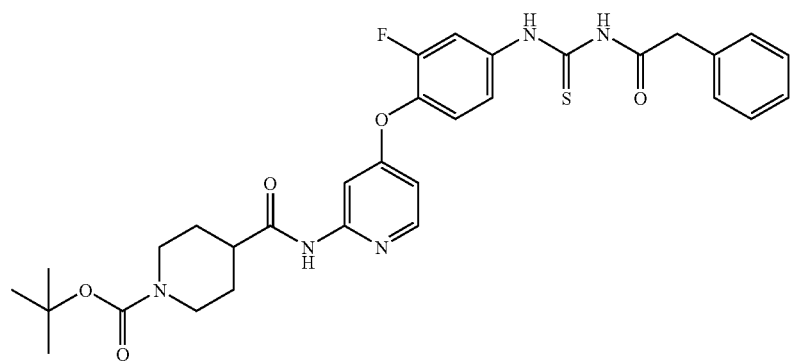
Pro. Ex. 39

TABLE 9-continued
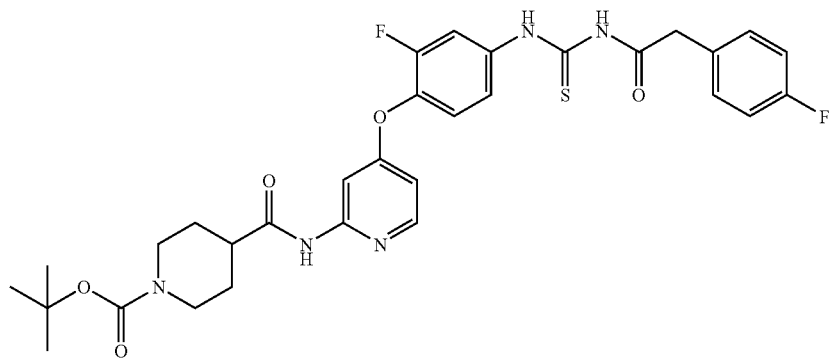
Pro. Ex. 40
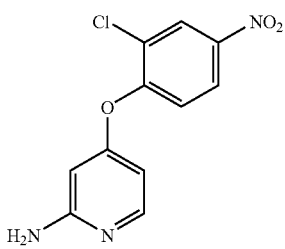
Pro. Ex. 41
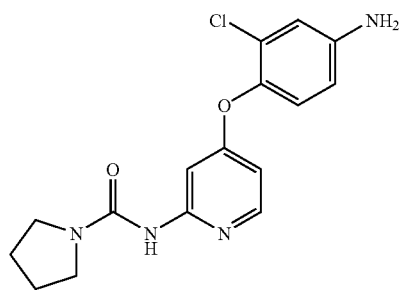
Pro. Ex. 42
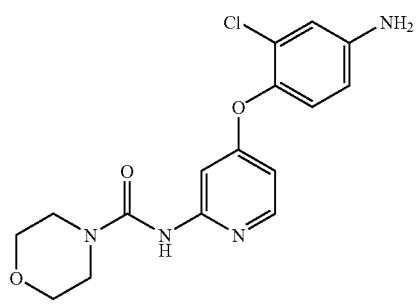
Pro. Ex. 43
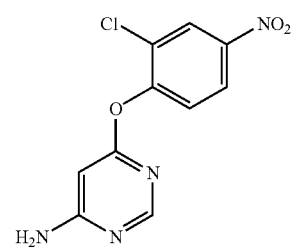
Pro. Ex. 44
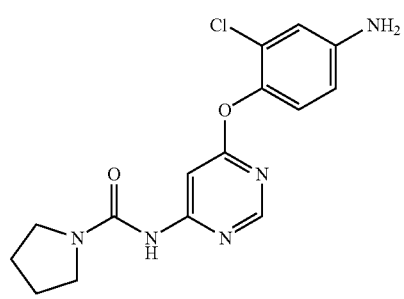
Pro. Ex. 45
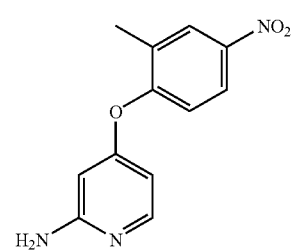
Pro. Ex. 46

TABLE 9-continued
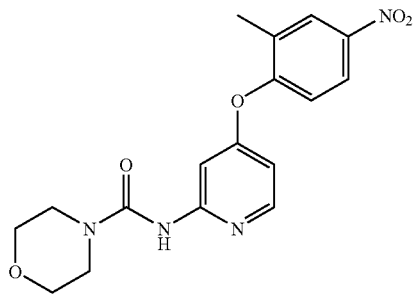
Pro. Ex. 47
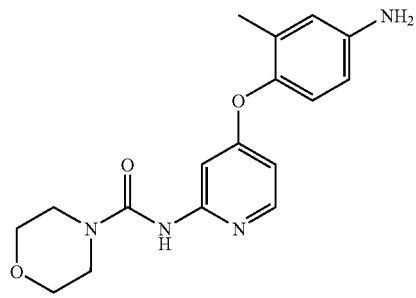
Pro. Ex. 48
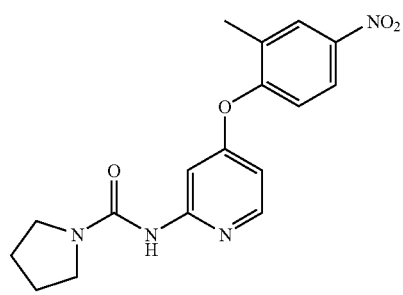
Pro. Ex. 49
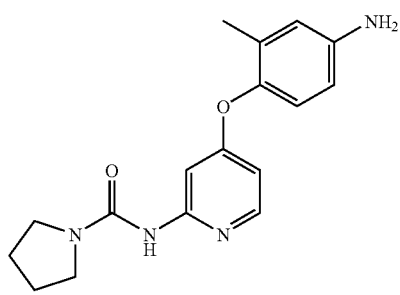
Pro. Ex. 50
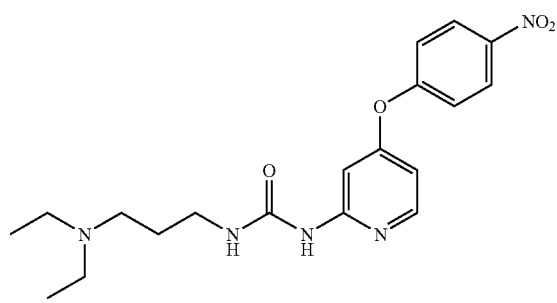
Pro. Ex. 51
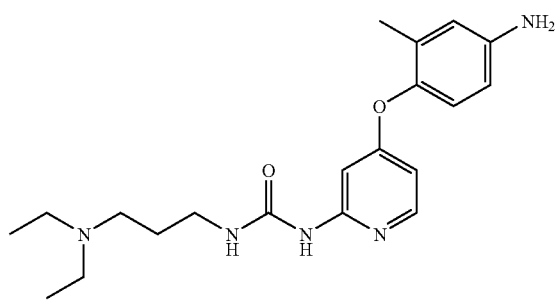
Pro. Ex. 52
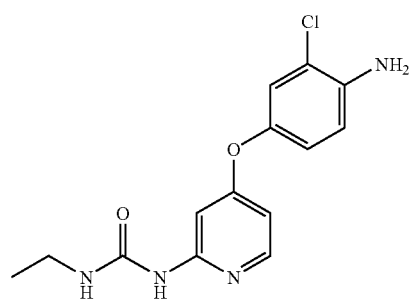
Pro. Ex. 53
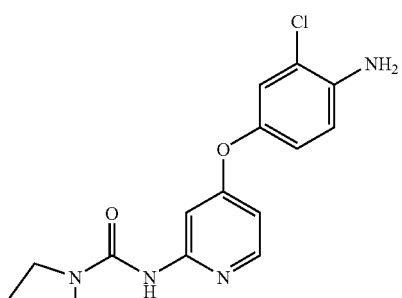
Pro. Ex. 54

TABLE 9-continued
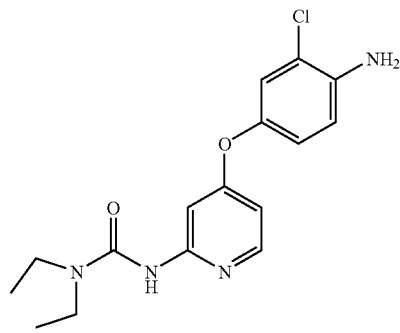
Pro. Ex. 55
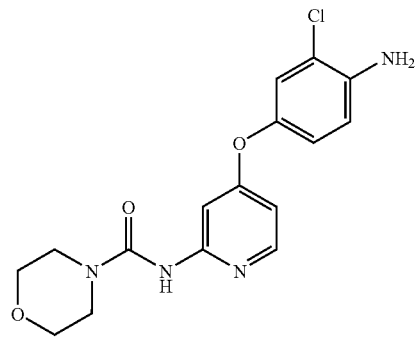
Pro. Ex. 56
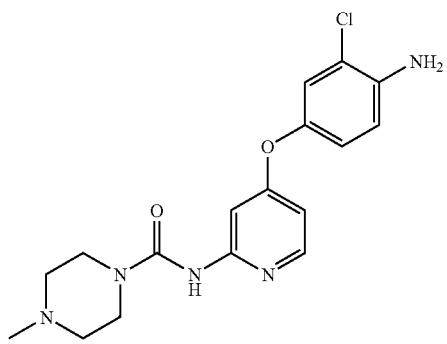
Pro. Ex. 57
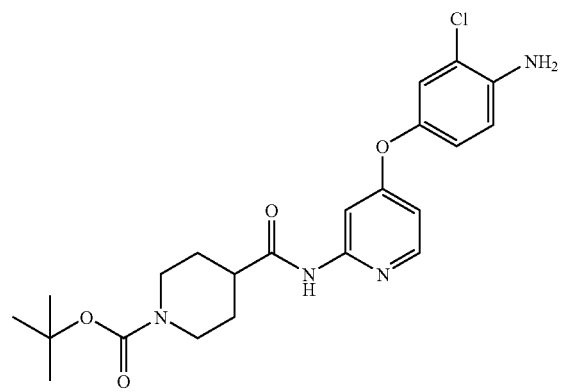
Pro. Ex. 58
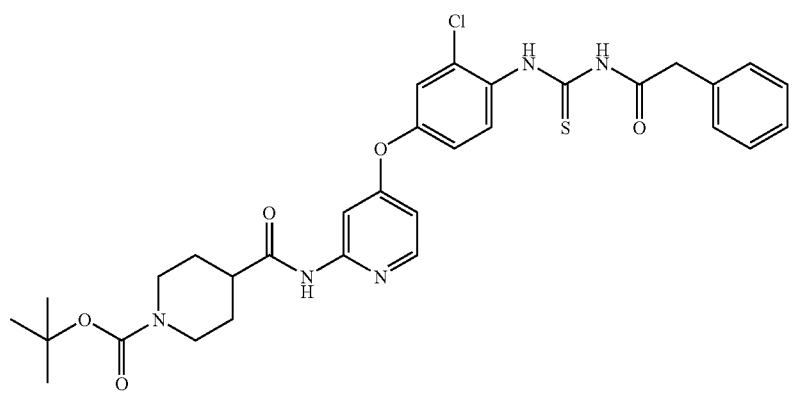
Pro. Ex. 59
TABLE 10
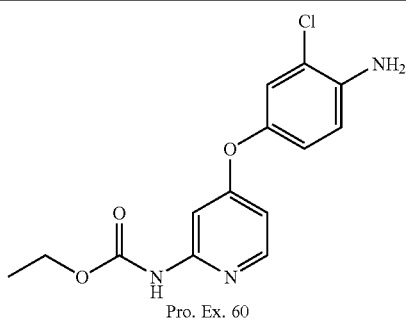
Pro. Ex. 60
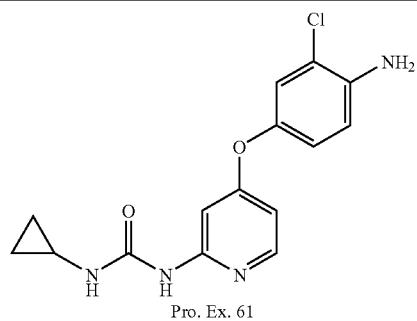
Pro. Ex. 61

TABLE 10-continued
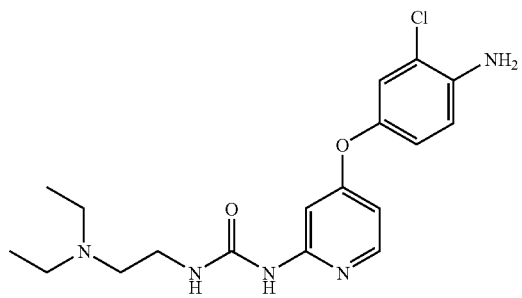
Pro. Ex. 62
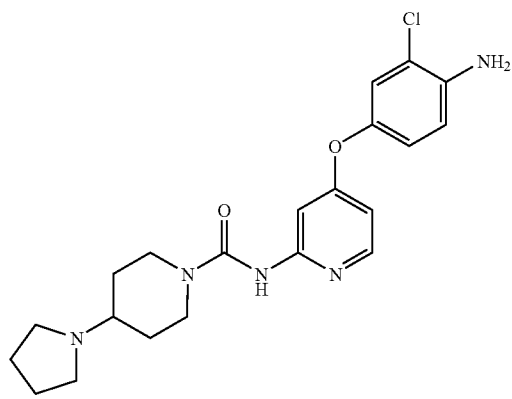
Pro. Ex. 63
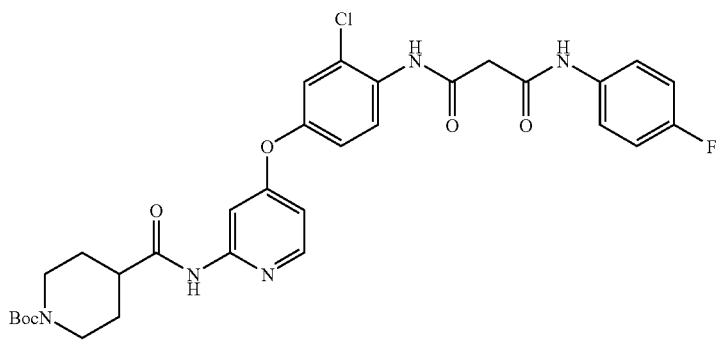
Pro. Ex. 64
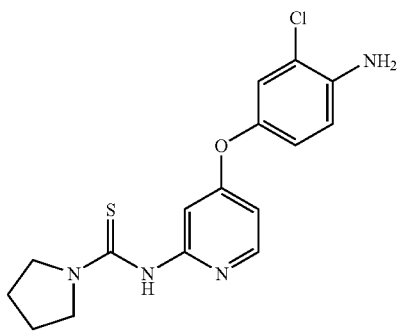
Pro. Ex. 65
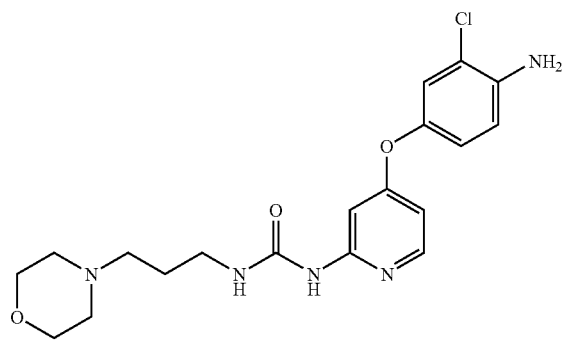
Pro. Ex. 66
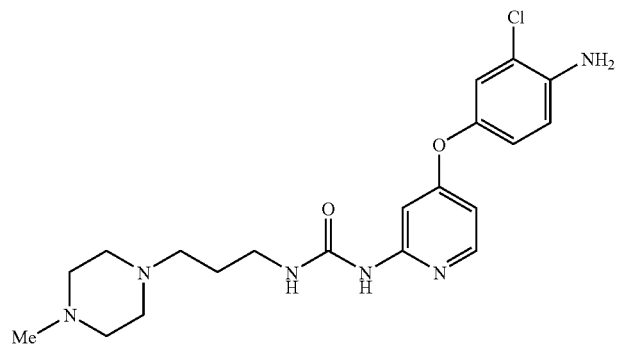
Pro. Ex. 67

TABLE 10-continued
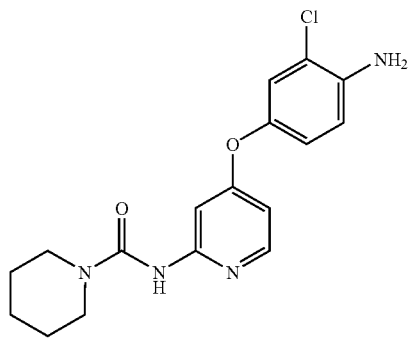
Pro. Ex. 68
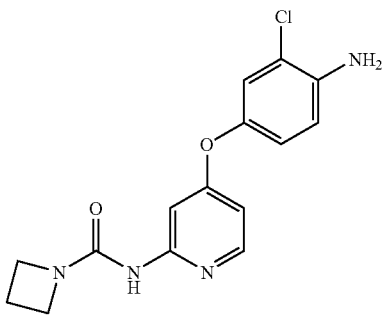
Pro. Ex. 69
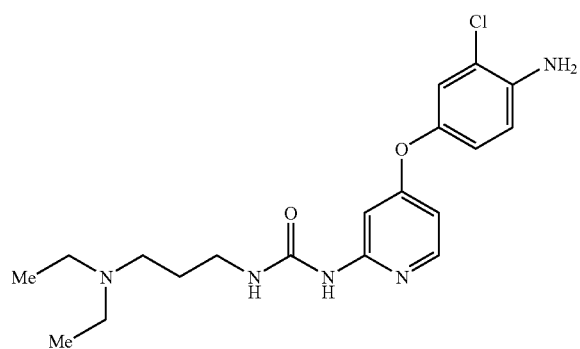
Pro. Ex. 70
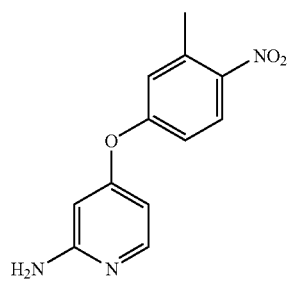
Pro. Ex. 71
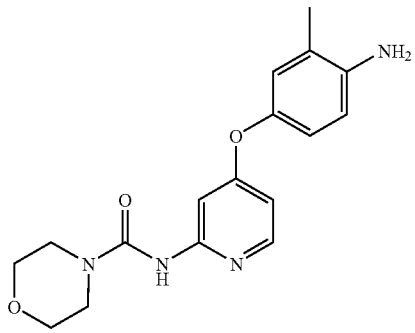
Pro. Ex. 72
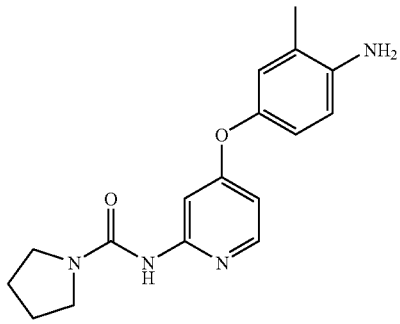
Pro. Ex. 73
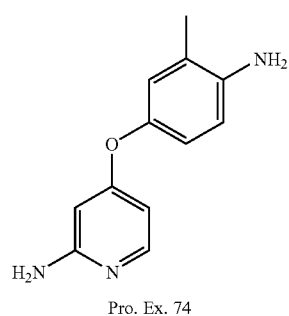
Pro. Ex. 74
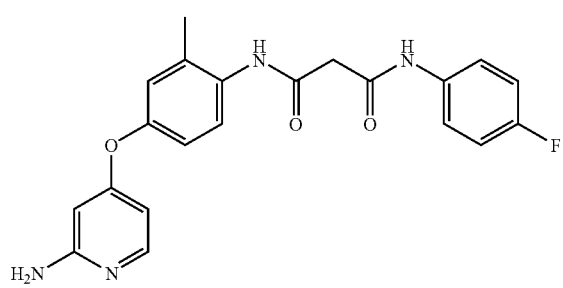
Pro. Ex. 75

TABLE 10-continued
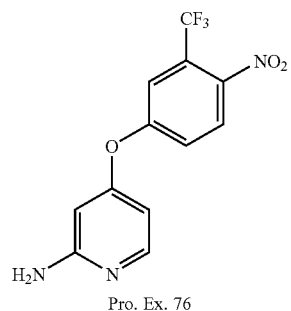
Pro. Ex. 76
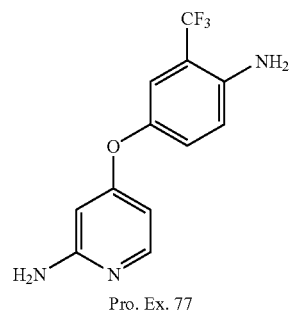
Pro. Ex. 77
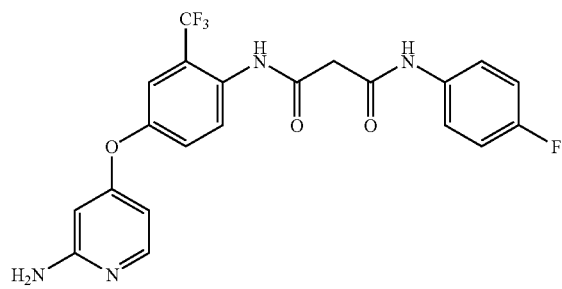
Pro. Ex. 78
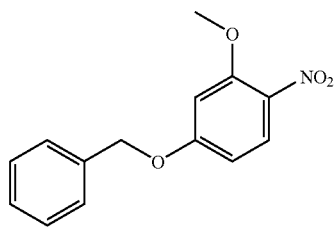
Pro. Ex. 79
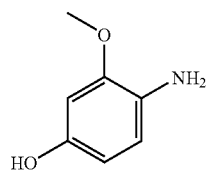
Pro. Ex. 80
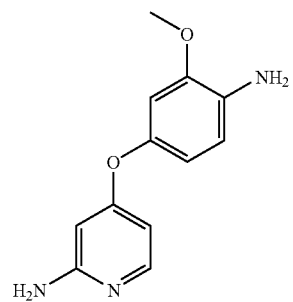
Pro. Ex. 81
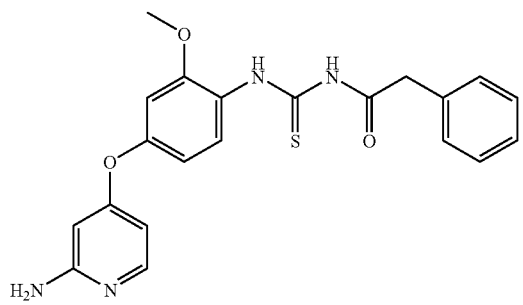
Pro. Ex. 82
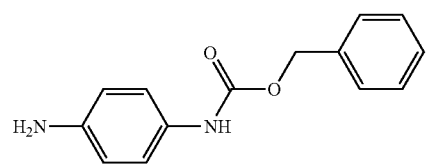
Pro. Ex. 83

TABLE 10-continued
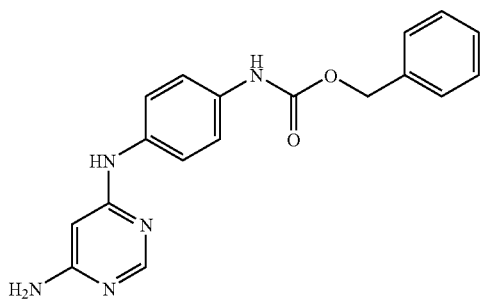
Pro. Ex. 84
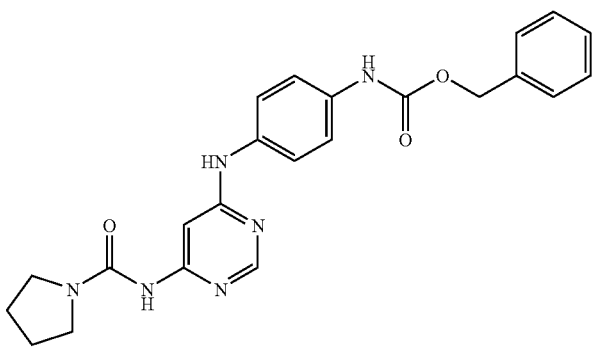
Pro. Ex. 85
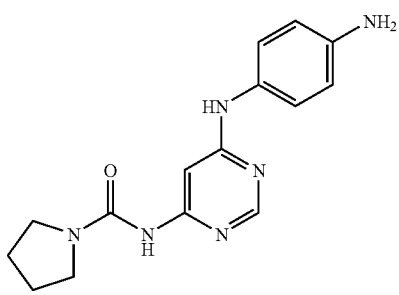
Pro. Ex. 86
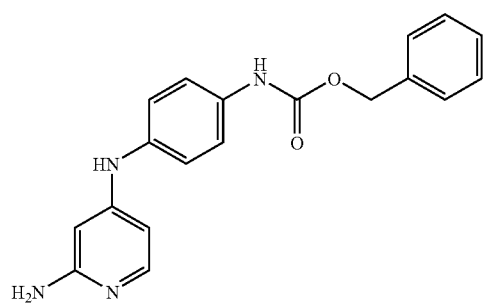
Pro. Ex. 87
TABLE 11
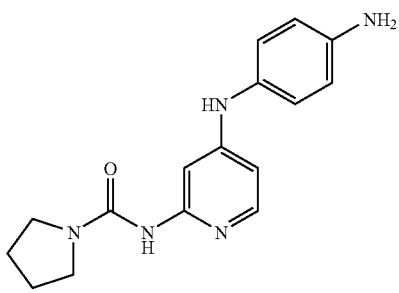
Pro. Ex. 88
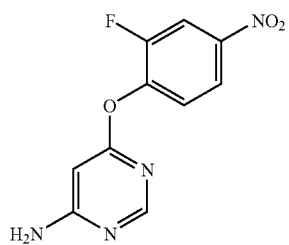
Pro. Ex. 89
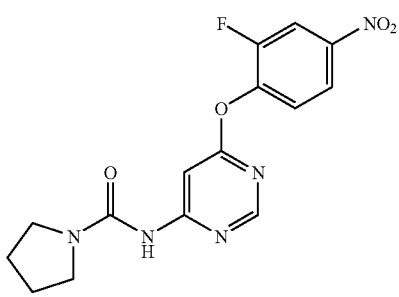
Pro. Ex. 90
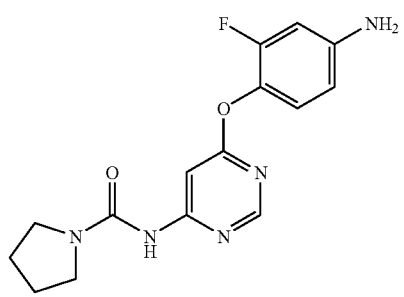
Pro. Ex. 91

TABLE 11-continued
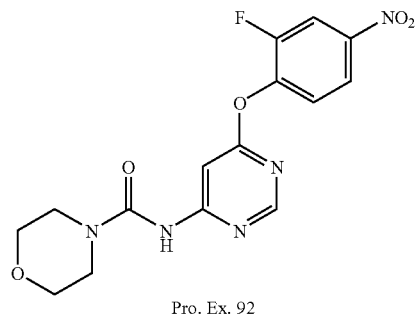
Pro. Ex. 92
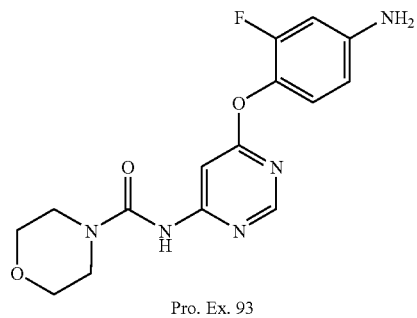
Pro. Ex. 93
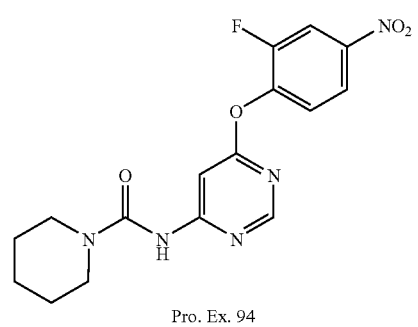
Pro. Ex. 94
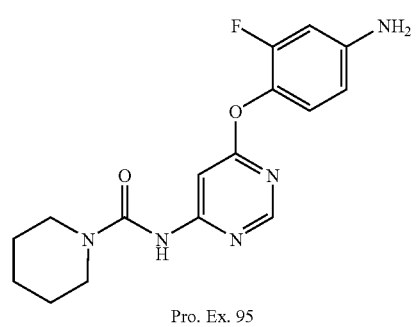
Pro. Ex. 95
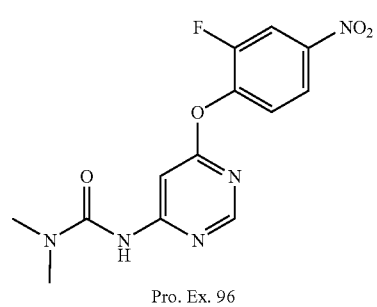
Pro. Ex. 96
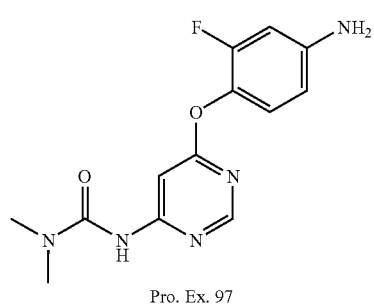
Pro. Ex. 97
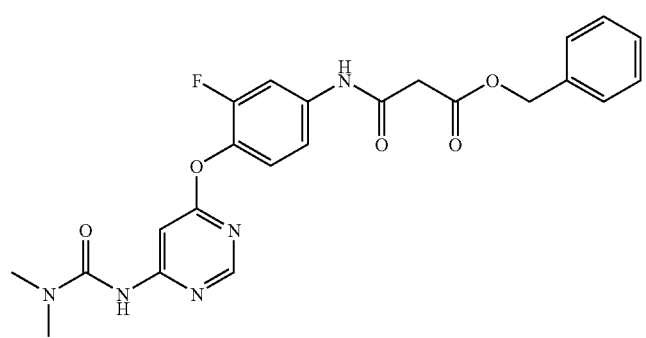
Pro. Ex. 98
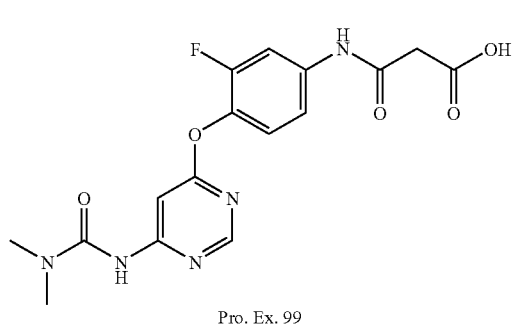
Pro. Ex. 99

TABLE 11-continued
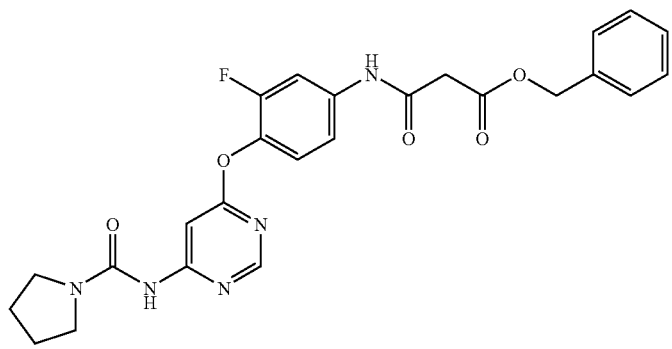
Pro. Ex. 100
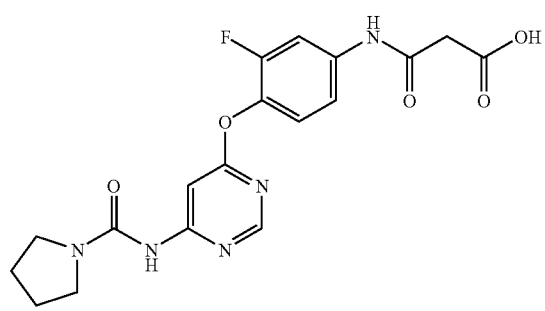
Pro. Ex. 101
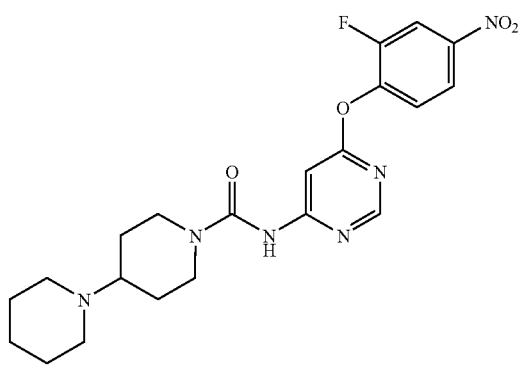
Pro. Ex. 102
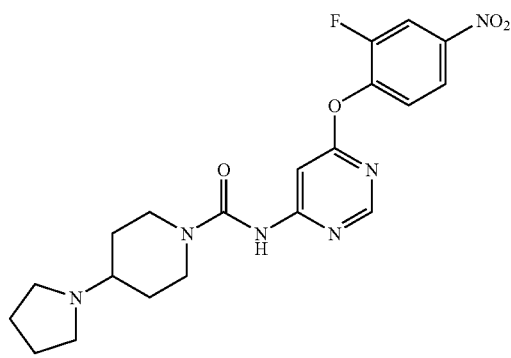
Pro. Ex. 103
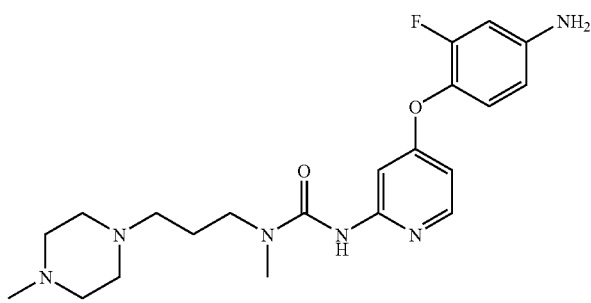
Pro. Ex. 104
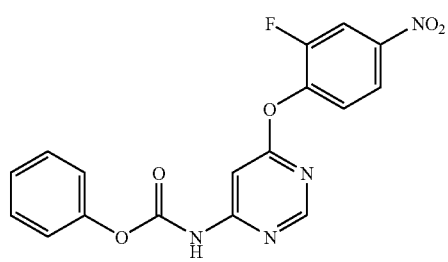
Pro. Ex. 105
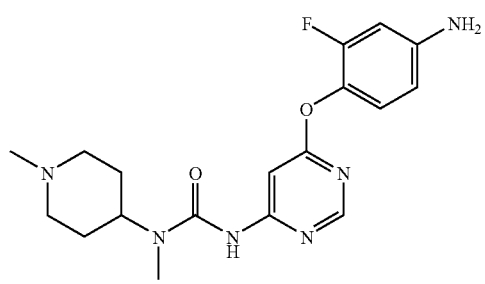
Pro. Ex. 106

TABLE 11-continued
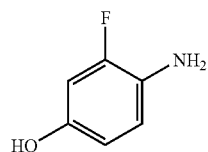
Pro. Ex. 107
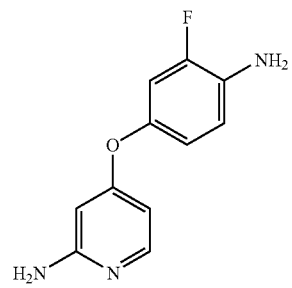
Pro. Ex. 108
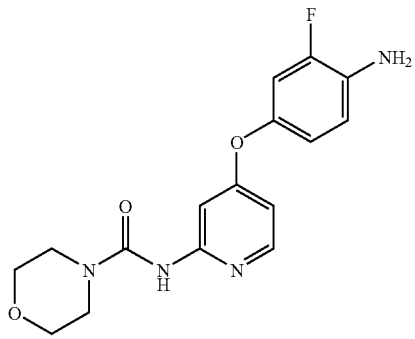
Pro. Ex. 109
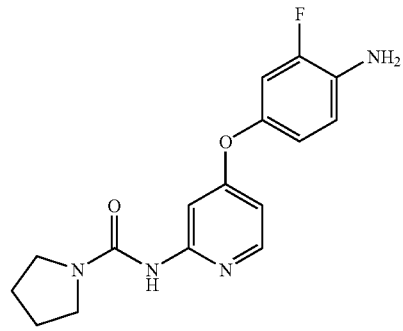
Pro. Ex. 110
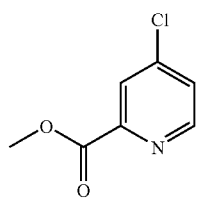
Pro. Ex. 111
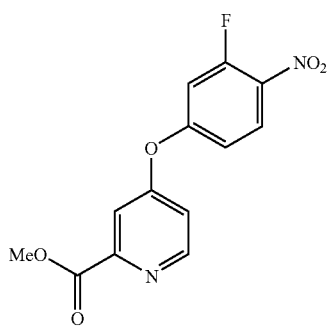
Pro. Ex. 112
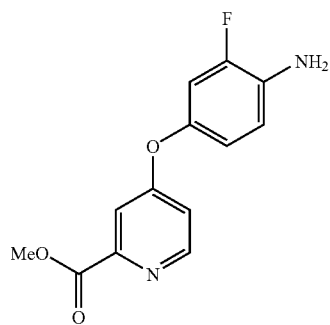
Pro. Ex. 113

TABLE 11-continued
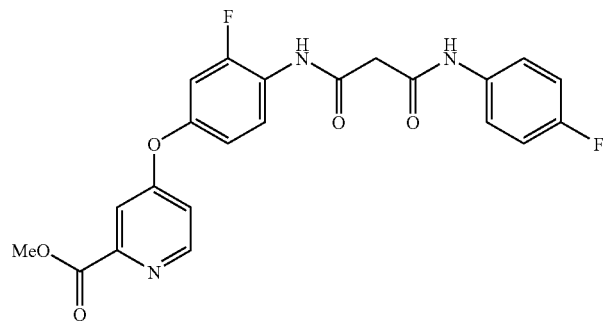
Pro. Ex. 114
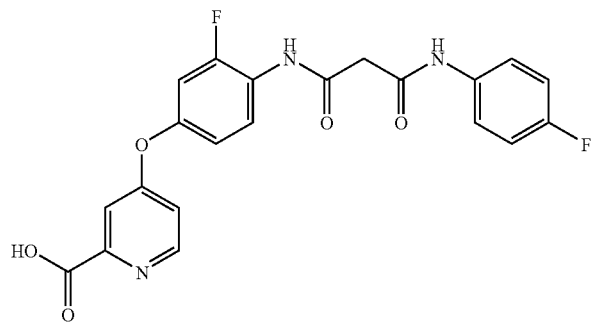
Pro. Ex. 115
TABLE 12
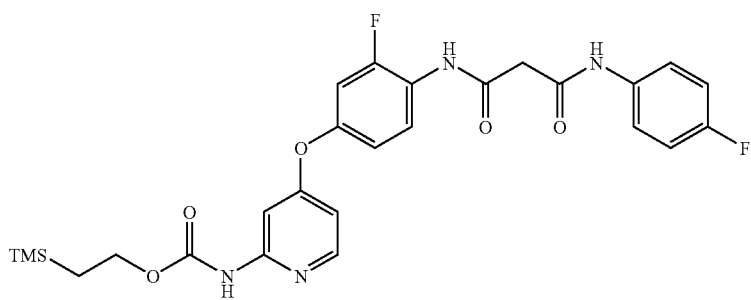
Pro. Ex. 116-1
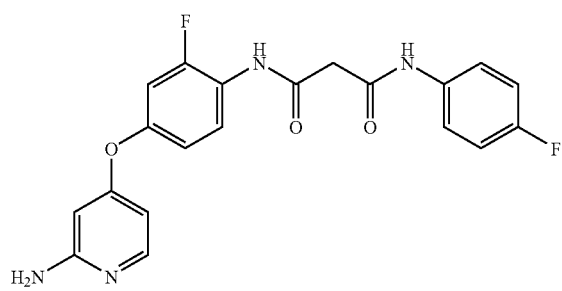
Pro. Ex. 116-2
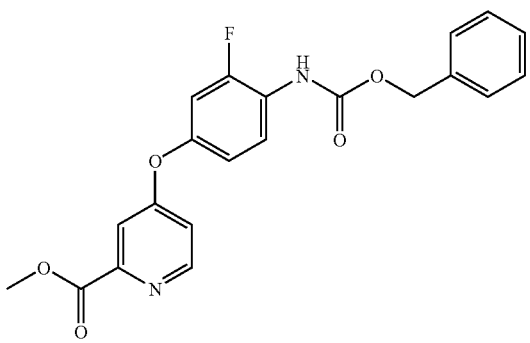
Pro. Ex. 117

TABLE 12-continued
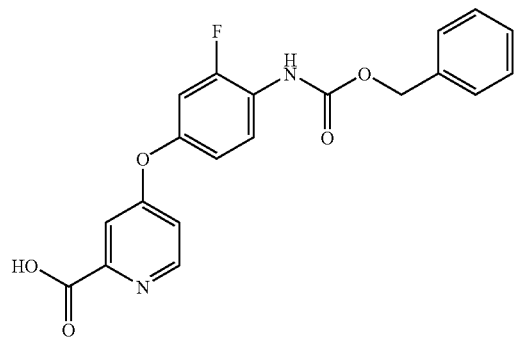
Pro. Ex. 118
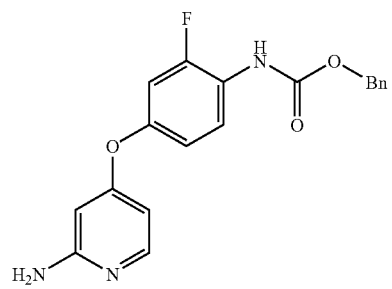
Pro. Ex. 119-1
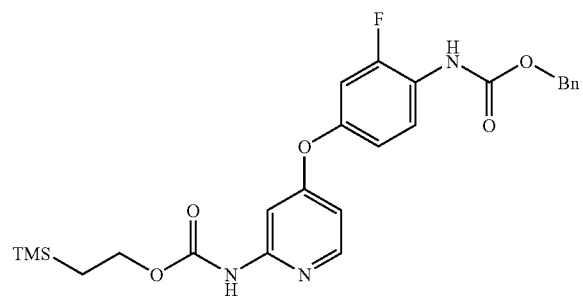
Pro. Ex. 119-2
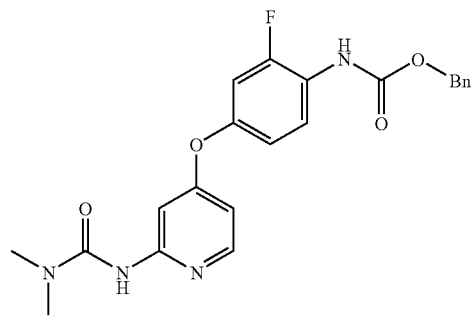
Pro. Ex. 120
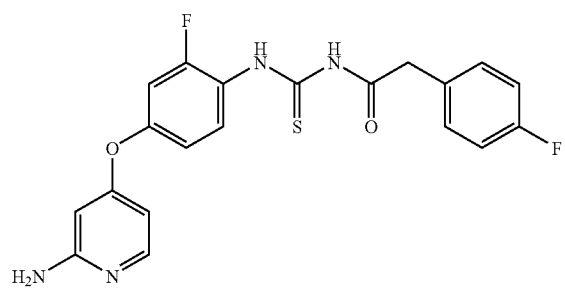
Pro. Ex. 121
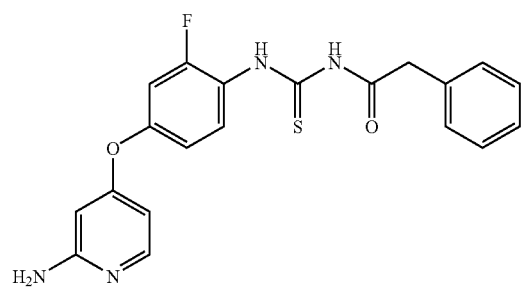
Pro. Ex. 122
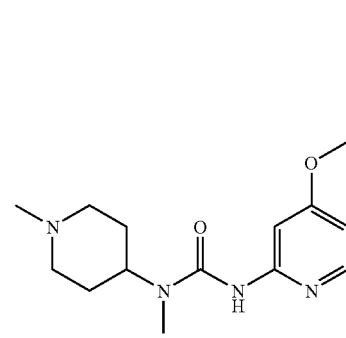
Pro. Ex. 123

TABLE 12-continued
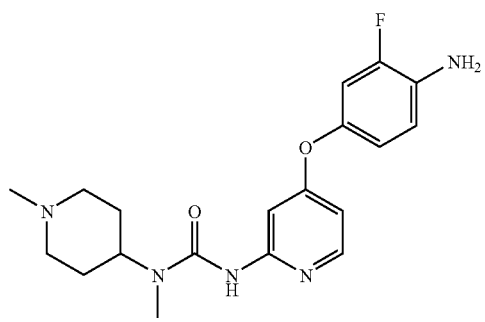
Pro. Ex. 124
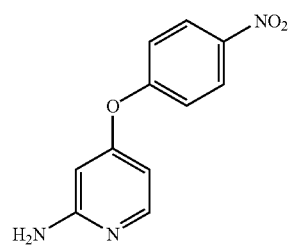
Pro. Ex. 125
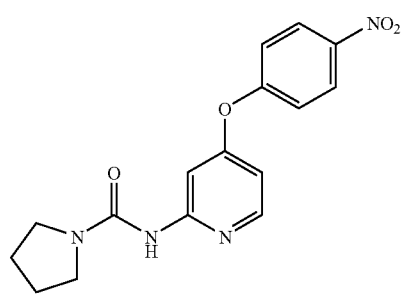
Pro. Ex. 126
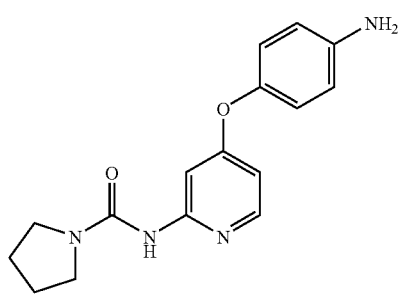
Pro. Ex. 127
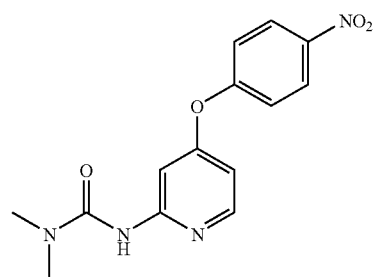
Pro. Ex. 128
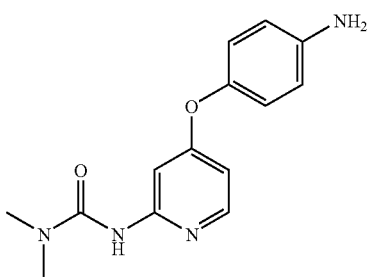
Pro. Ex. 129
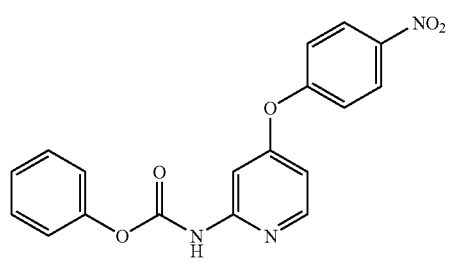
Pro. Ex. 130
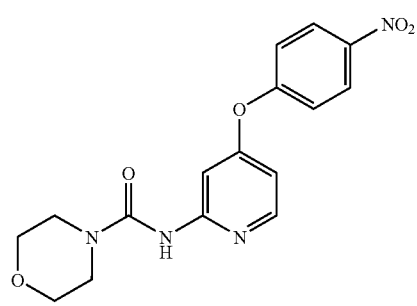
Pro. Ex. 131

TABLE 12-continued
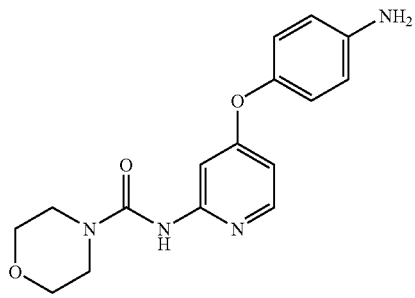
Pro. Ex. 132
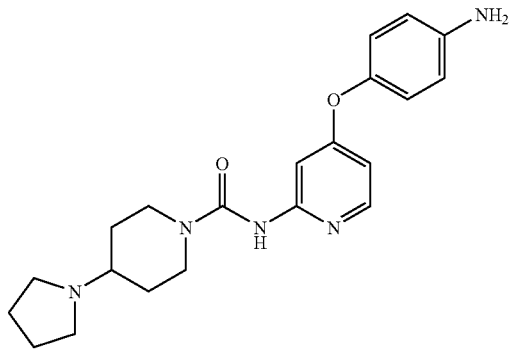
Pro. Ex. 133
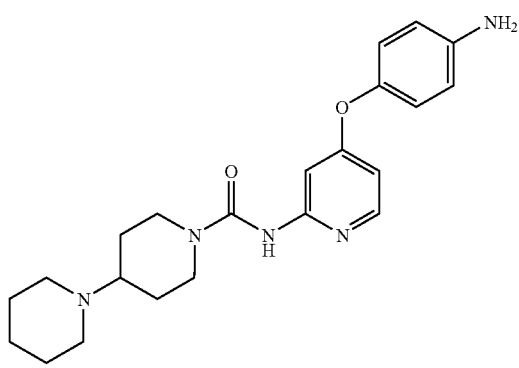
Pro. Ex. 134
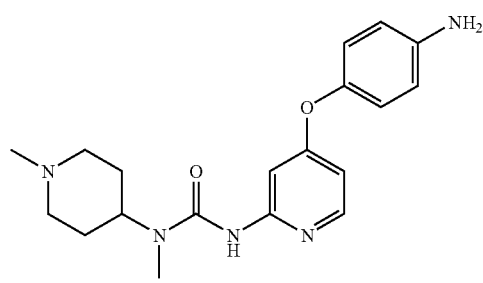
Pro. Ex. 135
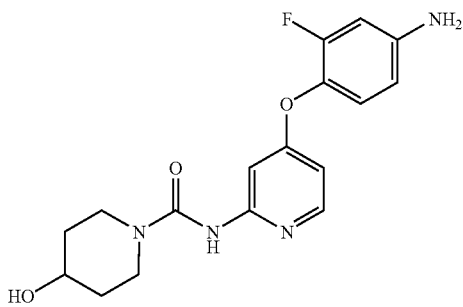
Pro. Ex. 136
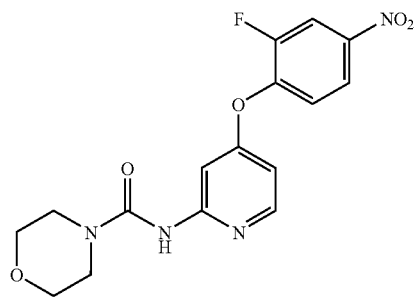
Pro. Ex. 137
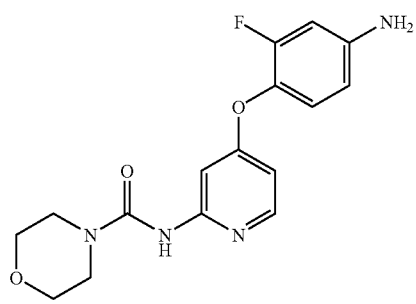
Pro. Ex. 138
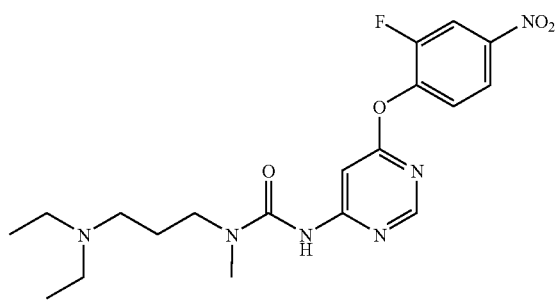
Pro. Ex. 139

TABLE 12-continued
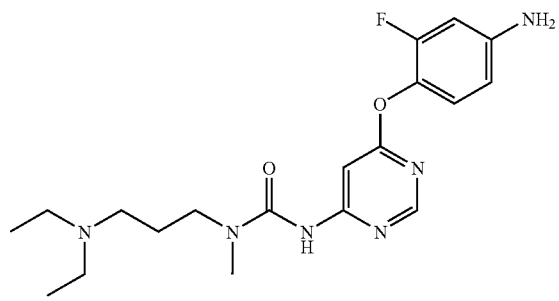
Pro. Ex. 140
TABLE 13
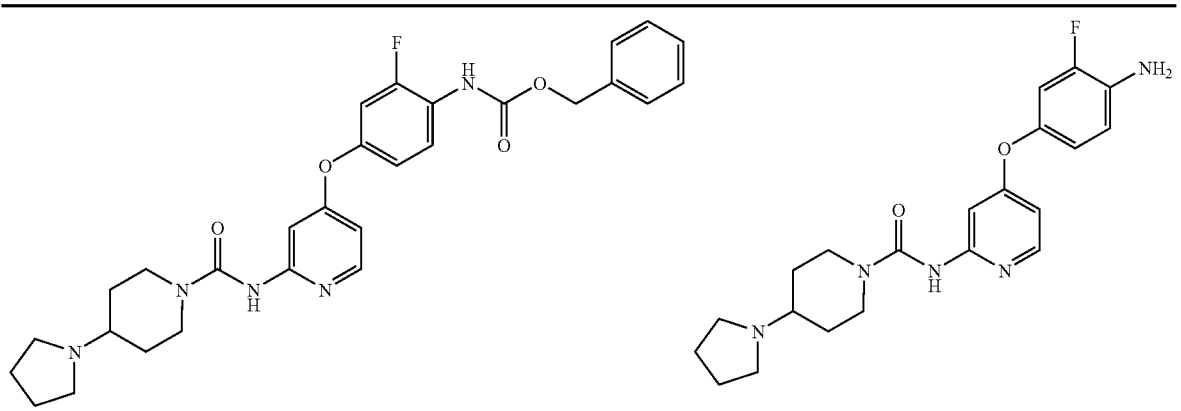
Pro. Ex. 141                                    Pro. Ex. 142
TABLE 14
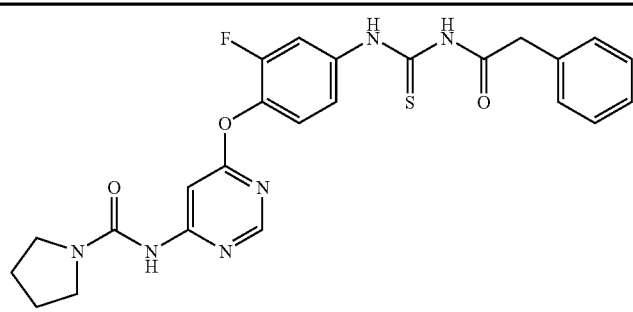
Ex. 1
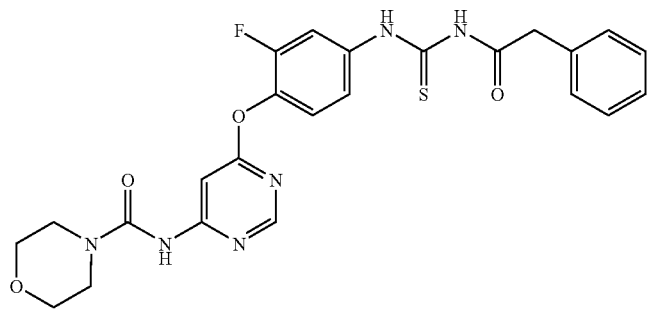
Ex. 2

TABLE 14-continued
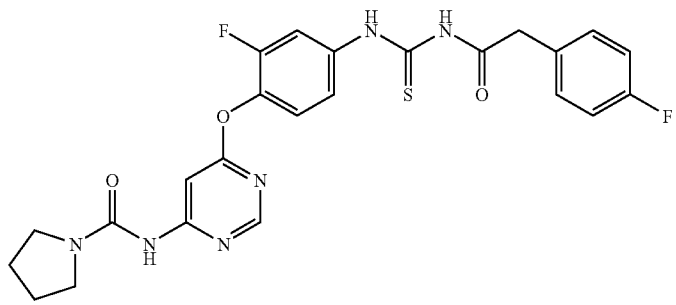
Ex. 3
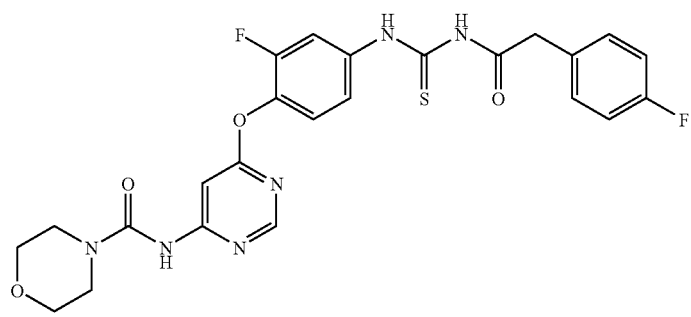
Ex. 4
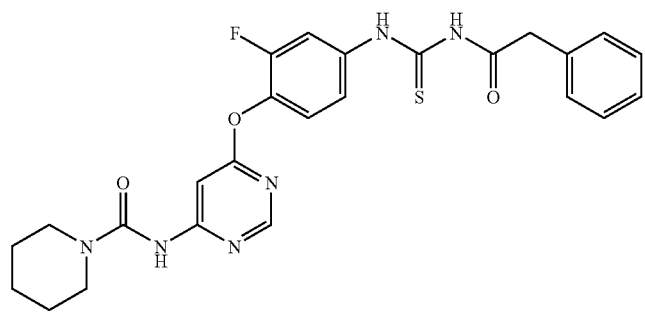
Ex. 5
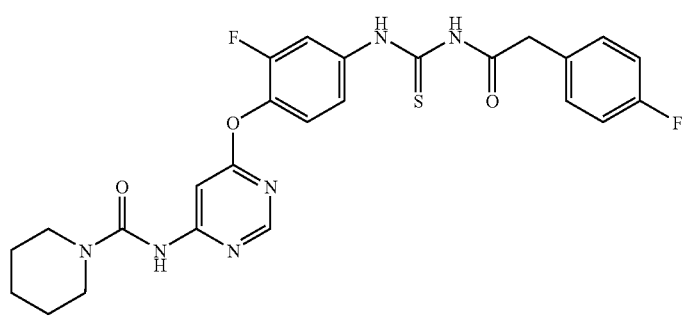
Ex. 6

TABLE 14-continued
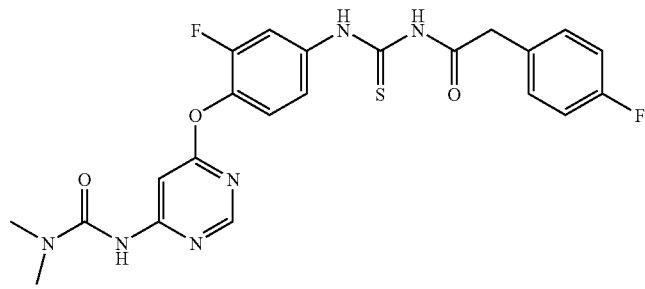
Ex. 7
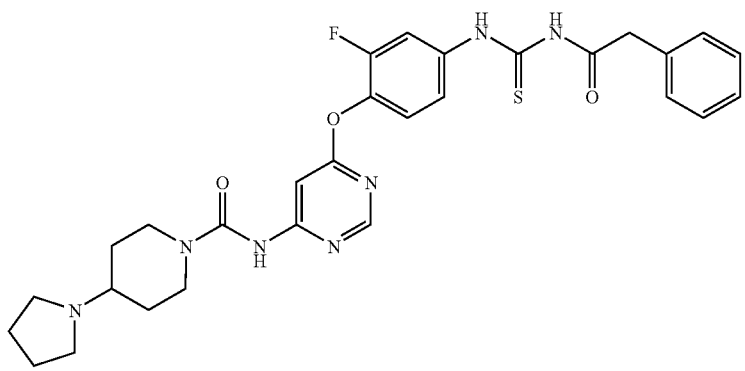
Ex. 8
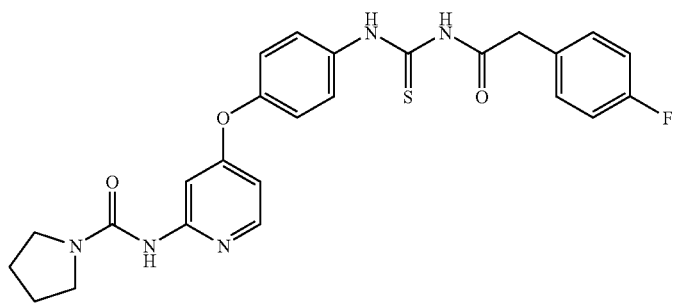
Ex. 9
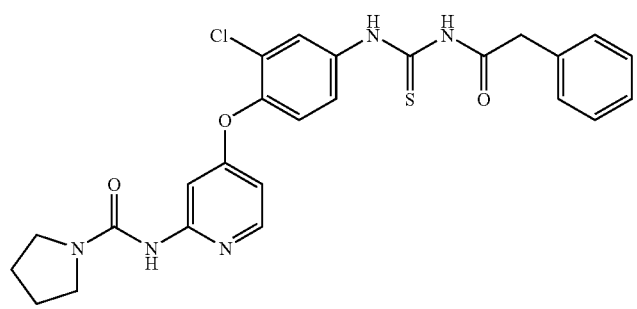
Ex. 10

TABLE 14-continued
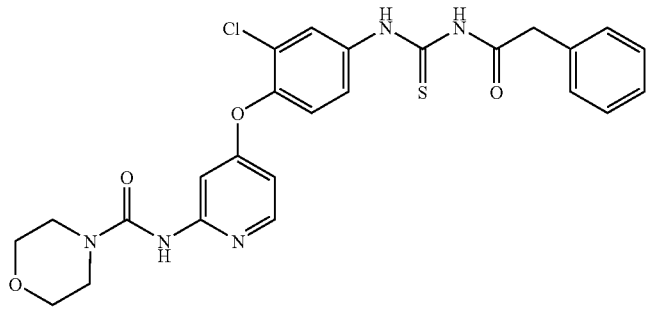
Ex. 11
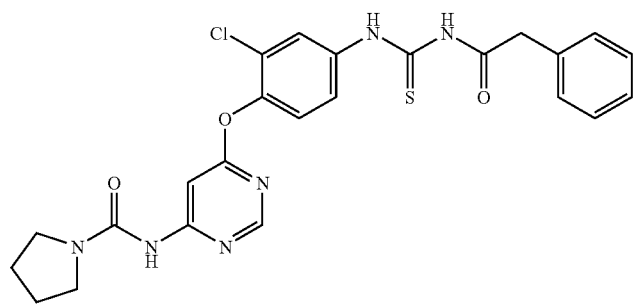
Ex. 12
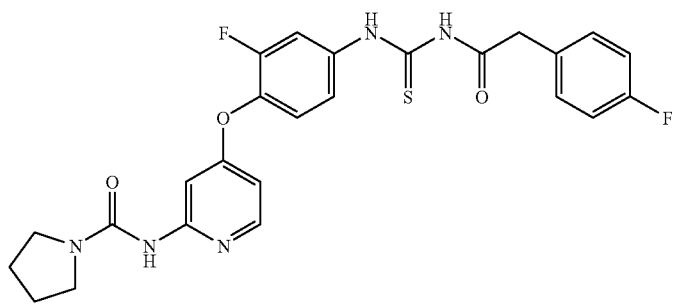
Ex. 13
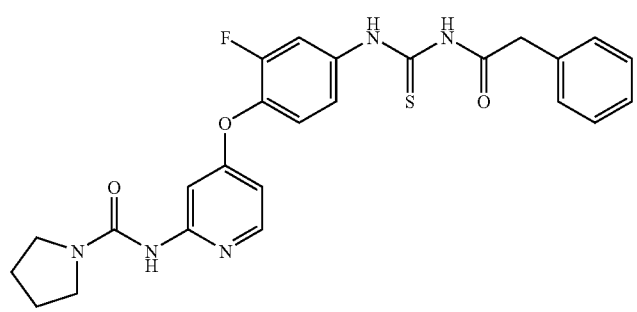
Ex. 14

TABLE 14-continued
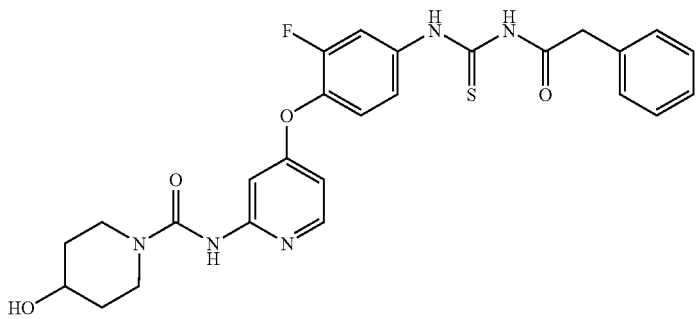
Ex. 15
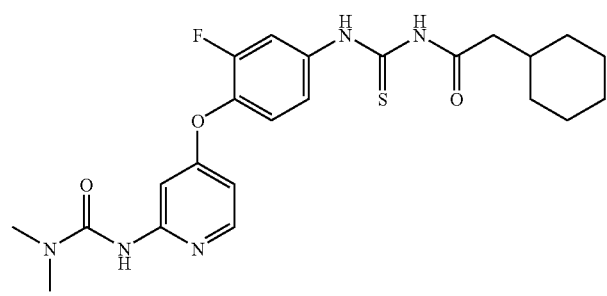
Ex. 16
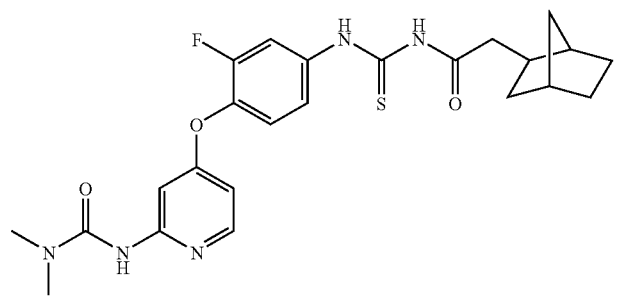
Ex. 17
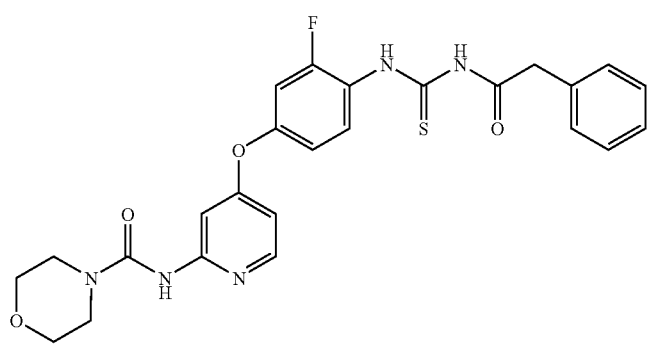
Ex. 18

TABLE 14-continued
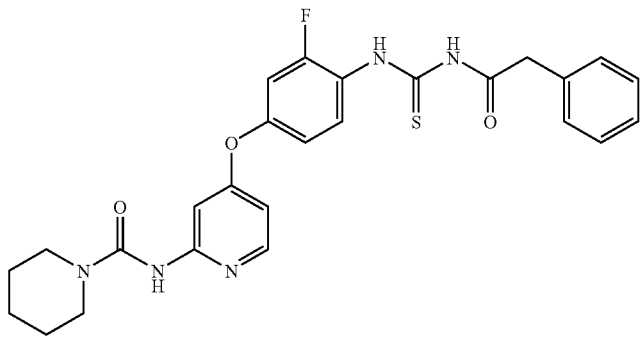
Ex. 19
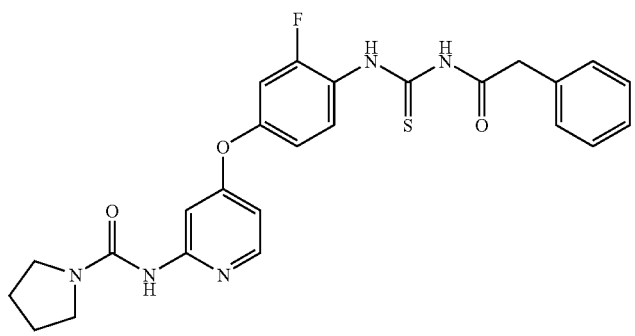
Ex. 20
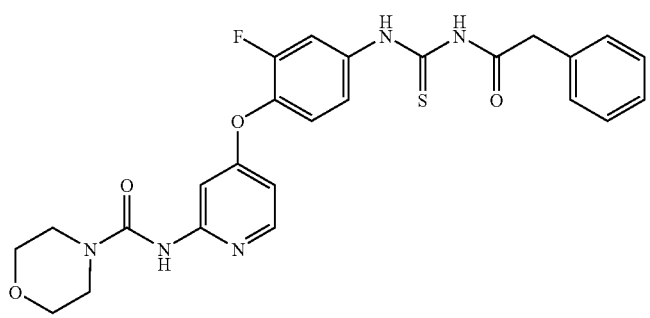
Ex. 21
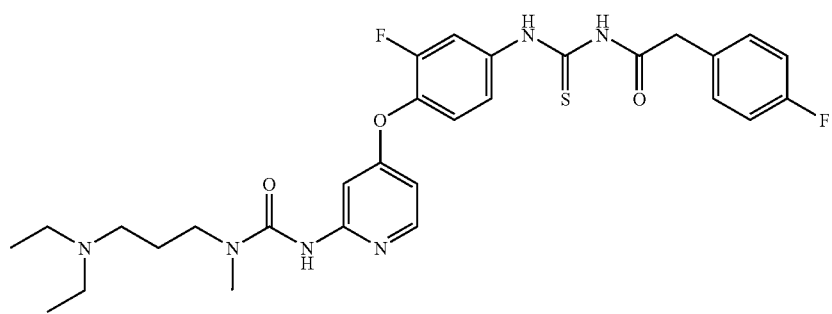
Ex. 22

TABLE 14-continued
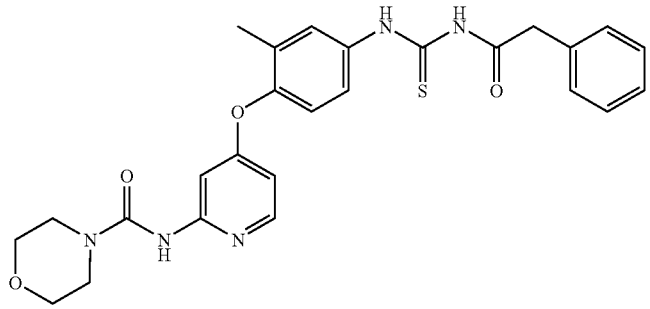
Ex. 23
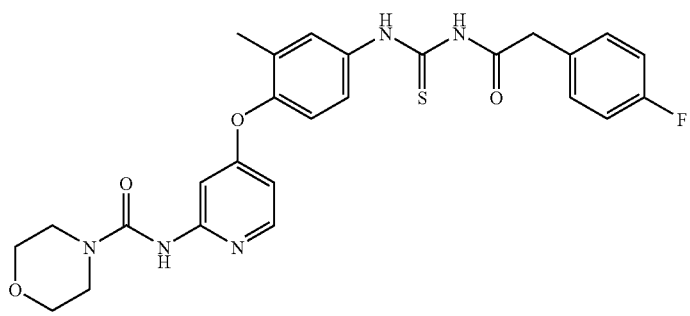
Ex. 24
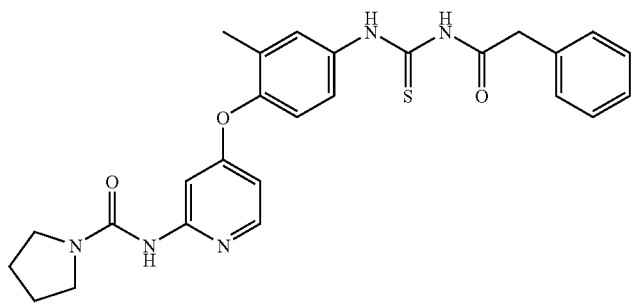
Ex. 25
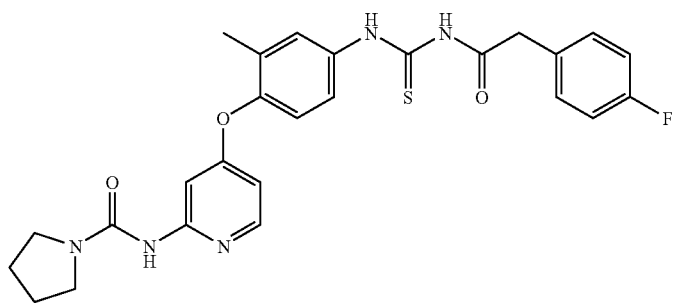
Ex. 26
Ex. 27

TABLE 15
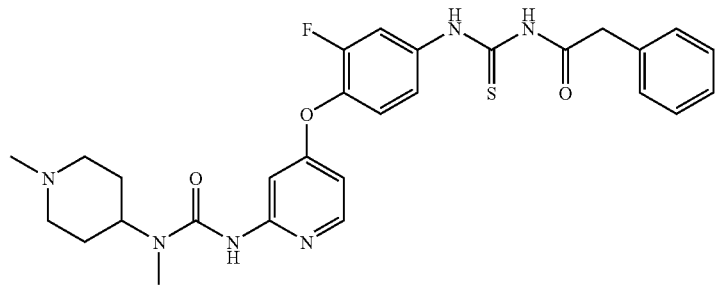
Ex. 28
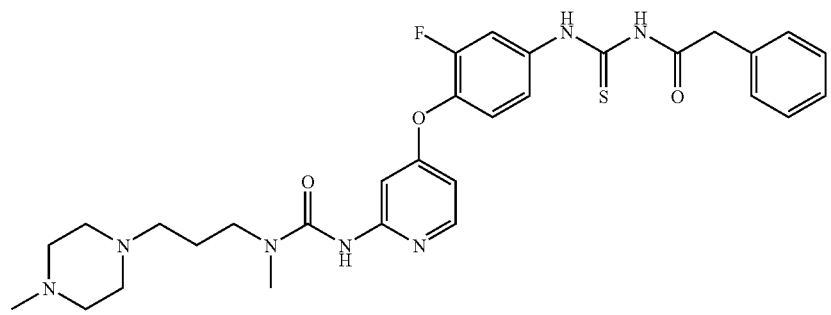
Ex. 29
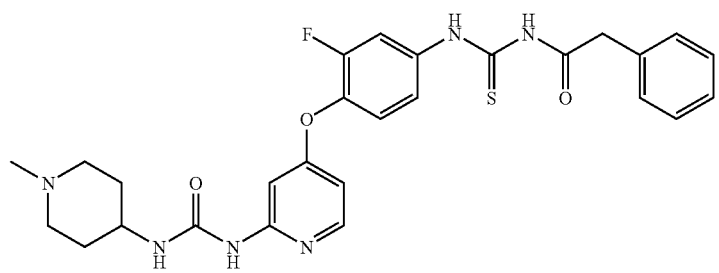
Ex. 30
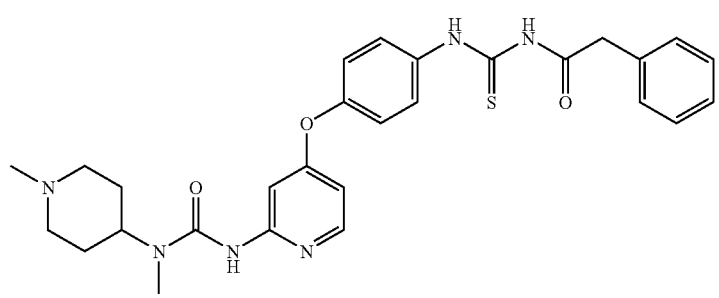
Ex. 31

TABLE 15-continued
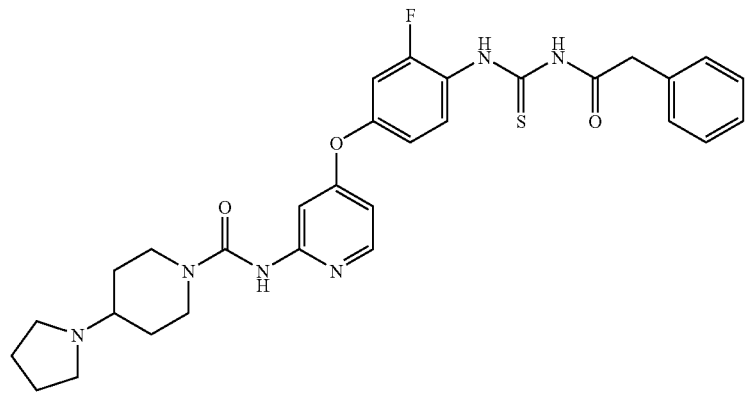
Ex. 32
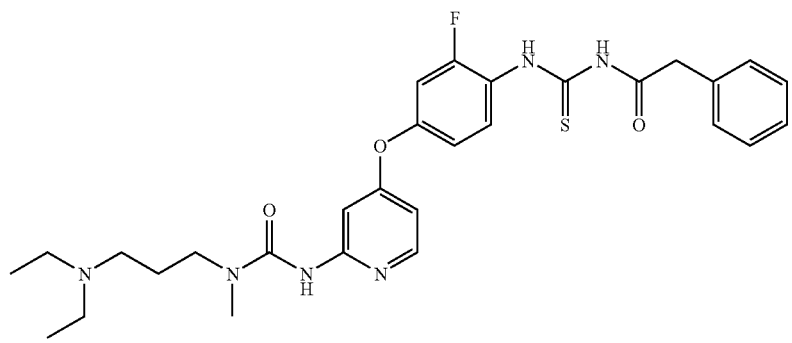
Ex. 33
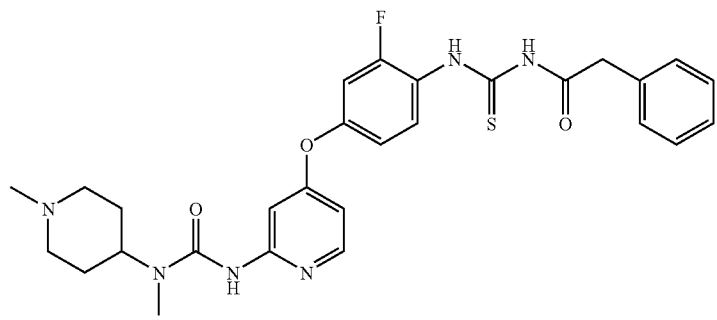
Ex. 34
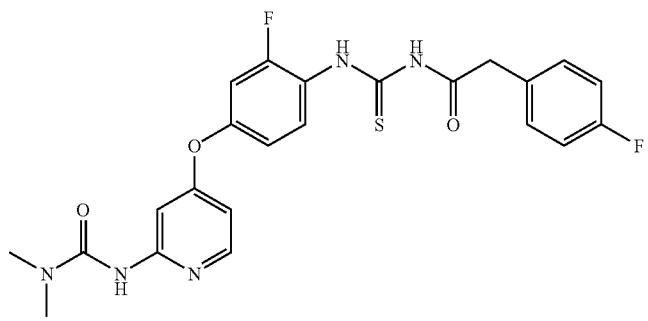
Ex. 35

TABLE 15-continued
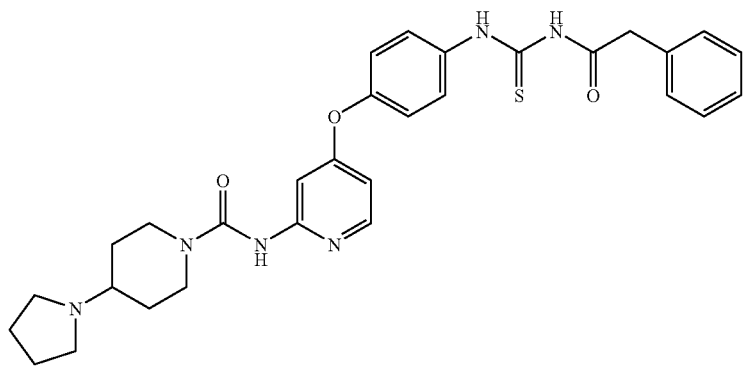
Ex. 36
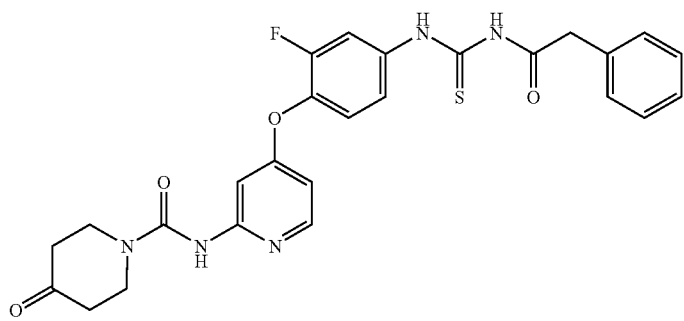
Ex. 37
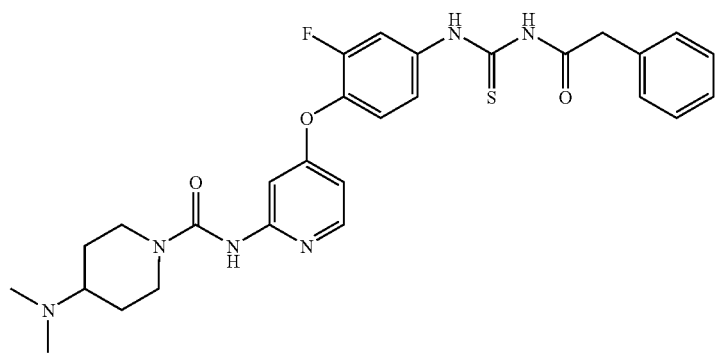
Ex. 38
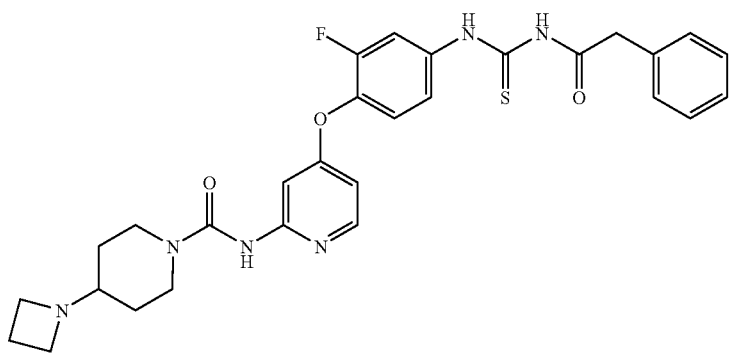
Ex. 39

TABLE 15-continued
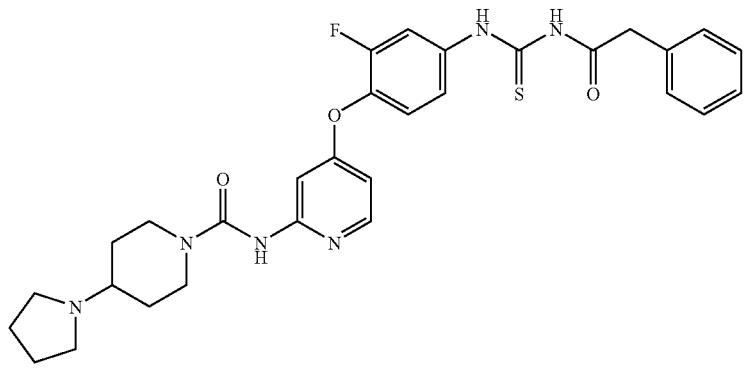
Ex. 40
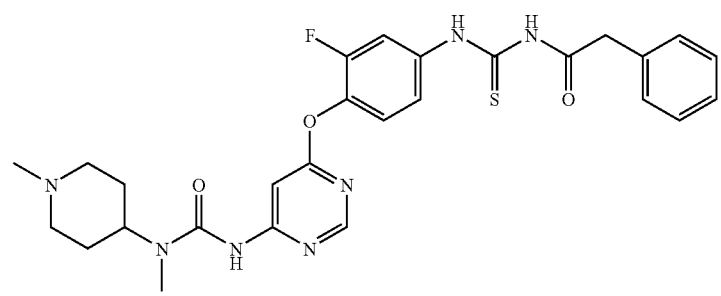
Ex. 41
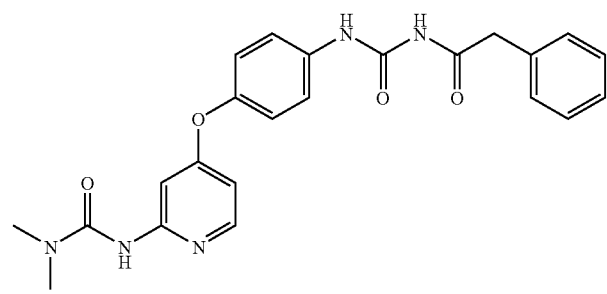
Ex. 42
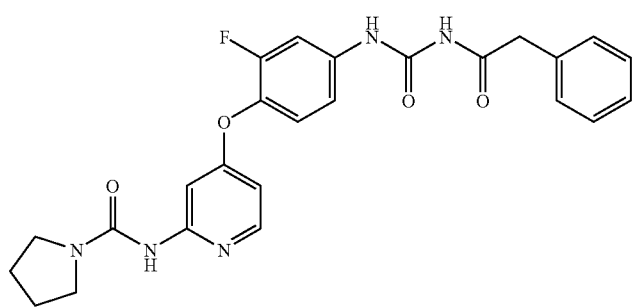
Ex. 43

TABLE 15-continued
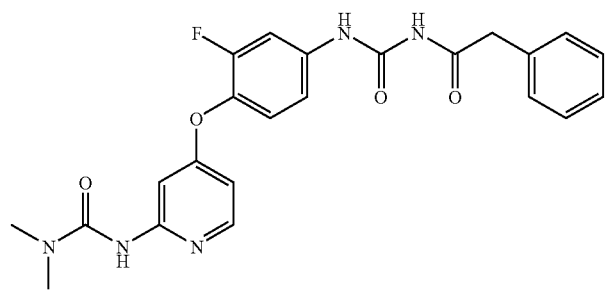
Ex. 44
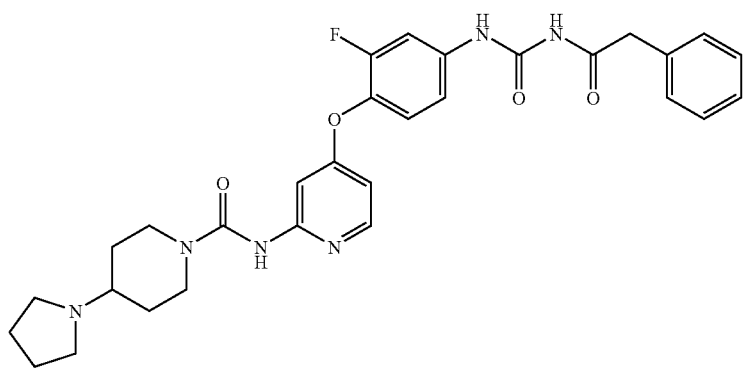
Ex. 45
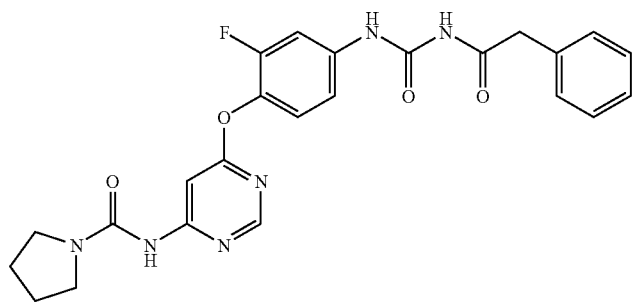
Ex. 46
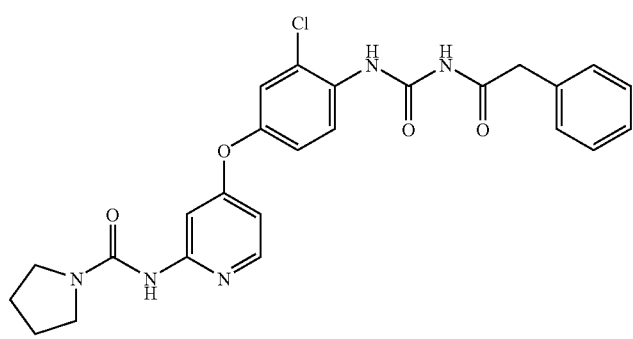
Ex. 47

TABLE 15-continued
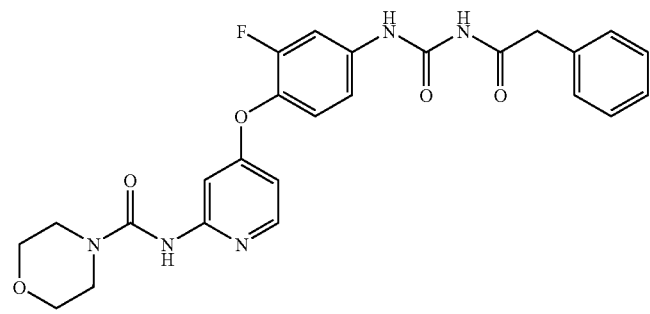
Ex. 48
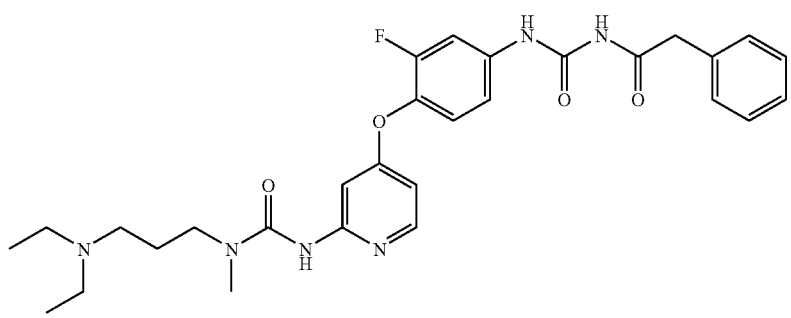
Ex. 49
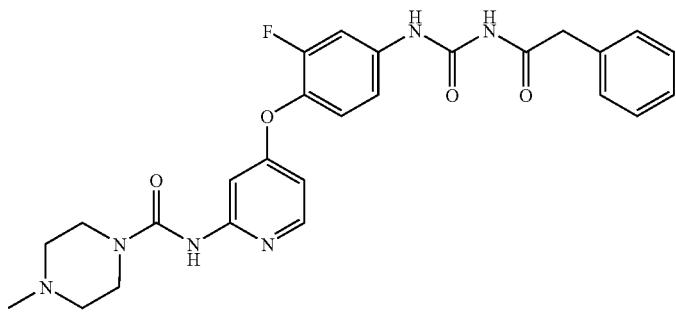
Ex. 50
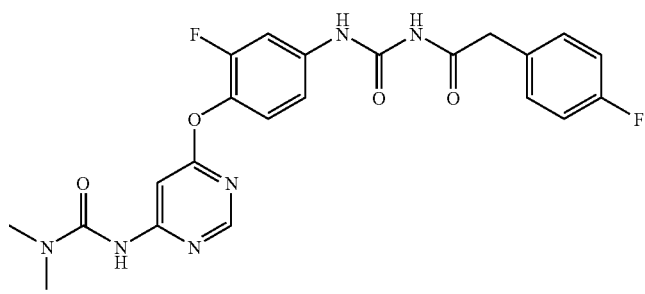
Ex. 51
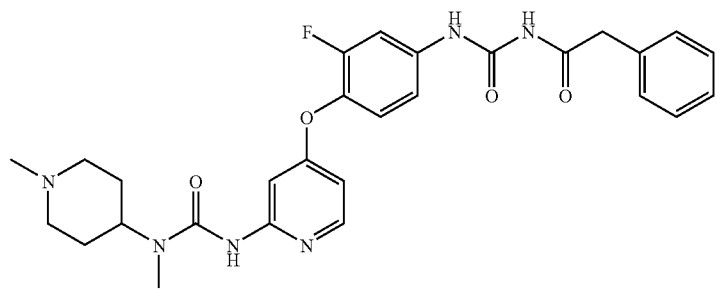
Ex. 52

TABLE 15-continued
TABLE 16
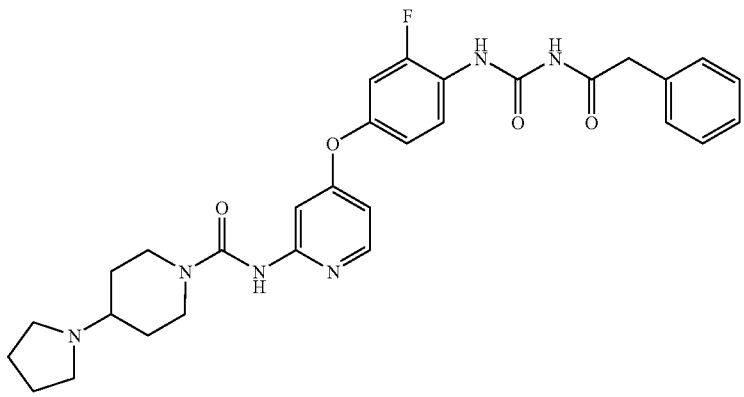
Ex. 53
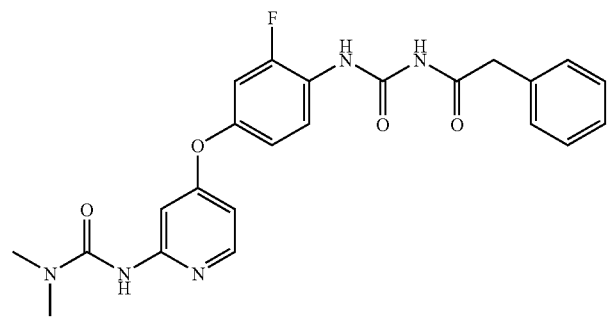
Ex. 54
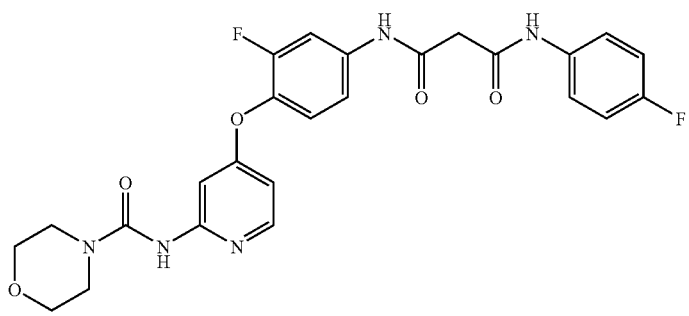
Ex. 55
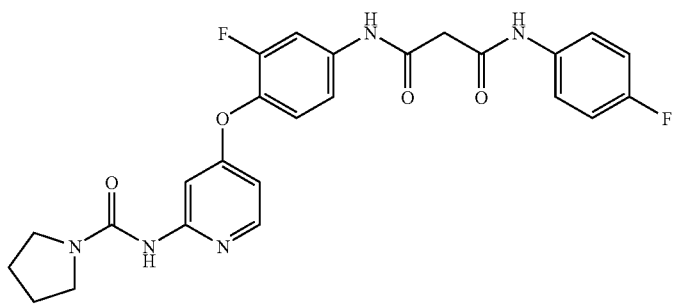
Ex. 56

TABLE 16-continued
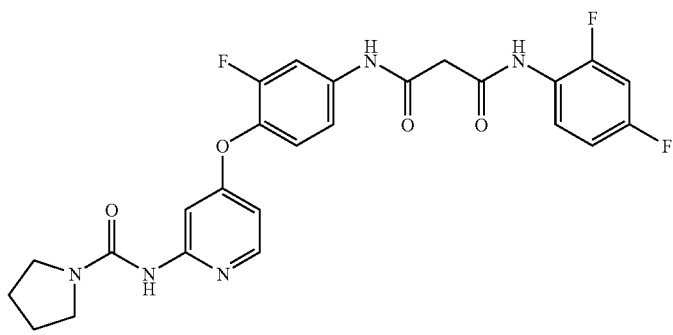
Ex. 57
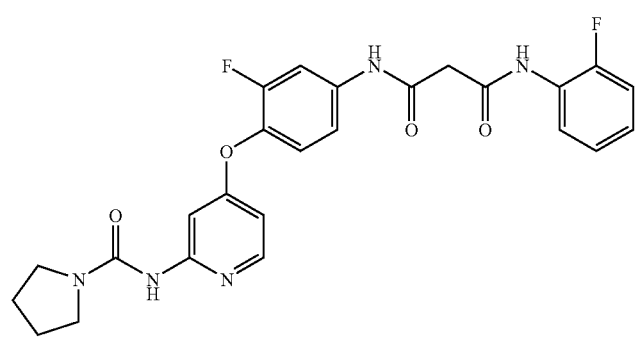
Ex. 58
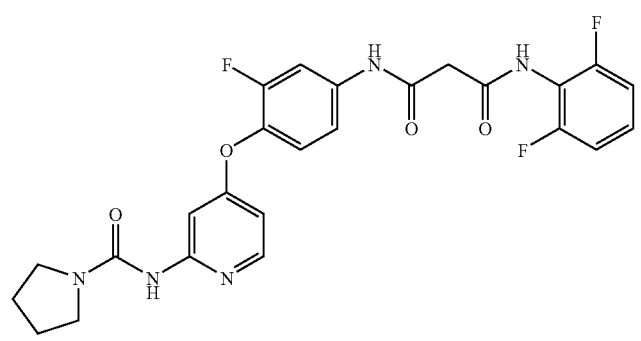
Ex. 59
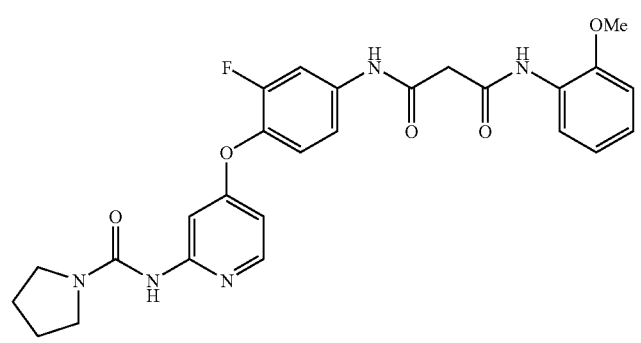
Ex. 60

TABLE 16-continued
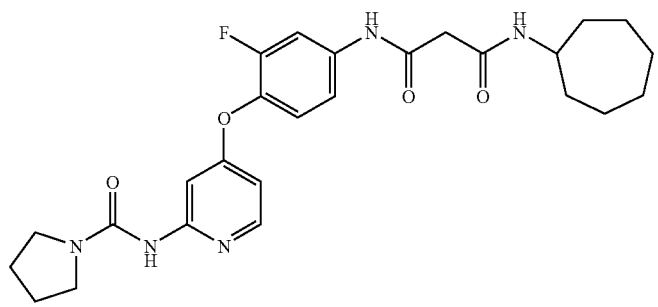
Ex. 61
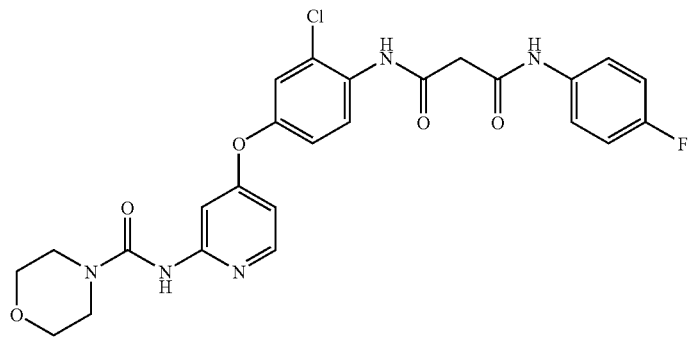
Ex. 62
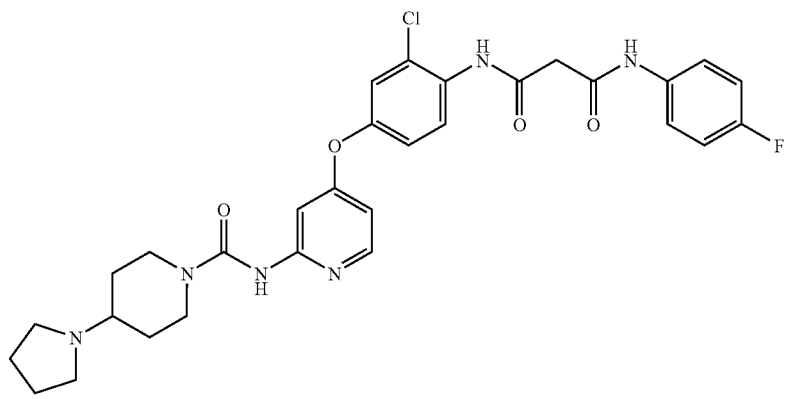
Ex. 63
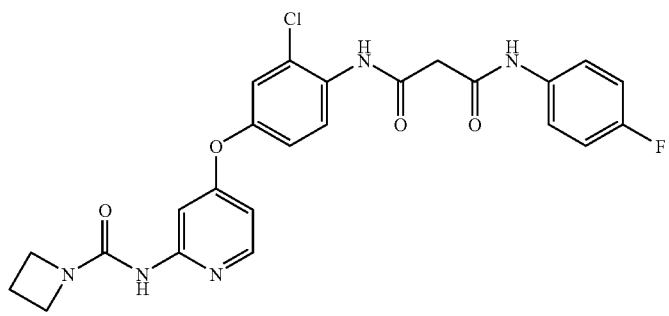
Ex. 64

TABLE 16-continued
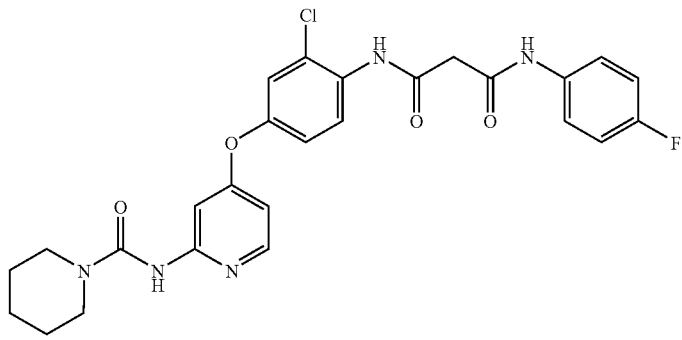
Ex. 65
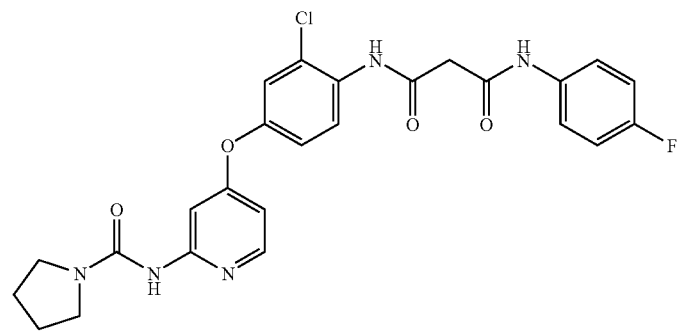
Ex. 66
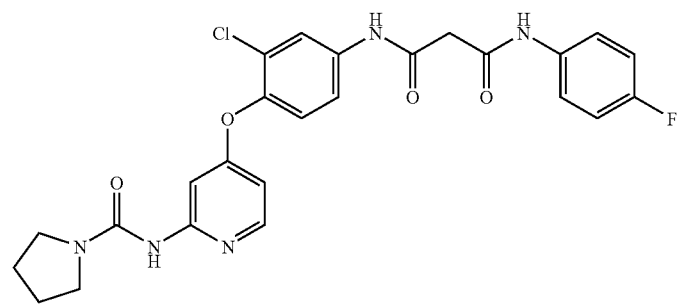
Ex. 67
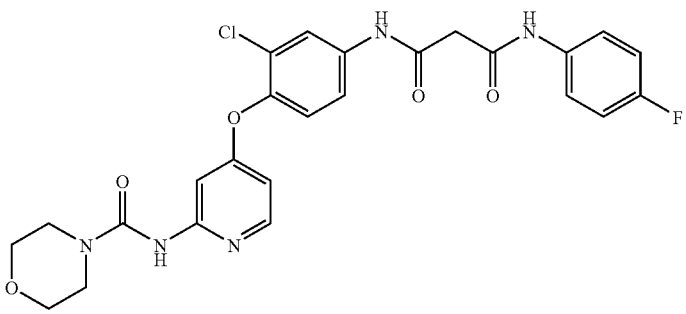
Ex. 68

TABLE 16-continued
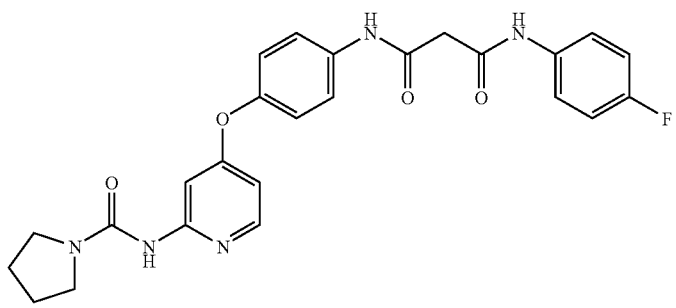
Ex. 69
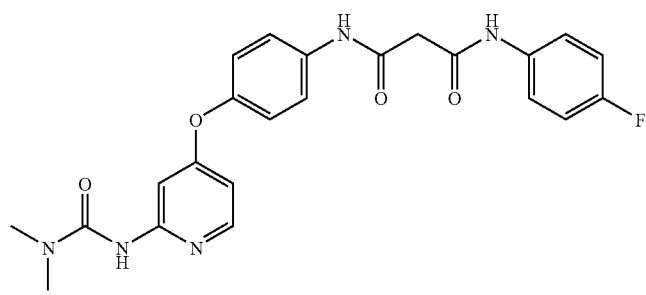
Ex. 70
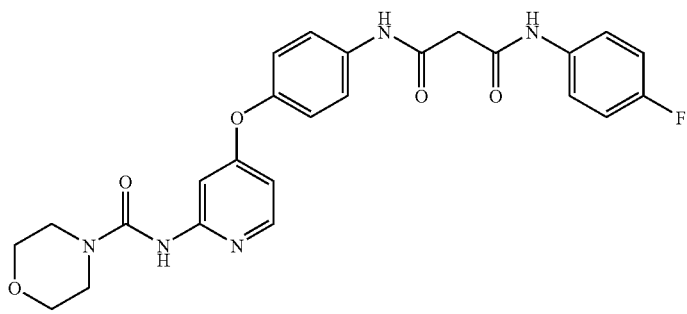
Ex. 71
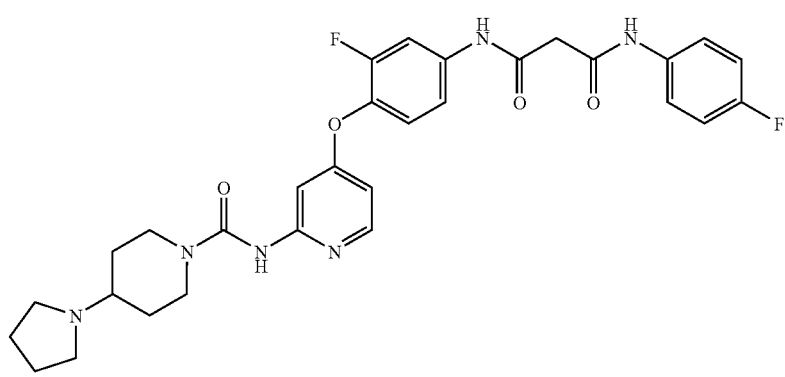
Ex. 72

TABLE 16-continued
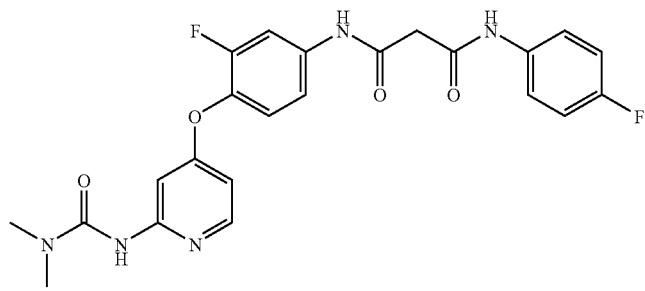
Ex. 73
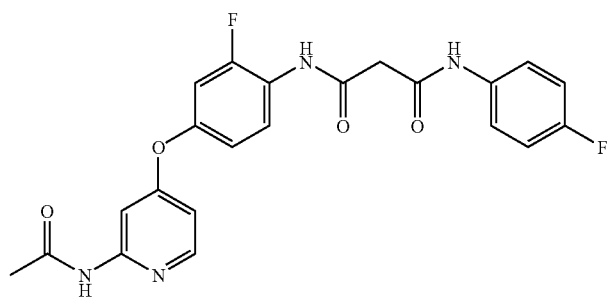
Ex. 74
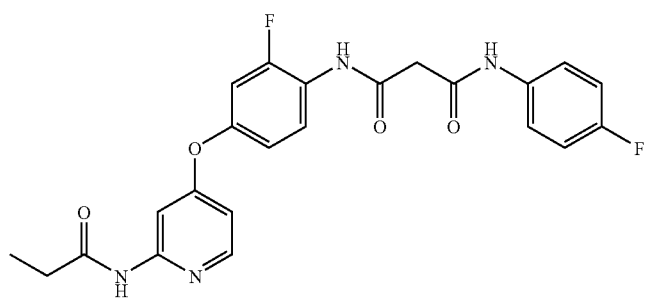
Ex. 75
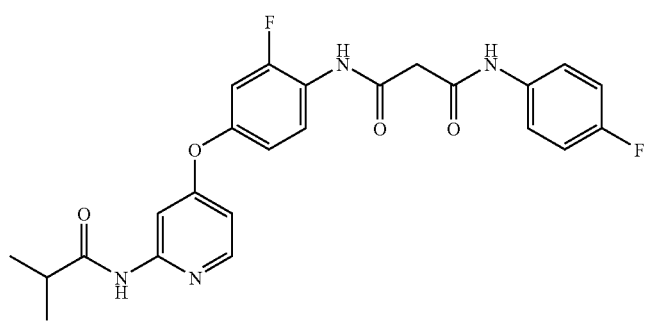
Ex. 76

TABLE 16-continued
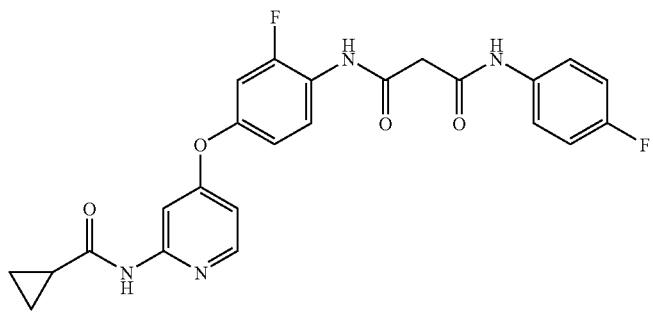
Ex. 77
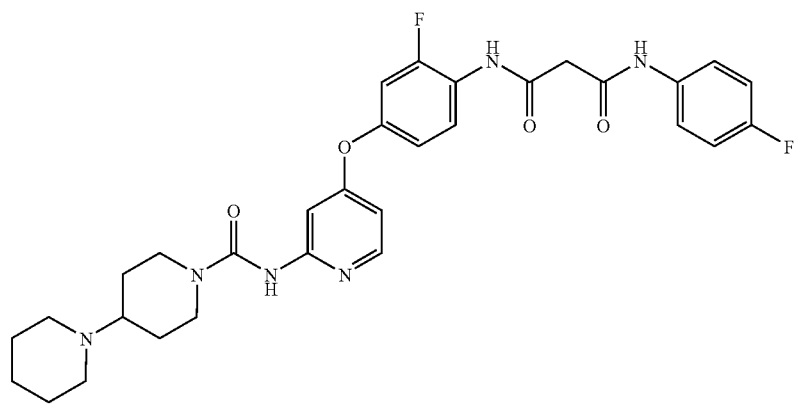
Ex. 78
TABLE 17
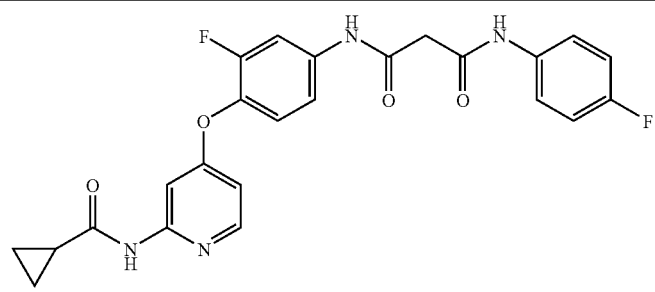
Ex. 79
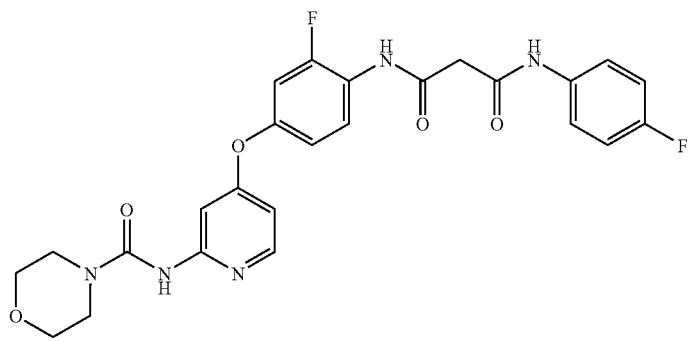
Ex. 80

TABLE 17-continued
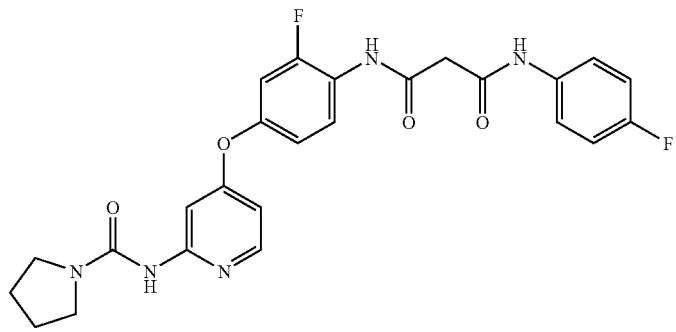
Ex. 81
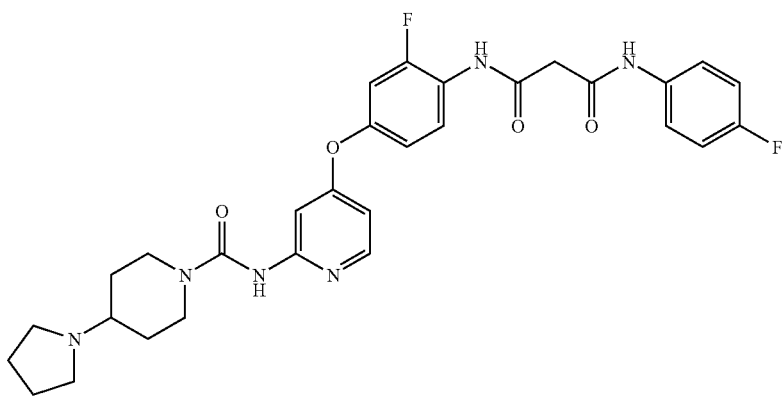
Ex. 82
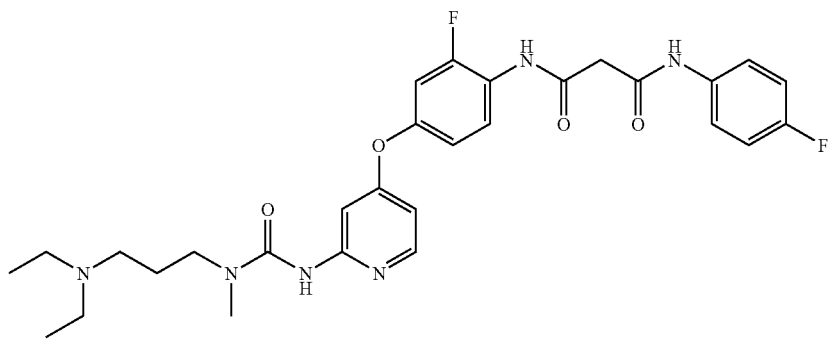
Ex. 83
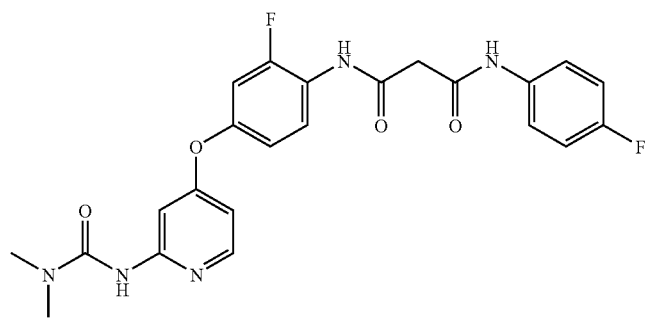
Ex. 84

TABLE 17-continued
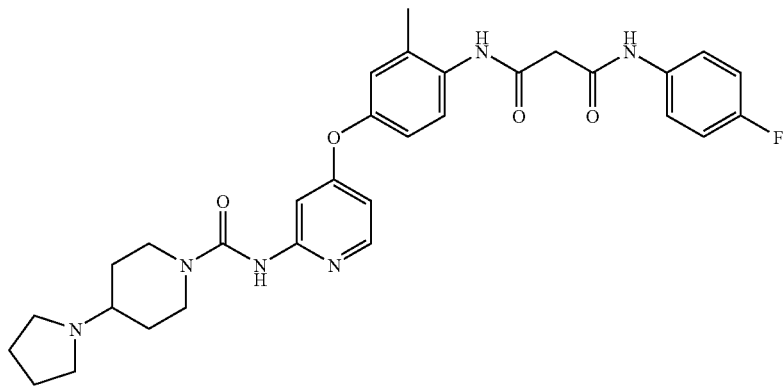
Ex. 85
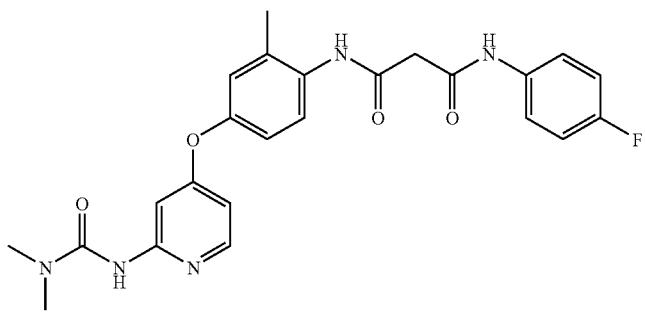
Ex. 86
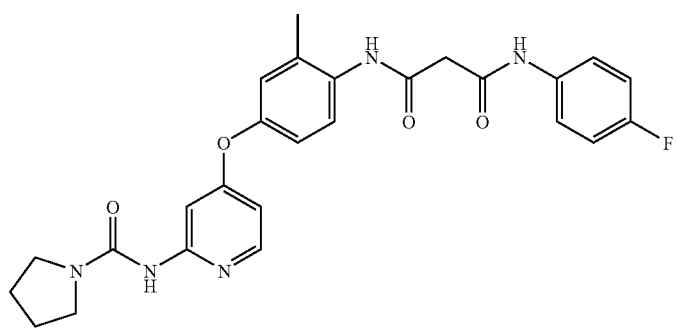
Ex. 87
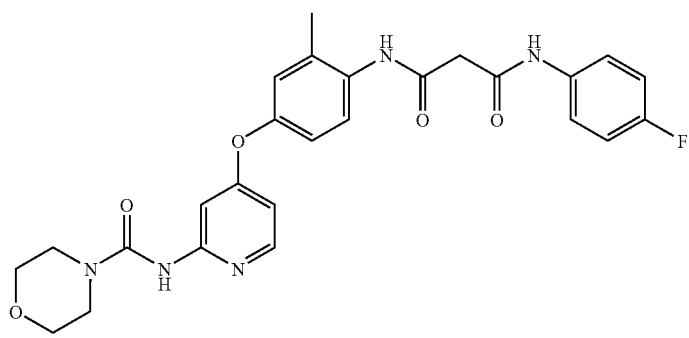
Ex. 88

TABLE 17-continued
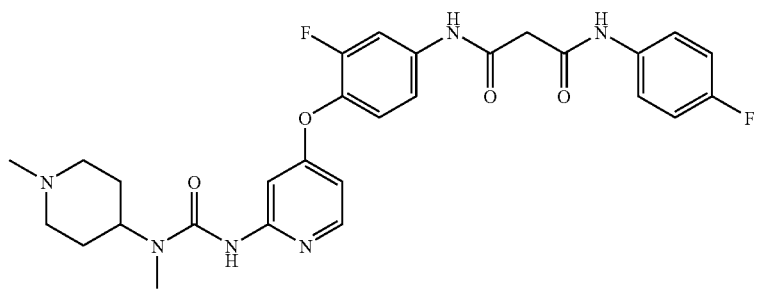
Ex. 89
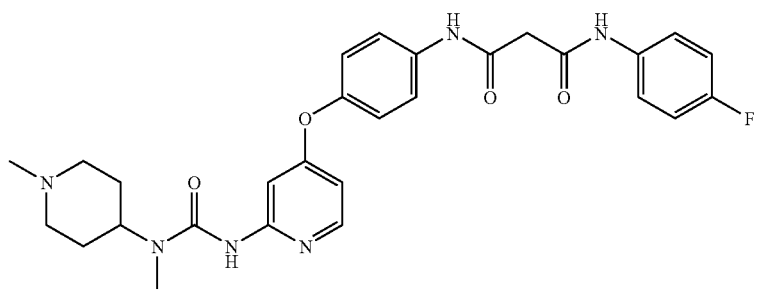
Ex. 90
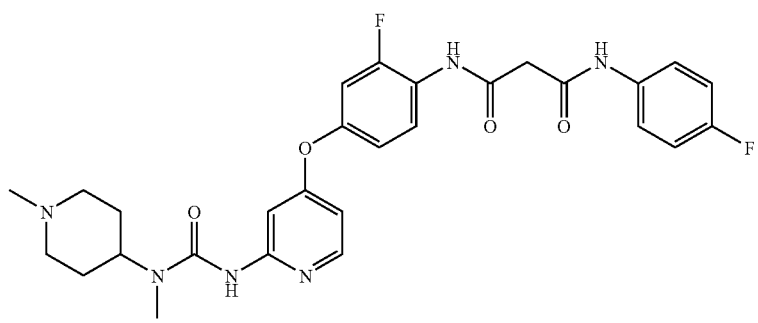
Ex. 91
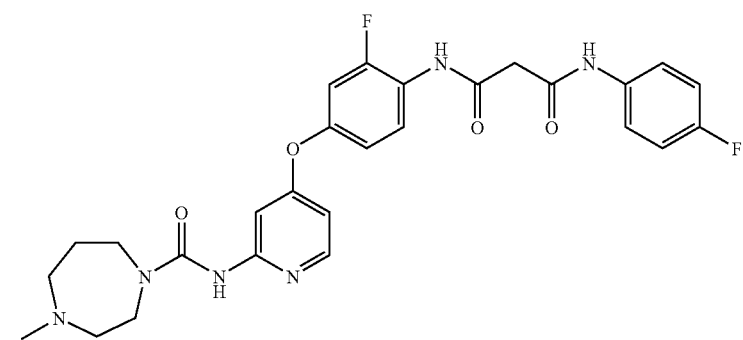
Ex. 92

TABLE 17-continued
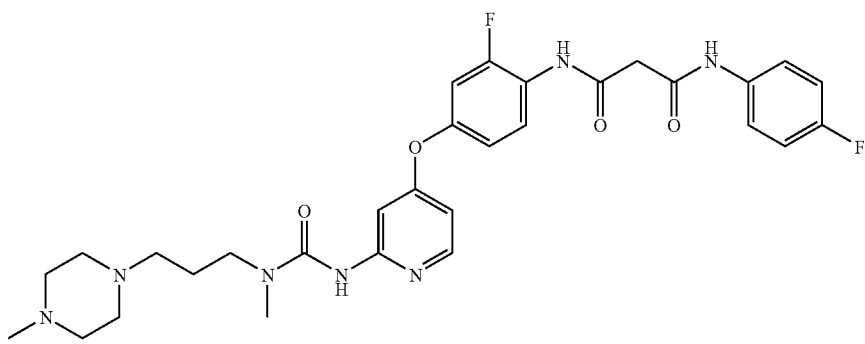
Ex. 93
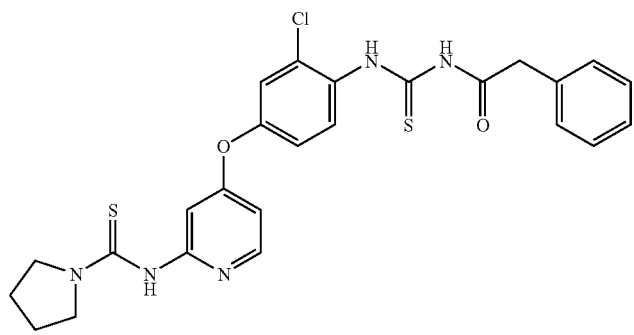
Ex. 94
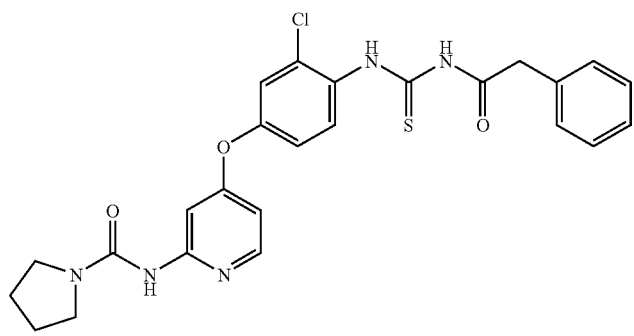
Ex. 95
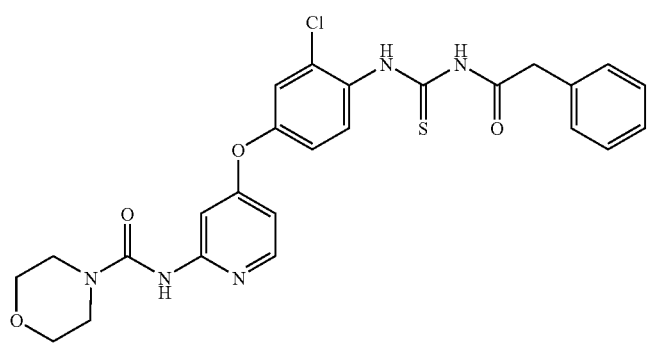
Ex. 96

TABLE 17-continued
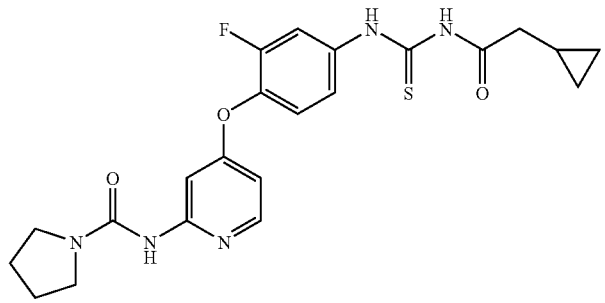
Ex. 97
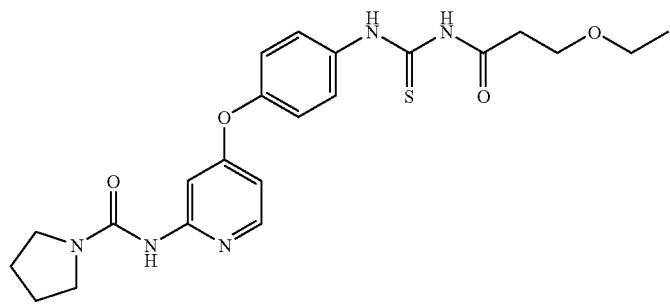
Ex. 98
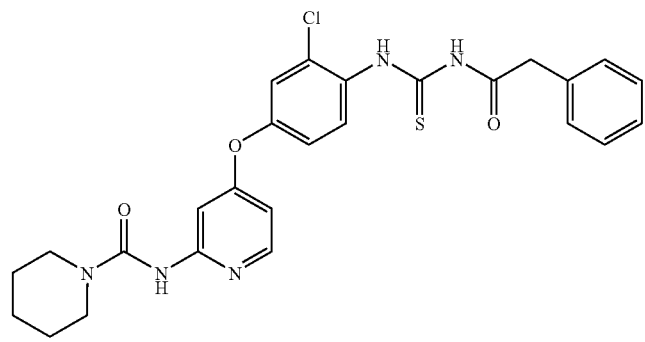
Ex. 99
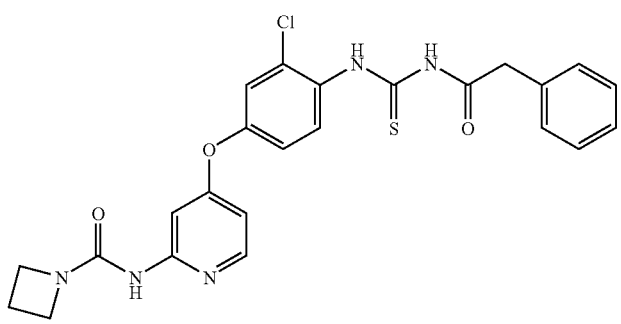
Ex. 100

TABLE 17-continued
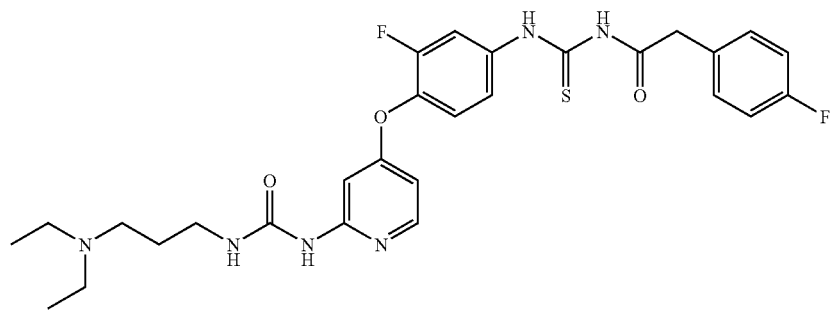
Ex. 101
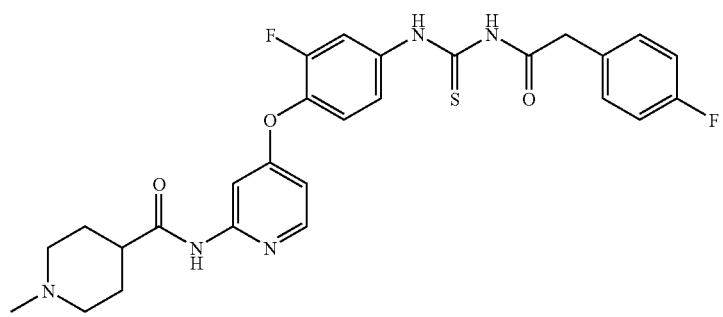
Ex. 102
TABLE 18
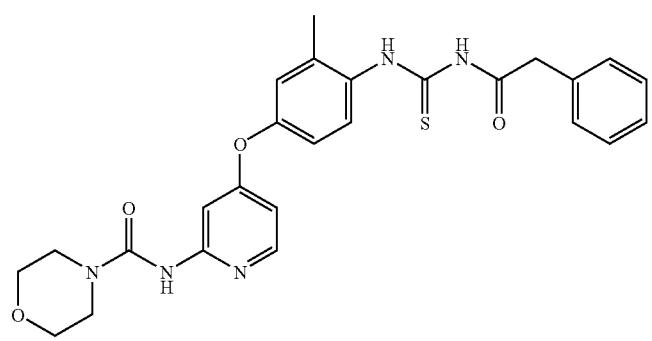
Ex. 103
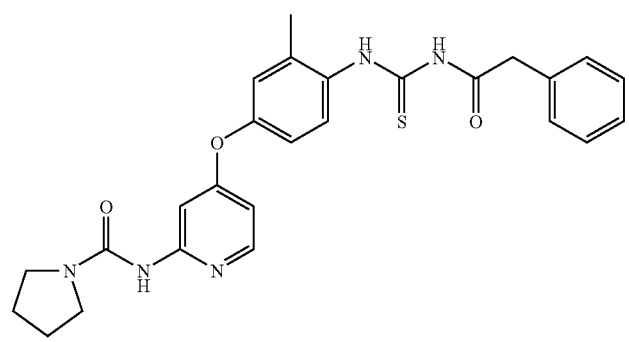
Ex. 104

TABLE 18-continued
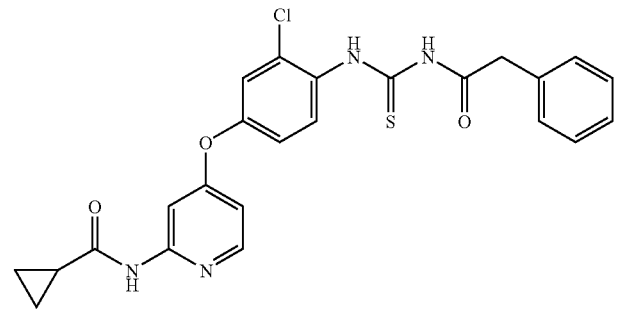
Ex. 105
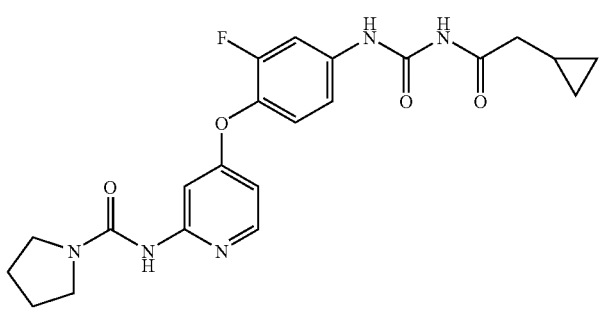
Ex. 106
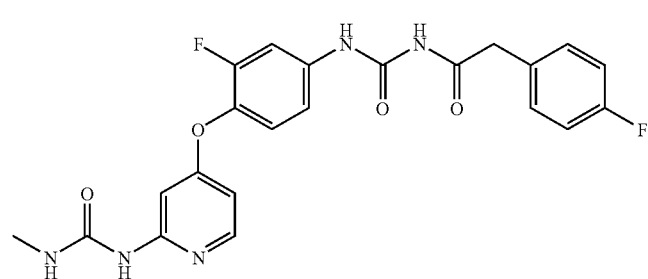
Ex. 107
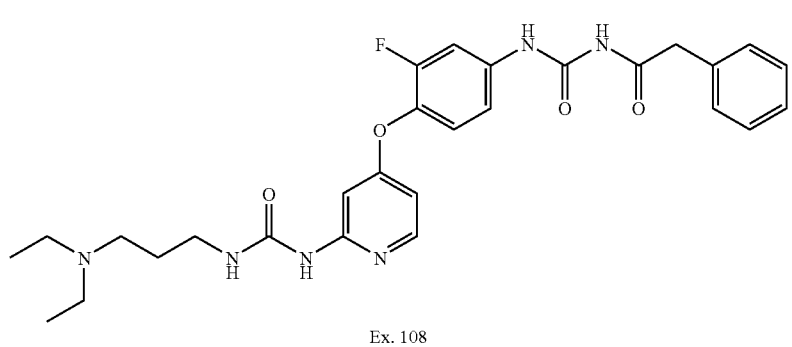
Ex. 108
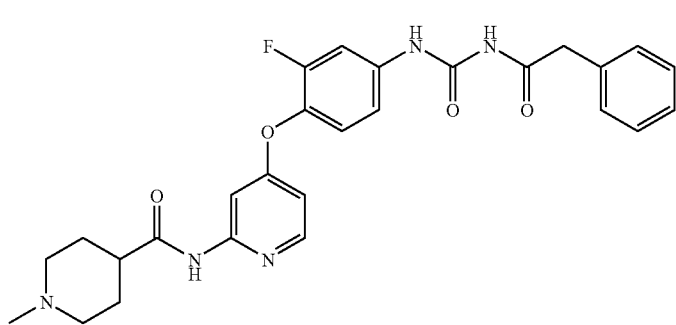
Ex. 109

TABLE 18-continued
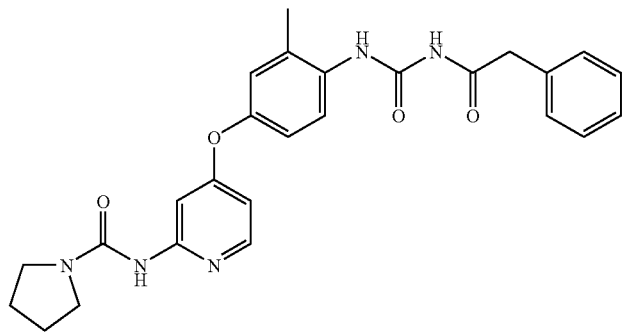
Ex. 110
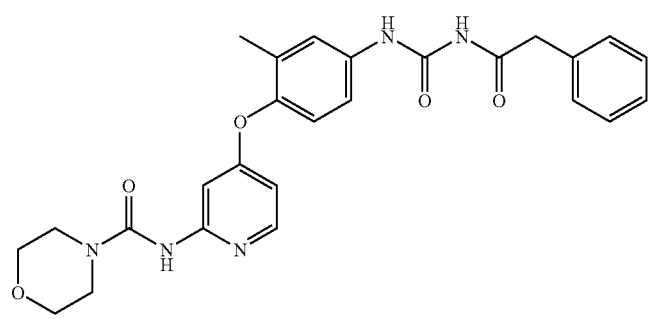
Ex. 111
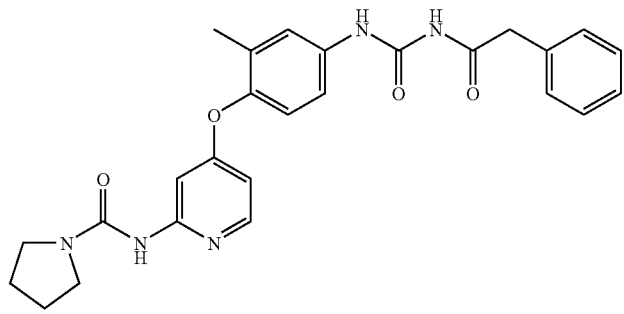
Ex. 112
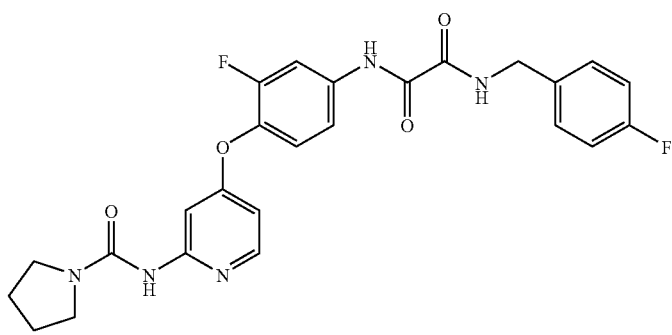
Ex. 113

TABLE 18-continued
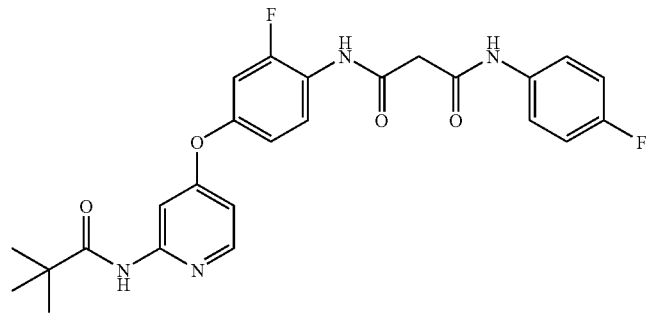
Ex. 114
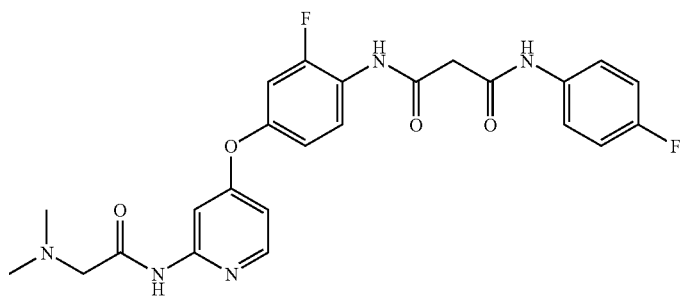
Ex. 115
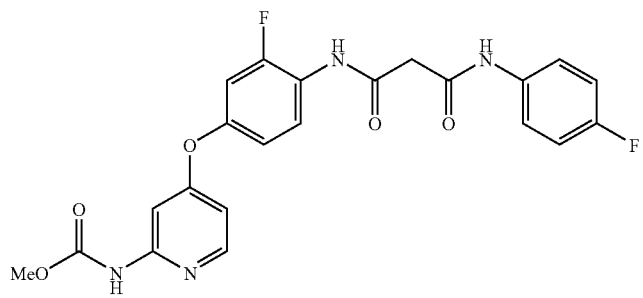
Ex. 116
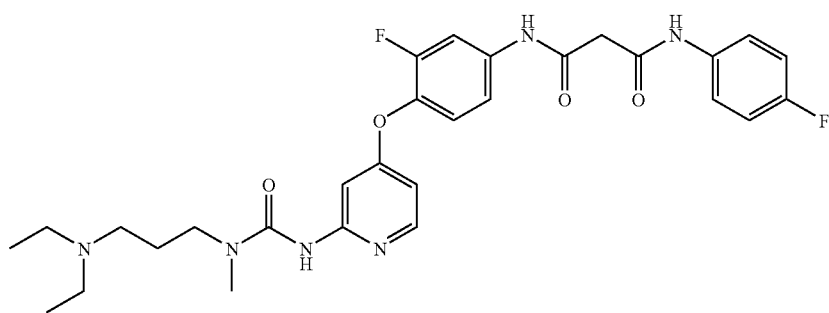
Ex. 117

TABLE 18-continued
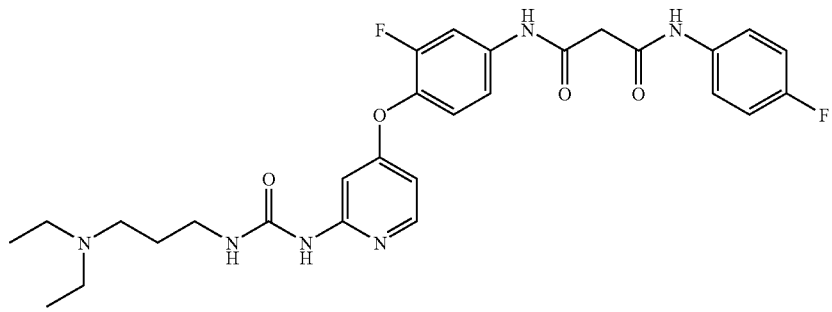
Ex. 118
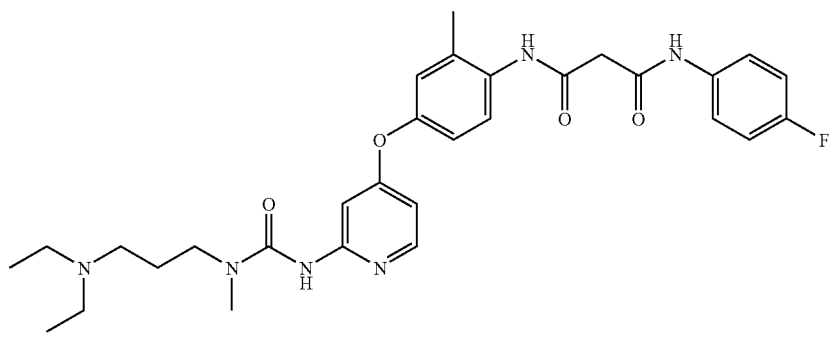
Ex. 119
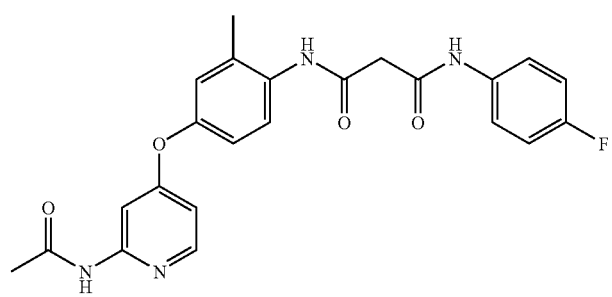
Ex. 120
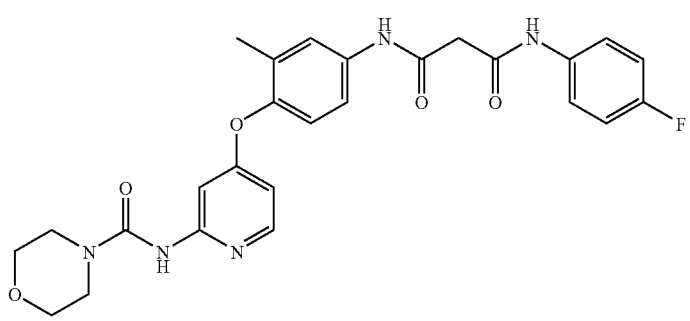
Ex. 121

TABLE 18-continued
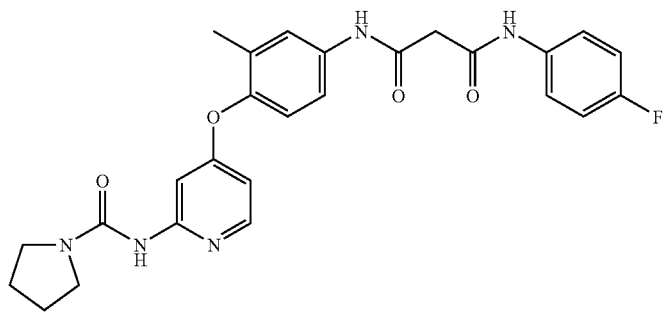
Ex. 122
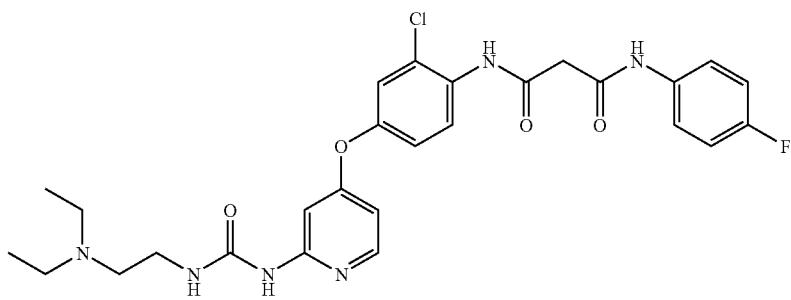
Ex. 123
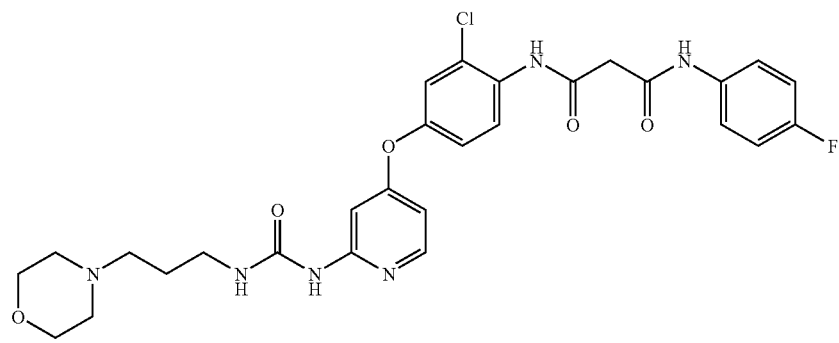
Ex. 124
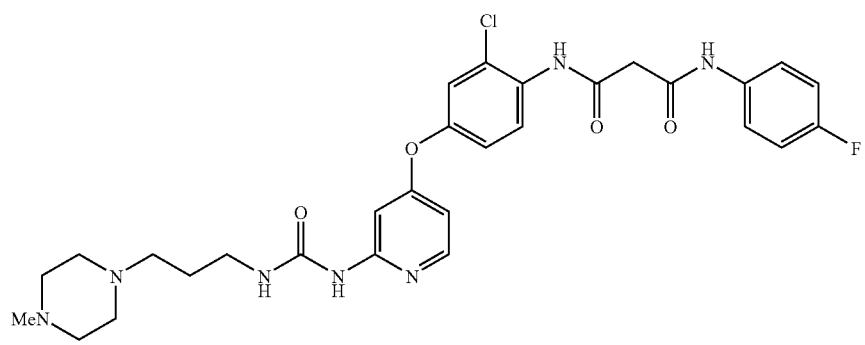
Ex. 125

TABLE 19
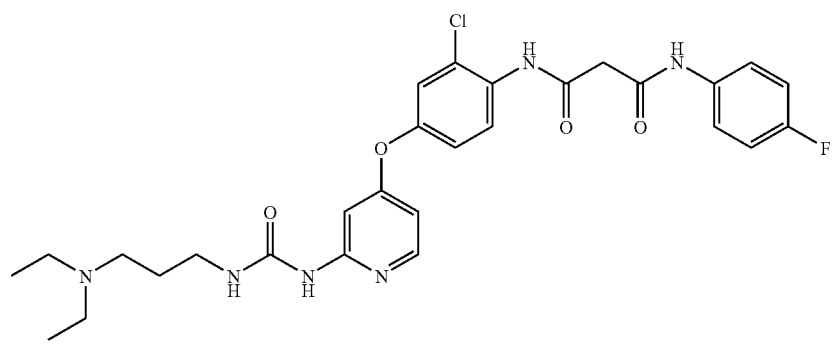
Ex. 126
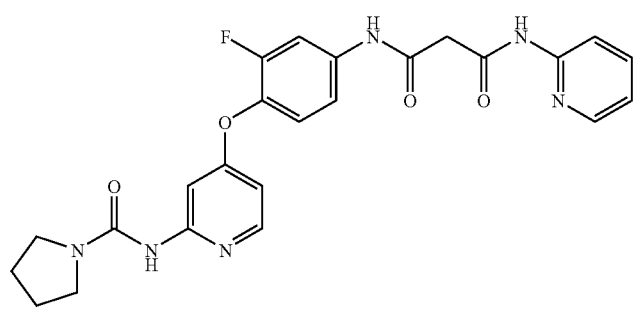
Ex. 127
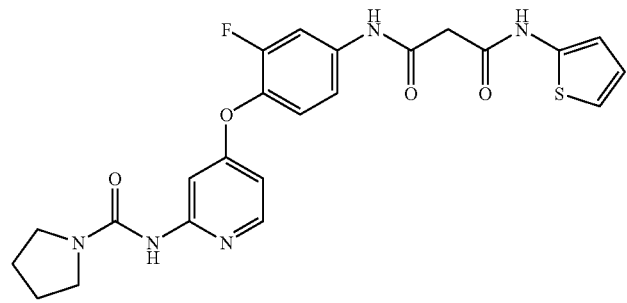
Ex. 128
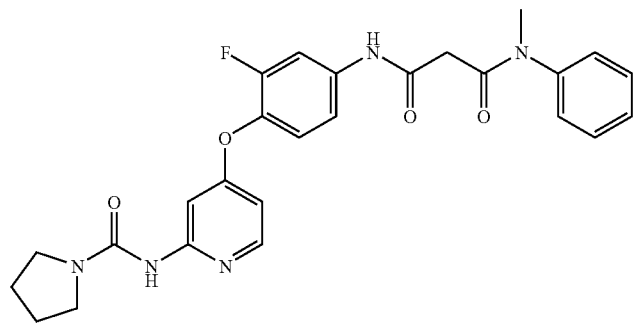
Ex. 129

TABLE 19-continued
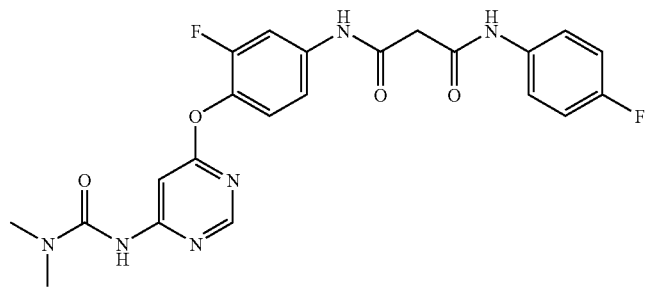
Ex. 130
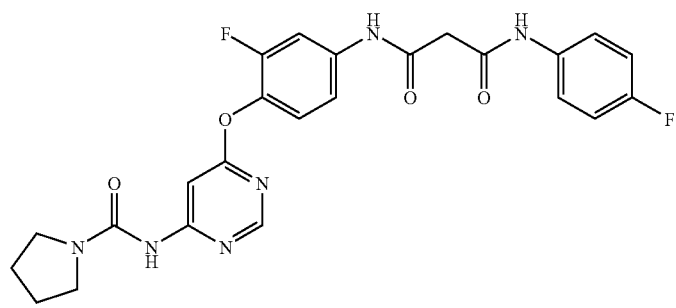
Ex. 131
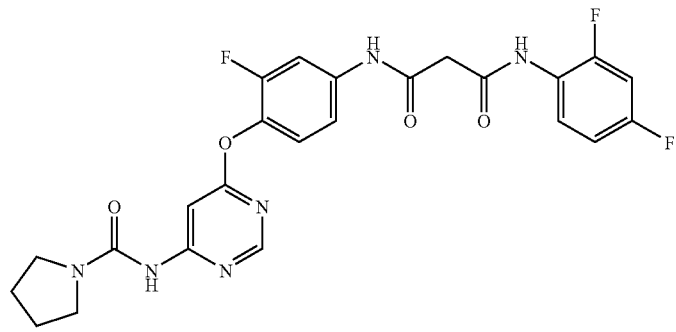
Ex. 132
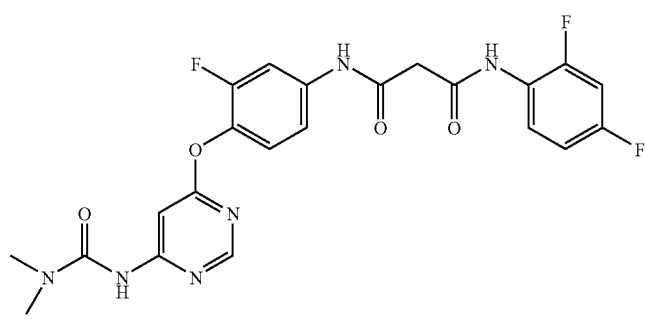
Ex. 133

TABLE 19-continued
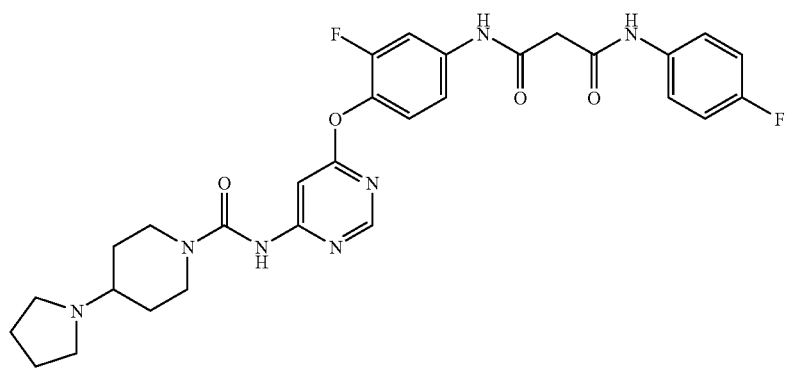
Ex. 134
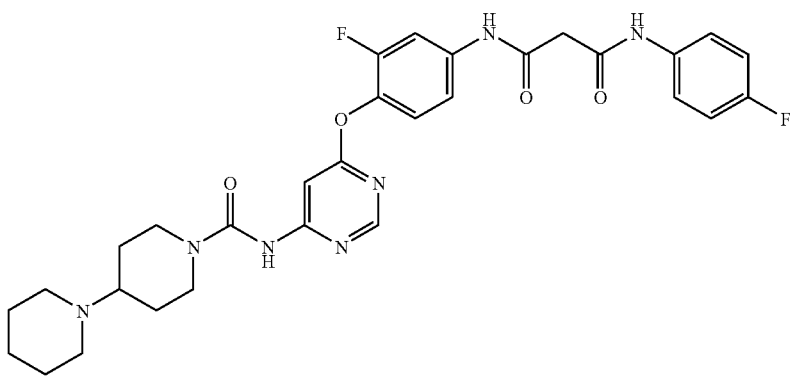
Ex. 135
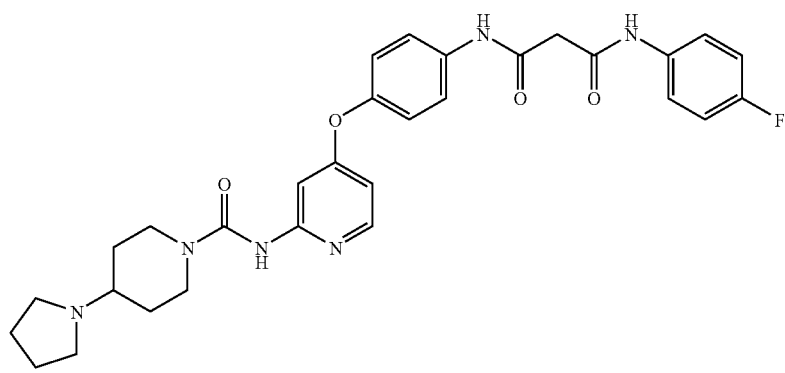
Ex. 136
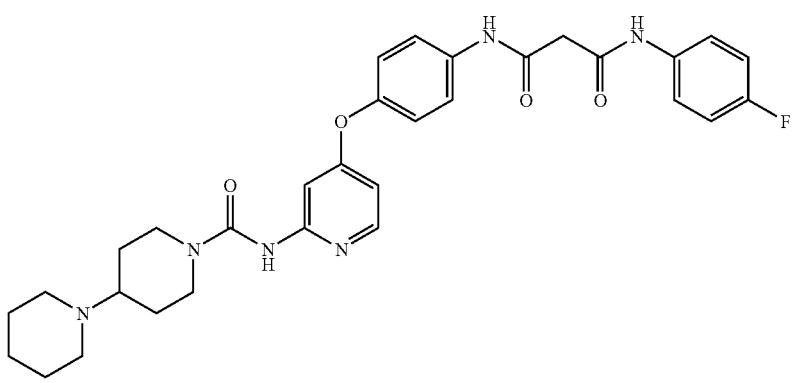
Ex. 137

TABLE 19-continued
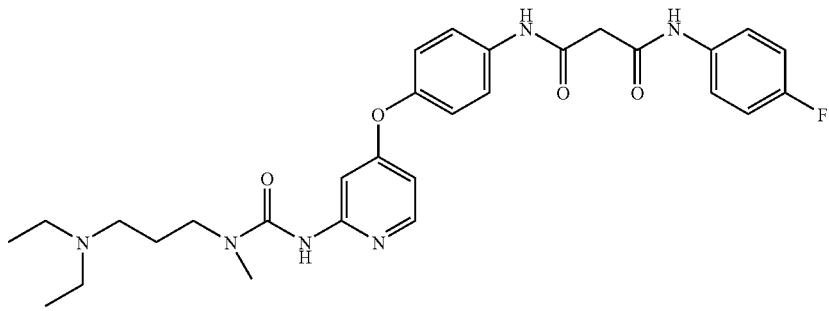
Ex. 138
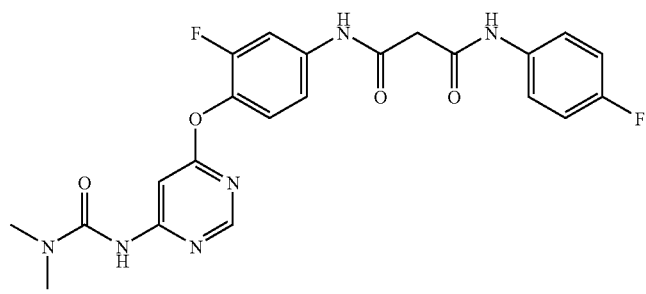
Ex. 139
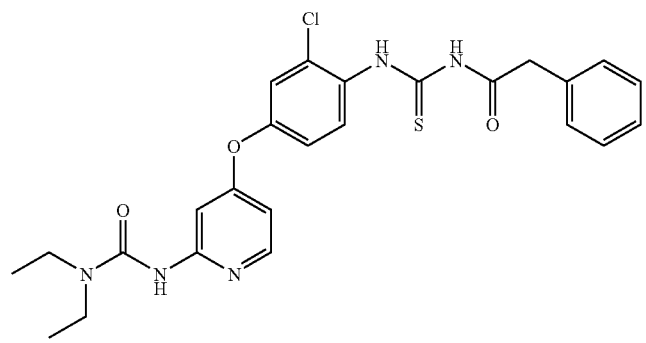
Ex. 140
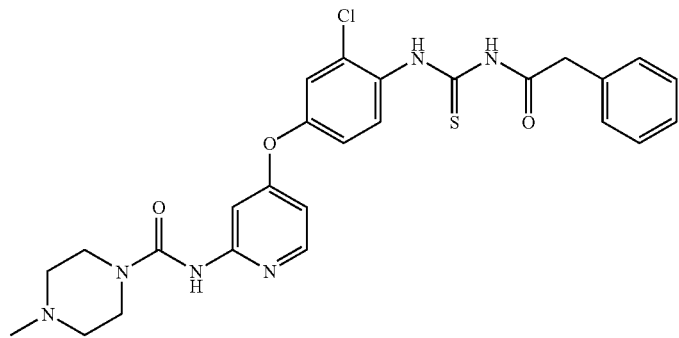
Ex. 141

TABLE 19-continued
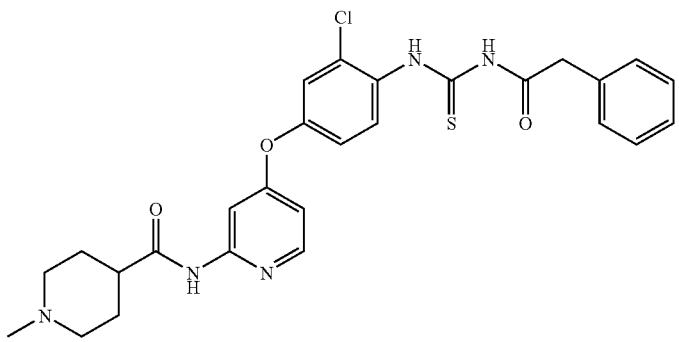
Ex. 142
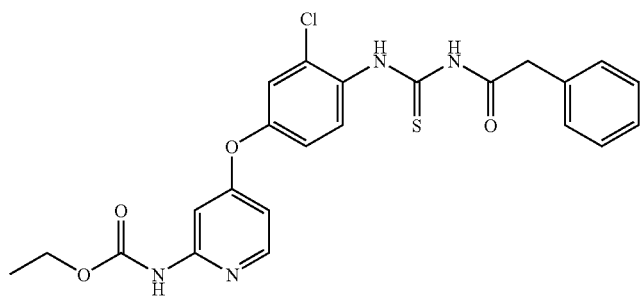
Ex. 143
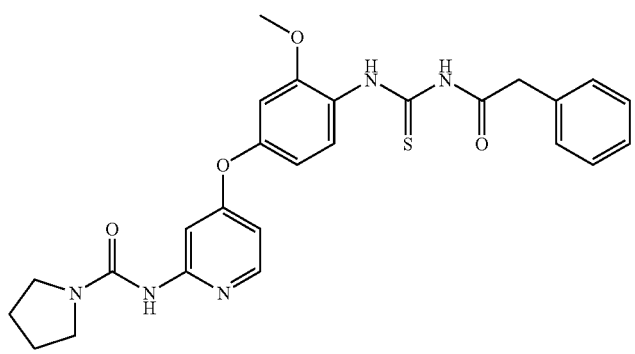
Ex. 144
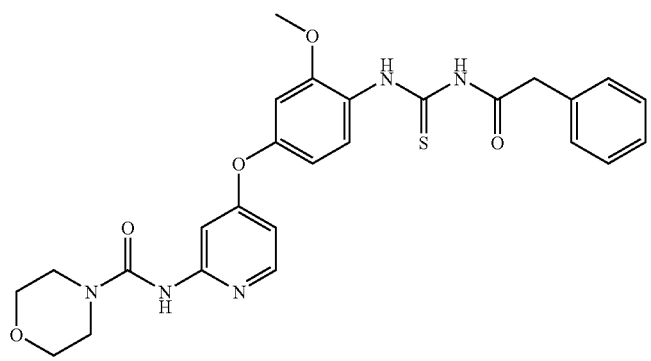
Ex. 145

TABLE 19-continued
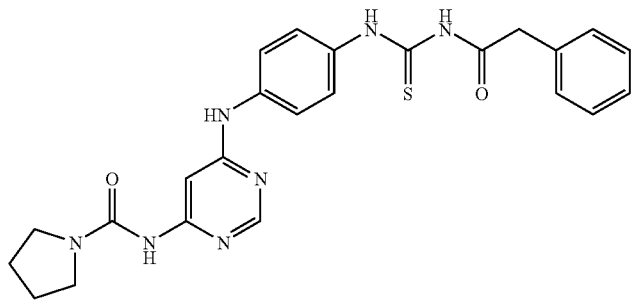
Ex. 146
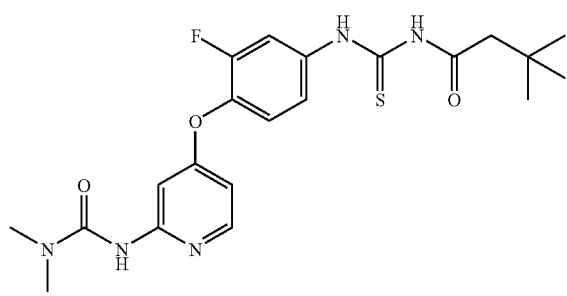
Ex. 147
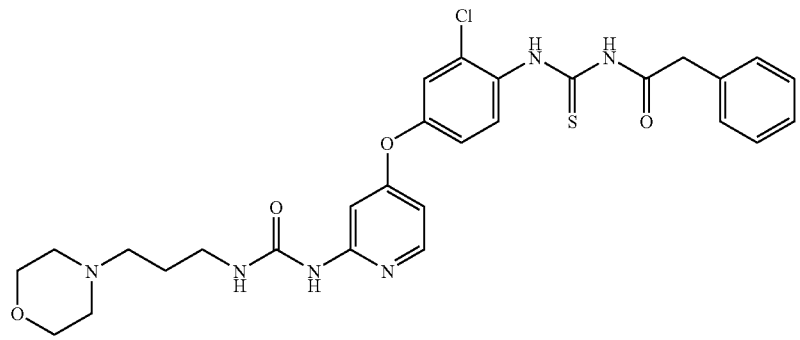
Ex. 148
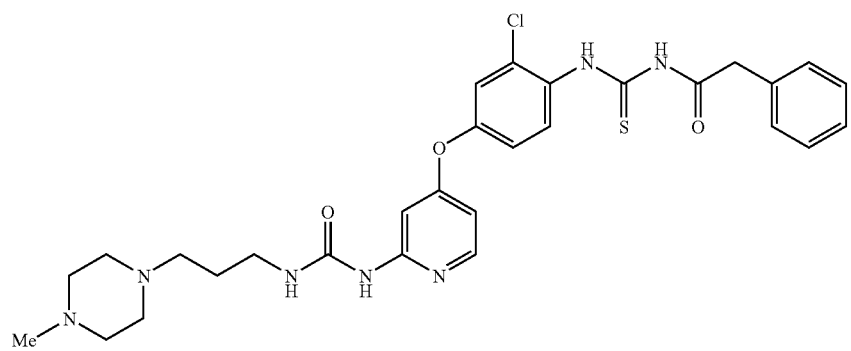
Ex. 149

TABLE 20
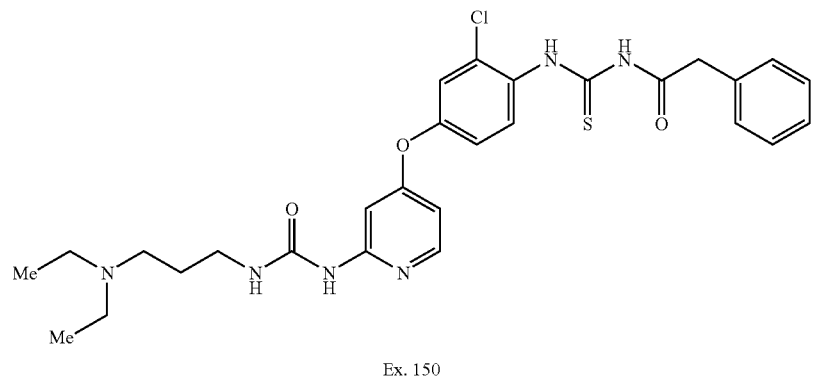
Ex. 150
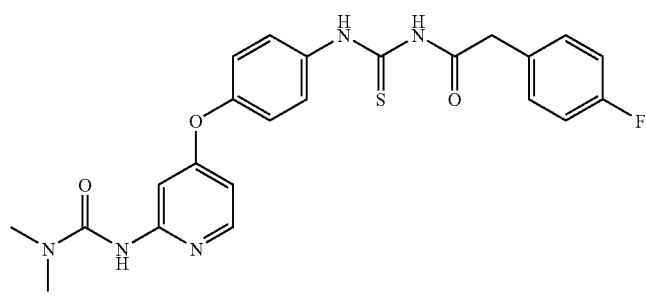
Ex. 151
Ex. 152
Ex. 153

TABLE 20-continued
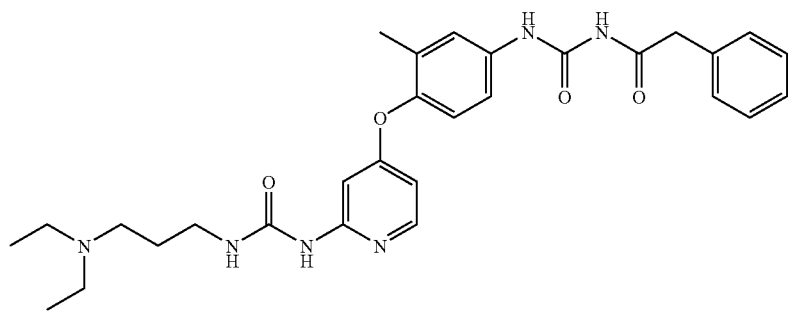
Ex. 154
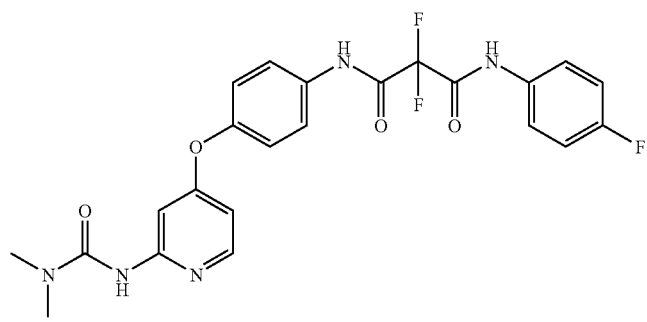
Ex. 155
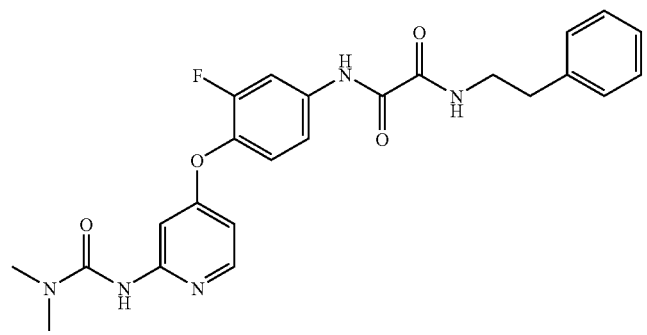
Ex. 156
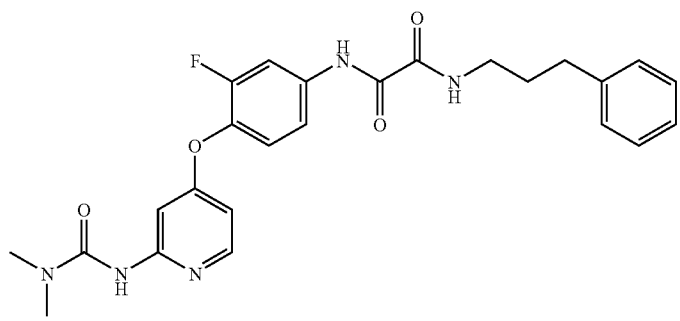
Ex. 157

TABLE 20-continued
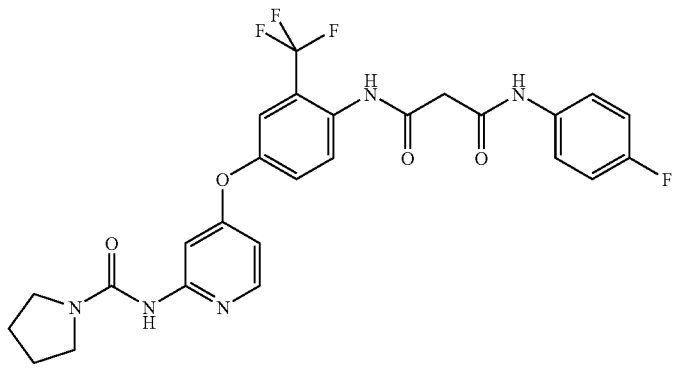
Ex. 158
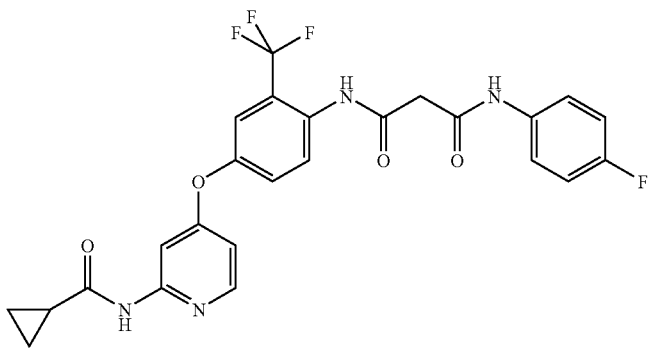
Ex. 159
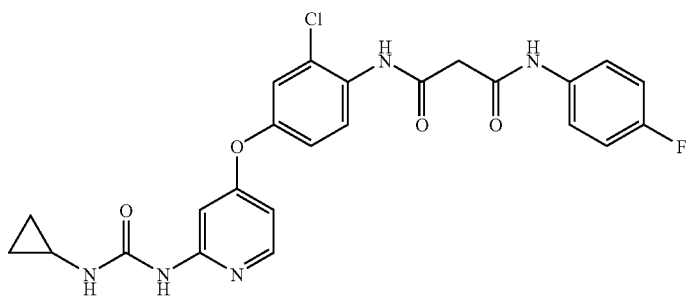
Ex. 160
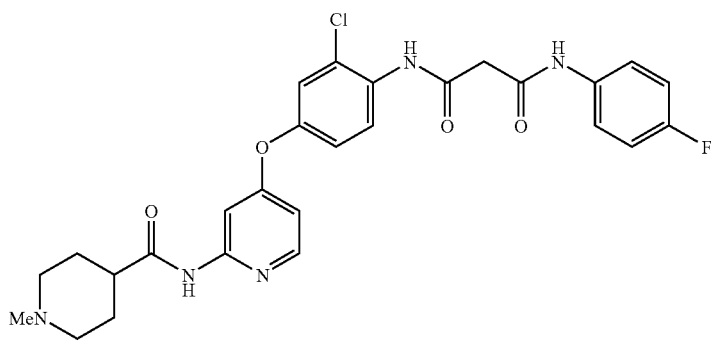
Ex. 161

TABLE 20-continued
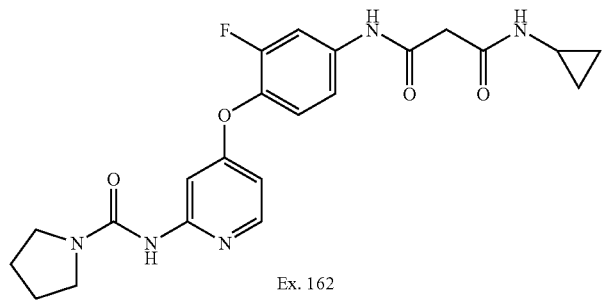
Ex. 162
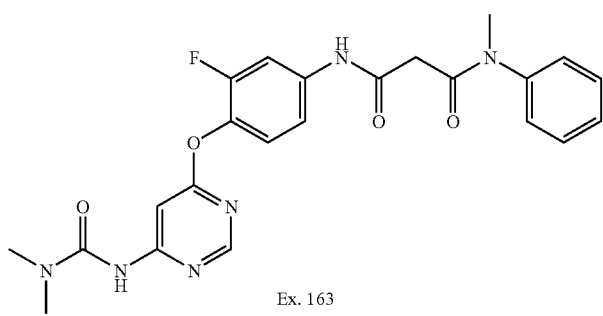
Ex. 163
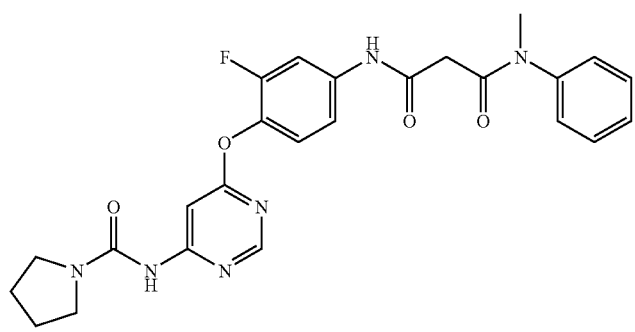
Ex. 164
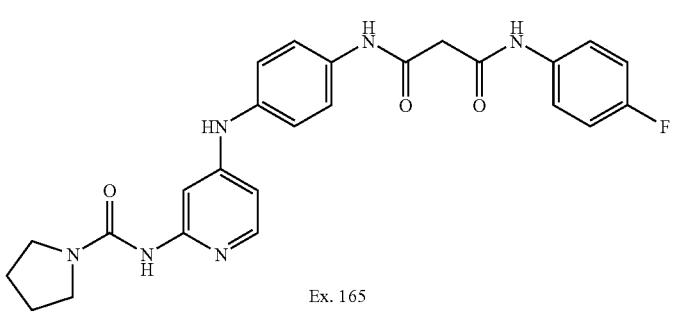
Ex. 165
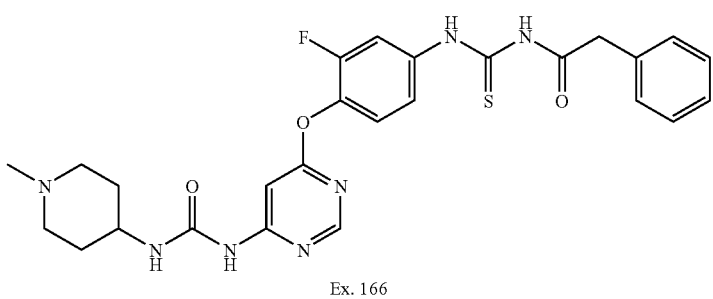
Ex. 166

TABLE 21
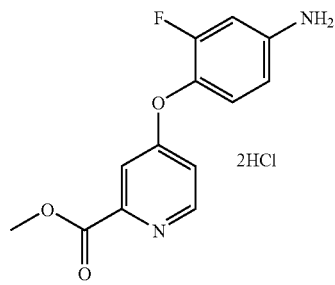
Pro. Ex. 29-1
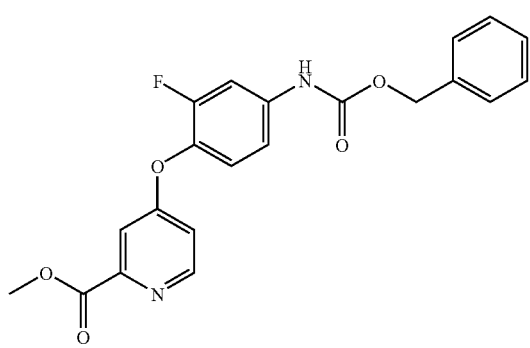
Pro. Ex. 29-2
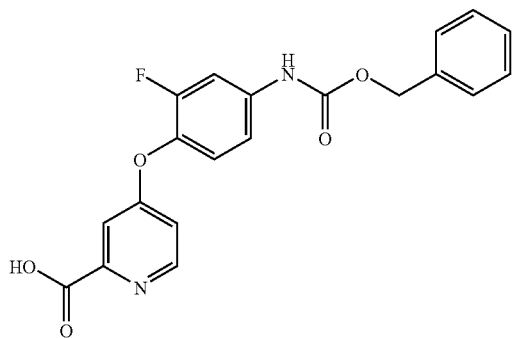
Pro. Ex. 29-3
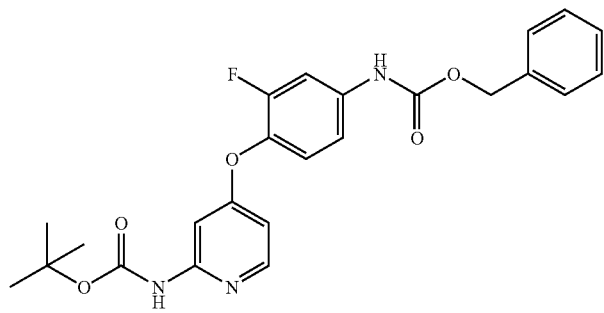
Pro. Ex. 29-4

TABLE 21-continued
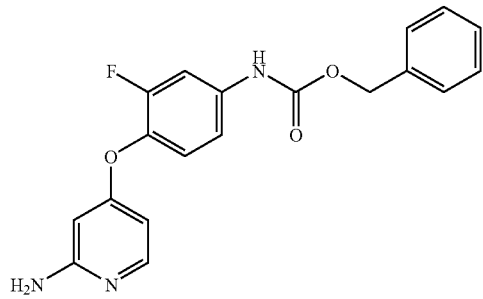
Pro. Ex. 29-5
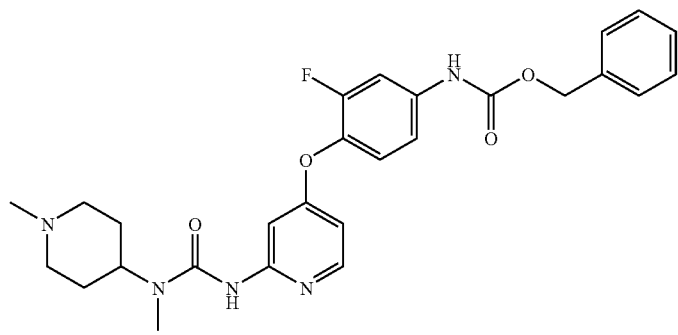
Pro. Ex. 29-6
| TABLE 22 |
| --- |
| 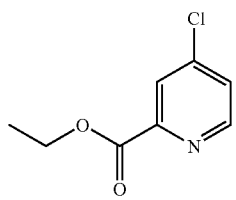<br>Pro. Ex. 118-1 |
| 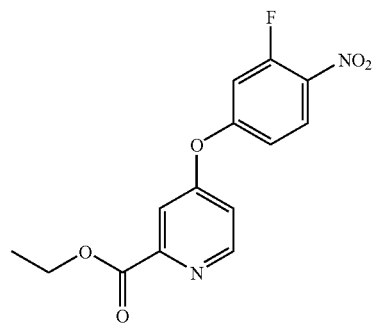<br>Pro. Ex. 118-2 |
| TABLE 22-continued |
| --- |
| 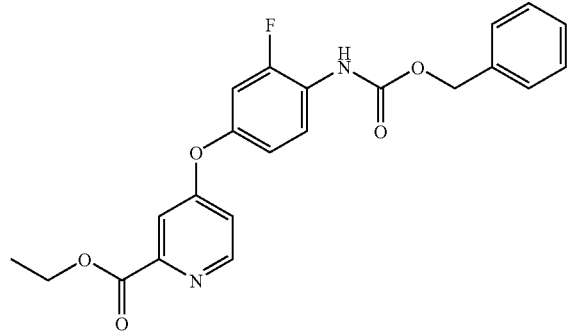<br>Pro. Ex. 118-3 |
| 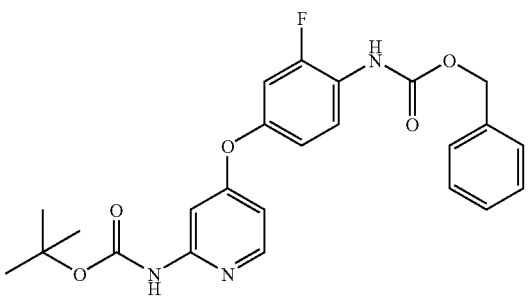<br>Pro. Ex 119-3 |

TABLE 23
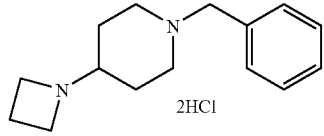
2HCl
Pro. Ex. 167-1
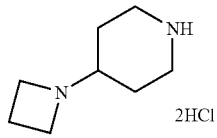
2HCl
Pro. Ex. 167-2
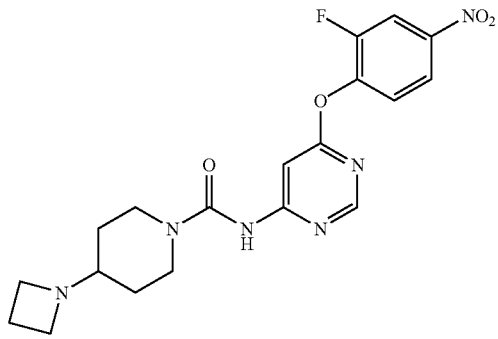
Pro. Ex. 167-3
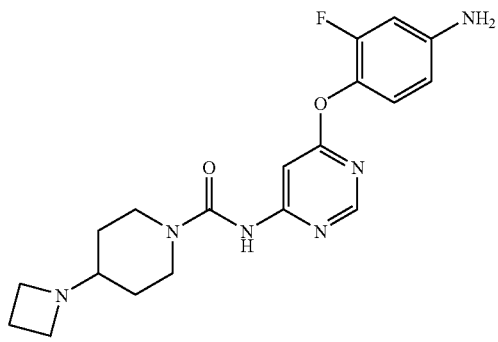
Pro. Ex. 167-4
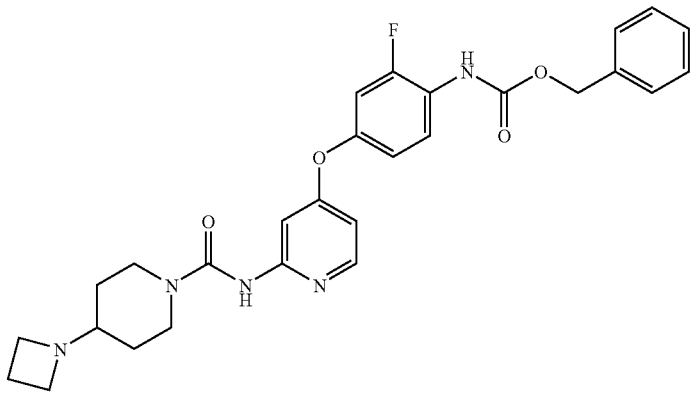
Pro. Ex. 168-1
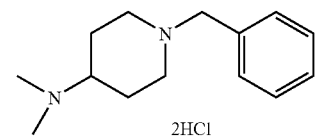
2HCl TABLE 23-continued
Pro. Ex. 169-1
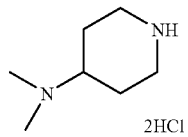
2HCl
Pro. Ex. 169-2
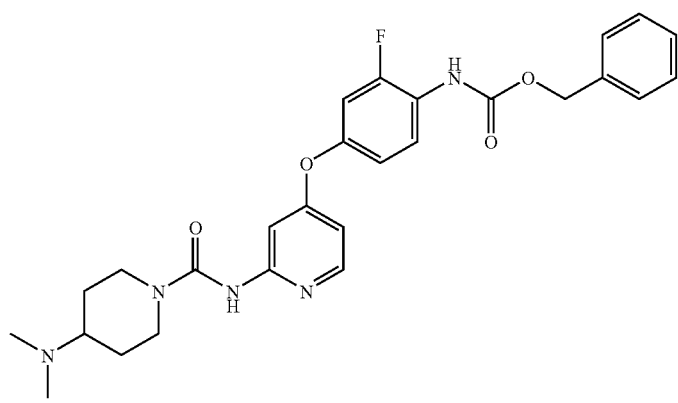
Pro. Ex. 169-3
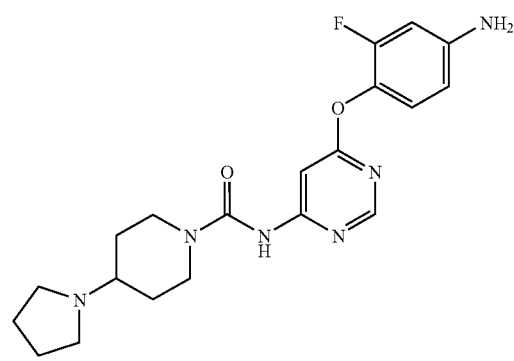
Pro. Ex. 173-1
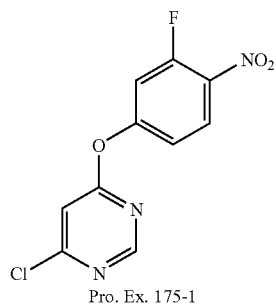
Pro. Ex. 175-1
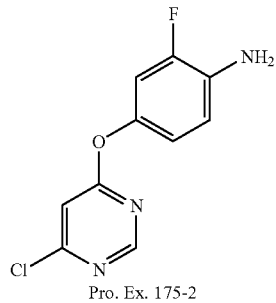
Pro. Ex. 175-2

TABLE 23-continued
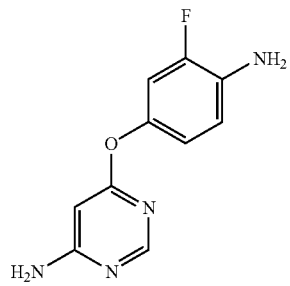
Pro. Ex. 175-3
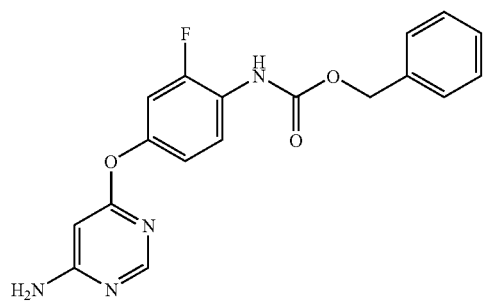
Pro. Ex. 175-4
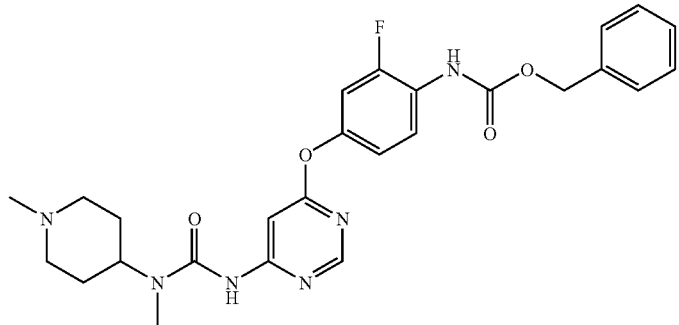
Pro. Ex. 175-5
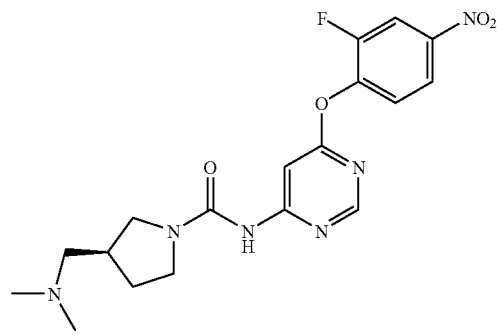
Pro. Ex. 179-1

TABLE 23-continued
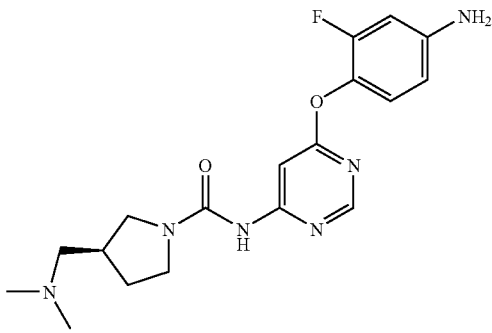
Pro. Ex. 179-2
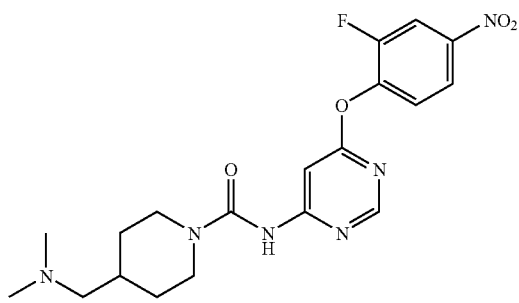
Pro. Ex. 180-1
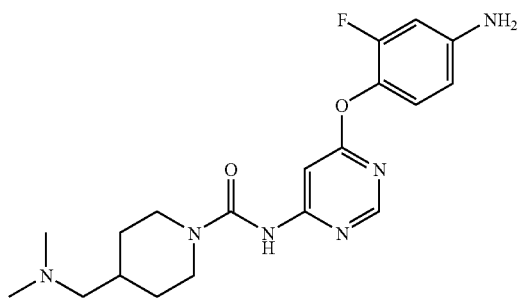
Pro. Ex. 180-2
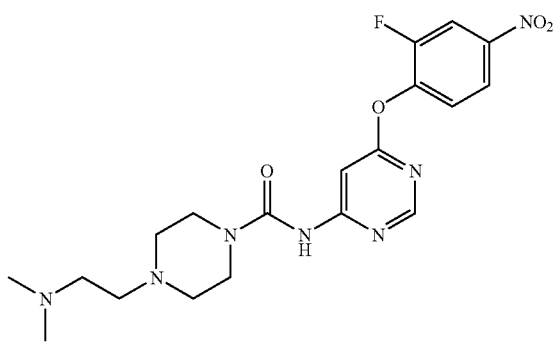
Pro. Ex. 181-1

TABLE 23-continued
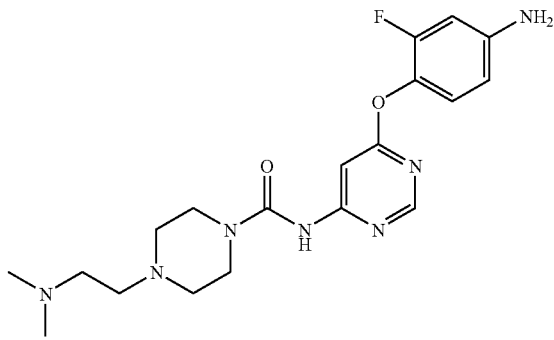
Pro. Ex. 181-2
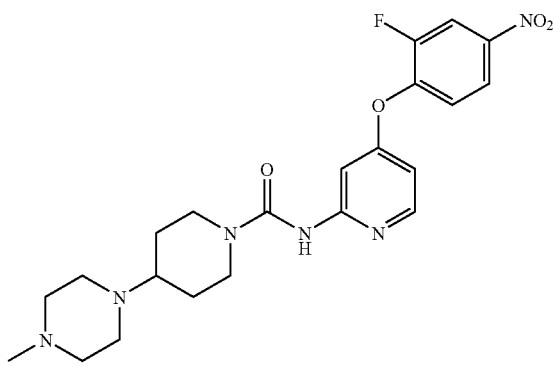
Pro. Ex. 182-1
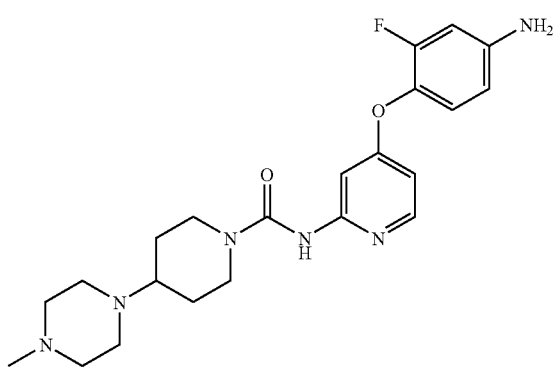
Pro. Ex. 182-2
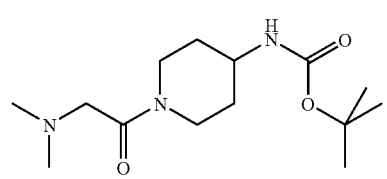
Pro. Ex. 183-1
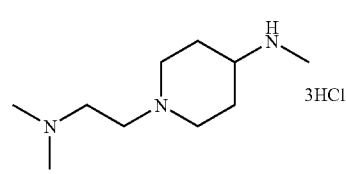
Pro. Ex. 180-3-2

TABLE 23-continued
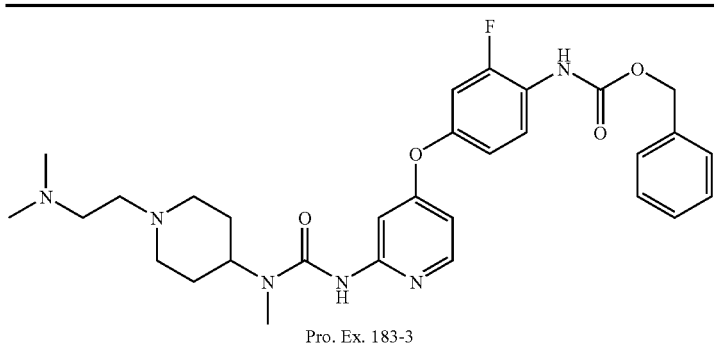
Pro. Ex. 183-3
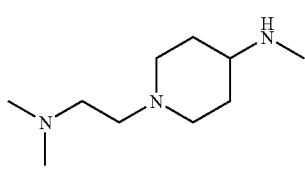
Pro. Ex. 184-1
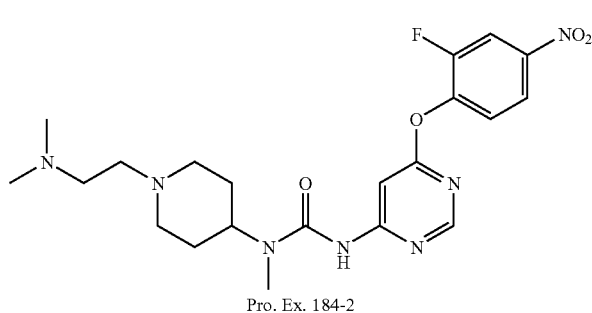
Pro. Ex. 184-2
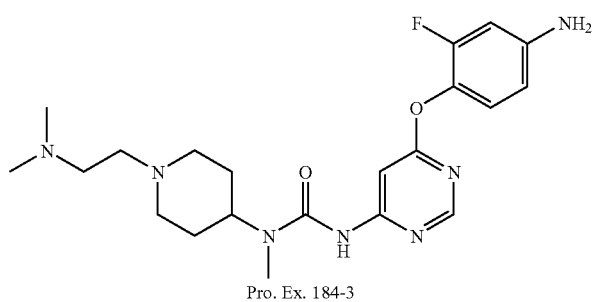
Pro. Ex. 184-3
TABLE 24
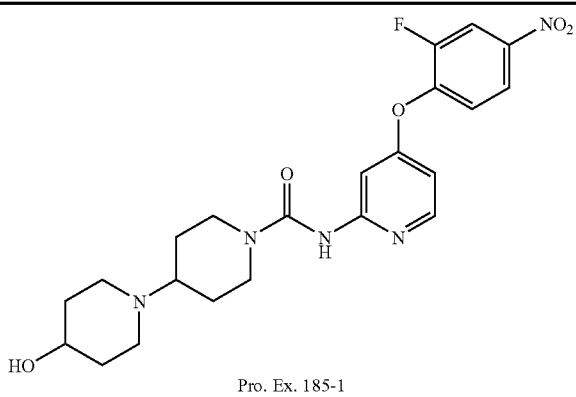
Pro. Ex. 185-1

TABLE 24-continued
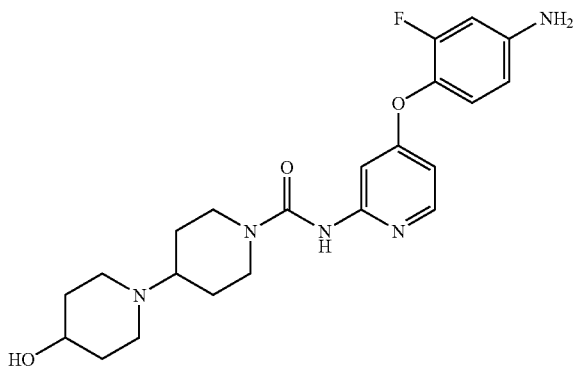
Pro. Ex. 185-2
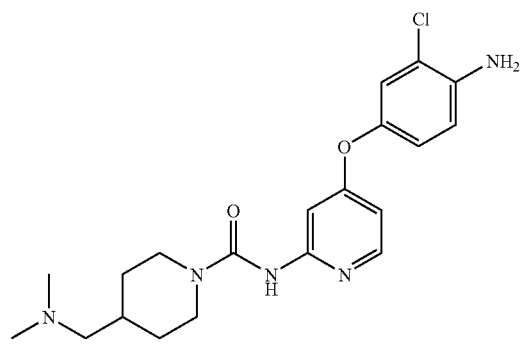
Pro. Ex. 188-1
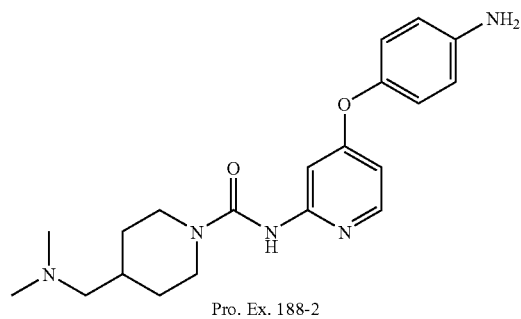
Pro. Ex. 188-2
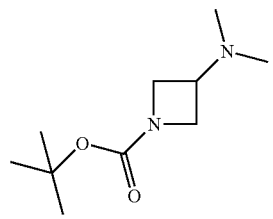
Pro. Ex. 189-1
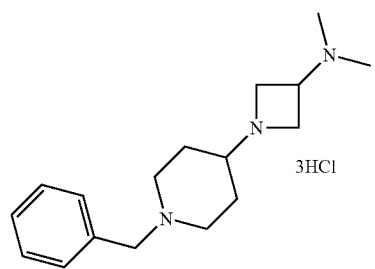
Pro. Ex. 189-2

TABLE 24-continued
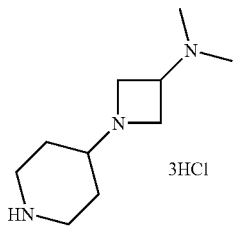
Pro. Ex. 189-3
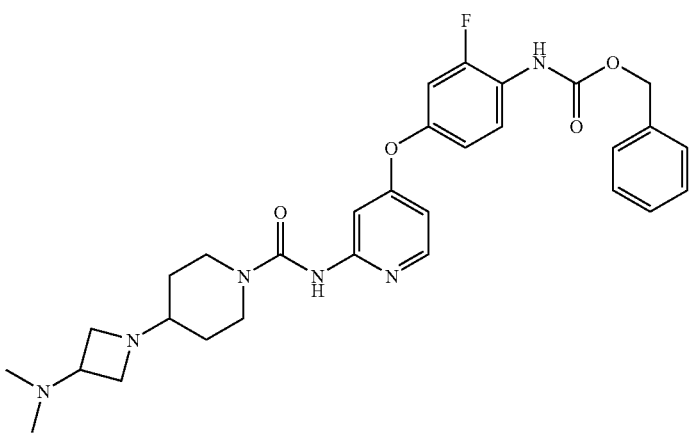
Pro. Ex. 189-4
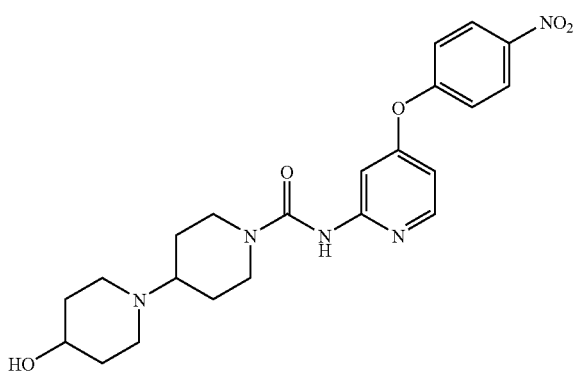
Pro. Ex. 190-1
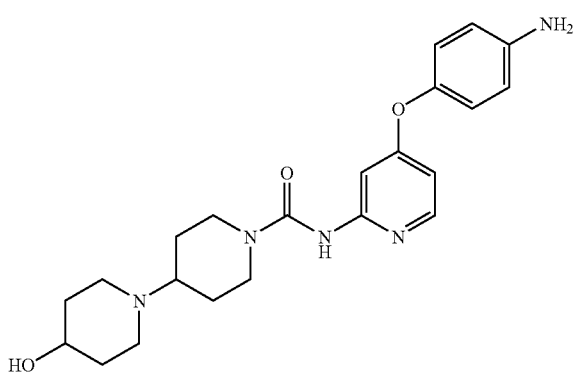
Pro. Ex. 190-2

TABLE 24-continued
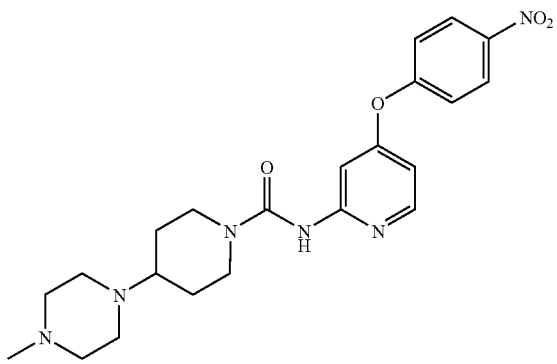
Pro. Ex. 191-1
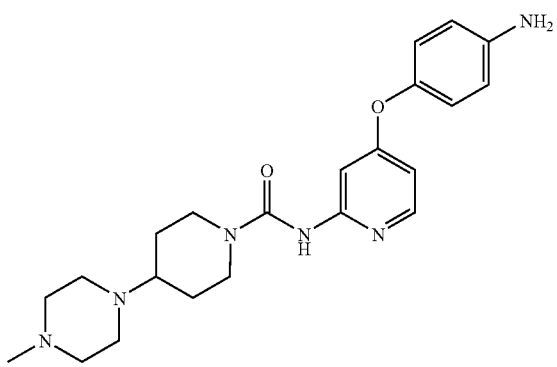
Pro. Ex. 191-2
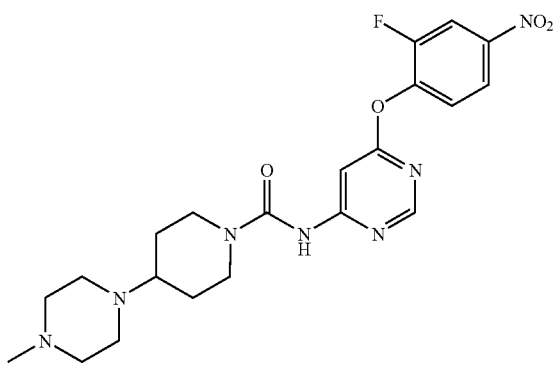
Pro. Ex. 192-1
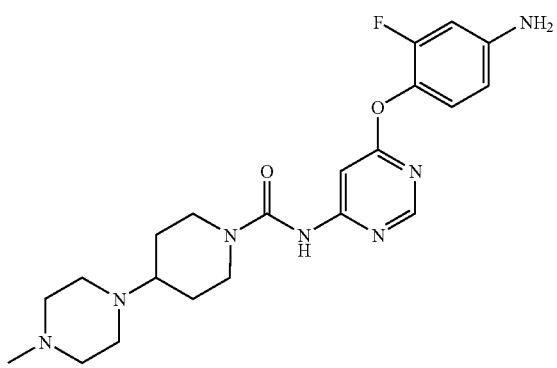
Pro. Ex. 192-2

TABLE 24-continued
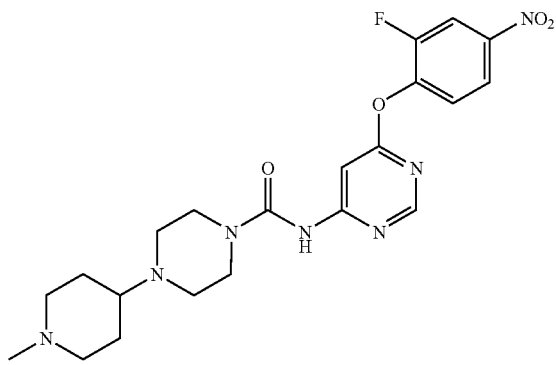
Pro. Ex. 193-1
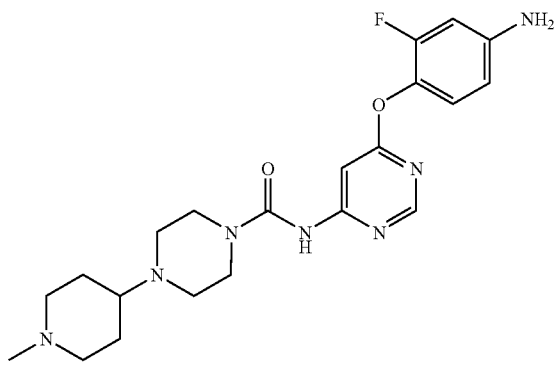
Pro. Ex. 193-2
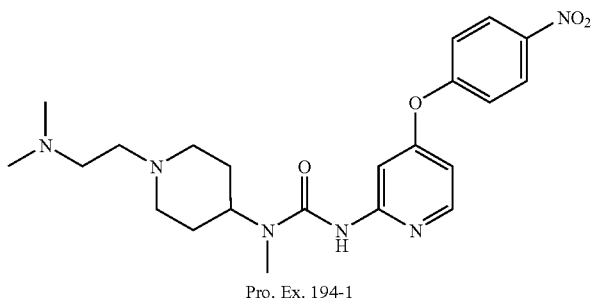
Pro. Ex. 194-1
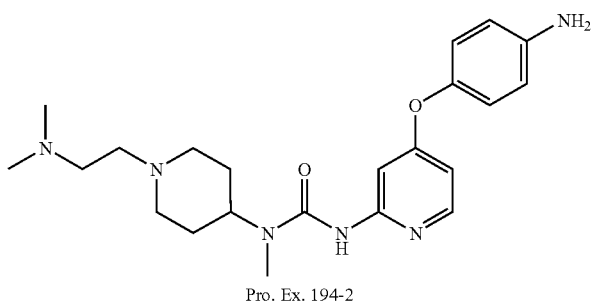
Pro. Ex. 194-2

TABLE 24-continued
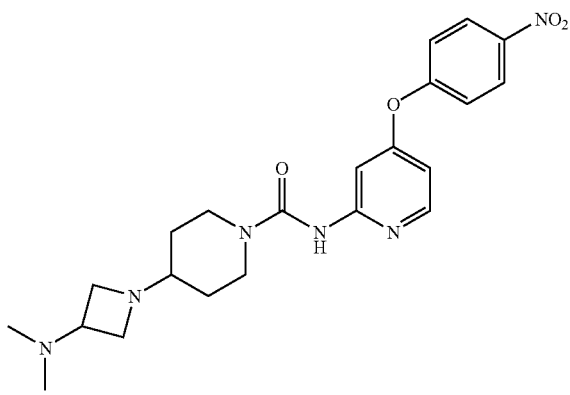
Pro. Ex. 195-1
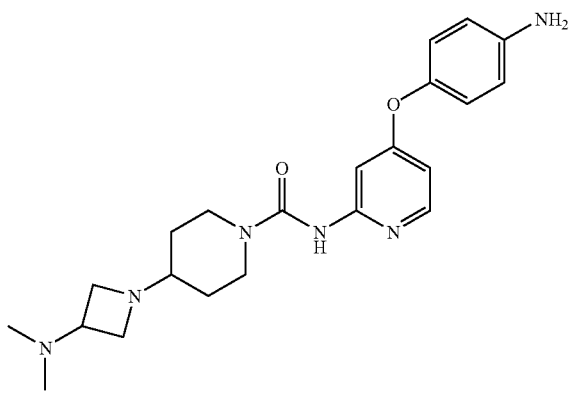
Pro. Ex. 195-2
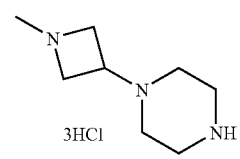
3HCl
Pro. Ex. 196-1
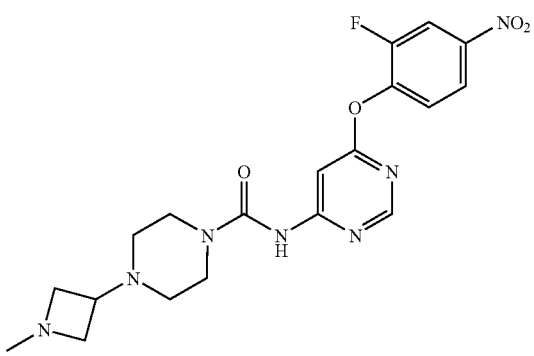
Pro. Ex. 196-2

TABLE 24-continued
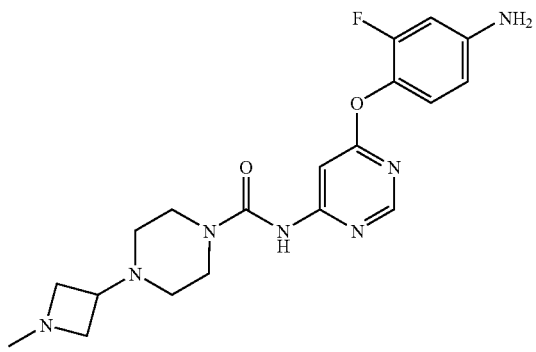
Pro. Ex. 196-3
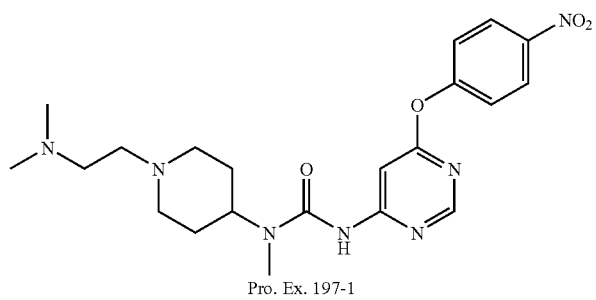
Pro. Ex. 197-1
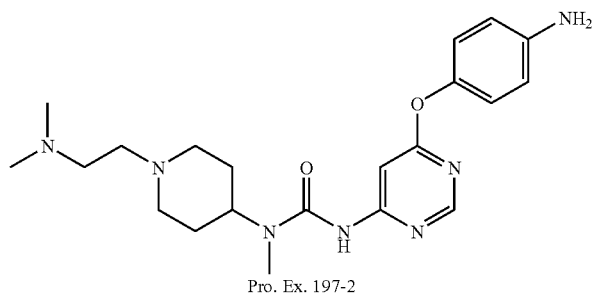
Pro. Ex. 197-2
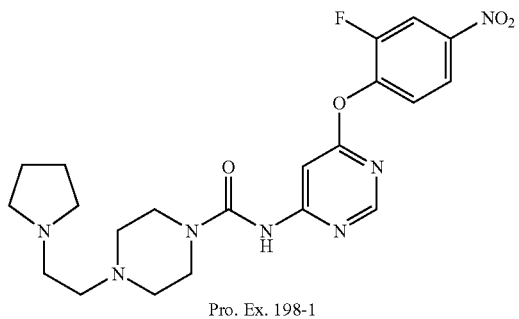
Pro. Ex. 198-1
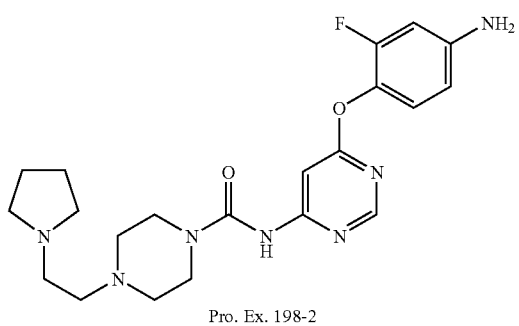
Pro. Ex. 198-2

TABLE 24-continued
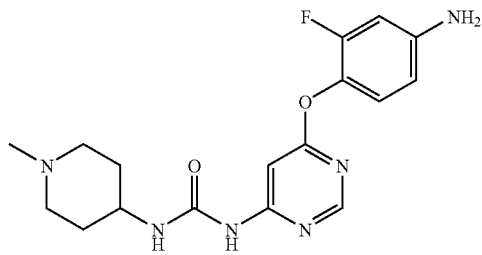
Pro. Ex. 199-1
TABLE 25
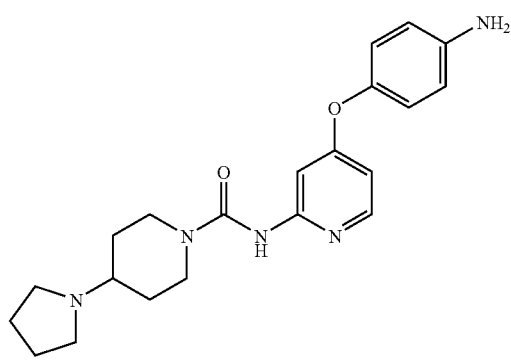
Pro Ex. 200-1
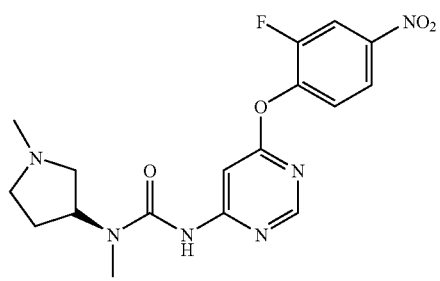
Pro. Ex. 201-1
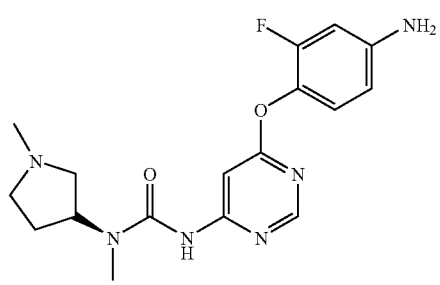
Pro. Ex. 201-2

TABLE 25-continued
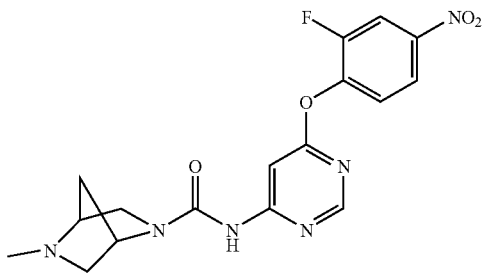
Pro. Ex. 202-1
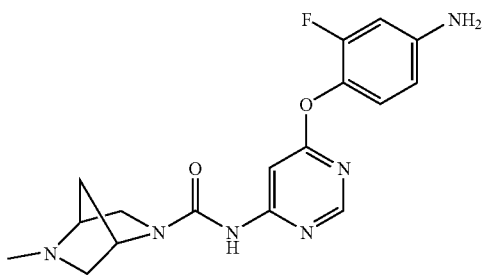
Pro. Ex. 202-2
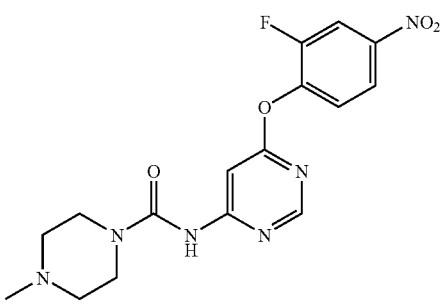
Pro. Ex. 205-1
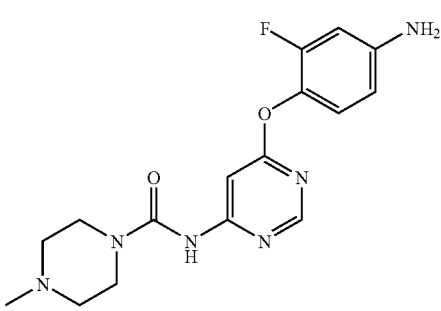
Pro. Ex. 205-2
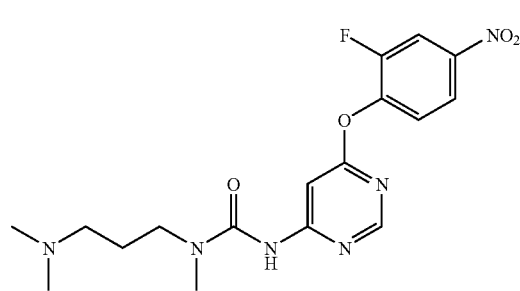
Pro. Ex. 206-1

TABLE 25-continued
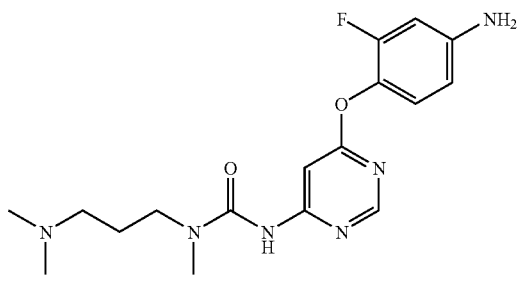
Pro. Ex. 206-2
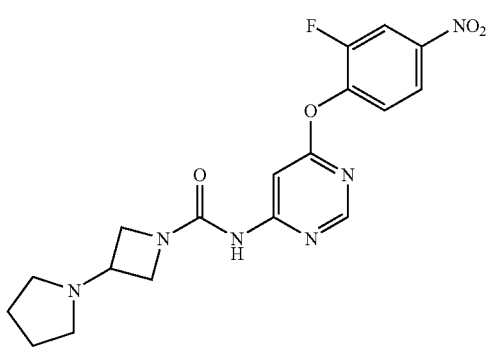
Pro. Ex. 207-1
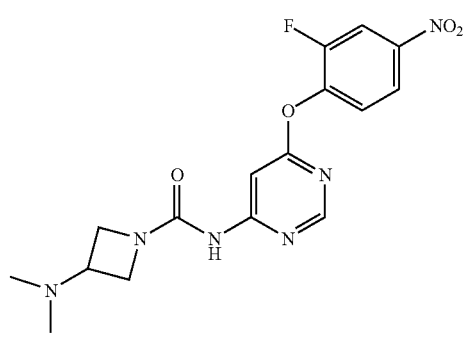
Pro. Ex. 208-1
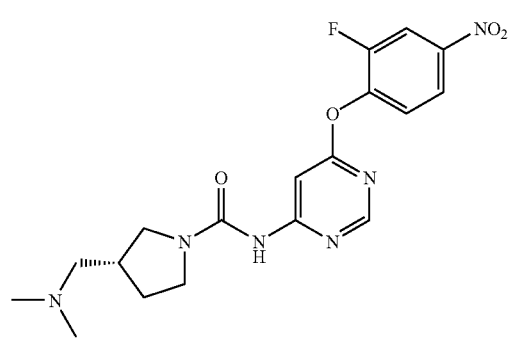
Pro. Ex. 209-1

TABLE 25-continued
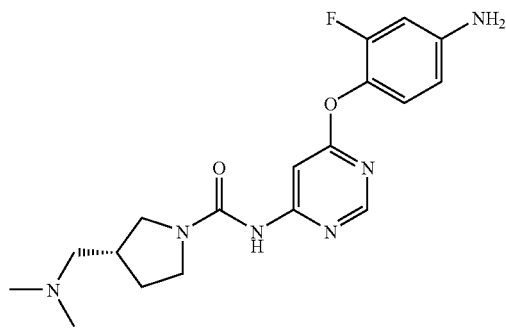
Pro. Ex. 209-2
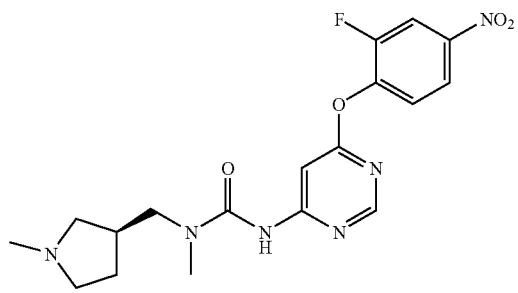
Pro. Ex. 210-1
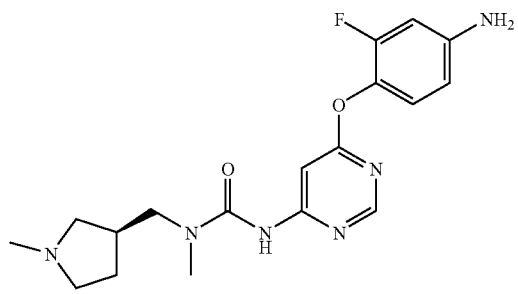
Pro. Ex. 210-2
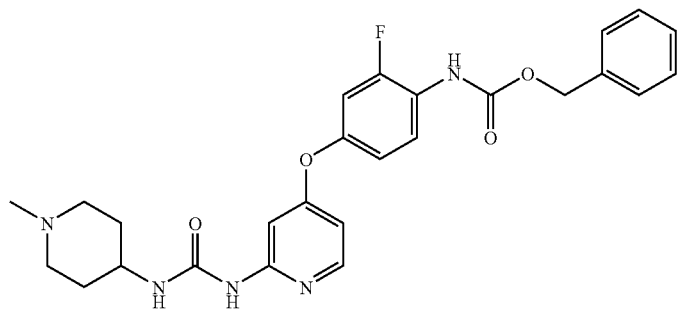
Pro. Ex. 215-1
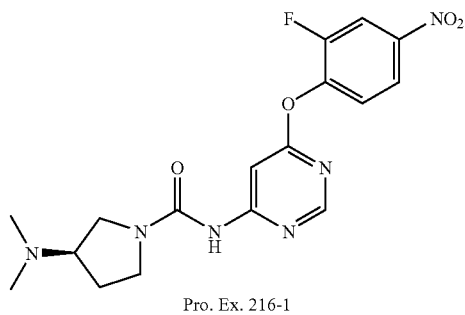
Pro. Ex. 216-1

TABLE 25-continued
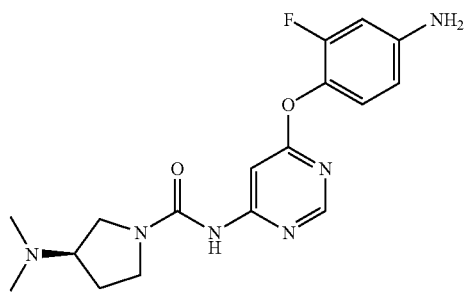
Pro. Ex. 216-2
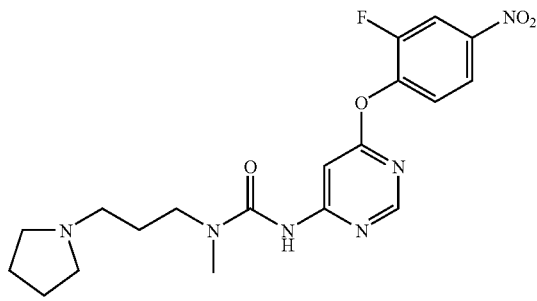
Pro. Ex. 217-1
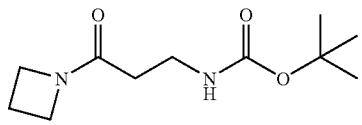
Pro. Ex. 218-1
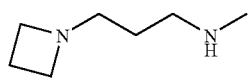
Pro. Ex. 218-2
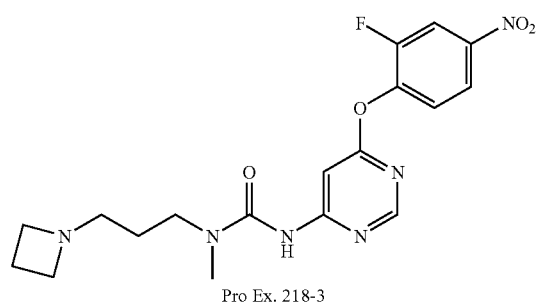
Pro Ex. 218-3
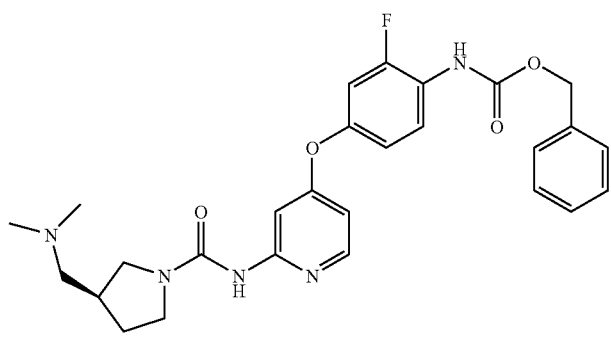
Pro. Ex. 219-1

TABLE 25-continued
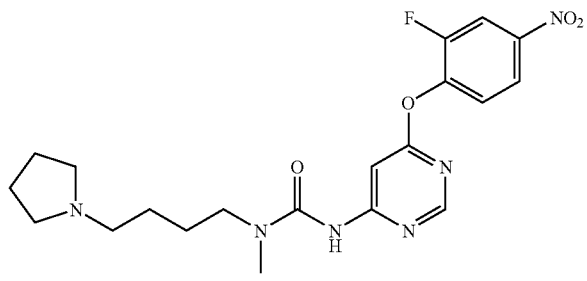
Pro. Ex. 220-1
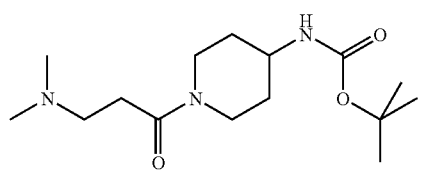
Pro. Ex. 221-1
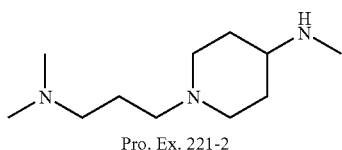
Pro. Ex. 221-2
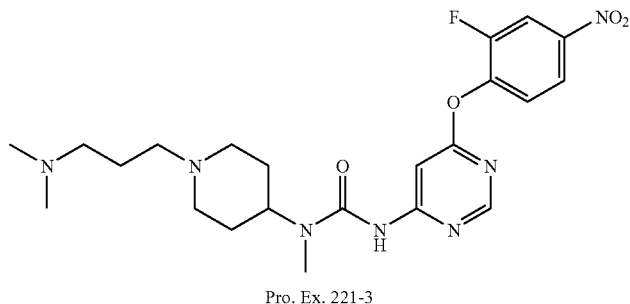
Pro. Ex. 221-3
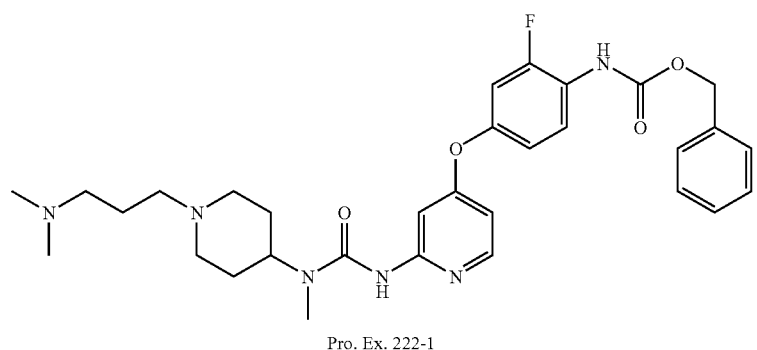
Pro. Ex. 222-1

TABLE 26
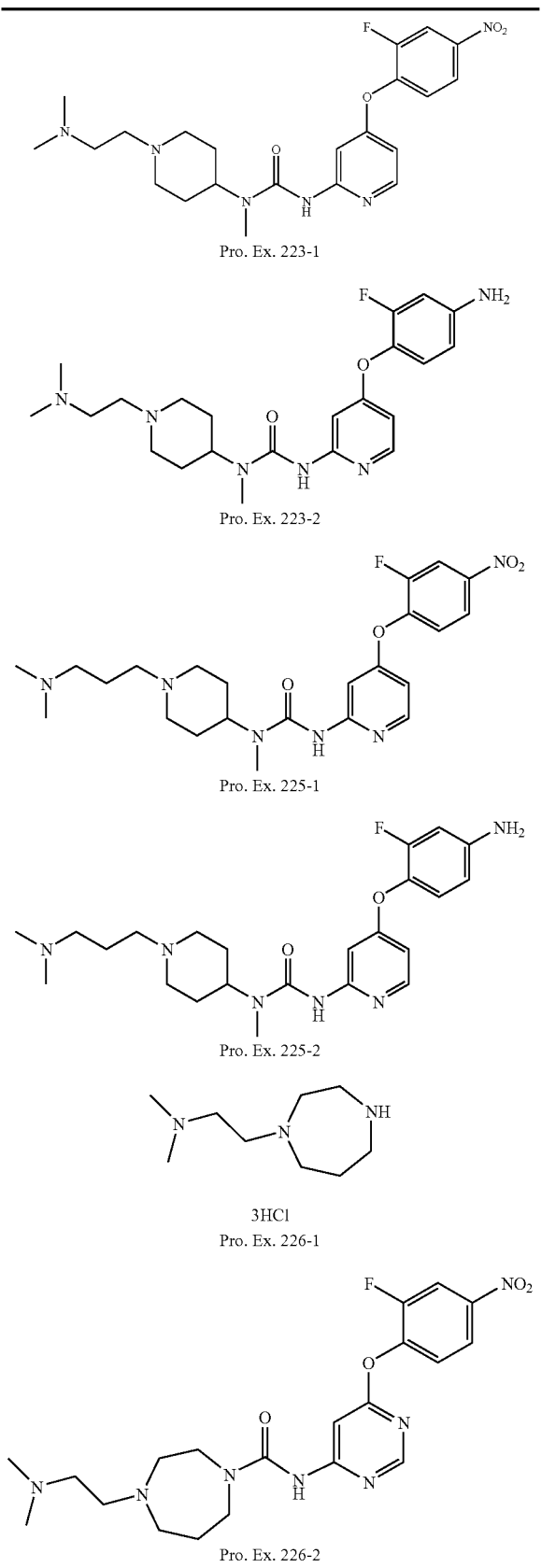
TABLE 26-continued
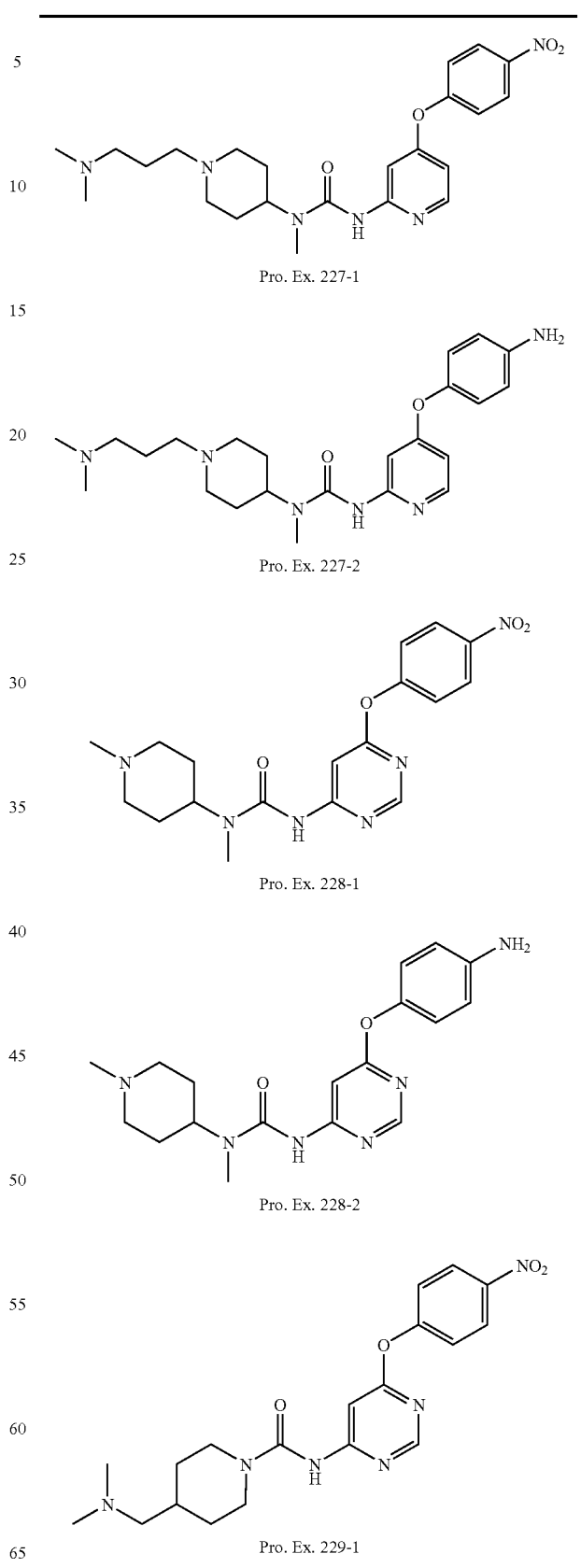

TABLE 26-continued
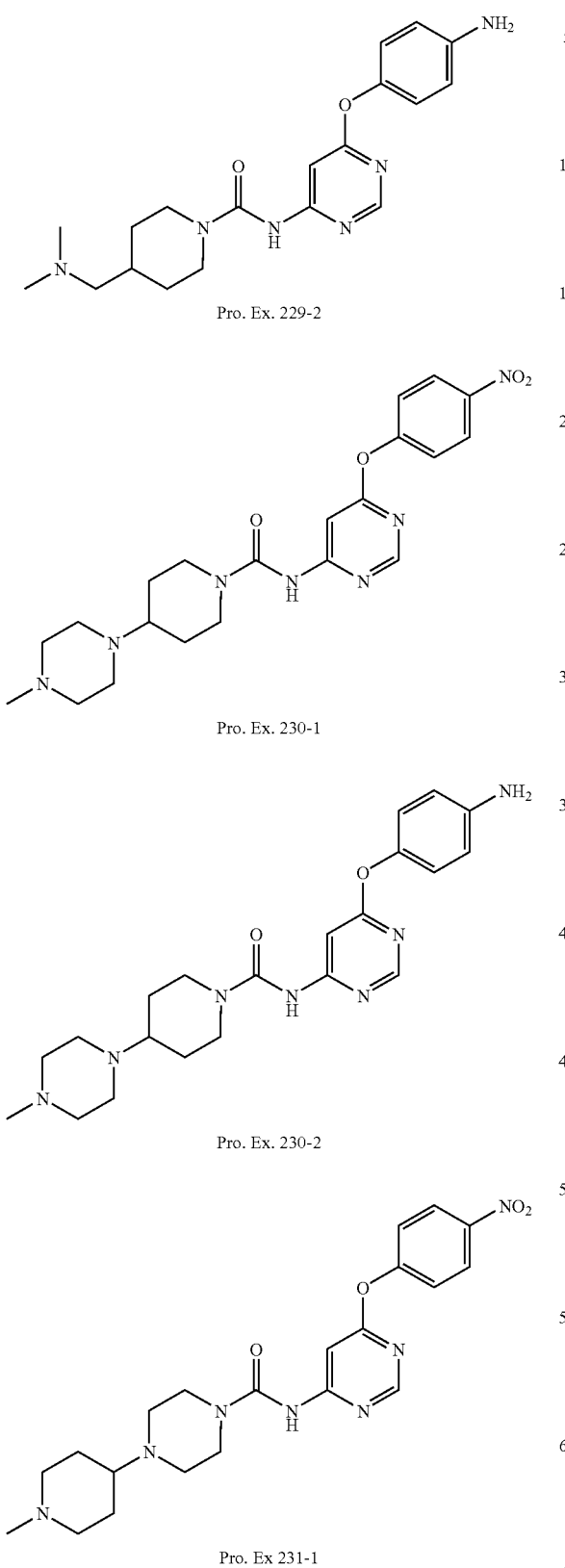
TABLE 26-continued
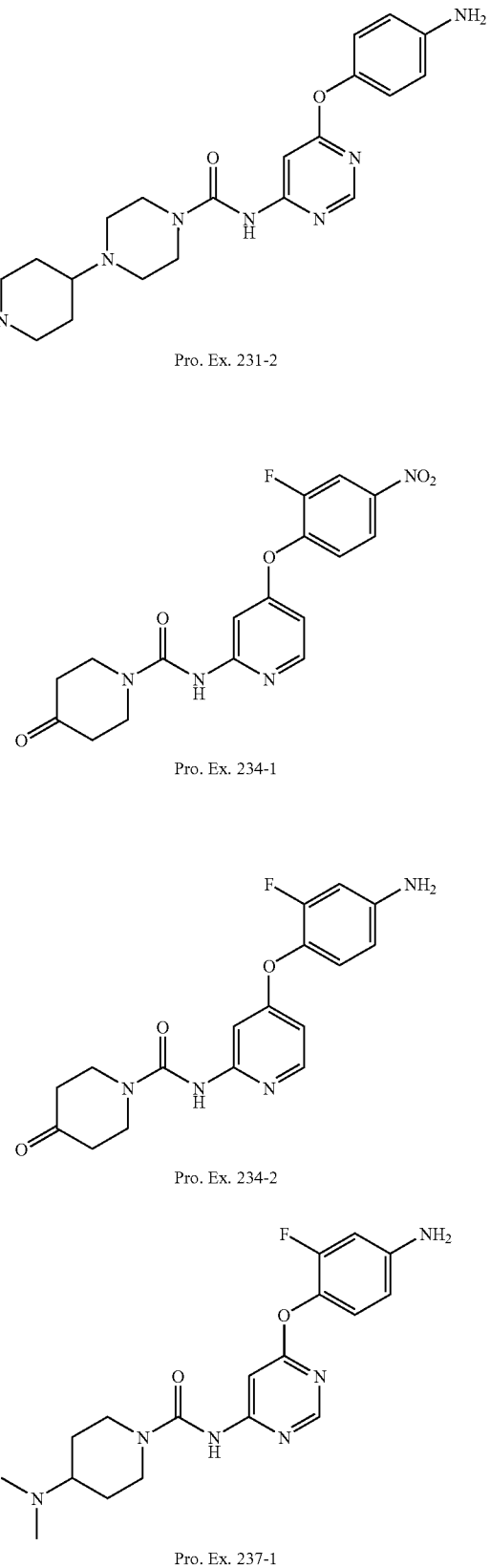

TABLE 26-continued
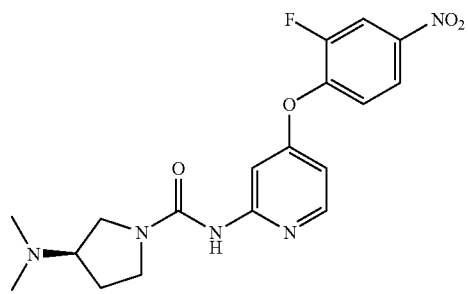
Pro. Ex. 245-1
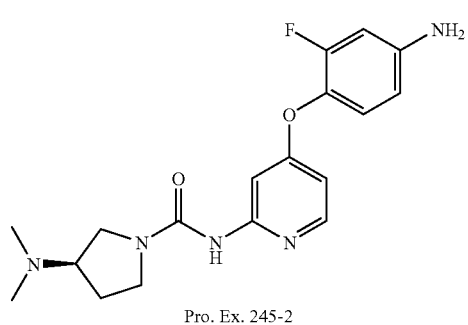
Pro. Ex. 245-2
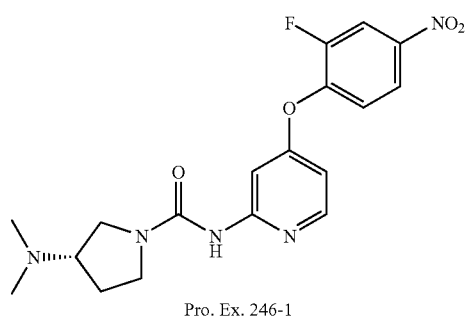
Pro. Ex. 246-1
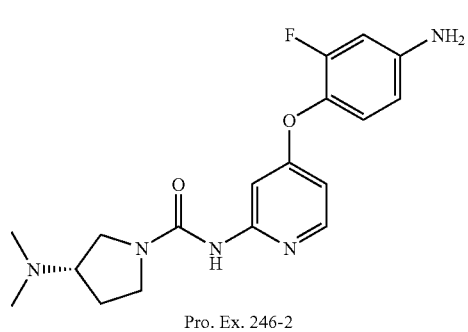
Pro. Ex. 246-2
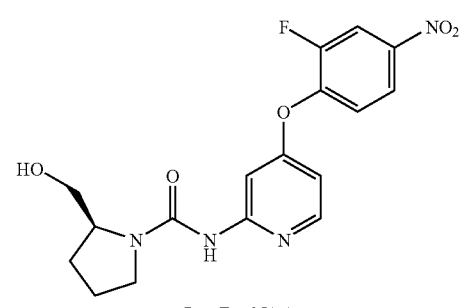
Pro. Ex. 251-1
TABLE 26-continued
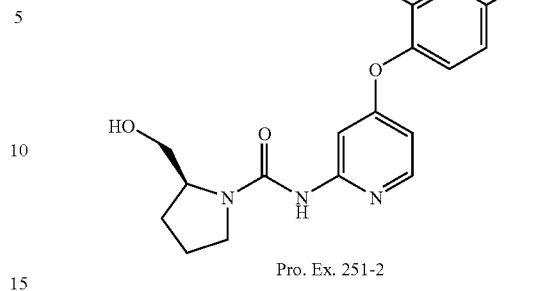
Pro. Ex. 251-2
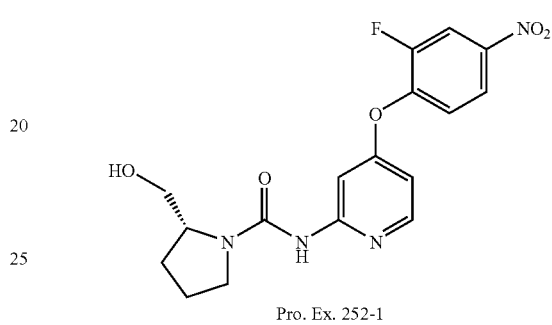
Pro. Ex. 252-1
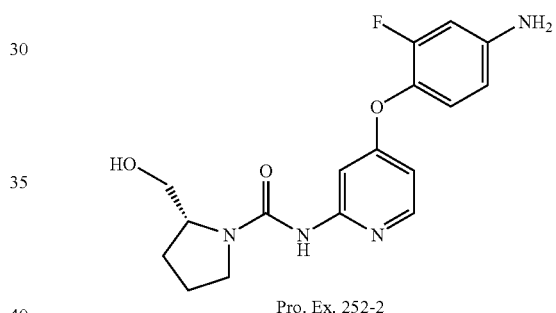
Pro. Ex. 252-2
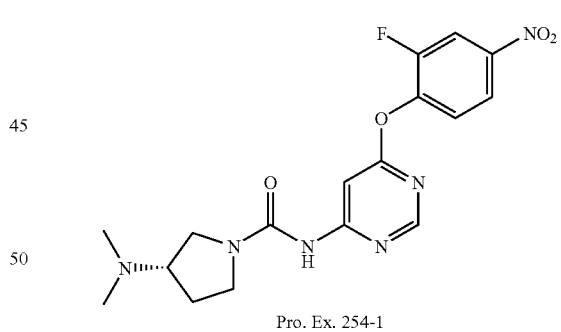
Pro. Ex. 254-1
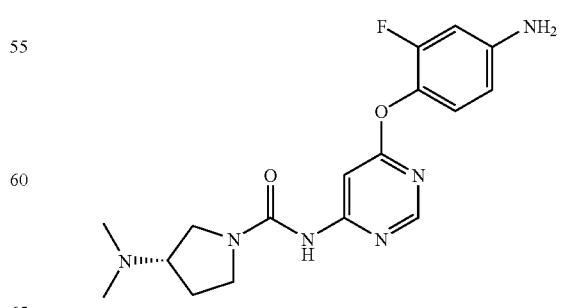
Pro. Ex. 254-2

TABLE 27
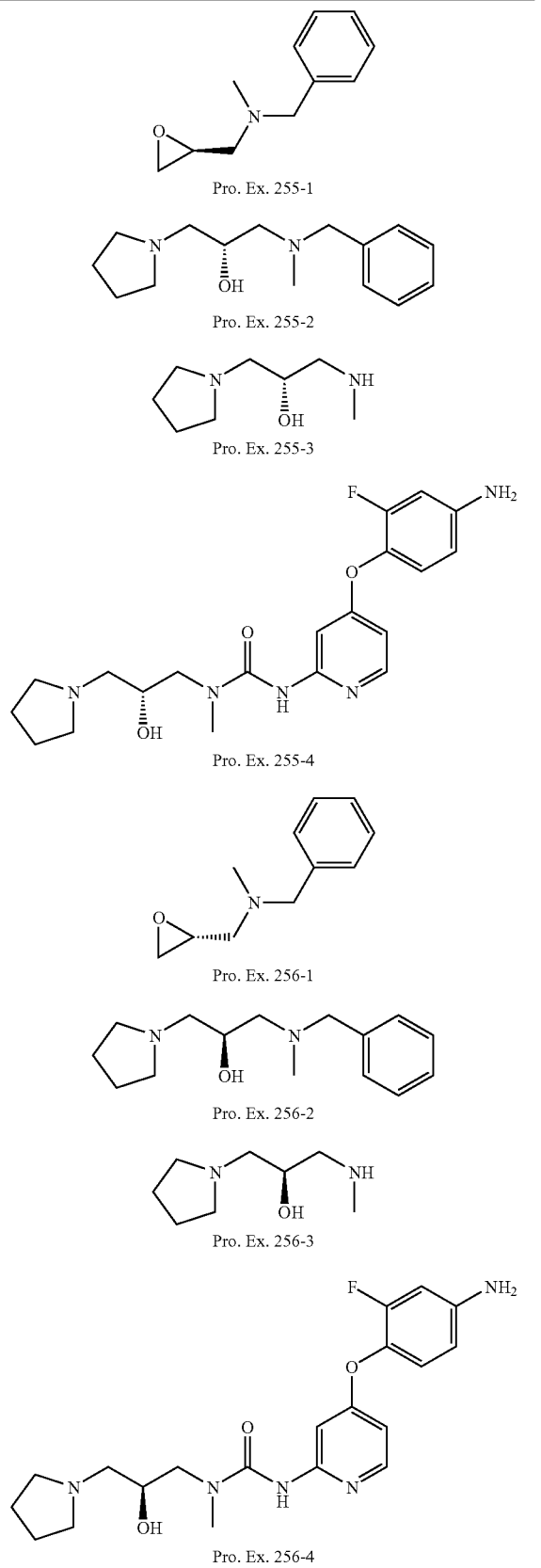
TABLE 27-continued
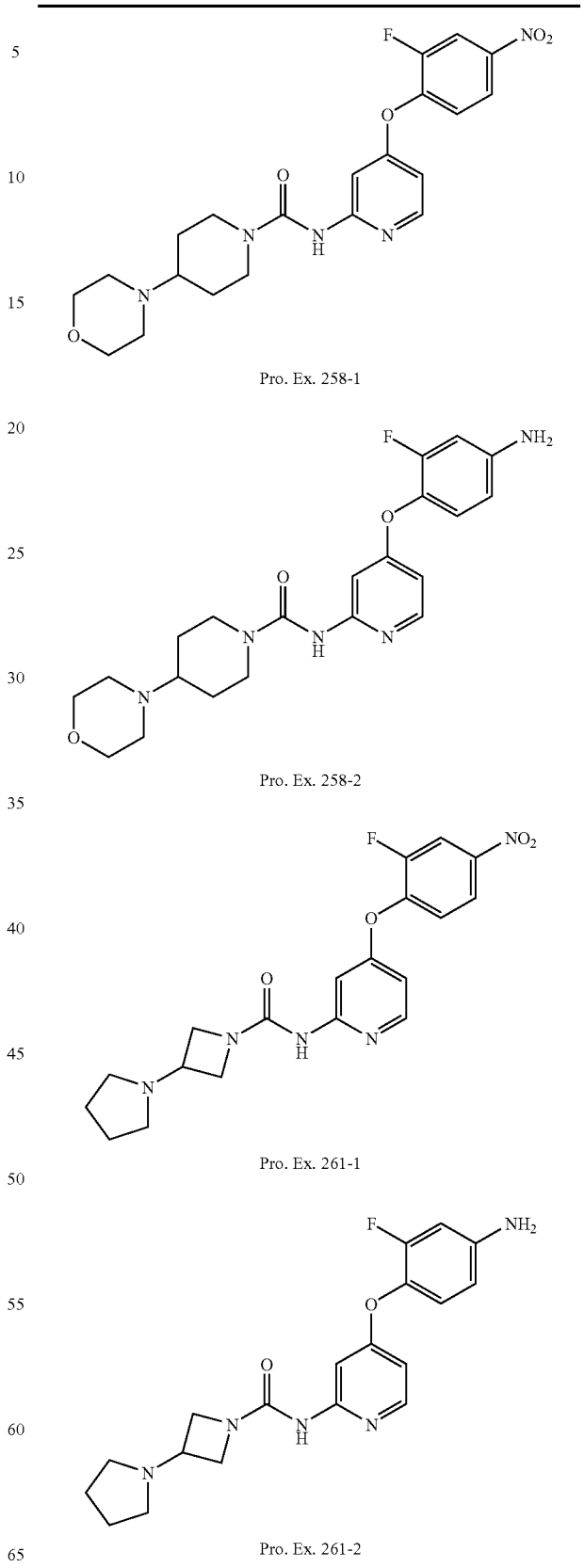

TABLE 27-continued
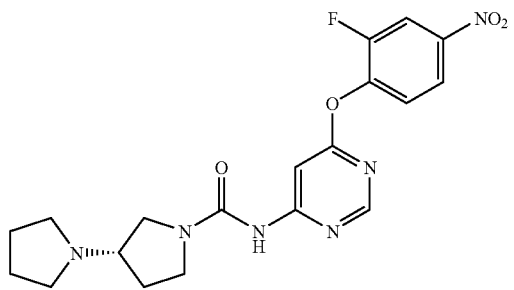
Pro. Ex. 267-1
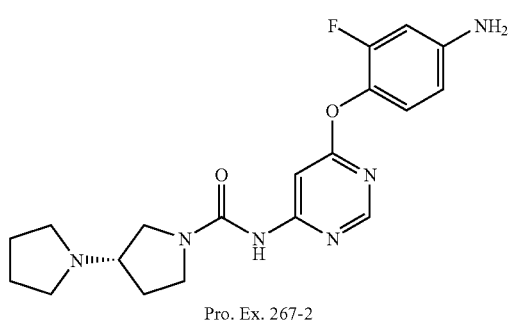
Pro. Ex. 267-2
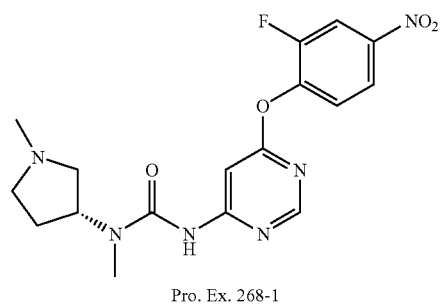
Pro. Ex. 268-1
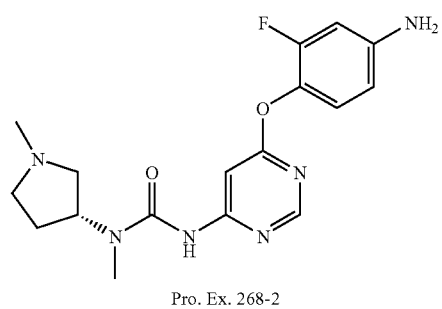
Pro. Ex. 268-2
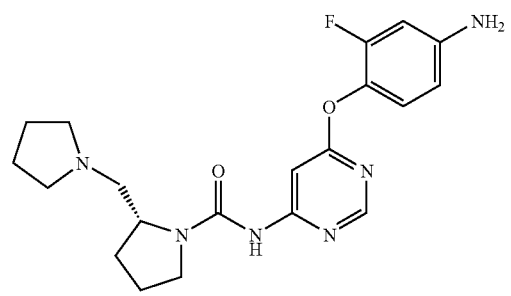
Pro. Ex. 272-1
TABLE 27-continued
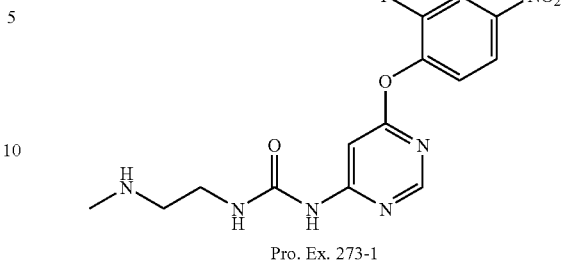
Pro. Ex. 273-1
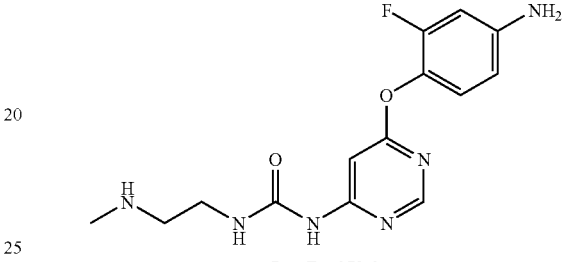
Pro. Ex. 273-2
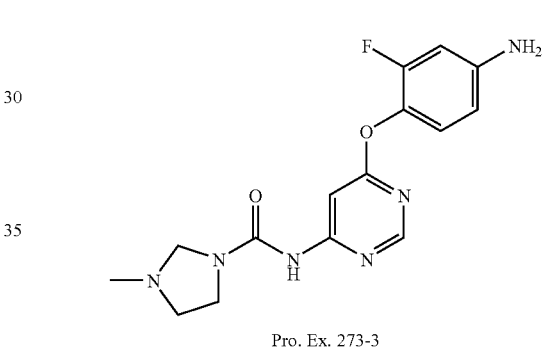
Pro. Ex. 273-3
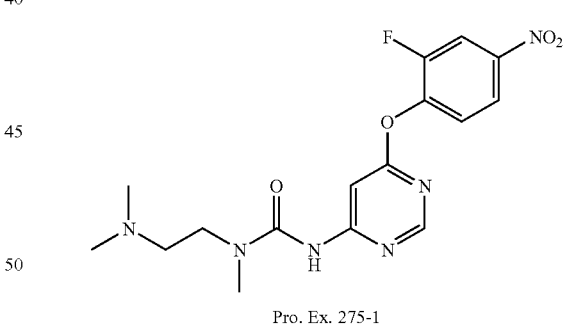
Pro. Ex. 275-1
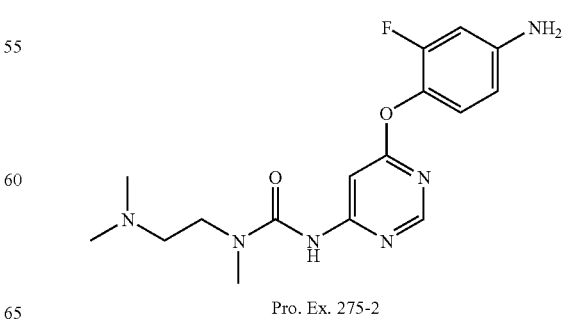
Pro. Ex. 275-2

TABLE 27-continued
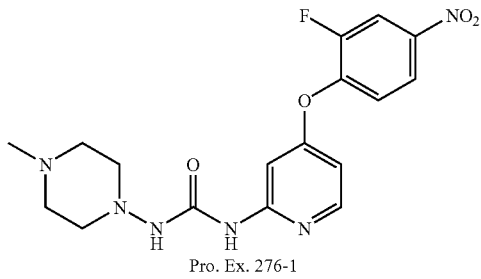
Pro. Ex. 276-1
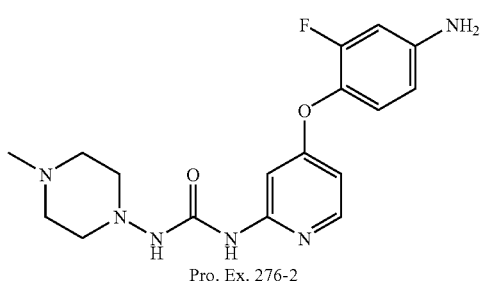
Pro. Ex. 276-2
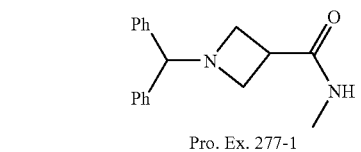
Pro. Ex. 277-1
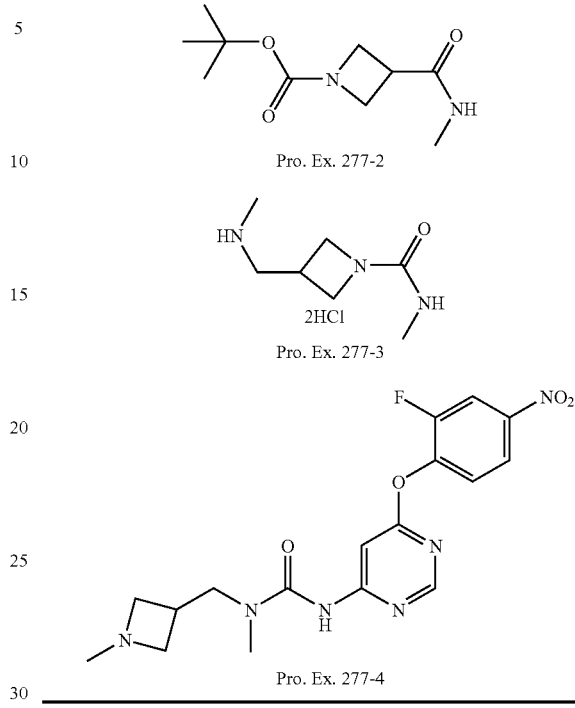
Pro. Ex. 277-2
Pro. Ex. 277-3
Pro. Ex. 277-4
TABLE 28
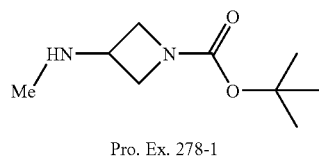
Pro. Ex. 278-1
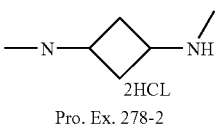
Pro. Ex. 278-2
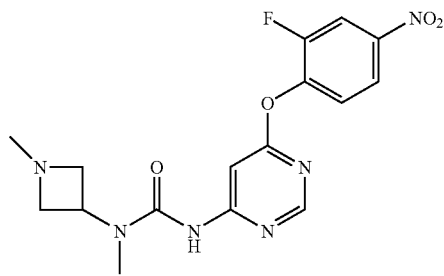
Pro. Ex. 278-3
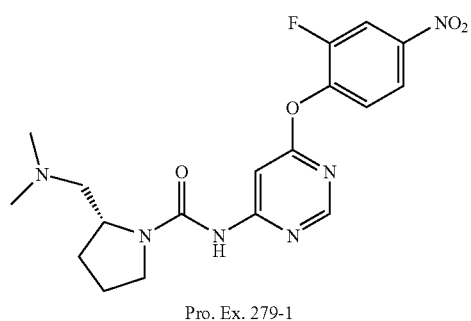
Pro. Ex. 279-1
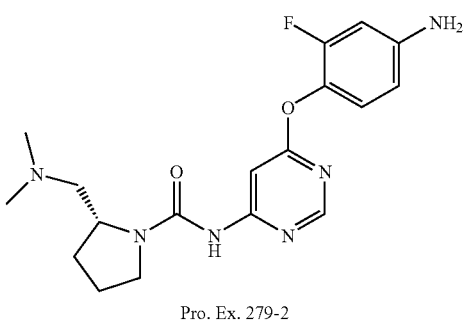
Pro. Ex. 279-2

TABLE 28-continued
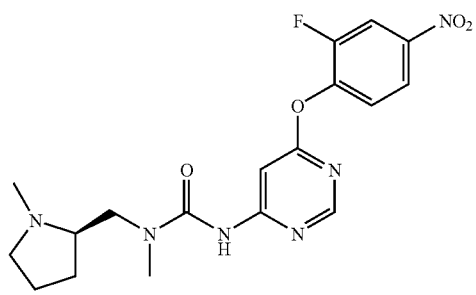
Pro. Ex. 280-1
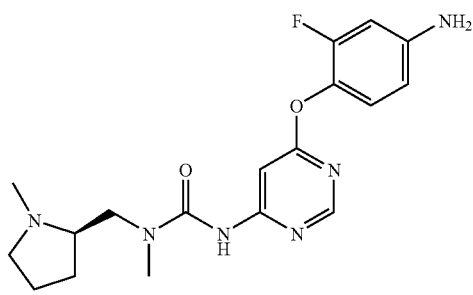
Pro. Ex. 280-2
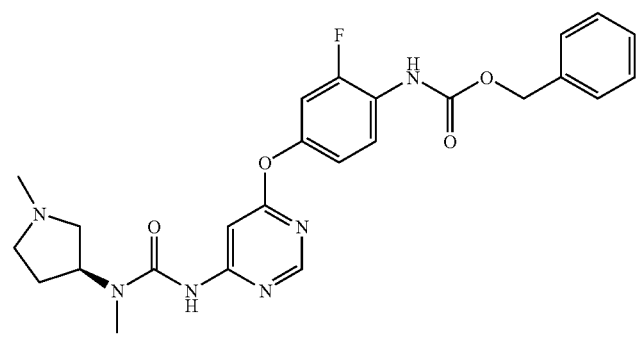
Pro. Ex. 281-1
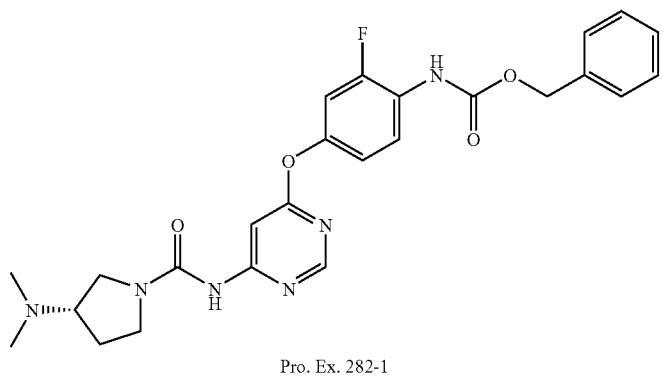
Pro. Ex. 282-1
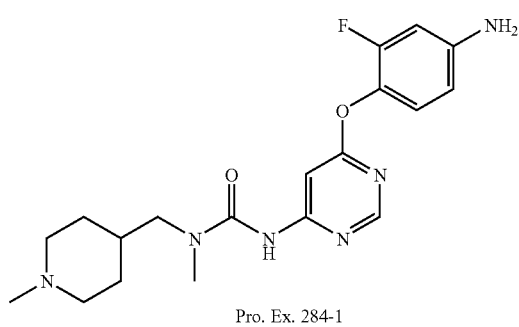
Pro. Ex. 284-1
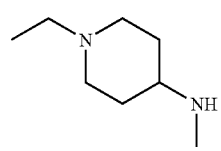
Pro. Ex. 285-1

TABLE 28-continued
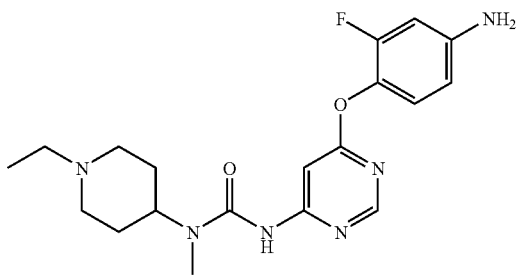
Pro. Ex. 285-2
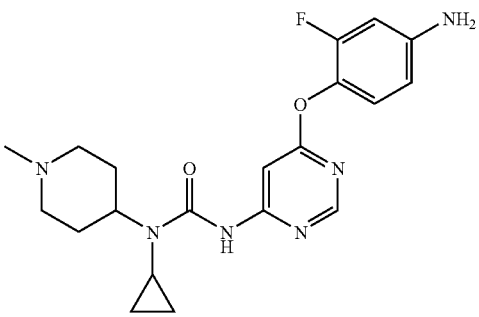
Pro. Ex. 286-1
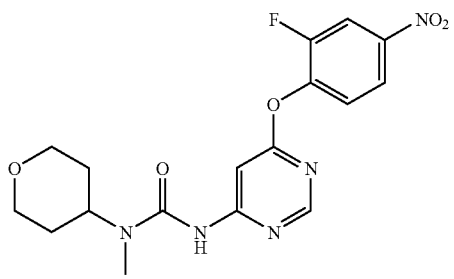
Pro. Ex. 288-1
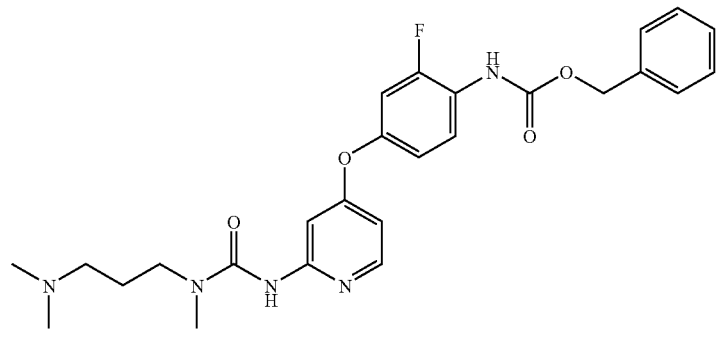
Pro. Ex. 291-1
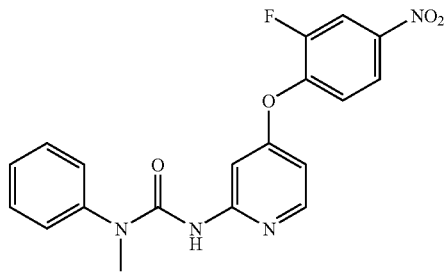
Pro. Ex. 295-1
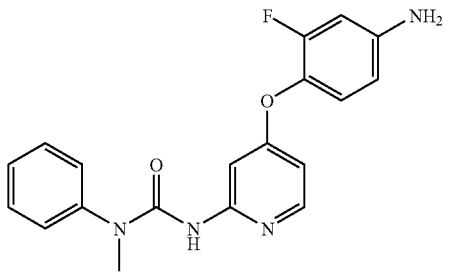
Pro. Ex. 295-2
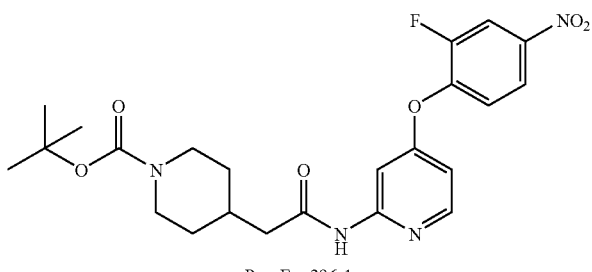
Pro. Ex. 296-1

TABLE 28-continued
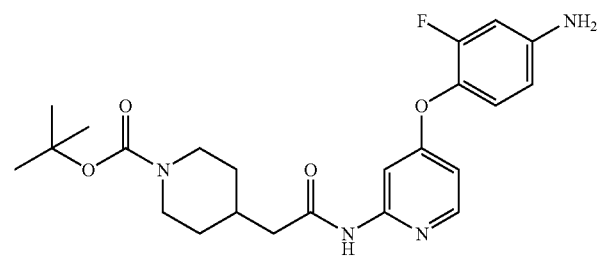
Pro. Ex. 296-2
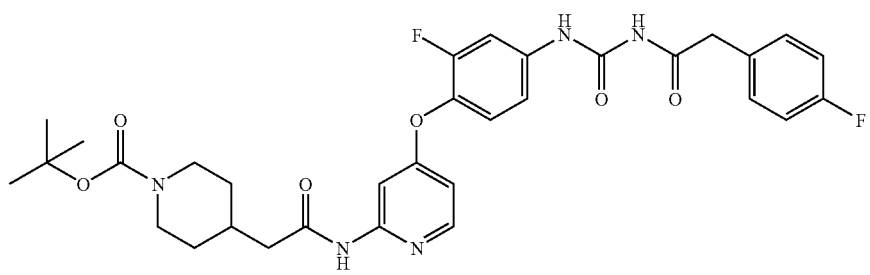
Pro. Ex. 296-3
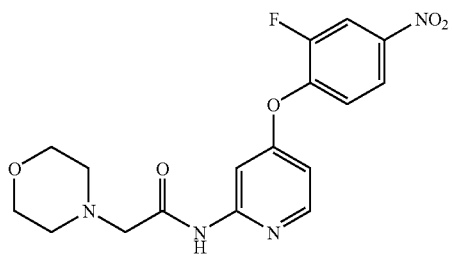
Pro. Ex. 297-1
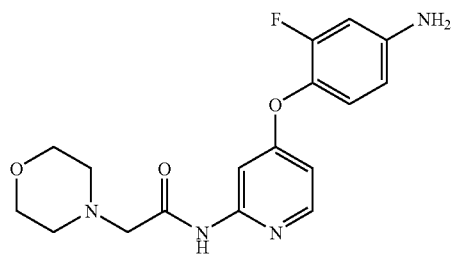
Pro. Ex. 297-2
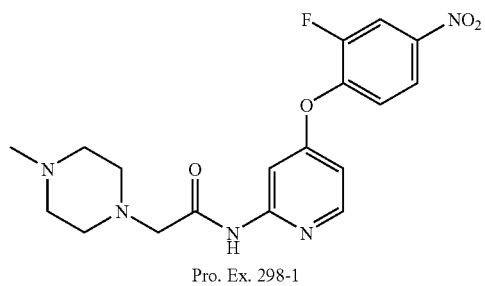
Pro. Ex. 298-1
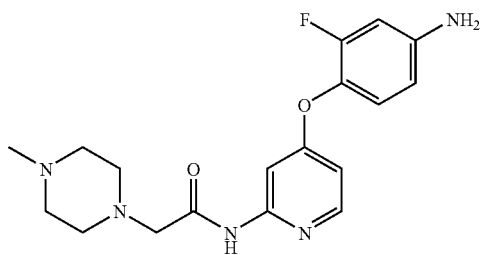
Pro. Ex. 298-2
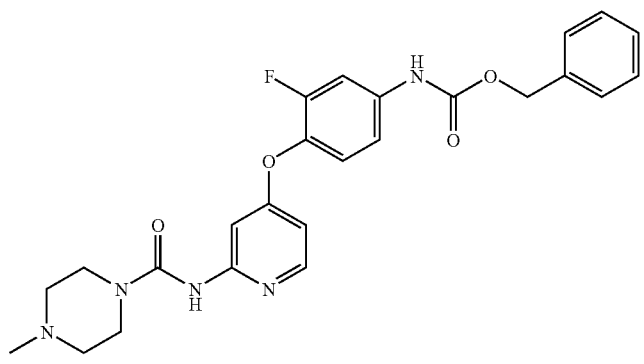
Pro. Ex. 299-1

TABLE 28-continued
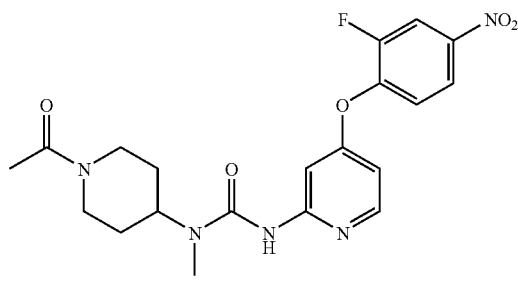
Pro. Ex. 301-1
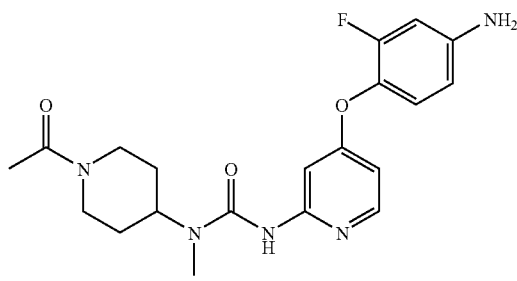
Pro. Ex. 301-2
TABLE 29
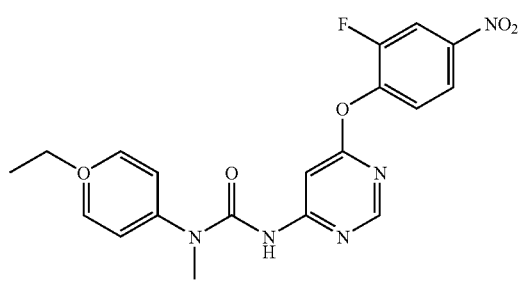
Pro. Ex. 302-1
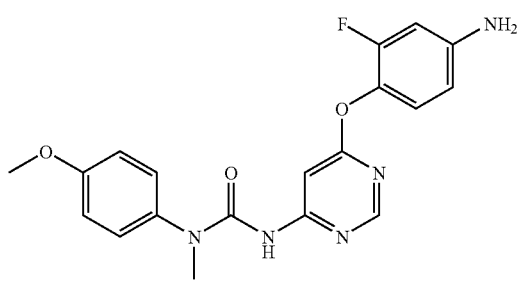
Pro. Ex. 302-2
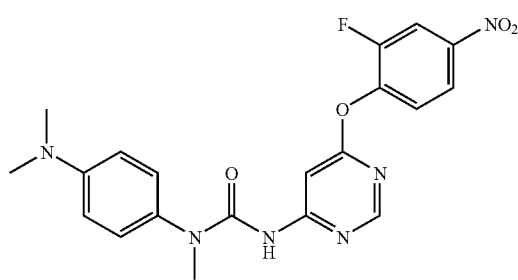
Pro. Ex. 303-1
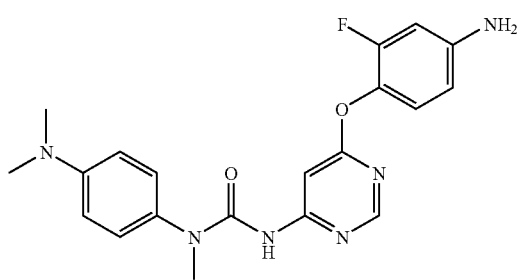
Pro. Ex. 303-2
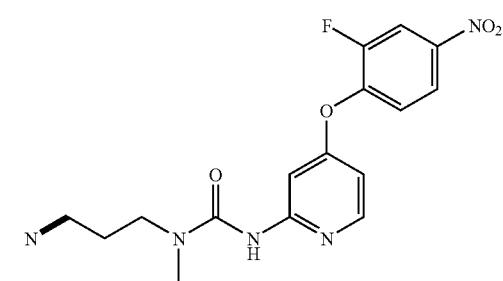
Pro. Ex. 304-1
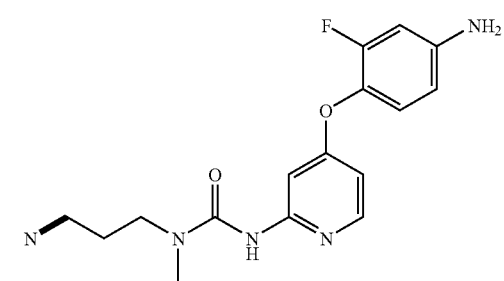
Pro. Ex. 304-2

TABLE 29-continued
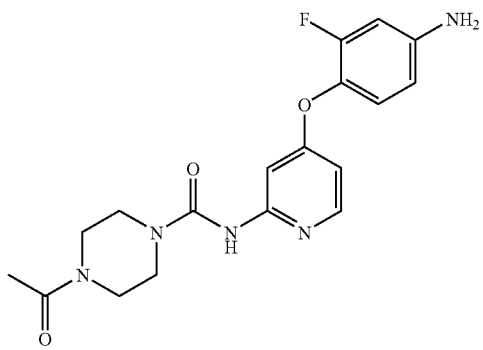
Pro. Ex. 305-1
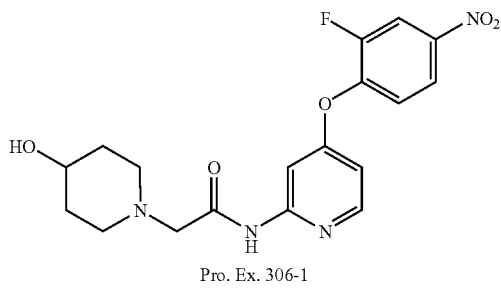
Pro. Ex. 306-1
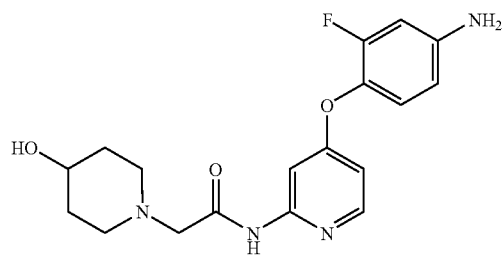
Pro. Ex. 306-2
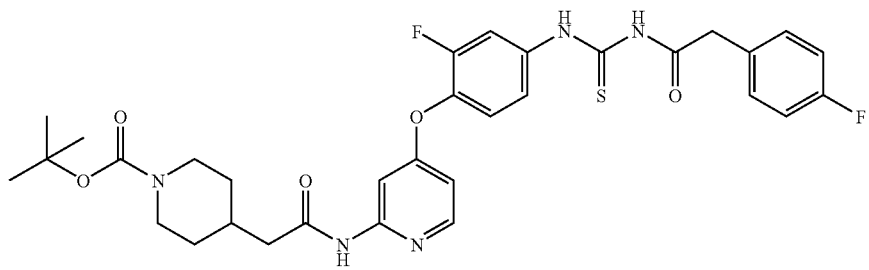
Pro. Ex. 307-1
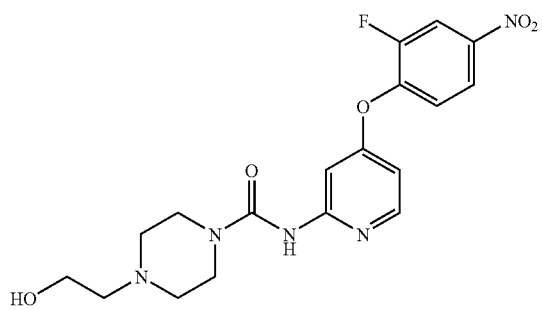
Pro. Ex. 308-1
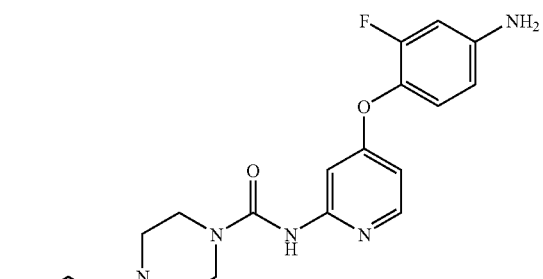
Pro. Ex. 308-2

TABLE 29-continued
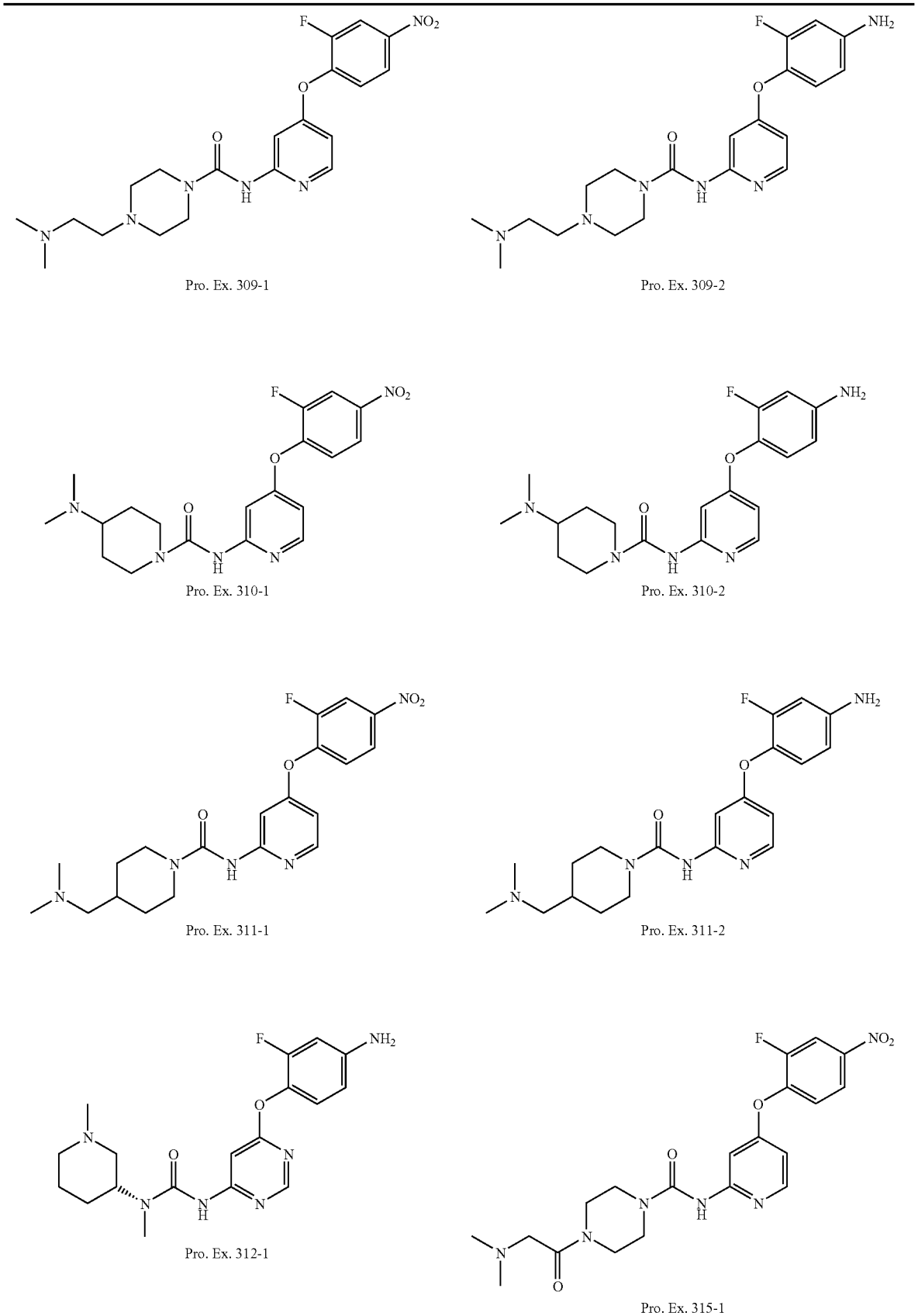

TABLE 29-continued
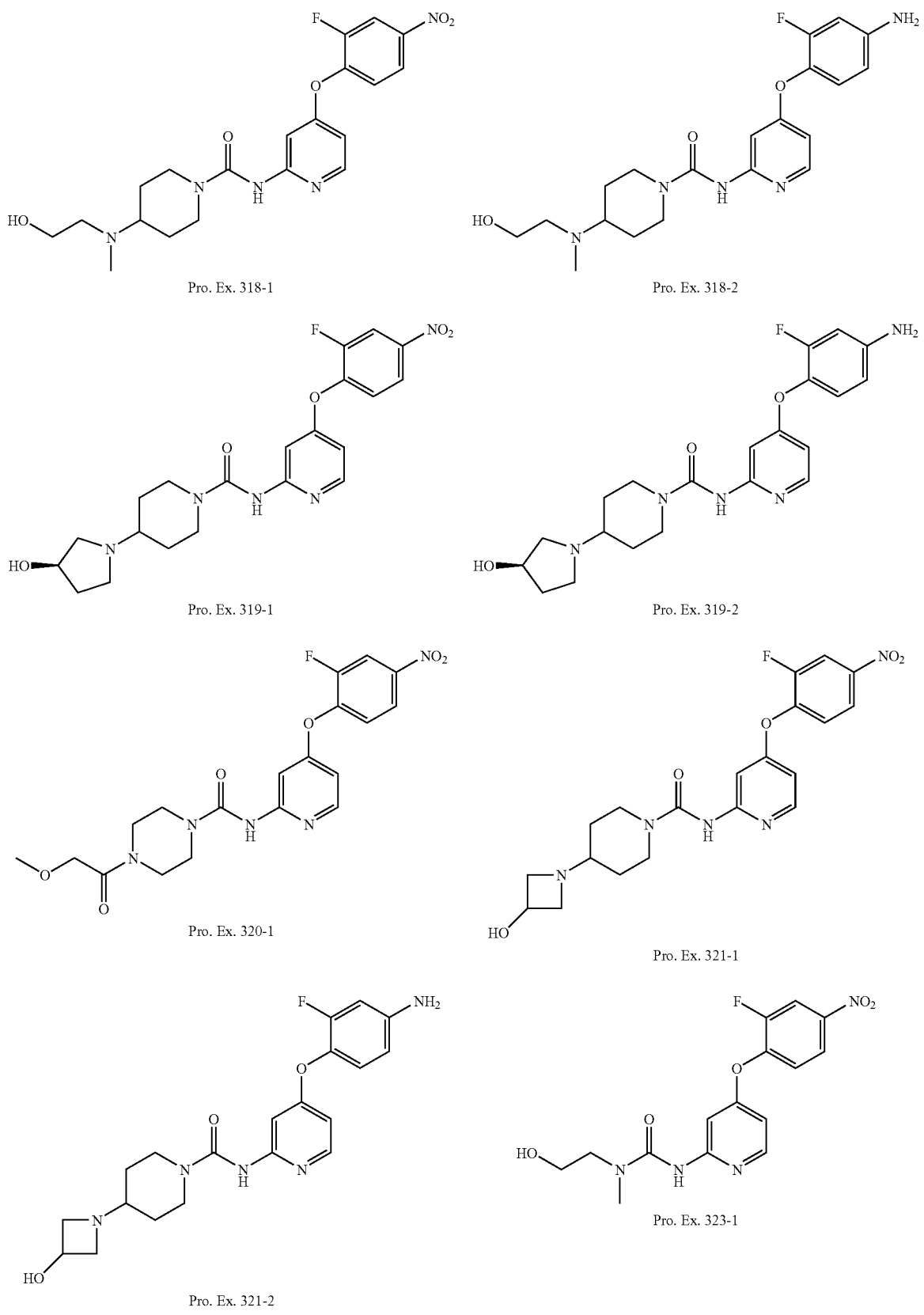

TABLE 30
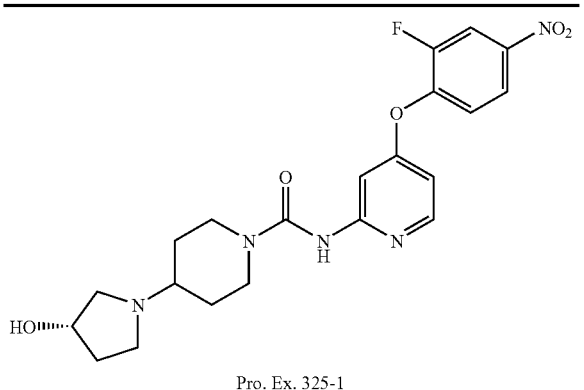
Pro. Ex. 325-1
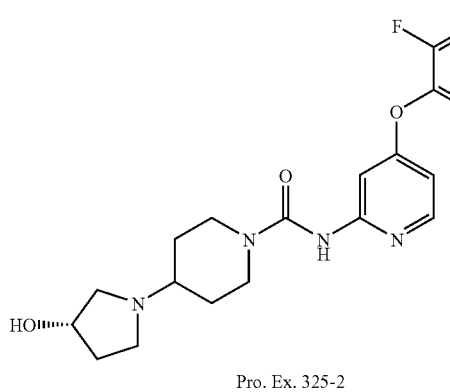
Pro. Ex. 325-2
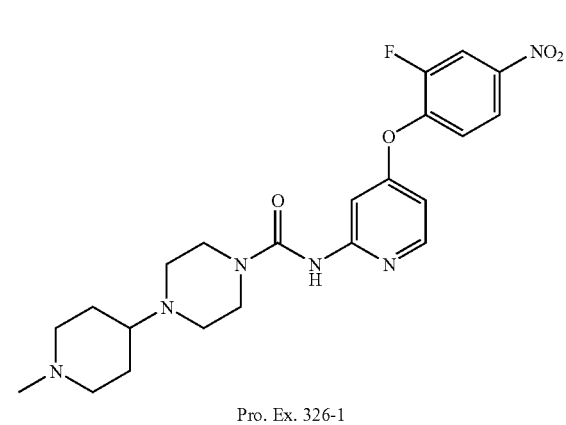
Pro. Ex. 326-1
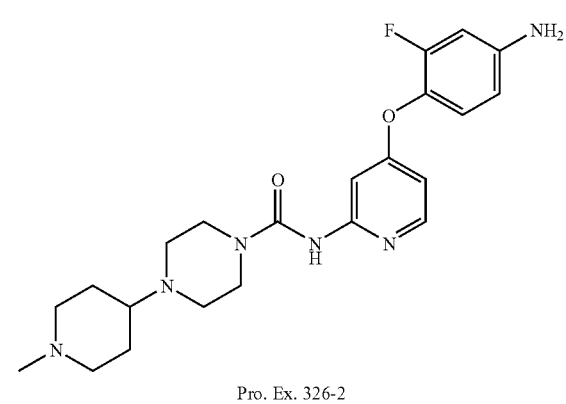
Pro. Ex. 326-2
TABLE 30-continued
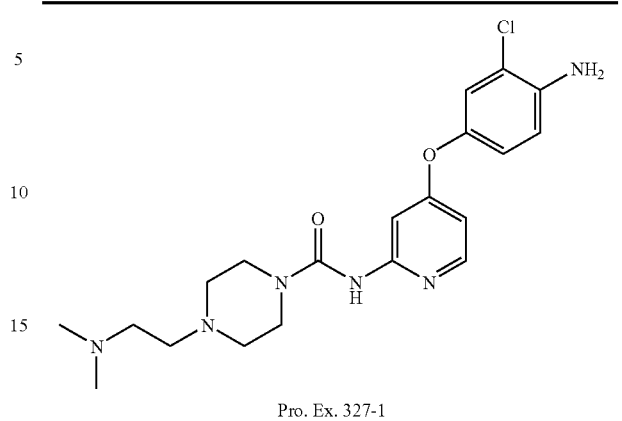
Pro. Ex. 327-1
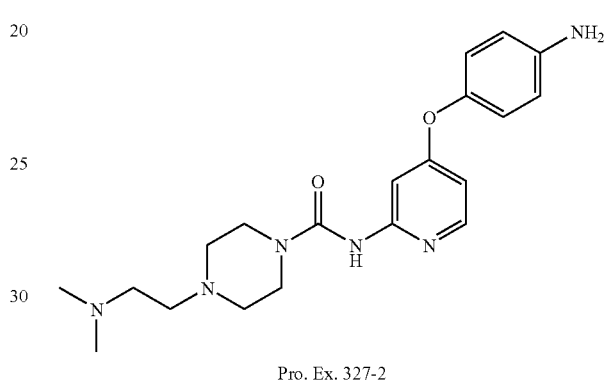
Pro. Ex. 327-2
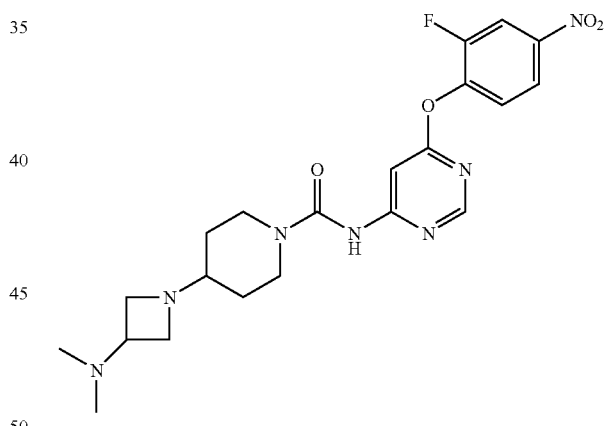
Pro. Ex. 328-1
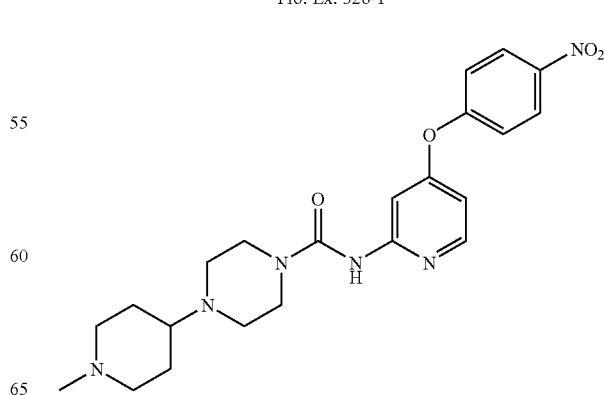
Pro. Ex. 329-1

TABLE 30-continued
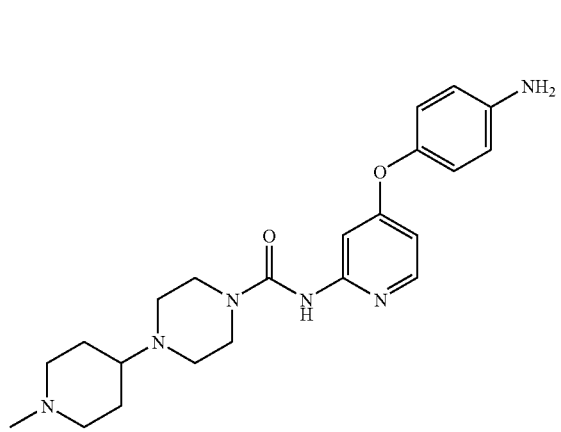
Pro. Ex. 329-2
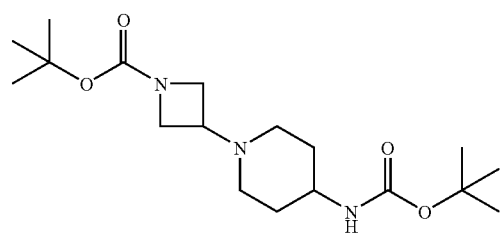
Pro. Ex. 330-1
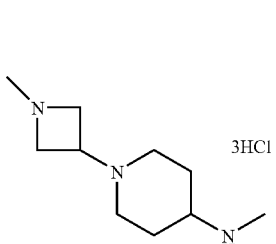
Pro. Ex. 330-2
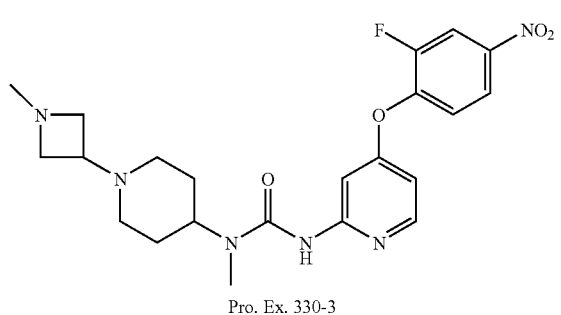
Pro. Ex. 330-3
TABLE 30-continued
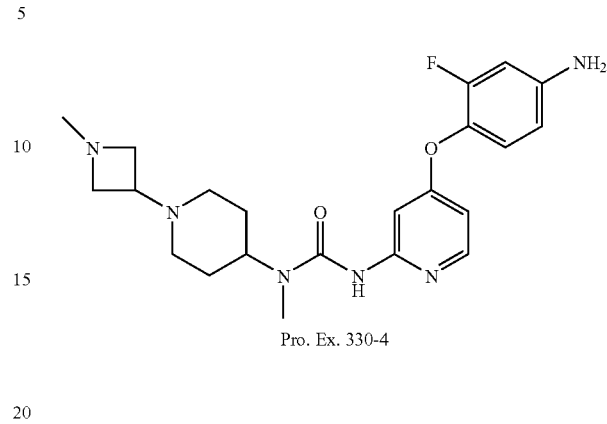
Pro. Ex. 330-4
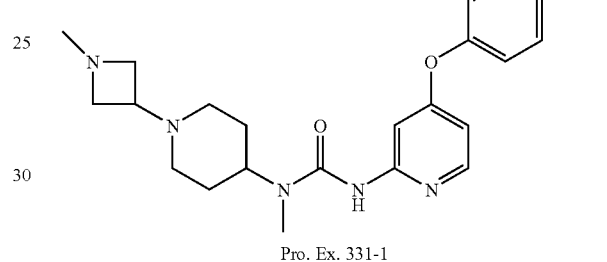
Pro. Ex. 331-1
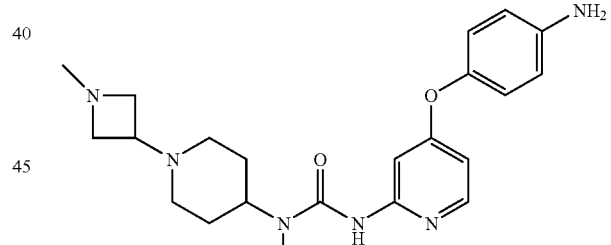
Pro. Ex. 331-2
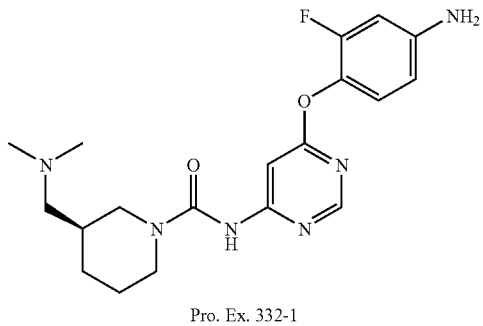
Pro. Ex. 332-1

TABLE 30-continued
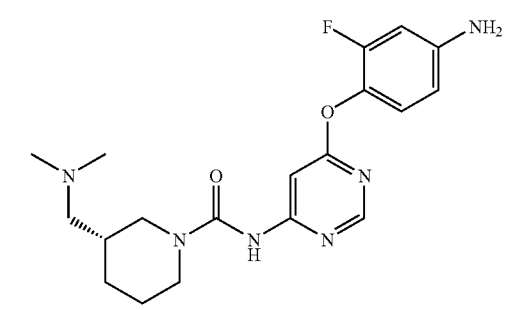
Pro. Ex. 333-1
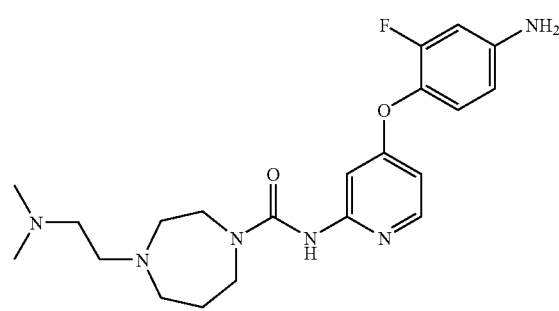
Pro. Ex. 334-1
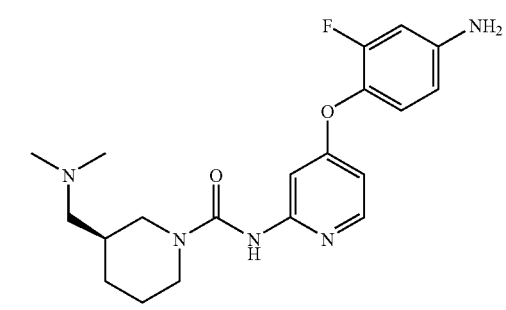
Pro. Ex. 335-1
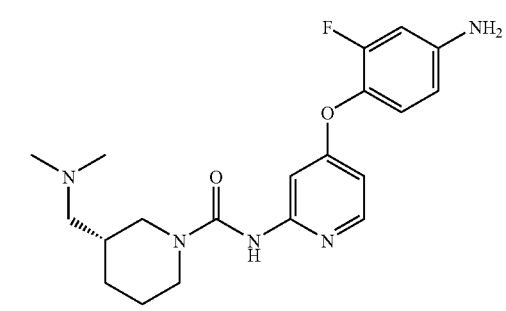
Pro. Ex. 336-1
TABLE 30-continued
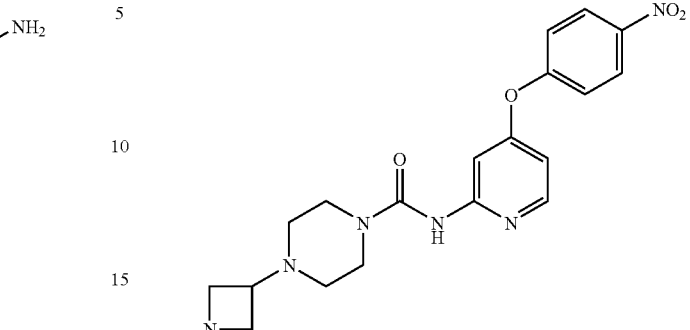
Pro. Ex. 337-1
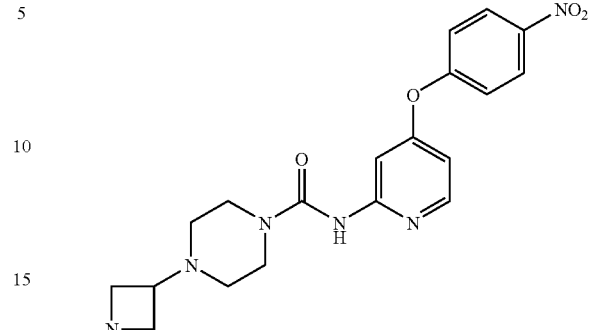
Pro. Ex. 337-2
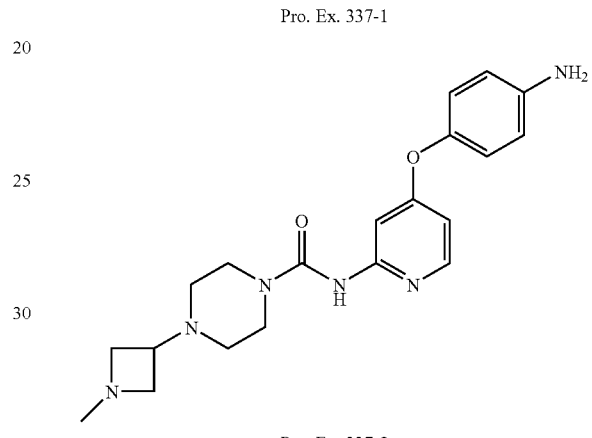
Pro. Ex. 338-1
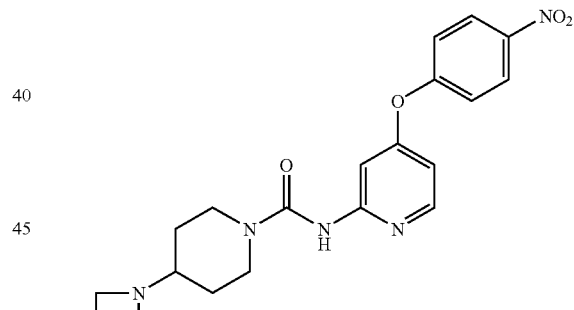
Pro. Ex. 338-2

TABLE 31
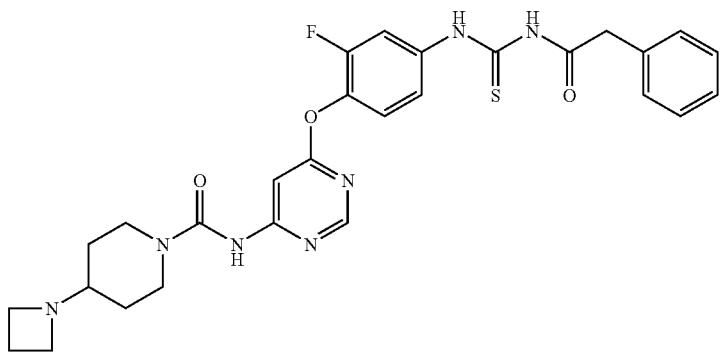
Ex. 167
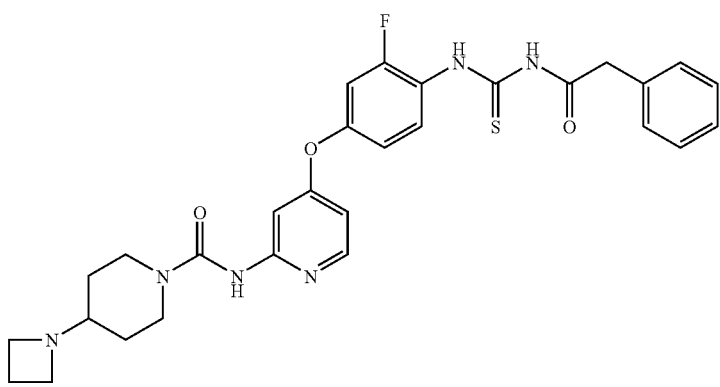
Ex. 168
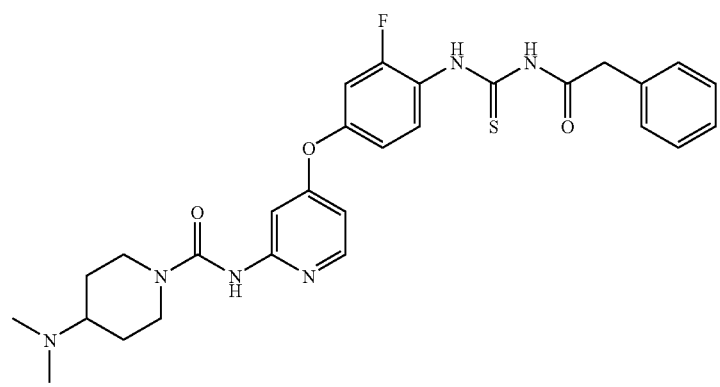
Ex. 169
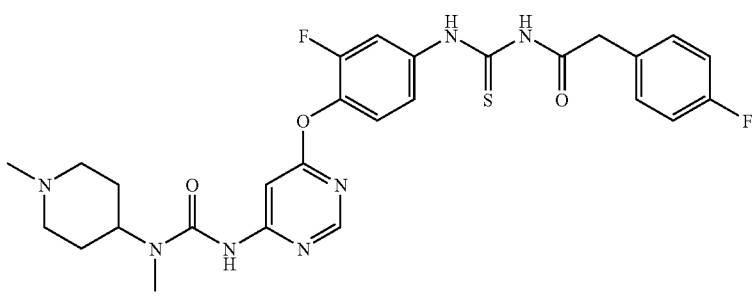
Ex. 170

TABLE 31-continued
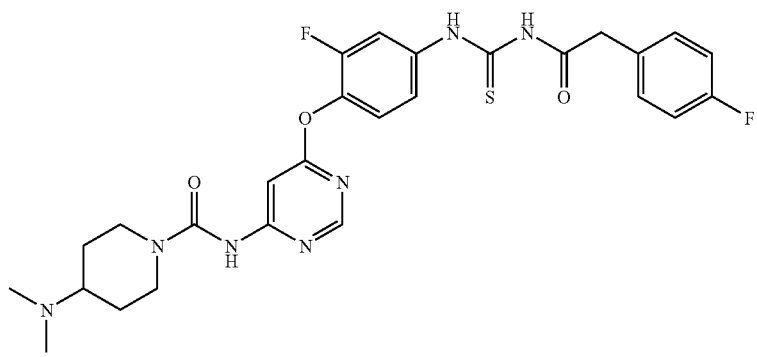
Ex. 171
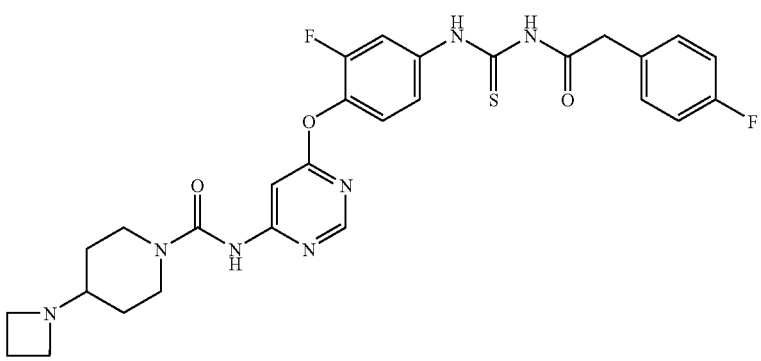
Ex. 172
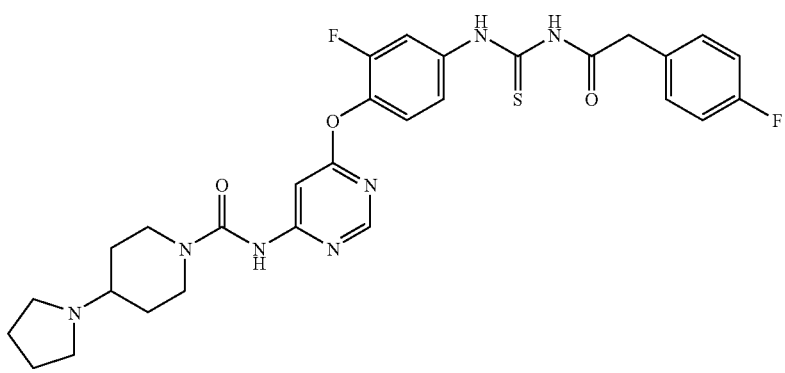
Ex. 173
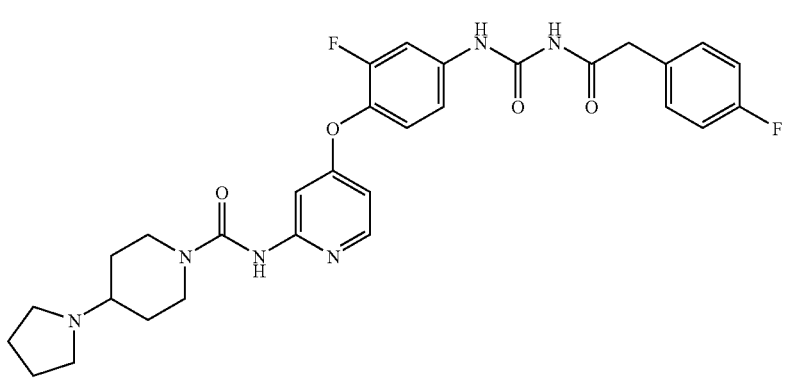
Ex. 174

TABLE 31-continued
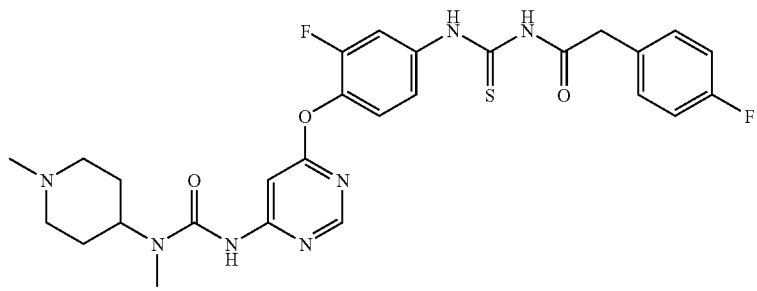
Ex. 175
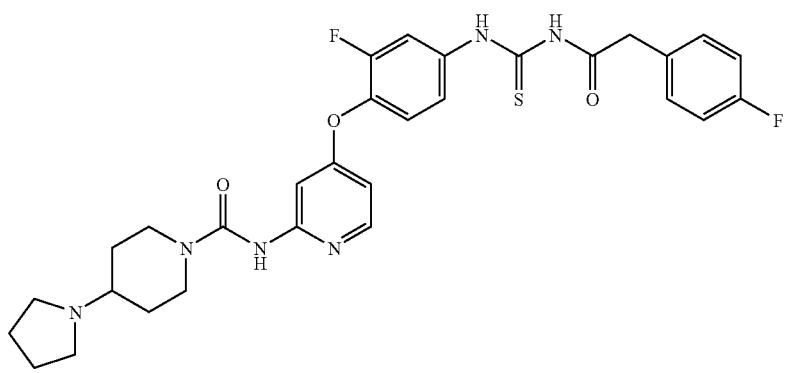
Ex. 176
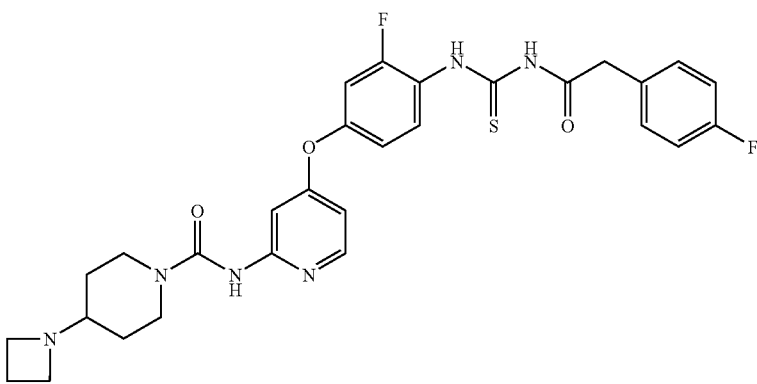
Ex. 177
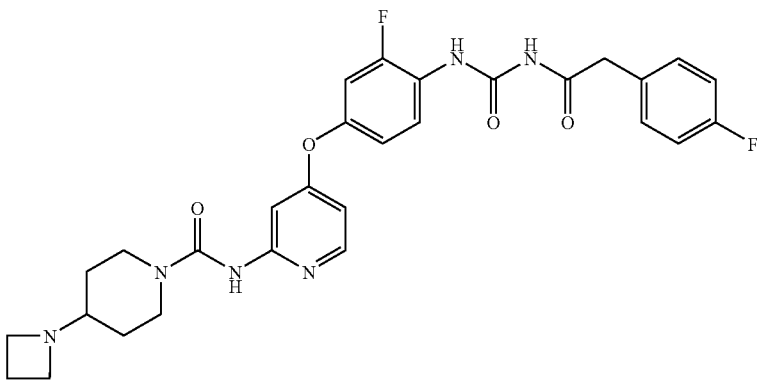
Ex. 178

TABLE 31-continued
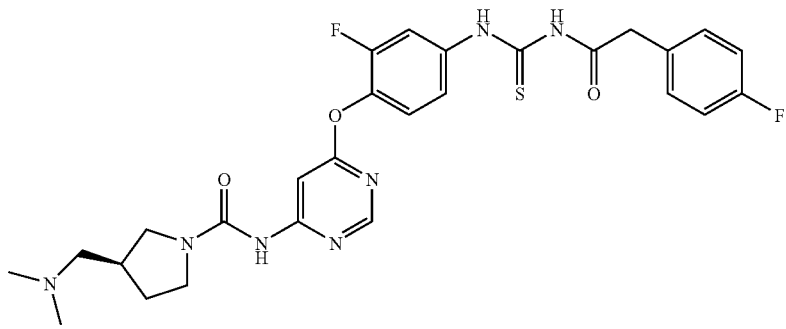
Ex. 179
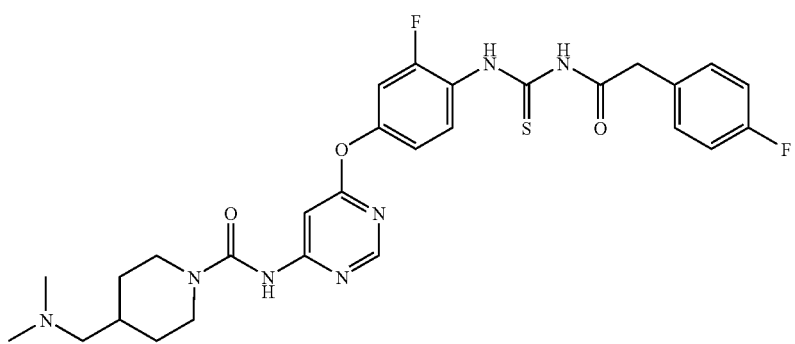
Ex. 180
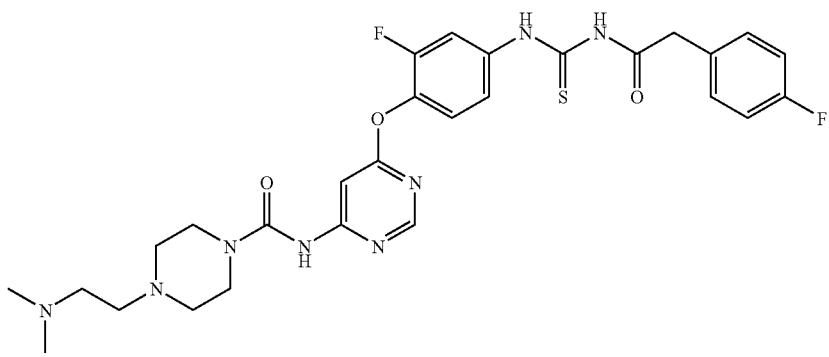
Ex. 181
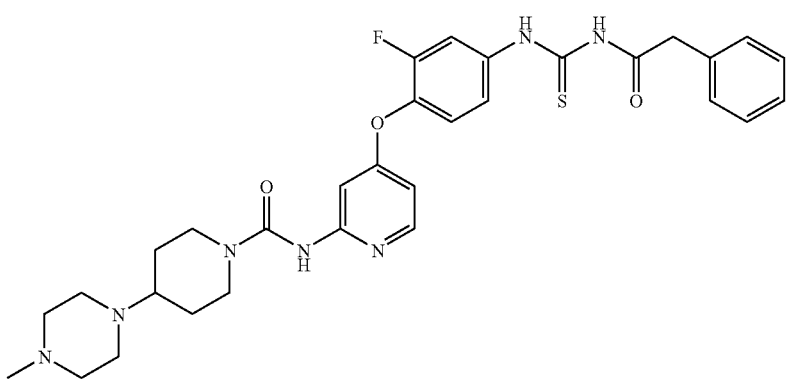
Ex. 182

TABLE 31-continued
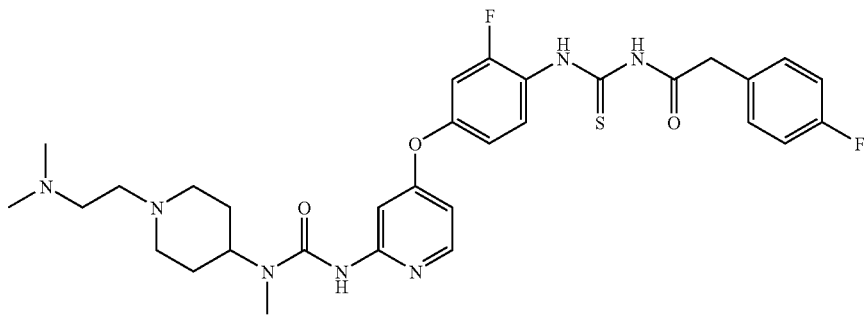
Ex. 183
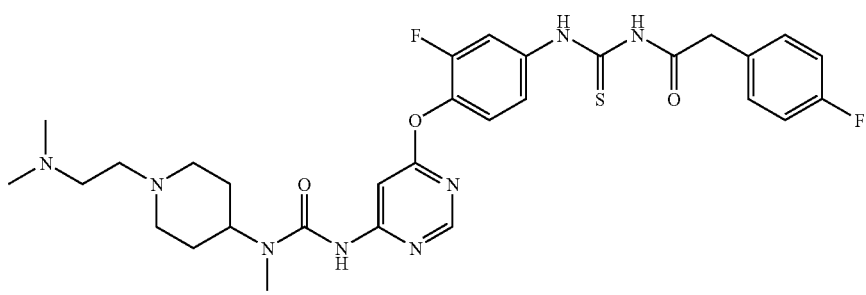
Ex. 184
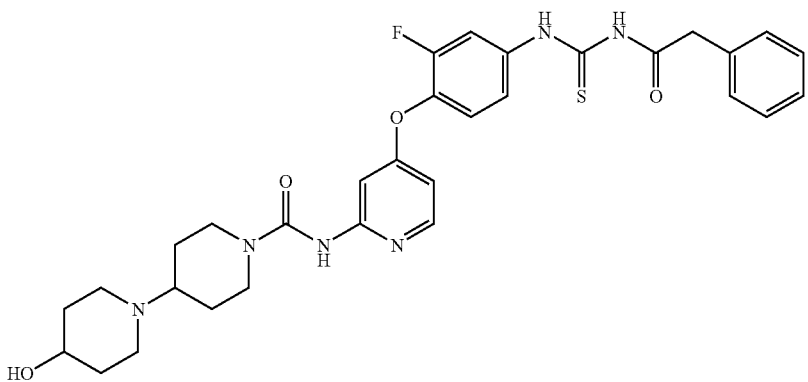
Ex. 185
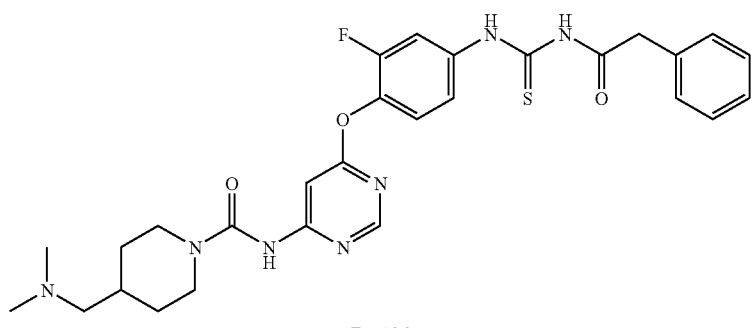
Ex. 186

TABLE 31-continued
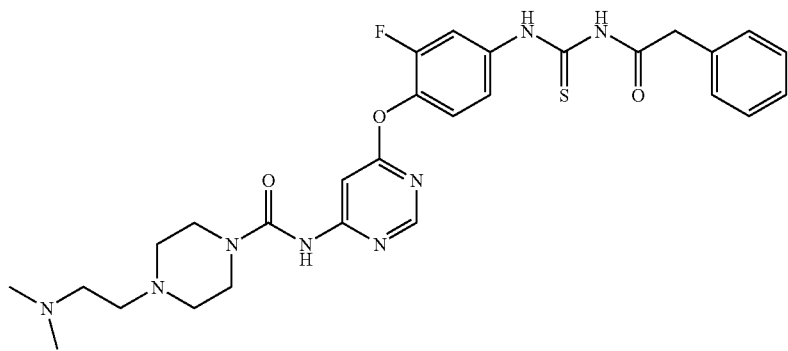
Ex. 187
TABLE 32
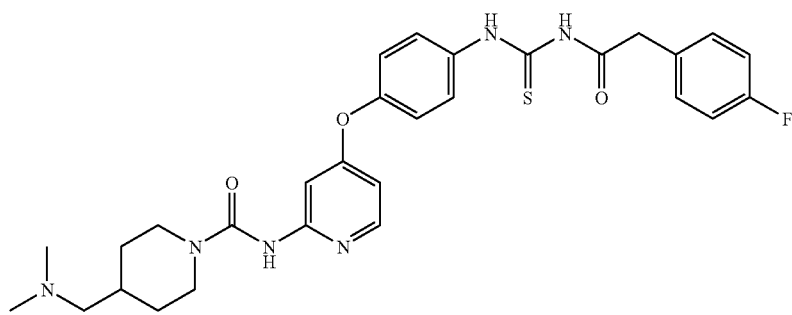
Ex. 188
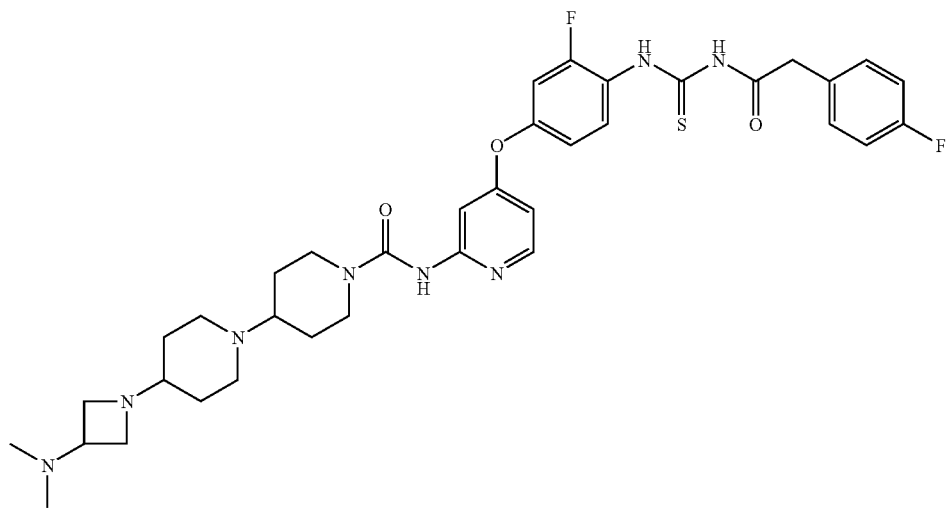
Ex. 189

TABLE 32-continued
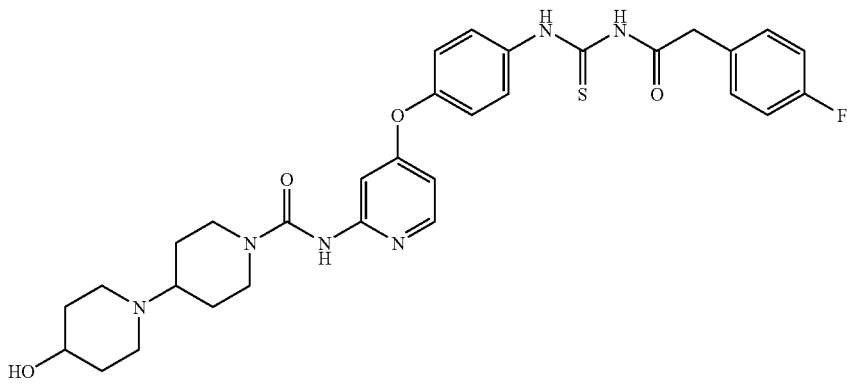
Ex. 190
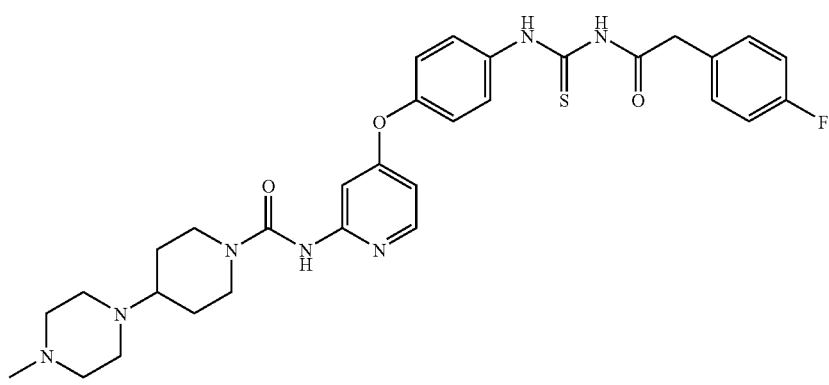
Ex. 191
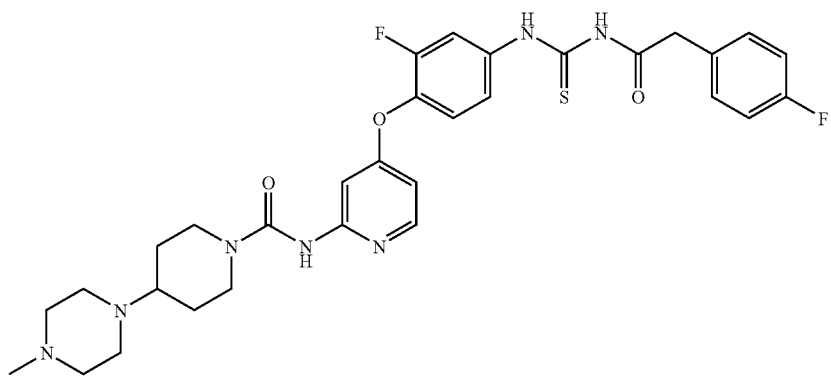
Ex. 192
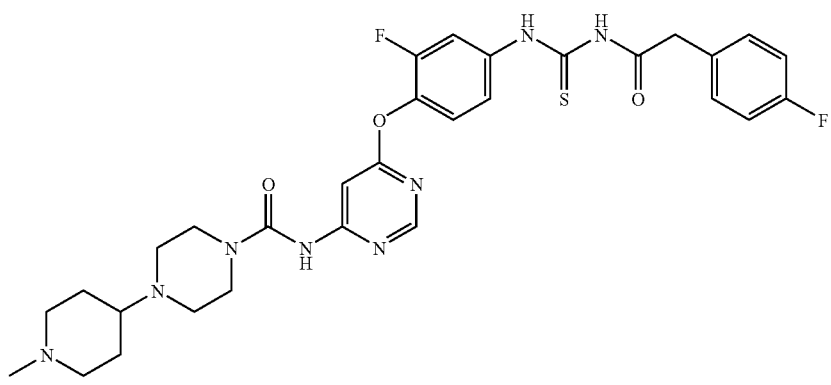
Ex. 193

TABLE 32-continued
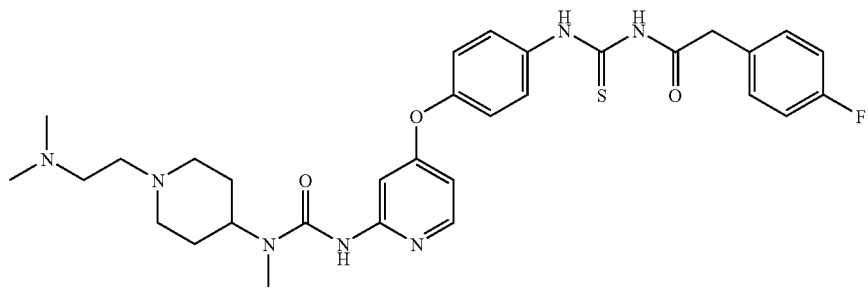
Ex. 194
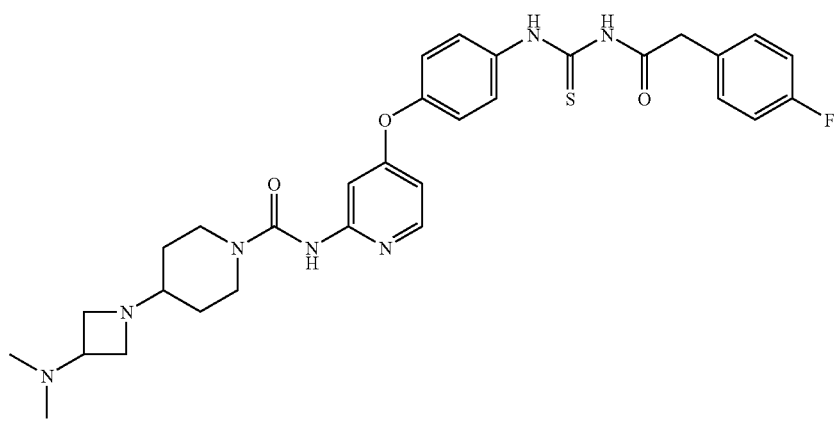
Ex. 195
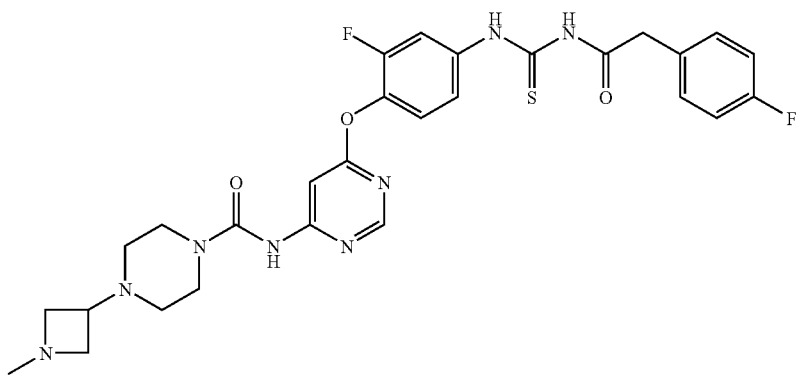
Ex. 196
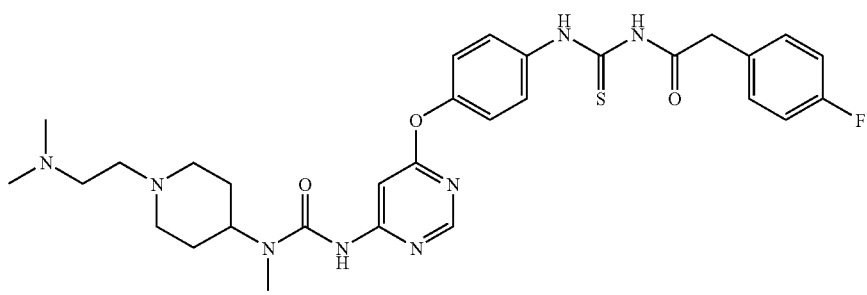
Ex. 197

TABLE 32-continued
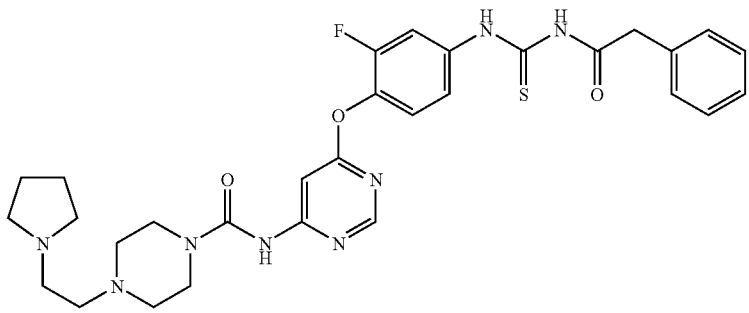
Ex. 198
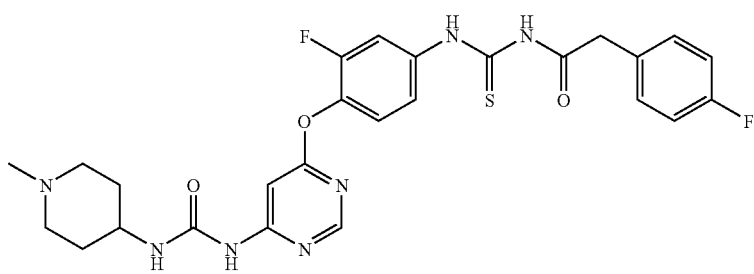
Ex. 199
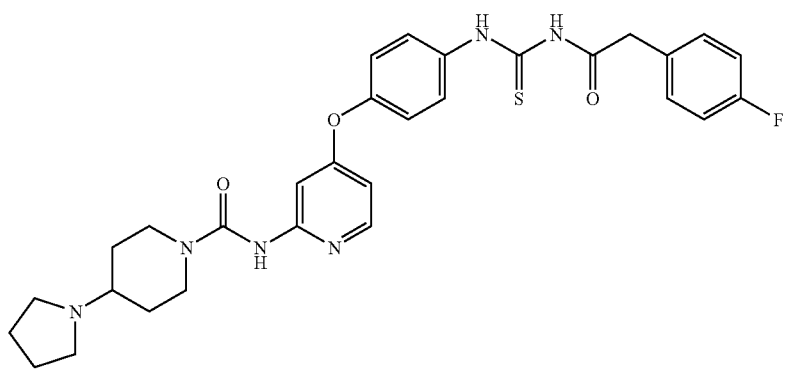
Ex. 200
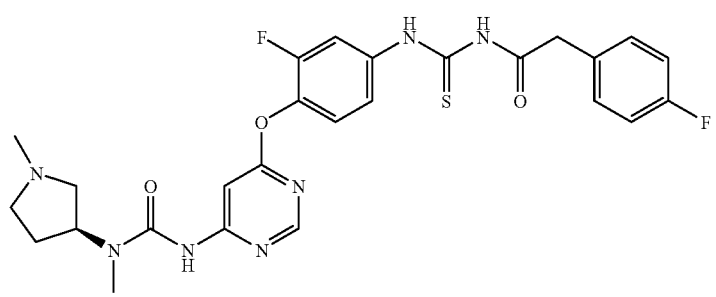
Ex. 201

TABLE 32-continued
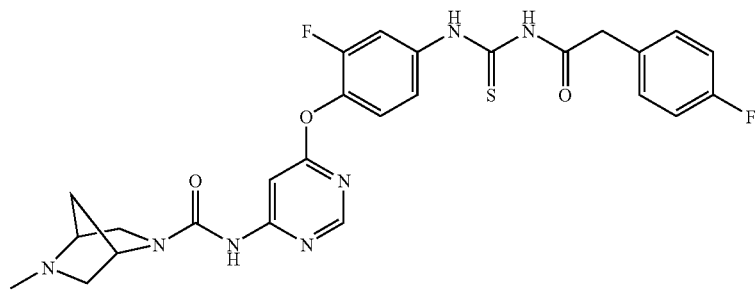
Ex. 202
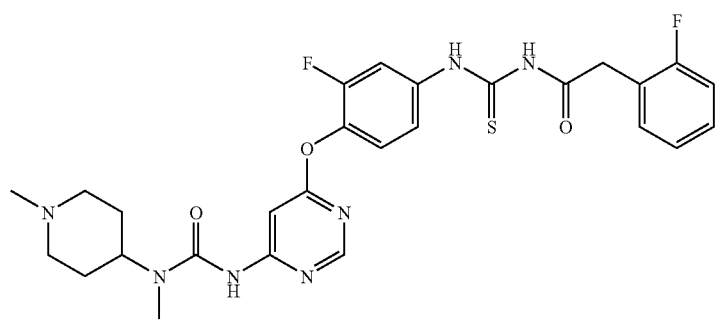
Ex. 203
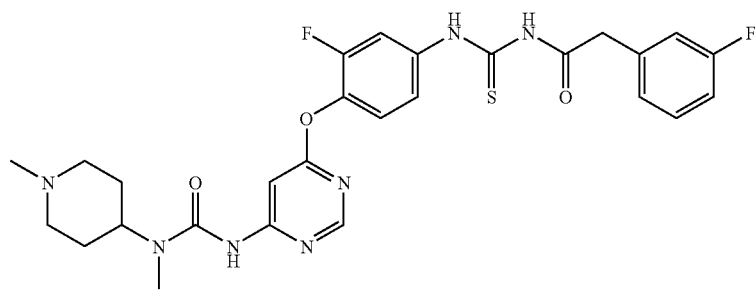
Ex. 204
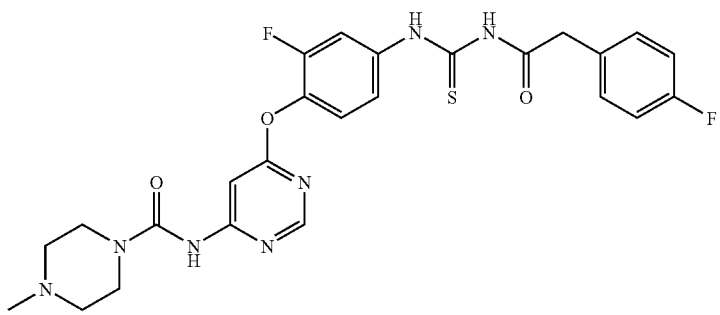
Ex. 205

TABLE 32-continued
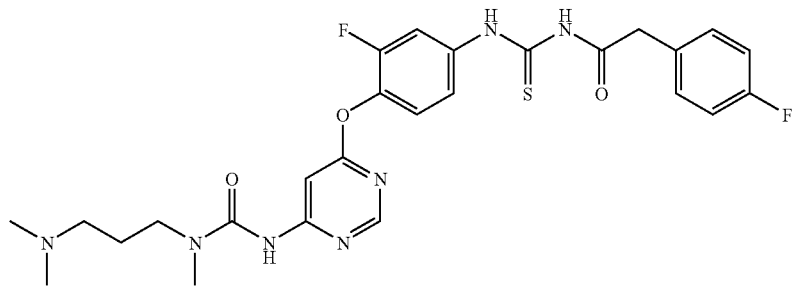
Ex. 206
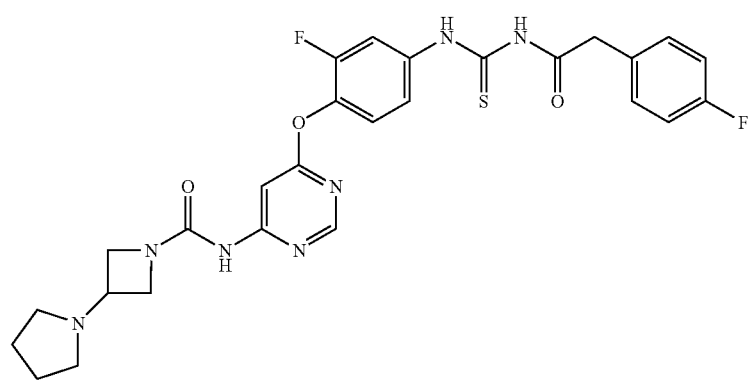
Ex. 207
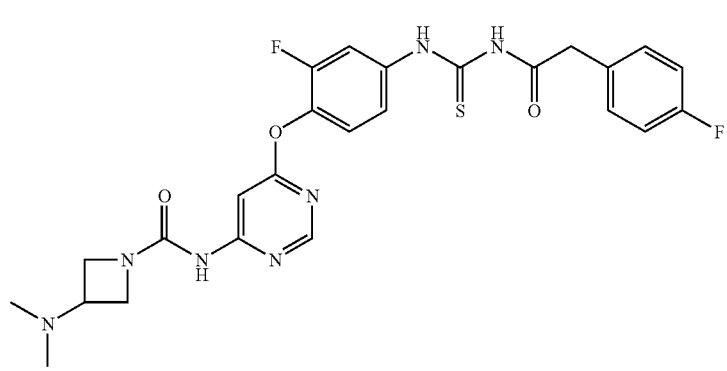
Ex. 208
TABLE 33
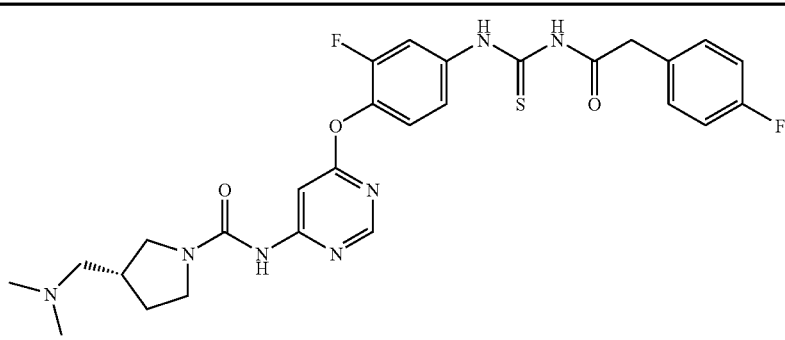
Ex. 209

TABLE 33-continued
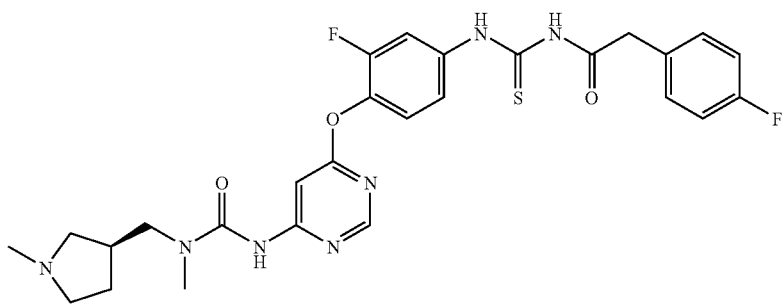
Ex. 210
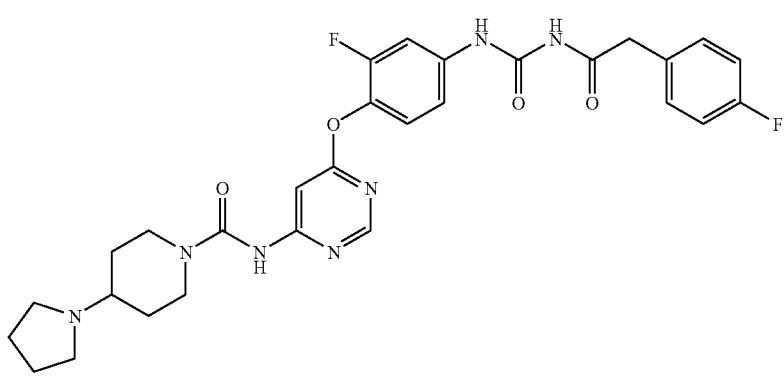
Ex. 211
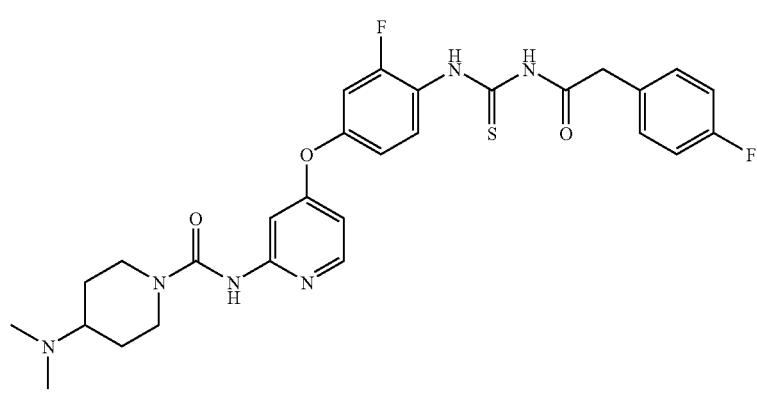
Ex. 212
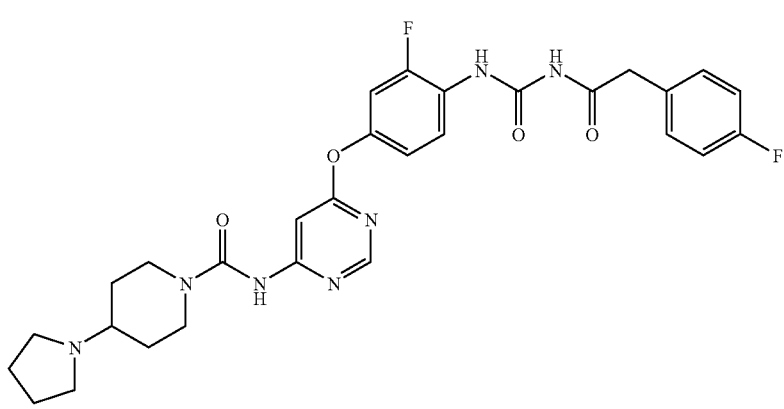
Ex. 213

TABLE 33-continued
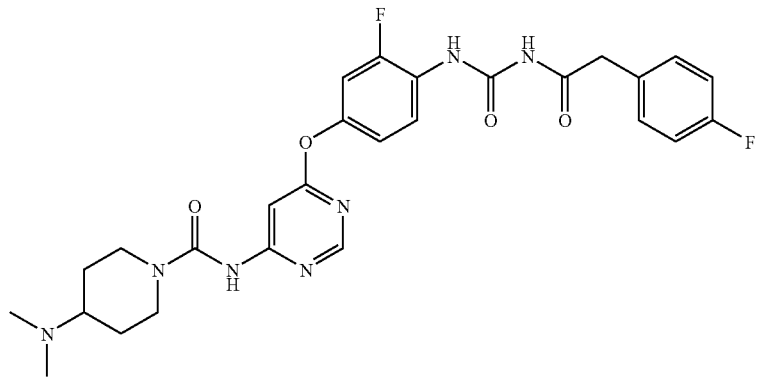
Ex. 214
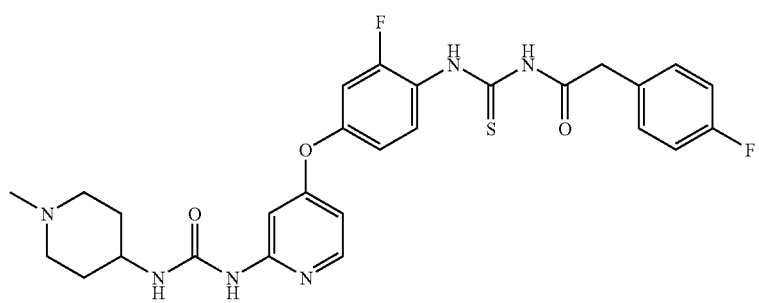
Ex. 215
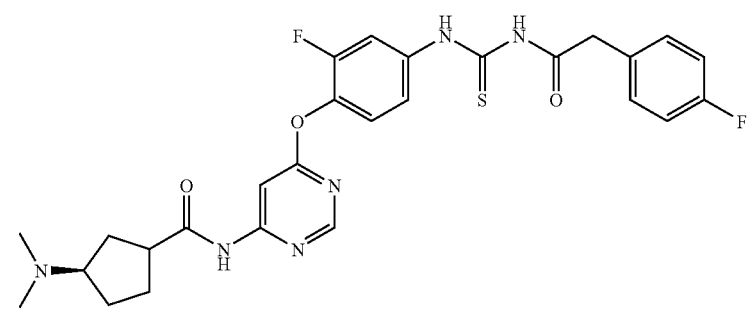
Ex. 216
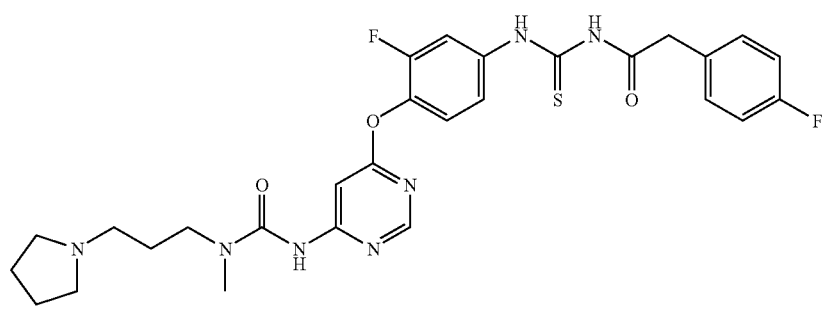
Ex. 217

TABLE 33-continued
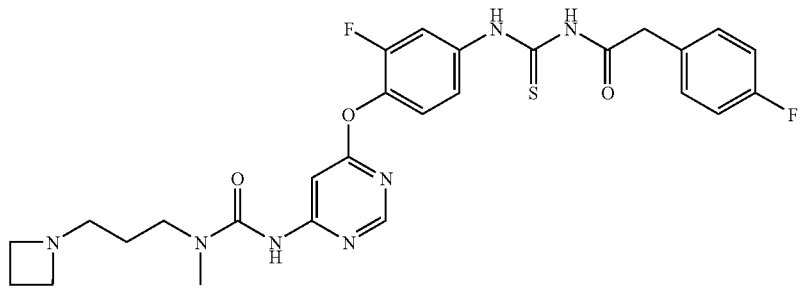
Ex. 218
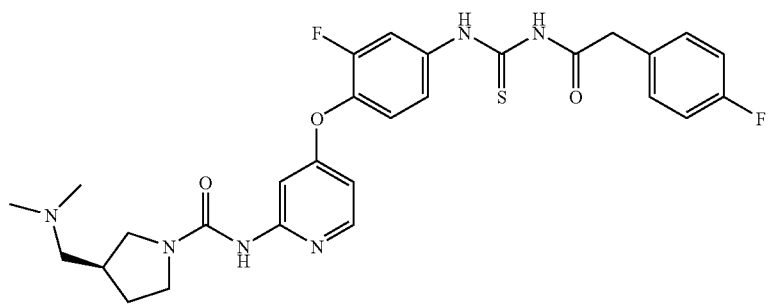
Ex. 219
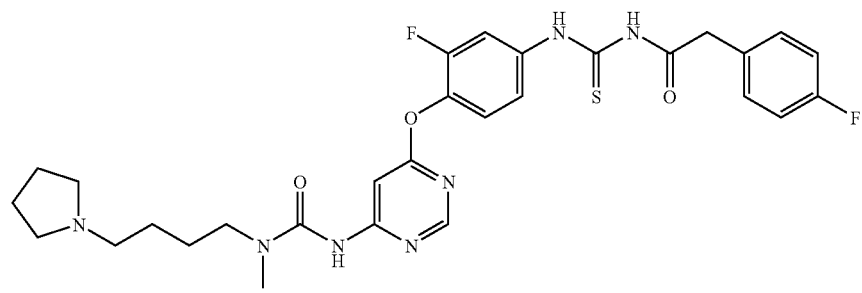
Ex. 220
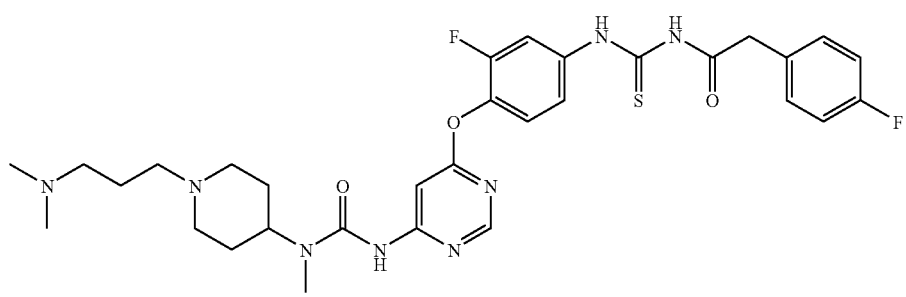
Ex. 221

TABLE 33-continued
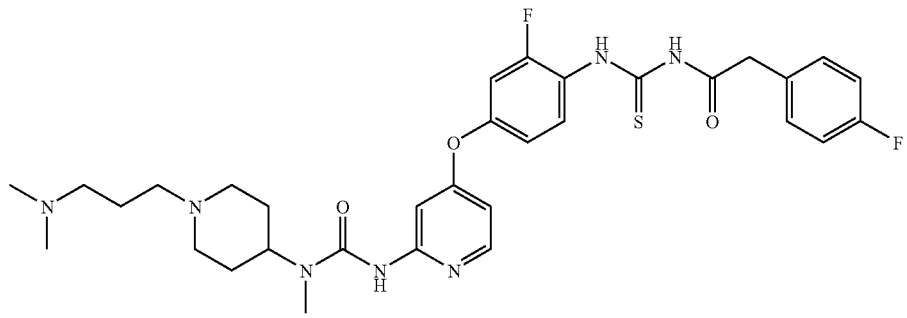
Ex. 222
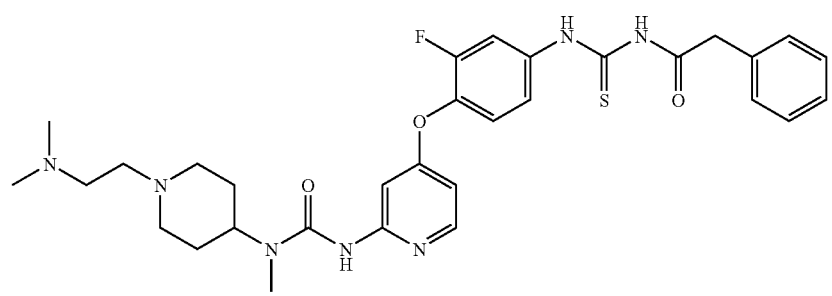
Ex. 223
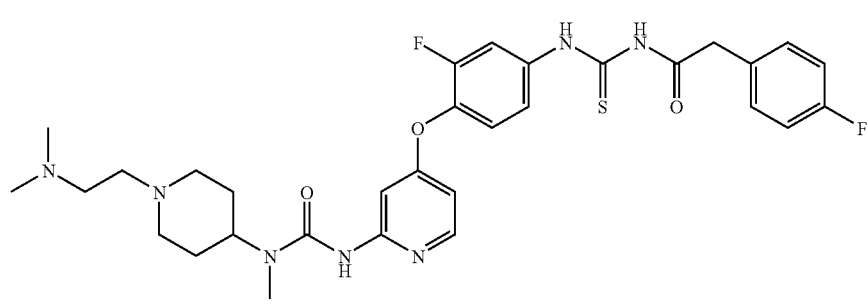
Ex. 224
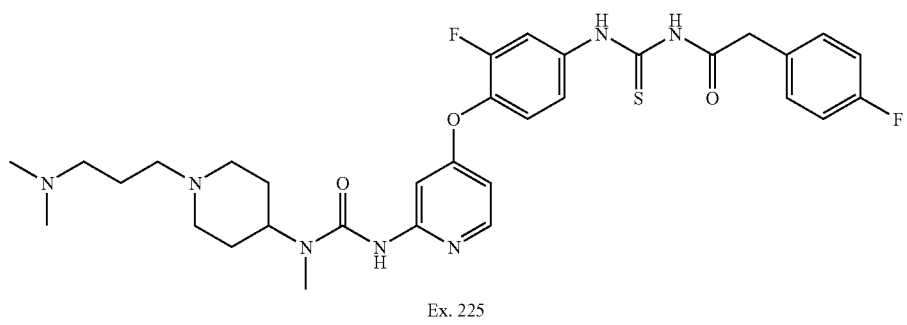
Ex. 225

TABLE 33-continued
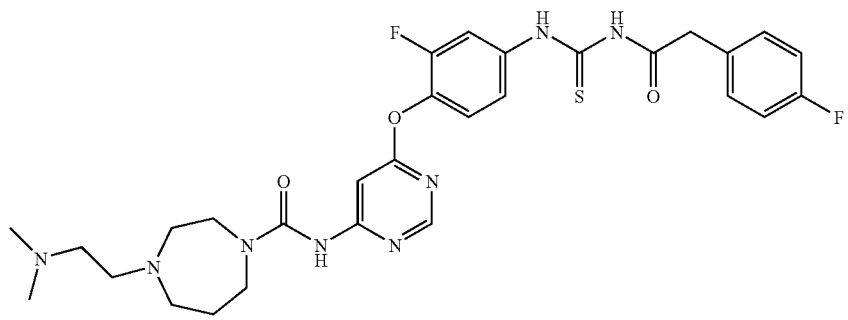
Ex. 226
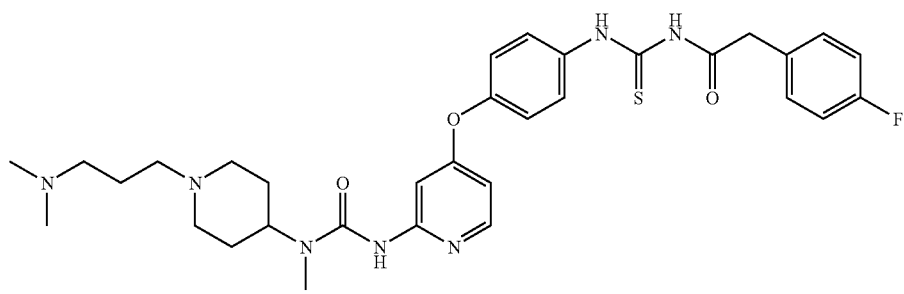
Ex. 227
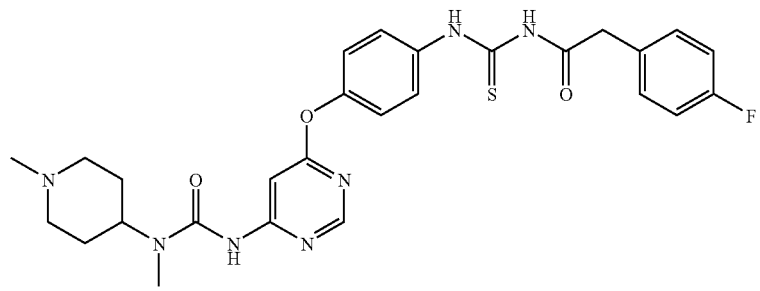
Ex. 228
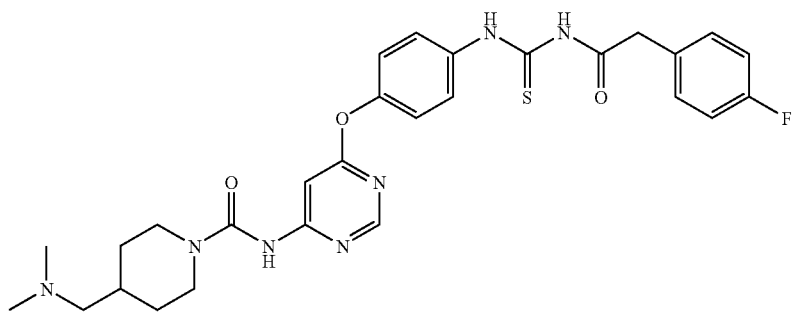
Ex. 229

TABLE 34
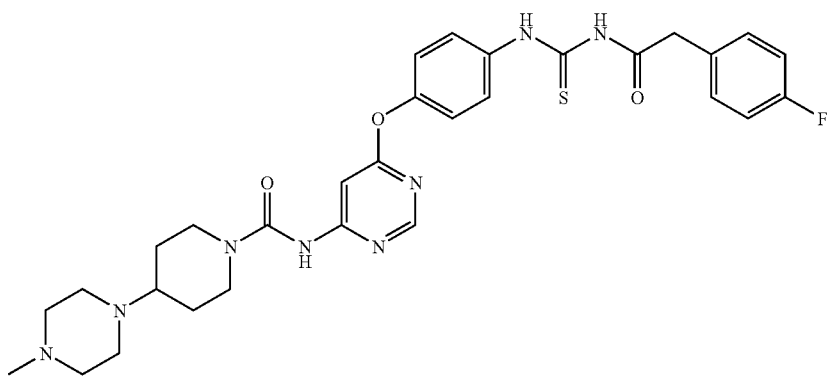
Ex. 230
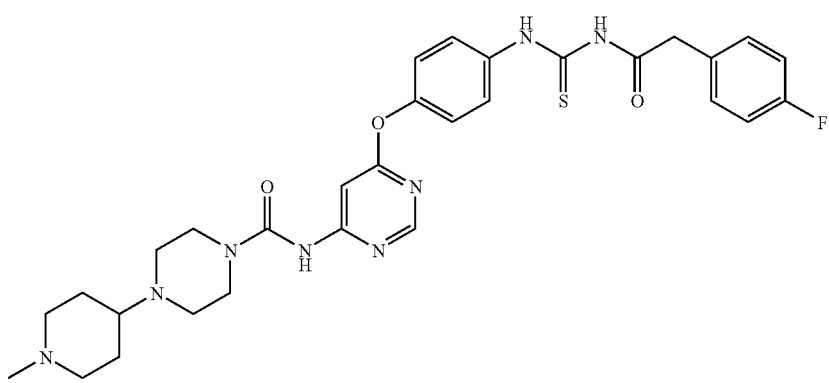
Ex. 231
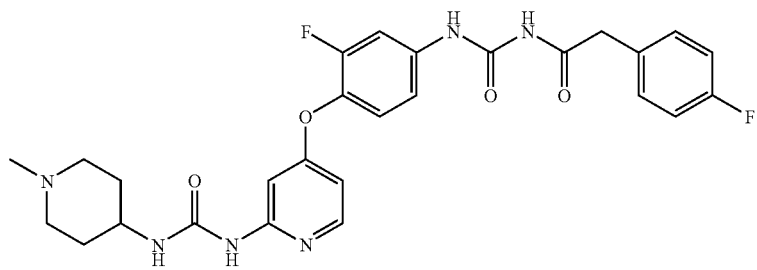
Ex. 232
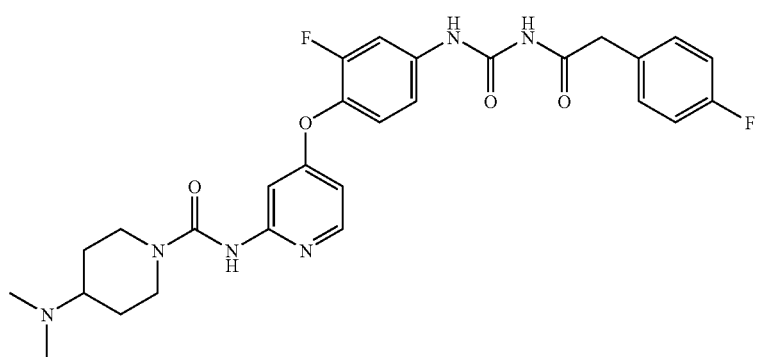
Ex. 233

TABLE 34-continued
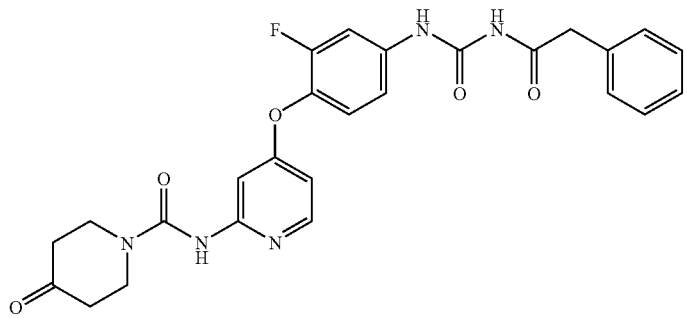
Ex. 234
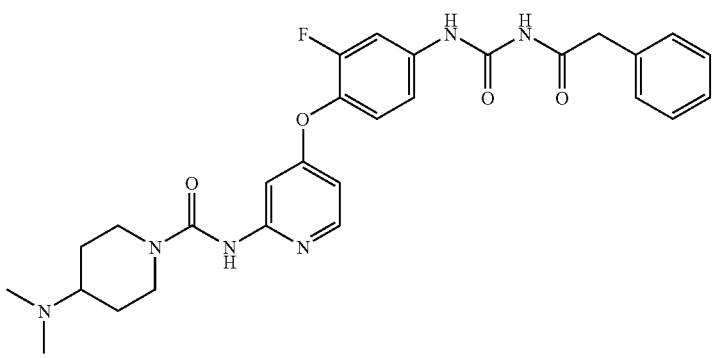
Ex. 235
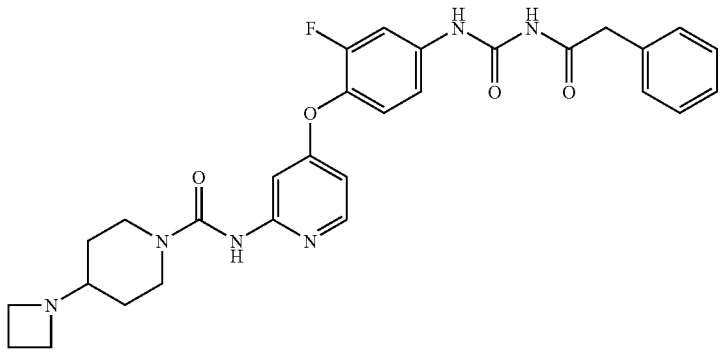
Ex. 236
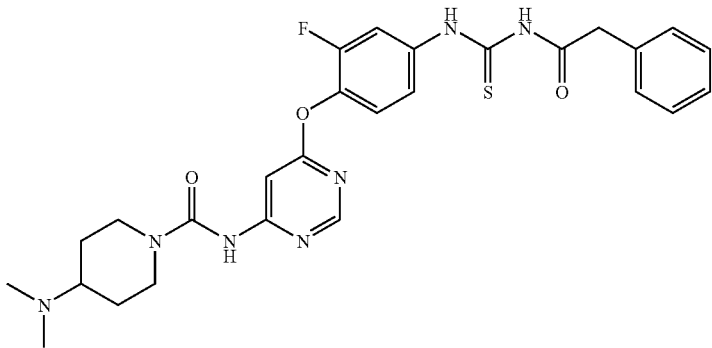
Ex. 237

TABLE 34-continued
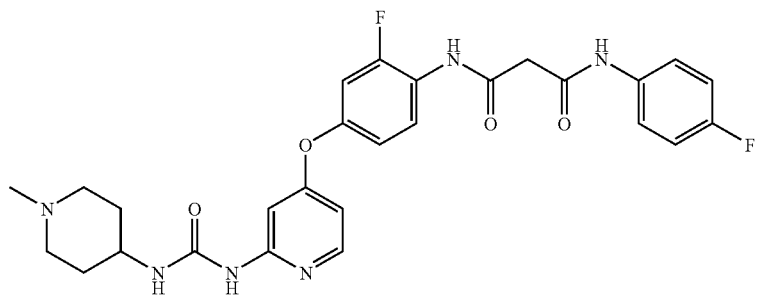
Ex. 238
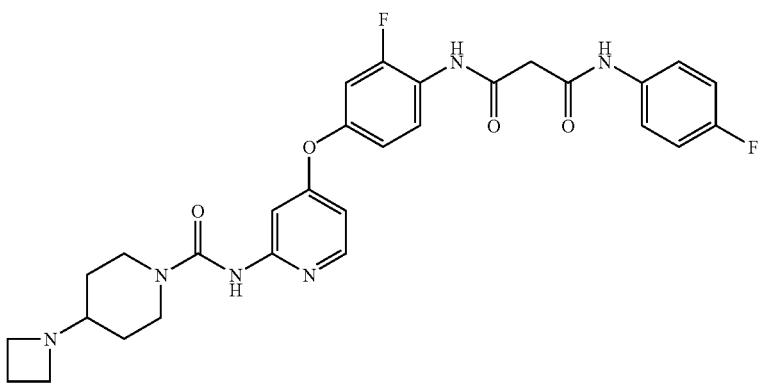
Ex. 239
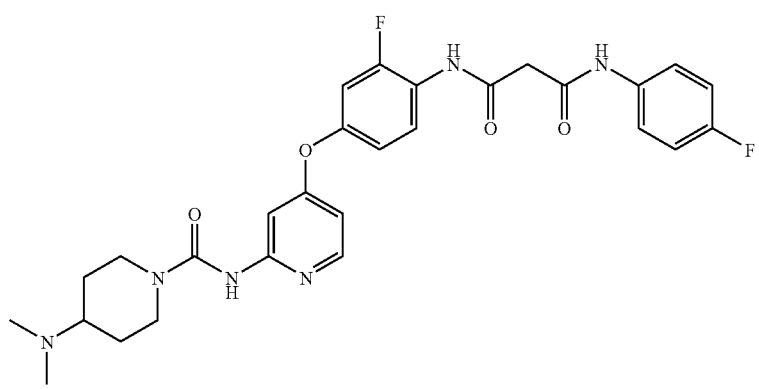
Ex. 240
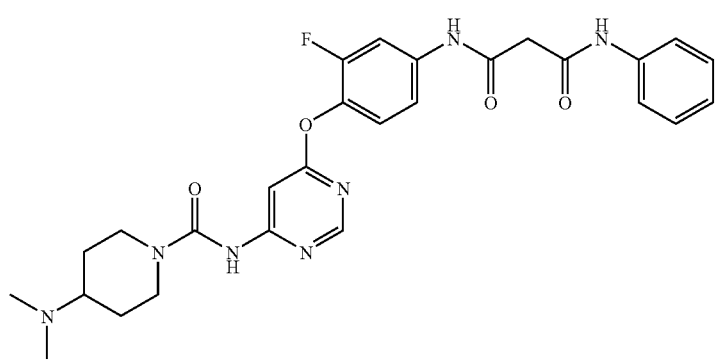
Ex. 241

TABLE 34-continued
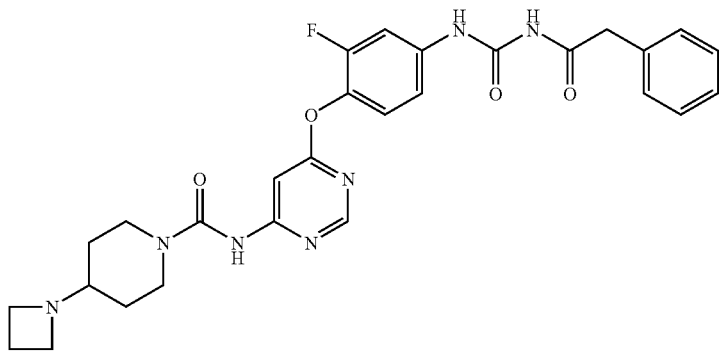
Ex. 242
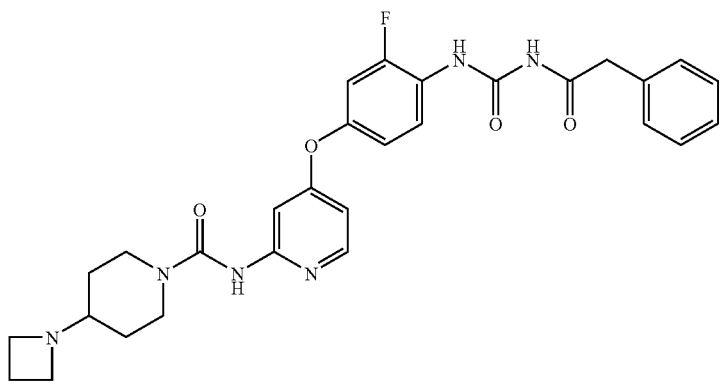
Ex. 243
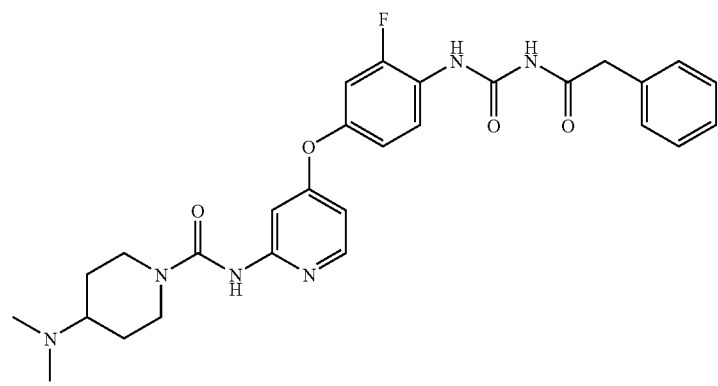
Ex. 244
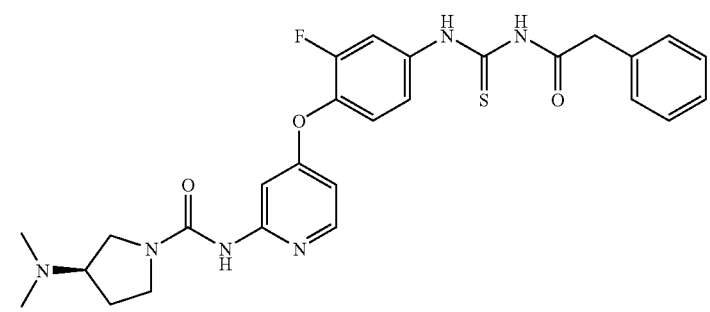
Ex. 245

TABLE 34-continued
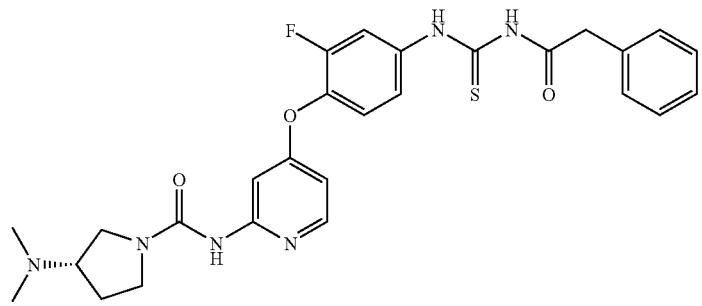
Ex. 246
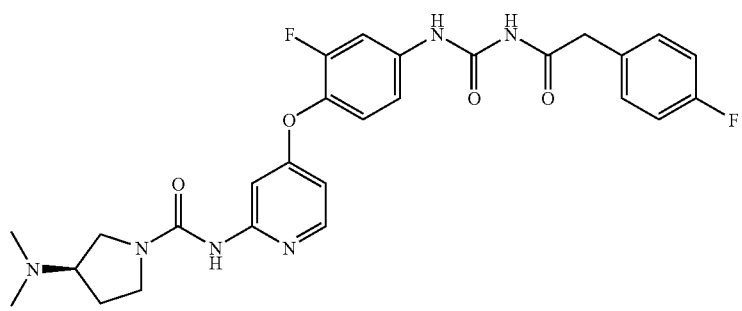
Ex. 247
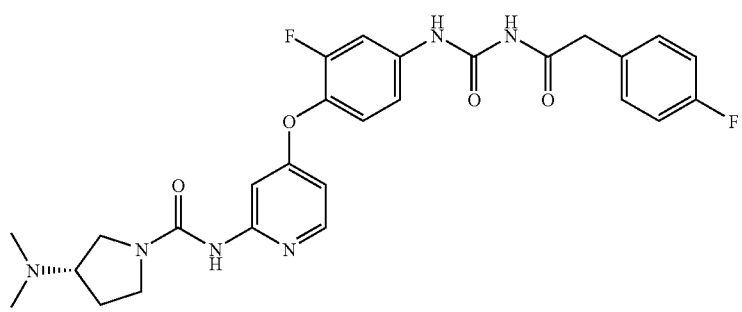
Ex. 248
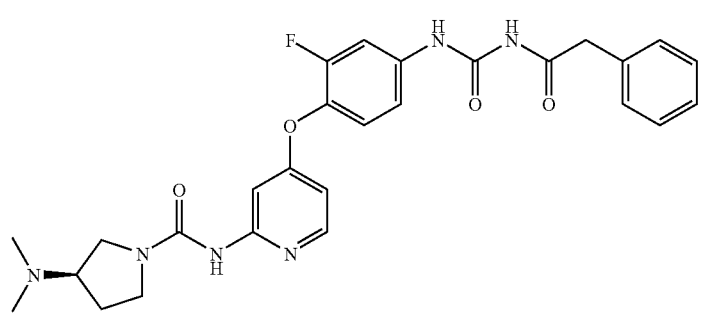
Ex. 249

TABLE 34-continued
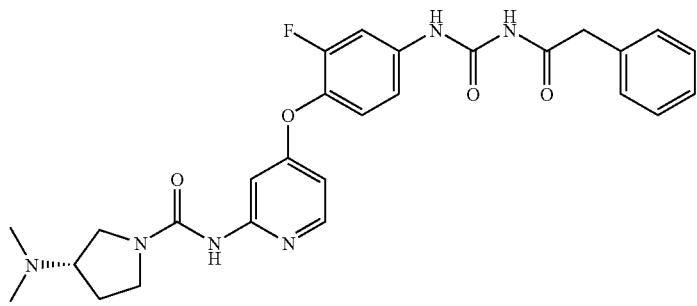
Ex. 250
TABLE 35
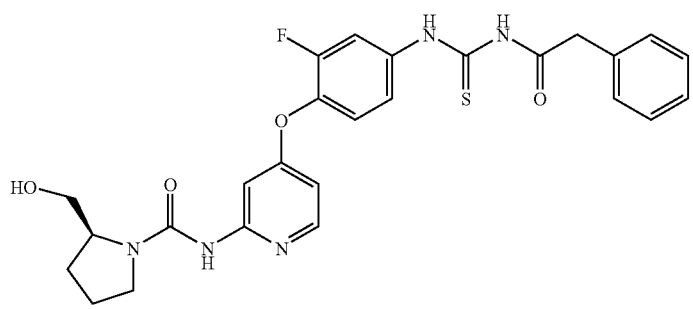
Ex. 251
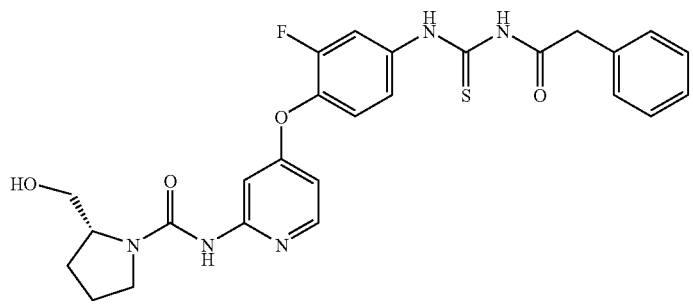
Ex. 252
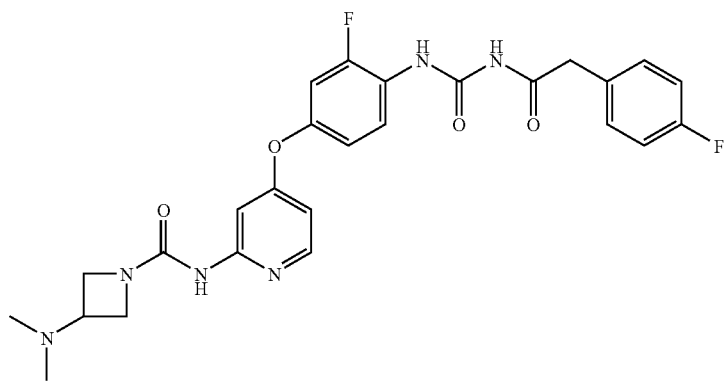
Ex. 253

TABLE 35-continued
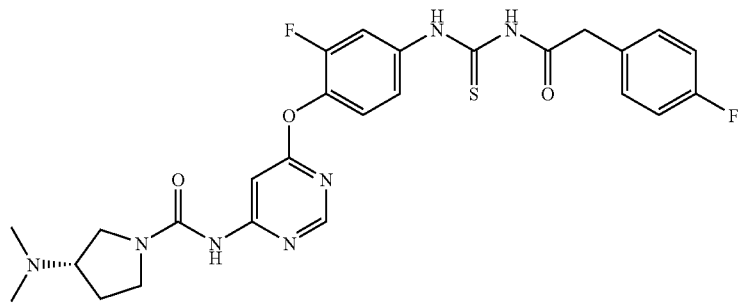
Ex. 254
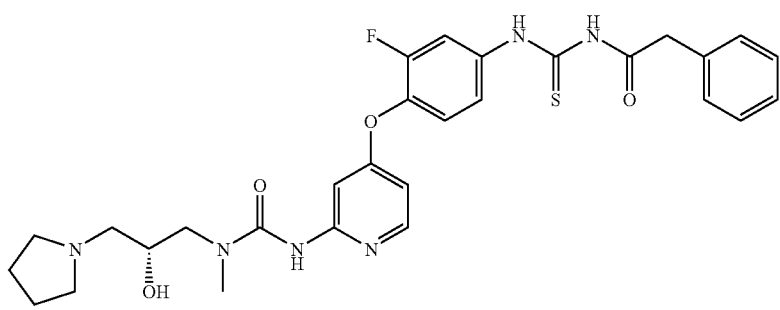
Ex. 255
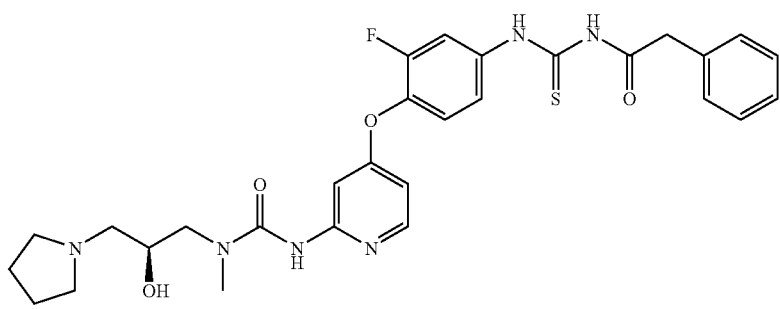
Ex. 256
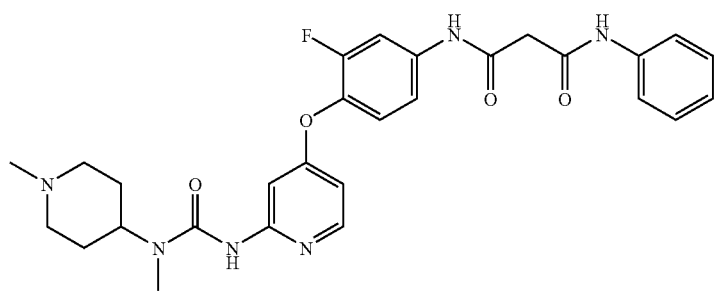
Ex. 257

TABLE 35-continued
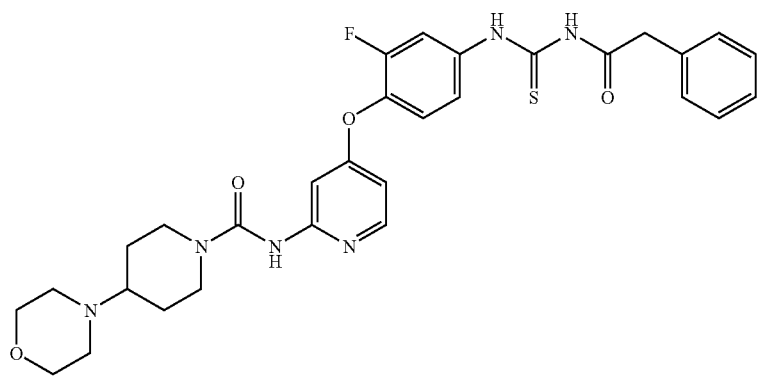
Ex. 258
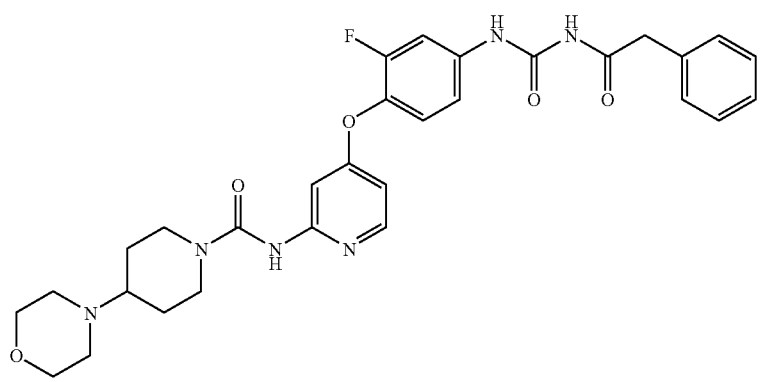
Ex. 259
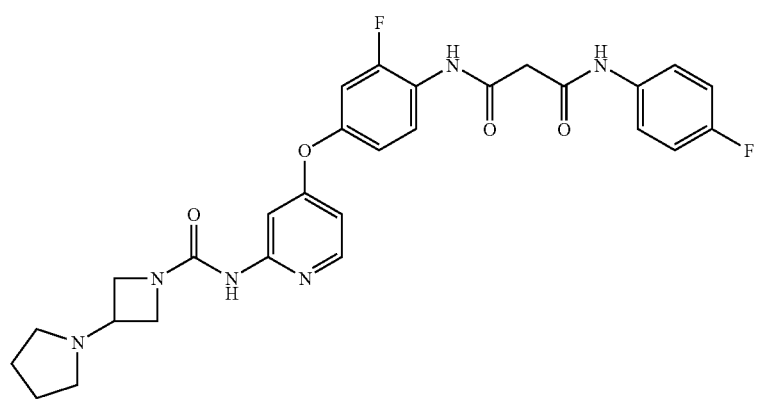
Ex. 260

TABLE 35-continued
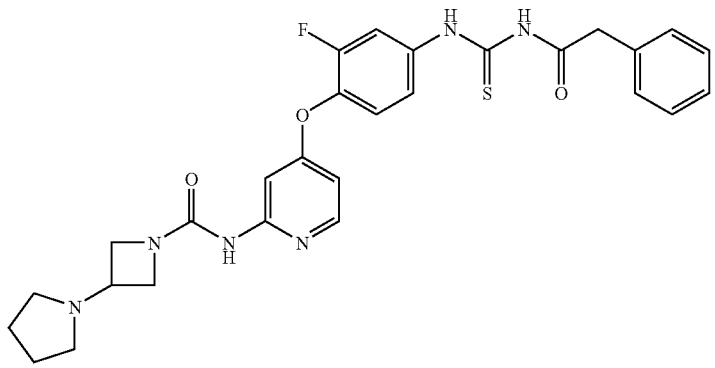
Ex. 261
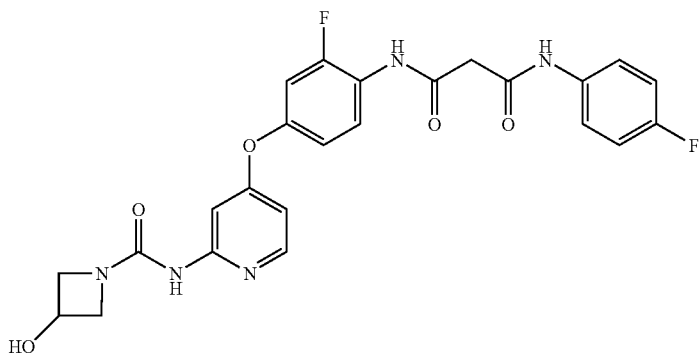
Ex. 262
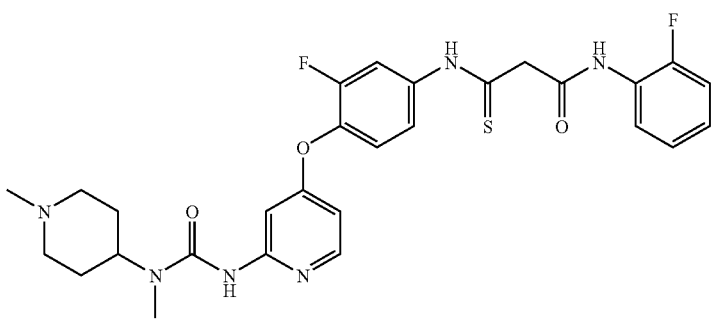
Ex. 263
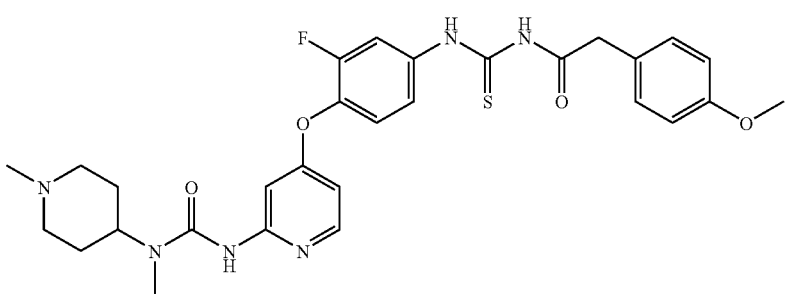
Ex. 264

TABLE 35-continued
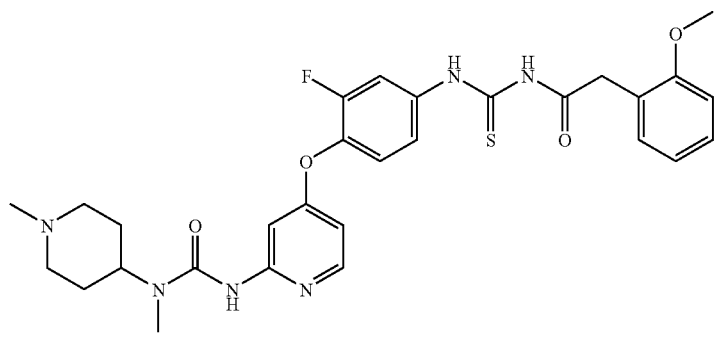
Ex. 265
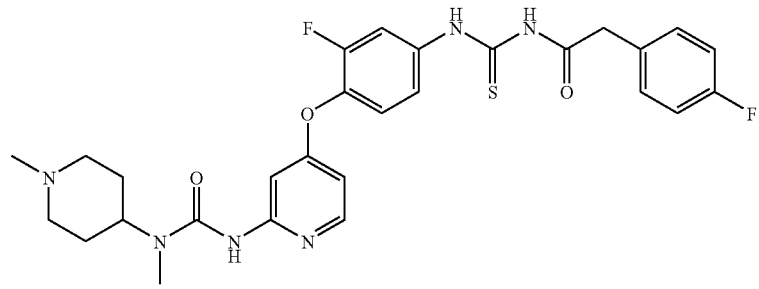
Ex. 266
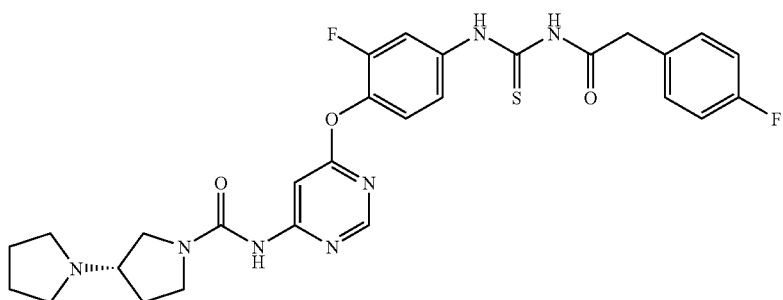
Ex. 267
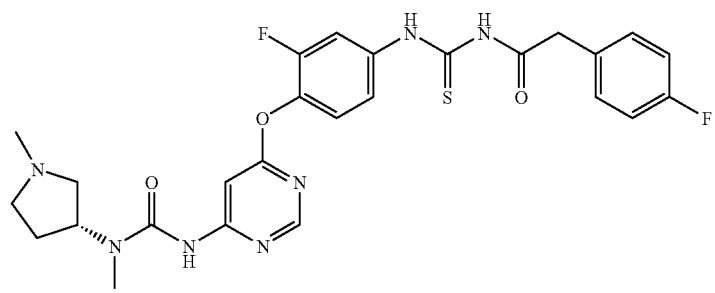
Ex. 268

TABLE 36
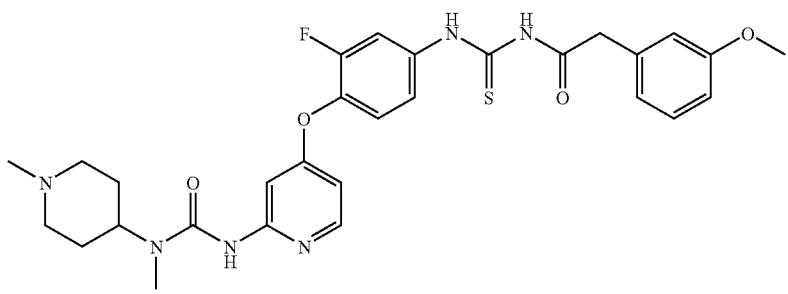
Ex. 269
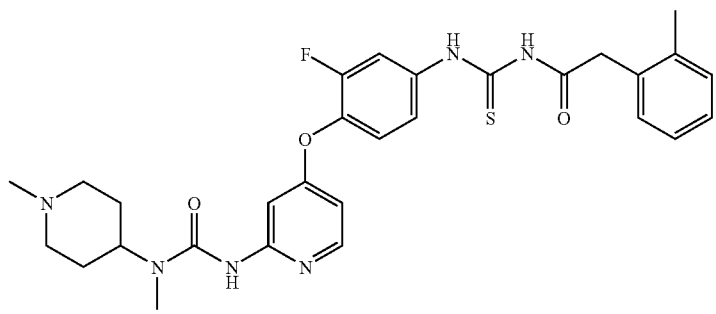
Ex. 270
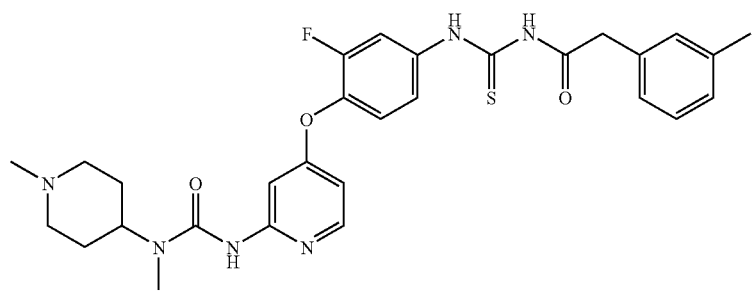
Ex. 271
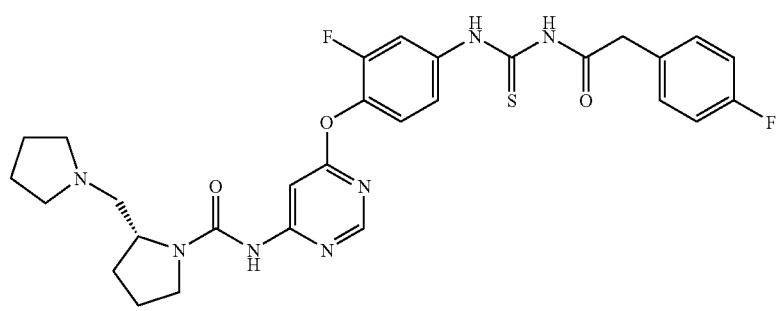
Ex. 272

TABLE 36-continued
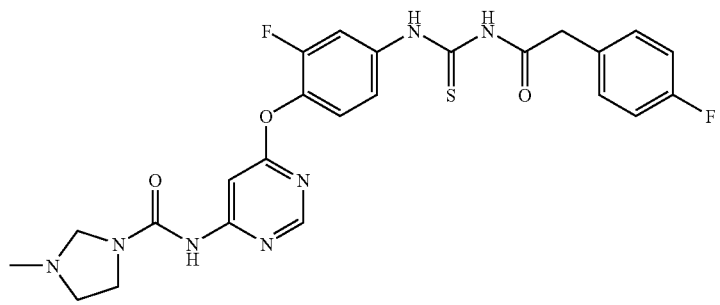
Ex. 273
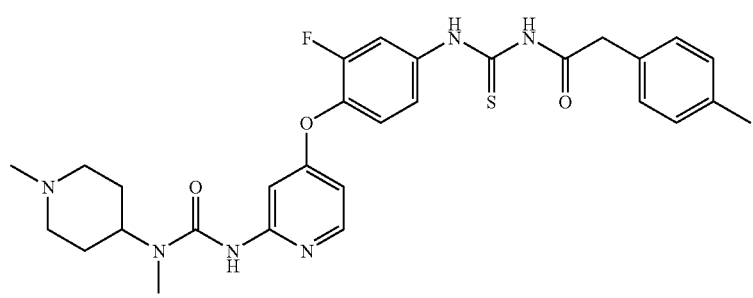
Ex. 274
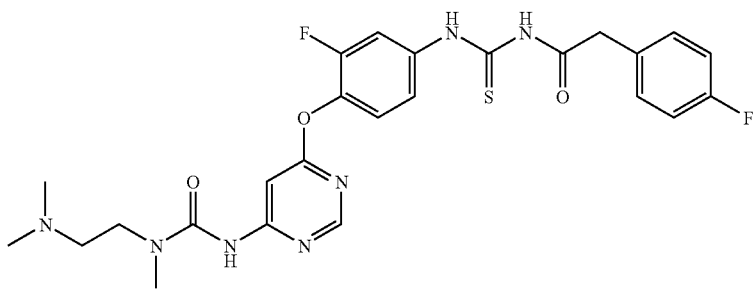
Ex. 275
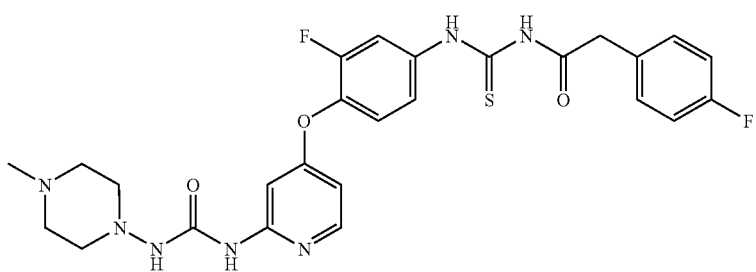
Ex. 276

TABLE 36-continued
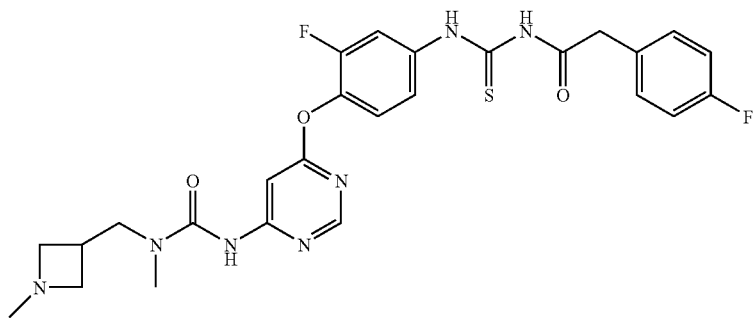
Ex. 277
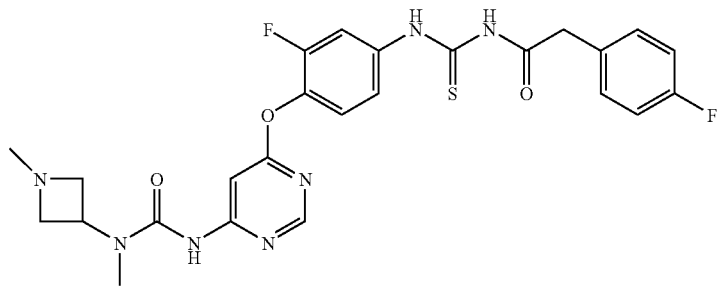
Ex. 278
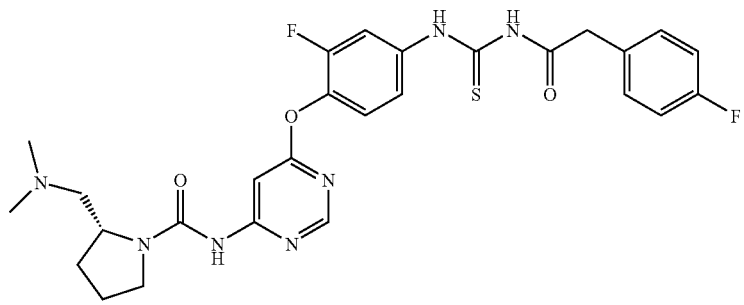
Ex. 279
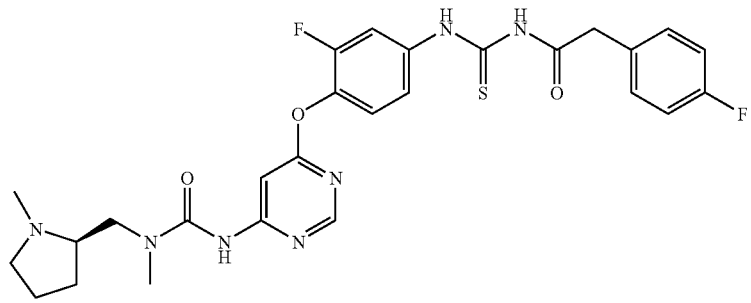
Ex. 280

TABLE 36-continued
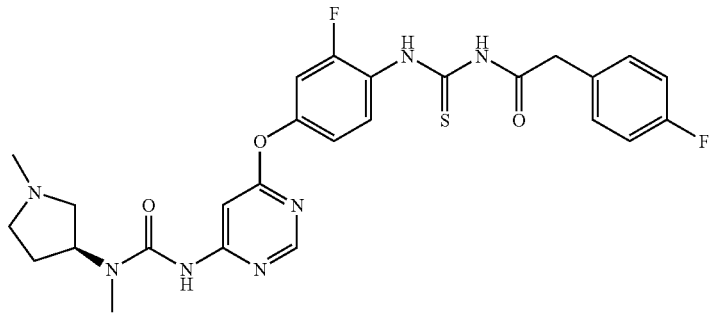
Ex. 281
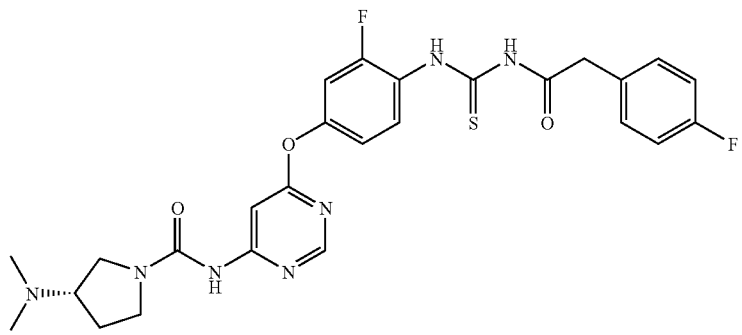
Ex. 282
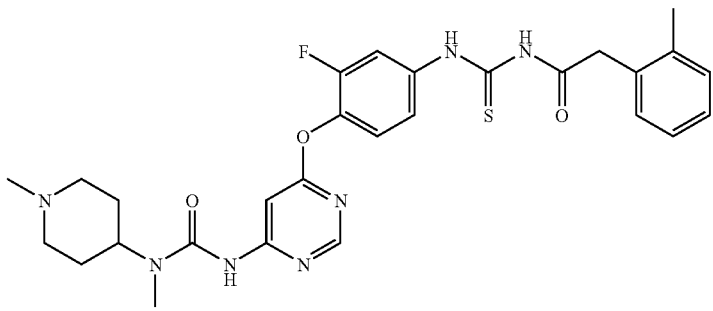
Ex. 283
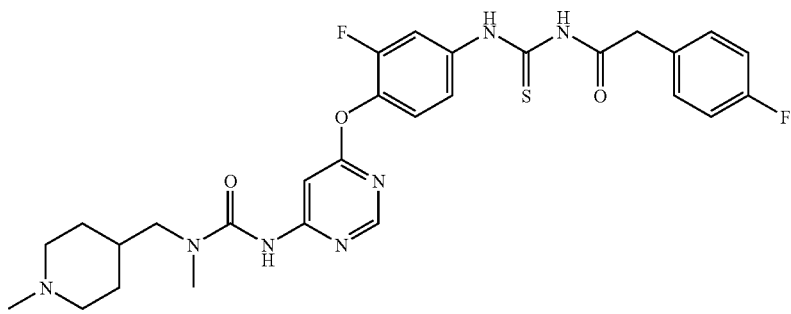
Ex. 284

TABLE 36-continued
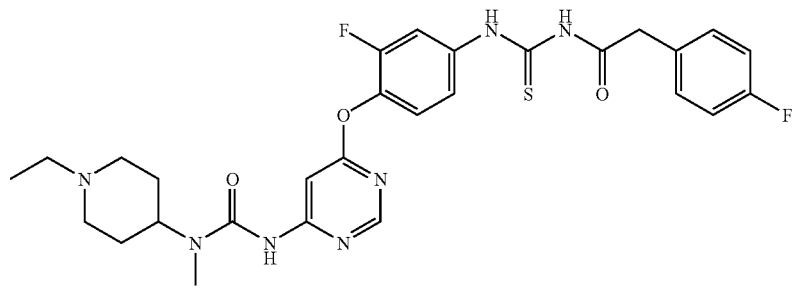
Ex. 285
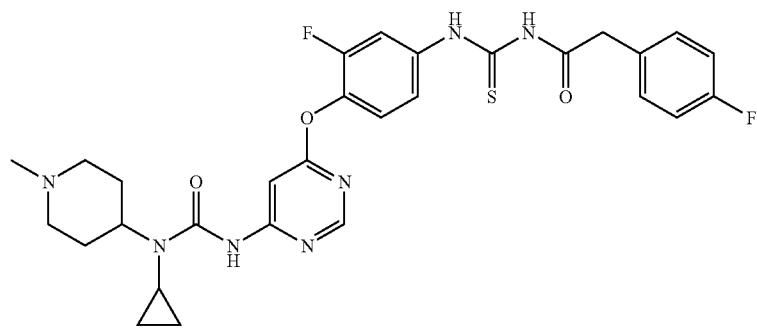
Ex. 286
TABLE 37
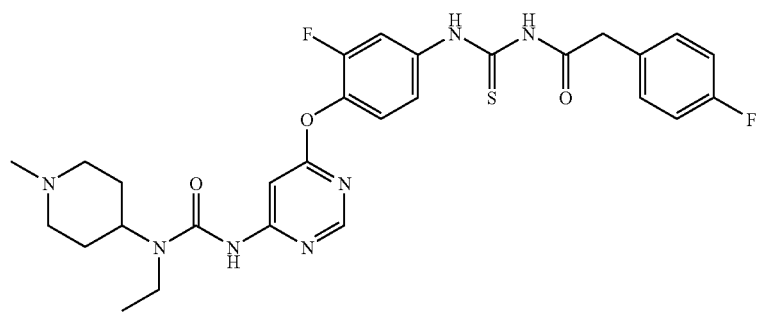
Ex. 287
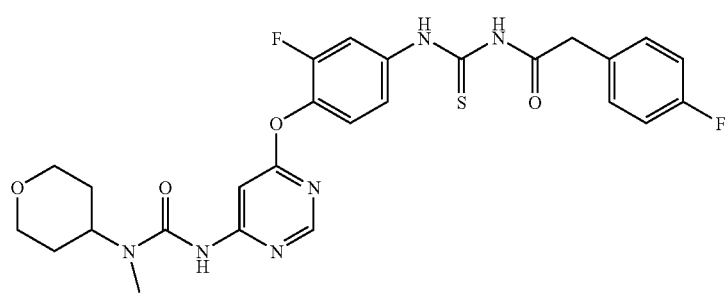
Ex. 288

TABLE 37-continued
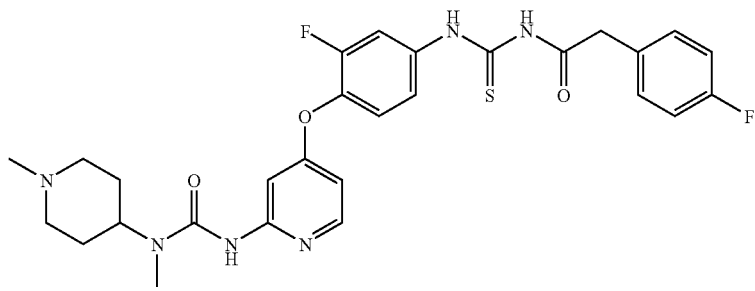
Ex. 289
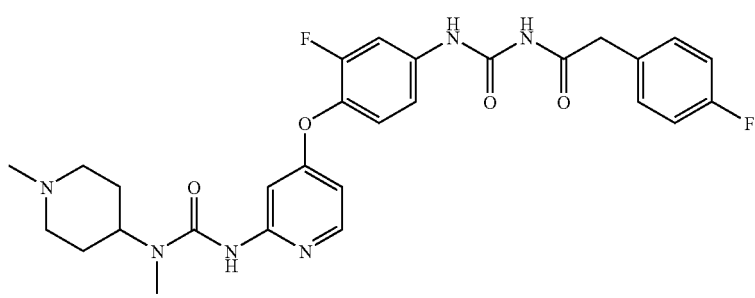
Ex. 290
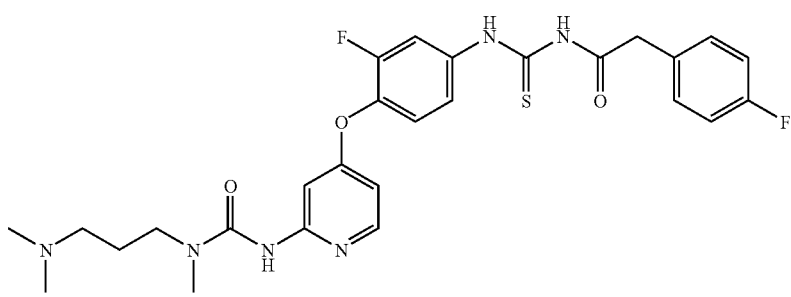
Ex. 291
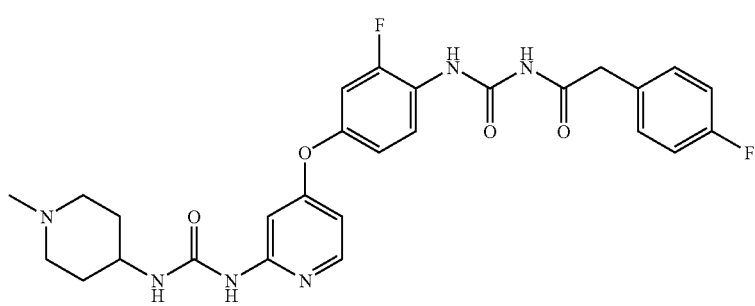
Ex. 292
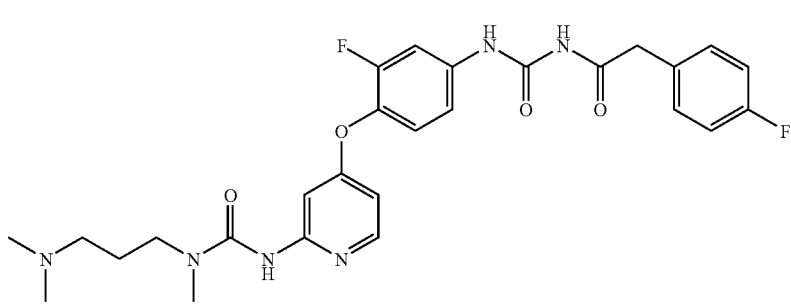
Ex. 293

TABLE 37-continued
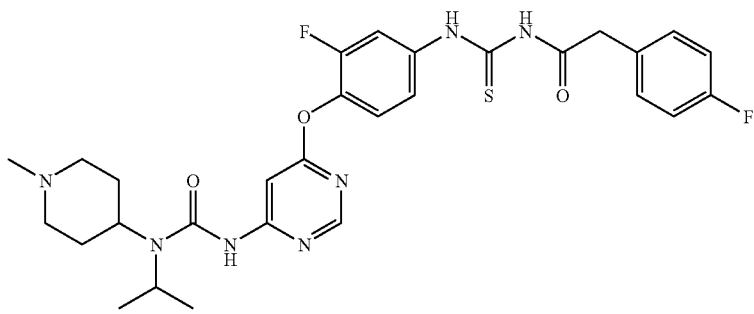
Ex. 294
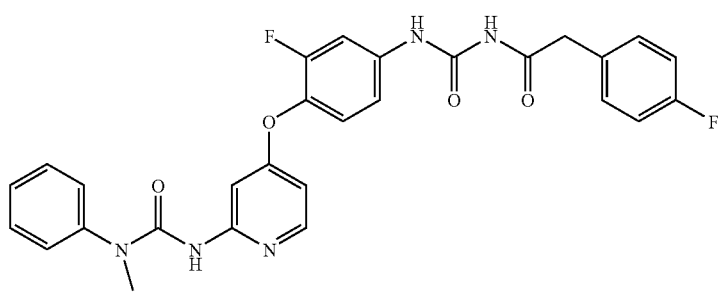
Ex. 295
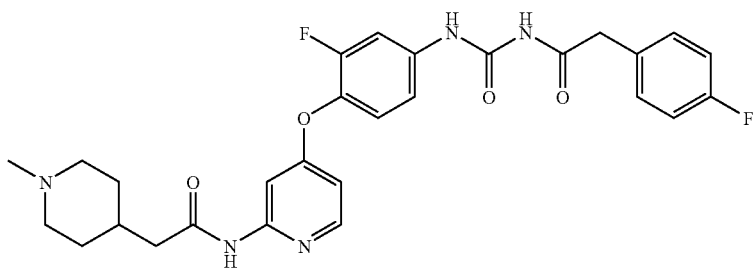
Ex. 296
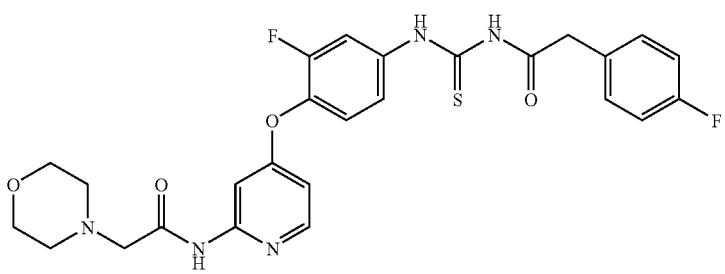
Ex. 297
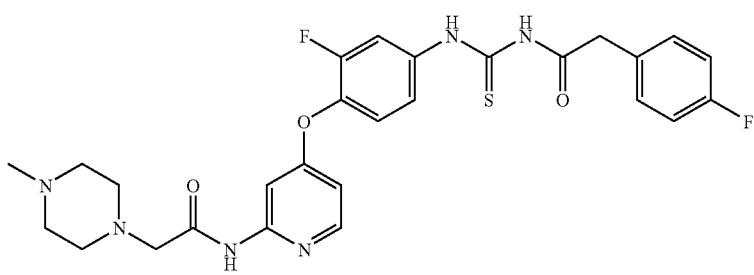
Ex. 298

TABLE 37-continued
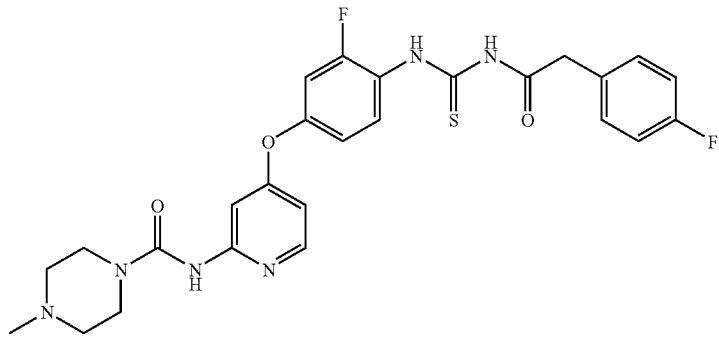
Ex. 299
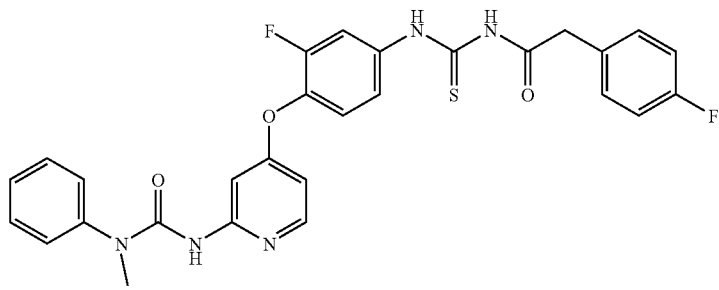
Ex. 300
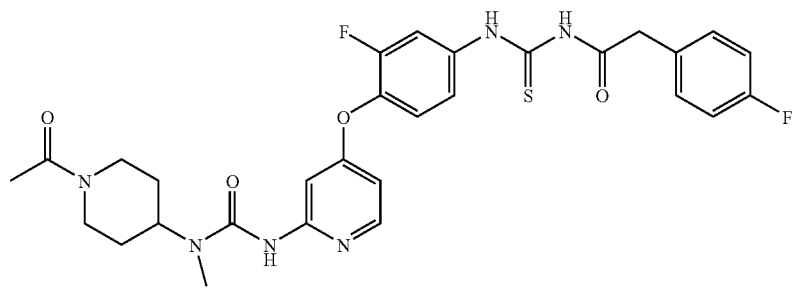
Ex. 301
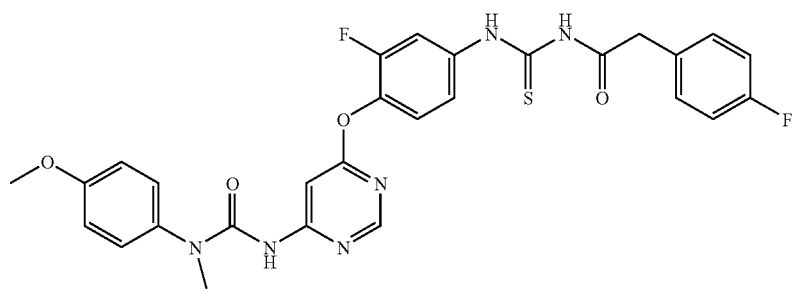
Ex. 302

TABLE 37-continued
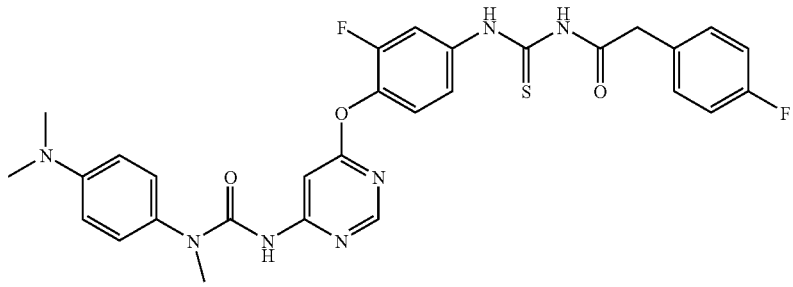
Ex. 303
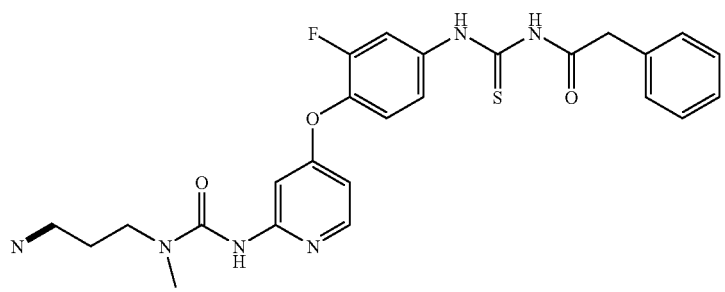
Ex. 304
TABLE 38
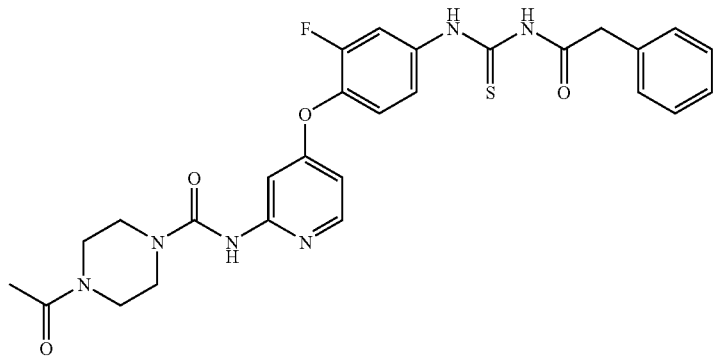
Ex. 305
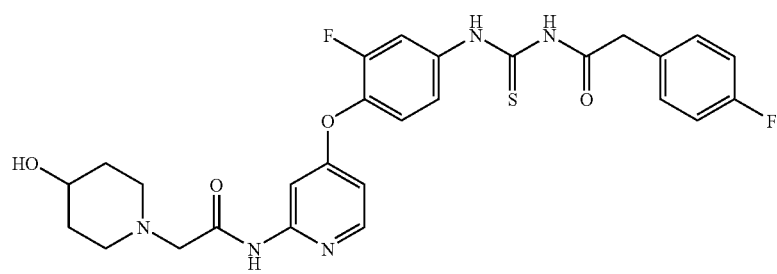
Ex. 306

TABLE 38-continued
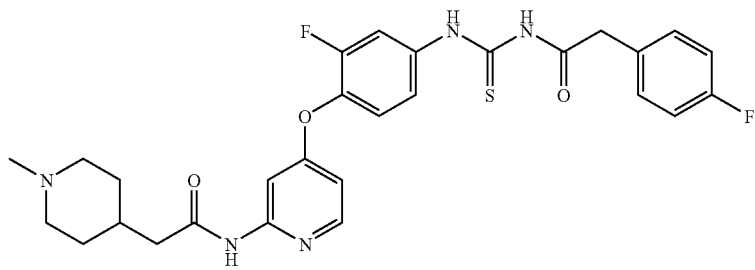
Ex. 307
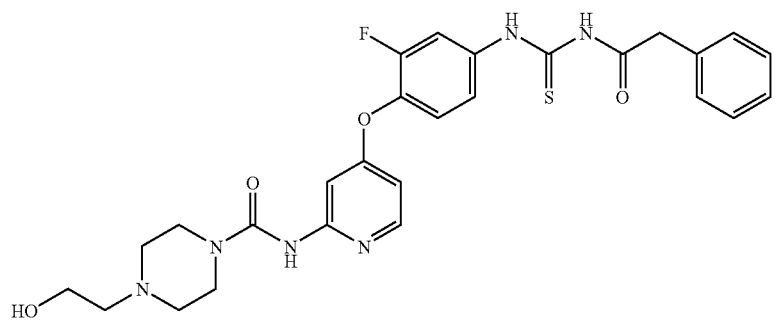
Ex. 308
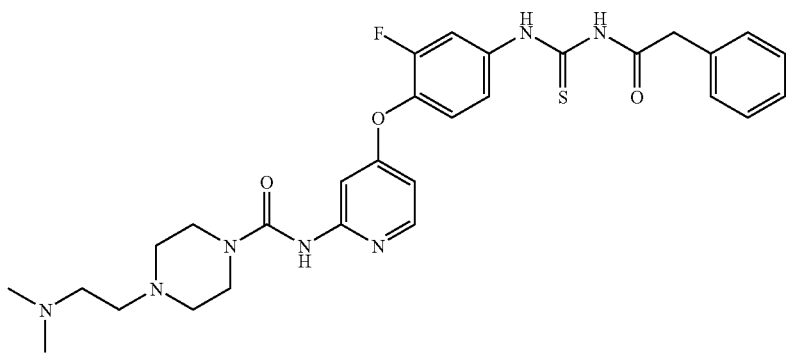
Ex. 309
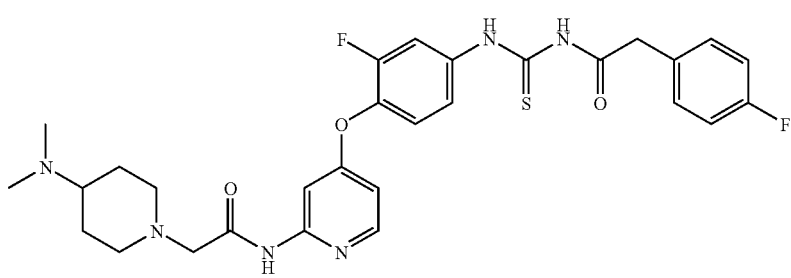
Ex. 310

TABLE 38-continued
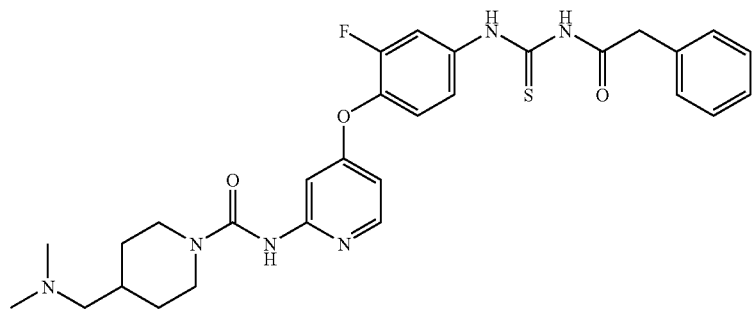
Ex. 311
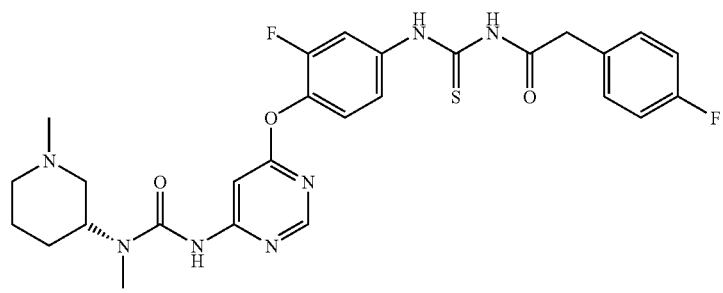
Ex. 312
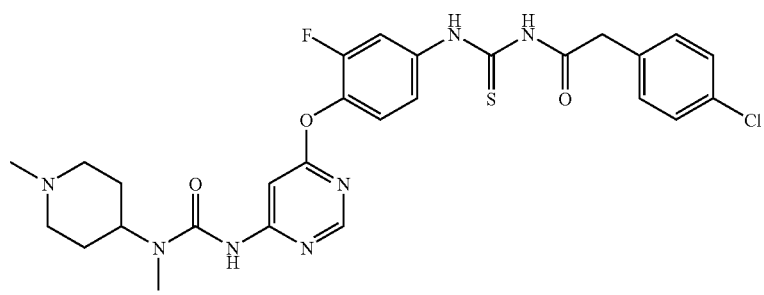
Ex. 313
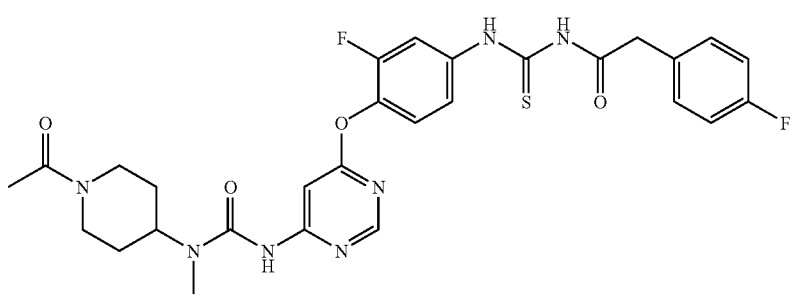
Ex. 314

TABLE 38-continued
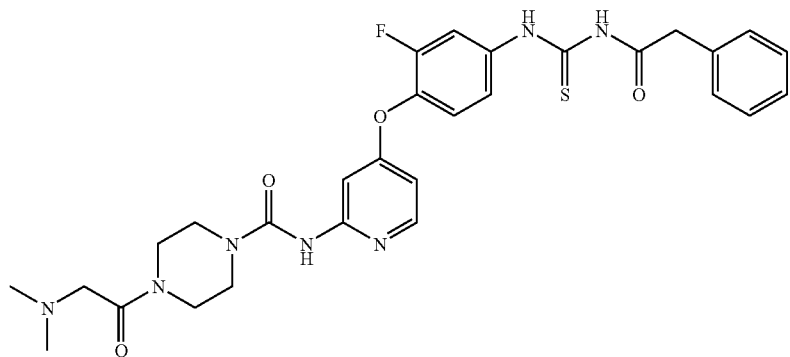
Ex. 315
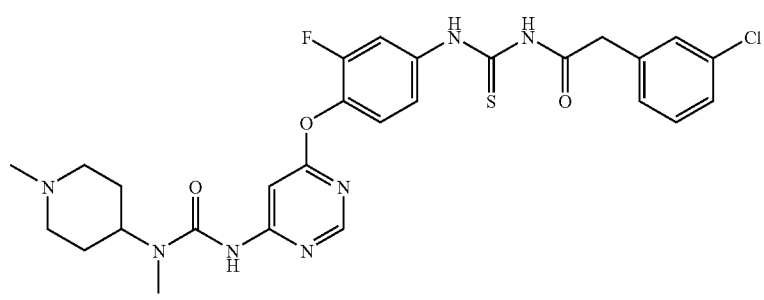
Ex. 316
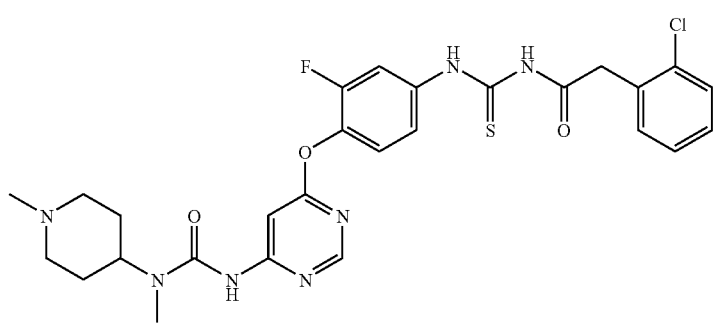
Ex. 317
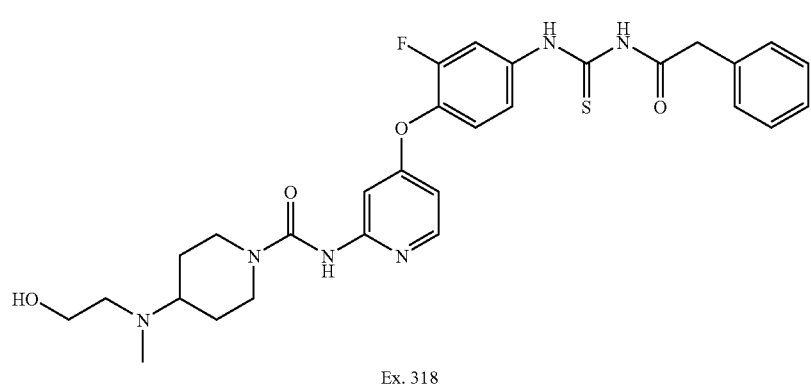
Ex. 318

TABLE 38-continued
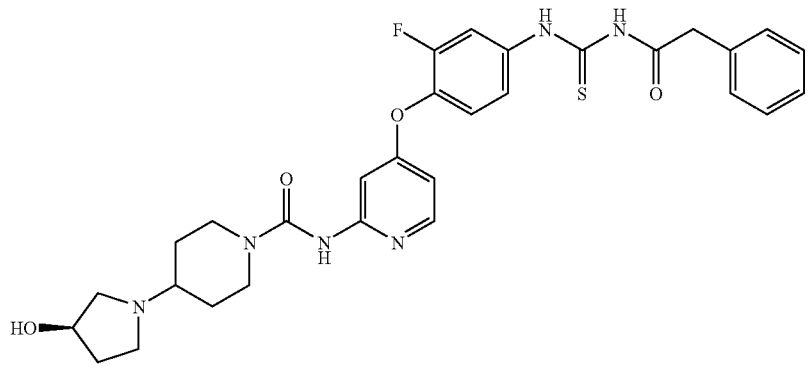
Ex. 319
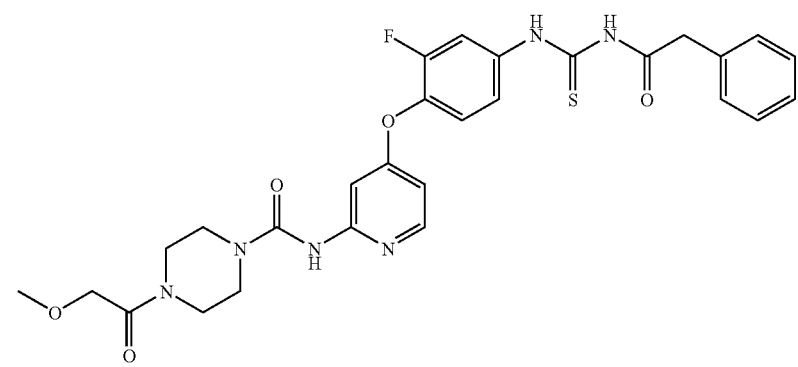
Ex. 320
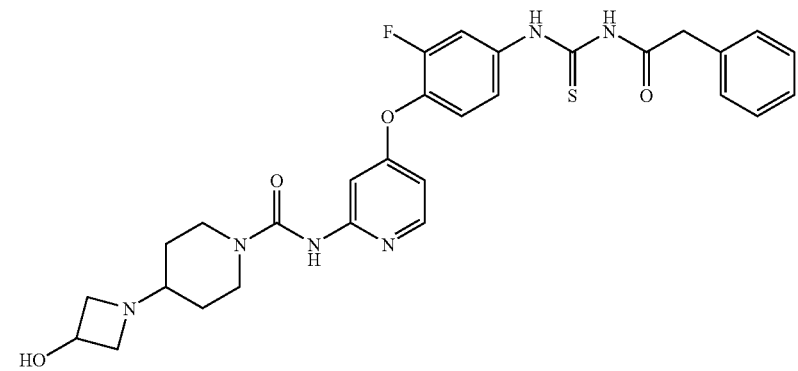
Ex. 321
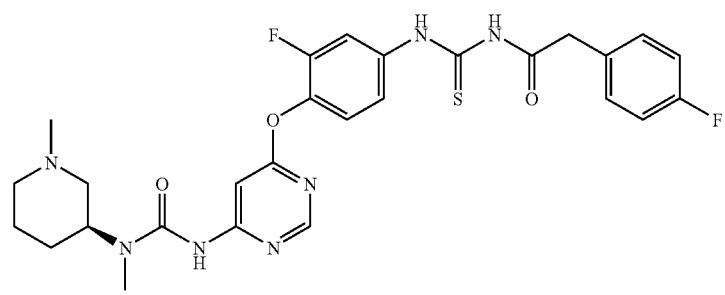
Ex. 322

TABLE 39
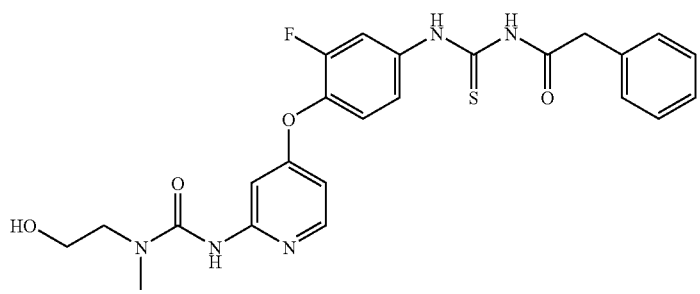
Ex. 323
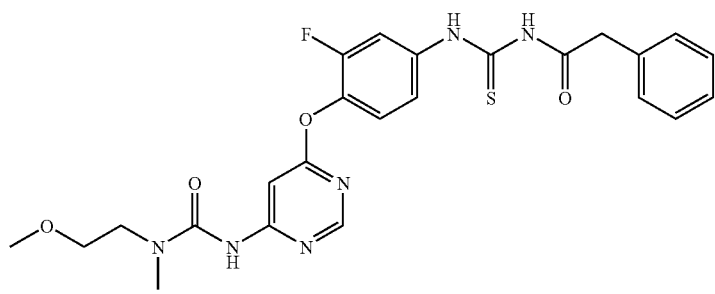
Ex. 324
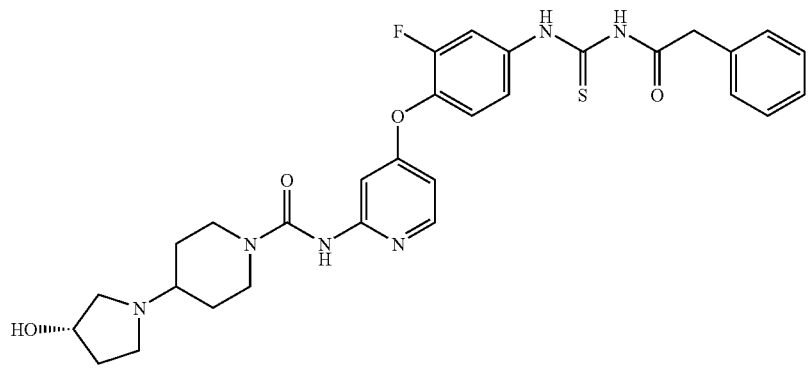
Ex. 325
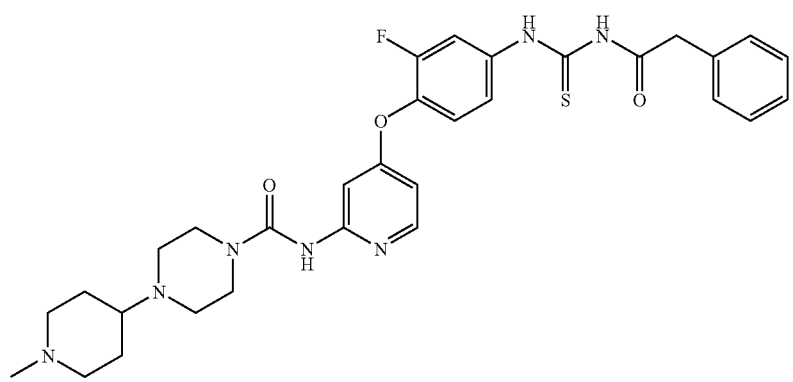
Ex. 326

TABLE 39-continued
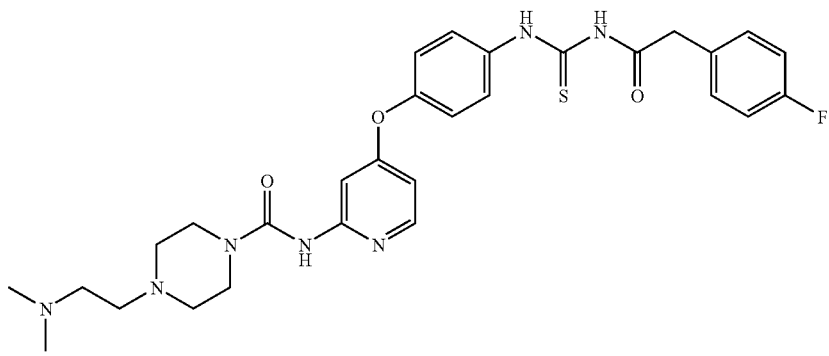
Ex. 327
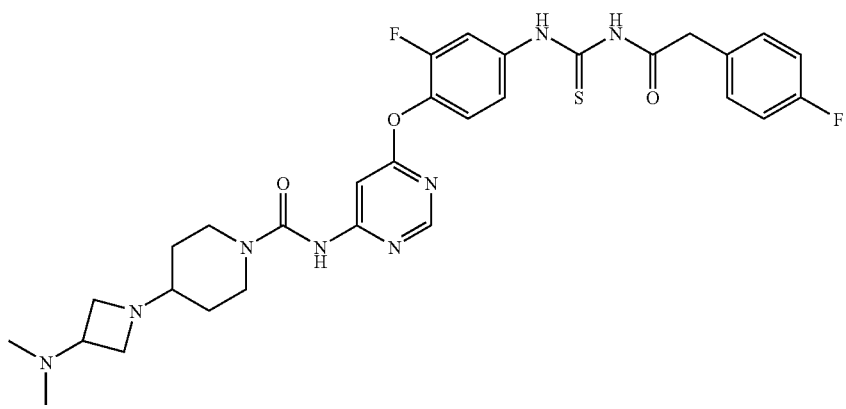
Ex. 328
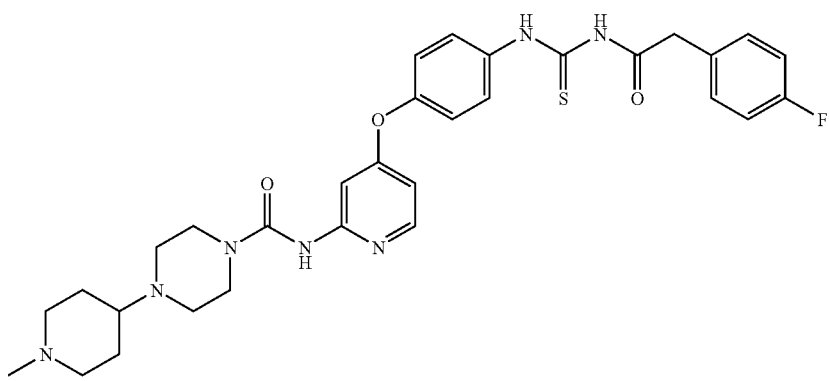
Ex. 329
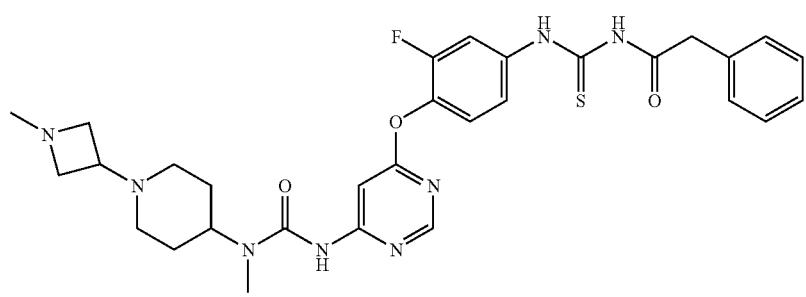
Ex. 330

TABLE 39-continued
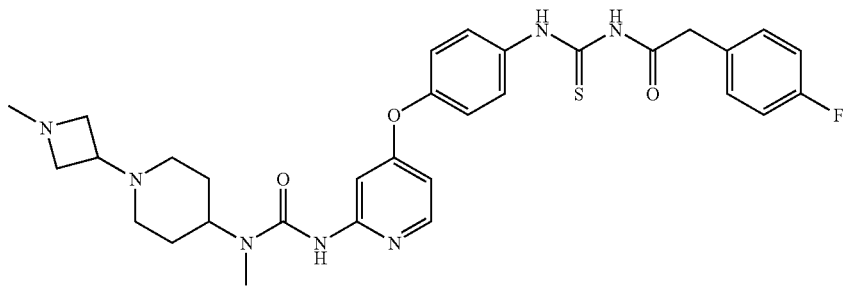
Ex. 331
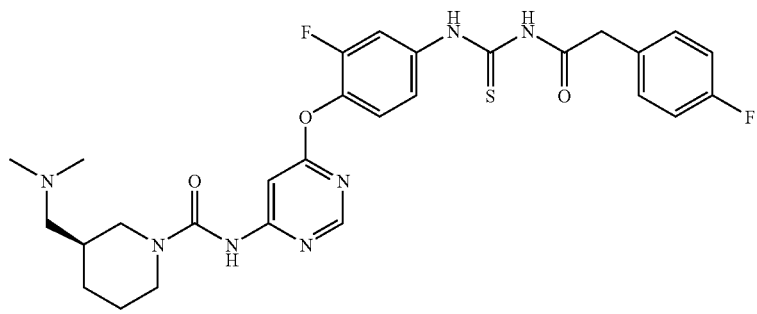
Ex. 332
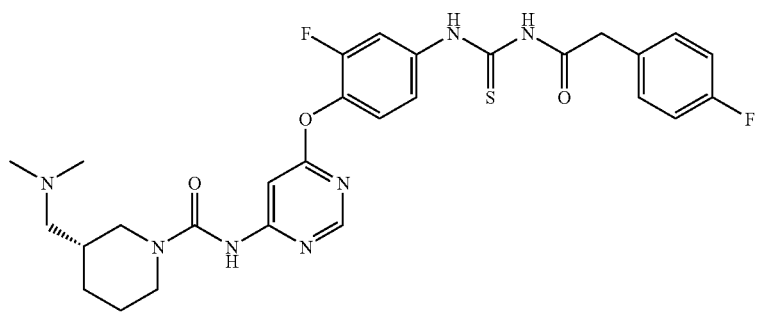
Ex. 333
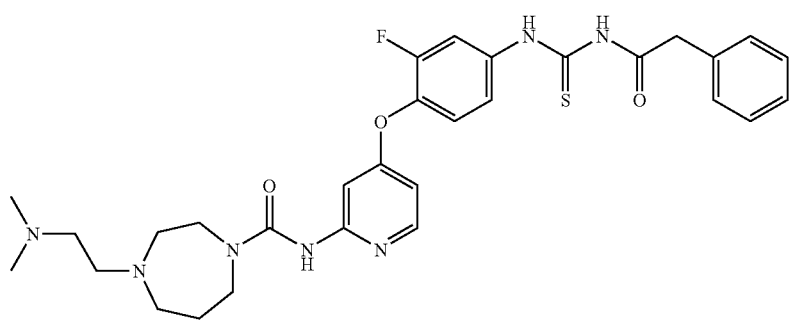
Ex. 334

TABLE 39-continued
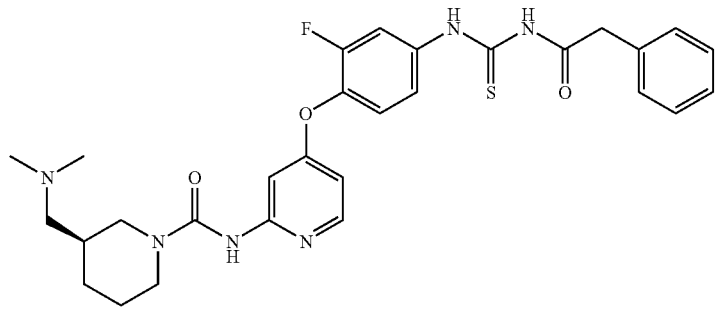
Ex. 335
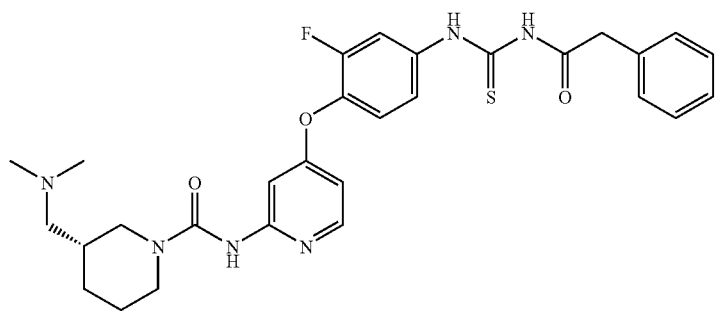
Ex. 336
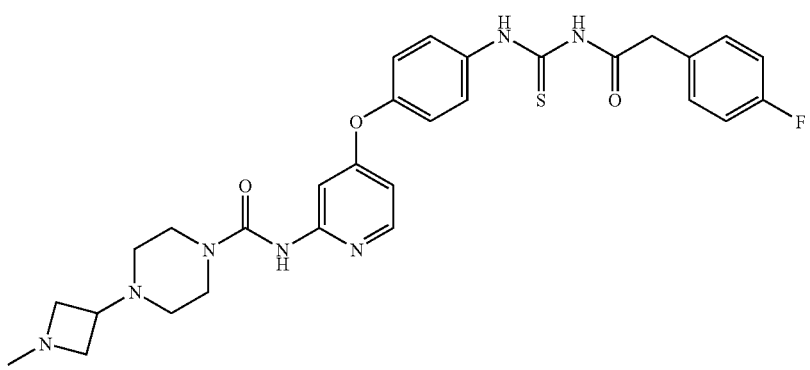
Ex. 337
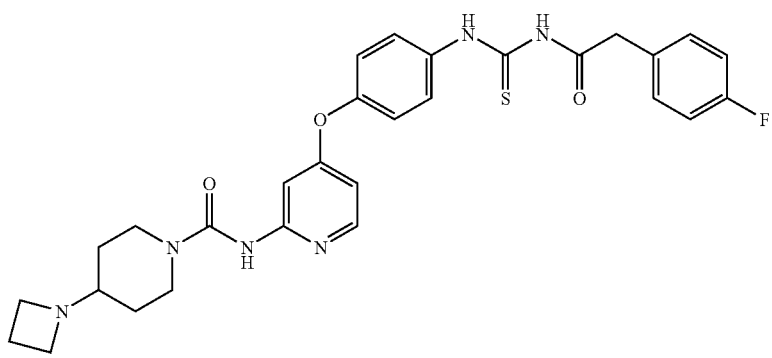
Ex. 338

TABLE 39-continued
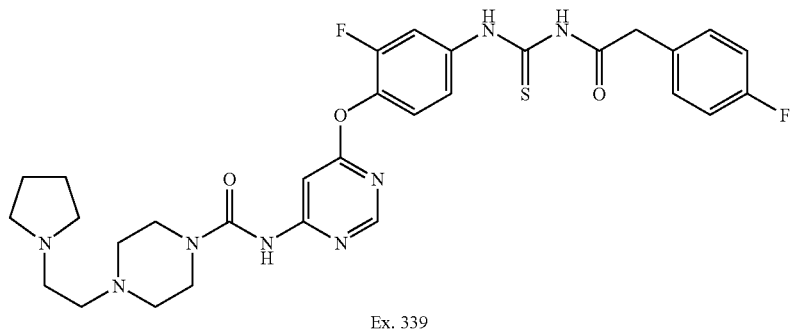
Ex. 339
| TABLE 40 | TABLE 40-continued |
|---|---|
| 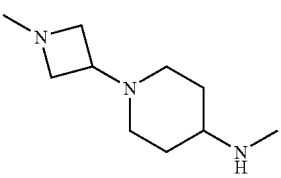<br>Pro. Ex. 355-1 | 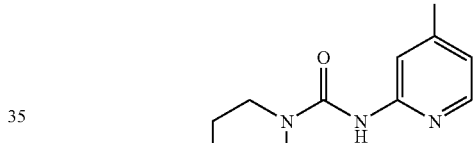<br>Pro. Ex. 373-1 |
| 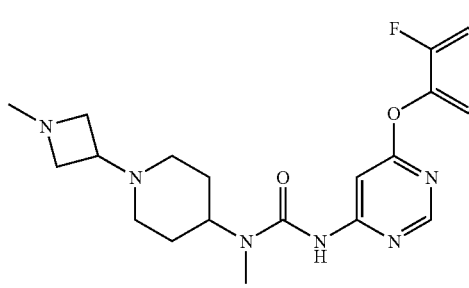<br>Pro. Ex. 355-2 | 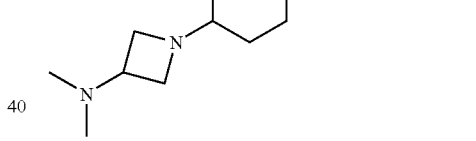<br> |
| 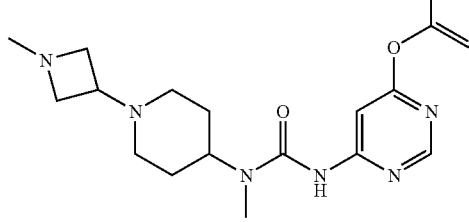<br>Pro. Ex. 355-3 | 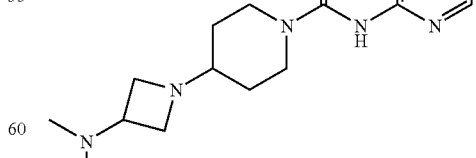<br>Pro. Ex. 373-2 |

TABLE 40-continued
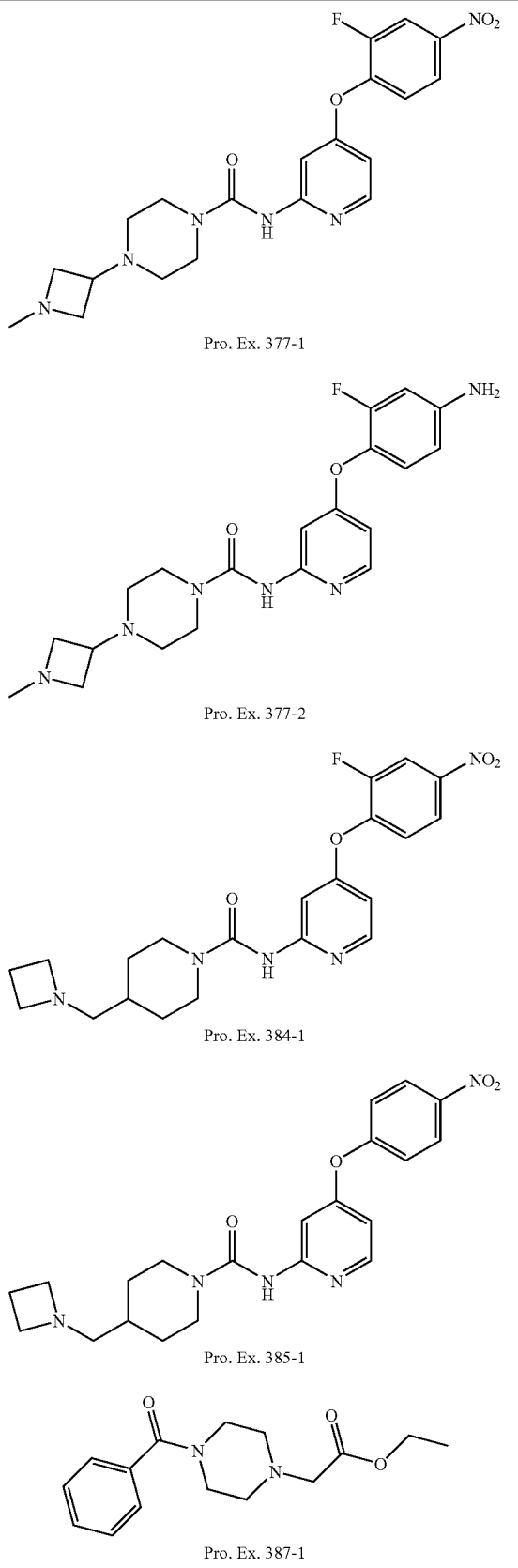
Pro. Ex. 377-1
Pro. Ex. 377-2
Pro. Ex. 384-1
Pro. Ex. 385-1
Pro. Ex. 387-1
TABLE 40-continued
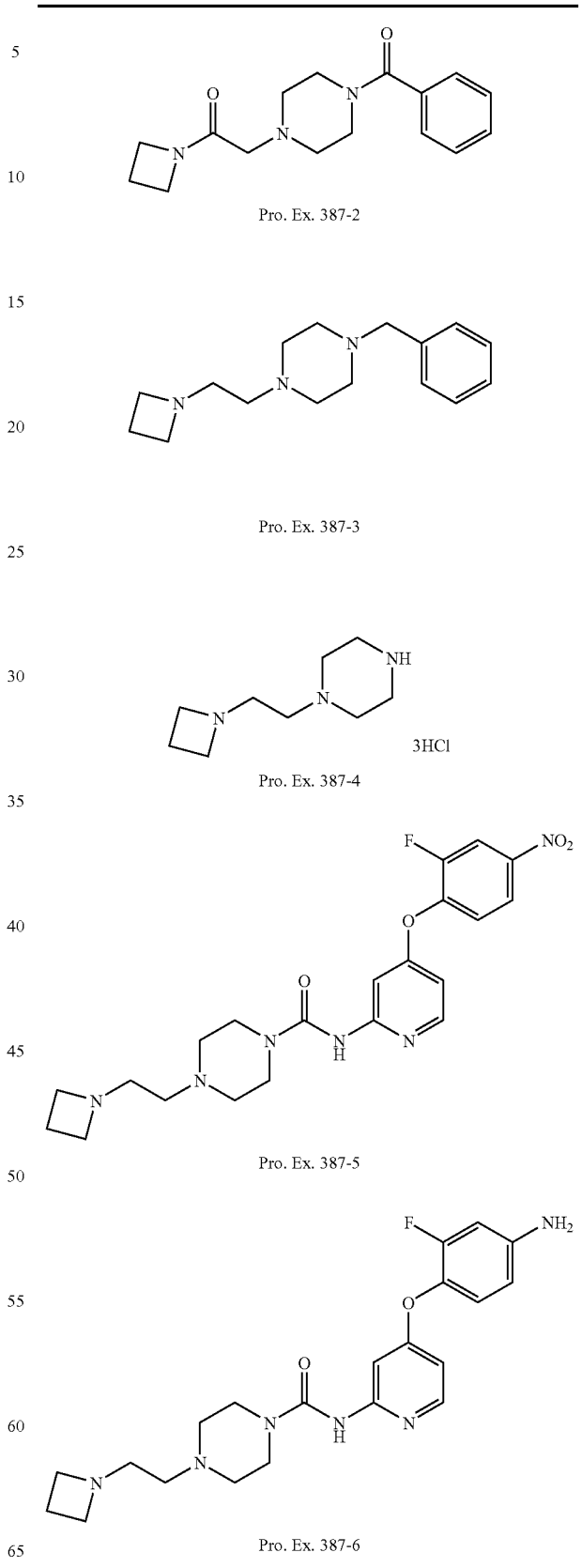
Pro. Ex. 387-2
Pro. Ex. 387-3
Pro. Ex. 387-4
Pro. Ex. 387-5
Pro. Ex. 387-6

TABLE 40-continued
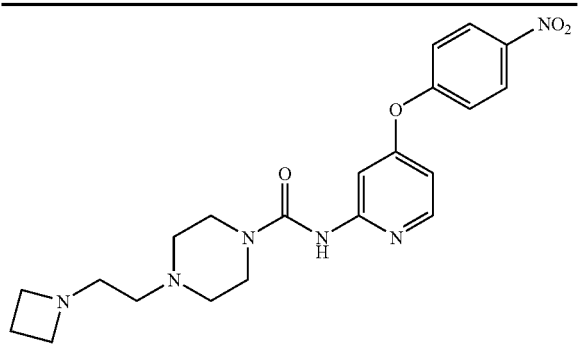
Pro. Ex. 388-1
TABLE 40-continued
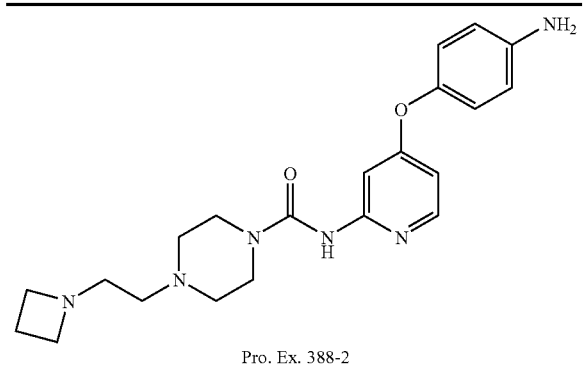
Pro. Ex. 388-2
TABLE 41
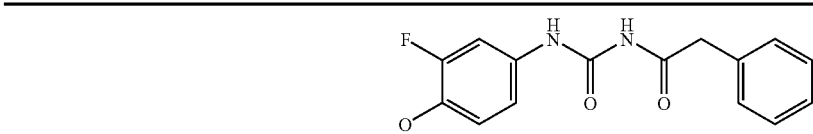
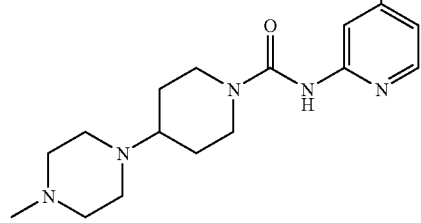
Ex. 340
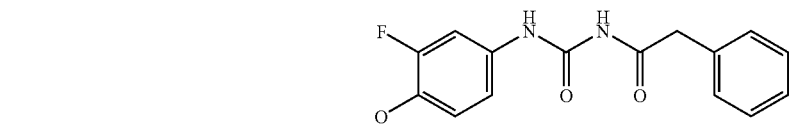
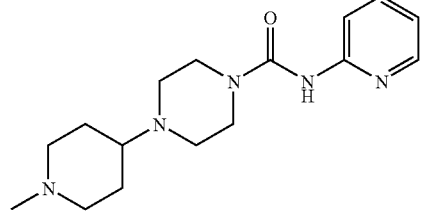
Ex. 341
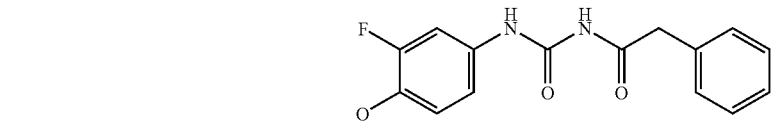
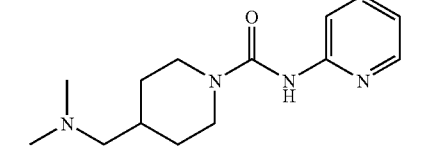
Ex. 342

TABLE 41-continued
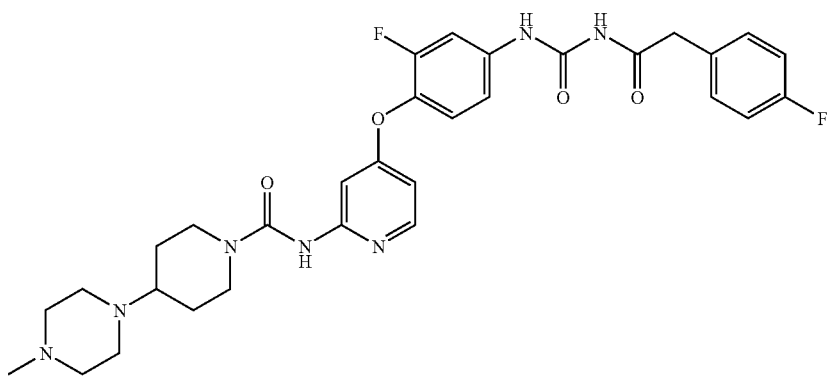
Ex. 343
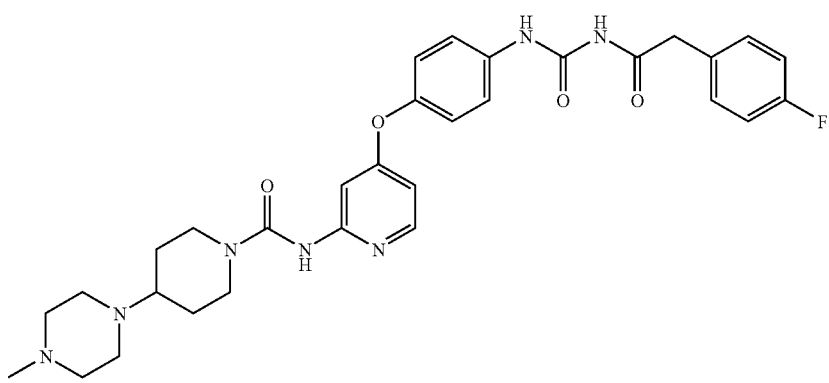
Ex. 344
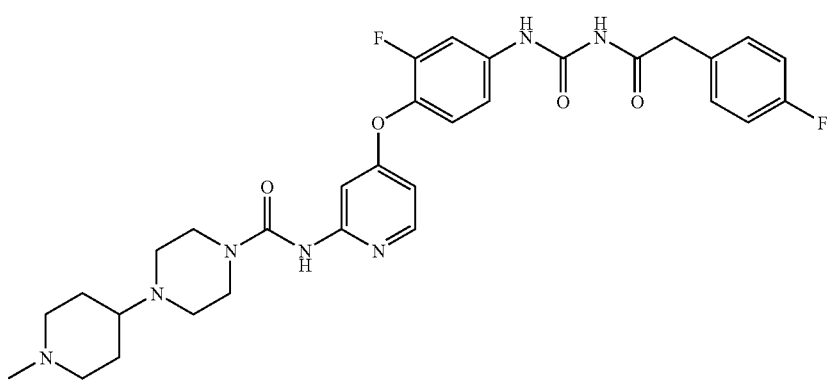
Ex. 345
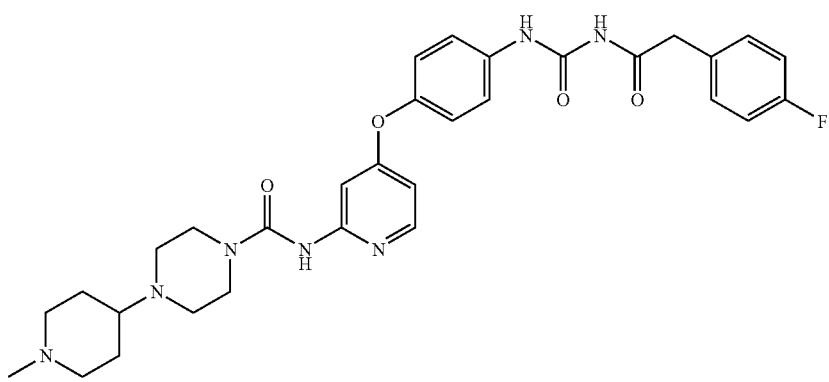
Ex. 346

TABLE 41-continued
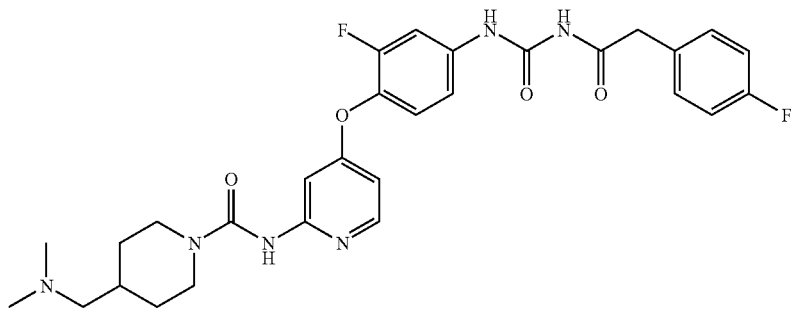
Ex. 347
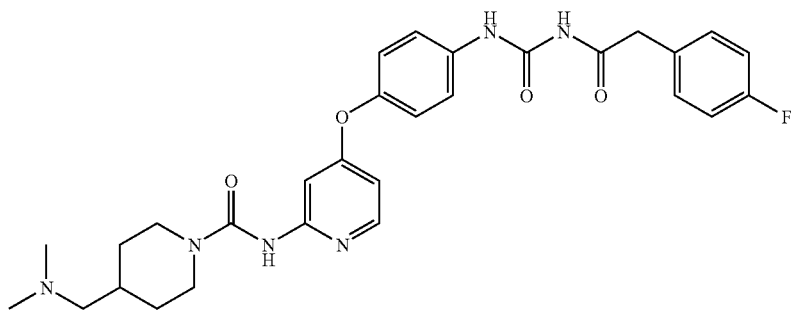
Ex. 348
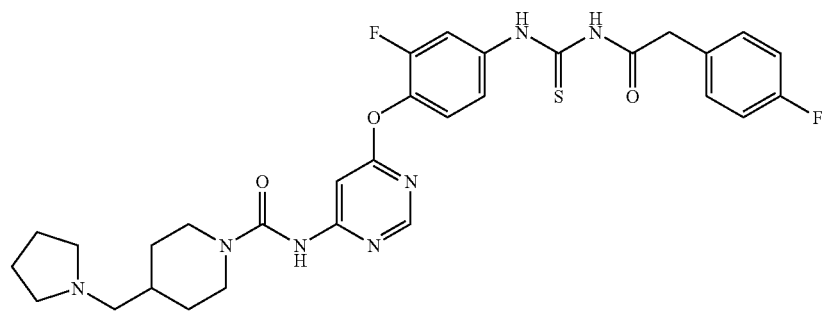
Ex. 349
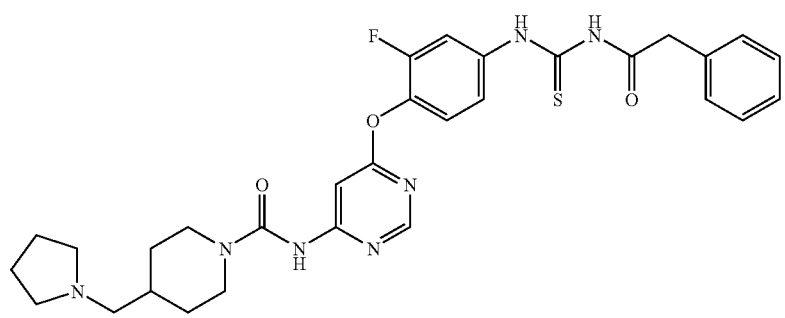
Ex. 350

TABLE 41-continued
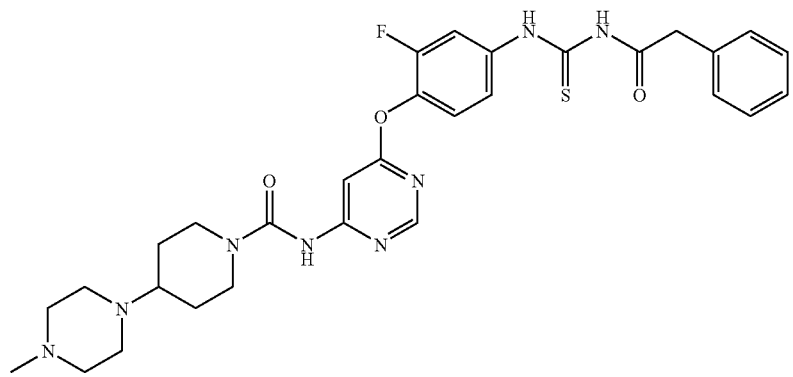
Ex. 351
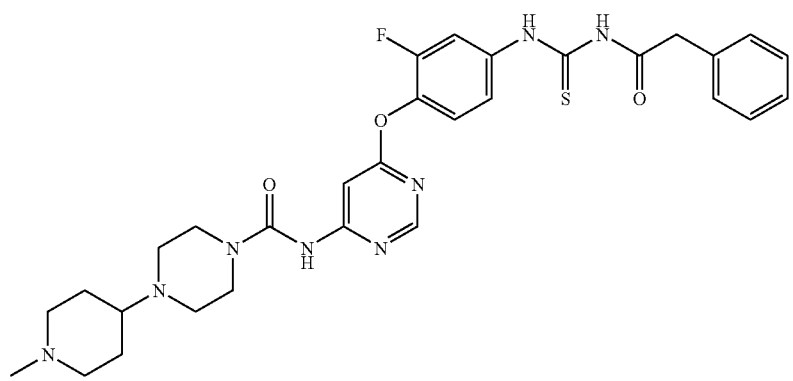
Ex. 352
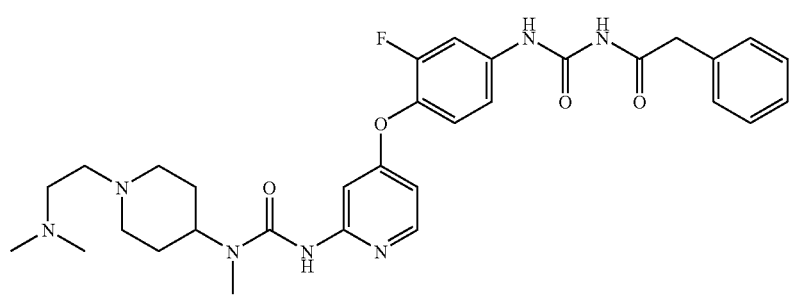
Ex. 353
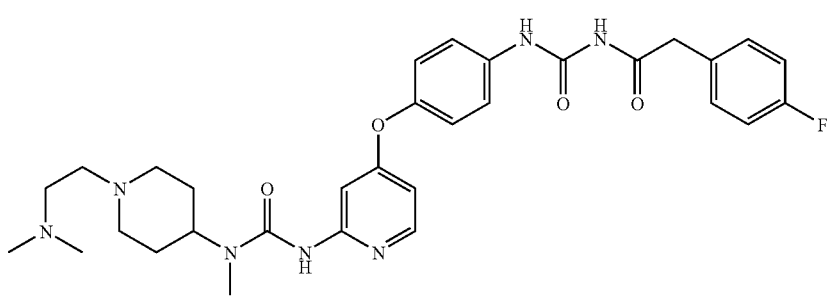
Ex. 354

TABLE 41-continued
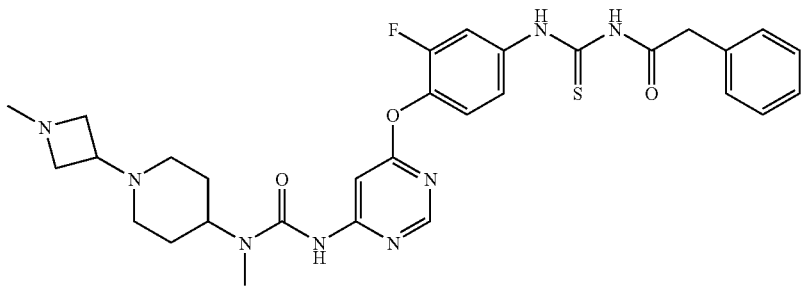
Ex. 355
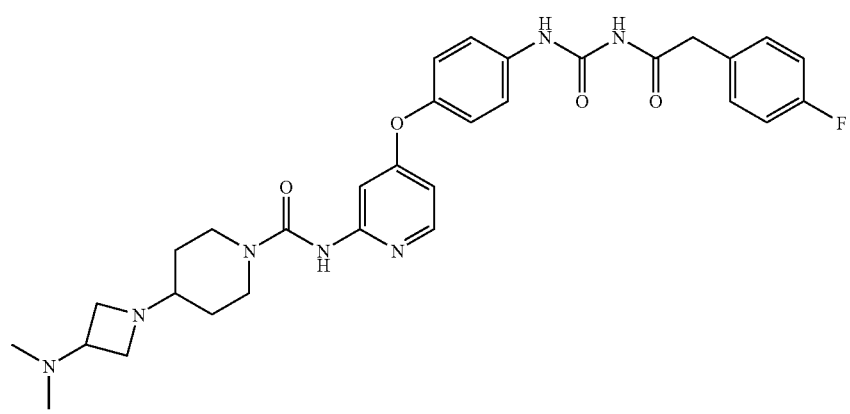
Ex. 356
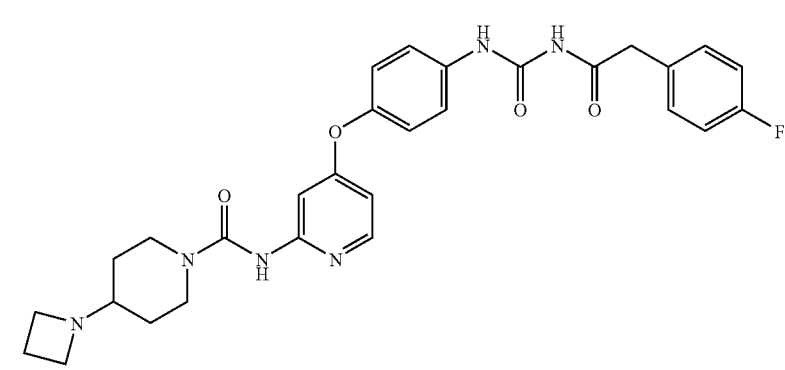
Ex. 357
TABLE 42
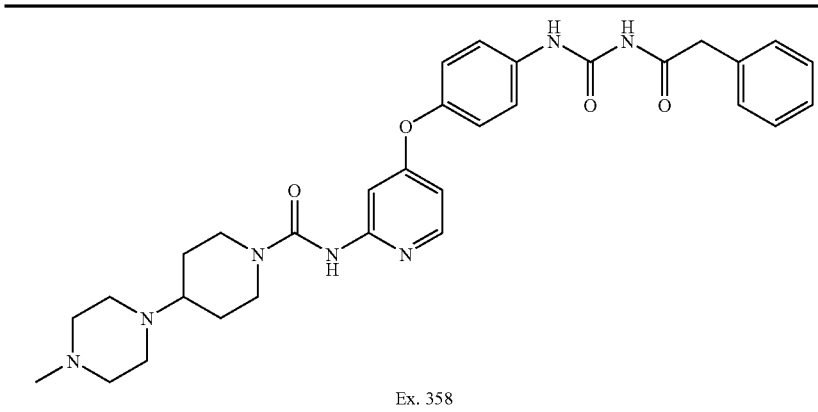
Ex. 358

TABLE 42-continued
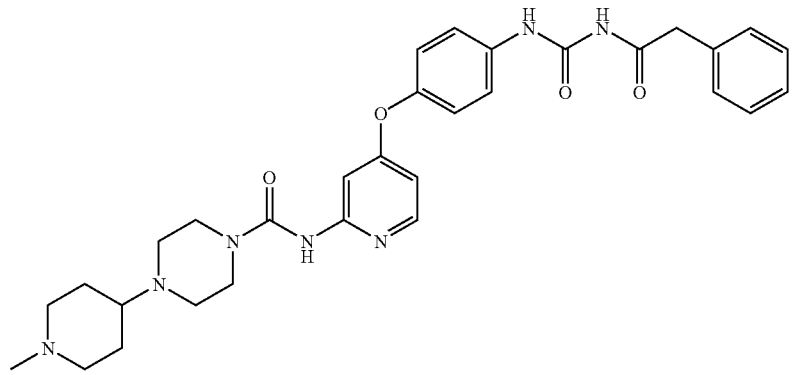
Ex. 359
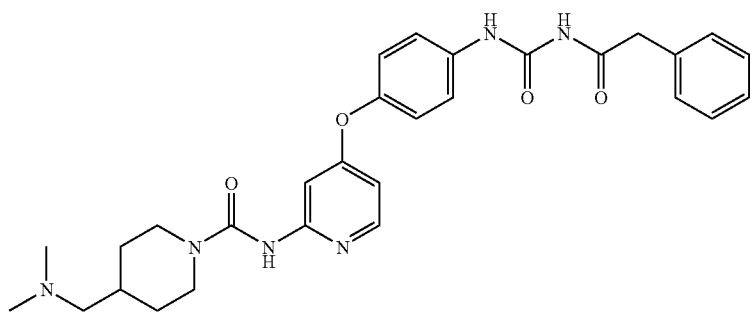
Ex. 360
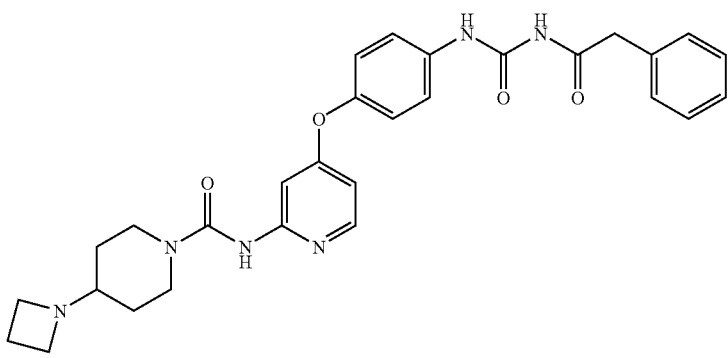
Ex. 361
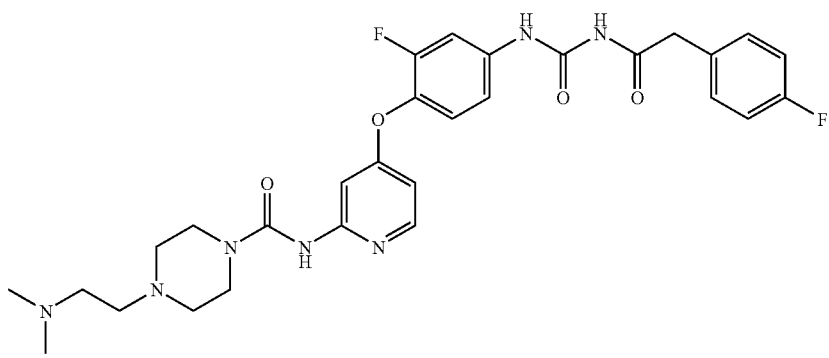
Ex. 362

TABLE 42-continued
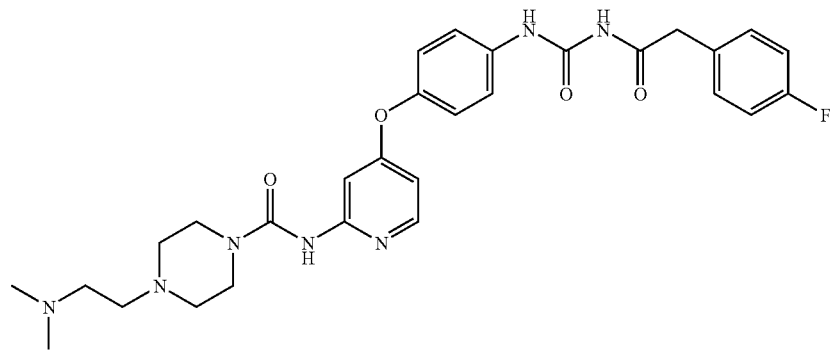
Ex. 363
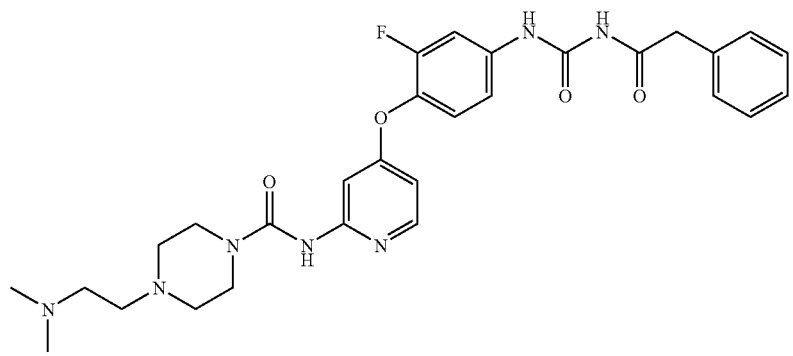
Ex. 364
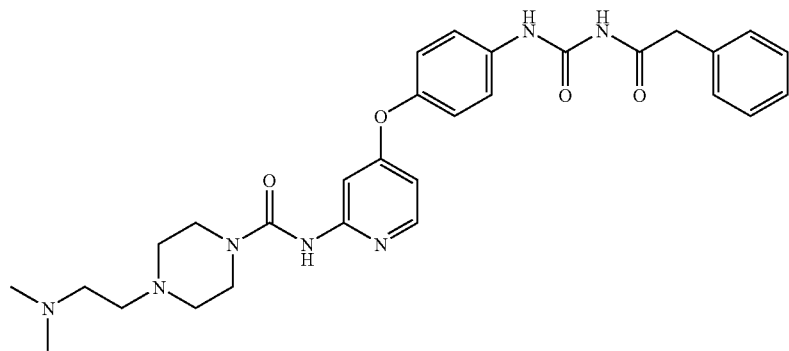
Ex. 365
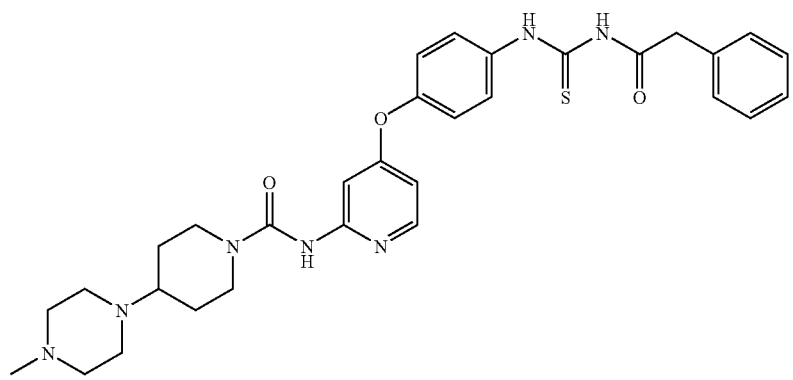
Ex. 366

TABLE 42-continued
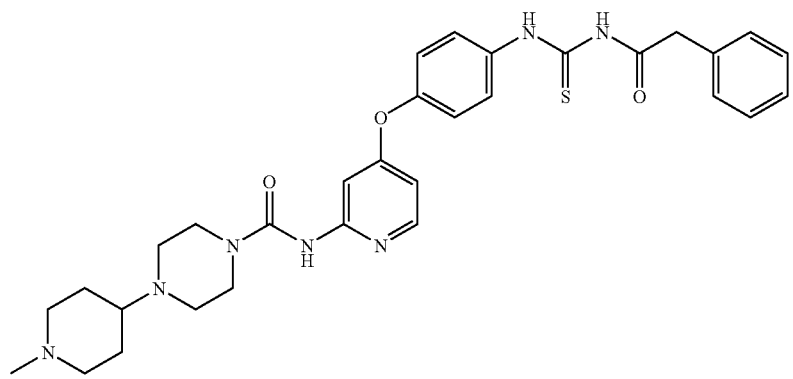
Ex. 367
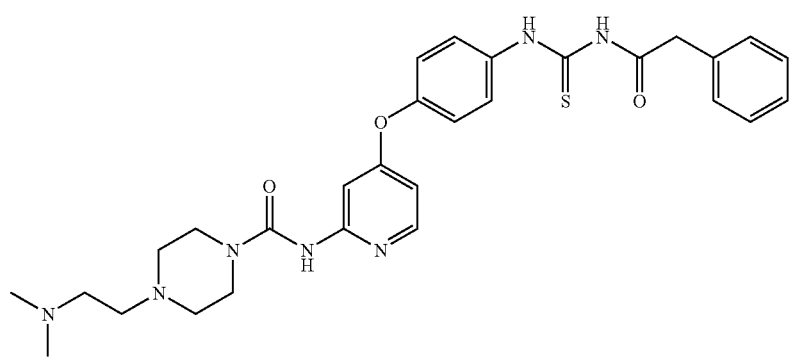
Ex. 368
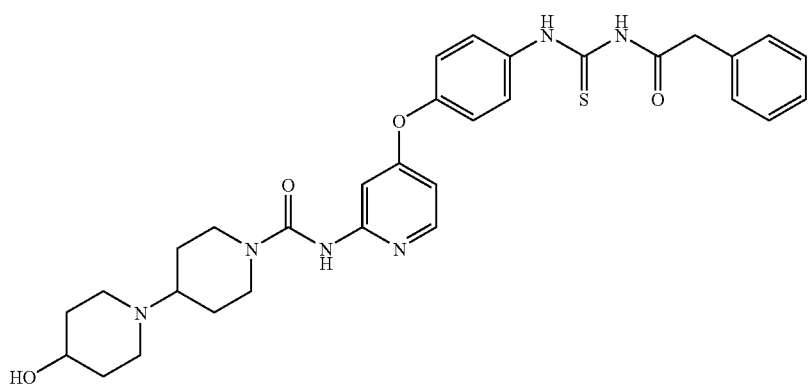
Ex. 369
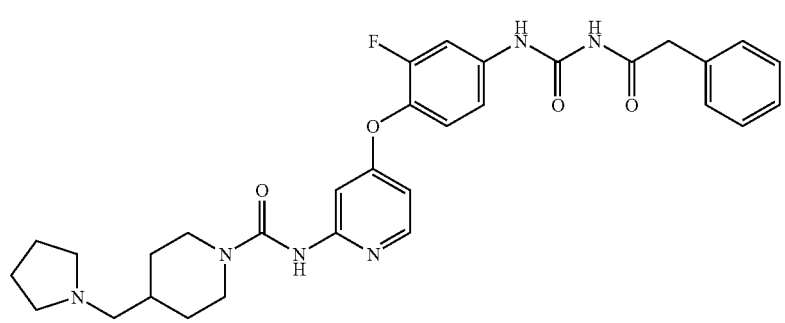
Ex. 370

TABLE 42-continued
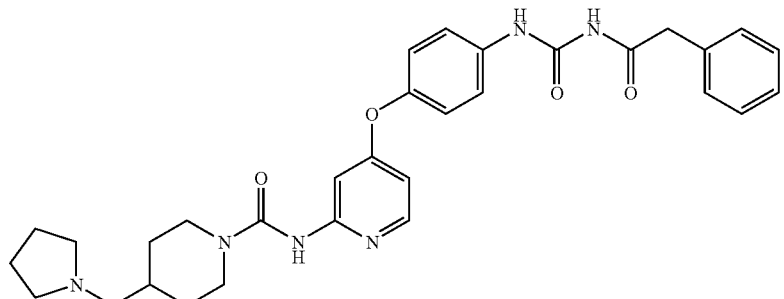
Ex. 371
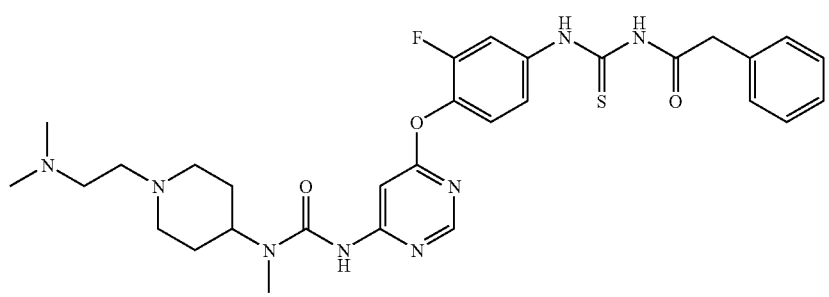
Ex. 372
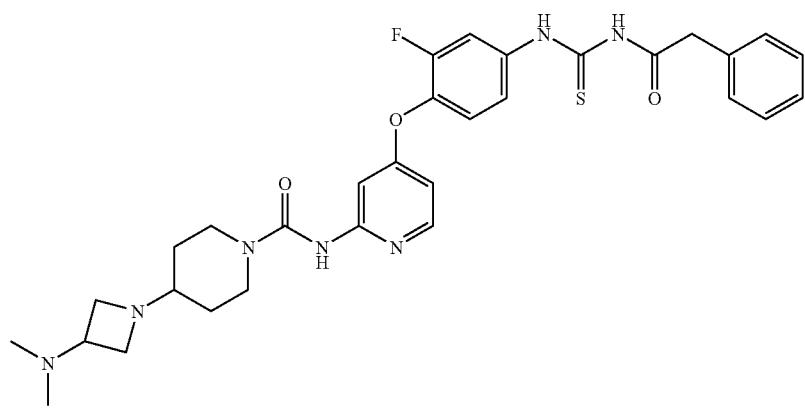
Ex. 373
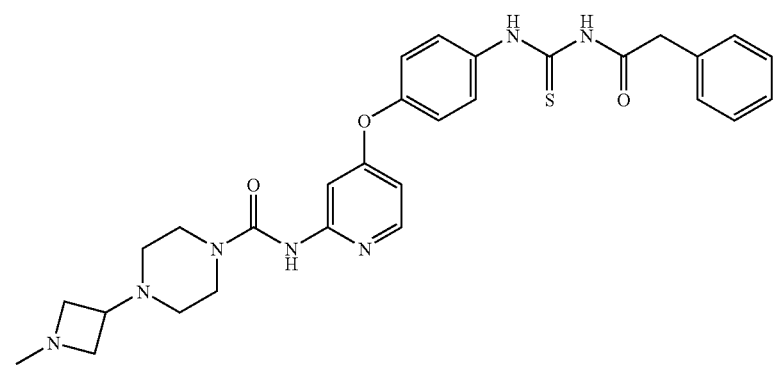
Ex. 374

TABLE 42-continued
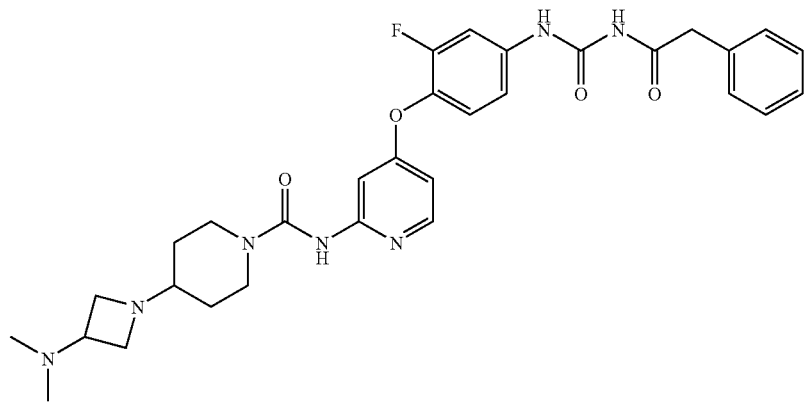
Ex. 375
TABLE 43
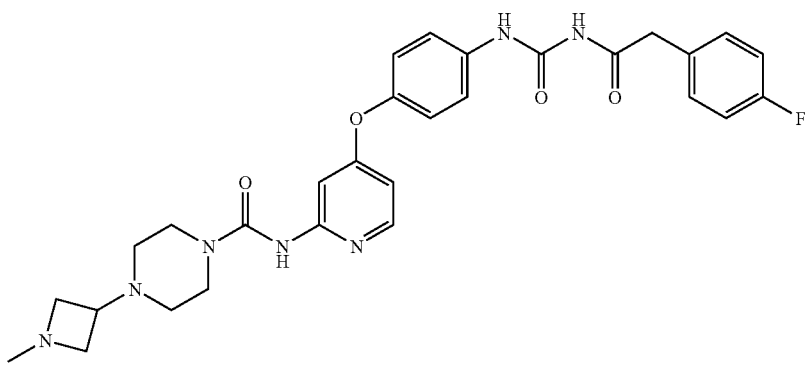
Ex. 376
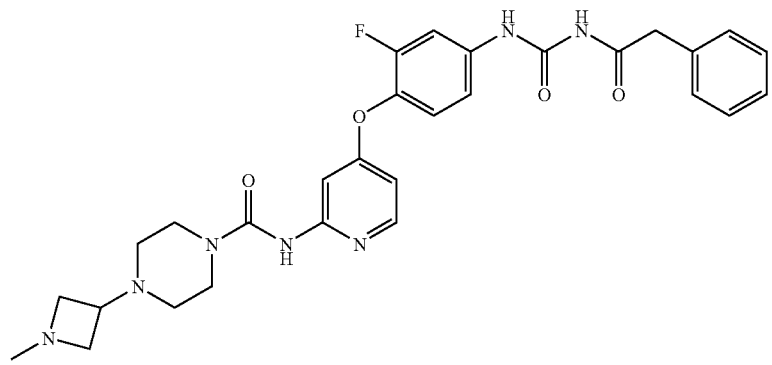
Ex. 377

TABLE 43-continued
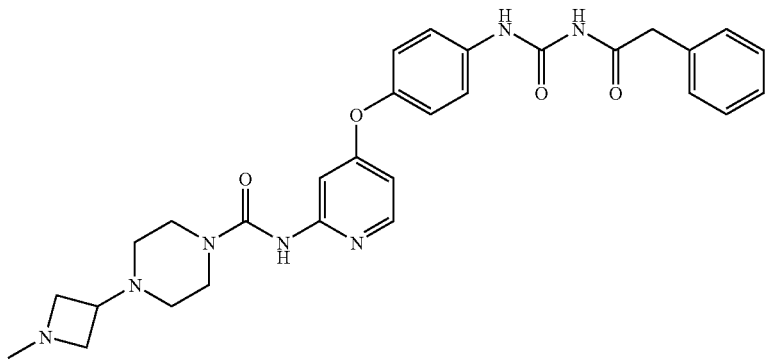
Ex. 378
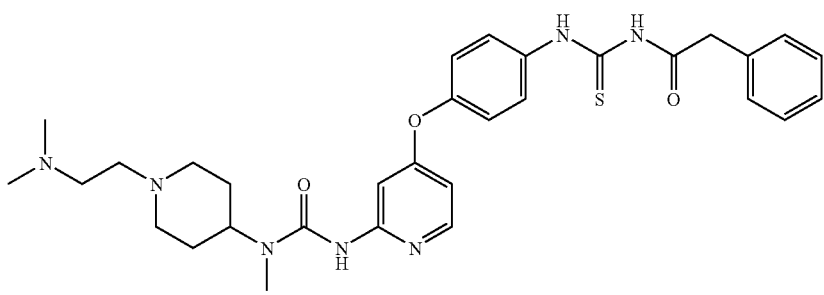
Ex. 379
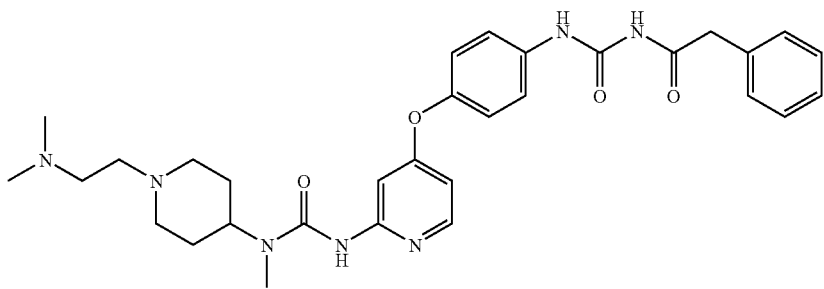
Ex. 380
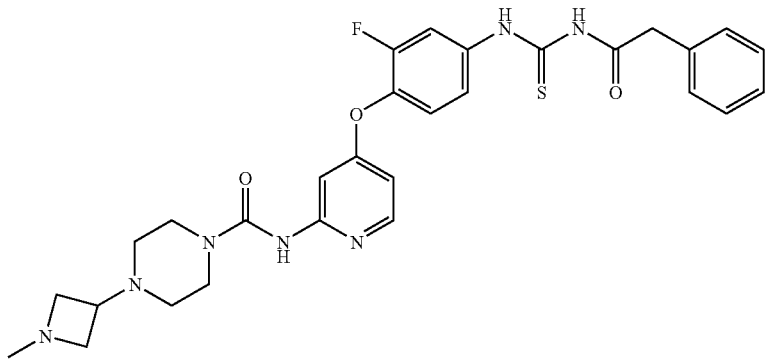
Ex. 381

TABLE 43-continued
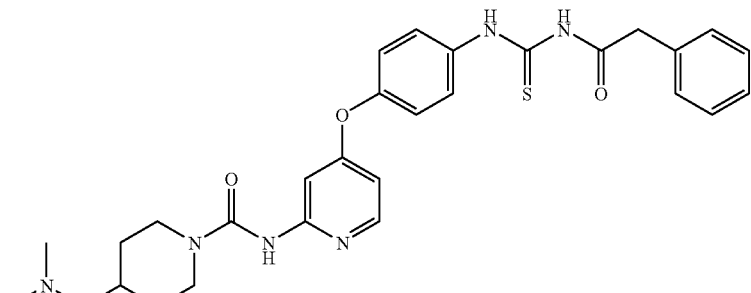
Ex. 382
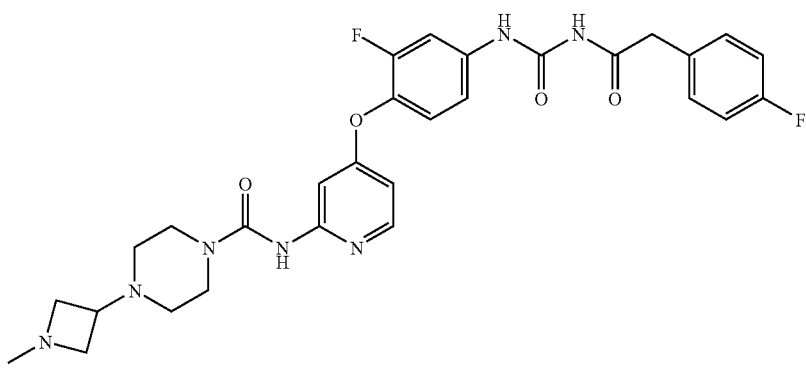
Ex. 383
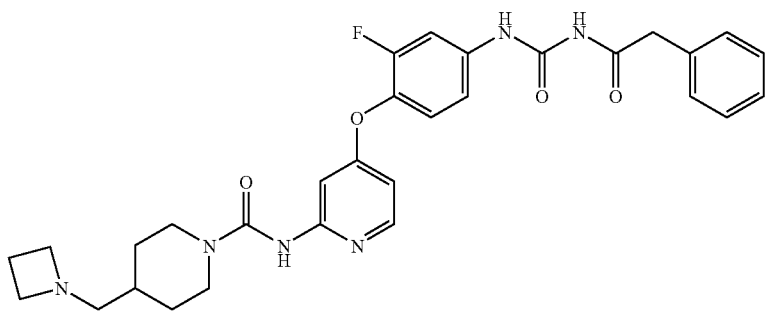
Ex. 384
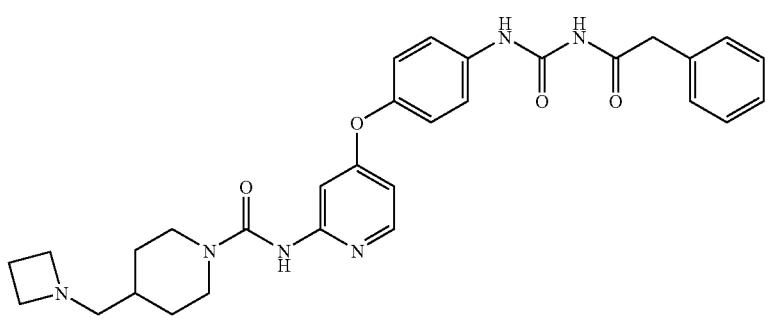
Ex. 385

TABLE 43-continued
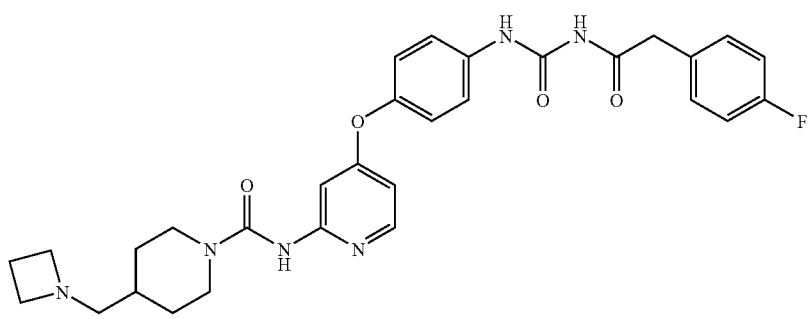
Ex. 386
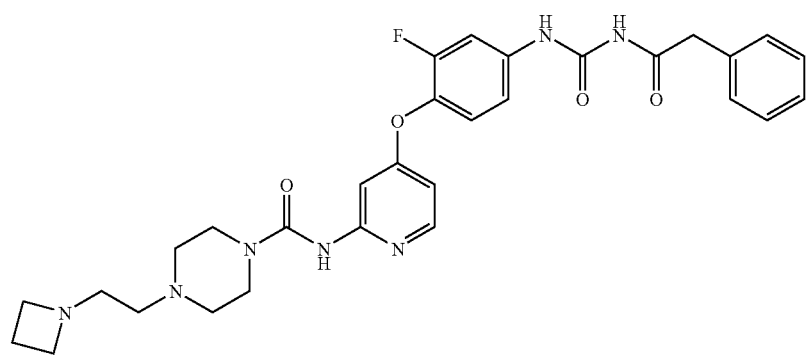
Ex. 387
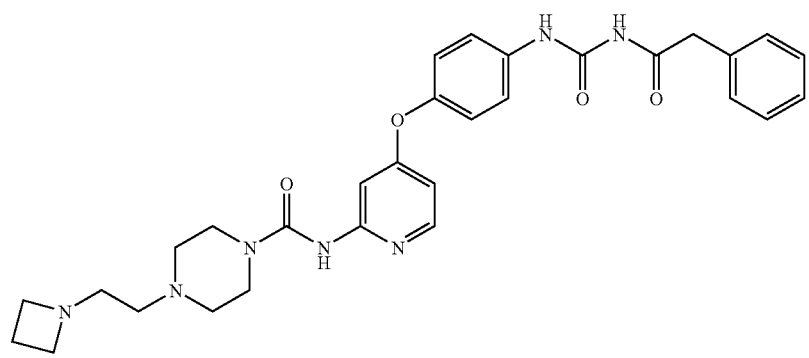
Ex. 388
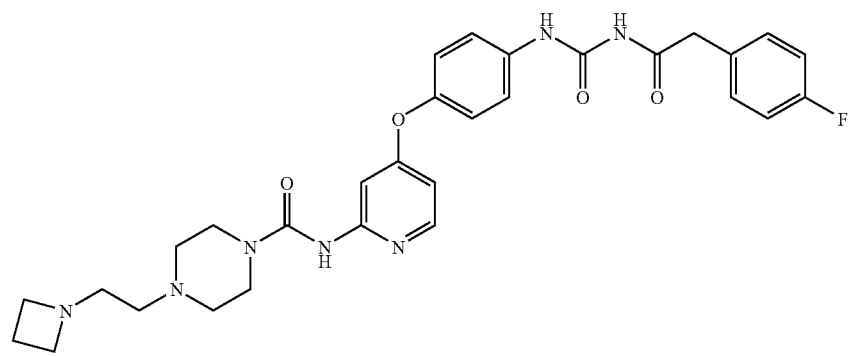
Ex. 389

TABLE 43-continued
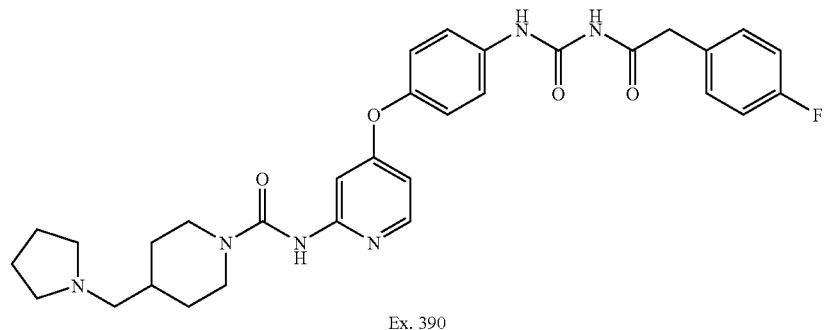
Ex. 390
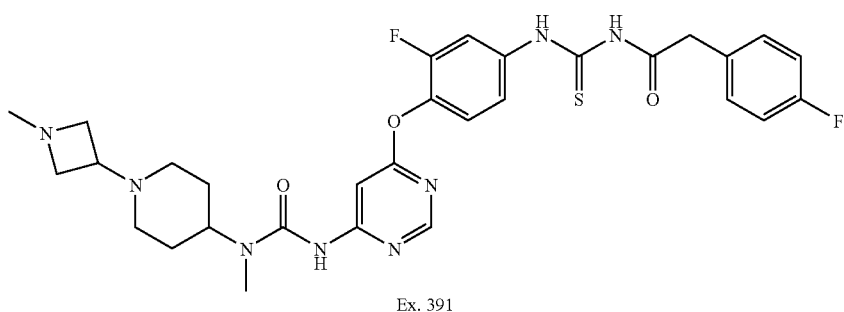
Ex. 391
TABLE 44
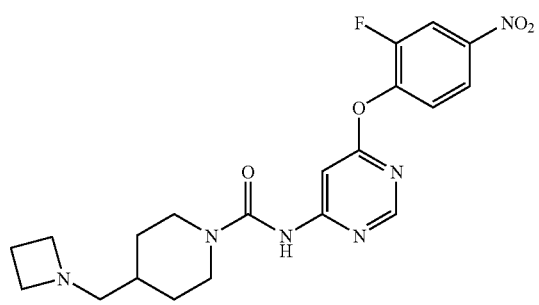
Pro. Ex. 392-1
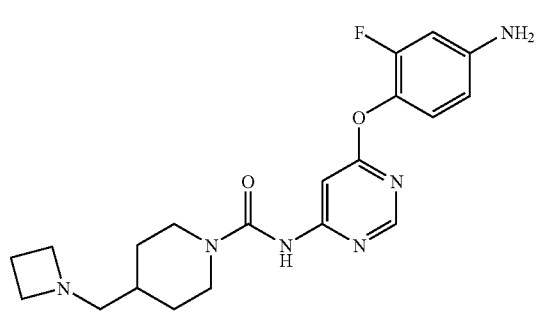
Pro. Ex. 392-2
TABLE 44-continued
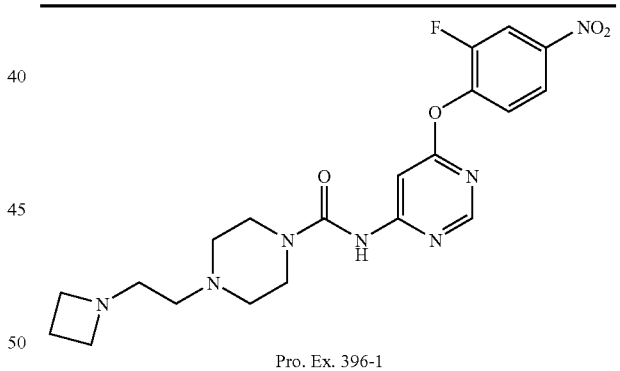
Pro. Ex. 396-1
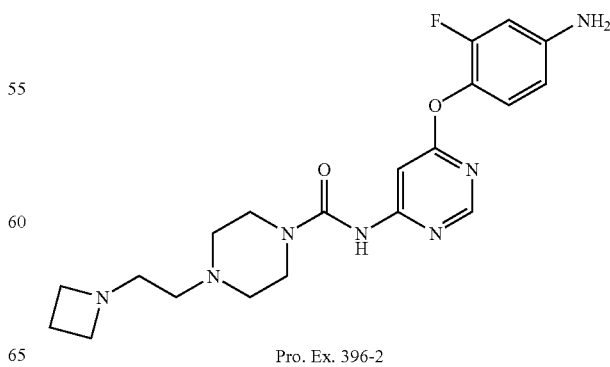
Pro. Ex. 396-2

TABLE 45
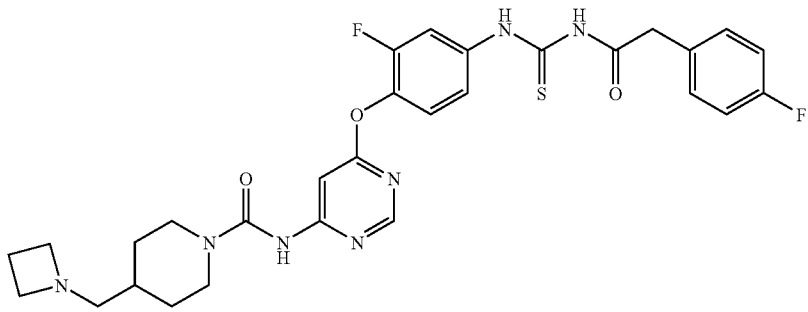
Ex. 392
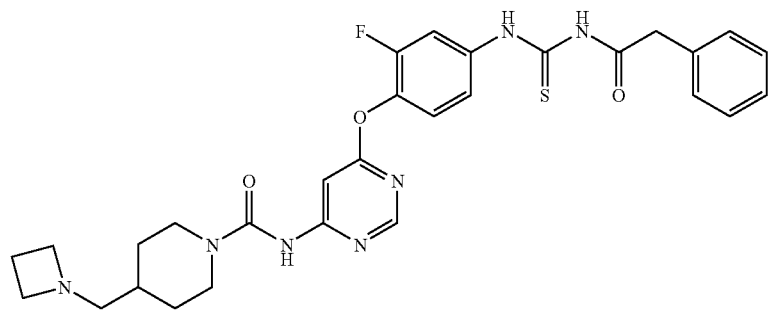
Ex. 393
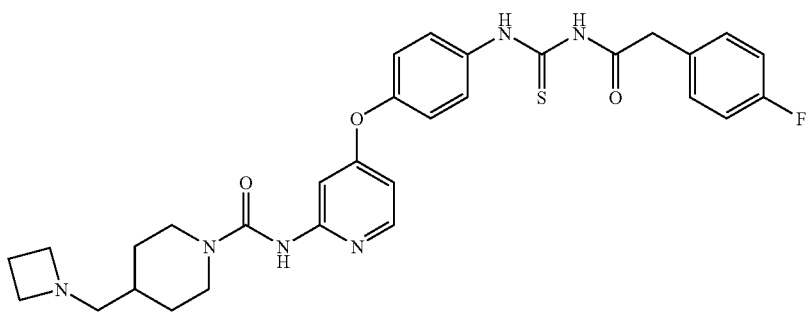
Ex. 394
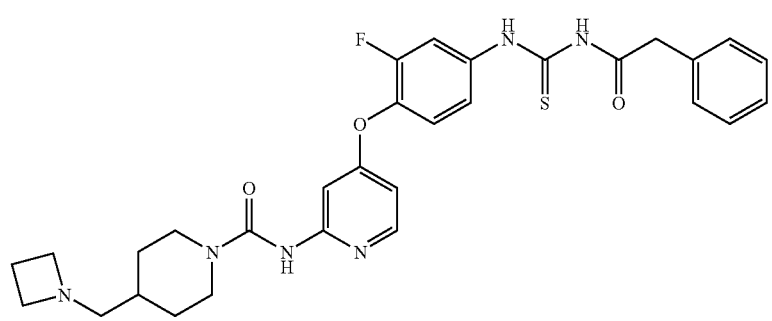
Ex. 395

TABLE 45-continued

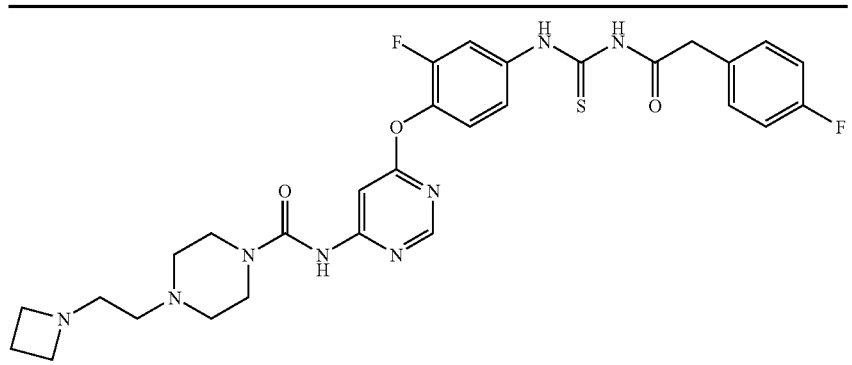

Ex. 396

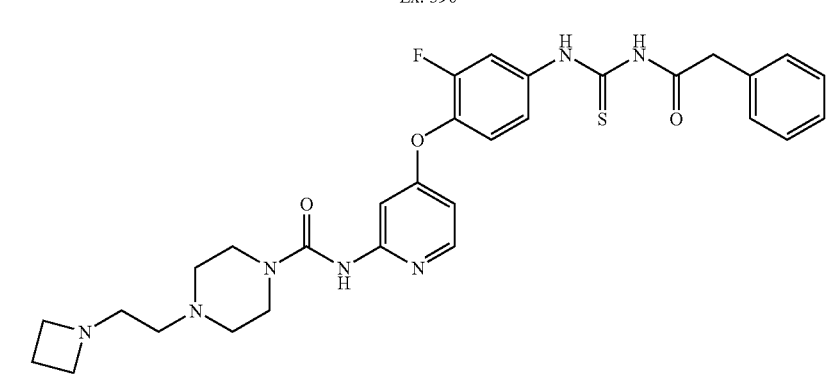

Ex. 397

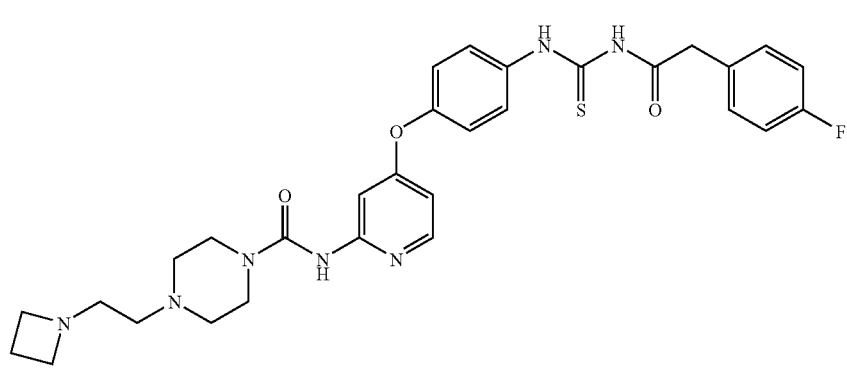

Ex. 398

A compound according to the present invention has excellent HGFR inhibitory activity, and is useful as an anti-tumor agent against various kinds of tumors such as a pancreatic cancer, a gastric cancer, a colorectal cancer, a breast cancer, a prostate cancer, a lung cancer, a renal cancer, a brain tumor and an ovarian cancer, an inhibitor against angiogenesis or a cancer metastasis inhibitor.

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: an artificially synthesized primer sequence
      used in PCR to isolate the cytoplasmic domain of HGFR from the -continued

```
       human placental cDNA library

<400> SEQUENCE: 1
ccggccggat ccaaaaagag aaagcaaatt aaa                         33

<210> SEQ ID NO 2
<211> LENGTH: 33
<212> TYPE: DNA
<213> ORGANISM: Artificial Sequence
<220> FEATURE:
<223> OTHER INFORMATION: an artificially synthesized primer sequence
      used in PCR to isolate the cytoplasmic domain of HGFR from the
      human placental cDNA library

<400> SEQUENCE: 2
ttaattctgc agctatgatg tctcccagaa gga                         33
```

What is claimed is:

1. A compound represented by the following formula, or a salt thereof:

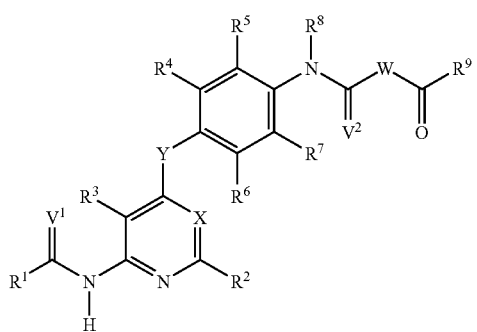

(I)

wherein $R^1$ represents $C_{1-6}$ alkyl, $C_{2-6}$ alkenyl, $C_{2-6}$ alkynyl, $C_{3-10}$ cycloalkyl, $C_{6-10}$ aryl, $C_{1-6}$ alkoxy, 5- to 10-membered heteroaryl, a 3- to 10-membered non-aromatic heterocyclic group or a group represented by the formula —$NR^{11a}R^{11b}$, and $R^1$ may be substituted with a substituent selected from the group consisting of Substituent Group A and Substituent Group B, wherein $R^{11a}$ and $R^{11b}$ may be the same or different and each represents hydrogen, $C_{1-6}$ alkyl, $C_{3-6}$ alkenyl, $C_{3-6}$ alkynyl, $C_{3-10}$ cycloalkyl, $C_{6-10}$ aryl, $C_{1-6}$ alkoxy, 5- to 10-membered heteroaryl or a 4- to 10-membered non-aromatic heterocyclic group, and $R^{11a}$ and $R^{11b}$ may be substituted with a substituent selected from the group consisting of Substituent Group A and Substituent Group B;

$R^2$ and $R^3$ represent hydrogen;

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino;

$R^8$ represents hydrogen or $C_{1-6}$ alkyl;

$R^9$ represents $C_{1-6}$ alkyl, $C_{2-6}$ alkenyl, $C_{2-6}$ alkynyl, $C_{3-10}$ cycloalkyl, $C_{6-10}$ aryl, $C_{3-10}$ cycloalkyl-$C_{1-6}$ alkyl, $C_{6-10}$ aryl-$C_{1-6}$ alkyl, $C_{1-6}$ alkoxy, 5- to 10-membered heteroaryl, a 3- to 10-membered non-aromatic heterocyclic group, 5- to 10-membered heteroaryl-$C_{1-6}$ alkyl, 3- to 10-membered non-aromatic heterocyclic-$C_{1-6}$ alkyl or a group represented by the formula —$NR^{11a}R^{11b}$, and $R^9$ may be substituted with a substituent selected from the group consisting of Substituent Group A and Substituent Group B, wherein $R^{11a}$ and $R^{11b}$ represent the same meaning as recited above;

$V^1$ and $V^2$ may be the same or different and each represents oxygen or sulfur;

W represents a group represented by the formula —$N(R^{W3})$—, wherein $R^{W3}$ represents hydrogen or $C_{1-6}$ alkyl;

X represents nitrogen; and

Y represents oxygen, sulfur, sulfinyl, sulfonyl or a group represented by the formula —$N(R^Y)$—, wherein $R^Y$ represents hydrogen or $C_{1-6}$ alkyl, wherein Substituent Group A is selected from the group consisting of halogen, hydroxyl, mercapto, nitro, cyano and oxo;

wherein Substituent Group B is selected from the group consisting of $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{3-6}$ alkenyloxy, $C_{3-6}$ alkynyloxy, $C_{3-10}$ cycloalkoxy, $C_{6-10}$ aryloxy, 5- to 10-membered heteroaryloxy, 4- to 10-membered non-aromatic heterocyclicoxy, $C_{1-6}$ alkylthio, $C_{3-6}$ alkenylthio, $C_{3-6}$ alkynylthio, $C_{3-10}$ cycloalkylthio, $C_{6-10}$ arylthio, 5- to 10-membered heteroarylthio, 4- to 10-membered non-aromatic heterocyclicthio and a group represented by the formula -$T^1$-$T^2$-$T^3$, and each group in Substituent Group B may be substituted with a substituent selected from the group consisting of Substituent Group C, wherein $T^1$ represents a direct bond or $C_{1-6}$ alkylene, $T^2$ represents carbonyl, sulfinyl, sulfonyl, a group represented by the formula —C(=O)—O—, a group represented by the formula —O—C(=O)—, a group represented by the formula —$SO_2$—O—, a group represented by the formula —O—$SO_2$—, a group represented by the formula —$NR^{T1}$—, a group represented by the formula —C(=O)—$NR^{T1}$—, a group represented by the formula —$NR^{T1}$—C(=O)—, a group represented by the formula —$SO_2$—$NR^{T1}$— or a group represented by the formula —$NR^{T1}$—$SO_2$—, $T^3$ represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{T1}$ represents hydrogen or $C_{1-6}$ alkyl; and wherein Substituent Group C is selected from the group consisting of halogen, hydroxyl, mercapto, nitro, cyano, oxo, $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy and $C_{1-6}$ alkylthio.

2. The compound according to claim 1, or a salt thereof, wherein $R^1$ represents $C_{1-6}$ alkyl optionally substituted with a substituent selected from the group consisting of Substituent Group A and Substituent Group B recited in claim 1.

3. A compound according to claim 1, or a salt thereof, wherein $R^1$ represents $C_{1-6}$ alkyl optionally substituted with a substituent selected from the group consisting of Substituent Group D, wherein Substituent Group D is selected from the group consisting of amino, mono-$C_{1-6}$ alkylamino and di-$C_{1-6}$ alkylamino.

4. The compound according to claim 1, or a salt thereof, wherein $R^1$ represents a 3- to 10-membered non-aromatic heterocyclic group optionally substituted with a substituent selected from the group consisting of Substituent Group A and Substituent Group B.

5. The compound according to claim 1, or a salt thereof, wherein $R^1$ represent a group represented by the formula (II):

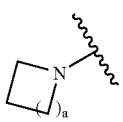

(II)

wherein a represents an integer of 1 to 4, or a group represented by the formula (III):

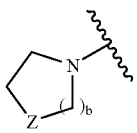

(III)

wherein b represents an integer of 1 to 3, and Z represents oxygen, sulfur, carbonyl, sulfonyl or a group represented by the formula —$NR^Z$—, wherein $R^Z$ represents hydrogen or $C_{1-6}$ alkyl, and the groups represented by the formula (II) or (III) may be substituted with a substituent selected from the group consisting of Substituent Group A and Substituent Group B.

6. The compound according to claim 1, or a salt thereof, wherein $R^1$ represents azetidin-1-yl, pyrrolidin-1-yl, piperidin-1-yl, azepan-1-yl, piperazin-1-yl, diazepan-1-yl, morpholin-4-yl, thiomorpholin-4-yl or 1,1-dioxothiomorpholin-4-yl optionally substituted with a substituent selected from the group consisting of Substituent Group E, wherein Substituent Group E is selected from the group consisting of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, diazepanyl and a group represented by -$T^4$-$T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino, wherein each group included in Substituent Group E may be substituted with hydroxyl, $C_{1-6}$ alkyl, di-$C_{1-6}$ alkylamino, azetidinyl or pyrrolidinyl.

7. The compound according to claim 1, or a salt thereof, wherein $R^1$ represents azetidin-1-yl, pyrrolidin-1-yl, piperidin-1-yl, azepan-1-yl, piperazin-1-yl, diazepan-1-yl or morpholin-4-yl optionally substituted with a substituent selected from the group consisting of Substituent Group E', wherein Substituent Group E' is selected from the group consisting of methyl, ethyl, dimethylamino, azetidinyl, pyrrolidinyl, piperidinyl and piperazinyl, and where each group included in Substituent Group E' may be substituted with hydroxyl, methyl, dimethylamino, azetidinyl or pyrrolidinyl.

8. The compound according to claim 1, or a salt thereof, wherein $R^1$ represents a group represented by the formula —$NR^{11a}R^{11b}$, wherein $R^{11a}$ and $R^{11b}$ represent the same meaning as recited in claim 1.

9. The compound according to claim 1, or a salt thereof, wherein $R^1$ represents a group represented by the formula —$NR^{11c}R^{11d}$, wherein $R^{11c}$ represents hydrogen or $C_{1-6}$ alkyl, and $R^{11d}$ represents $C_{1-6}$ alkyl or a group represented by the formula (IV):

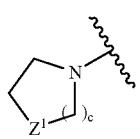

(IV)

wherein c represents an integer of 1 to 3, and $Z^1$ represents oxygen, sulfur, carbonyl, sulfonyl or a group represented by the formula —$NR^{Z1}$—, wherein $R^{Z1}$ represents hydrogen or $C_{1-6}$ alkyl, and $R^{11d}$ may be substituted with a substituent selected from the group consisting of Substituent Group A and Substituent Group B.

10. The compound according to claim 1, or a salt thereof, wherein $R^1$ represents a group represented by the formula —$NR^{11e}R^{11f}$, wherein $R^{11e}$ represents hydrogen or $C_{1-6}$ alkyl, and $R^{11f}$ represents $C_{1-6}$ alkyl, pyrrolidin-3-yl, piperidin-3-yl, piperidin-4-yl, piperazin-4-yl or tetrahydropyran-4-yl, and $R^{11f}$ may be substituted with a substituent selected from the group consisting of Substituent Group E, wherein Substituent Group E is selected from the group consisting of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$_{1-6}$ alkylamino, azetidinyl, pyrrolidinyl, piperidinyl, piperazinyl, diazeppanyl and a group represented by -$T^4$-$T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino, and wherein each group included in Substituent Group E may be substituted with hydroxyl, $C_{1-6}$ alkyl, di-$C_{1-6}$ alkylamino, azetidinyl or pyrrolidinyl.

11. The compound according to claim 1, or a salt thereof, wherein $R^1$ represents a group represented by the formula —$NR^{11g}R^{11h}$, wherein $R^{11g}$ represents hydrogen or methyl, and $R^{11h}$ represents n-propyl, n-butyl, pyrrolidin-3-yl, piperidin-3-yl, piperidin-4-yl or tetrahydropyran-4-yl, and $R^{11h}$ may be substituted with a substituent selected from the group consisting of Substituent Group E",
  wherein Substituent Group E" is selected from the group consisting of methyl, ethyl, n-propyl, acetyl, dimethylamino, diethylamino, azetidinyl, pyrrolidinyl and piperazinyl, and
  wherein each group included in Substituent Group E" may be substituted with methyl or diethylamino.

12. The compound according to claim 1, or a salt thereof, wherein $R^4$, $R^5$, $R^6$ and $R^7$ may be the same or different and each represents hydrogen, halogen or $C_{1-6}$ alkyl.

13. The compound according to claim 1, or a salt thereof, wherein $R^8$ represents hydrogen.

14. The compound according to claim 1, or a salt thereof, wherein $V^1$ represents oxygen.

15. The compound according to claim 1, or a salt thereof, wherein Y represents oxygen.

16. The compound according to claim 1, or a salt thereof, wherein $V^2$ represents sulfur.

17. The compound according to claim 1, or a salt thereof, wherein W represents a group represented by the formula —NH— and wherein $V^2$ represents sulfur.

18. The compound according to claim 1, or a salt thereof, wherein $V^2$ represents oxygen.

19. The compound according to claim 1, or a salt thereof, wherein W represents a group represented by the formula —NH— and wherein $V^2$ represents oxygen.

20. The compound according to claim 1, or a salt thereof, wherein $R^9$ represents $C_{1-6}$ alkyl, $C_{3-10}$ cycloalkyl, $C_{3-10}$ cycloalkyl-$C_{1-6}$ alkyl, $C_{6-10}$ aryl-$C_{1-6}$ alkyl, 5- to 10-membered heteroaryl-$C_{1-6}$ alkyl or 3- to 10-membered non-aromatic heterocyclic-$C_{1-6}$ alkyl, and $R^9$ may be substituted with a substituent selected from the group consisting of Substituent Group A and Substituent Group B.

21. The compound according to claim 1, or a salt thereof, wherein $R^9$ represents $C_{3-10}$ cycloalkyl-$C_{1-6}$ alkyl or $C_{6-10}$ aryl-$C_{1-6}$ alkyl, and $R^9$ may be substituted with a substituent selected from the group consisting of Substituent Group A and Substituent Group B.

22. A pharmaceutical composition comprising the compound according to claim 1, a salt thereof.

23. The compound according to claim 1, or a salt thereof, wherein said compound is selected from the group consisting of:
  1) Pyrrolidine-1-carboxylic acid [6-(2-fluoro-4-{3-[2-(4-fluorophenyl)acetyl]thioureido}phenoxy)pyrimidin-4-yl]amide,
  2) 3-[6-(2-Fluoro-4-{3-[2-(4-fluorophenyl)acetyl]thioureido}phenoxy)pyrimidin-4-yl]-1-methyl-1-(1-methylpiperidin-4-yl)urea,
  3) 4-(Azetidin-1-yl)piperidine-1-carboxylic acid [6-(2-fluoro-4-{3-[2-(4-fluorophenyl)acetyl]thioureido}phenoxy)pyrimidin-4-yl]amide,
  4) 4-{[(3 S)-3-Dimethylaminomethyl)pyrrolidin-1-yl]carbonylamino}-6-(2-fluoro-4-{3-[2-(4-fluorophenyl)acetyl]thioureido}phenoxy)pyrimidine,
  5) 4-{[4-(Dimethylaminomethyl)piperidin-1-yl]carbonylamino}-6-(2-fluoro-4-{3-[2-(4-fluorophenyl)acetyl]thioureido}phenoxy)pyrimidine,
  6) 4-{[4-(2-Dimethylaminoethyl)piperazin-1-yl]carbonylamino}-6-(2-fluoro-4-{3-[2-(4-fluorophenyl)acetyl]thioureido}phenoxy)pyrimidine,
  7) 1-[1-(2-Dimethylaminoethyl)piperidin-4-yl]-3-[6-(2-fluoro-4-{3-[2-(4-fluorophenyl)acetyl]thioureido}phenoxy)pyrimidin-4-yl]-1-methylurea,
  8) 4-(2-Fluoro-4-{3-[2-(4-fluorophenyl)acetyl]thioureido}phenoxy)-6-{[4-(1-methylpiperazin-4-yl)piperidin-1-yl]carbonylamino}pyrimidine,
  9) 4-(2-Fluoro-4-{3-[2-(4-fluorophenyl)acetyl]thioureido}phenoxy)-6-{[4-(1-methylpiperidin-4-yl)piperazin-1-yl]carbonylamino}pyrimidine,
  10) 4-(1-Methylazetidin-3-yl)piperazine-1-carboxylic acid [6-(2-fluoro-4-{3-[2-(4-fluorophenyl)acetyl]thioureido}phenoxy)pyrimidin-4-yl]amide,
  11) 3-[6-(2-Fluoro-4-{3-[2-(4-fluorophenyl)acetyl]thioureido}phenoxy)pyrimidin-4-yl]-1-methyl-1-[(3S)-1-methylpyrrolidin-3-yl]urea,
  12) 3-Dimethylaminoazetidine-1-carboxylic acid [6-(2-fluoro-4-{3-[2-(4-fluorophenyl)acetyl]thioureido}phenoxy)pyrimidin-4-yl]amide,
  13) 4-{[(3R)-3-(Dimethylaminomethyl)pyrrolidin-1-yl]carbonylamino}-6-(2-fluoro-4-{3-[2-(4-fluorophenyl)acetyl]thioureido}phenoxy)pyrimidine,
  14) 1-[1-(3-Dimethylaminopropyl)piperidin-4-yl]-3-[6-(2-fluoro-4-{3-[2-(4-fluorophenyl)acetyl]thioureido}phenoxy)pyrimidin-4-yl]-1-methylurea,
  15) 4-(Pyrrolidin-1-ylmethyl)piperidine-1-carboxylic acid [6-(2-fluoro-4-{3-[2-(4-fluorophenyl)acetyl]thioureido}phenoxy)pyrimidin-4-yl]amide,
  16) 3-(6-{2-Fluoro-4-[3-(4-fluorophenyl)acetylthioureido]phenoxy}pyrimidin-4-yl)-1-methyl-1-[1-(1-methylazetidin-3-yl)piperidin-4-yl]urea,
  17) 4-(Azetidin-1-ylmethyl)piperidine-1-carboxylic acid [6-(2-fluoro-4-{3-[2-(4-fluorophenyl)acetyl]thioureido}phenoxy)pyrimidin-4-yl]amide,
  18) 4-(Azetidin-1-ylmethyl)piperidine-1-carboxylic acid {6-[2-fluoro-4-(3-phenylacetylthioureido)phenoxy]pyrimidin-4-yl}amide, and
  19) 4-[2-(Azetidin-1-yl)ethyl]piperazine-1-carboxylic acid [6-(2-fluoro-4-{3-[2-(4-fluorophenyl)acetyl]thioureido}phenoxy)pyrimidin-4-yl]amide.

24. The compound according to claim 1 or a salt thereof, wherein said compound is 3-[6-(2-Fluoro-4-{3-[2-(4-fluorophenyl)acetyl]thioureido}phenoxy) pyrimidin-4-yl]-1-methyl-1-(1-methylpiperidin-4-yl)urea.

25. The compound according to claim 1 or a salt thereof, wherein said compound is 1-[1-(2-Dimethylaminoethyl)piperidin-4-yl]-3-[6-(2-fluoro-4-{3-[2-(4-fluorophenyl)acetyl]thioureido}phenoxy)pyrimidin-4-yl]-1-methylurea.

* * * * *